US010772962B2

(12) United States Patent
Qian et al.

(10) Patent No.: US 10,772,962 B2
(45) Date of Patent: Sep. 15, 2020

(54) COMPOUNDS AND METHODS FOR THE TARGETED DEGRADATION OF BROMODOMAIN-CONTAINING PROTEINS

(71) Applicants: Arvinas, Inc., New Haven, CT (US); Yale University, New Haven, CT (US)

(72) Inventors: Yimin Qian, Plainsboro, NJ (US); Hanqing Dong, Madison, CT (US); Jing Wang, Milford, CT (US); Michael Berlin, Flemington, NJ (US); Andrew P. Crew, Guilford, CT (US); Craig M. Crews, New Haven, CT (US)

(73) Assignees: ARVINAS OPERATIONS, INC., New Haven, CT (US); YALE UNIVERSITY, New Haven, CT (US)

( * ) Notice: Subject to any disclaimer, the term of this patent is extended or adjusted under 35 U.S.C. 154(b) by 0 days.

(21) Appl. No.: 15/230,354

(22) Filed: Aug. 5, 2016

(65) Prior Publication Data

US 2017/0065719 A1 Mar. 9, 2017

Related U.S. Application Data

(60) Provisional application No. 62/207,240, filed on Aug. 19, 2015, provisional application No. 62/324,804, filed on Apr. 19, 2016.

(51) Int. Cl.

| | |
|---|---|
| ***C07D 521/00*** | (2006.01) |
| ***A61K 45/06*** | (2006.01) |
| ***C07D 519/00*** | (2006.01) |
| ***C07D 417/14*** | (2006.01) |
| ***C07D 495/14*** | (2006.01) |
| ***A61K 47/55*** | (2017.01) |

(52) U.S. Cl.

CPC .............. *A61K 45/06* (2013.01); *A61K 47/55* (2017.08); *C07D 417/14* (2013.01); *C07D 495/14* (2013.01); *C07D 519/00* (2013.01)

(58) Field of Classification Search

CPC .................................................... C07D 521/00

See application file for complete search history.

(56) References Cited

U.S. PATENT DOCUMENTS

| | | | |
|---|---|---|---|
| 6,306,663 | B1 | 10/2001 | Kenten et al. |
| 6,670,348 | B1 | 12/2003 | Rosen et al. |
| 7,030,141 | B2 | 4/2006 | Bigge et al. |
| 7,041,298 | B2 | 5/2006 | Deshaies et al. |
| 7,208,157 | B2 | 4/2007 | Sakamoto et al. |
| 7,244,851 | B2 | 7/2007 | Cohen et al. |
| 7,345,081 | B2 | 3/2008 | Cohen et al. |
| 7,419,975 | B2 | 9/2008 | Palermo et al. |
| 7,517,906 | B2 | 4/2009 | Condon et al. |
| 7,915,293 | B2 | 3/2011 | Ramesh |
| 9,500,653 | B2 | 11/2016 | Crews et al. |
| 9,632,089 | B2 | 4/2017 | Crews et al. |
| 2006/0128632 | A1 | 6/2006 | Sharma et al. |
| 2008/0051432 | A1 | 2/2008 | Zhang |
| 2008/0214501 | A1 | 9/2008 | Zhengying et al. |
| 2008/0269140 | A1 | 10/2008 | Wang et al. |
| 2009/0035362 | A1 | 2/2009 | Shih et al. |
| 2010/0203012 | A1 | 8/2010 | Laurent et al. |
| 2010/0286127 | A1 | 11/2010 | Miyoshi et al. |
| 2011/0195043 | A1 | 8/2011 | Sun et al. |
| 2012/0270800 | A1 | 10/2012 | Verdine et al. |
| 2014/0066625 | A1 | 3/2014 | Mautiino et al. |
| 2014/0235629 | A1 | 8/2014 | Bartberger et al. |
| 2014/0243372 | A1 | 8/2014 | Rew |
| 2014/0256700 | A1 | 9/2014 | Poss |
| 2014/0296243 | A1 | 10/2014 | Albrecht et al. |
| 2014/0302523 | A1 | 10/2014 | Crews et al. |
| 2014/0356322 | A1 | 12/2014 | Crews et al. |
| 2014/0371206 | A1 | 12/2014 | Albrecht et al. |
| 2015/0119435 | A1 | 4/2015 | Crews et al. |
| 2015/0148342 | A1 | 5/2015 | Combs et al. |
| 2015/0291562 | A1 | 10/2015 | Crew et al. |
| 2015/0344473 | A1 | 10/2015 | Du et al. |
| 2016/0022642 | A1 | 1/2016 | Crews et al. |
| 2016/0045607 | A1 | 2/2016 | Crew et al. |
| 2016/0058872 | A1 | 3/2016 | Crew et al. |
| 2016/0136230 | A1 | 5/2016 | Campos et al. |
| 2016/0176864 | A1 | 6/2016 | Norris et al. |
| 2016/0214972 | A1 | 7/2016 | Jin et al. |
| 2016/0272639 | A1 | 9/2016 | Crew et al. |
| 2016/0368911 | A1 | 12/2016 | Campos et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2017/0121321 | A1 | 5/2017 | Crews et al. |
| 2017/0281784 | A1 | 10/2017 | Wang et al. |
| 2017/0307614 | A1 | 10/2017 | Crews et al. |
| 2017/0327469 | A1 | 11/2017 | Crew et al. |

(Continued)

FOREIGN PATENT DOCUMENTS

| | | | |
|---|---|---|---|
| CN | 103688176 | A | 3/2014 |
| EP | 2985285 | A1 | 2/2016 |

(Continued)

OTHER PUBLICATIONS

Zengerle et al. ( ACS Chemical Biology (2015), 10(8), 1770-1777).*

(Continued)

*Primary Examiner* — Bruck Kifle

(74) *Attorney, Agent, or Firm* — Bryan D. Zerhusen, Esq.; Nicholas R. Herrel, Esq.; Cantor Colburn LLP

(57) ABSTRACT

The present invention relates to bifunctional compounds, which find utility as modulators of targeted ubiquitination, especially inhibitors of a variety of polypeptides and other proteins which are degraded and/or otherwise inhibited by bifunctional compounds according to the present invention. In particular, the present invention is directed to compounds, which contain on one end a VHL ligand which binds to the ubiquitin ligase and on the other end a moiety which binds a target protein such that the target protein is placed in proximity to the ubiquitin ligase to effect degradation (and inhibition) of that protein. The present invention exhibits a broad range of pharmacological activities associated with compounds according to the present invention, consistent with the degradation/inhibition of targeted polypeptides.

23 Claims, 10 Drawing Sheets

(56) References Cited

U.S. PATENT DOCUMENTS

| | | | |
|---|---|---|---|
| 2018/0015087 | A1 | 1/2018 | Liu et al. |
| 2018/0072711 | A1 | 3/2018 | Crew et al. |
| 2018/0099940 | A1 | 4/2018 | Crew et al. |
| 2018/0125821 | A1 | 5/2018 | Crew et al. |
| 2018/0147202 | A1 | 5/2018 | Crew et al. |
| 2018/0155322 | A1 | 6/2018 | Crew et al. |
| 2018/0177750 | A1 | 6/2018 | Crew et al. |
| 2018/0179183 | A1 | 6/2018 | Crew et al. |
| 2018/0193470 | A1 | 7/2018 | Crew et al. |
| 2018/0215731 | A1 | 8/2018 | Crew et al. |
| 2018/0228907 | A1 | 8/2018 | Crew et al. |
| 2018/0237418 | A1 | 8/2018 | Crew et al. |
| 2018/0256586 | A1 | 9/2018 | Crew et al. |

FOREIGN PATENT DOCUMENTS

| | | | |
|---|---|---|---|
| JP | A 2004-525889 | | 8/2004 |
| JP | A 2010-502627 | | 1/2010 |
| RU | 2008/112221 | A | 10/2009 |
| RU | 2448101 | C2 | 4/2012 |
| RU | 2011/121567 | A | 10/2012 |
| RU | 2012/138709 | A | 3/2014 |
| WO | WO 1998/003502 | | 1/1998 |
| WO | WO 2000/066119 | | 11/2000 |
| WO | WO 2002/066512 | | 8/2002 |
| WO | WO 2002/100845 | | 12/2002 |
| WO | WO 2005/097791 | | 10/2005 |
| WO | WO 2006/069063 | | 6/2006 |
| WO | WO 2006/113942 | | 10/2006 |
| WO | WO 2007/101347 | | 9/2007 |
| WO | WO 2007/106670 | | 9/2007 |
| WO | WO 2007/130626 | | 11/2007 |
| WO | WO 2008/011392 | | 1/2008 |
| WO | WO 2008/014236 | | 1/2008 |
| WO | WO 2008/109057 | | 9/2008 |
| WO | WO 2008/128121 | | 10/2008 |
| WO | WO 2008/128171 | | 10/2008 |
| WO | WO 2008/134679 | | 11/2008 |
| WO | WO 2009/015254 | | 1/2009 |
| WO | WO 2009/060292 | | 5/2009 |
| WO | WO 2010/107485 | | 9/2010 |
| WO | WO 2010/141805 | | 12/2010 |
| WO | WO 2011/143660 | | 11/2011 |
| WO | WO 2011/143669 | | 11/2011 |
| WO | WO 2012/003281 | | 1/2012 |
| WO | WO 2012/040527 | | 3/2012 |
| WO | WO 2012/054110 | | 4/2012 |
| WO | WO 2012/078559 | | 6/2012 |
| WO | WO 2012/090104 | | 7/2012 |
| WO | WO 2013/071035 | | 5/2013 |
| WO | WO 2013/071039 | | 5/2013 |
| WO | WO 2013/106643 | | 7/2013 |
| WO | WO 2013/106646 | | 7/2013 |
| WO | WO 2013/170147 | | 11/2013 |
| WO | WO 2013/175417 | | 11/2013 |
| WO | WO 2013/178570 | | 12/2013 |
| WO | WO 2014/001356 | | 1/2014 |
| WO | WO 2014/011712 | | 1/2014 |
| WO | WO 2014/020502 | | 2/2014 |
| WO | WO 2014/025759 | | 2/2014 |
| WO | WO 2014/038606 | | 3/2014 |
| WO | WO 2014/047024 | | 3/2014 |
| WO | WO 2014/055461 | | 4/2014 |
| WO | WO 2014/074658 | | 5/2014 |
| WO | WO 2014/100065 | | 6/2014 |
| WO | WO 2014/100071 | | 6/2014 |
| WO | WO 2014/107713 | | 7/2014 |
| WO | WO 2014/108452 | | 7/2014 |
| WO | WO 2014/123418 | | 8/2014 |
| WO | WO 2014/128111 | | 8/2014 |
| WO | WO 2014/134201 | | 9/2014 |
| WO | WO 2014/151863 | | 9/2014 |
| WO | WO 2015/000868 | | 1/2015 |
| WO | WO 2015/006524 | | 1/2015 |
| WO | WO 2015/011084 | | 1/2015 |
| WO | WO 2015/022332 | | 2/2015 |
| WO | WO 2015/015318 | | 5/2015 |
| WO | WO 2015/067770 | | 5/2015 |
| WO | WO 2015/074064 | | 5/2015 |
| WO | 2015160845 | A2 | 10/2015 |
| WO | WO 2015/195863 | | 12/2015 |
| WO | WO 2016/050821 | | 4/2016 |
| WO | WO 2016/069578 | | 5/2016 |
| WO | WO 2016/105518 | | 6/2016 |
| WO | 2016118666 | A1 | 7/2016 |
| WO | WO 2016/146985 | | 9/2016 |
| WO | WO 2016/172134 | | 10/2016 |
| WO | WO 2016/197114 | | 12/2016 |
| WO | WO 2017/007612 | A1 | 1/2017 |
| WO | WO 2017/011590 | | 1/2017 |
| WO | WO 2017/024317 | | 2/2017 |
| WO | WO 2017/024318 | A1 | 2/2017 |
| WO | WO 2017/024319 | A1 | 2/2017 |
| WO | WO 2017/030814 | | 2/2017 |
| WO | WO 2017/079267 | | 5/2017 |

OTHER PUBLICATIONS

Zengerle et al. (ACS Chem. Biol. 2015, 10, 1770-1777).*

Ahn, et al., "HIF-lalpha peptide derivatives with modifications at the hydroxyproline residue as activators of HIF-lalpha", Bioorg Med Chem Lett. 19(15), 2009, 4403-4405.

Albrecht, B., et al., "Identification of a benzoisoxazoloazepine inhibitor (CPI-0610) of the bromodomain and extra-terminal (BETA) family as a candidate for human clinical trials", Journal Med. Chem. 59, 1330-1339 (2016).

Ardecky, RJ, et al., "Design, synthesis and evaluation of inhibitor of apoptosis protein (IAP) antagonists that are highly selective for the BIR2 domain of XIAP", Bioorg. Med. Chem., 23(14): 4253-4257 (2013).

Asangani, I.A. et al., "Therapeutic Targeting of BET Bromodomain Proteins in Castration-Resistant Prostate Cancer", Nature, 2014, 510: 278-282.

Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (2013).

Baratta, M.G. et al., "An in-tumor genetic screen reveals that the BET bromodomain protein, BRD4, is a potential therapeutic target in ovarian carcinonoma", PNAS, 112: 232-237 (2015).

Bargagna-Mohan, et al., "Use of PROTACS as molecular probes of angiogenesis", Bioorg Med Chem Left. 15(11) 2005, 2724-2727.

Belkina, A.C. et al., "BET domain co-regulators in obesity, inflammation and cancer", Nat. Rev. Cancer, 12 (2012) 465-477.

Boi, M. et al., "The BET Bromodomain inhibitor OTX015 Affects pathogenetic Pathways in Preclinical B-cell Tumor Models and synergizes with Targeted Drugs", Clin. Cancer Res., (2015) 21(7):1628-1638.

Bondeson, et al., "Catalytic in vivo protein knockdown by small-molecule PROTACS", National Chem Biol. 11(8) Aug. 2015, 611-617.

Buckley, et al., "HaloPROTACS: use of small molecule PROTACS to induce degradation of HaloTag fusion proteins", ACS Chem Biol. 10(8), 2015, 1831-1837.

Buckley, et al., "Small-molecule inhibitors of the interaction between the E3 ligase VHL and HIF1a", Angew Chem Int Ed Engl.51(46), Oct. 12, 2012, 11463-11467.

Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.

Capitosti, S., et al., "Thalidomide analogues demonstrate dual inhibition of both angiogenesis and prostate cancer", Bioorganic & Medicinal Chemistry 12, (2004) 327-336.

Carmony, KC, et al., "PROTAC-Induced Proteolytic Targeting", Methods Mol. Biol., 2012, vol. 832, pp. 627-638.

CAS Registry No. 1004933-70-3, which entered STN on Feb. 21, 2008.

CAS Registry No. 871986-52-6 entered STN Jan. 16, 2006.

(56) References Cited

OTHER PUBLICATIONS

Ceribelli, M. et al., "Blockade of oncongenic IKB kinase activity in diffuse large B-cell lymphoma by bromodomain and extraterminal domain protein inhibitors", PNAS, 111 (2014) 11365-11370.
Chapuy, B. et al., "Discovery and characterization of super-enhancer-associated dependencies in diffuse large B cell lymphoma", Cancer Cell, 24 (2013) 777-790.
Chene, P., et al., "Inhibiting the p53-MDM2 interaction: an important target for cancer therapy" Nat. Rev. Cancer (2003), 3, 102-109.
Chung, et al., "Discovery and Characterization of Small Molecule Inhibitors of the BET Family Bromodomains", J Med Chem. 54(11), Jun. 9, 2011, 3827-3838.
Cohen, F, et al., "Orally bioavailable antagonists of inhibitor of apoptosis proteins based on an azabicyclooctane scaffold", J. Med. Chem., 52(6), 1723-1730 (2009).
Cohen, F. et al., "Antogonists of inhibitors of apoptosis proteins based on thiazole amide isosteres", Bioorg. Med. Chem. Lett., 20(7), 2229-2233 (2010).
Contino-Pepin, Christiane, et al., "Preliminary biological evaluations of new thalidomide analogues for multiple sclerosis application", Bioorganic & Medicinal Chemistry Letter 19 (2009), 878-881.
Corson, et al., "Design and applications of bifunctional small molecules: why two heads are better than one", ACS Chemical Biology vol. 3 No. 11, pp. 677-692; Nov. 21, 2008.
Crews, C. M., "Targeting the undruggable proteome: the small molecules of my dreams", *Chem Biol 17*, 551-555, doi:S1074-5521(10)00196-1 [pii] 10.1016/j.chembio1.2010.05.011 (2010).
Cyrus, et al., "Jostling for position: optimizing linker location in the design of estrogen receptor-targeting PROTACs", Chem Med Chem. 5(7), Jul. 5, 2010, 979-985.
Cyrus, K. et al, "Impact of Linker Length on the Activity of PROTACs," Mol. Biosyst., 2011, vol. 7, No. 2, pp. 359-364.
Cyrus, K. et al, "Two-Headed PROTAC: An Effective New Tool for Targeted Protein Degradation," Chembiochem., 2010, vol. 11,pp. 1531-1534.
Dawson, et al., "Inhibition of BET recruitment to chromatin as an effective treatment for MLL-fusion leukemia", Nature 478, Oct. 2, 2011, 529-533.
Delmore, J.E. et al., "BET Bromodomain inhibition as a therapeutic strategy to target c-Myc", Cell, 146 (2011) 904-917 Platform.
Deroo, B.J., et al., "Estrogen receptors and human disease", Journal of Clinical Investigation, (2006), vol. 116(3), pp. 561-570.
Di, J et al. "Reactivation of p53 by inhibiting Mdm2 E3 Ligase: a novel antitumor approach", Current Cancer Drug Targets (2011), 11(8), 987-994.
Ding, Q, et al., "Discovery of RG7388, a potent and selective p53-MDM2 inhibitor in clinical development", J Med Chem. Jul. 25, 2013; 56(14):5979-83. doi: 10.1021/jm400487c. Epub Jul. 16, 1013. PubMed PMID: 23808545 (J. Med. Chem. (2013) 56, 5979-5983 Ding, et al).
Dixon, S. J. et al., "Identifying druggable disease-modifying gene products",. *Curr Opin Chem Biol 13*, 549-555, doi:S1367-5931(09)00107-0 [pii] 10.1016/j.cbpa.2009.08.003 (2009).
Filippakopoulos, et al., "Selective inhibition of BET bromodomains", Nature 468, Dec. 23, 2010, 1067-1073.
Fischer, et al., "Structure of the DDB1-DRBN E3 Ubiquitin ligase in complex with thalidomide", Nature, vol. 000, pp. 1-5 (2014).
Flygare, J.A., et al. "Small-molecule pan-IAP antagonists: a patent review", Expert Opin. Ther. Pat., 20 (2), 251-267 ( 2010).
French, C.A. et al., "BRD-NUT oncoproteins: a family of closely related nuclear proteins that block epithelial differentiation and maintain the growth of carcinoma cells", Oncogene, 27 (2008) 2237-2242.
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Gosink, M et al., "Redirecting the specificity of ubiquitination by modifying ubiquitin-conjugating enzymes", Pro. Natl. Acad Sci, vol. 92, pp. 9117-9121, 1995.
Haupt, Y. et al., "Mdm2 promotes the rapid degradation of p53", Nature 387, 296-299 (1997).
Hennessy, EJ, et al., "Discovery of aminopiperidine-based Smac mimetics as IAP antagonists", Bioorg. Med. Chem. Lett., 22(4), 1690-1694 (2012).
Hewings, et al., "3,5-Dimethylisoxazoles Act As Acetyllysine-mimetic Bromodomain", J Med Chem. 54(19), Oct. 13, 2011, 6761-6770.
Hines, J., et al., "Posttranslational protein knockdown coupled to receptor tyrosine kinase activation with phosphoPROTACs", Proc Natl Acad Sci USA 110, 8942-8947 (2013).
Hird, AW, et al., "Structure-based design and synthesis of tricyclic IAP (Inhibitors of Apoptosis Proteins) inhibitors", Bioorg. Med. Chem. Lett., 24(7): 1820-1824 (2014).
Hon, et al., "Structural basis for the recognition of hydroxyproline in H1f-1 alpha by pVHL", Nature 417, Jun. 27, 2002, 975-978.
Ivan, M., et al., "HIFa Targeted for VHL-Mediated Destruction by Proline Hydroxylation: Implications for O2 Sensing", Science, vol. 292, No. 5516, pp. 464-468, 2001.
Jang, E.R. et al., "Targeted Degradation of Proteins by PROTACs," Curr. Protoc. Chem. Biol., 2010, vol. 2, No. 2, pp. 71-87.
Kim, K.S., "Discovery of tetrahydroisoquinoline-based bivalent heterodimeric IAP antagonists", Bioorg. Med. Chem. Lett. 24(21), 5022-5029 (2014).
Knott, Edward (1955). "Compounds containing sulphur chromophores. Part I. The action of bases on heterocyclic sulphide quarternary salts", Journal of The Chemical Society (resumed). 10.1039/jr9550000916. 949-954) (USPTO summary attached).
Kronke, et al, "Lenalidomide Causes Selective Degradation of IKZF1 and IKZF3 in Multiple Myeloma Cells", Science 343, 301-305 (2014).
Kurimchak, A. M. et al.," Resistance to BET Bromodomain Inhibitors Is Mediated by Kinome Reprogramming in Ovarian Cancer", Cell Reports 16, 1273-1286 (2016).
Lai, A.C., et al., "Modular PROTAC Design for the Degradation of Oncogenic BCR-ABL", Angew Chem Int Ed Engl 55, 807-810 (2016).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Li, Yan, et al., "Single polymer-drug conjugate carrying two drugs for fixed-dose co-delivery", Medicinal Chemistry, 2014, vol. 4(10): 676-683.
Liu, K., et al., "Design and biological characterization of hybrid compounds of curcumin and thalidomide for multiple myeloma", Org. Biomol. Chem. 2013, 11, 4757-4763.
Lopez-Girona, A. et al., Cereblon is a direct protein target for immunomodulatory and antiproliferative activities of lenalidomide and pomalidomide, Leukemia 26: 2326-2335, 2012).
Loven, J. et al., "Selective Inhibition of Tumor Oncogenes by Disruption of Super Enhancers", Cell, 153 (2013) 320-334.
Lu, et al., "Hijacking the E3 ubiquitin ligase cereblon to efficiently target BRD4", Chem Biol 22(6), 2015, 755-763.
Lu, et al., "The myeloma drug lenalidomide promotes the cereblon-dependent destruction of ikaros proteins", Science 343, 305-309 (2014).
Mannhold, R., et al., "IAP antagonists: promising candidates for cancer therapy", Drug Discov. Today, 15 (5-6), 210-219 (2010).
Mertz, J.A. et al., "Targeting MYC dependence in cancer by inhibiting BET bromodomains", PNAS, 108 (2011) 16669-16674.
Min, Jung-hyun, et al., "Structure of an HIV-1-alpha—pVHL complex: hydroxyproline recognition in signaling", Jun. 7, 2002, 296: 1886-1889.
Miyazaki, M., et al., "Discovery of DS-5272 as a promising candidate: a potent and orally active p53-MDM2 interaction inhibitor", Bioorg. Med. Chem. Lett. (2015) 23, 2360-2367.

(56) References Cited

OTHER PUBLICATIONS

Muller, G., et al., "Amino-Substituted Thalodomide Analogs: Potent Inhibitors of TNF-α Production", Bioorganic & Medicinal Chemistry Letters 9 (1999) 1625-1630.
Ndubaku, C, et al., "Antagonism of c-IAP and XIAP proteins is required for efficient induction of cell death by small-molecule IAP antagonists", ACS Chem Biol. Jul. 17, 2009;4(7):557-566.
Neklesa, T.K., et al., "Chemical biology: Greasy tags for protein removal", Nature 487, 308-309 (2012).
Nicodeme, et al., "Suppression of inflammation by a synthetic histone mimic", Nature 468, Dec. 23, 2010, 1119-1123.
Nikolovska-Coleska, et al., "Interaction of a cyclic, Bivalent Smac Mimetic with the X-linked inhibitor of apoptosis protein", Biochemistry, 2008, 47(37), pp. 9811-9824.
Noel, J. Kay, Abstract C244: "Development of the BET Bromodomain inhibitor OTX015", Mol Cancer Ther 2013; 12(11 Suppl); C244 1-4.
Oost, T.K. et al., "Discovery of potent antagonists of the antiapoptotic protein XIAP for the treatment of cancer", Journal of Medicinal Chemistry 2004, 47, 4417-4426.
Perez, HL,"Discovery of potent heterodimeric antagonists of inhibitor of apoptosis proteins (IAPs) with sustained antitumor activity", J. Med. Chem. 58(3), 1556-1562 (2015).
Puissant, A. et al., "Targeting MYCN in neuroblastoma by BET bromodomain inhibition", Cancer discovery, 3 (2013) 308-323.
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Raina, K., et al., "PROTAC-induced BET protein degradation as a therapy for castration-resistant prostate cancer", Proc Natl Acad Sci USA 113, 7124-7129 (2016).
Rew, Y, et al., "Discovery of AM-7209, a potent and selective 4-amidobenzoic acid inhibitor of the MDM2-p53 interaction", J Med Chem. Dec. 26, 2014;57(24):10499-10511. doi: 10.1021/jm501550p. Epub Dec. 4, 2014. PubMed PMID: 25384157. (J. Med. Chem. (2014) 57, 10499-10511 Rew, et al.).
Rodriguez-Gonzalez, et al., "Targeting steroid hormone receptors for ubiquitination and degradation in breast and prostate cancer", Oncogene. 27(57), Dec. 4, 2008, 7201-7211 868.
Rotili, D., et al., "Photoactivable peptides for identifying enzyme-substrate and protein-protein interactions", Chem Commun (Carob) 47(5), Feb. 2011, 1488-1490.
Ruchelman, A., et al., "Isosteric analogs of lenalidominde and pomalidomide: Synthesis and biological activity", Bioorganic & Medicinal Chemistry Letters 23 (2013) 360-365.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1—Cullin-F box complex for ubiquitination and degradation", Proc Natl Acad Sci U S A.98(15), Jul. 17, 2001, 8554-8559.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Shi, J. et al., "The mechanisms behind the therapeutic activity of BET bromodomain inhabitation", Molecular cell, 54 (2014) 728-736.
Shimamura, et al. "Efficacy of BET bromodomain inhabitation in kras-mutant non-small cell lung cancer", Clinical Cancer Research 19(22), pp. 6183-6192 (2013) DOI:10.1158/1078-0432.CCR-12-3904.
Smith, et al., "Targeted Intracellular Protein Degradation Induced by a Small Molecule: En Route to Ghemical Proteomics", Bioorg Med Chem Lett. 18(22), Nov. 15, 2008, 5904-5908.
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
Stuhlmiller, Timothy J., et al., "Inhibition of Lapatinib-Induced Kinome Reprogramming in ERBB2-Positive Breast Cancer by Targeting BET Family Bromodomains", Cell Reports 11, 390-404 (2015).
Sun, D, et al., "Discovery of AMG 232, a potent, selective, and orally bioavailable MDM2-p53 inhibitor in clinical development", J Med Chem. Feb. 27, 2014;57(4):1454-72. doi: 10.1021/jm401753e. Epub Feb. 5, 2014. PubMed PMID: 24456472.
Sun, et al., "Potent bivalent Smac mimetics: effect of the linker on binding to inhibitor apoptosis proteins (IAPs) and anticancer activity", J. Med. Chem. 53, 3306-3318 (2011).
Turk, B. E., "Binding of thalidomide to alphal-acid glycoprotein may be involved in its inhibition of tumor necrosis factor alpha production", Proc. Natl. Acad. Sci. U.S.A. 1996, 93, 7552-7556.
Vamos M., et al., "Expedient synthesis of highly potent antagonists of inhibitor of apoptosis proteins (IAPs) with unique selectivity for ML-IAP", ACS Chem. Biol., 8(4), 725-732 (2013).
Van Molle, et al., "Dissecting fragment-based lead discovery at the von Hippel-Lindau protein:hypoxia inducible factor 1a protein-protein interface", Chem Biol. 19(10), Oct. 26, 2012, 1300-1312.
Vassilev, et al., "In vivo activation of the p53 pathway by small-molecule antagonists of MDM2", Science 303, Feb. 6, 2004, 844-848.
Vazquez, A. et al., "The genetics of the p53 pathway, apoptosis and cancer therapy", Nat. Rev. Drug. Dis., 7, 979-982 (2008).
Vu, B. et al. "Discovery of RG7112: a small-molecule MDM2 inhibitor in clinical development", ACS Med. Chem. Lett. (2013) 4, 466-469.
Wang J, et al., "Discovery of novel second mitochondrial-derived activator of caspase mimetics as selective inhibitor or apoptosis protein inhibitors", J. Pharmacol. Exp. Ther., 349(2): 319-29 (2014).
Wang, S., et al. "Small-molecule inhibitors of the MDM2-p53 protein-protein interaction (MDM2 inhibitors) in clinical trials for cancer treatment", J. Med. Chem. (2015) 58, 1038-1052.
Wang, S., et al. "Temporal activation of p53 by a specific MDM2 inhibitor is selectively toxic to tumors and leads to complete tumor growth inhabitation", PNAS USA (2008) 105, 3933-3938.
Weinmann, H., "Cancer Immunotherapy: Selected Targets and Small-Molecule Modulators", ChemMedChem (2016), 11, 450-466.
Winter, et al., "Phthalimide Conjugation as a strategy for in vivo target protein degradation", Science, 2015 vol. 348 (6241), pp. 1376-1381 [Pub online: May 21, 2015].
Wyce, A. et al., "Inhibition of BET bromodomain proteins as a therapeutic approach in prostate cancer", Oncotarget, 4 (2013) 2419-2429.
Zhang B.et al., "Small-molecule MDM2-p53 inhibitors: recent advances", Future Med. Chem. (2015) 7, 631-645.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
Golub, et al., "Molecular classification of cancer: class discovery and class prediction by gene expression monitoring", Science 286, 531-537 (1991).
Huang, et al., (2016) "Drugging the undruggables: exploring the ubiquitin system for drug development." Cell Res 26(4):484-498.
Lala, et al., "Role of nitric oxide in tumor progression: Lessons from experimental tumors", Cancer and Metastasis Reviews 17:91-106 (1998).
Levine, et al., Targeting the androgen receptor with steroid conjugates, J. Med. Chem., vol. 57., No. 20. pp. 8224-8237, (2014).
Medline Plus Trusted Health Information for You, www.nlm.nih.gov/medlineplus/cancer.html pp. 1-10, (2007).
Toure, et al., (2016) "Small-Molecule PROTACS: New Approaches to Protein Degradation." Angew Chem Int Ed Engl 55(6):1966-1973.

* cited by examiner

COMPOUNDS AND METHODS FOR THE TARGETED DEGRADATION OF BROMODOMAIN-CONTAINING PROTEINS

CROSS-REFERENCE TO RELATED APPLICATIONS

This application claims priority to U.S. Provisional Application No. 62/207,240, filed Aug. 19, 2015, and to U.S. Provisional Application No. 62/324,804, filed on Apr. 19, 2016, both of which are incorporated herein by reference in their entirety.

INCORPORATION BY REFERENCE

U.S. Patent Application Publications US 2015-0291562 entitled "Imide-Based Modulators of Proteolysis and Associated Methods of Use," and US 2014-0356322 entitled "Compounds and Methods for the Enhanced Degradation of Targeted Proteins and Other Polypeptides by an E3 ubiquitin ligase," as well as U.S. patent application Ser. No. 15/206,497 filed 11 Jul. 2016 entitled "MDM2-Based Modulators of Proteolysis and Associated Methods of Use," are incorporated herein by reference in their entirety. Furthermore, all references cited herein are incorporated by reference herein in their entirety.

BACKGROUND

1. Field of the Discovery

The present description relates to bifunctional compounds, which are useful for the modifying the ubiquitination and subsequent degradation of target polypeptides and proteins, in particular, bromodomain and extraterminal-containing (BET) proteins, e.g., BRD4. These compounds work in such way that the target protein/polypeptide is placed in proximity to the ubiquitin ligase to effect degradation (and inhibition) of that protein (e.g., BET/BRD4).

2. Background Information

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped.

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. We generated the first small molecule ligands of Von Hippel Lindau (VHL) to the substrate recognition subunit of the E3 ligase, VCB, an important target in cancer, chronic anemia and ischemia, and obtained crystal structures confirming that the compound mimics the binding mode of the transcription factor HIF-1α, the major substrate of VHL.

BRD4 has captured considerable attention from academia and pharmaceutical industry alike due to its great potential as a novel target in multiple disease settings, particularly in cancer. BRD4 belongs to the bromodomain and extra-terminal domain (BET) family, which is characterized by two bromodomains (BD domain) at the N-terminus and an extraterminal domain (ET domain) at the C-terminus (J. Shi, et al. *Molecular cell,* 54 (2014) 728-736 and A. C. Belkina, et al., *Nat. Rev. Cancer,* 12 (2012) 465-477). The two BD domains recognize and interact with acetylated-lysine residues at the N-terminal tail of histone protein; the ET domain is not yet fully characterized, and is largely considered to serve a scaffolding function in recruiting diverse transcriptional regulators. Thus, BRD4 plays a key role in regulating gene expression by recruiting relevant transcription modulators to specific genomic loci. Several studies have established that BRD4 is preferentially located at super-enhancer regions, which often reside upstream of important oncogenes, such as c-MYC, Bcl-xL and BCL-6, and play a key role in regulating their expressions (J. Loven, et al., *Cell,* 153 (2013) 320-334 and B. Chapuy, et al., *Cancer Cell,* 24 (2013) 777-790.). Owing to its pivotal role in modulating the expression of essential oncogenes, BRD4 emerges as a promising therapeutic target in multiple cancer types, including midline carcinoma, AML, MM, BL, and prostate cancer (J. Loven, et al., *Cell,* 153 (2013) 320-334; J. Zuber, et al., *Nature,* 478 (2011) 524-528; J. E. Delmore, et al., *Cell,* 146 (2011) 904-917; J. A. Mertz, et al., *PNAS,* 108 (2011) 16669-16674; A. Wyce, et al., *Oncotarget,* 4 (2013) 2419-2429; I. A. Asangani, et al., *Nature,* 510 (2014) 278-282; and C. A. French, et al., *Oncogene,* 27 (2008) 2237-2242). BRD4's distinct high occupancy of genomic loci proximal to specific oncogenes provide a potential therapeutic window that will allow specific targeting of tumor cells while sparing normal tissues. Particularly, BRD4 may serve as an alternative strategy of targeting c-MYC, which contributes to the development and maintenance of a majority of human cancers but has remained undruggable (J. E. Delmore, et al., *Cell,* 146 (2011) 904-917; J. A. Mertz, et al., *PNAS,* 108 (2011) 16669-16674; M. G. Baratta, et al., *PNAS,* 112 (2015) 232-237; and M. Gabay, et al., *Cold Spring Harb Perspect Med.* (2014) 4:a014241).

The development of small molecule BRD4 inhibitors, such as JQ1, iBET and OTX15, has demonstrated promising therapeutic potential in preclinical models of various cancers, including BL (J. Loven, et al., *Cell,* 153 (2013) 320-334; B. Chapuy, et al., *Cancer Cell,* 24 (2013) 777-790; J. E. Delmore, et al., *Cell,* 146 (2011) 904-917; J. A. Mertz, et al., *PNAS,* 108 (2011) 16669-16674; I. A. Asangani, et al., *Nature,* 510 (2014) 278-282; M. G. Baratta, et al., *PNAS,* 112 (2015) 232-237; M. Boi, et al., *Clin. Cancer Res.,* (2015) 21(7):1628-38; and A. Puissant, et al., *Cancer discovery,* 3 (2013) 308-323). Indeed, BRD4 inhibitors have shown various anti-tumor activities with good tolerability in different mouse tumor models and, not surprisingly, high sensitivity to BRD4 inhibitors, such as JQ1, has been associated with high levels of c-MYC and/or N-MYC in different tumor types, including c-MYC driven BL. Almost all BL cases contain c-myc gene translocation that places it under control of a super-enhancer located upstream of IgH, thus driving an abnormally high level of c-MYC expression, tumor development and maintenance (K. Klapproth, et al., *British journal of haematology,* 149 (2010) 484-497).

Currently, over 10 small molecule BET Bromodomain inhibitors are in the clinical studies. These include OTX-015, CPI-610, TEN-010, GSK525762, GSK2820151, ABBV-075, GS-5289, BMS986158, FT-1101, INCB057643, INCB054329, ZEN003694. Despite the rapid progress of BRD4 inhibitors, the effect of BRD4 inhibition has been encouraging, but less than ideal, as the effect is mostly cytostatic and requires relatively high concentration of inhibitors.

Bifunctional compounds such as those that are described in U.S. Patent Application Publications US 2015-0291562, and US 2014-0356322 (incorporated herein by reference), function to recruit endogenous proteins to an E3 ubiquiuin ligase for degradation. In particular, the publications describe bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds.

An ongoing need exists in the art for effective treatments for disease, especially hyperplasias and cancers, such as multiple myeloma. However, non-specific effects, and the inability to target and modulate certain classes of proteins altogether, such as transcription factors, remain as obstacles to the development of effective agents (e.g., anti-cancer agents). As such, small molecule therapeutic agents that demonstrate substrate specificity and, at the same time, are "tunable" such that a wide range of protein classes can be targeted and modulated with specificity would be very useful as a therapeutic.

SUMMARY

The present disclosure describes bifunctional compounds, including compositions comprising the same, which function to recruit endogenous proteins to anE3 ubiquitin ligase for ubiquitination and subsequent degradation, and methods of using the same. In particular, the present disclosure provides bifunctional or proteolysis targeting chimeric (PROTAC) compounds, which find utility as modulators of targeted ubiquitination and degradation of Bromodomain and extraterminal domain-containing protein (BET), e.g., BRD4. In addition, the description provides methods of using an effective amount of the compounds as described herein for the treatment or amelioration of a disease condition including cancer, e.g., diffused large B cell lymphoma (DLBCL), prostate cancer (PC), ovarian cancer, breast cancer, etc.

Thus, in one aspect, the disclosure provides compounds which function to recruit endogenous proteins, e.g., BRd4, to E3 Ubiquitin Ligase for ubiquintination and degradation.

In certain embodiments, the compounds have the following general structures (I)

PTM-L-UTM (I)

wherein, PTM represents protein targeting moiety, UTM represents E3 ubiquitin ligase targeting moiety including but not limited to VHL, cerebon, mouse double minute 2 (MDM2), and/or inhibitor of apoptosis protein (IAP) and L represents a linker, e.g., a bond or a chemical linker moiety. As would be understood by the skilled artisan, the bifunctional compounds as described herein can be synthesized such that any of the order (i.e., position), number or configuration can be varied as desired.

In certain embodiments, the PTMs in structure (I) are the ligands that bind to BRD4 as well as other BRDs, such as BRD2, BRD3, and BRDT and UTM are molecules that bind to VHL E3 ubiquitin ligase.

In certain embodiments, the compounds as described herein comprise multiple UTMs, multiple PTMs, multiple chemical linkers or a combination thereof. In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In yet another aspect, the present invention provides a method of ubiquitinating/degrading a target protein in a cell. In certain embodiments, the method comprises administering a bifunctional compound as described herein comprising an UTM and a PTM, preferably linked through a linker moiety, as otherwise described herein, wherein the UTM is coupled to the PTM and wherein the UTM recognizes a ubiquitin pathway protein (e.g., an ubiquitin ligase, preferably an E3 ubiquitin ligase) and the PTM recognizes the target protein such that degradation of the target protein will occur when the target protein (e.g., BRD4) is placed in proximity to the ubiquitin ligase, thus resulting in degradation/inhibition of the effects of the target protein and the control of protein levels. In another aspect, the target protein is BRD4. The control of protein levels afforded by the present invention provides treatment of a disease state or condition, which is modulated through the target protein by lowering the level of that protein in the cells of a patient.

In particular, PTM are molecules that bind to a BET-containing protein, e.g., BRD4, and UTM are molecules that bind to VHL E3 ubiquitin ligase with the following general structures (II):

(II)

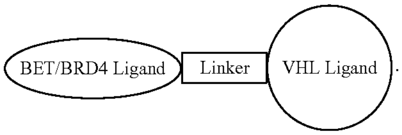

It will be understood that the general structures are exemplary and the respective moieties can be arranged spatially in any desired order, number or configuration.

In further embodiments, the description provides a bifunctional compound having a structure selected from the group consisting of Examples 1-368, a salt, a polymorph, and a prodrug thereof.

In another aspect, the description provides compositions comprising compounds as described herein, and a pharmaceutically acceptable carrier. In certain embodiments, the compositions are therapeutic or pharmaceutical compositions comprising an effective amount of a compound as described herein and a pharmaceutically acceptable carrier. In certain embodiments, the therapeutic or pharmaceutical compositions comprise an additional biologically active agent, e.g., an agent effective for the treatment of cancer.

In any of the aspects or embodiments described herein, the therapeutic compositions comprising compounds described herein can be in any suitable dosage form, e.g., solid, or liquid, and configured to be delivered by any suitable route, e.g., oral, parenteral, intravenous, intraperitoneal, subcutaneous, intramuscular, etc.

In another aspect, the description provides methods of modulating BET protein in general, and BRD4 in particular, their ubiquitination and the subsequent degradation in a subject, e.g., a cell, a tissue, mammal, or human patient, the method comprising administering an effective amount of a compound as described herein or a composition comprising an effective amount of the same to a subject, wherein the compound or composition comprising the same is effective in modulating BET/BRD4 ubiquitination and degradation in the subject.

In yet another aspect, the description provides methods of treating or ameliorating a symptom of a disease related to BET/BRD4 activity in a subject, e.g., a cell, a tissue, mammal, or human patient, the method comprising administering an effective amount of a compound as described herein or a composition comprising an effective amount of the same to a subject in need thereof, wherein the compound or composition comprising the same is effective in treating or ameliorating a symptom of a disease related to BET/BRD4 activity in the subject. In certain embodiments, the disease to be treated is cancer, e.g., diffused large B cell lymphoma, prostate cancer, ovarian cancer and breast cancer. In a preferred embodiment, the subject is a human.

In an additional aspect, the description provides methods for identifying the effects of the degradation of proteins of interest in a biological system using compounds according to the present invention.

Where applicable or not specifically disclaimed, any one of the embodiments described herein are contemplated to be able to combine with any other one or more embodiments, even though the embodiments are described under different aspects of the invention. As such, the preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages, objects, and embodiments are expressly included within the scope of the present invention. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

Figure 1:
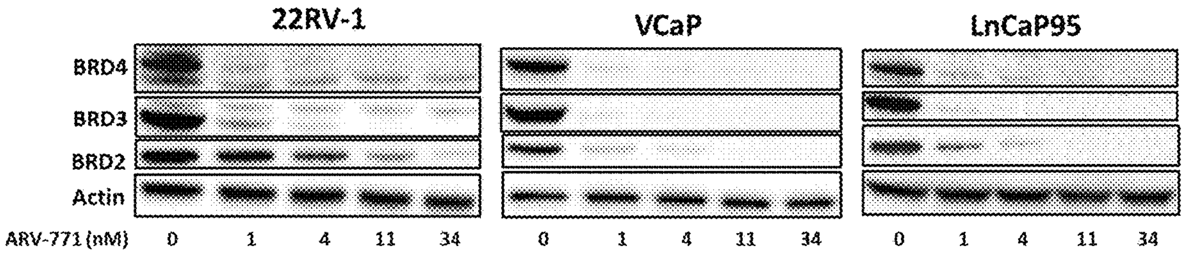
FIG. 1 shows the degradation of BRD2/3/4 in 22RV-1, VCaP, and LnCaP95 cells caused by Example 77 (ARV-771).

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

The present description relates to the surprising and unexpected discovery that an E3 ubiquitin ligase protein can ubiquitinate a target protein once the E3 ubiquitin ligase protein and the target protein are brought into proximity by a chimeric construct (e.g., PROTAC) as described herein, which binds the E3 ubiquitin ligase protein (e.g., VHL, cereblon, MDM2 or IAP E3 ligase) and the target protein e.g., BET/BRD4. Accordingly, the present description provides compounds, compositions comprising the same, and associated methods of use for ubiquitination and degradation of a chosen target protein.

The following terms are used to describe the present invention. In instances where a term is not specifically defined herein, that term is given an art-recognized meaning by those of ordinary skill applying that term in context to its use in describing the present invention. Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder.

When the bond 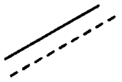 is shown, both a double bond and single bond are represented within the context of the compound shown.

The term "patient" or "subject" is used throughout the specification to describe an animal, preferably a human or a domesticated animal, to whom treatment, including prophylactic treatment, with the compositions according to the present invention is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present invention, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

The term "VCB E3 Ubiquitin Ligase", "Hippel-Lindau E3 Ubiquitin Ligase" or "Ubiquitin Ligase" is used to describe a target enzyme(s) binding site of ubiquitin ligase moieties in the bifunctional (chimeric) compounds according to the present invention. VCB E3 is a protein that in combination with an E2 ubiquitin-conjugating enzyme causes the attachment of ubiquitin to a lysine on a target protein; the E3 ubiquitin ligase targets specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first, a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include compounds targeting BRD4, estrogen-related receptor alpha (ERRα) binders, RIPK2 binders, AR binders, Hsp90 inhibitors, kinase inhibitors, MDM2 inhibitors, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of these nine types of small molecule target protein.

The term "target protein" is used to describe a protein or polypeptide, which is a target for binding to a compound according to the present invention and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to UTM groups through linker groups L.

Target proteins which may be bound to the protein target moiety and degraded by the ligase to which the ubiquitin ligase binding moiety is bound include structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes, including microbes, viruses, fungi and parasites, including humans, microbes, viruses, fungi and parasites, among numerous others, as targets for drug therapy, other animals, including domesticated animals, microbials for the determination of targets for antibiotics and other antimicrobials and plants, and even viruses, among numerous others.

More specifically, a number of drug targets for human therapeutics represent protein targets to which protein target moiety may be bound and incorporated into compounds according to the present invention. These include proteins which may be used to restore function in numerous polygenic diseases, including for example BRD4, ERRα, AR, RIPK2, B7.1 and B7, TINFR1m, TNFR2, NADPH oxidase, BclIBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

Haloalkane dehalogenase enzymes are another target of specific compounds according to the present invention. Compounds according to the present invention which contain chloroalkane peptide binding moieties ($C_1$-$C_{12}$ often about $C_2$-$C_{10}$ alkyl halo groups) may be used to inhibit and/or degrade haloalkane dehalogenase enzymes which are used in fusion proteins or related diagnostic proteins as described in PCT/US 2012/063401 filed Dec. 6, 2011 and published as WO 2012/078559 on Jun. 14, 2012, the contents of which is incorporated by reference herein.

These various protein targets (e.g., BRD4) may be used in screens that identify compound moieties which bind to the protein and by incorporation of the moiety into compounds according to the present invention, the level of activity of the protein may be altered for therapeutic end result.

The term "disease state or condition" is used to describe any disease state or condition wherein protein dysregulation (i.e., the amount of protein expressed in a patient is elevated) occurs and where degradation of one or more proteins (e.g., BRD4) in a patient may provide beneficial therapy or relief of symptoms to a patient in need thereof. In certain instances, the disease state or condition may be cured.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome, Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis, aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alström syndrome, Alexander disease, Amelogenesis imperfecta, ALA dehydratase deficiency, Anderson-Fabry disease, androgen insensitivity syndrome, Anemia, Angiokeratoma Corporis Diffusum, Angiomatosis retinae (von Hippel-Lindau disease), Apert syndrome, Arachnodactyly (Marfan syndrome), Stickler syndrome, Arthrochalasis multiplex congenital (Ehlers-Danlos syndrome # arthrochalasia type), ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria, Erythroid 5-aminolevulinate synthetase deficiency, Erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita), SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Weissenbacher-Zweymüller syndrome, Wolf-Hirschhorn syndrome, Wolff Periodic disease, Weissenbacher-Zweymüller syndrome and Xeroderma pigmentosum, among others.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "bioactive agent" is used to describe an agent, other than a compound according to the present invention, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present invention to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, $IPdR_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6,Azgly 10] (pyro-Glu-His-Trp-Ser-Tyr-D-Ser(Bu t)-Leu-Arg-Pro-Azgly-$NH_2$ acetate $[C_{59}H_{84}N_{18}Oi_4-(C_2H_4O_2)x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present invention.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

The term "independently" is used herein to indicate that the variable, which is independently applied, varies independently from application to application.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain preferred embodiments, compounds according to the present invention which may be used to covalently bind to dehalogenase enzymes. These compounds generally contain a side chain (often linked through a polyethylene glycol group) which terminates in an alkyl group which has a halogen substituent (often chlorine or bromine) on its distil end which results in covalent binding of the compound containing such a moiety to the protein.

The term "lower alkyl" means the alkyl groups with no more than six carbon atoms.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon. The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present invention and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or CO, amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted $—N(C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present invention may include, for example $—SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteraryl moiety) through an optionally substituted $—(CH_2)_m—$ or alternatively an optionally substituted $—(OCH_2)_m—$, $—(OCH_2CH_2)_m—$ or $—(CH_2CH_2O)_m—$ group, which may be substituted with any one or more of the above-described substituents. Alkylene groups $—(CH_2)_m—$ or $—(CH_2)_n—$ groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sideshain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$alkyl group, most often methyl or O-methyl groups or a sidechain of an amino acid as otherwise described herein. In the present invention, a moiety in a molecule may be optionally substituted with up to five substituents, preferably up to three substituents. Most often, in the present invention moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane $—O—C(O)—NR_1R_2$ or $—N(R_1)—C(O)—O—R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, $—(CH_2)_m$-(here, m and n are in context, 1, 2, 3, 4, 5 or 6), —S—, —S(O)—, $SO_2$- or —NH—C(O)—NH—, $—(CH_2)_nOH$, $—(CH_2)_nSH$, $—(CH_2)_nCOOH$, $C_1$-$C_6$ alkyl, $—(CH_2)_nO—(C_1$-$C_6$ alkyl), $—(CH_2)_nC(O)—(C_1$-$C_6$ alkyl), $—(CH_2)_nOC(O)—(C_1$-$C_6$ alkyl), $—(CH_2)_nC(O)O—(C_1$-$C_6$ alkyl), $—(CH_2)_nNHC(O)—R_1$, $—(CH_2)_nC(O)—NR_1R_2$, $—(OCH_2)_nOH$, $—(CH_2O)_nCOOH$, $C_1$-$C_6$ alkyl, $—(OCH_2)_nO—(C_1$-$C_6$ alkyl), $—(CH_2O)_nC(O)—(C_1$-$C_6$ alkyl), $—(OCH_2)_nNHC(O)—R_1$, $—(CH_2O)_nC(O)—NR_1R_2$, $—S(O)_2—R_S$, $—S(O)—R_S$ ($R_S$ is $C_1$-$C_6$ alkyl or a $—(CH_2)_m—NR_1R_2$ group), $NO_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group $O—C(O)—NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present invention at any available stable position on the ring(s) or as otherwise indicated in the chemical structure presented. Other examples of aryl groups, in context, may include heterocyclic aromatic ring systems "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "heterocycle" refers to a cyclic group which contains at least one heteroatom, i.e., O, N or S, and may be aromatic (heteroaryl) or non-aromatic. Thus, the heteroaryl moieties are subsumed under the definition of heterocycle, depending on the context of its use. Exemplary heteroaryl groups are described hereinabove. Exemplary non-aromatic heterocyclic groups for use in the present invention include, for example, pyrrolidinyl, pyrrolinyl, piperidinyl, piperazinyl, N-methylpiperazinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimide and succinimide, among others, as described herein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present invention are set forth hereinabove.

The term "coadministration" or "combination therapy" shall mean that at least two compounds or compositions are administered to the patient at the same time, such that effective amounts or concentrations of each of the two or more compounds may be found in the patient at a given point in time. Although compounds according to the present invention may be coadministered to a patient at the same time, the term embraces both administration of two or more agents at the same time or at different times, provided that effective concentrations of all coadministered compounds or compositions are found in the subject at a given time. In certain preferred aspects of the present invention, one or more of the present compounds described above, are coadministered in combination with at least one additional bioactive agent, especially including an anticancer agent. In particularly preferred aspects of the invention, the co-administration of compounds results in synergistic therapeutic, including anticancer therapy The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family.

As such, presently described are compositions and methods that relate to the surprising and unexpected discovery that an E3 ubiquitin ligase protein ubiquitinates a target protein once it and the target protein are placed in proximity by a bifunctional or chimeric construct (e.g., a PROTAC)

that binds the E3 ubiquitin ligase protein and the target protein. Accordingly, the present invention provides such compounds and compositions comprising an E3 ubiquintin ligase targeting moiety ("UTM") coupled to a protein target binding moiety ("PTM"), which result in the ubiquitination of a chosen target protein, which leads to degradation of the target protein by the proteasome. The present invention also provides a library of compositions and the use thereof.

In particular, the present application is directed to compounds which contain a ligand, e.g., a small molecule ligand (i.e., having a molecular weight of below 2,000, 1,000, 500, or 200 Daltons), which is capable of binding to a ubiquitin ligase, such as VHL, cereblon, IAP or MDM2, and a moiety that is capable of binding to a target protein, in such a way that the target protein is placed in proximity to the ubiquitin ligase to effect degradation (and/or inhibition) of that protein.

In one embodiment, the description provides a composition useful for regulating protein activity. The composition comprises a ubiquitin pathway protein binding moiety (preferably for a VHL, cereblon, MDM2, or IAP E3 ligase) according to a defined chemical structure and a protein targeting moiety which are linked together, preferably through a linker, wherein the ubiquitin pathway protein binding moiety recognizes an ubiquitin pathway protein and the targeting moiety recognizes a target protein (e.g., BRD4) and wherein the ubiquitin pathway protein binding moiety is coupled to the targeting moiety.

In another embodiment, the present invention provides a library of compounds. The library comprises more than one compound wherein each composition has a formula of A-B, wherein A is a ubiquitin pathway protein binding moiety (preferably, VHL, cereblon, MDM2, or IAP E3 ligase) and B is a protein binding member of a molecular library (e.g., BRD4), wherein A is coupled (preferably, through a linker moiety) to B, and wherein the ubiquitin pathway protein binding moiety recognizes an ubiquitin pathway protein, in particular, an E3 ubiquitin ligase. In a particular embodiment, the library contains a specific ubiquitination recognition peptide of VHL for an E3 ubiquitin ligase (ubiquitin pathway protein binding moiety as otherwise disclosed herein) with random target protein binding elements (e.g., a chemical compound library). As such, the target protein is not determined in advance and the method can be used to determine the activity of a putative protein binding element and its pharmacological value as a target upon degradation by ubiquitin ligase.

In still another embodiment, the present invention provides a method of screening a library of the present invention to identify a compound containing a targeting moiety, which recognizes a target protein (e.g., BRD4) associated with a predetermined function of a cell. The method comprises incubating a cell with a pool of entities from the library; monitoring the predetermined function of the cell; identifying a pool of entities that change the predetermined function of the cell; incubating the cell with a composition from the identified pool of entities; monitoring the predetermined function of the cell; and identifying a composition that changes the predetermined function of the cell, wherein the identified composition contains a targeting moiety which recognizes a target protein associated with the predetermined function.

In another embodiment, the present invention provides a method of screening a library of the present invention to identify a composition containing a targeting moiety, which recognizes a target protein (e.g., BRD4) associated with a predetermined function of a cell. The method comprises incubating a cell with each composition from the library; monitoring the predetermined function of the cell; identifying a composition that changes the predetermined function of the cell; wherein the identified composition contains a targeting moiety, which recognizes a target protein associated with the predetermined function.

In still another embodiment, the present invention provides a method of identifying a target protein (e.g., BRD4) associated with a predetermined function of a cell. The method comprises incubating a cell with a composition from the library of the present invention; monitoring the predetermined function of the cell; identifying a composition that changes the predetermined function of the cell; identifying a target protein that binds to the identified composition, wherein the target protein is associated with the predetermined function of the cell.

In yet another embodiment, the present invention provides a method of identifying a target protein (e.g., BRD4) associated with a predetermined function of a cell. The method comprises incubating a cell with a pool of entities from the library of the present invention; monitoring the predetermined function of the cell; identifying a pool of entities that change the predetermined function of the cell; incubating the cell with a composition from the identified pool of entities; monitoring the predetermined function of the cell; identifying a composition that changes the predetermined function of the cell; and identifying a target protein that binds to the identified composition, wherein the target protein is associated with the predetermined function of the cell.

In yet another embodiment, the present invention provides a method of ubiquitinating/degrading a target protein (e.g., BRD4) in a cell. The method comprises administering a bifunctional composition comprising an ubiquitin pathway protein binding moiety and a targeting moiety, preferably linked through a linker moiety, as otherwise described herein, wherein the ubiquitin pathway protein binding moiety is coupled to the targeting moiety and wherein the ubiquitin pathway protein binding moiety recognizes a ubiquitin pathway protein (e.g., VHL, cereblon, MDM2, or IAP E3 ligase) and the targeting moiety recognizes the target protein (e.g., BRD4) such that degradation of the target protein will occur when the target protein is placed in proximity to the ubiquitin ligase, thus resulting in degradation/inhibition of the effects of the target protein and the control of protein levels. The control of protein levels afforded by the present invention provides treatment of a disease state or condition, which is modulated through the target protein by lowering the level of that protein in the cells of a patient.

In another embodiment, the present invention is directed to a method of treating a patient in need for a disease state or condition modulated through a protein (e.g., BRD4) where the degradation of that protein will produce a therapeutic effect in that patient, the method comprising administering to a patient in need an effective amount of a compound according to the present invention, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In one embodiment, the present invention is directed to a compound according to the structure: L-UTM, where L is a linker group, and UTM is a ubiquitin ligase binding moiety, wherein said linker group is optionally further linked to a PTM group.

In one aspect, the description provides composition and structural details of the following general structure as shown in (II):

(II)

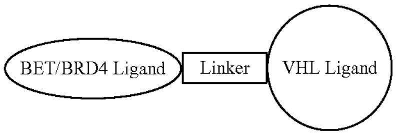

The details of chemical entities of each of the three components in (II) are further described in three sections and different embodiments below.

Section 1: VHL Ligand in Structure (II)

In certain embodiments of the compounds as described herein, the UTM comprises a VHL E3 ubiquitin ligase binding moiety (or VHL ligand) having a chemical structure as following

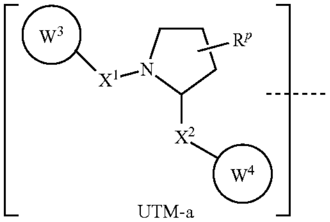

UTM-a

In certain embodiments of the compounds as described herein, the UTM comprises a chemical structure selected from the group UTM-a:

where a dashed line indicates the attachment of at least one PTM, another UTM or VLM (i.e., UTM' or VLM'), or a chemical linker moiety coupling at least one PTM, a UTM' or VLM' to the other end of the linker;

$X^1$, $X^2$ are each independently a bond, O, $NR^{Y3}$, $CR^{Y3}R^{Y4}$, C═O, C═S, SO, $SO_2$;

$R^{Y3}$, $R^{Y4}$ are each independently H, $C_{1-6}$ alkyl (linear, branched, optionally substituted by 1 or more halo, $C_{1-6}$ alkoxyl); optionally substituted by 1-3 RP groups in the pyrrolidine moiety, wherein each RP is independently H, halo, —OH, $C_{1-3}$alkyl;

$W^3$ is an optionally substituted -T-N($R^{1a}R^{1b}$), -T-Aryl, an optionally substituted -T-Heteroaryl, an optionally substituted -T-Heterocycle, an optionally substituted —$NR^1$-T-Aryl, an optionally substituted —$NR^1$-T-Heteroaryl or an optionally substituted —$NR^1$-T-Heterocycle, where T is covalently bonded to $X^1$;

$R^1$, $R^{1a}$, $R^{1b}$ are independently H, a $C_1$-$C_6$ alkyl group (linear, branched, optionally substituted by 1 or more halo, —OH), $R^{Y3}$C═O, $R^{Y3}$C═S, $R^{Y3}$SO, $R^{Y3}SO_2$, N($R^{Y3}R^{Y4}$)C═O, N($R^{Y3}R^{Y4}$)C═S, N($R^{Y3}R^{Y4}$)SO, N($R^{Y3}R^{Y4}$)$SO_2$;

$W^4$ is an optionally substituted —$NR^1$-T-Aryl, an optionally substituted —$NR^1$-T-Heteroaryl group or an optionally substituted —$NR^1$-T-Heterocycle, where —$NR^1$ is covalently bonded to $X^2$ where $R^1$ is H or $CH_3$, preferably H.

In any of the embodiments described herein, T is an optionally substituted —$(CH_2)_n$-group, wherein each one of the methylene groups (—$CH_2$-) may be optionally substituted with one or two substituents, preferably selected from halogen, an amino acid side chain, a $C_1$-$C_6$ alkyl group (linear, branched, optionally substituted by 1 or more halogen, —OH) or the sidechain of an amino acid as otherwise described herein, preferably methyl, which may be optionally substituted; and n is 0 to 6, often 0, 1, 2, or 3, preferably 0 or 1.

In certain embodiments, T may also be a —$(CH_2O)_n$— group, a —$(OCH2)_n$— group, a —$(CH_2CH_2O)_n$— group, a —$(OCH_2CH_2)_n$— group, each of which groups is optionally substituted.

In any of the embodiments described herein, $W^3$ and/or $W^4$ can be attached to a linker moiety as described herein.

In certain embodiments, aryl groups for $W^3$ include optionally substituted phenyl or naphthyl groups, preferably phenyl groups, wherein the phenyl or naphthyl group is optionally substituted with a linker group to which is attached a PTM group (including a UTM' group) and/or a halogen (preferably F or Cl), an amine, monoalkyl- or dialkyl amine (preferably, dimethylamine), an amido group (preferably a —$(CH_2)_m$—$NR_1C(O)R_2$ group where m, $R_1$ and $R_2$ are the same as for $R^1$), a halogen (often F or Cl), OH, $CH_3$, $CF_3$, OMe, $OCF_3$, $NO_2$, CN or a $S(O)_2R_S$ group ($R^S$ is a a $C_1$-$C_6$ alkyl group, an optionally substituted aryl, heteroaryl or heterocycle group or a —$(CH_2)_mNR_1R_2$ group), each of which may be substituted in ortho-, meta- and/or para-positions of the phenyl ring, preferably para-), or an Aryl (preferably phenyl), heteroaryl or heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a PTM group (including a UTM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo-(preferably, F) or methylsubstituted pyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally substituted with a linker group to which is attached a PTM group (including a UTM' group).

In certain embodiments, heteroaryl groups for $W^3$ include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted $—(CH_2)_m—O—C_1-C_6$ alkyl group or an optionally substituted $—(CH_2)_m—C(O)—O—C_1-C_6$ alkyl group), an optionally substituted pyridine (2-, 3, or 4-pyridine) or a group according to the chemical structure:

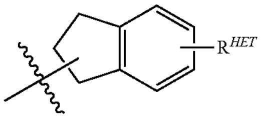
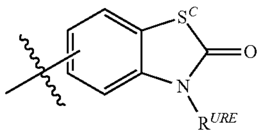
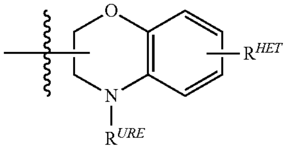
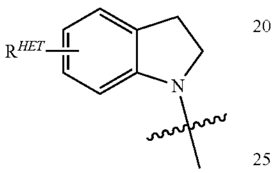
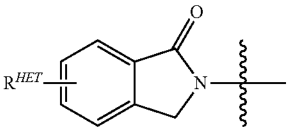
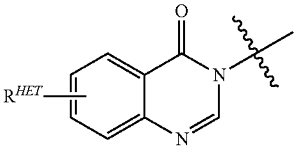
or
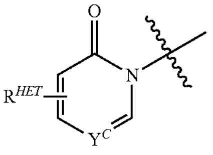

where $S^c$ is $CHR^{SS}$, $NR^{URE}$, or O;

$R^{HET}$ is H, CN, $NO_2$, halo (preferably Cl or F), optionally substituted $C_1-C_6$ alkyl (preferably substituted with one or two hydroxyl groups or up to three halo groups (e.g. $CF_3$), optionally substituted $O(C_1-C_6$ alkyl) (preferably substituted with one or two hydroxyl groups or up to three halo groups) or an optionally substituted acetylenic group $—C≡C—R_a$ where $R_a$ is H or a $C_1-C_6$ alkyl group (preferably $C_1-C_3$ alkyl);

$R^{SS}$ is H, CN, $NO_2$, halo (preferably F or Cl), optionally substituted $C_1-C_6$ alkyl (preferably substituted with one or two hydroxyl groups or up to three halo groups), optionally substituted $O—(C_1-C_6$ alkyl) (preferably substituted with one or two hydroxyl groups or up to three halo groups) or an optionally substituted $—C(O)(C_1-C_6$ alkyl) (preferably substituted with one or two hydroxyl groups or up to three halo groups);

$R^{URE}$ is H, a $C_1-C_6$ alkyl (preferably H or $C_1-C_3$ alkyl) or a $—C(O)(C_1-C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted; and $Y^C$ is N or $C—R^{YC}$, where $R^{YC}$ is H, OH, CN, $NO_2$, halo (preferably Cl or F), optionally substituted $C_1-C_6$ alkyl (preferably substituted with one or two hydroxyl groups or up to three halo groups (e.g. $CF_3$), optionally substituted $O(C_1-C_6$ alkyl) (preferably substituted with one or two hydroxyl groups or up to three halo groups) or an optionally substituted acetylenic group $—C≡C—R_a$ where $R_a$ is H or a $C_1-C_6$ alkyl group (preferably $C_1-C_3$ alkyl). Each of said heteroaryl groups may be optionally substituted with a linker group to which is attached a PTM group (including a UTM' group).

In additional embodiments, heterocycle groups for $W^3$ include tetrahydroquinoline, piperidine, piperazine, pyrrollidine, morpholine, tetrahydrofuran, tetrahydrothiophene, oxane and thiane, each of which groups may be optionally substituted or a group according to the chemical structure:

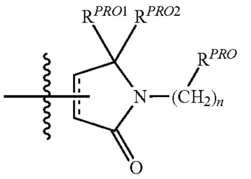
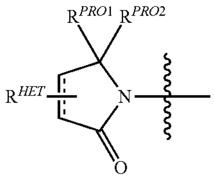
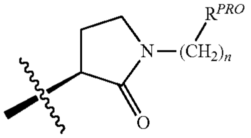
or
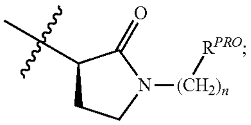

where $R^{PRO}$ is H, optionally substituted $C_1-C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1-C_3$ alkyl group, preferably methyl or a halo group, preferably F or Cl), benzofuran, indole, indolizine, azaindolizine;

$R^{PRO1}$ and $R^{PRO2}$ are each independently H, an optionally substituted $C_1-C_3$ alkyl group or together form a keto group, and each n is 0, 1, 2, 3, 4, 5, or 6 (preferably 0 or 1), wherein each of said Heterocycle groups may be optionally substituted with a linker group to which is attached a PTM group (including a UTM' group) or a pharmaceutically acceptable salt, stereoisomer, solvate or polymorph thereof.

In certain embodiments, $W^3$ substituents for use in the present invention also include specifically (and without limitation to the specific compound disclosed) the $W^3$ substituents which are found in the identified compounds disclosed herein (which includes the specific compounds which are disclosed in the present specification, and the figures which are attached hereto). Each of these $W^3$ substituents may be used in conjunction with any number of $W^4$ substituents, which are also disclosed herein.

In certain embodiments, Aryl groups for $W^4$ include optionally substituted phenyl or naphthyl groups, preferably phenyl groups, wherein the phenyl group is optionally substituted with a linker group to which is attached a PTM group (including a UTM' group), a halogen (preferably F or Cl), an amine, monoalkyl- or dialkyl amine (preferably, dimethylamine), F, Cl, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with a linker group attached to a PTM group, including a UTM' group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstituted pyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

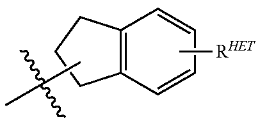

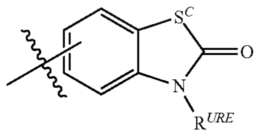

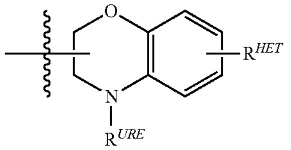

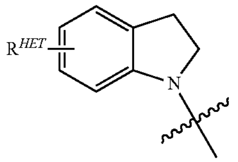

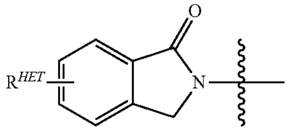

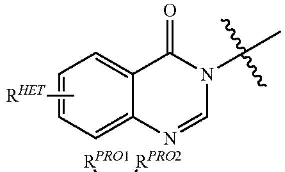

or

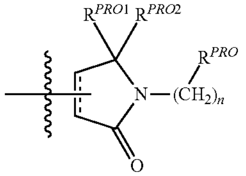

where $S^c$ is selected from $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);

$R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or CO, benzofuran, indole, indolizine, azaindolizine;

$R^{PRO1}$ and $R^{PRO2}$ are each independently H, an optionally substituted $C_1$-$C_3$ alkyl group or together form a keto group; and each n is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, CO, each of which groups may be optionally substituted with a linker group to which is attached a PTM group (including a UTM' group).

In certain preferred aspects,

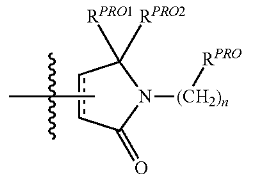

is a

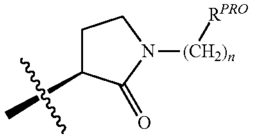

or

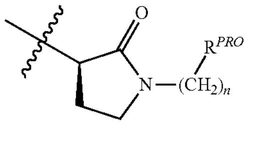

group, where $R^{PRO}$ and n are the same as above.

In certain embodiments, heteroaryl groups for $W^4$ include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

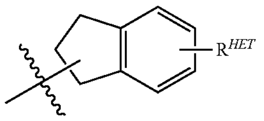
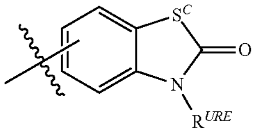
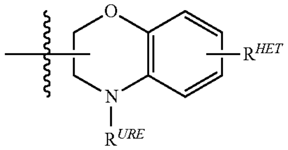
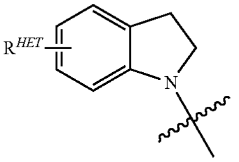
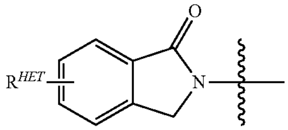
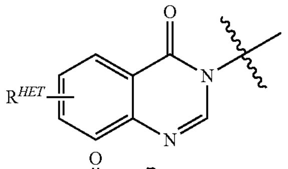
or
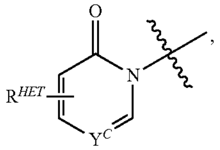
, Where, $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted; and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl), each of which groups may be optionally substituted with a linker group to which is attached a PTM group (including a UTM' group).

In certain embodiments, heterocycle groups for $W^4$ include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

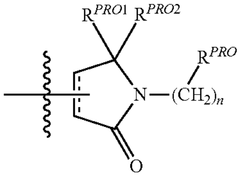
or
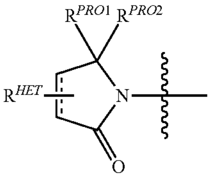

preferably, a

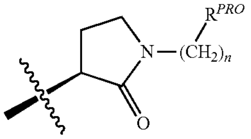
or
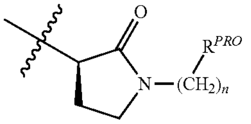
or group,

Where, $R^{PRO}$ is H, optionally substituted $C_1$-$C_6$ alkyl or an optionally substituted aryl, heteroaryl or heterocyclic group;

$R^{PRO1}$ and $R^{PRO2}$ are each independently H, an optionally substituted $C_1$-$C_3$ alkyl group or together form a keto group; and each n is independently 0, 1, 2, 3, 4, 5, or 6 (often 0 or 1), each of which groups may be optionally substituted with a linker group to which is attached a PTM group (including a UTM' group)

In additional embodiments, $W^4$ substituents for use in the present invention also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In certain additional embodiments, UTM-a, is optionally substituted by 1-3 $R^P$ groups in the pyrrolidine moiety. Each $R^P$ is independently H, halo, —OH, $C_{1-3}$alkyl.

In any of the embodiments described herein, the $W^3$, $W^4$ can independently be covalently coupled to a linker which is attached one or more PTM groups.

In certain embodiments, UTM is a group (derivatized or configured to be linked or coupled to an PTM via a linker (as indicated by the dashed line) according to the chemical structure:

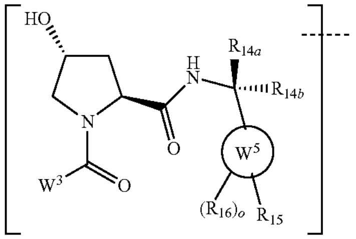

wherein, $W^3$ is optionally substituted aryl, optionally substituted heteroaryl, or

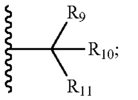

$R_9$ and $R_{10}$ are independently hydrogen, optionally substituted alkyl, optionally substituted cycloalkyl, optionally substituted hydroxyalkyl, optionally substituted heteroaryl, or haloalkyl; or $R_9$, $R_{10}$, and the carbon atom to which they are attached form an optionally substituted cycloalkyl;

$R_{11}$ is optionally substituted heterocyclic, optionally substituted alkoxy, optionally substituted heteroaryl, optionally substituted aryl,

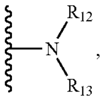 , 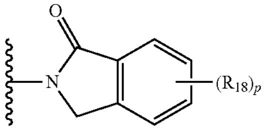 or

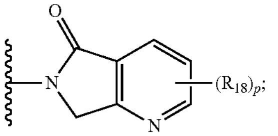

wherein, $R_{12}$ is H or optionally substituted alkyl;

$R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$, is each independently H, haloalkyl, or optionally substituted alkyl;

$W^5$ is a phenyl or a 5-10 membered heteroaryl, $R_{15}$ is H, halogen, CN, OH, $NO_2$, $NR_{14a}R^{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, optionally substituted heteroaryl, cycloalkyl, cycloheteroalkyl each $R_{16}$ is independently halo, optionally substituted alkyl, optionally substituted haloalkyl, hydroxy, or optionally substituted haloalkoxy;

p is 0, 1, 2, 3, or 4; and each $R_{18}$ is independently halo, optionally substituted alkoxy, cyano, optionally substituted alkyl, haloalkyl, haloalkoxy or a linker.

In certain embodiments, $R_{15}$ is

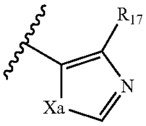

wherein $R_{17}$ is H, halo, optionally substituted $C_{3-6}$cycloalkyl, optionally substituted $C_{1-6}$alkyl, optionally substituted $C_{1-6}$alkenyl, and $C_{1-6}$haloalkyl; and Xa is S or O.

In certain embodiments, $R_{17}$ is selected from the group methyl, ethyl, isopropyl, and cyclopropyl.

In certain additional embodiments, $R_{15}$ is selected from the group consisting of:

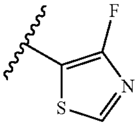 ; 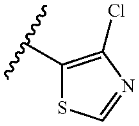 ; 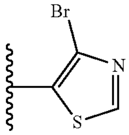 ;

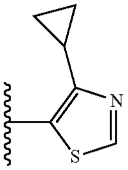 ; 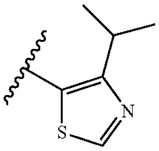 ;; 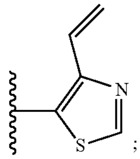 ;

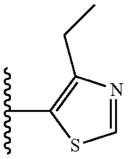 ; 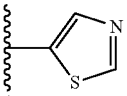 ; 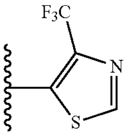 ;

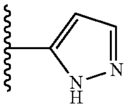 ; 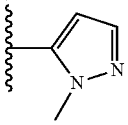 ; 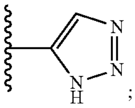 ;

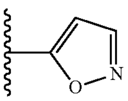 ; 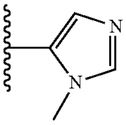 ; 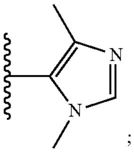 ;

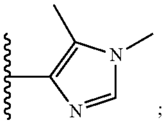 ; 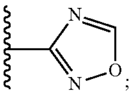 ; 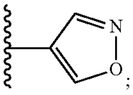 ;

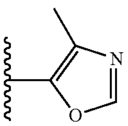 ; 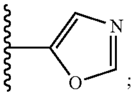 ; 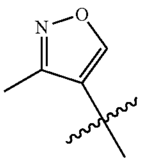 ;

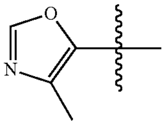 ; 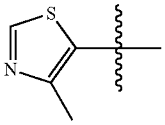 ;

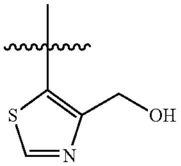 ; 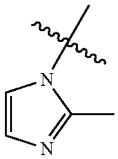 ; and

-continued

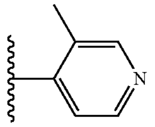

In certain embodiments, $R_{11}$ is selected from the group consisting of:

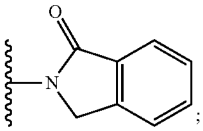 ; 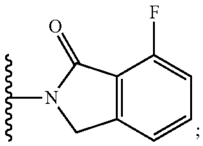 ;

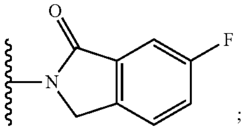 ; 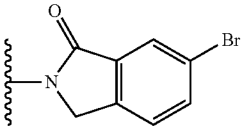 ;

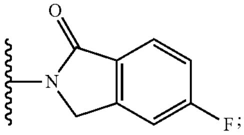 ; 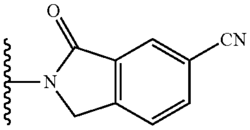 ;

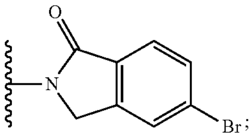 ; 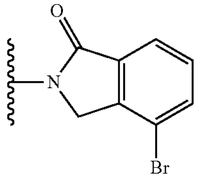 ;

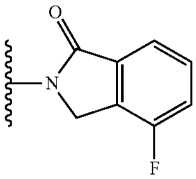 ; 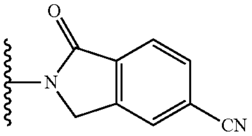 ;

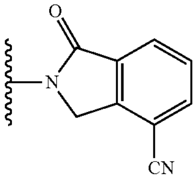 ; 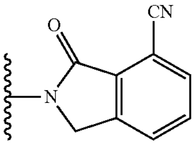 ;

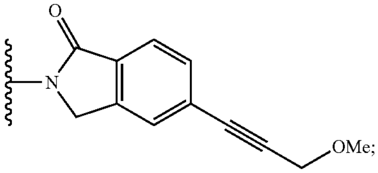 ;

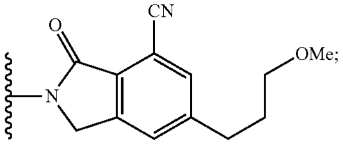 ;

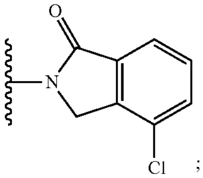 ; 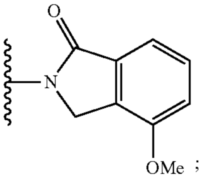 ;

-continued

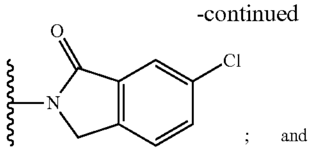 ; and

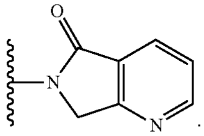 [SMILES: *N1Cc2ncccc2C1=O] .

In certain embodiments, the UTM has a chemical structure selected from the group of:

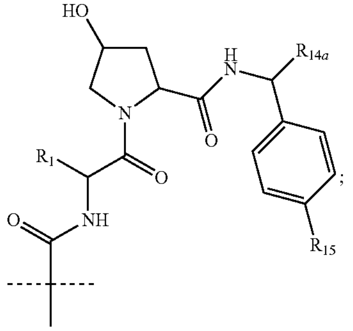 ;

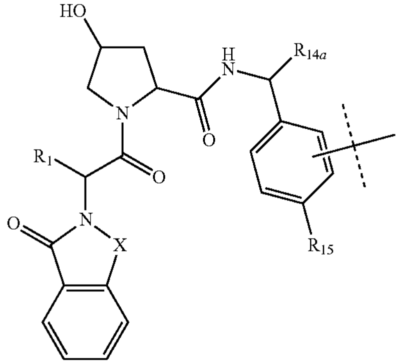 and

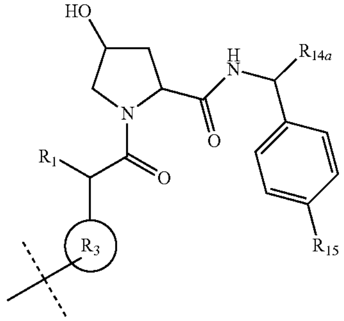

wherein $R_1$ is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

$R_{14a}$ is H, haloalkyl, optionally substituted alkyl, methyl, fluoromethyl, hydroxymethyl, ethyl, isopropyl, or cyclopropyl;

$R_{15}$ is selected from the group consisting of H, halogen, CN, OH, $NO_2$, optionally substituted heteroaryl, optionally substituted aryl; optionally substituted alkyl, optionally substituted haloalkyl, optionally substituted haloalkoxy, cycloalkyl, or cycloheteroalkyl;

X is C or C═O $R_3$ is an optionally substituted 5 or 6 membered heteroaryl; and wherein the dashed line indicates the site of attachment of at least one BET/BRD4 binding ligand, another UTM (UTM') or a chemical linker moiety coupling at least one BET/BRD4 binding ligand or a UTM' or both to UTM-a.

In certain embodiments, the UTM (derivatized or configured to be linked or coupled to an PTM via a linker (as indicated by the dashed line)) has the structure:

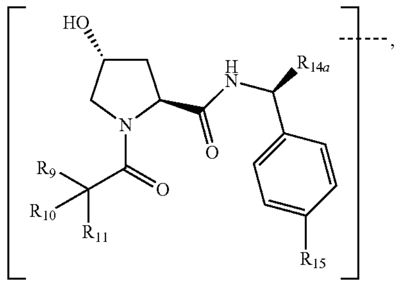

wherein

R14a is H, haloalkyl, optionally substituted alkyl, methyl, fluoromethyl, hydroxymethyl, ethyl, isopropyl, or cyclopropyl;

R9 is H;

R10 is H, ethyl, isopropyl, tert-butyl, sec-butyl, cyclopropyl, cyclobutyl, cyclopentyl, or cyclohexyl;

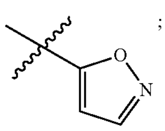
;
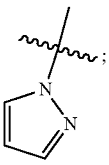
;

R11 is; optionally substituted heteroaryl,

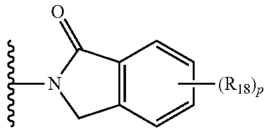
or
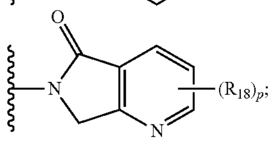

p is 0, 1, 2, 3, or 4; and each $R_{18}$ is independently halo, optionally substituted alkoxy, cyano, optionally substituted alkyl, haloalkyl, haloalkoxy or a linker;

R12 is H, C═O

R13 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl, $R_{15}$ is selected from the group consisting of H, halogen, Cl, CN, OH, $NO_2$, optionally substituted heteroaryl, optionally substituted aryl;

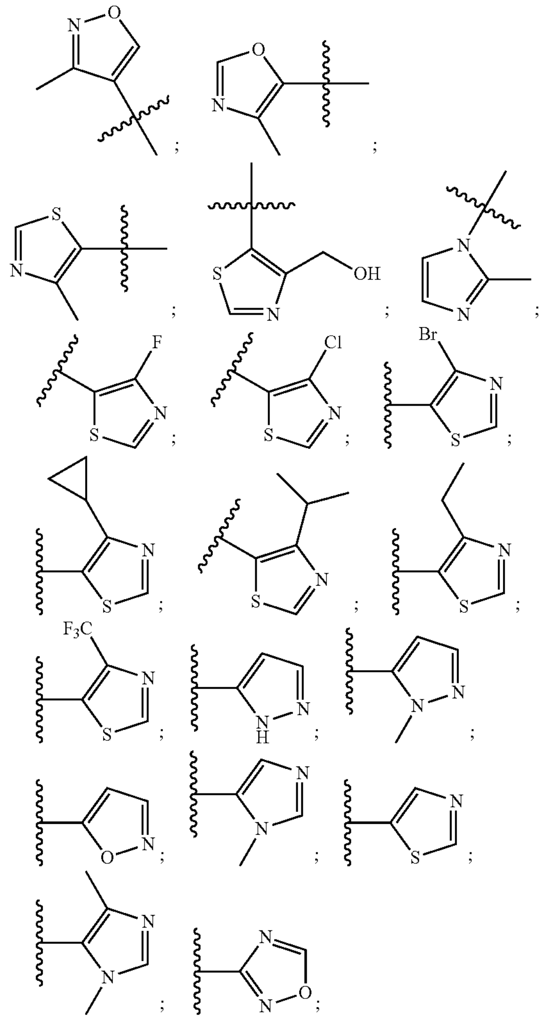

and wherein the dashed line indicates the site of attachment of at least one PTM, another UTM (UTM') or a chemical linker moiety coupling at least one PTM or a UTM' or both to UTM-a.

In certain embodiments, the present invention is directed to but not limited to UTMs with following structures: The actual UTM as VHL ligand in structure (II) are not limited to these UTM examples. The dotted line in the structure indicates the linker attachment point.

UTM-a1

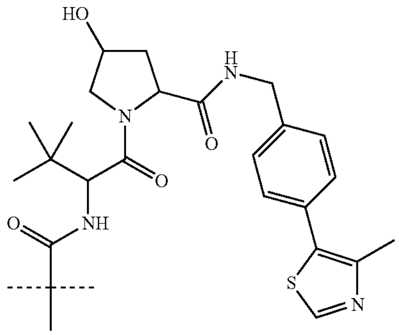

-continued
UTM-a2
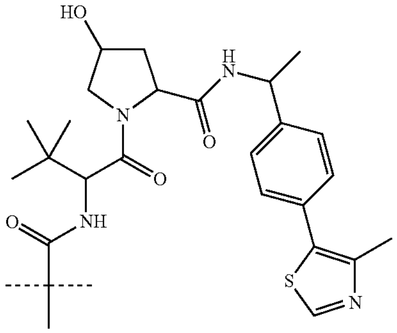
UTM-a3
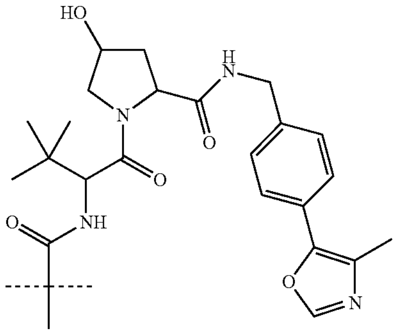
UTM-a4
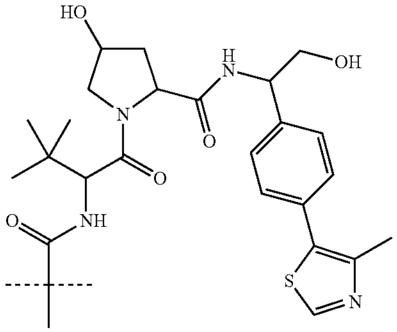
UTM-a5
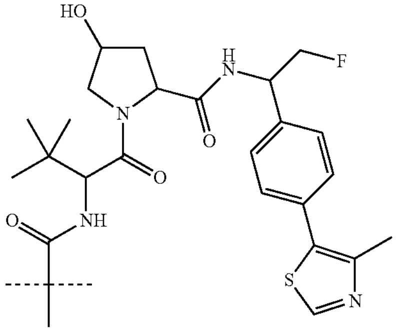
-continued
UTM-a6
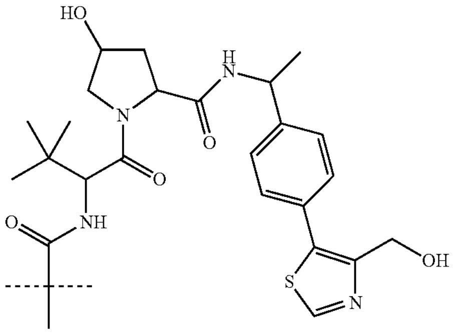
UTM-a7
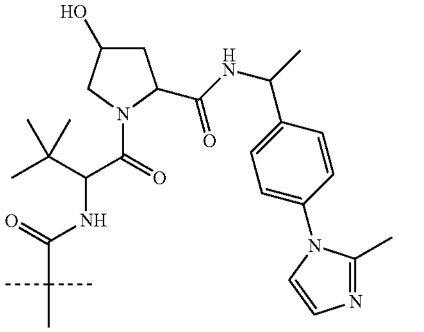
UTM-a8
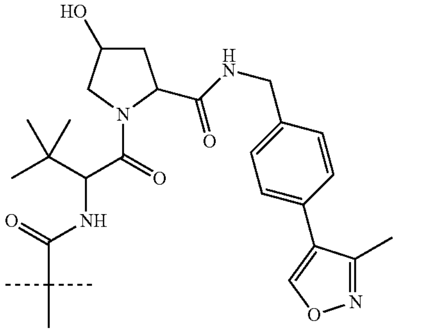
UTM-a9
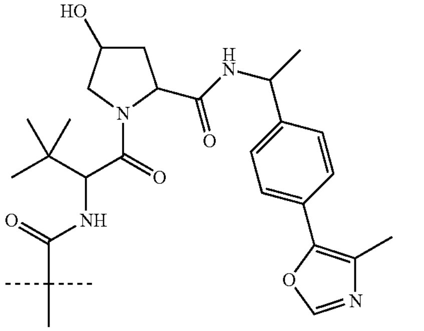

-continued
UTM-a10
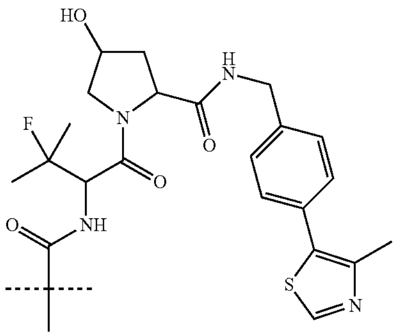
UTM-a11
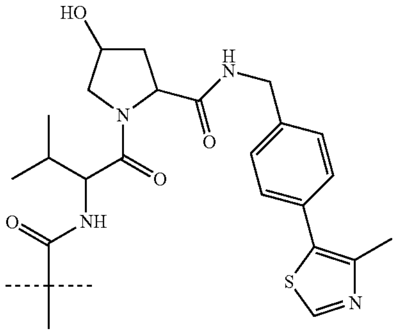
UTM-a12
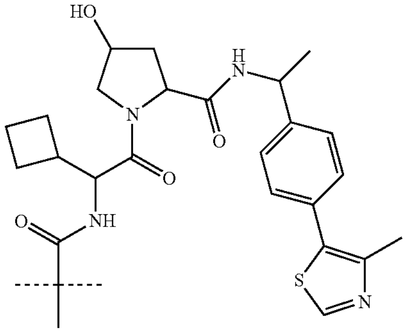
UTM-a13
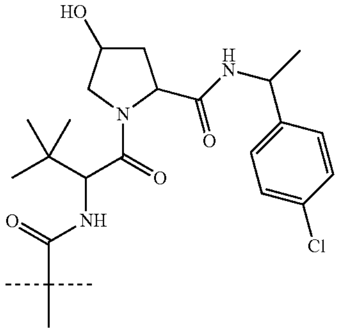
-continued
UTM-a14
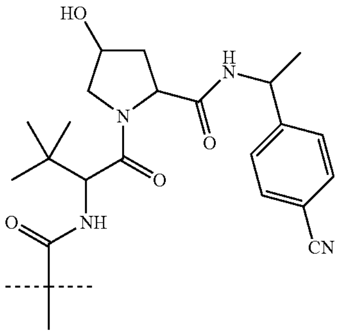
UTM-a15
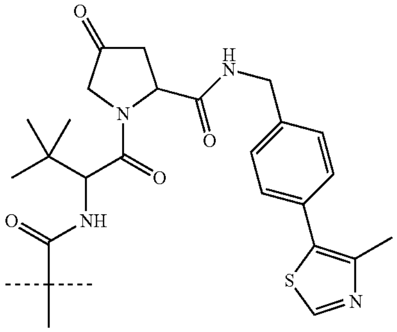
UTM-b1
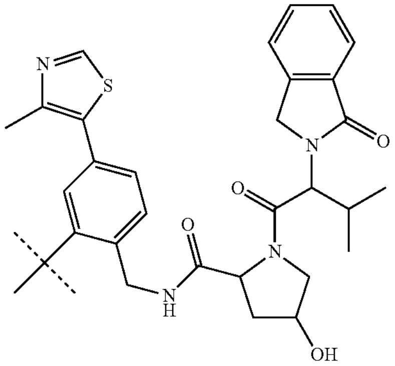
UTM-b2
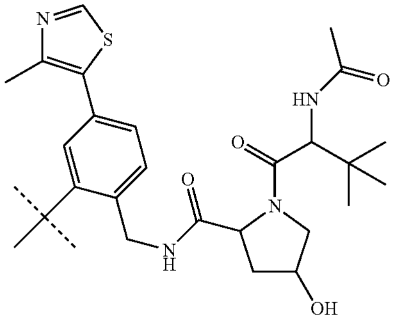

-continued
UTM-b3
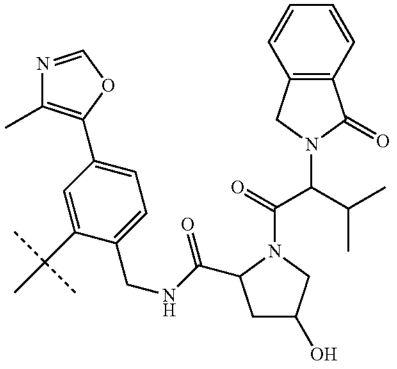
UTM-b4
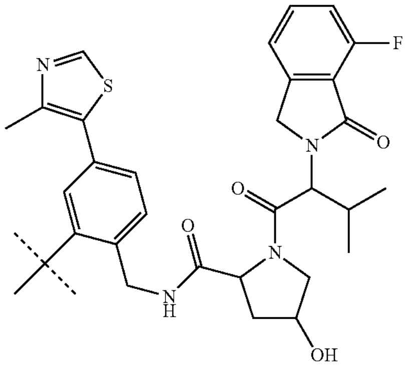
UTM-b5
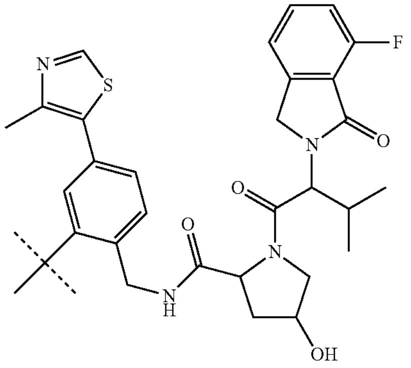
UTM-b6
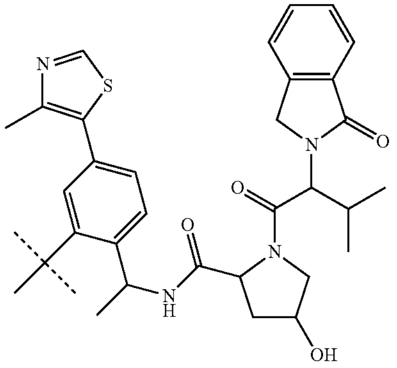
-continued
UTM-b7
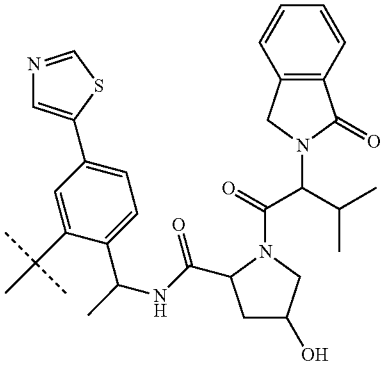
UTM-b8
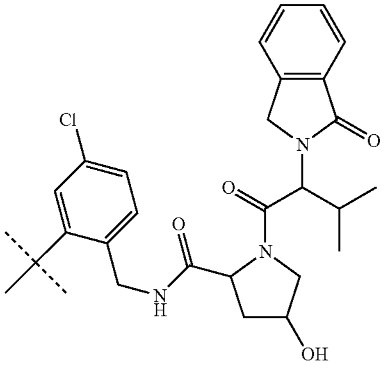
UTM-b9
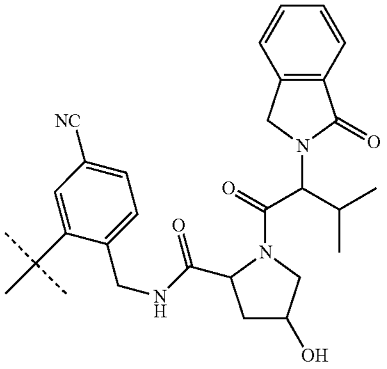
UTM-b10
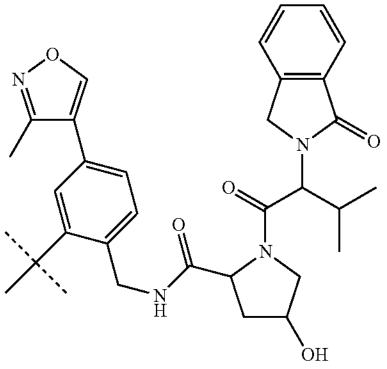

-continued
UTM-b11
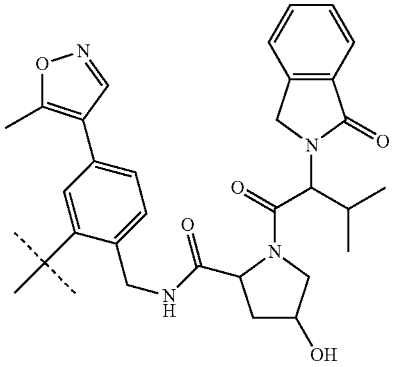
UTM-b12
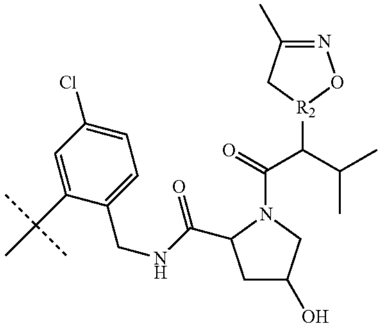
UTM-c1
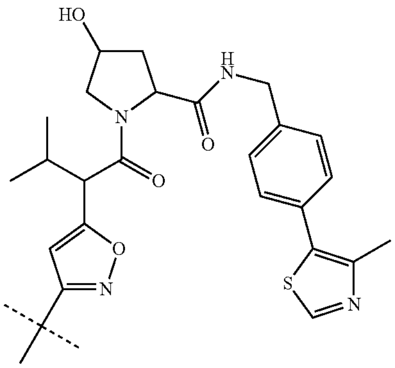
UTM-c2
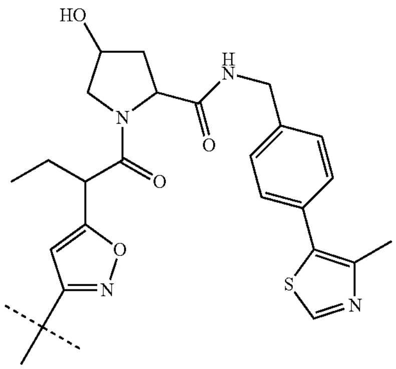
-continued
UTM-c3
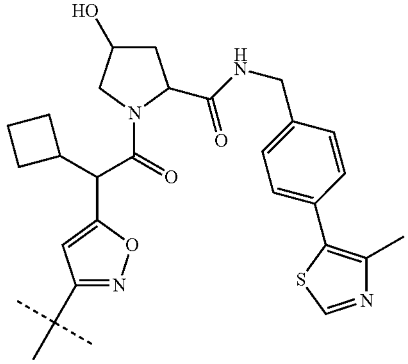
UTM-c4
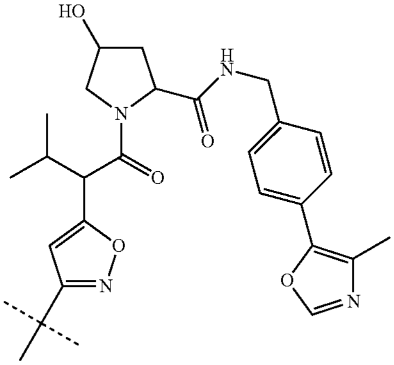
UTM-c5
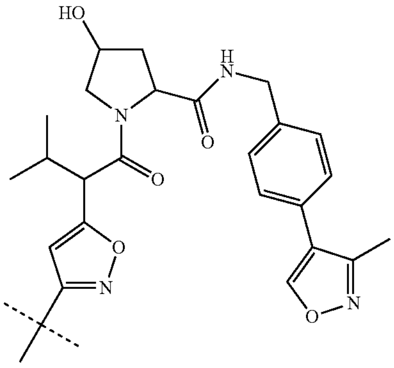
UTM-c6
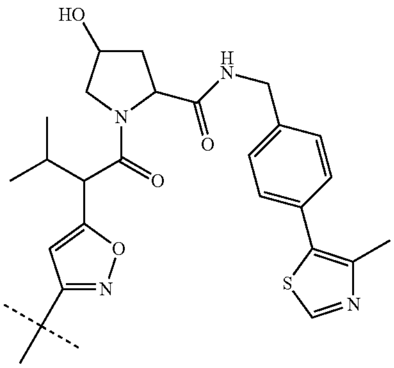

-continued
UTM-c7
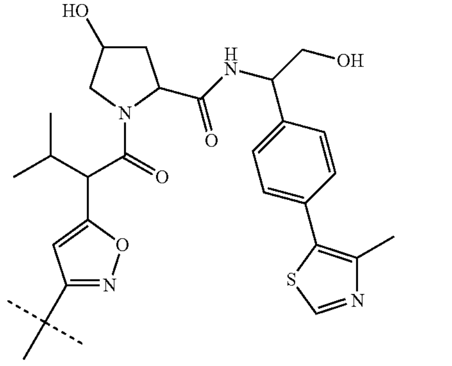
UTM-c8
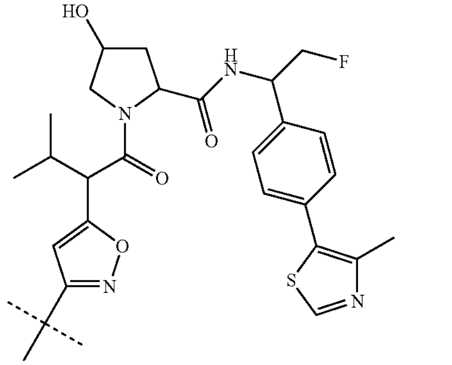
UTM-c9
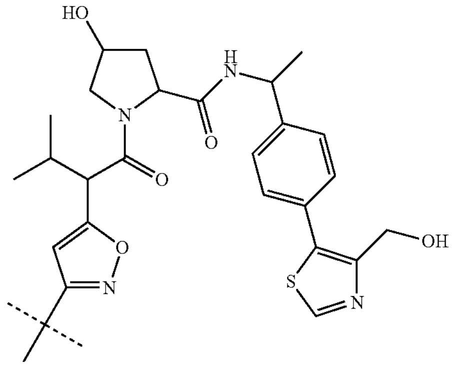
UTM-c10
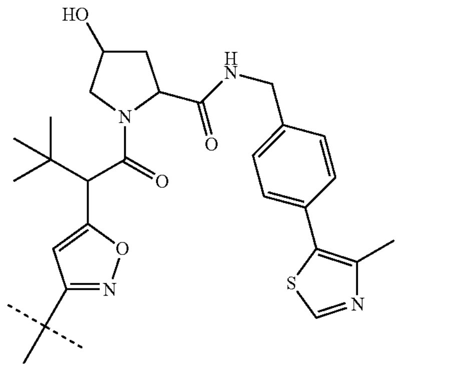
-continued
UTM-c11
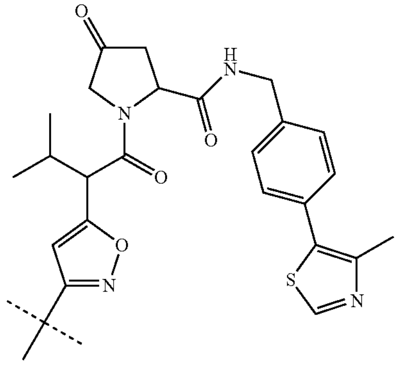
UTM-c12
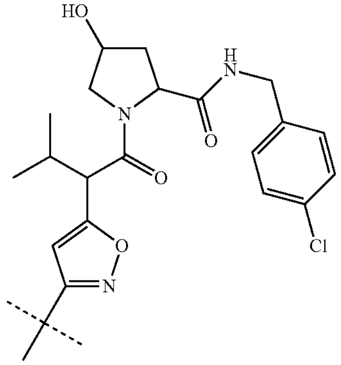
UTM-c13
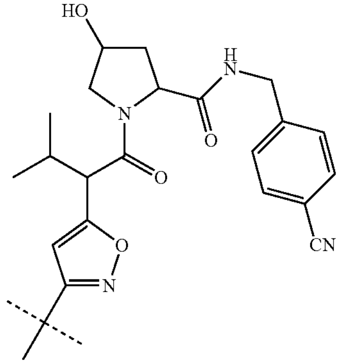
UTM-c14
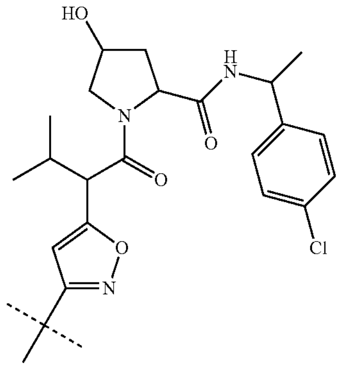

-continued
UTM-c15
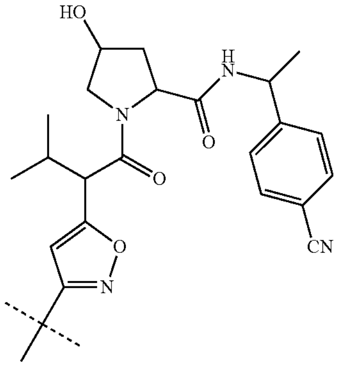
UTM-d1
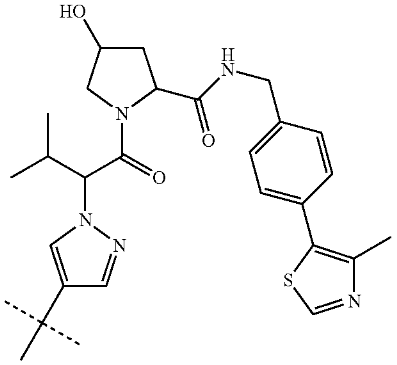
UTM-d2
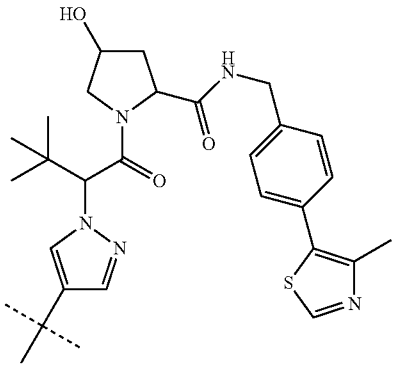
UTM-d3
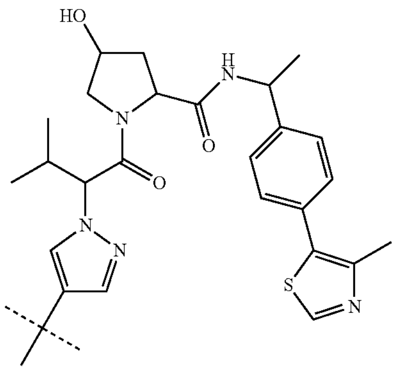
-continued
UTM-d4
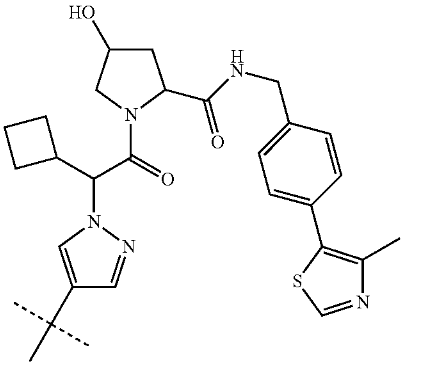
UTM-d5
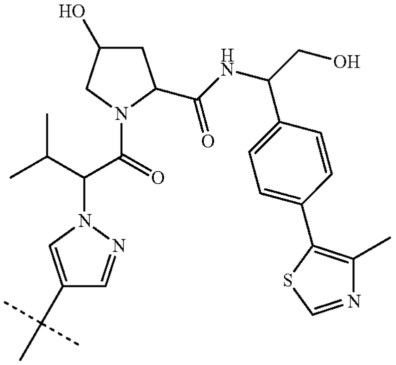
UTM-d6
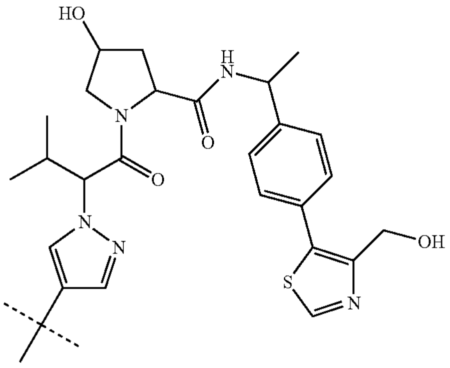
UTM-d7
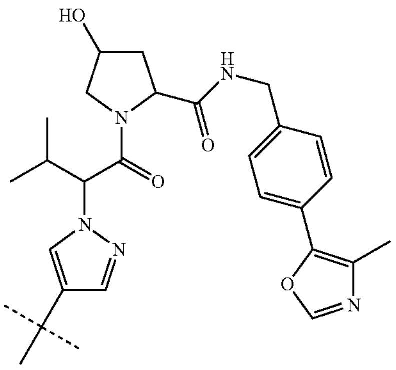

-continued

UTM-d8

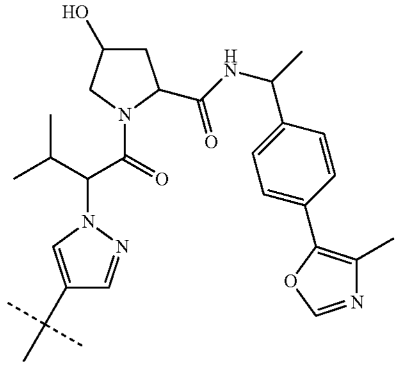

UTM-d9

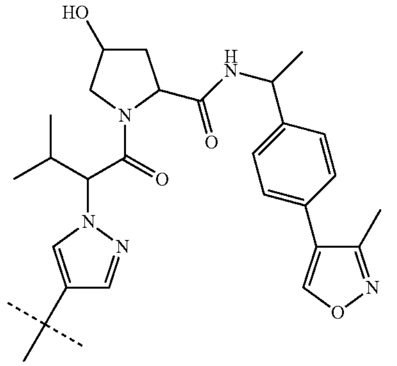

In one embodiment, the phenyl ring in UTM-a 1 through UTM-a15, UTM-b1 through UTM-b12, UTM-c1 through UTM-c15 and UTM-d1 through UTM-d9 can be substituted with fluorine or lower alkyl and alkoxy groups.

In another embodiment, the hydroxyl group on the pyrrolidine ring in UTM-a 1 through UTM-a15, UTM-b1 through UTM-b12, UTM-c1 through UTM-c15 and UTM-d1 through UTM-d9 can be functionalized as the ester to make it a part of the prodrug. The following are representative examples for UTM-a chemical type as VHL ligands.

UTM-a1′

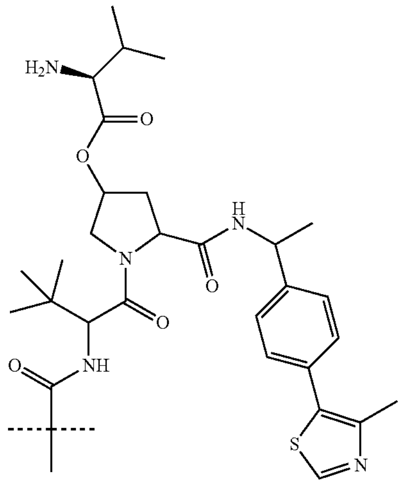

-continued

UTM-a2′

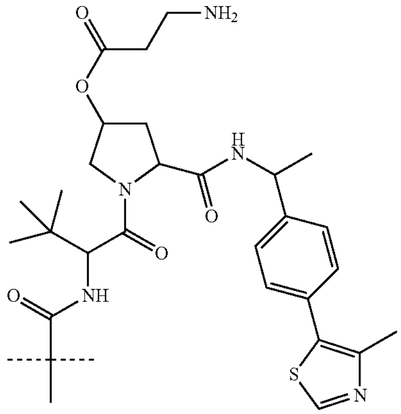

UTM-a3′

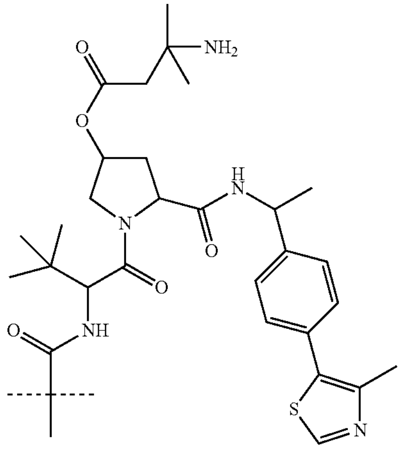

Wherein, dotted line represents the linker attachment point which may be further connected to another UTM (UTM') or a BET/BRD4 ligand.

UTM-a4′

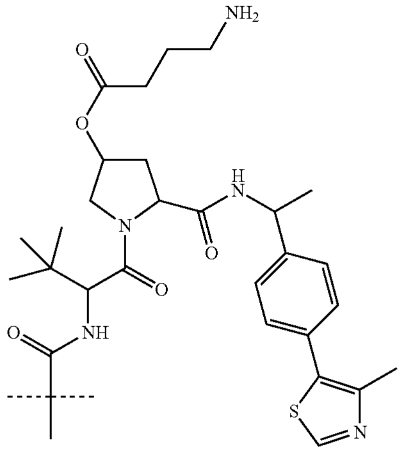

-continued

UTM-a5′

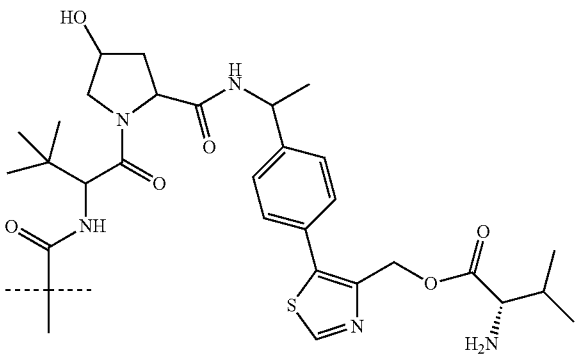

UTM-a6′

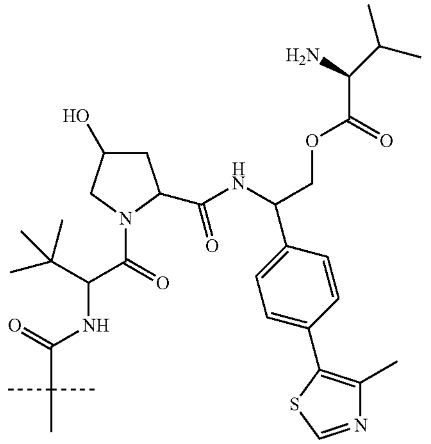

In certain embodiments, in structures from UTM-a1 through UTM-a15, the phenyl ring in UTM-a1' through UTM-a6' can be substituted with fluorine or lower alkyl and alkoxy groups.

In certain embodiments, UTM-a1 through UTM-a15, UTM-b1 through UTM-b12, UTM-c1 through UTM-c15 and UTM-d1 through UTM-d9 is connected to a BET/BRD4 ligand consisting of a tricyclic diazepine or azepine chemotype, carbazole derivative, pyrrolopyridone chemotype, tetrahydroquinoline chemotype, triazolopyrazine chemotype, pyridone chemotype, quinazolinone chemotype, dihydropyridopyrazinone chemotype directly or through a linker group L.

In certain embodiments, the hydroxyl group on the pyrrolidine ring of UTM-a1 through UTM-a15, UTM-b1 through UTM-b12, UTM-c1 through UTM-c15 and UTM-d1 through UTM-d9, respectively, comprises an ester-linked prodrug moiety.

Section 2: BET/BRD4 Ligand in Structure (II)

In certain embodiments of the compounds as described herein, the BET/BRD4 ligand in structure (II) can be known BET/BRD4 inhibitors reported in the literature. These ligands are referred as protein targeting moiety (PTM) and in this case the targeted protein or proteins are BET/BRD4. The following are some of the representative examples of PTM. The actual PTM as BET/BRD4 ligands in structure (II) are not limited to these PTM examples. The dotted line in the structure indicates the linker attachment point.

In one embodiment, the claimed structure (II) is composed of tricyclic diazepine or tricyclic azepine as BET/BRD4 ligand (PTM-a), where the dashed lines indicate the linker connection trajectory and three sites are defined to attach linkers.

PTM-a

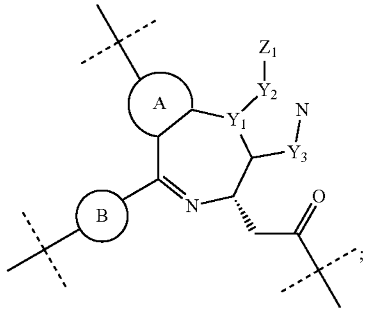

wherein,

A and B are independently an aromatic ring, a heteroaromatic ring, a 5-membered carbocyclic, a 6-membered carbocyclic, a 5-membered heterocyclic, a 6-membered heterocyclic, a thiophene, a pyrrole, a pyrazole, a pyridine, a pyrimidine, a pyrazine, optionally substituted by alkyl, aloxy, halogen, nitrile or another aromatic or heteroaromatic ring, where A is fused to the central azepine (Y1=C) or diazepine (Y1=N) moiety;

Y1, Y2, and Y3 and Y4 can be carbon, nitrogen or oxygen for to form a fused 5-membered aromatic ring as triazole or isoxazole; and Z1 is methyl, or lower alkyl group.

The fragment of PTM-a as BET/BRD4 ligand is described in the literature (WO 2016/069578; WO2014/001356; WO2016/050821; WO 2015/195863; WO 2014/128111).

In certain embodiments comprising the structure UTM-L-PTM-a, PTM-a can be represented by the following general structures, where dashed line indicates linker connection point. In structure PTM-aa through PTM-ai, the substitution pattern of X and Y can be mono- or bis-substitution.

PTM-aa

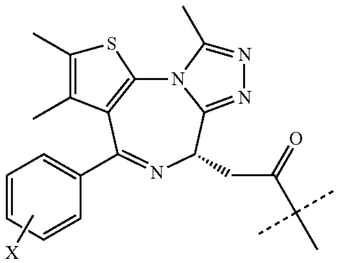

X = Cl, F, Br, H, CN, methyl, acetylene, methoxy

PTM-ab

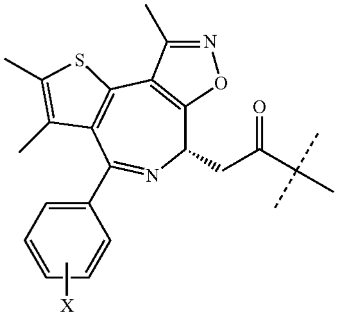

X = Cl, F, Br, H, CN, methyl, acetylene, methoxy

-continued

PTM-ac

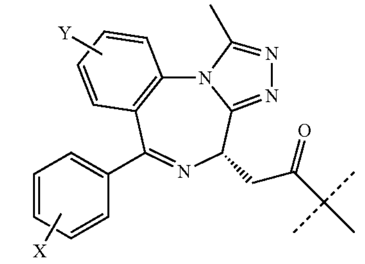

X = Cl, F, Br, H, CN, methyl, methoxy, acetylene
Y: mono- or di-substitution, Y = Me, OMe,
N-methypyrazole/imidazole PTM-ad

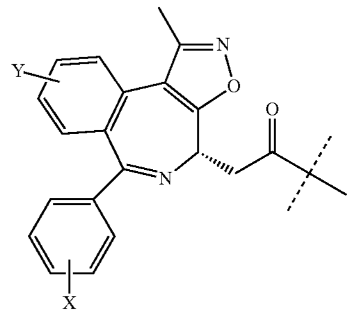

X = Cl, F, Br, H, CN, methyl, methoxy, acetylene
Y: mono- or di-substitution, Y = Me, OMe,
N-methypyrazole/imidazole PTM-ae

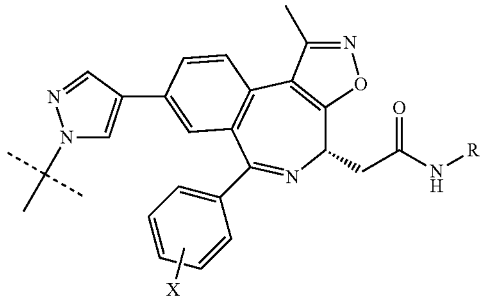

X = Cl, F, Br, H, CN, methyl, methoxy, acetylene
R = lower alkyl, aryl, substituted aryl PTM-af

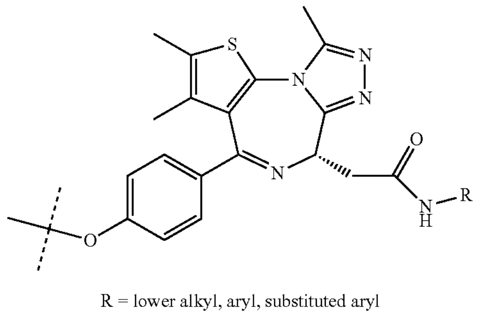

R = lower alkyl, aryl, substituted aryl

-continued

PTM-ag

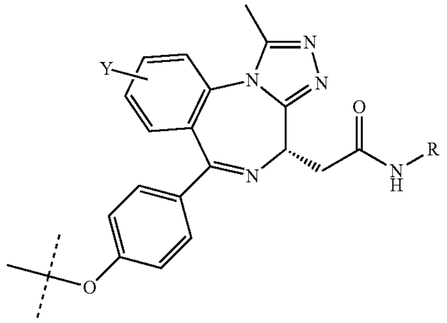

Y: mono- or di-substitutiion, Y = Me, OMe,
N-methylpyrazole/imidazole
R = lower alkyl, aryl, substituted aryl PTM-ah

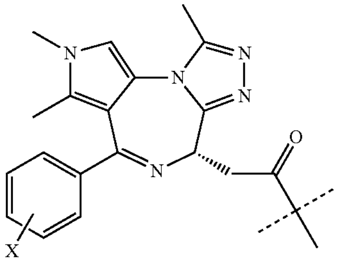

X = Cl, F, Br, H, CN, methyl, acetylene, methoxy

PTM-ai

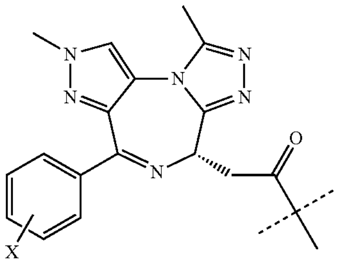

X = Cl, F, Br, H, CN, methyl, acetylene, methoxy

In certain embodiments, the structures are representatives of PTM-a as the BET/BRD4 ligand in structure (II). The dashed line indicates the connection point between BET/BRD4 ligand and the linkers. These are examples only and do not limit the ligand that can be used in structure (II) to degrade BET/BRD4.

PTM-al

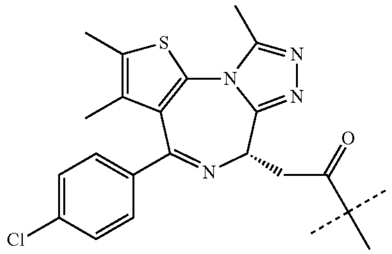

-continued
PTM-a2
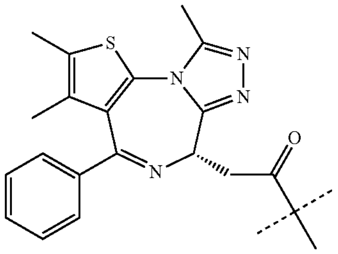
PTM-a3
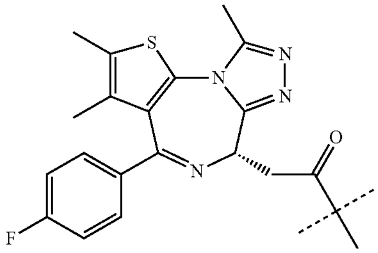
PTM-a4
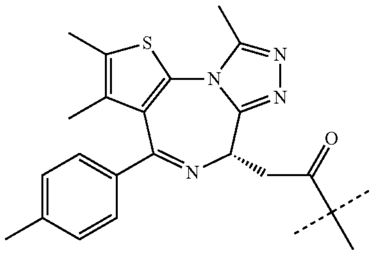
PTM-a5
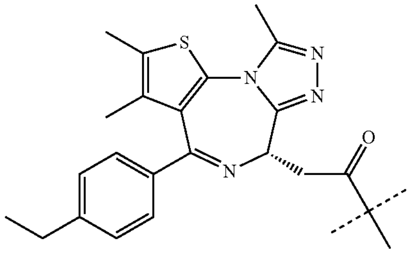
PTM-a6
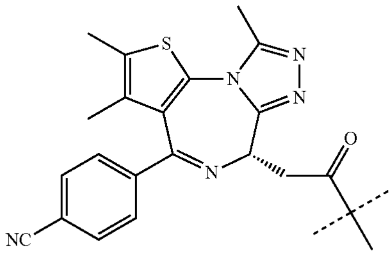
PTM-a7
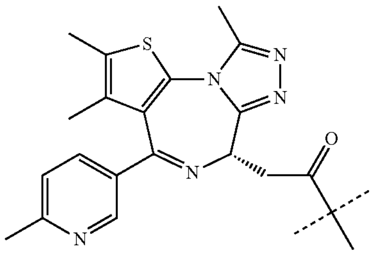
-continued
PTM-a8
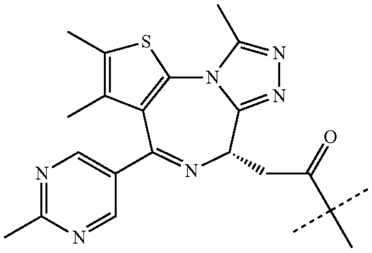
PTM-a9
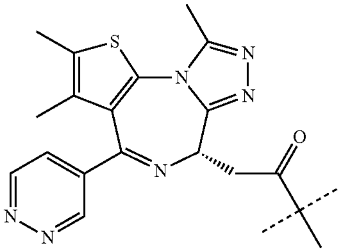
PTM-a10
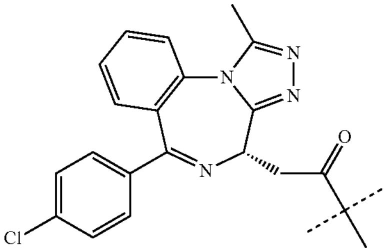
PTM-a11
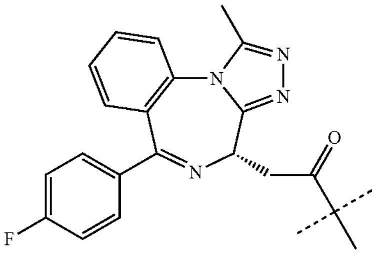
PTM-a12
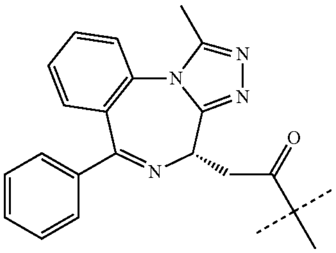
PTM-a13
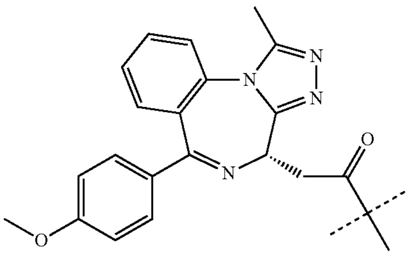

-continued
PTM-a14
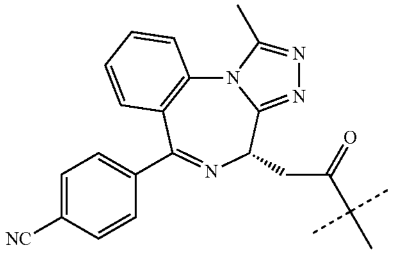
PTM-a15
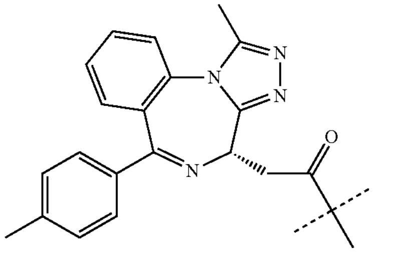
PTM-a16
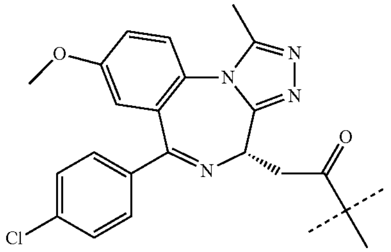
PTM-a17
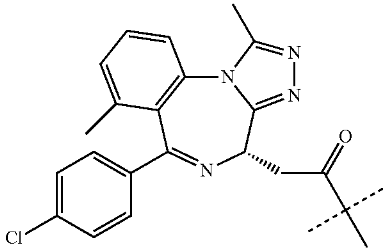
PTM-a18
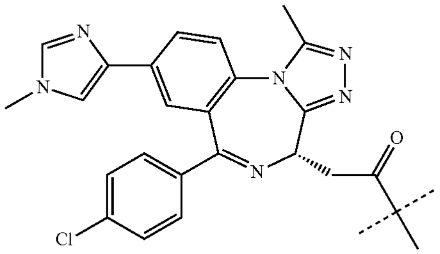
PTM-a19
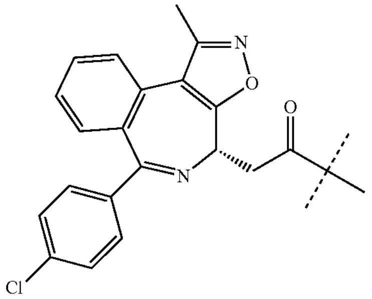
-continued
PTM-a20
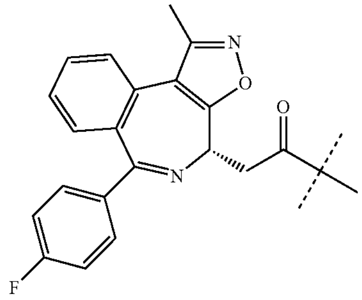
PTM-a21
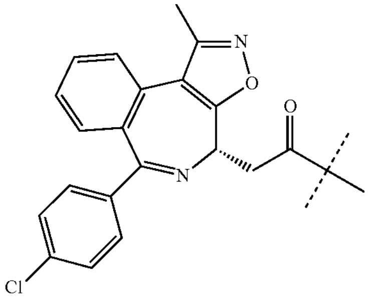
PTM-a22
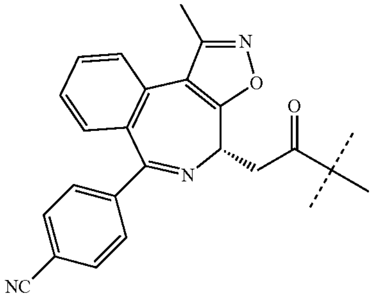
PTM-a23
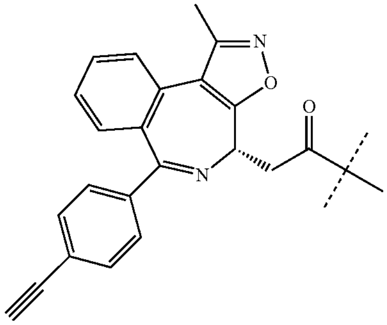
PTM-a24
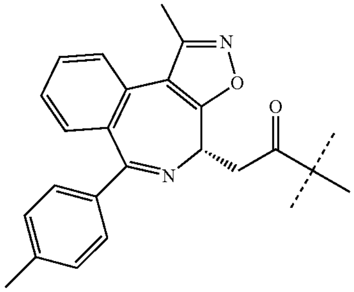

-continued
PTM-a25
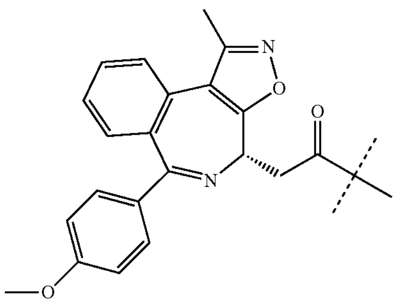
PTM-a26
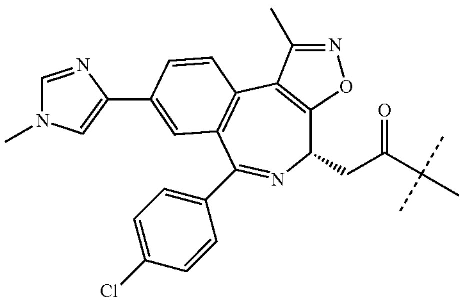
PTM-a27
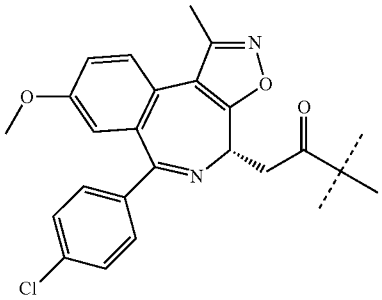
PTM-a28
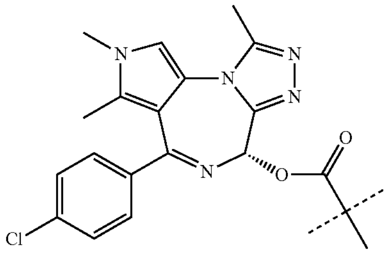
PTM-a29
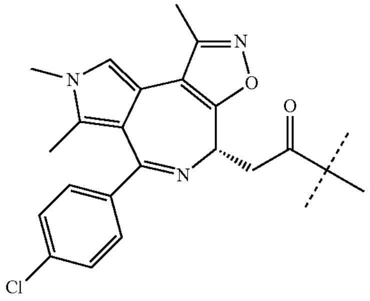
-continued
PTM-a30
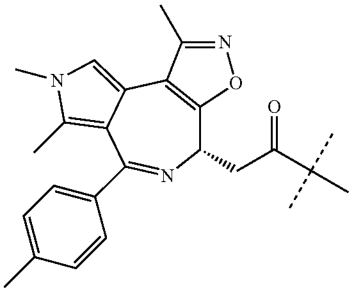
PTM-a31
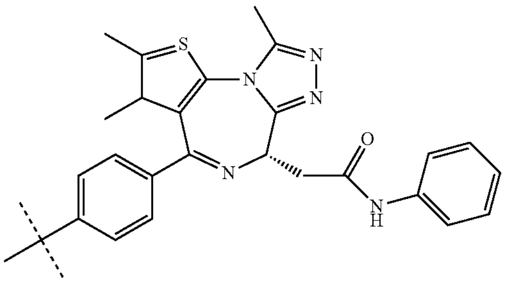
PTM-a32
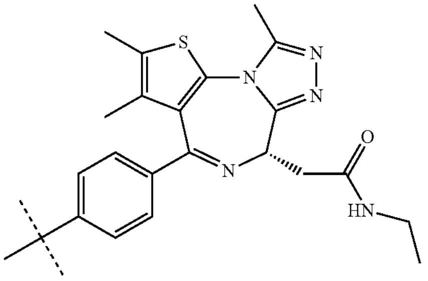
PTM-a33
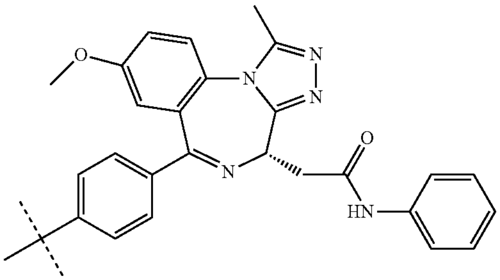
PTM-a34
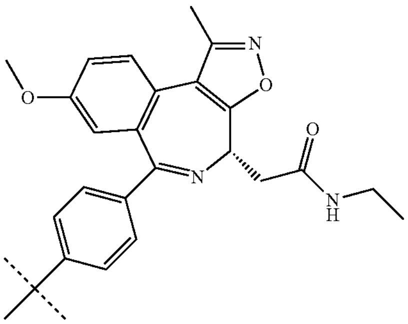

-continued

PTM-a35

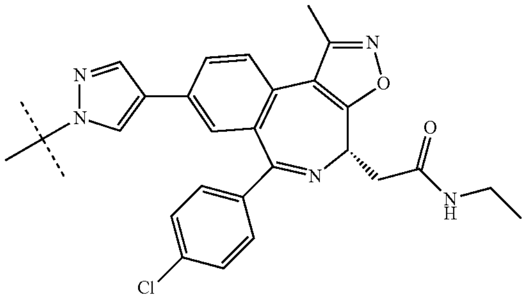

PTM-a36

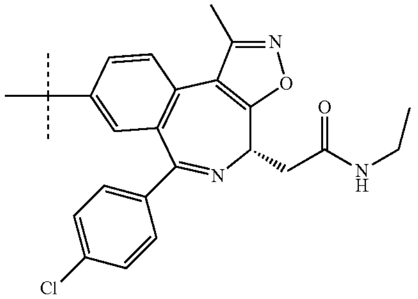

In certain embodiments, the structure (II) of the description comprises carbazole derived BET/BRD4 ligand with the general structure described as PTM-b. The fragment of PTM-b as BET/BRD4 ligand is described in the literature (US 2016/0176864).

PTM-b

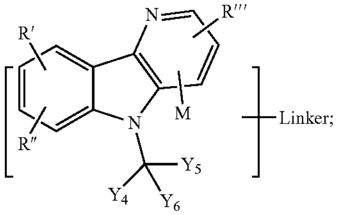

wherein,

M is a heterocyclic aromatic group, and can be further substituted with halogen, lower alkyl, fluorinated lower alkyl, CN, deuterium substitute lower alkyl. Preferably, M is optionally a 5-membered heteroaromatic, more preferably an isoxazole or a triazole, wherein the isoxazole ring can be substituted with halogen, lower alkyl, fluorinated lower alkyl, CN, deuterium substitute lower alkyl;

R' is a H, halogen, CN, lower alkyl, fluorine substituted lower alkyl, carboxylic acid, carboxamide, reverse amide, sulfonamide, hydroxyl alkyl, substituted hydroxyl alkyl, OH, alkoxy, fluorine substituted alkoxy;

R" is H, halogen, CN, lower alkyl, fluorine substituted lower alkyl, carboxylic acid, carboxamide, reverse amide, sulfonamide, hydroxyl alkyl, substituted hydroxyl alkyl, OH, alkoxy, fluorine substituted alkoxy;

R"' is H, CN, halogen, lower alkyl (C1-C6), fluorine substituted lower alkyl;

$Y_4$ and $Y_5$ are independently selected from H, lower alkyl, lower alkyl substituted with cycloalkyl, lower alkyl substituted with aryl, lower alkyl substituted with heterocycle, lower alkyl substituted with heteroaryl, aryl, heteroaryl;

$Y_6$ is selected from H, alkoxy, lower alkyl, substituted lower alkyl, heterocyclic alkyl, cyclic alkyl, carboxamide, sulfonamide, and carbamate.

In certain embodiments, PTM-b is described as a compound of formula:

PTM-b

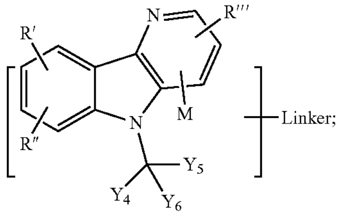

wherein

M is an optionally substituted heterocyclo or heteroaryl, wherein the substituents are one or more R; wherein, R is independently one or more hydrogen, CD3, halogen, haloalkyl, hydroxyalkyl, CN, $CF_3$, $CH_2F$, $CHF_2$, optionally substituted (Ci-C6)alkyl, optionally substituted (C1-C6) alkoxy, optionally substituted (C3-C6)cycloalkyl, optionally substituted heterocyclo, —OR4, —$CONR^3R^4$, —$NR^3R^4$, $NR^3R^4$(C1-C6)alkyl-, —$NR^6OCOR^3$, —$NR^6COR^3$, $NR^6COR^3$(C1-C6)alkyl-, —$NR^6CO_2R^3$, $NR^6CO_2R^3$(C1-C6)alkyl-, —$NR^6CONR^3R^4$, —$SO_2NR^3R^4$, $SO_2$(C1-C6) alkyl-, —$NR^6SO_2NR^3R^4$, —$NR^6SO_2R^4$ or $NR^6SO_2R^4$(C1-C6)alkyl-;

$Y^4$ and $Y^5$ are independently selected from hydrogen, optionally substituted (C1-C6)alkyl, optionally substituted (C3-C8)cycloalkyl, optionally substituted aryl, optionally substituted heteroaryl or optionally substituted heterocyclo;

Y6 is hydrogen, halogen, —OH, alkyl, substituted alkyl, cyclic alkyl, heterocyclic alkyl, (C1-C6)alkyl, (C1-C6) alkoxy, —NR3R4, —CONR3R4, —OCONR3R4, —NR6OCOR3, —NR6CONR3R4, —NR6SO2NR3R4 or —NR6SO2R4;

R' is, independently at each occurrence, one or more hydrogen, halogen, —CN, —$OR^4$, —$NR^3R^4$, —$CONR^3R^4$, —COOH, —$OCONR^3R^4$, —$NR^6OCOR^3$, —$NR^6CONR^3R^4$, —$NR^6SO_2NR^3R^4$, —$NR^6SO_2R^4$, optionally substituted (C1-C6)alkyl, optionally substituted, (C2-C6)alkenyl, optionally substituted (C2-C6)alkynyl, optionally substituted (C1-C6)alkoxy, optionally substituted (C3-C8)cycloalkyl, optionally substituted (C3-C8)cycloalkyl (C1-C6)alkyl, optionally substituted (C3-C8)cycloalkyl-CO—, optionally substituted (C3-C8)cycloalkyl-$SO_2$-, optionally substituted aryl (C1-C6)alkoxy, optionally substituted (C3-C8)cycloalkyl (C1-C6)alkoxy, optionally substituted heterocyclyl-CO—, optionally substituted heterocyclyl, optionally substituted (C1-C6)alkyl-$SO_2$-, —$NR^6SO_2$-, optionally substituted (C1-C6)alkyl, —NR6SO2-optionally substituted heterocyclo, optionally substituted (C1-C6)alkyl-$NR^6SO_2$- or optionally substituted heterocyclo-$NR^6SO_2$-;

R" is hydrogen, halogen, —CN, OH, —$CONR^3R^4$, —$NR^6COOR^4$, —$NR^6CONR^3R^4$, $NR^6COR^4$, —$NR^6SO_2R^3$, —$SO_2NR^3R^4$, —$NR^6SO_2NR^3R^4$, optionally substituted (C1-C6)alkyl, optionally substituted (C3-C8) cycloalkyl, optionally substituted (C1-C6) alkoxy, optionally substituted aryl, optionally substituted (C1-C6)alkyl-$SO_2$-, optionally substituted aryl-$SO_2$, optionally substituted heteroaryl or optionally substituted heterocyclo;

$R^3$ is hydrogen, optionally substituted (C1-C6)alkyl, optionally substituted (C3-C8)cycloalkyl, optionally substituted (C2-C6)alkenyl, optionally substituted (C2-C6)alkynyl, cyano(C1-C6)alkyl, hydroxy(C1-C6)alkyl, optionally substituted aryl, optionally substituted aryl(C1-C6)alkyl, optionally substituted aryloxy(C1-C6)alkyl, optionally substituted (C1-C6)alkyl-SO2-, optionally substituted heterocyclyl, optionally substituted heterocyclyl(C1-C6)alkyl, optionally substituted heteroaryl or optionally substituted heteroaryl(C1-C6)alkyl, $R^4$ is hydrogen, optionally substituted (C1-C6)alkyl or optionally substituted (C3-C8)cycloalkyl;

or $R^3$ and $R^4$ may be taken together with the nitrogen atom to which they are attached to form an optionally substituted (C4-C8) heteroaryl or (C4-C8) heterocyclic ring;

$R^5$ is hydrogen, optionally substituted (C1-C6)alkyl, optionally substituted (C3-C8)cycloalkyl, optionally substituted (C2-C6)alkenyl, optionally substituted (C2-C6)alkynyl, cyano(C1-C6)alkyl, hydroxy(C1-C6)alkyl, optionally substituted aryl, optionally substituted aryl(C1-C6)alkyl, optionally substituted aryloxy(C1-C6)alkyl, optionally substituted (C1-C6)alkyl-$SO_2$-, optionally substituted heterocyclyl, optionally substituted heterocyclyl(C1-C6)alkyl, optionally substituted heteroaryl or optionally substituted heteroaryl(C1-C6)alkyl;

$R^6$ is hydrogen or optionally substituted (C1-C6)alkyl;

R''' is hydrogen, optionally substituted (C1-C6)alkyl, —$OR^4$, CN or halogen;

and/or a pharmaceutically acceptable salt, tautomer or stereoisomer thereof.

In certain embodiments, the PTM-b is represented by the following structures as the BET/BRD4 ligand in structure (II). The dashed line indicates the site of linker attachment. These are examples only and do not limit the ligand that can be used in structure (II) to degrade BET/BRD4.

PTM-ba

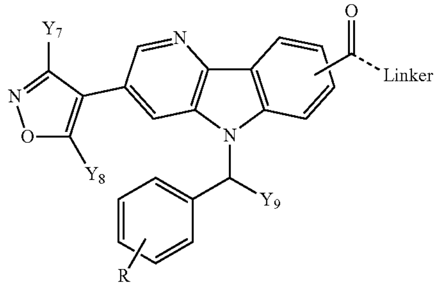

PTM-bb

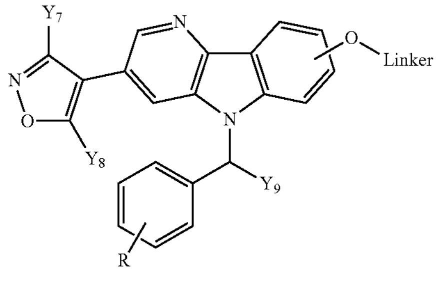

-continued

PTM-bc

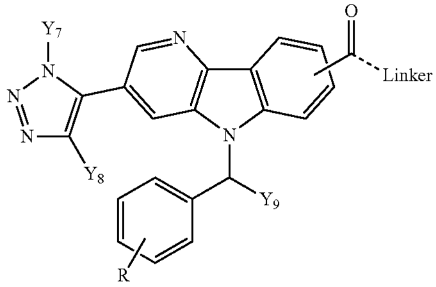

PTM-bd

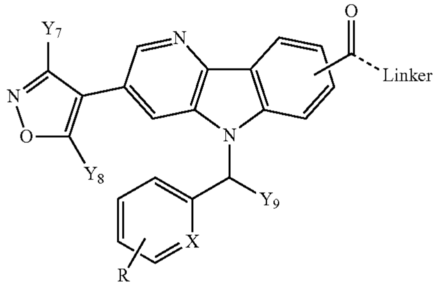

PTM-be

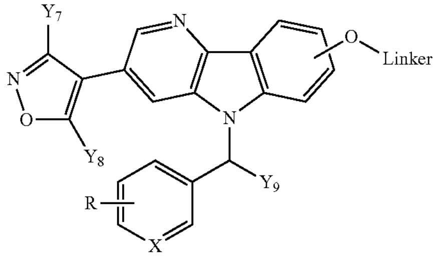

PTM-bf

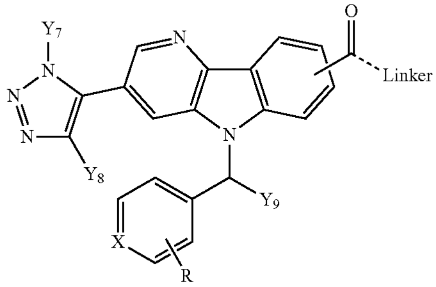

wherein, $Y_7$ is $CH_3$ or $CD_3$;

$Y_8$ is selected from H, $CH_3$, $CD_3$, $CF_3$;

R is independently selected from H, halogen, lower alkyl groups, wherein R can be mono-, bis- or tri-substituted; and $Y_9$ is selected from H, lower alkyl, cycloalkyl, heterocycle.

In certain embodiments, $Y_9$ is tetrahydropyran, cyclobutane, methyl, alkoxy, tetrahydrofuran, oxetane.

In another embodiment, the claimed structure (II) is composed of a carbazole derived BET/BRD4 ligand with the general structure described as PTM-c. The fragment of PTM-c as BET/BRD4 ligand is described in the literature (US 2014/0256700).

PTM-c

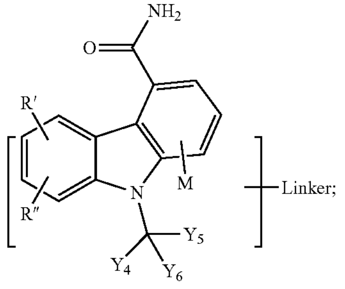

wherein

M is a heterocyclic aromatic group, preferably a 5-membered heteroaromatic, more preferably isoxazole or triazole, optionally substituted with halogen, lower alkyl, fluorinated lower alkyl, CN, deuterium substitute lower alkyl;

R' and R" are independently H, halogen, CN, lower alkyl, fluorine substituted lower alkyl, carboxylic acid, carboxamide, reverse amide, sulfonamide, hydroxyl alkyl, substituted hydroxyl alkyl, OH, alkoxy, fluorine substituted alkoxy;

$Y_4$ and $Y_5$ are independently selected from H, lower alkyl, lower alkyl substituted with cycloalkyl, lower alkyl substituted with aryl, lower alkyl substituted with heterocycle, lower alkyl substituted with heteroaryl, aryl, heteroaryl; and $Y_6$ is selected from H, alkyl, substituted alkyl, cyclic alkyl, heterocyclic alkyl, alkoxy, lower alkyl, carboxamide, sulfonamide, carbamate.

In certain embodiments PTM-c is represented by following structures as the BET/BRD4 ligand in structure (II). The dashed line indicates the site of linker attachment. These are examples only and do not limit the ligand that can be used in structure (II) to degrade BET/BRD4.

PTM-ca

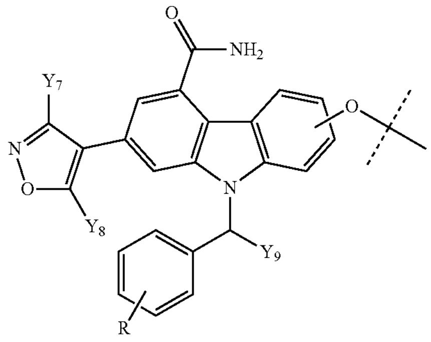

PTM-cb

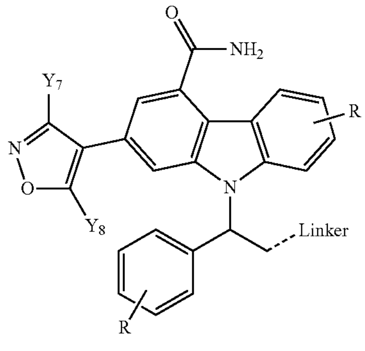

-continued

PTM-cc

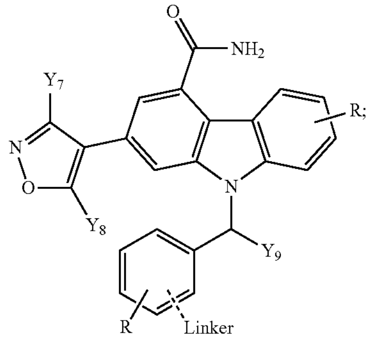

wherein $Y_7$ is $CH_3$ or $CD_3$;

$Y_8$ is selected from H, $CH_3$, $CD_3$, $CF_3$

R is independently selected from H, halogen, lower alkyl groups, wherein R can be mono-, bis- or tri-substituted;

$Y_9$ is selected from H, lower alkyl, cycloalkyl and heterocycle.

In certain embodiments, $Y_9$ is tetrahydropyran, cyclobutane, methyl, alkoxy, tetrahydrofuran, oxetane In certain embodiments, pyrrolopyridone chemotype PTM-d is represented by following structures as the BET/BRD4 ligand in structure (II). The dashed line indicates the site of linker attachment. These are examples only and do not limit the ligand that can be used in structure (II) to degrade BET/BRD4. The fragments of these ligands are described in the literature (US 2015/0148342).

PTM-da

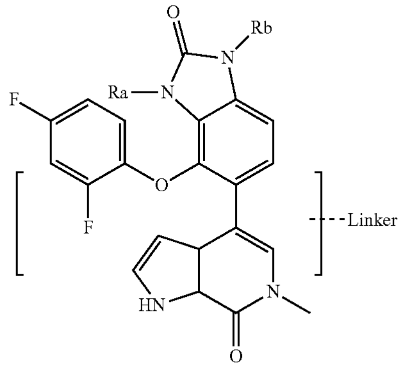

PTM-db

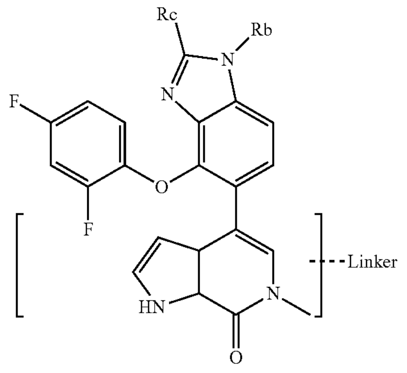

-continued

PTM-dc

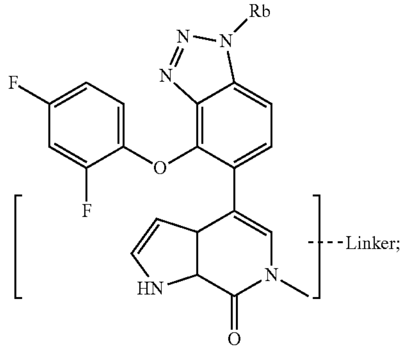

wherein

Ra, Rb and Rc are each independently selected from H, halo, C1-6 alkyl, C2-6 alkenyl, C2-6 alkynyl, C1-6 haloalkyl, C6-10 aryl, C3-10 cycloalkyl, 5-10 membered heteroaryl, 4-10 membered heterocycloalkyl, CN, NO2, $OR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C{=}NR^{e3})R^{b3}$, $C({=}NR^{e3})NR^{c3}R^{d3}$, $NR^{c3}C({=}NR^{e3})NR^{c3}R^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said C1-6 alkyl, C2-6 alkenyl, C2-6 alkynyl, C6-10 aryl, C3-10 cycloalkyl, 5-10 membered heteroaryl, and 4-10 membered heterocycloalkyl are each optionally substituted with 1, 2, 3, 4, or 5 substituents independently selected from halo, C1-6 alkyl, C2-6 alkenyl, C2-6 alkynyl, C1-6 haloalkyl, phenyl, C3-7 cycloalkyl, 5-6 membered heteroaryl, 4-7 membered heterocycloalkyl, CN, NO2, $OR^{a3}$, $SR^{a3}C(O)R^{b3}$, $C(O)NR^{c3}R^{d3}$, $C(O)OR^{a3}$, $OC(O)R^{b3}$, $OC(O)NR^{c3}R^{a3}$, $C({=}NR^{e3})NR^{c3}R^{d3}$, $NR^{c3}C({=}NR^{e3})$ $NR^{c3}R^{d3}$, $NR^{c3}R^{d3}$, $NR^{c3}C(O)R^{b3}$, $NR^{c3}C(O)OR^{e3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, and wherein said phenyl, C3-7 cycloalkyl, 5-6 membered heteroaryl, and 4-7 membered heterocycloalkyl are each independently substituted by 1, 2, or 3 substituents independently selected from halo, C1-6 alkyl, C2-6 alkenyl, C2-6 alkynyl, C1-6 haloalkyl, CN, $NO_2$, $OR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C{=}NR^{e3})R^{b3}$, $C({=}NR^{e3})NR^{c3}R^{d3}$, $NR^{c3}C({=}NR^{e3})NR^{c3}R^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein $R^{a3}$, $R^{b3}$, $R^{c3}$, $R^{d3}$ and $R^{e3}$ are independently selected from H, C1-6 alkyl, C1-4 haloalkyl, C2-6 alkenyl, C2-6 alkynyl, C6-10 aryl, C3-10 cycloalkyl, 5-10 membered heteroaryl, 4-10 membered heterocycloalkyl, C6-10 aryl-C1-6 alkyl, C3-10 cycloalky-C1-6 alkyl, (5-10 membered heteroaryl)-C1-6 alkyl, and (4-10 membered heterocycloalkyl)-C1-6 alkyl, wherein said C1-6 alkyl, C2-6 alkenyl, C2-6 alkynyl, C6-10 aryl, C3-10 cycloalkyl, 5-10 membered heteroaryl, 4-10 membered heterocycloalkyl, C6-10 aryl-C1-6 alkyl, C3-10 cycloalky-C1-6 alkyl, (5-10 membered heteroaryl)-C1-6 alkyl, and (4-10 membered heterocycloalkyl)-C1-6 alkyl is optionally substituted with 1, 2, 3, 4, or 5 substituents independently selected from C1-4 alkyl, C1-4 haloalkyl, halo, CN, OR's, SR's, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR$'s, $C({=}NR^{c5})NR^{c5}R^{d5}$, $NR^{c5}C({=}NR^{c5})NR^{c5}R^{d5}$, $S(O)\ R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$; and $R^{b5}$, $R^{c5}$, and $R^{d5}$ are independently selected from H, C1-4 alkyl, C1-4 haloalkyl, C2-4 alkenyl, and C2-4 alkynyl, optionally substituted with 1, 2, or 3 substituents independently selected from OH, CN, amino, halo, C1-4 alkyl, C1-4 alkoxy, C1-4 alkylthio, C1-4 alkylamino, di(C1-4 alkyl) amino, C1-4 haloalkyl, and C1-4 haloalkoxy.

In another embodiment, tetrahydroquinoline type of chemotype PTM-e is represented by following structures as the BET/BRD4 ligand. The fragments of these ligands are described in the literature (WO 2015/074064)

PTM-e

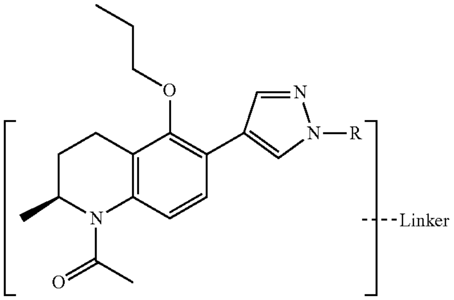

R is hydrogen or $C_1$-$C_6$ alkyl; $(CH_2)$, $R^a$, $(CH_2)$, $OR^a$, $C(O)R^a$, $C(O)OR^a$, $C(O)NR^aR^b$, $S(O)2R^a$, $S(O)_2NR^aR^b$, C1-C6 haloalkyl, C1-C6 haloalkoxy, aryl, heteroaryl, cycloalkyl, heterocycloalkyl, halo, cyano, or oxo;

In yet another embodiment, triazolopyrazine chemotype PTM-f is represented by following structures as the BET/BRD4 ligand (WO 2015/067770).

PTM-fa

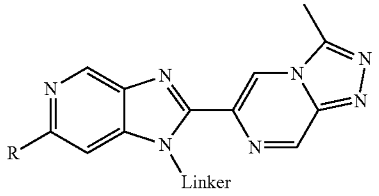

PTM-fb

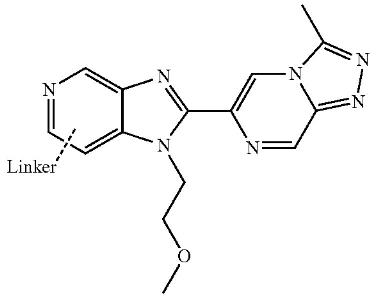

R is selected from halogen, CN, NH2, —O—C1-3 alkyl, $N(C1\text{-}3\ alkyl)_2$, $C(O)N(C1\text{-}3alkyl)_2$, a C1-5alkyl wherein, C1-5alkyl is optionally substituted with one or more groups selected from halogen or CN, a 4-7 membered heterocycloalkyl, wherein the heterocycloalkyl group can be optionally substituted with one or more C1-3alkyl, and a C3-6 cycloalkyl wherein the cycloalkyl group can be optionally substituted with one or more groups independently selected from C1-3 alkyl, C1-3 haloalkyl and halogen.

In certain embodiment, pyridone type of chemotype PTM-g is represented by following structure as the BET/BRD4 ligand The fragments of these ligands are described in the literature (WO 2015/022332).

PTM-g

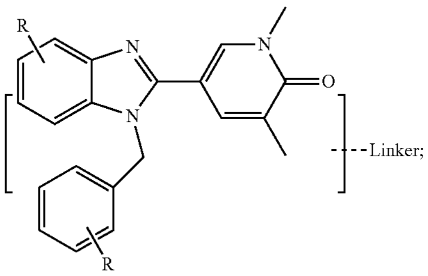

wherein,

R is selected from H, halogen, NH2, C1-3alkyl, C3-6cycloalkyl, SO2N(C1-3alkyl)$_2$ and 5-6 membered heterocycloalkyl, where heterocycloalkyl can be optionally substituted with one or more groups independently selected from ═O, C1-3alkyl, and C1-5haloalkyl; and the cycloalkyl group can be optionally and independently substituted with one or more groups independently selected from C1-3alkyl, C1-3haloalkyl and halogen.

In another embodiment, quinazolinone chemotype PTM-h is represented by following structures as the BET/BRD4 ligand. The fragments of these ligands are described in the literature (WO 2015/015318).

PTM-h

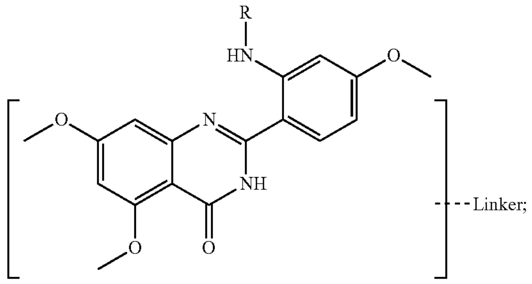

wherein,

R is selected from amino, 5- and 6-membered carbocycles and heterocycles.

In yet another embodiment, dihydropyridopyrazinone chemotype PTM-i is represented by following structure as the BET/BRD4 ligand. The fragments of these ligands are described in the literature (WO 2015/011084).

PTM-i

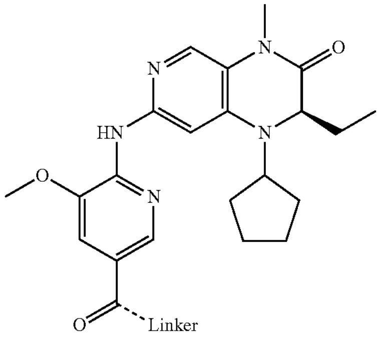

Section 3: Linker in Structure (II)

In certain embodiments, the compounds as described herein can be chemically linked or coupled via a chemical linker (L). Linker (L) can be covalently connected to PTM (e.g. BET/BRD4 ligand) on one end and to UTM on the other end as described in structure (II).

In certain embodiments, the linker group L is a group comprising one or more covalently connected structural units (e.g., -$A_1$ . . . $A_q$-), wherein Ai is a group coupled to PTM, and $A_q$ is a group coupled to UTM.

In certain embodiments, the linker group L is selected from $A_q$-;

Aq is a group which is connected to a UTM or PTM moiety; and q is an integer greater than or equal to 1, wherein $A_q$ is selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$═$CR^{L2}$, C≡C, $SiR^{L1}R^{L2}$, $P(O)R^{L1}$, $P(O)OR^{L1}$, $NR^{L3}C$(═NCN)$NR^{L4}$, $NR^{L3}C$(═NCN), $NR^{L3}C$(═$CNO_2$)$NR^{L4}$, $C_{3-11}$cycloalkyl optionally substituted with 0-6 $R^{L1}$ and/or $R^{L2}$ groups, $C_{3-11}$heterocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups;

$R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, CH═CH($C_{1-8}$alkyl), C($C_{1-8}$alkyl)═CH($C_{1-8}$alkyl), C($C_{1-8}$alkyl)═C($C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-8}alkyl)_2$, NH $SO_2NH_2$.

In certain embodiments, q is an integer greater than or equal to 0. In certain embodiments, q is an integer greater than or equal to 1.

In certain embodiments, e.g., where q is greater than 2, $A_q$ is a group which is connected to UTM, and $A_1$ and $A_q$ are connected via structural units of the linker (L).

In certain embodiments, e.g., where q is 2, $A_q$ is a group which is connected to $A_1$ and to a UTM.

In certain embodiments, e.g., where q is 1, the structure of the linker group L is -$A_1$-, and $A_1$ is a group which is connected to a UTM moiety and a PTM moiety.

In certain embodiments, the linker (L) comprises a group represented by a general structure selected from the group consisting of:

—$NR(CH_2)_n$-(lower alkyl)-, —$NR(CH_2)_n$-(lower alkoxyl)-, —$NR(CH_2)_n$-(lower alkoxyl)-$OCH_2$—, —$NR(CH_2)_n$-(lower alkoxyl)-(lower alkyl)-$OCH_2$—, —$NR(CH_2)_n$-(cycloalkyl)-(lower alkyl)-$OCH_2$—, —$NR(CH_2)_n$-(hetero cycloalkyl)-, —$NR(CH_2CH_2O)_n$-(lower alkyl)-O—$CH_2$—, —$NR(CH_2CH_2O)_n$-(hetero cycloalkyl)-O—$CH_2$—, —$NR(CH_2CH_2O)_n$-Aryl-O—$CH_2$—, —$NR(CH_2CH_2O)_n$-(hetero aryl)-O—$CH_2$—, —$NR(CH_2CH_2O)_n$-(cyclo alkyl)-O-(hetero aryl)-O—$CH_2$—, —$NR(CH_2CH_2O)_n$-(cyclo alkyl)-O-Aryl-O—$CH_2$—, —$NR(CH_2CH_2O)_n$-(lower alkyl)-NH-Aryl-O—$CH_2$—, —$NR(CH_2CH_2O)_n$-(lower alkyl)-O-Aryl-$CH_2$, —$NR(CH_2CH_2O)_n$-cycloalkyl-O-Aryl-, —$NR(CH_2CH_2O)_n$-cycloalkyl-O-(hetero aryl)l-, —NR(CH2CH2)$_n$-(cycloalkyl)-O-(heterocycle)-$CH_2$, —NR $(CH_2CH_2)_n$-(heterocycle)-(heterocycle)-$CH_2$, —N(R1R2)-(heterocycle)-CH2; where n can be 0 to 10;

R can be H, lower alkyl;

R1 and R2 can form a ring with the connecting N.

In certain embodiments, the linker (L) comprises a group represented by a general structure selected from the group consisting of:

—N(R)—(CH2)$_m$—O(CH2)$_n$-O(CH2)$_o$-O(CH2)$_p$-O (CH2)$_q$-O(CH2)$_r$-OCH2-,

—O—(CH2)$_m$—O(CH2)$_n$-O(CH2)$_o$-O(CH2)$_p$-O(CH2)$_q$-O(CH2)$_r$-OCH2-,

—O—(CH2)$_m$-O(CH2)$_n$-O(CH2)$_o$-O(CH2)$_p$-O(CH2)$_q$-O (CH2)$_r$-O—;

—N(R)—(CH2)$_m$-O(CH2)$_n$-O(CH2)$_o$-O(CH2)$_p$-O (CH2)$_q$-O(CH2)$_r$-O—; —CH2)$_m$-O(CH2)$_n$-O(CH2)$_o$-O (CH2)$_p$-O(CH2)$_q$-O(CH2)$_r$-O—; —CH2)$_m$-O(CH2)$_n$-O (CH2)$_o$-O(CH2)$_p$-O(CH2)$_q$-O(CH2)$_r$-OCH2-;

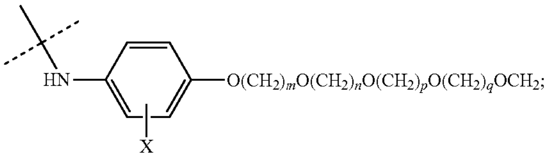

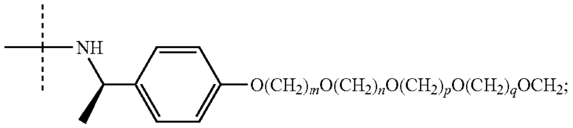

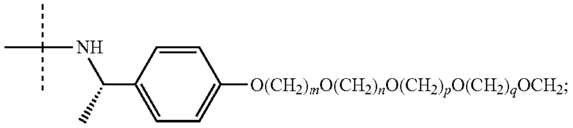

-continued

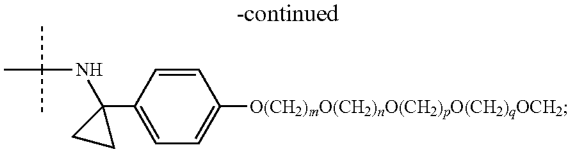

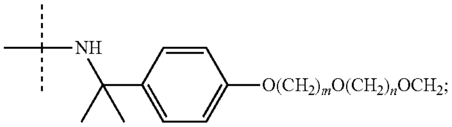

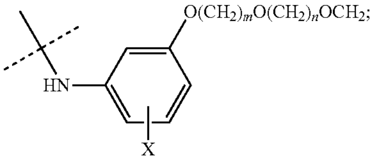

and

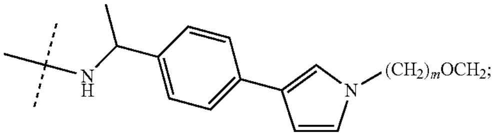

wherein m, n, o, p, q, and r are independently 0, 1, 2, 3, 4, 5;

when the number is zero, there is no N—O or O—O bond

R is H, methyl and ethyl;

X is H and F

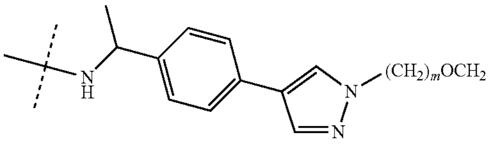

Where m can be 2, 3, 4, 5

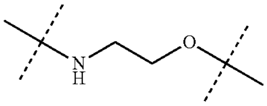

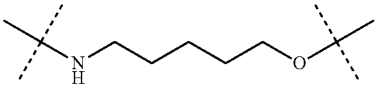

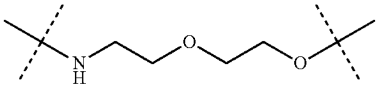

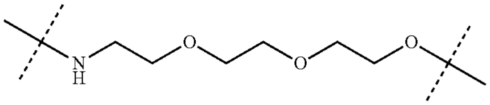

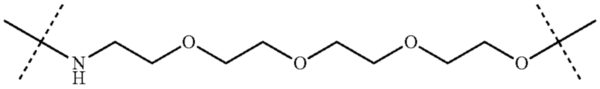

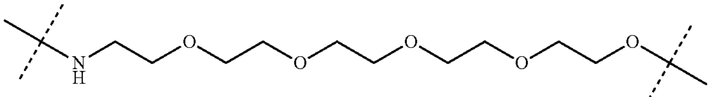

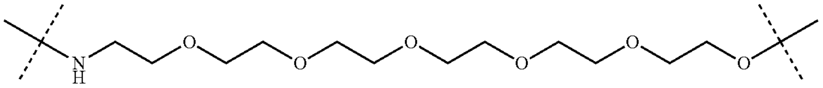

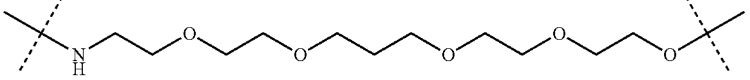

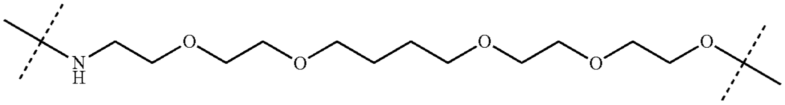

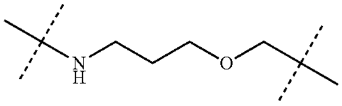

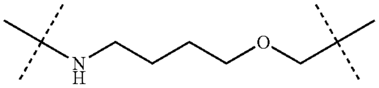

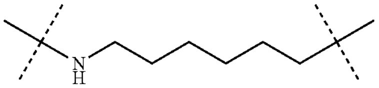

-continued
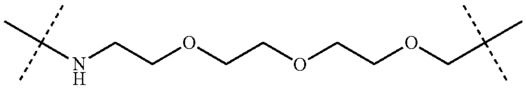
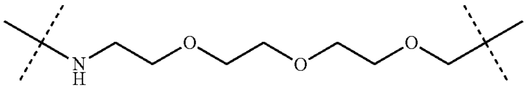
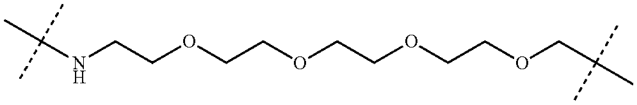
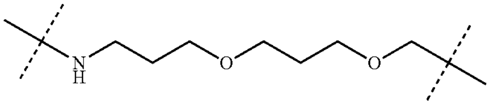
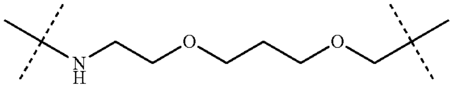
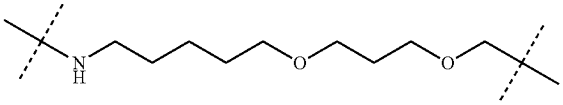
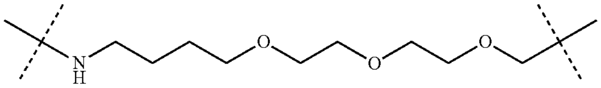
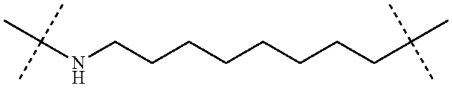
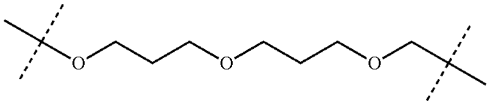
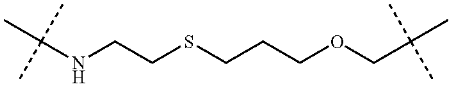
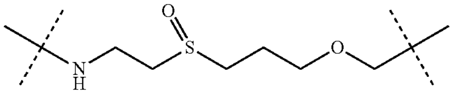
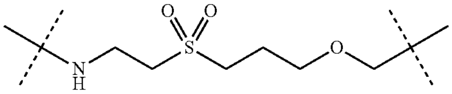
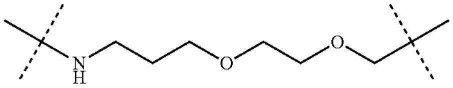
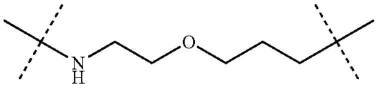
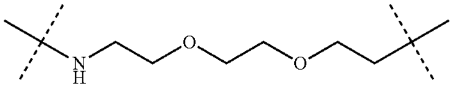
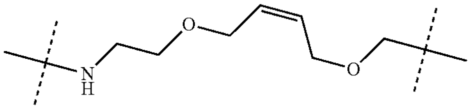
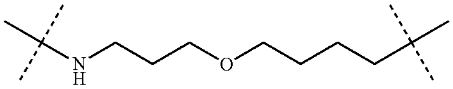
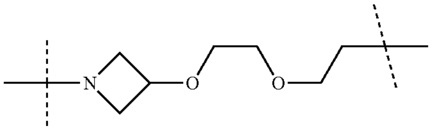
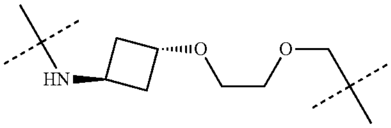
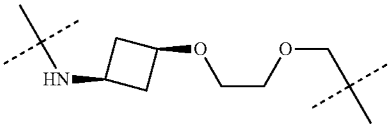
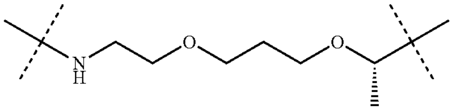
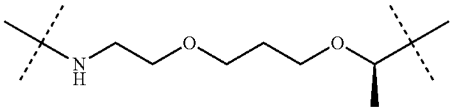
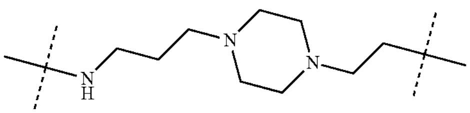
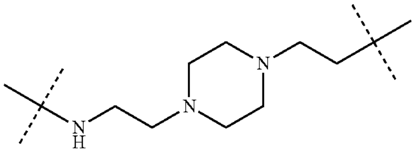
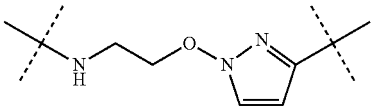
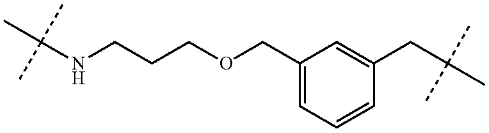
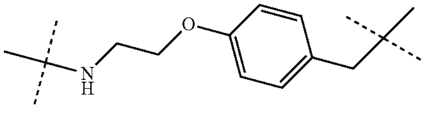
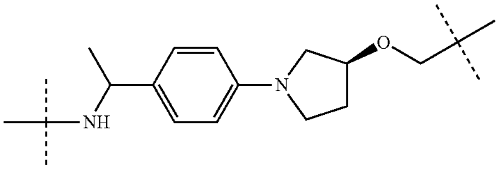

-continued
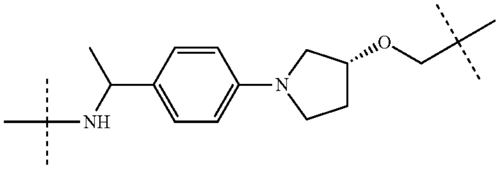
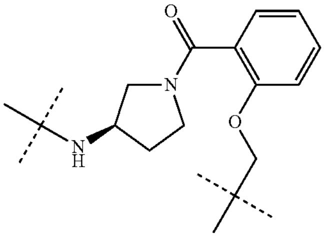
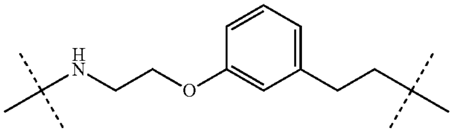
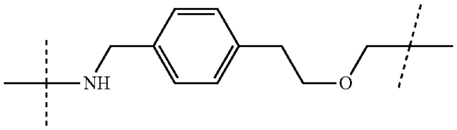
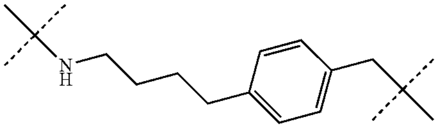
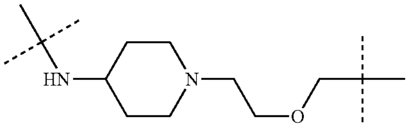
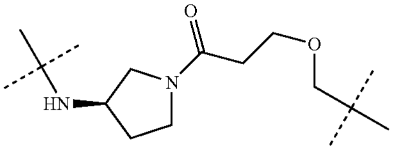
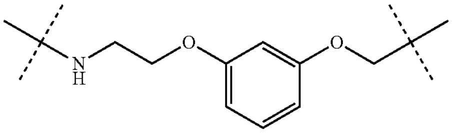
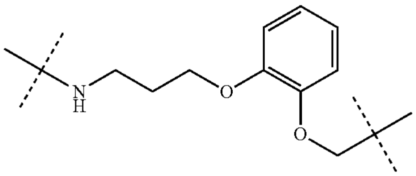
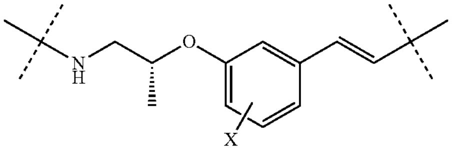
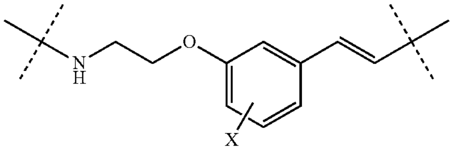
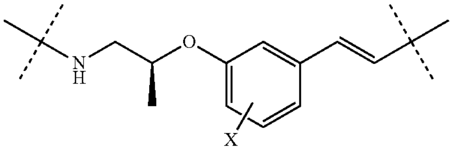
X = H, F
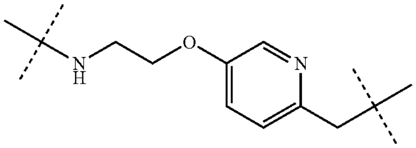
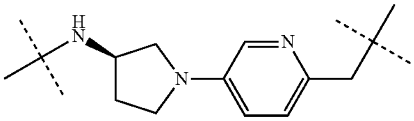
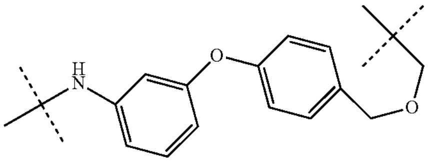
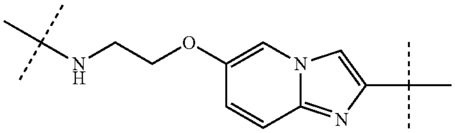
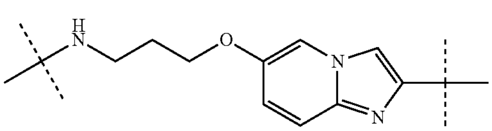
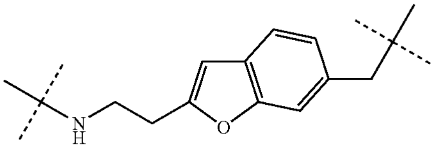
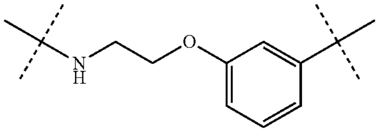
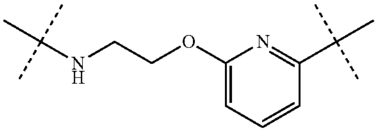

-continued
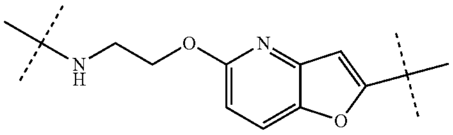 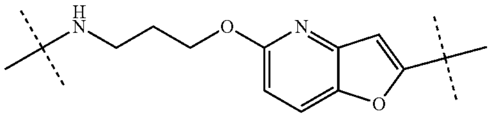
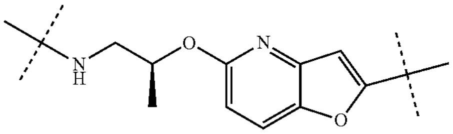 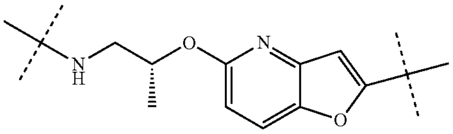
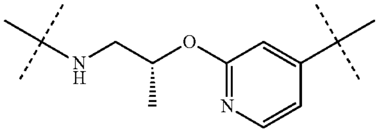 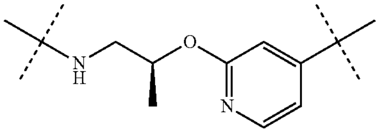
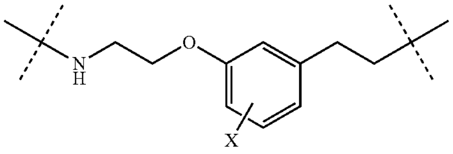 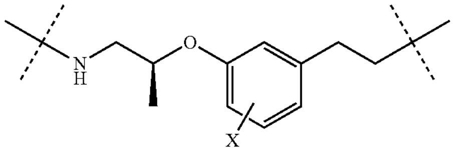
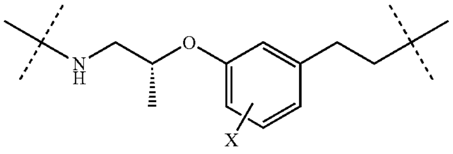 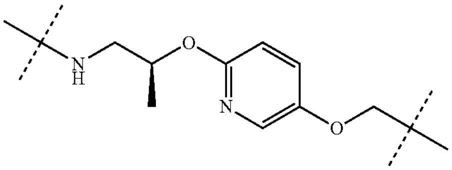
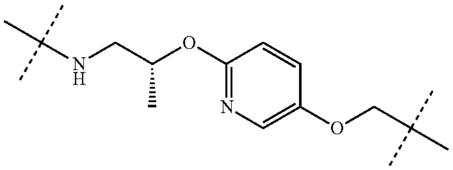 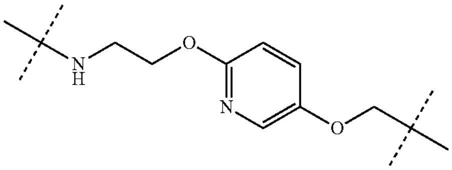
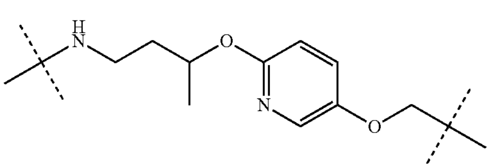 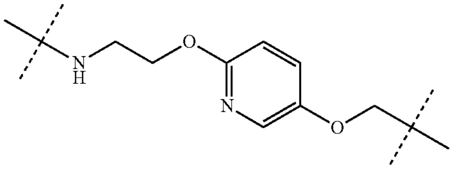
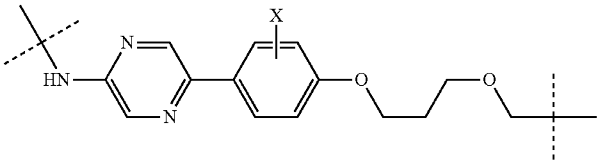
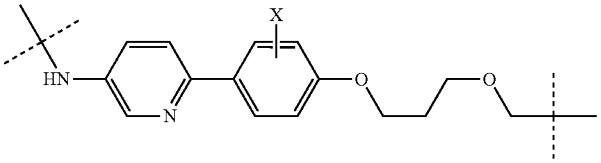
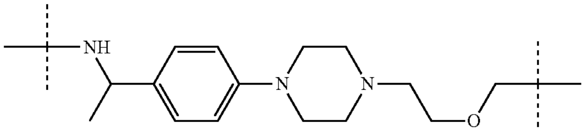
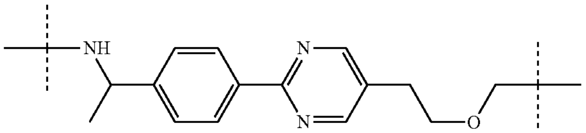

-continued
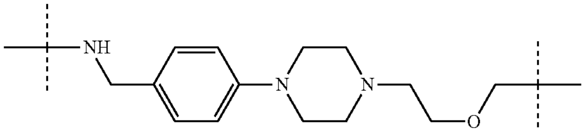
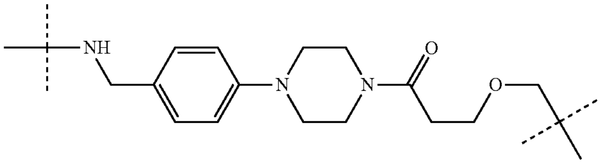
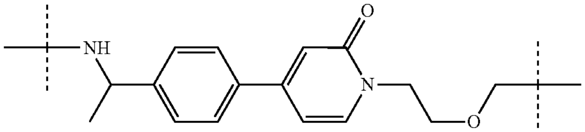
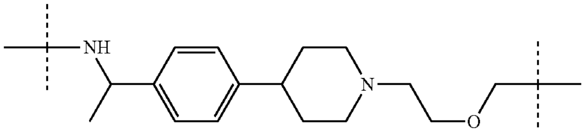
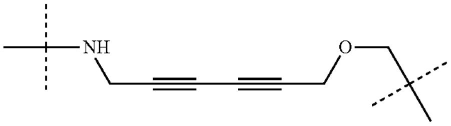
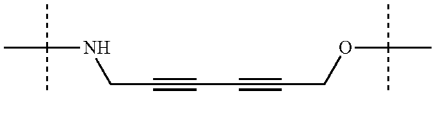
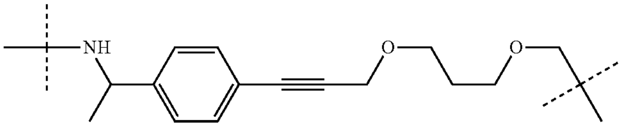
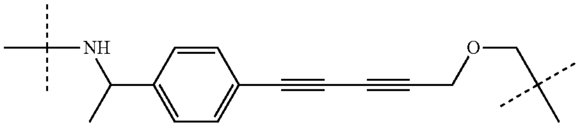
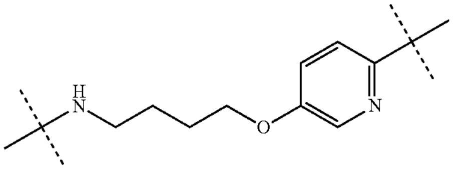
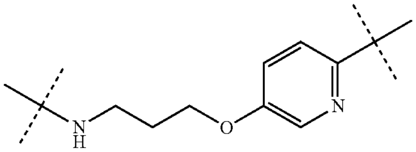
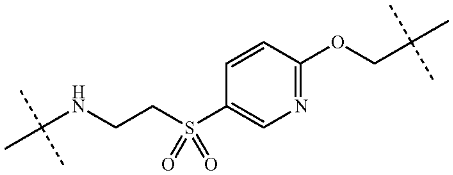
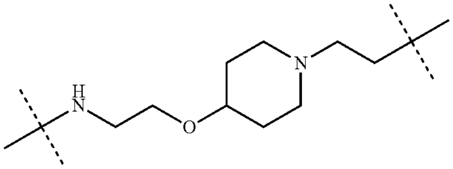
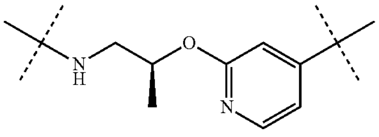
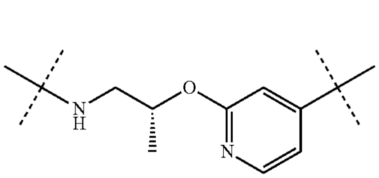
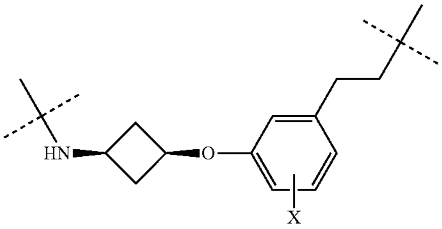
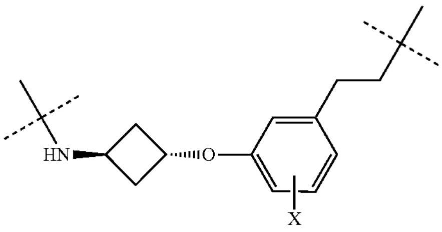
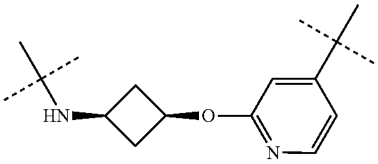
X = H, F -continued
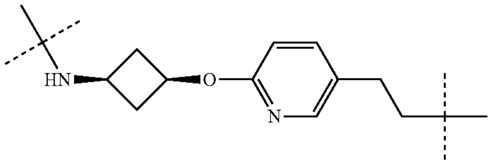
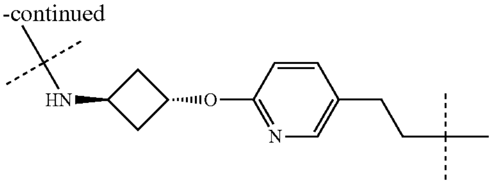
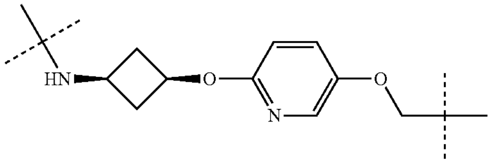
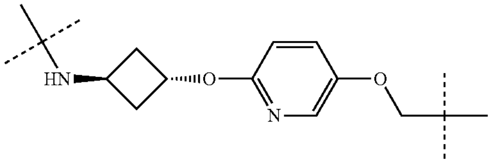
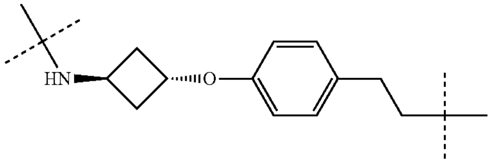
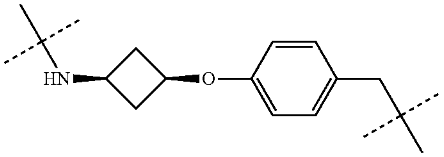
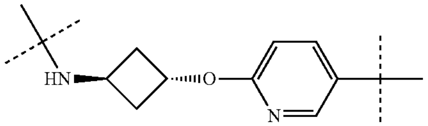
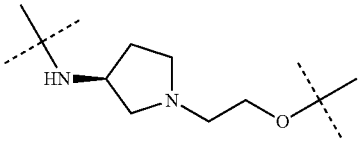
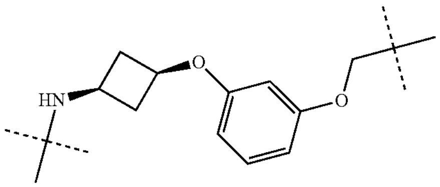
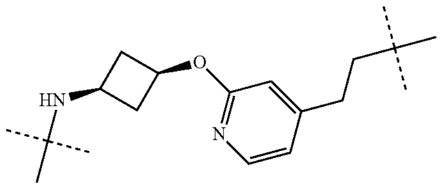
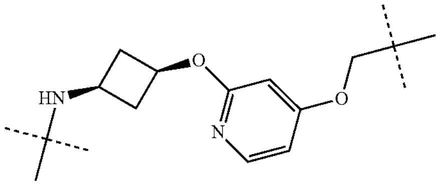
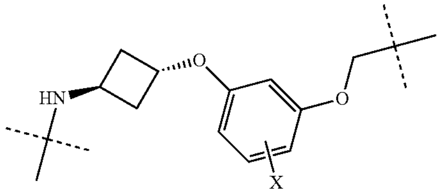
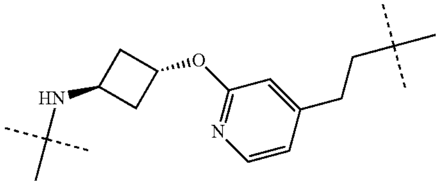
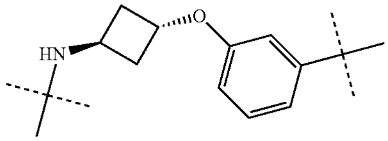
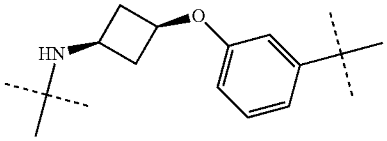
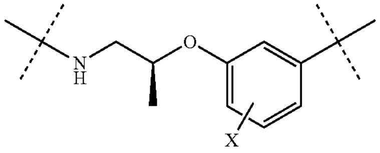
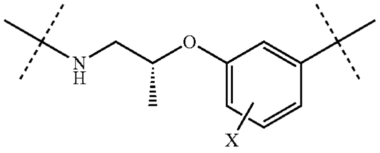
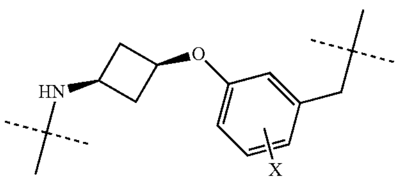
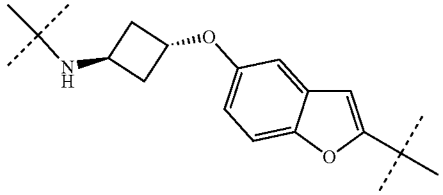
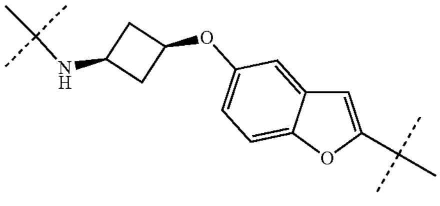
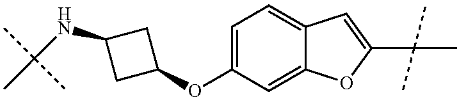

-continued
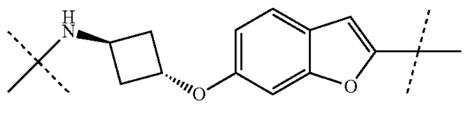
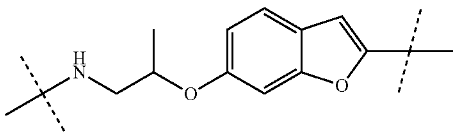
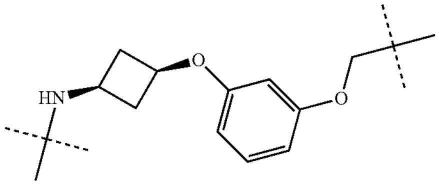
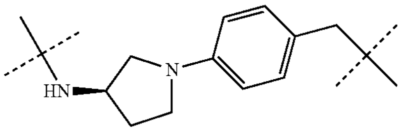
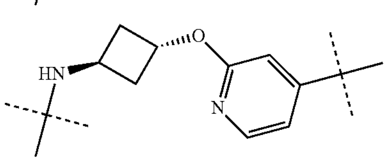
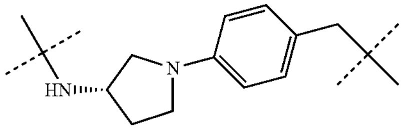
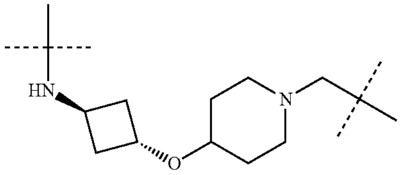
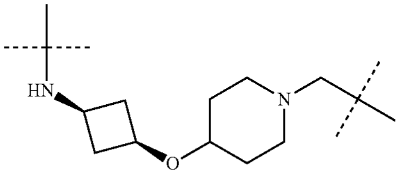
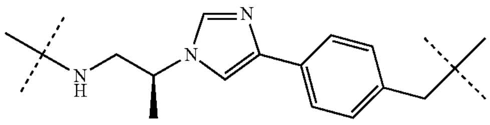
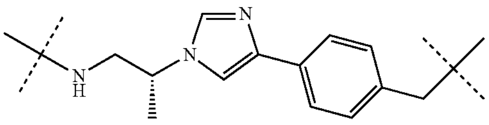
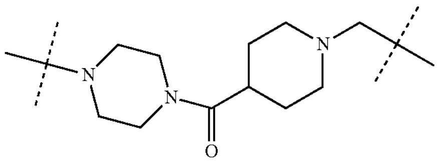
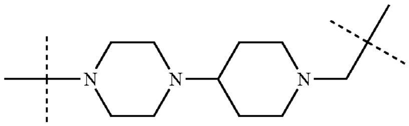
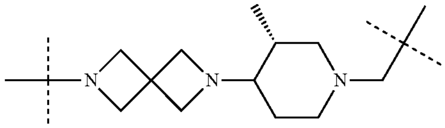
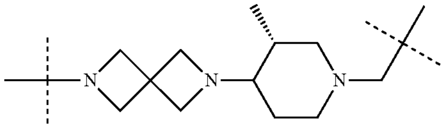
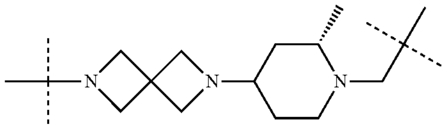
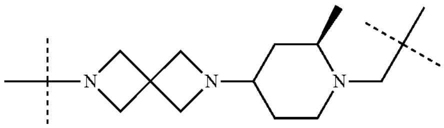
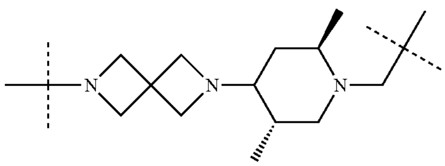
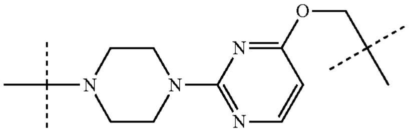
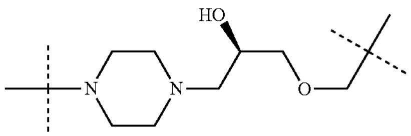
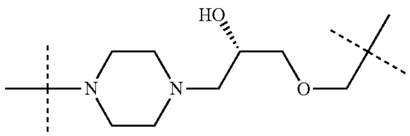
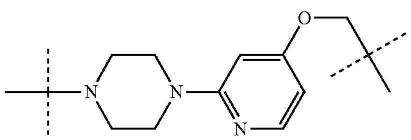
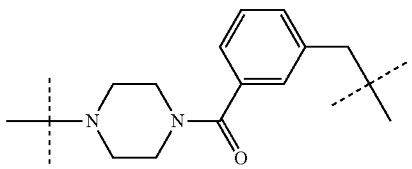

-continued

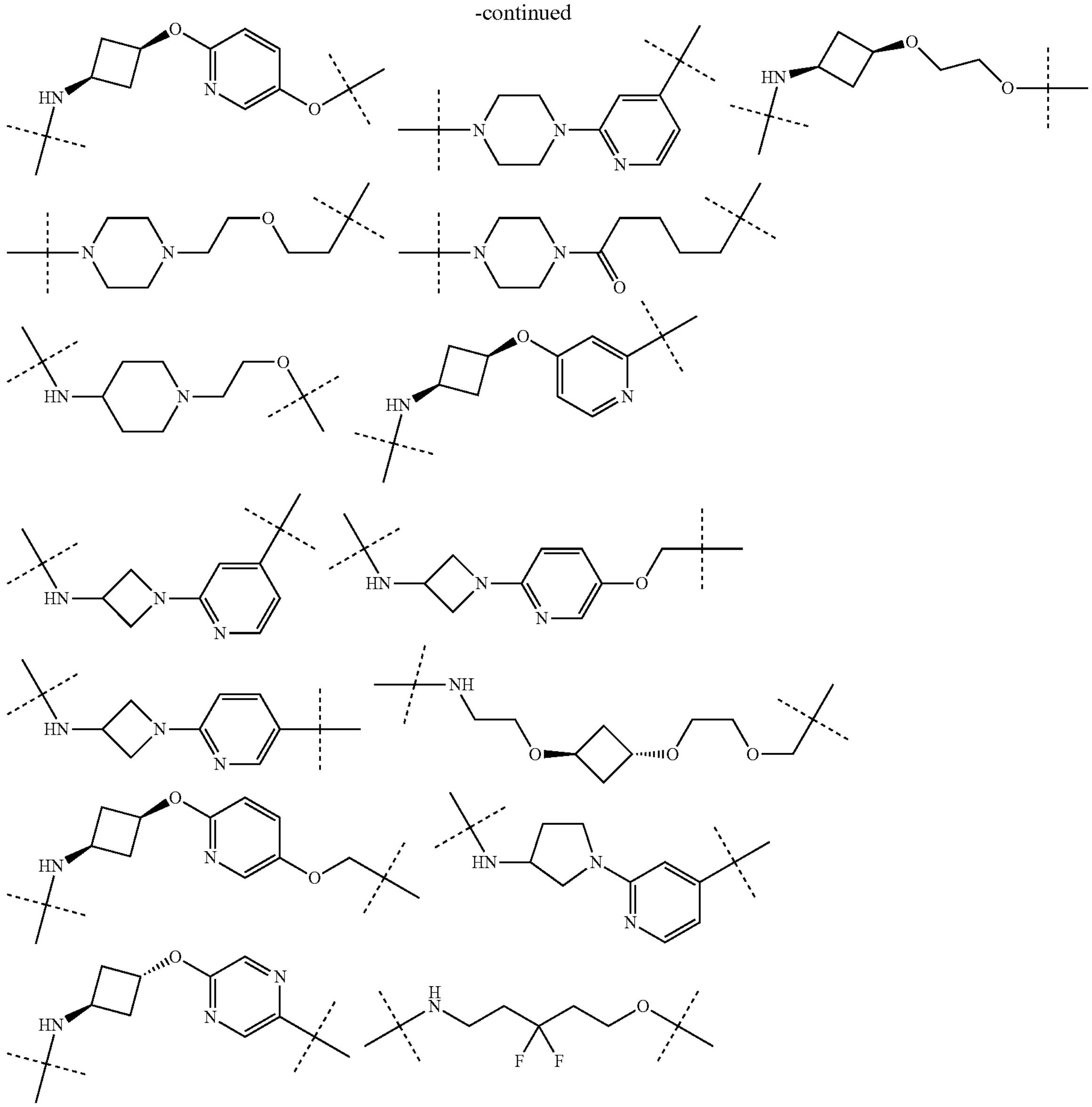

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In another embodiment, the present invention is directed to a compound which comprises a PTM group as described above which binds to a target protein (e.g., BRD4) or polypeptide, which is ubiquitinated by an ubiquitin ligase and is chemically linked directly to the UTM group or through a linker moiety L, or PTM is alternatively a UTM' group which is also an ubiquitin ligase binding moiety, which may be the same or different than the UTM group as described above and is linked directly to the UTM group directly or through the linker moiety; and L is a linker moiety as described above which may be present or absent and which chemically (covalently) links UTM to PTM, or a pharmaceutically acceptable salt, enantiomer, stereoisomer, solvate or polymorph thereof.

In certain embodiments, the UTM shows activity or binds to an E3 ubiquitin ligase with an $IC_{50}$ of less than about 200 μM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 μM, or less than about 100, 50, 10, 1, 0.5, 0.1, 0.05, 0.01, 0.005, 0.001 nM.

Although the UTM group and PTM group may be covalently linked to the linker group through any group which is appropriate and stable to the chemistry of the linker, in preferred aspects of the present invention, the linker is independently covalently bonded to the UTM group and the PTM group preferably through an amide, ester, thioester, keto group, carbamate (urethane), carbon or ether, each of which groups may be inserted anywhere on the UTM group and PTM group to provide maximum binding of the UTM group on the ubiquitin ligase and the PTM group on the target protein to be degraded. (It is noted that in certain aspects where the PTM group is a UTM group, the target protein for degradation may be the ubiquitin ligase itself). In certain preferred aspects, the linker may be linked to an optionally substituted alkyl, alkylene, alkene or alkyne group, an aryl group or a heterocyclic group on the UTM and/or PTM groups.

The present invention may be used to treat a number of disease states and/or conditions, including any disease state and/or condition in which proteins are dysregulated and where a patient would benefit from the degradation of proteins (e.g., BRD4).

In another aspect, the present invention relates to pharmaceutical compositions comprising an effective amount of a compound as set forth hereinabove, in combination with a pharmaceutically acceptable carrier, additive or excipient, and optionally an additional bioactive agent.

In alternative aspects, the present invention relates to a method for treating a disease state by degrading a protein (e.g., BRD4) or polypeptide through which a disease state or condition is modulated comprising administering to said patient or subject an effective amount of at least one compound as described hereinabove, optionally in combination with an additional bioactive agent. The method according to the present invention may be used to treat a large number of disease states or conditions including cancer, by virtue of the administration of effective amounts of at least one compound described herein.

Pharmaceutical compositions comprising combinations of an effective amount of at least one bifunctional compound according to the present invention, and one or more of the compounds otherwise described herein, all in effective amounts, in combination with a pharmaceutically effective amount of a carrier, additive or excipient, represents a further aspect of the present invention.

The present invention includes, where applicable, the compositions comprising the pharmaceutically acceptable salts, in particular, acid or base addition salts of compounds of the present invention. The acids which are used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds of the present invention may, in accordance with the invention, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present invention as sprays, mists, or aerosols for intra-nasal, intra-tracheal or pulmonary administration may also be used. The present invention therefore also is directed to pharmaceutical compositions comprising an effective amount of compound according to the present invention, optionally in combination with a pharmaceutically acceptable carrier, additive or excipient. Compounds according to the present invention may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions of this invention may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain preferred aspects of the invention, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease to be treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the present invention can be treated by administering to the patient (subject) an effective amount of the compound according to the present invention including pharmaceutically acceptable salts, solvates or polymorphs, thereof optionally in a pharmaceutically acceptable carrier or diluent, either alone, or in combination with other known erythropoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain preferred aspects of the invention, one or more compounds according to the present invention are coadministered with another bioactive agent, such as an erythropoietin stimulating agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachidoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Results

Figure 2:
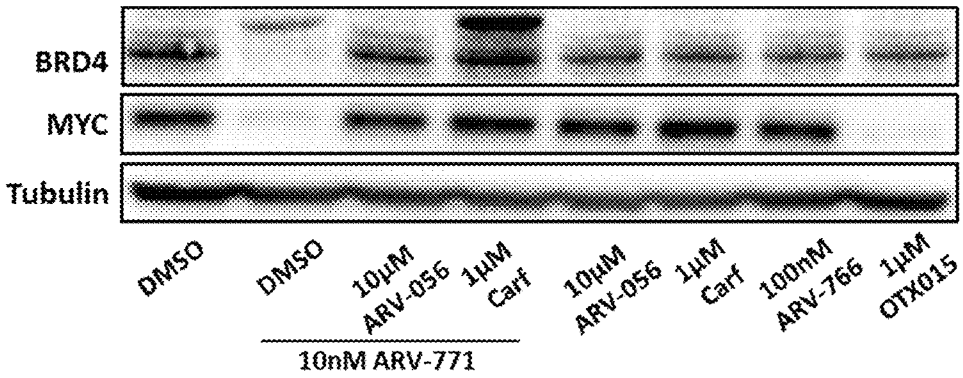
FIG. 2 shows BRD4 degradation mediated by Example 77 (ARV-771) is blocked by a pretreatment with an excess of VHL ligand ARV-056, and by a proteasome inhibitor carfilzomib to demonstrate ubiquitination pathway as the degradation mechanism.
Figure 3:
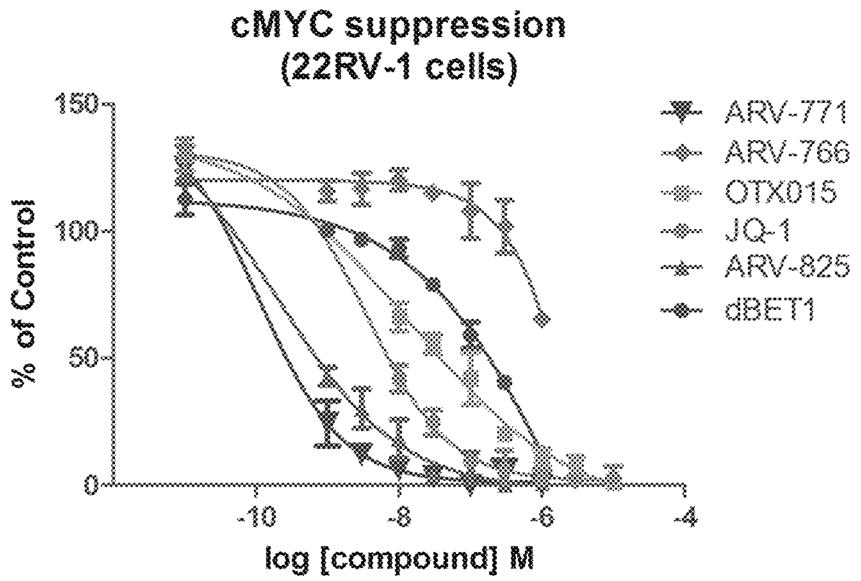
FIG. 3 shows the suppression of cellular c-MYC levels caused by Example 77 (ARV-771) and measured by ELISA. As a comparison, Example 72 (ARV-766), and literature reference compounds ARV-825, dBET1, OTX-015 and JQ1 were also included.
Figure 4:
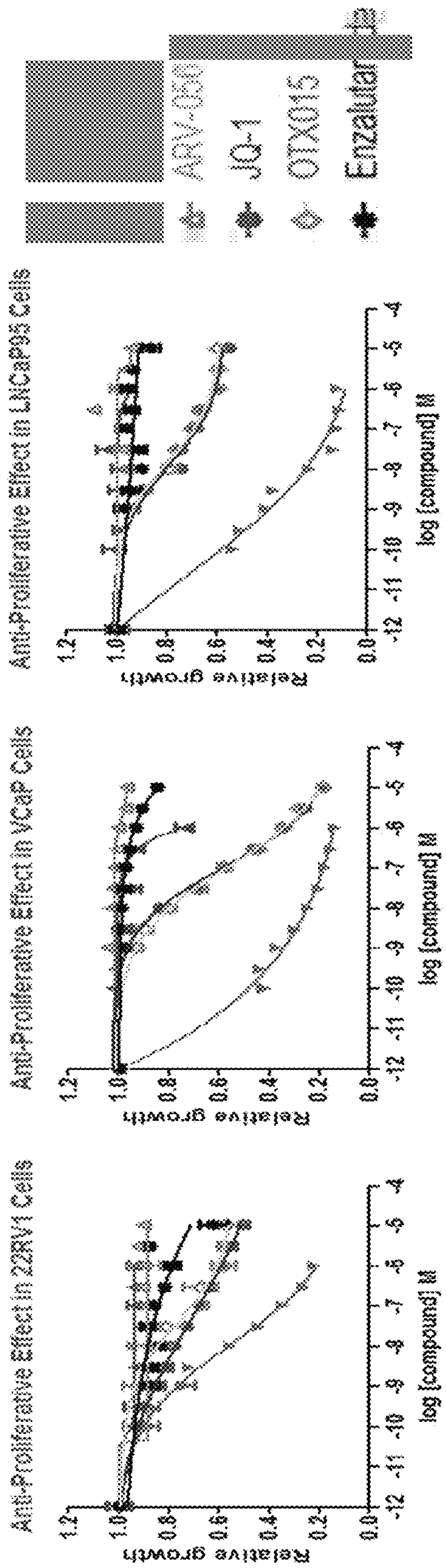
FIG. 4 shows the proliferation inhibition of prostate cancer cell growth by Example 77 (ARV-771). As a comparison, Example 72 (ARV-766), VHL ligand (ARV-056), JQ1, OTX-015 and enzalutamide were also included.
Figure 5:
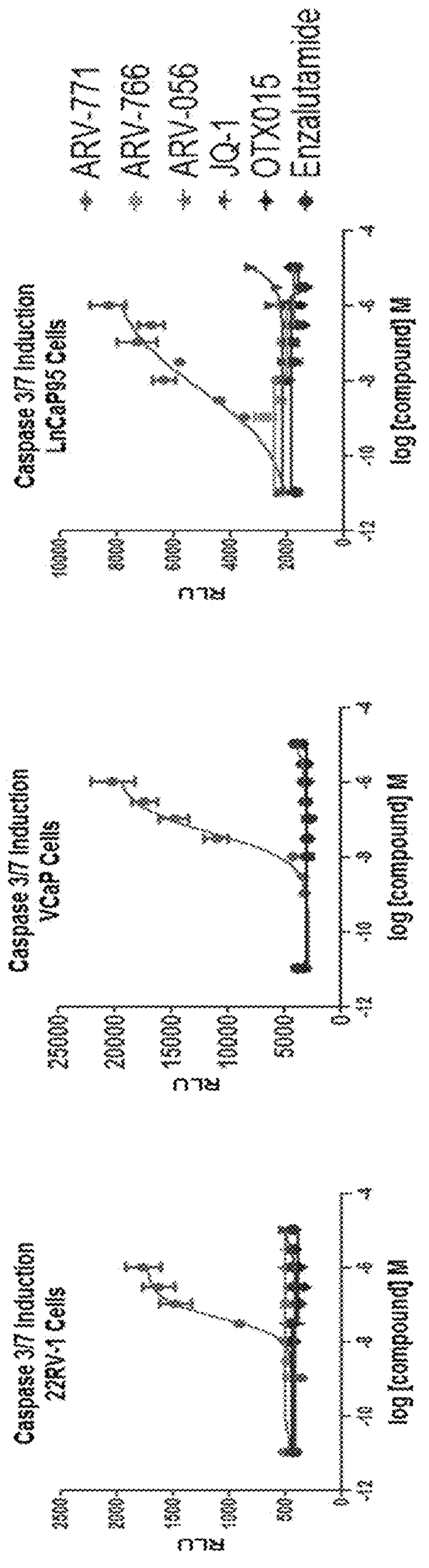
FIG. 5 shows the caspase activation in prostate cancer cell lines caused by Example 77 (ARV-771). As a comparison, Example 72 (ARV-766), VHL ligand (ARV-056), JQ1, OTX-015 and enzalutamide were also included.
Figure 6:
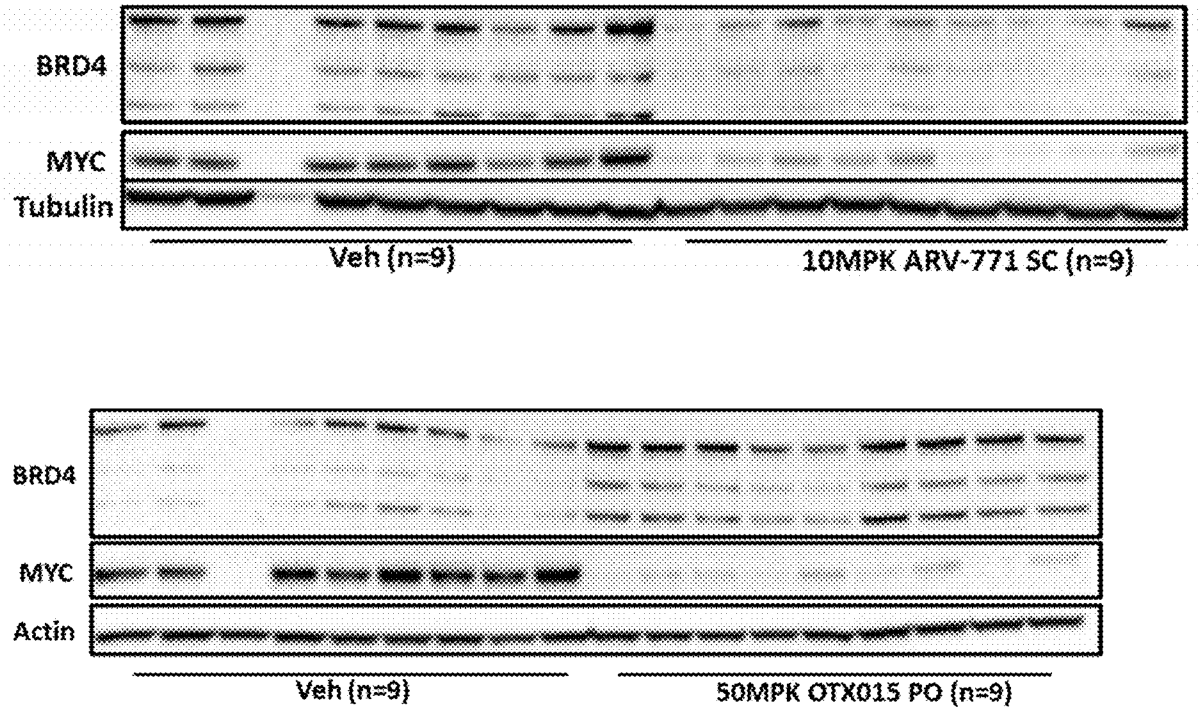
FIG. 6 shows the degradation of BRD4 caused by Example 77(ARV-771) in a 14-day 22RV-1 tumor xenograft study. As a comparison, OTX-015 was also included (50 mg/kg, p.o., qd). Example 77 was dosed subcutaneously to mice at 10 mg/kg (qd) for 2 weeks.
Figure 7:
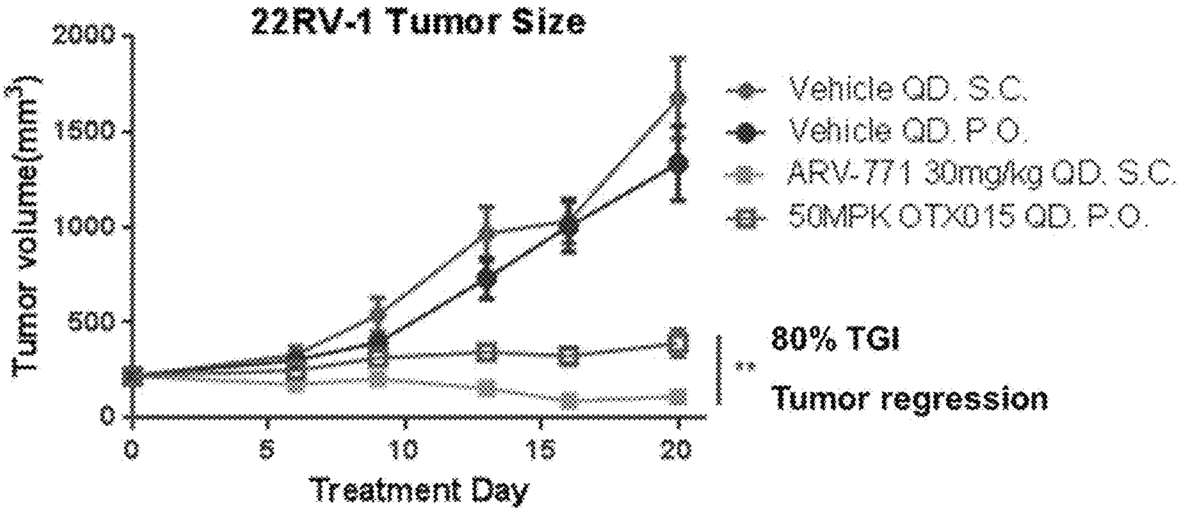
FIG. 7 shows the tumor regression caused by Example 77 (ARV-771) following subcutaneous dosing in a 14 day 22RV-1 mice tumor xenograft model. As a comparison, OTX-015 was also included and demonstrated tumor growth inhibition.
Figure 8:
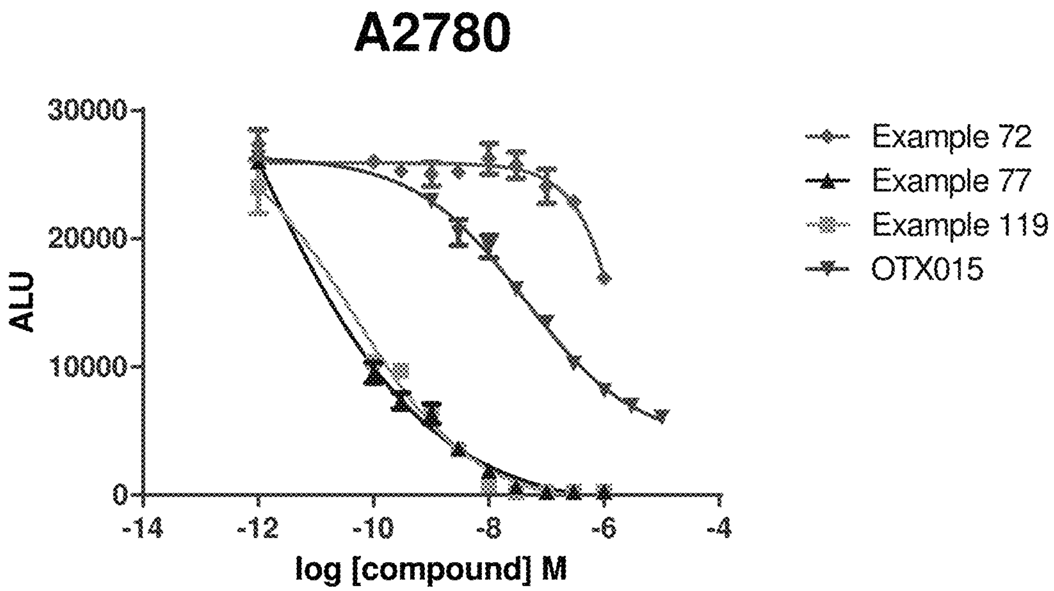
FIG. 8 shows ovarian cancer cell lines A2780 and COV434 treated with the indicated concentrations of compounds for 72 h, cell proliferation was measured using CellTiterGlo (Promega) following manufacturer's protocols.
Figure 8:
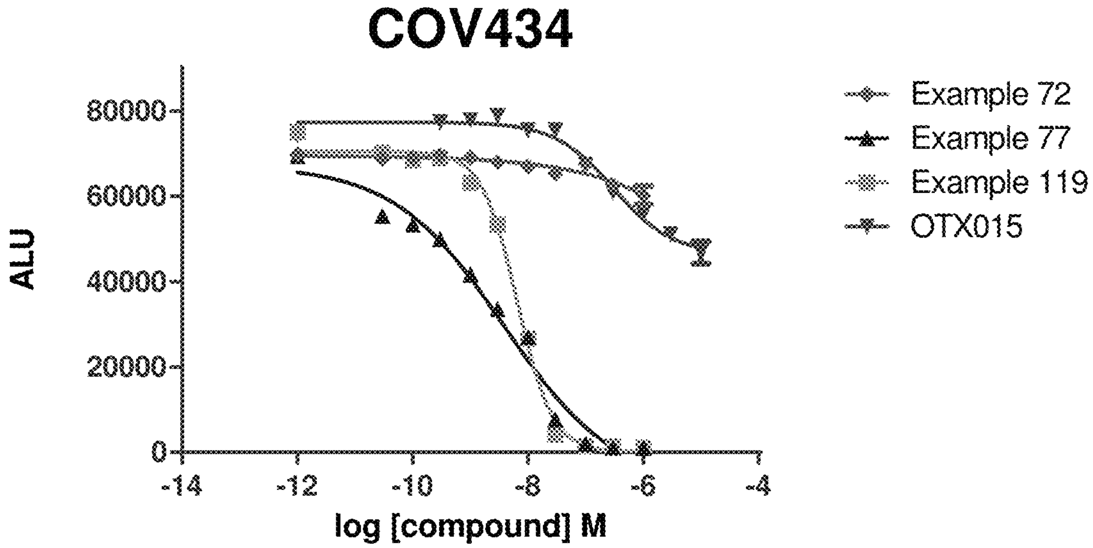
Figure 9:
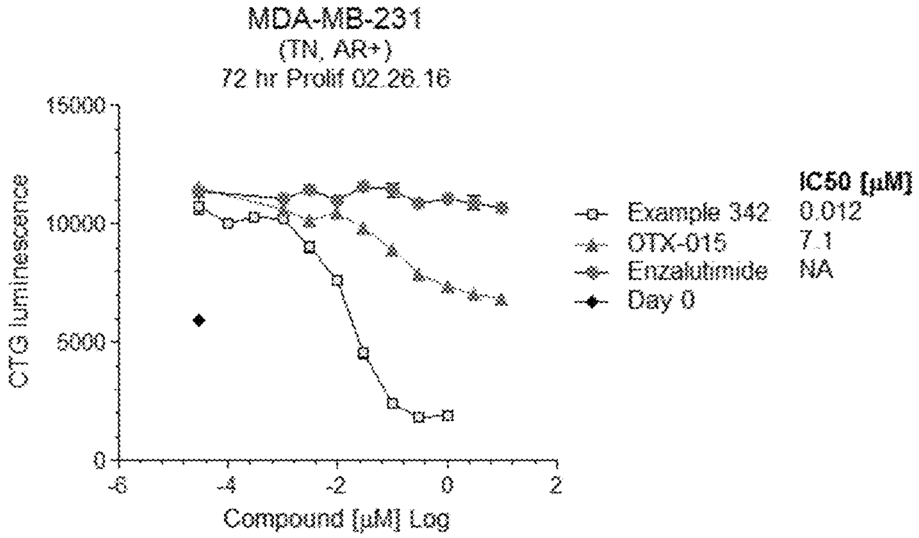
FIG. 9 shows the proliferative behavior of human breast cancer cell lines treated with PROTAC in Example 342 in comparison with small molecules OTX-015 and Enzalutimide. Top Figure: Triple negative, AR+ cell line MDA-MB-231; Bottom Figure: ER+, PR+/−, HER2−, AR+ cell line MCF7.
Figure 9:
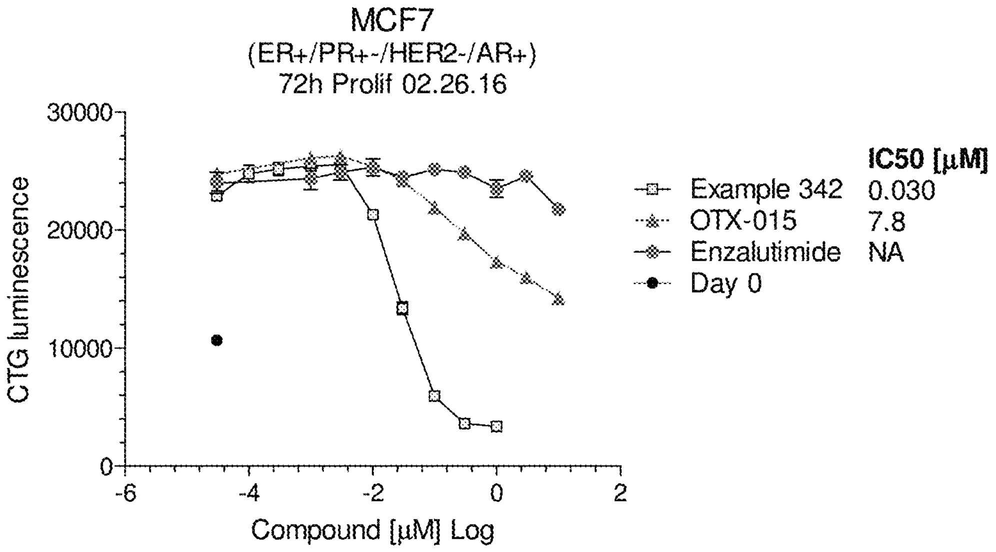
Figure 10:
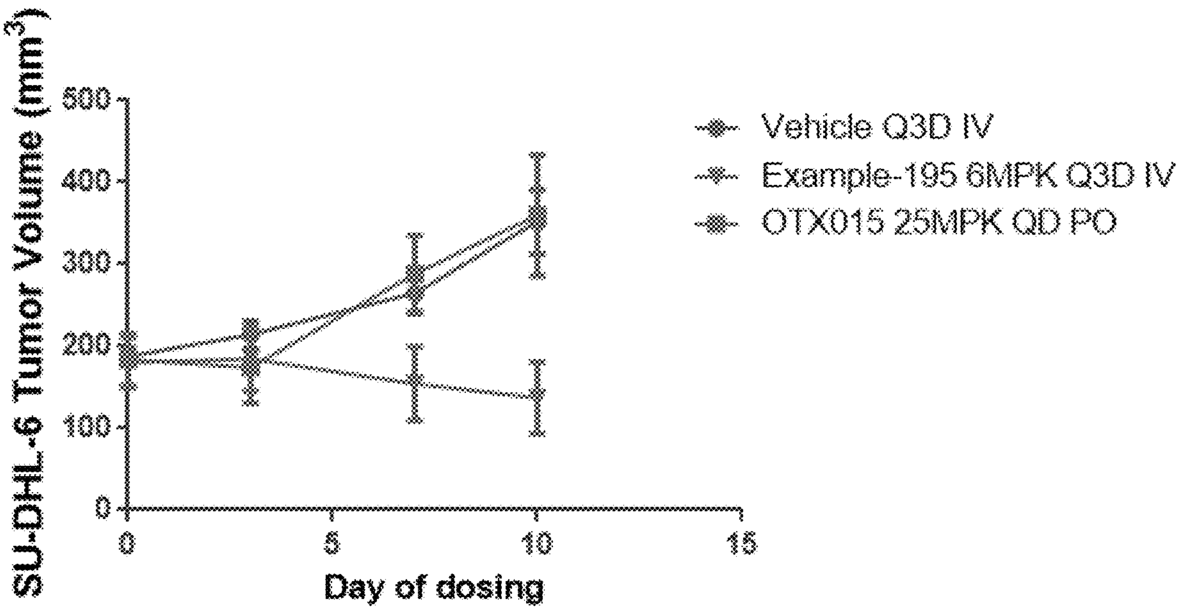
FIG. 10 shows PROTAC in Example 195 inhibited the in vivo growth of SU-DHL-6 xenografts. Results of an efficacy study in SU-DHL-6 tumor xenografts implanted in CB17 SCID mice showing tumor regression with 6MPK Q3D iv dosing. Each treatment cohort contained 10 animals (n=10). Daily po administration of 25MPK OTX015 had no effect of the growth of the SU-DHL-6 xenografts.

The PROTAC compounds of the instant invention are effective in affecting BET degradation, as illustrated in FIGS. 1-2. FIGS. 3,6,7, 8, 9 and 10 illustrate the effectiveness of PROTACs in suppression of cancer. FIGS. 4 and 5 illustrate the potential of the invention for cancer treatment with representative data on prostate cancer. FIGS. 8 and 9 illustrate the potential of the invention for cancer treatment with representative data on ovarian and breast cancers. FIG. 10 illustrate effectiveness of PROTAC in the treatment of diffused large B-cell lymphoma (DLBCL).

General Methods of Chemical Synthesis

The synthesis of the claimed chimeric compounds can be carried out according to the following schemes. Synthetic routes in the schemes are described as one of the methods that can be used to obtain the desired compounds. Other methods can also be used for those skilled in the art of synthesis. The UTM and PTM described in schemes only represent one of many UTMs and PTMs in this application.

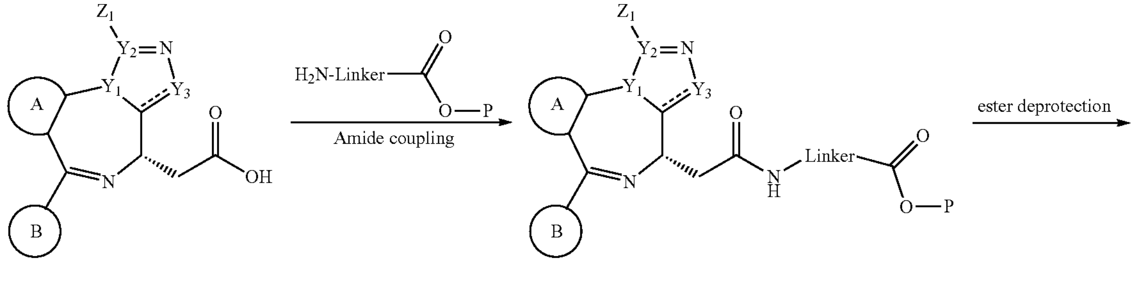

-continued
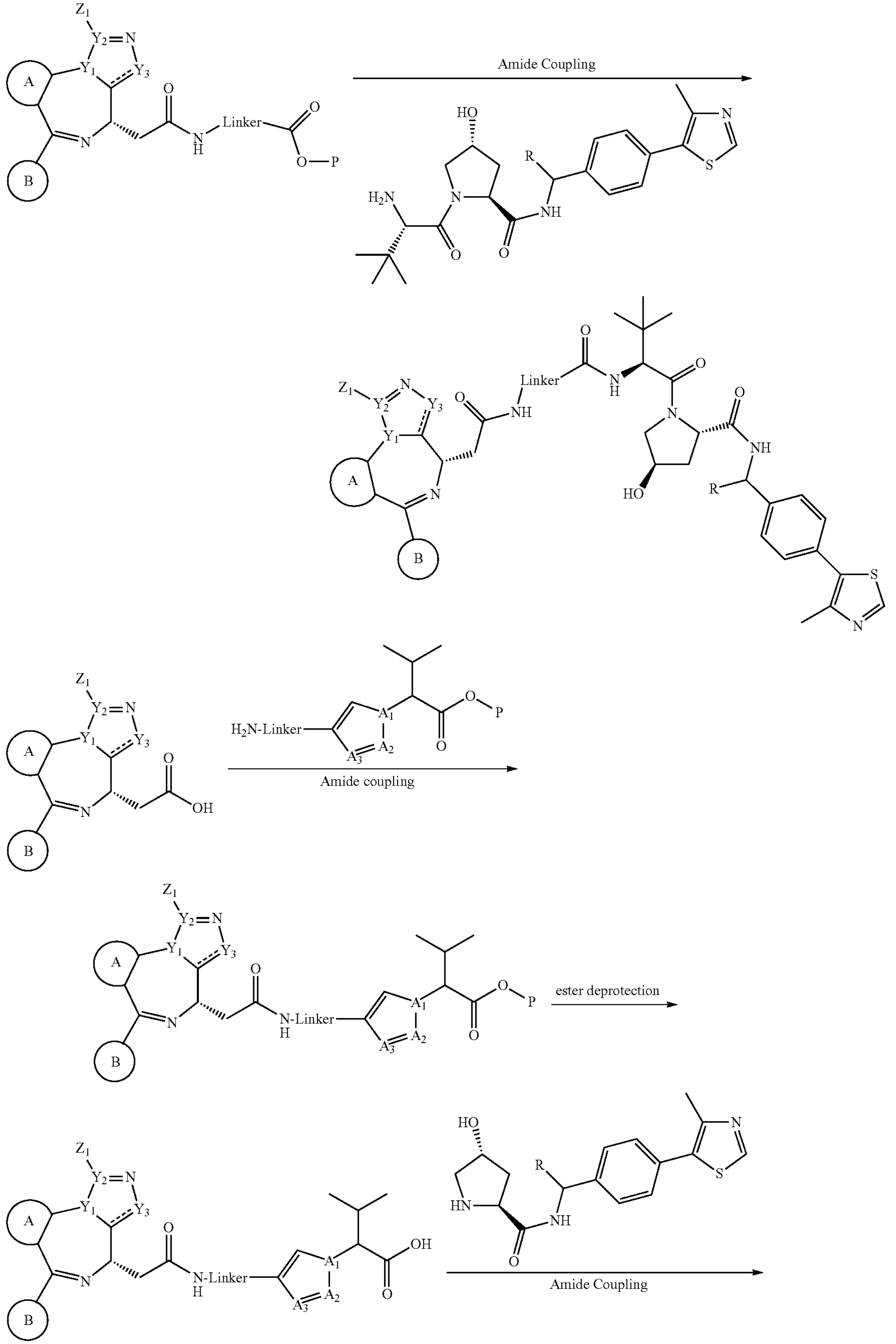

-continued

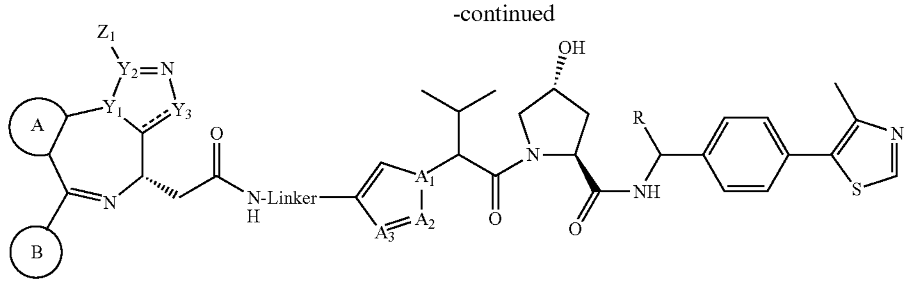

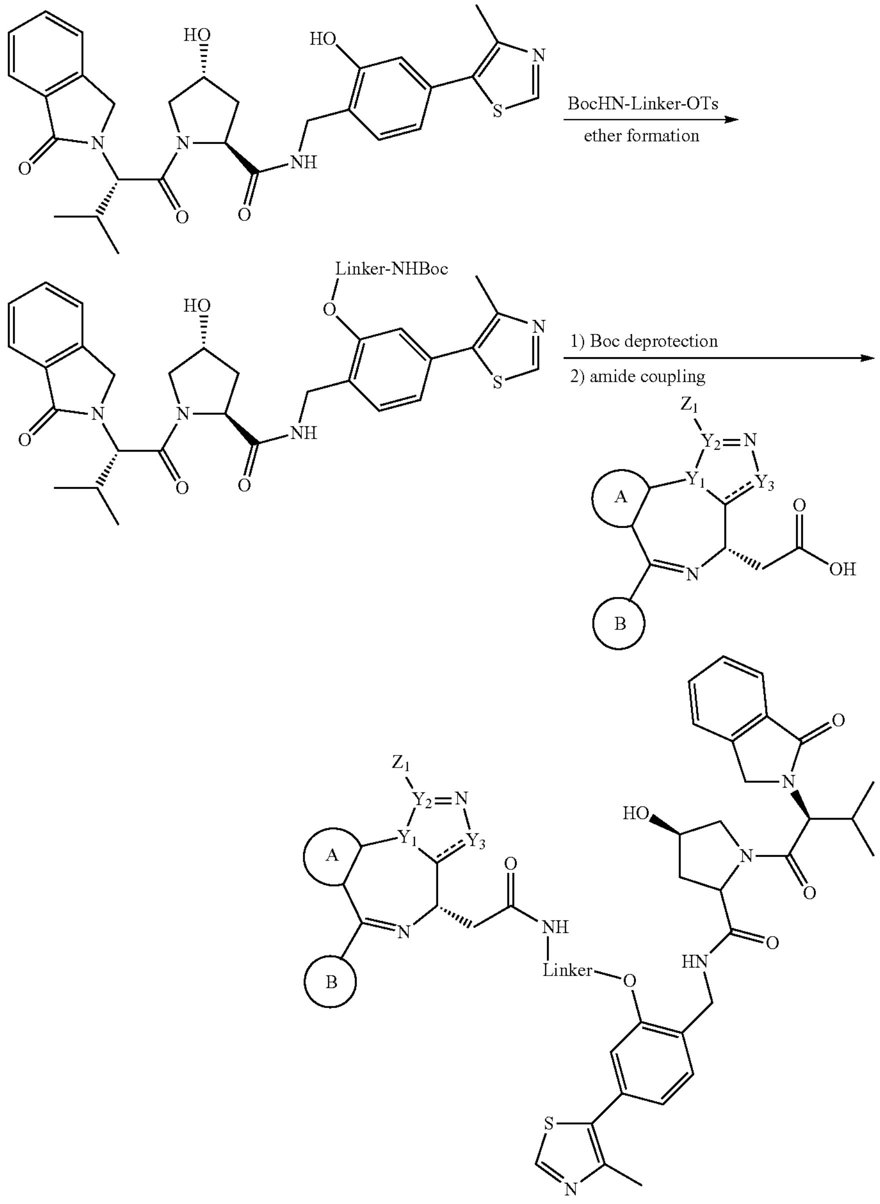

Synthesis of Claimed Compounds

Unless otherwise noted, all materials/reagents were obtained from commercial suppliers and used without further purification. Reactions were monitored by LC-MS and/or thin layer chromatography (TLC) on silica gel 60 F254 (0.2 mm) pre-coated aluminum foil or glass-backed and visualized using UV light.

1HNMR (400 MHz) spectra was recorded on Bruker spectrometers at rt with TMS or the residual solvent peak as the internal standard. The line positions or multiples are given in (δ) and the coupling constants (J) are given as absolute values in Hertz (Hz). The multiplicities in $^1$HNMR spectra are abbreviated as follows: s (singlet), d (doublet), t (triplet), q (quartet), m (multiplet), br or broad (broadened).

Preparative HPLC purifications were performed on Shimadzu LC-6AD. All purification work was completed using Shim-pack PREP-DDS(H)KIT Column. The mobile phases were water (with 0.1% $HCO_2H$) and acetonitrile; all reagents used were of HPLC grade. The flow rate was 10 ml/min.

LC-MS was performed on Shimadzu LCMS-2020 equipped with LC-20AD or 30AD pumps, SPD-M20A PDA and Alltech 3300 ELSD; Mobile Phase A: water (0.1% formic acid); Mobile Phase B: acetonitrile; 5 minute run; Column: Sepax BR-C18 4.6×50 mm, 3 um; Flow Rate: 1.0 mL/min; Oven Temperature: 40° C.; Gradient: 20% B for 0.2 min, increase to 70% B within 1.8 min, 70% B for 2.8 min, back to 20% B within 0.2 min, and 20% B for 2 min.

Preparative TLC was performed on Whatman LK6F Silica Gel 60A size 20×20 cm plates with a thickness of 1000 μm or equivalent.

LC-MS Method for Purity Analysis (Quality Control)

The analysis was conducted on an Acquity UPLC BEH C18 column (50 mm×2.1 mm internal diameter 1.7 μm packing diameter) at 40° C. The solvents employed were: A=0.1% v/v solution of formic acid in water; B=0.1% v/v solution of formic acid in acetonitrile. The gradient employed was as follows:

| Time (minutes) | Flow Rate (mL/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.

Other HPLC Purification Method

The following illustrates the mobile phases and gradients used when compounds underwent purification by mass-directed auto-preparative HPLC.

Mass-Directed Auto-Preparative HPLC (Formic Acid Modifier)

The HPLC analysis was conducted on a Sunfire C18 column (150 mm×30 mm internal diameter, 5 μm packing diameter) at ambient temperature. The solvents employed were:

A=0.1% v/v solution of formic acid in water

B=0.1% v/v solution of formic acid in acetonitrile

Mass-Directed Auto-Preparative HPLC (Trifluoroacetic Acid Modifier)

The HPLC analysis was conducted on a Sunfire C18 column (150 mm×30 mm internal diameter, 5 μm packing diameter) at ambient temperature. The solvents employed were:

A=0.1% v/v solution of trifluoroacetic acid in water

B=0.1% v/v solution of trifluoroacetic acid in acetonitrile

Mass-Directed Auto-Preparative HPLC (Ammonium Bicarbonate Modifier)

The HPLC analysis was conducted on an XBridge C18 column (150 mm×30 mm internal diameter, 5 μm packing diameter) at ambient temperature. The solvents employed were:

A=10 mM ammonium bicarbonate in water adjusted to pH 10 with ammonia solution

B=acetonitrile

For each of the mass-directed auto-preparative purifications, irrespective of the modifier used, the gradient employed was summarized below.

For compounds with an analytical LCMS retention time below 0.6 minutes the following gradient was one of the examples used in HPLC purification:

| Time (minutes) | Flow Rate (mL/min) | % A | % B |
|---|---|---|---|
| 0 | 40 | 99 | 1 |
| 1 | 40 | 99 | 1 |
| 10 | 40 | 70 | 30 |
| 11 | 40 | 1 | 99 |
| 15 | 40 | 1 | 99 |

For compounds with an analytical LCMS retention time between 0.6 and 0.9 minutes the following gradient was one of the examples used in HPLC purification:

| Time (minutes) | Flow Rate (mL/min) | % A | % B |
|---|---|---|---|
| 0 | 40 | 85 | 15 |
| 1 | 40 | 85 | 15 |
| 10 | 40 | 45 | 55 |
| 11 | 40 | 1 | 99 |
| 15 | 40 | 1 | 99 |

For compounds with an analytical LCMS retention time between 0.9 and 1.2 minutes the following gradient one of the examples used in HPLC purification:

| Time (minutes) | Flow Rate (mL/min) | % A | % B |
|---|---|---|---|
| 0 | 40 | 70 | 30 |
| 1 | 40 | 70 | 30 |
| 10 | 40 | 15 | 85 |
| 11 | 40 | 1 | 99 |
| 15 | 40 | 1 | 99 |

For compounds with an analytical LCMS retention time between 1.2 and 1.4 minutes the following gradient one of the examples used in HPLC purification:

| Time (minutes) | Flow Rate (mL/min) | % A | % B |
|---|---|---|---|
| 0 | 40 | 50 | 50 |
| 1 | 40 | 50 | 50 |
| 10 | 40 | 1 | 99 |
| 11 | 40 | 1 | 99 |
| 15 | 40 | 1 | 99 |

For compounds with an analytical LCMS retention time greater than 1.4 minutes or greater than 3.6 minutes, the following gradient one of the examples used in HPLC purification:

| Time (minutes) | Flow Rate (mL/min) | % A | % B |
|---|---|---|---|
| 0 | 40 | 20 | 80 |
| 1 | 40 | 20 | 80 |
| 10 | 40 | 1 | 99 |
| 11 | 40 | 1 | 99 |
| 15 | 40 | 1 | 99 |

The UV detection was an averaged signal from wavelength of 210 nm to 350 nm and mass spectra were recorded on a mass spectrometer using alternate-scan positive and negative mode electrospray ionization.

Abbreviations

ACN: acetonitrile
$Boc_2O$: di-tert-butyl dicarbonate
DCM: dichloromethane.
DIPEA: N,N-diisopropylethylamine
DMA: N,N-dimethylacetamide
DMF: N,N-dimethylformamide
EA: ethyl acetate
HATU: 2-(7-aza-1H-benzotriazole-1-yl)-1,1,3,3-tetramethyluronium hexafluorophosphate
HPLC: high-performance liquid chromatography
LC-MS: liquid chromatography-mass spectrometry
Min: minutes
MTBE: methyl tert-butyl ether
PE: petroleum ether
RT: room temperature
SPB: sodium perborate
tBu: tert-butyl
TBACl: tetra-butyl ammonium chloride
TFA: trifluoroacetic acid
THF: tetrahydrofuran
TLC: thin layer chromatography
TMS: trimethylsilyl
tR: retention rime
TsCl: p-toluene sulfonyl chloride Intermediates of Ubiquitin E3 Ligase Targeting Moiety (UTM) and Protein Targeting Moiety (PTM)

Intermediate 1: (2S, 4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide Hydrochloride (UTM-1)

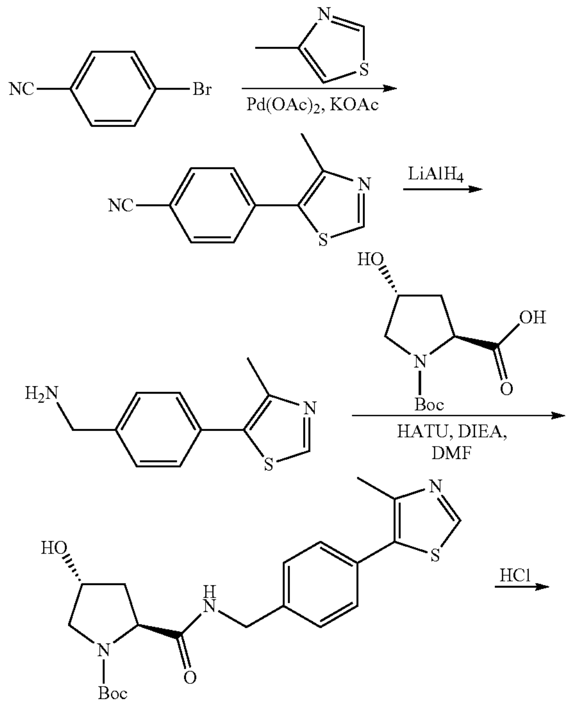

-continued

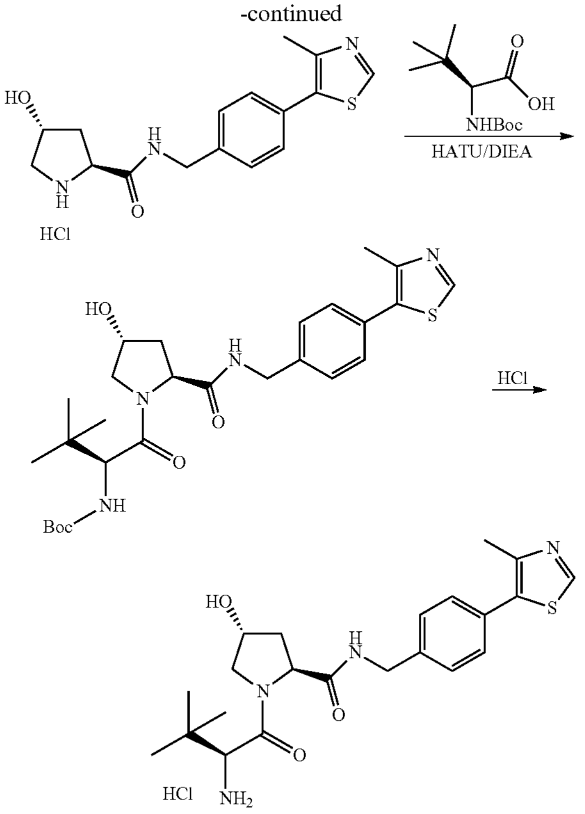

Step 1: Preparation of 4-(4-methyl-1,3-thiazol-5-yl)benzonitrile

To a stirred solution of 4-bromobenzonitrile (20 g, 109.88 mmol) in DMA (250 mL) under a nitrogen atmosphere was added 4-methyl-1,3-thiazole (21.88 g, 220.67 mmol), palladium (II) acetate (743 mg, 3.31 mmol) and potassium acetate (21.66 g, 220.71 mmol) at rt. The resulting mixture was heated to 150° C. and stirred at this temperature for 5 h, at which time LC-MS indicated completion of the reaction. The mixture was cooled to rt, diluted with 1 L of water and extracted with ethyl acetate (300 mL×3). The organic layers were combined, washed with brine (200 mL), dried over anhydrous sodium sulfate and then concentrated under reduced pressure to give a crude residue, which was purified by flash silica gel column chromatography (eluent: ethyl acetate/petroleum ether, v:v=1:5) to give the titled compound (yield: 91%) as a white solid.

Step 2: Preparation of [4-(4-methyl-1,3-thiazol-5-yl)phenyl]methanamine

To a stirred solution of 4-(4-methyl-1,3-thiazol-5-yl)benzonitrile (35 g, 174.77 mmol) in tetrahydrofuran (1000 mL) was added $LiAlH_4$ (20 g, 526.32 mmol) in portions at 0° C. in 10 min under a nitrogen atmosphere. The resulting mixture was then stirred at 60° C. for 3 h, at which time LC-MS indicated completion of reaction. The mixture was cooled to 0° C., then quenched by the addition of water (20 mL, added slowly), aq. solution of NaOH (15%, 20 mL) and water (60 mL). The resulting mixture was then extracted with ethyl acetate (300 mL×2). The organic layers were combined, washed with brine (100 mL), dried over anhydrous sodium sulfate and then concentrated under reduced pressure to give a crude residue, which was purified by flash silica gel column chromatography (eluent: dichloromethane/methanol (v:v=10:1)) to give the titled compound (yield: 56%) as a yellow oil.

Step 3: Preparation of tert-butyl (2S,4R)-4-hydroxy-2-([[4-(4-methyl-1,3-thiazol-5-yl)phenyl]methyl]carbamoyl)pyrrolidine-1-carboxylate To a stirred solution of (2S,4R)-1-[(tert-butoxy)carbonyl]-4-hydroxypyrrolidine-2-carboxylic acid (2.7 g, 11.68 mmol) in N,N-dimethylformamide (20 mL) was added DIPEA (2.52 g, 19.50 mmol), HATU (4.47 g, 11.76 mmol) and [4-(4-methyl-1,3-thiazol-5-yl)phenyl]methanamine (2 g, 9.79 mmol) at rt. The resulting mixture was stirred at rt overnight, at which time LC-MS indicated completion of reaction. The reaction mixture was diluted with 20 mL of water and extracted with ethyl acetate (50 mL×3). The organic layers were combined, washed with brine (50 mL), dried over anhydrous sodium sulfate and then concentrated under reduced pressure to give a crude residue, which was purified by flash silica gel column chromatography (eluent: dichloromethane/methanol (v:v=20:1)) to give the titled compound (yield: 56%) as a yellow solid.

Step 4: Preparation of (2S,4R)-4-hydroxy-N-[[4-(4-methyl-1,3-thiazol-5-yl)phenyl]methyl]pyrrolidine-2-carboxamide Hydrochloride To 1 L round bottom flask containing tert-butyl (2S,4R)-4-hydroxy-2-([[4-(4-methyl-1,3-thiazol-5-yl)phenyl]methyl]carbamoyl)pyrrolidine-1-carboxylate (45 g, 107.78 mmol) in dioxane was added hydrogen chloride in dioxane (4N, 300 mL). The resulting solution was stirred for 2 h at rt. The solids were collected by filtration to give the titled product (yield: 98%) as a yellow solid.

Step 5: Preparation of tert-butyl N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamate To a stirred solution of (2S)-2-{[(tert-butoxy)carbonyl]amino}-3,3-dimethylbutanoic acid (15.7 g, 68.0 mmol) in N,N-dimethylformamide (500 mL) was added DIPEA (29.2 g, 225.9 mmol), HATU (25.9 g, 68.1 mmol) and (2S,4R)-4-hydroxy-N-{[4-(4-methyl-1,3-thiazol-5-yl)-phenyl]methyl}pyrrolidine-2-carboxamide hydrochloride (20.0 g, 56.5 mmol) at rt.

The resulting solution was stirred at rt for 16 h, LC-MS indicated formation of the desired product. The reaction mixture was diluted by water (200 mL) and extracted with ethyl acetate (200 mL×3). The organic layers were combined, washed with saturated aqueous solution of sodium chloride (50 mL×2), dried over anhydrous sodium sulfate and then concentrated under reduced pressure to give a crude residue, which was purified by flash silica gel chromatography (eluent: ethyl acetate/petroleum ether (v:v=2:1)) to give the title compound (yield: 51%) as a yellow solid.

Step 6: Synthesis of (2S, 4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide Hydrochloride (UTM-1)

To a stirred solution of tert-butyl N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamate (12 g, 22.61 mmol) in dioxane (20 mL) was added a solution of hydrogen chloride in dioxane (4N, 80 mL) at rt. The resulting solution was stirred at rt for 2 h, at which time LC-MS indicated completion of reaction. Precipitated solids were collected by filtration to give the titled product (yield: 48%) as a yellow solid.

d: 48%) as a yellow solid.

$^1$HNMR (400 MHz, $CD_3OD$): δ 9.84-9.82 (s, 1H), 7.58-7.54 (m, 4H), 4.71-4.41 (m, 4H), 4.13-4.08 (m, 1H), 3.86-3.71 (m, 2H), 3.36 (s, 1H), 2.60-2.58 (s, 3H), 2.35-2.07 (m, 2H), 1.19-1.12 (m, 9H). LC-MS ($ES^+$): m/z 431.11 [$MH^+$], $t_R$=0.73 min.

Intermediate 2: (2S,4R)-1-[(S)-2-amino-3,3-dimethylbutanoyl]-4-hydroxy-N—[(S)-1-(4-(4-methylthiazol-5-yl)phenyl)ethyl]-pyrrolidine-2-carboxamide Hydrochloride (UTM-2)

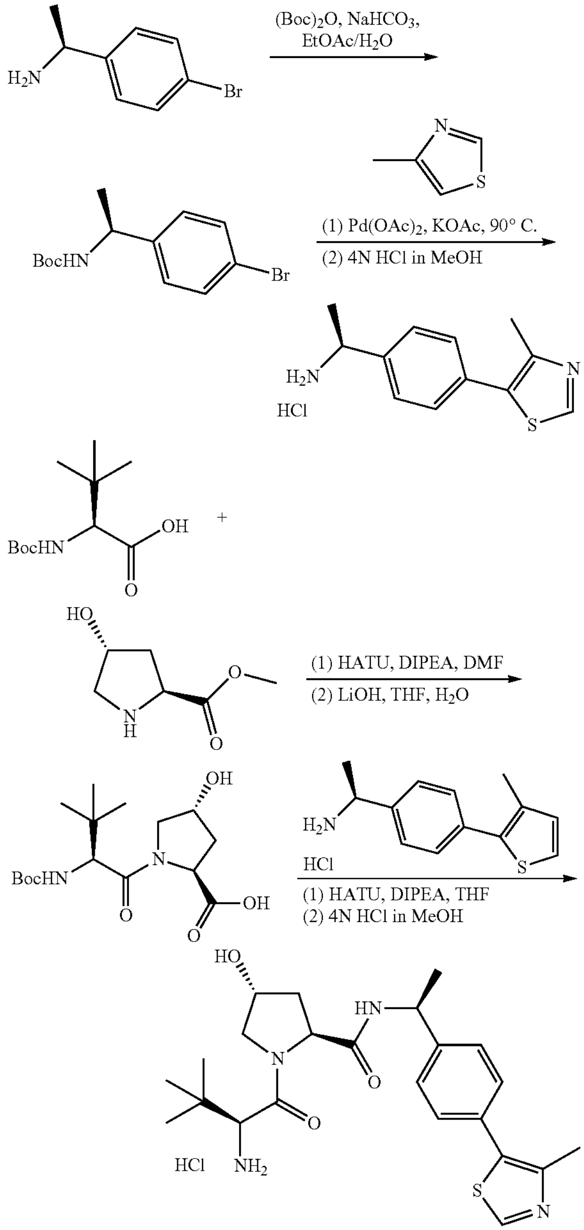

Step 1: Preparation of (S)-tert-butyl-1-(4-bromophenyl)-ethyl Carbamate

To a mixture of (S)-1-(4-bromophenyl)ethanamine (3.98 g, 19.9 mmol) and $NaHCO_3$(1.24 g, 14.8 mmol) in $H_2O$ (10 mL) and ethyl acetate (10 mL) was added $(Boc)_2O$ (5.20 g, 23.8 mmol) at 5° C. The reaction was continued to react for 2 h. TLC showed reaction was complete. The reaction mixture was filtered. The solid was collected and suspended in a mixture of hexane (10 mL) and $H_2O$ (10 mL) for 0.5 h. The mixture was filtered and the solid was collected and dried in oven at 50° C. to afford the title compound as white solid (5.9 g, 98.7%).

$^1$HNMR (400 MHz, DMSO-$d_6$): δ 1.28 (d, J=7.2 Hz, 3H), 1.36 (s, 9H), 4.55-4.60 (m, 1H), 7.25 (d, J=8.4 Hz, 2H), 7.39 (br, 1H), 7.49 (d, J=8.4 Hz, 2H).

Step 2: Preparation of (S)-1-(4-(4-methylthiazol-5-yl)phenyl)ethanamine Hydrochloride A mixture of (S)-tert-butyl-1-(4-bromophenyl)-ethyl carbamate (4.0 g, 13.3 mmol), 4-methylthiazole (2.64 g, 26.6 mmol), palladium (II) acetate (29.6 mg, 0.13 mmol) and potassium acetate (2.61 g, 26.6 mmol) in DMF (10 mL) was stirred at 90° C. under $N_2$ for 18 h. After cooling to ambient temperature, the reaction mixture was filtered. To the filtrate was added $H_2O$ (50 mL) and the resulting mixture was stirred at ambient temperature for 4 h. The reaction mixture was filtered. The solid was collected by filtration and dried in oven at 50° C. to afford (S)-tert-butyl 1-(4-(4-methylthiazol-5-yl)phenyl)ethylcarbamate (3.48 g, 82.3%) as gray solid.

$^1$HNMR (400 MHz, DMSO-$d_6$): δ 1.33 (d, J=7.2 Hz, 3H), 1.38 (s, 9H), 2.46 (s, 3H), 4.64-4.68 (m, 1H), 7.23 (br d, 0.5H), 7.39 (d, J=8 Hz, 2H), 7.44 (d, J=8.4 Hz, 2H), 7.50 (br d, 0.5H), 8.99 (s, 1H); LC-MS $[M+1]^+$: 319.5

This solid material (1.9 g, 6.0 mmol) was dissolved in 4N hydrochloride in methanol (5 mL, 20 mmol, prepared from acetyl chloride and methanol) and the mixture was stirred at ambient temperature for 3 h then concentrated and triturated with ether. The mixture was filtered and the solid was collected and dried in oven at 60° C. to afford (S)-1-(4-(4-methylthiazol-5-yl)phenyl)ethanamine hydrochloride (1.3 g, 85%) as a light green solid.

$^1$HNMR (400 MHz, DMSO-d6): δ 1.56 (d, J=6.8 Hz, 3H), 2.48 (s, 3H), 4.41-4.47 (m, 1H), 7.57 (d, J=8.4 Hz, 2H), 7.67 (d, J=8.4 Hz), 8.75 (s, 3H), 9.17 (s, 1H); LC-MS $[M+1]^+$: 219.2

Step 3: Preparation of (2S, 4R)-1-{(S)-2-[(tert-butoxycarbonyl)amino]-3,3-dimethylbutanoyl}-4-hydroxypyrrolidine-2-carboxylic Acid HATU (2.15 g, 5.7 mmol) was added to a solution of (S)-2-(tert-butoxycarbonyl)amino-3,3-dimethylbutanoic acid (1.25 g, 5.4 mol), (2S,4R)-methyl 4-hydroxypyrrolidine-2-carboxylate hydrochloride (0.98 g, 5.4 mmol) and DIPEA (2.43 g, 18.9 mmol) in DMF (10 mL) at 0° C. under nitrogen. The mixture was stirred at ambient temperature for 18 h. TLC showed the reaction complete. The reaction mixture was quenched with water (30 mL) and extracted with ethyl acetate (15 mL×4). The combined organic layer was washed with the 5% citric acid (10 mL×2), saturated $NaHCO_3$solution (10 mL×2), brine (10 mL×2) and dried over $Na_2SO_4$. The organic solution was filtered and concentrated to afford (2S, 4R)-methyl 1-{(S)-2-[(tert-butoxycarbonyl)amino]-3,3-dimethylbutanoyl}-4-hydroxypyrrolidine-2-carboxylate as pale yellow oil (1.93 g, 100% yield). This crude product (1.93 g) and lithium hydroxide hydrate (2.2 g, 54 mmol) were taken into THF (20 mL) and $H_2O$ (10 mL). The resulting mixture was stirred at ambient temperature for 18 h. THF was removed by concentration. The residue was diluted with ice-water (10 mL) and slowly adjusted to pH 2-3 with 3N HCl. The resulting suspension was filtered, washed with $H_2O$ (6 mL×2). The solid was collected by filtration and dried in oven at 50° C. to afford the title compound as a white solid (1.4 g, 75% for two steps).

$^1$HNMR (400 MHz, DMSO-d6): δ 6.50 (d, J=9.6 Hz, 1H), 5.19 (br s, 1H), 4.32 (br s, 1H), 4.25 (t, J=8.4 Hz, 1H), 4.16 (d, J=9.2 Hz, 1H), 3.57-3.66 (m, 2H), 2.08-2.13 (m, 1H), 1.85-1.91 (m, 1H), 1.38 (s, 9H), 0.94 (s, 9H).

Step 4: Preparation of (2S,4R)-1-[(S)-2-amino-3,3-dimethylbutanoyl]-4-hydroxy-N—[(S)-1-(4-(4-methylthiazol-5-yl)phenyl)ethyl]-pyrrolidine-2-carboxamide Hydrochloride (UTM-2)

HATU (1.6 g, 4.2 mmol) was added to a stirred solution containing (2S, 4R)-1-{(S)-2-[(tert-butoxycarbonyl)amino]-3,3-dimethylbutanoyl}-4-hydroxypyrrolidine-2-carboxylic acid (1.21 g, 3.5 mmol), (S)-1-(4-(4-methylthiazol-5-yl)phenyl)ethanamine hydrochloride (0.9 g, 3.5 mmol), and DIPEA (1.36 g, 10.5 mmol) in anhydrous THF (15 mL) at 0° C. The resulting mixture was allowed to warm up to ambient temperature and continued to stir for 2 h. TLC showed reaction completed. THF was removed by concentration. To the residue was added water (15 mL) and the resulting mixture was stirred for 4 h. The resulting mixture was filtered. The solid was collected and dried in oven at 50° C. to give a white solid. This solid was taken into methanol (10 mL) and activated carbon (150 mg) was added. The resulting mixture was heated at 80° C. and stirred for 1 h. The mixture was filtered while it was hot. Water (5 mL) was added to the filtrate at 80° C. The resulting mixture was cooled to ambient temperature and continued to stir for 18 h. The suspension was filtered. The solid was collected and dried in oven at 50° C. to afford tert-butyl-{(S)-1-[(2S,4R)-4-hydroxy]-2-[(S)-1-(4-(4-methylthiazol-5-yl)phenyl)-ethylcarbamoyl]pyrrolidin-1-yl}-3,3-dimethyl-1-oxobutan-2-yl-carbamate (1.41 g, 74.2%) as a white solid.

$^1$H NMR (400 MHz, $CDCl_3$): δ 1.05 (s, 9H), 1.42 (s, 9H), 1.47 (d, J=7.2 Hz, 3H), 2.04-2.10 (m, 1H), 2.53 (s, 3H), 2.58-2.64 (m, 1H), 3.23 (s, 1H), 3.58 (dd, J=11.2 Hz, 3.2 Hz, 1H), 4.11 (d, J=11.6 Hz, 1H), 4.22 (d, J=9.2 Hz, 1H), 4.51 (br, 1H), 4.79 (t, J=8.0 Hz, 1H), 5.04-5.11 (m, 1H), 5.22 (d, J=8.8 Hz, 1H), 7.36-7.42 (m, 4H), 7.61 (d, J=7.6 Hz 1H), 8.68 (s, 1H).

This solid (1.04 g, 1.9 mmol) was dissolved in 4N hydrogen chloride in methanol (3.0 mL) and the mixture was stirred at ambient temperature for 3 h. TLC showed reaction complete. The reaction mixture was concentrated to remove all volatiles under reduced pressure to give a light yellow solid. The solid was added to TBME (5 mL) and the resulting mixture was stirred at ambient temperature for 4 h. The reaction mixture was filtered and the solid was collected and dried in oven at 50° C. to afford the title compound (0.92 g, 100%).

$^1$H NMR (400 MHz, DMSO-d6): δ 1.03 (s, 9H), 1.38 (d, J=7.2 Hz, 3H), 1.72-1.79 (m, 1H), 2.09-2.14 (m, 1H), 2.49 (s, 3H), 3.48-3.52 (m, 1H), 3.75-3.79 (m, 1H), 3.88-3.90 (m, 1H), 4.31 (br, 1H), 4.56 (t, J=8.4 Hz, 1H), 4.89-4.95 (m, 1H), 7.41 (d, J=8.4 Hz, 2H), 7.47 (d, J=8.4 Hz, 2H), 8.20 (br, 3H), 8.67 (d, J=7.6 Hz, 1H), 9.22 (s, 1H); $^{13}$C NMR (400 MHz, DMSO-d6): δ 170.7, 167.1, 153.0, 146.5, 145.7, 132.5, 129.4, 129.3, 126.9, 69.4, 59.3, 58.5, 56.9, 48.3, 38.4, 34.8, 26.6, 23.0, 15.7; LC-MS $[M+1]^+$: 445.6

Intermediate 3: (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide (UTM-3)

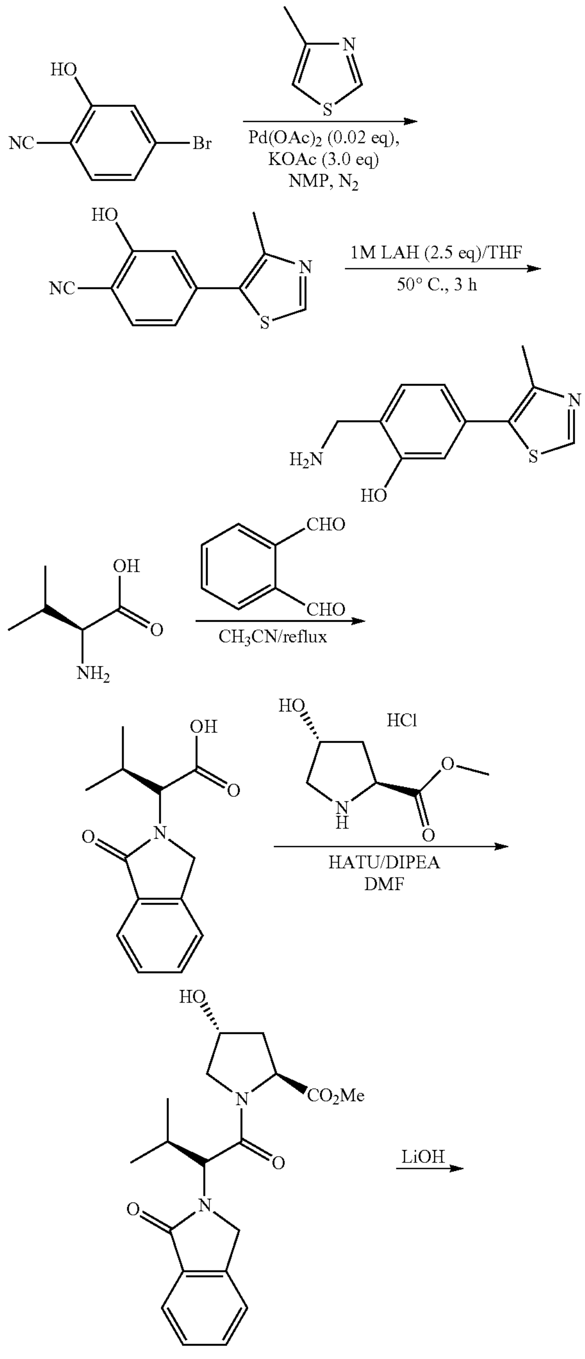

-continued

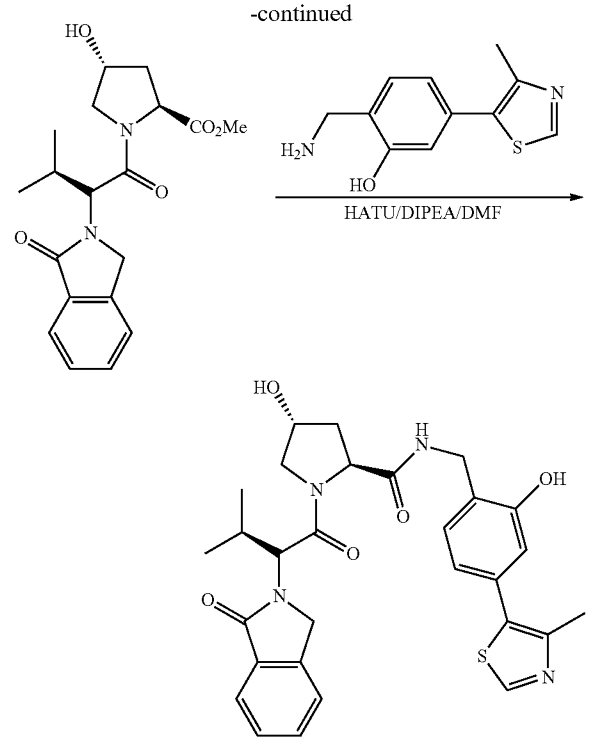

Step 1: Preparation of 2-hydroxy-4-(4-methylthiazol-5-yl) benzonitrile

A mixture of 4-bromo-2-hydroxybenzonitrile (15 g, 76 mmol), 4-methylthiazole (14 mL, 152 mmol), KOAc (14.9 g, 152 mmol) and $Pd(OAc)_2$ (0.34 g, 1.52 mmol) in dry NMP (125 mL) was stirred at 110° C. for 6 hours under nitrogen atmosphere. TLC showed the reaction was complete. The mixture was first cooled to room temperature, then partitioned between EtOAc and water. The combined organic fraction was filtered and the filtrate was washed with water, brine, dried over anhydrous $Na_2SO_4$, and concentrated. The residue was dissolved in toluene (100 mL) and re-evaporated to afford the crude product. The crude product was treated with cold MeOH (80 mL). The resulting precipitate was collected by filtration, washed with MeOH (20 mL), and dried under vacuum to afford the title compound as a light yellow solid (10.5 g, 64%).

LC/MS: 217.2 $[M+1]^+$.

$^1$HNMR (400 MHz, DMSO-d6): δ2.49 (s, 3H), 7.07 (dd, J=8.0, 1.6 Hz, 1H), 7.13 (d, J=1.6 Hz, 1H), 7.70 (d, J=8.0 Hz, 1H), 9.07 (s, 1H), 11.34 (s, 1H).

Step 2: Preparation of 2-(aminomethyl)-5-(4-methylthiazol-5-yl)phenol

To a solution of 2-hydroxy-4-(4-methylthiazol-5-yl)benzonitrile (2.9 g, 13.41 mmol) in dry THF (150 mL), was added $LiAlH_4$ (1.5 g, 40.23 mmol) in portions at 0° C. The resulting mixture was stirred at 50° C. for 3 h under nitrogen atmosphere. TLC showed the reaction was complete. The mixture was cooled in ice-water bath then $Na_2SO_4.10H_2O$ (5 g) was added carefully and stirred at this temperature for 1 h. The mixture was filtered and the filter cake was washed with 10% MeOH in DCM for four times. The combined filtrates were concentrated to afford the crude 2-(aminomethyl)-5-(4-methylthiazol-5-yl)phenol as a light yellow solid (2.0 g, 68%). It was used in next step without further purification.

LCMS: 221.2[M+H]$^+$.

$^1$HNMR (400 MHz, DMSO-d6): δ2.43 (s, 3H), 3.54 (br, 2H), 6.11 (d, J=7.2 Hz, 1H), 6.40 (d, J=11.6 Hz, 1H), 6.83 (d, J=7.6 Hz, 1H), 8.81 (s, 1H).

Step 3: Preparation of (S)-3-methyl-2-(1-oxoisoindolin-2-yl) butanoic Acid

L-Valine (4.37 g, 37.3 mmol) was added to a solution of phthalic dicarboxaldehyde (5.0 g, 37.3 mmol) in acetonitrile (350 mL). The resulting mixture was refluxed for 5 h. The reaction mixture was filtered whilst hot and the filtrate was cooled to room temperature slowly. The resulting precipitate was filtered and dried to afford (S)-3-methyl-2-(1-oxoisoindolin-2-yl)butanoic acid as a white solid (6.45 g, 74%).

$^1$HNMR (400 MHz, DMSO-d6): δ 0.85 (d, J=6.8 Hz, 3H), 1.0 (d, J=6.8 Hz, 3H), 2.25-2.34 (m, 1H), 4.51 (d, J=4.4 Hz, 1H), 4.54 (d, J=3.6 Hz, 1H), 4.64 (d, J=18.0 Hz, 1H), 7.48-7.54 (m, 1H), 7.63 (d, J=3.6 Hz, 2H), 7.72 (d, J=7.6 Hz, 1H), 13.01 (br, 1H).

Step 4: Preparation of (2S,4R)-methyl 4-hydroxy-1-((S)-3-methyl-2-(1-oxoisoindolin-2-yl)butanoyl) pyrrolidine-2-carboxylate To a solution containing 4-hydroxy-L-proline methyl ester hydrochloride (1.0 g, 5.52 mmol), (S)-3-methyl-2-(1-oxoisoindolin-2-yl)butanoic acid (1.16 g, 4.97 mmol), and DIPEA (2.58 g, 20 mmol) in dry DMF (15 mL) was added HATU (3.8 g, 10 mmol) at 0° C. The resulting mixture was stirred at room temperature for 2 h. The mixture was partitioned between EtOAc and water. The organic phase was washed with water, brine and dried over anhydrous $Na_2SO_4$. The residue was purified by silica gel chromatography using 30-50% EtOAc in hexane as eluent to afford the title compound as a light yellow solid (1.21 g, 67.6%).

LCMS: 361.3[M+1]$^+$.

Step 5: Preparation of (2S,4R)-4-hydroxy-1-((S)-3-methyl-2-(1-oxoisoindolin-2-yl)butanoyl)pyrrolidine-2-carboxylic Acid A mixture containing (2S,4R)-methyl 4-hydroxy-1-((S)-3-methyl-2-(1-oxoisoindolin-2-yl)butanoyl)pyrrolidine-2-carboxylate (1.2 g, 3.33 mmol), LiOH.$H_2O$ (559 mg, 13.32 mmol) in THF (20 mL) and $H_2O$ (10 mL) was stirred at room temperature for 2 h. TLC showed the reaction was complete. The reaction mixture was acidified with 1N HCl to pH 1-2, and extracted with EtOAc. The combined organic layer was washed with brine, dried over $Na_2SO_4$ and concentrated to afford the title compound as a light yellow solid (1.05 g, 91% yield).

$^1$HNMR (400 MHz, $CDCl_3$): δ0.91 (d, J=6.4 Hz, 3H), 1.05 (d, J=6.8 Hz, 3H), 2.30 (dd, J=8.4, 2.8 Hz, 2H), 2.44-2.50 (m, 1H), 3.75 (dd, J=11.2, 3.2 Hz, 1H), 4.42 (d, J=17.6 Hz, 1H), 4.50-4.55 (m, 2H), 4.66 (t, J=8.4 Hz, 1H), 4.75 (d, J=17.6 Hz, 1H), 4.83 (d, J=11.2 Hz, 1H), 7.42-7.45 (m, 2H), 7.51-7.56 (m, 1H), 7.78 (d, J=7.6 Hz, 1H).

Step 6: Preparation of (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide To a solution containing (2S,4R)-4-hydroxy-1-((S)-3-methyl-2-(1-oxoisoindolin-2-yl)butanoyl)pyrrolidine-2-carboxylic acid (1.0 g, 2.89 mmol), 2-(aminomethyl)-5-(4-methylthiazol-5-yl)phenol (954 mg, 4.33 mmol), and DIPEA (1.5 g, 11.55 mmol) in DMF (20 mL) was added HATU (2.2 g, 5.77 mmol) at 0° C. The resulting mixture was stirred at room temperature for 1 h. TLC showed the reaction was complete. The mixture was partitioned between EtOAc and water. The organic phase was washed with water, brine and dried over anhydrous $Na_2SO_4$. The residue was purified by silica gel column chromatography using 2-5% MeOH in DCM to afford the title compound as a light yellow solid (650 mg, 43% yield).

LCMS: 549.2[M+H]$^+$ $^1$HNMR (400 MHz, $CDCl_3$): δ0.80 (d, J=6.8 Hz, 3H), 0.88 (d, J=6.8 Hz, 3H), 1.96-2.01 (m, 1H), 2.34-2.40 (m, 1H), 2.47-2.53 (m, 4H), 3.61 (dd, J=11.6, 3.6 Hz, 1H), 4.29-4.37 (m, 2H), 4.38-4.41 (m, 1H), 4.47-4.50 (m, 2H), 4.64-4.69 (m, 2H), 4.72 (s, 1H), 6.90 (dd, J=8.0, 2.0 Hz, 1H), 7.01 (d, J=2.0 Hz, 1H), 7.14 (d, J=8.0 Hz, 1H), 7.39-7.44 (m, 2H), 7.51-7.54 (m, 1H), 7.76 (d, J=7.6 Hz, 1H), 8.03 (t, J=6.4 Hz, 1H), 8.66 (s, 1H), 9.27 (br, 1H).

Intermediate 4: (2R,4S)-1-[(S)-2-amino-3,3-dimethylbutanoyl]-4-hydroxy-N—[(S)-1-(4-(4-methylthiazol-5-yl)phenyl)ethyl]-pyrrolidine-2-carboxamide Hydrochloride (UTM-4)

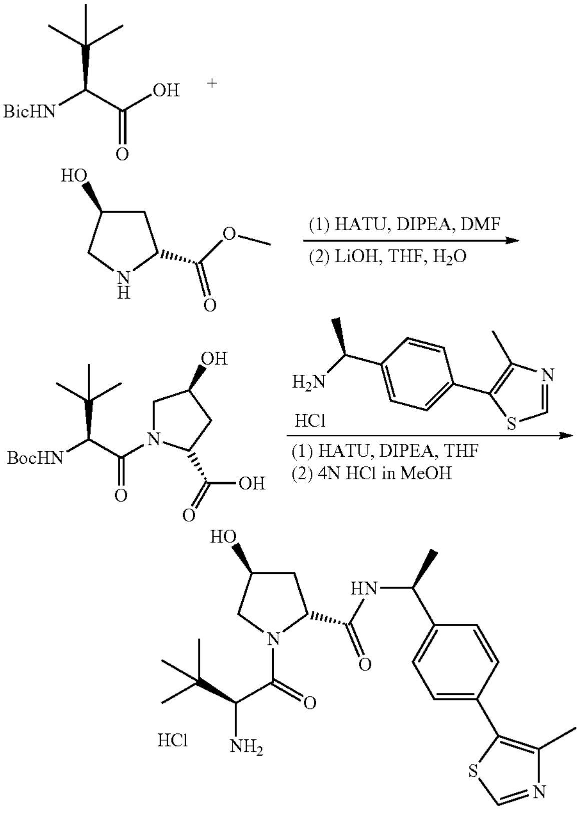

This compound was synthesized using the same method as descried in the preparation of UTM-2 using (2R,4S)-methyl 4-hydroxypyrrolidine-2-carboxylate hydrochloride. $^1$HNMR (400 MHz, $CD_3OD$): δ 1.14 (s, 9H), 1.55 (d, J=6.8 Hz, 3H), 2.00-2.05 (m, 1H), 2.51-2.58 (m, 1H), 2.65 (s, 3H), 3.77-3.81 (m, 1H), 3.88-3.92 (m, 1H), 4.06 (br, 1H), 4.41-

4.46 (m, 1H), 4.56-4.60 (m, 1H), 5.07-5.12 (m, 1H), 7.58 (d, J=8.0 Hz, 2H), 7.67 (d, J=8.0 Hz, 2H), 10.02 (s, 1H). LC-MS $[M+H]^+$: 445.3

Intermediate 5 and Intermediate 6: tert-butyl-N-[(2S)-1-[(2S,4R)-4-hydroxy-2-{[(1R)-2-hydroxy-1-[4-(4-methyl-1,3-thiazol-5-yl)phenyl]ethyl]carbamoyl}pyrrolidin-1-yl]-3,3-dimethyl-1-oxobutan-2-yl]carbamate (UTM-5-A) and tert-butyl N-[(2S)-1-[(2S,4R)-4-hydroxy-2-{[(1S)-2-hydroxy-1-[4-(4-methyl-1,3-thiazol-5-yl)phenyl]ethyl]carbamoyl}pyrrolidin-1-yl]-3,3-dimethyl-1-oxobutan-2-yl]carbamate (UTM-5-B)

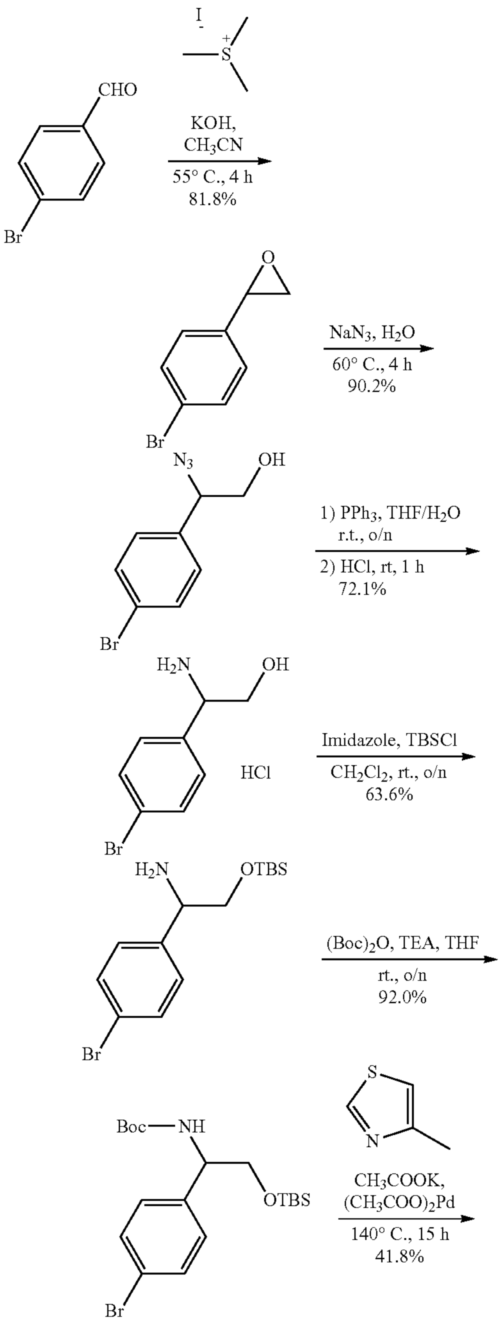

-continued

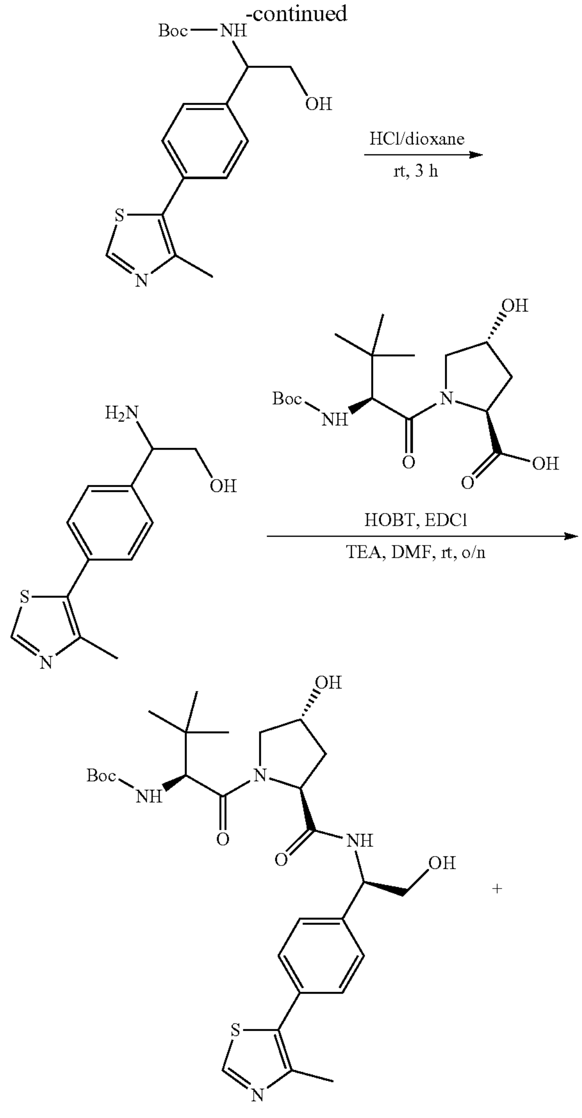

UTM-5-A

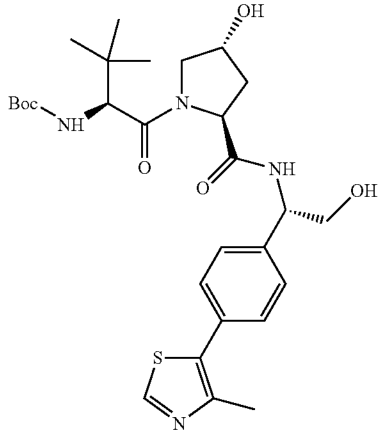

UTM-5-B

Step 1: The synthesis of 2-(4-bromophenyl)oxirane

A mixture of 4-bromobenzaldehyde (2.52 g, 13.6 mmol), trimethylsulfonium iodide (2.87 g, 14.1 mmol), water (0.65 mL, 36.1 mmol) and potassium hydroxide (1.56 g, 27.7 mmol) in acetonitrile (20 mL) was warmed to 55° C. for 4 hours. The resulting solution was partitioned between water and diethyl ether, and the organic layer was washed with water, diluted hydrochloric acid, and brine, and dried over sodium sulfate. Crude product of 2-(4-bromophenyl)oxirane (2.20 g, 81.8% yield) was obtained by removal of organic solvent under reduced pressure, which was used for next reaction without purification.

$^1$H NMR (400 MHz, $CDCl_3$) δ 2.74 (1H, q, J=2.8 Hz), 3.14 (1H, dd, J=4.0 Hz, 5.2 Hz), 3.82 (1H, dd, J=2.4 Hz, 4.0 Hz), 7.15 (2H, d, J=8.4 Hz), 7.47 (2H, d, J=8.8 Hz).

Step 2: The synthesis of 2-azido-2-(4-bromophenyl)ethanol

To a stirred suspension of 2-(4-bromophenyl)oxirane (5.0 g, 25.3 mmol) in distilled water (70 mL) was added the sodium azide (3.28 g, 50.5 mmol), the resulting mixture was stirred at 60° C. for 4 hour and was monitored by TLC. After reaction completion, the mixture was extracted with EtOAc, washed with brine, dried over anhydrous sodium sulfate, filtered, and concentrated in vacuo to give 2-azido-2-(4-bromophenyl)ethanol (5.5 g, 90.2%) as pale yellow oils. The crude product was used for next step directly.

$^1$H NMR (400 MHz, $CDCl_3$) δ 1.94 (1H, s), 3.63-3.66 (2H, m), 4.57 (1H, dd, J=5.2 Hz, 7.6 Hz), 7.15 (2H, d, J=8.4 Hz), 7.46 (2H, d, J=8.4 Hz).

Step 3: The synthesis of 2-amino-2-(4-bromophenyl)ethanol Hydrochloride

To a solution of 2-azido-2-(4-bromophenyl)ethanol (2.0 g, 8.30 mmol) in tetrahydrofuran (20.0 mL) and water (5.00 mL) was added triphenylphosphine (4.35 g, 16.6 mmol). The reaction mixture was stirred at room temperature overnight and the solvent was removed in vacuo. The residue was dissolved in HCl/dioxane (4M, 10.0 mL) and stirred at room temperature for 1 h. After being concentrated, the solid was washed with dichloromethane to give 2-amino-2-(4-bromophenyl)ethanol hydrochloride (1.5 g, 72.1% yield) as white solids.

$^1$H NMR (400 MHz, $CDCl_3$) δ 3.70 (2H, s), 4.28 (1H, s), 5.55 (1H, s), 7.47 (2H, d, J=8.4 Hz), 7.63 (2H, d, J=8.4 Hz), 8.61 (3H, s); LC/MS 216.2 $[M+H]^+$.

Step 4: The synthesis of 1-(4-bromophenyl)-2-(tert-butyldimethylsilyloxy)ethanamine To a solution of 2-amino-2-(4-bromophenyl)ethanol hydrochloride (1.80 g, 7.17 mmol) in dichloromethane (50 mL) was added imidazole (1.95 g, 2.87 mmol) and tert-butyldimethylsilyl chloride (TBSCl) (1.63 g, 10.8 mmol) are room temperature. The reaction mixture was stirred at room temperature overnight and then quenched with water. The aqueous phase was extracted with dichloromethane (30 mL×3), the combined organic phases were dried over anhydrous sodium sulfate, filtered, and concentrated in vacuo to give crude compound. The crude product was purified by silica gel column chromatography (petroether/ethyl acetate=5:1) to give 1-(4-bromophenyl)-2-(tert-butyldimethylsilyloxy)ethanamine (1.50 g, 63.6%) as white solids.

LC/MS: 330.1 $[M+H]^+$;

Step 5: The synthesis of tert-butyl 1-(4-bromophenyl)-2-(tert-butyldimethylsilyloxy)ethylcarbamate To a solution of 1-(4-bromophenyl)-2-(tert-butyldimethylsilyloxy)ethanamine (1.50 g, 4.56 mmol) in tetrahydrofuran (20 mL) was added triethylamine (0.69 g, 6.84 mmol) and di-tert-butyl dicarbonate (1.49 g, 6.84 mmol). The reaction mixture was stirred at room temperature overnight and then quenched with water. The aqueous phase was extracted with ethyl acetate (50 mL×3) and washed with brine. The combined organic phases were dried over anhydrous sodium sulfate, filtered, and concentrated in vacuo to give crude compound. The crude product was purified by silica gel column chromatography (petroether/ethyl acetate=100:1) to give tert-butyl 1-(4-bromophenyl)-2-(tert-butyldimethylsilyloxy)ethylcarbamate (1.80 g, 92.0%) as pale yellow oils.

$^1$H NMR (400 MHz, $CDCl_3$) δ 0.01 (6H, d, J=9.6 Hz), 0.86 (9H, s), 1.42 (9H, s), 3.65-3.70 (2H, m), 4.60-4.63 (1H, m), 7.34 (2H, d, J=8.0 Hz), 7.39 (1H, d, J=8.8 Hz), 7.56 (2H, d, J=8.4 Hz).

Step 6: The synthesis of tert-butyl 2-hydroxy-1-(4-(4-methylthiazol-5-yl)phenyl)-ethylcarbamate A mixture of tert-butyl 1-(4-bromophenyl)-2-(tert-butyldimethylsilyloxy)ethylcarbamate (4.0 g, 9.32 mmol), 4-methylthiazole (1.85 g, 18.6 mmol), potassium acetate (1.82 g, 18.6 mmol), palladium (II) acetate (0.11 g, 0.47 mmol) were dissolved in dimethylacetamide and stirred under argon. The mixture was heated to 140° C. and stirred for 15 hours, then diluted with water. The aqueous phase was extracted with ethyl acetate (50 mL×3) and washed with brine. The combined organic layer was dried over sodium sulfate, filtered and concentrated under vacuum to give crude compound which was purified by silica gel column chromatography (petroether/ethyl acetate=100:1) to give tert-butyl 2-hydroxy-1-(4-(4-methylthiazol-5-yl)phenyl) ethylcarbamate (1.30 g, 41.8%) as pale yellow solids.

$^1$H NMR (400 MHz, $CDCl_3$) δ 1.38 (9H, s), 2.46 (3H, s), 3.52 (2H, t, J=6.0 Hz), 4.55-4.58 (1H, m), 4.84 (1H, t, J=6.0 Hz), 7.30 (1H, d, J=8.0 Hz), 7.38-7.45 (4H, m), 8.99 (1H, s); LC/MS 335.2 $[M+H]^+$; Rt=1.859 min Step 7: The synthesis of 2-amino-2-(4-(4-methylthiazol-5-yl)phenyl)ethanol Hydrochloride The tert-butyl 2-hydroxy-1-(4-(4-methylthiazol-5-yl)phenyl)ethylcarbamate (300 mg, 0.536 mmol) was dissolved in hydrochloric acid/dioxane (5 mL, 4M). The resulting reaction mixture was stirred at room temperature for 3 h. The solvent was concentrated in vacuo to give 2-amino-2-(4-(4-methylthiazol-5-yl)phenyl)ethanol hydrochloride as white solids, which was used for the next step without further purification.

Step 8: The synthesis of tert-butyl N-[(2S)-1-[(2S,4R)-4-hydroxy-2-{[(1R)-2-hydroxy-1-[4-(4-methyl-1,3-thiazol-5-yl)phenyl]ethyl]carbamoyl}pyrrolidin-1-yl]-3,3-dimethyl-1-oxobutan-2-yl]carbamate (UTM-5-A) and tert-butyl N-[(2S)-1-[(2S,4R)-4-hydroxy-2-{[(1S)-2-hydroxy-1-[4-(4-methyl-1,3-thiazol-5-yl)phenyl]ethyl]carbamoyl}pyrrolidin-1-yl]-3,3-dimethyl-1-oxobutan-2-yl]carbamate (UTM-5-B)

A solution of 2-amino-2-(4-(4-methylthiazol-5-yl)phenyl) ethanol hydrochloride (1000 mg, 3.70 mmol), N-(3-dimethylaminopropyl)-N'-ethylcarbodiimide hydrochloride (EDCI) (995 mg, 5.19 mmol), 1-hydroxybenzotriazole (HOBT) (695 mg, 5.19 mmol), (2S,4R)-1-((S)-2-(tert-butoxycarbonylamino)-3,3-dimethylbutanoyl)-4-hydroxypyrrolidine-2-carboxylic acid (1273 mg, 3.70 mmol) and triethylamine (747 mg, 7.40 mmol) in N,N-dimethylformamide (50 mL) was stirred at room temperature overnight under agron, and then water (80 mL) was added to the mixture. The aqueous layer was extracted with ethyl acetate (50 mL×5). The combined organic layer was washed with brine (50 mL×3), dried over anhydrous sodium sulfate, and concentrated in vacuo. The crude product was purified by preparative TLC (dichloromethyl/methanol=15:1) to give tert-butyl (S)-1-((2S,4R)-4-hydroxy-2-((R)-2-hydroxy-1-(4-(4-methylthiazol-5-yl)phenyl) ethylcarbamoyl)pyrrolidin-1-yl)-3,3-dimethyl-1-oxobutan-2-ylcarbamate (700 mg) as pale yellow oils and tert-butyl (S)-1-((2S,4R)-4-hydroxy-2-((S)-2-hydroxy-1-(4-(4-methylthiazol-5-yl)phenyl) ethyl carbamoyl)pyrrolidin-1-yl)-3,3-dimethyl-1-oxobutan-2-ylcarbamate (500 mg) as pale yellow oils.

UTM-5-A:

$^1$H NMR (400 MHz, $CDCl_3$) δ 0.93 (9H, s), 1.39 (9H, s), 1.77-1.83 (1H, m), 2.01-2.06 (1H, m), 2.46 (3H, s), 3.54-3.60 (4H, m), 4.13-4.19 (1H, m), 4.29-4.36 (1H, m), 4.50 (1H, t, J=8.0 Hz), 4.78 (1H, t, J=5.6 Hz), 4.81-4.88 (1H, m), 5.12-5.16 (1H, m), 6.46 (1H, d, J=9.2 Hz), 7.36-7.46 (4H, m), 8.41 (1H, d, J=8.0 Hz), 8.99 (1H, s); LC/MS 561.2 $[M+H]^+$; Rt=1.897 min

UTM-5-B:

$^1$H NMR (400 MHz, $CDCl_3$) δ 0.87 (9H, s), 1.38 (9H, s), 1.92-2.06 (2H, m), 2.45 (3H, s), 3.56-3.69 (4H, m), 4.06-4.14 (1H, m), 4.36 (1H, s), 4.56 (1H, t, J=7.6 Hz), 4.76-4.81 (1H, m), 4.87 (1H, t, J=5.6 Hz), 5.146 (1H, d, J=2.8 Hz), 6.47 (1H, d, J=8.8 Hz), 7.37 (2H, d, J=8.0 Hz), 7.51 (2H, d, J=8.0 Hz), 8.37 (1H, d, J=7.6 Hz), 8.98 (1H, s); LC/MS 561.2 $[M+H]^+$; Rt=1.887 min Intermediate 7: (2S,4R)—N-[(4-chloro-2-hydroxyphenyl)methyl]-4-hydroxy-1-[3-methyl-2-(3-methyl-1,2-oxazol-5-yl)butanoyl]pyrrolidine-2-carboxamide (UTM-6)

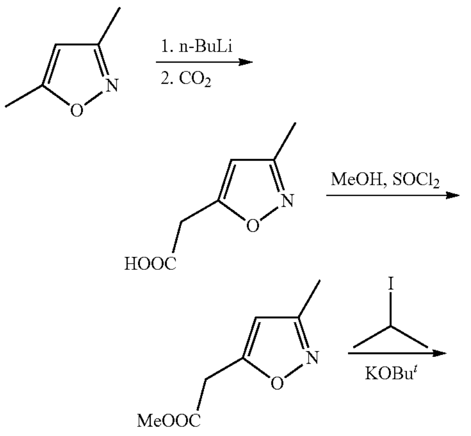

-continued

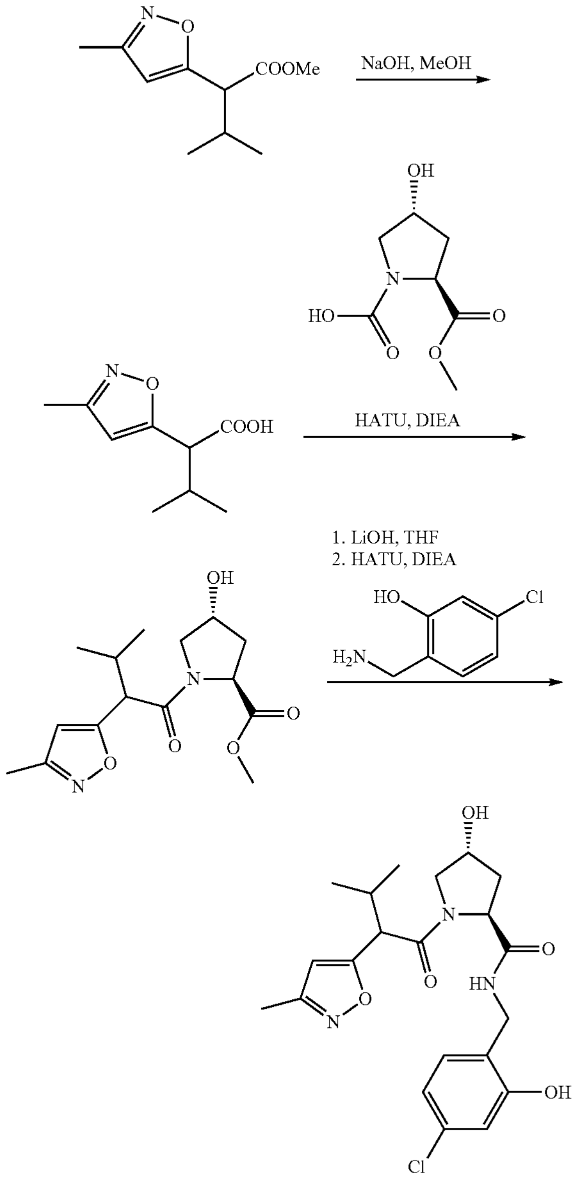

UTM-6

This key intermediate was prepared using the synthetic route above. The required 3-methylisoxazole-5-acetic acid was prepared according to the literature (J. Org. Chem. 66, 6595-6603, 2001). The alkylation with 2-iodopropane was described in Example 311. The desired UTM-6 was prepared using the same synthetic method as described in the preparation of intermediate UTM-3.

$^1$H NMR (400 MHz, $CDCl_3$): δ 9.33 (s, 0.5H), 9.20 (s, 0.5H), 8.07 (t, J=6.4 Hz, 0.5H), 7.83 (t, J=6.0 Hz, 0.5H), 6.99 (dd, J=2.4, 8.0 Hz, 1H), 6.89-6.90 (m, 1H), 6.76-6.78 (m, 1H), 6.02 (s, 0.5H), 5.99 (s, 0.5H), 5.80-5.83 (m, 0.5H), 4.35 (q, J=6.4 Hz, 1.5), 4.16-4.25 (m, 2H), 3.72-3.76 (m, 0.5H), 3.61 (d, J=9.2 Hz, 1.0H), 3.51-3.55 (m, 1.5H), 2.30-2.46 (m, 2.5H), 2.26 (s, 1.5H), 2.24 (s, 1.5H), 1.95-2.05 (m, 1H), 1.01 (d, J=6.8 Hz, 1.5H), 0.82-0.87 (m, 4.5H); LC-MS 436.1 $[M+1]^+$; Rt=3.57 min.

Intermediate 8: 2-[(9S)-7-(4-chlorophenyl)-4,5,13-trimethyl-3-thia-1,8,11,12-tetraazatricyclo[$8.3.0.0^{2},^{6}$]trideca-2(6),4,7,10,12-pentaen-9-yl]acetic Acid (PTM-1)

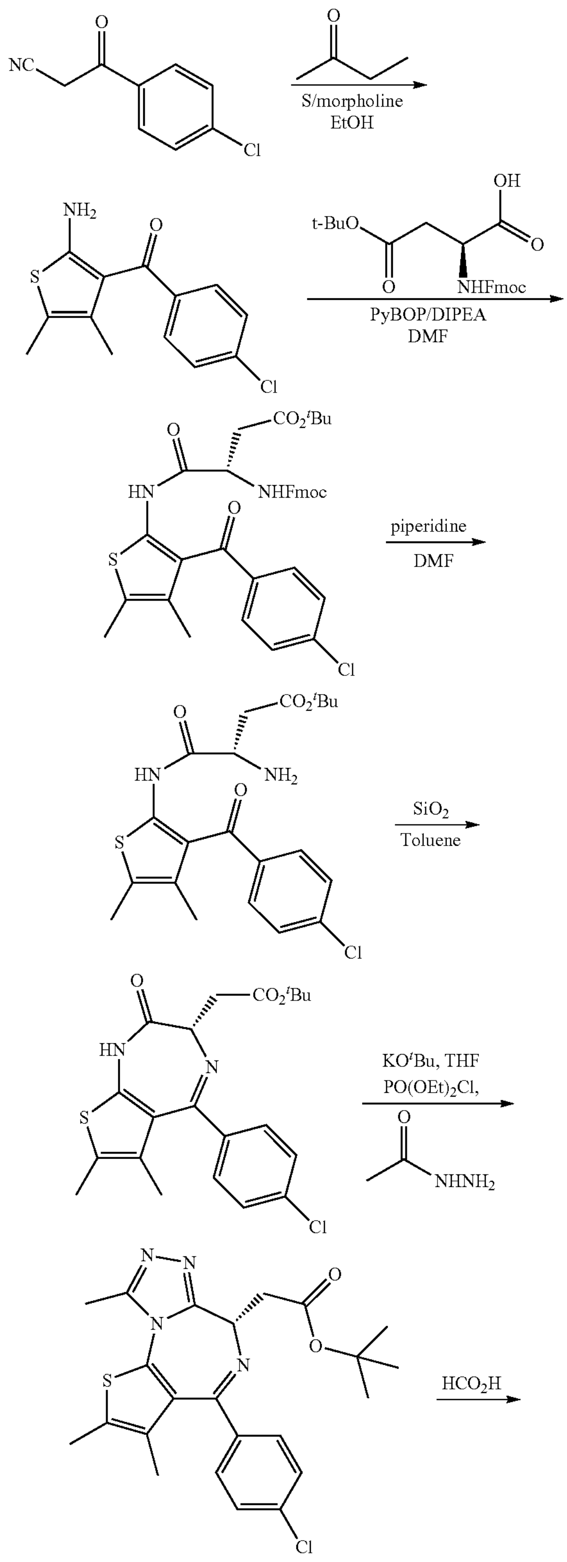

-continued

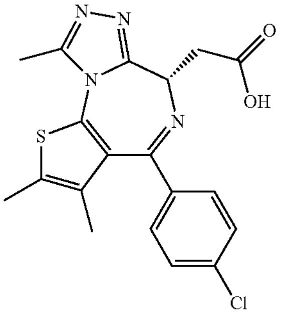

PTM-1

This chiral triazole-fused thiphenodiazepine acetic acid was prepared according to the literature using the synthetic scheme above (Nature 468, 1067-1073, 2010; PNAS 113, 7124-7129, 2016).

$^1$HNMR (400 MHz, DMSO_d6): δ 1.63 (s, 3H), 2.42 (s, 3H), 2.60 (s, 3H), 3.31-3.41 (m, 2H), 4.45 (t, J=7.2 Hz, 1H), 7.45-7.49 (m, 4H); LC/MS 401.1 $[M+1]^+$.

Intermediate 9: 2-[(9S)-7-(4-hydroxyphenyl)-4,5,13-trimethyl-3-thia-1,8,11,12-tetraazatricyclo[$8.3.0.0^{2},^{6}$]trideca-2(6),4,7,10,12-pentaen-9-yl]-N-phenylacetamide (PTM-1-A)

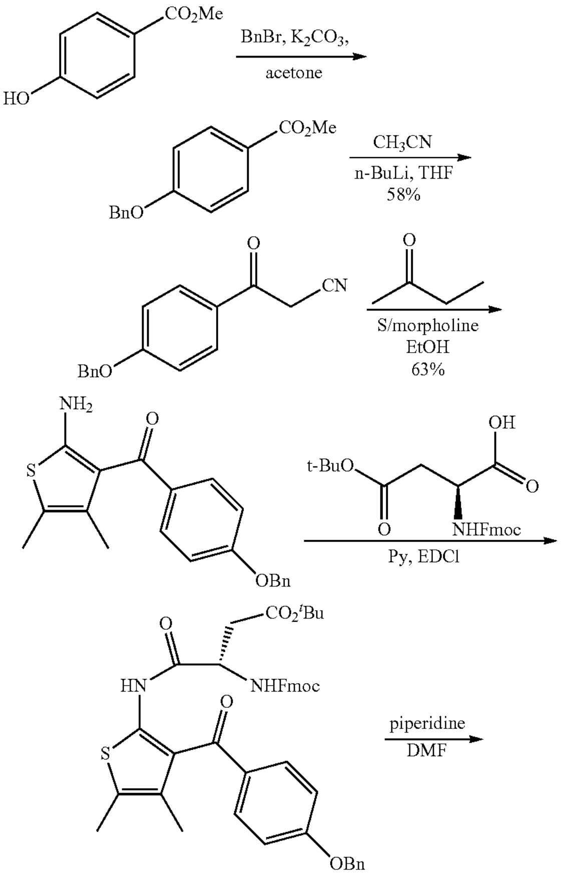

-continued
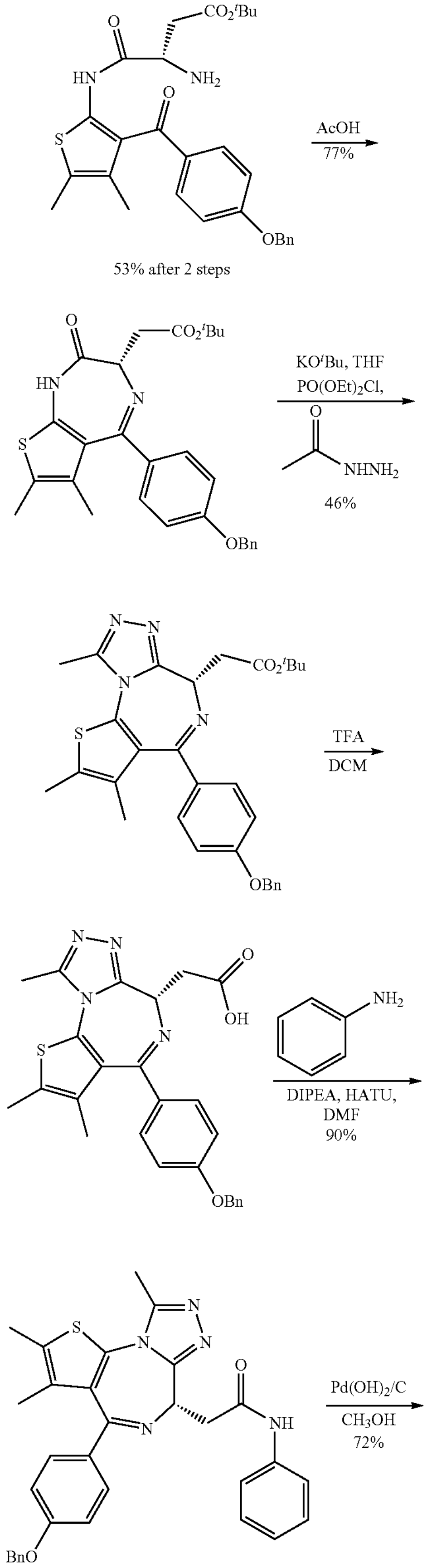
-continued
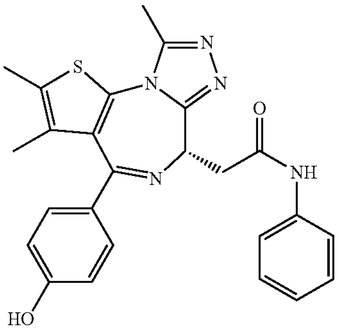
PTM-1-A
Similar to the preparation of intermediate 8, with the same synthetic method as described in the literature, intermediate PTM-1-A was prepared based on the scheme above.
LC/MS ($ES^+$): m/z 458.23 $[M+H]^+$; $t_R$=2.02 min.
Intermediate 10: 2-[(7S)-9-(4-chlorophenyl)-3-methyl-5-oxa-4,8-diazatricyclo[8.4.0.0$^{2,6}$]tetradeca-1(10),2(6),3,8,11,13-hexaen-7-yl]acetic Acid (PTM-1-B)
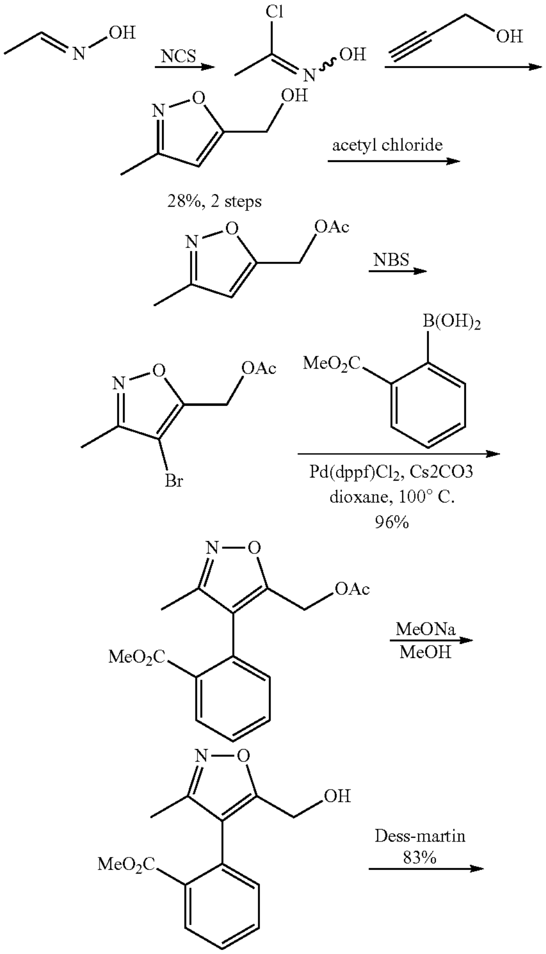

-continued
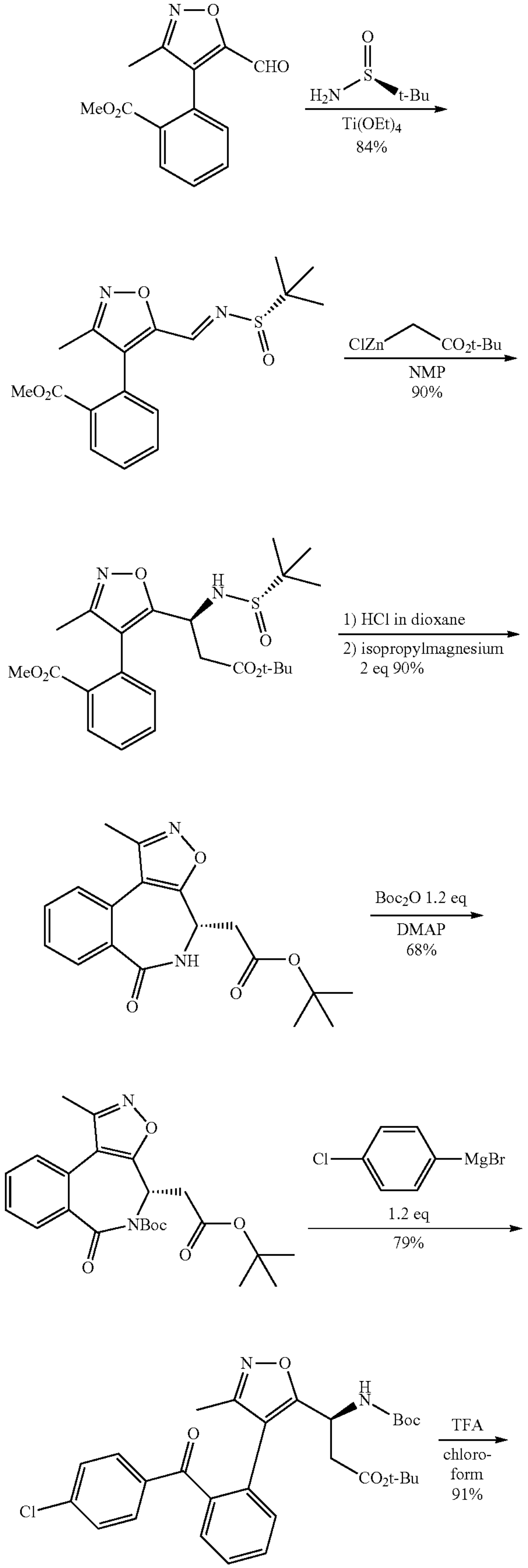
-continued
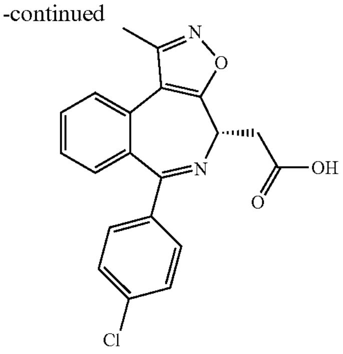
(PTM-1-B)
The synthesis of PTM-1-B was carried out according to the above scheme as described in the literature (J. Med. Chem. 2016, 59, 1330-1339). PTM-1-B is the carboxylic acid of CPI-0610 reported in the literature.
Intermediate 11: 9-Benzyl-2-(dimethyl-1,2-oxazol-4-yl)-6-hydroxy-9H-carbazole-4-carboxamide (PTM-2-1)
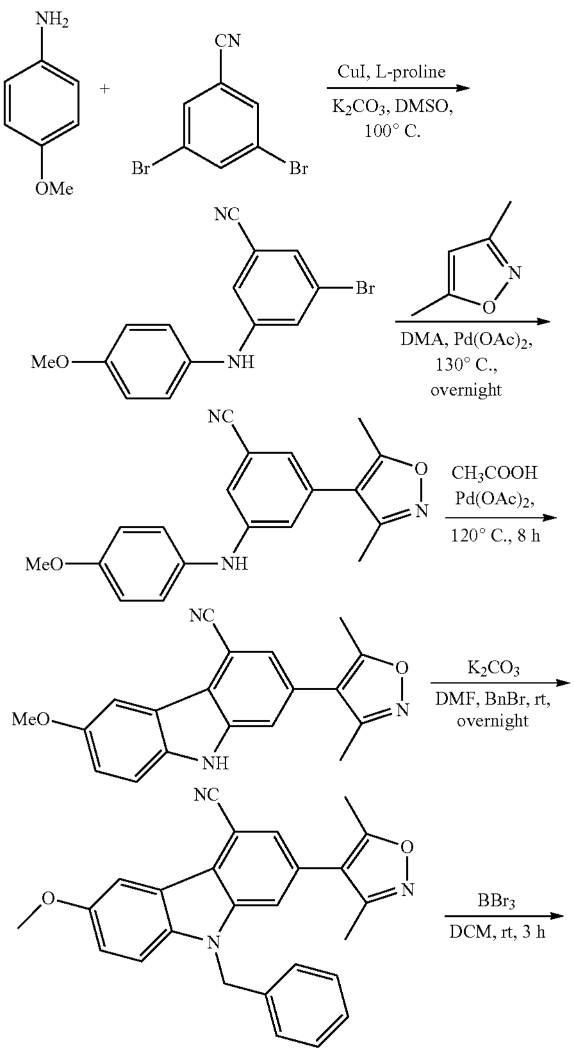

-continued

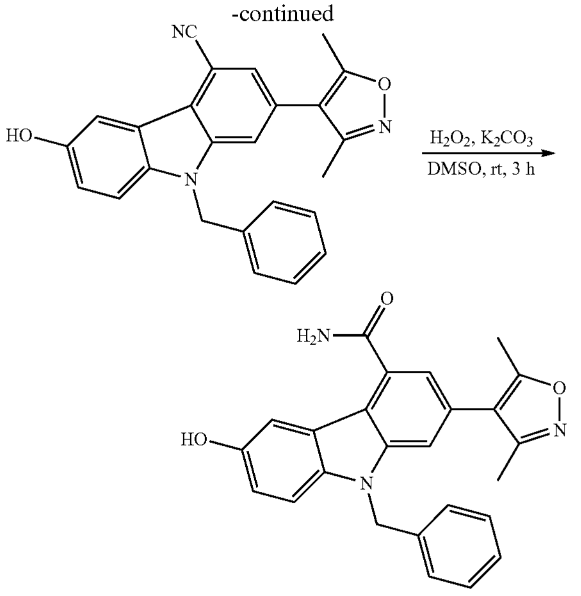

PTM-2-1

The synthetic sequence of PTM-2-1 was adapted from the literature procedure (US 2014/0256700)

Step 1: Preparation of 3-bromo-5-((4-methoxyphenyl)amino)benzonitrile

Into a 250 ml 3-necked round-bottom flask maintained with an inert atmosphere of nitrogen was placed a mixture of 4-methoxyaniline (1.23 g, 10.0 mmol, 1.00 equiv), 3,5-dibromobenzonitrile(2.59 g, 10 mmol, 1 equiv), L-proline (230 mg, 0.2 mmol, 0.2 eq), CuI (190 mg, 1 mmol, 0.1 eq), and $K_2CO_3$(2.76 g, 20 mmol, 2 eq) in DMSO (40 mL). The resulting mixture was stirred at 100° C. overnight in an oil bath. The resulting mixture was cooled to rt, and diluted with water (200 mL). The mixture was extracted with ethyl acetate (150 mL×2). The combined organic layers were washed with brine (50 mL), dried with $Na_2SO_4$, and concentrated under vacuum. The residue was applied onto a silica gel column with ethyl acetate/petroleum ether (1/4) to afford the title compound (0.68 g, 22.5% yield) as a yellow solid. $^1$HNMR (400 MHz, $CDCl_3$): δ7.08-7.13 (m, 4H), 6.92-6.94 (m, 3H), 5.66 (s, 1H), 3.83 (s, 3H).

Step 2: Preparation of 3-(3,5-dimethylisoxazol-4-yl)-5-((4-methoxyphenyl)amino)-benzonitrile Into a 50 mL round-bottom flask and maintained with an inert atmosphere of nitrogen were placed 3-bromo-5-((4-methoxyphenyl)amino)benzonitrile (678 mg, 2.25 mmol, 1.00 equiv), 3,5-dimethylisoxazole (1.09 g, 11.23 mmol, 5.00 eq), KOAc(441 mg, 4.50 mmol, 2 equiv), and $Pd(OAc)_2$ (13.1 mg, 0.058 mmol, 0.026 eq) in DMA (20 mL). The resulting solution was stirred at 130° C. overnight. It was then diluted with water (50 mL) and extracted with ethyl acetate (50 mL×2). The combined organic layers were washed with brine (2×30 mL), dried over anhydrous sodium sulfate and concentrated under vacuum. The residue was applied onto a silica gel column eluted with ethyl acetate/petroleum ether (1/5) to afford the title compound (0.48 g, 67.0% yield) as a yellow solid. $^1$HNMR (400 MHz, $CDCl_3$): δ 7.11 (d, J=8.0 Hz, 2H), 7.03 (s, 1H), 6.92 (d, J=8.0 Hz, 2H), 6.89 (s, 1H), 6.85 (s, 1H), 5.80 (s, 1H), 3.83 (s, 3H), 2.39 (s, 3H), 2.24 (s, 3H); LC/MS: 318 $[M-H]^-$; $t_R$=6.43

Step 3: Preparation of 2-(3,5-dimethylisoxazol-4-yl)-6-methoxy-9H-carbazole-4-carbonitrile A mixture of 3-(3,5-dimethylisoxazol-4-yl)-5-((4-methoxyphenyl)amino)benzonitrile (330 mg, 1.04 mmol, 1.0 eq) and $Pd(OAc)_2$ (232 mg, 1.04 mmol, 1.0 eq) in $CH_3COOH$ (15 mL) was stirred at 120° C. overnight under $O_2$ atmosphere. The reaction was cooled to room temperature. The mixture was diluted with water (40 mL) and extracted with ethyl acetate (50 mL). The combined EtOAc layers were washed with saturated $NaHCO_3$(20 mL×1), and brine (20 mL×1). The solution was dried over anhydrous sodium sulfate and concentrated under vacuum to afford a crude material as the title compound (150 mg, 0.47 mmol, 45.5% yield). LC/MS: 316 $[M-H]^-$

Step 4: Preparation of 9-benzyl-2-(3,5-dimethylisoxazol-4-yl)-6-methoxy-9H-carbazole-4-carbonitrile To a solution of 2-(3,5-dimethylisoxazol-4-yl)-6-methoxy-9H-carbazole-4-carbonitrile (150 mg, 0.47 mmol, 1 eq) in DMF (4 mL) were added $K_2CO_3$ (259.4 mg, 1.88 mmol, 4 eq) and benzyl bromide (160.7 mg, 0.94 mmol, 2 eq) at room temperature. The mixture was stirred overnight. The reaction mixture was extracted with ethyl acetate (100 mL). The organic phase was washed with water (50 mL×2), dried over anhydrous $Na_2SO_4$ and concentrated under vacuum. The residue was purified by column chromatography (PE:EA=3:1) to afford the title compound (130 mg, 0.32 mmol, 68% yield). $^1$HNMR (400 MHz, $CDCl_3$): δ 8.13 (d, J=2.0 Hz, 1H), 7.38-7.41 (m, 4H), 7.22-7.33 (m, 3H), 7.10 (d, J=5.6 Hz, 2H), 5.53 (s, 2H), 3.99 (s, 3H), 2.35 (s, 3H), 2.20 (s, 3H).

Step 5: Preparation of 9-benzyl-2-(3,5-dimethylisoxazol-4-yl)-6-hydroxy-9H-carbazole-4-carbonitrile To a solution of 9-benzyl-2-(3,5-dimethylisoxazol-4-yl)-6-methoxy-9H-carbazole-4-carbonitrile (110 mg, 0.27 mmol, 1 eq) in DCM (4 mL) was added $BBr_3$ (135 mg, 0.54 mmol, 2 eq) at 0° C. The mixture was stirred at rt for 2 h. The mixture was extracted with ethyl acetate (100 mL), washed with water (50 mL×2), and dried over anhydrous $Na_2SO_4$. The combined organic layers were concentrated under vacuum. The residue was purified by column chromatography (PE:EA=3:1) to afford the title compound (90 mg, 0.23 mmol, 85% yield). $^1$HNMR (400 MHz, $CDCl_3$): δ 8.10 (s, 1H), 7.36 (d, J=8.8 Hz, 3H), 7.26-7.28 (m, 3H), 7.21 (d, J=8.8 Hz, 1H), 7.11 (d, J=7.2 Hz, 2H), 6.89 (s, 1H), 5.52 (s, 2H), 2.35 (s, 3H), 2.22 (s, 3H); LC/MS: 394 $[M+H]^+$; $t_R$=6.13 min

Step 6: Preparation of 9-benzyl-2-(3,5-dimethylisoxazol-4-yl)-6-hydroxy-9H-carbazole-4-carboxamide (PTM-2-1)

To a solution of 9-benzyl-2-(3,5-dimethylisoxazol-4-yl)-6-hydroxy-9H-carbazole-4-carbonitrile (60 mg, 0.153 mmol, 1 equiv) in DMSO (4 mL) were added $K_2CO_3$ (105.6 mg, 0.765 mmol, 5 equiv) and $H_2O_2$ (30%) (86.7 mg, 0.765 mmol, 5 equiv). The mixture was stirred at rt for 2 h. The mixture was quenched by addition of saturated $Na_2SO_3$ (5 mL) and the solution was stirred for 10 min. The mixture was extracted with ethyl acetate (20 mL), washed with water (5 ml×2), and dried over anhydrous $Na_2SO_4$. The organic phase was concentrated under vacuum. The residue was purified by column chromatography (PE:EA=3:1) to afford the title compound (45 mg, 71.5% yield).

$^1$HNMR (400 MHz, MeOD): δ 7.87 (s, 1H), 7.44 (t, J=4.0 Hz, 2H), 7.23-7.27 (m, 4H), 7.14 (d, J=6.8 Hz, 2H), 7.05 (dd, J=2.0, 8.8 Hz, 1H), 5.64 (s, 2H), 2.39 (s, 3H), 2.22 (s, 3H); LC/MS: 410 [M−H]$^-$

Intermediate 12 and Intermediate 13: 3-(dimethyl-1,2-oxazol-4-yl)-5-[(R)-oxan-4-yl-(phenyl)methyl]-5H-pyrido[3,2-]indole-7-carboxylic Acid (PTM-3-1-A) and 3-(dimethyl-1,2-oxazol-4-yl)-5-[(S)-oxan-4-yl(phenyl)methyl]-5H-pyrido[3,2-b]indole-7-carboxylic Acid (PTM-3-1-B)

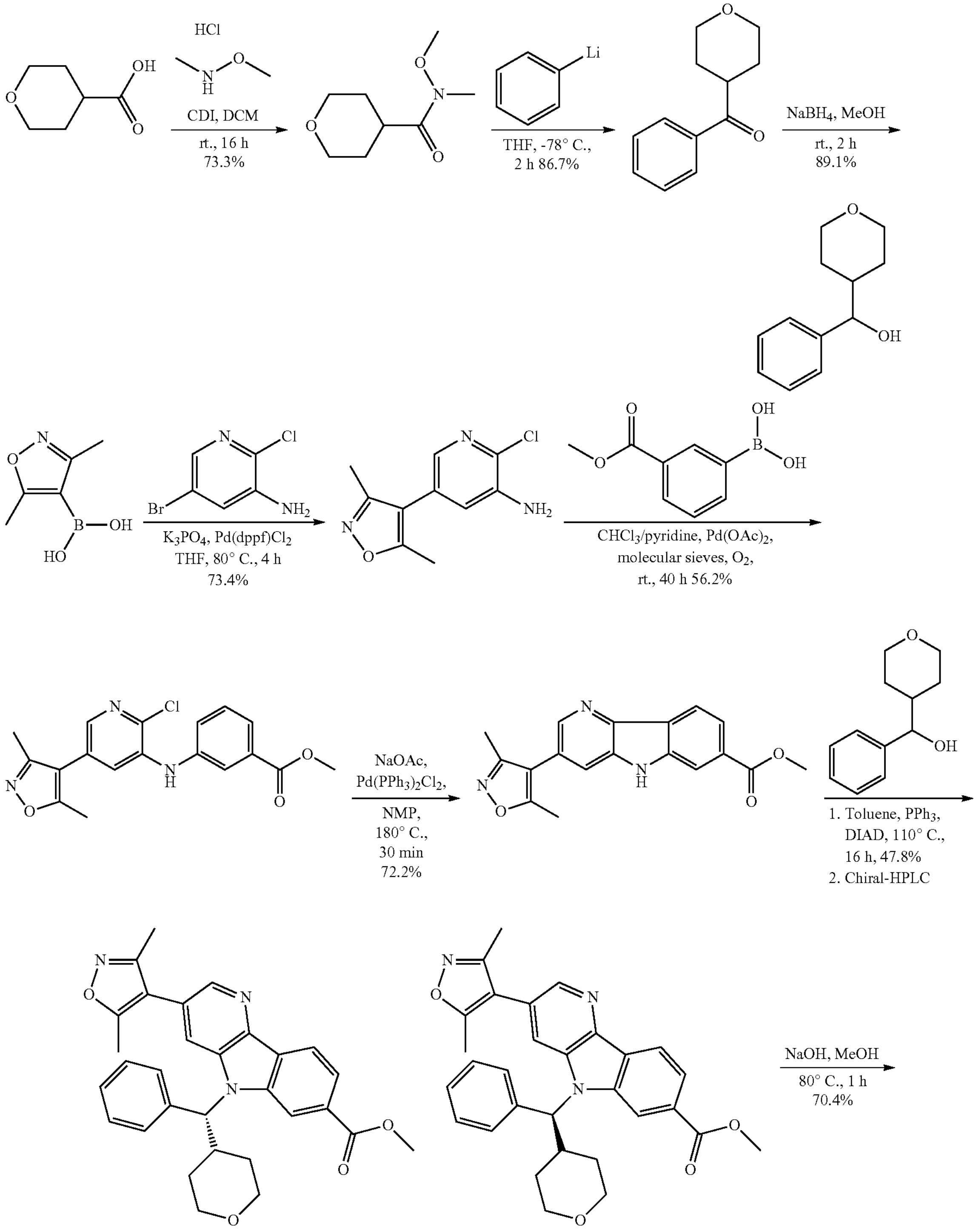

-continued

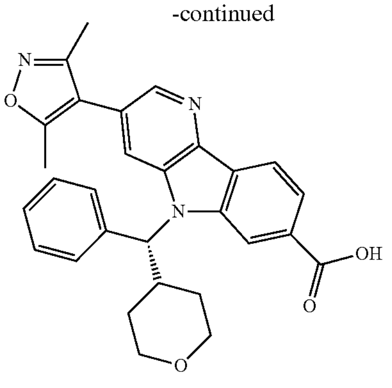

PTM-3-1-A

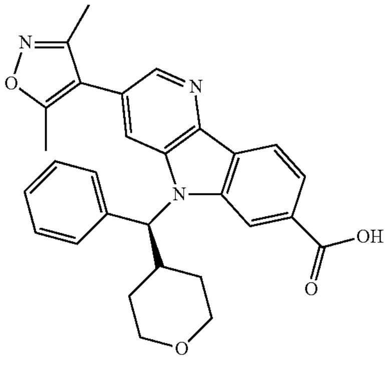

PTM-3-1-B

The racemate of the methyl ester of the title compound was prepared according the literature using the scheme described above (US 2016/0176864).

Methyl 3-(3,5-dimethylisoxazol-4-yl)-5-(phenyl(tetrahydro-2H-pyran-4-yl)methyl)-5H-pyrido[3,2-b]indole-7-carboxylate (0.22 g, prepared according to literature and the synthetic route above) was separated by chiral HPLC to give (R)-methyl 3-(3,5-dimethylisoxazol-4-yl)-5-(phenyl(tetrahydro-2H-pyran-4-yl)methyl)-5H-pyrido[3,2-b]indole-7-carboxylate (0.095 g) and (S)-methyl 3-(3,5-dimethylisoxazol-4-yl)-5-(phenyl(tetrahydro-2H-pyran-4-yl)methyl)-5H-pyrido[3,2-b]indole-7-carboxylate (0.090 g) as a yellow solid.

$^1$H NMR (racemate) (400 MHz, $CDCl_3$) δ 0.98-1.02 (1H, m), 1.32-1.36 (2H, m), 1.95 (1H, s), 2.15 (3H, s), 2.31 (3H, s), 3.00-3.08 (1H, m), 3.24-3.31 (1H, m), 3.45-3.51 (1H, m), 3.76-3.80 (1H, m), 3.96 (3H, s), 4.00-4.01 (1H, m), 5.52 (1H, d, J=10.8 Hz), 7.22-7.29 (3H, m), 7.38-7.40 (2H, m), 7.51 (1H, d, J=1.6 Hz), 7.99 (1H, dd, J=8.0, 1.2 Hz), 8.36 (1H, d, J=8.0 Hz), 8.39 (2H, s); LC/MS 496.3 $[M+H]^+$.

The chiral material ester was hydrolyzed under basic condition (aq. NaOH in MeOH) to provide (R)-PTM-3-1-A and (S)-PTM-3-1-B.

EXAMPLES

Example 1: (2S,4R)—N-{[2-(2-{2-[2-(2-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}ethoxy)ethoxy]ethoxy}ethoxy)-4-(4-methyl-1,3-thiazol-5-yl)phenyl]methyl}-4-hydroxy-1-[(2S)-3-methyl-2-(1-oxo-2,3-dihydro-M-isoindol-2-yl)butanoyl]pyrrolidine-2-carboxamide

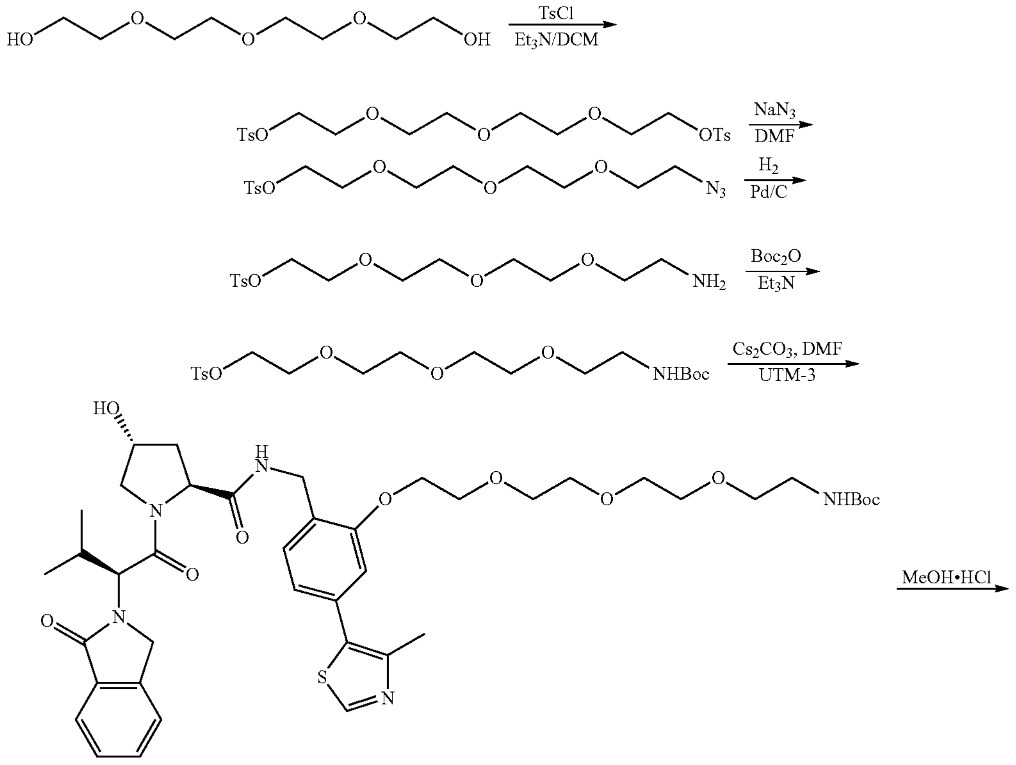

-continued

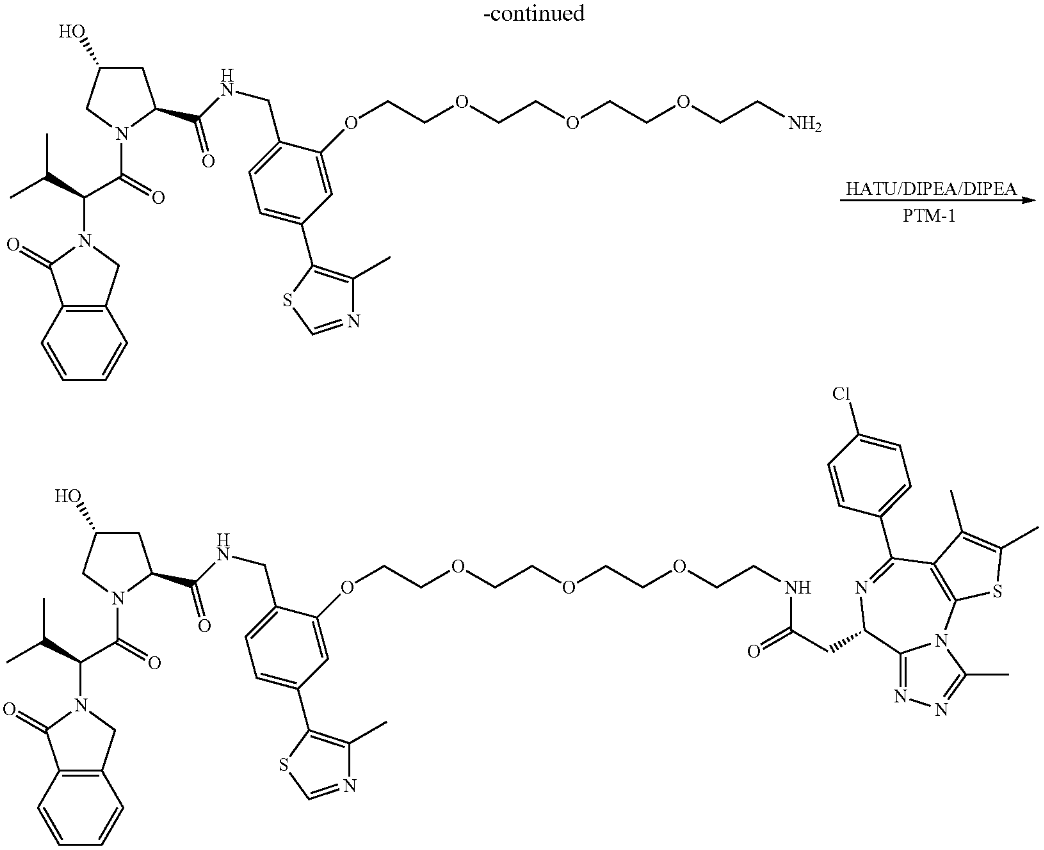

Step 1: Preparation of 2-[2-(2-{2-[(4-methylbenzenesulfonyl)oxy]ethoxy}ethoxy)-ethoxy]ethyl 4-methylbenzene-1-sulfonate To a solution of 2-{2-[2-(2-hydroxyethoxy)ethoxy] ethoxyl ethan-1-ol (13 g, 67.1 mmol), $Et_3N$ (13 mL) in DCM (100 mL) was added TsCl (25.5 g, 134.2 mmol) in portions at 0° C. The resulting mixture was allowed to stir at room temperature overnight. TLC showed the reaction completed. The mixture was partitioned between DCM and $H_2O$. The organic phase was washed with brine, dried over magnesium sulfate and evaporated to dryness. The crude product was purified by silica gel chromatography using with 10-20% EtOAc in hexane as eluent to afford the desired compound (25.0 g, 74.4%).

Step 2: Preparation of 2-(2-(2-(2-azidoethoxy) ethoxy)ethoxy)ethyl4-methylbenzenesulfonate The above compound (25.0 g, 49.8 mmol), $NaN_3$ (3.2 g, 49.8 mmol) in DMF (150 mL) was stirred at 50° C. overnight. TLC showed the reaction completed. The mixture was partitioned between EtOAc and $H_2O$. The organic phase was washed with brine, dried over magnesium sulfate and evaporated to dryness. The crude product was purified by silica gel chromatography using 20-40% EtOAc in hexane to afford the desired compound (7.5 g, 40.5%).

LC/MS: 396.2[M+Na]$^+$.

$^1$HNMR (400 MHz, $CDCl_3$): δ 2.45 (s, 3H), 3.38 (t, J=5.0 Hz, 2H), 3.58-3.63 (m, 4H), 3.66-3.70 (m, 8H), 4.16 (t, J=4.8 Hz, 2H), 7.35 (d, J=8.0 Hz, 2H), 7.80 (d, J=8.4 Hz, 2H).

Step 3: Preparation of 2-(2-(2-(2-aminoethoxy) ethoxy)ethoxy)ethyl 4-methylbenzenesulfonate Compound from step 2 (7.5 g, 20.1 mmol), 10% Pd/C (0.8 g) in MeOH (150 mL) was stirred at room temperature for 5 h under $H_2$ atmosphere. TLC showed the reaction completed. The mixture was filtered and the solid was washed with MeOH. The filtrate was concentrated to afford the desired compound (6.8 g, 97.1%) as colorless oil. It was used in next step without further purification.

LC/MS: 348.2 [M+H]$^+$.

Step 4: Preparation of 2,2-dimethyl-4-oxo-3,8,11,14-tetraoxa-5-azahexadecan-16-yl 4-methylbenzenesulfonate To a solution of the amine from step 3 (6.0 g, crude) in DCM (50 mL) was added $Boc_2O$ (19.0 mmol, 4.1 g) at 0° C. The resulting mixture was allowed to stir at room temperature overnight. The mixture was partitioned between DCM and $H_2O$. The organic phase was washed with brine, dried over magnesium sulfate and evaporated to dryness. The crude product was purified by silica gel chromatography using 30% EtOAc in hexane as eluent to afford the desired compound (2.2 g, 28%, step 3 and step 4).

LC/MS: 448.3 [M+H]$^+$.

$^1$HNMR (400 MHz, $CDCl_3$): δ 1.44 (s, 9H), 2.45 (s, 3H), 3.29-3.32 (m, 2H), 3.53 (t, J=5.2 Hz, 2H), 3.61 (br, 8H), 3.70 (t, J=4.8 Hz, 2H), 4.16 (t, J=5.2 Hz, 2H), 5.02 (br, 1H), 7.34 (d, J=8.0 Hz, 2H), 7.80 (d, J=8.4 Hz, 2H).

Step 5: Preparation of tert-butyl (2-(2-(2-(2-(((2S,4R)-4-hydroxy-1-((S)-3-methyl-2-(1-oxoisoindolin-2-yl)butanoyl)pyrrolidine-2-carboxamido)methyl)-5-(4-methylthiazol-5-yl)phenoxy)ethoxy)ethoxy)ethoxy)ethyl)carbamate A mixture of compound from step 4 (97 mg, 0.22 mmol), UTM-3 (118 mg, 0.22 mmol), and $K_2CO_3$ (19.0 mmol, 4.1 g) in DMF (5 mL) was stirred at 50° C. overnight. TLC showed the reaction completed. The mixture was cooled to room temperature and partitioned between EtOAc and $H_2O$. The organic phase was washed with brine, dried over anhydrous $Na_2SO_4$. The crude product was purified by silica gel chromatography using 2-5% MeOH in DCM as eluent to afford the desired product (130 mg, 72.2%).

LC/MS: 846.5 $[M+Na]^+$.

Step 6: Preparation of (2S,4R)—N-(2-(2-(2-(2-(2-aminoethoxy)ethoxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide The above compound from step 5 (120 mg, 0.15 mmol) in methanol (4 mL) was treated with 4M hydrochloric acid in MeOH (2 mL). The mixture was stirred at ambient temperature for 1 h. The volatiles were concentrated to afford a hydrochloride salt (110 mg, crude) as a white solid. It was used in next step without further purification.

LC/MS: 724.4$[M+1]^+$.

Step 7: Preparation of (2S,4R)—N-{[2-(2-{2-[2-(2-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}ethoxy)ethoxy]ethoxy}ethoxy)-4-(4-methyl-1,3-thiazol-5-yl)phenyl]methyl}-4-hydroxy-1-[(2S)-3-methyl-2-(1-oxo-2,3-dihydro-1H-isoindol-2-yl)butanoyl]pyrrolidine-2-carboxamide To an ice-cooled mixture of the hydrochloride salt from step 6 (110 mg, crude), PTM-1 (55 mg, 0.14 mmol), and DIPEA (0.09 mL, 0.54 mmol) in DMF (5 mL) was added HATU (15 mg, 0.21 mmol) at 0° C. The resulting mixture was allowed to stir at ambient temperature for 30 min. TLC showed the reaction completed. The mixture was treated with water and extracted with EtOAc. The combined organic phase was washed with brine, dried over magnesium sulfate and evaporated to dryness. The crude product was purified by preparative TLC to afford the desired compound (38 mg, 24.6%).

LC/MS: 1106.3 $[M+H]^+$.

$^1$HNMR (400 MHz, $CDCl_3$): δ 0.81 (d, J=6.8 Hz, 3H), 1.04 (d, J=6.8 Hz, 3H), 1.66 (s, 3H), 2.02-2.07 (m, 1H), 2.16-2.18 (m, 1H), 2.40-2.46 (m, 7H), 2.66 (s, 3H), 3.23-3.27 (m, 1H), 3.40-3.46 (m, 3H), 3.55-3.75 (m, 10H), 3.84-3.97 (m, 4H), 4.19-4.22 (m, 2H), 4.39-4.64 (m, 7H), 4.81-4.84 (m, 1H), 6.99-7.01 (m, 2H), 7.35-7.42 (m, 6H), 7.53-7.59 (m, 2H), 7.76 (d, J=7.6 Hz, 1H), 8.85 (s, 1H).

Compounds of Example 2, Example 3, Example 5 and Example 6 were synthesized using the same synthetic method as described in Example 1.

Example 4: (2S,4R)-1-[(2S)-2-(20-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}-3,6,9,12,15,18-hexaoxaicosanamido)-3,3-dimethylbutanoyl]-4-hydroxy-N-{[4-(4-methyl-1,3-thiazol-5-yl)phenyl]methyl}-pyrrolidine-2-carboxamide

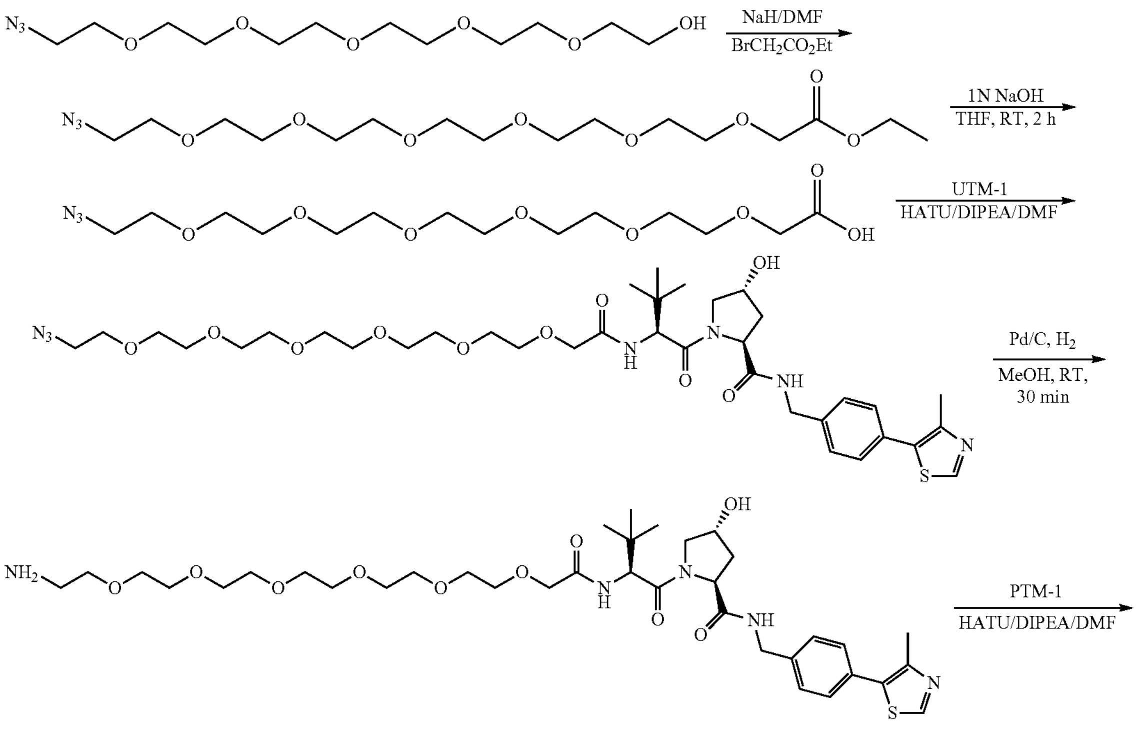

-continued

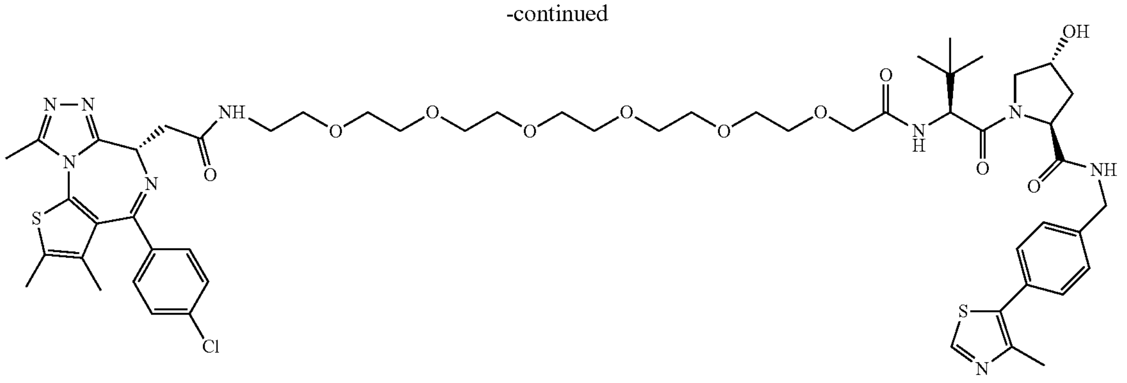

Step 1: Preparation of ethyl 20-azido-3,6,9,12,15,18-hexaoxaicosan-1-oate

60% NaH (130 mg, 3.26 mmol) was added to a stirred solution of 17-azido-3,6,9,12,15-pentaoxaheptadecan-1-ol (500 mg, 1.63 mmol) in dry DMF (5 mL) in portions at 0° C. The mixture was allowed to stir at room temperature for 40 min and then cooled to 0° C. $BrCH_2CO_2Et$ (0.41 g, 2.44 mmol) in dry DMF (1 mL) was added dropwise and the resulting mixture was allowed to stir at room temperature for 4 h. TLC showed the reaction completed. The mixture was carefully quenched with water and extracted with EtOAc. The organic phase was washed with water and brine, dried over $Na_2SO_4$ and concentrated. The crude product was purified by silica gel chromatography using 30-60% EtOAc in hexane as eluent to afford the desired ester (100 mg, 16%) as a colorless oil.

$^1$H NMR (400 MHz, $CDCl_3$): δ 1.29 (t, J=7.2 Hz, 3H), 3.39 (t, J=4.8 Hz, 2H), 3.66-3.74 (m, 22H), 4.15 (s, 2H), 4.22 (q, J=7.2 Hz, 2H).

Step 2: Preparation of 20-azido-3,6,9,12,15,18-hexaoxaicosan-1-oic Acid

A solution of the above ester (250 mg, 0.64 mmol) and 2N NaOH (1.8 mL) in THF (5 mL) was stirred at room temperature for 3 h. TLC showed the reaction was completed. The reaction mixture was acidified with 4 N HCl to pH 2-3. The volatiles were evaporated to afford the desired acid (300 mg, crude). This material was used in next step without further purification.

Step 3: Preparation of (2S,4R)-1-((S)-23-azido-2-tert-butyl-4-oxo-6,9,12,15,18,21-hexaoxa-3-azatricosane)-4-hydroxy-N-(4-(4-methylthiazol-5-yl)benzyl)pyrrolidine-2-carboxamide To a solution of the above carboxylic acid (300 mg, crude), UTM-1 (299 mg, 0.64 mmol), and DIPEA (248 mg, 1.92 mmol) in dry DMF (8 mL) was added HATU (364 mg, 0.96 mmol) at 0° C. The resulting mixture was allowed to stir at room temperature for 1 h. TLC showed the reaction completed. The mixture was partitioned between EtOAc and water. The organic phase was washed with water and brine, dried over anhydrous $Na_2SO_4$. The residue was purified by silica gel chromatography using 2-8% MeOH in DCM as eluent to afford the desired compound (260 mg, 51%) as a pale yellow solid.

LC/MS: 778.4 $[M+H]^+$ $^1$H NMR (400 MHz, DMSO-d6): δ 0.93-0.95 (m, 9H), 1.89-1.93 (m, 1H) 2.03-2.06 (m, 1H), 2.44-2.46 (m, 3H), 3.38 (t, J=4.8 Hz, 2H), 3.48-3.69 (m, 24H), 3.93-3.98 (m, 2H), 4.22-4.27 (m, 1H), 4.35-4.46 (m, 3H), 4.68 (d, J=9.6 Hz, 1H), 5.16 (d, J=3.2 Hz, 1H), 7.38-7.44 (m, 5H), 8.61 (t, J=6.0 Hz, 1H), 8.99 (s, 1H).

Step 4: Preparation of (2S,4R)-1-((S)-23-amino-2-tert-butyl-4-oxo-6,9,12,15,18,21-hexaoxa-3-azatricosane)-4-hydroxy-N-(4-(4-methylthiazol-5-yl)benzyl)pyrrolidine-2-carboxamide A mixture of the product from step 3 (100 mg, 0.13 mmol), 10% Pd/C (20 mg) in MeOH (5 mL) was stirred at room temperature for 30 min under $H_2$ atmosphere. The solid was removed by filtration and washed with MeOH. The filtrate was concentrated to afford the desired amine (70 mg, 74%) as colorless oil. This material was used in the next step without further purification.

LC/MS: 752.4 $[M+H]^+$ $^1$H NMR (400 MHz, DMSO-d6): δ 0.95 (s, 9H), 1.87-1.93 (m, 1H) 2.04-2.09 (m, 1H), 2.45 (s, 3H), 2.95 (t, J=5.2 HZ, 2H), 3.43-3.69 (m, 24H), 3.97 (s, 2H), 4.22-4.27 (m, 1H), 4.35-4.46 (m, 3H), 4.56 (d, J=8.8 HZ, 1H), 5.19 (br, 1H), 7.38-7.46 (m, 5H), 7.76-7.90 (m, 2H), 8.61-8.64 (m, 1H), 8.99 (s, 1H).

Step 5: Preparation of (2S,4R)-1-[(2S)-2-(20-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido-3,6,9,12,15,18-hexaoxaicosanamido)-3,3-dimethylbutanoyl]-4-hydroxy-N-[4-(4-methyl-1,3-thiazol-5-yl)phenyl]methyl}pyrrolidine-2-carboxamide To a solution of the hydrogenation product from step 4 (70 mg, 0.093 mmol), PTM-1 (37 mg, 0.093 mmol), and DIPEA (24 mg, 0.186 mmol) in dry DMF (3 mL) was added HATU (71 mg, 0.186 mmol) at 0° C. The resulting mixture was allowed to stir at room temperature for 1 h. TLC showed the reaction completed. The mixture was partitioned between EtOAc and water. The organic phase was washed with water, brine and dried over anhydrous $Na_2SO_4$. The residue was purified by preparative HPLC to afford the desired compound as a white solid (22 mg, 21%).

LC/MS: 1134.8 $[M+H]^+$.

$^1$H NMR (400 MHz, DMSO-d6): δ 0.94 (s, 9H), 1.62 (s, 3H), 1.87-1.93 (m, 1H) 2.04-2.09 (m, 1H), 2.41 (s, 3H), 2.44 (s, 3H), 2.60 (s, 3H), 3.20-3.27 (m, 3H), 3.45-3.62 (m, 24H), 3.97 (s, 2H), 4.22-4.27 (m, 2H), 4.34-4.57 (m, 6H), 7.40-7.50 (m, 9H), 8.28-8.31 (m, 1H), 8.60-8.63 (m, 1H), 8.99 (s, 1H).

Compounds of Example 7, Example 8, and Example 9 were synthesized using the same synthetic method as described in Example 4.

Example 10: (2S,4R)-1-[(2S)-2-(2-{2-[2-(4-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}phenoxy)ethoxy]ethoxy}acetamido)-3,3-dimethylbutanoyl]-4-hydroxy-N-{[4-(4-methyl-1,3-thiazol-5-yl)phenyl]methyl}pyrrolidine-2-carboxamide

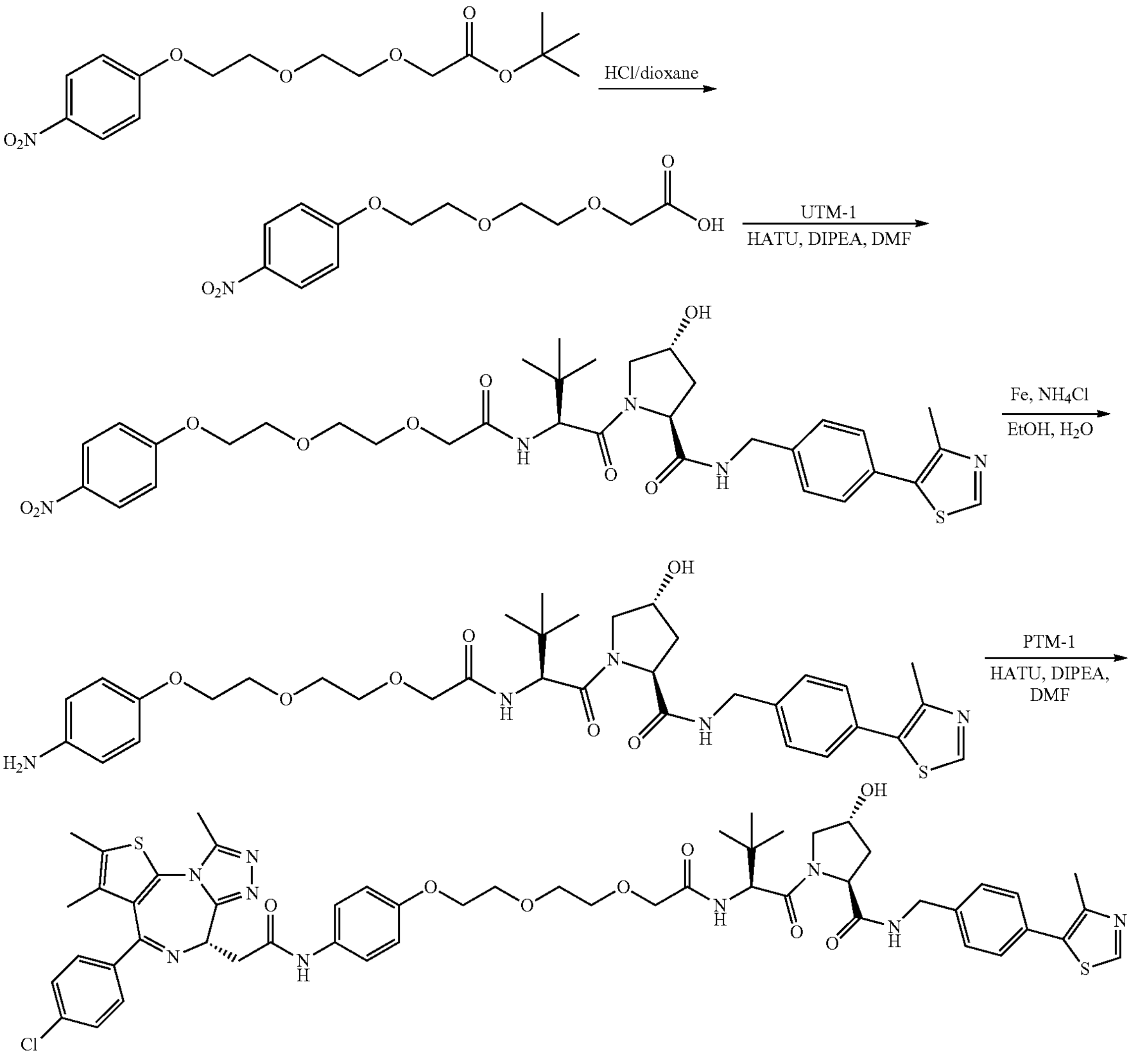

Step 1: Preparation of (2-(2-(2-(4-nitrophenoxy)ethoxy)ethoxy)acetic Acid

To a stirred solution of tert-butyl 2-(2-(2-(4-nitrophenoxy)ethoxy)ethoxy)acetate (450 mg, 1.32 mmol, prepared using the same method as described in *Chem. & Biol.* 22, 755-763, 2015) in dry dichloromethane (10 ml) was added 4M hydrochloride acid/dioxane (10 mL) at room temperature. The resulting mixture was stirred at room temperature for 1 hour. TLC showed the reaction completed. The volatiles were evaporated under reduced pressure to afford 2-(2-(2-(4-nitrophenoxy)ethoxy)ethoxy)acetic acid (380 mg, crude) as yellow oil which was used in next step without further purification.

LC/MS: ($ES^+$): m/z 286.20 [$M+H^+$]; $t_R$=2.575 min.

Step 2: Preparation of (2S,4R)-1-((S)-3,3-dimethyl-2-(2-(2-(2-(4-nitrophenoxy)ethoxy)ethoxy)acetamido)butanoyl)-4-hydroxy-N-(4-(4-methylthiazol-5-yl)benzyl)pyrrolidine-2-carboxamide To a stirred solution containing 2-(2-(2-(4-nitrophenoxy)ethoxy)ethoxy)acetic acid (380 mg, crude), (2S,4R)-1-((S)-2-amino-3,3-dimethylbutanoyl)-4-hydroxy-N-(4-(4-methylthiazol-5-yl)benzyl)pyrrolidine-2-carboxamide hydrochloric acid salt (490 mg, 1.05 mmol), and DIPEA (0.58 mL, 3.15 mmol) in dry N,N-dimethylformamide (10 mL) was added HATU (105 mg, 1.57 mmol) at room temperature, the resulting mixture was stirred at room temperature for 30 minutes. TLC showed formation of desired product. The reaction mixture was poured into water (70 ml)

and extracted with ethyl acetate (60 mL×3). The combined organic phase was washed with brine (30 mL), dried over anhydrous sodium sulfate, and concentrated under reduced pressure to give a crude residue which was purified by silica gel flash column chromatography (eluted with 1-5% methanol in dichloromethane) to afford (2S,4R)-1-((S)-3,3-dimethyl-2-(2-(2-(2-(4-nitrophenoxy)ethoxy)ethoxy)acetamido)butanoyl)-4-hydroxy-N-(4-(4-methylthiazol-5-yl)benzyl)pyrrolidine-2-carboxamide (600 mg, 82%) as light yellow solid.

LC/MS: ($ES^+$): m/z 698.40 [$M+H^+$]. $t_R$=2.142 min.

$^1$HNMR (400 MHz, $CDCl_3$): δ 0.94 (s, 9H), 2.09-2.15 (s, 1H), 2.51 (s, 3H), 2.58-2.61 (m, 1H), 2.86-2.87 (m, 1H), 3.59-3.63 (m, 2H), 3.69-3.76 (m, 4H), 3.88-3.90 (m, 2H), 3.96-4.06 (m, 2H), 4.21-4.23 (m, 2H), 4.32-4.37 (m, 1H), 4.47-4.49 (m, 1H), 4.53-4.60 (m, 2H), 4.74 (t, J=8.0 Hz, 1H), 6.96 (d, J=9.2 Hz, 2H), 7.28-7.37 (m, 6H), 8.18 (d, J=9.6 Hz, 2H), 8.68 (s, 1H).

Step 3: Preparation of (2S,4R)-1-((S)-2-(2-(2-(2-(4-aminophenoxy)ethoxy)ethoxy)-acetamido)-3,3-dimethylbutanoyl)-4-hydroxy-N-(4-(4-methylthiazol-5-yl)benzyl)pyrrolidine-2-carboxamide A mixture of the compound prepared in step 2 (418 mg, 0.60 mmol), iron powder (336 mg, 6.0 mmol) and ammonium chloride (318 mg, 6.0 mmol) in ethanol (10 mL) and water (10 mL) was stirred at refluxing temperature for 3 hours. TLC showed the formation of the desired product. The mixture was cooled to room temperature. The solid precipitate was filtered off, washed with ethyl acetate (10 mL×2), and the filtrates were partitioned between ethyl acetate (120 mL) and water (30 mL). The organic phase was separated, washed with brine (30 mL), dried over anhydrous sodium sulfate, and concentrated under reduced pressure. The residue was purified by silica gel flash column chromatography (eluted with 3-5% methanol in dichloromethane) to afford (2S,4R)-1-((S)-2-(2-(2-(2-(4-aminophenoxy)ethoxy)ethoxy)-acetamido)-3,3-dimethylbutanoyl)-4-hydroxy-N-(4-(4-methylthiazol-5-yl)benzyl)pyrrolidine-2-carboxamide (209 mg, 52.4%) as light yellow solid.

LC/MS: ($ES^+$): m/z 668.40 [$M+H^+$]; $t_R$=1.512 min.

$^1$HNMR (400 MHz, DMSO-$d_6$): δ 0.92 (s, 9H), 1.87-1.91 (m, 1H), 2.01-2.04 (m, 1H), 2.47 (s, 3H), 3.57-3.72 (m, 8H), 3.90-3.96 (m, 4H), 4.20-4.44 (m, 4H), 4.53-4.58 (m, 3H), 5.14 (d, J=3.2 Hz, 1H), 6.44-6.47 (m, 2H), 6.57-6.61 (m, 2H), 7.37-7.44 (m, 5H), 8.58 (t, J=6.0 Hz, 1H), 8.95 (s, 1H).

Step 4: Preparation of (2S,4R)-1-[(2S)-2-(2-{2-[2-(4-{2-[(9S)-7-(4-chlorophenyl)-4,5,13-trimethyl-3-thia-1,8,11,12-tetraazatricyclo[8.3.0.$0^{2}$,$^{6}$]trideca-2(6),4,7,10,12-pentaen-9-yl]acetamido}phenoxy)ethoxy]ethoxy}acetamido)-3,3-dimethylbutanoyl]-4-hydroxy-N-{[4-(4-methyl-1,3-thiazol-5-yl)phenyl]methyl}pyrrolidine-2-carboxamide To a stirred solution containing (2S,4R)-1-((S)-2-(2-(2-(2-(4-aminophenoxy)ethoxy)ethoxy)acetamido)-3,3-dimethylbutanoyl)-4-hydroxy-N-(4-(4-methylthiazol-5-yl)benzyl)pyrrolidine-2-carboxamide (50 mg, 0.09 mmol), (S)-2-(4-(4-chlorophenyl)-2,3,9-trimethyl-6H-thieno[3,2-f][1,2,4]triazolo[4,3-a][1,4]diazepin-6-yl)acetic acid (60 mg, 0.09 mmol), and DIPEA (0.05 mL, 0.27 mmol) in anhydrous N,N-dimethylformamide (3 ml) was added HATU (95 mg, 0.25 mmol) at 0° C. The resulting mixture was allowed to warm up to room temperature and stirred for 20 min. TLC showed formation of the desired product. The mixture was partitioned between ethyl acetate (60 mL) and water (20 mL). The organic layer was collected, washed with brine (10 mL), dried over anhydrous sodium sulfate, and concentrated under reduced pressure to give a crude residue which was purified by preparative TLC to afford (2S,4R)-1-[(2S)-2-(2-{2-[2-(4-{2-[(9S)-7-(4-chlorophenyl)-4,5,13-trimethyl-3-thia-1,8,11,12-tetraazatricyclo[8.3.0.$0^{2}$,$^{6}$]trideca-2(6),4,7,10,12-pentaen-9-yl]acetamido}phenoxy)ethoxy]ethoxy}acetamido)-3,3-dimethylbutanoyl]-4-hydroxy-N-{[4-(4-methyl-1,3-thiazol-5-yl)phenyl]methyl}pyrrolidine-2-carboxamide (42 mg, 44.4%) as a white solid.

LC/MS: ($ES^+$): m/z 1050.20 [$M+H^+$]; $t_R$=2.372 min.

$^1$HNMR (400 MHz, DMSO-$d_6$): δ 0.94 (s, 9H), 1.63 (s, 3H), 1.86-1.91 (m, 1H), 2.04-2.09 (m, 1H), 2.41-2.43 (m, 6H), 2.60 (s, 3H), 3.43-3.47 (m, 2H), 3.62-3.77 (m, 8H), 3.99 (s, 2H), 4.05-4.07 (m, 2H), 4.35-4.61 (m, 6H), 5.50 (d, J=2.8 Hz, 1H), 6.87 (d, J=8.8 Hz, 2H), 7.39-7.54 (m, 11H), 8.61-8.64 (m, 1H), 8.97 (s, 1H), 10.23 (br, 1H).

Compounds in Example 11-16, Example 18-20 were prepared using the same method as described in Example 10.

Example 17: (2S,4R)-1-[(2S)-2-(18-{2-[(9S)-7-(4-chlorophenyl)-4,5,13-trimethyl-3-thia-1,8,11,12-tetraazatricyclo[8.3.0.$0^{2}$,$^{6}$]trideca-2(6),4,7,10,12-pentaen-9-yl]-N-methylacetamido}-3,6,9,13,16-pentaoxaoctadecanamido)-3,3-dimethylbutanoyl]-4-hydroxy-N-{[4-(4-methyl-1,3-thiazol-5-yl)phenyl]methyl}pyrrolidine-2-carboxamide

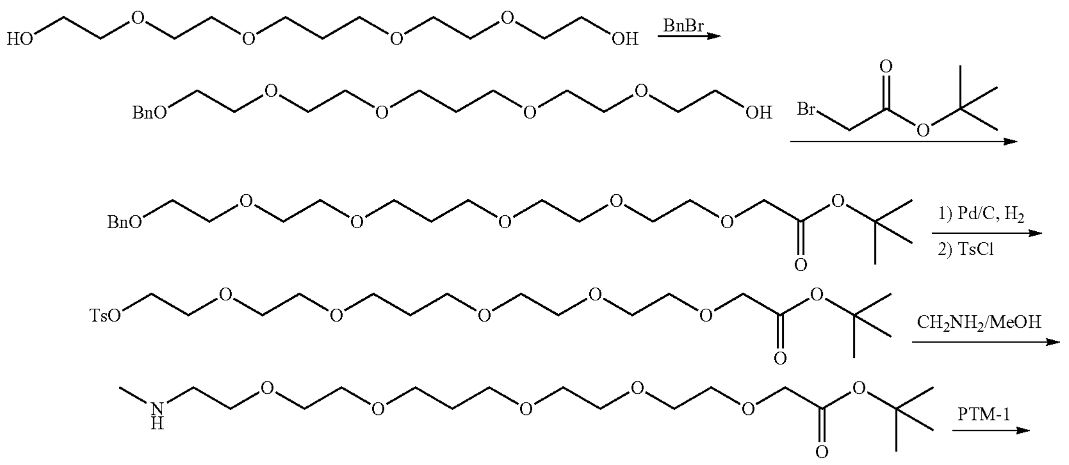

-continued

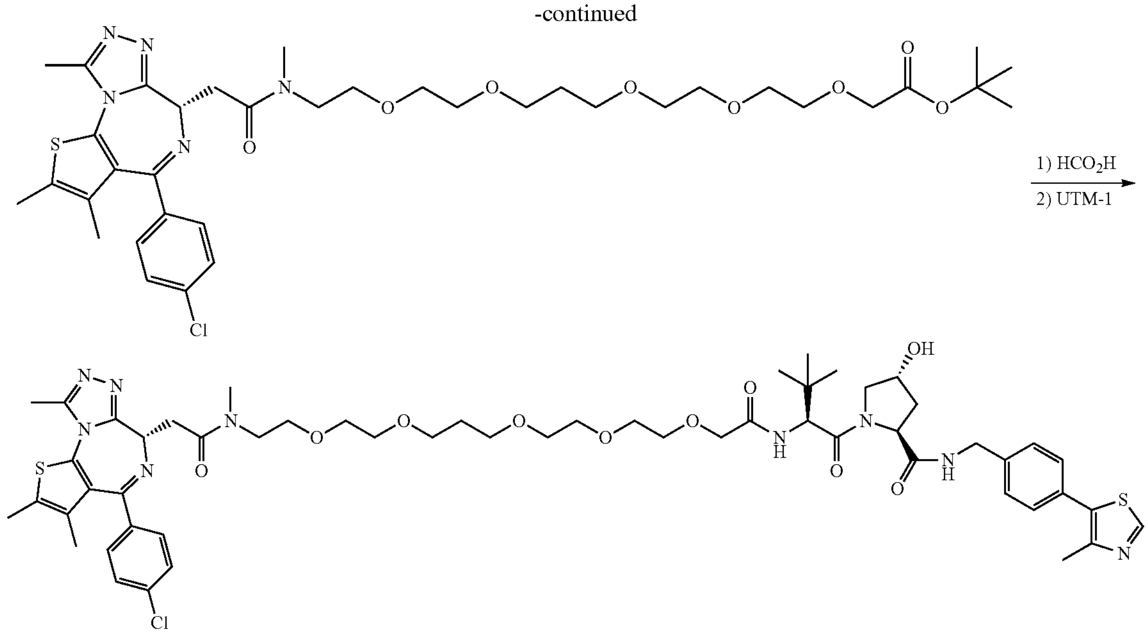

Step 1: Preparation of 1-phenyl-2,5,8,12,15-pentaoxaheptadecan-17-ol

To a stirred solution of silver(I) oxide (4.82 g, 20.81 mmol), potassium iodide (921 mg, 5.55 mmol), and 3,6,10,13-tetraoxapentadecane-1,15-diol(3.5 g, 13.87 mmol) in anhydrous dichloromethane (50 ml) was added-benzylbromide (2.61 g, 15.26 mmol) drop wise over 5 min at room temperature, the resulting mixture was stirred at room temperature for 2 hours. TLC showed formation of the desired product. The solid precipitate was filtered off, washed with dichloromethane (20 ml×2), and the combined organic phase was concentrated under reduced pressure to give a crude residue which was purified by silica gel flash column chromatography (eluted with 1-5% methanol in dichloromethane) to afford 1-phenyl-2,5,8,12,15-pentaoxaheptadecan-17-ol (2.3 g, 48%) as colorless oil.

LC/MS ($ES^+$): m/z 343.40 [$M+H^+$]; $t_R$=1.962 min.

Step 2: Preparation of tert-butyl 1-phenyl-2,5,8,12,15,18-hexaoxaicosan-20-oate

To a stirred solution of 1-phenyl-2,5,8,12,15-pentaoxaheptadecan-17-ol (2.3 g, 6.72 mmol) and aqueous sodium hydroxide (35%,40 mL) were added tetra-butyl ammonium chloride (1.87 g, 6.72 mmol) in dichloromethane (40 mL) followed by the addition of tert-butyl 2-bromoacetate (5.24 g, 26.87 mmol) at room temperature. The resulting mixture was stirred at room temperature overnight. The reaction mixture was poured into water (40 mL). The organic layer was separated, and the aqueous layer was extracted with dichloromethane (60 mL×2). The combined organic phase was washed with water (20 mL×2) and brine (30 mL), dried over anhydrous sodium sulfate, and concentrated under reduced pressure to give a crude residue which was purified by silica gel flash column chromatography (eluted with 1-6% ethyl acetate in hexane) to afford tert-butyl 1-phenyl-2,5,8,12,15,18-hexaoxaicosan-20-oate (2.15 g, 70%) as colorless oil.

$^1H$ NMR (400 MHz, $CDCl_3$): δ 1.47 (s, 9H), 1.83-1.90 (m, 2H), 3.52-3.72 (m, 20H), 4.02 (s, 2H), 4.57 (s, 2H), 7.28-7.35 (m, 5H).

Step 3: Preparation of tert-butyl 18-(tosyloxy)-3,6,9,13,16-pentaoxaoctadecan-1-oate A mixture of tert-butyl 1-phenyl-2,5,8,12,15,18-hexaoxaicosan-20-oate (2.15 g, 4.7 mmol) and palladium on carbon (10%, 250 mg) in ethanol (40 mL) was stirred at 50° C. overnight under hydrogen atmosphere (hydrogen balloon). TLC showed formation of the desired product. Palladium on carbon was removed through filtration and washed with ethanol (10 mL×2), and the combined filtrate was concentrated under reduced pressure. The residue was re-dissolved in anhydrous dichloromethane (20 mL), followed by sequential addition of triethylamine (1.60 g, 15.85 mmol) and tosyl chloride (950 mg, 4.98 mmol) at 0° C. The reaction mixture was allowed to warm up to room temperature and stirred at room temperature overnight. TLC showed formation of the desired product. The reaction mixture was diluted with dichloromethane (100 mL), washed with water (20 mL×2) and brine (20 mL), dried over anhydrous sodium sulfate, and concentrated under reduced pressure to give a crude residue which was purified by silica gel flash column chromatography (eluted with 10-30% ethyl acetate in hexane) to afford tert-butyl 18-(tosyloxy)-3,6,9,13,16-pentaoxaoctadecan-1-oate (1.8 g, 73%) as colorless oil.

LC/MS ($ES^+$): m/z 543.30 [$M+H^+$]; $t_R$=2.598 min.

Step 4: Preparation of tert-butyl 5,8,12,15,18-pentaoxa-2-azaicosan-20-oate

A solution of tert-butyl 18-(tosyloxy)-3,6,9,13,16-pentaoxaoctadecan-1-oate (100 mg, 0.19 mmol) in methylamine methanol solution (30%, 2 mL) was stirred at room temperature for 5 hours. TLC showed formation of the desired product. The volatiles were removed under reduced pressure to afford tert-butyl 5,8,12,15,18-pentaoxa-2-azaicosan-20- oate (110 mg, crude) as brown oil which was used in next step without further purification.

Step 5: Preparation of (S)-tert-butyl1-(4-(4-chlorophenyl)-2,3,9-trimethyl-6H-thieno[3,2-f][1,2,4]triazolo[4,3-a][1,4]diazepin-6-yl)-3-methyl-2-oxo-6,9,13,16,19-pentaoxa-3-azahenicosan-21-oate The tert-butyl 5,8,12,15,18-pentaoxa-2-azaicosan-20-oate (110 mg, crude) was combined with (S)-2-(4-(4-chlorophenyl)-2,3,9-trimethyl-6H-thieno[3,2-f][1,2,4]triazolo [4,3-a][1,4]diazepin-6-yl)acetic acid (76 mg, 0.19 mmol) and DIPEA (48 mg, 0.37 mmol) in dry N,N-dimethylformamide (2 mL). To this stirred solution was added HATU (141 mg, 0.37 mmol) at 0° C. The resulting mixture was allowed to warm up to room temperature and stirred at room temperature for 30 min. TLC showed formation of the desired product. The resulting mixture was partitioned between ethyl acetate (60 mL) and water (20 mL). The organic layer was collected, washed with brine (20-mL), dried over anhydrous sodium sulfate, and concentrated under reduced pressure to afford a crude residue which was purified by preparative TLC to afford (S)-tert-butyl1-(4-(4-chlorophenyl)-2,3,9-trimethyl-6H-thieno[3,2-f][1,2,4]triazolo[4,3-a][1,4]diazepin-6-yl)-3-methyl-2-oxo-6,9,13,16,19-pentaoxa-3-azahenicosan-21-oate (56 mg, 40%) as a yellow solid.

LC/MS ($ES^+$): m/z 762.4 [$M+H^+$]; $t_R$=2.635 min.

Step 6: Preparation of (2S,4R)-1-[(2S)-2-(18-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-methylacetamido}-3,6,9,13,16-pentaoxaoctadecanamido)-3,3-dimethylbutanoyl]-4-hydroxy-N-{[4-(4-methyl-1,3-thiazol-5-yl)phenyl]methyl}pyrrolidine-2-carboxamide A solution of (S)-tert-butyl1-(4-(4-chlorophenyl)-2,3,9-trimethyl-6H-thieno[3,2-f][1,2,4]triazolo[4,3-a][1,4]diazepin-6-yl)-3-methyl-2-oxo-6,9,13,16,19-pentaoxa-3-azahenicosan-21-oate (56 mg, 0.073 mmol) in formic acid (1 mL) was stirred at 60° C. for 30 min. The volatiles were removed under reduced pressure. The residue was re-dissolved in anhydrous N,N-dimethylformamide (1 mL), followed by sequential addition of (2S,4R)-1-((S)-2-amino-3,3-dimethylbutanoyl)-4-hydroxy-N-(4-(4-methylthiazol-5-yl) benzyl)pyrrolidine-2-carboxamide hydrochloric acid salt (40 mg, 0.085 mmol), DIPEA (36.6 mg, 0.283 mmol), and HATU (54 mg, 0.141 mmol) at 0° C. The resulting mixture was allowed to warm up to room temperature and stirred at room temperature for 30 min. TLC showed formation of the desired product. The mixture was partitioned between ethyl acetate (60 mL) and water (20 mL). The organic layer was collected, washed with brine (20 mL), dried over anhydrous sodium sulfate, and concentrated under reduced pressure to afford a crude residue which was purified by preparative TLC to afford the desired compound (33.8 mg, 43%) as a white solid.

LC/MS ($ES^+$): m/z 1118.40 [$M+H^+$]; $t_R$=2.447 min.

$^1$H NMR (400 MHz, $CD_3OD$): δ 0.94 (s, 9H), 1.60-1.72 (m, 5H), 1.94-2.01 (m, 1H), 2.09-2.14 (m, 1H), 2.35 (d, J=10.4 Hz, 6H), 2.59 (s, 3H), 2.92 (s, 2H), 3.34-3.76 (m, 24H), 3.93 (s, 2H), 4.24 (d, J=15.6 Hz, 1H), 4.39-4.47 (m, 3H), 4.56-4.61 (m, 2H), 7.30-7.35 (m, 8H), 8.77 (s, 1H).

Example 21: (2S,4R)-1-[(2S)-2-(2-{3-[4-(5-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}pyrazin-2-yl)phenoxy]propoxy}acetamido)-3,3-dimethylbutanoyl]-4-hydroxy-N-{[4-(4-methyl-1,3-thiazol-5-yl)phenyl]methyl}pyrrolidine-2-carboxamide

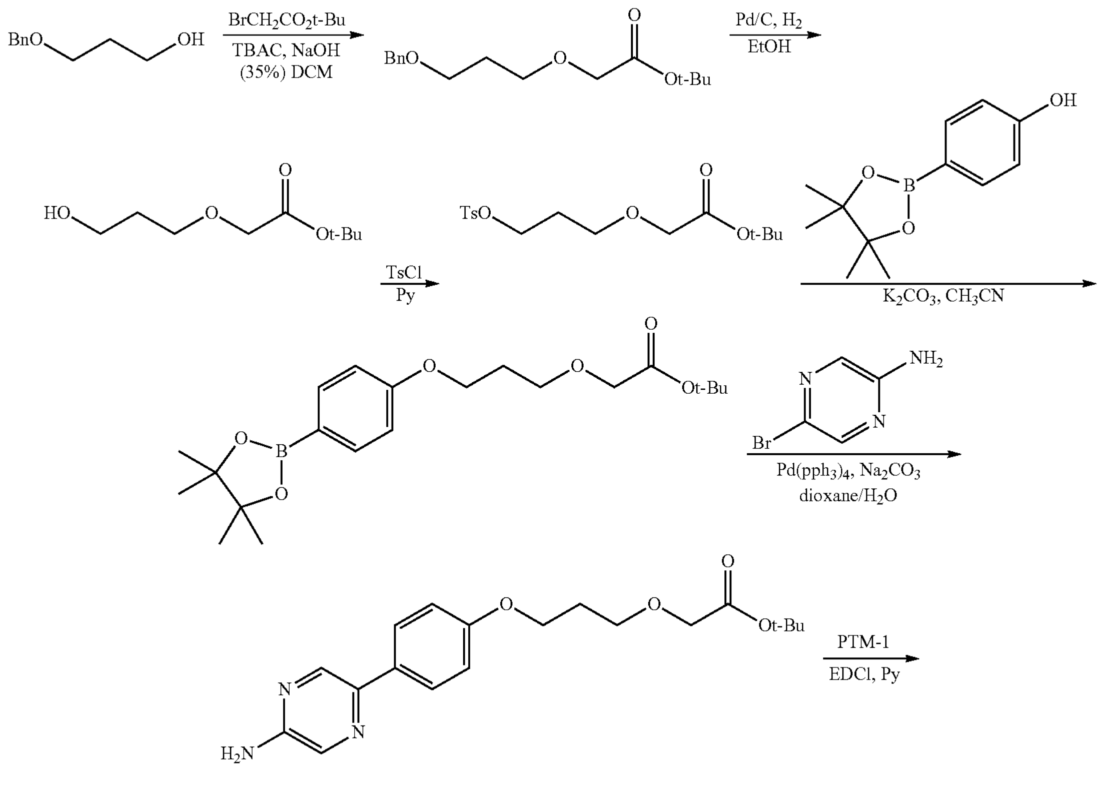

-continued

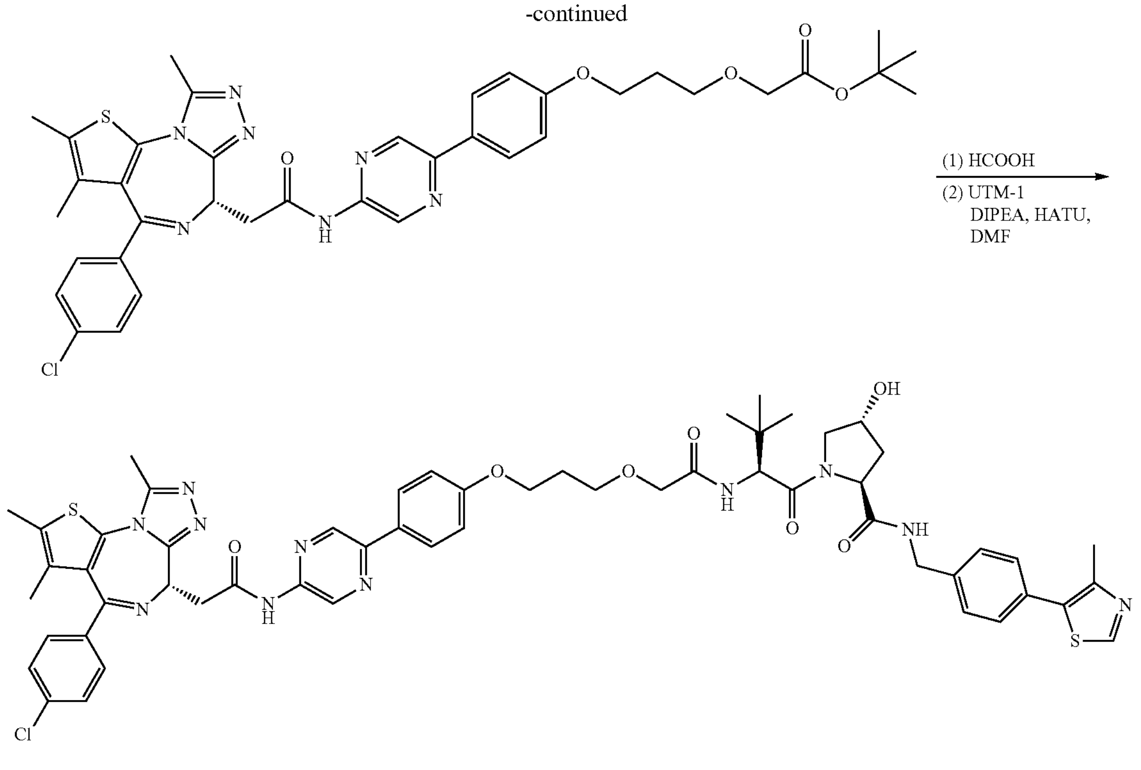

Step 1: Preparation of tert-butyl 2-(3-(benzyloxy)propoxy)acetate

A mixture containing 3-(benzyloxy)propan-1-ol (18 g, 108.43 mmol), tert-butyl 2-bromoacetate (84.6 g, 433.74 mmol), aqueous sodium hydroxide (35%, 360 mL), and tetra-butyl ammonium chloride (30.1 g, 108.43 mmol) in dichloromethane (360 mL) was stirred at room temperature overnight. The reaction mixture was poured into water (300 mL). The organic phase was separated, and the aqueous phase was extracted with dichloromethane (200 mL×2). The combined organic phase was washed with water (200×2 mL) and brine (200 mL), dried over anhydrous sodium sulfate, and concentrated under reduced pressure to give a crude residue which was purified by silica gel flash column chromatography (eluted with 0-20% ethyl acetate in hexane) to afford tert-butyl 2-(3-(benzyloxy)propoxy)acetate (25 g, yield 83%) as colorless oil.

LC/MS ($ES^+$): m/z 303.10 [$M+Na^+$]; $t_R$=3.128 min.

Step 2: Preparation of tert-butyl 2-(3-hydroxypropoxy)acetate

A mixture of tert-butyl 2-(3-(benzyloxy)propoxy)acetate (25 g, 89.3 mmol) and palladium on carbon (10%, 500 mg) in ethanol (250 mL) was stirred at room temperature overnight under hydrogen atmosphere. The mixture was filtered and the solid was washed with ethyl acetate (50 mL×2). The combined filtrate was concentrated under reduced pressure to afford tert-butyl 2-(3-hydroxypropoxy)acetate (16 g, yield 94%) as colorless oil which was used in next step without further purification.

$^1H$ NMR (400 MHz, $CDCl_3$): δ 1.48 (s, 9H), 1.84 (t, J=5.6 Hz, 2H), 2.50 (br, 1H), 3.68 (t, J=5.6 Hz, 2H), 3.81 (t, J=5.6 Hz, 2H), 3.97 (s, 2H).

Step 3: Preparation of tert-butyl 2-(3-(tosyloxy)propoxy)acetate

To a stirred solution of tert-butyl 2-(3-hydroxypropoxy) acetate (1.0 g, 5.26 mmol) in pyridine (5 mL) was added 4-toluenesulfonyl chloride (3 g, 15.77 mmol) at 0° C. The resulting mixture was allowed to warm up to room temperature and stirred at room temperature for 2 hours. The reaction mixture was diluted with dichloromethane (250 mL), washed with hydrochloric acid (1N, 60 mL×2), water (60 mL) and brine (50 mL), dried over anhydrous sodium sulfate, and concentrated under reduced pressure to give a crude residue which was purified by silica gel flash column chromatography (eluted with 10-50% ethyl acetate in hexane) to afford tert-butyl 2-(3-(tosyloxy)propoxy)acetate (1.0 g, yield 56%) as colorless oil.

LC/MS ($ES^+$): m/z 367.10 [$M+Na^+$]; $t_R$=2.917 min.

Step 4: Preparation of tert-butyl 2-(3-(4-(4,4,5,5-tetramethyl-1,3,2-dioxaborolan-2-yl)phenoxy)propoxy)acetate A mixture of tert-butyl 2-(3-(tosyloxy)propoxy)acetate (1 g, 2.9 mmol), 4-(4,4,5,5-tetramethyl-1,3,2-dioxaborolan-2-yl)phenol (830 mg, 3.5 mmol) and potassium carbonate (802 mg, 5.8 mmol) in acetonitrile (20 ml) was stirred at refluxing temperature overnight. The reaction mixture was cooled and partitioned between ethyl acetate(150 mL) and water (50 mL). The organic layer was collected, washed with brine (50 mL), dried over anhydrous sodium sulfate, and concentrated under reduced pressure to give a crude residue which was purified by silica gel flash column chromatography (eluted with 30-100% ethyl acetate in hexane) to afford tert-butyl 2-(3-(4-(4,4,5,5-tetramethyl-1,3,2-dioxaborolan-2-yl)phenoxy)propoxy)acetate (650 mg, yield 57%) as colorless oil.

LC/MS ($ES^+$): m/z 415.10 [$M+Na^+$]; $t_R$=4.185 min.

$^1H$ NMR (400 MHz, $CDCl_3$): δ 1.33 (s, 12H), 1.47 (s, 9H), 2.07-2.13 (m, 2H), 3.70 (t, J=6.0 Hz, 2H), 3.96 (s, 2H), 4.12 (t, J=6.0 Hz, 2H), 6.89 (d, J=8.8 Hz, 2H), 7.73 (d, J=8.8 Hz, 2H).

Step 5: Preparation of tert-butyl 2-(3-(4-(5-aminopyrazin-2-yl)phenoxy)propoxy)acetate To a solution containing tert-butyl 2-(3-(4-(4,4,5,5-tetramethyl-1,3,2-dioxaborolan-2-yl)phenoxy)propoxy)acetate (525 mg, 1.34 mmol), 5-bromopyrazin-2-amine (233 mg, 1.34 mmol), and sodium carbonate (284 mg, 2.68 mmol) in 1,4-dioxane (4 mL) and water (1 mL) was added tetrakis(triphenylphosphine)palladium (59 mg, 0.051 mmol) at room temperature under nitrogen atmosphere. The reaction mixture was then heated to 100° C. and stirred for 2 hours. The mixture was cooled to room temperature. The suspension solid was removed by filtration and washed with ethyl acetate (20 mL×2). The filtrates were partitioned between ethyl acetate (150 mL) and water (50 mL). The organic phase was separated, washed with brine (50 mL), dried over anhydrous sodium sulfate, and concentrated under reduced pressure to afford a crude residue which was purified by silica gel flash column chromatography (eluted with 30-100% ethyl acetate in hexane) to afford tert-butyl 2-(3-(4-(5-aminopyrazin-2-yl)phenoxy)propoxy)acetate (400 mg, yield 83%) as a white solid.

LC/MS ($ES^+$): m/z 360.40 [$M+H^+$]; $t_R$=2.532 min.

Step 6: Preparation of tert-butyl 2-{3-[4-(5-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}pyrazin-2-yl)phenoxy]propoxy}acetate A mixture containing tert-butyl 2-(3-(4-(5-aminopyrazin-2-yl)phenoxy)propoxy)acetate (100 mg, 0.28 mmol), 2-[(9S)-7-(4-chlorophenyl)-4,5,13-trimethyl-3-thia-1,8,11,12-tetraazatricyclo-[8.3.0.0$^{2,6}$]trideca-2(6),4,7,10,12-pentaen-9-yl]acetic acid (112 mg, 0.28 mmol) and 1-(3-dimethylaminopropyl)-3-ethylcarbodiimide hydrochloride (176 mg, 0.92 mmol) in pyridine (1 mL) was stirred at room temperature overnight. TLC showed formation of desired product. The reaction mixture was partitioned between ethyl acetate (150 mL) and water (50 mL). The organic layer was collected, washed with brine (50 mL), dried over anhydrous sodium sulfate, and concentrated under reduced pressure to give a crude residue which was purified by silica gel flash column chromatography (eluted with 0-4% methanol in dichloromethane) to afford tert-butyl 2-{3-[4-(5-{2-[(9S)-7-(4-chlorophenyl)-4,5,13-trimethyl-3-thia-1,8,11,12-tetraazatricyclo-[8.3.0.0$^{2,6}$]trideca-2(6),4,7,10,12-pentaen-9-yl]acetamido}pyrazin-2-yl)phenoxy]propoxy}acetate (82 mg, yield 40%) as colorless oil.

LC/MS ($ES^+$): m/z 742.20 [$M+H^+$]; $t_R$=3.585 min.

$^1H$ NMR (400 MHz, DMSO-d6): δ 1.42 (s, 9H), 1.64 (s, 3H), 1.96-2.02 (m, 2H), 2.43 (s, 3H), 2.61 (s, 3H), 3.31-3.33 (m, 1H), 3.60-3.72 (m, 4H), 3.99 (s, 2H), 4.11 (t, J=6.4 Hz, 2H), 4.65 (t, J=7.2 Hz, 1H), 7.06 (d, J=8.8 Hz, 2H), 7.43-7.50 (m, 4H), 8.05 (d, J=8.8 Hz, 2H), 8.97 (br, 1H), 9.32 (s, 1H).

Step 7: Preparation of (2S,4R)-1-[(2S)-2-(2-{3-[4-(5-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}pyrazin-2-yl)phenoxy]propoxy}acetamido)-3,3-dimethylbutanoyl]-4-hydroxy-N-{[4-(4-methyl-1,3-thiazol-5-yl)phenyl]methyl}pyrrolidine-2-carboxamide The isolated oily material from Step 6 (82 mg, 0.11 mmol) in formic acid (2 mL) was stirred at 60° C. for 2 hours. The volatiles were evaporated under reduced pressure. The residue was re-dissolved in anhydrous N,N-dimethylformamide (2 mL), followed by sequential addition of (2S,4R)-1-((S)-2-amino-3,3-dimethylbutanoyl)-4-hydroxy-N-(4-(4-methylthiazol-5-yl) benzyl)pyrrolidine-2-carboxamide hydrochloric acid salt (51 mg, 0.11 mmol), DIPEA (56 mg, 0.43 mmol), and HATU (102 mg, 0.27 mmol) at 0° C. The resulting mixture was allowed to warm up to room temperature and stirred at room temperature for 30 min. The mixture was partitioned between ethyl acetate (30 mL) and water (20 mL). The organic layer was collected, washed with brine (30 mL), dried over anhydrous sodium sulfate, and concentrated under reduced pressure to afford a crude residue which was purified by preparative TLC (eluting with 5% methanol in dichloromethane) to afford the desired compound (30 mg, yield 25%) as light yellow solid.

LC/MS ($ES^+$): m/z 1098.20 [$M+H^+$]; $t_R$=2.772 min.

$^1H$ NMR (400 MHz, $CD_3OD$): δ 1.03, 1.05 (two singles, 9H), 1.73 (s, 3H), 2.07-2.28 (m, 4H), 2.44, 2.48 (two singles, 6H), 2.74 (s, 3H), 3.65-3.67 (m, 1H), 3.73-3.91 (m, 5H), 4.00-4.10 (m, 2H), 4.22-4.26 (m, 2H), 4.34-4.39 (m, 1H), 4.52-4.63 (m, 3H), 4.72-4.80 (m, 2H), 7.08-7.11 (m, 2H), 7.37-7.50 (m, 8H), 7.60-7.63 (m, 1H), 7.92-7.94 (m, 2H), 8.75 (m, 1H), 8.85 (s, 1H), 9.36 (s, 1H).

Example 25: (2S,4R)-1-[(2S)-2-{2-[3-(3-{4-[(1S)-1-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethyl]phenoxy}propoxy)propoxy]acetamido}-3,3-dimethylbutanoyl]-4-hydroxy-N-{[4-(4-methyl-1,3-thiazol-5-yl)phenyl]methyl}pyrrolidine-2-carboxamide

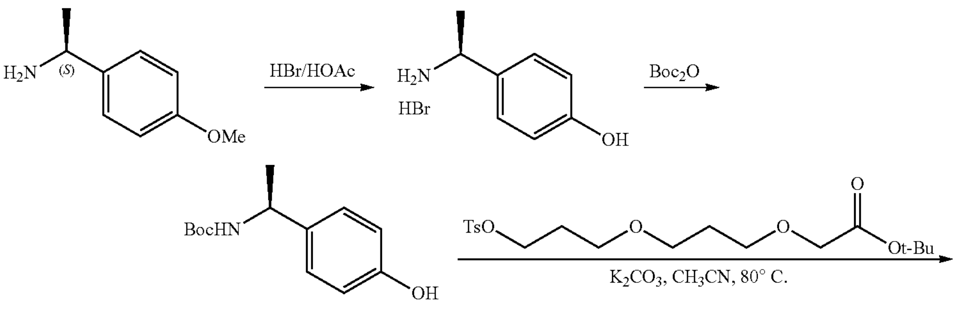

-continued
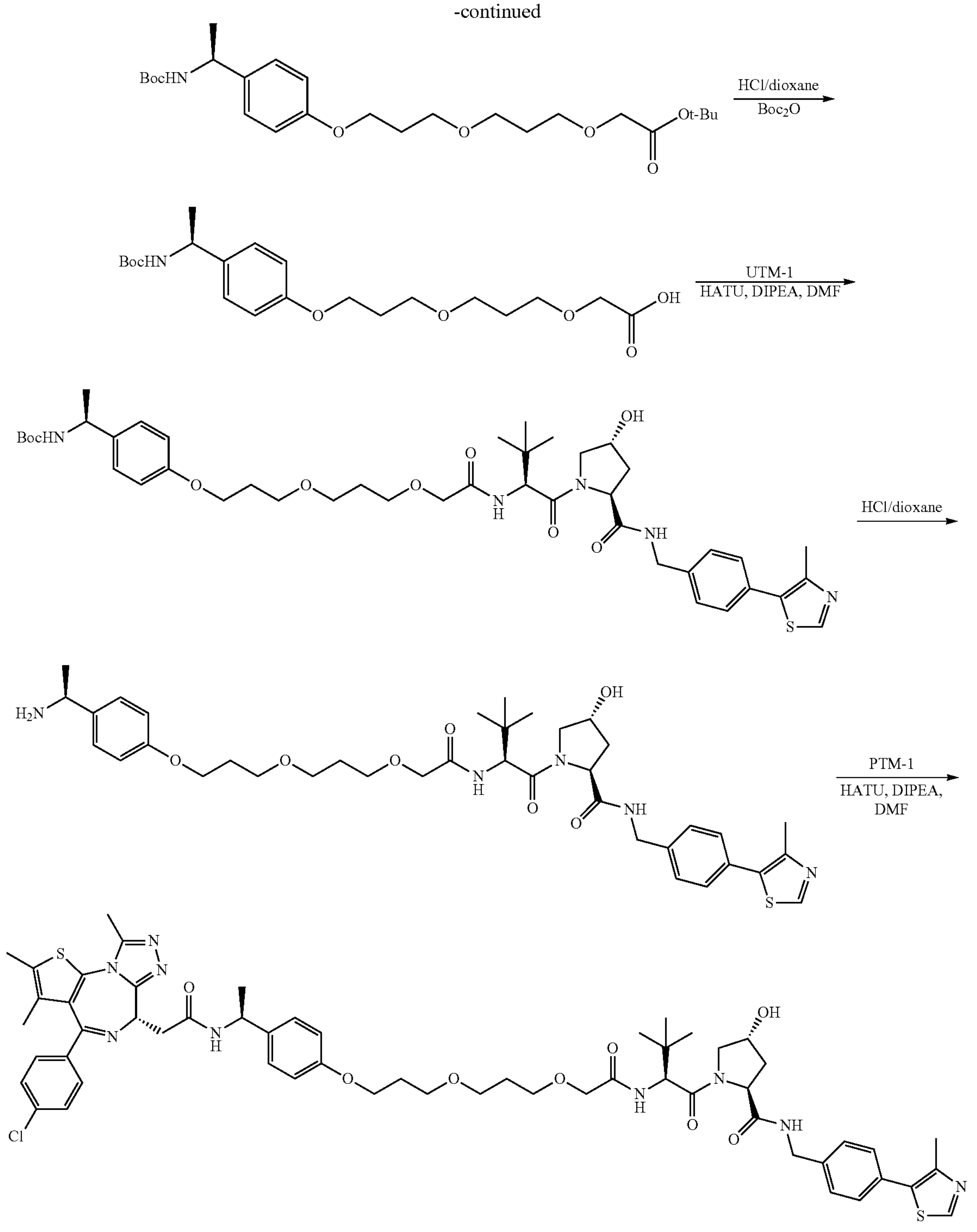
This molecule was prepared according the scheme above.
$^1$HNMR (400 MHz, $CDCl_3$): δ 0.93 (s, 9H), 1.44-1.51 (m, 2H), 1.57 (d, J=6.4 Hz, 3H), 1.68 (s, 3H), 1.99-2.02 (m, 4H), 2.41 (s, 3H), 2.52 (s, 3H), 2.67 (s, 3H), 3.21-3.25 (m, 1H), 3.40-3.64 (m, 11H), 3.99-4.13 (m, 3H), 4.31-4.41 (m, 2H), 4.50-4.56 (m, 1H), 4.62-4.66 (m, 2H), 4.72-4.75 (m, 1H), 5.07-5.10 (m, 1H), 6.84 (d, J=8.4 Hz, 2H), 7.09-7.11 (m, 1H), 7.21-7.24 (m, 2H), 7.34-7.42 (m, 9H), 7.65-7.67 (m, 1H), 8.69 (s, 1H).
LC/MS ($ES^+$): m/z 1106.3 [$M+H^+$]; to =2.719 min.

Example 27: (2S,4R)-1-[(2S)-2-[2-(3-{3-[4-(1-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}cyclopropyl)phenoxy]propoxy}propoxy)acetamido]-3,3-dimethylbutanoyl]-4-hydroxy-N-{[4-(4-methyl-1,3-thiazol-5-yl)phenyl]methyl}pyrrolidine-2-carboxamide
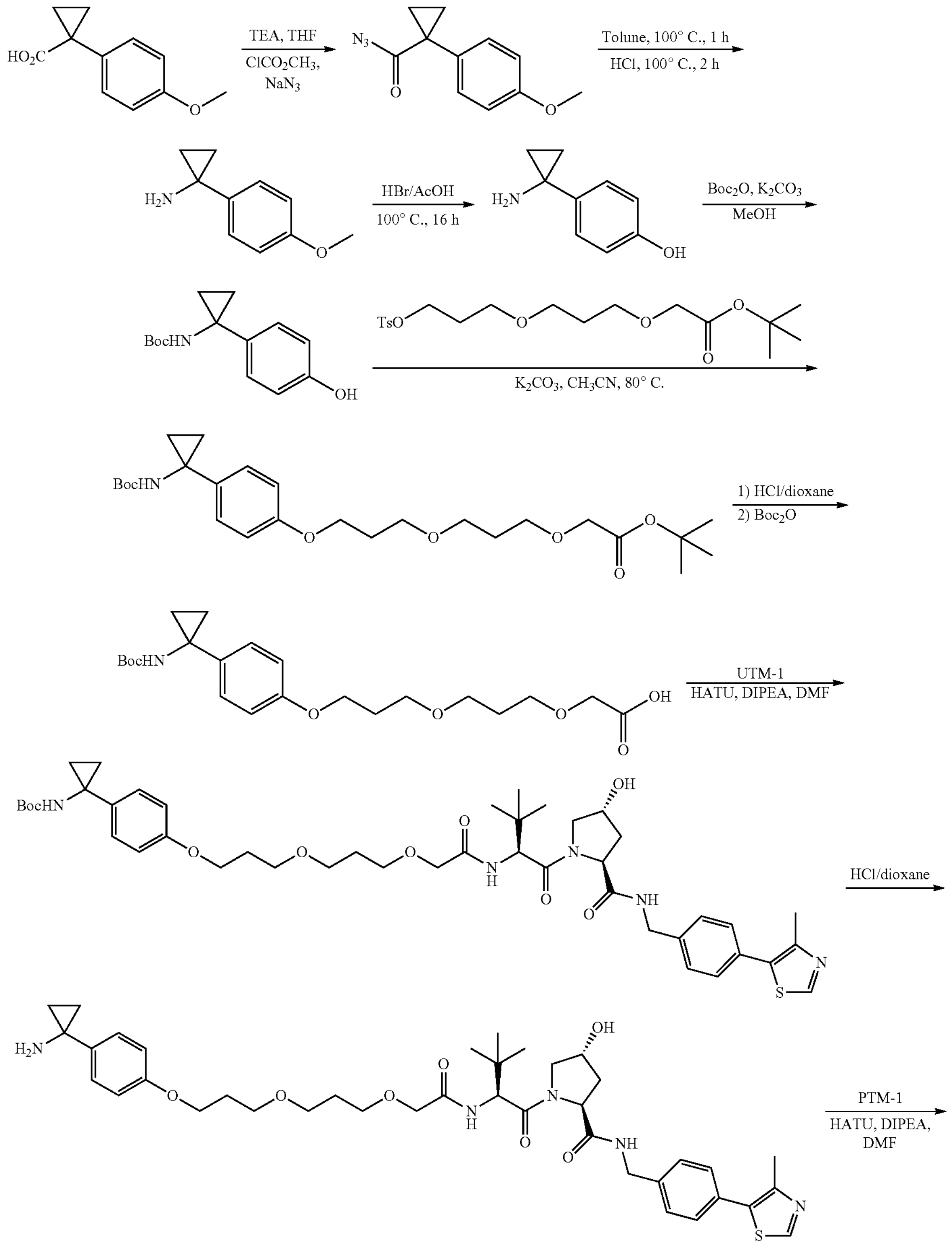

-continued

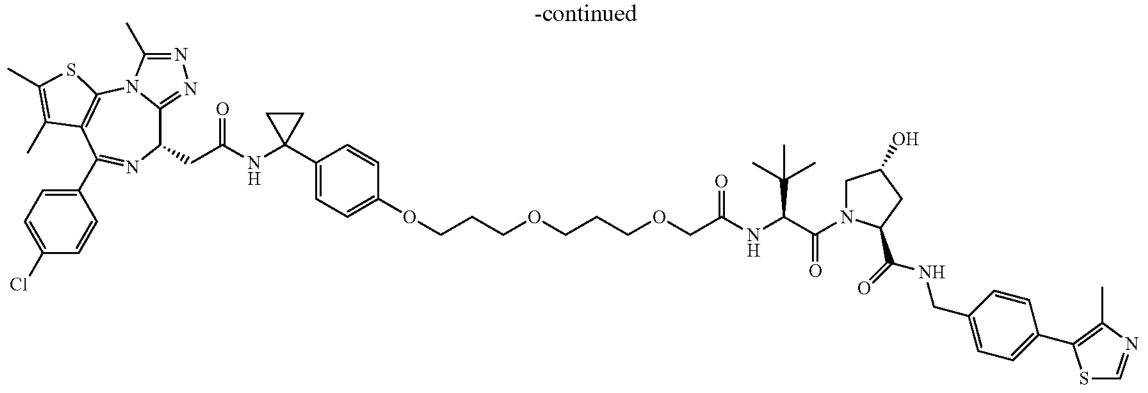

This molecule was prepared according to the scheme above.

LC/MS (ES$^+$): m/z 1118.3 [M+H$^+$]; $t_R$=2.510 min.

$^1$HNMR (400 MHz, $CDCl_3$): δ 0.96 (s, 9H), 1.18-1.25 (m, 3H), 1.32-1.42 (m, 1H), 1.66-1.76 (m, 5H), 1.99-2.01 (m, 3H), 2.12-2.16 (m, 1H), 2.41 (s, 4H), 2.51 (s, 3H), 2.67 (br, 3H), 3.30-3.66 (m, 11H), 4.04-4.08 (m, 3H), 4.29-4.32 (m, 1H), 4.53-4.56 (m, 3H), 4.72-4.74 (m, 2H), 6.80-6.82 (m, 2H), 7.09-7.11 (m, 2H), 7.28-7.35 (m, 10H), 7.92 (br, 1H), 8.78 (br, 1H).

Example 33: (2S,4R)-1-[(2S)-2-{2-[4-(4-{4-[(1R)-1-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethyl]phenyl}-1H-pyrazol-1-yl)butoxy]acetamido}-3,3-dimethylbutanoyl]-4-hydroxy-N-{[4-(4-methyl-1,3-thiazol-5-yl)phenyl]methyl}pyrrolidine-2-carboxamide

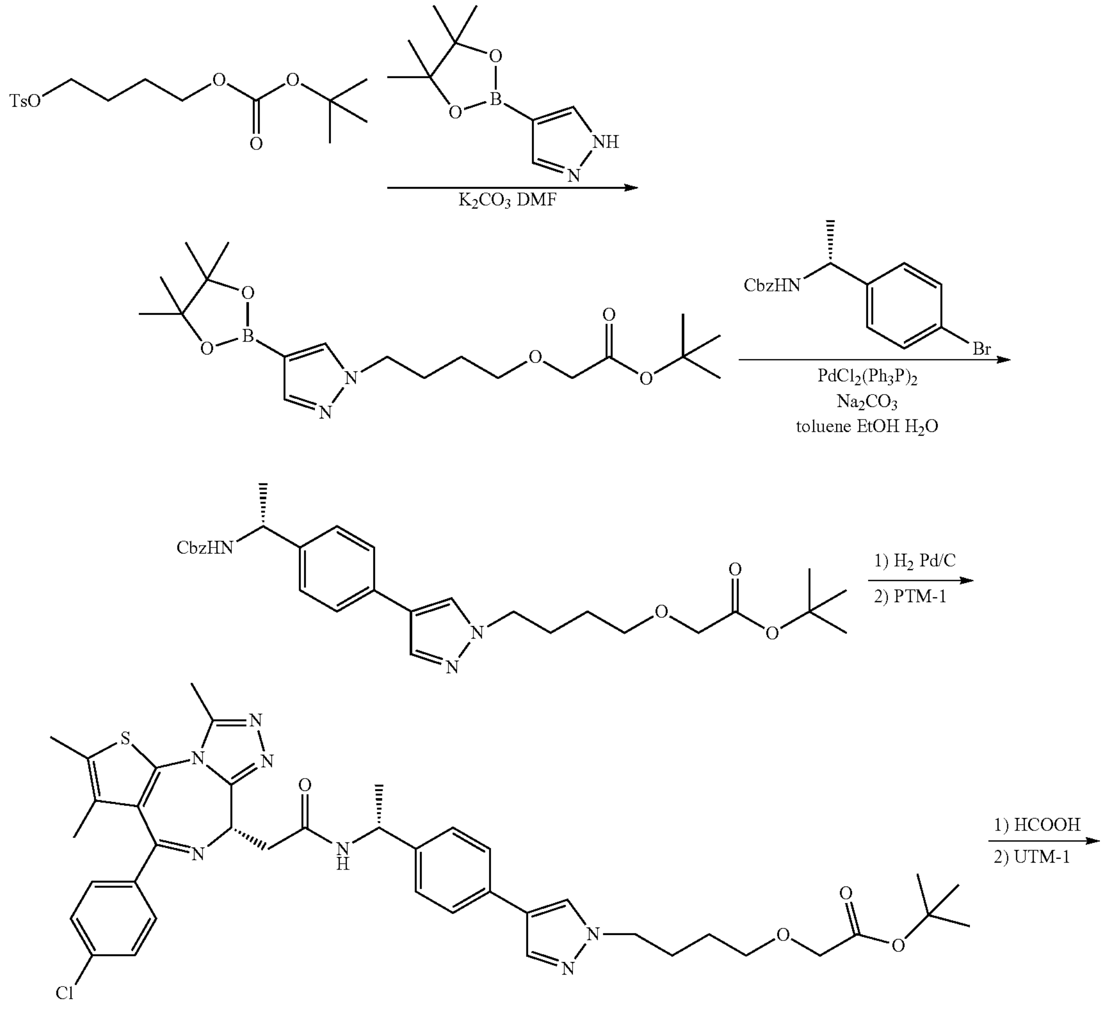

-continued

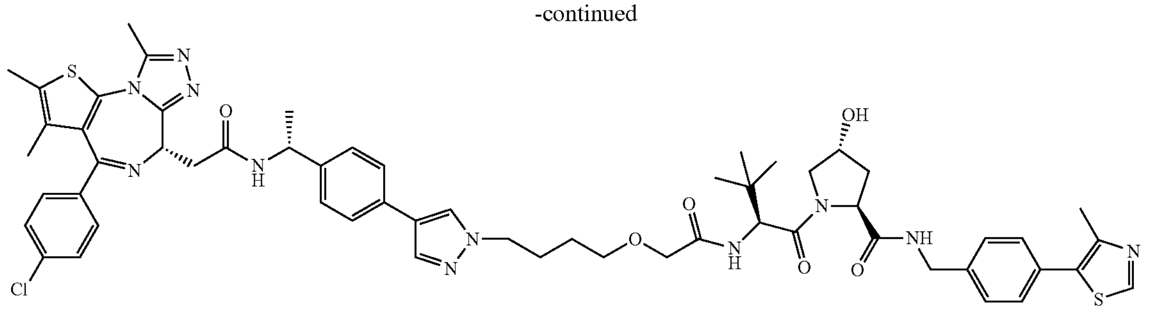

Step 1: Preparation of tert-butyl 5-(4-(4,4,5,5-tetramethyl-1,3,2-dioxaborolan-2-yl)-1H-pyrazol-1-yl) pentanoate)

A mixture of tert-butyl 5-(tosyloxy)pentanoate (600 mg, 1.67 mmol), 4-(4,4,5,5-tetramethyl-1,3,2-dioxaborolan-2-yl)-1H-pyrazole (357 mg, 1.84 mmol), and potassium carbonate (463 mg, 3.35 mmol) in acetonitrile (8 mL) was stirred at 80° C. overnight. The reaction mixture was partitioned between ethyl acetate (30 mL) and water (20 mL). The organic layer was collected, and the aqueous layer was extracted with ethyl acetate (20 mL×2). The combined organic layers were washed with brine (40 mL), dried over anhydrous sodium sulfate, and concentrated under reduced pressure to give a crude residue which was purified by silica gel flash column chromatography (eluted with 10-20% ethyl acetate in hexane) to afford tert-butyl 5-(4-(4,4,5,5-tetramethyl-1,3,2-dioxaborolan-2-yl)-1H-pyrazol-1-yl)pentanoate (500 mg, yield 78%) as colorless oil.

LC/MS (ES$^+$): m/z 381.1 [M+H]$^+$; $t_R$=1.511 min.

$^1$H NMR (400 MHz, $CDCl_3$): δ 1.32 (s, 12H), 1.47 (s, 9H), 1.55-1.62 (m, 2H), 1.95-2.02 (m, 2H), 3.51 (t, J=6.0 Hz, 2H), 3.93 (s, 2H), 4.18 (t, J=6.8 Hz, 2H), 7.69 (s, 1H), 7.77 (s, 1H).

Step 2: Preparation of (R)-tert-butyl 5-(4-(4-(1-(benzyloxycarbonylamino)ethyl)phenyl)-1H-pyrazol-1-yl)pentanoate To a stirred solution of tert-butyl 5-(4-(4,4,5,5-tetramethyl-1,3,2-dioxaborolan-2-yl)-1H-pyrazol-1-yl)pentanoate (200 mg, 0.52 mmol), (R)-benzyl 1-(4-bromophenyl)ethylcarbamate (160 mg, 0.48 mmol), and sodium carbonate (102 mg, 0.96 mmol) in toluene (10 mL)/ethanol (4 mL)/water (2 mL) was added bis(triphenylphosphine)palladium(II) chloride (68 mg, 0.10 mmol) at room temperature under nitrogen atmosphere. The mixture was degassed and refilled with nitrogen atmosphere for three times. The resulting mixture was refluxed for 2 hours. The reaction mixture was partitioned between ethyl acetate (30 mL) and water (20 mL). The organic layer was collected and the aqueous layer was extracted with ethyl acetate (20 mL×2). The combined organic layers were washed with brine (40 mL), dried over anhydrous sodium sulfate, and concentrated under reduced pressure to give a crude residue which was purified by silica gel flash column chromatography (eluted with 10-33% ethyl acetate in hexane) to afford (R)-tert-butyl 5-(4-(4-(1-(benzyloxycarbonylamino)ethyl)phenyl)-1H-pyrazol-1-yl)pentanoate (135 mg, yield 56%) as white solid.

LC/MS (ES$^+$): m/z 508.6 [M+H]$^+$; $t_R$=2.855 min.

$^1$H NMR (400 MHz, $CDCl_3$): δ 1.47-1.50 (m, 12H), 1.60-1.67 (m, 2H), 1.99-2.06 (m, 2H), 3.54 (t, J=6.0 Hz, 2H), 3.94 (s, 2H), 4.02 (t, J=6.8 Hz, 2H), 4.84-4.87 (m, 1H), 5.04-5.09 (m, 2H), 7.28-7.35 (m, 7H), 7.44 (d, J=8.0 Hz, 2H), 7.65 (s, 1H), 7.74 (s, 1H).

Step 3: Preparation of tert-butyl 2-[4-(4-{4-[(1R)-1-{2-[(9S)-7-(4-chlorophenyl)-4,5,13-trimethyl-3-thia-1,8,11,12-tetraazatricyclo[8.3.0.0$^2$,$^6$]trideca-2(6),4,7,10,12-pentaen-9-yl]acetamido}ethyl]phenyl}-1H-pyrazol-1-yl)butoxy]acetate A mixture of (R)-tert-butyl 5-(4-(4-(1-(benzyloxycarbonylamino)ethyl)phenyl)-1H-pyrazol-1-yl)pentanoate (135 mg, 0.27 mmol) and palladium on carbon (10%, 20 mg) in ethanol (5 mL) was stirred at 30° C. for 2 hours under hydrogen atmosphere (hydrogen balloon). The solid was removed through filtration and washed with ethyl acetate (10 mL×2). The filtrate was concentrated under reduced pressure. The residue was taken up in dry N,N-dimethylformamide (1 mL), followed by sequential addition of (S)-2-(4-(4-chlorophenyl)-2,3,9-trimethyl-6H-thieno[3,2-f][1,2,4]triazolo[4,3-a][1,4]diazepin-6-yl)acetic acid (63 mg, 0.16 mmol), DIPEA (115 mg, 0.89 mmol), and HATU (253 mg, 0.67 mmol) at 0° C. The resulting mixture was allowed to warm up to room temperature and stirred at room temperature for 30 min. The reaction mixture was partitioned between ethyl acetate (50 mL) and water (30 mL). The organic layer was collected, washed with brine (30 ml), dried over anhydrous sodium sulfate, and concentrated under reduced pressure to give a crude residue which was purified by silica gel flash column chromatography (eluted with 1-2.5% methanol in dichloromethane) to afford tert-butyl-2-[4-(4-{4-[(1R)-1-{2-[(9S)-7-(4-chlorophenyl)-4,5,13-trimethyl-3-thia-1,8,11,12-tetraazatricyclo[8.3.0.0$^2$,$^6$]trideca-2(6),4,7,10,12-pentaen-9-yl]acetamido}ethyl]phenyl}-1H-pyrazol-1-yl)butoxy]acetate (80.4 mg, yield 40.0%) as a brown solid. LC/MS (ES$^+$): m/z 756.2 [M+H]$^+$; $t_R$=2.690 min.

Step 4: Preparation of (2S,4R)-1-[(2S)-2-{2-[4-(4-{4-[(1R)-1-{2-[(9S)-7-(4-chlorophenyl)-4,5,13-trimethyl-3-thia-1,8,11,12-tetraazatricyclo[8.3.0.0$^2$,$^6$]trideca-2(6),4,7,10,12-pentaen-9-yl]acetamidoethyl]phenyl}-1H-pyrazol-1-yl)butoxy]acetamido}-3,3-dimethylbutanoyl]-4-hydroxy-N-{[4-(4-methyl-1,3-thiazol-5-yl)phenyl]methyl}pyrrolidine-2-carboxamide The isolated solid from step 3 (80.4 mg, 0.11 mmol) in formic acid (1 mL) was stirred at 60° C. for 1 hour. The volatiles were evaporated under reduced pressure. The residue was taken up in dry N,N-dimethylformamide (1 mL), followed by sequential addition of (2S,4R)-1-((S)-2-amino-3,3-dimethylbutanoyl)-4-hydroxy-N-(4-(4-methylthiazol-5-yl)benzyl)pyrrolidine-2-carboxamide hydrochloric acid salt (99 mg, 0.21 mmol), DIPEA (69 mg, 0.53 mmol), and HATU (122 mg, 0.32 mmol) at 0° C. The resulting mixture was allowed to warm up to room temperature and stirred at room temperature for 30 min. The reaction mixture was worked up and the crude product was purified by preparative TLC (eluted with 10% methanol in anhydrous dichloromethane) to afford the desired product (30.9 mg, 26.1% yield) as white solid.

LC/MS ($ES^+$): m/z 1112.3 $[M+H]^+$; $t_R$=2.235 min.

$^1H$ NMR (400 MHz, $CD_3OD$): δ 1.01, 1.03 (two singles, 9H), 1.37-1.40 (m, 2H), 1.52-1.55 (m, 3H), 1.59, 1.60 (two singles, 3H), 1.66-1.73 (m, 2H), 2.02-2.13 (m, 3H), 2.22-2.27 (m, 1H), 2.42 (s, 3H), 2.46, 2.49 (two singles, 3H), 2.70 (s, 3H), 3.15-3.22 (m, 1H), 3.49-3.62 (m, 3H), 3.80-4.06 (m, 4H), 4.26-4.39 (m, 3H), 4.49-4.61 (m, 4H), 4.70-4.72 (m, 1H), 5.12-5.16 (m, 1H), 7.06-7.08 (m, 2H), 7.17-7.20 (m, 2H), 7.39-7.48 (m, 6H), 7.57-7.60 (m, 2H), 7.86, 7.88 (two singles, 1H), 8.12, 8.16 (two singles, 1H), 8.86, 8.89 (two singles, 1H).

Example 36: (2S,4R)-1-[(2S)-2-(2-{2-[(4-{4-[(1R)-1-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethyl]phenyl}pyridin-2-yl)oxy]ethoxy}acetamido)-3,3-dimethylbutanoyl]-4-hydroxy-N-{[4-(4-methyl-1,3-thiazol-5-yl)phenyl]methyl}pyrrolidine-2-carboxamide

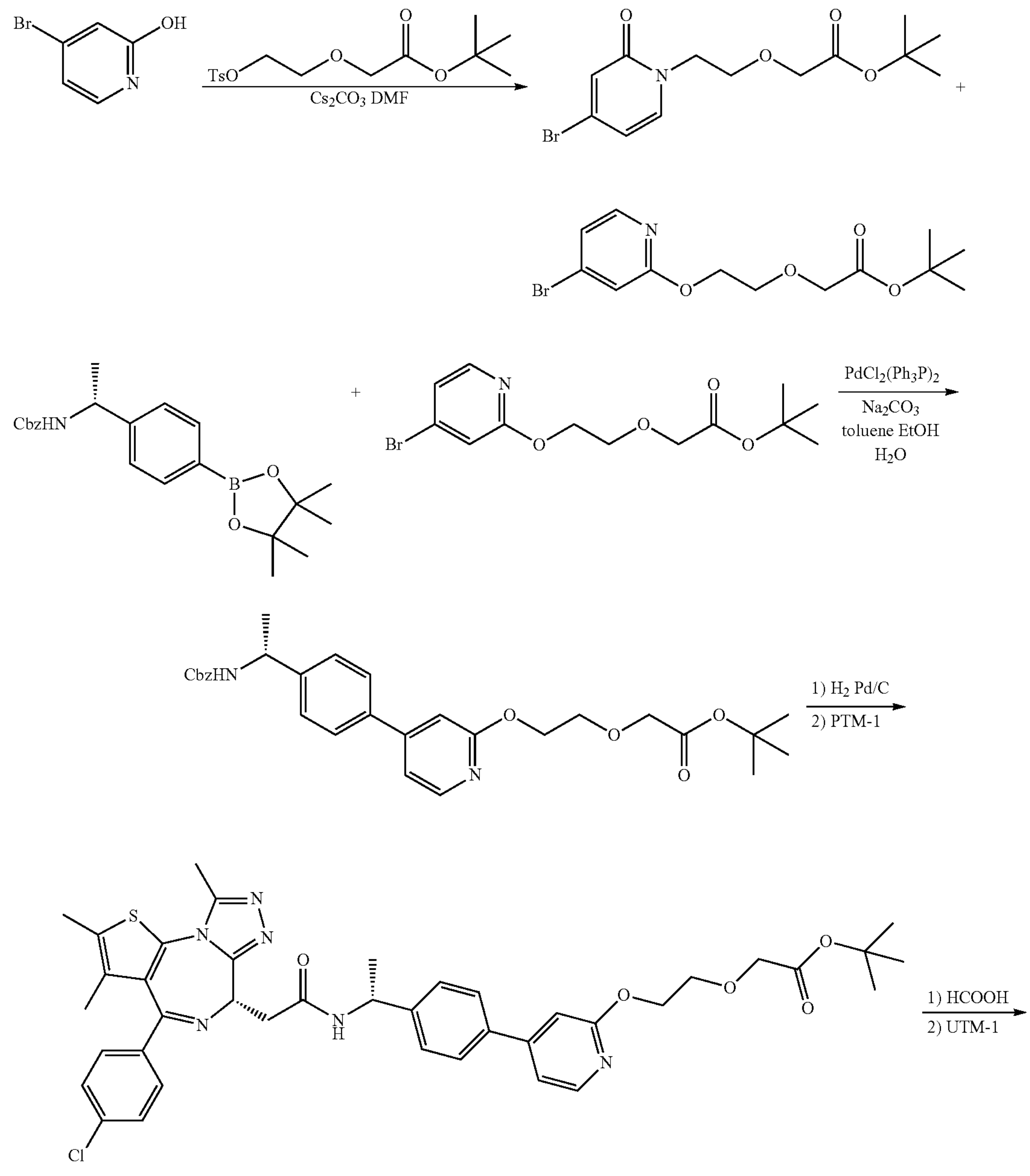

-continued

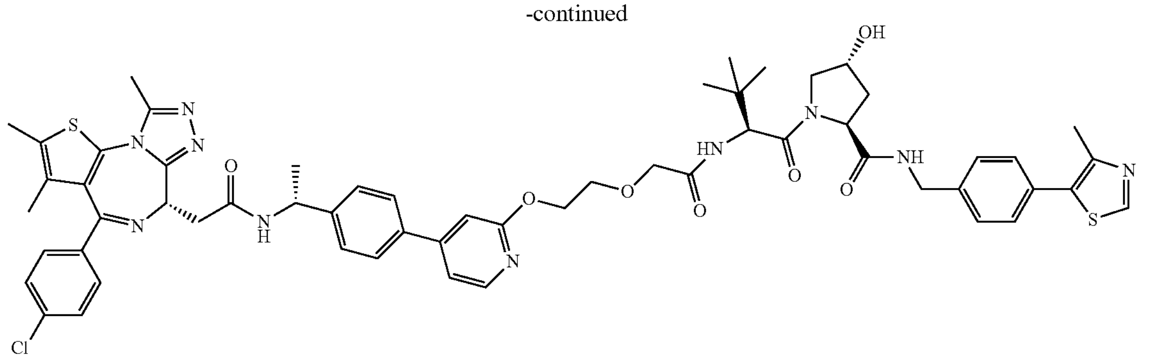

This compound was prepared using the synthetic route described above.

$^1$H NMR (400 MHz, $CD_3OD$): δ 1.02, 1.03 (two singles, 9H), 1.53-1.56 (m, 3H), 1.60, 1.62 (two singles, 3H), 2.07-2.13 (m, 1H), 2.21-2.26 (m, 1H), 2.42-2.49 (m, 6H), 2.70 (s, 3H), 3.22-3.27 (m, 1H), 3.48-3.54 (m, 1H), 3.80-3.90 (m, 2H), 3.98 (t, J=4.4 Hz, 2H), 4.15 (s, 2H), 4.32-4.37 (m, 1H), 4.47-4.60 (m, 6H), 4.74 (d, J=9.6 Hz, 1H), 5.13-5.20 (m, 1H), 7.12-7.19 (m, 4H), 7.25-7.30 (m, 2H), 7.33-7.46 (m, 4H), 7.56-7.61 (m, 2H), 7.71-7.83 (m, 3H), 8.18-8.20 (m, 1H), 8.62 (t, J=5.6 Hz, 1H), 8.85, 8.89 (two singles, 1H), 8.97 (d, J=8.0 Hz, 1H).

LC/MS ($ES^+$): m/z 1111.2 $[M+H]^+$; $t_R$=2.328 min.

Example 39: (2S,4R)-1-[(2S)-2-(2-{3-[(3-{4-[(1R)-1-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}-ethyl]phenyl}prop-2-yn-1-yl)oxy]propoxy}acetamido)-3,3-dimethylbutanoyl]-4-hydroxy-N-{[4-(4-methyl-1,3-thiazol-5-yl)phenyl]methyl}pyrrolidine-2-carboxamide

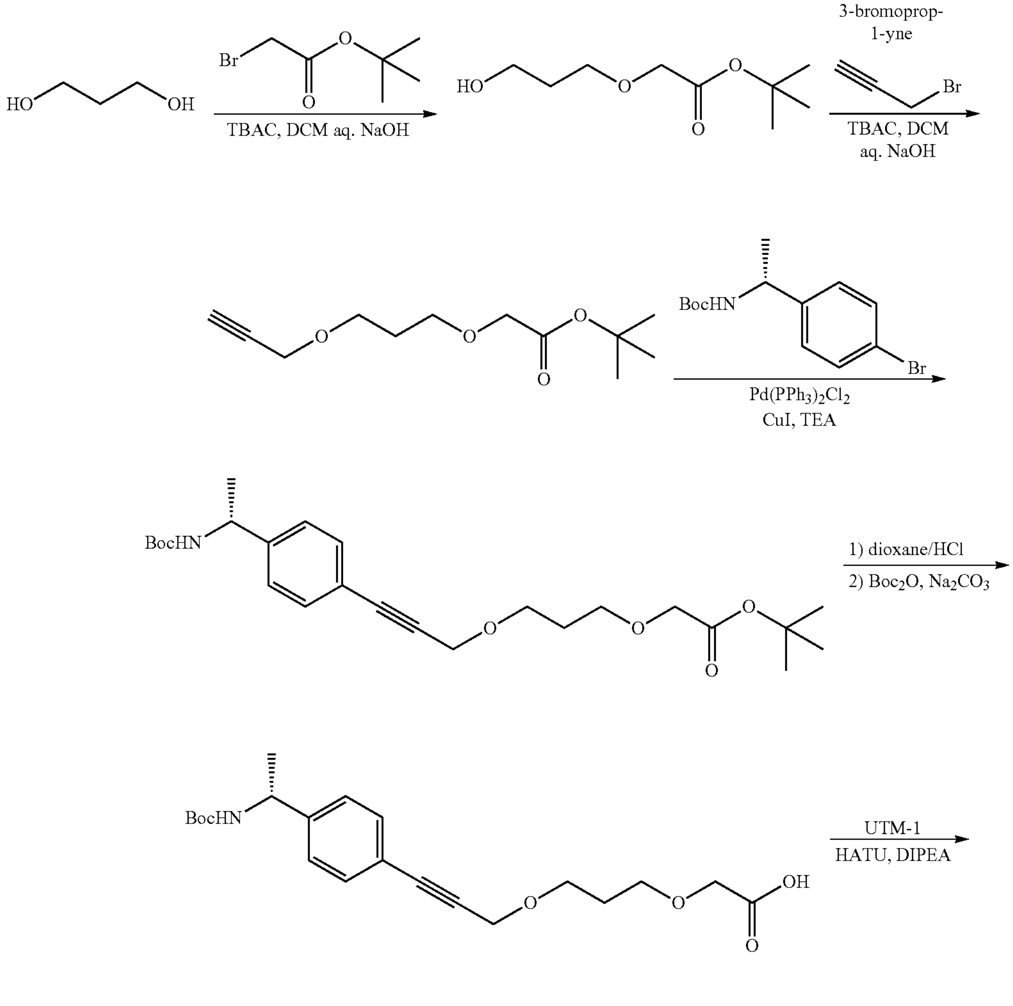

-continued

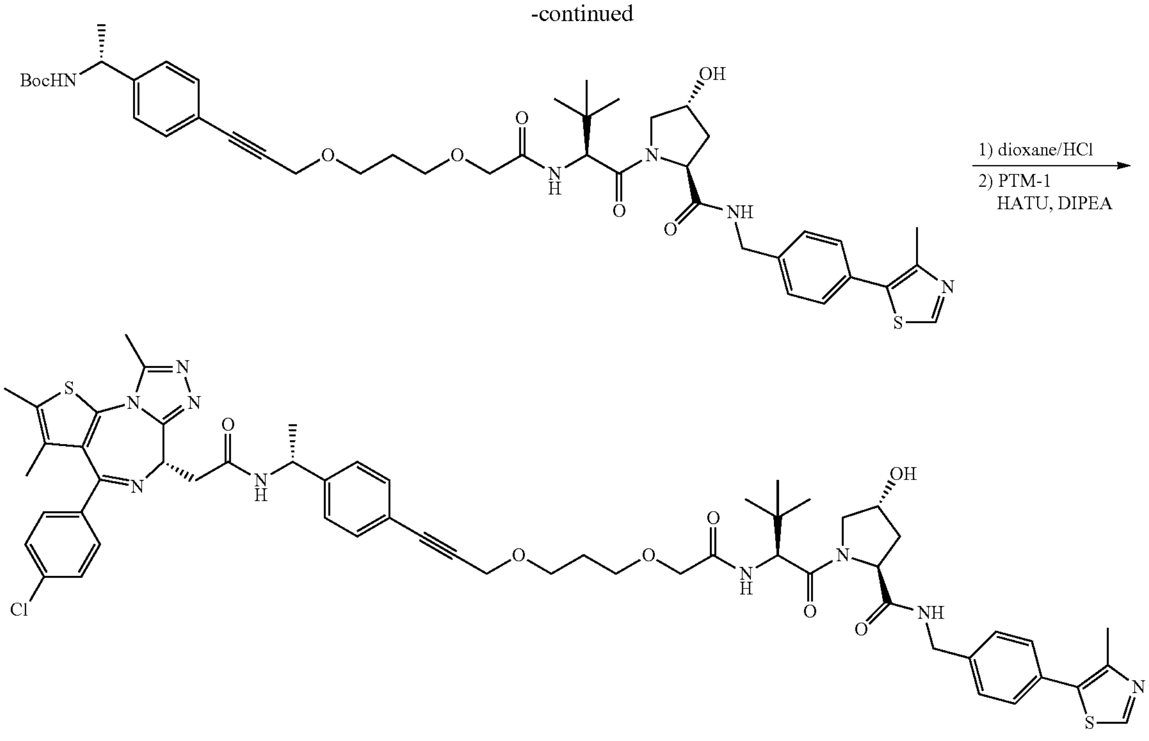

This compound was prepared using the synthetic sequence described above. The title compound was isolated as a white solid.

$^1$H NMR (400 MHz, $CD_3OD$): δ 0.90, 0.92 (two singles, 9H), 1.40 (d, J=6.8 Hz, 3H), 1.58 (s, 3H), 1.81-1.87 (m, 2H), 1.95-2.01 (m, 1H), 2.09-2.15 (m, 1H), 2.33-2.37 (m, 6H), 2.58 (s, 3H), 3.23-3.27 (m, 1H), 3.32-3.38 (m, 1H), 3.54-3.63 (m, 4H), 3.68-3.71 (m, 1H), 3.76, 3.78 (two singles, 1H), 3.84-3.93 (m, 2H), 4.20-4.25 (m, 1H), 4.27, 4.28 (two singles, 2H), 4.40-4.53 (m, 4H), 4.59-4.61 (m, 1H), 4.92-4.97 (m, 1H), 7.22-7.26 (m, 4H), 7.29-7.36 (m, 8H), 7.47 (d, J=9.2 Hz, 1H), 8.55-8.71 (m, 1H), 8.74, 8.78 (two singles, 1H); LC/MS 1086.20 $[M+H]^+$; $t_R$=2.623 min.

Example 43: (2S,4R)-1-[(2S)-2-{2-[(6-{4-[(1R)-1-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethyl]phenoxy}hexa-2,4-diyn-1-yl)oxy]acetamido}-3,3-dimethylbutanoyl]-4-hydroxy-N-{[4-(4-methyl-1,3-thiazol-5-yl)phenyl]methyl}pyrrolidine-2-carboxamide

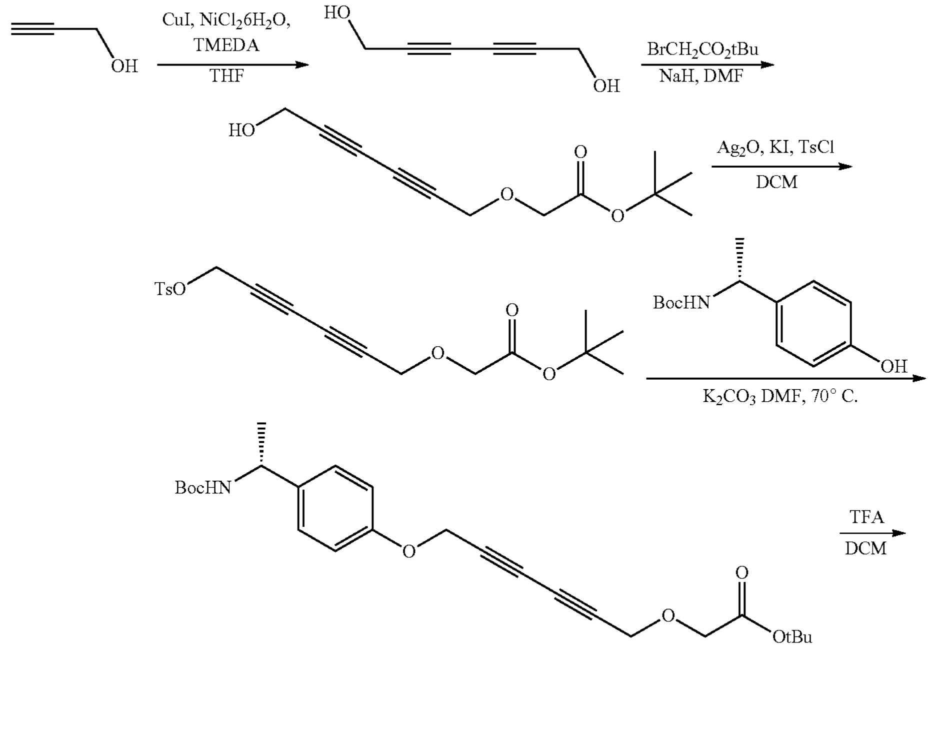

-continued
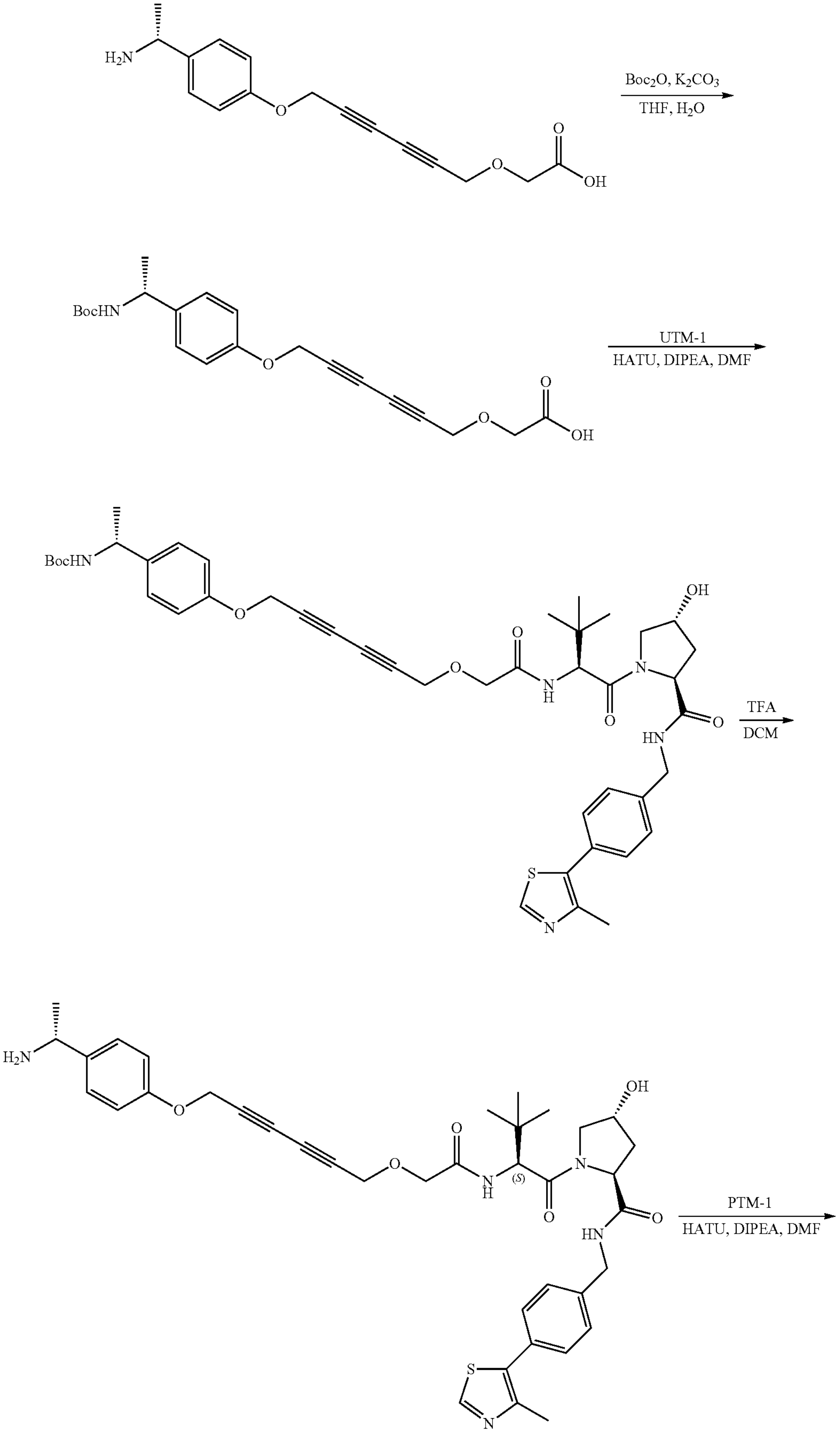

-continued

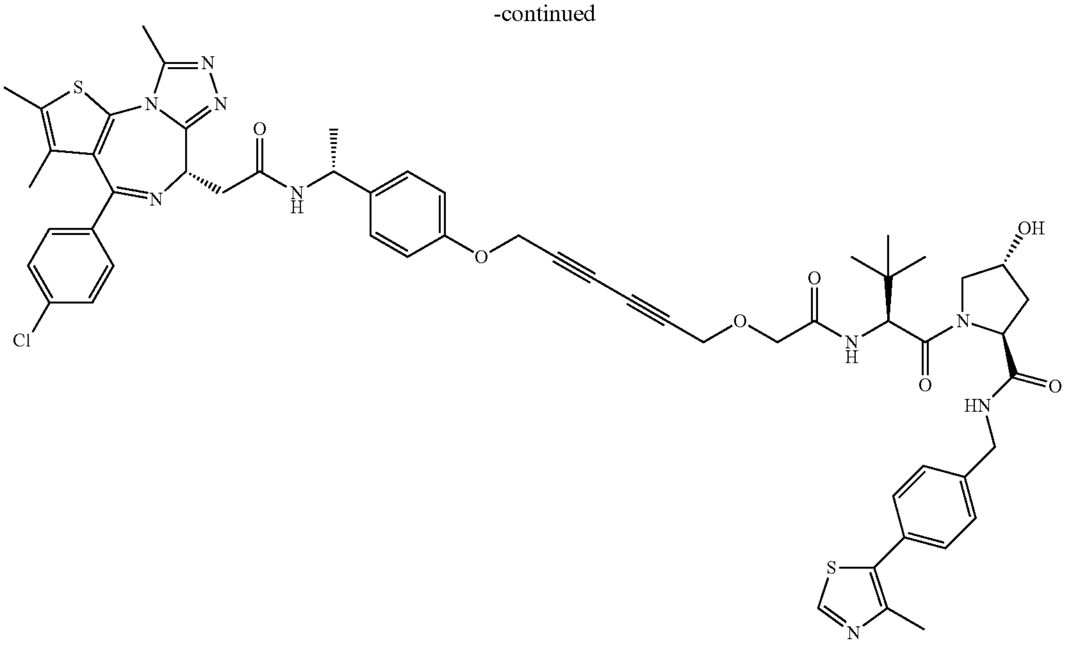

This compound was prepared using the synthetic sequence described above. The title compound was isolated as a white solid.

$^{1}$H NMR (400 MHz, $CD_3OD$): δ 1.01, 1.03 (two singles, 9H), 1.50 (d, J=6.8 Hz, 3H), 1.65 (s, 3H), 2.07-2.13 (m, 1H), 2.21-2.26 (m, 1H), 2.43 (s, 3H), 2.48 (s, 3H), 2.68 (s, 3H), 3.15-3.22 (m, 1H), 3.46-3.52 (m, 1H), 3.79-3.89 (m, 2H), 4.05 (s, 2H), 4.33-4.40 (m, 3H), 4.51-4.60 (m, 4H), 4.70 (d, J=9.2 Hz, 1H), 4.86 (s, 2H), 5.08-5.11 (m, 1H), 6.99 (d, J=8.8 Hz, 2H), 7.16 (d, J=8.8 Hz, 2H), 7.31 (d, J=8.4 Hz, 2H), 7.39-7.48 (m, 6H), 7.53 (d, J=9.2 Hz, 1H), 8.66 (t, J=6.0 Hz, 1H), 8.81 (br, 1H), 8.91 (br, 1H); LC/MS (ES 1082.2 $[M+H]^+$; $t_R$=2.503 min.

Example 48: (2S,4R)-1-[(2S)-2-{2-[3-(4-{4-[(1S)-1-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}ethyl]phenyl}piperazin-1-yl)-3-oxopropoxy]acetamido}-3,3-dimethylbutanoyl]-4-hydroxy-N-[(1S)-1-[4-(4-methyl-1,3-thiazol-5-yl)phenyl]ethyl]pyrrolidine-2-carboxamide

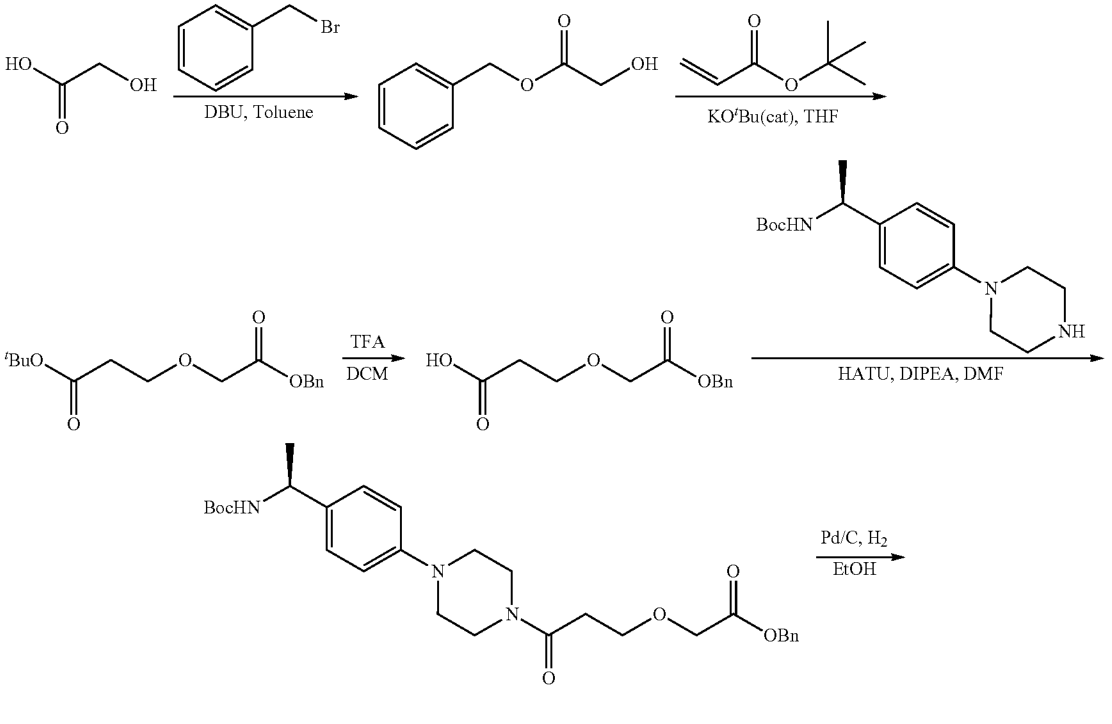

-continued
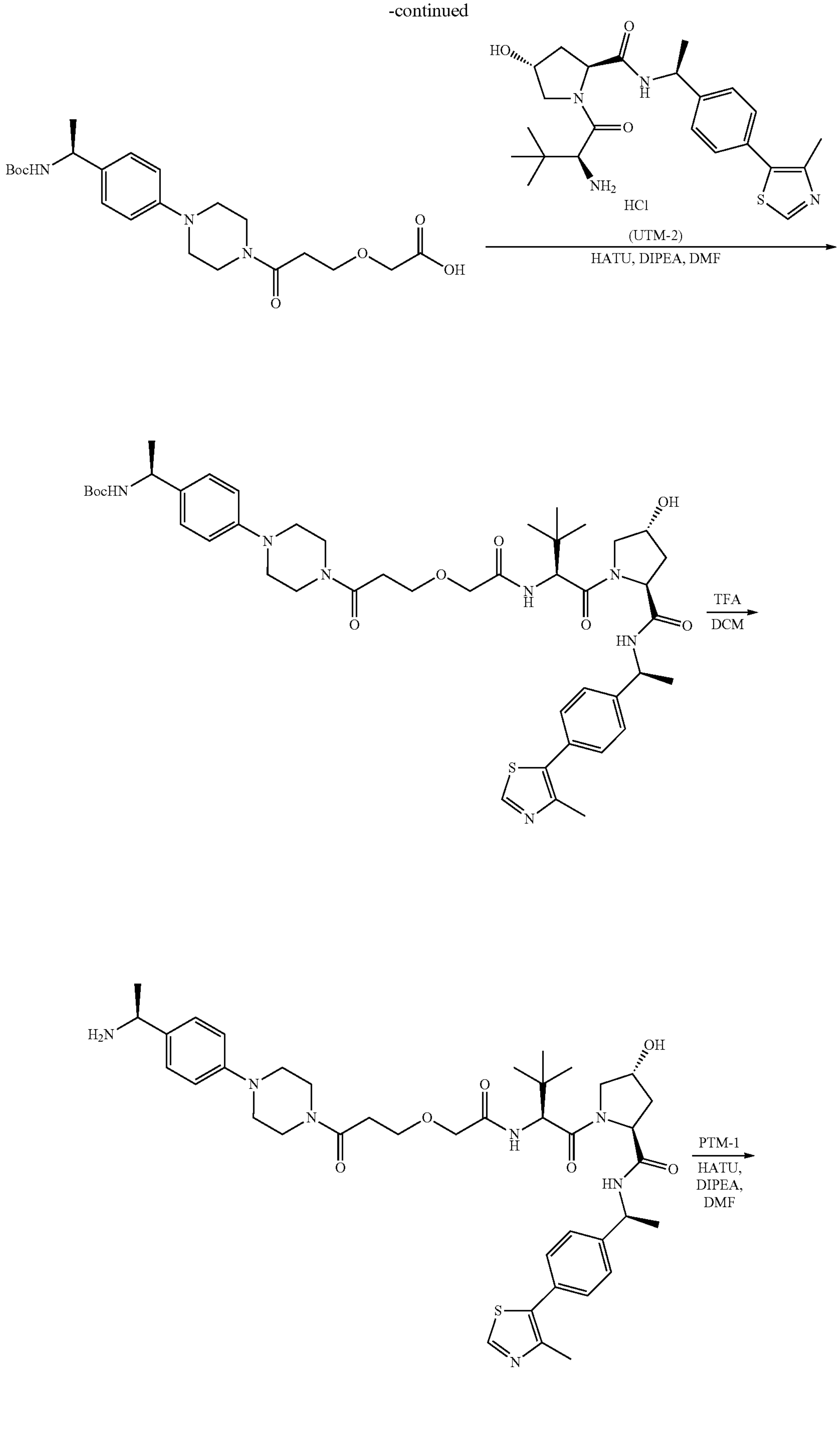

-continued

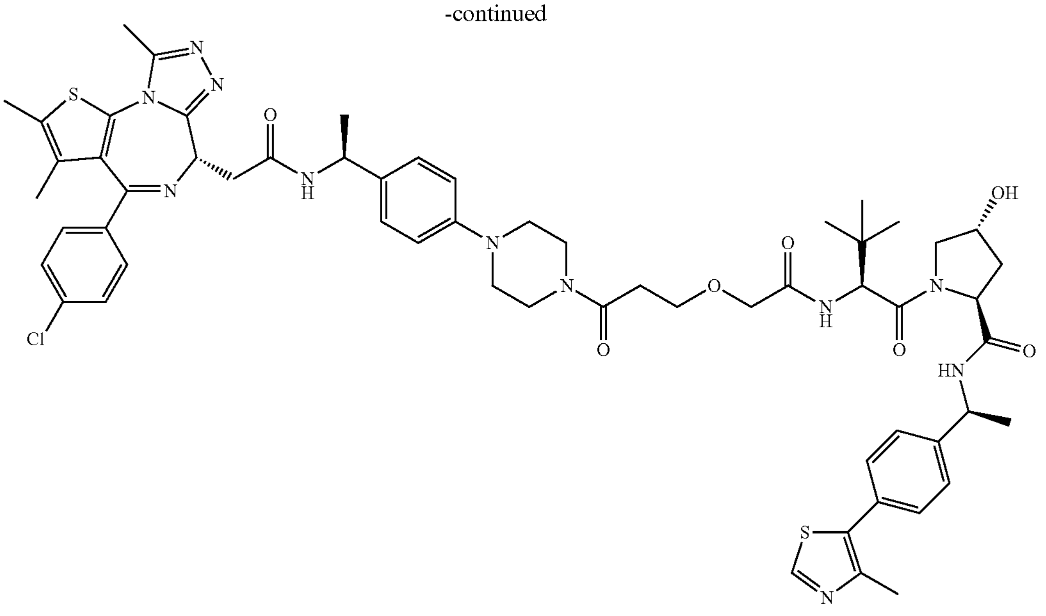

Step 1: Preparation of benzyl 2-hydroxyacetate

A mixture of 2-hydroxyacetic acid (5.0 g, 65.7 mmol), 1,8-diazabicyclo[5.4.0]undec-7-ene (9.9 g, 65.7 mmol) and benzyl bromide (13.0 g, 78.9.mmol) in toluene (150 mL) was refluxed overnight. The reaction mixture was worked up and the crude product was purified by silica gel flash column chromatography (eluent 20-50% ethyl acetate in hexane) to give tert-butyl benzyl 2-hydroxyacetate (6.9 g, yield 63%) as a colorless oil.

$^1$H NMR (400 MHz, $CDCl_3$): δ 2.60 (t, J=5.6 Hz, 1H), 4.19 (d, J=5.6 Hz, 2H), 5.21 (s, 2H), 7.35-7.37 (m, 5H).

Step 2: Preparation of tert-butyl 3-(2-(benzyloxy)-2-oxoethoxy)propanoate

To a mixture of benzyl 2-hydroxyacetate (5.0 g, 31.3 mmol) and tert-butyl acrylate (4.0 g, 31.3 mmol) in tetrahydrofuran (20 mL) was added potassium tert-butanolate (350 mg, 3.13 mmol) at room temperature. The resulting mixture was stirred at room temperature overnight. The mixture was concentrated to give a crude residue which was purified by silica gel flash column chromatography (eluent 30-60% ethyl acetate in hexane) to afford tert-butyl 3-(2-(benzyloxy)-2-oxoethoxy)propanoate (1.5 g, yield 16%) as colorless oil.

$^1$H NMR (400 MHz, $CDCl_3$): δ 1.45 (s, 9H), 2.54 (t, J=6.6 Hz, 2H), 3.79 (t, J=6.6 Hz, 2H), 4.14 (s, 2H), 5.18 (s, 2H), 7.32-7.36 (m, 5H).

Step 3: Preparation of 3-(2-(benzyloxy)-2-oxoethoxy)propanoic Acid

A mixture of tert-butyl 3-(2-(benzyloxy)-2-oxoethoxy) propanoate (200 mg, 0.714 mmol) and 2,2,2-trifluoroacetic acid (2 mL) in dichloromethane (2 mL) was stirred at room temperature for 1 hour. The volatiles were evaporated under reduced pressure to afford 3-(2-(benzyloxy)-2-oxoethoxy) propanoic acid (150 mg, crude) as yellow oil which was used in next step without further purification.

Step 4: Preparation of (S)-benzyl 2-(3-(4-(4-(1-((tert-butoxycarbonyl)amino)ethyl)phenyl)piperazin-1-yl)-3-oxopropoxy)acetate To a stirred solution of 3-(2-(benzyloxy)-2-oxoethoxy) propanoic acid (150 mg, 0.63 mmol), (S)-tert-butyl (1-(4-(piperazin-1-yl)phenyl)ethyl)carbamate (217 mg, 0.71 mmol), and DIPEA (362 mg, 2.8 mmol) in anhydrous N,N-dimethylformamide (5 mL) was added HATU (678 mg, 1.78 mmol) at 0° C. The resulting mixture was allowed to warm to room temperature and stirred at room temperature for 30 min. The mixture was worked up and the crude product was purified by silica gel flash column chromatography (eluted with 20-50% ethyl acetate in hexane) to afford (S)-benzyl 2-(3-(4-(4-(1-((tert-butoxycarbonyl)amino) ethyl)phenyl)piperazin-1-yl)-3-oxopropoxy)acetate (209 mg, yield 63%) as colorless oil.

$^1$H NMR (400 MHz, $CDCl_3$): δ 1.41-1.43 (m, 12H), 2.71 (t, J=6.6 Hz, 2H), 3.10-3.15 (m, 4H), 3.62-3.64 (m, 2H), 3.75-3.77 (m, 2H), 3.90 (t, J=6.4 Hz, 2H), 4.16 (s, 2H), 4.71 (br, 1H), 5.18 (s, 2H), 6.87 (d, J=8.8 Hz, 2H), 7.21 (d, J=8.4 Hz, 2H), 7.32-7.36 (m, 5H).

Step 5: Preparation of (S)-2-(3-(4-(4-(1-((tert-butoxycarbonyl)amino)ethyl)phenyl)piperazin-1-yl)-3-oxopropoxy)acetic Acid To a solution containing (S)-benzyl 2-(3-(4-(4-(1-((tert-butoxycarbonyl)amino)ethyl)phenyl)piperazin-1-yl)-3-oxopropoxy)acetate (170 mg, 0.323 mmol) in ethanol (10 mL) was added palladium on carbon (10%, 20 mg) and the mixture was stirred at room temperature overnight under hydrogen atmosphere (hydrogen balloon). The mixture was filtered and the filter cake was washed with ethanol (10 mL×2). The filtrates were concentrated under reduced pressure to afford (S)-2-(3-(4-(4-(1-((tert-butoxycarbonyl) amino)ethyl)phenyl)piperazin-1-yl)-3-oxopropoxy)acetic acid (130 mg, yield 95%) as colorless oil.

LC/MS ($ES^+$): m/z 458.20 $[M+H]^+$; $t_R$=2.075 min.

Step 6: Preparation of tert-butyl ((S)-1-(4-(4-(3-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)propanoyl)piperazin-1-yl)phenyl)ethyl)carbamate To a stirred solution of (S)-2-(3-(4-(4-(1-((tert-butoxycarbonyl)amino)ethyl)phenyl)piperazin-1-yl)-3-oxopropoxy)acetic acid (150 mg, 0.3 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (144 mg, 0.3 mmol), and DIPEA (322 mg, 2.5 mmol) in anhydrous N,N-dimethylformamide (2 mL) was added HATU (285 mg, 0.49 mmol) at 0° C. The resulting mixture was allowed to warm to room temperature and stirred at room temperature for 20 min. The mixture was partitioned between ethyl acetate (50 mL) and water (30 mL). The organic layer was collected, washed with brine (20 mL), dried over anhydrous sodium sulfate, and concentrated under reduced pressure to give a crude residue which was purified by silica gel flash column chromatography (eluted with 1-8% methanol in dichloromethane) to afford tert-butyl ((S)-1-(4-(4-(3-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)propanoyl)piperazin-1-yl)phenyl)ethyl)carbamate (170 mg, yield 65%) as a white solid.

LC/MS ($ES^+$): m/z 862.4 $[M+H]^+$; $t_R$=2.390 min.

$^1$H NMR (400 MHz, $CD_3OD$): δ 1.07 (s, 9H), 1.37 (d, J=6.8 Hz, 3H), 1.42 (s, 9H), 1.49 (d, J=7.2 Hz, 3H), 1.99-2.02 (m, 1H), 2.19-2.23 (m, 1H), 2.49 (s, 3H), 3.14-3.28 (m, 4H), 3.74-3.81 (m, 6H), 3.86-3.91 (m, 4H), 4.04-3.13 (m, 2H), 4.46 (br, 1H), 4.65-4.68 (m, 3H), 4.99-5.03 (m, 1H), 6.96 (d, J=8.8 Hz, 2H), 7.22 (d, J=8.8 Hz, 2H), 7.40-7.46 (m, 5H), 8.50 (d, J=7.2 Hz, 1H), 8.88 (s, 1H).

Step 7: Preparation of (2S,4R)-1-((S)-2-(2-(3-(4-(4-((S)-1-aminoethyl)phenyl)piperazin-1-yl)-3-oxopropoxy)acetamido)-3,3-dimethylbutanoyl)-4-hydroxy-N—((S)-1-(4-(4-methylthiazol-5-yl)phenyl)ethyl)pyrrolidine-2-carboxamide A mixture of tert-butyl ((S)-1-(4-(4-(3-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)propanoyl)piperazin-1-yl)phenyl)ethyl)carbamate (150 mg, 0.71 mmol) and 2,2,2-trifluoroacetic acid (2 mL) in dichloromethane (2 mL) was stirred at room temperature for 1 hour. The volatiles were evaporated under reduced pressure to afford (2S,4R)-1-((S)-2-(2-(3-(4-(4-((S)-1-aminoethyl)phenyl)piperazin-1-yl)-3-oxopropoxy)acetamido)-3,3-dimethylbutanoyl)-4-hydroxy-N—((S)-1-(4-(4-methylthiazol-5-yl)phenyl)ethyl)pyrrolidine-2-carboxamide (100 mg, crude) as yellow oil which was used in next step without further purification.

LC/MS ($ES^+$): m/z 785.20 $[M+Na]^+$; $t_R$=1.487 min.

Step 8: Preparation of (2S,4R)-1-[(2S)-2-{2-[3-(4-{4-[(1S)-1-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethyl]phenyl}piperazin-1-yl)-3-oxopropoxy]acetamido}-3,3-dimethylbutanoyl]-4-hydroxy-N-[(1S)-1-[4-(4-methyl-1,3-thiazol-5-yl)phenyl]ethyl]pyrrolidine-2-carboxamide The amide coupling of the amine from Step 7 with carboxylic acid PTM-1 afforded the desired product (yield 28%) as a white solid.

LC/MS: ($ES^+$) m/z 1144.3 $[M+H]^+$; $t_R$=2.430 min.

$^1$H NMR (400 MHz, $CD_3OD$): δ 1.04, 1.07 (two singles, 9H), 1.47-1.52 (m, 6H), 1.70 (s, 3H), 1.98-2.05 (m, 1H), 2.17-2.23 (m, 1H), 2.44-2.47 (m, 6H), 2.69 (s, 3H), 2.77-2.83 (m, 2H), 3.14-3.20 (m, 4H), 3.28-3.29 (m, 1H), 3.42-3.46 (m, 1H), 3.77-3.88 (m, 8H), 4.00-4.05 (m, 2H), 4.45-4.46 (m, 1H), 4.58-4.68 (m, 3H), 4.99-5.03 (m, 2H), 6.96 (d, J=8.4 Hz, 2H), 7.29 (d, J=8.0 Hz, 2H), 7.41-7.43 (m, 8H), 8.47-8.49 (m, 1H), 8.63-8.65 (m, 1H), 8.86 (s, 1H).

Example 55: (2S,4R)-1-[(2S)-3,3-dimethyl-2-(2-{3-[3-(4-{2-[(9S)-4,5,13-trimethyl-7-phenyl-3-thia-1,8,11,12-tetraazatricyclo[8.3.0.0$^{2,6}$]trideca-2(6),4,7,10,12-pentaen-9-yl]acetamido}phenoxy)propoxy]propoxy}acetamido)butanoyl]-4-hydroxy-N-{[4-(4-methyl-1,3-thiazol-5-yl)phenyl]methyl}pyrrolidine-2-carboxamide

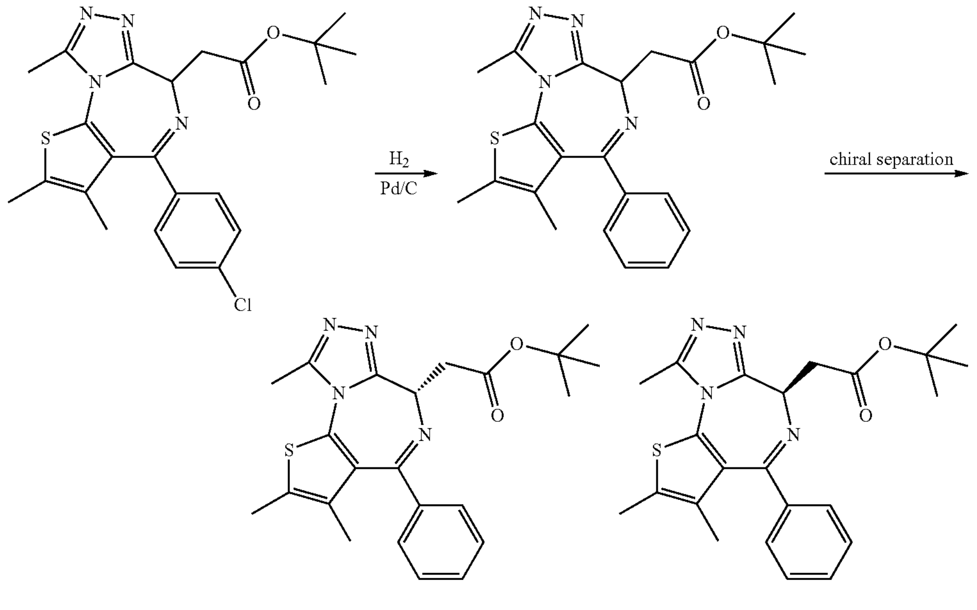

-continued

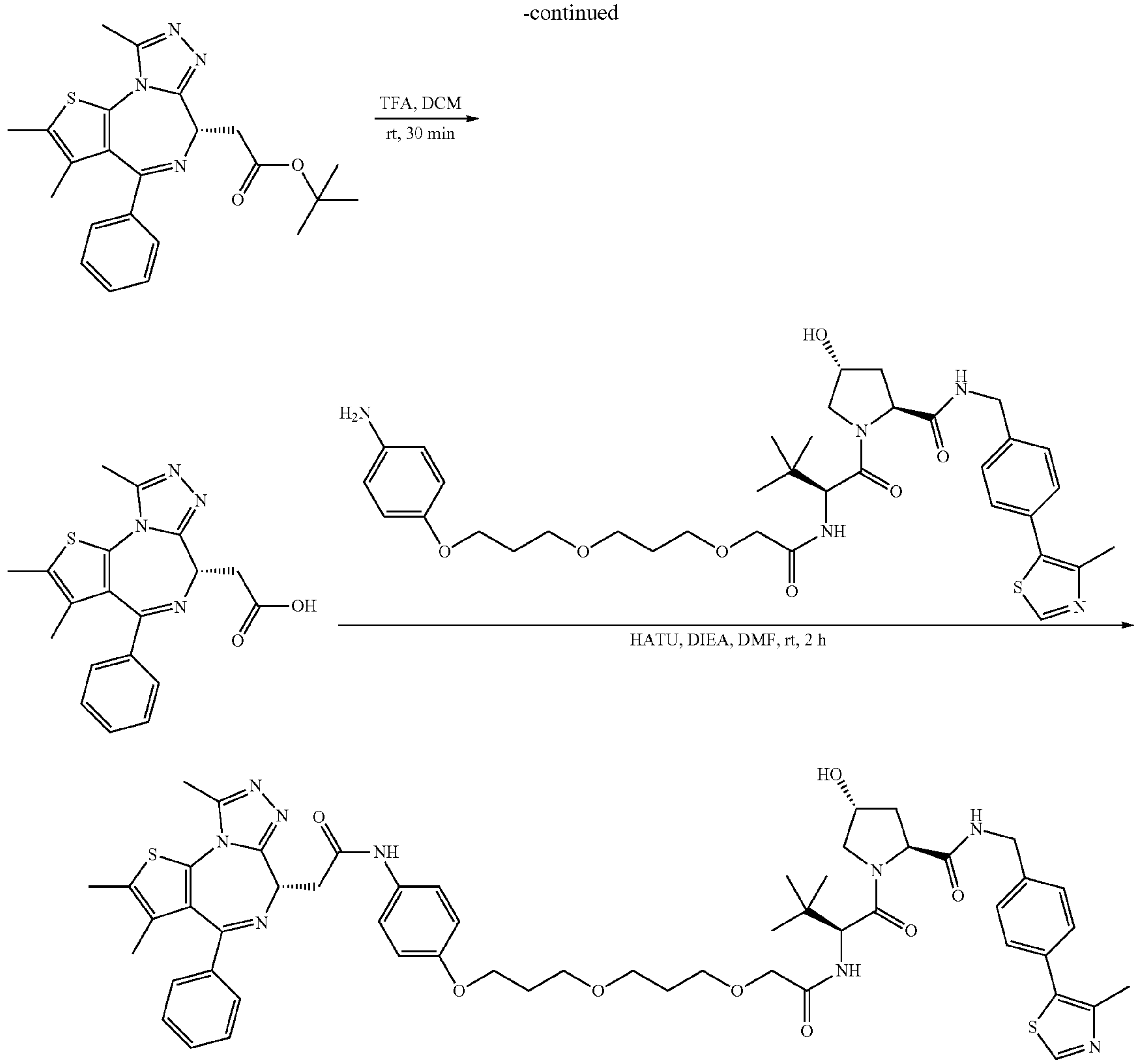

The (+/−)-JQ1 (prepared according to literature) was hydrogenated in the presence of catalytic amount of palladium on carbon to provide tert-butyl 2-[4,5,13-trimethyl-7-phenyl-3-thia-1,8,11,12-tetraazatricyclo[8.3.0.0$^{[2,6]}$]trideca-2(6),4,7,10,12-pentaen-9-yl]acetate. This material (30 mg) was separated by chiral HPLC (Hex:EtOH=70:30, column: ChiralPAK IC-3, Size: 0.46*5 cm, 3 um). The chiral separation resulted in 14.2 mg of tert-butyl 2-[(9R)-4,5,13-trimethyl-7-phenyl-3-thia-1,8,11,12-tetraazatricyclo [8.3.0.0$^{2,6}$]]trideca-2(6),4,7,10,12-pentaen-9-yl]acetate as an off-white solid and 5.9 mg of tert-butyl 2-[(9S)-4,5,13-trimethyl-7-phenyl-3-thia-1,8,11,12-tetraazatricyclo [8.3.0.0$^{2,6}$]]trideca-2(6),4,7,10,12-pentaen-9-yl]acetate as an off-white solid.

$^{1}$H NMR (400 MHz, $CD_3OD$): δ 7.52-7.40 (m, 5H), 4.60-4.56 (m, 1H), 3.52-3.41 (m, 2H), 2.73 (s, 3H), 2.47 (s, 3H), 1.69 (s, 3H), 1.51 (s, 9H); LC-MS ($ES^+$): m/z 423.10 [$MH^+$].

The chiral ester from the chiral separation was first converted to the corresponding carboxylic acid and then coupled with the aniline derivative (prepared with the same synthetic method as described in Example 10) to provide crude (2S,4R)-1-[(2S)-3,3-dimethyl-2-(2-{3-[3-(4-{2-[(9S)-4,5,13-trimethyl-7-phenyl-3-thia-1,8,11,12-tetraazatricyclo [8.3.0.0$^{2,6}$]trideca-2(6),4,7,10,12-pentaen-9-yl] acetamido}phenoxy)propoxy]propoxy}acetamido) butanoyl]-4-hydroxy-N-{[4-(4-methyl-1,3-thiazol-5-yl) phenyl]methyl}pyrrolidine-2-carboxamide. The crude product was purified by prep-HPLC (Column, Gemini-NX 5 um C18, 110A, AXIA Packed 150×21.2 mm; mobile phase, water with 0.5% TFA and ACN (5.0% ACN up to 95.0% in 8 min); Detector, uv 254 nm). This resulted in the desired compound as a white solid.

$^{1}$H NMR (400 MHz, $CD_3OD$): δ 8.87 (s, 1H), 7.51-7.38 (m, 11H), 6.89 (d, J=6.8 Hz, 2H), 4.73-4.72 (m, 2H), 4.62-4.52 (m, 3H), 4.33-4.30 (m, 1H), 4.07-3.70 (m, 6H), 3.65-3.59 (m, 7H), 3.52-3.45 (m, 1H), 2.73 (s, 3H), 2.49-2.48 (s, 6H), 2.30-2.20 (m, 1H), 2.15-2.10 (m, 1H),2.12-1.95 (m, 2H), 1.95-1.85 (m, 2H), 1.68 (s, 3H), 1.03 (s, 9H); LC-MS ($ES^+$): m/z 1044.25 [$MH^+$].

Example 56: (2S,4R)-1-[(2S)-2-(2-{2-[(2-{4-[(1S)-1-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethyl]phenyl}pyrimidin-5-yl)oxy]ethoxy}acetamido)-3,3-dimethylbutanoyl]-4-hydroxy-N-[(1S)-1-(4-(4-methyl-1,3-thiazol-5-yl)phenyl]ethyl]pyrrolidine-2-carboxamide
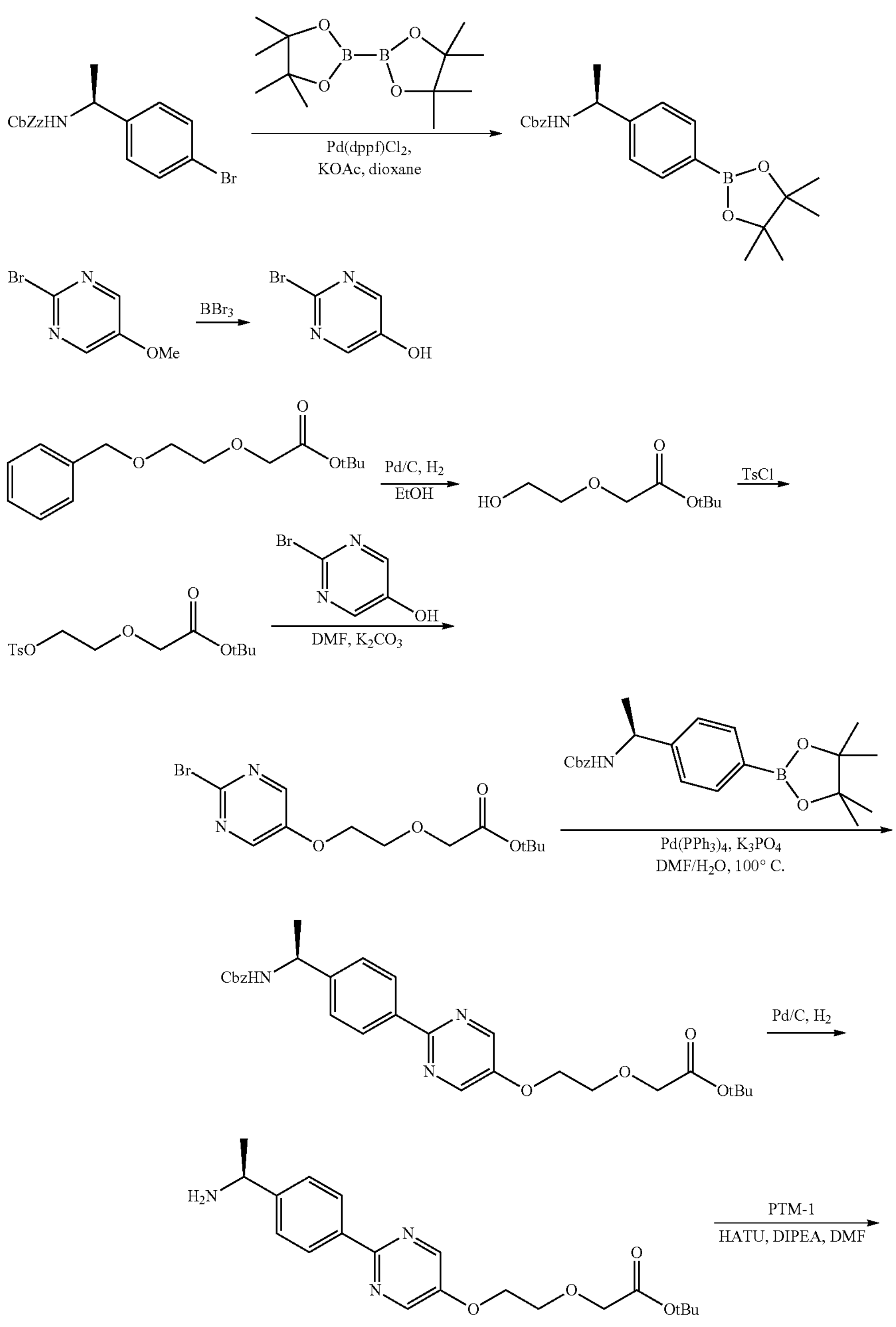

-continued

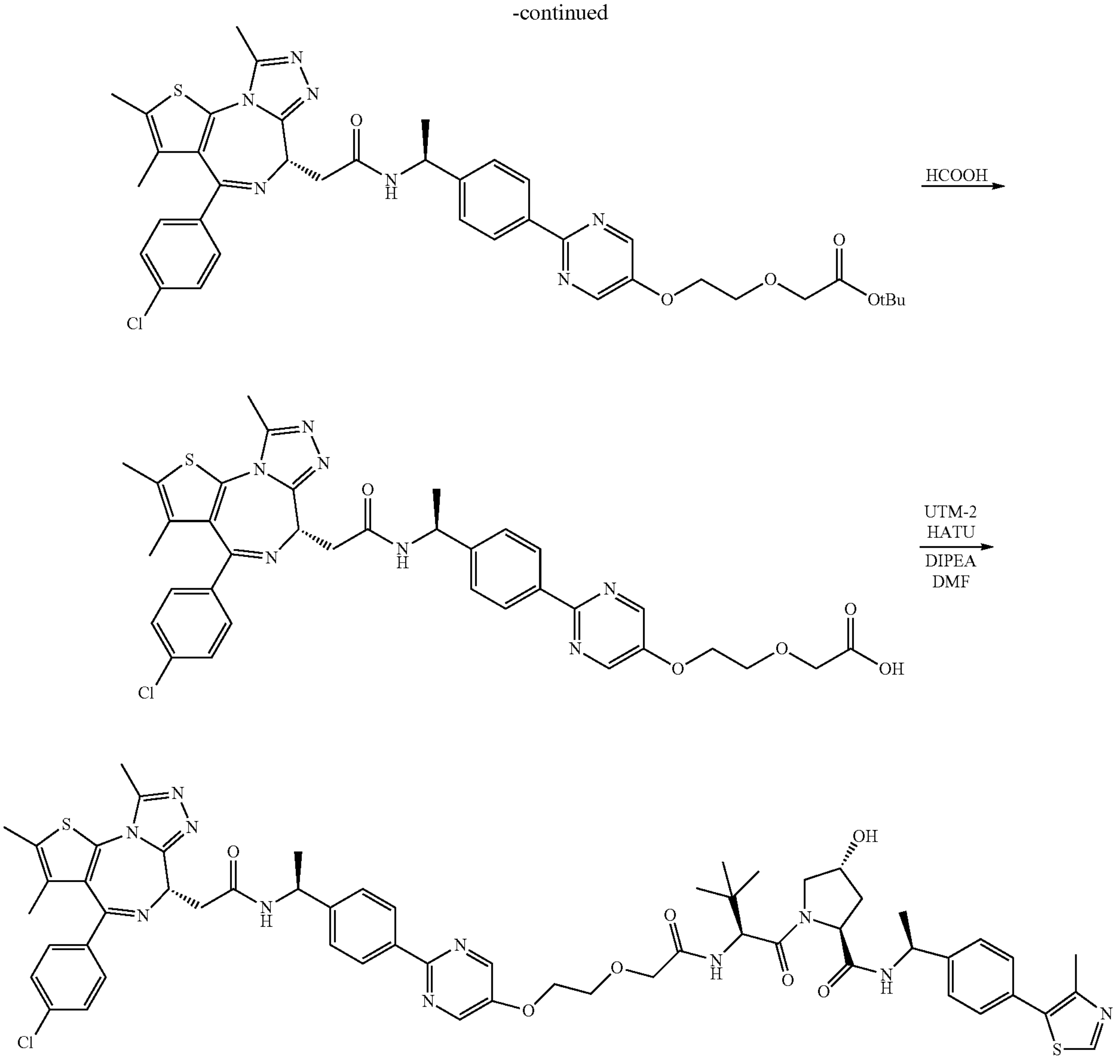

This compound was prepared using the synthetic route described above.

$^1$H NMR (400 MHz, $CDCl_3$): δ 1.05 1.07 (two singles, 9H), 1.54-1.59 (m, 6H), 1.70 (s, 3H), 1.99-2.04 (m, 1H), 2.17-2.22 (m, 1H), 2.44 (s, 3H), 2.47, 2.48 (two singles, 3H), 2.69, 2.70 (two singles, 3H), 3.37 (d, J=5.2 Hz, 1H), 3.46-3.52 (m, 1H), 3.75-3.86 (m, 2H), 4.00-4.02 (m, 2H), 4.14-4.16 (m, 2H), 4.39-4.46 (m, 3H), 4.58-4.64 (m, 2H), 4.73-4.76 (m, 1H), 5.02-2.17 (m, 2H), 7.41-7.48 (m, 10H), 8.28 (d, J=8.4 Hz, 2H), 8.67, 8.68 (two singles, 2H), 8.86, 8.87 (two singles, 1H).

LC/MS ($ES^+$): m/z 1126.4 $[M+H]^+$; $t_R$=2.550 min.

Example 61: (2S,4R)-1-[(2S)-2-{2-[3-(3-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}propoxy)phenyl] acetamido}-3,3-dimethylbutanoyl]-4-hydroxy-N-{[4-(4-methyl-1,3-thiazol-5-yl)phenyl] methyl}pyrrolidine-2-carboxamide

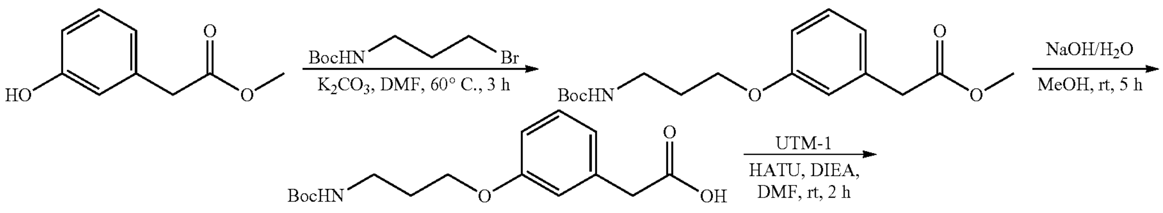

-continued
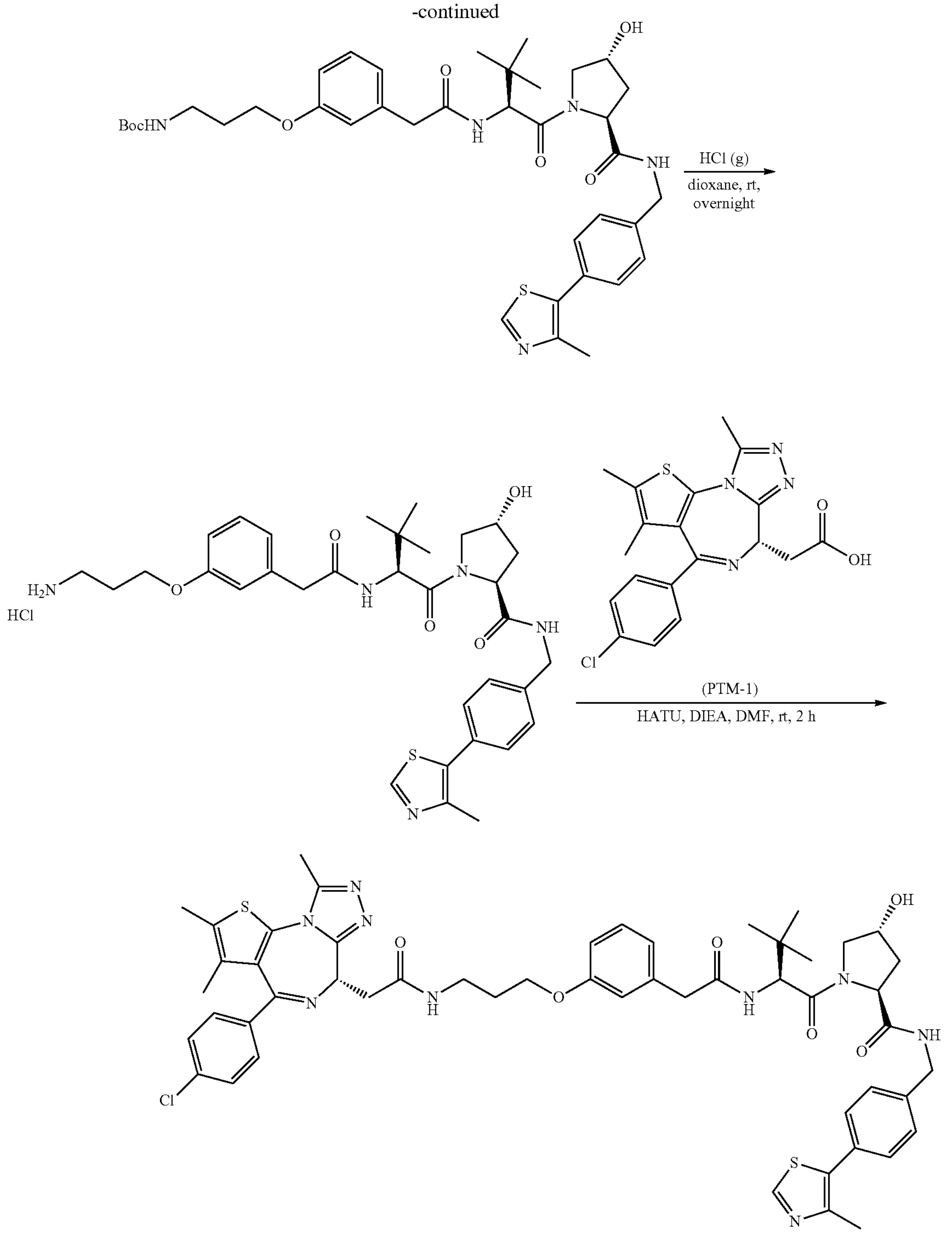
This compound was prepared using the synthetic route described above.
$^1$H NMR (300 MHz, $CD_3OD$) δ 8.89 (s, 1H), 8.42-8.29 (m, 8H), 7.19-7.14 (m, 1H), 4.61-4.55 (m, 3H), 4.49-4.41 (m, 2H), 4.39-4.22 (m, 1H), 4.04-4.01 (m, 2H), 3.86-3.82 (m, 2H), 3.76-3.75 (m, 2H), 3.53-3.32 (m, 3H), 3.35-3.28 (m, 1H), 2.65 (s, 3H), 2.43-2.41 (m, 6H), 2.16-2.13 (m, 1H), 2.06-1.97 (m, 3H), 1.64 (s, 3H), 0.96 (s, 9H). LC-MS ($ES^+$): m/z 501.10/503.10 [$M/2+H^+$], $t_R$=2.97 min, (5.6 minute run).

Example 64: (2S,4R)-1-[(2S)-2-(2-{3-[3-(4-{2-[(9S)-7-(4-ethylphenyl)-4,5,13-trimethyl-3-thia-1,8,11,12-tetraazatricyclo[8.3.0.0$^{2,6}$]trideca-2(6),4,7,10,12-pentaen-9-yl]acetamido}phenoxy)propoxy]propoxy}acetamido)-3,3-dimethylbutanoyl]-4-hydroxy-N-{[4-(4-methyl-1,3-thiazol-5-yl)phenyl]methyl}pyrrolidine-2-carboxamide
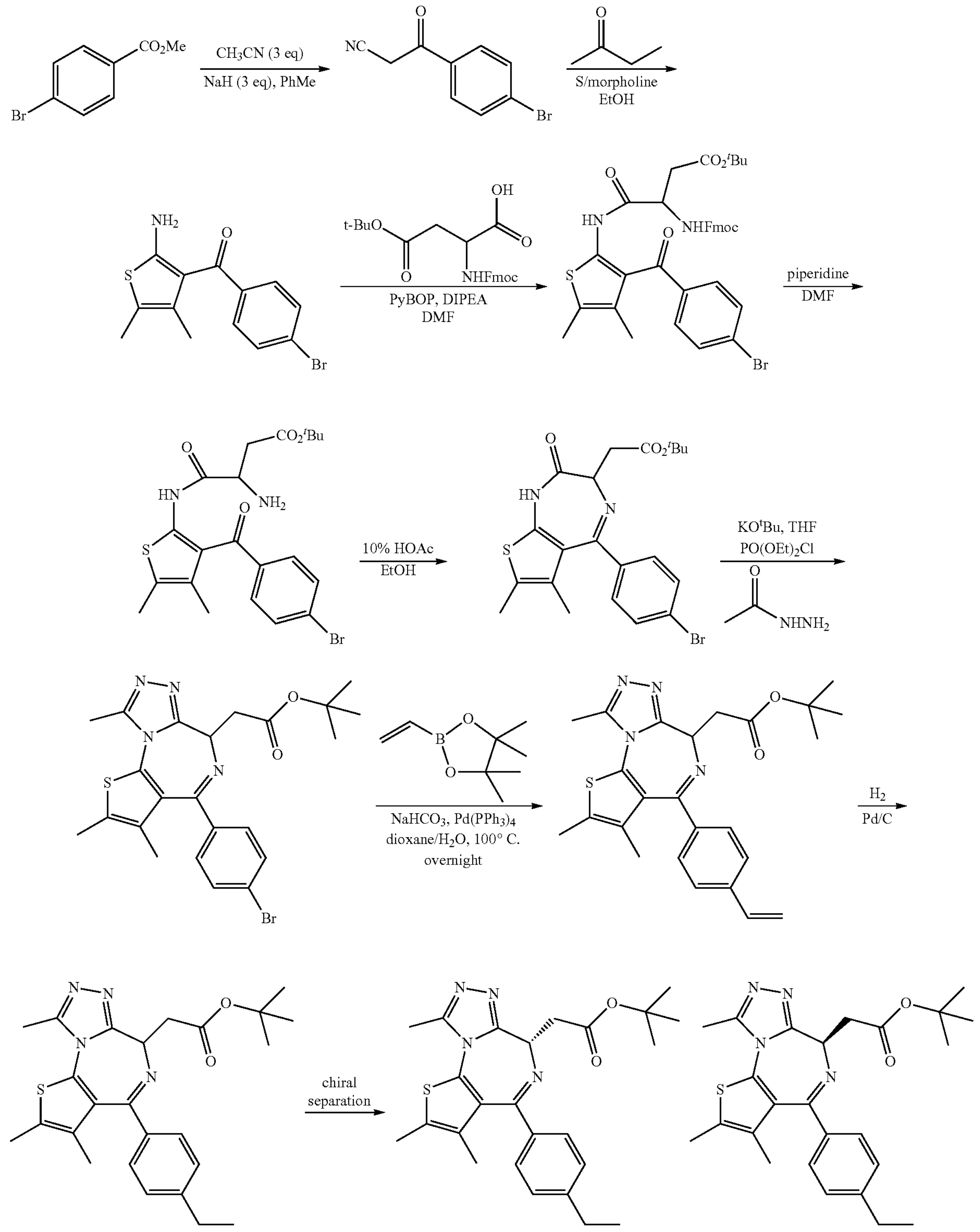

-continued

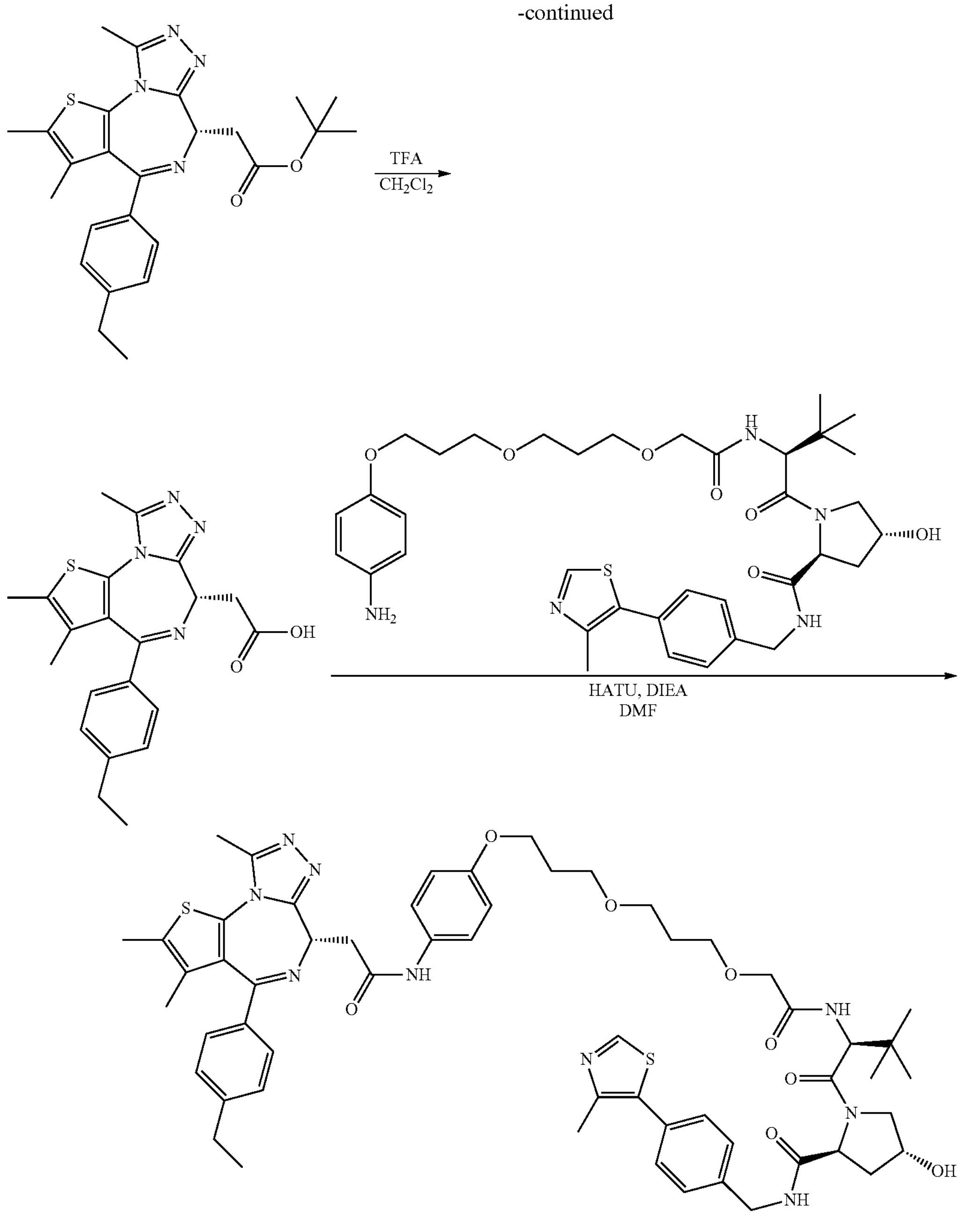

The racemic tert-butyl 2-[7-(4-ethylphenyl)-4,5,13-trimethyl-3-thia-1,8,11,12-tetraazatricyclo[8.3.0.$0^{2,6}$]trideca-2(6),4,7,10,12-pentaen-9-yl]acetate was prepared using the synthetic sequence similar to JQ1 as described above. This racemic tert-butyl ester (30.0 mg, 0.06 mmol, 1.0 equiv) in ethanol (5.0 mL) was separated by chiral HPLC (column: Chiralpak IA 2*25 cm, Sum; Mobile Phase A: Hexane-HPLC, Mobile Phase B: isopropyl alcohol-HPLC; Flow rate: 20 mL/min; 254/220 nm; RT1:10.8 min; RT2:14.8 min). This resulted in 8.6 mg of tert-butyl2-[(9R)-7-(4-ethylphenyl)-4,5,13-trimethyl-3-thia-1,8,11,12-tetraazatricyclo[8.3.0.$0^{2,6}$]-trideca-2(6),4,7,10,12-pentaen-9-yl]acetate as a white solid and 10.2 mg of tert-butyl 2-[(9S)-7-(4-ethylphenyl)-4,5,13-trimethyl-3-thia-1,8,11,12-tetraazatricyclo[8.3.0.$0^{2,6}$]trideca-2(6),4,7,10,12-pentaen-9-yl]acetate as a white solid.

$^1$H NMR (400 MHz, $CDCl_3$): δ 7.41 (d, J=7.6 Hz, 2H), 7.21 (d, J=8.0 Hz, 2H), 4.63-4.59 (m, 1H), 3.61-3.59 (m, 2H), 2.75 (s, 3H), 2.71-2.66 (m, 2H), 2.44 (s, 3H), 1.72 (s, 3H), 1.52 (s, 9H), 1.26-1.22 (m, 3H); LC-MS ($ES^+$): m/z 451.05 [$MH^+$].

The chiral ester from the chiral separation was first converted to the corresponding carboxylic acid and then coupled with the aniline derivative (prepared with the same synthetic method as described in Example 10) to provide crude (2S,4R)-1-[(2S)-2-(2-{3-[3-(4-{2-[(9S)-7-(4-ethylphenyl)-4,5,13-trimethyl-3-thia-1,8,11,12-tetraazatricyclo[8.3.0.$0^2$,$^6$]trideca-2(6),4,7,10,12-pentaen-9-yl]acetamido}phenoxy)propoxy]propoxy}acetamido)-3,3-dimethylbutanoyl]-4-hydroxy-N-{[4-(4-methyl-1,3-thiazol-5-yl)phenyl]methyl}pyrrolidine-2-carboxamide. The crude product was purified by preparative HPLC (column, XBridge Shield RP18 OBD column, 5 um, 19*150 mm; mobile phase, water with 10 mmol $NH_4HCO_3$ and ACN (47.0% ACN up to 50.0% in 10 min); detector, UV 254 nm) to provide the desired compound as a white solid.

$^1H$ NMR (400 MHz, $CD_3OD$): δ 8.87 (s, 1H), 7.52-7.35 (m, 8H), 7.27-7.22 (m, 2H), 6.91-6.88 (m, 2H), 4.72-4.68 (m, 2H), 4.63-5.45 (m, 3H), 4.38-4.34 (m, 1H), 4.09-4.03 (m, 2H), 3.96-4.76 (m, 4H), 3.68-3.55 (m, 7H), 3.53-3.42 (m, 1H), 2.76-2.63 (m, 5H), 2.49-2.43 (m, 6H), 2.28-2.20 (m, 1H), 2.16-1.98 (m, 3H), 1.97-1.88 (m, 2H), 1.71-1.68 (m, 3H), 1.27-1.21 (m, 3H), 1.03 (s, 9H); LC-MS ($ES^+$): m/z 1072.40 [$MH^+$].

Example 67: (2S,4R)-1-[(2S)-2-(2-{[(3R)-1-{4-[(1R)-1-{2-[(9S)-7-(4-chlorophenyl)-4,5,13-trimethyl-3-thia-1,8,11,12-tetraazatricyclo[$8.3.0.0^{2,6}$]trideca-2(6),4,7,10,12-pentaen-9-yl]acetamido}ethyl]phenyl}pyrrolidin-3-yl]oxy}acetamido)-3,3-dimethylbutanoyl]-4-hydroxy-N-{[4-(4-methyl-1,3-thiazol-5-yl)phenyl]methyl}pyrrolidine-2-carboxamide

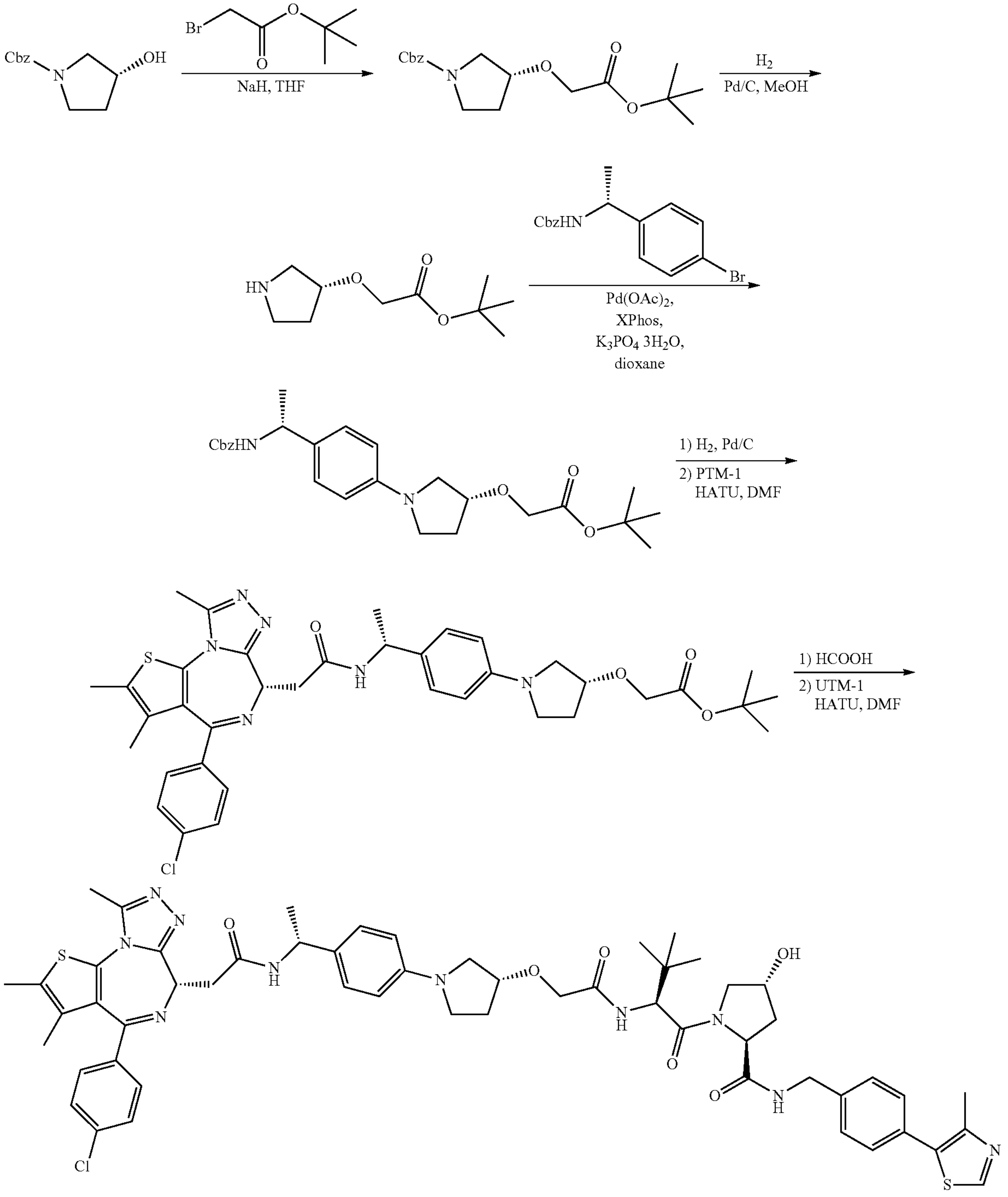

This compound was prepared using the synthetic sequence described above. The title compound was isolated as a light yellow solid.

$^1H$ NMR (400 MHz, $CD_3OD$): δ 0.94 (s, 9H), 1.34 (d, J=6.8 Hz, 3H), 1.58 (s, 3H), 1.87-1.93 (m, 1H), 2.03-2.18 (m, 3H), 2.39, 2.44 (two singles, 6H), 2.59 (s, 3H), 3.07-3.12 (m, 1H), 3.20-3.26 (m, 2H), 3.35-3.38 (m, 1H), 3.44-3.48 (m, 1H), 3.59-3.69 (m, 2H), 3.98-4.08 (m, 2H), 4.23-4.57 (m, 7H), 4.88-4.96 (m, 1H), 5.12-5.13 (m, 1H), 6.53 (d, J=8.4 Hz, 2H), 7.18-7.23 (m, 4H), 7.34-7.43 (m, 7H), 8.49-8.58 (m, 2H), 8.97 (s, 1H); LC/MS 1059.3 $[M+H]^+$; $t_R$=2.3908 min.

Example 70: (2S,4R)-1-[(2S)-2-{2-[3-(4-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}butyl)phenyl]acetamido}-3,3-dimethylbutanoyl]-4-hydroxy-N-{[4-(4-methyl-1,3-thiazol-5-yl)phenyl]methyl}pyrrolidine-2-carboxamide

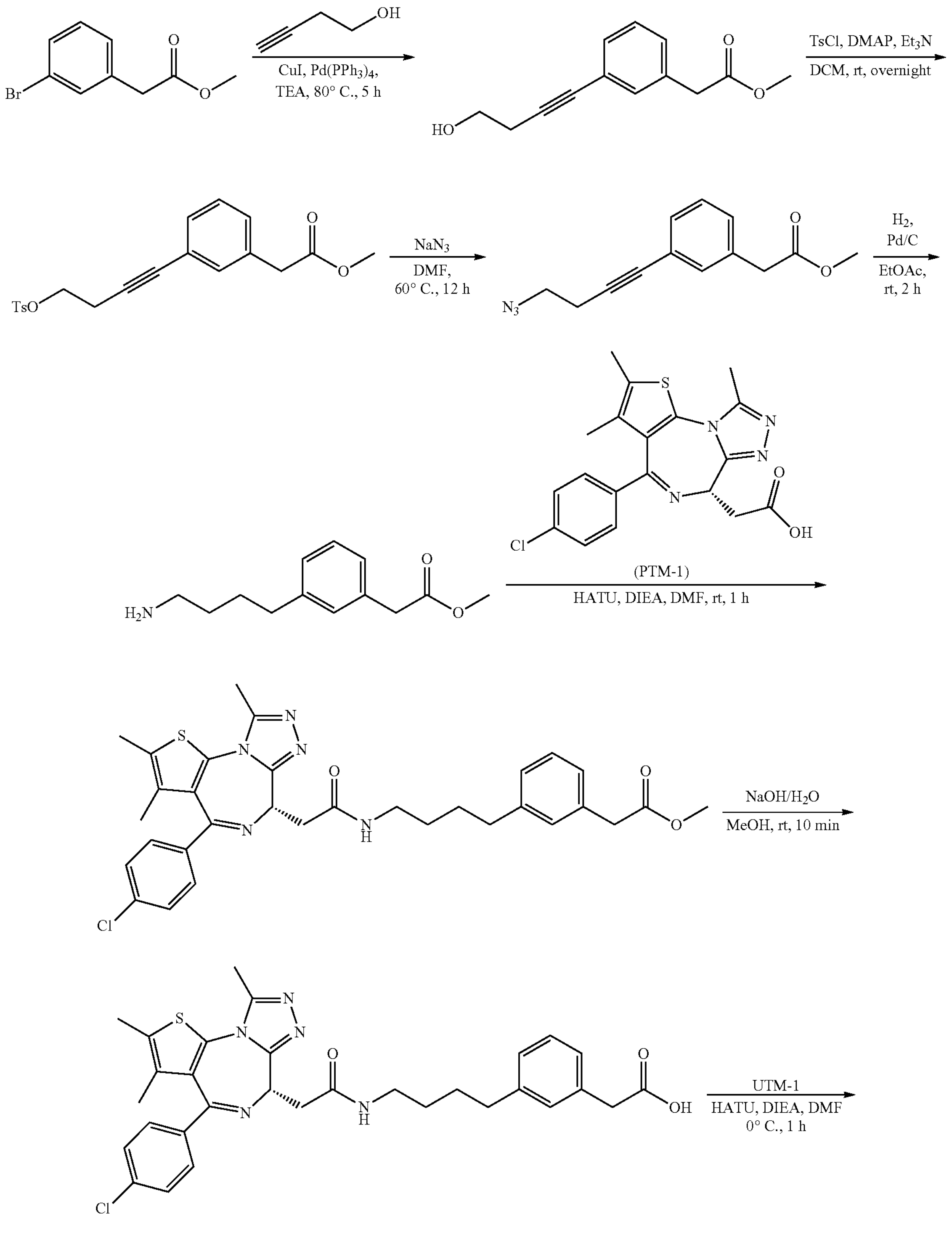

-continued

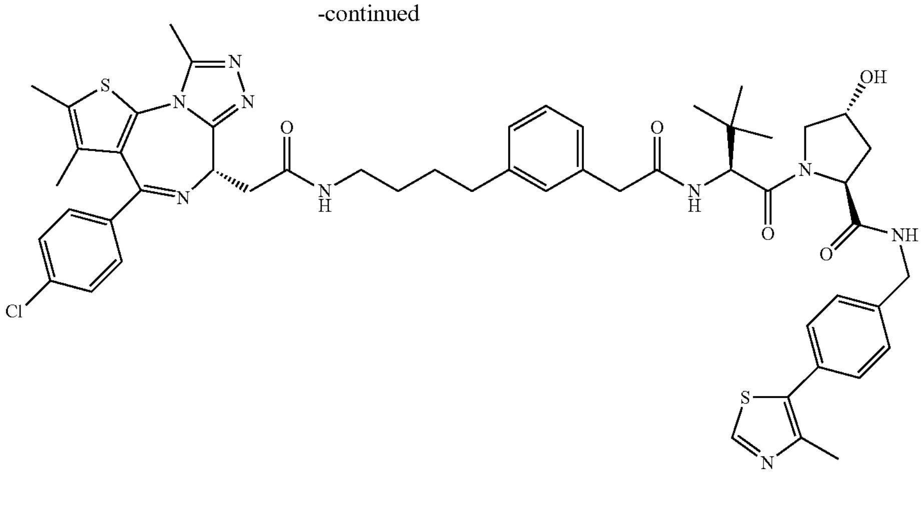

Step 1: Preparation of methyl 2-[3-(4-hydroxybut-1-yn-1-yl) phenyl]acetate

Into a 100-mL round-bottom flask purged and maintained with an inert atmosphere of nitrogen, was placed a solution of methyl 2-(3-bromophenyl) acetate (5.0 g, 21.83 mmol, 1.00 equiv), but-3-yn-1-ol (4.6 g, 65.63 mmol, 3.00 equiv), iodocopper (417.0 mg, 2.19 mmol, 0.10 equiv) in N, N-dimethylformamide (1 mL). This was followed by the addition of $Pd(PPh_3)_2Cl_2$ (1.5 g, 2.20 mmol, 0.10 equiv) and triethylamine (3 mL). The resulting solution was stirred for 5 hours at 80° C. The reaction was then quenched by the addition of 50 mL of water. The resulting solution was extracted with ethyl acetate (30 mL×2), and the organic layers combined. The resulting mixture was washed with brine. The mixture was dried over anhydrous sodium sulfate. The solids were filtered out. The resulting mixture was concentrated under vacuum. The residue was applied onto a silica gel column eluted with ethyl acetate/petroleum ether (v:v=1:3). This resulted in 3.6 g (76%) of methyl 2-[3-(4-hydroxybut-1-yn-1-yl)phenyl]acetate as yellow oil.

$^1$H NMR (300 MHz, DMSO): δ 7.32-7.21 (m, 4H), 4.90 (t, J=5.7 Hz, 1H), 3.68 (s, 2H), 3.57-3.50 (m, 5H), 2.53 (t, J=5.7 Hz, 1H).

Step 2: Preparation of methyl 2-[3-(4-[[(4-methylbenzene)sulfonyl]oxy]but-1-yn-1-yl) phenyl]acetate Into a 100-mL round-bottom flask, was placed a solution of methyl 2-[3-(4-hydroxybut-1-yn-1-yl)phenyl]acetate (3.6 g, 16.49 mmol, 1.00 equiv), triethylamine (3.33 g, 32.91 mmol, 2.00 equiv), 4-methylbenzene-1-sulfonyl chloride (3.45 g, 18.10 mmol, 1.10 equiv), 4-dimethylaminopyridine (200 mg, 1.64 mmol, 0.10 equiv) in dichloromethane (40 mL). The resulting solution was stirred overnight at room temperature. The reaction was worked up and the crude product was applied onto a silica gel column eluted with ethyl acetate/petroleum ether (v:v=1:2). This resulted in 2.9 g (47%) of methyl 2-[3-(4-[[(4-methylbenzene)sulfonyl]oxy]but-1-yn-1-yl)phenyl]acetate as yellow oil.

Step 3: Preparation of methyl 2-[3-(4-azidobut-1-yn-1-yl) phenyl]acetate

Into a 50-mL round-bottom flask, was placed a solution of methyl 2-[3-(4-[[(4-methylbenzene)sulfonyl]oxy]but-1-yn-1-yl)phenyl]acetate (1.4 g, 3.76 mmol, 1.00 equiv), azidosodium (1.74 g, 26.77 mmol, 3.00 equiv) in N, N-dimethylformamide (20 mL). The resulting solution was stirred for 12 hours at 60° C. The reaction was then quenched by the addition of water. The resulting solution was extracted with ethyl acetate (50 mL×2), and the organic layers were combined and concentrated. The residue was applied onto a silica gel column eluted with ethyl acetate/petroleum ether (v:v=1:1). This resulted in 900.0 mg (98%) of methyl 2-[3-(4-azidobut-1-yn-1-yl)phenyl]acetate as a yellow solid.

Step 4: Preparation of 2-(3-(4-aminobutyl)phenyl)acetate

Into a 100-mL round-bottom flask, palladium on carbon (10%, 500 mg) was added to a solution of methyl 2-(3-(4-azidobut-1-ynyl) phenyl) acetate (900.0 mg, 3.76 mmol, 1.00 equiv) in ethyl acetate (10 mL) at room temperature under nitrogen atmosphere. The reaction flask was vacuumed and charged with a hydrogen balloon. The resulting solution was stirred for 2 hours at room temperature. The solids were filtered out. The resulting mixture was concentrated under vacuum. This resulted in 790.0 mg (97%) of methyl 2-(3-(4-aminobutyl)phenyl)acetate as a yellow solid. LC-MS ($ES^+$): m/z 222.00 [$MH^+$], $t_R$=0.53 min (1.90 minute run).

Step 5: Preparation of 2-[3-(4-[2-[(9S)-7-(4-chlorophenyl)-4,5,13-trimethyl-3-thia-1,8,11,12-tetraazatricyclo[8.3.0.0^[2,6]]trideca-2(6),4,7,10,12-pentaen-9-yl]acetamido]butyl)phenyl]acetate Into a 50-mL round-bottom flask, was placed a solution of 2-[7-(4-chlorophenyl)-4,5,13-trimethyl-3-thia-1,8,11,12-tetraazatricyclo[8.3.0.0^[2,6]]trideca-2(6),4,7,10,12-pentaen-9-yl]acetic acid (81 mg, 0.20 mmol, 1.00 equiv), HATU (93.0 mg, 0.24 mmol, 1.20 equiv), N,N-diisopropylethylamine (79.0 mg, 0.61 mmol, 3.00 equiv) in N,N-dimethylformamide (5 mL). The resulting solution was stirred for 10 minutes at room temperature. Then methyl 2-(3-(4-aminobutyl) phenyl) acetate (45.0 mg, 0.20 mmol, 1.00 equiv) was added and the mixture was stirred for another 1 hour. The mixture was worked up and the crude product was applied onto a silica gel column eluted with dichloromethane/methanol (v:v=10:1). This resulted in 60.0 mg (50%) of methyl 2-[3-(4-[2-[(9S)-7-(4-chlorophenyl)-4,5,13-trimethyl-3-thia-1,8,11,12-tetraazatricyclo[8.3.0.0^[2,6]]trideca-2(6),4,7,10,12-pentaen-9-yl]acetamido]butyl)phenyl]acetate as a yellow oil.

LC-MS ($ES^+$): m/z 604.20 [$MH^+$], $t_R$=1.03 min (1.90 minute run).

Step 6: Preparation of 2-[3-(4-[2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido]butyl)phenyl]acetic acid Into a 50-mL round-bottom flask, was placed a solution of methyl 2-[3-(4-[2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido]butyl)phenyl]acetate (60.0 mg, 0.10 mmol, 1.00 equiv), 1 N sodium hydroxide solution (0.5 mL) in methanol (2 mL). The resulting solution was stirred for 10 minutes at room temperature. The pH value of the solution was adjusted to 1 with 1 N HCl. The resulting solution was extracted with ethyl acetate (50 mL×3), and the organic layers were combined. The resulting mixture was washed with brine. The mixture was dried over anhydrous sodium sulfate. The solids were filtered out. The resulting mixture was concentrated under vacuum. This resulted in 45.0 mg (77%) of 2-[3-(4-[2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9yl]acetamido]butyl)phenyl]-acetic acid as yellow oil. LC-MS (ES$^+$): m/z 590.15 [MH$^+$], $t_R$=0.93 min (1.90 minute run).

Step 7: Preparation of (2S,4R)-1-[(2S)-2-{2-[3-(4-{2-[(9S)-7-(4-chlorophenyl)-4,5,13-trimethyl-3-thia-1,8,11,12-tetraazatricyclo[8.3.0.0$^2$,$^6$]trideca-2(6),4,7,10,12-pentaen-9-yl]acetamido}butyl)phenyl]acetamido}-3,3-dimethylbutanoyl]-4-hydroxy-N-{[4-(4-methyl-1,3-thiazol-5-yl)phenyl]methyl}pyrrolidine-2-carboxamide Into a 50-mL round-bottom flask, was placed a solution of 2-[3-(4-[2-[(9S)-7-(4-chlorophenyl)-4,5,13-trimethyl-3-thia-1,8,11,12-tetraazatricyclo[8.3.0.0$^2$]trideca-2(6),4,7,10,12-pentaen-9-yl]acetamido]butyl)phenyl]acetic acid (40.0 mg, 0.07 mmol, 1.00 equiv), HATU (45.6 mg, 0.08 mmol, 1.20 equiv), N,N-diisopropylethylamine (27.0 mg, 0.21 mmol, 3.00 equiv) in N,N-dimethylformamide (2 mL). The resulting solution was stirred for 10 minutes at room temperature. Then (2S, 4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (29.0 mg, 0.07 mmol, 1.00 equiv) was added the mixture was stirred for another 1 hour. The reaction mixture was worked up and the crude product was purified by preparative HPLC (column: X Bridge C18, 19*150 mm, 5 urn; Mobile Phase A: water/10 mM ammonium bicarbonate, Mobile Phase B: acetonitrile; Flow rate: 20 mL/min; Gradient: 55% B to 80% B in 10 min; 254 nm). This resulted in 18.5 mg (27%) of (2S,4R)-1-[(2S)-2-{2-[3-(4-{2-[(9S)-7-(4-chlorophenyl)-4,5,13-trimethyl-3-thia-1,8,11,12-tetraazatricyclo[8.3.0.0$^2$,$^6$]trideca-2(6),4,7,10,12-pentaen-9-yl]acetamido}butyl)phenyl]acetamido}-3,3-dimethylbutanoyl]-4-hydroxy-N-{[4-(4-methyl-1,3-thiazol-5-yl)phenyl]methyl}pyrrolidine-2-carboxamide as a white solid.

$^1$H NMR (400 MHz, CD$_3$OD): δ 8.89 (s, 1H), 7.46-7.31 (m, 9H), 7.27-7.09 (m, 4H), 4.68-4.50 (m, 6H), 4.42-4.31 (m, 1H), 3.92-3.89 (m, 1H), 3.73-3.68 (m, 1H), 3.64-3.53 (m, 2H), 3.47-3.40 (m, 1H), 3.30-3.21 (m, 2H), 2.70-2.65 (m, 5H), 2.48 (s, 3H), 2.45 (s, 3H), 2.27-2.20 (m, 1H), 2.17-2.03 (m, 1H), 1.73-1.55 (m, 7H), 0.98 (s, 9H); LC-MS (ES$^+$): m/z 1002.50 [MH$^+$], $t_R$=1.45 min (3.00 minute run).

Example 72: (2R, 4S)-1-[(2S)-2-{2-[3-(2-{2-[(9S)-7-(4-chlorophenyl)-4,5,13-trimethyl-3-thia-1,8,11,12-tetraazatricyclo[8.3.0.0$^2$,$^6$]trideca-2(6),4,7,10,12-pentaen-9-yl]acetamido}ethoxy)propoxy]acetamido}-3,3-dimethylbutanoyl]-4-hydroxy-N-[(1S)-1-[4-(4-methyl-1,3-thiazol-5-yl)phenyl]ethyl]pyrrolidine-2-carboxamide Example 77: (2S, 4R)-1-[(2S)-2-{2-[3-(2-{2-[(9S)-7-(4-chlorophenyl)-4,5,13-trimethyl-3-thia-1,8,11,12-tetraazatricyclo[8.3.0.0$^2$,$^6$]trideca-2(6),4,7,10,12-pentaen-9-yl]acetamido}ethoxy)propoxy]acetamido}-3,3-dimethylbutanoyl]-4-hydroxy-N-[(1S)-1-[4-(4-methyl-1,3-thiazol-5-yl)phenyl]ethyl]pyrrolidine-2-carboxamide

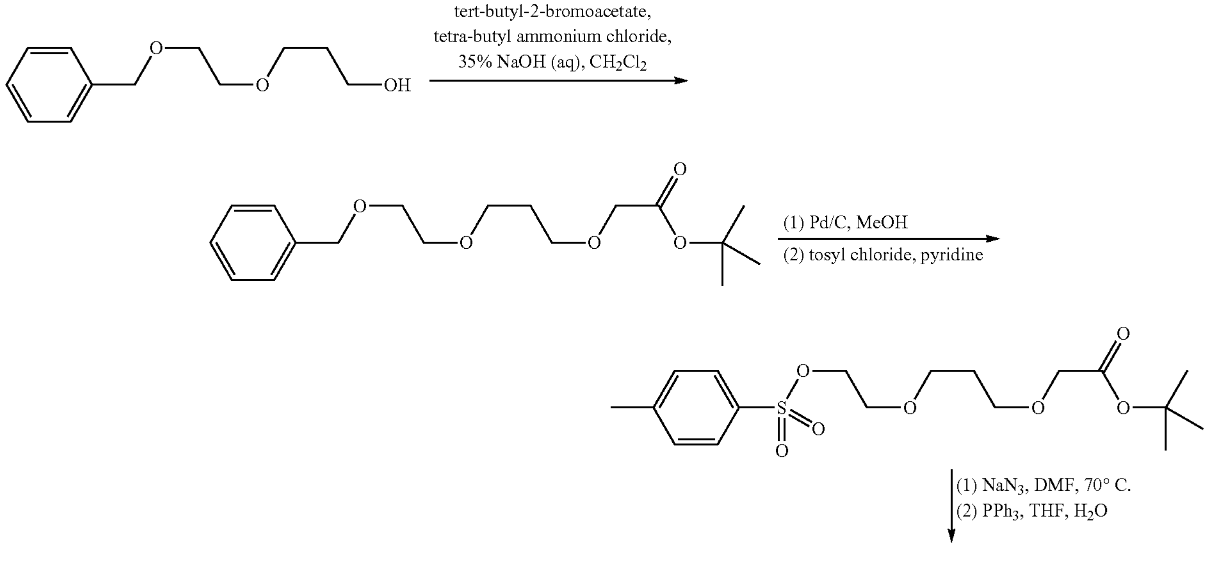

-continued

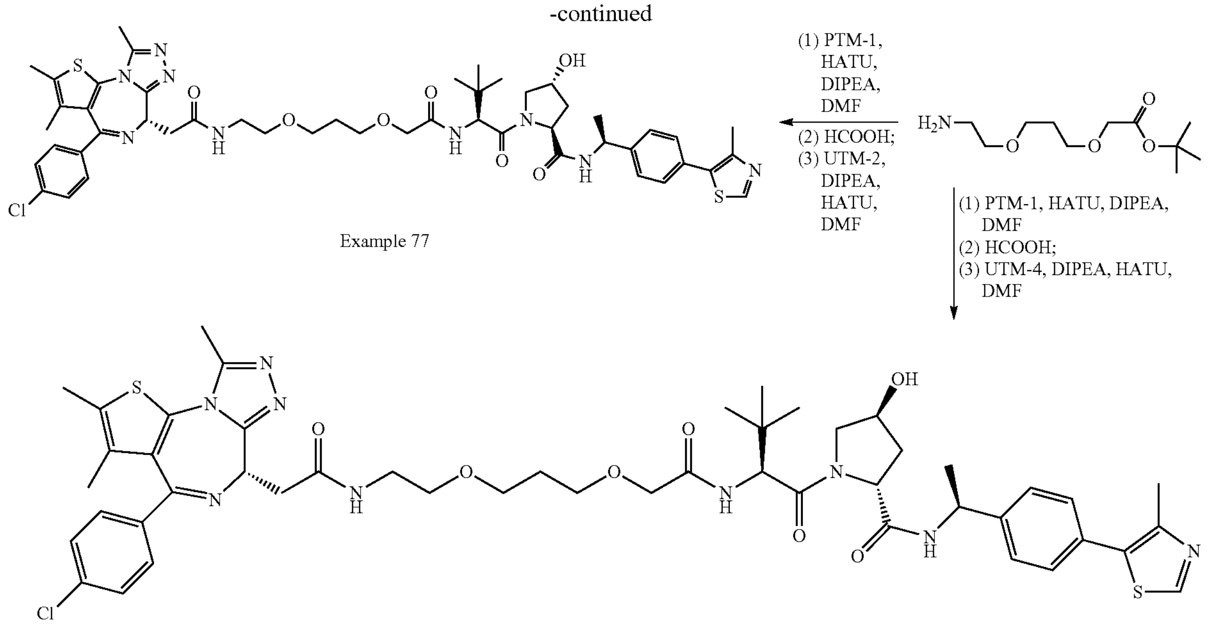

Example 77

Example 72

Step 1: Preparation of tert-butyl 2-(3-(2-(benzyloxy)ethoxy)propoxy)acetate

A mixture of 3-(2-(benzyloxy)ethoxy)propan-1-ol (6.7 g, 31.86 mmol, prepared from 2-benzyloxyethanol and allyl bromide in two steps of ether formation and hydroboration), tert-butyl 2-bromoacetate (12.4 g, 63.73 mmol), tetra-butyl ammonium chloride (8.9 g, 31.86 mmol) and 35% sodium hydroxide aqueous solution (35 mL) in dichloromethane (35 mL) was stirred at room temperature overnight. TLC showed the reaction was completed. The mixture was partitioned between DCM (100 mL) and water (100 mL). The organic layer was collected, washed with brine (100 mL), dried over anhydrous sodium sulfate, and concentrated under reduced pressure to give a residue which was purified by silica gel flash column chromatography (eluted with 10-20% ethyl acetate in hexane) to afford tert-butyl 2-(3-(2-(benzyloxy)ethoxy)propoxy)acetate (4.1 g, yield 40%) as yellow oil.

$^1$H NMR (400 MHz, $CDCl_3$): δ 1.47 (s, 9H), 1.88-1.95 (m, 2H), 3.57-3.63 (m, 8H), 3.94 (s, 2H), 4.57 (s, 2H), 7.27-7.35 (m, 5H).

Step 2: Preparation of tert-butyl 2-(3-{2-[(4-methylbenzenesulfonyl)oxy]ethoxy}propoxy)acetate A mixture of tert-butyl 2-{3-[2-(benzyloxy)ethoxy]propoxy}acetate (4.1 g, 12.64 mmol) and palladium on carbon (10%, 160 mg) in MeOH (30 mL) was stirred at 40° C. overnight under hydrogen atmosphere (hydrogen balloon). TLC showed the reaction was completed. Palladium on carbon was removed through filtration and washed with MeOH (20 mL×2). The combined filtrate was concentrated under reduced pressure to afford tert-butyl 2-[3-(2-hydroxyethoxy)propoxy]acetate (2.81 g, crude) as colorless oil which was used in the next step without further purification.

$^1$H NMR (400 MHz, $CDCl_3$): δ 1.48 (s, 9H), 1.87-1.93 (m, 2H), 2.36 (br, 1H), 3.56-3.58 (m, 2H), 3.60-3.64 (m, 4H), 3.72-3.74 (m, 2H), 3.96 (s, 2H).

This oily material (2.81 g, crude) and tosyl chloride (2.7 g, 14.21 mmol) in pyridine (8 mL) was stirred at rt for 1 hour. TLC showed the reaction was completed. The reaction mixture was partitioned between ethyl acetate (70 mL) and water (60 mL). The organic layer was collected, washed with cold hydrochloric acid (1N, 80 mL) and then brine (100 mL), dried over anhydrous sodium sulfate, and concentrated under reduced pressure to give a crude residue which was purified by silica gel flash column chromatography (eluted with 10-20% ethyl acetate in hexane) to afford tert-butyl 2-(3-{2-[(4-methylbenzenesulfonyl)oxy]ethoxy}propoxy)acetate (3.9 g, yield 84%) as yellow oil.

$^1$H NMR (400 MHz, $CDCl_3$): δ 1.48 (s, 9H), 1.78-1.85 (m, 2H), 2.45 (s, 3H), 3.49-3.56 (m, 4H), 3.62 (t, J=4.8 Hz, 2H), 3.93 (s, 2H), 4.15 (t, J=4.8 Hz, 2H), 7.35 (d, J=8.0 Hz, 2H), 7.80 (d, J=8.4 Hz, 2H).

Step 3: Preparation of tert-butyl 2-(3-(2-aminoethoxy)propoxy)acetate

A mixture of tert-butyl 2-(3-{2-[(4-methylbenzenesulfonyl)oxy]ethoxy}propoxy)acetate (3.9 g, 10.04 mmol) and sodium azide (783 mg, 12.04 mmol) in anhydrous N,N-dimethylformamide (10 mL) was stirred at 70° C. for 2 hours. TLC showed the reaction was completed. The reaction mixture was allowed to cool to room temperature, and partitioned between ethyl acetate (70 mL) and water (30 mL). The organic layer was collected, washed with brine (50 mL), dried over anhydrous sodium sulfate, and concentrated under reduced pressure to give a crude residue which was purified by silica gel flash column chromatography (eluted with 10-20% ethyl acetate in hexane) to afford tert-butyl 2-(3-(2-azidoethoxy)propoxy)acetate (1.89 g, yield 73%) as colorless oil.

$^1$H NMR (400 MHz, $CDCl_3$): δ 1.48 (s, 9H), 1.89-1.94 (m, 2H), 3.36 (t, J=5.0 Hz, 2H), 3.59-3.64 (m, 6H), 3.96 (s, 2H).

This oily material (1.79 g, 6.9 mmol), triphenylphosphine (2.71 g, 10.35 mmol) and water (0.6 mL) in THF (20 mL)

was stirred at rt for 3 hours. TLC showed the reaction was completed. The reaction mixture was partitioned between ethyl acetate (60 mL) and water (30 mL). The organic layer was collected, washed with brine (50 mL), dried over anhydrous sodium sulfate, and concentrated under reduced pressure to give a crude residue which was purified by silica gel flash column chromatography (eluted with 50-80% ethyl acetate in hexane) to afford tert-butyl 2-(3-(2-aminoethoxy) propoxy)acetate (1.37 g, yield 85%) as yellow oil.

$^1$H NMR (400 MHz, $CDCl_3$): δ 1.48 (s, 9H), 1.87-1.94 (m, 2H), 2.85 (t, J=5.2 Hz, 2H), 3.45-3.48 (m, 2H), 3.57 (t, J=6.4 Hz, 2H), 3.61 (t, J=6.4 Hz, 2H), 3.95 (s, 2H).

Step 4: Preparation of (2S, 4R)-1-[(2S)-2-{2-[3-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)propoxy]acetamido}-3,3-dimethylbutanoyl]-4-hydroxy-N-[(15)-1-[4-(4-methyl-1,3-thiazol-5-yl)phenyl]ethyl]pyrrolidine-2-carboxamide (Example 77)

To a stirred solution of (S)-2-(4-(4-chlorophenyl)-2,3,9-trimethyl-6H-thieno[3,2-f][1,2,4]triazolo[4,3-a][1,4]diazepin-6-yl) acetic acid (900 mg, 2.32 mmol), tert-butyl 2-(3-(2-aminoethoxy)propoxy)acetate (650 mg, 2.79 mmol), and DIPEA (1.5 g, 11.61 mmol) in anhydrous N,N-dimethylformamide (6 mL) was added HATU (2.65 mg, 6.97 mmol) at 0° C., the resulting mixture was stirred at rt for 20 min. LC-MS showed the reaction was completed. The mixture was partitioned between ethyl acetate (100 mL) and water (40 mL). The aqueous layer was extracted with ethyl acetate (50 mL×2). The combined organic layers were collected, washed with brine (100 mL), dried over anhydrous sodium sulfate, and concentrated under reduced pressure to give a crude residue which was purified by silica gel flash column chromatography (eluted with 2-10% MeOH in DCM) to afford (S)-tert-butyl 2-(3-(2-(2-(4-(4-chlorophenyl)-2,3,9-trimethyl-6H-thieno[3,2-f][1,2,4]triazolo[4,3-a][1,4]diazepin-6-yl)acetamido)ethoxy)propoxy)acetate (800 mg, yield 58%) as white solid. This solid (800 mg, 1.30 mmol) in formic acid (5 mL) was stirred at 60° C. for 1 h. TLC showed the reaction was completed. The volatiles were evaporated under reduced pressure to afford (S)-2-(3-(2-(2-(4-(4-chlorophenyl)-2,3,9-trimethyl-6H-thieno[3,2-f][1,2,4]triazolo[4,3-a][1,4]diazepin-6-yl)acetamido)ethoxy)propoxy)acetic acid as a crude yellow oil without further purification. The oily material (700 mg, Crude) was mixed with (2S,4R)-1-[(5)-2-amino-3,3-dimethylbutanoyl]-4-hydroxy-N—[(S)-1-(4-(4-methylthiazol-5-yl)phenyl)ethyl]-pyrrolidine-2-carboxamide hydrochloride (UTM-2, 920 mg, 1.91 mmol), DIPEA (1.05 g, 8.11 mmol), HATU (1.85 g, 4.87 mmol) in anhydrous N,N-dimethylformamide (8 mL) at 0° C., the resulting mixture was stirred at room temperature for 20 min. LC-MS showed the reaction was completed. The mixture was partitioned between ethyl acetate (60 mL) and water (30 mL). The aqueous layer was extracted with ethyl acetate (30 mL×2). The combined organic layers were collected, washed with brine (50 mL), dried over anhydrous sodium sulfate, and concentrated under reduced pressure to give a crude residue which was purified by preparative HPLC to afford the title compound in Example 77 (404.1 mg, yield 32%) as white solid.

$^1$H NMR (400 MHz, $CD_3OD$): δ 1.06 (s, 9H), 1.51 & 1.59 (d, J=6.8 Hz, 3H), 1.72 (s, 3H), 1.93-2.00 (m, 3H), 2.20-2.25 (m, 1H), 2.46 (s, 3H), 2.49 (s, 3H), 2.71 (s, 3H), 3.45-3.67 (m, 10H), 3.75-3.78 (m, 1H), 3.85-3.88 (m, 1H), 3.95-4.05 (m, 2H), 4.45 (br, 1H), 4.59-4.71 (m, 3H), 4.99-5.04 (m, 1H), 7.40-7.49 (m, 8H), 7.57 (d, J=9.6 Hz, 1H), 8.89 (s, 1H); LC-MS ($ES^+$): m/z 986.4/988.4 $[M+H^+]$

With the same method and UTM-4, compound in Example 72 was prepared as an off white powder.

$^1$H NMR (400 MHz, $CDCl_3$) δ 8.71-8.75 (m, 1H), 8.01 (d, J=7.83 Hz, 1H), 7.58-7.64 (m, 1H), 7.29-7.43 (m, 9H), 7.21 (d, J=8.02 Hz, 1H), 5.13 (t, J=7.34 Hz, 1H), 4.80 (dd, J=4.70, 8.61 Hz, 1H), 4.57-4.63 (m, 2H), 4.04-4.10 (m, 2H), 3.90 (d, J=15.65 Hz, 1H), 3.75 (dd, J=4.21, 10.66 Hz, 1H), 3.48-3.69 (m, 9H), 3.45 (d, J=6.46 Hz, 1H), 3.27 (dd, J=5.67, 14.87 Hz, 1H), 2.69 (s, 3H), 2.49-2.54 (m, 3H), 2.35-2.42 (m, 4H), 2.19 (s, 1H), 1.81-1.92 (m, 2H), 1.68 (s, 3H), 1.47 (d, J=7.04 Hz, 3H), 1.02-1.12 (m, 9H). LC-MS ($ES^+$): m/z 986.30/988.31 $[M+H^+]$

Compounds in the following Examples were prepared using the same method as described in Example 77.

| | | |
|---|---|---|
| Example 38 | (2S,4R)-1-[(2S)-2-(14-12-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}-3,6,9,12-tetraoxatetradecanamido)-3,3-dimethylbutanoyl]-4-hydroxy-N-{[4-(4-methyl-1,3-thiazol-5-yl)phenyl]methyl}pyrrolidine-2-carboxamide | $^1$HNMR (400 MHz, $CD_3OD$): δ 1.03, 1.05 (two singles, 9H), 1.71 (s, 3H), 2.06-2.13 (m, 1H), 2.21-2.26 (m, 1H), 2.46-2.48 (m, 6H), 2.70 (m, 3H), 3.29-3.30 (m, 1H), 3.44-3.50 (m, 3H), 3.60-3.70 (m, 14H), 3.80-3.90 (m, 2H), 4.01-4.09 (m, 2H), 4.35-4.39 (m, 1H), 4.51-4.70 (m, 5H), 7.41-7.46 (m, 8H), 8.88, 8.89 (two singles, 1H). |
| Example 41 | (2S,4R)-1-[(2S)-2-{2-[2-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)ethoxy]acetamido}-3,3-dimethylbutanoyl]-4-hydroxy-N-{[4-(4-methyl-1,3-thiazo 1-5-yl)phenyl]methyl}pyrrolidine-2-carboxamide | $^1$HNMR (400 MHz, $CD_3OD$): δ 1.04, 1.10 (two singles, 9H), 2.09-2.15 (m, 1H), 2.26-2.30 (m, 1H), 2.44 (s, 6H), 2.65 (s, 3H), 3.39-4.04 (m, 15H), 4.30-4.43 (m, 2H), 4.52-4.69 (m, 3H), 7.26-7.42 (m, 8H), 7.75-7.81 (m, 1H), 8.50 (br, 1H), 8.77 (br, 1H), 8.87 (s, 1H). |
| Example 42 | (2S,4R)-1-[(2S)-2-(2-{2-[2-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)ethoxy]ethoxy}acetamido)-3,3-dimethylbutanoyl]-4-hydroxy-N-{[4-(4-methyl-1,3-thiazol-5-yl)phenyl]methyl}pyrrolidine-2-carboxamide | $^1$HNMR (400 MHz, $CD_3OD$): δ 1.04, 1.06 (two singles, 9H), 1.71 2.70 (s, 3H), 2.06-2.13 (m, 1H), 2.21-2.24 (m, 1H), 2.46-2.48 (m, 6H), (s, 3H), 3.43-3.49 (m, 3H), 3.60-3.74 (m, 11H), 3.80-3.90 (m, 2H), 4.03-4.12 (m, 2H), 4.34-4.39 (m, 1H), 4.51-4.55 (m, 2H), 5.58-4.65 (m, 2H), 4.71-4.73 (m, 1H), 7.40-7.48 (m, 8H), 7.66-7.68 (m, 1H), 8.67-8.70 (m, 1H), 8.88 (s, 1H). |

-continued

| | | |
|---|---|---|
| Example 45 | (2S,4R)-1-[(2S)-2-[2-(4-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}butoxy)acetamido]-3,3-dimethylbutanoyl]-4-hydroxy-N-{[4-(4-methyl-1,3-thiazol-5-yl)phenyl]methyl}pyrrolidine-2-carboxamide | $^{1}$HNMR (400 MHz, $CD_3OD$): δ 0.91, 0.93 (two singles, 9H), 1.56-1.66 (m, 7H), 1.96-2.02 (m, 1H), 2.11-2.16 (m, 1H), 2.33-2.37 (two singles, 6H), 2.57-2.58 (two singles, 3H), 3.24-3.33 (m, 4H), 3.47-3.51 (m, 2H), 3.68-3.94 (m, 4H), 4.24-4.28 (m, 1H), 4.38-4.42 (m, 2H), 4.48-4.53 (m, 2H), 4.59-4.61 (m, 1H), 7.25-7.46 (m, 9H), 8.20-8.26 (m, 1H), 8.74, 8.76 (two singles, 1H). |
| Example 49 | (2S,4R)-1-[(2S)-2-{2-[3-(2-{2-[(9S)-7-(4-chlorophenyl)-4,5,13-trimethyl-3-thia-1,8,11,12-tetraazatricyclo[8.3.0.0$^{2}$,$^{6}$]trdeca-2(6),4,7,10,12-pentaen-9-yl]acetamido}ethoxy)propoxy]acetamido}-3,3-dimethyl-butanoyl]-4-hydroxy-N-{[4-(4-methyl-1,3-thiazol-5-yl)phenyl]methyl}pyrrolidine-2-carboxamide | $^{1}$HNMR (400 MHz, $CD_3OD$): δ 0.91,0.93 (two singles, 9H), 1.59 (s, 3H), 1.78-1.81 (m, 2H), 1.95-2.02 (m, 1H), 2.10-2.15 (m, 1H), 2.34-2.36 (m, 6H), 2.58 (s, 3H), 3.25 (s, 1H), 3.33 (s, 3H), 3.46-3.55 (m, 6H), 3.69-3.93 (m, 4H), 4.22-4.26 (m, 1H), 4.38-4.62 (m, 5H), 7.27-7.35 (m, 8H), 8.75 (s, 1H). |
| Example 50 | (2S,4R)-1-[(2S)-2-(2-{3-[(5-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7, 10,12-pentaen-9-yl]acetamido}pentyl)oxy]propoxy}acetamido)-3,3-dimethyl-butanoyl]-4-hydroxy-N-{[4-(4-methyl-1,3-thiazol-5-yl)phenyl]methyl}pyrrolidine-2-carboxamide | $^{1}$HNMR (400 MHz, $CD_3OD$): δ 1.05, 1.03 (two singles, 9H), 1.41-1.48 (m, 2H), 1.56-1.65 (m, 4H), 1.71 (s, 3H), 1.87-1.93 (m, 2H), 2.07-2.14 (m, 1H), 2.20-2.27 (m, 1H), 2.46 (s, 3H), 2.48, 2.49 (two singles, 3H), 2.71 (s, 3H), 3.22-3.30 (m, 3H), 3.40-3.48 (m, 3H), 3.54-3.67 (m, 4H), 3.80-4.03 (m, 4H), 4.35-4.40 (m, 1H), 4.52-4.73 (m, 5H), 7.40-7.48 (m, 8H), 7.54 (d, J = 9.6 Hz, 1H), 8.31-8.34 (m, 1H), 8.66-8.69 (m, 1H), 8.88, 8.89 (two singles, 1H). |
| Example 51 | (2S,4R)-1-[(2S)-2-(2-{2-[2-(4-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}butoxy)ethoxy]ethoxy}acetamido)-3,3-dimethylbutanoyl]-4-hydroxy-N-{[4-(4-methyl-1,3-thiazol-5-yl)phenyl]methyl}pyrrolidine-2-carboxamide | $^{1}$HNMR (400 MHz, $CD_3OD$): δ 0.98 (s, 9H), 1.65-1.69 (m, 7H), 2.09-2.15 (m, 1H), 2.40 (s, 3H), 2.42-2.49 (m, 1H) 2.51 (s, 3H), 2.63 (s, 3H), 3.15-3.19 (m, 1H), 3.31-3.66 (m, 15H), 4.00-4.11 (m, 2H), 4.25-4.30 (m, 2H), 4.43 (br, 1H), 4.51-4.56 (m, 1H), 4.67 (t, J = 7.6 Hz, 2H), 4.81 (t, J = 7.8 Hz, 1H), 7.28-7.39 (m, 10H), 7.23-7.51 (m, 1H), 8.68 (s, 1H). |
| Example 58 | (2S,4R)-1-[(2S)-2-{2-[2-(4-{4-[(1S)-1-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}ethyl]phenyl}piperazin-1-yl)ethoxy]acetamido}-3,3-dimethylbutanoyl]-4-hydroxy-N-{[4-(4-methyl-1,3-thiazol-5-yl)phenyl]methyl}pyrrolidine-2-carboxamide | $^{1}$HNMR (400 MHz, $CD_3OD$): δ 1.05, 1.07 (two singles, 9H), 1.51 (d, J = 6.8 Hz, 3H), 1.71 (s, 3H), 2.07-2.15 (m, 1H), 2.20-2.28 (m, 1H), 2.45, 2.48 (two singles, 6H), 2.70 (s, 3H), 3.04-3.18 (m, 6H), 3.23-3.32 (m, 5H), 3.43-3.52 (m, 1H), 3.73-3.97 (m, 4H), 4.07-4.18 (m, 2H), 4.34-4.40 (m,1H), 4.52-4.71 (m, 5H), 4.98-5.07 (m, 1H), 6.94 (d, J = 8.0 Hz, 2H), 7.26-7.47 (m, 10H), 8.39 (br, 1H), 8.65 (d, J = 8.0 Hz, 1H), 8.84, 8.88 (two singles, 1H). |
| Example 80 | (2S,4R)-1-[(2S)-2-{2-[4-(2-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}ethoxy)phenyl]acetamido}-3,3-dimethyl-butanoyl]-4-hydroxy-N-{[4-(4-methyl-1,3-thiazol-5-yl)phenyl]methyl}pyrrolidine-2-carboxamide | $^{1}$HNMR (400 MHz, $CD_3OD$): δ 0.84 (s, 9H), 1.67 (s, 3H), 2.10-2.15 (m, 1H), 2.40 (s, 3H), 2.49 (s, 4H), 2.65 (s, 3H), 3.39-3.68 (m, 8H), 4.04-4.08 (m, 3H), 4.30-4.73 (m, 6H), 6.14-6.16 (m, 1H), 6.84 (d, J = 7.6 Hz, 2H), 7.12 (d, J = 7.2 Hz, 3H), 7.33-7.37 (m, 7H), 8.71 (s, 1H). |

Example 83: 9-Benzyl-2-(dimethyl-1,2-oxazol-4-yl)-6-(2-{2-{2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]ethoxy}ethoxy)-9H-carbazole-4-carboxamide
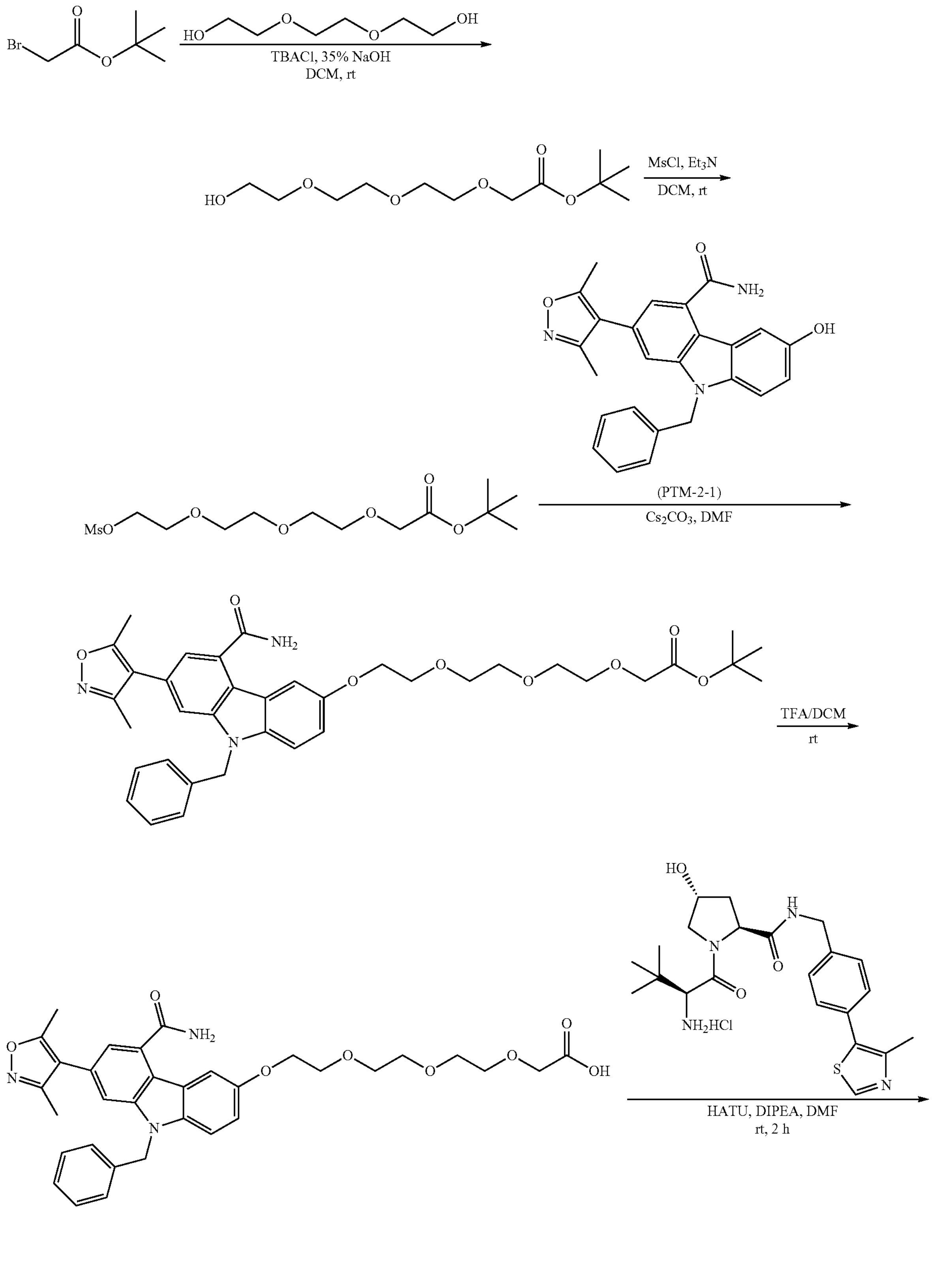

-continued

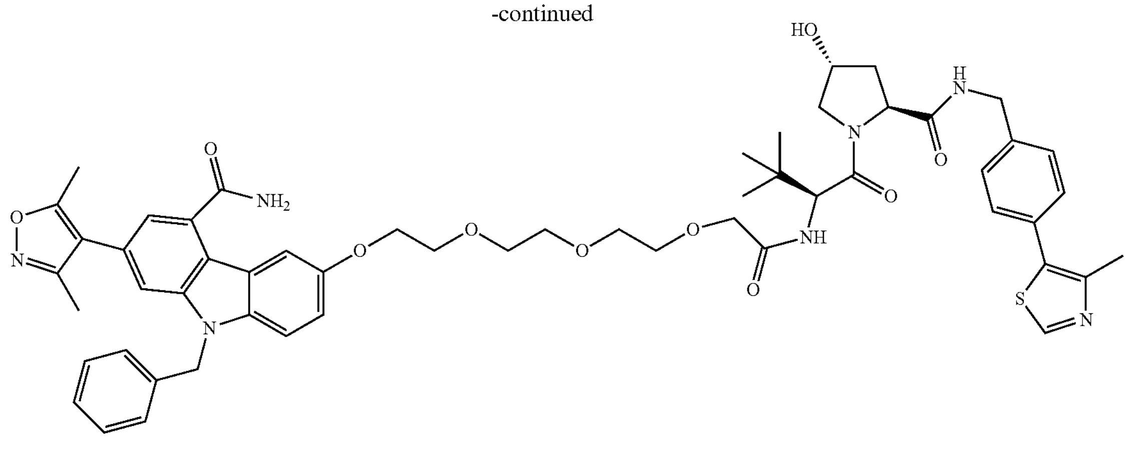

Step 1: Preparation of tert-butyl 2-(2-(2-(2-hydroxyethoxy)ethoxy)ethoxy)acetate To a solution containing 2,2'-(ethane-1,2-diylbis(oxy)) diethanol (4.2 g, 28 mmol, 1.4 eq), 35% NaOH (38 mL), and TBACl (5.84 g, 21 mmol, 1.05 eq) in DCM (50 mL) was added tert-butyl 2-bromoacetate (3.9 g, 20 mmol, 1 equiv). The resulting solution was stirred at rt for 0.5 h. Then water (20 mL) was added. The mixture was extracted with ethyl acetate (150 mL×2). The combined organic layers were washed with brine (20 mL), dried over anhydrous sodium sulfate and concentrated under vacuum. The residue was applied onto a silica gel column eluted with ethyl acetate/petroleum ether (1/3) to afford the title compound (0.85 g, 16.1% yield) as a colorless oil.

$^1$HNMR (400 MHz, $CDCl_3$): δ: 4.09 (s, 2H), 3.70-3.64 (m, 10H), 3.58-3.56 (m, 2H), 2.70 (s, 1H), 1.44 (s, 9H).

Step 2: Preparation of tert-butyl 2-(2-{2-[2-(methanesulfonyloxy)-ethoxy]ethoxy}ethoxy)acetate To a solution of tert-butyl 2-(2-(2-(2-hydroxyethoxy) ethoxy)ethoxy)acetate (350 mg, 1.33 mmol, 1.00 equiv) and $Et_3N$ (537 mg, 5.3 mmol, 4 eq) in DCM (8 mL) was added MSCl (304 mg, 2.7 mmol, 2.0 eq). The resulting solution was stirred at 25° C. for 1 h and quenched with water (5 mL). The mixture was extracted with ethyl acetate (30 mL×2). The combined organic layers were washed with brine (5 mL), dried over anhydrous sodium sulfate and concentrated under vacuum. The residue was applied onto a silica gel column eluted with ethyl acetate/petroleum ether (1/2) to afford the title compound (0.35 g, 77.0% yield) as colorless oil. $^1$HNMR (400 MHz, $CDCl_3$): δ 4.37-4.36 (m, 2H), 4.00 (s, 2H), 3.76-3.75 (m, 2H), 3.67-3.65 (m, 8H), 3.07 (s, 3H), 1.46 (s, 9H).

Step 3: Preparation of tert-butyl 2-(2-(2-(2-((9-benzyl-5-carbamoyl-7-(3,5-dimethylisoxazol-4-yl)-9H-carbazol-3-yl)oxy)ethoxy)ethoxy)ethoxy)acetate To a solution of 9-benzyl-2-(3,5-dimethylisoxazol-4-yl)-6-hydroxy-9H-carbazole-4-carboxamide (41.1 mg, 0.1 mmol, 1 eq, PTM-2-1) and tert-butyl 2-(2-{2-[2-(methanesulfonyloxy)-ethoxy]ethoxyl ethoxy)acetate (68.4 mg, 0.2 mmol, 2 eq) in DMF (4 mL) was added $Cs_2CO_3$ (97.7 mg, 0.3 mmol, 3 equiv) at 25° C. The mixture was stirred at 90° C. for 1 h and then cooled to room temperature. The mixture was extracted with ethyl acetate (30 mL×2). The combined organic layers were washed with water (10 mL), brine (5 mL), and concentrated under vacuum. The resulting residue was purified by column chromatography (PE:EA=1:1) to afford the title compound (42 mg, 64% yield).

Step 4 and Step 5: Preparation of 9-benzyl-2-(dimethyl-1,2-oxazol-4-yl)-6-(2-{2-[2-({[(2S)-1-[(2S, 4R)-4-hydroxy-2-({[4-(4-methyl-1,3-thiazol-5-yl) phenyl]methyl}carbamoyl)pyrrolidin-1-yl]-3,3-dimethyl-1-oxobutan-2-yl]carbamoyl}methoxy) ethoxy]ethoxy}ethoxy)-9H-carbazole-4-carboxamide To a solution of tert-butyl 2-(2-(2-(2-((9-benzyl-5-carbamoyl-7-(3,5-dimethylisoxazol-4-yl)-9H-carbazol-3-yl) oxy)ethoxy)ethoxy)ethoxy)acetate (42 mg, 0.064 mmol, 1 eq) in DCM (2 mL) was added TFA (1 mL) at room temperature. The mixture was stirred at rt for 1 h and then evaporated to dryness and dried under vacuum to afford an intermediate carboxylic acid (38.5 mg, 100% yield), which was used without further purification. This acid (38.5 mg, 0.064 mmol, 1 eq) was combined with (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (35.8 mg, 0.077 mmol, 1.2 eq), DIPEA (33.5 mg, 0.26 mmol, 4 equiv) in DMF (4 mL). To this stirred solution was added HATU (49.4 mg, 0.13 mmol, 2 eq) at 25° C. The mixture was stirred at rt for 1 h and then quenched with water. The solution was extracted with ethyl acetate (2×10 mL). The combined organic layers were washed with water (5 mL) and brine (5 mL). The organic phase was concentrated and purified by preparative TLC (MeOH:DCM=1:10) to afford the title compound (25 mg, 39.1% yield).

$^1$HNMR (400 MHz, $CD_3OD$): δ 8.90 (s, 1H), 8.00 (s, 1H), 7.36-7.47 (m, 6H), 7.10-7.23 (m, 7H), 5.62 (s, 2H), 4.89 (s, 1H), 4.46-4.68 (m, 3H), 4.18-4.30 (m, 3H), 4.06-4.08 (m, 2H), 3.82-3.88 (m, 3H), 3.62-3.80 (m, 9H), 2.44 (s, 3H), 2.36 (s, 3H), 2.19-2.20 (m, 1H), 2.18 (s, 3H), 2.00-2.12 (m, 1H), 1.65 (d, J=6.8 Hz, 1H), 1.02 (s, 9H). LC/MS: 1015 $[M+H]^+$; $t_R$=5.51 min With the same method the following compounds were prepared:

| | | |
|---|---|---|
| Example 89 | 9-Benzyl-2-(dimethyl-1,2-oxazol-4-yl)-6{[1-({1-[4-hydroxy-2-({[4-(4-methyl-1,3-thiazol-5-yl)phenyl] methyl}carbamoyl)pyrrolidin-1-yl]-3,3-dimethyl-1-oxobutan-2-yl}carbamoyl)-2,5,8,11-tetraoxatridecan-13-yl]oxy}-9H-carbazole-4-carboxamide | $^{1}$HNMR (400 MHz, $CD_3OD$): δ 8.92 (s, 1H), 8.02 (s, 1H), 7.36-7.49 (m, 6H), 7.10-7.27 (m, 7H), 5.63 (s, 2H), 4.67 (s, 1H), 4.47-4.56(m, 3H), 4.28-4.32(m, 1H), 4.21(m, 2H), 4.00 (s, 2H), 3.82-3.87 (m, 3H), 3.62-3.71 (m, 14H), 2.44 (s, 3H), 2.36 (s, 3H), 2.19(s, 3H), 2.05(m, 1H), 1.01(s, 9H) |
| Example 116 | 9-benzyl-2-(dimethyl-1,2-oxazol-4-yl)-6-{2-[3-({[(2S)-1-[(2S,4R)-4-hydroxy-2-({[4-(4-methyl-1,3-thiazol-5-yl)phenyl]methyl}carbamoyl) pyrrolidin-1-yl]-3,3-dimethyl-1-oxobutan-2-yl]carbamoyl}methoxy) propoxy]ethoxy}-9H-carbazole-4-carboxamide | $^{1}$HNMR (400 MHz, $CD_3OD$): δ 8.97 (s, 1H), 8.00 (d, J = 2.4 Hz, 1H), 7.36-7.48 (m, 6H), 7.10-7.26 (m, 7H), 5.62 (s, 2H), 4.69 (s, 1H), 4.48-4.52(m, 3H), 3.97-3.99 (m, 2H), 3.84-3.86 (m, 3H), 3.82-3.09 (m, 3H), 3.66-3.72 (m, 5H), 2.44 (s, 3H), 2.36 (s, 3H), 2.19(s, 3H), 2.03-2.12(m, 1H), 1.93-1.94 (m, 2H), 1.65 (d, J = 7.2 Hz, 1H), 1.01 (s, 9H) |
| Example 117 | 9-benzyl-2-(dimethyl-1,2-oxazol-4-yl)-6-{4-[3-({[(2S)-1- [(2S,4R)-4-hydroxy-2-({[4-(4-methyl-1,3-thiazol-5-yl) phenyl]methyl}carbamoyl)pyrrolidin-1-yl]-3,3-dimethyl-1-oxobutan-2-yl]c arbamoyl}methoxy)propoxy]butoxy}-9H-carbazole-4-carboxamide | $^{1}$HNMR (400 MHz, $CD_3OD$): δ 8.98 (s, 1H), 7.98 (s, 1H), 7.26-7.47 (m, 6H), 7.21-7.26 (m, 4H), 7.11(d, J = 6.8 Hz, 2H), 5.62 (s, 2H), 4.70 (s, 1H), 4.48-4.54(m, 4H), 4.29-4.31(m, 1H), 4.07-4.09(m, 2H), 3.96-3.97 (m, 2H), 3.75-3.85 (m, 2H), 3.54-3.64 (m, 7H), 2.45 (s, 3H), 2.36 (s, 3H), 2.19(s, 3H), 2.03-2.12(m, 1H), 2.05-2.10(m, 1H), 1.78-1.92 (m, 6H), 1.66 (d, J = 6,8 Hz, 3H), 1.02(s, 9H) |
| Example 133 | 9-benzyl-2-(dimethyl-1,2-oxazol-4-yl)-6-{3-[3-({[(2S)-1-[(2S,4R)-4-hydroxy-2-({[4-(4-methyl-1,3-thiazol-5-yl) phenyl]methyl}carbamoyl)pyrrolidin-1-yl]-3,3-dimethyl-1-oxobutan-2-yl]c arbamoyl}methoxy)propoxy]propoxy}-9H-carbazole-4-carboxamide | $^{1}$HNMR (400 MHz, $CD_3OD$): δ 1.03 (s, 9H), 1.74-1.93 (m, 3H), 2.06-2.08 (m, 3H), 2.20 (s, 3H), 2.37-2.47 (m, 6H), 3.41-3.46 (m, 1H), 3.55-3.70 (m, 6H), 3.72-3.83 (m, 2H), 3.87-3.93 (m, 1H), 3.97 (d, J = 5.2 Hz, 1H), 4.09-4.19 (m, 3H), 4.29-4.33 (m, 1H), 4.40-4.62 (m, 3H), 4.69-4.76 (m, 1H), 5.63 (s, 2H), 7.12-7.27 (m, 6H), 7.37-7.48 (m, 6H), 7.59 (d, J = 9.2 Hz, 1H), 7.80 (d, J = 8.0 Hz, 1H), 8.01 (s, 1H), 8.84, 8.87 (two singles, 1H). |
| Example 143 | 9-benzyl-2-(dimethyl-1,2-oxazol-4-yl)-6-({5-[3-({[(2S)-1-[(2S,4R)-4-hydroxy-2-({[4-(4-methyl-1,3-thiazol-5-yl) phenyl]methyl}carbamoyl)pyrrolidin-1-yl]-3,3-dimethyl-1-oxobutan-2-yl]carbamoyl}methoxy)propoxy]pent yl}oxy)-9H-carbazole-4-carboxamide | $^{1}$HNMR (400 MHz, $CD_3OD$): δ 1.02, 1.04 (two singles, 9H), 1.56-1.69 (m, 4H), 1.82-1.94 (m, 4H), 2.05-2.11 (m, 1H), 2.21-2.26 (m, 4H), 2.38 (s, 3H), 2.46, 2.47 (two singles, 3H), 3.51 (t, J = 6.4 Hz, 2H), 3.57-3.60 (m, 2H), 3.63-3.68 (m, 2H), 3.77-3.81 (m, 1H), 3.87, 3.89 (two singles, 1H), 3.99 (d, J = 4.0 Hz, 2H), 4.05-4.10 (m, 2H), 4.31-4.38 (m, 1H), 4.47-4.61 (m, 3H), 4.70-4.72 (m, 1H), 5.64 (s, 2H), 7.12-7.15 (m, 3H), 7.21-7.28 (m, 4H), 7.38-7.49 (m, 6H), 7.57 (d, J = 9.6 Hz, 1H), 8.00 (d, J = 2.4 Hz, 1H), 8.85, 8.87 (two singles, 1H). |
| Example 152 | 9-benzyl-2-(dimethyl-1,2-oxazol-4-yl)-6-(4-{2-[2-({[2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]ethoxy} butoxy)-9H-carbazole-4-carboxamide | $^{1}$HNMR (400 MHz, $CD_3OD$): δ 1.02, 1.04 (two singles, 9H), 1.75-1.82 (m, 2H), 1.85-1.92 (m, 2H), 2.05-2.11 (m, 1H), 2.18-2.26 (m, 4H), 2.38 (s, 3H), 2.46, 2.47 (two singles, 3H), 3.56 (t, J = 6.4 Hz, 2H), 3.62-3.70 (m, 8H), 3.77-3.81 (m, 1H), 3.87, 3.90 (two singles, 1H), 4.03-4.13 (m, 4H), 4.29-4.34 (m, 1H), 4.47-4.61 (m, 3H), 4.70 (d, J = 9.6 Hz, 1H), 5.64 (s, 2H), 7.12-7.16 (m, 3H), 7.21-7.28 (m, 4H), 7.38-7.49 (m, 6H), 7.68 (d, J = 9.2 Hz, 1H), 8.00 (d, J = 2.0 Hz, 1H), 8.85, 8.87 (two singles, 1H). |
| Example 166 | 9-benzyl-2-(dimethyl-1,2-oxazol-4-yl)-6-{4-[3-({[2S)-1-[(2S,4R)-4-hydroxy-2-{[(1S)-1-[4-(4-methyl-1,3-thiazol-5-yl)phenyl]ethyl]carbamoyl} pyrrolidin-1-yl]-3,3-dimethyl-1-oxobutan-2-yl]carbamoyl}methoxy)propoxy] butoxy}-9H-carbazole-4-carboxamide | $^{1}$HNMR (400 MHz, $CD_3OD$): δ 1.04 (s, 9H), 1.27-1.36 (m, 2H), 1.48 (d, J = 6.0 Hz, 3H), 1.77-2.00 (m, 6H), 2.20 (s, 3H), 2.37 (s, 3H), 2.47 (s, 3H), 3.57-3.66 (m, 6H), 3.73-3.75 (m, 1H), 3.84-3.87 (m, 1H), 3.94-4.03 (m, 2H), 4.06-4.18 (m, 2H), 4.35-4.44 (m, 1H), 4.56-4.64 (m, 1H), 4.67-4.71 (m, 1H), 4.98-5.03 (m, 1H), 5.64 (s, 2H), 7.11-7.28 (m, 7H), 7.40-7.57 (m, 7H), 8.02 (s, 1H), 8.87 (s, 1H). |

Example 118: (2S,4R)-1-[(2S)-3,3-dimethyl-2-[2-({6-[(1,3-cis)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido)cyclobutoxy]pyridin-3-yl}oxy)acetamido]butanoyl]-4-hydroxy-N-{[4-(4-methyl-1,3-thiazol-5-yl)phenyl]methyl}pyrrolidine-2-carboxamide
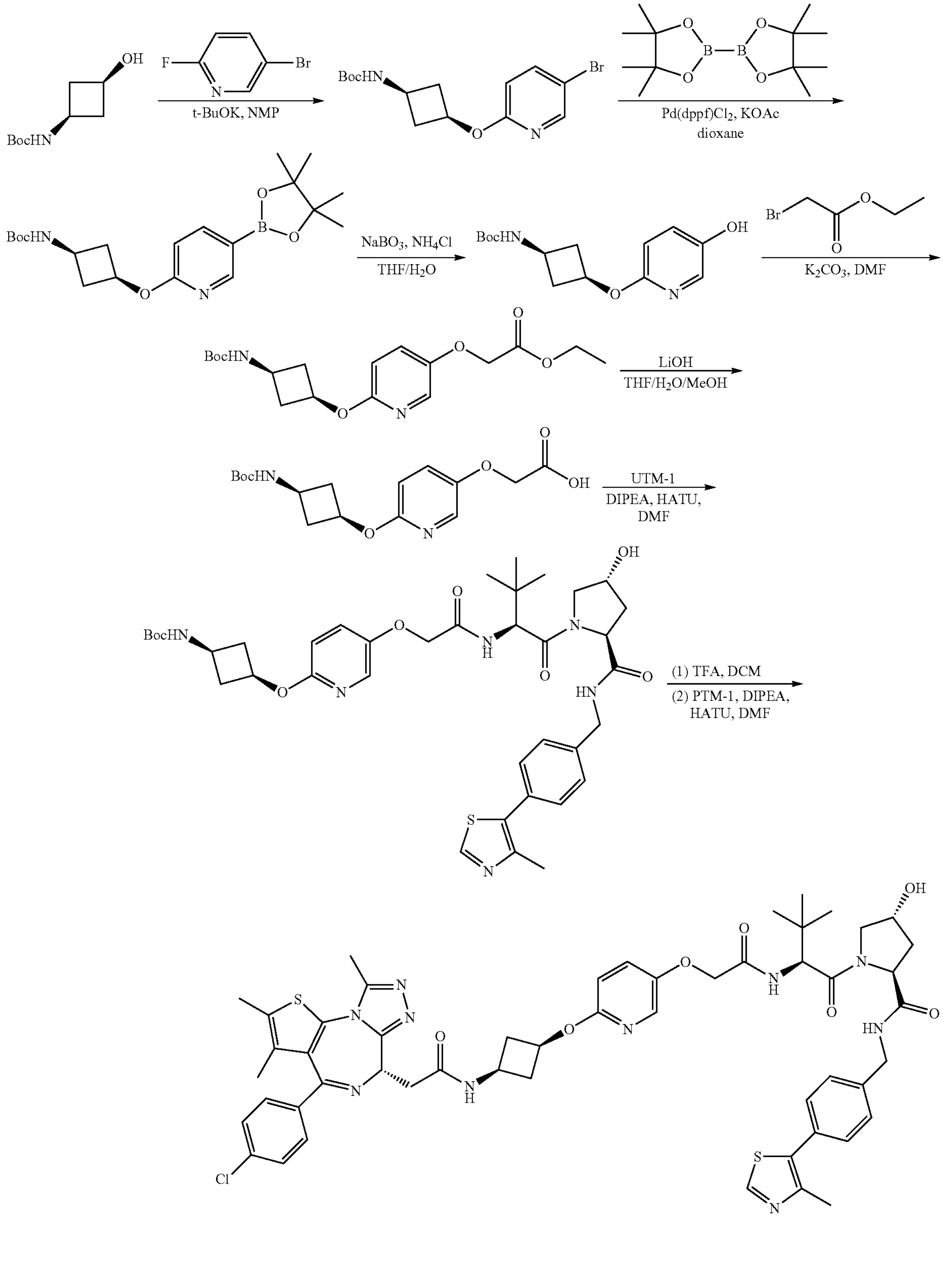

Step 1: Preparation of tert-butyl (1,3-cis)-3-((5-bromopyridin-2-yl)oxy)cyclobutylcarbamate To a stirred solution of 5-bromo-2-fluoropyridine (376 mg, 2.14 mmol) and tert-butyl (1,3-cis)-3-hydroxycyclobutyl)carbamate (400 mg, 2.14 mmol) in 1-methyl-2-pyrrolidinone (4 mL) was added potassium tert-butoxide (2.8 mL, 2.78 mmol, 1M in tetrahydrofuran) at room temperature. The reaction mixture was stirred at room temperature for 2 hours. TLC showed the reaction was complete. The reaction mixture was quenched with saturated ammonium chloride (10 mL), and the resulting mixture was extracted with ethyl acetate (20 mL×2). The combined organic layers were washed with brine (20 mL), dried over anhydrous sodium sulfate, filtered and concentrated under reduced pressure to afford crude residue which was purified by silica gel flash column chromatography (eluted with 30-100% ethyl acetate in hexane) to afford tert-butyl (1,3-cis)-3-((5-bromopyridin-2-yl)oxy)cyclobutylcarbamate (640 mg, crude) as white solid.

LC/MS (ES+): m/z 364.9 $[M+Na]^+$; to =3.007 min.

Step 2: Preparation of tert-butyl ((1,3-cis)-3-((5-(4,4,5,5-tetramethyl-1,3,2-dioxaborolan-2-yl)pyridin-2-yl)oxy)cyclobutyl)carbamate To a stirred solution containing tert-butyl ((1,3-cis)-3-((5-bromopyridin-2-yl)oxy)cyclobutyl)carbamate (640 mg, 1.87 mmol), 4,4,4',4',5,5,5',5'-octamethyl-2,2'-bi(1,3,2-dioxaborolane) (711 mg, 2.80 mmol), and potassium acetate (549 mg, 5.60 mmol) in dioxane (10 mL) was added [1,1'-bis(diphenylphosphino)ferrocene]dichloropalladium (II) (137 mg, 0.19 mmol) at rt under nitrogen atmosphere. The mixture was degassed with nitrogen three times. The resulting mixture was stirred at 90° C. overnight. TLC showed the reaction was complete. The reaction mixture was partitioned between ethyl acetate (100 mL) and water (50 mL). The organic layer was collected and the aqueous layer was extracted with ethyl acetate (50 mL×2). The combined organic layers were washed with brine (80 mL), dried over anhydrous sodium sulfate, and concentrated under reduced pressure to give a crude residue which was purified by silica gel flash column chromatography (eluted with 10-33% ethyl acetate in hexane) to afford tert-butyl ((1,3-cis)-3-((5-(4,4,5,5-tetramethyl-1,3,2-dioxaborolan-2-yl)pyridin-2-yl)oxy)cyclobutyl)-carbamate (800 mg, crude) as colorless oil.

LC/MS (ES+): m/z 413.0 $[M+Na]^+$; $t_R$=2.807 min.

Step 3: Preparation of tert-butyl ((1,3-cis)-3-((5-hydroxypyridin-2-yl)oxy)cyclobutyl)carbamate A mixture of tert-butyl ((1,3-cis)-3-((5-(4,4,5,5-tetramethyl-1,3,2-dioxaborolan-2-yl)pyridin-2-yl)oxy)cyclobutyl)carbamate (800 mg, crude) and sodium perborate tetrahydrate (632 mg, 4.10 mmol) in THF (8 mL)/water (4 mL) was stirred at room temperature for 6 h. TLC showed the reaction was complete. To the reaction mixture was added ammonium chloride (1.1 g, 20.51 mmol) at room temperature and the mixture was stirred for 30 min. The resulting reaction mixture was partitioned between ethyl acetate (80 mL) and water (60 mL). The organic layer was collected and the aqueous layer was extracted with ethyl acetate (30 mL×2). The combined organic layers were washed with brine (100 mL), dried over anhydrous sodium sulfate, and concentrated under reduced pressure to give a crude residue which was purified by silica gel flash column chromatography (eluted with 30-100% ethyl acetate in hexane) to afford tert-butyl ((1,3-cis)-3-((5-hydroxypyridin-2-yl)oxy)cyclobutyl)carbamate (350 mg, yield 67%) as white solid.

$^1$H NMR (400 MHz, $CDCl_3$): δ 1.44 (s, 9H), 1.90-1.97 (m, 2H), 2.85-3.00 (m, 2H), 3.79-3.94 (m, 1H), 4.75-4.82 (m, 1H), 5.86 (br, 1H), 6.58-6.60 (m, 1H), 7.15-7.19 (m, 1H), 7.74-7.75 (m, 1H).

LC/MS (ES+): m/z 281.2 $[M+H]^+$. $t_R$=1.912 min.

Step 4: Preparation of ethyl 2-((6-((1,3-cis)-3-((tert-butoxycarbonyl)amino)cyclobutoxy)pyridin-3-yl)oxy)acetate A mixture of tert-butyl((1s,3s)-3-((5-hydroxypyridin-2-yl)oxy)cyclobutyl)carbamate (400 mg, 1.43 mmol), ethyl 2-bromoacetate (477 mg, 2.86 mmol) and potassium carbonate (591 mg, 4.29 mmol) in N,N-dimethylformamide (3 mL) was stirred at room temperature for 4 hours. TLC showed the reaction was complete. The reaction mixture was partitioned between ethyl acetate (80 mL) and water (30 mL). The combined organic layer was collected and washed with brine (30 mL), dried over anhydrous sodium sulfate, and concentrated under reduced pressure to give a crude residue which was purified by silica gel flash column chromatography (eluted with 10-33% ethyl acetate in hexane) to afford ethyl 2-((6-((1,3-cis)-3-((tert-butoxycarbonyl)amino)cyclobutoxy)pyridin-3-yl)oxy)acetate (400 mg, yield 76%) as colorless oil.

$^1$H NMR (400 MHz, $CDCl_3$): δ 1.30 (t, J=7.0 Hz, 3H), 1.44 (s, 9H), 1.90-1.98 (m, 2H), 2.86-3.01 (m, 2H), 3.89 (br, 1H), 4.27 (q, J=7.1 Hz, 2H), 4.58 (s, 2H), 4.79-4.86 (m, 1H), 6.62-6.65 (m, 1H), 7.24-7.26 (m, 1H), 7.77-7.79 (m, 1H).

LC/MS (ES+): m/z 367.4 $[M+H]^+$. $t_R$=2.348 min.

Step 5: Preparation of 2-((6-((1,3-cis)-3-((tert-butoxycarbonyl)amino)cyclobutoxy)pyridin-3-yl)oxy)acetic acid A mixture of ethyl 2-((6-((1,3-cis)-3-((tert-butoxycarbonyl)amino)cyclobutoxy)pyridin-3-yl)oxy)acetate (350 mg, 0.95 mmol) and lithium hydroxide monohydrate (80 mg, 1.91 mmol) in THF (4 mL)/water (1 mL)/methanol (1 mL) was stirred at room temperature for 2 hours. TLC showed the reaction was complete. The reaction mixture was acidified with hydrochloride acid (1N) and extracted with dichloromethane (10 mL×3). The combined organic layers were dried over sodium sulfate and concentrated under reduced pressure to give 2-((6-((1,3-cis)-3-((tert-butoxycarbonyl)amino)cyclobutoxy)pyridin-3-yl)oxy)acetic acid (450 mg, crude) as white solid which was used in next step without further purification.

Step 6: Preparation of tert-butyl ((1,3-cis)-3-((5-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)pyridin-2-yl)oxy)cyclobutyl)carbamate To a stirred solution containing 2-(((6-((1,3-cis)-3-((tert-butoxycarbonyl)amino)cyclobutoxy)pyridin-3-yl)oxy)acetic acid (230 mg, crude), (2S,4R)-1-((S)-2-amino-3,3-dimethylbutanoyl)-4-hydroxy-N-(4-(4-methylthiazol-5-yl)

benzyl)pyrrolidine-2-carboxamide hydrochloric acid salt (223 mg, 0.48 mmol, UTM-1), and DIPEA (246 mg, 1.91 mmol) in anhydrous N,N-dimethylformamide (2 mL) was added HATU (634 mg, 1.67 mmol) at 0° C., the resulting mixture was allowed to warm to rt and stirred for 30 min. TLC showed the reaction was complete. The mixture was partitioned between ethyl acetate (50 mL) and water (30 mL). The organic layer was collected, and the aqueous layer was extracted with ethyl acetate (20 mL×2). The combined organic layers were washed with brine (100 mL), dried over anhydrous sodium sulfate, and concentrated under reduced pressure to give a crude residue which was purified by silica gel flash column chromatography (eluted with 2-10% methanol in dichloromethane) to afford tert-butyl ((1,3-cis)-3-((5-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)pyridin-2-yl)oxy)cyclobutyl)carbamate (230 mg, yield 56% over 2 steps) as a yellow solid.

LC/MS (ES+): m/z 751.3 [M+H]$^+$; $t_R$=2.300 min.

Step 7: Preparation of (2S,4R)-1-[(2S)-3,3-dimethyl-2-[2-({6-[(1s,3s)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}cyclobutoxy]pyridin-3-yl}oxy)acetamido]butanoyl]-4-hydroxy-N-{[4-(4-methyl-1,3-thiazol-5-yl)phenyl]methyl}pyrrolidine-2-carboxamide A mixture of tert-butyl ((1,3-cis)-3-((5-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)pyridin-2-yl)oxy)cyclobutyl)carbamate (100 mg, 0.13 mmol) and 2,2,2-trifluoroacetic acid (2 mL) in dichloromethane (2 mL) was stirred at room temperature for 1 hour. TLC showed the reaction was complete. The volatiles were evaporated under reduced pressure. The residue was taken up in dry N,N-dimethylformamide (2 mL), followed by sequential addition of (S)-2-(4-(4-chlorophenyl)-2,3,9-trimethyl-6H-thieno[3,2-f][1,2,4]triazolo[4,3-a][1,4]diazepin-6-yl)acetic acid (53 mg, 0.13 mmol, PTM-1), NDIPEA (69 mg, 0.53 mmol), and HATU (127 mg, 0.33 mmol) at 0° C. The resulting mixture was allowed to warm up to room temperature and stirred for 30 min. TLC showed the reaction was complete. The reaction mixture was partitioned between ethyl acetate (30 mL) and water (20 mL). The organic layer was collected and the aqueous layer was extracted with ethyl acetate (20 mL×2). The combined organic layers were washed with brine (30 mL), dried over anhydrous sodium sulfate, and concentrated under reduced pressure to give a crude residue which was purified by preparative TLC (eluted with 10% methanol in dichloromethane) to afford the title compound (32.6 mg, yield 30%) as a light yellow solid.

$^1$H NMR (400 MHz, $CD_3OD$): δ 1.02, 1.04 (two singles, 9H), 1.71 (s, 3H), 2.08-2.18 (m, 3H), 2.23-2.28 (m, 1H), 2.46 (s, 3H), 2.49 (s, 3H), 2.51-2.58 (m, 1H), 2.71, 2.72 (two singles, 3H), 2.87-3.04 (m, 2H), 3.27-3.33 (m, 1H), 3.37-3.46 (m, 1H), 3.81-3.85 (m, 1H), 3.89-3.92 (m, 1H), 4.08-4.17 (m, 1H), 4.35-4.39 (m, 1H), 4.52-4.67 (m, 6H), 4.76 (s, 1H), 4.81-4.87 (m, 1H), 6.76-6.80 (m, 1H), 7.39-7.50 (m, 9H), 7.87-7.90 (m, 1H), 8.89 (s, 1H).

LC/MS (ES+): m/z 1033.5 [M+H]$^+$; $t_R$=2.337 min.

Example 119: (2S,4R)-1-[(2S)-3,3-dimethyl-2-[2-({6-[(1,3-cis)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}cyclobutoxy]pyridin-3-yl}oxy)acetamido]butanoyl]-4-hydroxy-N-[(1S)-1-[4-(4-methyl-1,3-thiazol-5-yl)phenyl]ethyl]pyrrolidine-2-carboxamide

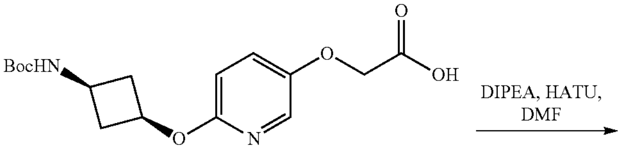

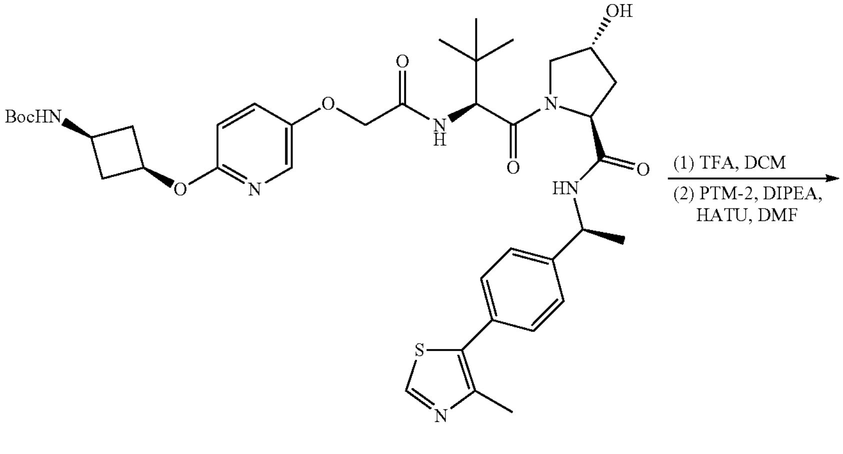

-continued

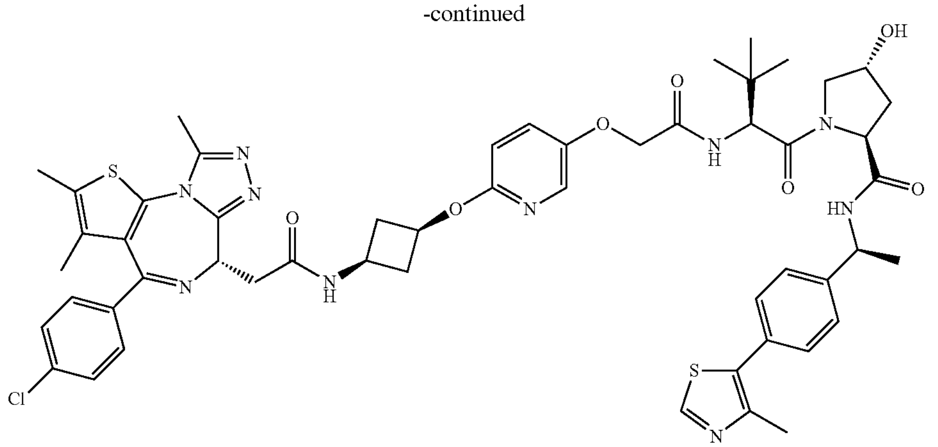

This compound was prepared according to the scheme above using the same method as described in Example 118. The title compound was obtained as a light yellow solid.

$^1$H NMR (400 MHz, $CD_3OD$): δ 1.03, 1.05 (two singles, 9H), 1.53-1.58 (m, 3H), 1.71 (s, 3H), 1.94-2.01 (m, 1H), 2.10-2.26 (m, 3H), 2.47 (s, 3H), 2.49, 2.50 (two singles, 3H), 2.52-2.59 (m, 1H), 2.71, 2.72 (two singles, 3H), 2.90-3.04 (m, 2H), 3.26-3.32 (m, 1H), 3.40-3.46 (m, 1H), 3.76-3.79 (m, 1H), 3.87-3.89 (m, 1H), 4.08-4.18 (m, 1H), 4.40-4.46 (m, 1H), 4.58-4.68 (m, 4H), 4.75 (s, 1H), 4.77-4.87 (m, 1H), 5.00-5.06 (m, 1H), 6.77-6.81 (m, 1H), 7.39-7.48 (m, 9H), 7.87-7.92 (m, 1H), 8.88, 8.89 (two singles, 1H).

LC/MS (ES+): m/z 1047.4 $[M+H]^+$; $t_R$=2.422 min.

Example 128: (2S,4R)-1-[(2S)-2-(2-{[6-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)pyridin-3-yl]oxy}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide

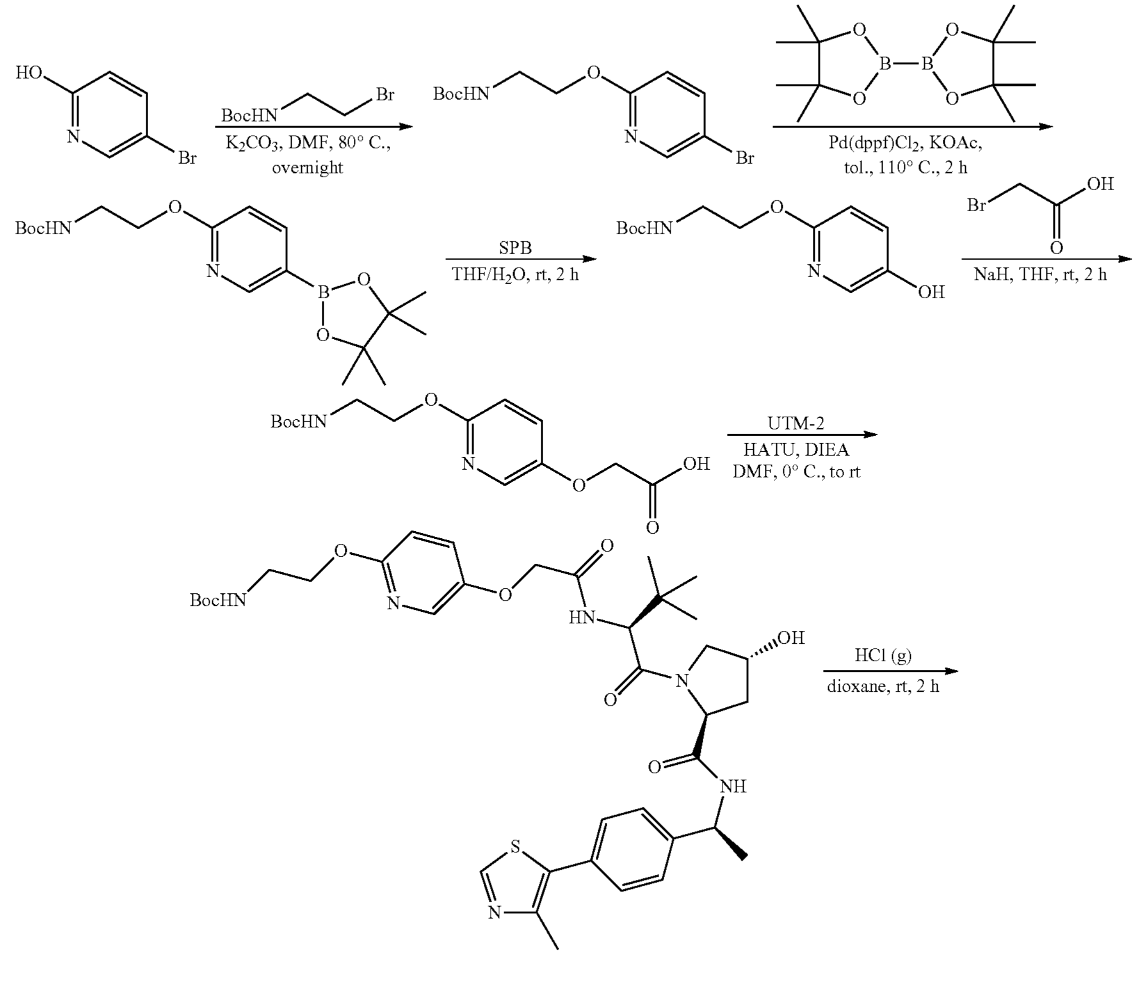

-continued

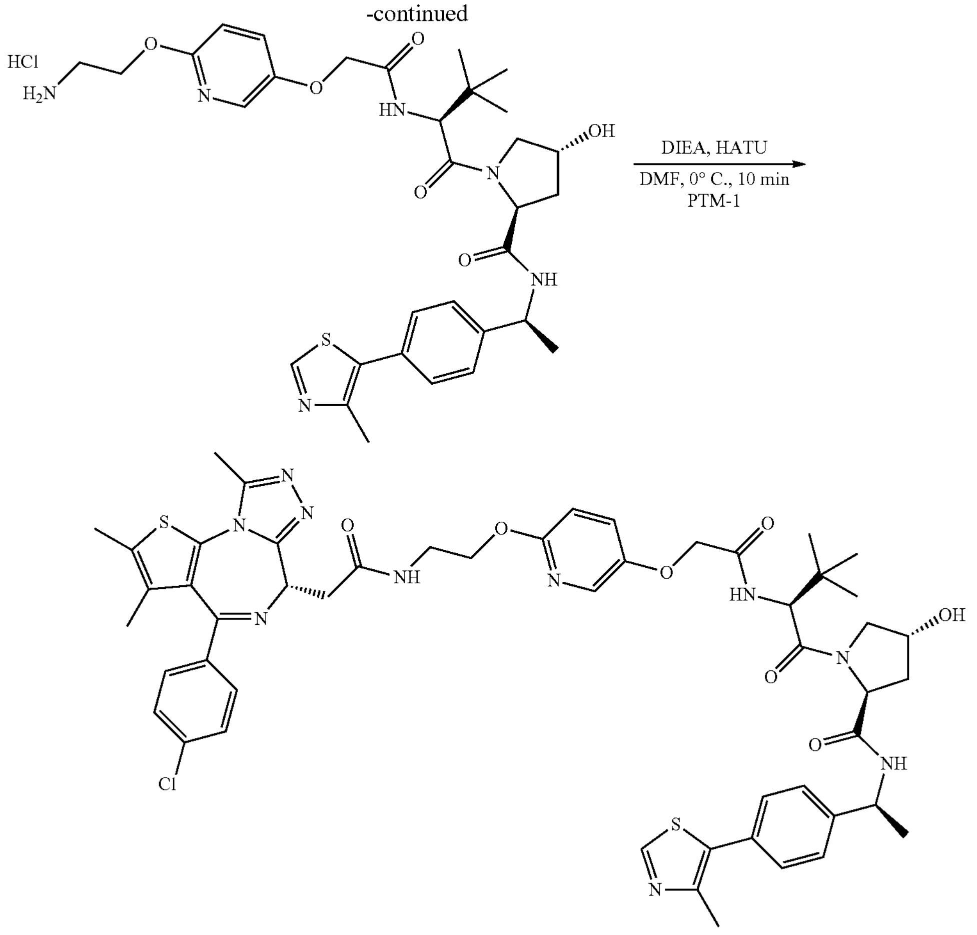

Step 1: Preparation of tert-butyl N-[2-[(5-bromopyridin-2-yl)oxy]ethyl]carbamate Into a 250-mL round-bottom flask, was placed a solution of 5-bromopyridin-2-ol (2.3 g, 13.22 mmol, 1.00 equiv), tert-butyl N-(2-bromoethyl) carbamate (3.0 g, 13.39 mmol, 1.00 equiv), potassium carbonate (5.5 g, 39.79 mmol, 3.00 equiv) in N, N-dimethylformamide (100 mL). The resulting solution was stirred overnight at 80° C. The reaction mixture was cooled. The resulting solution was extracted with ethyl acetate (200 mL×3), and the organic layers were combined. The resulting mixture was washed with brine. The mixture was dried over anhydrous sodium sulfate. The solids were filtered out. The resulting mixture was concentrated under vacuum. The crude product was purified by re-crystallization from ethyl acetate. This resulted in 2.1 g (50%) of tert-butyl N-[2-[(5-bromopyridin-2-yl)oxy]ethyl]carbamate as a white solid.

LC-MS ($ES^+$): m/z 316.85/318.85 [$MH^+$], to =0.99 min (1.90 minute run).

Step 2: Preparation of Synthesis of tert-butyl N-(2-[[5-(tetramethyl-1, 3, 2-dioxaborolan-2-yl) pyridin-2-yl]oxy]ethyl) carbamate Into a 250-mL round-bottom flask, was placed a solution of tert-butyl N-[2-[(5-bromopyridin-2-yl)oxy]ethyl]carbamate (2.5 g, 7.88 mmol, 1.00 equiv), 4,4,5,5-tetramethyl-2-(tetramethyl-1,3,2-dioxaborolan-2-yl)-1,3,2-dioxaborolane (3.0 g, 11.81 mmol, 1.50 equiv), Pd(dppf)C12 (600.0 mg, 0.82 mmol, 0.10 equiv), potassium acetate (3.1 g, 31.59 mmol, 4.00 equiv) in toluene (100 mL). The resulting solution was stirred for 2 h at 110° C. The reaction mixture was cooled. The solids were filtered out. The resulting solution was extracted with ethyl acetate (200 mL×2), and the organic layers were combined. The resulting mixture was washed with brine. The mixture was dried over anhydrous sodium sulfate. The solids were filtered out. The resulting mixture was concentrated under vacuum. The residue was applied onto a silica gel column with ethyl acetate/petroleum ether (v:v=1:2). This resulted in 2.7 g (94%) of tert-butyl N-(2-[[5-(tetramethyl-1,3,2-dioxaborolan-2-yl)pyridin-2-yl]oxy]ethyl)carbamate as yellow oil.

LC/MS ($ES^+$): m/z 365.05 [$MH^+$], $t_R$=1.09 min (1.90 minute run).

Step 3: Preparation of tert-butyl N-[2-[(5-hydroxypyridin-2-yl)oxy]ethyl]carbamate Into a 100-mL round-bottom flask, was placed a solution of tert-butyl N-(2-[[5-(tetramethyl-1, 3, 2-dioxaborolan-2-yl) pyridin-2-yl]oxy]ethyl)carbamate (500.0 mg, 1.37 mmol, 1.00 eq), sodium peroxyborate (225.0 mg, 2.00 eq) in THF/water (5/5 mL). The mixture was stirred for 2 h at rt. The solids were filtered out. The resulting solution was extracted with ethyl acetate (200 mL×2), and the organic layers were combined. The solution was washed with brine, dried over anhydrous sodium sulfate and filtered. Solvents were evaporated under vacuum. The residue was applied onto a silica gel column eluted with ethyl acetate/petroleum ether (v:v=1:2). This resulted in 260.0 mg (74%) of tert-butyl N-[2-[(5-hydroxypyridin-2-yl)oxy]ethyl]carbamate as a white solid.

$^1$H NMR (400 MHz, DMSO): δ 9.28 (s, 1H), 7.66 (d, J=4.0 Hz, 1H), 7.17 (d, J=4.0 Hz, 1H), 6.96-6.93 (m, 1H), 6.64 (d, J=4.0 Hz, 1H), 4.13-4.10 (m, 2H), 3.27-3.23 (m, 2H), 1.38 (s, 9H); LC/MS (ES$^+$): m/z 255.05 [MH$^+$], $t_R$=0.75 min (1.90 minute run).

Step 4: Preparation of 2-[[6-(2-[[(tert-butoxy)carbonyl]amino]ethoxy)pyridin-3-yl]oxy]acetic Acid Into a 50-mL round-bottom flask, sodium hydride (60%, 95.0 mg, 3.96 mmol, 2.50 eq) was added to a solution of tert-butyl N-[2-[(5-hydroxypyridin-2-yl)oxy]ethyl]carbamate (240.0 mg, 0.94 mmol, 1.00 eq) in THF (10 mL). The resulting solution was stirred for 20 minutes at room temperature. Then 2-bromoacetic acid (130.0 mg, 0.94 mmol, 1.00 eq) was added. The resulting solution was stirred for 2 hours at room temperature. The reaction was then quenched by the addition of water. The resulting solution was extracted with ethyl acetate (20 mL×2) and the aqueous layers combined. The pH value of the solution was adjusted to 1 with hydrochloric acid (1 mol/L). The resulting solution was extracted with ethyl acetate (20 mL×3) and the organic layers were combined and dried over anhydrous sodium sulfate. The solids were filtered out. The resulting solution was concentrated under vacuum. This resulted in 150.0 mg (51%) of 2-[[6-(2-[[(tert-butoxy)carbonyl]amino]ethoxy)pyridin-3-yl]oxy]acetic acid as a yellow solid.

LC-MS (ES$^+$): m/z 313.10 [MH$^+$], $t_R$=0.81 min (1.90 minute run).

Step 5 through step 7: Preparation of (2S,4R)-1-[(2S)-2-(2-{[6-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)pyridin-3-yl]oxy}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide The key intermediate from step 4 was used to prepare the title compound using the same method as described in Example 119. (2S,4R)-1-[(2S)-2-(2-{[6-(2-{2-[(9S)-7-(4-chlorophenyl-)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)pyridin-3-yl]oxy}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide was obtained as a white solid.

$^1$H NMR (400 MHz, $CD_3OD$): δ 8.87 (s, 1H), 7.89-7.87 (m, 1H), 7.46-7.29 (m, 9H), 6.79 (d, J=9.0 Hz, 1H), 5.02-4.97 (m, 1H), 4.74 (s, 1H), 4.67-4.55 (m, 4H), 4.45-4.34 (m, 3H), 3.84-3.81 (m, 1H), 3.78-3.67 (m, 2H), 3.65-3.40 (m, 2H), 3.31-3.25 (m, 1H), 2.68 (s, 3H), 2.48 (s, 3H), 2.44 (s, 3H), 2.25-2.18 (m, 1H), 2.06-1.91 (m, 1H), 1.68 (s, 3H), 1.54 (d, J=7.2 Hz, 3H), 1.04 (s, 9H); LC/MS (ES$^+$): m/z 1021.90/1023.90 [MH$^+$], $t_R$=2.73 min (5.60 minute run).

With the similar synthetic routes, the following compounds were prepared and their IUPAC names and H-NMR data are listed

| | | |
|---|---|---|
| Example 114 | 5-(3-{2-[(9S)-7-(4-chlorophenyl)-4,5,13-trimethyl-3-thia-1,8,11,12-tetra azatricyclo[8.3.0.0$^{2,6}$]trideca-2(6),4,7,10,12-pentaen-9-yl]acetamido}propoxy)-N-[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]pyridine-2-carboxamide | $^1$HNMR (400 MHz, $CD_3OD$): δ 8.24 (s, 1H) 8.27-8.20 (m, 1H), 8.04-7.97 (m, 1H), 7.46-7.32 (m, 9H), 5.03-5.00 (m, 1H), 4.82 (s, 1H), 4.70-4.55 (m, 2H), 4.45-4.40 (m, 1H), 4.21-4.11 (m, 2H), 3.96-3.91 (m, 1H), 3.85-7.76 (m, 1H), 3.58-3.33 (m, 4H), 2.68 (s, 3H), 2.48 (s, 3H), 2.45 (s, 3H), 2.22-2.17 (m, 1H), 2.15-2.05 (m, 2H), 2.02-1.93 (m, 1H), 1.68 (s, 3H), 1.52 (d, J = 6.8 Hz, 3H), 1.10(s, 9H). |
| Example 127 | (2S,4R)-1-[(2S)-2-{2-[3-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)phenoxy]acetamido}-3,3-dimethylbutanoyl]-4-hydroxy-N-[(1S)-1-[4-(4-methyl-1,3-thiazol-5-yl)phenyl]ethyl]pyrrolidine-2-carboxamide | $^1$HNMR (400 MHz, $CD_3OD$): 8.87 (s, 1H),7.30-7.43 (m, 6H),7.15-7.22 (m, 3H), 6.55-6.65 (m, 3H), 4.92-5.02 (m, 1H),4.63-4.68(m,1 H), 4.50-4.62(m, 4 H), 4.32-4.41 (m, 1 H), 4.00-4.11 (m, 2 H), 3.65-3.90(m, 3 H), 3.34-3.60(m, 3 H), 2.62-2.72 (s, 3 H), 2.35-2.45 (m, 6H), 2.05-2.28 (m, 1 H), 1.81-2.02 (m, 1 H), 1.60-1.70 (s, 3 H),1.40-1.50 (m, 3 H), 0.90-1.00 (s, 9H), |
| Example 132 | (2S,4R)-1-[(2S)-2-{[4-(3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}propoxy)phenyl]formamido}-3,3-dimethylbutanoyl]-4-hydroxy-N-[(1S)-1-[4-(4-methyl-1,3-thiazol-5-yl)phenyl]ethyl]pyrrolidine-2-carboxamide | $^1$HNMR (400 MHz, $CD_3OD$): δ 1.11, 1.13 (two singles, 9H), 1.53-1.64 (m, 3H), 1.69, 1.73 (two singles, 3H), 1.96-2.03 (m, 1H), 2.06-2.12 (m, 2H), 2.21-2.26 (m, 1H), 2.45, 2.46 (two singles, 3H), 2.48, 2.50 (two singles, 3H), 2.70, 2.72 (two singles, 3H), 3.41-3.52 (m, 3H), 3.81-3.85 (m, 1H), 3.97 (d, J = 10.8 Hz, 1H), 4.12-4.16 (m, 2H), 4.48 (br, 1H), 4.60-4.67 (m, 2H), 4.93 (s, 2H), 5.02-5.06 (m, 1H), 7.01 (d, J = 8.8 Hz, 2H), 7.34-7.37 (m, 2H), 7.40-7.50 (m, 7H), 7.69 (d, J = 9.2 Hz, 1H), 7.81 (d, J = 8.8 Hz, 2H), 8.89, 8.90 (two singles, 1H). |

-continued

| | | |
|---|---|---|
| Example 134 | (2S,4R)-1-[(2S)-2-{2-[(6-{[(2R)-1-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamido}propan-2-yl]oxy}pyridin-3-yl)oxy]acetamido}-3,3-dimethylbutanoyl]-4-hydroxy-N-[(1S)-1-[4-(4-methyl-1,3-thiazol-5-yl)phenyl]ethyl]pyrrolidine-2-carboxamide | $^{1}$HNMR (400 MHz, $CD_3OD$): δ8.86-8.78 (m, 1 H), 7.83-7.79 (m, 1 H), 7.50-7.40 (m, 7 H), 7.30-7.28 (m, 2 H), 6.71-6.65 (m, 1 H), 5.21-5.10 (m, 1 H), 5.02-4.90 (m, 1 H), 4.65 (s, 1 H), 4.58-4.48 (m, 4 H), 4.40-3.35 (m, 1 H), 3.82-3.73 (m, 1 H), 3.72-3.68 (m, 1 H), 3.60-3.50 (m, 1 H), 3.41-3.30 (m, 2 H), 3.22-3.10 (m, 1 H), 2.62 (s, 3 H), 2.55-2.46 (m, 6 H), 2.20-2.00 (m, 1 H), 1.99-1.80 (m, 1H), 1.65 (s, 3 H), 1.53-1.46 (m, 3 H), 1.30-1.10 (m, 3 H), 0.98 (s, 9 H); LC-MS ($ES^+$): m/z, 1035.47 |
| Example 135 | (2S,4R)-1-[(2S)-2-{2-[(6-{[(2S)-1-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamido}propan-2-yl]oxy}pyridin-3-yl)oxy]acetamido}-3,3-dimethylbutanoyl]-4-hydroxy-N-[(1S)-1-[4-(4-methyl-1,3-thiazol-5-yl)phenyl]ethyl]pyrrolidine-2-carboxamide | $^{1}$HNMR (400 MHz, $CD_3OD$): δ8.86-8.78 (m, 1 H), 7.83-7.79 (m, 1 H), 7.60-7.30 (m, 9 H), 6.71-6.65 (m, 1 H), 5.21-5.10 (m, 1 H), 5.02-4.90 (m, 1 H), 4.65 (s, 1 H), 4.58-4.48 (m, 4 H), 4.40-3.35 (m, 1 H), 3.82-3.73 (m, 1 H) 3.72-3.68 (m, 1 H) 3.60-3.50 (m, 2 H), 3.41-3.30 (m, 1 H), 3.22-3.10 (m, 1 H), 2.62 (s, 3 H), 2.55-2.46 (m, 6 H), 2.20-2.00 (m, 1 H), 1.99-1.80 (m, 1H), 1.65 (s, 3 H), 1.53-1.46 (m, 3 H), 1.30-1.10 (m, 3 H), 0.98 (s, 9 H) |
| Example 139 | (2S,4R)-1-[(2S)-2-{3-[6-(2-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-n-9-yl]acetamido}ethoxy)pyridin-3-yl]propanamido}-3,3-dimethylbutanoyl]-4-hydroxy-N-{[4-(4-methyl-1,3-thiazol-5-yl)phenyl]methyl}pyrrolidine-2-carboxamide | $^{1}$HNMR (400 MHz, $CD_3OD$): δ 0.96 (s, 9H), 1.69 (s, 3H), 2.05-2.13 (m, 1H), 2.20-2.27 (m, 1H), 2.46-2.49 (m, 6H), 2.51-2.62 (m, 2H), 2.71 (s, 3H), 2.80 (t, J = 7.0 Hz, 2H), 3.54-3.65 (m, 4H), 3.78-3.92 (m, 2H), 4.31-4.39 (m, 3H), 4.51-4.63 (m, 5H), 6.65 (d, J = 8.8 Hz, 1H), 7.38-7.47 (m, 9H), 7.78-7.85 (m, 2H), 8.29 (s, 1H), 8.63 (t, J = 5.8 Hz, 1H), 8.89 (s, 1H). |
| Example 141 | (2S,4R)-1-[(2S)-3,3-dimethyl-2-[2-({6-[(1,3trans)-3-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamido}cyclobutoxy]pyridin-3-yl}oxy)acetamido]butanoyl]-4-hydroxy-N-[(1S)-1-[4-(4-methyl-1,3-thiazol-5-yl)phenyl]ethyl]pyrrolidine-2-carboxamide | $^{1}$HNMR (400 MHz, $CD_3OD$): δ 1.03, 1.05 (two singles, 9H), 1.52-1.57 (m, 3H), 1.72 (s, 3H), 1.94-2.01 (m, 1H), 2.21-2.26 (m, 1H), 2.46 (s, 3H), 2.49, 2.50 (two singles, 3H), 2.52-2.56 (m, 4H), 2.71, 2.72 (two singles, 3H), 3.28-3.32 (m, 1H), 3.43-3.68 (m, 2H), 3.76-3.79 (m, 1H), 3.86-3.89 (m, 1H), 4.40-4.52 (m, 1H), 4.58-4.68 (m, 4H), 4.75-4.81 (m, 1H), 5.03 (q, J = 7.1 Hz, 1H), 5.28-5.33 (m, 1H), 6.78-6.81 (m, 1H), 7.37-7.49 (m, 10H), 7.87-7.90 (m, 1H), 8.88, 8.89 (two singles, 1H). |
| Example 142 | (2S,4R)-1-[(2S)-2-{3-[5-(2-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamido}ethoxy)-2-fluorophenyl]propanamido}-3,3-dimethylbutanoyl]-4-hydroxy-N-[(1S)-1-[4-(4-methyl-1,3-thiazol-5-yl)phenyl]ethyl]pyrrolidine-2-carboxamide | $^{1}$HNMR (400 MHz, $CD_3OD$): δ 0.97, 0.99 (two singles, 9H), 1.49-1.51 (m, 3H), 1.68 (s, 3H), 1.96-1.98 (m, 1H), 2.19-2.22 (m, 1H), 2.45-2.49 (m, 6H), 2.57-2.64 (m, 2H), 2.70 (s, 3H) 2.91-2.95 (m, 2H) 3.47-3.53 (m, 1H), 3.63-3.64 (m, 1H), 3.72-3.77 (m, 2H), 3.87-3.90 (m, 1H) 4.06-4.09 (m, 2H), 4.44 (s, 1H), 4.59-4.67 (m, 3H), 4.99-5.03 (m, 1H), 6.78-6.88 (m, 2H), 6.96-7.00 (m, 1H), 7.26-7.28 (m, 2H), 7.41-7.46 (m, 6H), 7.88-7.90 (m, 1H), 8.59-8.60 (m, 1H),8.86-8.89 (two singles, 1H). |
| Example 146 | (2S,4R)-1-[(2S)-2-(2-{[(2Z)-4-(2-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamido}ethoxy)but-2-en-1-yl]oxy}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide | $^{1}$HNMR (400 MHz, $CD_3OD$): δ 8.97 (s, 1H), 8.43-8.41 (d, J = 7.6 Hz, 1H), 8.28-8.26 (m, 1H), 7.48-7.40 (m, 6H), 7.36-7.33 (m, 3H), 5.68-5.66 (m, 2H), 5.12-5.11 (m, 1H), 4.90-4.81 (m, 1H), 4.54-4.51 (m, 2H), 4.49-4.48 (m, 1H), 4.26-4.19 (m, 1H), 4.11-4.04 (m, 4H), 3.92-3.91 (m, 2H), 3.57-3.56 (m, 2H), 3.44-3.42 (m, 2H), 3.31-3.28 (m, 3H), 2.58 (s, 3H), 2.49 (s, 3H), 2.48 (s, 3H), 2.10-2.00 (m, 1H), 1.79-1.61 (m, 1H), 1.60 (s, 3H), 1.33-1.31 (m, 3H), 0.91 (s, 9H). |

Example 150: (2S,4R)-1-[(2S)-2-{3-[3-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)-5-fluorophenyl]propanamido}-3,3-dimethylbutanoyl]-4-hydroxy-N-[(1S)-1-[4-(4-methyl-1,3-thiazol-5-yl)phenyl]ethyl]pyrrolidine-2-carboxamide
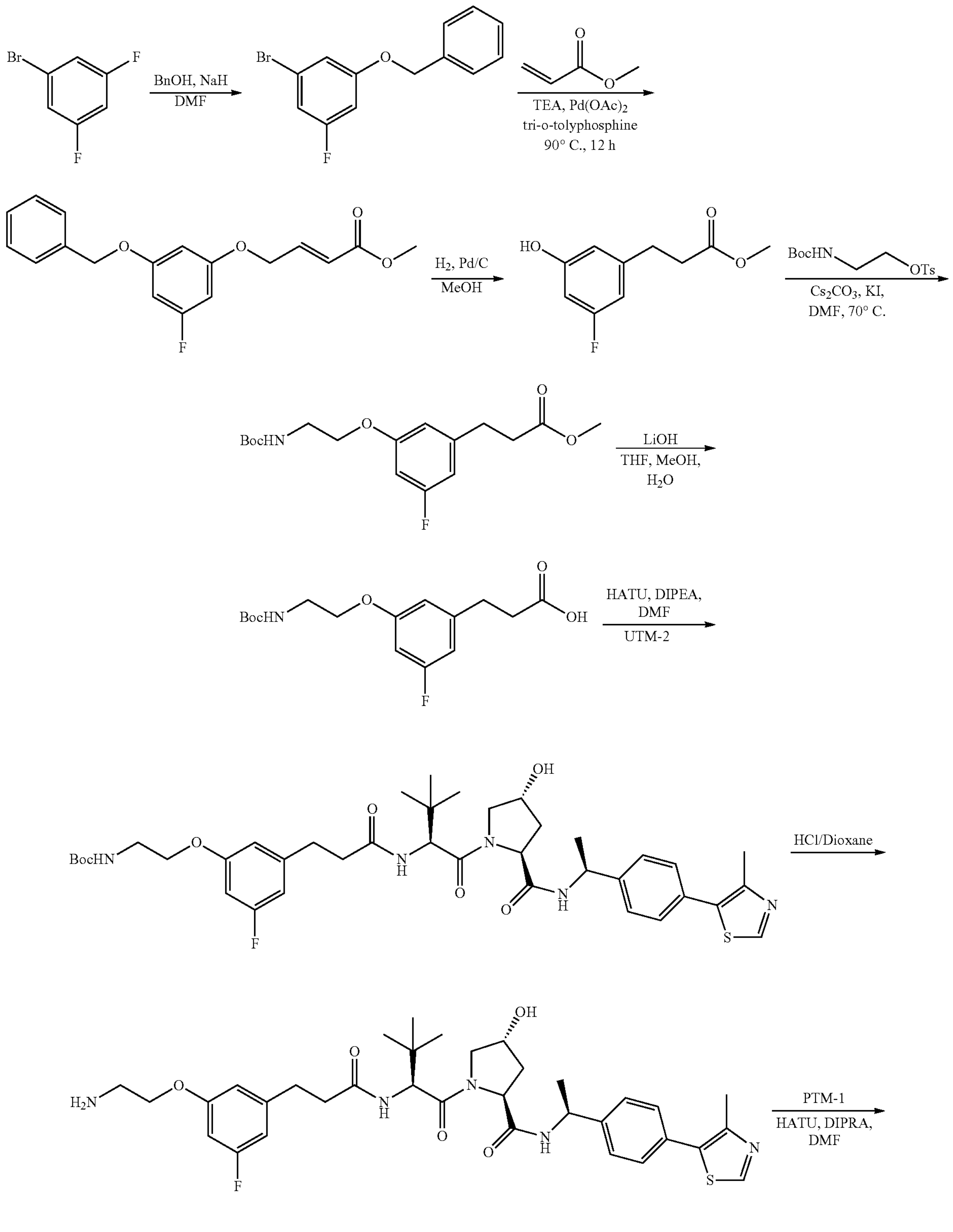

-continued

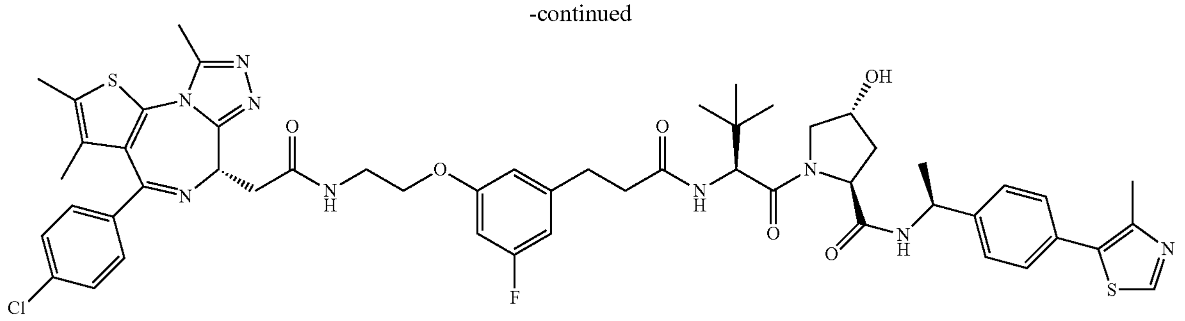

MN-ARV-YQ-048-A

This compound was prepared using the above synthetic scheme. The title compound was isolated as a white solid. $^1$HNMR (400 MHz, $CD_3OD$): δ 0.97, 0.99 (two singles, 9H), 1.50-1.60 (m, 3H), 1.69 (s, 3H), 1.93-1.99 (m, 1H), 2.18-2.23 (m, 1H), 2.45 (s, 3H), 2.49 (s, 3H), 2.55-2.66 (m, 2H), 2.70 (s, 3H), 2.88-2.94 (m, 2H), 3.28-3.30 (m, 1H), 3.47-3.53 (m, 1H), 3.57-3.65 (m, 1H), 3.73-3.78 (m, 2H), 3.87 (d, J=11.2 Hz, 1H), 4.07-4.11 (m, 2H), 4.37-4.44 (m, 1H), 4.56-4.67 (m, 3H), 4.95-5.04 (m, 1H), 6.54-6.73 (m, 3H), 7.25-7.28 (m, 2H), 7.39-7.46 (m, 6H), 7.88 (d, J=8.8 Hz, 1H), 8.60 (d, J=7.6 Hz, 1H), 8.91 (two singles, 1H); LC/MS 1036.3 $[M+H]^+$; $t_R$=2.502 min.

Example 165: (2S,4R)-1-[(2S)-2-{[5-(2-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}ethoxy)-1-benzofuran-2-yl]formamido}-3,3-dimethylbutanoyl]-4-hydroxy-N-[(1S)-1-[4-(4-methyl-1,3-thiazol-5-yl)phenyl]ethyl]pyrrolidine-2-carboxamide

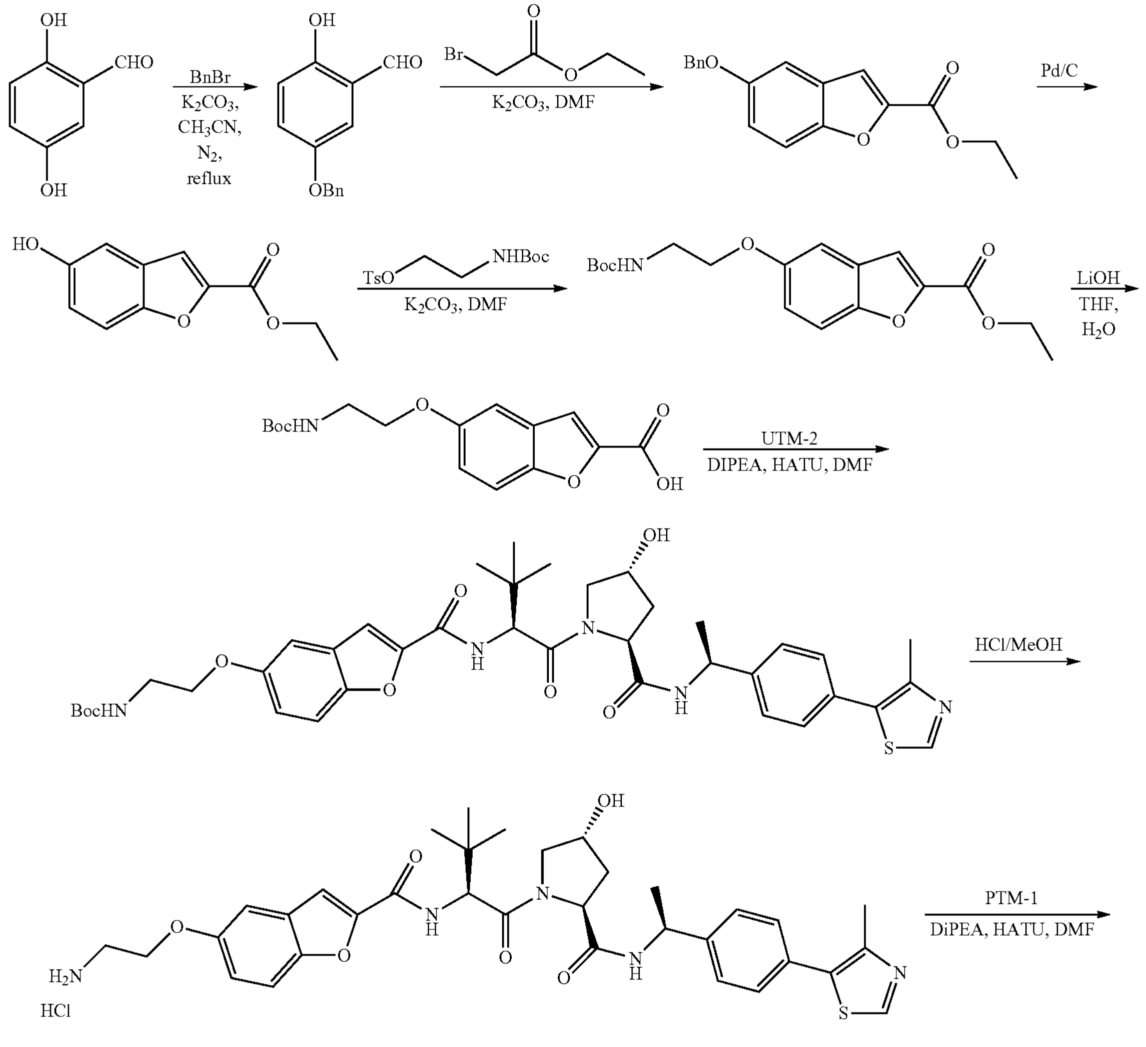

-continued

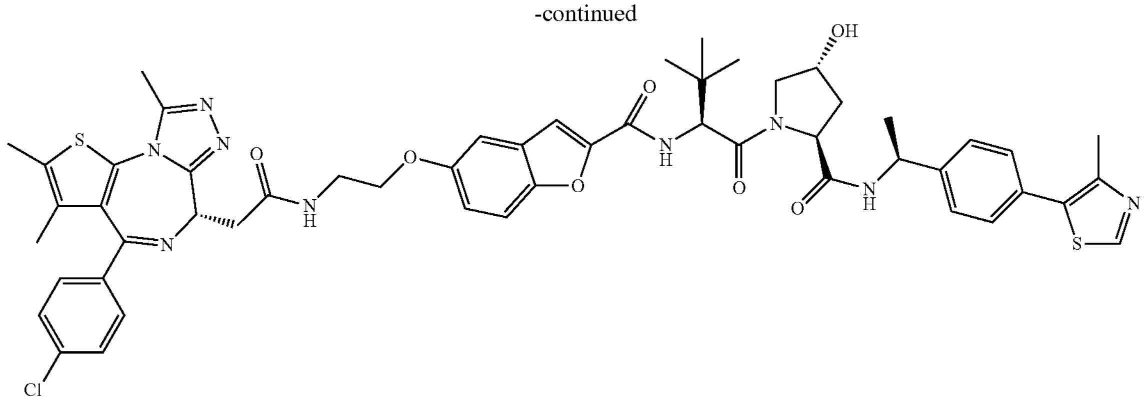

Step 1: Preparation of 5-(benzyloxy)-2-hydroxybenzaldehyde

A mixture of 2,5-dihydroxybenzaldehyde (5.0 g, 36.2 mmol), potassium carbonate (5.0 g, 36.2 mmol) and benzyl bromide (6.2 g, 36.2 mmol) in acetonitrile (25 mL) was refluxed at 90° C. for 5 hours under nitrogen atmosphere. TLC showed the reaction was complete. The cooled reaction mixture was partitioned between ethyl acetate (100 mL) and water (80 mL). The organic layer was collected, and the aqueous layer was extracted with ethyl acetate (50 mL×2). The combined organic layers were washed with brine (150 mL), dried over anhydrous sodium sulfate and concentrated under reduced pressure to afford crude residue which was purified by silica gel flash column chromatography (eluted with 10-30% ethyl acetate in hexane) to afford 5-(benzyloxy)-2-hydroxybenzaldehyde (2.8 g, yield 34%) as a yellow solid.

$^1$HNMR (400 MHz, $CDCl_3$): δ 5.06 (s, 2H), 6.94 (d, J=8.8 Hz, 1H), 7.08 (d, J=2.8 Hz, 1H), 7.21-7.24 (m, 1H), 7.36-7.42 (m, 5H), 9.84 (s, 1H), 10.67 (s, 1H).

Step 2: Preparation of ethyl 5-(benzyloxy)benzofuran-2-carboxylate

A mixture of 5-(benzyloxy)-2-hydroxybenzaldehyde (2.8 g, 12.3 mmol), ethyl 2-bromoacetate (2.05 g, 12.3 mmol) and potassium carbonate (3.4 g, 24.5 mmol) in N,N-dimethylformamide (30 mL) was stirred at 80° C. overnight under nitrogen atmosphere. TLC showed the reaction was complete. The reaction mixture was worked up and the crude residue was purified by silica gel flash column chromatography (eluted with 20-40% ethyl acetate in hexane) to afford ethyl 5-(benzyloxy)benzofuran-2-carboxylate (2.0 g, yield 55%) as a white solid.

$^1$HNMR (400 MHz, $CDCl_3$): δ 1.43 (t, J=7.2 Hz, 3H), 4.43 (q, J=7.2 Hz, 2H), 5.10 (s, 2H), 7.13-7.15 (m, 2H), 7.34-7.50 (m, 7H).

Step 3: Preparation of ethyl 5-hydroxybenzofuran-2-carboxylate

A mixture of ethyl 5-(benzyloxy)benzofuran-2-carboxylate (2.0 g, 6.75 mmol) and palladium on carbon (10%, 100 mg) in ethanol (10 mL)/ethyl acetate (10 mL) was stirred at room temperature for 1 h under hydrogen atmosphere (hydrogen balloon). TLC showed the reaction was complete. The mixture was filtered and the filter cake was washed with ethanol (20 mL×2). The combined filtrates were concentrated under reduced pressure to afford ethyl 5-hydroxybenzofuran-2-carboxylate (1.39 g, yield 99%) as a white solid.

LC/MS ($ES^+$): m/z 207.1 $[M+H]^+$. $t_R$=2.063 min.

Step 4: Preparation of ethyl 5-(2-((tert-butoxycarbonyl)amino)ethoxy)benzofuran-2-carboxylate A mixture containing 2-((tert-butoxycarbonyl)amino)ethyl 4-methylbenzenesulfonate (306 mg, 0.96 mmol), potassium carbonate (268 mg, 1.94 mmol), and ethyl 5-hydroxybenzofuran-2-carboxylate (200 mg, 0.96 mmol) in N,N-dimethylformamide (2 mL) was stirred at 50° C. overnight. TLC showed the reaction was complete. The reaction mixture was worked up and the crude residue was purified by silica gel flash column chromatography (eluted with 30% ethyl acetate in hexane) to afford ethyl 5-(2-((tert-butoxycarbonyl)amino)ethoxy)benzofuran-2-carboxylate (200 mg, yield 59%) as a white solid.

LC/MS ($ES^+$): m/z 372.1 [M+Na]+. $t_R$=2.725 min.

Step 5: Preparation of 5-(2-((tert-butoxycarbonyl)amino)ethoxy)benzofuran-2-carboxylic Acid A mixture of ethyl 5-(2-((tert-butoxycarbonyl)amino)ethoxy)benzofuran-2-carboxylate (200 mg, 0.57 mmol) and lithium hydroxide monohydrate (72 mg, 1.72 mmol) in THF (2.4 mL)/water (0.6 mL)/methanol (0.6 mL) was stirred at 25° C. for 3 h. TLC showed the reaction was complete. The reaction mixture was acidified with diluted hydrochloric acid, and extracted with dichloromethane (10 mL×3). The combined organic layers were dried over sodium sulfate and concentrated under reduced pressure to afford 5-(2-((tert-butoxycarbonyl)amino)ethoxy)benzofuran-2-carboxylic acid (135 mg, yield 74%) as a white solid.

LC/MS ($ES^+$): m/z 344.1 $[M+Na]^+$. $t_R$=2.492 min.

Step 6 through Step 8: Preparation of (2S,4R)-1-[(2S)-2-{[5-(2-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamido}ethoxy)-1-benzofuran-2-yl]formamido}-3,3-dimethylbutanoyl]-4-hydroxy-N-[(1S)-1-[4-(4-methyl-1,3-thiazol-5-yl)phenyl]ethyl]pyrrolidine-2-carboxamide Step 6 through step 8 were carried out using the same method as described in Example 119 to afford the title compound as a white solid.

LC/MS ($ES^+$): m/z 1030.5 $[M+H]^+$. $t_R$=2.855 min.

$^1$HNMR (400 MHz, $CD_3OD$): δ 1.00, 1.03 (two singles, 9H), 1.42-1.56 (m, 6H), 1.85-1.91 (m, 1H), 2.07-2.15 (m, 1H), 2.33-2.38 (m, 6H), 2.57 (s, 3H), 3.15-3.17 (m, 1H), 3.36-3.42 (m, 1H), 3.47-3.55 (m, 1H), 3.69-3.73 (m, 2H), 3.80-3.82 (m, 1H), 4.05 (t, J=5.0 Hz, 2H), 4.30-4.37 (m, 1H), 4.51-4.55 (m, 2H), 4.90-4.98 (m, 1H), 6.98-7.03 (m, 3H), 7.14-7.15 (m, 1H), 7.23-7.25 (m, 3H), 7.32-7.43 (m, 6H), 8.75, 8.78 (two singles, 1H).

The following compounds were prepared using the same synthetic method.

| | | |
|---|---|---|
| Example 170 | (2S,4R)-1-[(2S)-2-{[5-(3-{2-[(9S)-7-(4-chlorophenyl)-4,5,13-trimethyl-3-thia-1,8,11,12-tetraazatricyclo[8.3.0.$0^2$,$^6$]trideca-2(6),4,7,10,12-pentaen-9-yl]acetamido}propoxy)-1-benzofuran-2-yl]formamido}-3,3-dimethylbutanoyl]-4-hydroxy-N-[(1S)-1-[4-(4-methyl-1,3-thiazol-5-yl)phenyl]ethyl]pyrrolidine-2-carboxamide | $^1$HNMR (400 MHz, $CD_3OD$): δ 1.00, 1.02 (two singles, 9H), 1.42-1.55 (m, 6H), 1.88-1.92 (m, 1H), 1.93-2.0 (m, 2H), 2.07-2.15 (m, 1H), 2.31-2.38 (m, 6H), 2.57 (s, 3H), 3.03-3.17 (m, 1H), 3.30-3.46 (m, 4H), 3.39-4.03 (m, 4H), 4.28-4.37 (m, 1H), 4.49-4.54 (m, 2H), 4.90-4.96(m, 1H), 6.98-7.00 (m,1H), 7.09-7.15 (m, 3H), 7.27-7.40 (m, 8H), 8.75, 8.78 (two singles, 1H). |
| Example 171 | (2S,4R)-1-[(2S)-3,3-dimethyl-2-(3-{6-[(1,3-cis)-3-{2-[(9S)-7-4-chlorophenyl)-4,5,13-trimethyl-3-thia-1,8,11,12-tetraazatricyclo[8.3.0.$0^2$,$^6$]trideca-2(6),4,7,10,12-pentaen-9-yl]acetamido}cyclobutoxy]pyridin-3-yl}propanamido)butanoyl]-4-hydroxy-N-[(1S)-1-[4-(4-methyl-1,3-thiazol-5-yl)phenyl]ethyl]pyrrolidine-2-carboxamide | $^1$HNMR (400 MHz, $CD_3OD$): δ 0.96 (s, 9H), 1.52 (d, J = 7.2 Hz, 3H), 1.68, 1.71 (two singles, 3H), 1.94-2.01 (m, 1H), 2.14-2.23 (m, 3H), 2.48 (d, J = 10.4 Hz, 6H), 2.56-2.63 (m, 2H), 2.71 (s, 3H), 2.87-3.02 (m, 4H), 3.27-3.29 (m, 1H), 3.40-3.46 (m, 1H), 3.74-3.78 (m, 1H), 3.88-3.90 (m, 1H), 4.14-4.16 (m, 1H), 4.46 (br, 1H), 4.56-4.66 (m, 3H), 5.00-5.05 (m, 1H), 6.76-6.80 (m, 1H), 7.40-7.47 (m, 8H), 7.61-7.63 (m, 1H), 7.87 (d, J = 9.2 Hz, 1H), 7.99 (s, 1H), 8.55 (d, J = 7.2 Hz, 1H), 8.75 (d, J = 6.8 Hz, 1H), 8.90 (s, 1H). |
| Example 173 | (2S,4R)-1-[(2S)-2-(3-{3-fluoro-5-[(1,3-trans)-3-{2-[(9S)-7-(4-chlorophenyl)-4,5,13-trimethyl-3-thia-1,8,11,12-tetraazatricyclo[8.3.0.$0^2$,$^6$]trideca-2(6),4,7,10,12-pentaen-9-yl]acetamido}cyclobutoxy]phenyl}propanamido)-3,3-dimethylbutanoyl]-4-hydroxy-N-[(1S)-1-[4-(4-methyl-1,3-thiazol-5-yl)phenyl]ethyl]pyrrolidine-2-carboxamide | $^1$HNMR (400 MHz, $CD_3OD$): δ 0.95, 0.98 (two singles, 9H), 1.50-1.61 (s, 3H), 1.71 (s, 3H), 1.93-1.99 (m, 1H), 2.18-2.23 (m, 1H), 2.46 (s, 3H), 2.48, 2.49 (two singles, 3H), 2.51-2.69 (m, 6H), 2.72, 2.74 (two singles, 3H), 2.88-2.96 (m, 2H), 3.36-3.37 (m, 1H), 3.42-3.48 (m, 1H), 3.74-3.77 (m, 1H), 3.86-3.89 (m, 1H), 4.37-4.44 (m, 1H), 4.47-4.54 (m, 1H), 4.56-4.67 (m, 3H), 4.77-4.89 (m, 1H), 4.98-5.03 (m, 1H), 6.40-6.44 (m, 1H), 6.56-6.66 (m, 2H),7.41-7.48 (m, 8H), 7.87-7.89 (m, 1H), 8.88, 8.89 (two singles, 1H). |
| Example 183 | (2S,4R)-1-[(2S)-2-(3-{3-fluoro-5-[(1,3-cis)-3-{2-[(9S)-7-(4-chlorophenyl)-4,5,13-trimethyl-3-thia-1,8,11,12-tetraazatricyclo[8.3.0.$0^2$,$^6$]trideca-2(6),4,7,10,12-pentaen-9-yl]acetamido}cyclobutoxy]phenyl}propanamido)-3,3-dimethylbutanoyl]-4-hydroxy-N-[(1S)-1-[4-(4-methyl-1,3-thiazol-5-yl)phenyl]ethyl]pyrrolidine-2-carboxamide | $^1$HNMR (400 MHz, $CD_3OD$): δ 0.96, 0.99 (two singles, 9H), 1.50-1.62 (s, 3H), 1.70 (s, 3H), 1.93-2.00 (m, 1H), 2.11-2.24 (m, 3H), 2.46 (s, 3H), 2.49 (s, 3H), 2.53-2.71 (m, 5H), 2.88-3.06 (m, 4H), 3.13-3.30 (m, 1H), 3.40-3.46(m, 1H), 3.74-3.78 (m, 1H), 3.87-3.90 (m, 1H), 4.12-4.20 (m, 1H), 4.49-4.542 (m, 2H), 4.56-4.66 (m, 3H), 5.00-5.05 (m, 1H), 6.45-6.48 (m, 1H), 6.58-6.66 (m, 2H),7.40-7.47 (m, 8H), 7.88 (d, J = 8.8 Hz, 1H), 8.60 (d, J = 7.2 Hz, 1H), 8.88, 8.89 (two singles, 1H). |
| Example 185 | (2S,4R)-1-[(2S)-3,3-dimethyl-2-(2-{4-[(1s,35)-3-{2-[(9S)-7-(4-chlorophenyl)-4,5,13-trimethyl-3-thia-1,8,11,12-tetraa tetraazatricyclo[8.3.0.$0^2$,$^6$]trideca-2(6),4,7,10,12-pentaen-9-yl]acetamido}cyclobutoxy]phenyl}acetamido)butanoyl]-4-hydroxy-N-[(1S)-1-[4-(4-methyl-1,3-thiazol-5-yl)phenyl]ethyl]pyrrolidine-2-carboxamide | $^1$HNMR (400 MHz, $CD_3OD$): δ 0.99, 1.02 (two singles, 9H), 1.52 (d, J = 7.2 Hz, 3H), 1.71 (s, 3H), 1.91-2.00 (m, 1H), 2.10-2.26 (m, 3H), 2.46 (s, 3H), 2.50 (s, 3H), 2.71 (s, 3H), 2.90-3.06 (m, 2H), 3.26-3.31 (m, 1H), 3.39-3.47 (m, 1H), 3.53-3.61 (m, 2H), 3.71-3.78 (m, 1H), 3.83-3.92 (m, 1H), 4.11-4.20 (m, 1H), 4.41-4.47 (m, 1H), 4.48-4.67 (m, 4H), 4.99-5.06 (m, 1H), 6.80-6.89 (m, 2H), 7.20-7.30 (m, 2H), 7.34-7.49 (m, 8H), 7.76 (d, J = 9.2 Hz, 1H), 8.61 (d, J = 7.2 Hz, 1H), 8.61 (d, J = 7.2 Hz, 1H), 8.87, 8.89 (two singles, 1H). |

Example 177: (2S,4R)-4-hydroxy-N-{[4-(4-methyl-1,3-thiazol-5-yl)phenyl]methyl}-1-[(2R)-3-methyl-2-(4-{2-[(1,3-cis)-3-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}cyclobutoxy]pyridin-4-yl}-1H-pyrazol-1-yl)butanoyl]pyrrolidine-2-carboxamide Example 178: (2S,4R)-4-hydroxy-N-{[4-(4-methyl-1,3-thiazol-5-yl)phenyl]methyl}-1-[(2S)-3-methyl-2-(4-{2-[(1,3-cis)-3-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}cyclobutoxy]pyridin-4-yl}-1H-pyrazol-1-yl)butanoyl]pyrrolidine-2-carboxamide

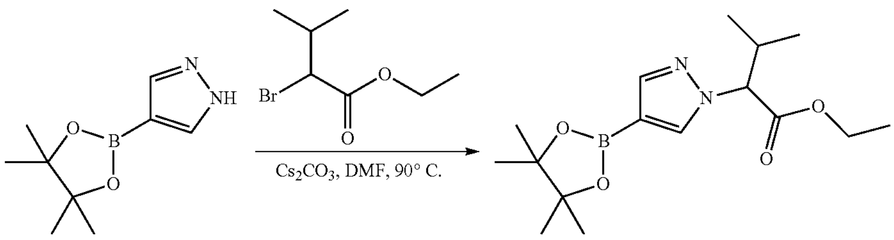

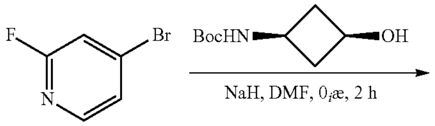

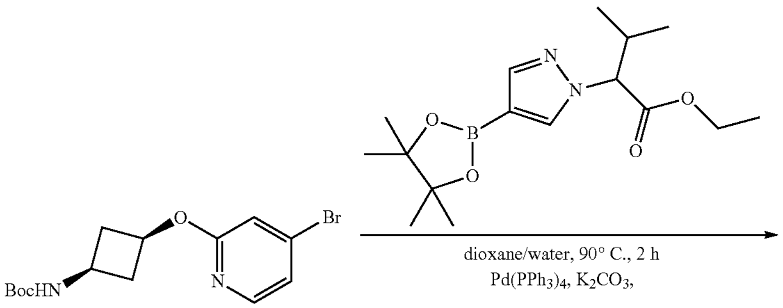

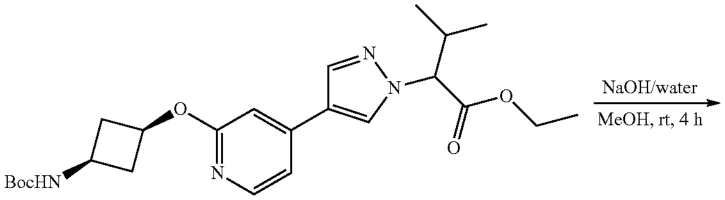

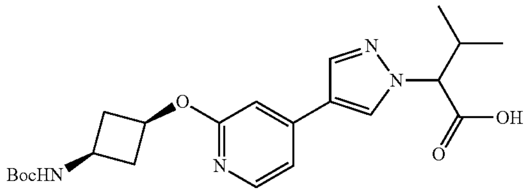

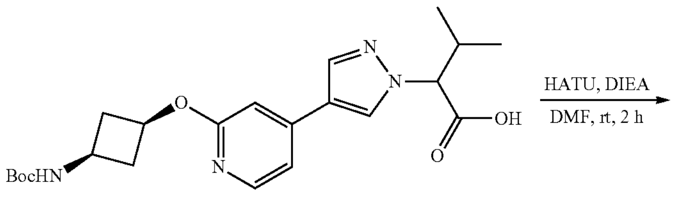

-continued
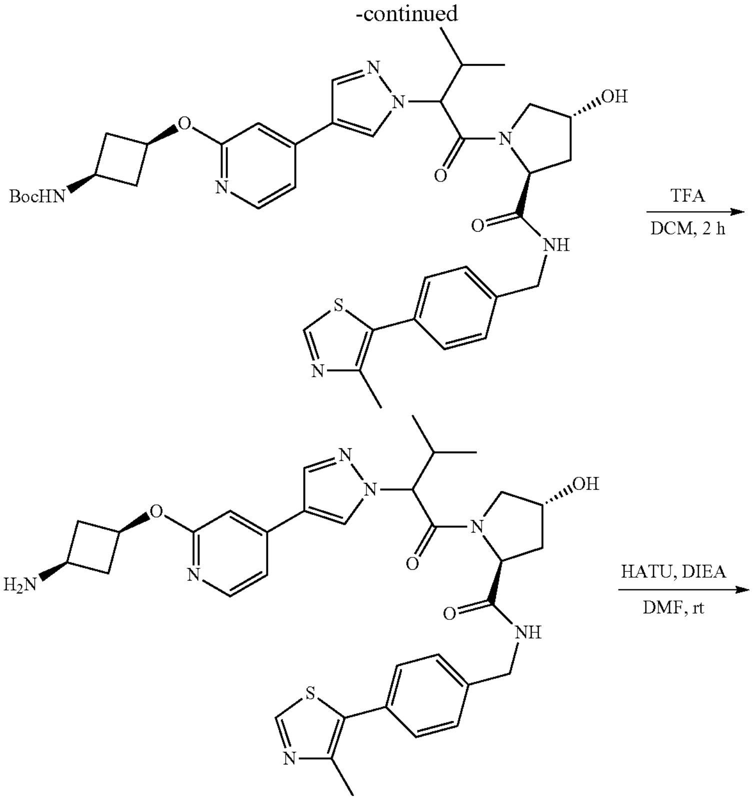
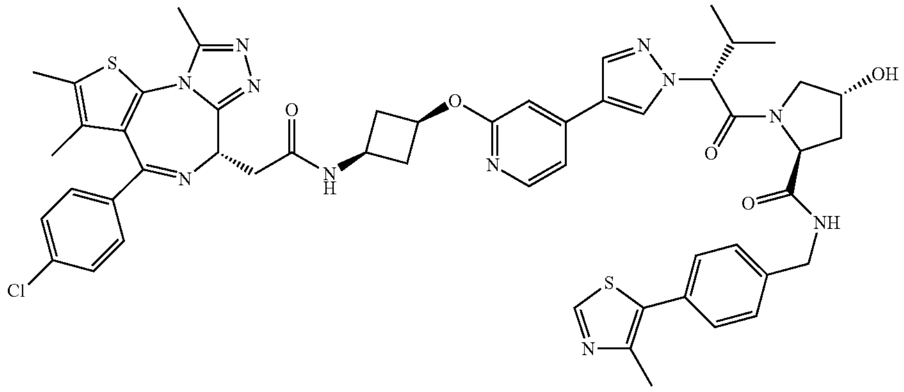
Example 177
+
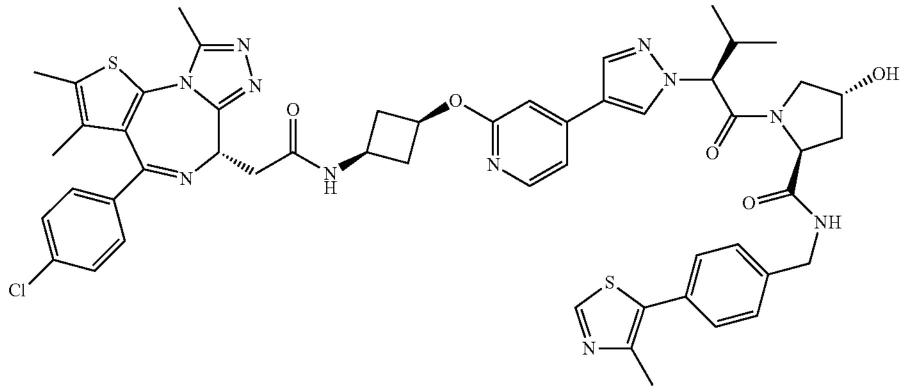
Example 178

Step 1: Preparation of ethyl 3-methyl-2-[4-(tetramethyl-1,3,2-dioxaborolan-2-yl)-1H-pyrazol-1-yl] butanoate To a solution of 4-(tetramethyl-1,3,2-dioxaborolan-2-yl)-1H-pyrazole (10 g, 51.5 mmol, 1.0 eq) in acetonitrile (150 mL) was added ethyl 2-bromo-3-methylbutanoate (11.9 g, 56.9 mmol, 1.1 eq) and cesium carbonate (33.5 g, 103 mmol, 2.0 eq). The reaction was then allowed to stir at reflux for 4 h. Reaction was monitored by TLC. After completion of the reaction, the mixture was poured in water and extracted with ethyl acetate (2×500 mL). Organic layer was combined, washed with brine solution, dried over sodium sulfate and concentrated under reduced pressure to obtain crude material. This was further purified by column chromatography. Product was eluted with 25% ethyl acetate in hexane to obtain pure title compound 13.1 g, 79%). MS(ES): m/z 323.3 $[M+H]^+$

Step 2: Preparation of tert-butyl N-[(1,3-cis)-3-[(4-bromopyridin-2-yl)oxy]cyclobutyl]carbamate Into a 100-mL 3-necked round-bottom flask purged and maintained with an inert atmosphere of nitrogen, was placed tert-butyl N-[(1,3-cis)-3-hydroxycyclobutyl]carbamate (300.0 mg, 1.60 mmol, 1.00 eq), N,N-dimethylformamide (5 mL). This was followed by the addition of sodium hydride (128.0 mg, 5.33 mmol, 2.00 eq) at 0° C. The mixture was stirred for 20 min. To this mixture was added 4-bromo-2-fluoropyridine (282.0 mg, 1.60 mmol, 1.00 eq) at 0° C. The resulting solution was stirred for 2 h at 0° C. in a water/ice bath. The reaction was then quenched by the addition of 20 mL of water/ice. The resulting solution was extracted with ethyl acetate (50 mL×3) and the organic layers were combined and dried over anhydrous sodium sulfate. After the evaporation of solvents, the residue was applied onto a silica gel column eluted with ethyl acetate/petroleum ether (1/4). This resulted in 540.0 mg (98%) of tert-butyl N-[(1,3-cis)-3-[(4-bromopyridin-2-yl)oxy]cyclobutyl]carbamate as a white solid.

LC/MS ($ES^+$): m/z 342.90/344.90 [$MH^+$], $t_R$=1.52 min, (2.60 minute run)

Step 3: Preparation of ethyl 3-methyl-2-(4-[2-[(1,3-cis)-3-[[(tert-butoxy)carbonyl]amino]cyclobutoxy] pyridin-4-yl]-1H-pyrazol-1-yl)butanoate Into a 50-mL round-bottom flask purged and maintained with an inert atmosphere of nitrogen, was placed tert-butyl N-[(1,3-cis)-3-[(4-bromopyridin-2-yl)oxy]cyclobutyl]carbamate (250.0 mg, 0.73 mmol, 1.00 eq), dioxane/water(4/1) (10 mL), ethyl 3-methyl-2-[4-(tetramethyl-1,3,2-dioxaborolan-2-yl)-1H-pyrazol-1-yl]butanoate (282.0 mg, 0.88 mmol, 1.20 equiv), potassium carbonate (151.0 mg, 1.09 mmol, 1.50 eq), $Pd(PPh_3)_4$ (84.5 mg, 0.07 mmol, 0.10 eq). The resulting solution was stirred for 2 h at 90° C. in an oil bath. The resulting solution was extracted with ethyl acetate (50 mL×3) and the organic layers were combined. The resulting mixture was washed with brine (50 mL×3). The mixture was dried over anhydrous sodium sulfate. The residue was applied onto a silica gel column eluted with ethyl acetate/petroleum ether (1/2). This resulted in 452.0 mg (crude) of ethyl 3-methyl-2-(4-[2-[(1,3-cis)-3-[[(tert-butoxy)carbonyl]amino]cyclobutoxy]pyridin-4-yl]-1H-pyrazol-1-yl)butanoate as light yellow oil.

LC/MS ($ES^+$): m/z 458.25 [$MH^+$], $t_R$=1.41 min, (2.60 minute run)

Step 4: Preparation of 3-methyl-2-(4-[2-[(1,3-cis)-3-[[(tert-butoxy)carbonyl]amino]cyclobutoxy]pyridin-4-yl]-1H-pyrazol-1-yl)butanoic Acid Into a 50-mL round-bottom flask, was placed ethyl 3-methyl-2-(4-[2-[(1,3-cis)-3-[[(tert-butoxy)carbonyl]amino]cyclobutoxy]pyridin-4-yl]-1H-pyrazol-1-yl)butanoate (452.0 mg, 0.99 mmol, 1.00 eq), methanol/water (4/1) (10 mL), sodium hydroxide (59.0 mg, 1.48 mmol, 1.50 eq). The resulting solution was stirred for 4 h at room temperature. The resulting mixture was concentrated under vacuum. The pH value of the solution was adjusted to 5 with hydrochloric acid (1 mol/L). The resulting solution was extracted with ethyl acetate (50 mL×3) and the organic layers were combined and dried over anhydrous sodium sulfate. This resulted in 430.0 mg of 3-methyl-2-(4-[2-[(1,3-cis)-3-[[(tert-butoxy)carbonyl]amino]cyclobutoxy]pyridin-4-yl]-1H-pyrazol-1-yl)butanoic acid as light yellow oil.

LC-MS ($ES^+$): m/z 431.15 [$MH^+$], $t_R$=1.16 min, (2.60 minute run). Step 5: Preparation of tert-butyl N-[(1,3-cis)-3-[[4-(1-[1-[(2S,4R)-4-hydroxy-2-([[4-(4-methyl-1,3-thiazol-5-yl)phenyl]methyl]carbamoyl)pyrrolidin-1-yl]-3-methyl-1-oxobutan-2-yl]-1H-pyrazol-4-yl)pyridin-2-yl]oxy]cyclobutyl]carbamate Into a 25-mL round-bottom flask, was placed 3-methyl-2-(4-[2-[(1,3-cis)-3-[[(tert-butoxy)carbonyl]amino]cyclobutoxy]pyridin-4-yl]-1H-pyrazol-1-yl)butanoic acid (185 mg, 0.43 mmol, 1.00 eq), N,N-dimethylformamide (5.0 mL), HATU (196.0 mg, 0.52 mmol, 1.20 eq), DIPEA (166.5 mg, 1.29 mmol, 3.00 eq), (2S,4R)-4-hydroxy-N-(4-(4-methylthiazol-5-yl)benzyl)pyrrolidine-2-carboxamide (182 mg, 0.52 mmol, 1.20 eq). The mixture was stirred for 2 h at room temperature. The resulting solution was extracted with ethyl acetate (50 mL×3) and the organic layers were combined. The resulting mixture was washed with brine (50 mL×3). The mixture was dried over anhydrous sodium sulfate. The residue was applied onto a silica gel column eluted with dichloromethane/methanol (19/1). This resulted in 180.0 mg (57%) of tert-butylN-[(1,3-cis)-3-[[4-(1-1-[(2S,4R)-4-hydroxy-2-([[4-(4-methyl-1,3-thiazol-5-yl)phenyl]-methyl]carbamoyl)pyrrolidin-1-yl]-3-methyl-1-oxobutan-2-yl]-1H-pyrazol-4-yl)pyridin-2-yl]oxy]cyclobutyl]carbamate as light yellow oil.

LC-MS ($ES^+$): m/z 730.25 [$MH^+$], $t_R$=1.14 min, (2.60 minute run).

Step 6: Preparation of (2S,4R)-4-hydroxy-N-[[4-(4-methyl-1,3-thiazol-5-yl)phenyl]methyl]-1-[3-methyl-2-(4-[2-[(1,3-cis)-3-aminocyclobutoxy]pyridin-4-yl]-1H-pyrazol-1-yl)butanoyl]pyrrolidine-2-carboxamide Into a 25-mL round-bottom flask, was placed tert-butyl N-[(1,3-cis)-3-[[4-(1-[1-[(2S,4R)-4-hydroxy-2-([[4-(4-methyl-1,3-thiazol-5-yl)phenyl]methyl]carbamoyl)pyrrolidin-1-yl]-3-methyl-1-oxobutan-2-yl]-1H-pyrazol-4-yl)pyridin-2-yl]oxy]cyclobutyl]carbamate (190.0 mg, 0.26 mmol, 1.00 eq), dichloromethane (10 mL), trifluoroacetic acid (5 mL). The solution was stirred for 2 h at room temperature. The resulting mixture was concentrated under vacuum. This resulted in 164 mg (100%) of (2S,4R)-4-hydroxy-N-[[4-(4-methyl-1,3-thiazol-5-yl)phenyl]methyl]-1-[3-methyl-2-(4-[2-[(1,3-cis)-3-aminocyclobutoxy]pyridin-4-yl]-1H-pyrazol-1-yl)butanoyl]pyrrolidine-2-carboxamide trifluoroacetic acid salt.

Step 7: Preparation of (2S,4R)-4-hydroxy-N-{[4-(4-methyl-1,3-thiazol-5-yl)phenyl]methyl}-1-[(2R)-3-methyl-2-(4-{2-[(1,3cis)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}cyclobutoxy]pyridin-4-yl)-1H-pyrazol-1-yl)butanoyl]pyrrolidine-2-carboxamide and (2S,4R)-4-hydroxy-N-{[4-(4-methyl-1,3-thiazol-5-yl)phenyl]methyl}-1-[(2S)-3-methyl-2-(4-{2-[(1,3-cis)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}cyclobutoxy]pyridin-4-yl}-1H-pyrazol-1-yl)butanoyl]pyrrolidine-2-carboxamide Into a 25-mL round-bottom flask, was placed 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl] acetic acid (87.0 mg, 0.22 mmol, 1.00 equiv), N,N-dimethylformamide (5.0 mL), HATU (98.9 mg, 0.26 mmol, 1.20 equiv), DIPEA (139.9 mg, 1.08 mmol, 5.00 eq), (2S,4R)-4-hydroxy-N-[[4-(4-methyl-1,3-thiazol-5-yl)phenyl]methyl]-1-[3-methyl-2-(4-[2-[(1,3-cis)-3-aminocyclobutoxy]pyridin-4-yl]-1H-pyrazol-1-yl)butanoyl]pyrrolidine-2-carboxamide trifluoroacetic acid salt (164.0 mg, 0.26 mmol, 1.20 equiv). The resulting solution was stirred for 2 h at r.t. This mixture was extracted with ethyl acetate (50 mL×3) and the organic layers were combined. The solution was washed with brine (50 mL×3), dried over anhydrous sodium sulfate and concentrated under vacuum. The crude product was purified by preparative HPLC with the following conditions (Column, XBridge Shield RP18 OBD Column, 5 um, 19*150 mm; mobile phase, acetonitrile and waters(10 mmol/L $NH_4HCO_3$); Detector, UV 254 nm). This resulted in 17.6 mg of (2S,4R)-4-hydroxy-N-[[4-(4-methyl-1,3-thiazol-5-yl)phenyl]methyl]-1-[(2S)-3-methyl-2-(4-[2-[(1,3-cis)-3-[2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido]cyclobutoxy]pyridin-4-yl]-1H-pyrazol-1-yl)butanoyl]pyrrolidine-2-carboxamide as a white solid (Example 178) as well as 20 mg of (2S,4R)-4-hydroxy-N-[[4-(4-methyl-1,3-thiazol-5-yl)phenyl]methyl]-1-[(2R)-3-methyl-2-(4-[2-[(1,3-cis)-3-[2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido]cyclobutoxy]pyridin-4-yl]-1H-pyrazol-1-yl)butanoyl]pyrrolidine-2-carboxamide as a white solid (Example 177).

$^1$H NMR (400 MHz, $CD_3OD$): δ 8.88 (s, 1H), 8.35 (s, 1H), 7.99-7.98 (d, J=5.2 Hz, 1H), 7.84 (s, 1H), 7.47-7.45 (d, J=8.4 Hz, 2H), 7.40-7.36 (m, 6H), 7.10 (d, J=1.2 Hz, 1H), 6.91 (s, 1H), 5.01-4.93 (m, 2H), 4.68-4.62 (m, 2H), 4.47-4.43 (m, 3H), 4.14-4.10 (m, 1H), 3.78-3.75 (d, J=10.8 Hz, 1H), 3.53-3.41 (m, 2H), 3.27-3.26 (m, 1H), 3.01-2.99 (m, 2H), 2.71 (s, 3H), 2.63-2.55 (m, 1H), 2.49-2.43 (m, 6H), 2.30-2.20 (m, 1H), 2.19-2.05 (m, 3H), 1.71 (s, 3H), 1.14-1.12 (d, J=6.8 Hz, 3H), 0.84-0.82 (d, J=8.0 Hz, 3H); LC-MS ($ES^+$): m/z 1034.55/1036.35 [$M+Na^+$], $t_R$=1.64 min, (3.60 minute run).

$^1$H NMR (400 MHz, $CD_3OD$): δ 8.89 (s, 1H), 8.36 (s, 1H), 8.08-8.06 (d, J=5.6 Hz, 1H), 7.99 (s, 1H), 7.48-7.45 (m, 6H), 7.41-7.39 (d, J=8.8 Hz, 2H), 7.19-7.18 (d, J=1.2 Hz, 1H), 6.99 (s, 1H), 4.98-4.92 (m, 2H), 4.66-4.62 (m, 1H), 4.57-4.52 (m, 3H), 4.47-4.43 (m, 1H), 4.15-4.10 (m, 1H), 3.96-3.95 (d, J=4.0 Hz, 1H), 3.85 (m, 1H), 3.47-3.32 (m, 1H), 3.30-3.28 (m, 1H), 3.05-2.95 (m, 2H), 2.71 (s, 3H), 2.63-2.55 (m, 1H), 2.50 (s, 3H), 2.46 (s, 3H), 2.23-2.12 (m, 4H), 1.70 (s, 3H), 1.14-1.12 (d, J=6.8 Hz, 3H), 0.83-0.82 (d, J=6.4 Hz, 3H); LC-MS ($ES^+$): m/z 1034.35/1036.35 [$M+Na^+$], $t_R$=1.65 min, (3.60 minute run).

Example 181: (2S,4R)-1-[(2S)-2-acetamido-3,3-dimethylbutanoyl]-4-hydroxy-N-{[4-(4-methyl-1,3-thiazol-5-yl)-2-[2-(3-{4-[(9S)-4,5,13-trimethyl-9-[(phenylcarbamoyl)methyl]-3-thia-1,8,11,12-tetraazatricyclo[8.3.0.0$^{2,6}$]trideca-2(6),4,7,10,12-pentaen-7-yl]phenoxy}propoxy)ethoxy]phenyl]methyl}pyrrolidine-2-carboxamide

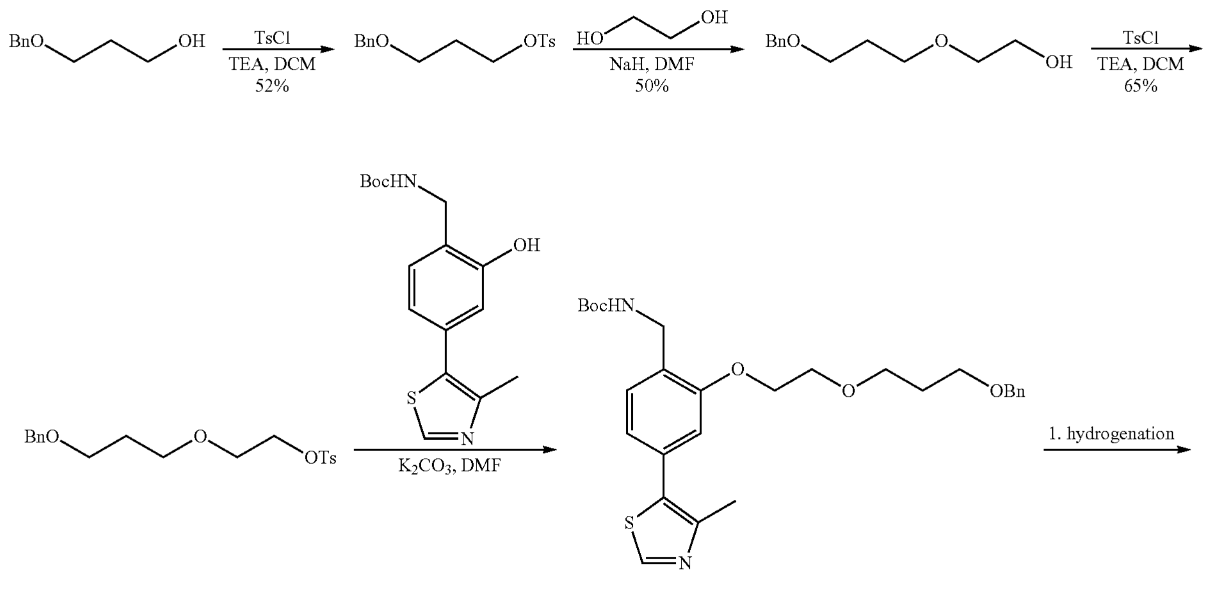

-continued
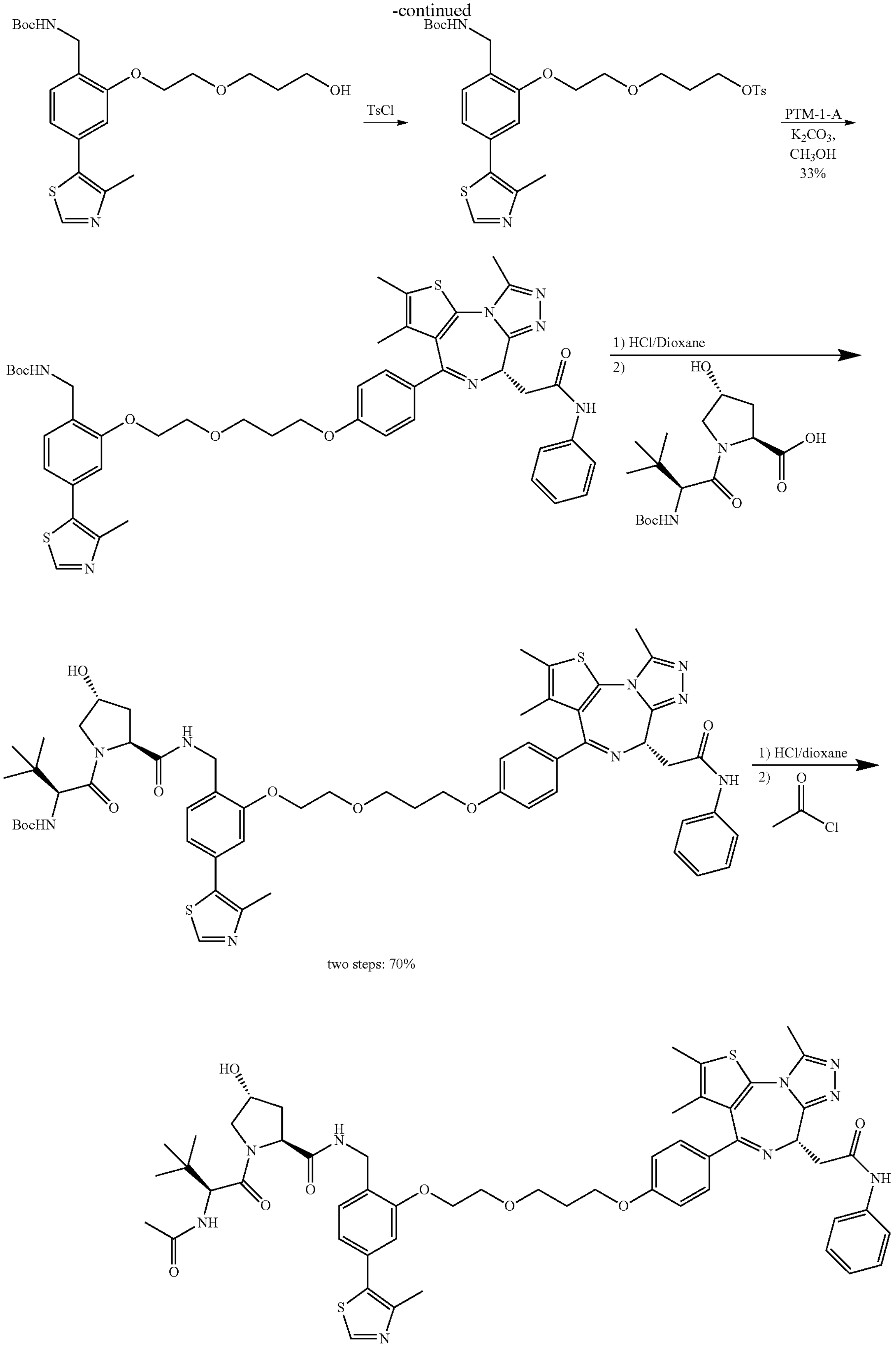

This compound was prepared using the key intermediate PTM-1-A as described in the synthetic scheme above. The synthetic procedure was similar to the preparation in Example 1.

$^1$H NMR (400 MHz, $CD_3OD$): δ 0.89 (s, 9H), 1.58 (s, 3H), 1.85-1.89 (m, 3H), 1.90-1.97 (m, 3H), 2.01-2.08 (m, 1H), 2.30-2.40 (m, 6H), 2.58-2.65 (m, 3H), 3.36-3.44 (m, 1H), 3.47-3.54 (m, 1H), 3.62-3.68 (m, 3H), 3.72-3.81 (m, 3H), 3.97 (t, J=6.0 Hz, 2H), 4.07-4.14 (m, 2H), 4.21-4.38 (m, 3H), 4.44-4.52 (m, 2H), 4.54-4.60 (m, 1H), 6.72-6.78 (m, 2H), 6.80-6.85 (m, 1H), 6.87-6.93 (m, 1H), 6.70 (t, J=7.2 Hz, 1H), 7.19-7.26 (m, 4H), 7.30-7.35 (m, 1H), 7.47-7.55 (m, 2H), 7.80-7.90 (m, 1H), 8.71, 8.73 (two singles, 1H); LC/MS 1030.5 $[M+H]^+$. $t_R$=2.713 min.

Example 193: (2S,4R)-1-[(2S)-3,3-dimethyl-2-(2-{4-[(1,3trans)-3-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}cyclobutoxy]phenyl}acetamido)butanoyl]-4-hydroxy-N-[(1S)-1-[4-(4-methyl-1,3-thiazol-5-yl)phenyl]ethyl]pyrrolidine-2-carboxamide

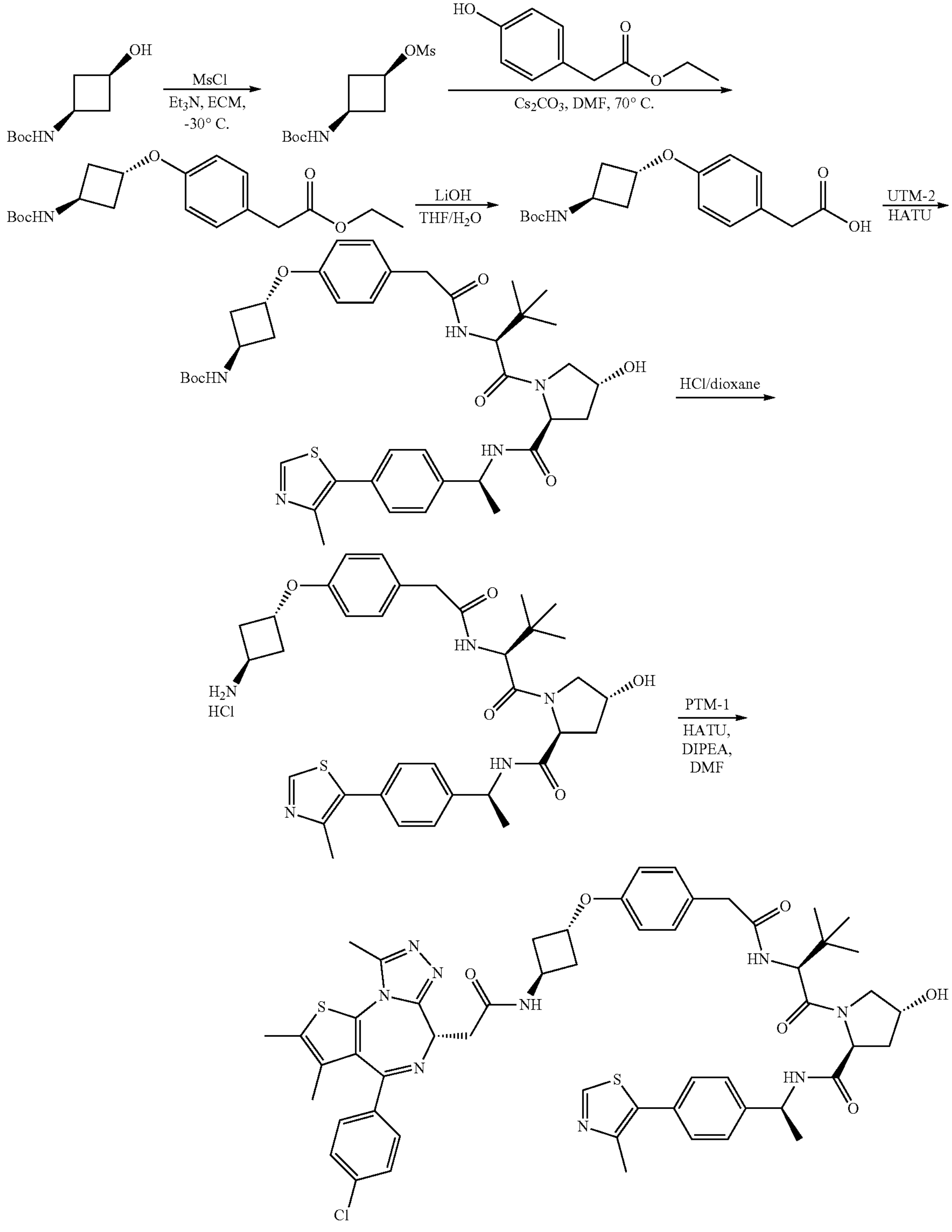

Step 1: Preparation of (1,3-cis)-3-(tert-butoxycarbonylamino)cyclobutyl Methanesulfonate To a solution of tert-butyl (1,3-cis)-3-hydroxycyclobutylcarbamate (200 mg, 1.07 mmol) and triethylamine (162 mg, 1.60 mmol) in DCM (10 mL) was added methanesulfonyl chloride (147 mg, 1.28 mmol) slowly at −30° C. The resulting mixture was stirred at −30° C. for 30 min. TLC showed the reaction was complete. The reaction was quenched with water (5 mL) at 0° C. The organic layer was collected and the aqueous layer was extracted with dichloromethane (10 mL×2). The combined organic layers were washed with water (5 mL×2) and then brine (5 mL), dried over anhydrous sodium sulfate, and concentrated under reduced pressure to afford (1,3-cis)-3-(tert-butoxycarbonylamino)cyclobutyl methanesulfonate (280 mg, crude) as a white solid. The product was used in the next step without further purification.

Step 2: Preparation of ethyl 2-(4-((1,3-trans)-3-(tert-butoxycarbonylamino)cyclobutoxy)phenyl) acetate A mixture containing (1,3-cis)-3-(tert-butoxycarbonylamino)cyclobutyl methanesulfonate (280 mg, crude), ethyl 2-(4-hydroxyphenyl)acetate (127 mg, 0.71 mmol) and cesium carbonate (458 mg, 1.41 mmol) in N,N-dimethylformamide (3 mL) was stirred at 70° C. overnight. TLC showed the reaction was complete. The reaction was partitioned between ethyl acetate and water. The organic layer was collected and the aqueous layer was extracted with ethyl acetate. The combined organic layers were washed with brine, dried over anhydrous sodium sulfate, and concentrated under reduced pressure to afford ethyl 2-(4-((1,3-trans)-3-(tert-butoxycarbonylamino)cyclobutoxy)phenyl) acetate (200 mg, crude) as colorless oil. The product was used in the next step without further purification.

Step 3: Preparation of 2-(4-((1,3-trans)-3-(tert-butoxycarbonylamino)cyclobutoxy)-phenyl)acetic Acid A mixture of ethyl 2-(4-((1,3-trans)-3-(tert-butoxycarbonylamino)-cyclobutoxy)phenyl)acetate (200 mg, crude) and lithium hydroxide monohydrate (120 mg, 2.86 mmol) in THF (5 mL)/water (1 mL)/methanol (1 mL) was stirred at rt for 2 h. TLC showed the reaction was complete. The mixture solution was acidified with diluted hydrochloric acid, and extracted with dichloromethane (10 mL×2). The combined organic layers were washed with brine (5 mL), dried over sodium sulfate and concentrated under reduced pressure to afford 2-(4-((1,3-trans)-3-(tert-butoxycarbonylamino)cyclobutoxy)phenyl)acetic acid (80 mg, crude) as a white solid.

Step 4 Through Step 6: Preparation of (2S,4R)-1-[(2S)-3,3-dimethyl-2-(2-{4-[(1,3-trans)-3-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}cyclobutoxy]phenyl}acetamido)butanoyl]-4-hydroxy-N-[(1S)-1-[4-(4-methyl-1,3-thiazol-5-yl)phenyl]ethyl]pyrrolidine-2-carboxamide Step 6 through step 8 were carried out using the same method as described in Example 119 to afford the title compound as a white solid.

LC/MS ($ES^+$): m/z 1030.4 $[M+H]^+$; $t_R$=2.842 min.

$^1$H NMR (400 MHz, $CD_3OD$): δ 0.99, 1.02 (two singles, 9H), 1.52 (d, J=6.8 Hz, 3H), 1.71 (s, 3H), 1.90-2.00 (m, 1H), 2.16-2.24 (m, 1H), 2.46 (s, 3H), 2.48-2.60 (m, 7H), 2.72 (s, 3H), 3.41-3.61 (m, 4H), 3.72-3.78 (m, 1H), 3.84-3.91 (m, 1H), 4.40-4.68 (m, 6H), 4.99-5.04 (m, 1H), 6.79-6.85 (m, 2H), 7.20-7.28 (m, 2H), 7.40-7.50 (m, 8H), 7.72-7.77 (m, 1H), 8.60 (d, J=7.2 Hz, 1H), 8.80-8.86 (m, 1H), 8.87, 8.89 (two singles, 1H).

Example 195: (2S,4R)-1-[(2S)-3,3-dimethyl-2-({5-[(1,3cis)-3-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}cyclobutoxy]-1-benzofuran-2-yl}formamido)butanoyl]-4-hydroxy-N-[(1S)-1-[4-(4-methyl-1,3-thiazol-5-yl)phenyl]ethyl]pyrrolidine-2-carboxamide

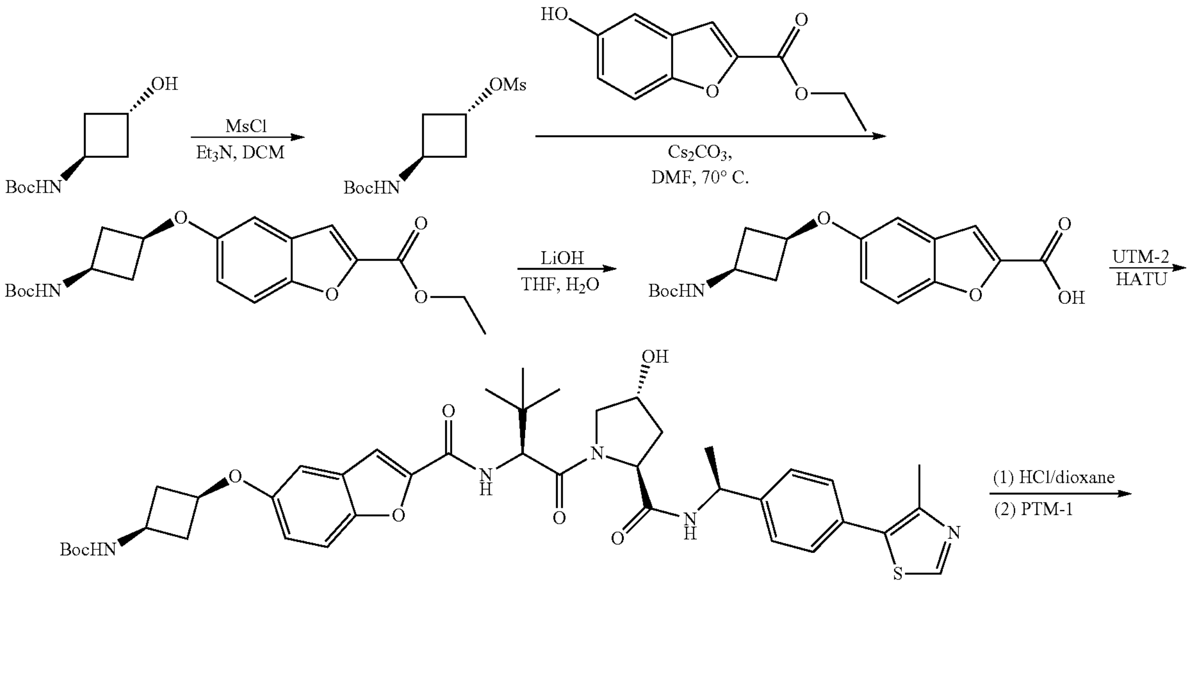

-continued

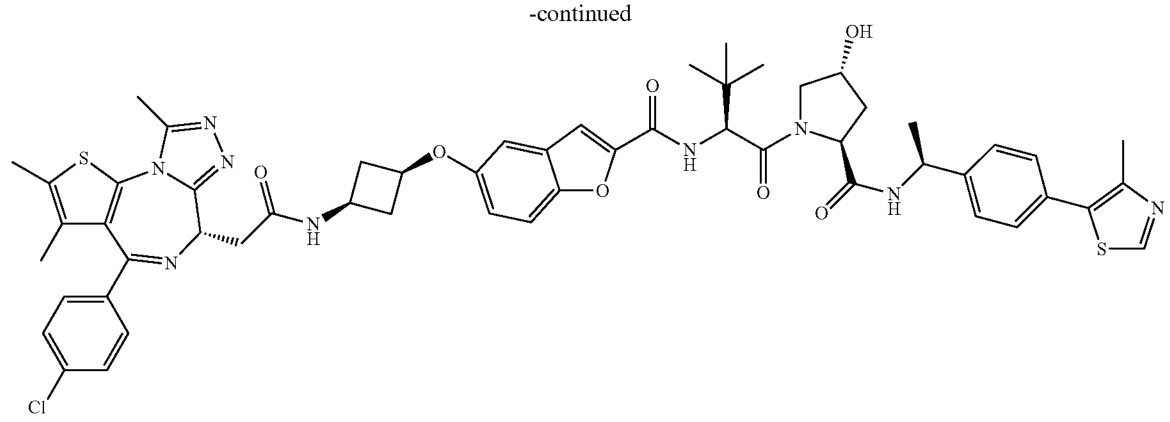

This compound was prepared according the scheme above using the same method as described in Example 165 and Example 193.

LC/MS ($ES^+$): m/z 1056.3 $[M+H]^+$. $t_R$=2.932 min.

$^1H$ NMR (400 MHz, $CD_3OD$): δ 1.12, 1.15 (two singles, 9H), 1.54 and 1.64 (2d, 3H), 1.70 (s, 3H), 1.97-2.06 (m, 1H), 2.16-2.27 (m, 3H), 2.46 (s, 3H), 2.49 (s, 3H), 2.71 (s, 3H), 2.98-3.10 (m, 2H), 3.26-3.29 (m, 1H), 3.41-3.50 (m, 1H), 3.81-3.84 (m, 1H), 3.92-3.95 (m, 1H), 4.12-4.23 (m, 1H), 4.41-4.66 (m, 5H), 5.03-5.10 (m, 1H), 7.05-7.09 (m, 1H), 7.15 (d, J=2.0 Hz, 1H), 7.36-7.55 (m, 10H), 8.87, 8.89 (two singles, 1H).

Example 206: (2S,4R)-1-[(2S)-2-[(5-{[(2R)-1-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}propan-2-yl]oxy}-1-benzofuran-2-yl)formamido]-3,3-dimethylbutanoyl]-4-hydroxy-N-[(1S)-1-[4-(4-methyl-1,3-thiazol-5-yl)phenyl]ethyl]pyrrolidine-2-carboxamide

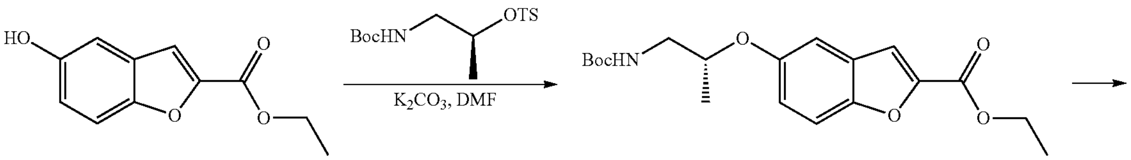

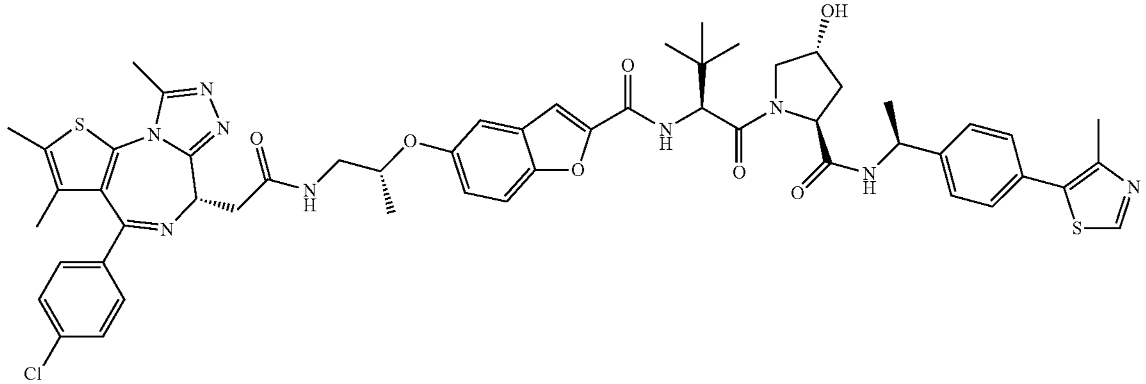

With the same method as described in Example 195, the title compound was prepared as a yellow solid.

LC/MS ($ES^+$): m/z 1044.40 $[M+H]^+$. $t_R$=3.012 min.

$^1H$ NMR (400 MHz, $CD_3OD$): δ 1.12, 1.14 (two singles, 9H), 1.34 (d, J=6.0 Hz, 3H), 1.55 (d, J=6.8 Hz, 3H), 1.69 (s, 3H), 1.97-2.03 (m, 1H), 2.22-2.27 (m, 1H), 2.45, 2.50 (two singles, 6H), 2.66, 2.67 (two singles, 3H), 3.44-3.63 (m, 3H), 3.81-3.86 (m, 1H), 3.90-3.96 (m, 1H), 4.48 (brs, 1H), 4.59-4.65 (m, 3H), 4.92 (s, 1H), 5.02-5.10 (m, 1H), 7.07-7.10 (m, 1H), 7.28-7.33 (m, 3H), 7.40-7.50 (m, 8H), 8.64-8.69 (m, 1H), 8.87, 8.90 (two singles, 1H).

Example 210: (2S,4R)-1-[(2S)-2-{[6-(2-{2-[(9S)-7-(4-chlorophenyl)-4,5,13-trimethyl-3-thia-1,8,11,12-tetraazatricyclo$[8.3.0.0^{2,6}]$trideca-2(6),4,7,10,12-pentaen-9-yl]acetamido}ethoxy)-1-benzofuran-2-yl]formamido}-3,3-dimethylbutanoyl]-4-hydroxy-N-[(1S)-1-[4-(4-methyl-1,3-thiazol-5-yl)phenyl]ethyl]pyrrolidine-2-carboxamide

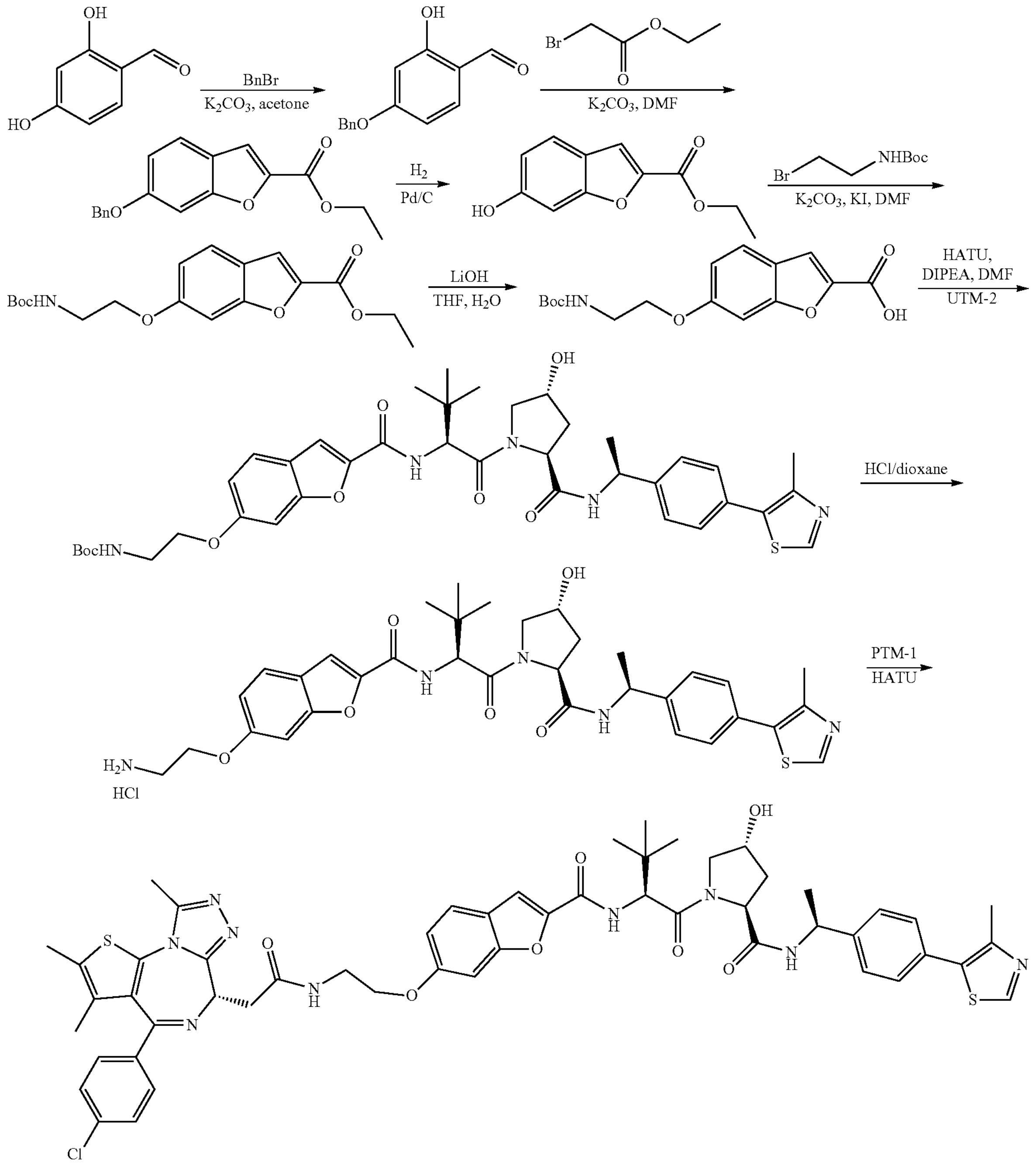

Using the synthetic route above and the similar procedure described in Example 165, the title compound was prepared as a light yellow solid.

LC/MS ($ES^+$): m/z 1030.3 $[M+H]^+$; $t_R$=2.846 min $^1$HNMR (400 MHz, $CD_3OD$): δ 1.12, 1.14 (two singles, 9H), 1.54-1.66 (m, 3H), 1.69 (s, 3H), 2.00-2.04 (m, 1H), 2.21-2.25 (m, 1H), 2.46-2.50 (m, 6H), 2.69 (s, 3H), 3.27-3.32 (m, 1H), 3.47-3.53 (m, 1H), 3.63-3.68 (m, 1H), 3.81-3.86 (m, 2H), 3.93-3.95 (m, 1H), 4.20 (d, J=5.2 Hz, 2H), 4.49 (br, 1H), 4.61-4.67 (m, 2H), 4.92 (s, 1H), 5.02-5.08 (m, 1H), 7.00-7.02 (m, 1H), 7.13-7.17 (m, 2H), 7.22-7.23 (m, 1H), 7.35-7.37 (m, 2H), 7.41-7.48 (m, 4H), 7.52 (s, 1H), 7.62 (d, J=8.4 Hz, 1H), 8.87, 8.90 (two singles, 1H).

Example 212: (2S,4R)-1-[(2S)-3,3-dimethyl-2-({6-[(1,3cis)-3-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}cyclobutoxy]-1-benzofuran-2-yl}formamido)butanoyl]-4-hydroxy-N-[(1S)-1-[4-(4-methyl-1,3-thiazol-5-yl)phenyl]ethyl]pyrrolidine-2-carboxamide

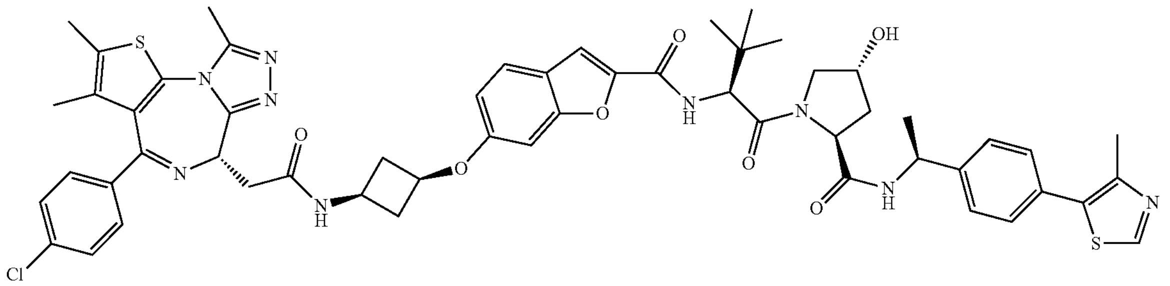 [SMILES: Cc1ncsc1-c1ccc([C@H](C)NC(=O)[C@@H]2C[C@@H](O)CN2C(=O)[C@@H](NC(=O)c2cc3ccc(O[C@H]4C[C@@H](NC(=O)C[C@@H]5N=C(c6ccc(Cl)cc6)c6c(sc(C)c6C)-n6c(C)nnc65)C4)cc3o2)C(C)(C)C)cc1]

With the same method as described in Example 195, the title compound was prepared as a light brown solid.

LC/MS (ES$^{+}$): m/z 1056.4 [M+H]$^{+}$; $t_R$=2.933 min $^{1}$HNMR (400 MHz, $CD_3OD$): δ 1.11, 1.14 (two singles, 9H), 1.55 (d, J=7.2 Hz, 3H), 1.63-1.78 (m, 4H), 1.88-2.13 (m, 2H), 2.18-2.26 (m, 3H), 2.45-2.50 (m, 6H), 2.70 (s, 3H), 3.00-3.12 (m, 2H), 3.28-3.29 (m, 1H), 3.41-3.51 (m, 1H), 3.72-3.84 (m, 1H), 3.92-3.93 (m, 1H), 4.17-4.23 (m, 1H), 4.59-4.67 (m, 3H), 5.04-5.07 (m, 1H), 6.93-6.96 (m, 1H), 7.13 (s, 1H), 7.39-7.50 (m, 9H), 7.62 (d, J=8.4 Hz, 1H), 8.87, 8.89 (two singles, 1H).

Compounds in the following Examples were prepared with the same method as described in Example 195.

| | | |
|---|---|---|
| Example 205 | (2S,4R)-1-[(2S)-2-[(5-{[(2S)-1-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}propan-2-yl]oxy}-1-benzofuran-2-yl)formamido]-3,3-dimethylbutanoyl]-4-hydroxy-N-[(1S)-1-[4-(4-methyl-1,3-thiazol-5-yl)phenyl]ethyl]pyrrolidine-2-carboxamide | $^{1}$HNMR (400 MHz, $CD_3OD$): δ 1.14 (s, 9H), 1.36 (d, J = 5.6 Hz, 3H), 1.55 (d, J = 6.8 Hz, 3H), 1.68 (s, 3H), 1.97-2.05 (m, 1H), 2.22-2.27 (m, 1H), 2.46, 2.50 (two singles, 6H), 2.69 (s, 3H), 3.27-3.29 (m, 1H), 3.45-3.50 (m, 2H), 3.59-3.63 (m, 1H), 3.81-3.84 (m, 1H), 3.92-3.95 (m, 1H), 4.40-4.51 (m, 1H), 4.61-4.65 (m, 3H), 4.98-5.09 (m, 1H), 7.12-7.18 (m, 3H), 7.30-7.53 (m, 9H), 8.67-8.74 (m, 1H), 8.87, 8.90 (two singles, 1H). |
| Example 207 | (2S,4R)-1-[(2S)-3,3-dimethyl-2-({5-[(1,3trans)-3-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}cyclobutoxy]-1-benzofuran-2-yl}formamido)butanoyl]-4-hydroxy-N-[(1S)-1-[4-(4-methyl-1,3-thiazol-5-yl)phenyl]ethyl]pyrrolidine-2-carboxamide | $^{1}$HNMR (400 MHz, $CD_3OD$): δ 1.12, 1.14 (two singles, 9H), 1.55 (d, J = 6.8 Hz, 3H), 1.71 (s, 3H), 1.96-2.03 (m, 1H), 2.21-2.27 (m, 1H), 2.46-2.50 (m, 6H), 2.56-2.63 (m, 4H), 2.72 (s, 3H), 3.33-3.36 (m, 1H), 3.43-3.49 (m, 1H), 3.80-3.84 (m, 1H), 3.93 (d, J = 8.0 Hz, 1H), 4.84-4.56 (m, 2H), 4.60-4.68 (m, 2H), 4.91-4.99 (m, 2H), 5.02-5.07 (m, 1H), 7.06-7.09 (m, 2H), 7.40-7.55 (m, 11H), 8.87, 8.89 (two singles, 1H). |
| Example 211 | (2S,4R)-1-[(2S)-2-[(6-{[(2R)-1-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}propan-2-yl]oxy}-1-benzofuran-2-yl)formamido]-3,3-dimethylbutanoyl]-4-hydroxy-N-[(1S)-1-[4-(4-methyl-1,3-thiazol-5-yl)phenyl]ethyl]pyrrolidine-2-carboxamide | $^{1}$HNMR (400 MHz, $CD_3OD$): δ 1.14 (s, 9H), 1.36-1.38 (m, 3H), 1.54-1.65 (m, 3H), 1.70 (s, 3H), 1.99-2.03 (m, 1H), 2.21-2.27 (m, 1H) 2.45, 2.50 (two single peaks,6H), 2.66 (s, 3H), 3.41-3.47 (m, 1H), 3.80-3.84 (m, 1H), 3.93 (d, J = 11.2 Hz, 1H), 4.48 (s, 1H), 4.61-4.69 (m, 3H), 4.92 (s, 1H), 5.03-5.07 (m, 1H), 6.92-6.95 (m, 1H), 7.23 (s, 1H), 7.32 (d, J = 8.8 Hz, 2H), 7.40-7.49 (m, 7H), 7.57 (d, J = 8.8 Hz, 1H), 7.73 (d, J = 9.2 Hz, 1H), 8.65-8.69 (m, 2H), 8.90 (s, 1H). |

-continued

| | | |
|---|---|---|
| Example 221 | (2S,4R)-1-[(2S)-2-[(6-{[(2S)-1-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}propan-2-yl]oxy}-1-benzofuran-2-yl)formamido]-3,3-dimethylbutanoyl]-4-hydroxy-N-[(1S)-1-[4-(4-methyl-1,3-thiazol-5-yl)phenyl]ethyl]pyrrolidine-2-carboxamide | $^{1}$HNMR (400 MHz, $CD_3OD$): δ 1.12, 1.14 (two singles, 9H), 1.38 (d, J = 6.4 Hz, 3H), 1.54 (d, J = 7.2 Hz, 3H), 1.70 (s, 3H), 2.00-2.04 (m, 1H), 2.21-2.25 (m, 1H), 2.46-2.50(m, 6H), 2.67 (d, J = 7.2 Hz, 3H), 3.44-3.63 (m, 3H), 3.81-3.85 (m, 1H), 3.93 (d, J = 10.8 Hz, 1H), 4.49 (s, 1H), 4.61-4.71 (m, 3H), 5.03-5.07 (m, 1H), 6.98-7.01 (m, 1H), 7.19-7.25 (m, 3H), 7.36 (d, J = 8.4 Hz, 2H), 7.41-7.51 (m, 5H), 7.60 (d, J = 8.4 Hz, 1H), 7.73 (d, J = 9.2 Hz, 1H), 8.66 (d, J = 7.6 Hz, 1H), 8.92, 8.93 (two singles, 1H). |

Example 218: (2S,4R)-4-hydroxy-N-[(1S)-1-[4-(4-methyl-1,3-thiazol-5-yl)phenyl]ethyl]-1-[(2R)-3-methyl-2-(4-{2-[(1,3-cis)-3-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}cyclobutoxy]pyridin-4-yl}-1H-pyrazol-1-yl)butanoyl]pyrrolidine-2-carboxamide Example 219: (2S,4R)-4-hydroxy-N-[(1S)-1-[4-(4-methyl-1,3-thiazol-5-yl)phenyl]ethyl]-1-[(2S)-3-methyl-2-(4-{2-[(1,3-cis)-3-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}cyclobutoxy]pyridin-4-yl}-1H-pyrazol-1-yl)butanoyl]pyrrolidine-2-carboxamide These two compounds were prepared using the same method as described in Example 177 and Example 178.

Example 218: $^{1}$H NMR (400 MHz, $CD_3OD$): δ 8.86 (s, 1H), 8.38 (s, 1H), 8.06-8.04 (d, J=5.6 Hz, 1H), 8.00 (s, 1H), 7.47-7.45 (d, J=8.8 Hz, 2H), 7.42-7.40 (d, J=4.4 Hz, 2H), 7.38 (s, 4H), 7.19-7.18 (d, J=1.2 Hz, 1H), 7.00 (s, 1H), 5.03-4.93 (m, 3H), 4.65-4.60 (m, 2H), 4.42 (s, 1H), 4.16-4.10 (m, 1H), 3.73-3.70 (m, 1H), 3.48-3.41 (m, 2H), 3.29-3.27 (m, 1H), 3.10-2.90 (m, 2H), 2.71 (s, 3H), 2.70-2.60 (m, 1H), 2.46 (s, 3H), 2.43 (s, 3H), 2.30-2.17 (m, 3H), 1.97-1.90 (m, 1H), 1.71 (s, 3H), 1.53-1.51 (d, J=7.2 Hz, 3H), 1.15-1.13 (d, J=6.8 Hz, 3H), 0.86-0.84 (d, J=6.8 Hz, 3H); LC-MS ($ES^+$): m/z 1026.00/1028.00 [$MH^+$], $t_R$=3.15 min, (5.60 minute run).

Example 219: $^{1}$H NMR (400 MHz, $CD_3OD$): δ8.89 (s, 1H), 8.36 (s, 1H), 8.08-8.07 (d, J=5.2 Hz, 1H), 7.48-7.40 (m, 9H), 7.19 (d, J=1.6 Hz, 2H), 7.00 (s, 1H), 5.07-5.06 (m, 1H), 4.96-4.90 (m, 2H), 4.66-4.63 (m, 1H), 4.57-4.53 (m, 1H), 4.48 (s, 1H), 4.16-4.10 (m, 1H), 3.90-3.84 (m, 2H), 3.47-3.41 (m, 1H), 3.32-3.28 (m, 1H), 3.10-2.90 (m, 2H), 2.71 (s, 3H), 2.65-2.50 (m, 1H), 2.47 (s, 3H), 2.46 (s, 3H), 2.20-2.18 (m, 3H), 2.00-1.99 (m, 1H), 1.71 (s, 3H), 1.56-1.54 (d, J=6.8 Hz, 3H), 1.15-1.14 (d, J=6.4 Hz, 1H), 0.84-0.82 (d, J=6.8 Hz, 3H); LC-MS ($ES^+$): m/z 1026.10/1028.10 [$MH^+$], $t_R$=1.89 min, (3.60 minute run).

With the same synthetic method following by chiral separation as described in Example 177 and Example 178, compounds in Example 225, Example 226, Example 220 and Example 228 were prepared.

| | | |
|---|---|---|
| Example 225 | (2S,4R)-4-hydroxy-N-{[4-(4-methyl-1,3-thiazol-5-yl)phenyl]methyl}-1-[(2R)-3-methyl-2-(4-{2-[(1,3trans)-3-{2-[(9 S)-7-(4-chlorophenyl)-4,5,13-trimethyl-3-thia-1,8,11, 12-tetraazatricyclo[8.3.0.0$^{2}$,$^{6}$]trideca-2(6),4,7,10,12-pentaen-9-yl]acetamido}cyclobutoxy]pyridin-4-yl}-1H-pyrazol-1-yl)butanoyl]pyrrolidine-2-carboxamide | $^{1}$HNMR (400 MHz, $CD_3OD$): δ 8.89 (s, 1H), 8.34 (s, 1H), 7.98-7.97 (d, J = 5.2 Hz, 1H), 7.84 (s, 1H), 7.49-7.41 (m, 4H), 7.35 (s, 4H), 7.10-7.09 (d, J = 1.6 Hz, 1H), 6.92 (s, 1H), 5.32 (s, 1H), 5.01-4.98 (m, 1H), 4.68-4.64 (m, 2H), 4.52-4.43 (m, 4H), 3.78-3.75 (m, 1H),3.54-3.43 (m, 2H), 2.72 (s, 3H), 2.61-2.49 (m, 5H), 2.46 (s, 3H), 2.42 (s, 3H), 2.30-2.25 (m, 1H), 2.10-2.00 (m, 3H), 1.71 (s, 3H), 1.14-1.12 (d, J = 6.8 Hz, 3H), 0.84-0.82 (d, J = 6.8 Hz, 3H) |
| Example 226 | (2S,4R)-4-hydroxy-N-{[4-(4-methyl-1,3-thiazol-5-yl)phenyl]methyl}-1-[(2S)-3-methyl-2-(4-{2-[(1,3trans)-3-{2-[(9 S)-7-(4-chlorophenyl)-4,5,13-trimethyl-3-thia-1,8,11,12-tetraazatricyclo[8.3.0.0$^{2}$,$^{6}$]trideca-2 (6),4,7,10,12-pentaen-9-yl]acetamido}cyclobutoxylpyridin-4-yl}-1H-pyrazol-1-yl)butanoyl]pyrrolidine-2-carboxamide | $^{1}$HNMR (400 MHz, $CD_3OD$): δ 8.89 (s, 1H), 8.36 (s, 1H), 8.07-8.05 (d, J = 5.6 Hz, 1H), 7.99 (s, 1H), 7.49-7.42 (m, 8H), 7.18 (d, J = 1.6 Hz, 1H), 7.00 (s, 1H), 5.38-5.35 (m, 1H), 4.92-4.89 (m, 2H), 4.67-4.64 (m, 1H), 4.57-4.43 (m, 5H), 3.95-3.94 (m, 1H), 3.85-3.82 (d, J = 11.2 Hz, 1H), 3.49-3.43 (m, 1H), 2.72 (s, 3H), 2.62-2.55(m, 5H), 2.50 (s, 3H), 2.46 (s, 3H), 2.39-2.11 (m, 2H), 1.71 (s, 3H), 1.13-1.12 (d, J = 6.4 Hz, 3H), 0.83-0.81 (d, J = 6.4 Hz, 3H) |
| Example 220 | (2S,4R)-4-hydroxy-N-[(1S)-1-[4-(4-methyl-1,3-thiazol-5-yl)phenyl]ethyl]-1-[(2R)-3-methyl-2-(4-{2-[(1r,3r)-3-{2-[(9S)-7-(4-chlorophenyl)-4,5,13-trimethyl-3-thia-1,8,11,12-tetraazatricyclo[8.3.0.0$^{2}$,$^{6}$]trideca-2 (6),4,7,10,12-pentaen-9-yl]acetamido}cyclobutoxylpyridin-4-yl}-1H-pyrazol-1-yl)butanoyl]pyrrolidine-2-carboxamide | $^{1}$HNMR (400 MHz, $CD_3OD$): δ 8.86 (s, 1H), 8.38 (s, 1H), 8.05-8.03 (d, J = 5.2 Hz, 1H), 8.00 (s, 1H), 7.50-7.41 (m,4H), 7.35 (s, 4H), 7.19-7.18 (d, J = 5.2 Hz, 1H), 7.01 (s, 1H), 5.37-5.35 (m, 1H), 5.03-4.99 (m, 2H), 4.67-4.60(m, 2H), 4.55-4.53 (m, 1H), 4.42 (s, 1H), 3.76-3.73 (m, 1H), 3.50-3.44 (m, 2H), 3.35-3.32 (m, 1H), 2.72 (s, 3H), 2.63-2.51 (m, 5H), 2.46 (s, 3H), 2.43 (s, 3H), 2.30-2.20(m, 1H), 1.97-1.90 (m, 1H), 1.71 (s, 3H), 1.52-1.50 (d, J = 6.8 Hz, 3H), 1.14-1.13 (d, J = 6.8 Hz, 3H), 0.86-0.84 (d, J = 6.4 Hz, 3H) |

-continued

| | | |
|---|---|---|
| Example 228 | (2S,4R)-4-hydroxy-N-[(1S)-1-[4-(4-methyl-1,3-thiazol-5-yl)phenyl]ethyl]-1-[(2S)-3-methyl-2-(4-{2-[(1r,3r)-3-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}cyclobutoxy]pyridin-4-yl}-1H-pyrazol-1-yl)butanoyl]pyrrolidine-2-carboxamide | $^{1}$HNMR (400 MHz, $CD_3OD$): δ 8.89 (s, 1H), 8.36 (s, 1H), 8.06-8.05 (d, J = 5.6 Hz, 1H), 7.98 (s, 1H), 7.48-7.41 (m,8H), 7.19-7.18 (d, J = 5.2 Hz, 1H), 7.00 (s, 1H), 5.36-5.35 (m, 1H), 5.07-4.92 (m, 3H), 4.67-4.64(m, 1H), 4.55-4.53 (m, 2H), 4.48 (s, 1H) 3.90-3.84(m 2H) 3.50-3.44 (m, 1H), 2.71 (s, 3H), 2.61-2.49 (m, 5H), 2.46 (s, 3H), 2.45 (s, 3H), 2.25-2.15 (m, 1H), 1.99-1.90 (m, 1H), 1.71 (s, 3H), 1.55-1.53 (d, J = 7.2 Hz, 3H), 1.15-1.13 (d, J = 6.4 Hz, 3H), 0.83-0.81 (d, J = 6.8 Hz, 3H) |

Example 224: (2S,4R)-1-[(2S)-2-{4-[3-(2-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido}ethoxy)-5-fluorophenyl]-1H-pyrazol-1-yl}-3-methylbutanoyl]-4-hydroxy-N-[(1S)-1-[4-(4-methyl-1,3-thiazol-5-yl)phenyl]ethyl]pyrrolidine-2-carboxamide

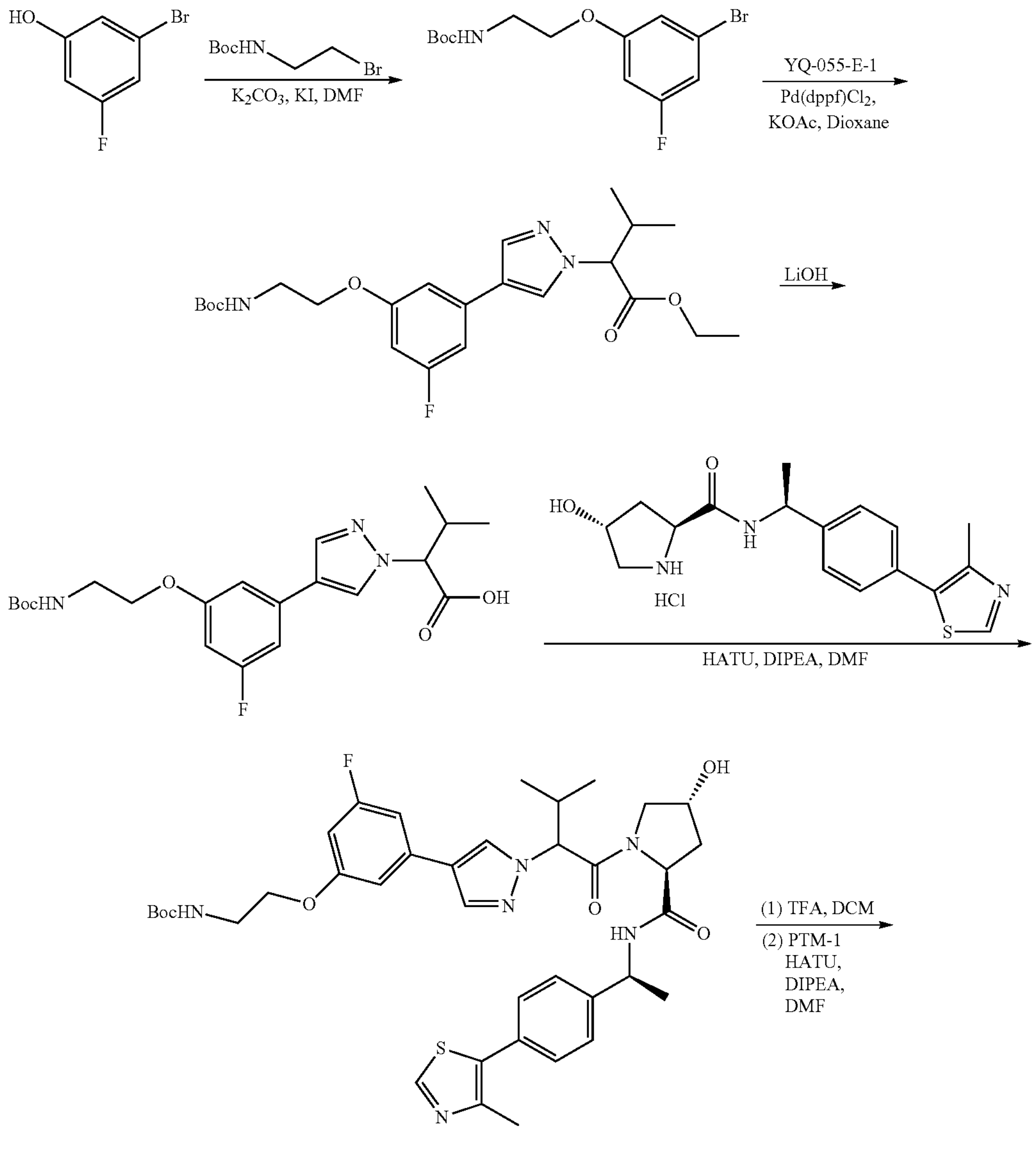

-continued

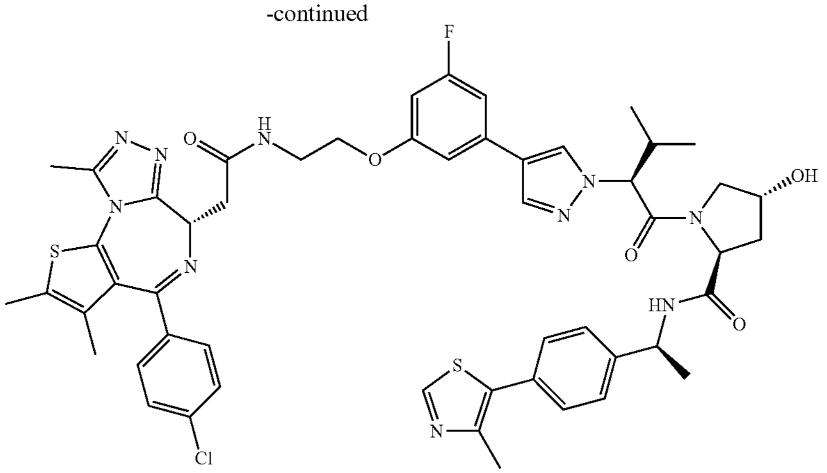

Example 224

+

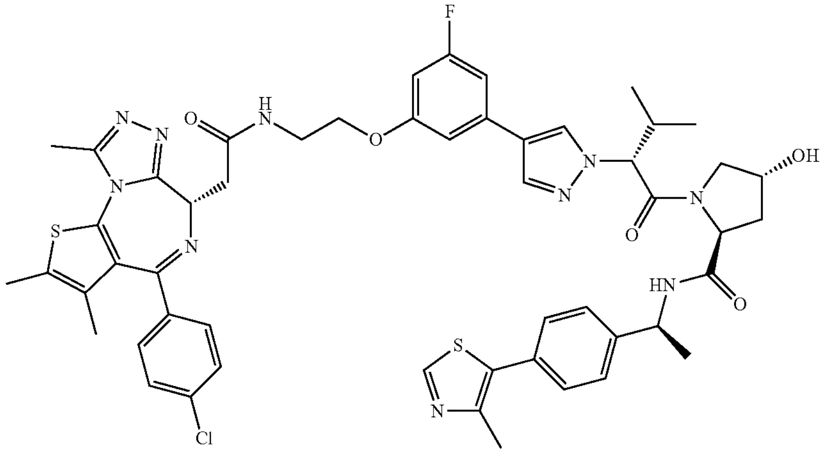 [SMILES: Cc1ncsc1-c1ccc([C@H](C)NC(=O)[C@@H]2C[C@@H](O)CN2C(=O)[C@@H](C(C)C)n2cc(-c3cc(F)cc(OCCNC(=O)C[C@@H]4N=C(c5ccc(Cl)cc5)c5c(sc(C)c5C)-n5c(C)nnc54)c3)cn2)cc1]

This molecule was prepared with the synthetic method described in the above scheme. The title compound was isolated as a white solid.

$^1$H NMR (400 MHz, $CD_3OD$): δ 0.80 (d, J=6.8 Hz, 3H), 1.12 (d, J=6.4 Hz, 3H), 1.54 (d, J=6.8 Hz, 3H), 1.67 (s, 3H), 1.96-2.06 (s, 2H), 2.17-2.23 (m, 1H), 2.44 (s, 3H), 2.50 (s, 3H), 2.56-2.61 (m, 1H), 2.69 (s, 3H), 3.27-3.28 (m, 1H), 3.47-3.65 (m, 2H), 3.78-3.91 (m, 3H), 4.15-4.17 (m, 2H), 4.48-4.67 (m, 3H), 5.04-5.09 (m, 1H), 6.58-6.60 (m, 1H), 6.95-7.00 (m, 2H), 7.22-7.24 (m, 2H), 7.38-7.48 (m, 5H), 7.85 (s, 1H), 8.20 (s, 1H), 8.69-8.71 (m, 1H), 8.90 (s, 1H); LC/MS 1017.00 $[M+H]^+$; $t_R$=2.898 min.

Example 229: (2S,4R)-1-[(2S)-3,3-dimethyl-2-({6-[(1,3-trans)-3-{2-[(9S)-7-(4-chlorophenyl)-4,5,13-trimethyl-3-thia-1,8,11,12-tetraazatricyclo[8.3.0.0$^2$,$^6$]trideca-2(6),4,7,10,12-pentaen-9-yl]acetamido}cyclobutoxy]-1-benzofuran-2-yl}formamido)butanoyl]-4-hydroxy-N-[(1S)-1-[4-(4-methyl-1,3-thiazol-5-yl)phenyl]ethyl]pyrrolidine-2-carboxamide

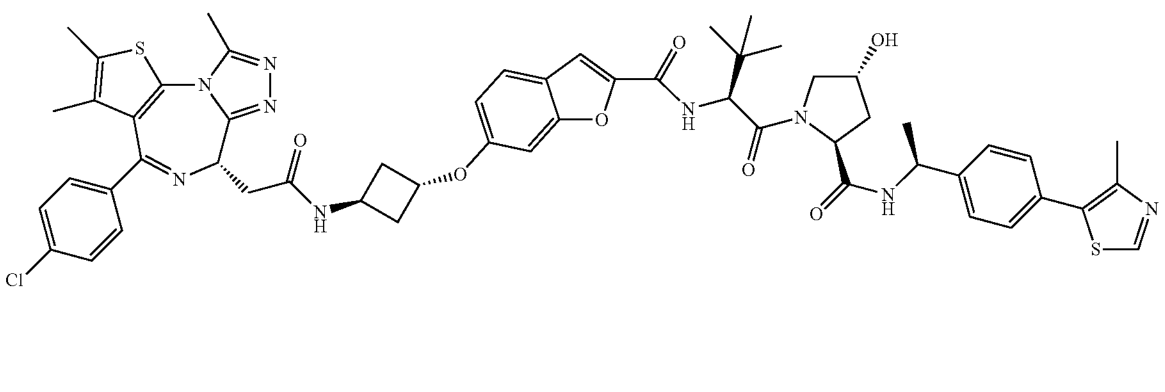 [SMILES: Cc1ncsc1-c1ccc([C@H](C)NC(=O)[C@@H]2C[C@@H](O)CN2C(=O)[C@@H](NC(=O)c2cc3ccc(O[C@H]4C[C@H](NC(=O)C[C@@H]5N=C(c6ccc(Cl)cc6)c6c(sc(C)c6C)-n6c(C)nnc65)C4)cc3o2)C(C)(C)C)cc1]

With the same method as described in Example 195, the title compound was prepared as a white solid.

LC/MS (ES+): m/z 1056.3 [M+H]+; $t_R$=2.978 min $^1$HNMR (400 MHz, $CD_3OD$): δ 1.00, 1.02 (two singles, 9H), 1.42 (d, J=6.8 Hz, 3H), 1.59 (s, 3H), 1.84-1.91 (m, 1H), 2.09-2.15 (m, 1H), 2.35-2.37 (m, 6H), 2.46-2.53 (m, 4H), 2.60 (s, 3H), 3.22-3.26 (m, 1H), 3.32-3.38 (m, 1H), 3.68-3.72 (m, 1H), 3.80-3.83 (m, 1H), 4.36-4.44 (m, 2H), 4.49-4.56 (m, 5H), 4.87-4.93 (m, 2H), 6.81-6.84 (m, 1H), 6.93 (s, 1H), 7.27-7.38 (m, 9H), 7.50 (d, J=8.8 Hz, 1H), 8.74, 8.77 (two singles, 1H).

The following compounds were prepared using the same synthetic method.

| | | |
|---|---|---|
| Example 230 | (2S,4R)-1-[(2S)-2-(2-{4-[(3R)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}pyrrolidin-1-yl]phenyl}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide | $^1$HNMR (400 MHz, $CD_3OD$): δ 0.84, 0.87 (two singles, 9H), 1.39 (d, J = 7.2 Hz, 3H), 1.58, 1.59 (two singles, 3H), 1.80-1.87 (m, 1H), 1.89-2.06 (m, 2H), 2.07-2.11(m, 1H), 2.19-2.25 (m, 1H), 2.34-2.37 (m, 6H), 2.58 (s, 3H), 3.10-3.15 (m, 1H), 3.23-3.29 (m, 1H), 3.32-3.51 (m, 6H), 3.60-3.64 (m, 1H), 3.74, 3.77 (two singles, 1H), 4.32 (brs, 1H), 4.43-4.53 (m, 5H), 4.85-4.91 (m, 1H), 6.48-6.52 (m, 2H), 7.05-7.11 (m, 4H), 7.23-7.35 (m, 7H), 8.75, 8.77 (two singles, 1H). |
| Example 235 | (2S,4R)-1-[(2S)-2-(2-{4-[(3S)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}pyrrolidin-1-yl]phenyl}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide | $^1$HNMR (400 MHz, $CD_3OD$): δ 0.84, 0.87 (two singles, 9H), 1.39 (d, J = 6.8 Hz, 3H), 1.59 (s, 3H), 1.80-1.86 (m, 1H), 1.97-2.11 (m, 2H), 2.21-2.27 (m, 1H), 2.35, 2.37 (two singles, 6H), 2.58 (s, 3H), 3.11-3.17 (m, 1H), 3.23-3.27 (m, 1H), 3.31-3.47 (m, 5H), 3.60-3.64 (m, 1H), 3.73, 3.76 (two singles, 1H), 4.31 (brs, 1H), 4.42-4.55 (m, 4H), 4.87-4.90 (m, 1H), 6.45 (d, J = 8.4 Hz, 2H), 7.02 (d, J = 8.4 Hz, 2H), 7.28-7.36 (m, 8H), 8.45-8.59 (m, 1H), 8.75, 8.77 (two singles, 1H). |
| Example 270 | (2S,4R)-1-[(2S)-3,3-dimethyl-2-(2-{6-[(1,3cis)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}cyclobutoxy]pyridin-3-yl}acetamido)butanoyl]-4-hydroxy-N-[(1S)-1-[4-(4-methyl-1,3-thiazol-5-yl)phenyl]ethyl]pyrrolidine-2-carboxamide | $^1$HNMR (400 MHz, $CD_3OD$): δ 0.90, 0.94 (two singles, 9H), 1.36-1.42 (m, 3H), 1.58, 1.59 (two singles, 3H), 1.81-1.87 (m, 1H), 1.91-1.95 (m, 1H), 2.04-2.09 (m, 2H), 2.35-2.38 (m, 6H), 2.59 (s, 3H), 2.83-2.91 (m, 2H), 3.15-3.17 (m, 1H), 3.28-3.34 (m, 1H), 3.45-3.47 (m, 2H), 3.61-3.65 (m, 1H), 3.74-3.77 (m, 1H), 3.99-4.07 (m, 1H), 4.31 (br, 1H), 4.44-4.54 (m, 4H), 4.88-4.92 (m, 1H), 5.24 (t, J = 4.8 Hz, 1H), 6.64-6.68 (m, 1H), 7.28-7.35 (m, 7H), 7.55 (dd, J = 8.4, 2.4 Hz, 1H), 7.93-7.95 (m, 1H), 7.97-6.01 (m, 1H), 8.49 (d, J = 7.6 Hz, 1H), 8.74, 8.77 (two singles, 1H). |

Example 249: (2S,4R)-1-[(2S)-2-(2-{2-fluoro-4-[1r,3r)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido)cyclobutoxy]phenyl}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide This molecule was prepared with the same method as described in Example 193. The title compound was isolated as a white solid.

$^1$H NMR (400 MHz, $CD_3OD$): δ 1.05 (s, 9H), 1.52 (br, 3H), 1.72 (s, 3H), 1.96-2.04 (m, 1H), 2.21 (br, 1H), 2.47-2.58 (m, 10H), 2.72 (s, 3H), 3.42-3.88 (m, 6H), 4.44-4.66 (m, 6H), 5.02 (br, 1H), 6.63-6.68 (m, 2H), 7.24 (br, 1H), 7.45 (s, 7H), 7.74-7.78 (m, 1H), 8.59 (br, 1H), 8.90 (s, 1H); LC/MS 1084.4 [M+H]+; $t_R$=2.845 min.

Example 251: (2S,4R)-1-[(2S)-2-(2-{[6-(3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}azetidin-1-yl)pyridin-3-yl]oxy}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide This compound was prepared with the same method as described in Example 178. The title compound was isolated as a light yellow solid.

$^1$HNMR (400 MHz, $CD_3OD$): δ 1.06 (s, 9H), 1.52-1.58 (m, 3H), 1.72 (s, 3H), 1.97-2.05 (m, 1H), 2.21-2.26 (m, 1H), 2.48 (d, J=10.8 Hz, 6H), 2.71 (s, 6H), 3.45-3.51 (m, 2H), 3.76-3.81 (m, 1H), 3.86-3.92 (m, 3H), 4.58-4.65 (m, 6H), 5.01-5.05 (m, 1H), 6.51 (d, J=8.8 Hz, 1H), 7.83-7.45 (m, 9H), 7.88-7.92 (m, 1H), 8.87, 8.89 (two singles, 1H); LC_MS: (ES+): m/z 1032.4 [M+H]+. $t_R$=2.395 min Example 257: (2S,4R)-1-[(2S)-3,3-dimethyl-2-(2-{4-[(1,3-cis)-3-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetamido)cyclobutoxy]piperidin-1-yl)acetamido)butanoyl]-4-hydroxy-N-[(1S)-1-[4-(4-methyl-1,3-thiazol-5-yl)phenyl]ethyl]pyrrolidine-2-carboxamide

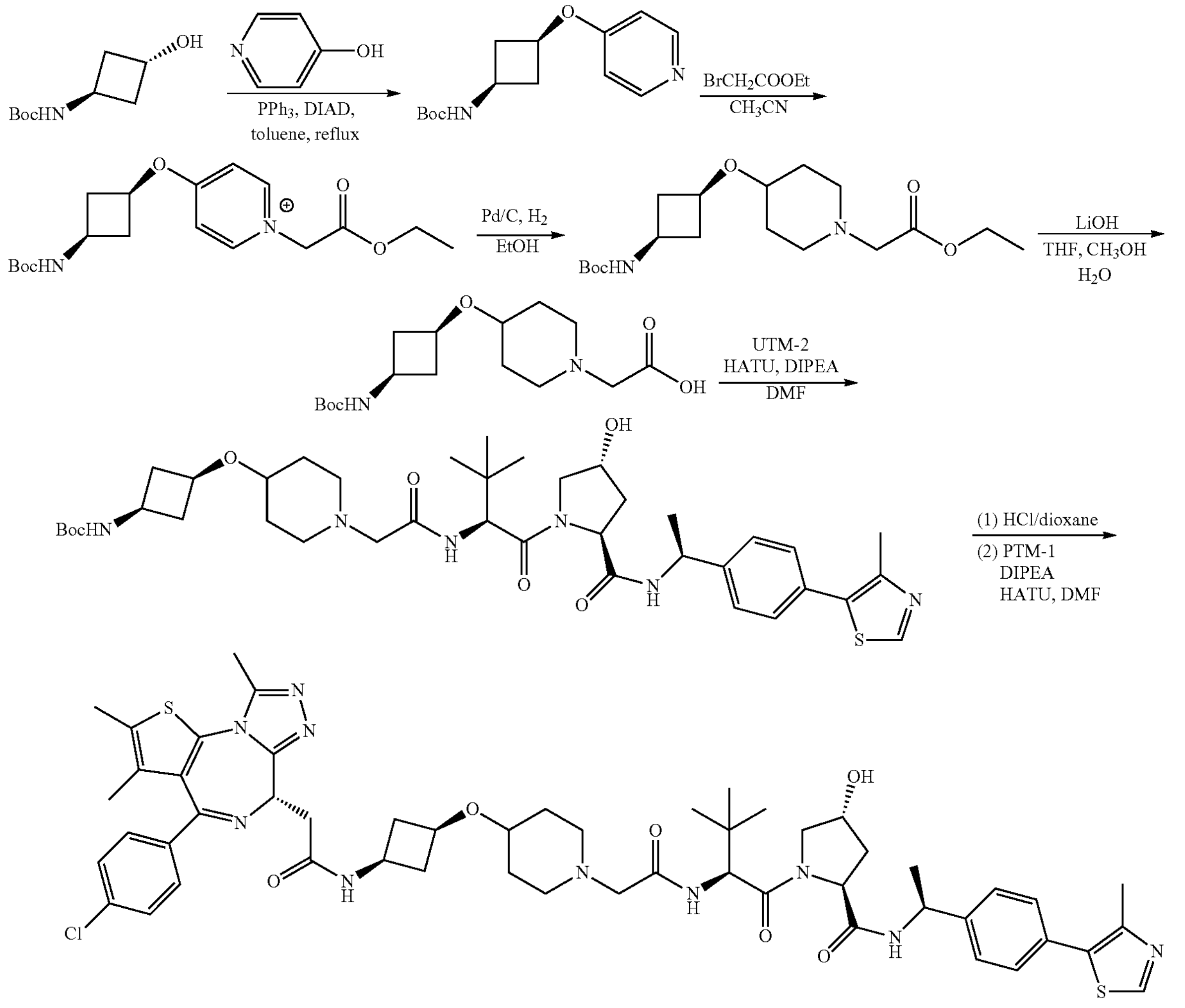

Step 1: Preparation of tert-butyl ((1,3-cis)-3-(pyridin-4-yloxy)cyclobutyl)carbamate To a stirred solution of tert-butyl ((1,3-trans)-3-hydroxycyclobutyl)carbamate (250 mg, 1.34 mmol) and triphenylphosphine (1.05 g, 4.01 mmol) in toluene (10 mL) was added diisopropyl azodicarboxylate (1.35 g, 6.68 mmol) slowly at 0° C. under nitrogen atmosphere. The reaction mixture was stirred at 0° C. for 10 min. To the reaction mixture was added pyridin-4-ol (127 mg, 1.34 mmol) at 0° C., and the resulting reaction mixture was heated to 110° C. and stirred at 110° C. overnight. The reaction mixture was concentrated under reduced pressure to afford a crude residue which was purified by silica gel flash column chromatography (eluted with 20-50% ethyl acetate in hexane) to afford tert-butyl ((1,3-cis)-3-(pyridin-4-yloxy)cyclobutyl)carbamate (100 mg, yield 28%) as a white solid.

$^{1}$H NMR (400 MHz, $CDCl_3$): δ 1.45 (s, 9H), 2.00-2.09 (m, 2H), 2.95-3.01 (m, 2H), 3.94 (br, 1H), 4.40-4.46 (m, 1H), 4.72 (br, 1H), 6.70-6.71 (m, 2H), 8.41-8.42 (m, 2H). LC/MS (ES+): m/z 265.3 $[M+H]^+$; $t_R$=1.735 min.

Step 2: Preparation of 4-((1,3-cis)-3-((tert-butoxycarbonyl)amino)cyclobutoxy)-1-(2-ethoxy-2-oxoethyl)pyridin-1-ium A mixture of tert-butyl ((1,3-cis)-3-(pyridin-4-yloxy)cyclobutyl)carbamate (70 mg, 0.27 mmol) and ethyl 2-bromoacetate (58 mg, 0.34 mmol) in acetonitrile (2 mL) was stirred at rt overnight. TLC showed the reaction was complete. The volatiles were removed under reduced pressure to give a crude residue which was triturated with ethyl acetate (1 mL). The solid precipitation was collected by filtration and dried under vacuum to afford crude 4-((1,3-cis)-3-((tert-butoxycarbonyl)amino)cyclobutoxy)-1-(2-ethoxy-2-oxoethyl)pyridin-1-ium (90 mg, crude) as a yellow solid which was used in next step without further purification.

LC/MS: ($ES^+$): m/z 351.2 $[M]^+$; $t_R$=1.958 min.

Step 3: Preparation of ethyl 2-(4-((1,3-cis)-3-((tert-butoxycarbonyl)amino)cyclobutoxy)-piperidin-1-yl) acetate A mixture of 4-((1,3-cis)-3-((tert-butoxycarbonyl)amino) cyclobutoxy)-1-(2-ethoxy-2-oxoethyl)pyridin-1-ium (90 mg, crude) and palladium on carbon (10%, 10 mg) in ethanol (20 mL) was stirred at 50° C. overnight under hydrogen atmosphere. TLC showed the reaction was complete. The mixture was filtered and the insoluble material was washed with ethanol (10 mL×2). The combined filtrate was concentrated under reduced pressure to give ethyl 2-(4-((1,3-cis)-3-((tert-butoxycarbonyl)amino)cyclobutoxy)piperidin-1-yl) acetate (80 mg, crude) as colorless oil which was used in next step without further purification.

Step 4: Preparation of 2-(4-((1,3-cis)-3-((tert-butoxycarbonyl)amino)cyclobutoxy)-piperidin-1-yl) acetic Acid A mixture of ethyl 2-(4-((1,3-cis)-3-((tert-butoxycarbonyl)amino)cyclobutoxy)piperidin-1-yl)acetate (80 mg, crude) and lithium hydroxide monohydrate (23 mg, 0.54 mmol) in THF (2 mL)/methanol (0.5 mL)/water (0.5 mL) was stirred at rt for 2 h. TLC showed the reaction was complete. The reaction mixture was acidified with diluted hydrochloride acid and the resulting mixture was concentrated under reduced pressure to give 2-(4-((1,3-cis)-3-((tert-butoxycarbonyl)amino)cyclobutoxy)piperidin-1-yl)acetic acid (130 mg, crude) as a white solid which was used in next step without further purification.

Step 5: Preparation of tert-butyl ((1,3-cis)-3-((1-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperidin-4-yl)oxy)cyclobutyl)carbamate]

To a stirred solution containing 2-(4-((1,3-cis)-3-((tert-butoxycarbonyl)amino)cyclobutoxy)piperidin-1-yl)acetic acid (130 mg, crude), (2S,4R)-1-((S)-2-amino-3,3-dimethylbutanoyl)-4-hydroxy-N—((S)-1-(4-(4-methylthiazol-5-yl) phenyl)ethyl)pyrrolidine-2-carboxamide hydrochloric acid salt (130 mg, 0.27 mmol), and N-ethyl-N-isopropylpropan-2-amine (140 mg, 1.08 mmol) in anhydrous N,N-dimethylformamide (2 ml) was added HATU (154 mg, 0.41 mmol) at 0° C. The resulting mixture was allowed to warm to rt and stirred for 30 min. TLC showed the reaction was complete. The mixture was partitioned between ethyl acetate (50 mL) and water (30 mL). The organic layer was collected, washed with brine (30 mL), dried over anhydrous sodium sulfate, and concentrated under reduced pressure to give a crude residue which was purified by silica gel flash column chromatography (eluted with 10% methanol in dichloromethane) to afford tert-butyl-((1,3-cis)-3-((1-(2-(((S)-1-((2S,4R)-4-hydroxy-2-(((S)-1-(4-(4-methylthiazol-5-yl) phenyl)ethyl)carbamoyl)pyrrolidin-1-yl)-3,3-dimethyl-1-oxobutan-2-yl)amino)-2-oxoethyl)piperidin-4-yl)oxy) cyclobutyl)carbamate (78 mg, yield: 38%) as a light yellow solid.

LC/MS (ES+): m/z 755.4 $[M+H]^+$; $t_R$=2.173 min.

Step 6: Preparation of (2S,4R)-1-[(2S)-3,3-dimethyl-2-(2-{4-[(1,3-cis)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl] acetamido}cyclobutoxy]piperidin-1-yl}acetamido) butanoyl]-4-hydroxy-N-[(1S)-1-[4-(4-methyl-1,3-thiazol-5-yl)phenyl]ethyl]pyrrolidine-2-carboxamide A mixture of tert-butyl ((1,3-cis)-3-((1-(2-(((S)-1-((2S, 4R)-4-hydroxy-2-(((S)-1-(4-(4-methylthiazol-5-yl)phenyl) ethyl)carbamoyl)pyrrolidin-1-yl)-3,3-dimethyl-1-oxobutan-2-yl)amino)-2-oxoethyl)piperidin-4-yl)oxy)cyclobutyl) carbamate (78 mg, 0.10 mmol) and 2,2,2-trifluoroacetic acid (2 mL) in dichloromethane (2 mL) was stirred at rt for 1 hour. The volatiles were evaporated under reduced pressure. The residue was taken up with dry N,N-dimethylformamide (2 mL), followed by sequential addition of (S)-2-(4-(4-chlorophenyl)-2,3,9-trimethyl-6H-thieno[3,2-f][1,2,4]triazolo[4,3-a][1,4]diazepin-6-yl)acetic acid (41 mg, 0.10 mmol), N-ethyl-N-isopropylpropan-2-amine (53 mg, 0.41 mmol), and HATU (59 mg, 0.16 mmol) at 0° C. The resulting mixture was allowed to warm up to room temperature and stirred at for 30 min. TLC showed the reaction was completed. The reaction mixture was partitioned between ethyl acetate (50 mL) and water (30 mL). The organic layer was collected, washed with brine (30 mL), dried over anhydrous sodium sulfate, and concentrated under reduced pressure to give a crude residue which was purified by preparative TLC (eluted with 10% methanol in anhydrous dichloromethane) to afford the title compound (26.1 mg, yield 25%) as light yellow solid.

$^1H$ NMR (400 MHz, $CD_3OD$): δ 1.05, 1.07 (two singles, 9H), 1.53-1.60 (m, 3H), 1.63-1.75 (m, 5H), 1.89-2.03 (m, 5H), 2.20-2.25 (m, 1H), 2.35-2.44 (m, 2H), 2.47 (s, 3H), 2.50 (s, 3H), 2.68-2.88 (m, 7H), 3.04-3.13 (m, 2H), 3.25-3.30 (m, 1H), 3.37-3.43 (m, 1H), 3.45-3.65 (m, 2H), 3.75-3.79 (m, 1H), 3.87-4.02 (m, 3H), 4.40-4.49 (m, 1H), 4.52-4.65 (m, 3H), 5.01-5.05 (m, 1H), 7.41-7.48 (m, 8H), 8.88, 8.89 (two singles, 1H).

LC/MS (ES+): m/z 1037.5 $[M+H]^+$. $t_R$=2.323 min.

Example 296: (2S,4R)-1-[(2S)-2-{3-[(5-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}-3,3-difluoropentyl)oxy]-1,2-oxazol-5-yl}-3-methylbutanoyl]-4-hydroxy-N-{[4-(4-methyl-1,3-thiazol-5-yl)phenyl]methyl}pyrrolidine-2-carboxamide Example 297: (2S,4R)-1-[(2R)-2-{3-[(5-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}-3,3-difluoropentyl)oxy]-1,2-oxazol-5-yl}-3-methylbutanoyl]-4-hydroxy-N-{[4-(4-methyl-1,3-thiazol-5-yl)phenyl]methyl}pyrrolidine-2-carboxamide

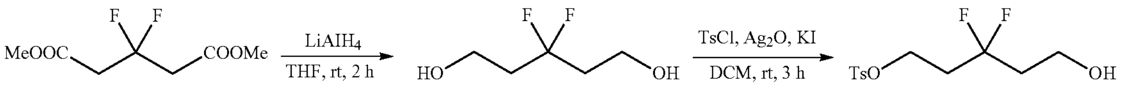

-continued
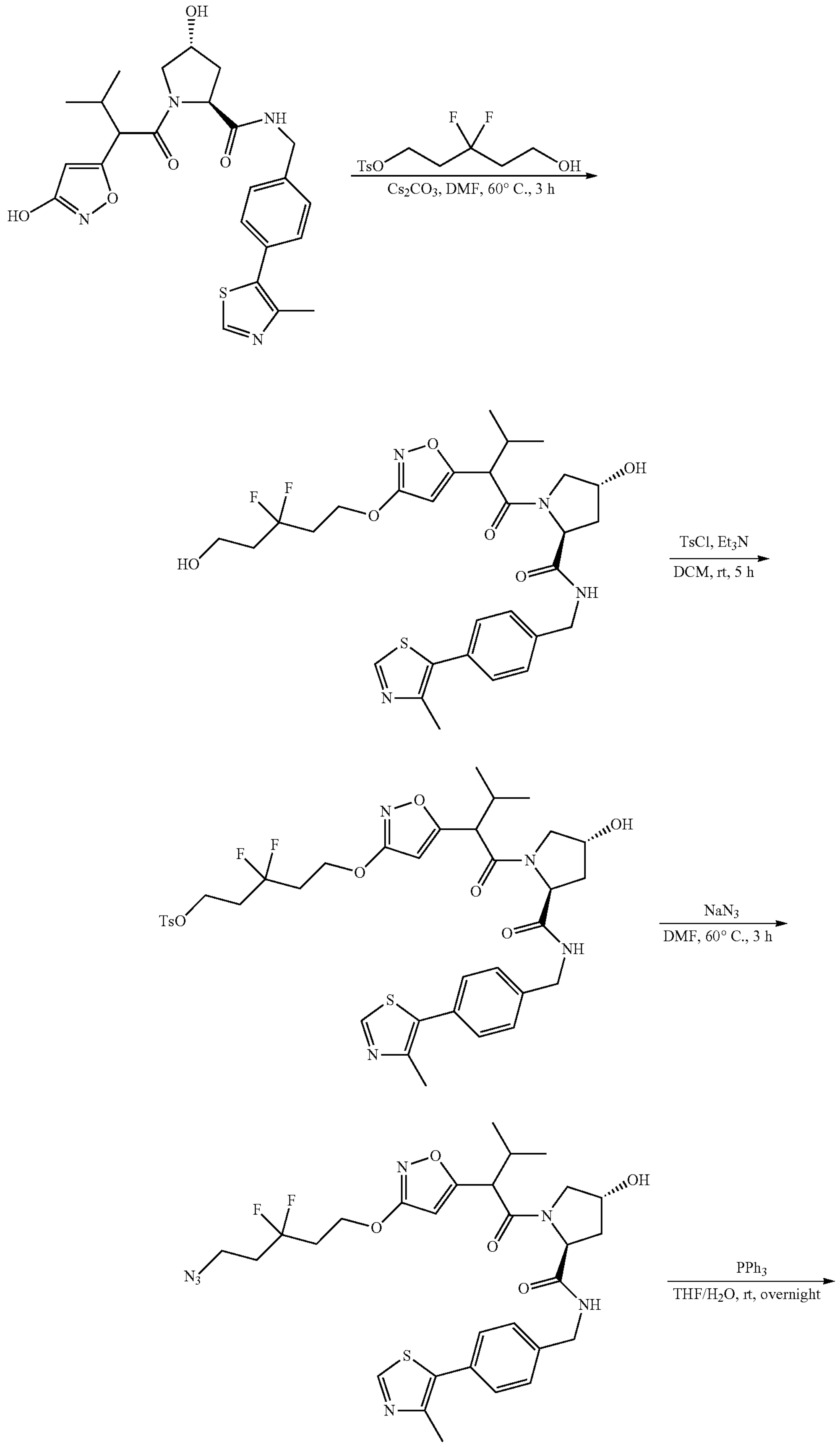

-continued

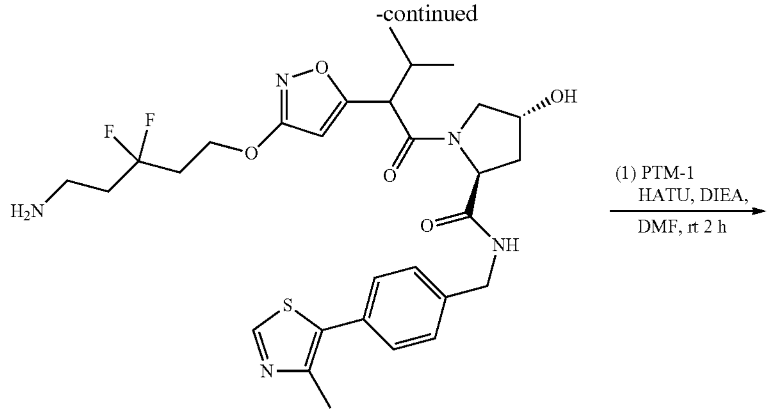

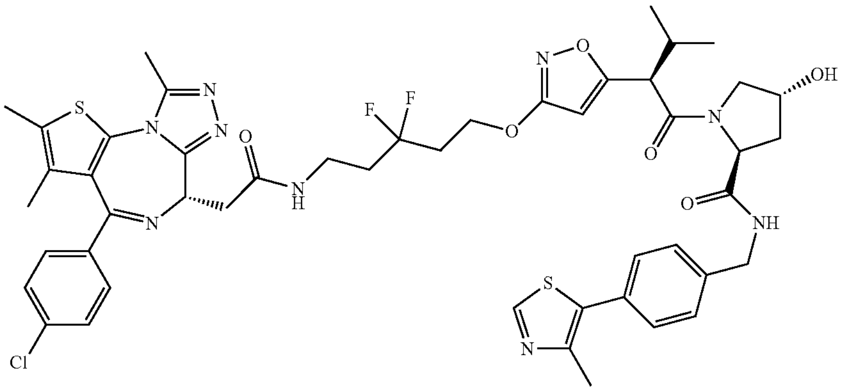

+

Example 297

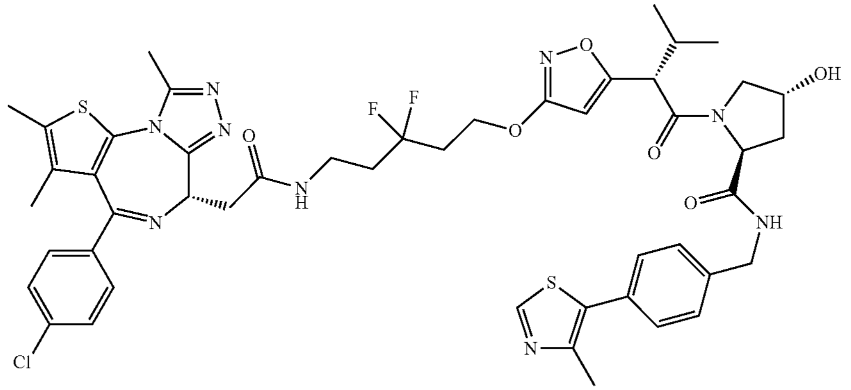

Example 296

Step 1: Synthesis of 3,3-difluoropentane-1,5-diol

Into a 100-mL round-bottom flask purged and maintained with an inert atmosphere of nitrogen, was placed 1,5-dimethyl 3,3-difluoropentanedioate (900.0 mg, 4.59 mmol, 1.00 eq), THF (15 mL), lithium aluminum hydride (872.0 mg, 22.98 mmol, 5.00 eq). The resulting solution was stirred for 2 h at rt. The reaction was then quenched by the addition of 1 mL of water. The mixture was filtered through a layer of Celite and rinsed with THF. The filtrate was dried over anhydrous sodium sulfate and concentrated under vacuum. The residue was applied onto a silica gel column eluted with dichloromethane/methanol (10:1). This resulted in 520.0 mg (81%) of 3,3-difluoropentane-1,5-diol as yellow oil.

Step 2: Synthesis of 3,3-difluoro-5-[[(4-methylbenzene)sulfonyl]oxy]pentan-1-ol

Into a 50-mL round-bottom flask purged and maintained with an inert atmosphere of nitrogen, was placed 3,3-difluoropentane-1,5-diol (520.0 mg, 3.71 mmol, 1.00 eq), dichloromethane (15 mL), silver oxide (1.3 g, 1.50 eq), 4-methylbenzene-1-sulfonyl chloride (705.0 mg, 3.70 mmol, 1.00 eq), and potassium iodide (184 mg, 0.30 eq). The mixture was stirred for 3 h at room temperature and then filtered. The filtrate was dried over anhydrous sodium sulfate and concentrated under vacuum. The residue was applied onto a silica gel column eluted with ethyl acetate/petroleum ether (1:3). This resulted in 650.0 mg (60%) of 3,3-difluoro-5-[[(4-methylbenzene)sulfonyl]oxy]pentan-1-ol as light yellow oil.

Step 3: Synthesis of (2S,4R)-1-(2-[3-[(3,3-difluoro-5-hydroxypentyl)oxy]-1,2-oxazol-5-yl]-3-methylbutanoyl)-4-hydroxy-N-[[4-(4-methyl-1,3-thiazol-5-yl)phenyl]methyl]pyrrolidine-2-carboxamide Into a 25-mL round-bottom flask purged and maintained with an inert atmosphere of nitrogen, was placed DMF (5 mL), 3,3-difluoro-5-[(4-methylbenzene)sulfonyl]oxypentan-1-ol (487.0 mg, 1.65 mol, 1.50 eq), (2S,4R)-4-hydroxy-1-[2-(3-hydroxy-1,2-oxazol-5-yl)-3-methylbutanoyl]-N-[[4-(4-methyl-1,3-thiazol-5-yl)phenyl]methyl]pyrrolidine-2-carboxamide (533.0 mg, 1.10 mmol, 1.00 eq, see preparation of this key intermediate in Example 311 and Example 312), and cesium carbonate (715.0 mg, 2.19 mmol, 2.00 eq). The resulting solution was stirred for 3 h at 60° C. The reaction was then quenched by the addition of water (20 mL). The mixture was extracted with ethyl acetate (20 mL×3). The organic layers were combined and dried over anhydrous sodium sulfate and concentrated under vacuum. The residue was applied onto a silica gel column eluted with dichloromethane/methanol (10:1). This resulted in 270.0 mg (40%) of (2S,4R)-1-(2-[3-[(3,3-difluoro-5-hydroxypentyl)oxy]-1,2-oxazol-5-yl]-3-methylbutanoyl)-4-hydroxy-N-[[4-(4-methyl-1,3-thiazol-5-yl)phenyl]methyl]pyrrolidine-2-carboxamide as yellow oil.

LC-MS ($ES^+$): m/z 607.20 [$MH^+$], $t_R$=1.11 min, (2.5 minute run).

Step 4: Synthesis of 3,3-difluoro-5-[(5-[1-[(2S,4R)-4-hydroxy-2-([[4-(4-methyl-1,3-thiazol-5-yl)phenyl]methyl]carbamoyl)pyrrolidin-1-yl]-3-methyl-1-oxobutan-2-yl]-1,2-oxazol-3-yl)oxy]pentyl 4-methylbenzene-1-sulfonate Into a 50-mL round-bottom flask, was placed (2S,4R)-1-(2-[3-[(3,3-difluoro-5-hydroxypentyl)oxy]-1,2-oxazol-5-yl]-3-methylbutanoyl)-4-hydroxy-N-[[4-(4-methyl-1,3-thiazol-5-yl)phenyl]methyl]pyrrolidine-2-carboxamide (270.0 mg, 0.45 mmol, 1.00 eq), dichloromethane (15 mL), 4-methylbenzene-1-sulfonyl chloride (85.0 mg, 0.45 mmol, 1.00 eq), triethylamine (133.0 mg, 1.31 mmol, 3.00 eq), and 4-dimethylaminopyridine (10.0 mg, 0.08 mmol, 0.18 eq). The mixture was stirred for 5 h at room temperature. The reaction was then quenched by the addition of water (20 mL) and extracted with dichloromethane (20 mL×3). The organic layers were dried over anhydrous sodium sulfate and concentrated under vacuum. The residue was applied onto a silica gel column eluted with dichloromethane/methanol (10:1). This resulted in 160.0 mg (47%) of 3,3-difluoro-5-[(5-[1-[(2S,4R)-4-hydroxy-2-([[4-(4-methyl-1,3-thiazol-5-yl)phenyl]methyl]carbamoyl)pyrrolidin-1-yl]-3-methyl-1-oxobutan-2-yl]-1,2-oxazol-3-yl)oxy]pentyl 4-methylbenzene-1-sulfonate as yellow oil.

LC-MS ($ES^+$): m/z 761.2 [$MH^+$], $t_R$=0.93 min, (2.0 minute run).

Step 5: Synthesis of (2S,4R)-1-(2-[3-[(5-azido-3,3-difluoropentyl)oxy]-1,2-oxazol-5-yl]-3-methylbutanoyl)-4-hydroxy-N-[[4-(4-methyl-1,3-thiazol-5-yl)phenyl]methyl]pyrrolidine-2-carboxamide Into a 25-mL round-bottom flask, was placed 3,3-difluoro-5-[(5-[1-[(2S,4R)-4-hydroxy-2-([[4-(4-methyl-1,3-thiazol-5-yl)phenyl]methyl]carbamoyl)pyrrolidin-1-yl]-3-methyl-1-oxobutan-2-yl]-1,2-oxazol-3-yl)oxy]pentyl 4-methylbenzene-1-sulfonate (160.0 mg, 0.21 mmol, 1.00 eq), DMF (3 mL), and sodium azide (28.0 mg, 0.43 mmol, 2.00 eq). The mixture was stirred for 3 h at 60° C. and then quenched by the addition of water (20 mL×3). The resulting solution was extracted with ethyl acetate (20 mL×3). The organic layers were combined and dried over anhydrous sodium sulfate and concentrated under vacuum. This resulted in 102.0 mg (77%) of (2S,4R)-1-(2-[3-[(5-azido-3,3-difluoropentyl)oxy]-1,2-oxazol-5-yl]-3-methylbutanoyl)-4-hydroxy-N-[[4-(4-methyl-1,3-thiazol-5-yl)phenyl]methyl]pyrrolidine-2-carboxamide as yellow oil.

LC-MS ($ES^+$): m/z 632.1 [$MH^+$], $t_R$=0.93 min, (2.0 minute run).

Step 6: Synthesis of (2S,4R)-1-(2-[3-[(5-amino-3,3-difluoropentyl)oxy]-1,2-oxazol-5-yl]-3-methylbutanoyl)-4-hydroxy-N-[[4-(4-methyl-1,3-thiazol-5-yl)phenyl]methyl]pyrrolidine-2-carboxamide Into a 25-mL round-bottom flask, was placed (2S,4R)-1-(2-[3-[(5-azido-3,3-difluoropentyl)oxy]-1,2-oxazol-5-yl]-3-methylbutanoyl)-4-hydroxy-N-[[4-(4-methyl-1,3-thiazol-5-yl)phenyl]methyl]pyrrolidine-2-carboxamide (102.0 mg, 0.16 mmol, 1.00 eq), THF/water (3.0/0.1 mL), triphenylphosphine (50.0 mg, 0.19 mmol, 1.20 eq). The solution was stirred overnight at room temperature and concentrated under vacuum. The residue was applied onto a silica gel column eluted with dichloromethane/methanol (10:1). This resulted in 90.0 mg (92%) of (2S,4R)-1-(2-[3-[(5-amino-3,3-difluoropentyl)oxy]-1,2-oxazol-5-yl]-3-methylbutanoyl)-4-hydroxy-N-[[4-(4-methyl-1,3-thiazol-5-yl)phenyl]methyl]pyrrolidine-2-carboxamide as yellow oil.

LC-MS ($ES^+$): m/z 606.2 [$MH^+$], $t_R$=1.07 min, (2.5 minute run).

Step 7: synthesis of (2S,4R)-1-[(2R)-2-{3-[(5-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamido}-3,3-difluoropentyl)oxy]-1,2-oxazol-5-yl}-3-methylbutanoyl]-4-hydroxy-N-{[4-(4-methyl-1,3-thiazol-5-yl)phenyl]methyl}pyrrolidine-2-carboxamide and (2S,4R)-1-[(2S)-2-{3-[(5-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamido}-3,3-difluoropentyl)oxy]-1,2-oxazol-5-yl}-3-methylbutanoyl]-4-hydroxy-N-{[4-(4-methyl-1,3-thiazol-5-yl)phenyl]methyl}pyrrolidine-2-carboxamide The above amine from step 6 (80.0 mg, 0.13 mmol, 1.10 eq) was combined with 2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetic acid (48.0 mg, 0.12 mmol, 1.00 eq), DMF (2 mL), 2-(7-aza-1H-benzotriazole-1-yl)-1,1,3,3-tetramethyluronium hexafluorophosphate (68.0 mg, 0.18 mmol, 1.50 eq) and DIPEA (46.0 mg, 0.36 mmol). The resulting mixture was stirred for 2 h at rt and then quenched by the addition of water (20 mL). The mixture was extracted with ethyl acetate (20 mL×3). The organic layers were combined, dried over anhydrous sodium sulfate and concentrated under vacuum. The residue was purified by preparative HPLC (column: XBridge Prep OBD C18 Column, 19*250 mm, 5 um; Mobile Phase A: water with 0.05% ammonium hydroxide; Mobile Phase B: acetonitrile; Flow rate: 20 mL/min; Gradient: 47% B to 62% B in 8 min; UV detection at 254 nm). This resulted in 33.0 mg (35%) of a white solid as the tile compound of Example 296 as well as 33.0 mg (35%) of a white solid as the tile compound of Example 297.

Example 296: $^1H$ NMR (400 MHz, $CD_3OD$) δ 8.87 (s, 1H), 7.47-7.35 (m, 9H), 5.99 and 5.91 (2s, 1H), 4.72-4.62

(m, 2H), 4.62-4.60 (m, 1H), 4.59-4.31 (m, 4H), 3.78-3.70 (m, 3H), 3.47-3.39 (m, 3H), 2.69 (s, 3H), 2.47 (s, 3H), 2.43 (s, 3H), 2.42-2.35 (m, 3H), 2.29-2.12 (m, 3H), 2.06-2.01 (m, 1H), 1.69 (s, 3H), 1.04 and 0.78 (2d, 3H), 0.89 and 0.64 (2d, 3H); LC-MS (ES$^+$): m/z 988.50/990.50 [MH$^+$], $t_R$=1.56 min, (3.0 minute run).

Example 297: $^1$H NMR (400 MHz, $CD_3OD$) δ 8.87 (s, 1H), 7.51-7.38 (m, 9H), 6.01 and 5.77 (2s, 1H), 4.72-4.62 (m, 1H), 4.51-4.43 (m, 3H), 4.40-4.38 (m, 3H), 3.88-3.78 (m, 1H), 3.67-3.59 (m, 2H), 3.50-3.30 (m, 3H), 2.69 (s, 3H), 2.47 (s, 3H), 2.43 (m, 4H), 2.42-2.31 (m, 2H), 2.36-2.15 (m, 3H), 2.12-2.00 (m, 1H), 1.70 (s, 3H), 1.00 (d, J=6.4 Hz, 3H), 0.89 (d, J=6.4 Hz, 3H); LC-MS (ES$^+$): m/z 988.45/990.45 [MH$^+$], $t_R$=1.43 min, (2.9 minute run).

Example 306: (2S,4R)-1-[(2S)-3,3-dimethyl-2-(2-{4-[(1,3-trans)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}cyclobutoxy]piperidin-1-yl}acetamido)butanoyl]-4-hydroxy-N-[(1S)-1-[4-(4-methyl-1,3-thiazol-5-yl)phenyl]ethyl]pyrrolidine-2-carboxamide Step 1: Preparation of tert-butyl ((1,3-trans)-3-(pyridin-4-yloxy)cyclobutyl)carbamate To a stirred solution of tert-butyl ((1,3-cis)-3-hydroxycyclobutyl)carbamate (300 mg, 1.60 mmol) and triphenylphosphine (1.26 g, 4.81 mmol) in toluene (10 mL) was added diisopropyl azodicarboxylate (972 mg, 4.81 mmol) slowly at 0° C. under nitrogen atmosphere. The reaction mixture was stirred at 0° C. for 10 min. To the reaction mixture was added pyridin-4-ol (152 mg, 1.60 mmol) at 0° C., and the resulting reaction mixture was heated to 110° C. and stirred at 110° C. overnight. TLC showed the reaction was complete. The reaction mixture was concentrated under reduced pressure to afford crude residue which was purified by silica gel flash column chromatography (eluted with 20-50% ethyl acetate in hexane) to afford tert-butyl ((1,3-trans)-3-(pyridin-4-yloxy)cyclobutyl)carbamate (140 mg, yield 33%) as a white solid.

$^1$H NMR (400 MHz, $CDCl_3$): δ 1.45 (s, 9H), 2.38-2.49 (m, 2H), 2.55-2.60 (m, 2H), 4.31 (br, 1H), 4.73-4.86 (m, 2H), 6.67-6.69 (m, 2H), 8.40-8.42 (m, 2H).

LC/MS (ES+): m/z 265.1 [M+H]$^+$; $t_R$=1.782 min.

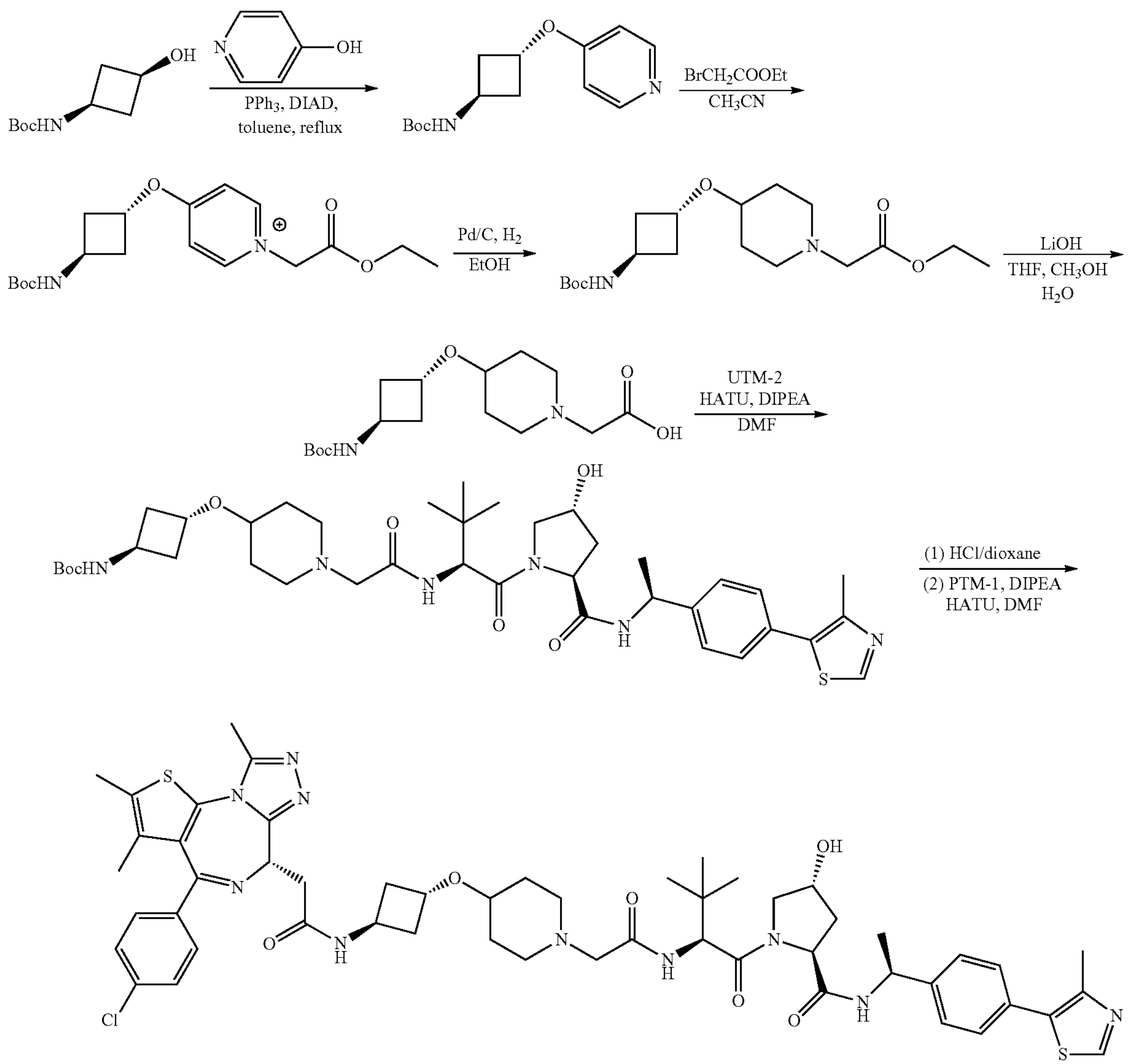

Step 2: Preparation of 4-((1,3-trans)-3-((tert-butoxy-carbonyl)amino)cyclobutoxy)-1-(2-ethoxy-2-oxo-ethyl)pyridin-1-ium A mixture of tert-butyl ((1,3-trans)-3-(pyridin-4-yloxy) cyclobutyl)carbamate (140 mg, 0.53 mmol) and ethyl 2-bromoacetate (116 mg, 0.69 mmol) in acetonitrile (4 mL) was stirred at rt overnight. TLC showed the reaction was complete. The volatiles were removed under reduced pressure to give a crude residue which was triturated with ethyl acetate (1 mL). The solid precipitation was collected by filtration and dried under vacuum to afford crude 4-((1,3-trans)-3-((tert-butoxycarbonyl)amino)cyclobutoxy)-1-(2-ethoxy-2-oxoethyl)pyridin-1-ium (180 mg, crude) as yellow oil which was used in next step without further purification.

LC/MS (ES$^+$): m/z 351.2 [M]$^+$; $t_R$=1.942 min.

Step 3: Preparation of ethyl 2-(4-((1,3-trans)-3-((tert-butoxycarbonyl)amino)cyclobutoxy)-piperidin-1-yl)acetate A mixture of 4-((1,3-trans)-3-((tert-butoxycarbonyl) amino)cyclobutoxy)-1-(2-ethoxy-2-oxoethyl)pyridin-1-ium (180 mg, crude) and palladium on carbon (10%, 20 mg) in ethanol (30 mL) was stirred at 50° C. overnight under hydrogen atmosphere. TLC showed the reaction was complete. The mixture was filtered and the solid was washed with ethanol (10 mL×2). The combined filtrates were concentrated under reduced pressure to afford crude ethyl 2-(4-((1,3-trans)-3-((tert-butoxycarbonyl)amino)cyclobutoxy)piperidin-1-yl)acetate (160 mg, crude) as colorless oil which was used in next step without further purification.

Step 4: Preparation of 2-(4-((1,3-trans)-3-((tert-butoxycarbonyl)amino)cyclobutoxy)piperidin-1-yl) acetic Acid A mixture of ethyl 2-(4-((1,3-trans)-3-((tert-butoxycarbonyl)amino)cyclobutoxy)piperidin-1-yl)acetate (160 mg, crude) and lithium hydroxide monohydrate (45 mg, 1.06 mmol) in THF (2 mL)/methanol (0.5 mL)/water (0.5 mL) was stirred at room temperature for 2 hours. TLC showed the reaction was complete. The reaction mixture was acidified with hydrochloride acid and the resulting mixture was extracted into ethyl acetate. The solution was concentrated under reduced pressure to give a crude 2-(4-((1,3-trans)-3-((tert-butoxycarbonyl)amino)cyclobutoxy)piperidin-1-yl) acetic acid (250 mg, crude) as a white solid which was used in next step without further purification.

Step 5: Preparation of tert-butyl ((1,3-trans)-3-((1-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperidin-4-yl)oxy)cyclobutyl)carbamate To a stirred solution containing 2-(4-((1,3-trans)-3-((tert-butoxycarbonyl)amino)cyclobutoxy)piperidin-1-yl)acetic acid (250 mg, crude), (2S,4R)-1-((S)-2-amino-3,3-dimethylbutanoyl)-4-hydroxy-N—((S)-1-(4-(4-methylthiazol-5-yl) phenyl)ethyl)pyrrolidine-2-carboxamide hydrochloric acid salt (255 mg, 0.53 mmol, UTM-2), and N-ethyl-N-isopropylpropan-2-amine (274 mg, 2.12 mmol) in anhydrous N,N-dimethylformamide (3 mL) was added HATU (302 mg, 0.80 mmol) at 0° C. The resulting mixture was allowed to warm to room temperature and stirred at room temperature for 30 min. TLC showed the reaction was complete. The mixture was partitioned between ethyl acetate (50 mL) and water (30 mL). The organic layer was collected, washed with brine (30 mL), dried over anhydrous sodium sulfate, and concentrated under reduced pressure to give a crude residue which was purified by silica gel flash column chromatography (eluted with 5-10% methanol in dichloromethane) to afford tert-butyl ((1,3-trans)-3-((1-(2-(((S)-1-((2S,4R)-4-hydroxy-2-(((S)-1-(4-(4-methylthiazol-5-yl)phenyl)ethyl)carbamoyl) pyrrolidin-1-yl)-3,3-dimethyl-1-oxobutan-2-yl)amino)-2-oxoethyl)piperidin-4-yl)oxy)cyclobutyl)carbamate (127 mg, yield: 32%) as a white solid.

LC/MS (ES+): m/z 755.4 [M+H]$^+$; $t_R$=2.170 min.

Step 6: Preparation of (2S,4R)-1-[(2S)-3,3-dimethyl-2-(2-{4-[(1,3-trans)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl] acetamido}cyclobutoxy]piperidin-1-yl}acetamido) butanoyl]-4-hydroxy-N-[(1S)-1-[4-(4-methyl-1,3-thiazol-5-yl)phenyl]ethyl]pyrrolidine-2-carboxamide A mixture of tert-butyl ((1,3-trans)-3-((1-(2-(((S)-1-((2S, 4R)-4-hydroxy-2-(((S)-1-(4-(4-methylthiazol-5-yl)phenyl) ethyl)carbamoyl)pyrrolidin-1-yl)-3,3-dimethyl-1-oxobutan-2-yl)amino)-2-oxoethyl)piperidin-4-yl)oxy)cyclobutyl) carbamate (127 mg, 0.17 mmol) and 2,2,2-trifluoroacetic acid (3 mL) in dichloromethane (3 mL) was stirred at rt for 1 h. TLC showed the reaction was complete. The volatiles were evaporated under reduced pressure. The residue was taken up with dry N,N-dimethylformamide (2 mL), followed by sequential addition of (S)-2-(4-(4-chlorophenyl)-2,3,9-trimethyl-6H-thieno[3,2-f][1,2,4]triazolo[4,3-a][1,4]diazepin-6-yl)acetic acid (67 mg, 0.17 mmol, PTM-1), N-ethyl-N-isopropylpropan-2-amine (87 mg, 0.67 mmol), and HATU (96 mg, 0.25 mmol) at 0° C. The resulting mixture was allowed to warm up to room temperature and stirred at room temperature for 30 min. TLC showed the reaction was complete. The reaction mixture was partitioned between ethyl acetate (80 mL) and water (50 mL). The organic layer was collected, washed with brine (50 mL), dried over anhydrous sodium sulfate, and concentrated under reduced pressure to give a crude residue which was purified by preparative TLC (eluted with 10% methanol in anhydrous dichloromethane) to afford the title compound (43.5 mg, yield 25%) as a light yellow solid.

$^1$H NMR (400 MHz, $CD_3OD$): S 1.00 and 1.02 (two singlets, 9H), 1.50 and 1.55 (two doublets, 3H), 1.56-1.72 (m, 5H), 1.84-1.98 (m, 3H), 2.15-2.25 (m, 1H), 2.26-2.40 (m, 6H), 2.44 (s, 3H), 2.48 (s, 3H), 2.68 (s, 3H), 2.73-2.84 (m, 2H), 3.04 (s, 2H), 3.25-3.65 (m, 3H), 3.68-3.75 (m, 1H), 3.87-3.90 (m, 1H), 4.25-4.45 (m, 3H), 4.50-4.66 (m, 3H), 5.01 (m, 1H), 7.30-7.50 (m, 8H), 8.85 (s, 1H).

LC/MS (ES+): m/z 1037.5 [M+H]$^+$; $t_R$=2.330 min.

Example 311: (2S,4R)-1-[(2S)-2-(3-{2-[(3R)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}pyrrolidin-1-yl]ethoxy}-1,2-oxazol-5-yl)-3-methylbutanoyl]-4-hydroxy-N-{[4-(4-methyl-1,3-thiazol-5-yl)phenyl]methyl}pyrrolidine-2-carboxamide Example 312: (2S,4R)-1-[(2R)-2-(3-{2-[(3R)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}pyrrolidin-1-yl]ethoxy}-1,2-oxazol-5-yl)-3-methylbutanoyl]-4-hydroxy-N-{[4-(4-methyl-1,3-thiazol-5-yl)phenyl]methyl}pyrrolidine-2-carboxamide

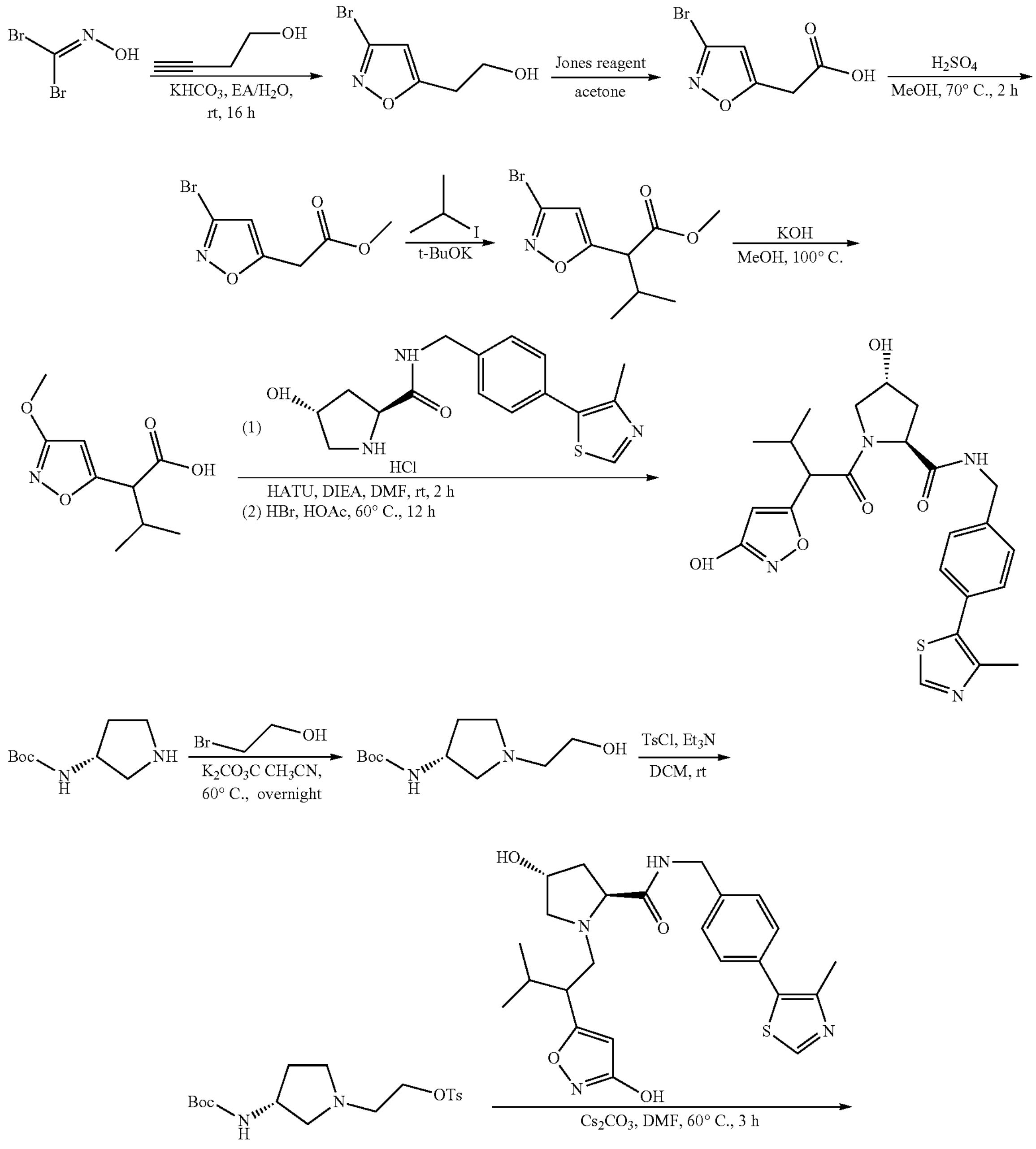

-continued
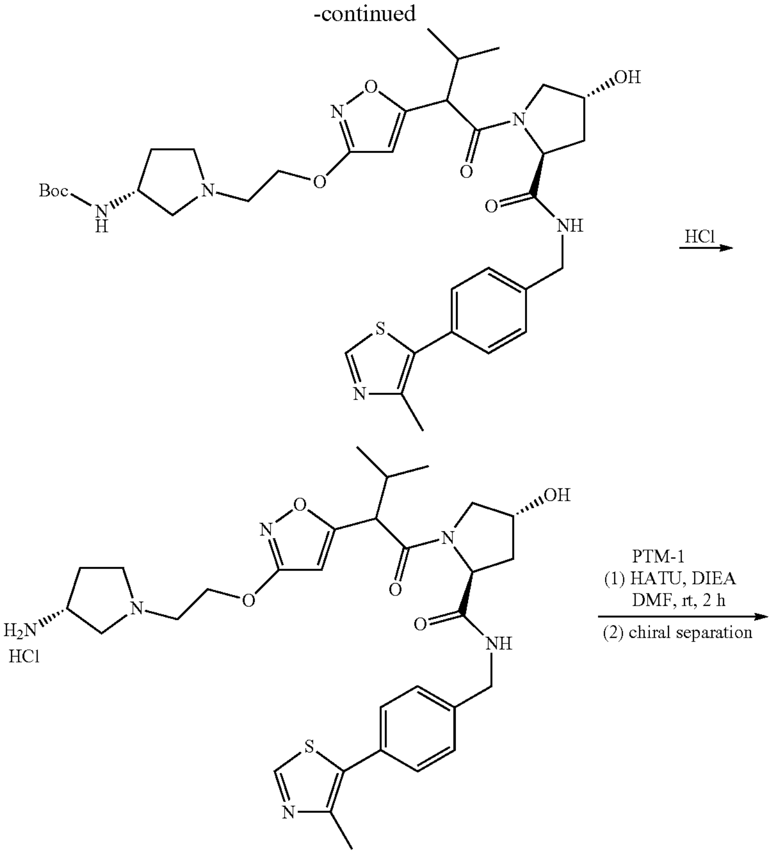
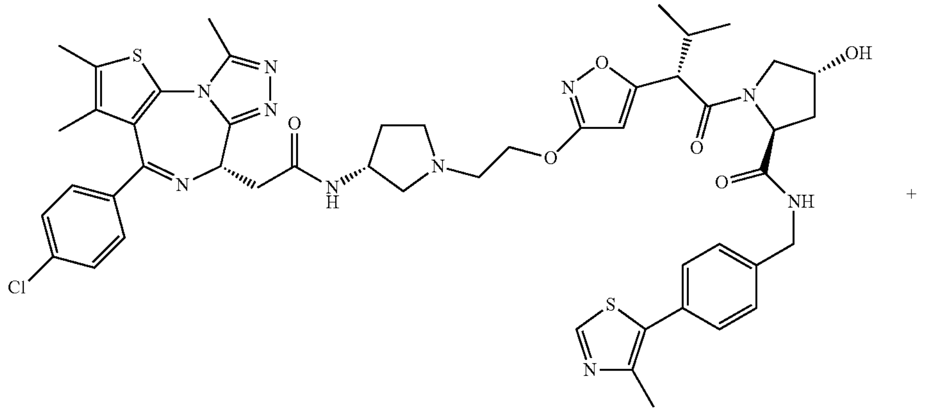
Example 311
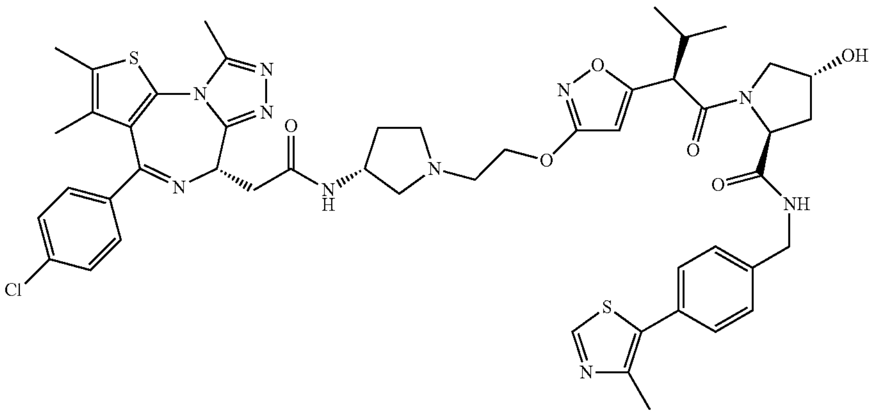
Example 312

Step 1: Synthesis of 2-(3-bromo-1,2-oxazol-5-yl)ethan-1-ol

Into a 1000-mL 3-necked round-bottom flask, was placed a solution of but-3-yn-1-ol (56.0 g, 798.98 mmol, 4.00 equiv) in ethyl acetate/water (400/40 mL) and potassium bicarbonate (60.0 g, 600.00 mmol, 3.0 eq). This was followed by the addition of a solution of 1-bromo-N-hydroxymethanecarbonimidoyl bromide (40.0 g, 197.21 mmol, 1.00 eq) in ethyl acetate (100 mL) dropwise with stirring at 20° C. The resulting solution was stirred for 16 h at 25° C. The reaction was then quenched by the addition of water (500 mL). The resulting solution was extracted with ethyl acetate (300 mL×3) and the organic layers were combined. The solution was washed with water (500 mL×1) and brine (300 mL×1), dried over anhydrous sodium sulfate and concentrated under vacuum. The residue was applied onto a silica gel column eluted with ethyl acetate/petroleum ether (1:4). This resulted in 46.0 g (crude) of 2-(3-bromo-1,2-oxazol-5-yl)ethan-1-ol as yellow oil.

Step 2: Synthesis of 2-(3-bromo-1,2-oxazol-5-yl)acetic Acid

Into a 100-mL round-bottom flask, was placed a solution of 2-(3-bromo-1,2-oxazol-5-yl)ethan-1-ol (45.0 g, 234.36 mmol, 1.00 eq) in acetone (500 mL). Jones reagent (200 mL) was added dropwise at 0° C. The resulting solution was stirred for 12 h at 25° C. This mixture was diluted with 500 mL of water. The resulting solution was extracted with ethyl acetate (300 mL×3) and the organic layers were combined. The solution was washed with water (300 mL×1) and brine (100 mL×1), dried over anhydrous sodium sulfate and concentrated under vacuum. This resulted in 40.0 g (crude) of 2-(3-bromo-1,2-oxazol-5-yl)acetic acid as yellow oil.

Step 3: Synthesis of methyl 2-(3-bromo-1,2-oxazol-5-yl)acetate

Into a 1000-mL round-bottom flask, was placed a solution of 2-(3-bromo-1,2-oxazol-5-yl)acetic acid (40.0 g, 194.18 mmol, 1.00 eq) in methanol (300 mL). Sulfuric acid (3 mL) was added slowly. The resulting solution was stirred for 2 h at 70° C. The mixture was concentrated under vacuum and then diluted with water (100 mL). The resulting mixture was extracted with ethyl acetate (100 mL×3) and the organic layers were combined. The solution was washed with brine, dried over anhydrous sodium sulfate and concentrated under vacuum. The residue was applied onto a silica gel column eluted with ethyl acetate/petroleum ether (1:4). This resulted in 31.0 g (73%) of methyl 2-(3-bromo-1,2-oxazol-5-yl) acetate as yellow oil.

LC-MS ($ES^+$): m/z 219.80/221.80 [$MH^+$], $t_R$=0.73 min, (1.9 minute run).

Step 4: Synthesis of methyl 2-(3-bromo-1,2-oxazol-5-yl)-3-methylbutanoate

Into a 500-mL 3-necked round-bottom flask, was placed a solution of methyl 2-(3-bromo-1,2-oxazol-5-yl)acetate (31.0 g, 140.90 mmol, 1.00 eq) in THF (300 mL), and potassium tert-butyl alcohol (23.0 g, 204.97 mmol, 1.50 eq) was added slowly. This was followed by the addition of 2-iodopropane (30.5 g, 179.42 mmol, 1.30 eq) dropwise with stirring at 0° C. The resulting solution was stirred for 16 h at 25° C. The reaction was then quenched by the addition of water/ice (500 mL). The mixture was extracted with ethyl acetate (200 mL×3) and the organic layers were combined. The resulting mixture was washed with brine (300 mL×1). The mixture was dried over anhydrous sodium sulfate and concentrated under vacuum. The residue was applied onto a silica gel column eluted with ethyl acetate/petroleum ether (1:6). This resulted in 17.0 g (46%) of methyl 2-(3-bromo-1,2-oxazol-5-yl)-3-methylbutanoate as yellow oil.

LC-MS ($ES^+$): m/z 263.90/265.90 [$MH^+$], $t_R$=0.94 min, (1.9 minute run).

Step 5: Synthesis of 2-(3-methoxy-1,2-oxazol-5-yl)-3-methylbutanoic Acid

Into a 500-mL round-bottom flask, was placed a solution of methyl 2-(3-bromo-1,2-oxazol-5-yl)-3-methylbutanoate (14.0 g, 53.41 mmol, 1.00 eq) in methanol (100 mL), and potassium hydroxide (29.4 g, 525.00 mmol, 10.00 eq) was added. The mixture was stirred for 4 h at 100° C. in a MW bath. The mixture was concentrated under vacuum and then diluted with water (100 mL). The resulting solution was extracted with ethyl acetate (100 mL×2) and the aqueous layers were combined. The pH value of the solution was adjusted to 5 with 1 N hydrochloric acid. This mixture was extracted with ethyl acetate (100 mL×3) and the organic layers were combined. The solution was washed with brine (30 mL×1) and dried over anhydrous sodium sulfate. The residue was applied onto a silica gel column eluted with ethyl acetate/petroleum ether (1:3). This resulted in 10.0 g (94%) of 2-(3-methoxy-1,2-oxazol-5-yl)-3-methylbutanoic acid as yellow oil.

LC-MS ($ES^+$): m/z 200.00 [$MH^+$], $t_R$=1.48 min, (1.9 minute run).

Step 6: Synthesis of (2S,4R)-4-hydroxy-1-[2-(3-methoxy-1,2-oxazol-5-yl)-3-methylbutanoyl]-N [[4-(4-methyl-1,3-thiazol-5-yl)phenyl]methyl]pyrrolidine-2-carboxamide Into a 250-mL 3-necked round-bottom flask, was placed a solution of 2-(3-methoxy-1,2-oxazol-5-yl)-3-methylbutanoic acid (6.0 g, 30.12 mmol, 1.00 eq) in DMF (100 mL), (2S,4R)-4-hydroxy-N-[4-(4-methyl-1,3-thiazol-5-yl)phenyl]methylpyrrolidine-2-carboxamide hydrogen chloride (10.6 g, 33.40 mmol, 1.00 eq) was added. This was followed by the addition of 0-(7-azabenzotriazol-1-yl)-N,N,N,N-tetramethyluronium hexafluorophosphate (14.9 g, 39.19 mmol, 1.30 eq) in several batches at 0° C. To this stirred mixture was added N,N-diisopropylethylamine (20.0 g, 154.75 mmol, 5.00 eq) dropwise at 0° C. The resulting solution was stirred for 2 h at rt. The reaction was then quenched by the addition of ice water (200 mL). The mixture was extracted with ethyl acetate (50 mL×3) and the organic layers were combined. The solution was washed with water and brine, dried over anhydrous sodium sulfate and concentrated under vacuum. The residue was applied onto a silica gel column eluted with dichloromethane/methanol (10:1). This resulted in 4.75 g (32%) of (2S,4R)-4-hydroxy-1-[2-(3-methoxy-1,2-oxazol-5-yl)-3-methylbutanoyl]-N-[[4-(4-methyl-1,3-thiazol-5-yl)phenyl]methyl]pyrrolidine-2-carboxamide as a solid.

$^1H$ NMR (300 MHz, $CD_3OD$) δ 8.90 (s, 1H), 7.50-7.39 (m, 4H), 6.01-5.99 (d, J=8.0 Hz, 1H), 4.86-4.42 (m, 4H), 3.93-3.62 (m, 6H), 2.42 (s, 3H), 2.38-2.00 (m, 3H), (t, J=6.3 Hz, 3H), 0.94-0.90 (t, J=6.3 Hz, 3H). LC-MS ($ES^+$): m/z 499.20 [$MH^+$], $t_R$=1.45 min, (3.6 minute run).

The above solid (2.0 g, 4.01 mmol, 1.00 eq) was mixed with hydrobromic acid in acetic acid (10 mL). The resulting solution was stirred for 12 h at 60° C. The solution was concentrated under vacuum. The crude product was purified by preparative HPLC (column, C18 silica gel; mobile phase, acetonitrile/Water, detector, UV 254 nm). This resulted in 1.7 g (87%) of (2S,4R)-4-hydroxy-1-[2-(3-hydroxy-1,2-oxazol-5-yl)-3-methylbutanoyl]-N-[[4-(4-methyl-1,3-thiazol-5-yl)phenyl]methyl]pyrrolidine-2-carboxamide as a white solid.

LC-MS (ES+): m/z 485.20 [$MH^+$], $t_R$=0.67 min, (2.0 minute run)

Step 7: Synthesis of tert-butyl N-[(3R)-1-(2-hydroxyethyl)pyrrolidin-3-yl]carbamate Into a 100-mL round-bottom flask, was placed tert-butyl N-[(3R)-pyrrolidin-3-yl]carboxamate (1.86 g, 9.99 mmol, 1.00 eq), acetonitrile (30 mL), 2-bromoethan-1-ol (1.87 g, 14.96 mmol, 1.50 eq), and potassium carbonate (1.5 g, 10.85 mmol, 1.10 eq). The mixture was stirred for 16 h at 60° C. in an oil bath. The solids were filtered out. The resulting mixture was concentrated under vacuum and extracted with ethyl acetate (60×3 mL). The organic layers were combined, washed with water, dried and concentrated. This resulted in 2.0 g (crude) of tert-butyl N-[(3R)-1-(2-hydroxyethyl)pyrrolidin-3-yl]carbamate as a solid.

Step 8: Synthesis of tert-butyl N-[(3R)-1-(2-[[(4-methylbenzene)sulfonyl]oxy]-ethyl)pyrrolidin-3-yl]carbamate Into a 100-mL round-bottom flask, was placed tert-butyl N-[(3R)-1-(2-hydroxyethyl)pyrrolidin-3-yl]carbamate (320.0 mg, 1.39 mmol, 1.00 eq), dichloromethane (5 mL), 4-toluene sulfonyl chloride (395.0 mg, 2.07 mmol, 1.20 eq), triethylamine (281.0 mg, 2.78 mmol, 2.00 eq), 4-dimethylaminopyridine (16.9 mg, 0.14 mmol, 0.10 equiv). The resulting mixture was stirred overnight at 25° C. The mixture was quenched with water and extracted with dichloromethane (40×3 mL). The organic layers were combined, washed with water and brine, dried and concentrated. The residue was applied onto a silica gel column eluted with ethyl acetate/petroleum ether (2/1). This resulted in 180 mg (34%) of tert-butyl N-[(3R)-1-(2-[[(4-methylbenzene)sulfonyl]oxy]ethyl)pyrrolidin-3-yl]carbamate as light yellow oil.

Step 9: Synthesis of tert-butyl N-[(3R)-1-[2-[(5-[1-[(2S,4R)-4-hydroxy-2-([[4-(4-methyl-1,3-thiazol-5-yl)phenyl]methyl]carbamoyl)pyrrolidin-1-yl]-3-methyl-1-oxobutan-2-yl]-1,2-oxazol-3-yl)oxy]ethyl]pyrrolidin-3-yl]carbamate Into a 100-mL round-bottom flask, was placed tert-butyl N-[(3R)-1-(2-[[(4-methylbenzene)sulfonyl]oxy]ethyl)pyrrolidin-3-yl]carbamate (180.0 mg, 0.47 mmol, 1.00 eq), DMF (10 mL), cesium carbonate (306.0 mg, 0.94 mmol, 2.00 eq), (2S,4R)-4-hydroxy-1-[2-(3-hydroxy-1,2-oxazol-5-yl)-3-methylbutanoyl]-N-[4-(4-methyl-1,3-thiazol-5-yl)phenyl]methylpyrrolidine-2-carboxamide (227.0 mg, 0.47 mmol, 1.00 eq). The resulting solution was stirred for 3 h at 25° C. After the workup and purification by flash column chromatography, 230.0 mg (71%) of tert-butyl N-[(3R)-1-[2-[(5-[1-[(2S,4R)-4-hydroxy-2-([[4-(4-methyl-1,3-thiazol-5-yl)phenyl]methyl]carbamoyl)pyrrolidin-1-yl]-3-methyl-1-oxobutan-2-yl]-1,2-oxazol-3-yl)oxy]ethyl]pyrrolidin-3-yl]carbamate was obtained as a white solid.

Step 10: Synthesis of (2S,4R)-1-[2-(3-[2-[(3R)-3-aminopyrrolidin-1-yl]ethoxy]-1,2-oxazol-5-yl)-3-methylbutanoyl]-4-hydroxy-N-[[4-(4-methyl-1,3-thiazol-5-yl)phenyl]methyl]pyrrolidine-2-carboxamide Into a 100-mL round-bottom flask, was placed tert-butyl N-[(3R)-1-[2-[(5-[1-[(2S,4R)-4-hydroxy-2-([[4-(4-methyl-1,3-thiazol-5-yl)phenyl]methyl]carbamoyl)pyrrolidin-1-yl]-3-methyl-1-oxobutan-2-yl]-1,2-oxazol-3-yl)oxy]ethyl]pyrrolidin-3-yl]carbamate (130.0 mg, 0.19 mmol, 1.00 eq), methanol (3 mL), hydrogen chloride in dioxane (4N, 1 mL). The resulting solution was stirred for 2 h at 25° C. The mixture was concentrated under vacuum to provide the title compound as a hydrochloride salt (108 mg).

Step 11: preparation of (2S,4R)-1-[(2S)-2-(3-{2-[(3R)-3-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamido}pyrrolidin-1-yl]ethoxy}-1,2-oxazol-5-yl)-3-methylbutanoyl]-4-hydroxy-N-{[4-(4-methyl-1,3-thiazol-5-yl)phenyl]methyl}pyrrolidine-2-carboxamide and (2S,4R)-1-[(2R)-2-(3-{2-[(3R)-3-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetamido}pyrrolidin-1-yl]ethoxyl-1,2-oxazol-5-yl)-3-methylbutanoyl]-4-hydroxy-N-{[4-(4-methyl-1,3-thiazol-5-yl)phenyl]methyl}pyrrolidine-2-carboxamide The hydrochloride salt from step 10 was mixed with 2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetic acid (87 mg, 0.22 mmol), DMF (5 mL), HATU (100.0 mg, 0.26 mmol), DIPEA (113.0 mg, 0.87 mmol). The resulting solution was stirred for 1 h at 25° C. The crude product was purified by flash column chromatography first then by preparative HPLC using a chiral column (column, Chiralpak IA, 2*25 cm, Sum; mobile phase, MTBE and ethanol, hold 40.0% ethanol in 19 min); detector, UV 254/220 nm) to provide two batches as white solids (25.6 mg for Example 311 and 33.7 mg for Example 312).

Fraction 1 (Example 311): $^1H$ NMR (400 MHz, $CD_3OD$): 8.87 (s, 1H), 7.28-7.50 (m, 8H), 5.98 and 5.88 (2s, 1H), 4.50-4.68 (m, 2H), 4.20-4.45 (m, 6H), 3.61-3.82 (m, 3H), 3.32-3.46 (m, 1H), 3.08-3.18 (m, 1H), 2.70-3.00 (m, 4H), 2.65 (s, 3H), 2.50-2.63 (m, 2H), 2.45 (s, 3H), 2.42 (s, 3H), 2.18-2.40 (m, 3H), 2.03-2.16 (m, 1H), 1.67-1.80 (m, 1H), 1.66 (s, 3H), 1.03 and 0.76 (2d, 3H), 0.88 and 0.60 (2d, 3H); LC-MS ($ES^+$): m/z 979.40[$MH^+$], $t_R$=2.058 min.

Fraction 2 (Example 312): $^1H$ NMR (400 MHz, $CD_3OD$): 8.87 (s, 1H), 7.35-7.50 (m, 8H), 5.98 and 5.78 (2s, 1H), 4.55-4.65 (m, 1H), 4.30-4.53 (m, 7H), 3.86 (m, 1H), 3.50-3.80 (m, 2H), 3.32-3.46 (m, 1H), 3.20-3.30 (m, 1H), 2.70-3.00 (m, 4H), 2.67 (s, 3H), 2.58-2.64 (m, 2H), 2.45 (s, 3H), 2.42 (s, 3H), 2.31-2.40 (m, 1H), 2.12-2.28 (m, 2H), 1.98-2.10 (m, 1H), 1.67-1.80 (m, 1H), 1.66 (s, 3H), 1.00 (d, 3H), 0.86 (d, 3H); LC-MS ($ES^+$): m/z 979.40[$MH^+$], $t_R$=1.515 min.

Example 327: (2S,4R)-1-[(2S)-2-(2-{[2-(4-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetyl}piperazin-1-yl)pyridin-4-yl]oxy}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide
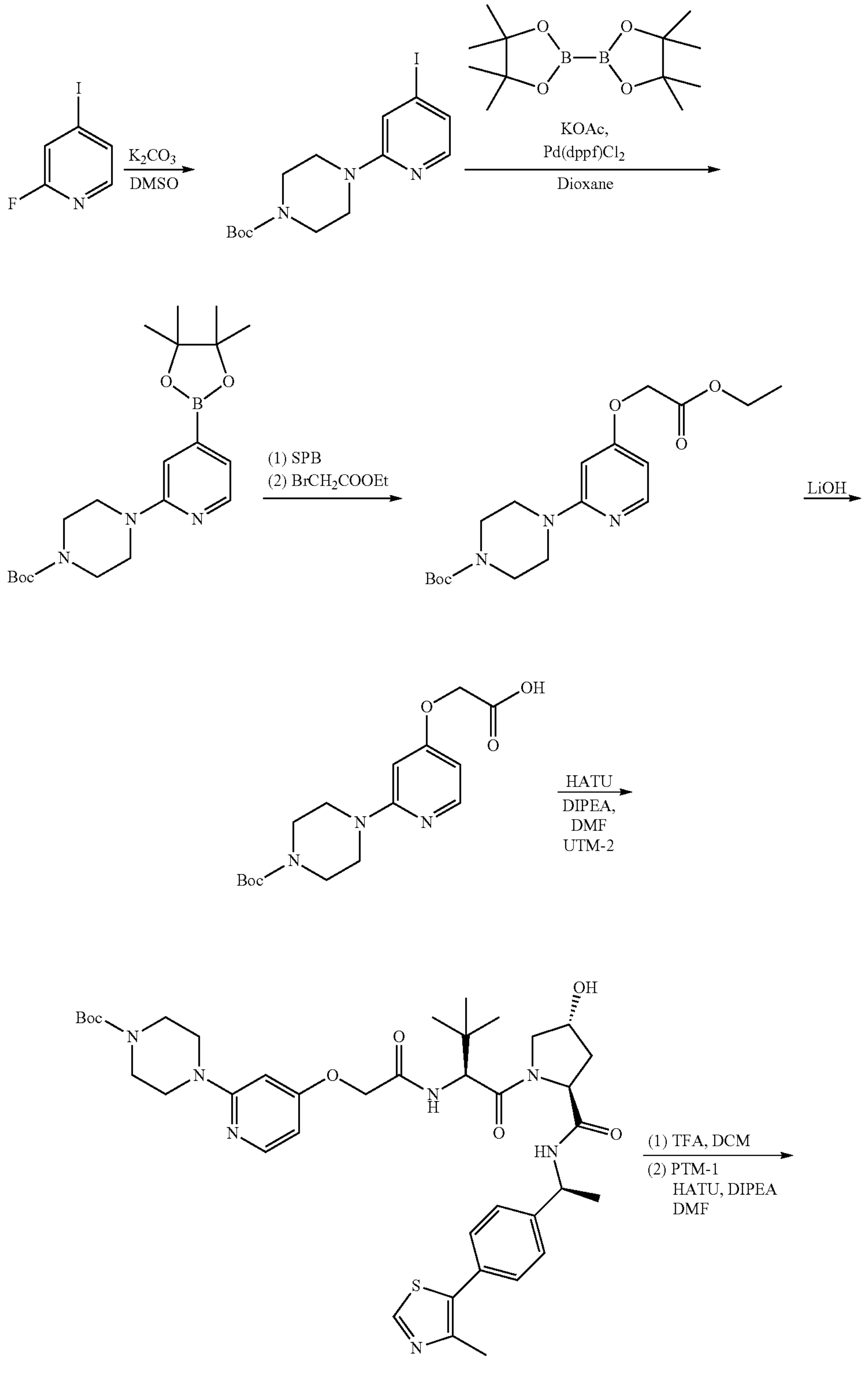

-continued

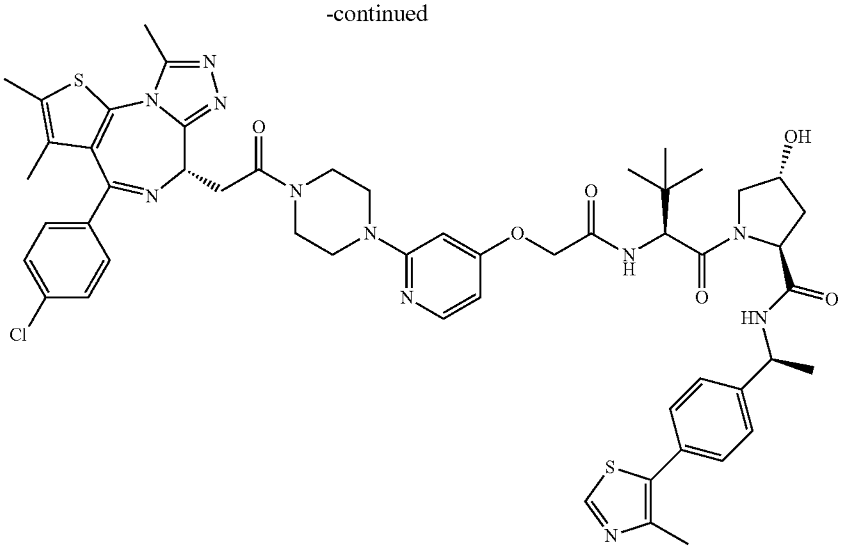

This compound was prepared using the synthetic route above. The title compound was isolated as a light yellow solid.

$^1$HNMR (400 MHz, $CD_3OD$): δ 1.03, 1.06 (two singles, 9H), 1.50-1.51 (m, 3H), 1.71 (s, 3H), 1.91-1.95 (m, 1H), 2.12-2.21 (m, 1H), 2.45-2.49 (m, 6H), 2.71, 2.72 (two singles, 3H), 3.57-3.94 (m, 12H), 4.44-4.46 (m, 1H), 4.57-4.61 (m, 1H), 4.69-4.79 (m, 4H), 5.00-5.04 (m, 1H), 6.40-6.51 (m, 2H), 7.33-7.48 (m, 8H), 8.00-8.02 (m, 1H), 8.30 (s, 1H), 8.68 (d, J=7.2 Hz, 1H), 8.86, 8.90 (two singles, 1H); LC/MS 1046.4 $[M+H]^+$. $t_R$=2.299

Example 342: (2S,4R)-1-[(2S)-3,3-dimethyl-2-({5-[(1,3-cis)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}cyclobutoxy]-1-benzofuran-2-yl}formamido)butanoyl]-4-hydroxy-N-[(1S)-1-{4-[4-(hydroxymethyl)-1,3-thiazol-5-yl]phenyl}ethyl]pyrrolidine-2-carboxamide

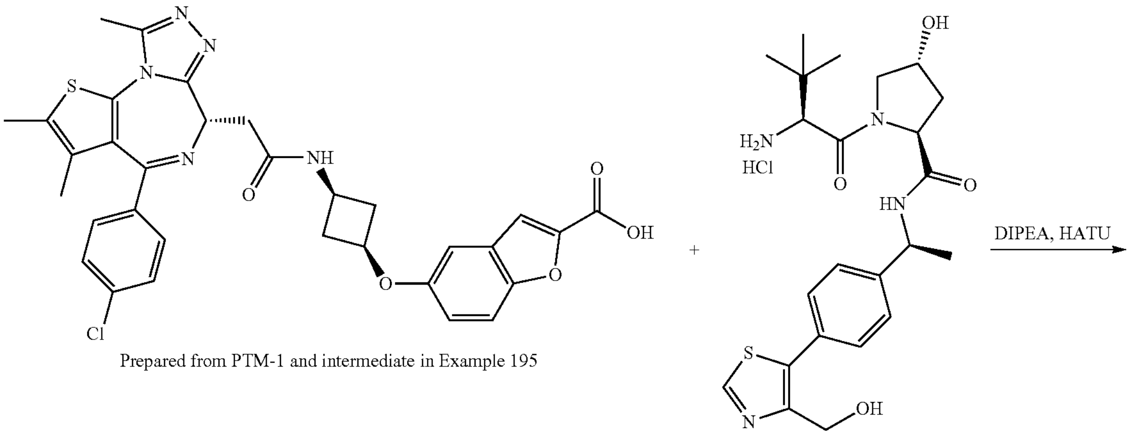

Prepared from PTM-1 and intermediate in Example 195

UTM-5-A

-continued

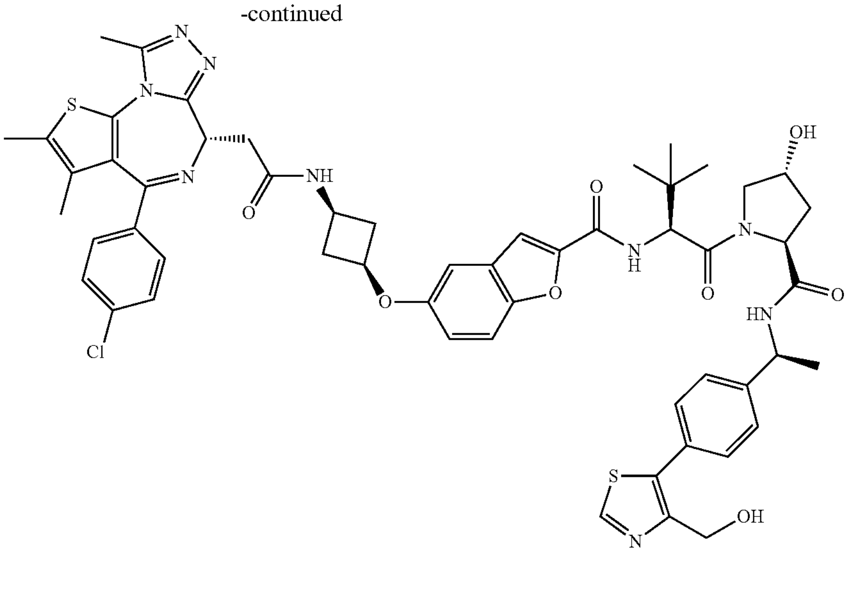

To a stirred solution of (2S,4R)-1-((S)-2-amino-3,3-dimethylbutanoyl)-4-hydroxy-N—((S)-1-(4-(4-(hydroxymethyl)thiazol-5-yl)phenyl)ethyl)pyrrolidine-2-carboxamide hydrochloride (UTM-5-A, 32 mg, 0.064 mmol), 5-((1,3-cis)-3-(2-((S)-4-(4-chlorophenyl)-2,3,9-trimethyl-611-thieno[3,2-f][1,2,4]triazolo[4,3-a][1,4]diazepin-6-yl)acetamido)cyclobutoxy)benzofuran-2-carboxylic acid (40 mg, 0.064 mmol, prepared from PTM-1 and the intermediate in Example 195), and DIPEA (0.04 ml, 0.256 mmol) in anhydrous DMF (2 mL) was added HATU (37 mg, 0.096 mmol) at 0° C., the resulting mixture was allowed to warm to room temperature and stirred at room temperature for 30 min. TLC showed the reaction was complete. The mixture was partitioned between ethyl acetate (5 mL) and water (5 mL). The organic layer was collected, washed with brine (5 mL), dried over anhydrous sodium sulfate, and concentrated under reduced pressure to give a crude residue which was purified by silica gel flash column chromatography (eluted with 10% methanol in dichloromethane) to afford the title compound (18.7 mg, 0.017 mmol, yield 27%) as a yellow solid.

$^1$HNMR (400 MHz, $CD_3OD$): δ 1.13 (s, 9H), 1.53 (d, J=7.2 Hz, 3H), 1.68 (s, 3H), 1.94-2.00 (m, 1H), 2.14-2.26 (m, 3H), 2.44 (s, 3H), 2.68 (s, 3H), 2.97-3.08 (m, 2H), 2.22-2.26 (m, 1H), 3.39-3.48 (m, 1H), 3.80 (dd, J=11.2 Hz, 1H), 3.93 (d, J=7.2 Hz, 1H), 4.17 (t, J=8.0 Hz, 1H), 4.47 (br, 1H), 4.52-4.65 (m, 4H), 4.90 (s, 2H), 5.01-5.06 (m, 1H), 7.05 (dd, J=2.4 Hz, 1H), 7.13 (d, J=2.0 Hz, 1H), 7.34-7.37 (m, 2H), 7.40-7.45 (m, 4H), 7.50-7.57 (m, 4H), 8.71 (d, J=7.2 Hz, 1H); LC/MS 1072.5 $[M+H]^+$; $t_R$=2.702 min.

Example 350: (2S,4R)-1-[(2S)-3,3-dimethyl-2-(2-{4-[(1,3-trans)-3-{2-[(7S)-9-(4-chlorophenyl)-3-methyl-5-oxa-4,8-diazatricyclo[8.4.0.0$^{2,6}$]tetradeca-1(10),2(6),3,8,11,13-hexaen-7-yl]acetamido}cyclobutoxy]piperidin-1-yl}acetamido)butanoyl]-4-hydroxy-N-[(1S)-1-[4-(4-methyl-1,3-thiazol-5-yl)phenyl]ethyl]pyrrolidine-2-carboxamide

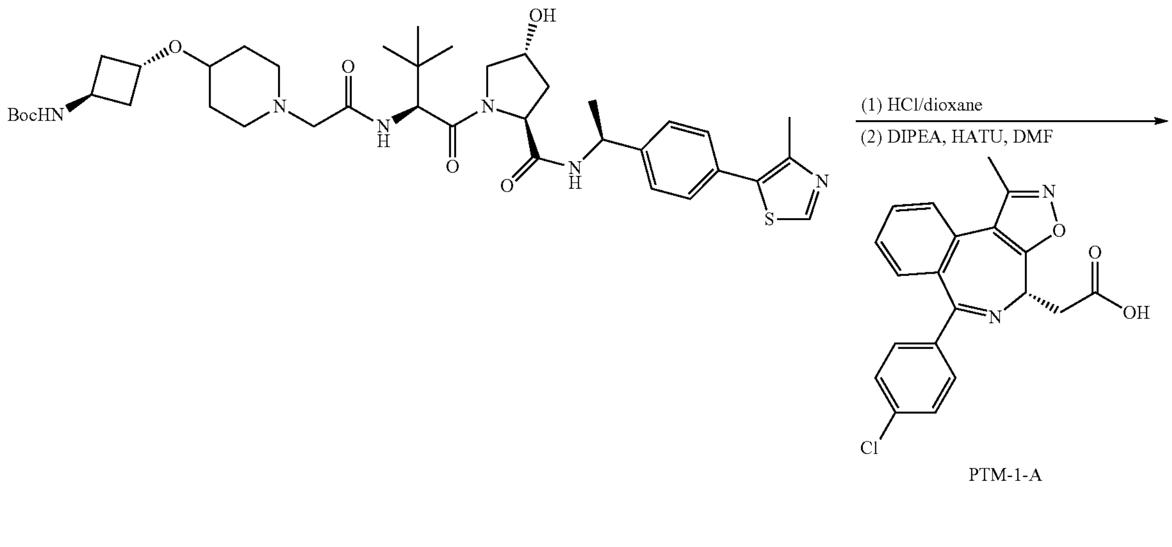

PTM-1-A

-continued

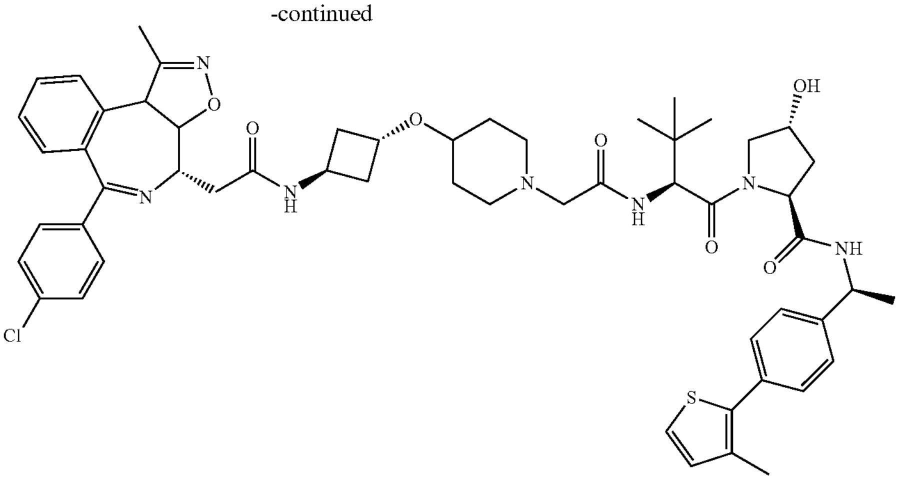

This compound was prepared using the same method as described in Example 306.

LC/MS 1026 [M+Na]$^+$ $^1$H-NMR (400 MHz, $CD_3OD$) δ 1.03 and 1.05 (2s, 9H), 1.52 and 1.57 (2d, 3H), 1.59-1.75 (m, 2H), 1.84-2.06 (m, 3H), 2.15-2.44 (m, 7H), 2.48 (s, 3H), 2.56 (s, 3H), 2.79 (br s, 2H), 3.04 (s, 2H), 3.14-3.26 (m, 1H), 3.36-3.47 (m, 1H), 3.49-3.62 (m, 1H), 3.75 (dd, J=3.7 and 11.1 Hz, 1H), 3.86 (d, J=11.1 Hz, 1H), 4.24-4.51 (m, 3H), 4.52-4.65 (m, 3H), 5.01 (q, J=6.9 Hz, 1H), 7.28-7.49 (m, 10H), 7.70 (dt, J=4.1 and 8.1 Hz, 1H), 7.80 (d, J=8.1 Hz, 1H), 8.87 (s, 1H).

Example 351: (2S,4R)-1-[(2S)-3,3-dimethyl-2-(2-{4-[(1,3-trans)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido)cyclobutoxy]piperidin-1-yl]acetamido)butanoyl]-4-hydroxy-N-[(1R)-2-hydroxy-1-[4-(4-methyl-1,3-thiazol-5-yl)phenyl]ethyl]pyrrolidine-2-carboxamide Example 352: (2S,4R)-1-[(2S)-3,3-dimethyl-2-(2-{4-[(1,3-trans)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}cyclobutoxy]piperidin-1-yl}acetamido)butanoyl]-4-hydroxy-N-[(1S)-2-hydroxy-1-[4-(4-methyl-1,3-thiazol-5-yl)phenyl]ethyl]pyrrolidine-2-carboxamide These two compounds were prepared using the same synthetic route and procedure as described in Example 306 except that UTM-5-A and UTM-5-B were used instead of UTM-2.

Example 351: $^1$H NMR (400 MHz, DMSO-$d_6$) δ 0.94 (9H, s), 1.43-1.50 (2H, m), 1.62 (3H, s), 1.75-1.81 (3H, m), 2.04-2.09 (1H, m), 2.13-2.30 (7H, m), 2.41 (3H, s), 2.46 (3H, s), 2.59 (3H, s), 2.66-2.72 (2H, m), 2.87-2.91 (1H, m), 3.01-3.05 (1H, m), 3.15-3.25 (2H, m), 3.56-3.64 (4H, m), 4.15-4.19 (1H, m), 4.24-4.28 (2H, m), 4.47-4.51 (3H, m), 4.79-4.87 (2H, m), 5.13 (1H, t, J=3.6 Hz), 7.38-7.51 (8H, m), 7.76 (1H, d, J=9.6 Hz), 8.44 (1H, d, J=8.0 Hz), 8.52 (1H, d, J=6.8 Hz), 8.99 (1H, s); LC/MS 1053.3 [M+H]$^+$.

Example 352: $^1$H NMR (400 MHz, DMSO-$d_6$) δ 0.87 (9H, s), 1.41-1.52 (2H, m), 1.62 (3H, s), 1.77-1.81 (2H, m), 1.92-1.98 (1H, m), 2.02-2.08 (1H, m), 2.12-2.30 (7H, m), 2.41 (3H, s), 2.45 (3H, s), 2.59 (3H, s), 2.66-2.72 (2H, m), 2.86-2.91 (1H, m), 2.99-3.04 (1H, m), 3.14-3.26 (2H, m), 3.56-3.68 (4H, m), 4.13-4.18 (1H, m), 4.23-4.27 (1H, m), 4.36 (1H, s), 4.44-4.50 (2H, m), 4.54 (1H, t, J=8.0 Hz), 4.77-4.82 (1H, m), 4.88 (1H, t, J=5.6 Hz), 5.14 (1H, d, J=3.2 Hz), 7.36-7.42 (4H, m), 7.48-7.55 (4H, m), 7.79 (1H, d, J=10.0 Hz), 8.41 (1H, d, J=8.0 Hz), 8.51 (1H, d, J=6.4 Hz), 8.97 (1H, s); LC/MS 1076.5 [M+Na]$^+$.

Example 353: (2S,4R)-1-[(2S)-2-{2-{4-(4-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}piperidin-1-yl)piperidin-1-yl]acetamido}-3,3-dimethylbutanoyl]-4-hydroxy-N-[(1S)-1-[4-(4-methyl-1,3-thiazol-5-yl)phenyl]ethyl]pyrrolidine-2-carboxamide

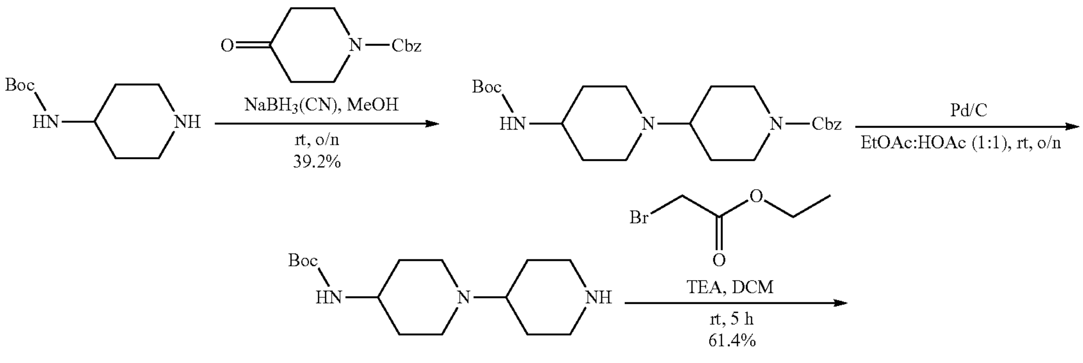

-continued

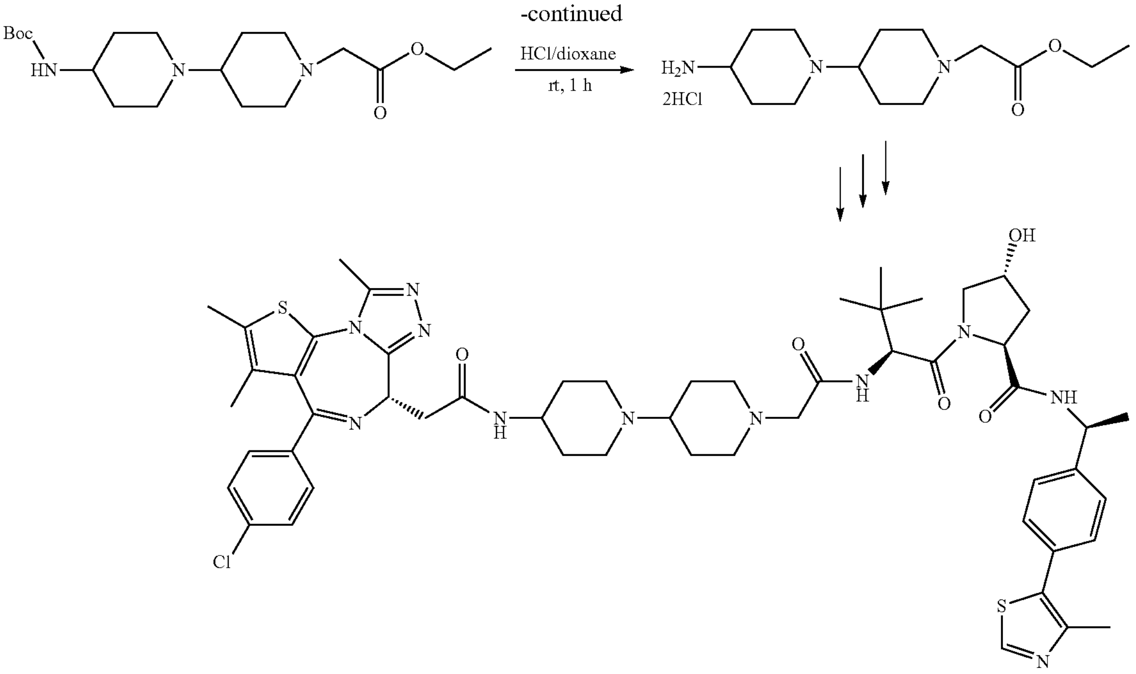

Compound in Example 353 was synthesized according to the scheme above. This compound was isolated as a white solid. $^1$H NMR (400 MHz, $CDCl_3$) δ 1.00 (9H, s), 1.17 (1H, s), 1.40-1.48 (4H, m), 1.60 (4H, s), 1.80-1.87 (3H, m), 1.92-2.02 (2H, m), 2.05-2.20 (5H, m), 2.34 (3H, s), 2.47 (3H, s), 2.52-2.57 (1H, m), 2.60 (3H, s), 2.80-2.98 (7H, m), 3.22-3.27 (1H, m), 3.42-3.52 (2H, m), 3.72-3.75 (1H, m), 4.15 (1H, d, J=11.6 Hz), 4.34 (1H, d, J=8.0 Hz), 4.44 (1H, brs), 4.53 (1H, t, J=6.8 Hz), 4.71 (1H, t, J=7.8 Hz), 5.01 (1H, t, J=7.2 Hz), 6.29 (1H, d, J=7.6 Hz), 7.25-7.29 (3H, m), 7.32-7.36 (6H, m), 7.44-7.46 (1H, m), 7.82 (1H, d, J=8.4 Hz), 8.61 (1H, s); LC/MS 525.8 $[(M+2H)/2]^+$ With the similar synthetic routes, the following compounds were prepared.

| | | |
|---|---|---|
| Example 354 | (2S,4R)-1-[(2S)-2-{2-[(3S)-4-(2-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetyl}-2-azaspiro[3.3]heptan-6-yl)-3-methyl-piperazin-1-yl]acetamido}-3,3-dimethylbutanoyl]-4-hydroxy-N-[(1S)-1-[4-(4-methyl-1,3-thiazol-5-yl)phenyl]ethyl]pyrrolidine-2-carboxamide | $^1$HNMR (400 MHz, $CD_3OD$): δ 1.01 (9H, s), 1.01 (3H, s), 1.41 (3H, d, J = 6.8 Hz), 1.59 (3H, d, J = 2.8 Hz), 1.98-2.30 (7H, m), 2.32 (3H, s), 2.37-2.47 (5H, m), 2.50-2.56 (3H, m), 2.59 (3H, d, J = 2.0 Hz), 2.62-2.65 (1H, m), 2.86-2.99 (4H, m), 3.17-3.35 (2H, m), 3.50 (1H, dd, J = 14.3 Hz, 3.2 Hz), 3.87 (1H, s), 3.97-4.03 (1H, m), 4.14-4.22 (1.5H, s), 4.30-4.38 (2H, m), 4.44 (1H, brs), 4.53-4.55 (0.5H, m), 4.61-4.65 (1H, m), 4.70 (1H, t, J = 7.8 Hz), 4.97-5.05 (1H, m), 7.24-7.27 (2H, m), 7.29-7.35 (6H, m), 7.41 (1H, d, J = 7.6 Hz), 7.75 (1H, d, J = 8.4 Hz), 8.61 (1H, s). |
| Example 357 | (2S,4R)-1-[(2S)-2-{2-[(2S,5R)-4-(2-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetyl}-2-azaspiro[3.3]heptan-6-yl)-2,5-dimethylpiperazin-1-yl]acetamido}-3,3-dimethylbutanoyl}-4-hydroxy-N-[(1S)-1-[4-(4-methyl-1,3-thiazol-5-yl)phenyl]ethyl]pyrrolidine-2-carboxamide | $^1$HNMR (400 MHz, $CD_3OD$): δ 0.94-0.99 (15H, m), 1.41 (3H, d, J = 7.2 Hz), 1.58-1.59 (3H, m), 1.70-1.74 (1H, m), 1.96-2.30 (6H, m), 2.32 (3H, s), 2.35-2.44 (2H, m), 2.47 (3H, s), 2.49-2.57 (2H, m), 2.59 (3H, d, J = 2.0 Hz), 2.65-2.89 (4H, m), 3.16-3.35 (3H, m), 3.49-3.52 (1H, m), 3.87 (1H, s), 4.00 (1H, s), 4.13-4.55 (5H, m), 4.61-4.65 (1H, s), 4.70 (1H, t, J = 7.6 Hz), 4.97-5.04 (1H, m), 7.24-7.41 (9H, m), 7.89 (1H, d, J = 8.4 Hz), 8.61 (1H, s). |
| Example 358 | (2S,4R)-1-[(2S)-2-{2-[(2S,4-(2-{2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]acetyl}-2-azaspiro[3.3]heptan-6-yl)-2-methyl piperazin-1-yl]acetamido}-3,3-dimethylbutanoyl]-4-hydroxy-N-[(1S)-1-[4-(4-methyl-1,3-thiazol-5-yl)phenyl]ethyl]pyrrolidine-2-carboxamide | $^1$HNMR (400 MHz, $CD_3OD$): δ 0.94-0.99 (15H, m), 1.41 (3H, d, J = 7.2 Hz), 1.58-1.59 (3H, m), 1.70-1.74 (1H, m), 1.96-2.30 (6H, m), 2.32 (3H, s), 2.35-2.44 (2H, m), 2.47 (3H, s), 2.49-2.57 (2H, m), 2.59 (3H, d, J = 2.0 Hz), 2.65-2.89 (4H, m), 3.16-3.35 (3H, m), 3.49-3.52 (1H, m), 3.87 (1H, s), 4.00 (1H, s), 4.13-4.55 (5H, m), 4.61-4.65 (1H, s), 4.70 (1H, t, J = 7.6 Hz), 4.97-5.04 (1H, m), 7.24-7.41 (9H, m), 7.89 (1H, d, J = 8.4 Hz), 8.61 (1H, s). |

Example 364: (2S,4R)-1-[(2S)-3,3-bis($^2H_3$)methyl-2-({5-[(1,3-cis)-3-{2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamido}cyclobutoxy]-1-benzofuran-2-yl}formamido)(4,4,4-$^2H_3$)butanoyl]-4-hydroxy-N-[(1S)-1-[4-(4-methyl-1,3-thiazol-5-yl)phenyl]ethyl]pyrrolidine-2-carboxamide This compound was prepared using the same synthetic method as described in Example 229. Instead of using chiral tert-butylglycine to prepare the right hand UTM, racemic D9-substituted tert-butylglycine was used.

$^1H$ NMR (400 MHz, $CD_3OD$) δ 1.53 and 1.63 (2d, J=8.0 Hz, 3H), 1.69 (s, 3H), 1.97 (dt, J=4.6, 8.9 Hz, 1H), 2.14-2.25 (m, 3H), 2.45 (s, 3H), 2.48 (s, 3H), 2.70 (s, 3H), 2.96-3.07 (m, 2H), 3.25-3.29 (m, 1H), 3.42 (dd, J=9.0, 15.1 Hz, 1H), 3.80 (dd, J=3.8, 11.0 Hz, 1H), 3.92 (d, J=11.0 Hz, 1H), 4.13-4.20 (m, 1H), 4.47-4.65 (m, 5H), 5.00-5.06 (m, 1H), 7.06 (dd, J=2.5, 9.0 Hz, 1H), 7.14 (d, J=2.5 Hz, 1H), 7.30-7.58 (m, 10H), 8.88 and 8.86 (2s, 1H); LC/MS 1065.4 $[M+H]^+$.

Example 365: (2S,4R)-1-[(2S)-3,3-dimethyl-2-(2-{4-[(1,3-trans)-3-[3-(dimethyl-1,2-oxazol-4-yl)-5-[(S)-oxan-4-yl(phenyl)methyl]-5H-pyrido[3,2-b]indole-7-amido]cyclobutoxy]piperidin-1-yl}acetamido)butanoyl]-4-hydroxy-N-[(1S)-1-[4-(4-methyl-1,3-thiazol-5-yl)phenyl]ethyl]pyrrolidine-2-carboxamide Example 366: (2S,4R)-1-[(2S)-3,3-dimethyl-2-(2-{4-[(1,3-trans)-3-{3-(dimethyl-1,2-oxazol-4-yl)-5-[(R)-oxan-4-yl(phenyl)methyl]-5H-pyrido[3,2-b]indole-7-amido]cyclobutoxy]piperidin-1-yl}acetamido)butanoyl]-4-hydroxy-N-[(1S)-1-[4-(4-methyl-1,3-thiazol-5-yl)phenyl]ethyl]pyrrolidine-2-carboxamide

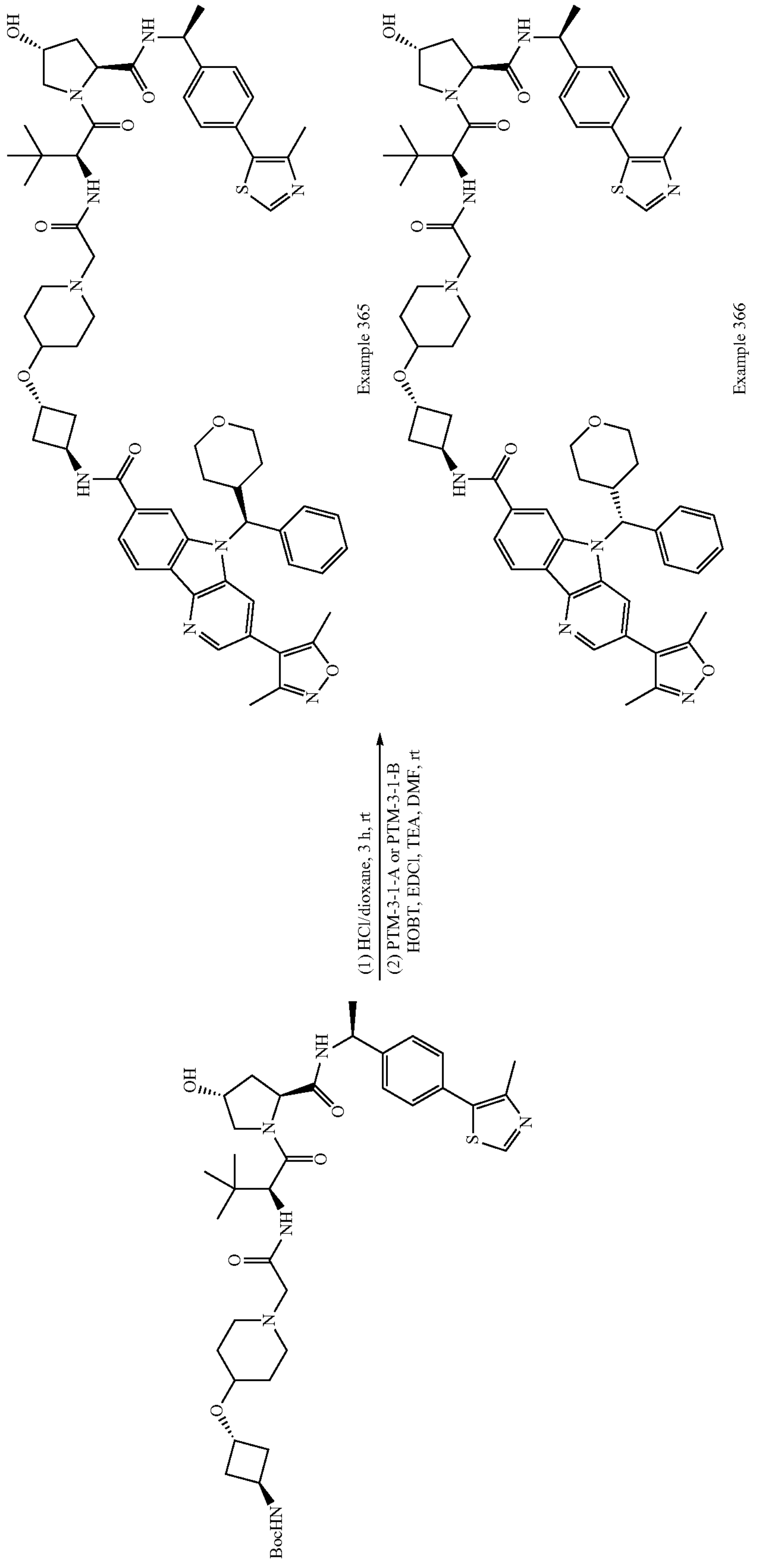
Example 365
Example 366

Compounds in Example 365 and Example 366 were prepared with the similar synthetic procedures as described in Example 257 using the intermediates PTM-3-1-A and PTM-3-1-B.

Example 365 $^{1}H$ NMR (400 MHz, $CDCl_3$) δ 1.08 (9H, s), 1.27-1.43 (3H, m), 1.48 (3H, d, J=6.8 Hz), 1.52-1.60 (2H, m), 1.69-1.77 (2H, m), 1.92-2.08 (4H, m), 2.23 (3H, s), 2.25-2.32 (2H, m), 2.39 (3H, s), 2.40-2.42 (1H, m), 2.54 (3H, s), 2.56-2.60 (2H, m), 2.81-2.83 (2H, m), 2.95-3.13 (3H, m), 3.31-3.36 (2H, m), 3.50-3.59 (2H, m), 3.81-3.84 (1H, m), 4.03-4.05 (1H, m), 4.20-4.23 (1H, m), 4.36-4.43 (2H, m), 4.51 (1H, s), 4.64-4.67 (1H, m), 4.78 (1H, t, J=8.0 Hz), 5.06-5.10 (1H, m), 5.59 (1H, d, J=10.4 Hz), 6.50-6.52 (1H, m), 7.28-7.61 (13H, m), 7.96 (1H, d, J=8.0 Hz), 8.37-8.45 (3H, m), 8.67 (111, s); LC/MS 1119 $[M+H]^+$ $^{1}H$ NMR (400 MHz, $CDCl_3$) δ 1.08 (9H, s), 1.30-1.52 (8H, m), 1.57-1.69 (2H, m), 1.91-2.02 (4H, m), 2.23 (3H, s), 2.29-2.33 (2H, m), 2.36 (3H, s), 2.39-2.42 (1H, m), 2.54 (3H, s), 2.55-2.60 (2H, m), 2.81-2.84 (2H, m), 2.96-3.14 (3H, m), 3.31-3.37 (2H, m), 3.50-3.59 (2H, m), 3.81-3.85 (1H, m), 4.03-4.06 (1H, m), 4.22-4.25 (1H, mz), 4.36-4.42 (2H, m), 4.51 (1H, s), 4.65-4.67 (1H, m), 4.77-4.81 (1H, m), 5.06-5.10 (1H, m), 5.59 (1H, d, J=10.4 Hz), 6.47 (1H, d, J=6.4 Hz), 7.28-7.60 (13H, m), 8.04-8.06 (1H, m), 8.36-8.45 (3H, m), 8.67 (1H, s); LC/MS 1119 $[M+H]^+$ Example 367: (2S,4R)-1-[(2S)-2-(2-{4-[(1R,4R)-5-{2-[(9S)-7-(4-chlorophenyl)-4,5,13 trimethyl-3-thia-1,8,11,12-tetraazatricyclo[8.3.0.0$^{2}$,$^{6}$]trideca-2(6),4,7,10,12-pentaen-9-yl]acetyl}-2,5-diazabicyclo[2.2.1]heptan-2-yl]piperidin-1-yl}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide Example 368 (2S,4R)-1-[(2S)-2-(2-{4-[(1S,4S)-5-{2-[(9S)-7-(4-chlorophenyl)-4,5,13-trimethyl-3-thia-1,8,11,12-tetraazatricyclo[8.3.0.0$^{2}$,$^{6}$]trideca-2(6),4,7,10,12-pentaen-9-yl]acetyl}-2,5-diazabicyclo[2.2.1]heptan-2-yl]piperidin-1-yl]acetamido)-3,3-dimethylbutanoyl]-4-hydroxy-N-[(1S)-1-[4-(4-methyl-1,3-thiazol-5-yl)phenyl]ethyl]pyrrolidine-2-carboxamide

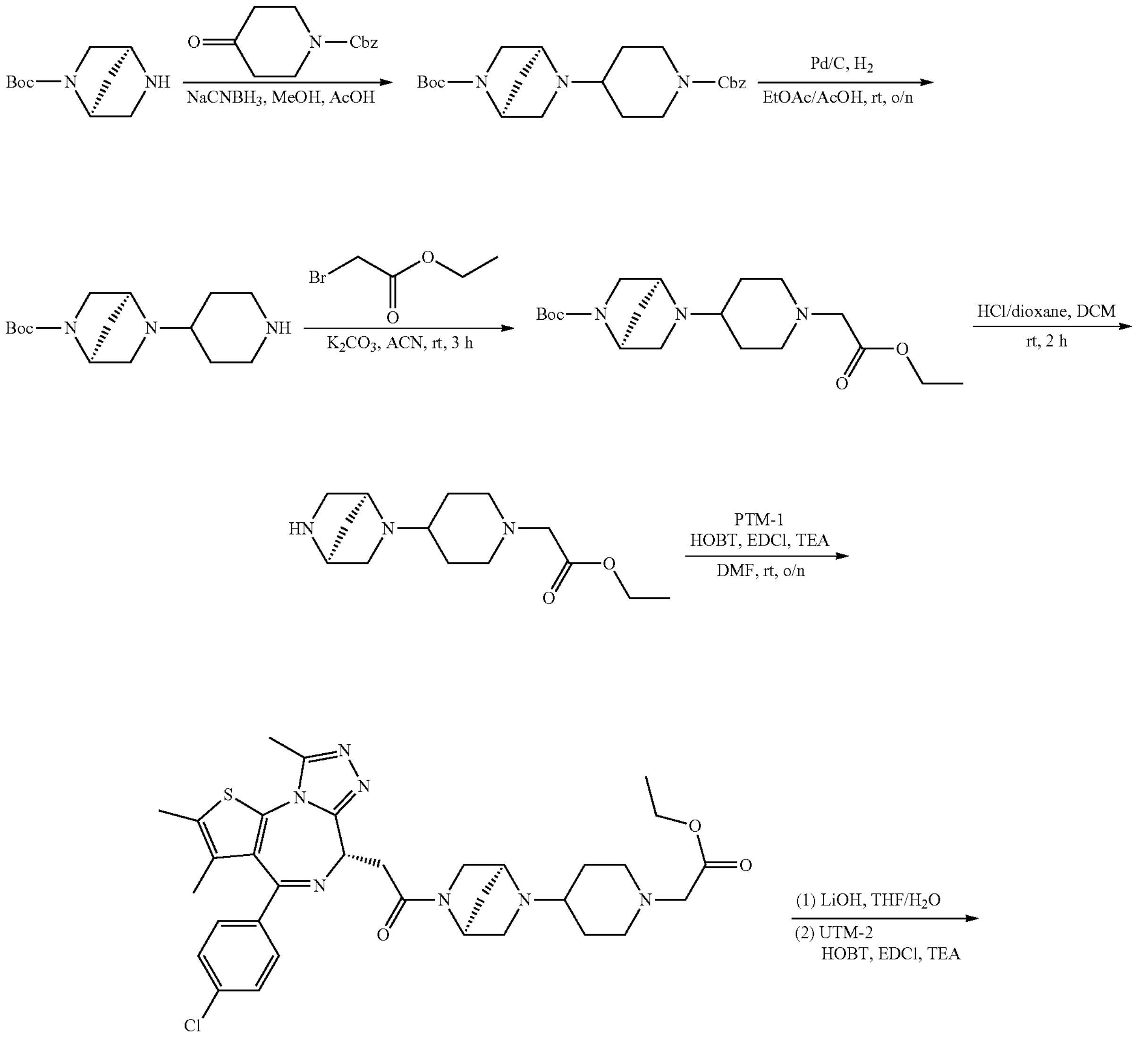

-continued

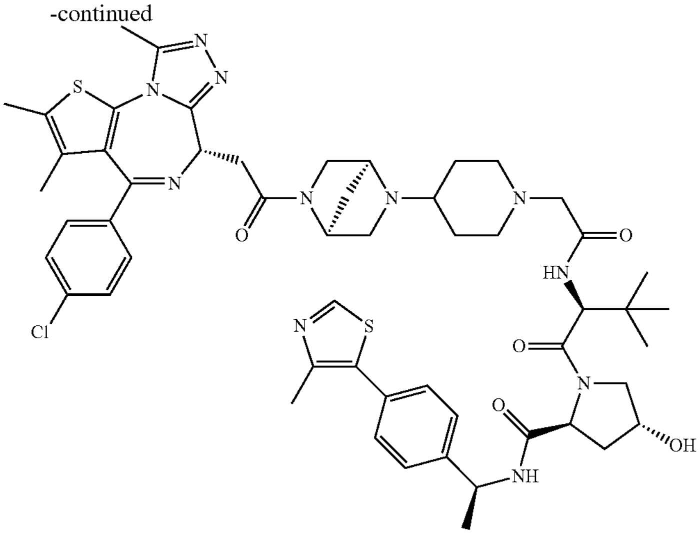

Compounds in Example 367 and Example 368 were prepared using the synthetic route described above.

Example 367: $^1$H NMR (400 MHz, $CDCl_3$) δ 1.07 (9H, d, J=3.2 Hz), 1.48 (4H, d, J=6.8 Hz), 1.67 (4H, d, J=4.4 Hz), 1.85-1.94 (3H, m), 2.04-2.09 (2H, m), 2.19-2.26 (2H, m), 2.40 (3H, s), 2.53 (3H, s), 2.59-2.64 (2H, m), 2.66 (3H, s), 2.76-3.07 (6H, m), 3.29-3.39 (1H, m), 3.55-3.61 (3H, m), 3.82-3.88 (2H, m), 4.20-4.24 (1H, m), 4.39-4.42 (1H, m), 4.51 (1H, brs), 4.77-4.81 (3H, m), 5.06-5.10 (1H, m), 7.31-7.35 (2H, m), 7.37-7.43 (7H, m), 7.52-7.57 (1H, m), 7.90-7.93 (1H, m), 8.67-8.68 (1H, m); LC/MS 1049 $[M+H]^+$ Example 368: $^1$H NMR (400 MHz, $CDCl_3$) δ 1.06-1.07 (10H, m), 1.48 (3H, d, J=6.8 Hz), 1.67 (3H, s), 1.85-2.09 (6H, m), 2.21-2.33 (2H, m), 2.40 (3H, s), 2.42-2.52 (2H, m), 2.54 (3H, s), 2.58-2.63 (2H, m), 2.66 (3H, d, J=5.2 Hz), 2.83-2.90 (2H, m), 3.00-3.15 (3H, m), 3.25-3.30 (1H, m), 3.36-3.47 (1H, m), 3.52-3.59 (2H, m), 3.69-3.88 (2H, m), 4.16-4.24 (1H, m), 4.41-4.43 (1H, m), 4.50 (1H, s), 4.75-4.85 (3H, m), 5.07-5.10 (1H, m), 7.31-7.34 (2H, m), 7.37-7.43 (6H, m), 7.52-7.58 (1H, m), 7.92-7.98 (1H, m), 8.68 (1H, s); LC/MS 1049 $[M+H]^+$ Human c-myc ELISA Assay 22RV-1 cells are seeded at 30,000 cells/well at a volume of 75 μL/well in RPMI+10% FBS media in 96-well plates and grown overnight at 37 C. Cells are dosed with compounds at 4× concentration diluted in 0.4% DMSO; compounds are serially diluted 1:3 for 8-point dose curve. 25 ul of compounds is added to cells for a final concentration starting at 300 nM-0.3 nM or 1 uM-1 nM in 0.1% DMSO and incubated for 18 hrs. Media is aspirated, cells washed 1× with PBS and aspirated. Cells are lysed in 50 ul RIPA buffer (50 mM Tris pH8, 150 mM NaCl, 1% Tx-100, 0.1% SDS, 0.5% sodium deoxycholate) supplemented with protease and phosphatase inhibitors. Plates are incubated on ice for 15 minutes then centrifuged at 4 C for 10 min at 4000 rpm. Add 50 ul of cleared lysate from 96-well assay plate into 96-well c-myc ELISA plate (Novex, Life Technologies Catalog # KH02041). Reconstitute c-myc standard with standard diluent buffer; standard curve range is 333 pg/ml-0 pg/ml, diluted 1:2 for 8-point dose curve. The rest of the assay was performed following the protocol from the c-myc ELISA kit. Data is analyzed and plotted using GraphPad Prism software. Compounds described in this application were assayed and c-myc suppression potency is listed in the following Table (A: $DC_{50}$<10 nM; B: $DC_{50}$ 10-100 nM; C: $DC_{50}$: 100-1000 nM; D: $DC_{50}$>1000 nM)

Immunoblotting

22Rv1 and VCaP cell lines were purchased from ATCC. LnCap95 cells were a generous gift from Dr. Alan Meeker at The Johns Hopkins University School of Medicine. BRD2 (#5848), BRD4 (#13440), PARP (#9532), c-Myc (#5605) antibodies were purchased from cell signaling. BRD3 (sc-81202) antibody was purchased from Santa Cruz Biotech. Antibodies used for immunohistochemistry were c-MYC (abcam # ab32072) and BRD4 (Bethyl Laboratories # a301-985a50). Actin and Tubulin antibodies were purchased from Sigma.

Cells were lysed in RIPA buffer (Thermo Fisher Cat #89900) supplemented with protease inhibitors (Pierce™ Protease Inhibitor Tablets, EDTA-free Cat #88266). Lysates were centrifuged at 16,000×g and supernatants were used for SDS-PAGE. Western blotting was carried out following standard protocols.

Cell Proliferation Assay

22RV-1 cells are seeded at 5,000 cells/well at a volume of 75 μL/well in RPMI+10% FBS media in 96-well plates and grown overnight at 37 C. Cells are dosed with compounds at 4× concentration diluted in 0.4% DMSO; compounds are serially diluted 1:3 for 10-point dose curve. 25 ul of compounds is added to cells for a final concentration starting at 300 nM-0.3 nM in 0.1% DMSO and incubated for 72 hrs. In a separate plate, 100 ul of 5,000 cells/well are plated in 8 wells, 100 ul of CellTiter-Glo (CellTiter-Glo® Luminescent Cell Viability Assay, Promega # G7573) is added and incubated for 30 minutes, then read on luminometer to assess initial signal for cell growth. After 72 hrs, 100 ul of CellTiter-Glo is added and incubated for 30 minutes, then read on luminometer. Data is analyzed and plotted using GraphPad Prism software.

Apoptosis Assay

22RV-1 cells are seeded at 5,000cells/well at a volume of 75 μL/well in RPMI+10% FBS media in 96-well plates and grown overnight at 37 C. Cells are dosed with compounds at 4× concentration diluted in 0.4% DMSO; compounds are serially diluted 1:3 for 8-point dose curve. 25 ul of compounds is added to cells for a final concentration starting at 300 nM-0.3 nM in 0.1% DMSO and incubated for 48 hrs. After 48 hrs, 100 ul of Caspase-Glo® 3/7 (Promega Caspase-Glo® 3/7 Assay # G8093 is added and incubated for 30 minutes, then read on luminometer. Data is analyzed and plotted using GraphPad Prism software.

Treatment of Ovarian Cancer with BRD4 PROTACs

BRD4 is a member of the bromodomain and extraterminal domain (BET) family of proteins, and has emerged as an attractive oncology target. BET inhibitors have shown promising results in a number of preclinical settings, including ovarian cancer (OvCa). Treatment with BRD4 PROTAC leads to the rapid and efficient degradation of BRD4 across OvCa cell lines. Furthermore, the BRD4 PROTAC has a more potent anti-proliferative activity (CellTiter-Glo® Assay (Promega)) than BET inhibitor OTX015 on OvCa cell lines, and results in pronounced apoptosis in sensitive OvCa cell lines.

A genetic signature that correlate with sensitivity to BRD4 PROTACs has been identified by performing RNA-sequencing on five OvCa cell lines. Genes with known roles in OvCa tumorigenesis and progression are differentially expressed in highly PROTAC sensitive, as compared to less sensitive OvCa cell lines. In particular, BCLxL was determined to be a clinical biomarker as BRD4 PROTAC sensitive OvCa, which was also recently shown to predict BET inhibitor sensitivity.

As such, the PROTACs are a potent BRD4 degrader in ovarian cancer cell lines and in tumor xenografts. BRD4 PROTACs are efficacious degraders in vitro and in vivo, and resulted in stasis in an A2780 tumor model following intermittent IV dosing (FIG. 8). Ovarian cancer lines show differential sensitivity to PROTAC mediated BRD4 degradation, which the present application has found to be linked with a number of genes known to be associated with chemo-resistance and disease outcome in ovarian cancer to be differentially regulated in highly PROTAC sensitive cell lines. In particular, BCLxL may be used as a clinical biomarker, with low levels being predictive of tumor sensitivity to BRD4 degradation in ovarian cancer Treatment of Breast Cancer with BRD4 PROTACs Breast cancer cells were treated with BRD4 PROTACs using the same experimental procedure as described in cell proliferation assay. Representative results were listed in FIG. 9.

Animal Studies

Mice were housed in pathogen-free animal facilities at New England Life Sciences (NELS, New Haven, Conn.). All experiments were conducted under an IACUC protocol that was approved by the NELS IACUC committee. Male Nu/Nu mice and CB17 SCID mice were obtained at 4-5 weeks age from Charles River Laboratories and implanted subcutaneously with $5\times10^6$ 22Rv1 cells or $5\times10^6$ VCaP cells in Matrigel (Corning Life Sciences). After 10-14 days, mice bearing >200 $mm^3$ tumors were randomized into indicated number of groups with ten mice in each group while ensuring identical (±5 $mm^3$) mean tumor volume in each group. Dosing was carried out through the indicated route and with the indicated schedule for each drug for up to three weeks, depending on the experiment. Mice were sacrificed eight hours after the final dose. Blood was collected, processed to plasma, and flash frozen for PK analysis. Tissues were harvested and flash frozen for further analysis. All PK analysis was carried out at Drumetix Laboratories (Greensboro, N.C.). 2 out of 10 animals in each study arm were randomly excluded in pharmacodynamic analysis, for greater technical ease of running a 20-well protein gel. For PSA ELISA, only samples with at least 25 uL plasma remaining after PK analysis were utilized using the Cell Signaling PathScan Total PSA/KLK3 Sandwich ELISA Kit #14119 following the manufacturer's protocol.

In Vivo SU-DHL-6 Xenografts Efficacy

The 4-5 weeks old male CB17 SCID mice were implanted subcutaneously with 5 million SU-DH-L6 GCB-DLBCL cells (in 200 ul volume of 3:1 matrigel: PBS). After 14 days, mice bearing 180-200 $mm^3$ tumors were randomized into three groups with ten mice in each group while ensuring identical (±5 $mm^3$) mean tumor volume in each group. Mice were either dosed via (i) intravenous (iv) administration every third day (Q3D) for a total of 10 days with example 195 (FIG. 10); (ii) oral gavage (po) administration daily (QD) for a total of 10 days with OTX015; or (iii) intravenous administration every third day (Q3D) for a total of 10 days with vehicle (previous studies have shown that SU-DHL-6 xenografts demonstrated similar growth kinetics in mice treated with vehicle administered either daily via oral gavage or every third day via intravenous injections, the tumor growth inhibition studies were conducted using only Q3D, iv administration of vehicle). Tumor volume was monitored twice per week using calipers and body weights were determined daily during the course of the study.

In Vivo 22Rv1 Xenografts Efficacy

The in vivo 22Rv1 xenograft efficacy study procedure was followed as described in the literature (Proc. Natl. Acad. Sci. 2016, 113, 7124-7129)

BRD4 Degradation Data for Exemplary Compounds of the Invention

| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 1 | 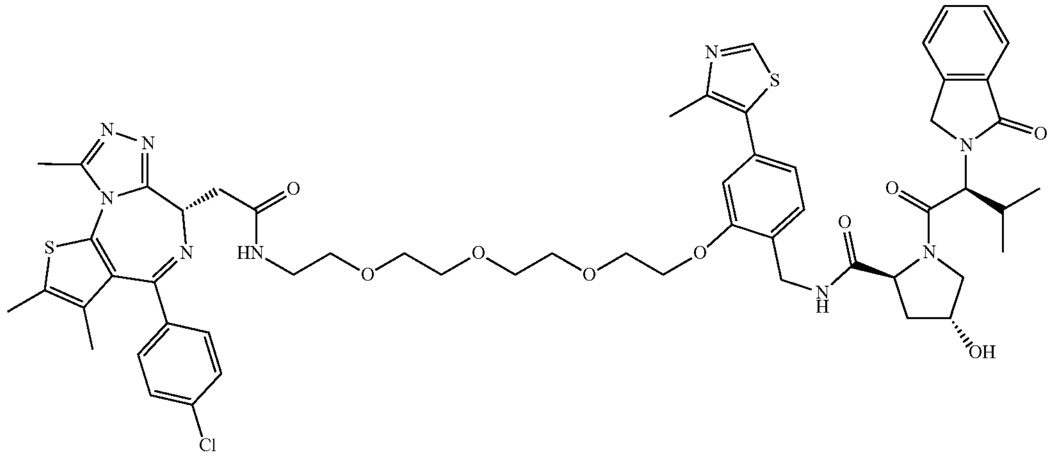 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCNC(=O)C[C@@H]2N=C(c3ccc(Cl)cc3)c3c(sc(C)c3C)-n3c(C)nnc32)c1] | 1106.7 | 1106.3 | C | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 2 | 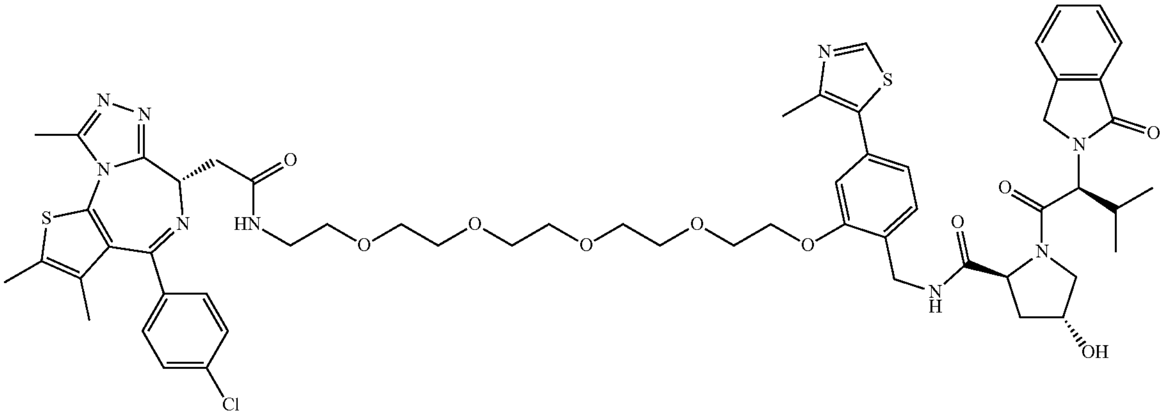 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCOCCNC(=O)C[C@@H]2N=C(c3ccc(Cl)cc3)c3c(sc(C)c3C)-n3c(C)nnc32)c1] | 1150.8 | 1150.6 | D | 41.0 |
| 3 | 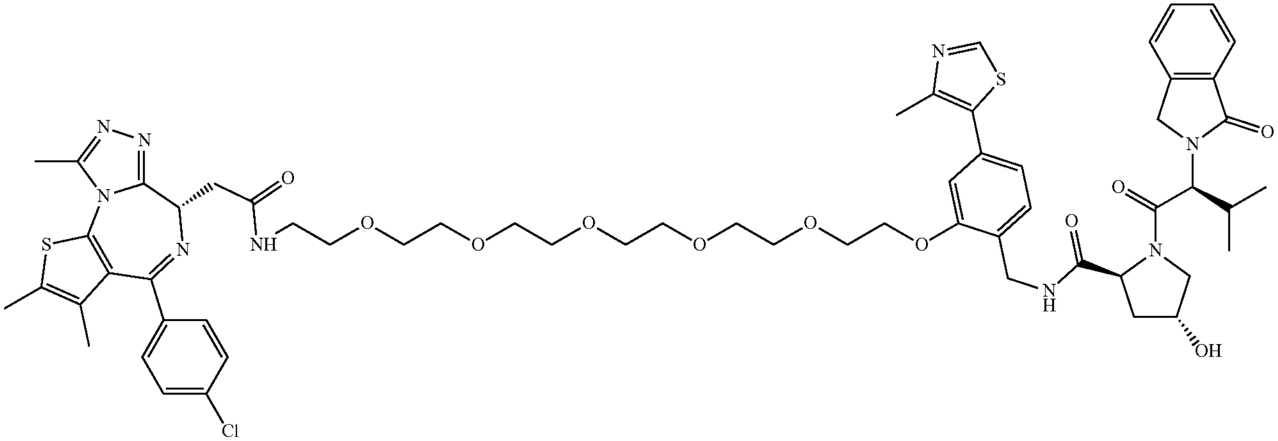 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCOCCOCCNC(=O)C[C@@H]2N=C(c3ccc(Cl)cc3)c3c(sc(C)c3C)-n3c(C)nnc32)c1] | 1194.9 | 1194.2 | C | 100 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 4 | 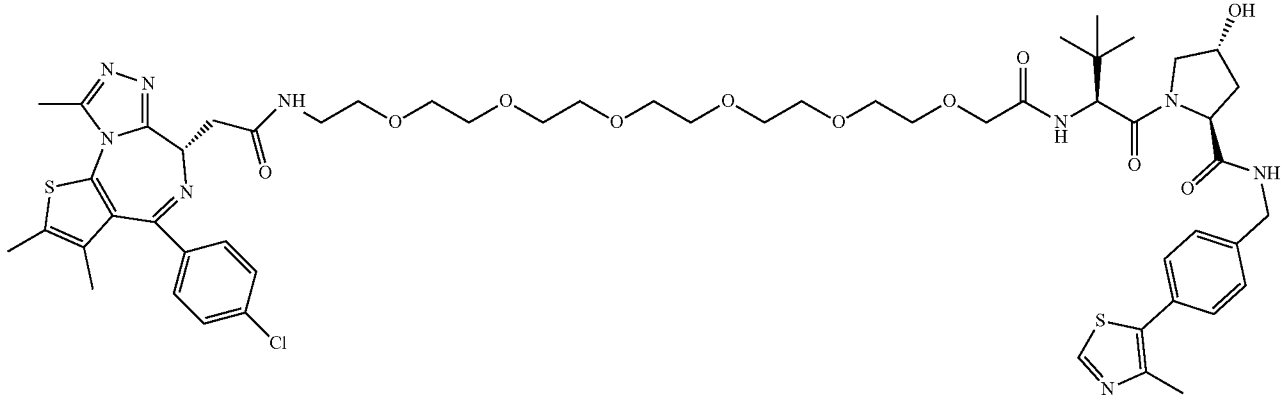 [SMILES: Cc1ncsc1-c1ccc(CNC(=O)[C@@H]2C[C@@H](O)CN2C(=O)[C@@H](NC(=O)COCCOCCOCCOCCOCCOCCNC(=O)C[C@@H]2N=C(c3ccc(Cl)cc3)c3c(sc(C)c3C)-n3c(C)nnc32)C(C)(C)C)cc1] | 1134.8 | 1134.8 | C | 62.2 |
| 5 | 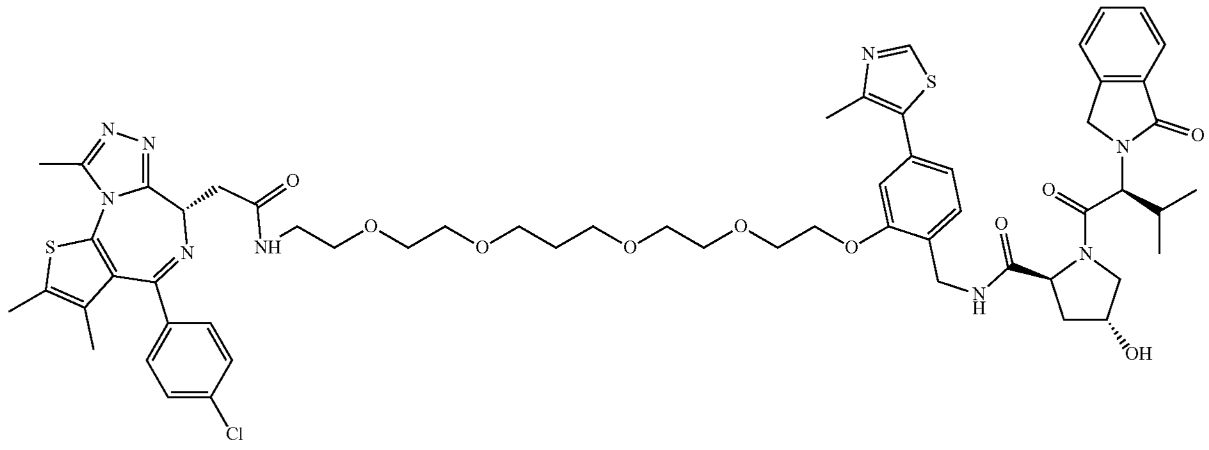 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCCOCCOCCNC(=O)C[C@@H]2N=C(c3ccc(Cl)cc3)c3c(sc(C)c3C)-n3c(C)nnc32)c1] | 1164.8 | 1164.6 | D | 25.0 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 6 | 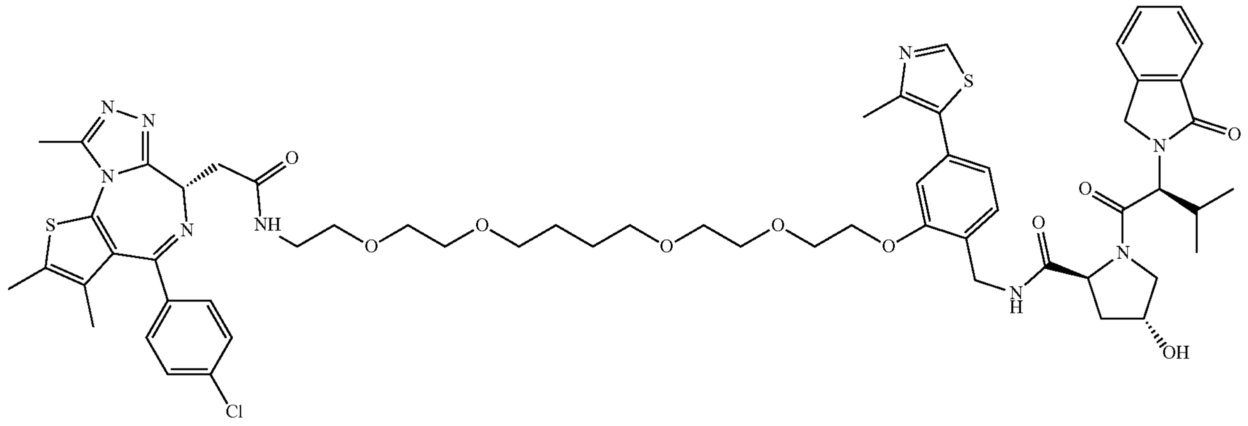 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCCCOCCOCCNC(=O)C[C@@H]2N=C(c3ccc(Cl)cc3)c3c(sc(C)c3C)-n3c(C)nnc32)c1] | 1178.9 | 1178.4 | C | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 7 | 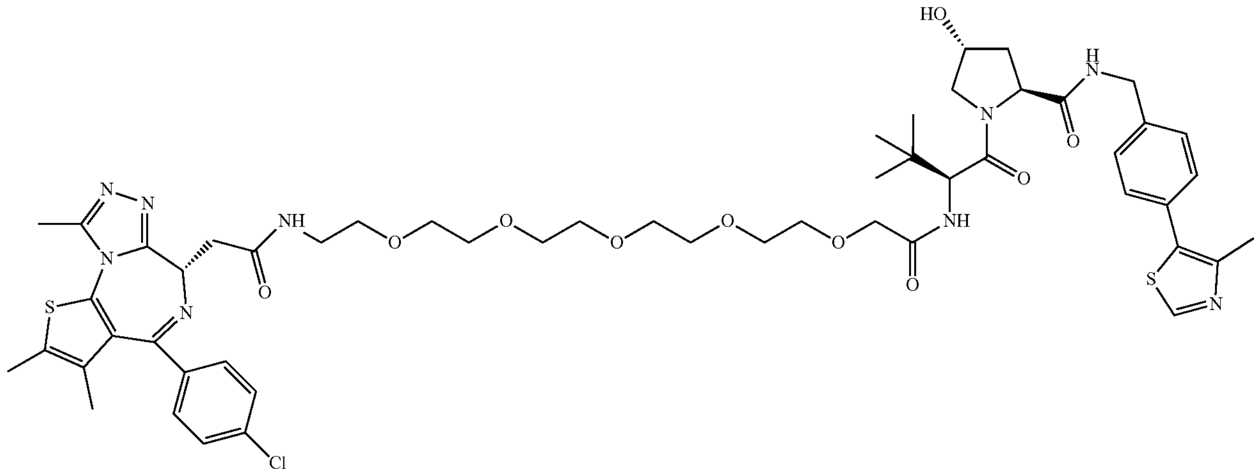 | 1090.7 | 1090.4 | C | 93.0 |
| 8 | 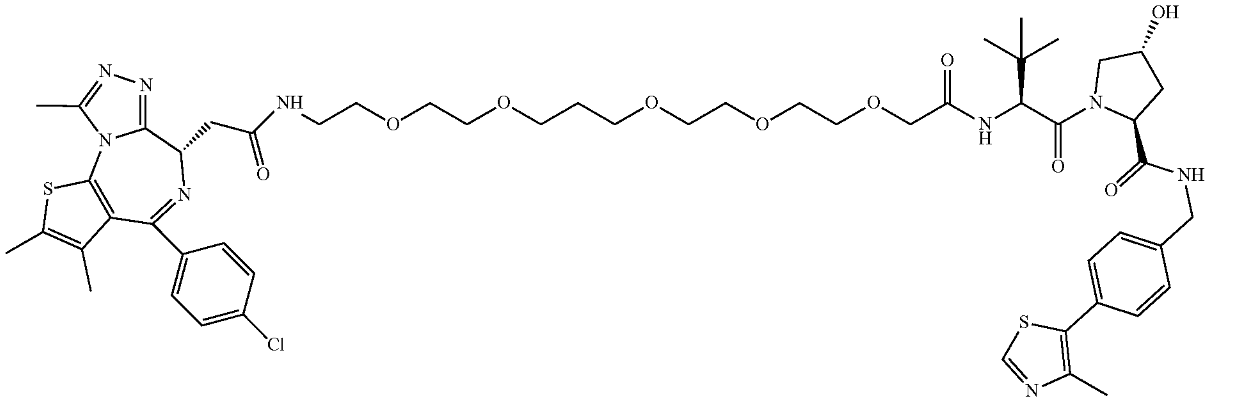 [SMILES: Cc1ncsc1-c1ccc(CNC(=O)[C@@H]2C[C@@H](O)CN2C(=O)[C@@H](NC(=O)COCCOCCOCCCOCCOCCNC(=O)C[C@@H]2N=C(c3ccc(Cl)cc3)c3c(sc(C)c3C)-n3c(C)nnc32)C(C)(C)C)cc1] | 1104.8 | 1104.7 | C | 95.9 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 9 | 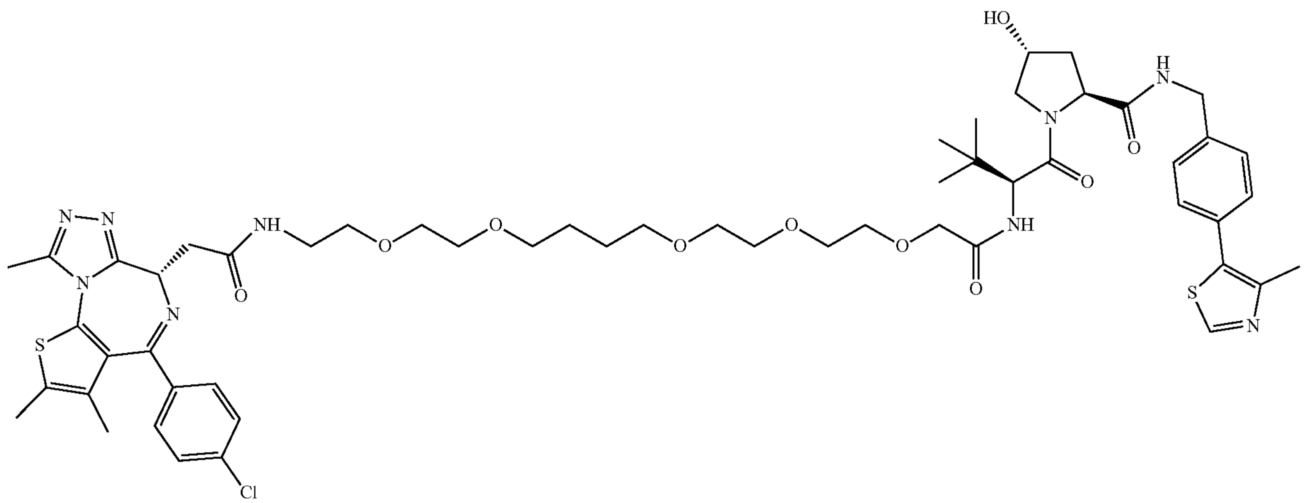 | 1118.8 | 1118.9 | C | 96.4 |
| 10 | 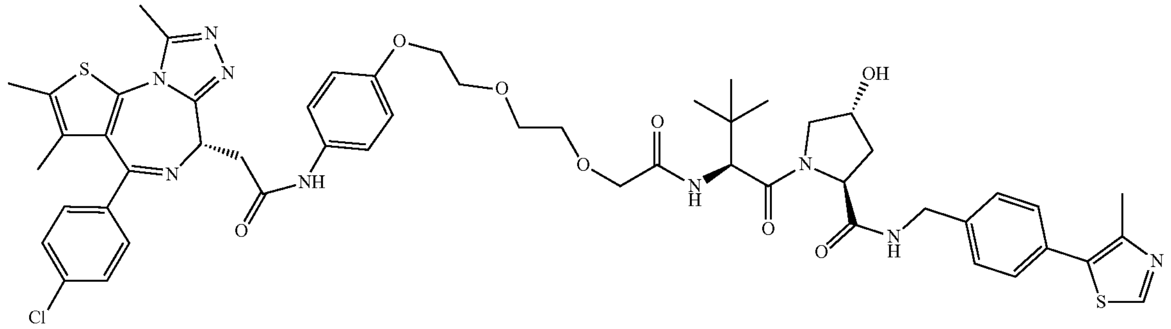 [SMILES: Cc1ncsc1-c1ccc(CNC(=O)[C@@H]2C[C@@H](O)CN2C(=O)[C@@H](NC(=O)COCCOCCOc2ccc(NC(=O)C[C@@H]3N=C(c4ccc(Cl)cc4)c4c(sc(C)c4C)-n4c(C)nnc43)cc2)C(C)(C)C)cc1] | 1050.7 | 1050.2 | B | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 11 | 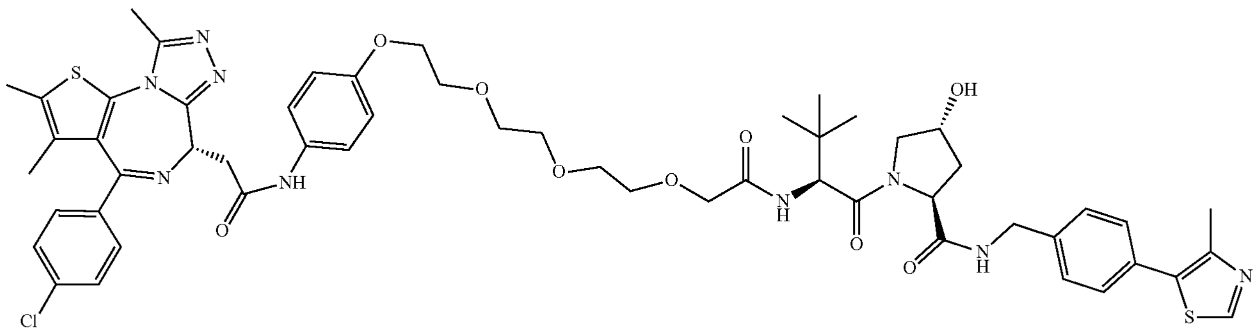 [SMILES: Cc1ncsc1-c1ccc(CNC(=O)[C@@H]2C[C@@H](O)CN2C(=O)[C@@H](NC(=O)COCCOCCOCCOc2ccc(NC(=O)C[C@@H]3N=C(c4ccc(Cl)cc4)c4c(sc(C)c4C)-n4c(C)nnc43)cc2)C(C)(C)C)cc1] | 1094.7 | 1094.2 | B | 99.5 |
| 12 | 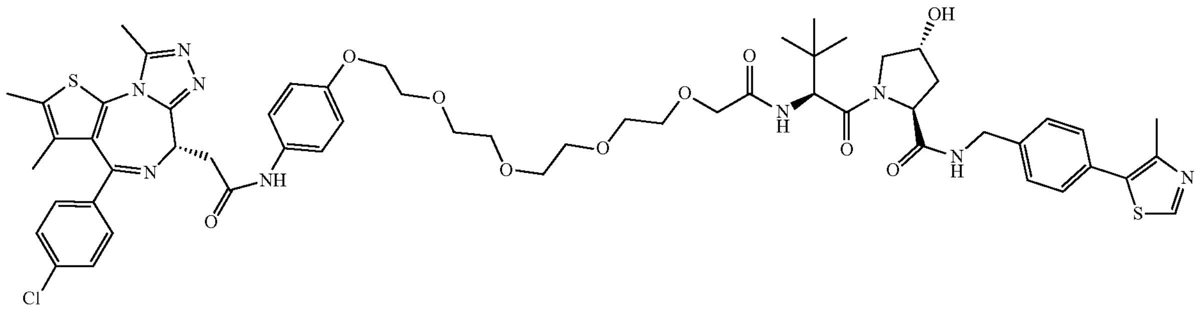 [SMILES: Cc1ncsc1-c1ccc(CNC(=O)[C@@H]2C[C@@H](O)CN2C(=O)[C@@H](NC(=O)COCCOCCOCCOCCOc2ccc(NC(=O)C[C@@H]3N=C(c4ccc(Cl)cc4)c4c(sc(C)c4C)-n4c(C)nnc43)cc2)C(C)(C)C)cc1] | 1138.8 | 1138.5 | B | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 13 | 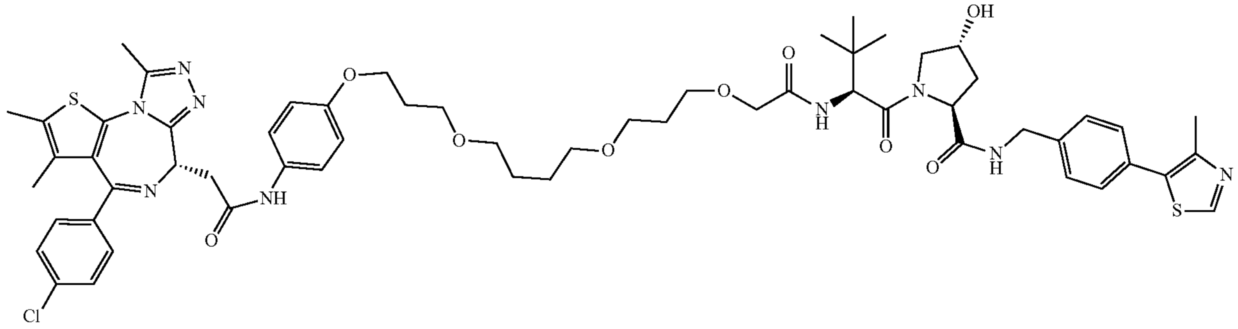 [SMILES: Cc1ncsc1-c1ccc(CNC(=O)[C@@H]2C[C@@H](O)CN2C(=O)[C@@H](NC(=O)COCCCOCCCCOCCCOc2ccc(NC(=O)C[C@@H]3N=C(c4ccc(Cl)cc4)c4c(sc(C)c4C)-n4c(C)nnc43)cc2)C(C)(C)C)cc1] | 1150.8 | 1150.3 | B | 100 |
| 14 | 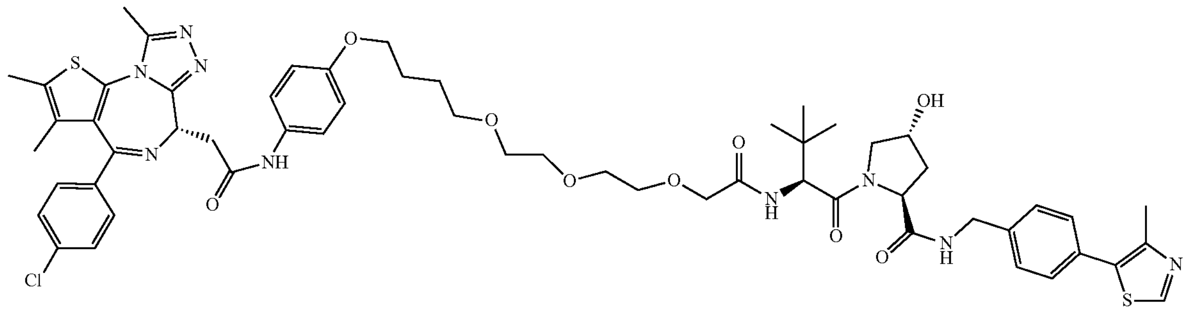 [SMILES: Cc1ncsc1-c1ccc(CNC(=O)[C@@H]2C[C@@H](O)CN2C(=O)[C@@H](NC(=O)COCCOCCOCCCCOc2ccc(NC(=O)C[C@@H]3N=C(c4ccc(Cl)cc4)c4c(sc(C)c4C)-n4c(C)nnc43)cc2)C(C)(C)C)cc1] | 1122.8 | 1122.2 | B | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 15 | 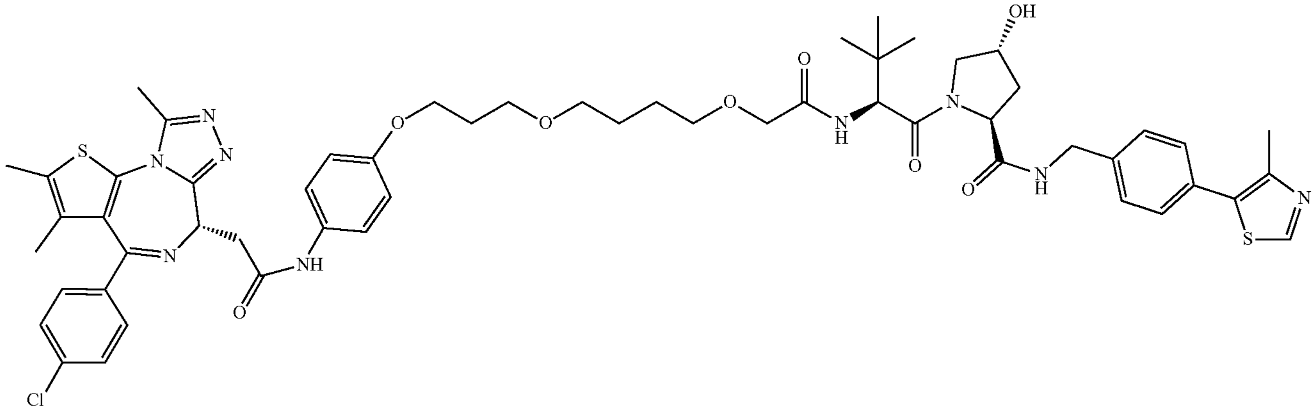 [SMILES: Cc1ncsc1-c1ccc(CNC(=O)[C@@H]2C[C@@H](O)CN2C(=O)[C@@H](NC(=O)COCCCCOCCCOc2ccc(NC(=O)C[C@@H]3N=C(c4ccc(Cl)cc4)c4c(sc(C)c4C)-n4c(C)nnc43)cc2)C(C)(C)C)cc1] | 1092.8 | 1092.4 | B | 100 |
| 16 | 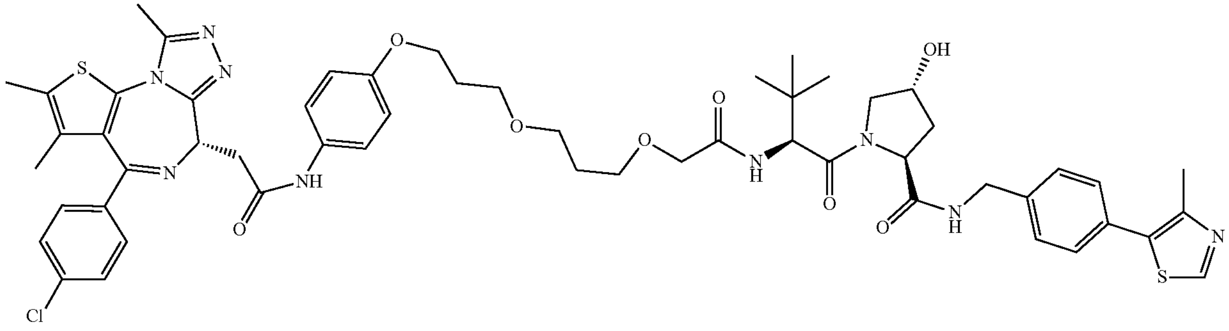 [SMILES: Cc1ncsc1-c1ccc(CNC(=O)[C@@H]2C[C@@H](O)CN2C(=O)[C@@H](NC(=O)COCCCOCCCOc2ccc(NC(=O)C[C@@H]3N=C(c4ccc(Cl)cc4)c4c(sc(C)c4C)-n4c(C)nnc43)cc2)C(C)(C)C)cc1] | 1078.7 | 1078.3 | B | 98.6 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 17 | 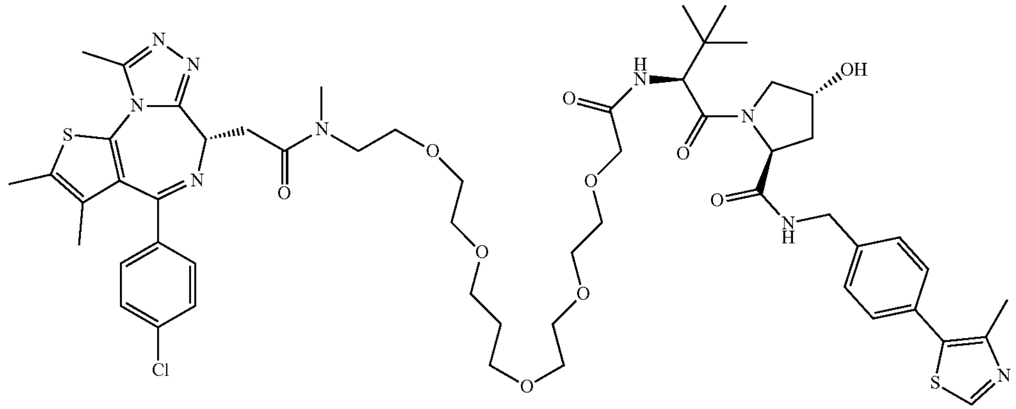 | 1118.8 | 1118.4 | C | 85.0 |
| 18 | 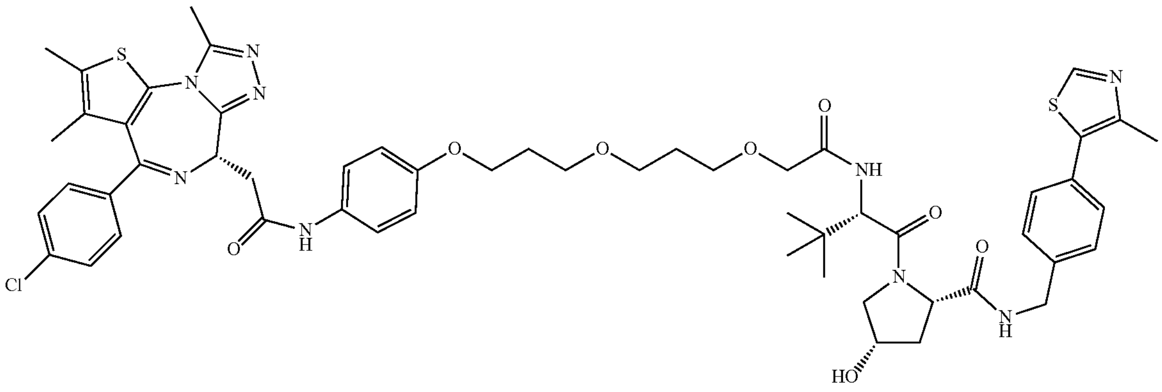 [SMILES: Cc1ncsc1-c1ccc(CNC(=O)[C@@H]2C[C@H](O)CN2C(=O)[C@@H](NC(=O)COCCCOCCCOc2ccc(NC(=O)C[C@@H]3N=C(c4ccc(Cl)cc4)c4c(sc(C)c4C)-n4c(C)nnc43)cc2)C(C)(C)C)cc1] | 1078.7 | 1078.0 | D | 39.0 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 19 | 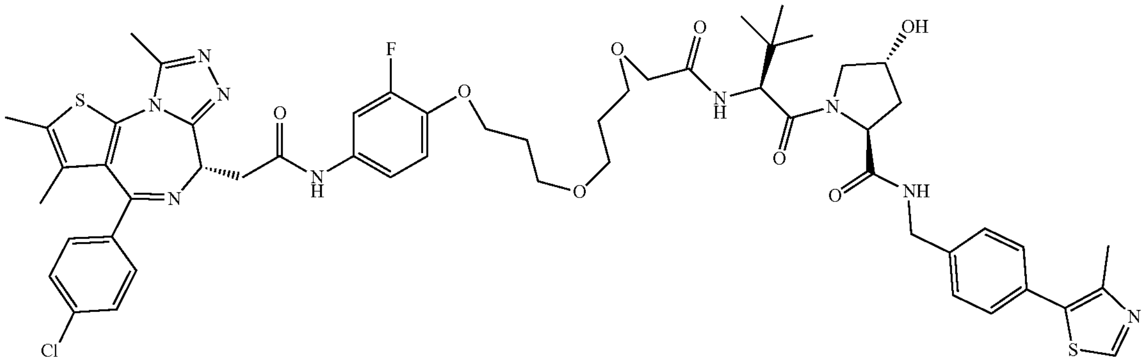 [SMILES: Cc1ncsc1-c1ccc(CNC(=O)[C@@H]2C[C@@H](O)CN2C(=O)[C@@H](NC(=O)COCCCOCCCOc2ccc(NC(=O)C[C@@H]3N=C(c4ccc(Cl)cc4)c4c(sc(C)c4C)-n4c(C)nnc43)cc2F)C(C)(C)C)cc1] | 1096.7 | 1096.2 | B | 92.0 |
| 20 | 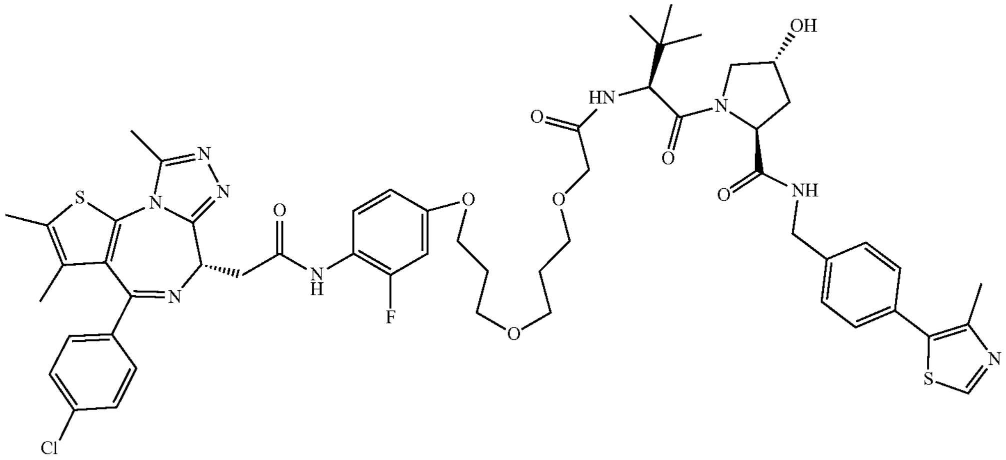 [SMILES: Cc1ncsc1-c1ccc(CNC(=O)[C@@H]2C[C@@H](O)CN2C(=O)[C@@H](NC(=O)COCCCOCCCOc2ccc(NC(=O)C[C@@H]3N=C(c4ccc(Cl)cc4)c4c(sc(C)c4C)-n4c(C)nnc43)c(F)c2)C(C)(C)C)cc1] | 1096.7 | 1096.2 | B | 94.0 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 21 | 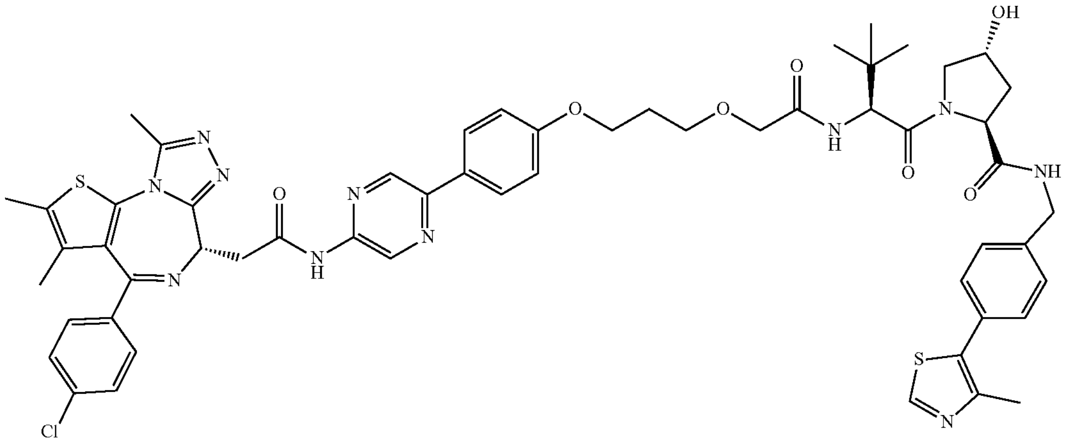 [SMILES: Cc1ncsc1-c1ccc(CNC(=O)[C@@H]2C[C@@H](O)CN2C(=O)[C@@H](NC(=O)COCCCOc2ccc(-c3cnc(NC(=O)C[C@@H]4N=C(c5ccc(Cl)cc5)c5c(sc(C)c5C)-n5c(C)nnc54)cn3)cc2)C(C)(C)C)cc1] | 1098.7 | 1098.2 | B | 91.0 |
| 22 | 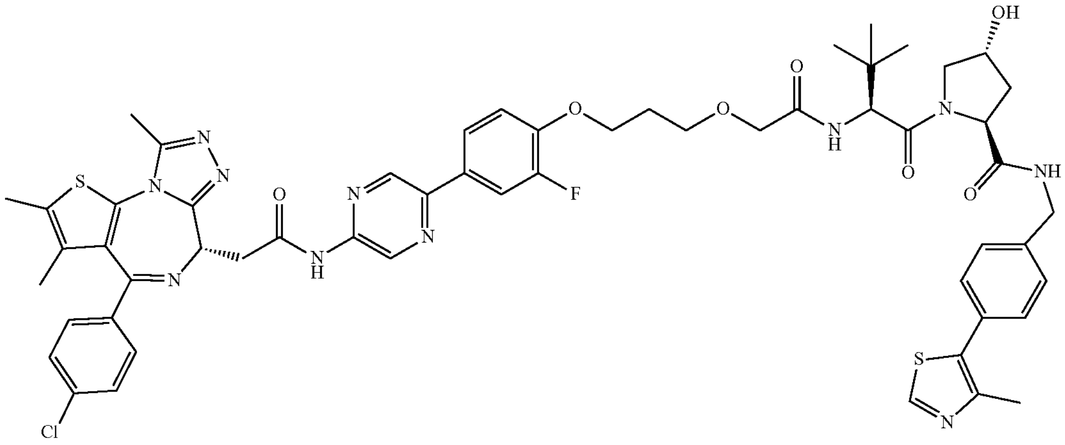 [SMILES: Cc1ncsc1-c1ccc(CNC(=O)[C@@H]2C[C@@H](O)CN2C(=O)[C@@H](NC(=O)COCCCOc2ccc(-c3cnc(NC(=O)C[C@@H]4N=C(c5ccc(Cl)cc5)c5c(sc(C)c5C)-n5c(C)nnc54)cn3)cc2F)C(C)(C)C)cc1] | 1116.7 | 1116.2 | B | 94.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 23 | 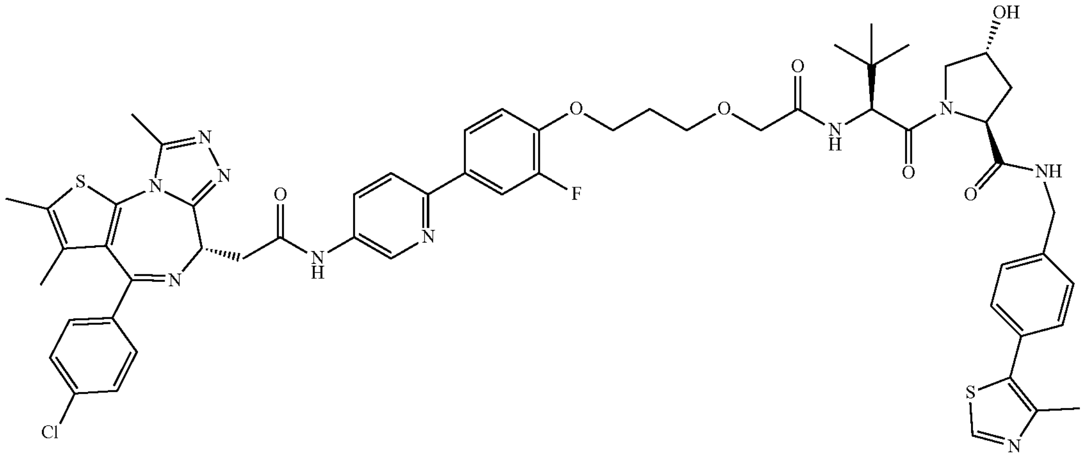 | 1115.7 | 1115.4 | B | 91.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 24 | 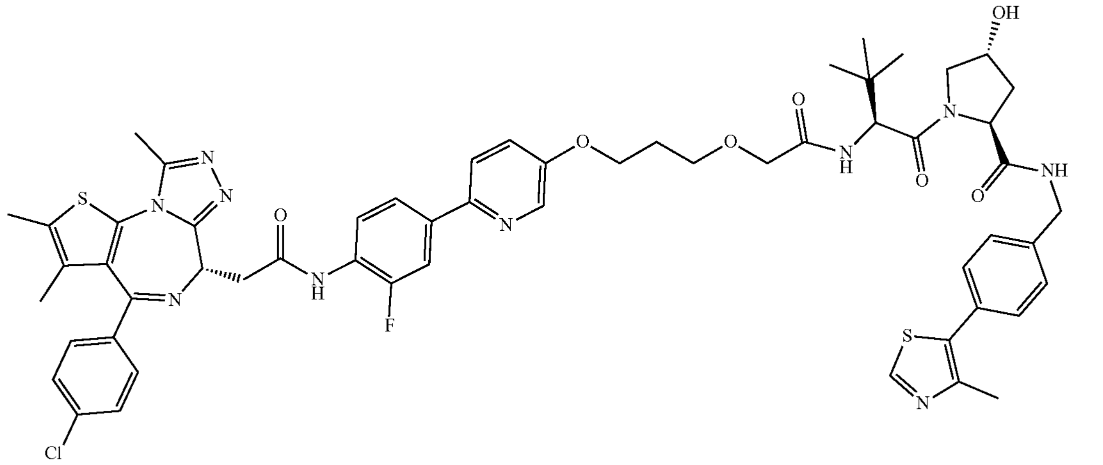 [SMILES: Cc1ncsc1-c1ccc(CNC(=O)[C@@H]2C[C@@H](O)CN2C(=O)[C@@H](NC(=O)COCCCOc2ccc(-c3ccc(NC(=O)C[C@@H]4N=C(c5ccc(Cl)cc5)c5c(sc(C)c5C)-n5c(C)nnc54)c(F)c3)nc2)C(C)(C)C)cc1] | 1116.0 | 1115.2 | B | 87.5 |
| 25 | 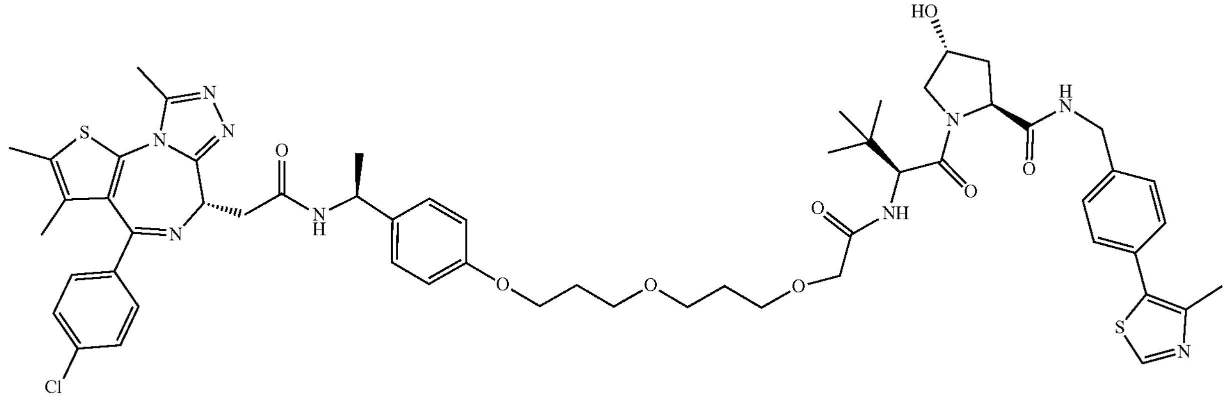 | 1106.8 | 1106.3 | B | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 26 | 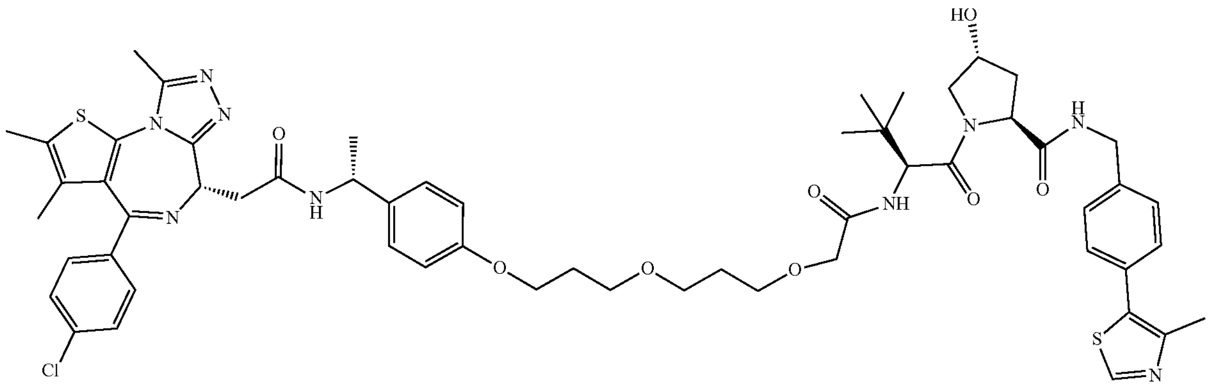 | 1106.8 | 1106.3 | B | 100 |
| 27 | 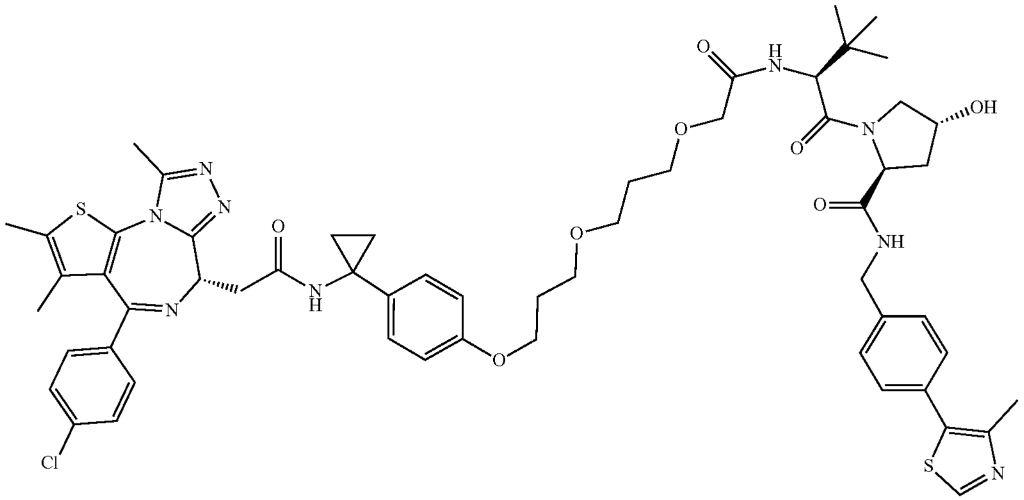 | 1118.8 | 1118.3 | B | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 28 | 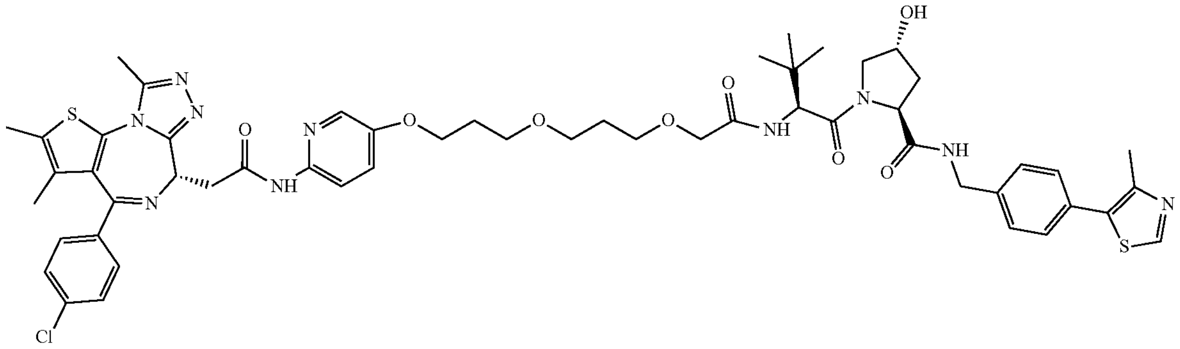 [SMILES: Cc1ncsc1-c1ccc(CNC(=O)[C@@H]2C[C@@H](O)CN2C(=O)[C@@H](NC(=O)COCCCOCCCOc2ccc(NC(=O)C[C@@H]3N=C(c4ccc(Cl)cc4)c4c(sc(C)c4C)-n4c(C)nnc43)nc2)C(C)(C)C)cc1] | 1079.7 | 1079.7 | B | 100 |
| 29 | 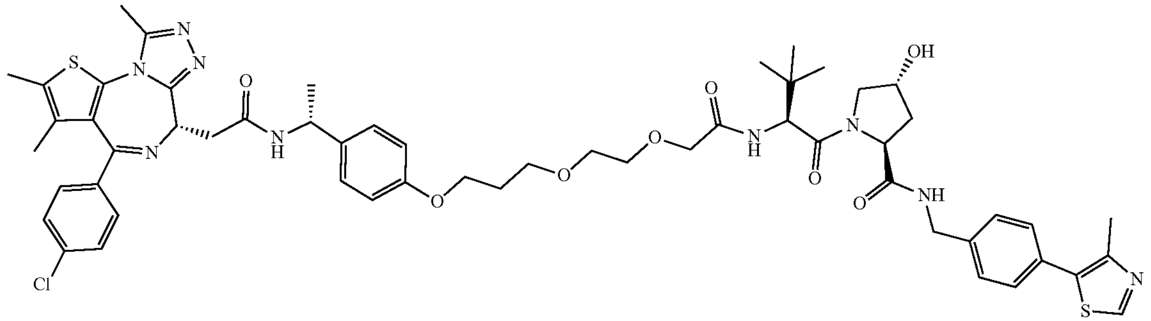 [SMILES: Cc1ncsc1-c1ccc(CNC(=O)[C@@H]2C[C@@H](O)CN2C(=O)[C@@H](NC(=O)COCCOCCCOc2ccc([C@@H](C)NC(=O)C[C@@H]3N=C(c4ccc(Cl)cc4)c4c(sc(C)c4C)-n4c(C)nnc43)cc2)C(C)(C)C)cc1] | 1093.0 | 1092.2 | B | 96.8 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 30 | 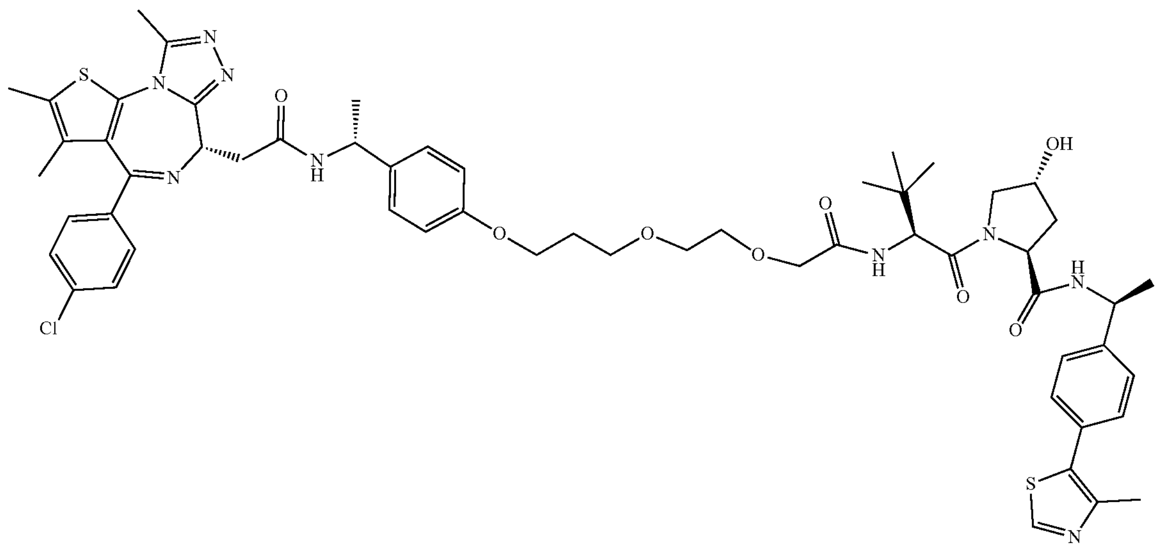 [SMILES: Cc1ncsc1-c1ccc([C@H](C)NC(=O)[C@@H]2C[C@@H](O)CN2C(=O)[C@@H](NC(=O)COCCOCCCOc2ccc([C@@H](C)NC(=O)C[C@@H]3N=C(c4ccc(Cl)cc4)c4c(sc(C)c4C)-n4c(C)nnc43)cc2)C(C)(C)C)cc1] | 1106.8 | 1106.3 | B | 96.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 31 | 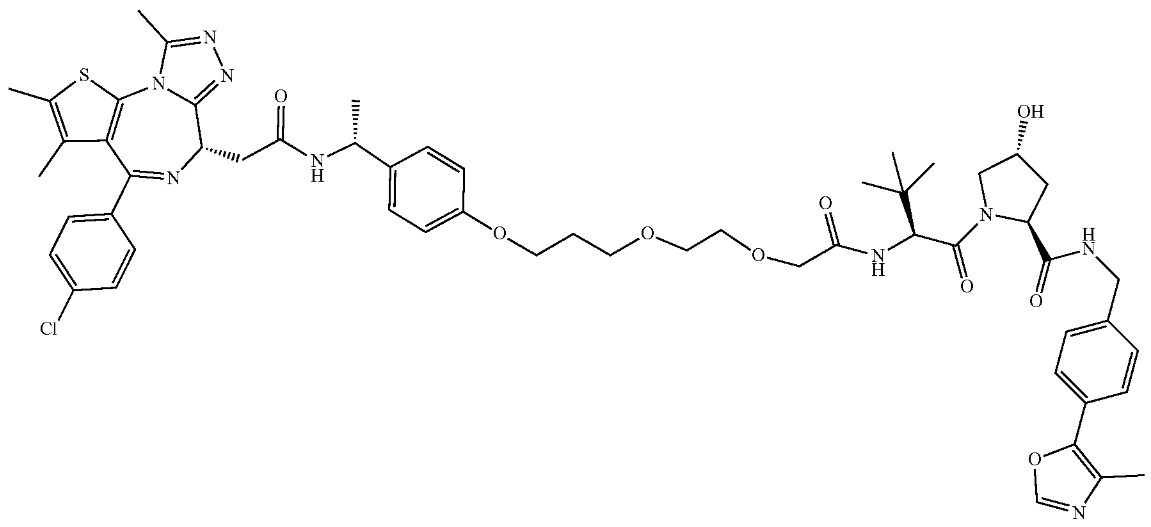 | 1076.7 | 1076.3 | C | 65.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 32 | 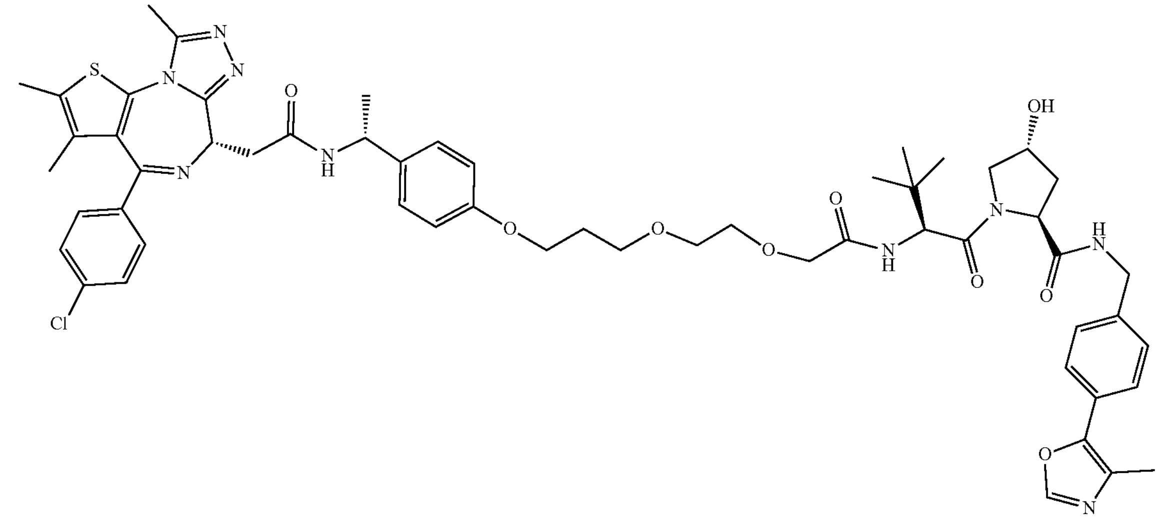 | 1090.7 | 1090.3 | B | 100 |
| 33 | 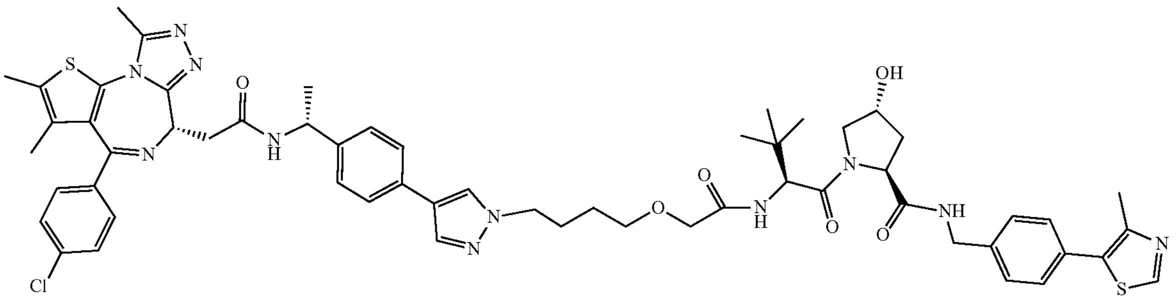 [SMILES: Cc1ncsc1-c1ccc(CNC(=O)[C@@H]2C[C@@H](O)CN2C(=O)[C@@H](NC(=O)COCCCCn2cc(-c3ccc([C@@H](C)NC(=O)C[C@@H]4N=C(c5ccc(Cl)cc5)c5c(sc(C)c5C)-n5c(C)nnc54)cc3)cn2)C(C)(C)C)cc1] | 1112.8 | 1112.3 | B | 100 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 34 | 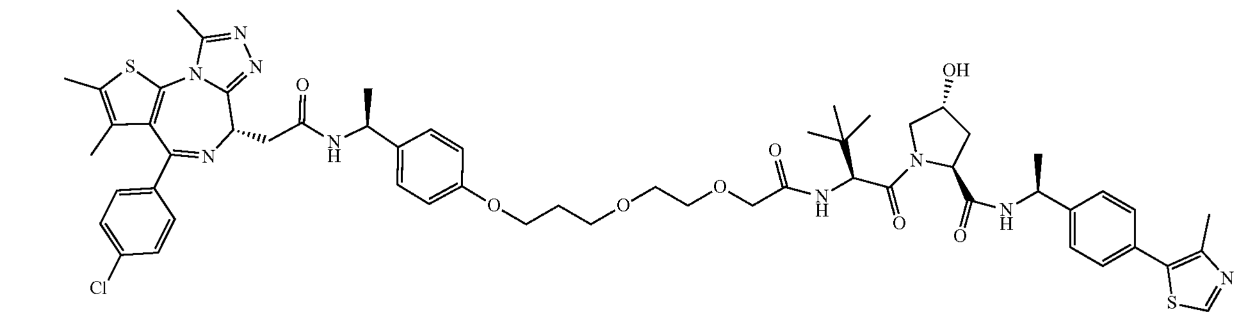 [SMILES: Cc1ncsc1-c1ccc([C@H](C)NC(=O)[C@@H]2C[C@@H](O)CN2C(=O)[C@@H](NC(=O)COCCOCCCOc2ccc([C@H](C)NC(=O)C[C@@H]3N=C(c4ccc(Cl)cc4)c4c(sc(C)c4C)-n4c(C)nnc43)cc2)C(C)(C)C)cc1] | 1106.8 | 1106.2 | B | 99.7 |
| 35 | 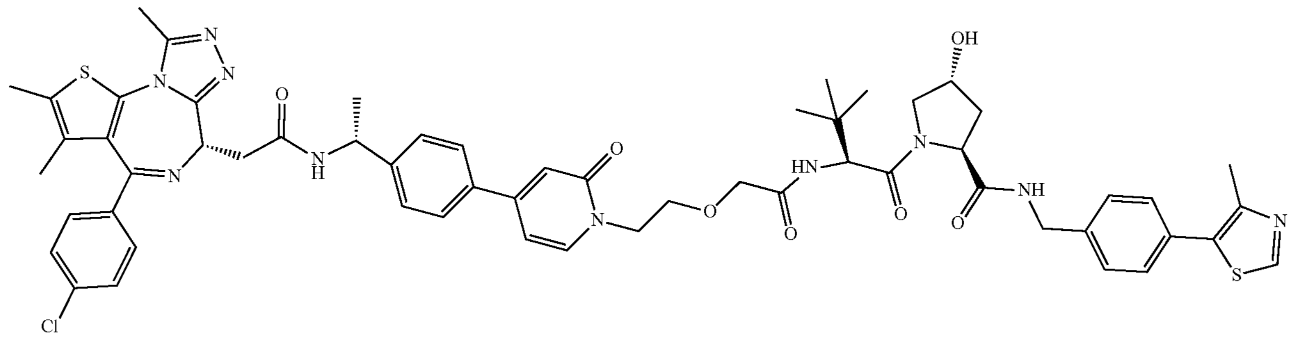 [SMILES: Cc1ncsc1-c1ccc(CNC(=O)[C@@H]2C[C@@H](O)CN2C(=O)[C@@H](NC(=O)COCCn2ccc(-c3ccc([C@@H](C)NC(=O)C[C@@H]4N=C(c5ccc(Cl)cc5)c5c(sc(C)c5C)-n5c(C)nnc54)cc3)cc2=O)C(C)(C)C)cc1] | 1111.8 | 556.7* | D | 37.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 36 | 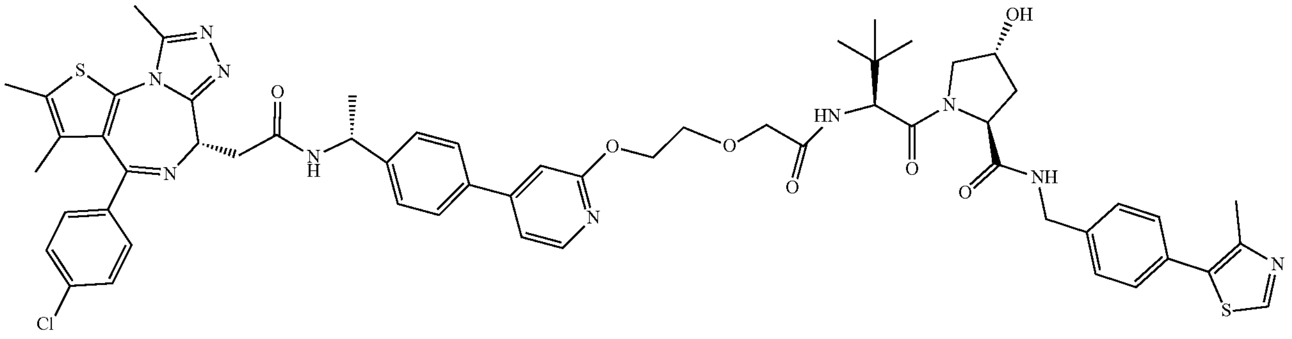 [SMILES: Cc1ncsc1-c1ccc(CNC(=O)[C@@H]2C[C@@H](O)CN2C(=O)[C@@H](NC(=O)COCCOc2cc(-c3ccc([C@@H](C)NC(=O)C[C@@H]4N=C(c5ccc(Cl)cc5)c5c(sc(C)c5C)-n5c(C)nnc54)cc3)ccn2)C(C)(C)C)cc1] | 1111.8 | 1111.2 | B | 97.0 |
| 37 | 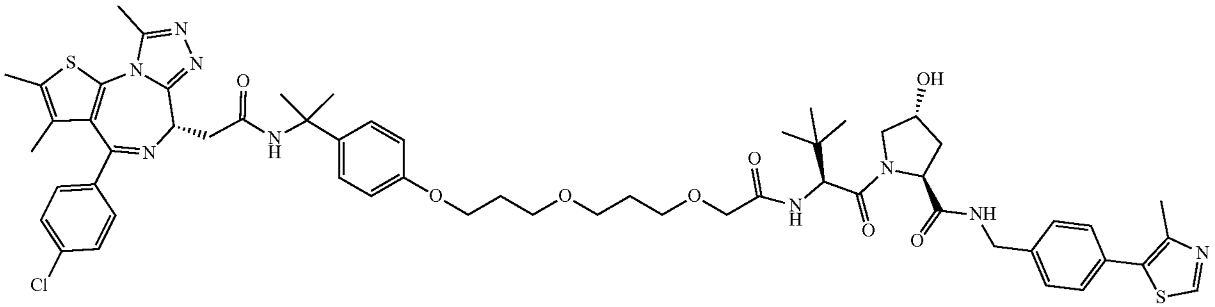 [SMILES: Cc1ncsc1-c1ccc(CNC(=O)[C@@H]2C[C@@H](O)CN2C(=O)[C@@H](NC(=O)COCCCOCCCOc2ccc(C(C)(C)NC(=O)C[C@@H]3N=C(c4ccc(Cl)cc4)c4c(sc(C)c4C)-n4c(C)nnc43)cc2)C(C)(C)C)cc1] | 1120.8 | 1120.8 | B | 96.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 38 | 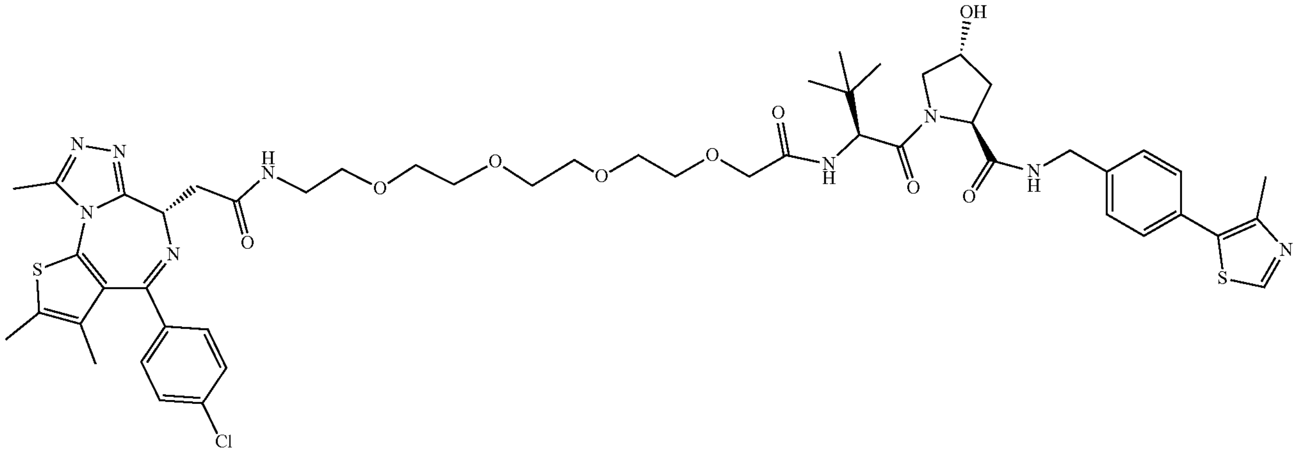 [SMILES: Cc1ncsc1-c1ccc(CNC(=O)[C@@H]2C[C@@H](O)CN2C(=O)[C@@H](NC(=O)COCCOCCOCCOCCNC(=O)C[C@@H]2N=C(c3ccc(Cl)cc3)c3c(sc(C)c3C)-n3c(C)nnc32)C(C)(C)C)cc1] | 1046.7 | 1046.7 | B | 94.0 |
| 39 | 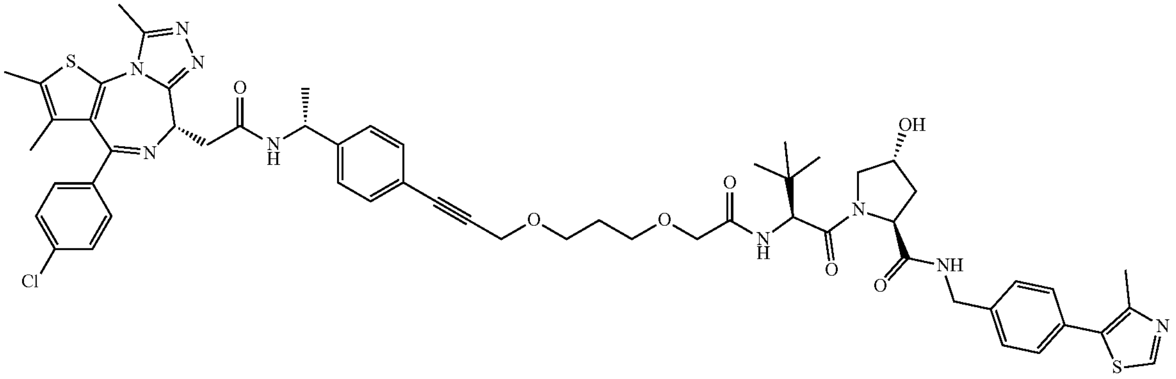 [SMILES: Cc1ncsc1-c1ccc(CNC(=O)[C@@H]2C[C@@H](O)CN2C(=O)[C@@H](NC(=O)COCCCOCC#Cc2ccc([C@@H](C)NC(=O)C[C@@H]3N=C(c4ccc(Cl)cc4)c4c(sc(C)c4C)-n4c(C)nnc43)cc2)C(C)(C)C)cc1] | 1086.8 | 1086.2 | B | 99.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 40 | 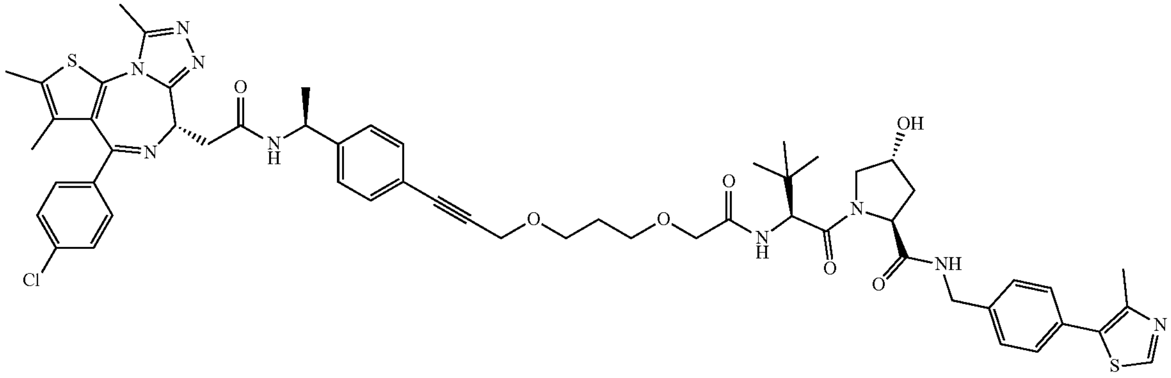 [SMILES: Cc1ncsc1-c1ccc(CNC(=O)[C@@H]2C[C@@H](O)CN2C(=O)[C@@H](NC(=O)COCCCOCC#Cc2ccc([C@H](C)NC(=O)C[C@@H]3N=C(c4ccc(Cl)cc4)c4c(sc(C)c4C)-n4c(C)nnc43)cc2)C(C)(C)C)cc1] | 1086.8 | 1086.2 | B | 97.5 |
| 41 | 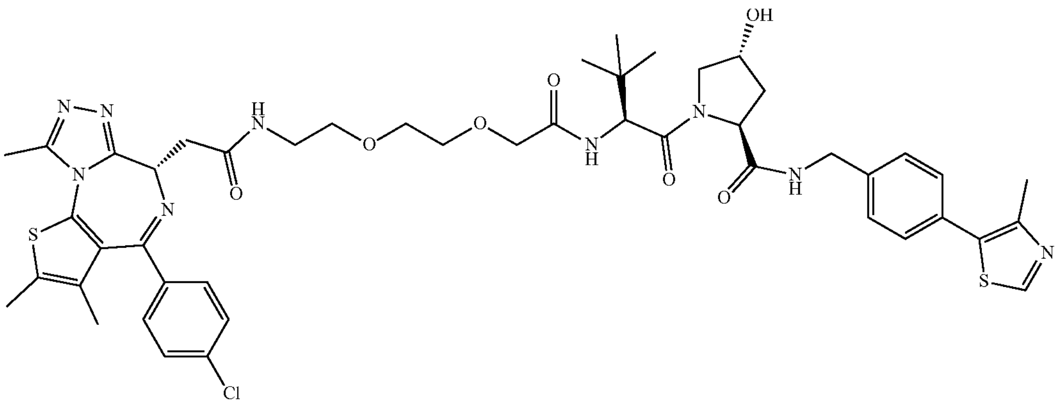 [SMILES: Cc1ncsc1-c1ccc(CNC(=O)[C@@H]2C[C@@H](O)CN2C(=O)[C@@H](NC(=O)COCCOCCNC(=O)C[C@@H]2N=C(c3ccc(Cl)cc3)c3c(sc(C)c3C)-n3c(C)nnc32)C(C)(C)C)cc1] | 0958.6 | 0958.6 | C | 94.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 42 | 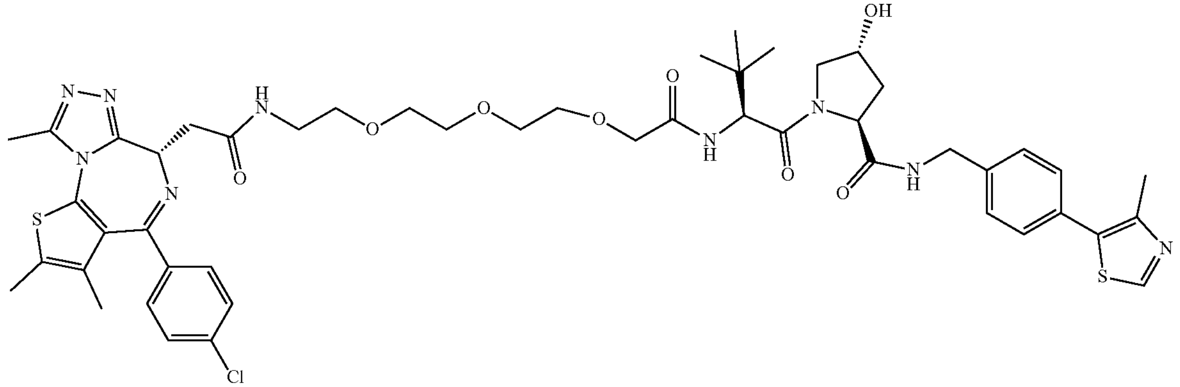 [SMILES: Cc1ncsc1-c1ccc(CNC(=O)[C@@H]2C[C@@H](O)CN2C(=O)[C@@H](NC(=O)COCCOCCOCCNC(=O)C[C@@H]2N=C(c3ccc(Cl)cc3)c3c(sc(C)c3C)-n3c(C)nnc32)C(C)(C)C)cc1] | 1002.6 | 1002.3 | B | 98.6 |
| 43 | 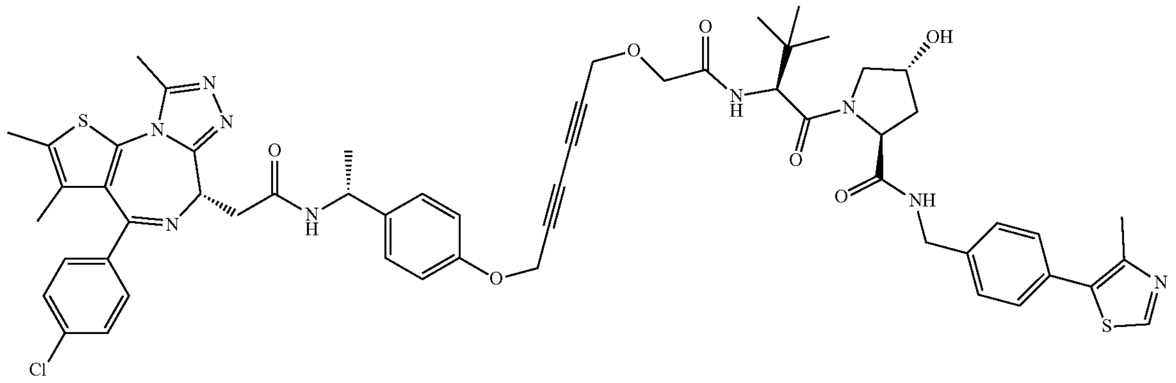 [SMILES: Cc1ncsc1-c1ccc(CNC(=O)[C@@H]2C[C@@H](O)CN2C(=O)[C@@H](NC(=O)COCC#CC#CCOc2ccc([C@@H](C)NC(=O)C[C@@H]3N=C(c4ccc(Cl)cc4)c4c(sc(C)c4C)-n4c(C)nnc43)cc2)C(C)(C)C)cc1] | 1082.7 | 1082.2 | B | 100 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 44 | 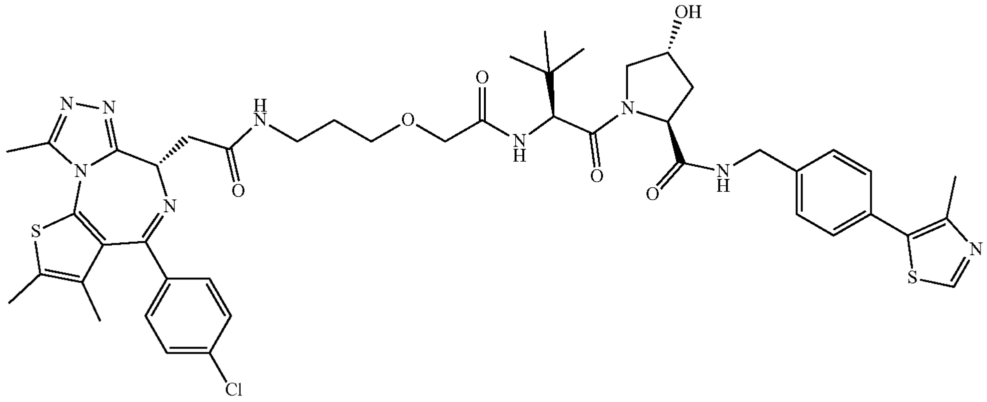 [SMILES: Cc1ncsc1-c1ccc(CNC(=O)[C@@H]2C[C@@H](O)CN2C(=O)[C@@H](NC(=O)COCCCNC(=O)C[C@@H]2N=C(c3ccc(Cl)cc3)c3c(sc(C)c3C)-n3c(C)nnc32)C(C)(C)C)cc1] | 0928.6 | 0928.6 | C | 98.0 |
| 45 | 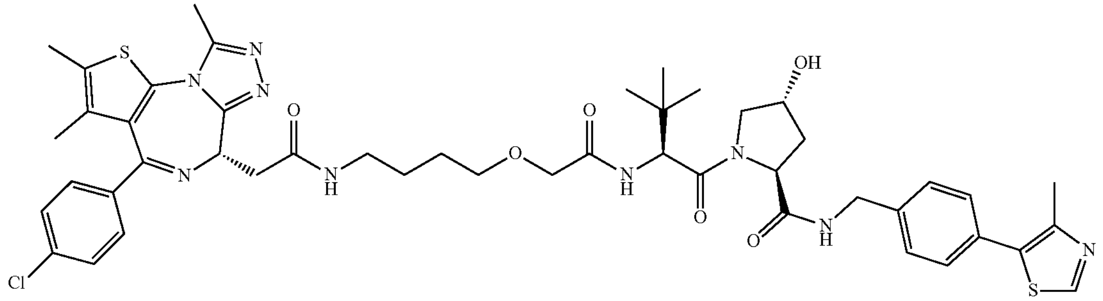 [SMILES: Cc1ncsc1-c1ccc(CNC(=O)[C@@H]2C[C@@H](O)CN2C(=O)[C@@H](NC(=O)COCCCCNC(=O)C[C@@H]2N=C(c3ccc(Cl)cc3)c3c(sc(C)c3C)-n3c(C)nnc32)C(C)(C)C)cc1] | 0942.6 | 0942.2 | C | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 46 | 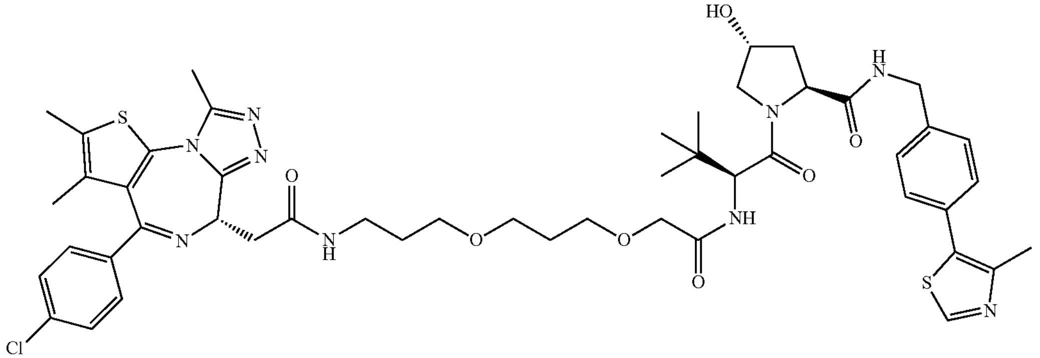 [SMILES: Cc1ncsc1-c1ccc(CNC(=O)[C@@H]2C[C@@H](O)CN2C(=O)[C@@H](NC(=O)COCCCOCCCNC(=O)C[C@@H]2N=C(c3ccc(Cl)cc3)c3c(sc(C)c3C)-n3c(C)nnc32)C(C)(C)C)cc1] | 0986.6 | 0986.7 | B | 100 |
| 47 | 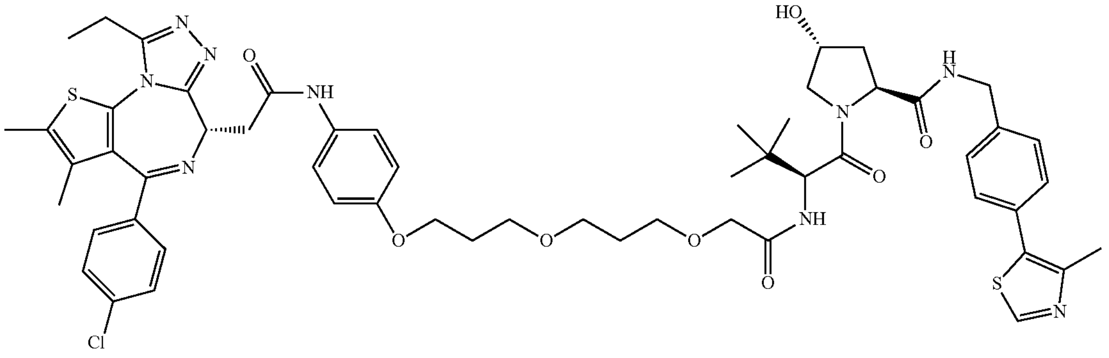 | 1092.8 | 1092.4 | C | 89.0 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 48 | 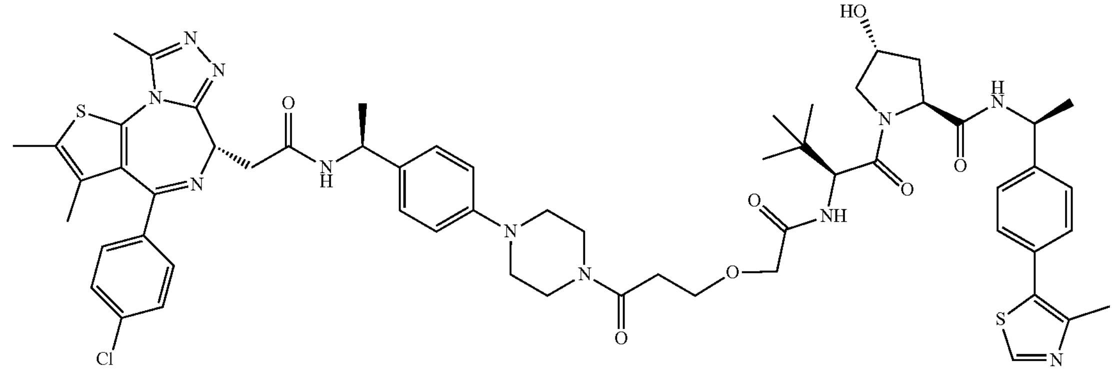 | 1144.8 | 1144.3 | B | 98.0 |
| 49 | 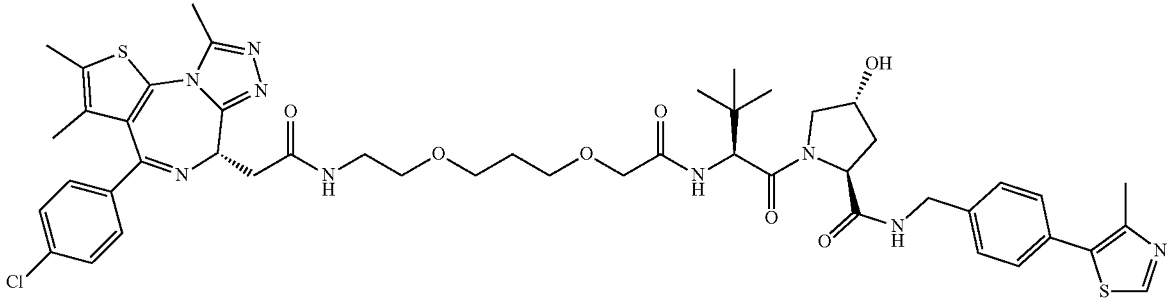 [SMILES: Cc1ncsc1-c1ccc(CNC(=O)[C@@H]2C[C@@H](O)CN2C(=O)[C@@H](NC(=O)COCCCOCCNC(=O)C[C@@H]2N=C(c3ccc(Cl)cc3)c3c(sc(C)c3C)-n3c(C)nnc32)C(C)(C)C)cc1] | 0972.6 | 0972.4 | A | 99.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 50 | 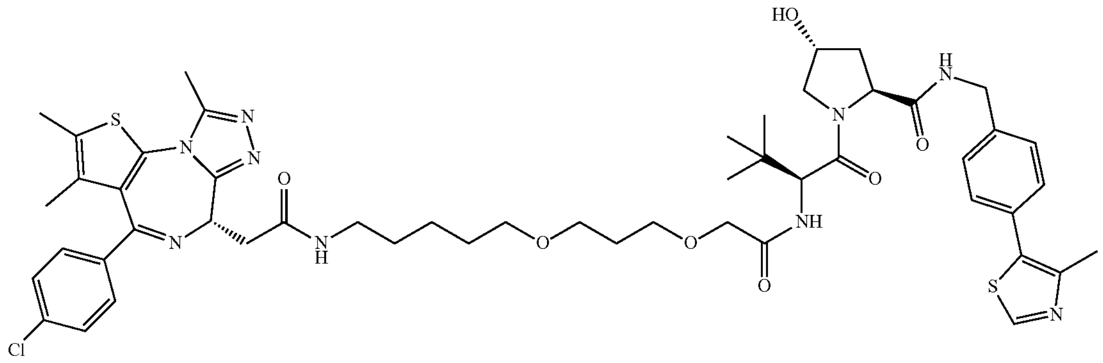 [SMILES: Cc1ncsc1-c1ccc(CNC(=O)[C@@H]2C[C@@H](O)CN2C(=O)[C@@H](NC(=O)COCCCOCCCCCNC(=O)C[C@@H]2N=C(c3ccc(Cl)cc3)c3c(sc(C)c3C)-n3c(C)nnc32)C(C)(C)C)cc1] | 1014.7 | 1014.3 | A | 98.0 |
| 51 | 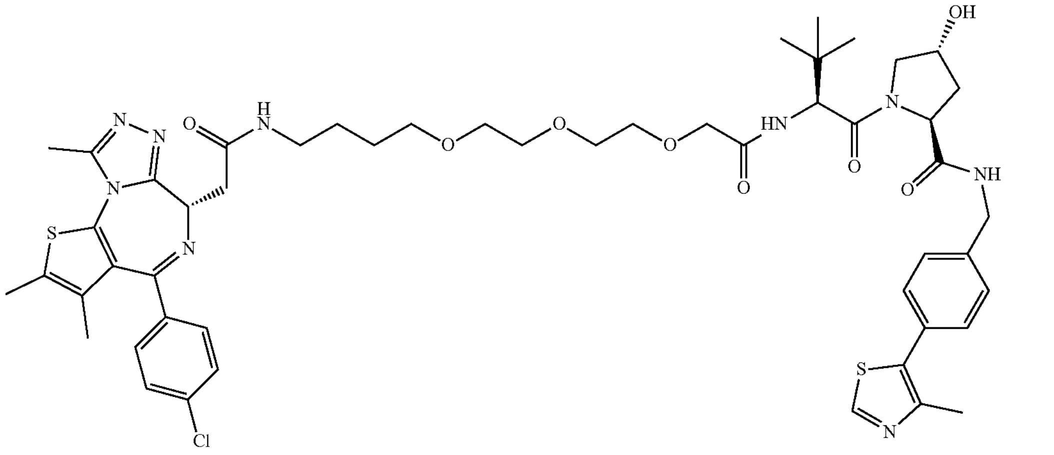 [SMILES: Cc1ncsc1-c1ccc(CNC(=O)[C@@H]2C[C@@H](O)CN2C(=O)[C@@H](NC(=O)COCCOCCOCCCCNC(=O)C[C@@H]2N=C(c3ccc(Cl)cc3)c3c(sc(C)c3C)-n3c(C)nnc32)C(C)(C)C)cc1] | 1030.7 | 1030.2 | A | 97.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 52 | 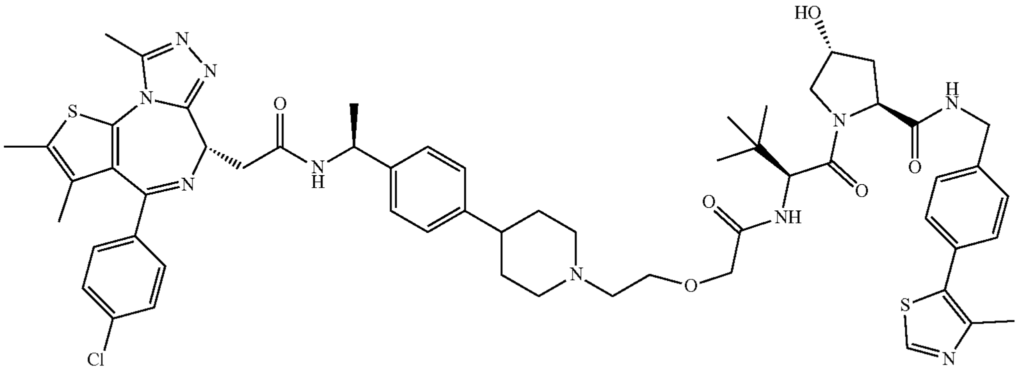 | 1101.8 | 1101.2 | C | 93.0 |
| 53 | 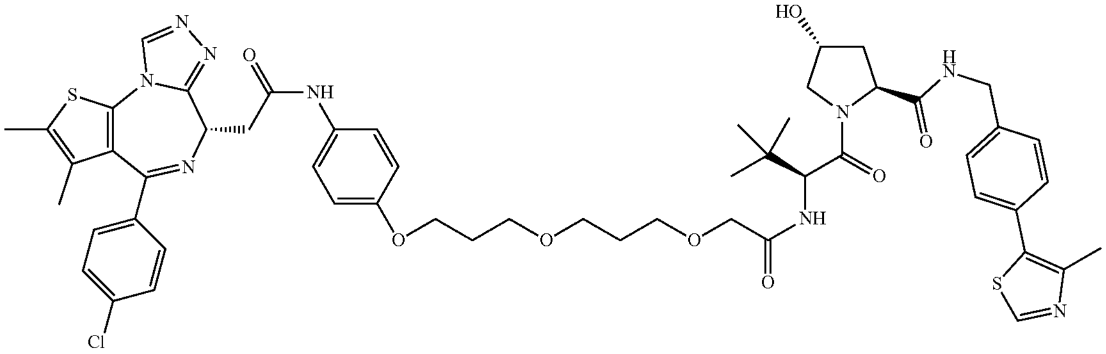 | 1064.7 | 1064.2 | D | 56.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 54 | 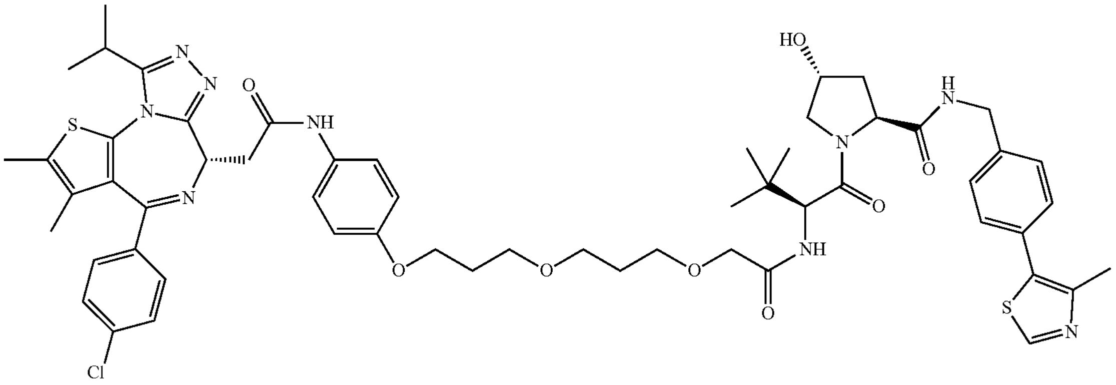 | 1106.8 | 1106.3 | D | 63.0 |
| 55 | 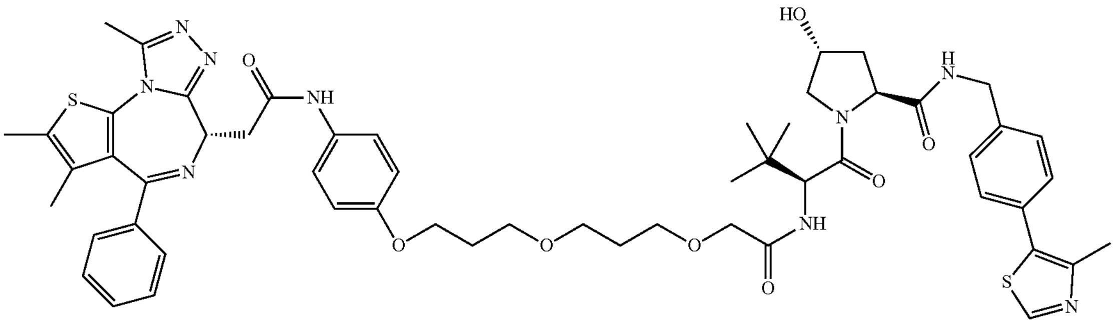 | 1044.3 | 1044.3 | A | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 56 | 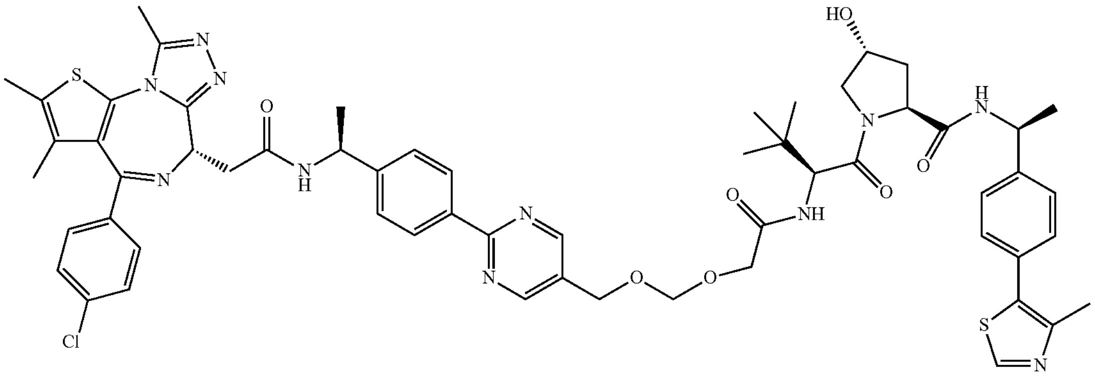 | 1126.8 | 1126.4 | B | 99.4 |
| 57 | 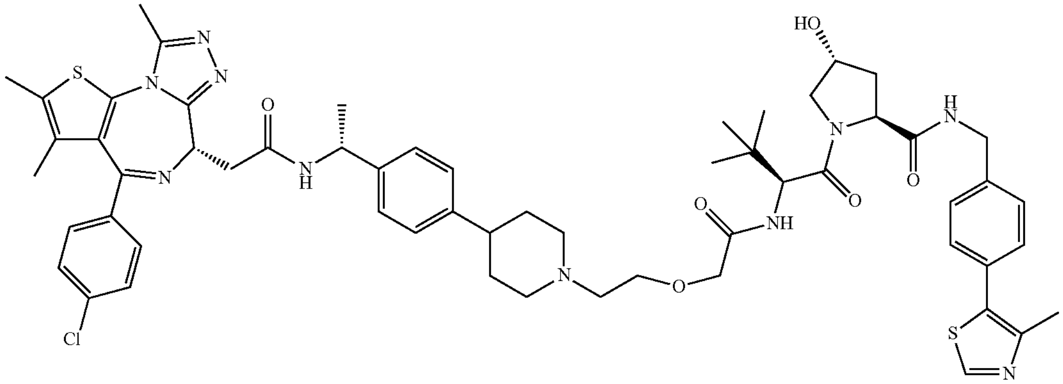 | 1101.8 | 1101.3 | C | 94.0 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 58 | 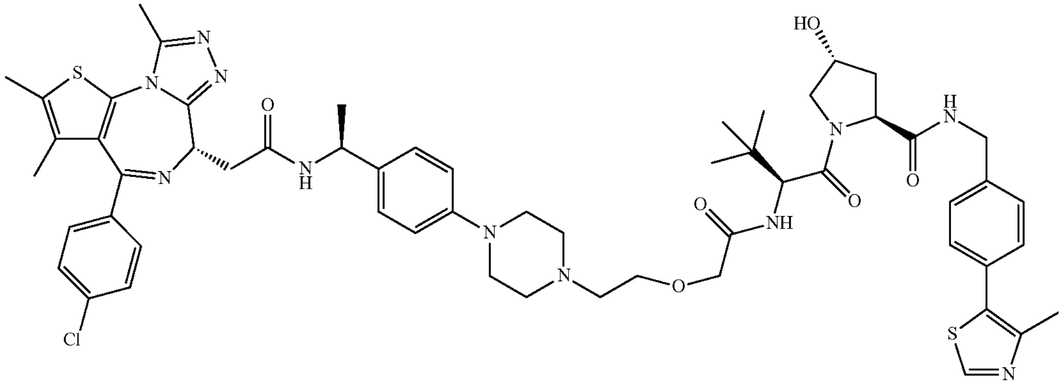 | 1102.8 | 1102.3 | C | 88.0 |
| 59 | 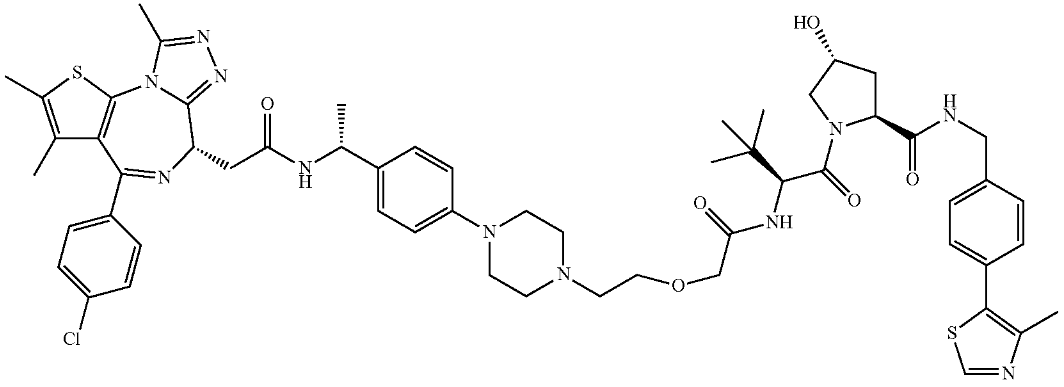 | 1102.8 | 1102.4 | C | 95.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 60 | 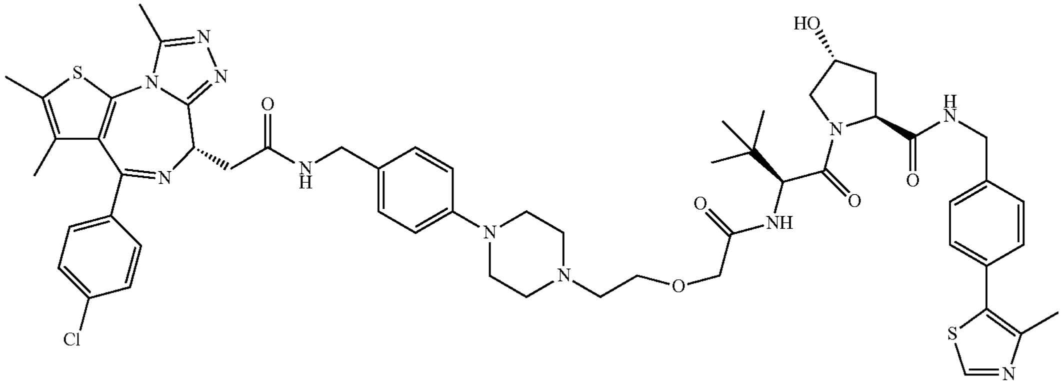 | 1088.8 | 1088.3 | C | 91.0 |
| 61 | 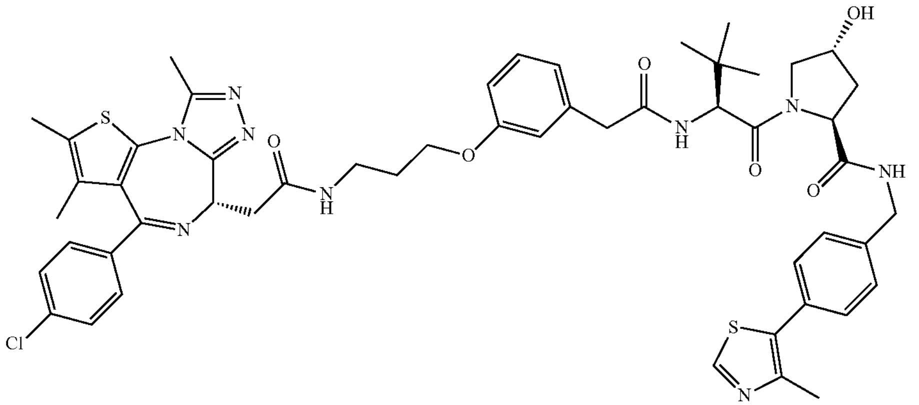 [SMILES: Cc1ncsc1-c1ccc(CNC(=O)[C@@H]2C[C@@H](O)CN2C(=O)[C@@H](NC(=O)Cc2cccc(OCCCNC(=O)C[C@@H]3N=C(c4ccc(Cl)cc4)c4c(sc(C)c4C)-n4c(C)nnc43)c2)C(C)(C)C)cc1] | 1004.7 | 503.1* | B | 96.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 62 | 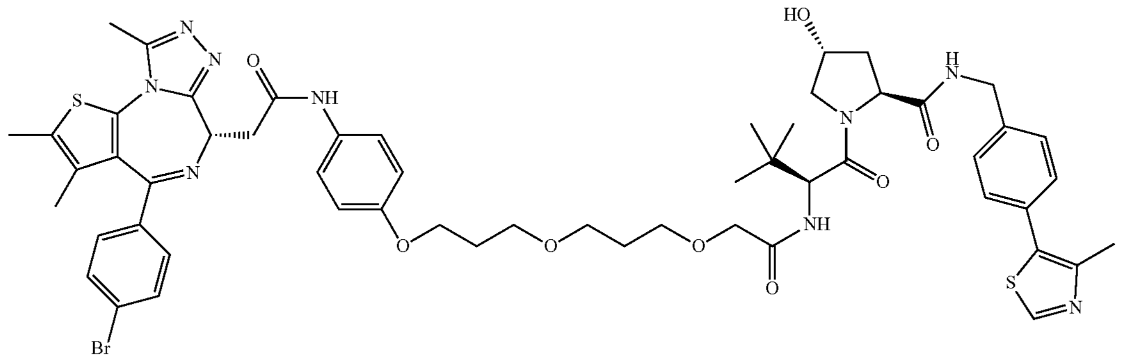 | 1123.2 | 562.7* | B | 98.5 |
| 63 | 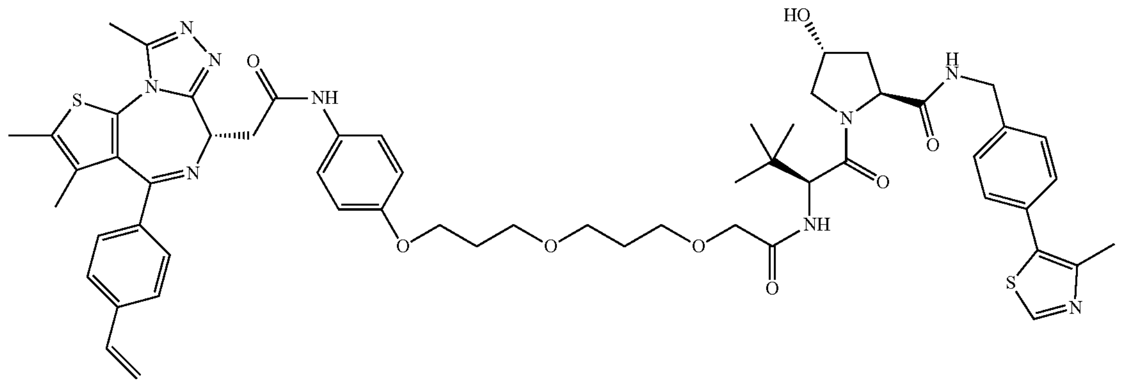 | 1070.3 | 1070.2 | B | 98.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 64 | 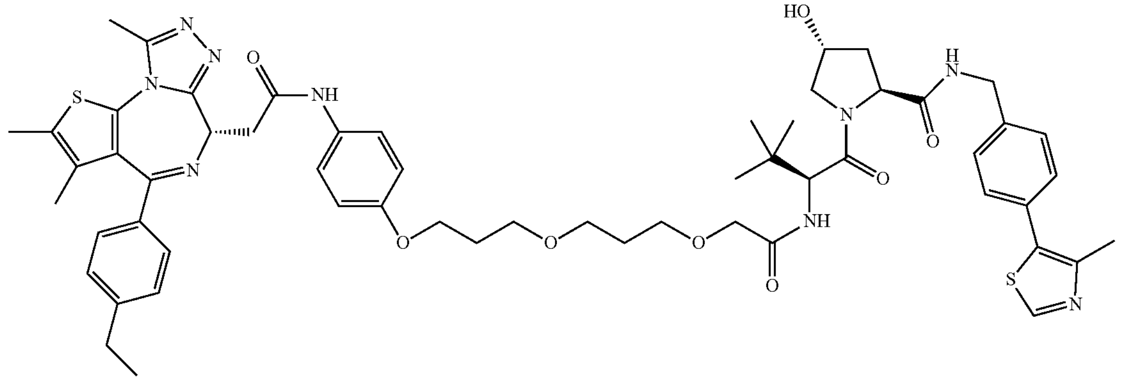 | 1072.3 | 1072.4 | B | 96.5 |
| 65 | 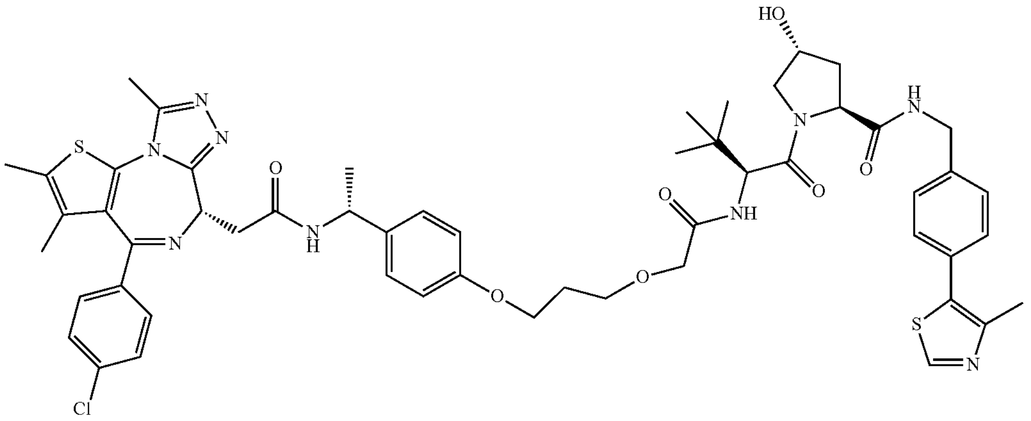 | 1048.7 | 1048.3 | B | 95.4 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 66 | 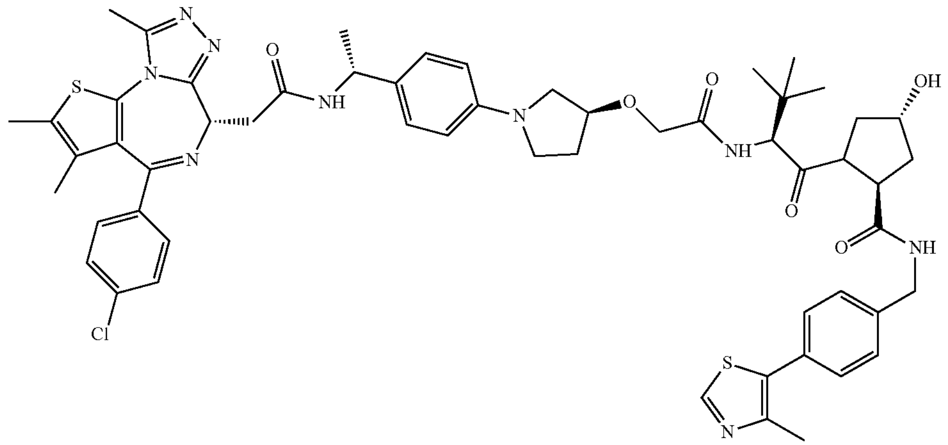 [SMILES: Cc1ncsc1-c1ccc(CNC(=O)[C@@H]2C[C@@H](O)CC2C(=O)[C@@H](NC(=O)CO[C@H]2CCN(c3ccc([C@@H](C)NC(=O)C[C@@H]4N=C(c5ccc(Cl)cc5)c5c(sc(C)c5C)-n5c(C)nnc54)cc3)C2)C(C)(C)C)cc1] | 1059.7 | 1059.3 | B | 89.4 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 67 | 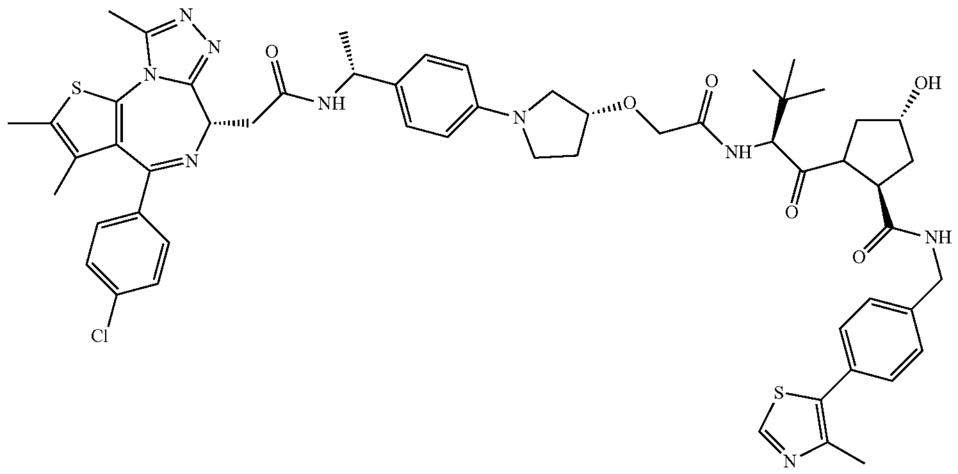 [SMILES: Cc1ncsc1-c1ccc(CNC(=O)[C@@H]2C[C@@H](O)CC2C(=O)[C@@H](NC(=O)CO[C@@H]2CCN(c3ccc([C@@H](C)NC(=O)C[C@@H]4N=C(c5ccc(Cl)cc5)c5c(sc(C)c5C)-n5c(C)nnc54)cc3)C2)C(C)(C)C)cc1] | 1059.7 | 1059.3 | B | 93.3 |
| 68 | 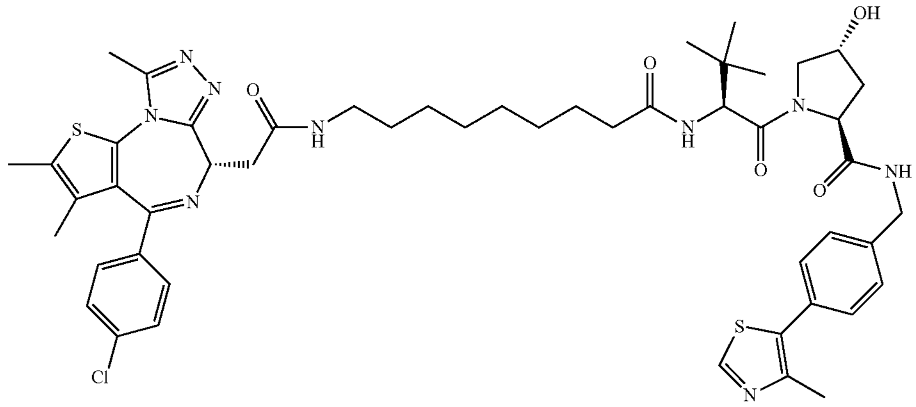 [SMILES: Cc1ncsc1-c1ccc(CNC(=O)[C@@H]2C[C@@H](O)CN2C(=O)[C@@H](NC(=O)CCCCCCCCNC(=O)C[C@@H]2N=C(c3ccc(Cl)cc3)c3c(sc(C)c3C)-n3c(C)nnc32)C(C)(C)C)cc1] | 0968.7 | 0968.4 | B | 95.4 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 69 | 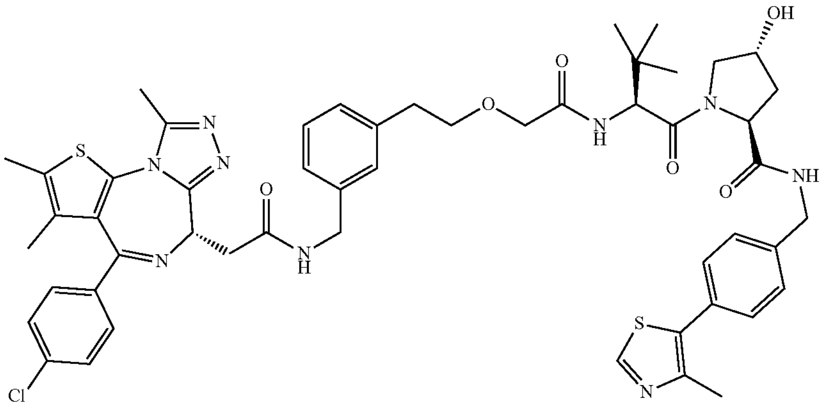 [SMILES: Cc1ncsc1-c1ccc(CNC(=O)[C@@H]2C[C@@H](O)CN2C(=O)[C@@H](NC(=O)COCCc2cccc(CNC(=O)C[C@@H]3N=C(c4ccc(Cl)cc4)c4c(sc(C)c4C)-n4c(C)nnc43)c2)C(C)(C)C)cc1] | 1004.7 | 1004.4 | B | 93.4 |
| 70 | 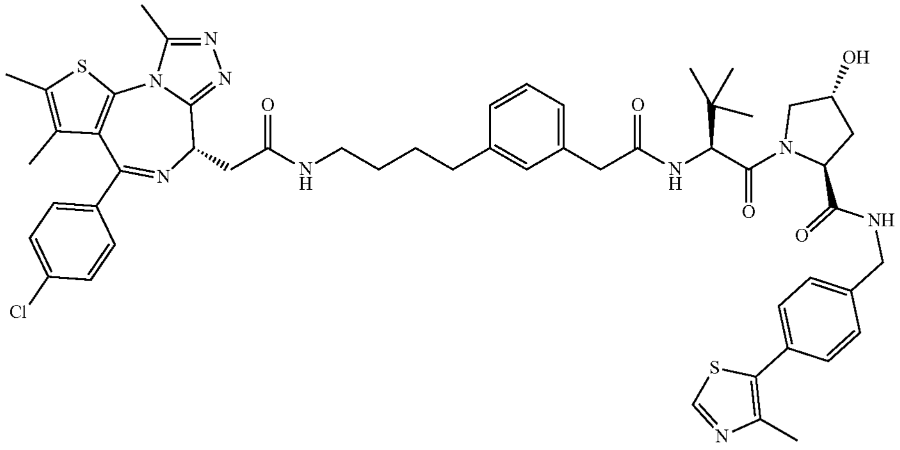 [SMILES: Cc1ncsc1-c1ccc(CNC(=O)[C@@H]2C[C@@H](O)CN2C(=O)[C@@H](NC(=O)Cc2cccc(CCCCNC(=O)C[C@@H]3N=C(c4ccc(Cl)cc4)c4c(sc(C)c4C)-n4c(C)nnc43)c2)C(C)(C)C)cc1] | 1002.7 | 1002.5 | B | 88.8 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 71 | 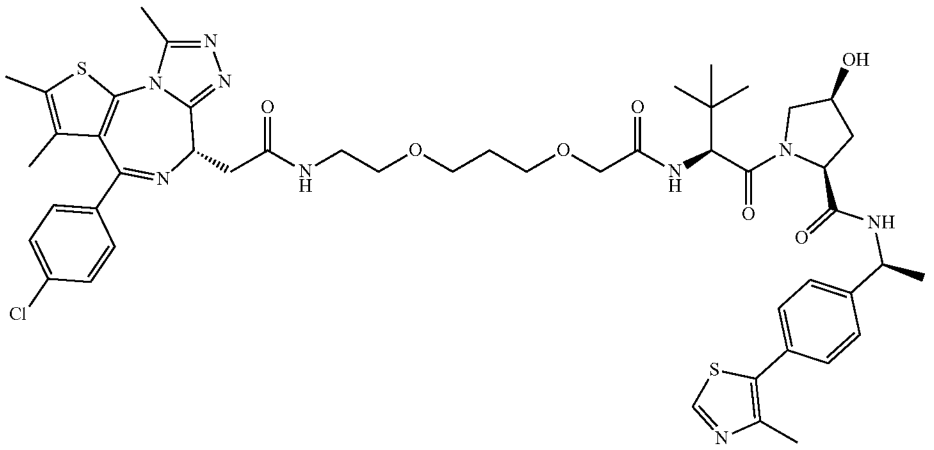 [SMILES: Cc1ncsc1-c1ccc([C@H](C)NC(=O)[C@@H]2C[C@H](O)CN2C(=O)[C@@H](NC(=O)COCCCOCCNC(=O)C[C@@H]2N=C(c3ccc(Cl)cc3)c3c(sc(C)c3C)-n3c(C)nnc32)C(C)(C)C)cc1] | 0986.6 | 0986.0 | D | 11.2 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 72 | 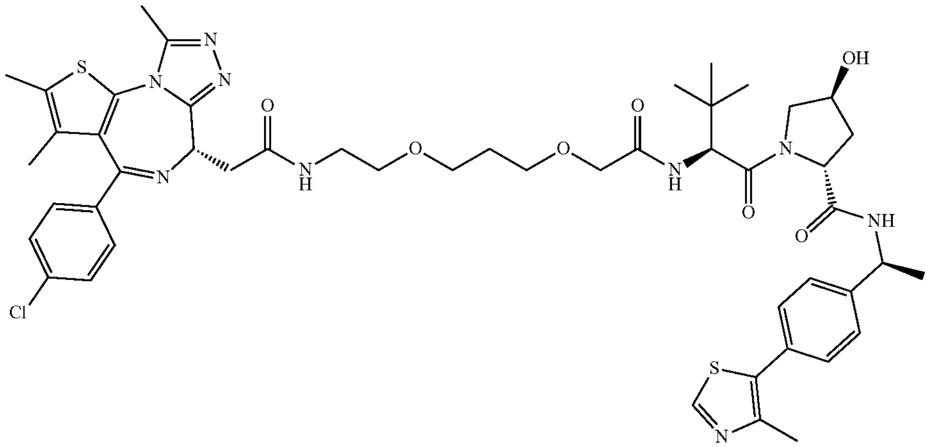 [SMILES: Cc1ncsc1-c1ccc([C@H](C)NC(=O)[C@H]2C[C@H](O)CN2C(=O)[C@@H](NC(=O)COCCCOCCNC(=O)C[C@@H]2N=C(c3ccc(Cl)cc3)c3c(sc(C)c3C)-n3c(C)nnc32)C(C)(C)C)cc1] | 0986.6 | 0986.0 | D | 10.2 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 73 | 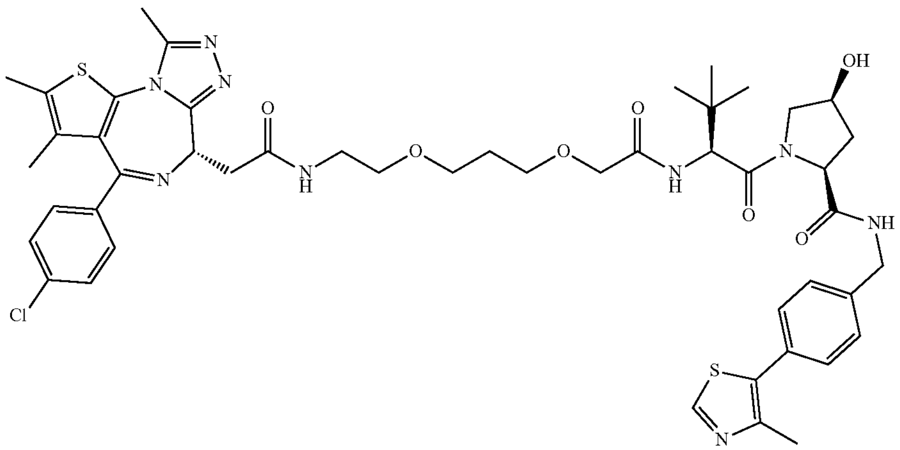 [SMILES: Cc1ncsc1-c1ccc(CNC(=O)[C@@H]2C[C@H](O)CN2C(=O)[C@@H](NC(=O)COCCCOCCNC(=O)C[C@@H]2N=C(c3ccc(Cl)cc3)c3c(sc(C)c3C)-n3c(C)nnc32)C(C)(C)C)cc1] | 0972.6 | 0973.0 | D | 21.4 |
| 74 | 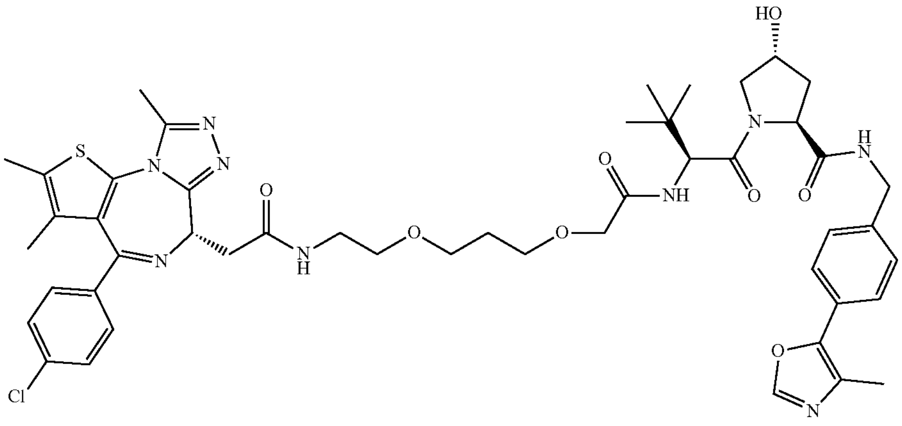 [SMILES: Cc1ncoc1-c1ccc(CNC(=O)[C@@H]2C[C@@H](O)CN2C(=O)[C@@H](NC(=O)COCCCOCCNC(=O)C[C@@H]2N=C(c3ccc(Cl)cc3)c3c(sc(C)c3C)-n3c(C)nnc32)C(C)(C)C)cc1] | 0956.5 | 0957.0 | B | 97.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 75 | 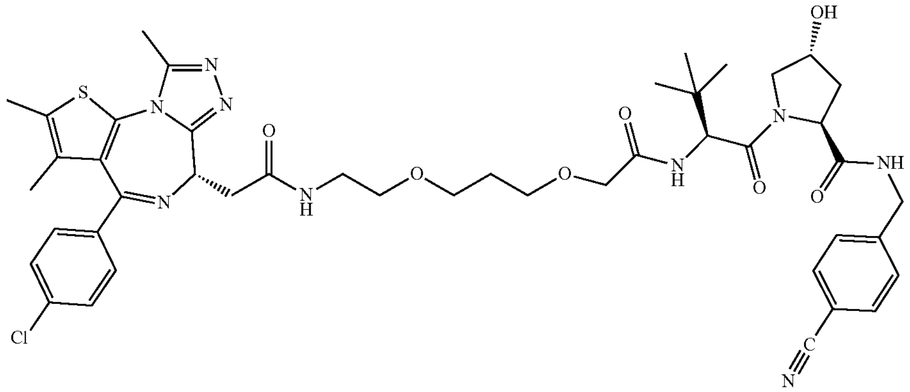 [SMILES: Cc1sc2c(c1C)C(c1ccc(Cl)cc1)=N[C@@H](CC(=O)NCCOCCCOCC(=O)N[C@H](C(=O)N1C[C@H](O)C[C@H]1C(=O)NCc1ccc(C#N)cc1)C(C)(C)C)c1nnc(C)n1-2] | 0900.5 | 0901.0 | C | 58.5 |
| 76 | 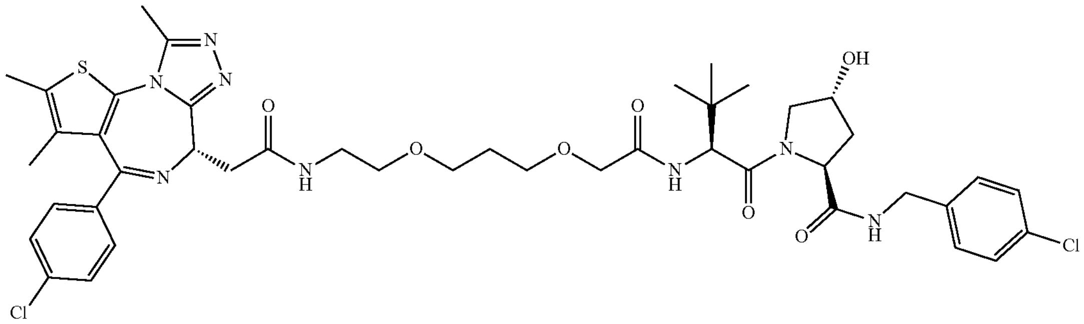 [SMILES: Cc1sc2c(c1C)C(c1ccc(Cl)cc1)=N[C@@H](CC(=O)NCCOCCCOCC(=O)N[C@H](C(=O)N1C[C@H](O)C[C@H]1C(=O)NCc1ccc(Cl)cc1)C(C)(C)C)c1nnc(C)n1-2] | 0909.9 | 0911.0 | C | 58.6 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 77 | 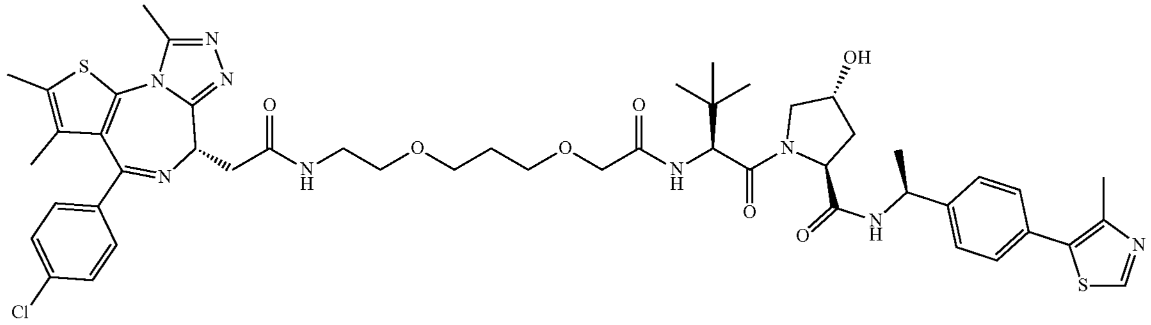 [SMILES: Cc1ncsc1-c1ccc([C@H](C)NC(=O)[C@@H]2C[C@@H](O)CN2C(=O)[C@@H](NC(=O)COCCCOCCNC(=O)C[C@@H]2N=C(c3ccc(Cl)cc3)c3c(sc(C)c3C)-n3c(C)nnc32)C(C)(C)C)cc1] | 0986.6 | 0986.4 | A | 100.0 |
| 78 | 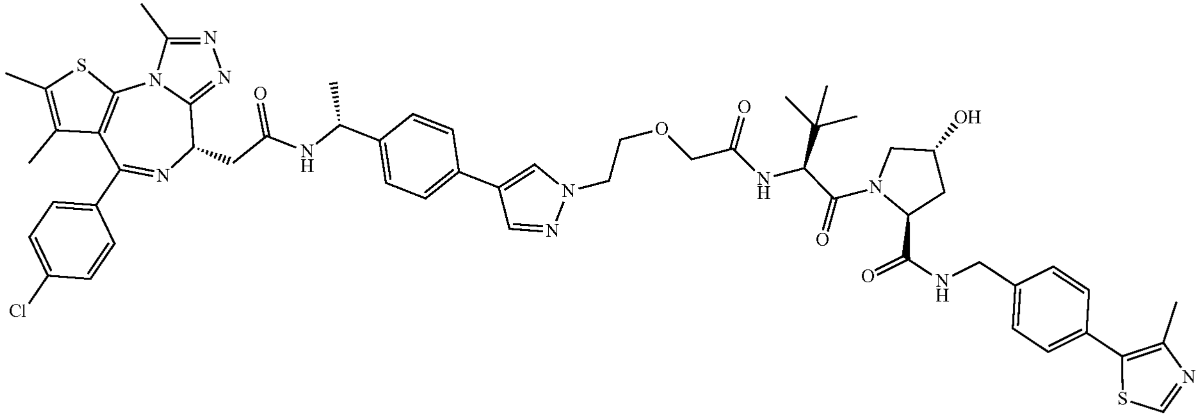 [SMILES: Cc1ncsc1-c1ccc(CNC(=O)[C@@H]2C[C@@H](O)CN2C(=O)[C@@H](NC(=O)COCCn2cc(-c3ccc([C@@H](C)NC(=O)C[C@@H]4N=C(c5ccc(Cl)cc5)c5c(sc(C)c5C)-n5c(C)nnc54)cc3)cn2)C(C)(C)C)cc1] | 1084.7 | 1084.2 | C | 86.7 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 79 | 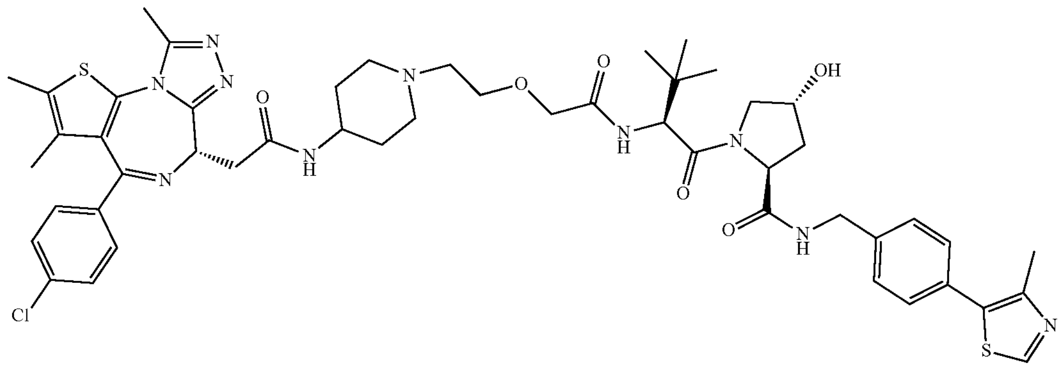 [SMILES: Cc1ncsc1-c1ccc(CNC(=O)[C@@H]2C[C@@H](O)CN2C(=O)[C@@H](NC(=O)COCCN2CCC(NC(=O)C[C@@H]3N=C(c4ccc(Cl)cc4)c4c(sc(C)c4C)-n4c(C)nnc43)CC2)C(C)(C)C)cc1] | 0997.7 | 0997.2 | D | 50.8 |
| 80 | 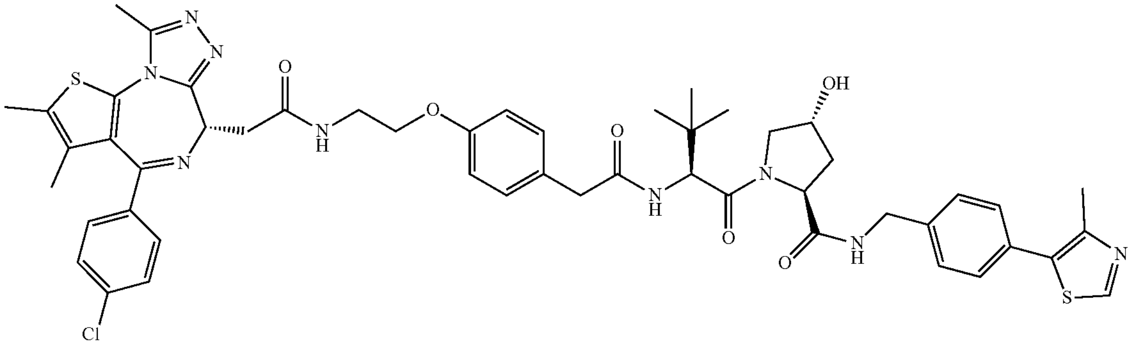 [SMILES: Cc1ncsc1-c1ccc(CNC(=O)[C@@H]2C[C@@H](O)CN2C(=O)[C@@H](NC(=O)Cc2ccc(OCCNC(=O)C[C@@H]3N=C(c4ccc(Cl)cc4)c4c(sc(C)c4C)-n4c(C)nnc43)cc2)C(C)(C)C)cc1] | 0990.6 | 0990.3 | B | 97.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 81 | 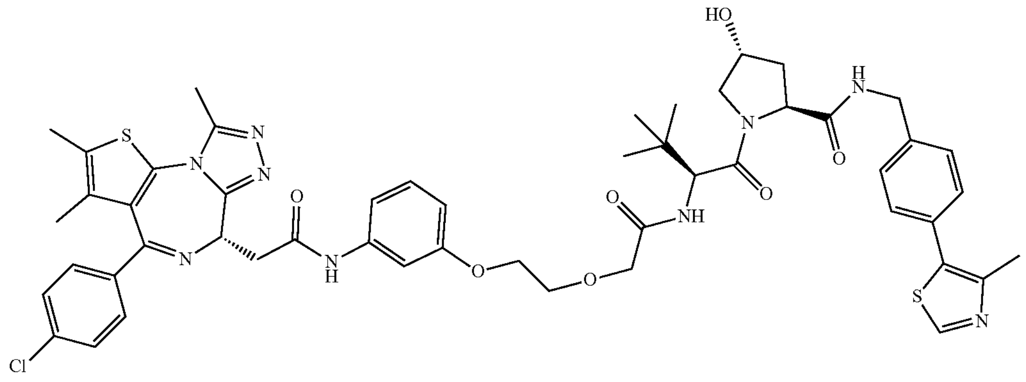 [SMILES: Cc1ncsc1-c1ccc(CNC(=O)[C@@H]2C[C@@H](O)CN2C(=O)[C@@H](NC(=O)COCCOc2cccc(NC(=O)C[C@@H]3N=C(c4ccc(Cl)cc4)c4c(sc(C)c4C)-n4c(C)nnc43)c2)C(C)(C)C)cc1] | 1006.6 | 1006.3 | B | 99.0 |
| 82 | 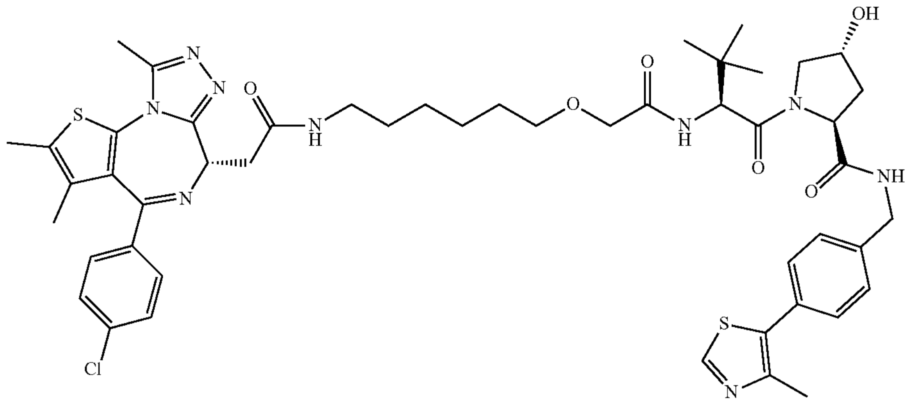 [SMILES: Cc1ncsc1-c1ccc(CNC(=O)[C@@H]2C[C@@H](O)CN2C(=O)[C@@H](NC(=O)COCCCCCCNC(=O)C[C@@H]2N=C(c3ccc(Cl)cc3)c3c(sc(C)c3C)-n3c(C)nnc32)C(C)(C)C)cc1] | 0970.6 | 0970.7 | B | 100 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 83 | 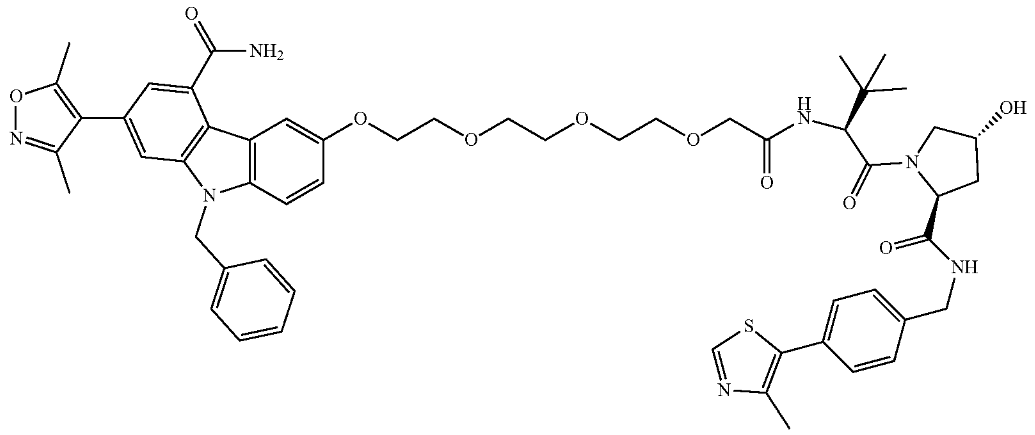 [SMILES: Cc1ncsc1-c1ccc(CNC(=O)[C@@H]2C[C@@H](O)CN2C(=O)[C@@H](NC(=O)COCCOCCOCCOc2ccc3c(c2)c2c(C(N)=O)cc(-c4c(C)noc4C)cc2n3Cc2ccccc2)C(C)(C)C)cc1] | 1014.2 | 1015.3 | B | 98.0 |
| 84 | 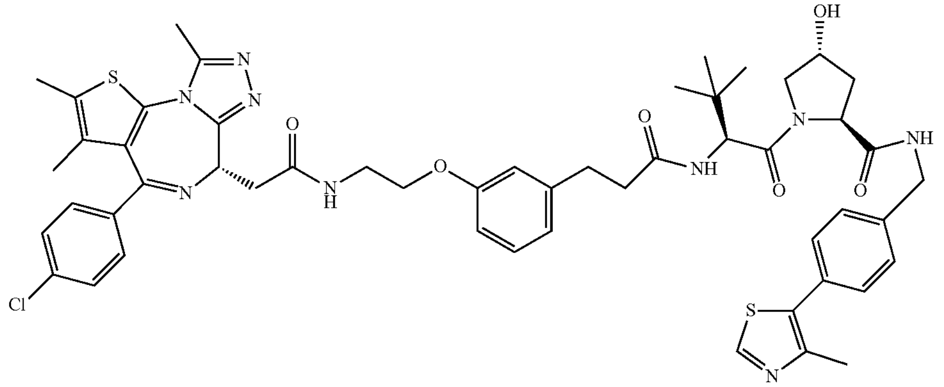 [SMILES: Cc1ncsc1-c1ccc(CNC(=O)[C@@H]2C[C@@H](O)CN2C(=O)[C@@H](NC(=O)CCc2cccc(OCCNC(=O)C[C@@H]3N=C(c4ccc(Cl)cc4)c4c(sc(C)c4C)-n4c(C)nnc43)c2)C(C)(C)C)cc1] | 1004.7 | 1005.0 | A | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 85 | 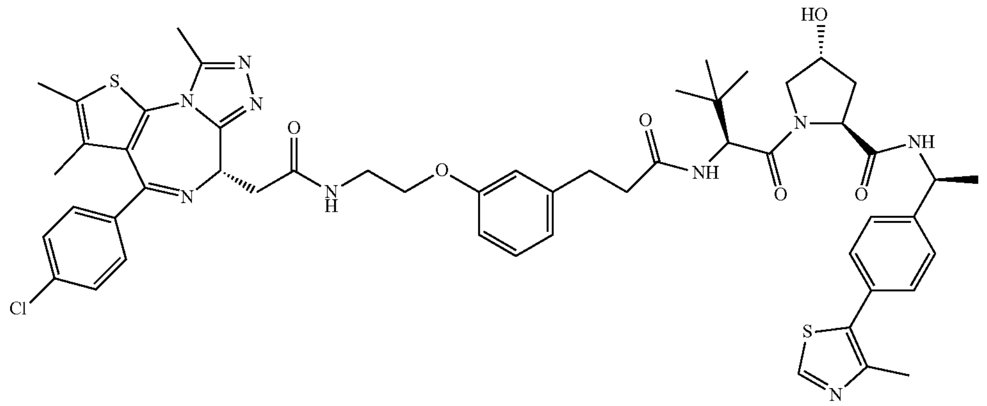 [SMILES: Cc1ncsc1-c1ccc([C@H](C)NC(=O)[C@@H]2C[C@@H](O)CN2C(=O)[C@@H](NC(=O)CCc2cccc(OCCNC(=O)C[C@@H]3N=C(c4ccc(Cl)cc4)c4c(sc(C)c4C)-n4c(C)nnc43)c2)C(C)(C)C)cc1] | 1018.7 | 1019.0 | A | 100 |
| 86 | 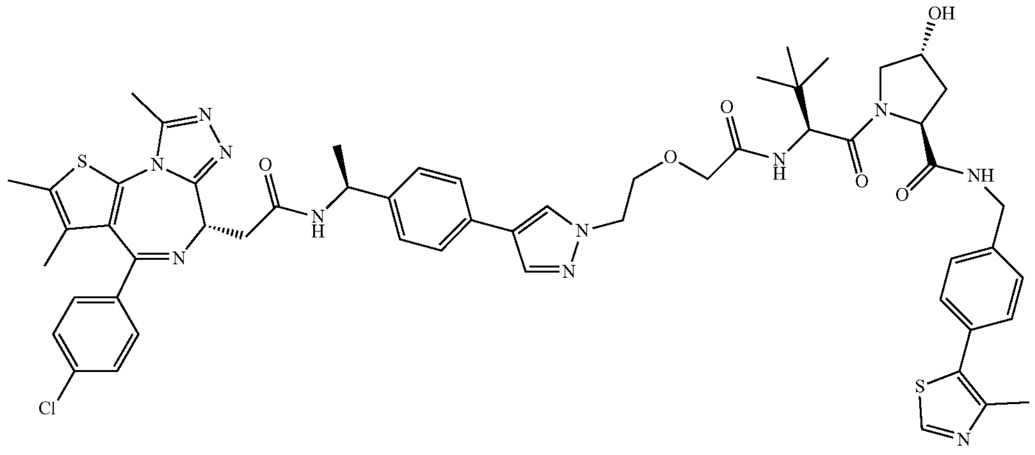 | 1084.7 | 1084.4 | C | 80.0 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 87 | 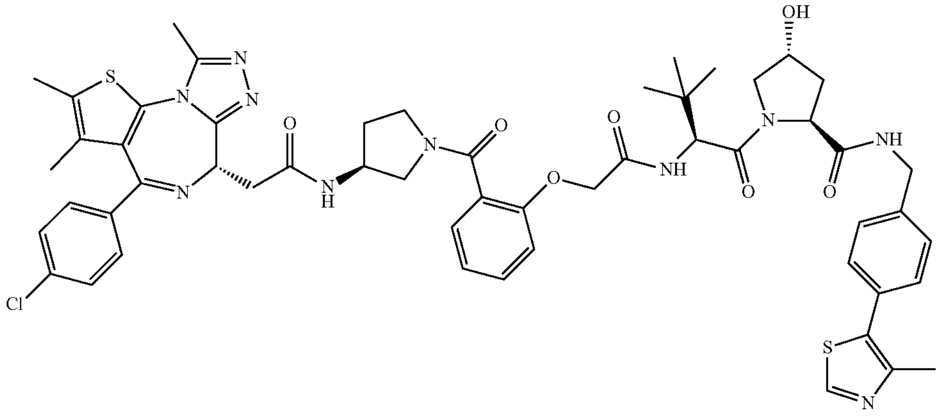 [SMILES: Cc1ncsc1-c1ccc(CNC(=O)[C@@H]2C[C@@H](O)CN2C(=O)[C@@H](NC(=O)COc2ccccc2C(=O)N2CC[C@H](NC(=O)C[C@@H]3N=C(c4ccc(Cl)cc4)c4c(sc(C)c4C)-n4c(C)nnc43)C2)C(C)(C)C)cc1] | 1059.7 | 1059.3 | B | 96.4 |
| 88 | 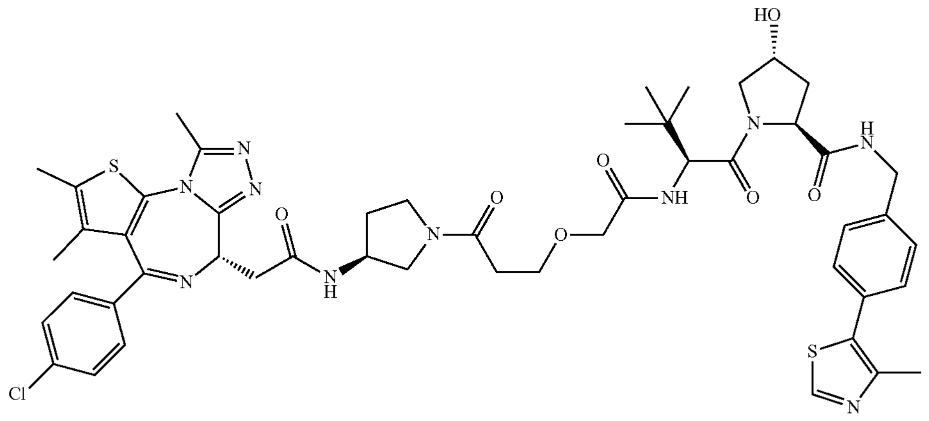 [SMILES: Cc1ncsc1-c1ccc(CNC(=O)[C@@H]2C[C@@H](O)CN2C(=O)[C@@H](NC(=O)COCCC(=O)N2CC[C@H](NC(=O)C[C@@H]3N=C(c4ccc(Cl)cc4)c4c(sc(C)c4C)-n4c(C)nnc43)C2)C(C)(C)C)cc1] | 1011.6 | 1011.4 | C | 85.9 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 89 | 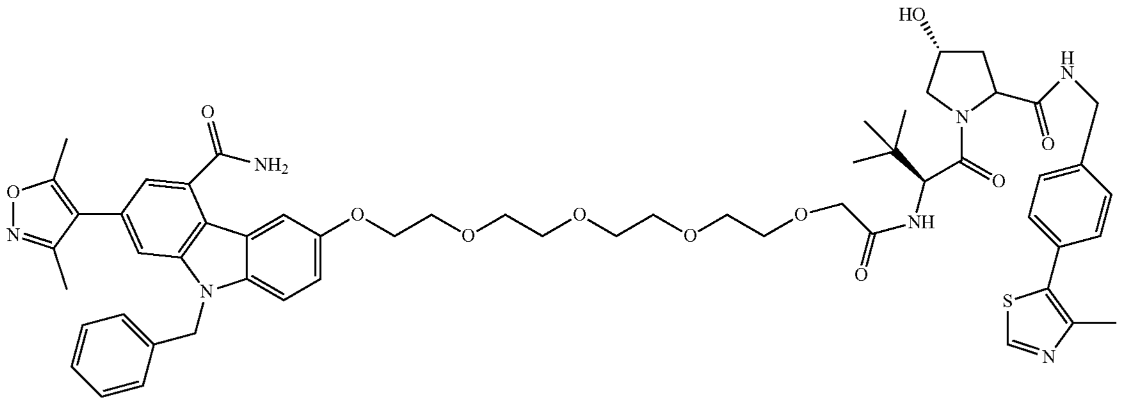 [SMILES: Cc1ncsc1-c1ccc(CNC(=O)C2C[C@@H](O)CN2C(=O)[C@@H](NC(=O)COCCOCCOCCOCCOc2ccc3c(c2)c2c(C(N)=O)cc(-c4c(C)noc4C)cc2n3Cc2ccccc2)C(C)(C)C)cc1] | 1058.2 | 1058.3 | B | 99.5 |
| 90 | 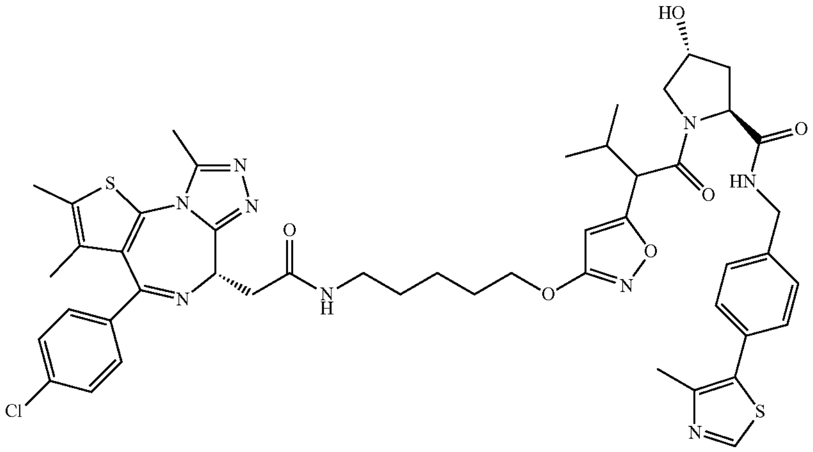 [SMILES: Cc1ncsc1-c1ccc(CNC(=O)[C@@H]2C[C@@H](O)CN2C(=O)C(c2cc(OCCCCCNC(=O)C[C@@H]3N=C(c4ccc(Cl)cc4)c4c(sc(C)c4C)-n4c(C)nnc43)no2)C(C)C)cc1] | 0952.6 | 0952.3 | A | 100 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 91 | 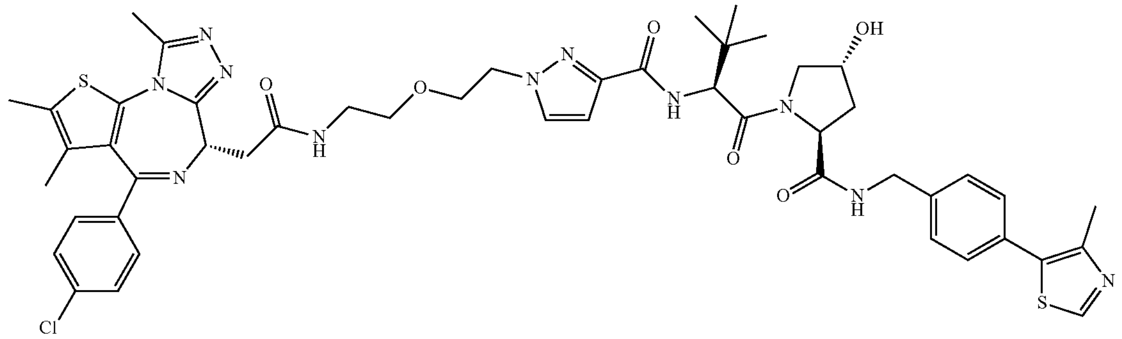 [SMILES: Cc1ncsc1-c1ccc(CNC(=O)[C@@H]2C[C@@H](O)CN2C(=O)[C@@H](NC(=O)c2ccn(CCOCCNC(=O)C[C@@H]3N=C(c4ccc(Cl)cc4)c4c(sc(C)c4C)-n4c(C)nnc43)n2)C(C)(C)C)cc1] | 0994.6 | 0994.4 | D | <5 |
| 92 | 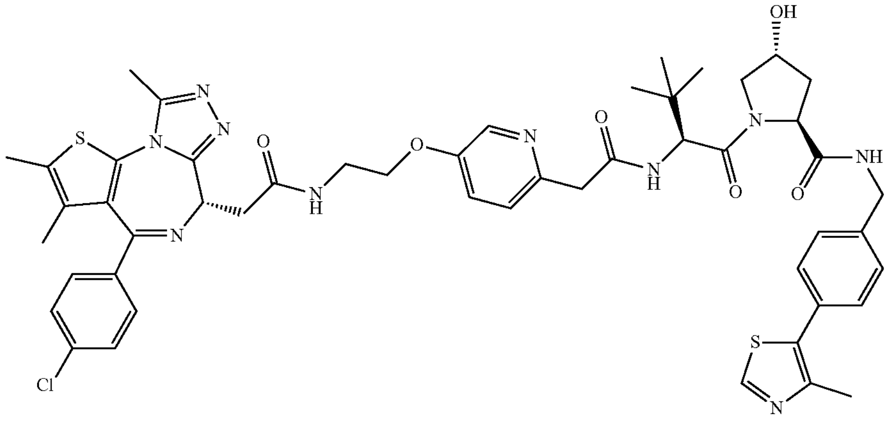 [SMILES: Cc1ncsc1-c1ccc(CNC(=O)[C@@H]2C[C@@H](O)CN2C(=O)[C@@H](NC(=O)Cc2ccc(OCCNC(=O)C[C@@H]3N=C(c4ccc(Cl)cc4)c4c(sc(C)c4C)-n4c(C)nnc43)cn2)C(C)(C)C)cc1] | 0991.6 | 0991.3 | C | 91.1 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 93 | 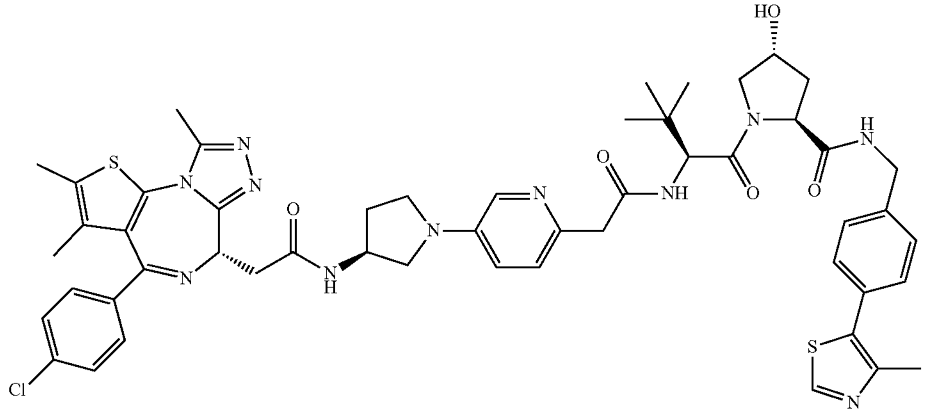 [SMILES: Cc1ncsc1-c1ccc(CNC(=O)[C@@H]2C[C@@H](O)CN2C(=O)[C@@H](NC(=O)Cc2ccc(N3CC[C@H](NC(=O)C[C@@H]4N=C(c5ccc(Cl)cc5)c5c(sc(C)c5C)-n5c(C)nnc54)C3)cn2)C(C)(C)C)cc1] | 1016.7 | 1016.4 | C | 74.2 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 94 | 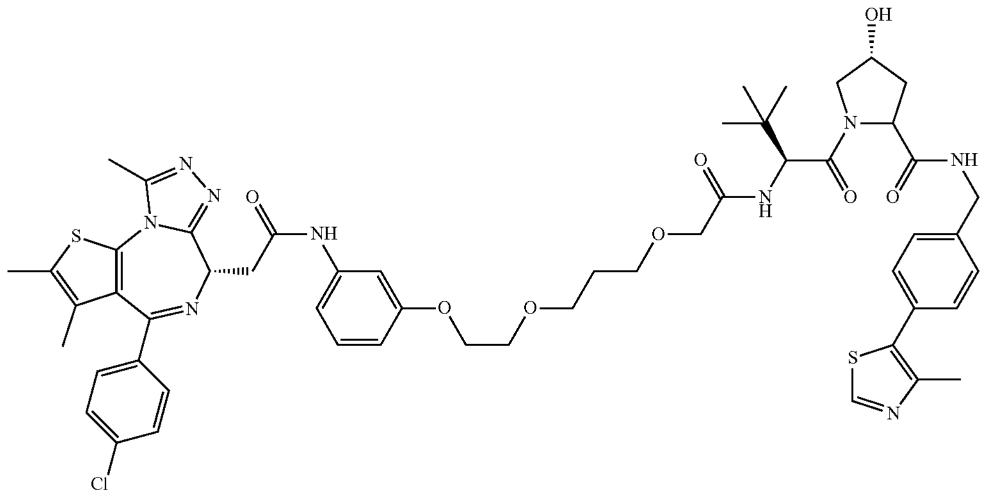 [SMILES: Cc1ncsc1-c1ccc(CNC(=O)C2C[C@@H](O)CN2C(=O)[C@@H](NC(=O)COCCCOCCOc2cccc(NC(=O)C[C@@H]3N=C(c4ccc(Cl)cc4)c4c(sc(C)c4C)-n4c(C)nnc43)c2)C(C)(C)C)cc1] | 1064.7 | 1064.4 | A | 98.5 |
| 95 | 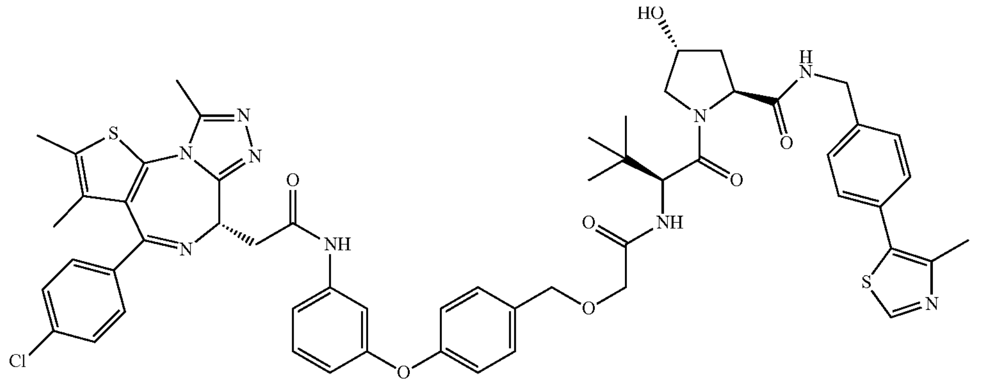 [SMILES: Cc1ncsc1-c1ccc(CNC(=O)[C@@H]2C[C@@H](O)CN2C(=O)[C@@H](NC(=O)COCc2ccc(Oc3cccc(NC(=O)C[C@@H]4N=C(c5ccc(Cl)cc5)c5c(sc(C)c5C)-n5c(C)nnc54)c3)cc2)C(C)(C)C)cc1] | 1068.7 | 1068.3 | A | 99.5 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 96 | 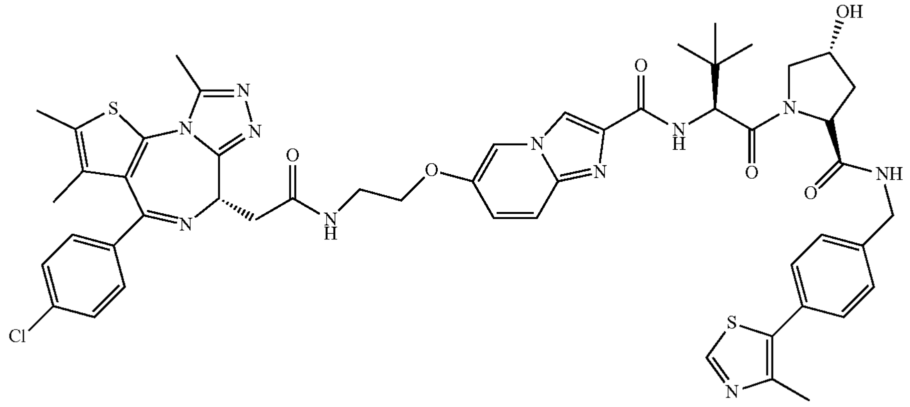 | 1016.6 | 1016.4 | C | 67.9 |
| 97 | 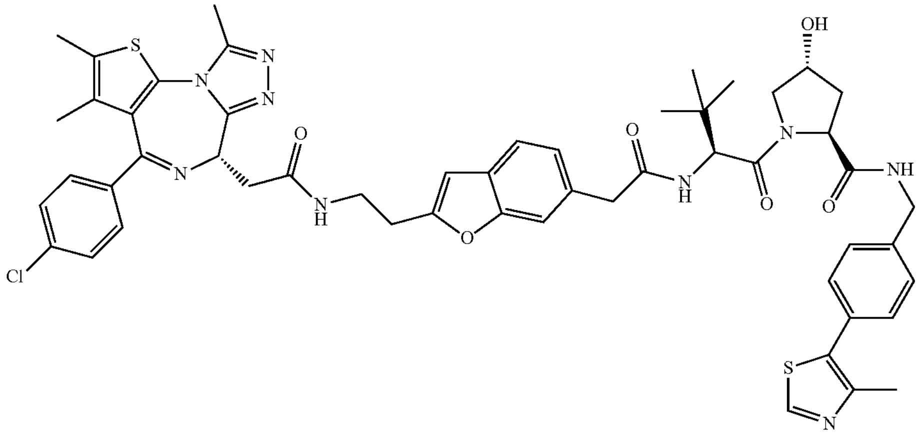 [SMILES: Cc1ncsc1-c1ccc(CNC(=O)[C@@H]2C[C@@H](O)CN2C(=O)[C@@H](NC(=O)Cc2ccc3cc(CCNC(=O)C[C@@H]4N=C(c5ccc(Cl)cc5)c5c(sc(C)c5C)-n5c(C)nnc54)oc3c2)C(C)(C)C)cc1] | 1014.7 | 1014.5 | A | 100 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 98 | 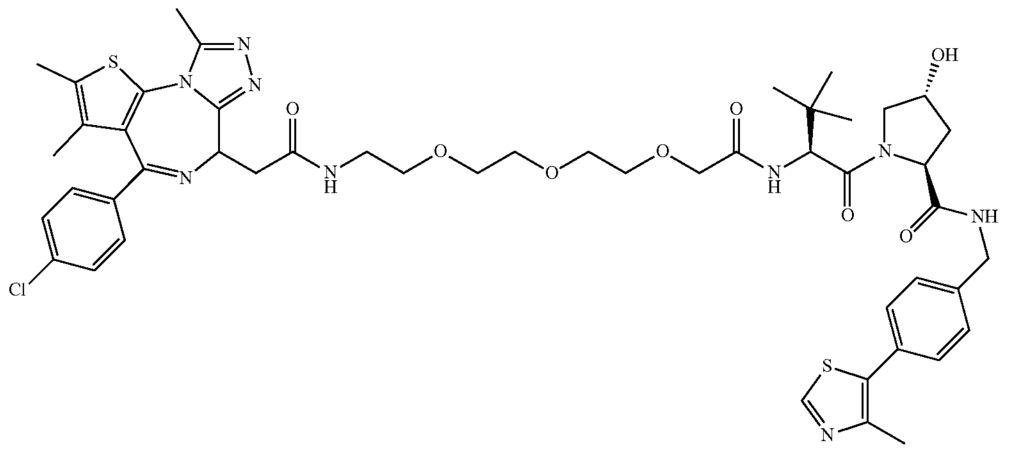 [SMILES: Cc1ncsc1-c1ccc(CNC(=O)[C@@H]2C[C@@H](O)CN2C(=O)[C@@H](NC(=O)COCCOCCOCCNC(=O)CC2N=C(c3ccc(Cl)cc3)c3c(sc(C)c3C)-n3c(C)nnc32)C(C)(C)C)cc1] | 1002.6 | 1002.4 | B | 100 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 99 | 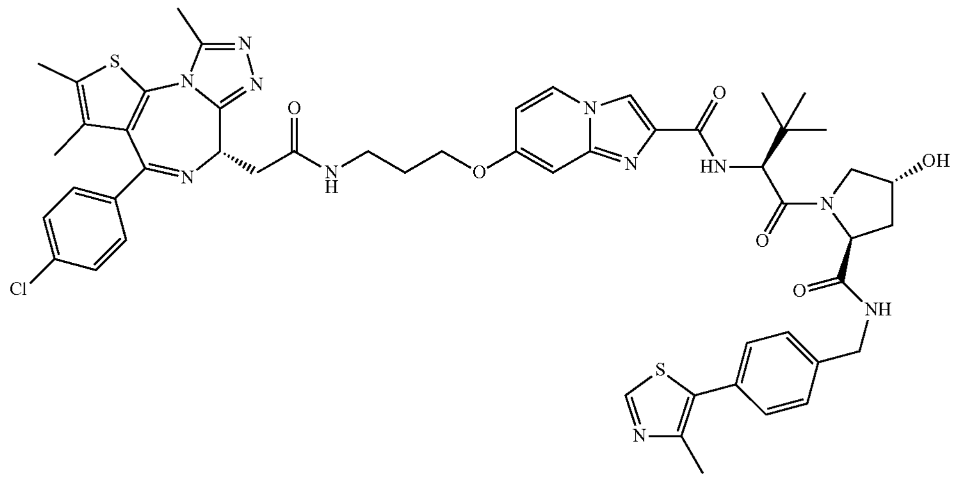 [SMILES: Cc1ncsc1-c1ccc(CNC(=O)[C@@H]2C[C@@H](O)CN2C(=O)[C@@H](NC(=O)c2cn3ccc(OCCCNC(=O)C[C@@H]4N=C(c5ccc(Cl)cc5)c5c(sc(C)c5C)-n5c(C)nnc54)cc3n2)C(C)(C)C)cc1] | 1030.7 | 1030.4 | C | 67.0 |
| 100 | 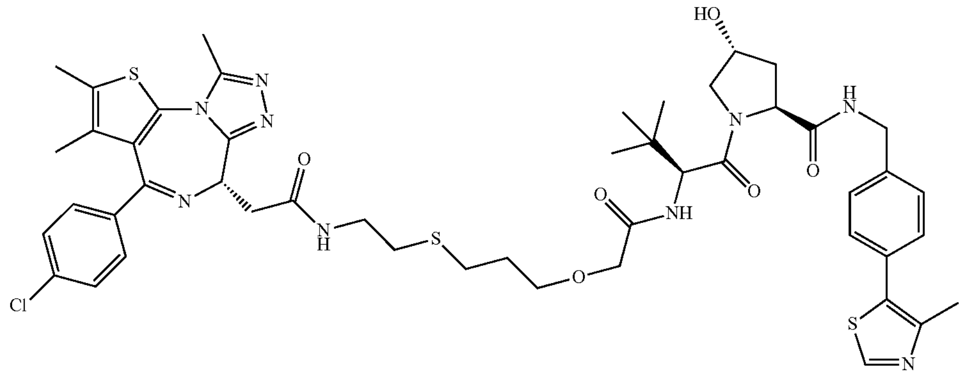 [SMILES: Cc1ncsc1-c1ccc(CNC(=O)[C@@H]2C[C@@H](O)CN2C(=O)[C@@H](NC(=O)COCCCSCCNC(=O)C[C@@H]2N=C(c3ccc(Cl)cc3)c3c(sc(C)c3C)-n3c(C)nnc32)C(C)(C)C)cc1] | 0988.7 | 0988.4 | B | 99.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 101 | 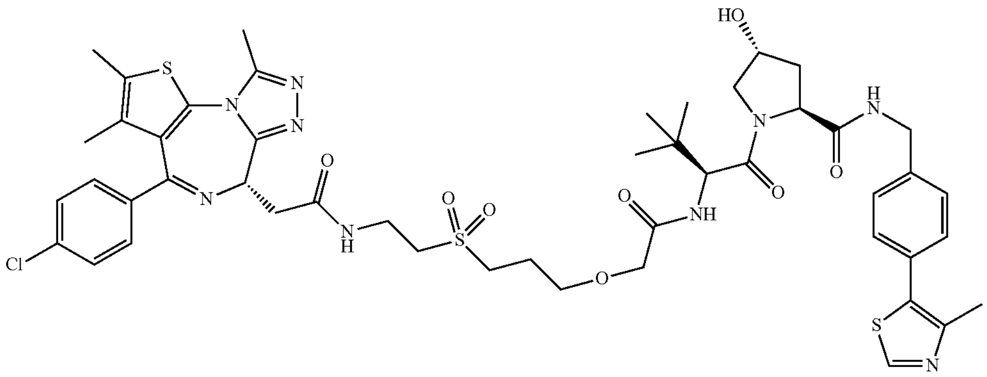 [SMILES: Cc1ncsc1-c1ccc(CNC(=O)[C@@H]2C[C@@H](O)CN2C(=O)[C@@H](NC(=O)COCCCS(=O)(=O)CCNC(=O)C[C@@H]2N=C(c3ccc(Cl)cc3)c3c(sc(C)c3C)-n3c(C)nnc32)C(C)(C)C)cc1] | 1020.7 | 1020.3 | C | 88.3 |
| 102 | 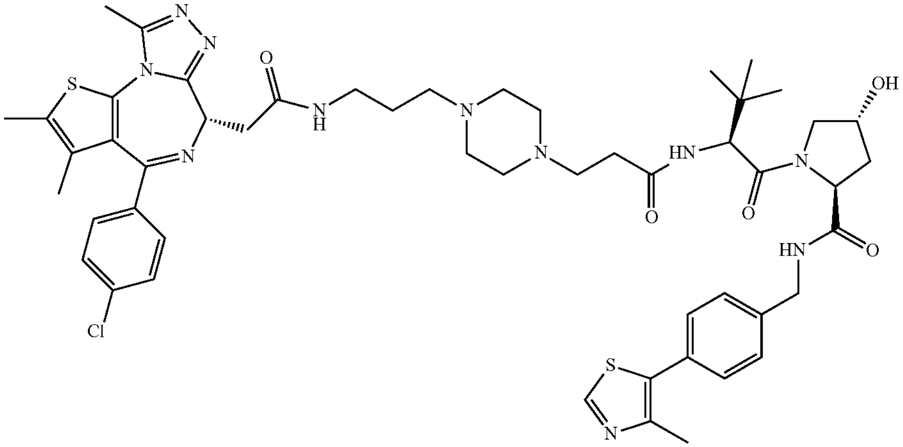 [SMILES: Cc1ncsc1-c1ccc(CNC(=O)[C@@H]2C[C@@H](O)CN2C(=O)[C@@H](NC(=O)CCN2CCN(CCCNC(=O)C[C@@H]3N=C(c4ccc(Cl)cc4)c4c(sc(C)c4C)-n4c(C)nnc43)CC2)C(C)(C)C)cc1] | 1010.7 | 1010.5 | D | 34.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 103 | 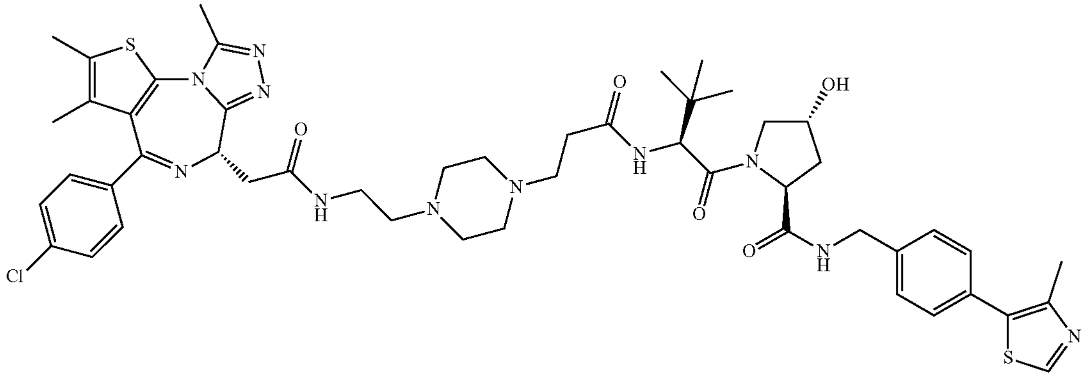 [SMILES: Cc1ncsc1-c1ccc(CNC(=O)[C@@H]2C[C@@H](O)CN2C(=O)[C@@H](NC(=O)CCN2CCN(CCNC(=O)C[C@@H]3N=C(c4ccc(Cl)cc4)c4c(sc(C)c4C)-n4c(C)nnc43)CC2)C(C)(C)C)cc1] | 0996.7 | 0996.4 | C | 62.5 |
| 104 | 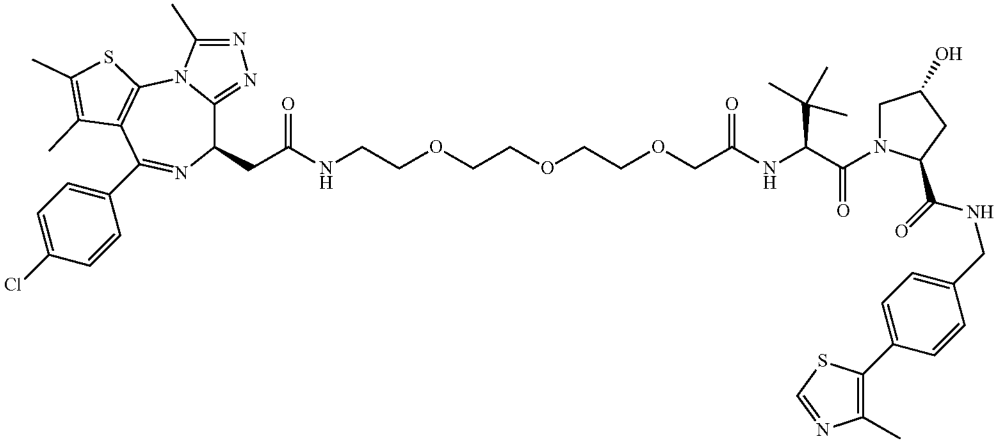 [SMILES: Cc1ncsc1-c1ccc(CNC(=O)[C@@H]2C[C@@H](O)CN2C(=O)[C@@H](NC(=O)COCCOCCOCCNC(=O)C[C@H]2N=C(c3ccc(Cl)cc3)c3c(sc(C)c3C)-n3c(C)nnc32)C(C)(C)C)cc1] | 1002.6 | 1002.1 | D | <5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 105 | 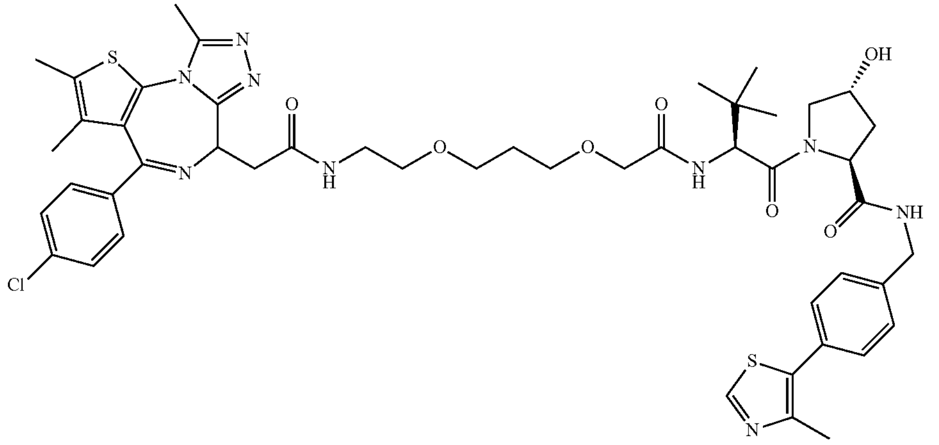 [SMILES: Cc1ncsc1-c1ccc(CNC(=O)[C@@H]2C[C@@H](O)CN2C(=O)[C@@H](NC(=O)COCCCOCCNC(=O)CC2N=C(c3ccc(Cl)cc3)c3c(sc(C)c3C)-n3c(C)nnc32)C(C)(C)C)cc1] | 0972.6 | 0972.4 | B | 97.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 106 | 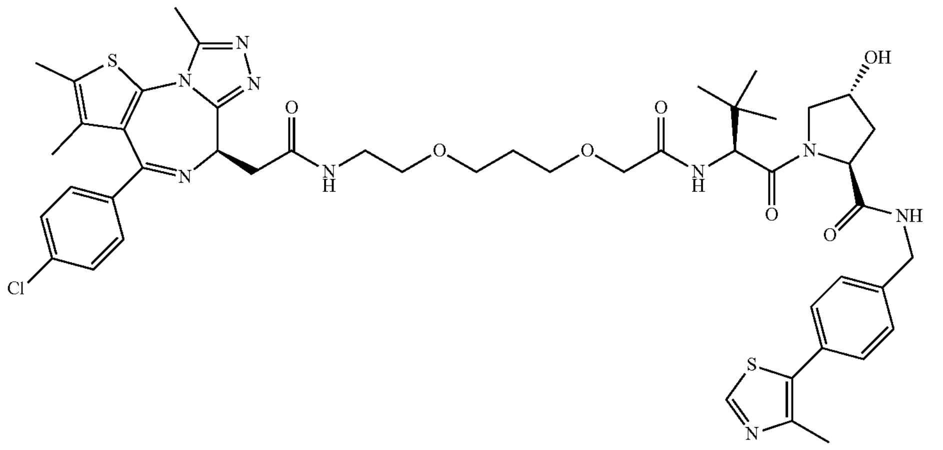 [SMILES: Cc1ncsc1-c1ccc(CNC(=O)[C@@H]2C[C@@H](O)CN2C(=O)[C@@H](NC(=O)COCCCOCCNC(=O)C[C@H]2N=C(c3ccc(Cl)cc3)c3c(sc(C)c3C)-n3c(C)nnc32)C(C)(C)C)cc1] | 0972.6 | 0972.4 | D | <5 |
| 107 | 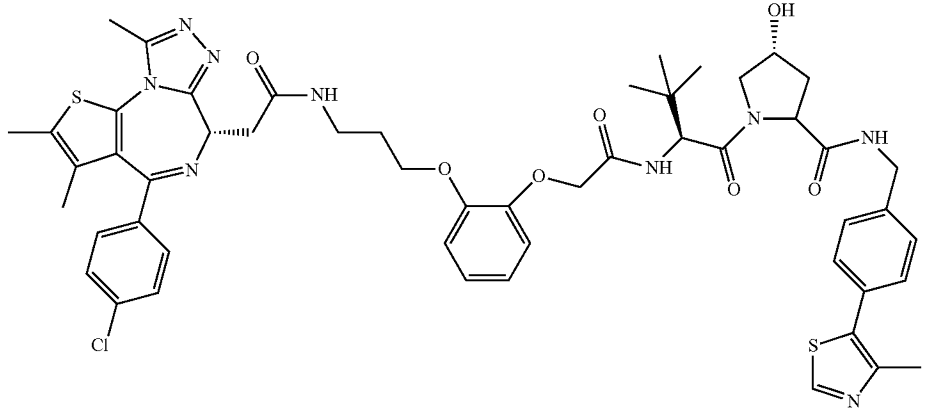 | 1020.7 | 1020.4 | B | 86.6 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 108 | 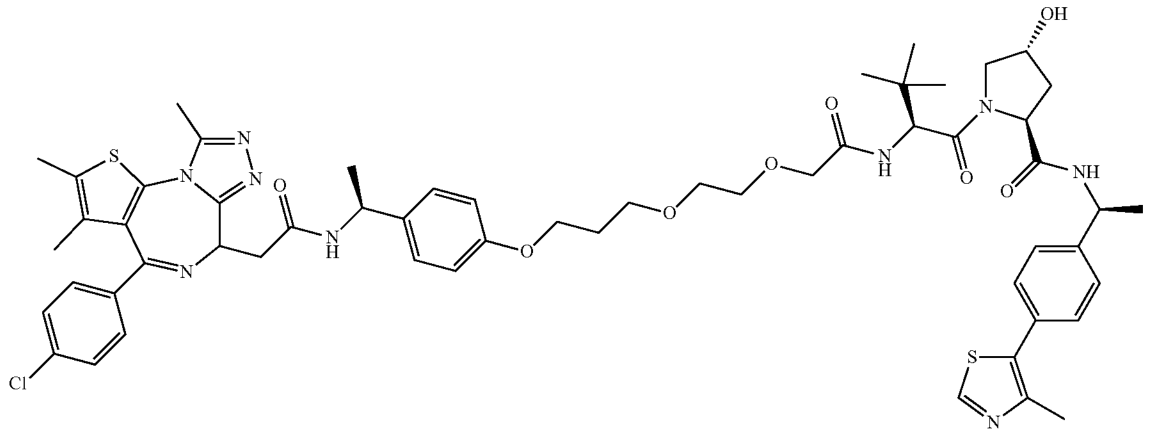 [SMILES: Cc1ncsc1-c1ccc([C@H](C)NC(=O)[C@@H]2C[C@@H](O)CN2C(=O)[C@@H](NC(=O)COCCOCCCOc2ccc([C@H](C)NC(=O)CC3N=C(c4ccc(Cl)cc4)c4c(sc(C)c4C)-n4c(C)nnc43)cc2)C(C)(C)C)cc1] | 1106.8 | 1106.4 | C | 95.4 |
| 109 | 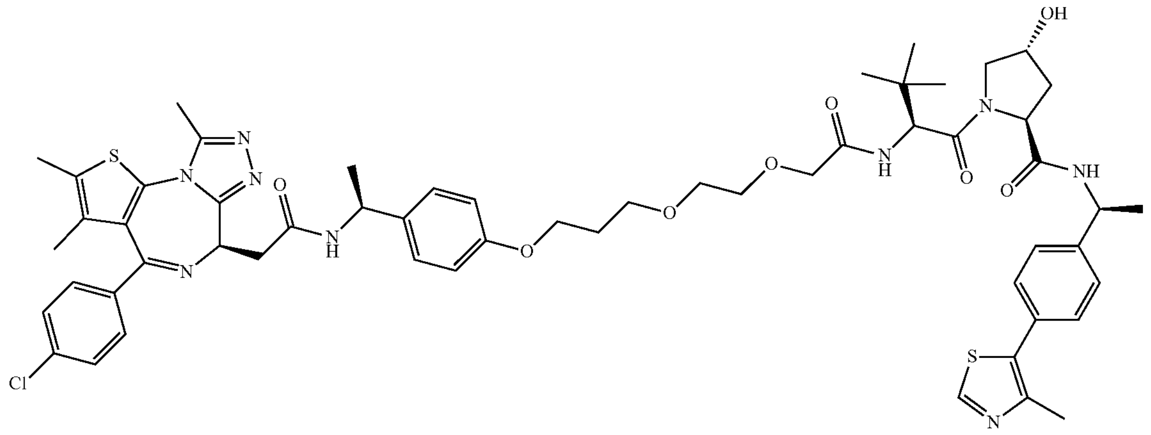 [SMILES: Cc1ncsc1-c1ccc([C@H](C)NC(=O)[C@@H]2C[C@@H](O)CN2C(=O)[C@@H](NC(=O)COCCOCCCOc2ccc([C@H](C)NC(=O)C[C@H]3N=C(c4ccc(Cl)cc4)c4c(sc(C)c4C)-n4c(C)nnc43)cc2)C(C)(C)C)cc1] | 1106.8 | 1106.4 | D | <5 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 110 | 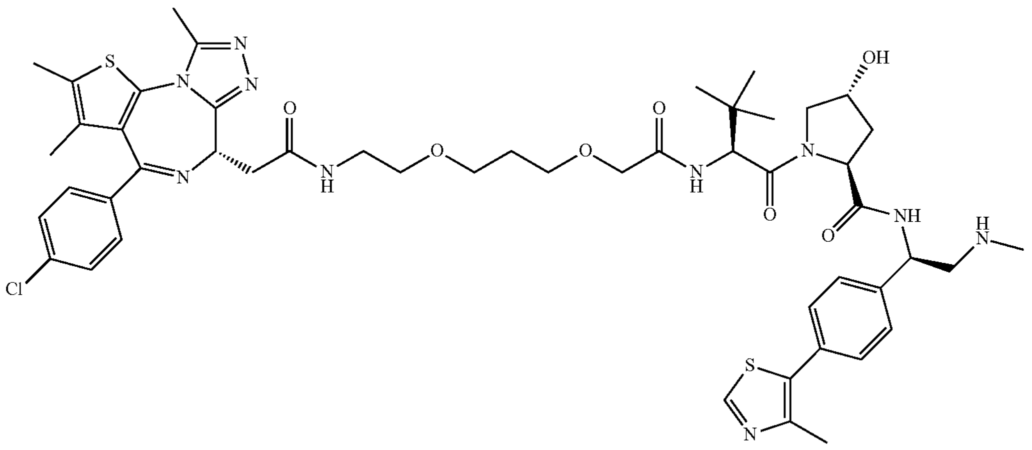 [SMILES: CNC[C@H](NC(=O)[C@@H]1C[C@@H](O)CN1C(=O)[C@@H](NC(=O)COCCCOCCNC(=O)C[C@@H]1N=C(c2ccc(Cl)cc2)c2c(sc(C)c2C)-n2c(C)nnc21)C(C)(C)C)c1ccc(-c2scnc2C)cc1] | 1015.7 | 1015.2 | D | 7.14 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 111 | 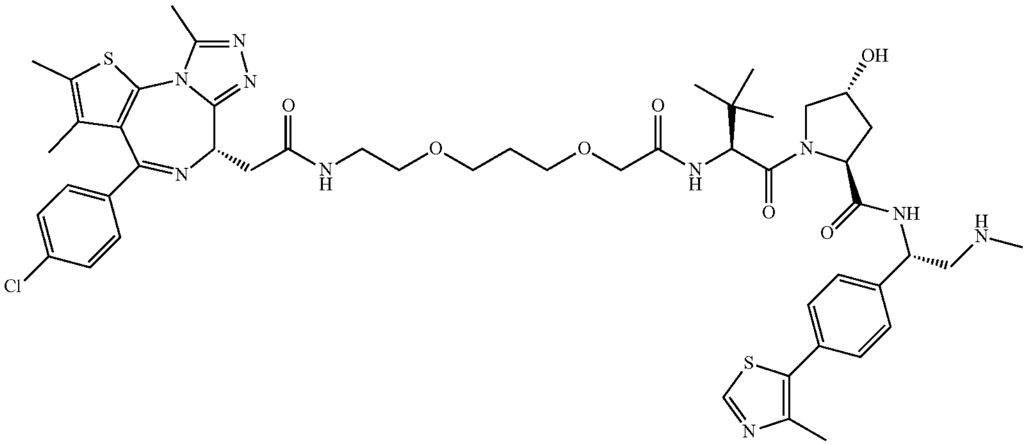 [SMILES: CNC[C@@H](NC(=O)[C@@H]1C[C@@H](O)CN1C(=O)[C@@H](NC(=O)COCCCOCCNC(=O)C[C@@H]1N=C(c2ccc(Cl)cc2)c2c(sc(C)c2C)-n2c(C)nnc21)C(C)(C)C)c1ccc(-c2scnc2C)cc1] | 1015.7 | 1015.2 | D | 47.3 |
| 112 | 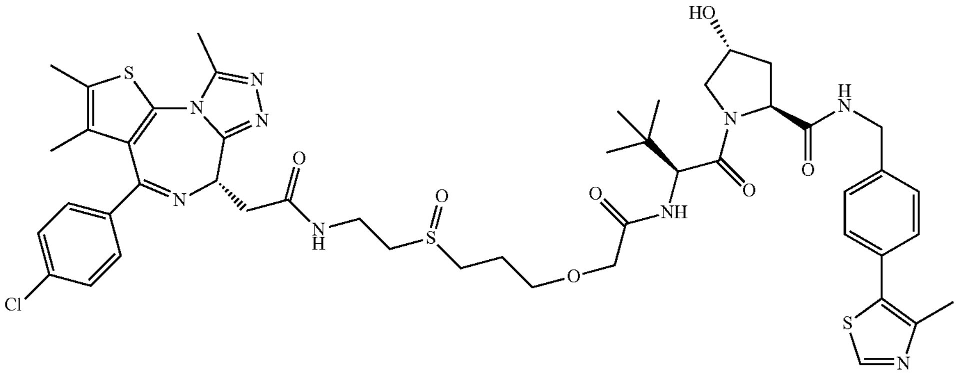 [SMILES: Cc1ncsc1-c1ccc(CNC(=O)[C@@H]2C[C@@H](O)CN2C(=O)[C@@H](NC(=O)COCCCS(=O)CCNC(=O)C[C@@H]2N=C(c3ccc(Cl)cc3)c3c(sc(C)c3C)-n3c(C)nnc32)C(C)(C)C)cc1] | 1004.7 | 1004.3 | D | 26.8 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 113 | 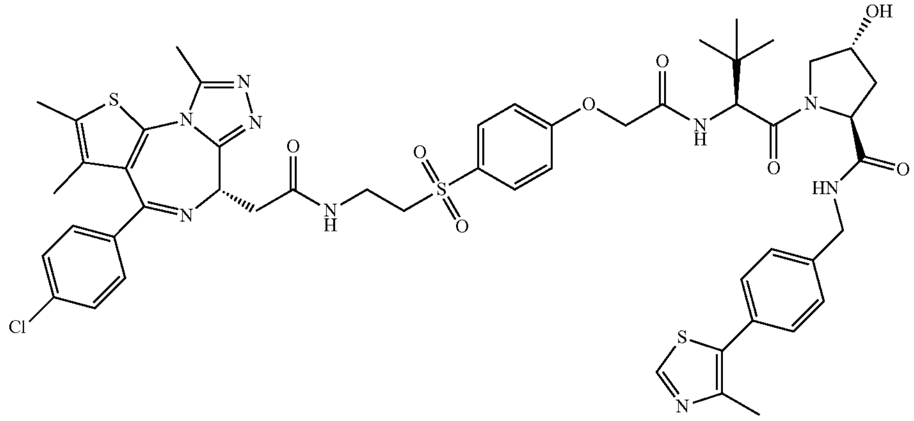 [SMILES: Cc1ncsc1-c1ccc(CNC(=O)[C@@H]2C[C@@H](O)CN2C(=O)[C@@H](NC(=O)COc2ccc(S(=O)(=O)CCNC(=O)C[C@@H]3N=C(c4ccc(Cl)cc4)c4c(sc(C)c4C)-n4c(C)nnc43)cc2)C(C)(C)C)cc1] | 1054.7 | 1054.3 | B | 88.5 |
| 114 | 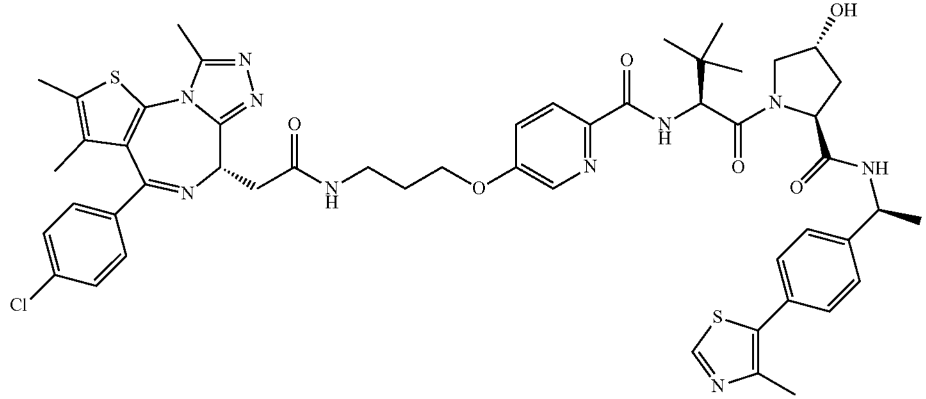 [SMILES: Cc1ncsc1-c1ccc([C@H](C)NC(=O)[C@@H]2C[C@@H](O)CN2C(=O)[C@@H](NC(=O)c2ccc(OCCCNC(=O)C[C@@H]3N=C(c4ccc(Cl)cc4)c4c(sc(C)c4C)-n4c(C)nnc43)cn2)C(C)(C)C)cc1] | 1005.6 | 1005.4 | A | 99.5 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 115 | 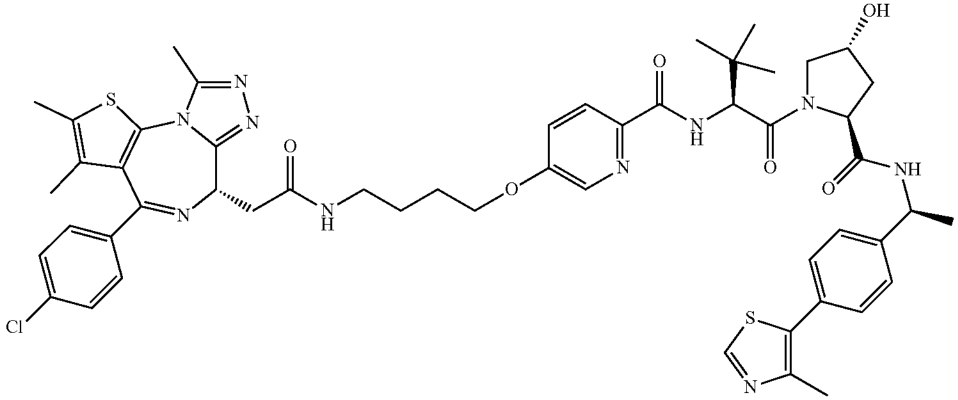 [SMILES: Cc1ncsc1-c1ccc([C@H](C)NC(=O)[C@@H]2C[C@@H](O)CN2C(=O)[C@@H](NC(=O)c2ccc(OCCCCNC(=O)C[C@@H]3N=C(c4ccc(Cl)cc4)c4c(sc(C)c4C)-n4c(C)nnc43)cn2)C(C)(C)C)cc1] | 1019.7 | 1019.1 | A | 100 |
| 116 | 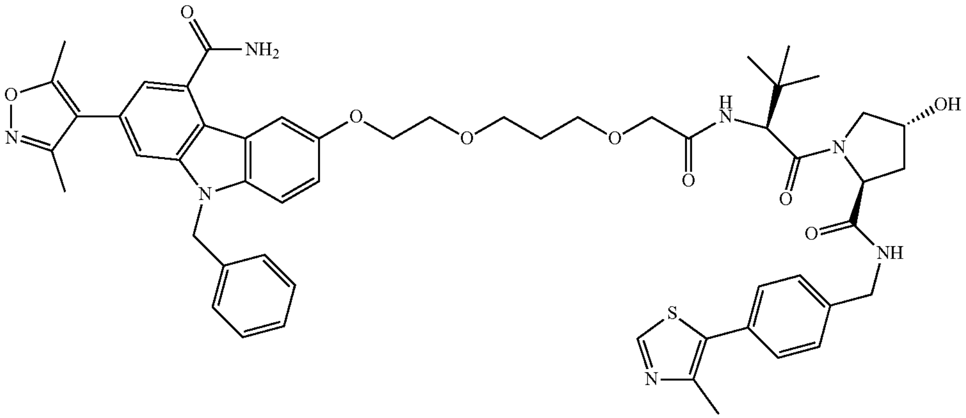 [SMILES: Cc1ncsc1-c1ccc(CNC(=O)[C@@H]2C[C@@H](O)CN2C(=O)[C@@H](NC(=O)COCCCOCCOc2ccc3c(c2)c2c(C(N)=O)cc(-c4c(C)noc4C)cc2n3Cc2ccccc2)C(C)(C)C)cc1] | 0984.2 | 0985.3 | B | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 117 | 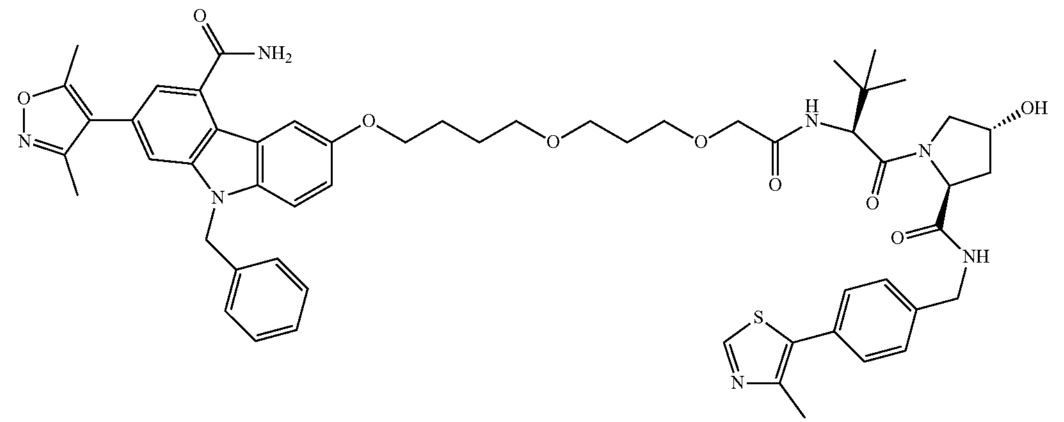 [SMILES: Cc1ncsc1-c1ccc(CNC(=O)[C@@H]2C[C@@H](O)CN2C(=O)[C@@H](NC(=O)COCCCOCCCCOc2ccc3c(c2)c2c(C(N)=O)cc(-c4c(C)noc4C)cc2n3Cc2ccccc2)C(C)(C)C)cc1] | 1012.2 | 1014.3 | A | 100 |
| 118 | 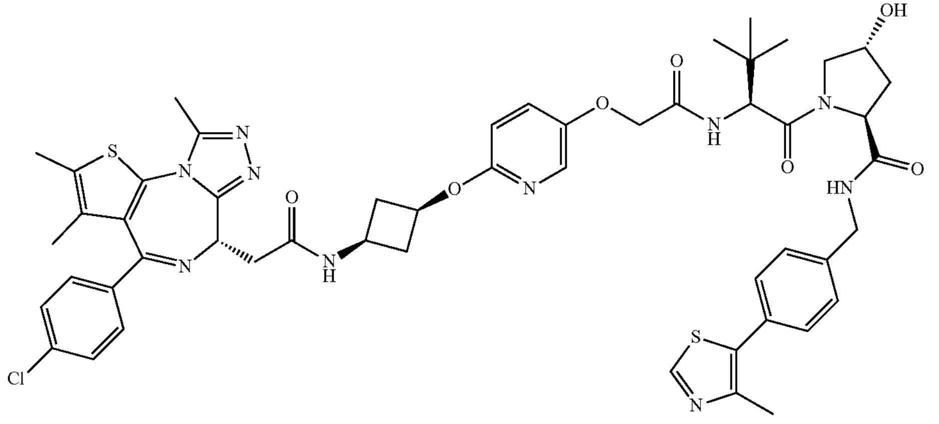 [SMILES: Cc1ncsc1-c1ccc(CNC(=O)[C@@H]2C[C@@H](O)CN2C(=O)[C@@H](NC(=O)COc2ccc(O[C@H]3C[C@@H](NC(=O)C[C@@H]4N=C(c5ccc(Cl)cc5)c5c(sc(C)c5C)-n5c(C)nnc54)C3)nc2)C(C)(C)C)cc1] | 1033.7 | 1033.5 | A | 94.4 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 119 | 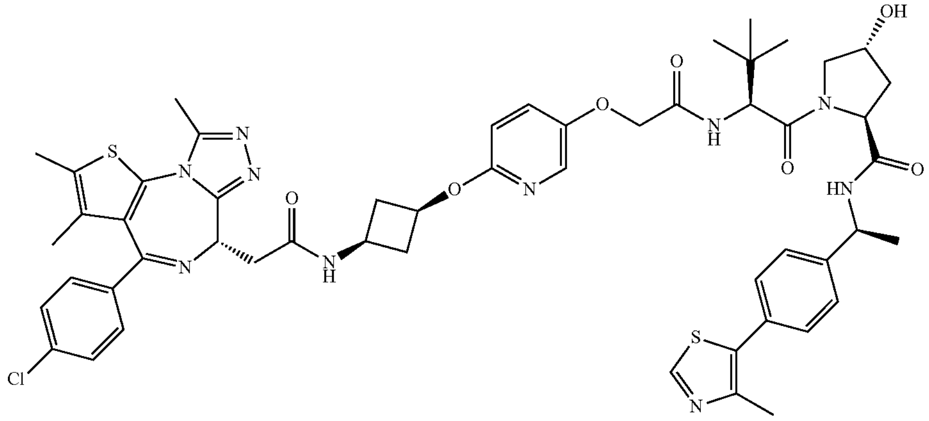 [SMILES: Cc1ncsc1-c1ccc([C@H](C)NC(=O)[C@@H]2C[C@@H](O)CN2C(=O)[C@@H](NC(=O)COc2ccc(O[C@H]3C[C@@H](NC(=O)C[C@@H]4N=C(c5ccc(Cl)cc5)c5c(sc(C)c5C)-n5c(C)nnc54)C3)nc2)C(C)(C)C)cc1] | 1047.7 | 1047.3 | A | 96.0 |
| 120 | 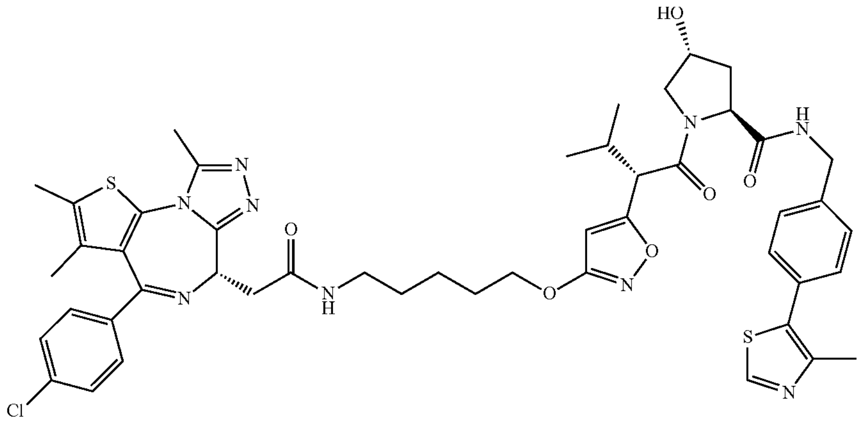 [SMILES: Cc1ncsc1-c1ccc(CNC(=O)[C@@H]2C[C@@H](O)CN2C(=O)[C@H](c2cc(OCCCCCNC(=O)C[C@@H]3N=C(c4ccc(Cl)cc4)c4c(sc(C)c4C)-n4c(C)nnc43)no2)C(C)C)cc1] | 0952.6 | 0952.3 | C | 79.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 121 | 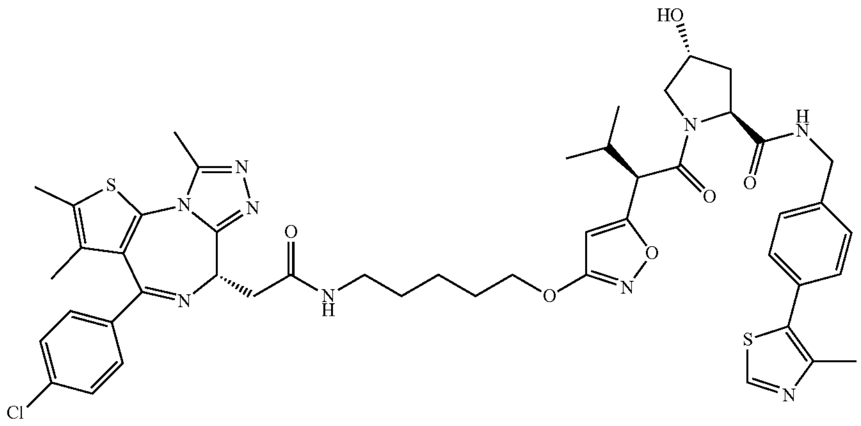 [SMILES: Cc1ncsc1-c1ccc(CNC(=O)[C@@H]2C[C@@H](O)CN2C(=O)[C@@H](c2cc(OCCCCCNC(=O)C[C@@H]3N=C(c4ccc(Cl)cc4)c4c(sc(C)c4C)-n4c(C)nnc43)no2)C(C)C)cc1] | 0952.6 | 0952.3 | A | 98.5 |
| 122 | 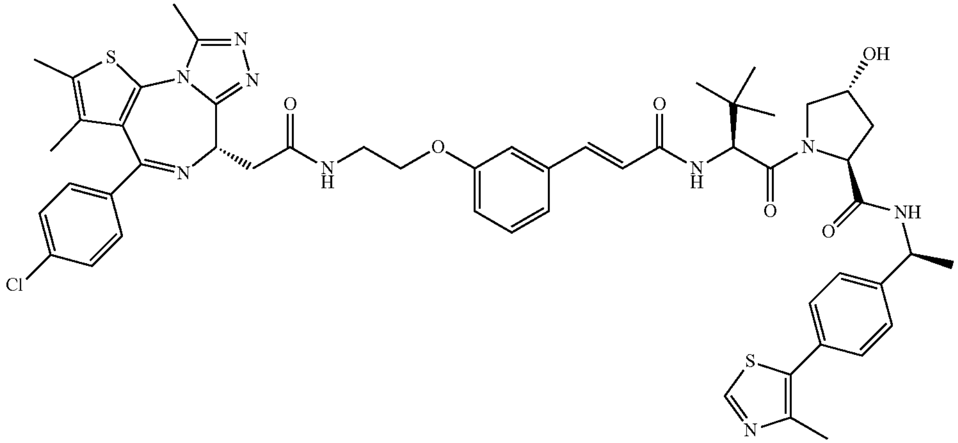 [SMILES: Cc1ncsc1-c1ccc([C@H](C)NC(=O)[C@@H]2C[C@@H](O)CN2C(=O)[C@@H](NC(=O)/C=C/c2cccc(OCCNC(=O)C[C@@H]3N=C(c4ccc(Cl)cc4)c4c(sc(C)c4C)-n4c(C)nnc43)c2)C(C)(C)C)cc1] | 1016.7 | 1016.1 | A | 100 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 123 | 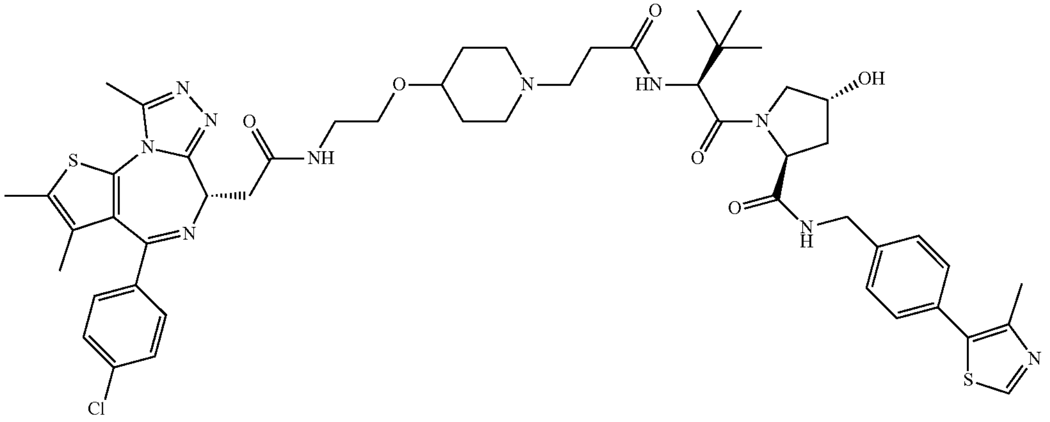 [SMILES: Cc1ncsc1-c1ccc(CNC(=O)[C@@H]2C[C@@H](O)CN2C(=O)[C@@H](NC(=O)CCN2CCC(OCCNC(=O)C[C@@H]3N=C(c4ccc(Cl)cc4)c4c(sc(C)c4C)-n4c(C)nnc43)CC2)C(C)(C)C)cc1] | 1011.7 | 1011.4 | D | 19.7 |
| 124 | 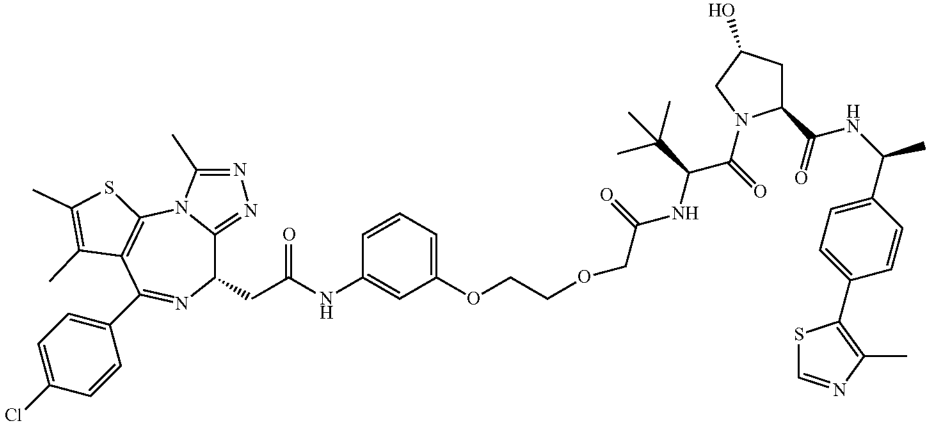 [SMILES: Cc1ncsc1-c1ccc([C@H](C)NC(=O)[C@@H]2C[C@@H](O)CN2C(=O)[C@@H](NC(=O)COCCOc2cccc(NC(=O)C[C@@H]3N=C(c4ccc(Cl)cc4)c4c(sc(C)c4C)-n4c(C)nnc43)c2)C(C)(C)C)cc1] | 1020.7 | 1020.3 | A | 98.0 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 125 | 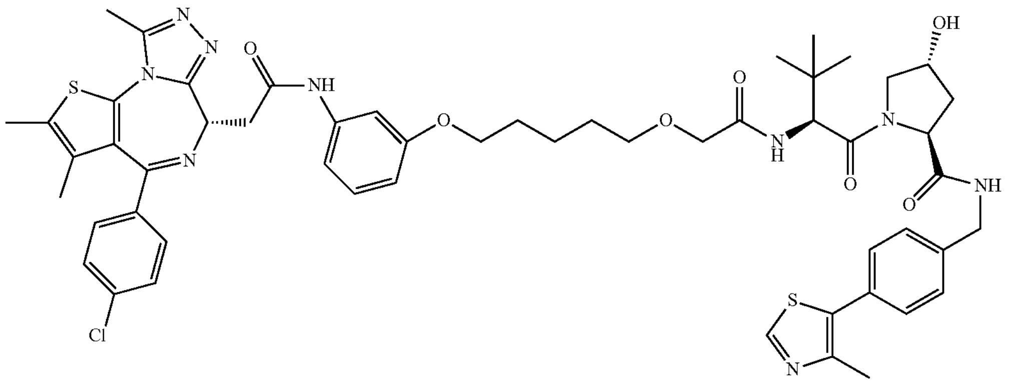 [SMILES: Cc1ncsc1-c1ccc(CNC(=O)[C@@H]2C[C@@H](O)CN2C(=O)[C@@H](NC(=O)COCCCCCOc2cccc(NC(=O)C[C@@H]3N=C(c4ccc(Cl)cc4)c4c(sc(C)c4C)-n4c(C)nnc43)c2)C(C)(C)C)cc1] | 1048.7 | 1048.4 | A | 99.5 |
| 126 | 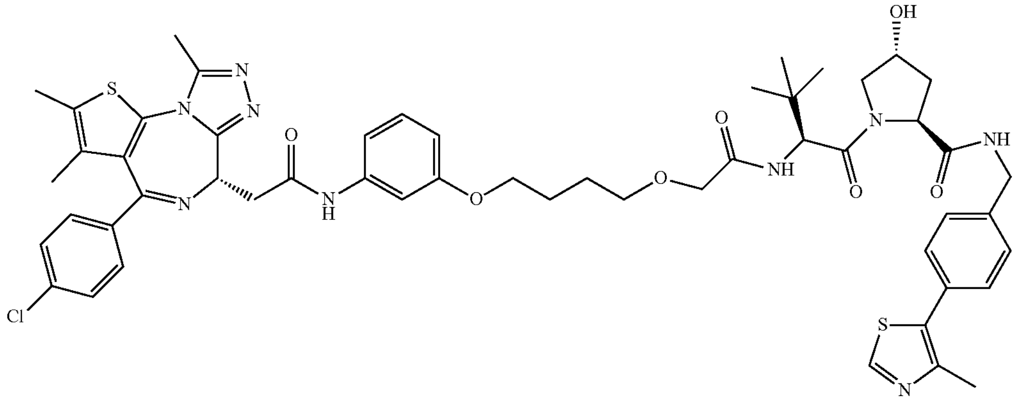 [SMILES: Cc1ncsc1-c1ccc(CNC(=O)[C@@H]2C[C@@H](O)CN2C(=O)[C@@H](NC(=O)COCCCCOc2cccc(NC(=O)C[C@@H]3N=C(c4ccc(Cl)cc4)c4c(sc(C)c4C)-n4c(C)nnc43)c2)C(C)(C)C)cc1] | 1034.7 | 1034.4 | A | 99.0 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 127 | 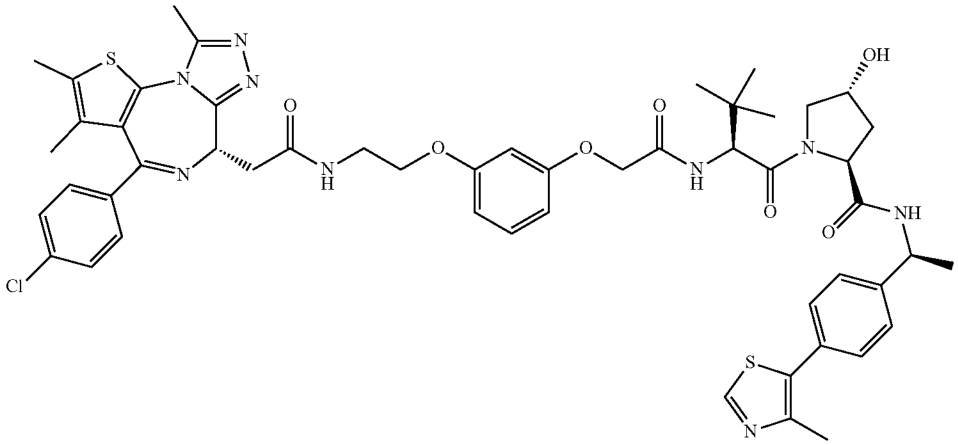 [SMILES: Cc1ncsc1-c1ccc([C@H](C)NC(=O)[C@@H]2C[C@@H](O)CN2C(=O)[C@@H](NC(=O)COc2cccc(OCCNC(=O)C[C@@H]3N=C(c4ccc(Cl)cc4)c4c(sc(C)c4C)-n4c(C)nnc43)c2)C(C)(C)C)cc1] | 1020.7 | 1020.5 | A | 99.0 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 128 | 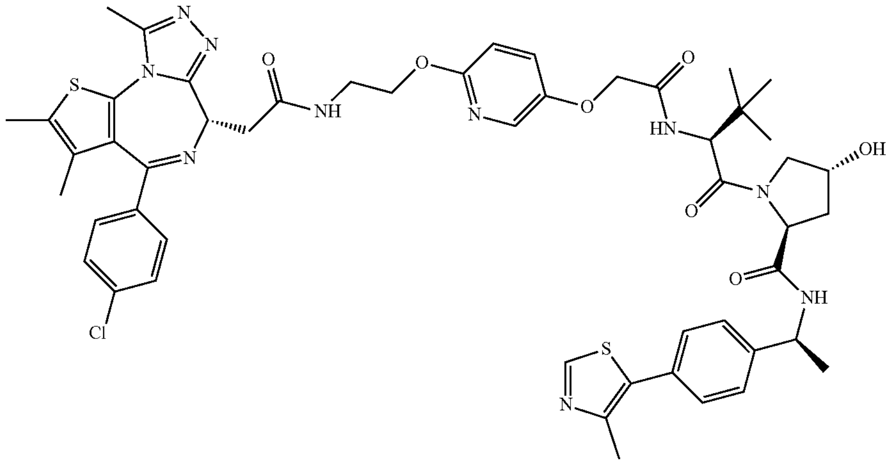 [SMILES: Cc1ncsc1-c1ccc([C@H](C)NC(=O)[C@@H]2C[C@@H](O)CN2C(=O)[C@@H](NC(=O)COc2ccc(OCCNC(=O)C[C@@H]3N=C(c4ccc(Cl)cc4)c4c(sc(C)c4C)-n4c(C)nnc43)nc2)C(C)(C)C)cc1] | 1021.6 | 1021.3 | A | 100 |
| 129 | 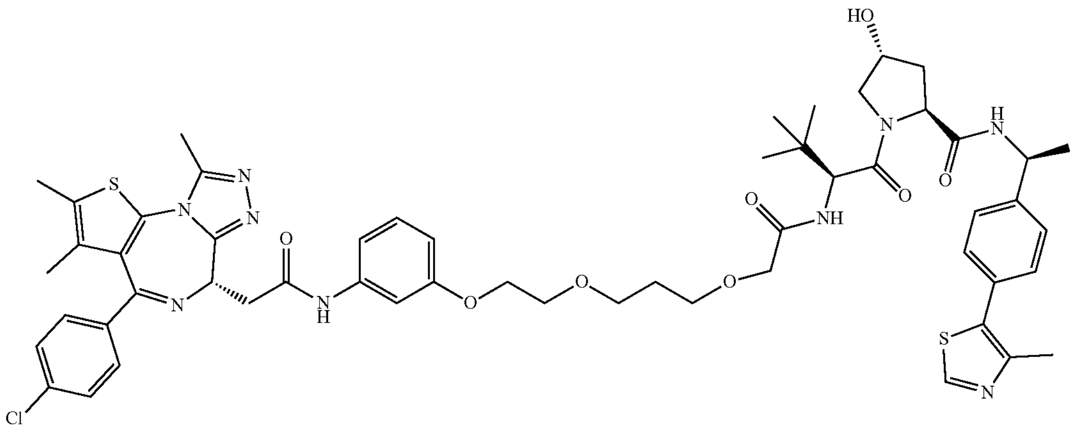 [SMILES: Cc1ncsc1-c1ccc([C@H](C)NC(=O)[C@@H]2C[C@@H](O)CN2C(=O)[C@@H](NC(=O)COCCCOCCOc2cccc(NC(=O)C[C@@H]3N=C(c4ccc(Cl)cc4)c4c(sc(C)c4C)-n4c(C)nnc43)c2)C(C)(C)C)cc1] | 1078.7 | 1078.4 | A | 96 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 130 | 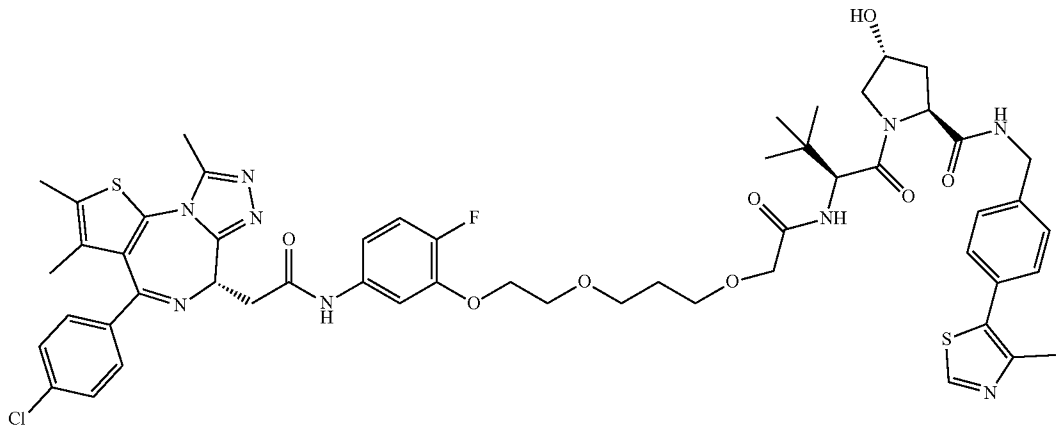 [SMILES: Cc1ncsc1-c1ccc(CNC(=O)[C@@H]2C[C@@H](O)CN2C(=O)[C@@H](NC(=O)COCCCOCCOc2cc(NC(=O)C[C@@H]3N=C(c4ccc(Cl)cc4)c4c(sc(C)c4C)-n4c(C)nnc43)ccc2F)C(C)(C)C)cc1] | 1082.7 | 1082.4 | A | 99 |
| 131 | 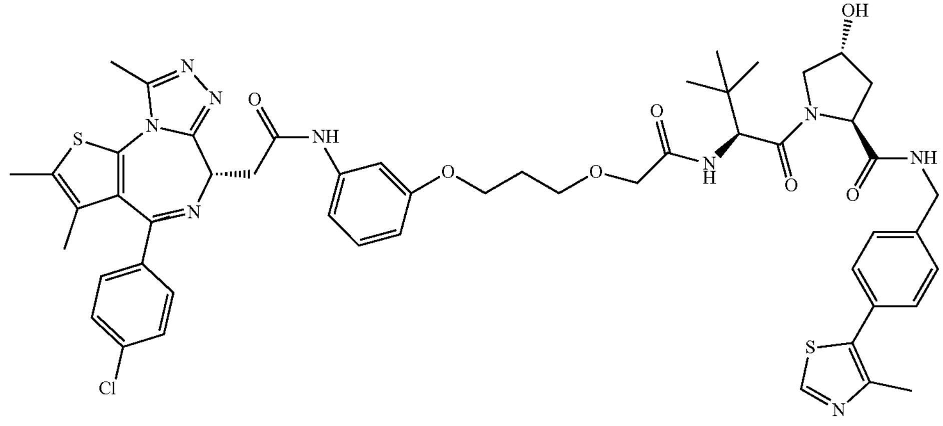 | 1020.7 | 1020.4 | B | 98 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 132 | 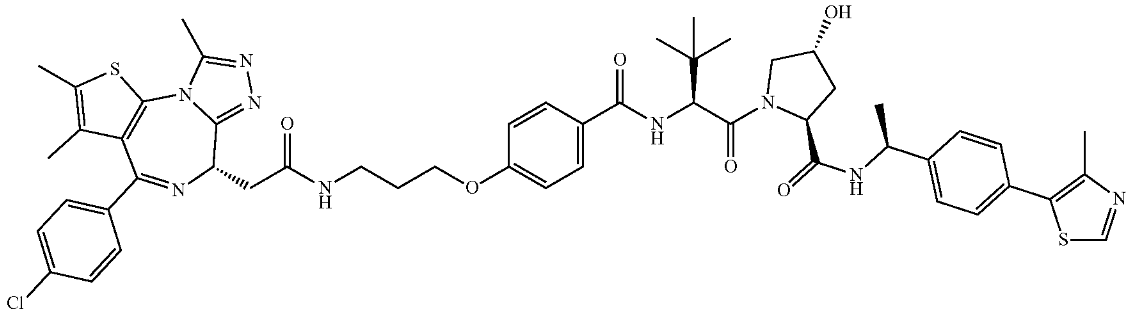 [SMILES: Cc1ncsc1-c1ccc([C@H](C)NC(=O)[C@@H]2C[C@@H](O)CN2C(=O)[C@@H](NC(=O)c2ccc(OCCCNC(=O)C[C@@H]3N=C(c4ccc(Cl)cc4)c4c(sc(C)c4C)-n4c(C)nnc43)cc2)C(C)(C)C)cc1] | 1004.7 | 1004.4 | A | 99 |
| 133 | 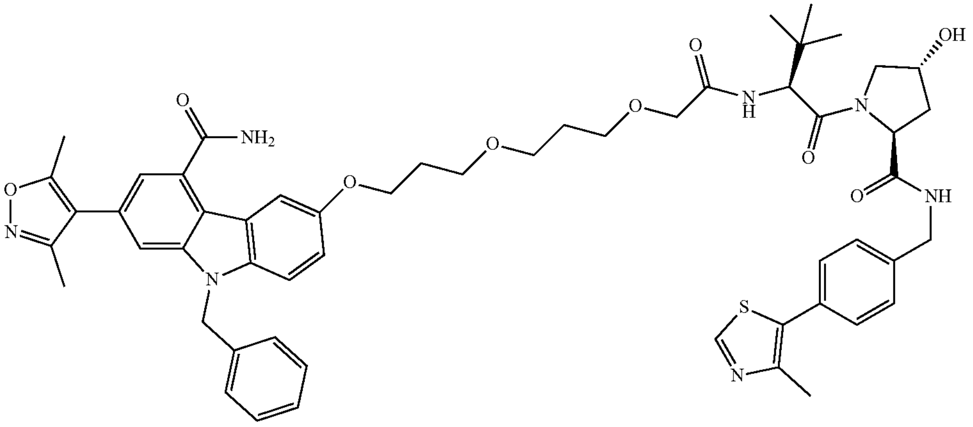 [SMILES: Cc1ncsc1-c1ccc(CNC(=O)[C@@H]2C[C@@H](O)CN2C(=O)[C@@H](NC(=O)COCCCOCCCOc2ccc3c(c2)c2c(C(N)=O)cc(-c4c(C)noc4C)cc2n3Cc2ccccc2)C(C)(C)C)cc1] | 0998.2 | 0998.5 | B | 98 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 134 | 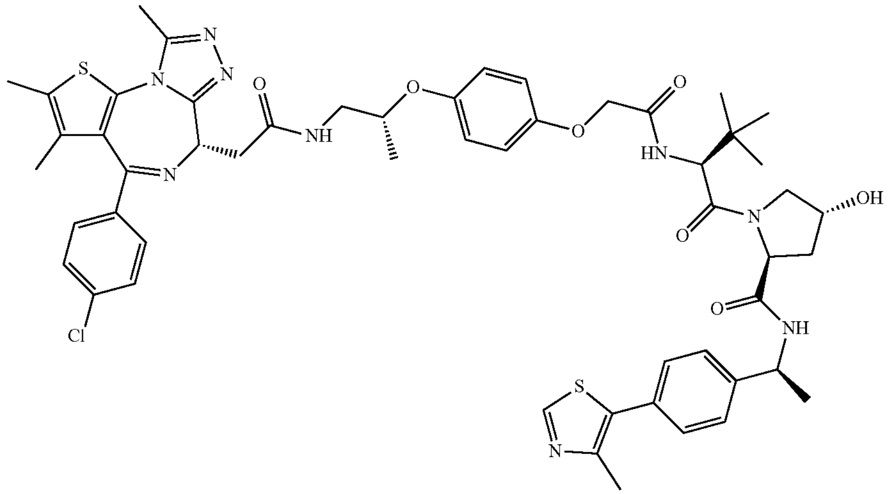 [SMILES: Cc1ncsc1-c1ccc([C@H](C)NC(=O)[C@@H]2C[C@@H](O)CN2C(=O)[C@@H](NC(=O)COc2ccc(O[C@H](C)CNC(=O)C[C@@H]3N=C(c4ccc(Cl)cc4)c4c(sc(C)c4C)-n4c(C)nnc43)cc2)C(C)(C)C)cc1] | 1035.7 | 1035.3 | A | 99 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 135 | 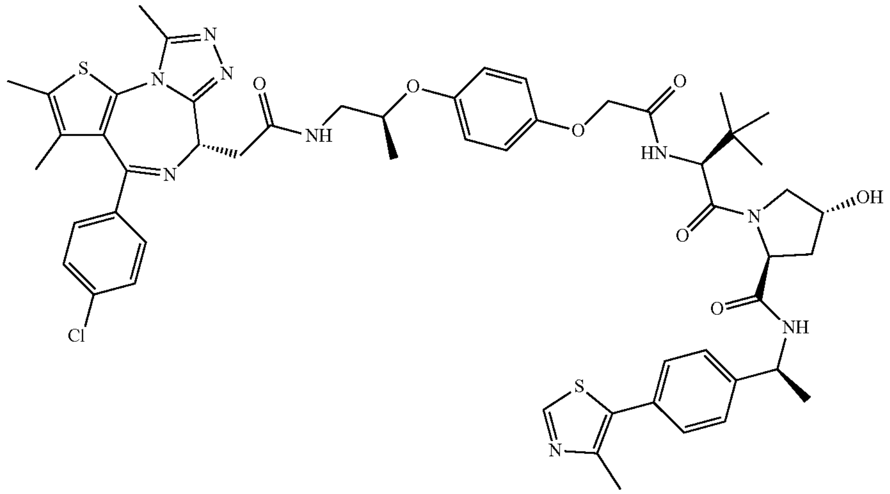 [SMILES: Cc1ncsc1-c1ccc([C@H](C)NC(=O)[C@@H]2C[C@@H](O)CN2C(=O)[C@@H](NC(=O)COc2ccc(O[C@@H](C)CNC(=O)C[C@@H]3N=C(c4ccc(Cl)cc4)c4c(sc(C)c4C)-n4c(C)nnc43)cc2)C(C)(C)C)cc1] | 1035.7 | 1035.3 | A | 99 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 136 | 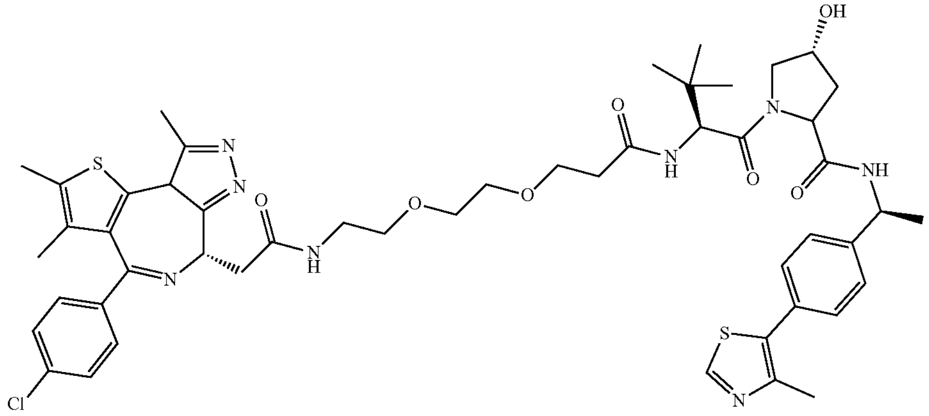 [SMILES: CC1=NN=C2C1c1sc(C)c(C)c1C(c1ccc(Cl)cc1)=N[C@H]2CC(=O)NCCOCCOCCC(=O)N[C@H](C(=O)N1C[C@H](O)CC1C(=O)N[C@@H](C)c1ccc(-c2scnc2C)cc1)C(C)(C)C] | 0986.6 | 0986.4 | B | 96 |
| 137 | 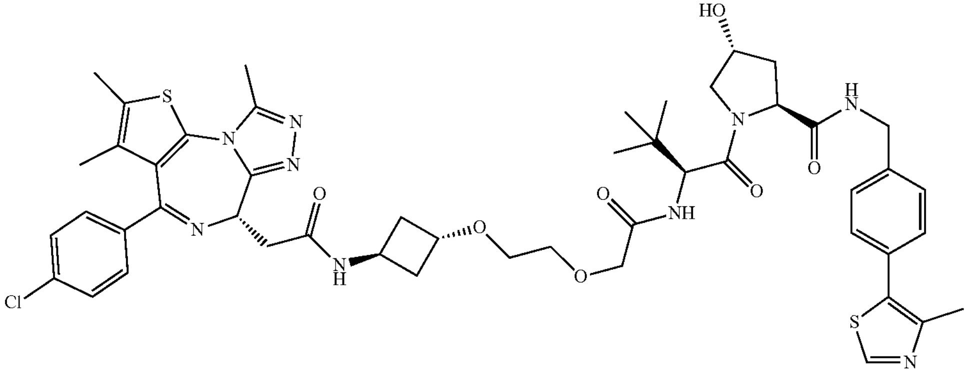 [SMILES: Cc1ncsc1-c1ccc(CNC(=O)[C@@H]2C[C@@H](O)CN2C(=O)[C@@H](NC(=O)COCCO[C@H]2C[C@H](NC(=O)C[C@@H]3N=C(c4ccc(Cl)cc4)c4c(sc(C)c4C)-n4c(C)nnc43)C2)C(C)(C)C)cc1] | 0984.6 | 0984.4 | C | 86.9 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 138 | 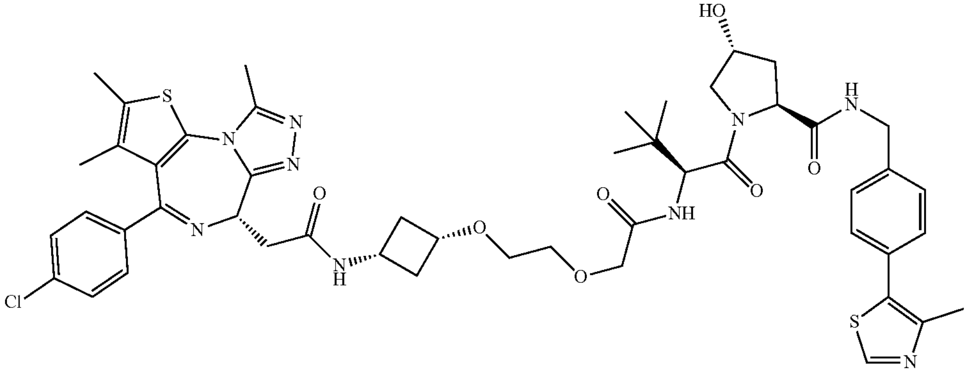 [SMILES: Cc1ncsc1-c1ccc(CNC(=O)[C@@H]2C[C@@H](O)CN2C(=O)[C@@H](NC(=O)COCCO[C@H]2C[C@@H](NC(=O)C[C@@H]3N=C(c4ccc(Cl)cc4)c4c(sc(C)c4C)-n4c(C)nnc43)C2)C(C)(C)C)cc1] | 0984.6 | 0984.5 | C | 89.4 |
| 139 | 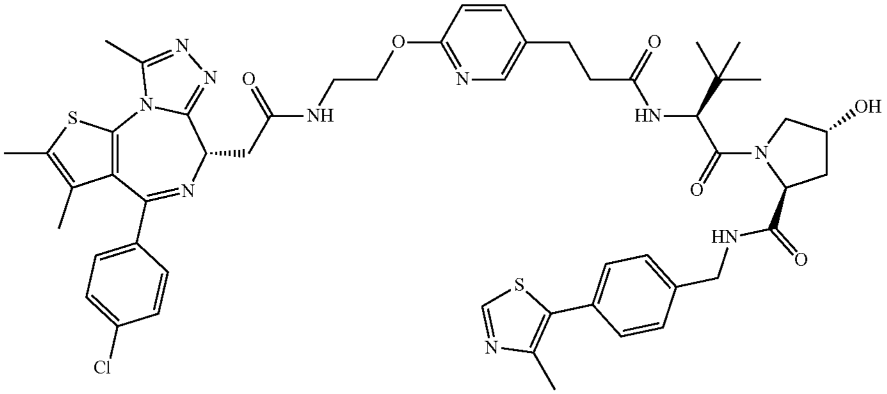 [SMILES: Cc1ncsc1-c1ccc(CNC(=O)[C@@H]2C[C@@H](O)CN2C(=O)[C@@H](NC(=O)CCc2ccc(OCCNC(=O)C[C@@H]3N=C(c4ccc(Cl)cc4)c4c(sc(C)c4C)-n4c(C)nnc43)nc2)C(C)(C)C)cc1] | 1005.6 | 1005.3 | A | 98 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 140 | 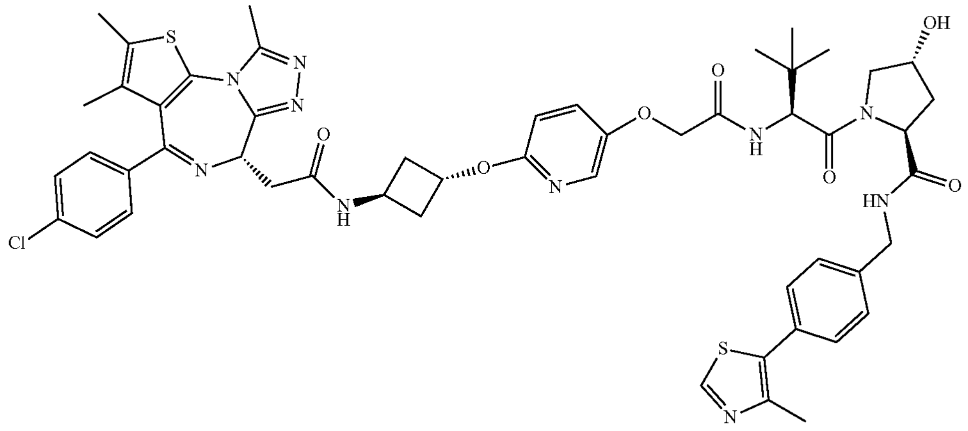 [SMILES: Cc1ncsc1-c1ccc(CNC(=O)[C@@H]2C[C@@H](O)CN2C(=O)[C@@H](NC(=O)COc2ccc(O[C@H]3C[C@H](NC(=O)C[C@@H]4N=C(c5ccc(Cl)cc5)c5c(sc(C)c5C)-n5c(C)nnc54)C3)nc2)C(C)(C)C)cc1] | 1033.7 | 1033.4 | A | 98 |
| 141 | 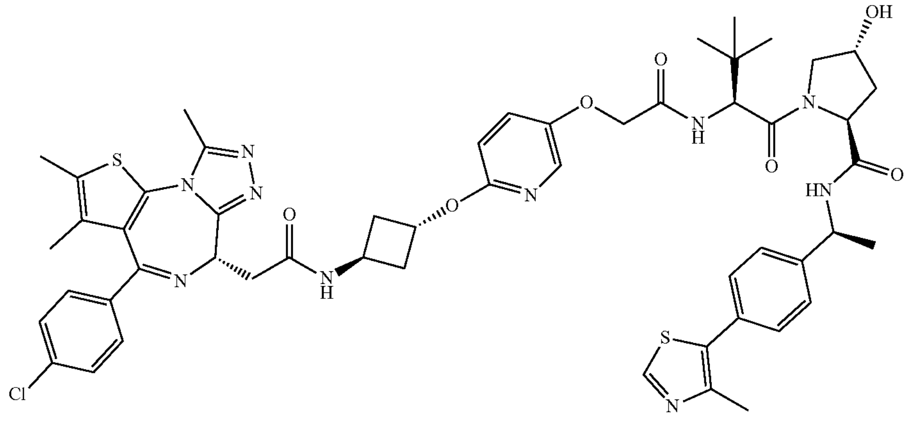 [SMILES: Cc1ncsc1-c1ccc([C@H](C)NC(=O)[C@@H]2C[C@@H](O)CN2C(=O)[C@@H](NC(=O)COc2ccc(O[C@H]3C[C@H](NC(=O)C[C@@H]4N=C(c5ccc(Cl)cc5)c5c(sc(C)c5C)-n5c(C)nnc54)C3)nc2)C(C)(C)C)cc1] | 1047.7 | 1047.4 | A | 98 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 142 | 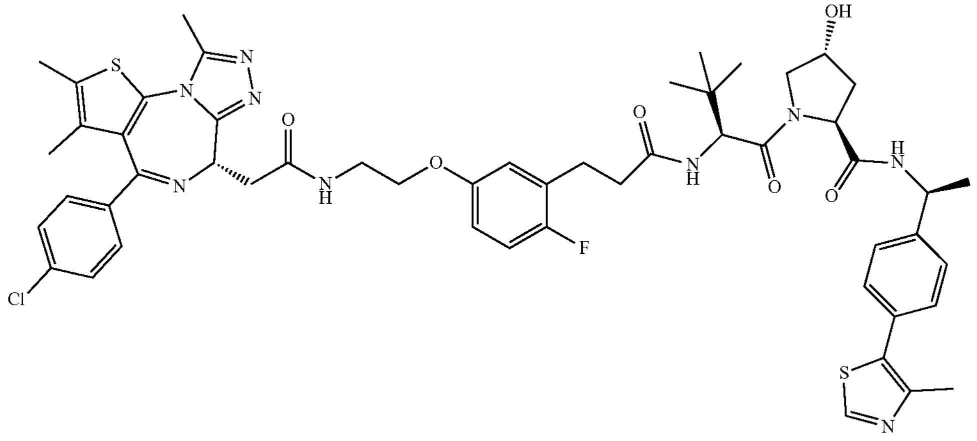 [SMILES: Cc1ncsc1-c1ccc([C@H](C)NC(=O)[C@@H]2C[C@@H](O)CN2C(=O)[C@@H](NC(=O)CCc2cc(OCCNC(=O)C[C@@H]3N=C(c4ccc(Cl)cc4)c4c(sc(C)c4C)-n4c(C)nnc43)ccc2F)C(C)(C)C)cc1] | 1036.7 | 1036.4 | A | 98 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 143 | 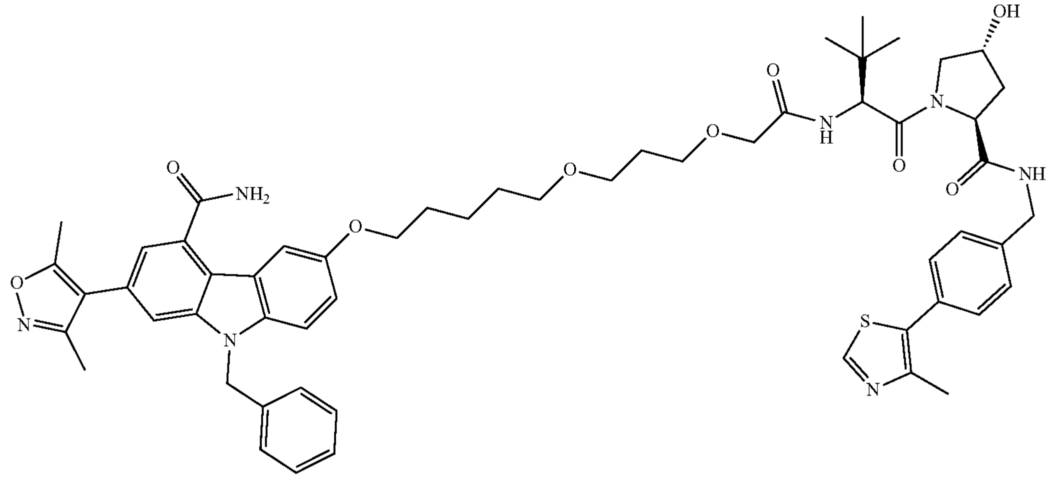 [SMILES: Cc1ncsc1-c1ccc(CNC(=O)[C@@H]2C[C@@H](O)CN2C(=O)[C@@H](NC(=O)COCCCOCCCCCOc2ccc3c(c2)c2c(C(N)=O)cc(-c4c(C)noc4C)cc2n3Cc2ccccc2)C(C)(C)C)cc1] | 1026.2 | 1026.5 | A | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 144 | 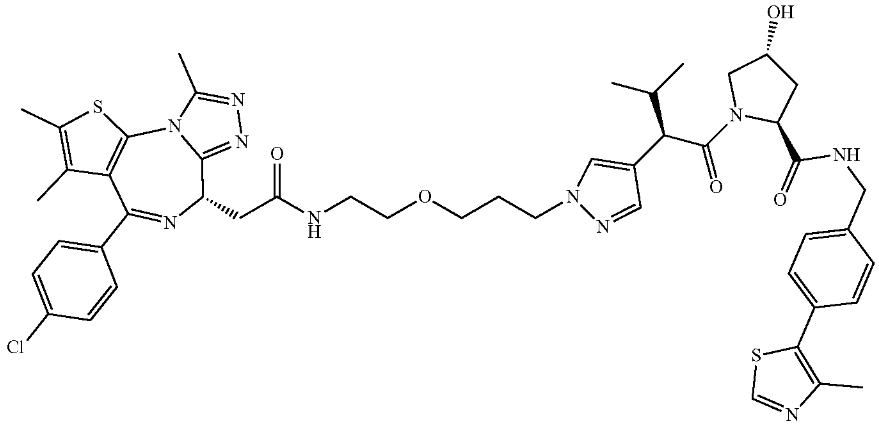 [SMILES: Cc1ncsc1-c1ccc(CNC(=O)[C@@H]2C[C@@H](O)CN2C(=O)[C@@H](c2cnn(CCCOCCNC(=O)C[C@@H]3N=C(c4ccc(Cl)cc4)c4c(sc(C)c4C)-n4c(C)nnc43)c2)C(C)C)cc1] | 0951.6 | 0951.3 | C | 73 |
| 145 | 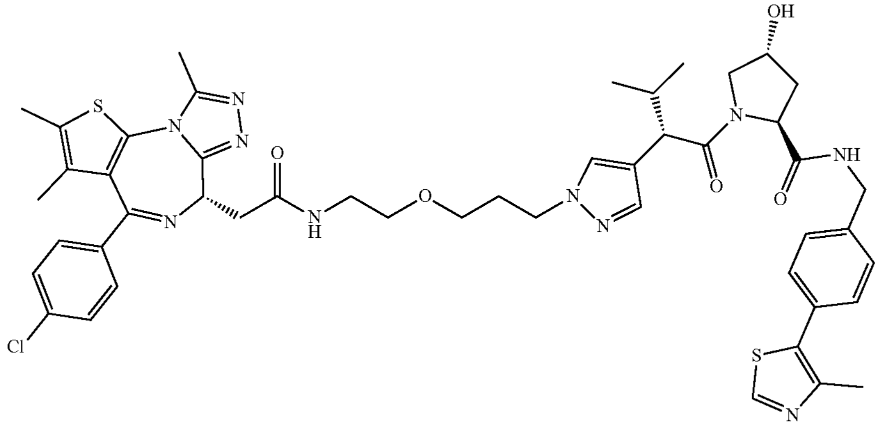 [SMILES: Cc1ncsc1-c1ccc(CNC(=O)[C@@H]2C[C@@H](O)CN2C(=O)[C@H](c2cnn(CCCOCCNC(=O)C[C@@H]3N=C(c4ccc(Cl)cc4)c4c(sc(C)c4C)-n4c(C)nnc43)c2)C(C)C)cc1] | 0951.6 | 0951.3 | D | 15.9 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 146 | 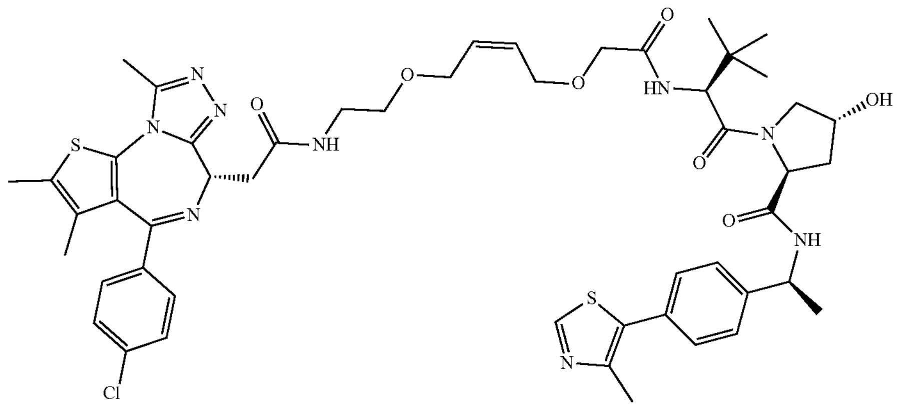 [SMILES: Cc1ncsc1-c1ccc([C@H](C)NC(=O)[C@@H]2C[C@@H](O)CN2C(=O)[C@@H](NC(=O)COC/C=C\COCCNC(=O)C[C@@H]2N=C(c3ccc(Cl)cc3)c3c(sc(C)c3C)-n3c(C)nnc32)C(C)(C)C)cc1] | 0998.7 | 0998.4 | A | 100 |
| 147 | 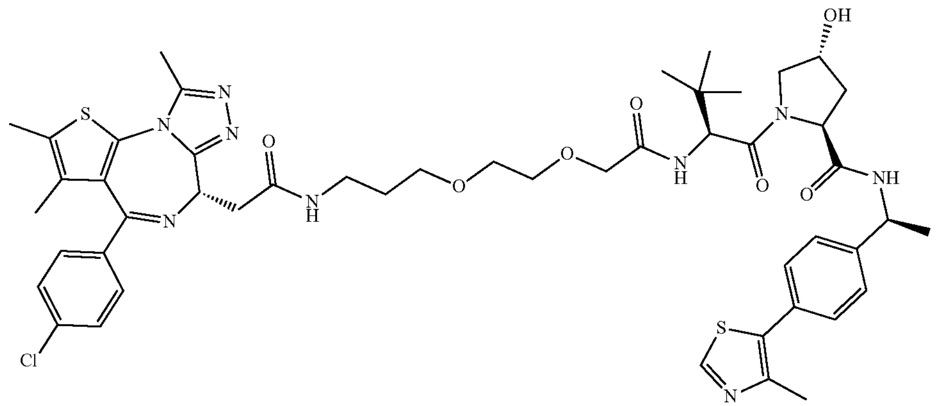 [SMILES: Cc1ncsc1-c1ccc([C@H](C)NC(=O)[C@@H]2C[C@@H](O)CN2C(=O)[C@@H](NC(=O)COCCOCCCNC(=O)C[C@@H]2N=C(c3ccc(Cl)cc3)c3c(sc(C)c3C)-n3c(C)nnc32)C(C)(C)C)cc1] | 0986.6 | 0986.4 | A | 98.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 148 | 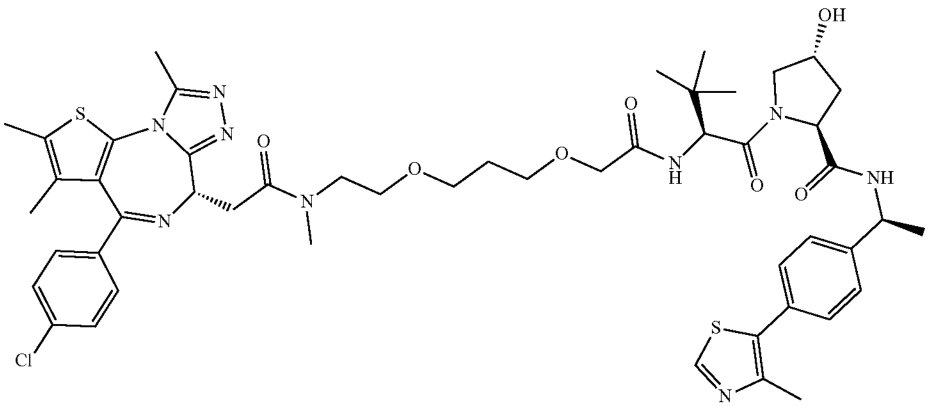 [SMILES: Cc1ncsc1-c1ccc([C@H](C)NC(=O)[C@@H]2C[C@@H](O)CN2C(=O)[C@@H](NC(=O)COCCCOCCN(C)C(=O)C[C@@H]2N=C(c3ccc(Cl)cc3)c3c(sc(C)c3C)-n3c(C)nnc32)C(C)(C)C)cc1] | 1000.7 | 1000.4 | A | 100 |
| 149 | 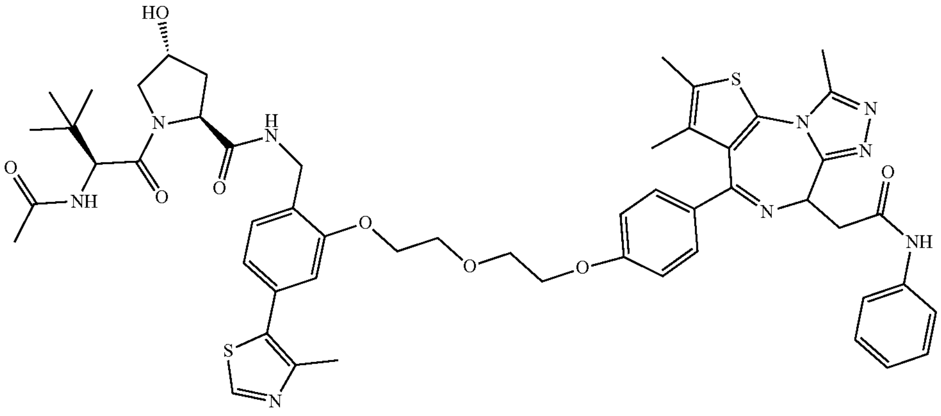 [SMILES: CC(=O)N[C@H](C(=O)N1C[C@H](O)C[C@H]1C(=O)NCc1ccc(-c2scnc2C)cc1OCCOCCOc1ccc(C2=NC(CC(=O)Nc3ccccc3)c3nnc(C)n3-c3sc(C)c(C)c32)cc1)C(C)(C)C] | 1016.2 | 1016.4 | C | 57.3 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 150 | 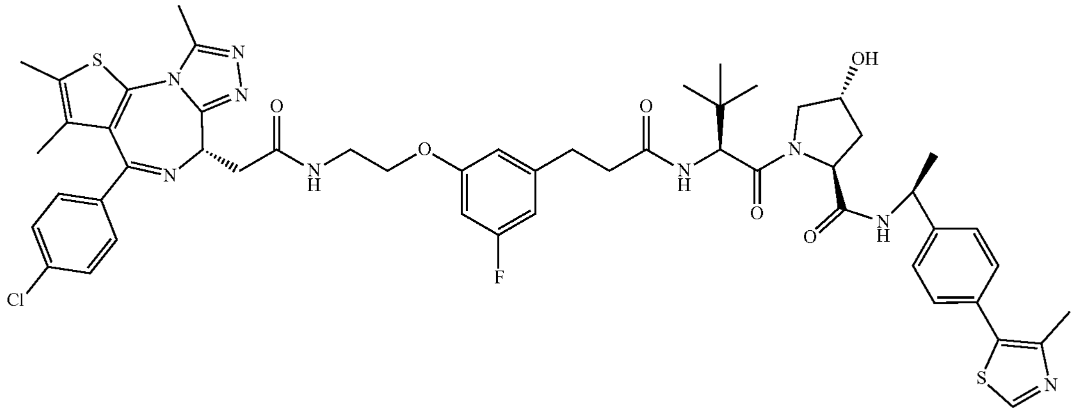 | 1036.7 | 1036.3 | A | 93.9 |
| 151 | 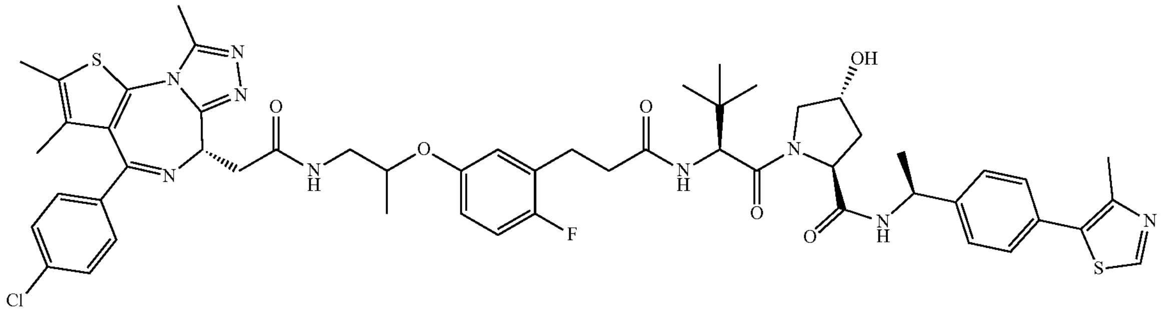 [SMILES: Cc1ncsc1-c1ccc([C@H](C)NC(=O)[C@@H]2C[C@@H](O)CN2C(=O)[C@@H](NC(=O)CCc2cc(OC(C)CNC(=O)C[C@@H]3N=C(c4ccc(Cl)cc4)c4c(sc(C)c4C)-n4c(C)nnc43)ccc2F)C(C)(C)C)cc1] | 1050.7 | 1050.4 | A | 96 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 152 | 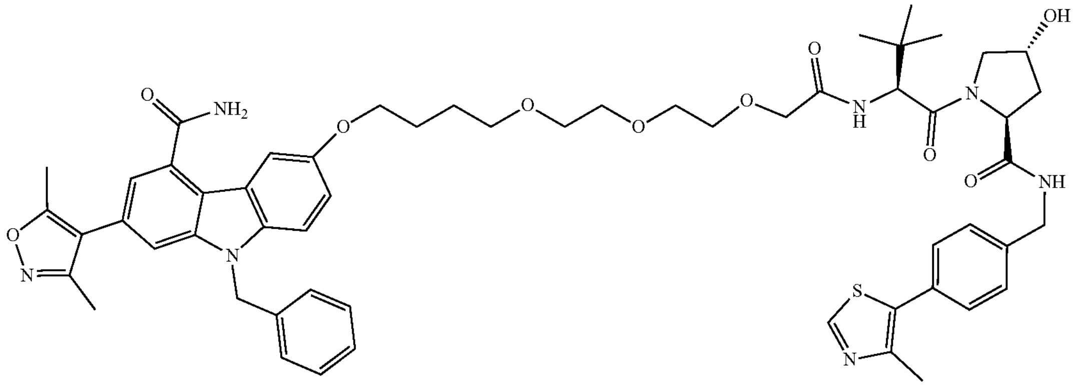 [SMILES: Cc1ncsc1-c1ccc(CNC(=O)[C@@H]2C[C@@H](O)CN2C(=O)[C@@H](NC(=O)COCCOCCOCCCCOc2ccc3c(c2)c2c(C(N)=O)cc(-c4c(C)noc4C)cc2n3Cc2ccccc2)C(C)(C)C)cc1] | 1042.2 | 1042.5 | B | 95 |
| 153 | 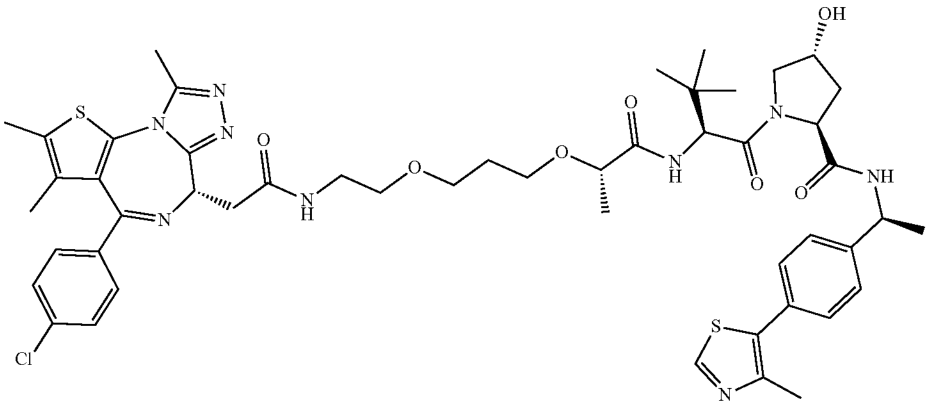 [SMILES: Cc1ncsc1-c1ccc([C@H](C)NC(=O)[C@@H]2C[C@@H](O)CN2C(=O)[C@@H](NC(=O)[C@H](C)OCCCOCCNC(=O)C[C@@H]2N=C(c3ccc(Cl)cc3)c3c(sc(C)c3C)-n3c(C)nnc32)C(C)(C)C)cc1] | 1000.7 | 1000.2 | A | 92 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 154 | 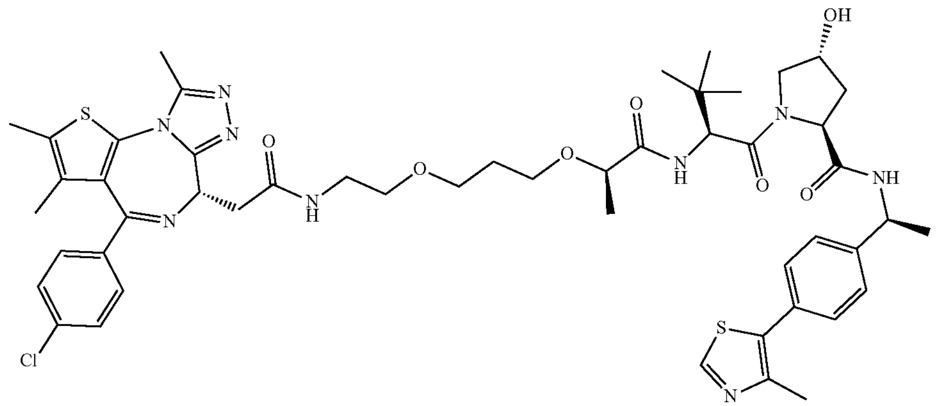 [SMILES: Cc1ncsc1-c1ccc([C@H](C)NC(=O)[C@@H]2C[C@@H](O)CN2C(=O)[C@@H](NC(=O)[C@@H](C)OCCCOCCNC(=O)C[C@@H]2N=C(c3ccc(Cl)cc3)c3c(sc(C)c3C)-n3c(C)nnc32)C(C)(C)C)cc1] | 1000.7 | 1000.2 | A | 94.5 |
| 155 | 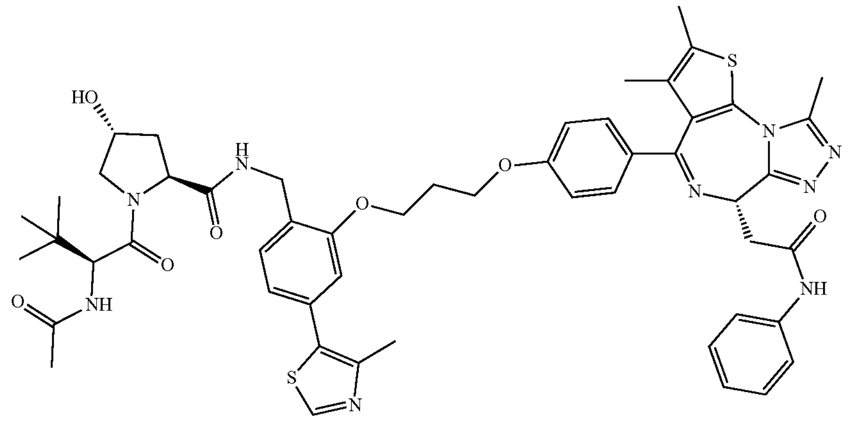 [SMILES: CC(=O)N[C@H](C(=O)N1C[C@H](O)C[C@H]1C(=O)NCc1ccc(-c2scnc2C)cc1OCCCOc1ccc(C2=N[C@@H](CC(=O)Nc3ccccc3)c3nnc(C)n3-c3sc(C)c(C)c32)cc1)C(C)(C)C] | 0986.2 | 0986.4 | C | 65.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 156 | 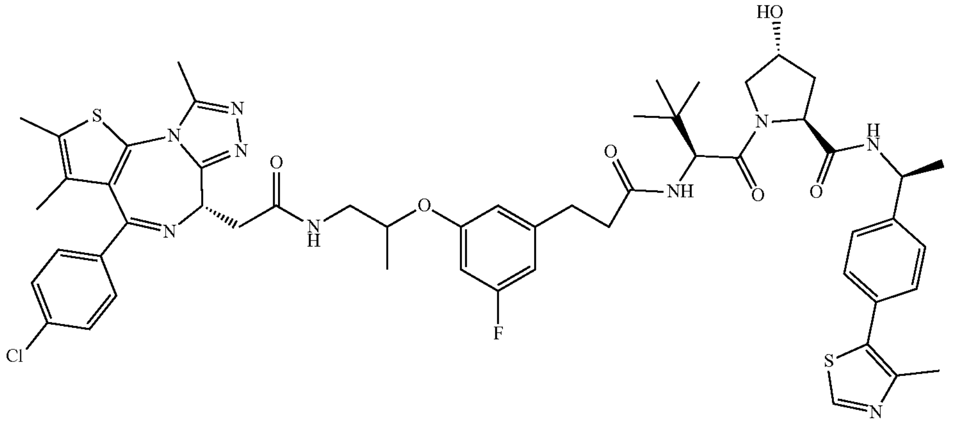 [SMILES: Cc1ncsc1-c1ccc([C@H](C)NC(=O)[C@@H]2C[C@@H](O)CN2C(=O)[C@@H](NC(=O)CCc2cc(F)cc(OC(C)CNC(=O)C[C@@H]3N=C(c4ccc(Cl)cc4)c4c(sc(C)c4C)-n4c(C)nnc43)c2)C(C)(C)C)cc1] | 1050.7 | 1050.4 | A | 96.5 |
| 157 | 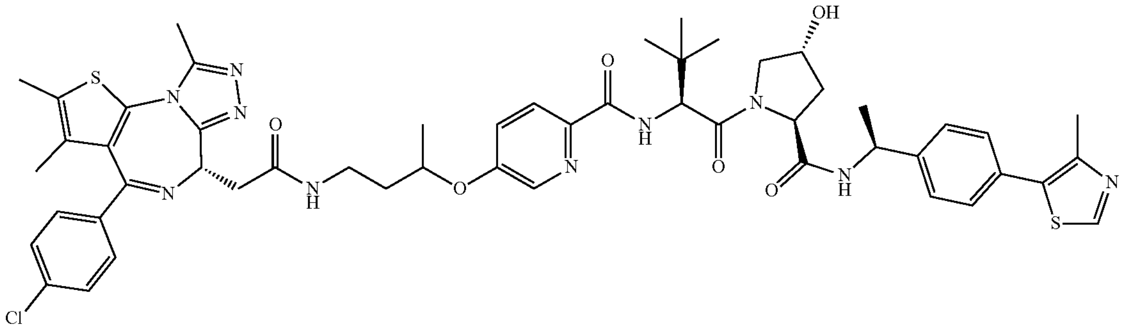 [SMILES: Cc1ncsc1-c1ccc([C@H](C)NC(=O)[C@@H]2C[C@@H](O)CN2C(=O)[C@@H](NC(=O)c2ccc(OC(C)CCNC(=O)C[C@@H]3N=C(c4ccc(Cl)cc4)c4c(sc(C)c4C)-n4c(C)nnc43)cn2)C(C)(C)C)cc1] | 1019.7 | 1019.5 | A | 97 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 158 | 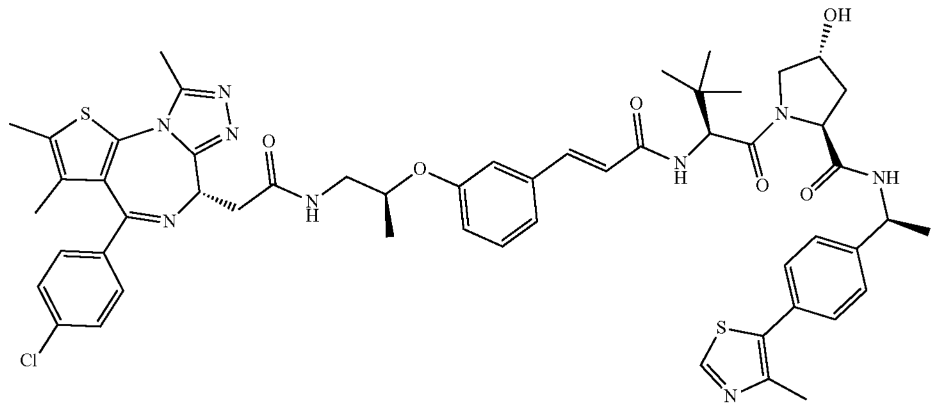 [SMILES: Cc1ncsc1-c1ccc([C@H](C)NC(=O)[C@@H]2C[C@@H](O)CN2C(=O)[C@@H](NC(=O)/C=C/c2cccc(O[C@@H](C)CNC(=O)C[C@@H]3N=C(c4ccc(Cl)cc4)c4c(sc(C)c4C)-n4c(C)nnc43)c2)C(C)(C)C)cc1] | 1030.7 | 1030.3 | A | 96.5 |
| 159 | 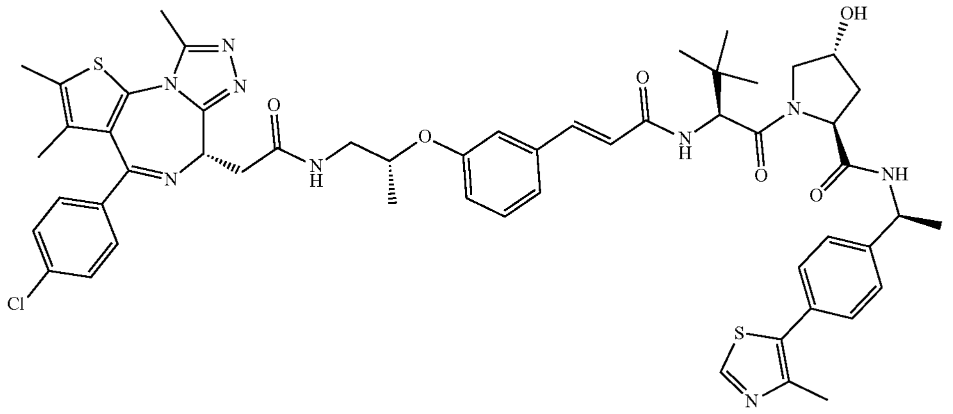 [SMILES: Cc1ncsc1-c1ccc([C@H](C)NC(=O)[C@@H]2C[C@@H](O)CN2C(=O)[C@@H](NC(=O)/C=C/c2cccc(O[C@H](C)CNC(=O)C[C@@H]3N=C(c4ccc(Cl)cc4)c4c(sc(C)c4C)-n4c(C)nnc43)c2)C(C)(C)C)cc1] | 1030.7 | 1030.3 | A | 96.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 160 | 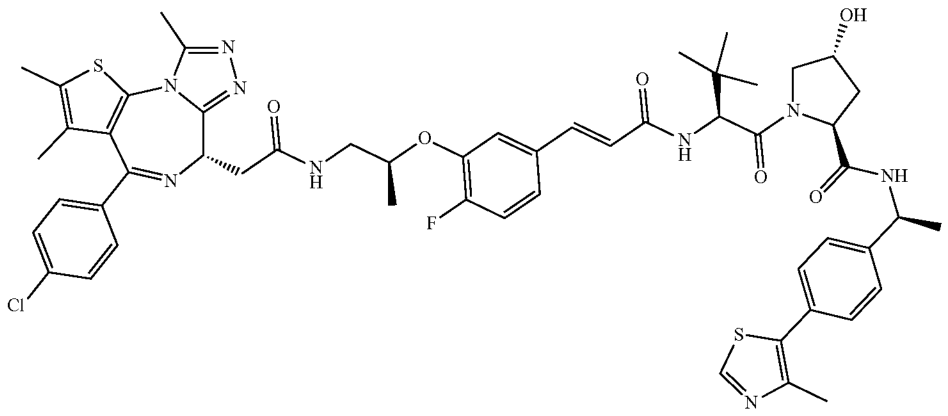 [SMILES: Cc1ncsc1-c1ccc([C@H](C)NC(=O)[C@@H]2C[C@@H](O)CN2C(=O)[C@@H](NC(=O)/C=C/c2ccc(F)c(O[C@@H](C)CNC(=O)C[C@@H]3N=C(c4ccc(Cl)cc4)c4c(sc(C)c4C)-n4c(C)nnc43)c2)C(C)(C)C)cc1] | 1048.7 | 1048.3 | A | 94.5 |
| 161 | 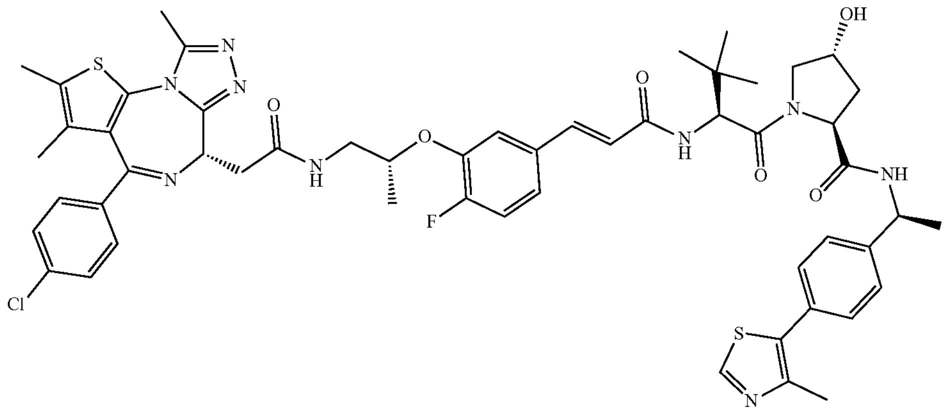 [SMILES: Cc1ncsc1-c1ccc([C@H](C)NC(=O)[C@@H]2C[C@@H](O)CN2C(=O)[C@@H](NC(=O)/C=C/c2ccc(F)c(O[C@H](C)CNC(=O)C[C@@H]3N=C(c4ccc(Cl)cc4)c4c(sc(C)c4C)-n4c(C)nnc43)c2)C(C)(C)C)cc1] | 1048.7 | 1048.3 | A | 97 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 162 | 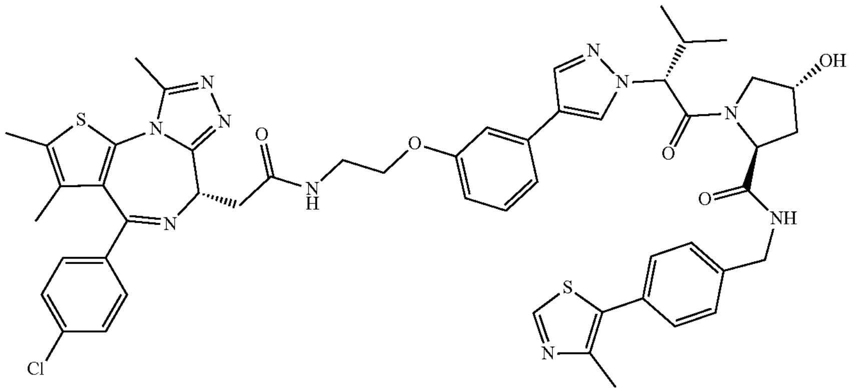 [SMILES: Cc1ncsc1-c1ccc(CNC(=O)[C@@H]2C[C@@H](O)CN2C(=O)[C@@H](C(C)C)n2cc(-c3cccc(OCCNC(=O)C[C@@H]4N=C(c5ccc(Cl)cc5)c5c(sc(C)c5C)-n5c(C)nnc54)c3)cn2)cc1] | 0985.6 | 0985.4 | D | 7.62 |
| 163 | 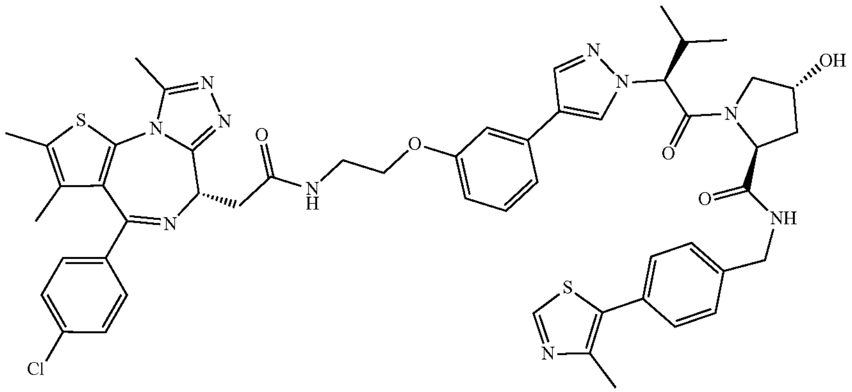 [SMILES: Cc1ncsc1-c1ccc(CNC(=O)[C@@H]2C[C@@H](O)CN2C(=O)[C@H](C(C)C)n2cc(-c3cccc(OCCNC(=O)C[C@@H]4N=C(c5ccc(Cl)cc5)c5c(sc(C)c5C)-n5c(C)nnc54)c3)cn2)cc1] | 0985.6 | 0985.4 | A | 96.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 164 | 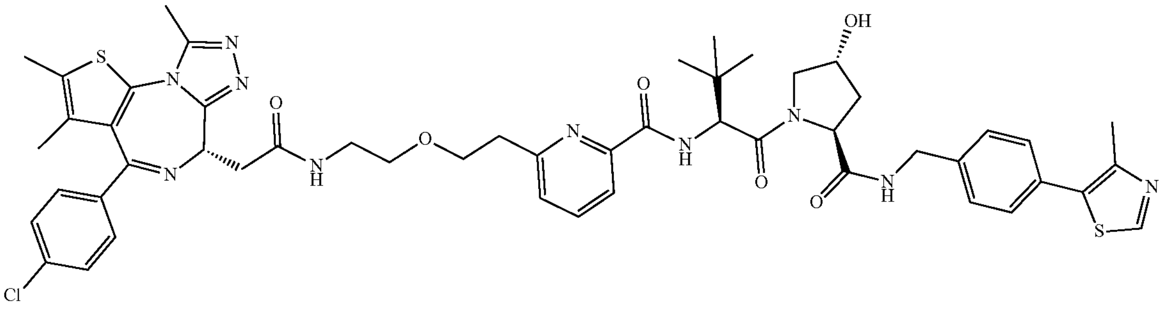 [SMILES: Cc1ncsc1-c1ccc(CNC(=O)[C@@H]2C[C@@H](O)CN2C(=O)[C@@H](NC(=O)c2cccc(CCOCCNC(=O)C[C@@H]3N=C(c4ccc(Cl)cc4)c4c(sc(C)c4C)-n4c(C)nnc43)n2)C(C)(C)C)cc1] | 1005.6 | 1005.4 | B | 96 |
| 165 | 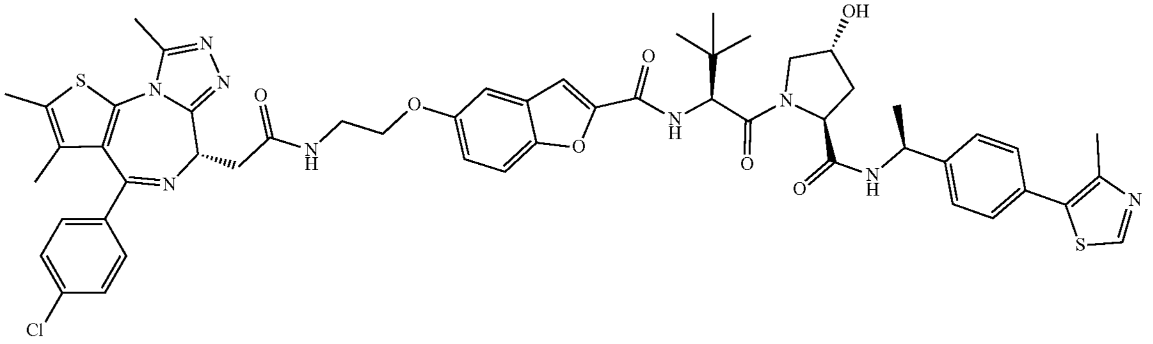 [SMILES: Cc1ncsc1-c1ccc([C@H](C)NC(=O)[C@@H]2C[C@@H](O)CN2C(=O)[C@@H](NC(=O)c2cc3cc(OCCNC(=O)C[C@@H]4N=C(c5ccc(Cl)cc5)c5c(sc(C)c5C)-n5c(C)nnc54)ccc3o2)C(C)(C)C)cc1] | 1030.7 | 1030.5 | A | 97 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 166 | 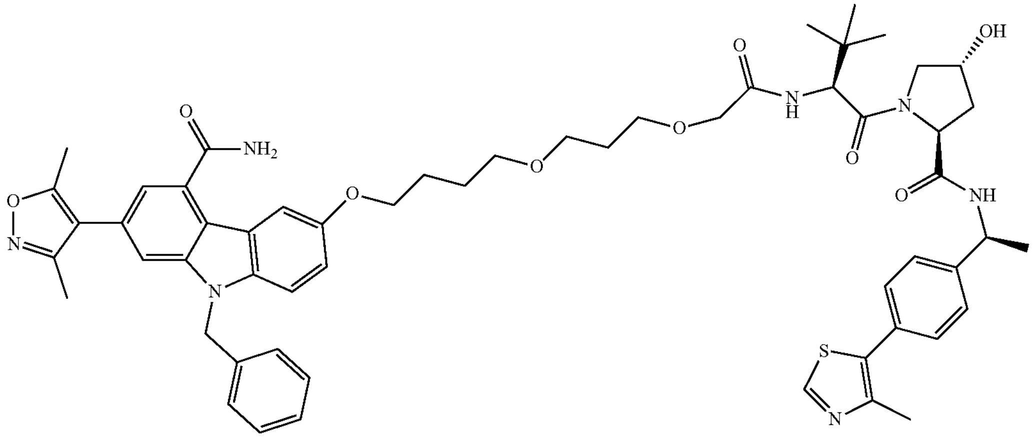 [SMILES: Cc1ncsc1-c1ccc([C@H](C)NC(=O)[C@@H]2C[C@@H](O)CN2C(=O)[C@@H](NC(=O)COCCCOCCCCOc2ccc3c(c2)c2c(C(N)=O)cc(-c4c(C)noc4C)cc2n3Cc2ccccc2)C(C)(C)C)cc1] | 1026.2 | 1026.5 | A | 97 |
| 167 | 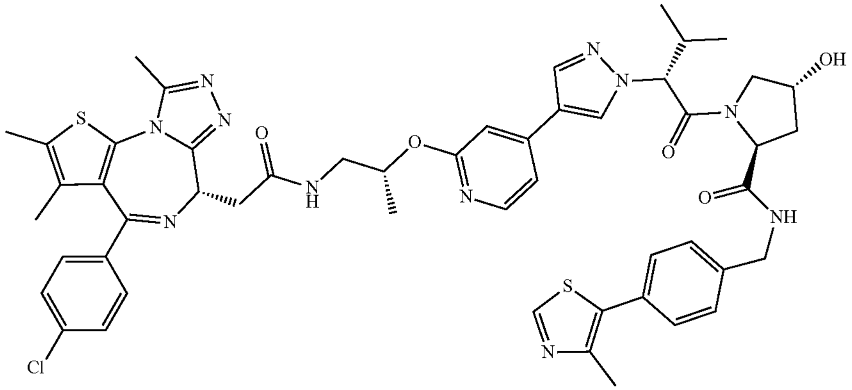 [SMILES: Cc1ncsc1-c1ccc(CNC(=O)[C@@H]2C[C@@H](O)CN2C(=O)[C@@H](C(C)C)n2cc(-c3ccnc(O[C@H](C)CNC(=O)C[C@@H]4N=C(c5ccc(Cl)cc5)c5c(sc(C)c5C)-n5c(C)nnc54)c3)cn2)cc1] | 1000.6 | 1000.4 | D | 27.6 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 168 | 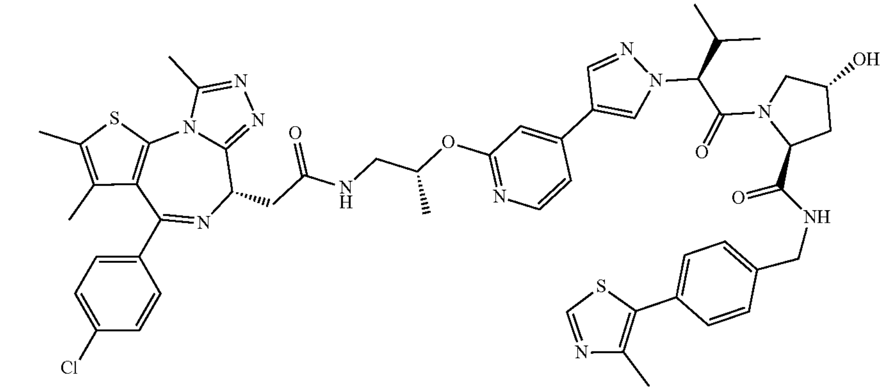 [SMILES: Cc1ncsc1-c1ccc(CNC(=O)[C@@H]2C[C@@H](O)CN2C(=O)[C@H](C(C)C)n2cc(-c3ccnc(O[C@H](C)CNC(=O)C[C@@H]4N=C(c5ccc(Cl)cc5)c5c(sc(C)c5C)-n5c(C)nnc54)c3)cn2)cc1] | 1000.6 | 1000.4 | B | 92 |
| 169 | 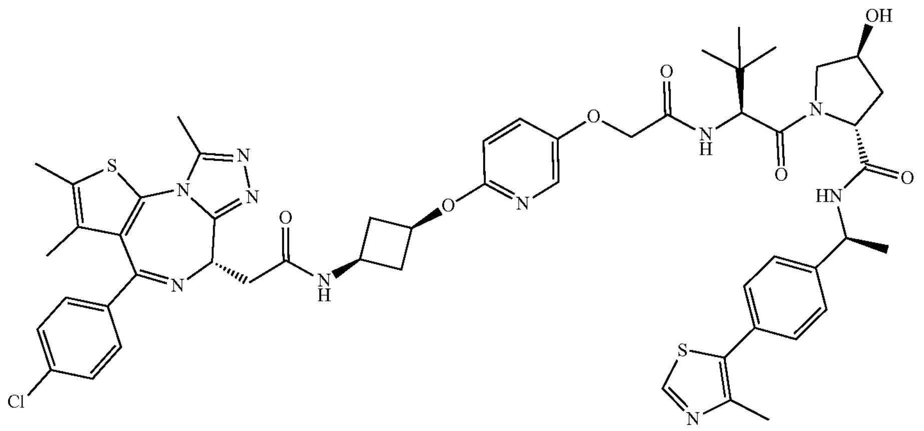 [SMILES: Cc1ncsc1-c1ccc([C@H](C)NC(=O)[C@H]2C[C@H](O)CN2C(=O)[C@@H](NC(=O)COc2ccc(O[C@H]3C[C@@H](NC(=O)C[C@@H]4N=C(c5ccc(Cl)cc5)c5c(sc(C)c5C)-n5c(C)nnc54)C3)nc2)C(C)(C)C)cc1] | 1047.7 | 1047.5 | D | 42.2 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 170 | 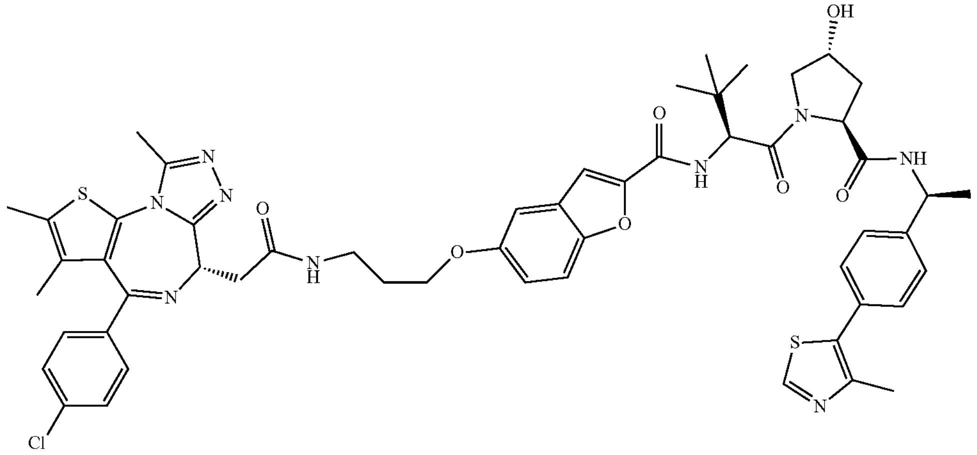 [SMILES: Cc1ncsc1-c1ccc([C@H](C)NC(=O)[C@@H]2C[C@@H](O)CN2C(=O)[C@@H](NC(=O)c2cc3cc(OCCCNC(=O)C[C@@H]4N=C(c5ccc(Cl)cc5)c5c(sc(C)c5C)-n5c(C)nnc54)ccc3o2)C(C)(C)C)cc1] | 1044.7 | 1044.4 | A | 97 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 171 | 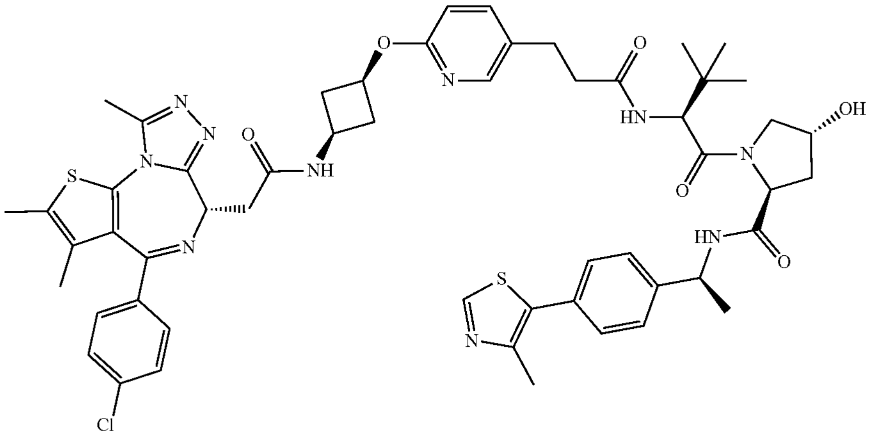 [SMILES: Cc1ncsc1-c1ccc([C@H](C)NC(=O)[C@@H]2C[C@@H](O)CN2C(=O)[C@@H](NC(=O)CCc2ccc(O[C@H]3C[C@@H](NC(=O)C[C@@H]4N=C(c5ccc(Cl)cc5)c5c(sc(C)c5C)-n5c(C)nnc54)C3)nc2)C(C)(C)C)cc1] | 1045.7 | 1045.4 | A | 97 |
| 172 | 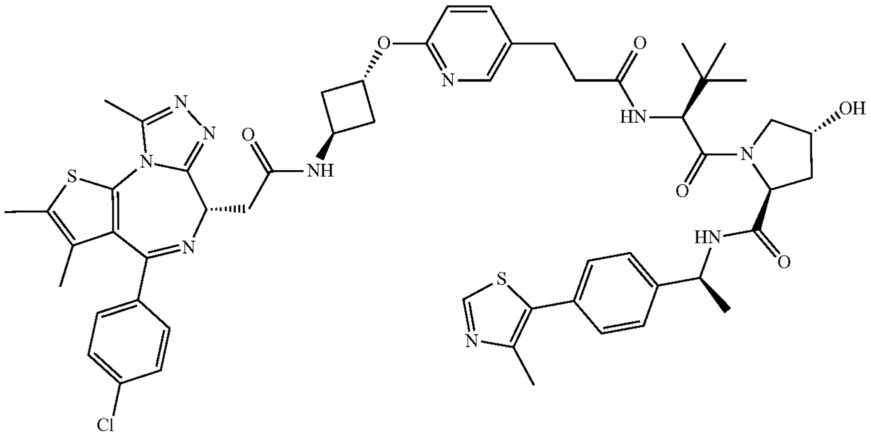 [SMILES: Cc1ncsc1-c1ccc([C@H](C)NC(=O)[C@@H]2C[C@@H](O)CN2C(=O)[C@@H](NC(=O)CCc2ccc(O[C@H]3C[C@H](NC(=O)C[C@@H]4N=C(c5ccc(Cl)cc5)c5c(sc(C)c5C)-n5c(C)nnc54)C3)nc2)C(C)(C)C)cc1] | 1045.7 | 1045.4 | A | 96 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 173 | 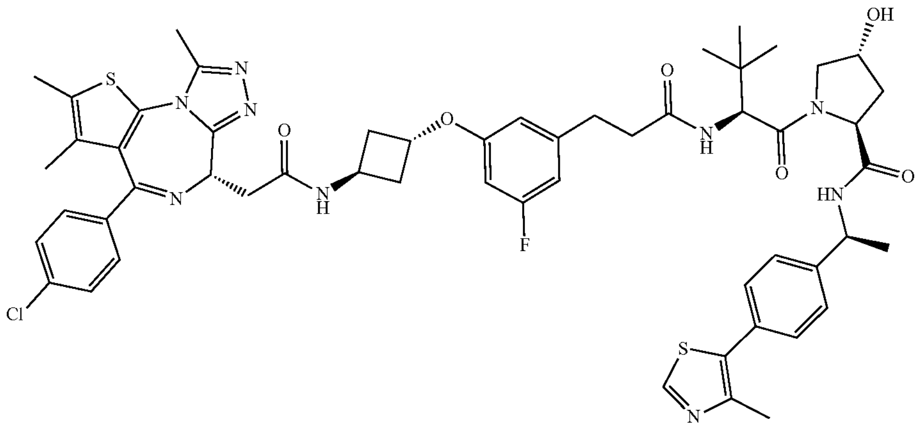 [SMILES: Cc1ncsc1-c1ccc([C@H](C)NC(=O)[C@@H]2C[C@@H](O)CN2C(=O)[C@@H](NC(=O)CCc2cc(F)cc(O[C@H]3C[C@H](NC(=O)C[C@@H]4N=C(c5ccc(Cl)cc5)c5c(sc(C)c5C)-n5c(C)nnc54)C3)c2)C(C)(C)C)cc1] | 1062.7 | 1062.4 | A | 98 |
| 174 | 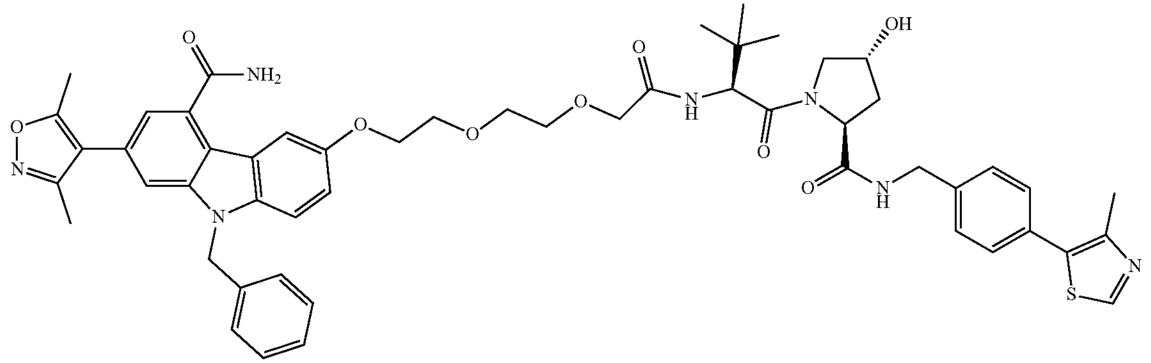 [SMILES: Cc1ncsc1-c1ccc(CNC(=O)[C@@H]2C[C@@H](O)CN2C(=O)[C@@H](NC(=O)COCCOCCOc2ccc3c(c2)c2c(C(N)=O)cc(-c4c(C)noc4C)cc2n3Cc2ccccc2)C(C)(C)C)cc1] | 0970.1 | 0970.5 | B | 96.4 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 175 | 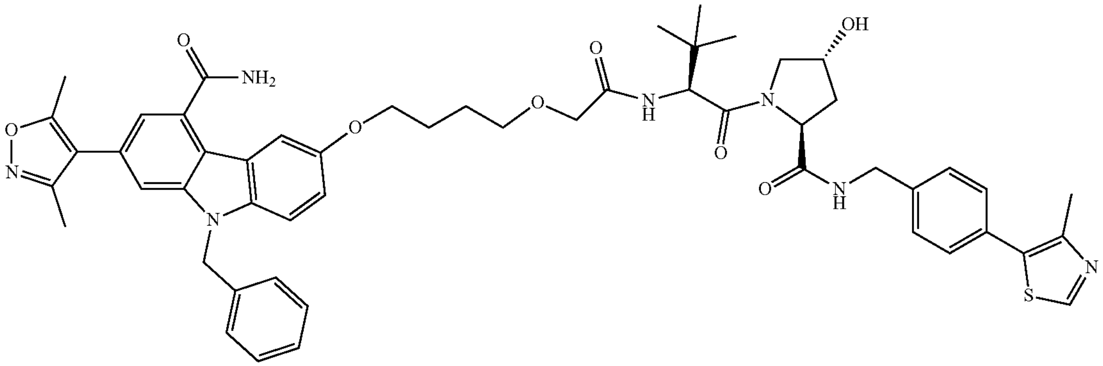 [SMILES: Cc1ncsc1-c1ccc(CNC(=O)[C@@H]2C[C@@H](O)CN2C(=O)[C@@H](NC(=O)COCCCCOc2ccc3c(c2)c2c(C(N)=O)cc(-c4c(C)noc4C)cc2n3Cc2ccccc2)C(C)(C)C)cc1] | 0954.1 | 0954.5 | B | 92 |
| 176 | 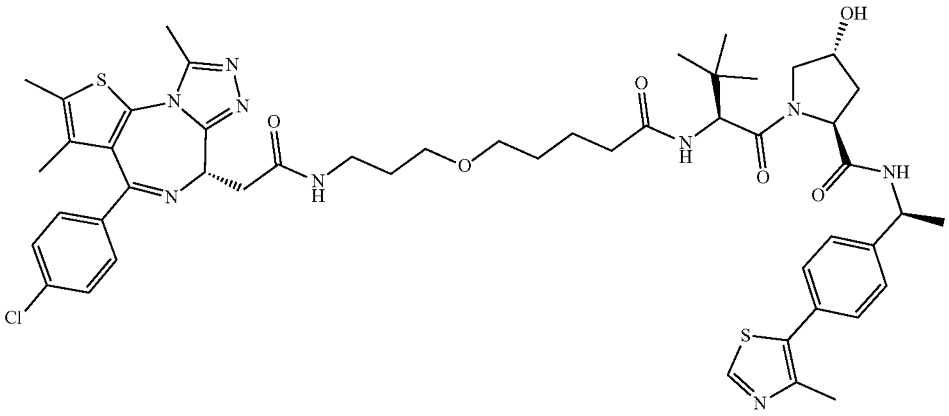 [SMILES: Cc1ncsc1-c1ccc([C@H](C)NC(=O)[C@@H]2C[C@@H](O)CN2C(=O)[C@@H](NC(=O)CCCCOCCCNC(=O)C[C@@H]2N=C(c3ccc(Cl)cc3)c3c(sc(C)c3C)-n3c(C)nnc32)C(C)(C)C)cc1] | 0984.7 | 0984.4 | A | 90.3 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 177 | 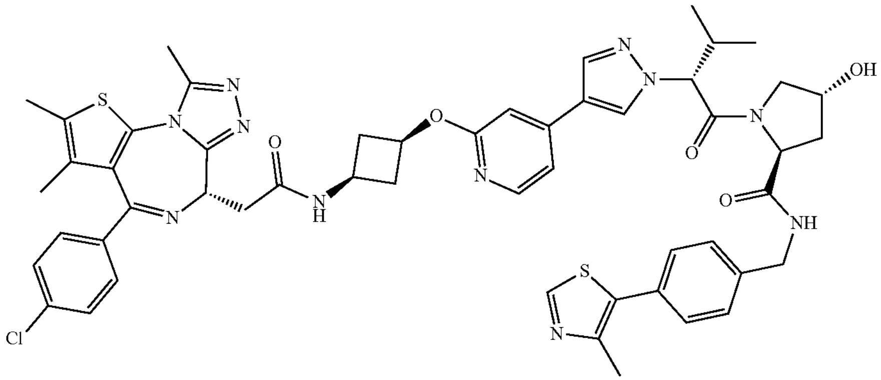 [SMILES: Cc1ncsc1-c1ccc(CNC(=O)[C@@H]2C[C@@H](O)CN2C(=O)[C@@H](C(C)C)n2cc(-c3ccnc(O[C@H]4C[C@@H](NC(=O)C[C@@H]5N=C(c6ccc(Cl)cc6)c6c(sc(C)c6C)-n6c(C)nnc65)C4)c3)cn2)cc1] | 1012.6 | 1012.3 | D | 39.3 |
| 178 | 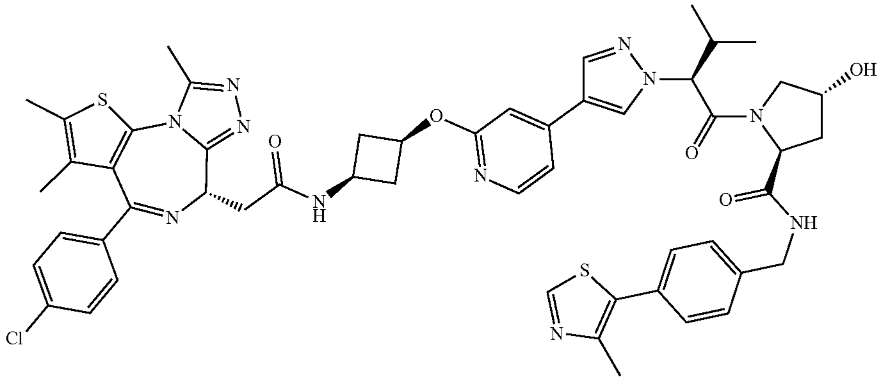 [SMILES: Cc1ncsc1-c1ccc(CNC(=O)[C@@H]2C[C@@H](O)CN2C(=O)[C@H](C(C)C)n2cc(-c3ccnc(O[C@H]4C[C@@H](NC(=O)C[C@@H]5N=C(c6ccc(Cl)cc6)c6c(sc(C)c6C)-n6c(C)nnc65)C4)c3)cn2)cc1] | 1012.6 | 1012.3 | B | 99 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 179 | 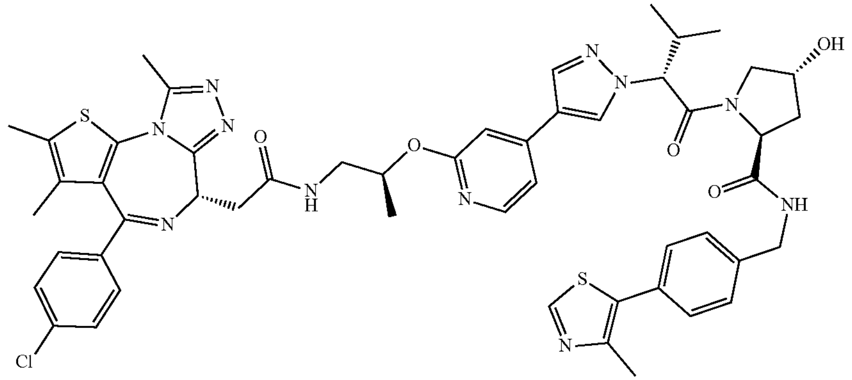 [SMILES: Cc1ncsc1-c1ccc(CNC(=O)[C@@H]2C[C@@H](O)CN2C(=O)[C@@H](C(C)C)n2cc(-c3ccnc(O[C@@H](C)CNC(=O)C[C@@H]4N=C(c5ccc(Cl)cc5)c5c(sc(C)c5C)-n5c(C)nnc54)c3)cn2)cc1] | 1000.6 | 1000.4 | D | 13.9 |
| 180 | 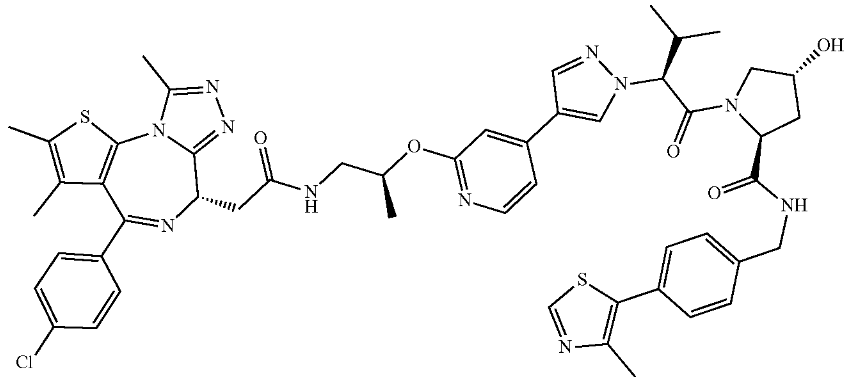 [SMILES: Cc1ncsc1-c1ccc(CNC(=O)[C@@H]2C[C@@H](O)CN2C(=O)[C@H](C(C)C)n2cc(-c3ccnc(O[C@@H](C)CNC(=O)C[C@@H]4N=C(c5ccc(Cl)cc5)c5c(sc(C)c5C)-n5c(C)nnc54)c3)cn2)cc1] | 1000.6 | 1000.5 | B | 98.5 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 181 | 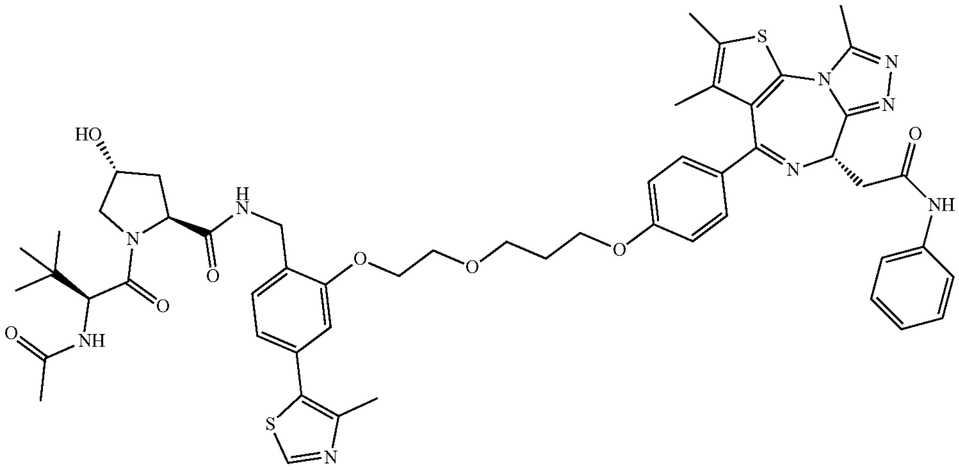 [SMILES: CC(=O)N[C@H](C(=O)N1C[C@H](O)C[C@H]1C(=O)NCc1ccc(-c2scnc2C)cc1OCCOCCCOc1ccc(C2=N[C@@H](CC(=O)Nc3ccccc3)c3nnc(C)n3-c3sc(C)c(C)c32)cc1)C(C)(C)C] | 1030.3 | 1030.5 | C | 80.5 |
| 182 | 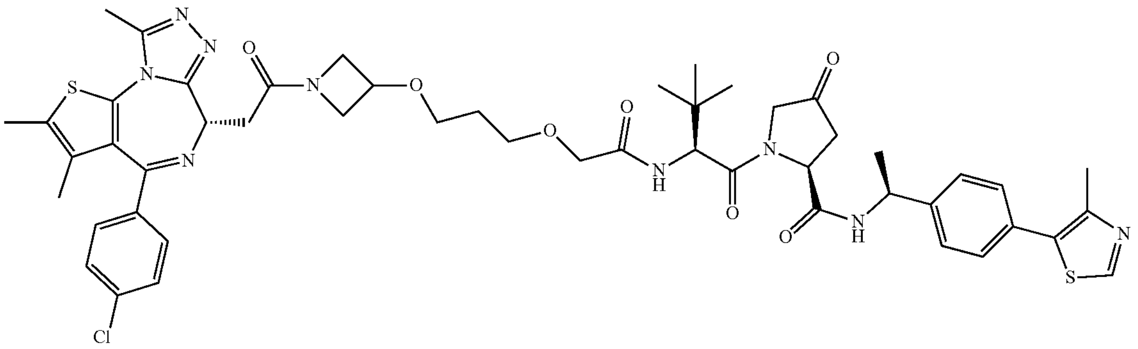 [SMILES: Cc1ncsc1-c1ccc([C@H](C)NC(=O)[C@@H]2CC(=O)CN2C(=O)[C@@H](NC(=O)COCCCOC2CN(C(=O)C[C@@H]3N=C(c4ccc(Cl)cc4)c4c(sc(C)c4C)-n4c(C)nnc43)C2)C(C)(C)C)cc1] | 0998.7 | 0998.4 | A | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 183 | 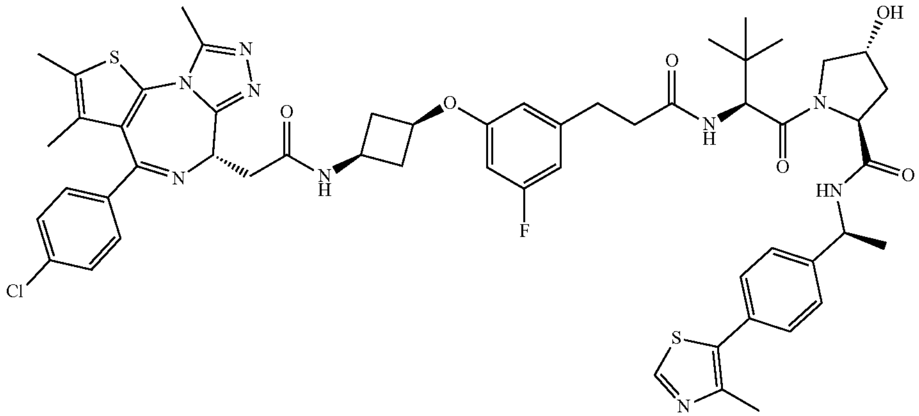 [SMILES: Cc1ncsc1-c1ccc([C@H](C)NC(=O)[C@@H]2C[C@@H](O)CN2C(=O)[C@@H](NC(=O)CCc2cc(F)cc(O[C@H]3C[C@@H](NC(=O)C[C@@H]4N=C(c5ccc(Cl)cc5)c5c(sc(C)c5C)-n5c(C)nnc54)C3)c2)C(C)(C)C)cc1] | 1062.7 | 1062.5 | A | 99 |
| 184 | 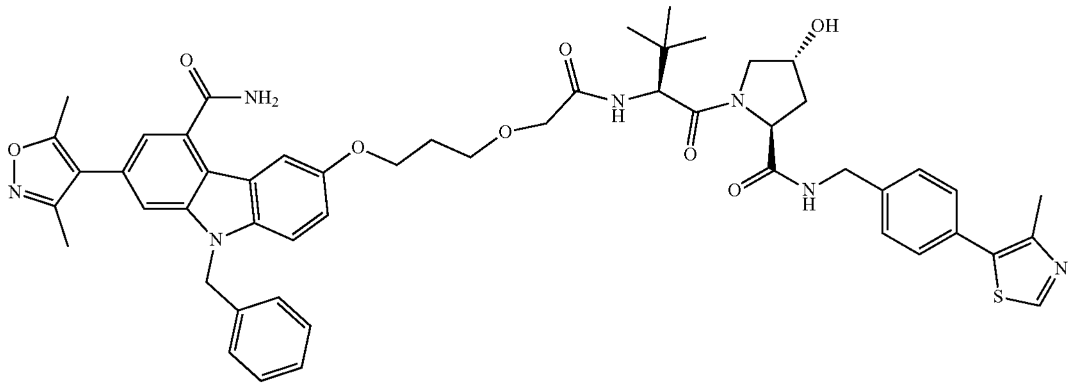 [SMILES: Cc1ncsc1-c1ccc(CNC(=O)[C@@H]2C[C@@H](O)CN2C(=O)[C@@H](NC(=O)COCCCOc2ccc3c(c2)c2c(C(N)=O)cc(-c4c(C)noc4C)cc2n3Cc2ccccc2)C(C)(C)C)cc1] | 0940.1 | 0940.5 | B | 91.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 185 | 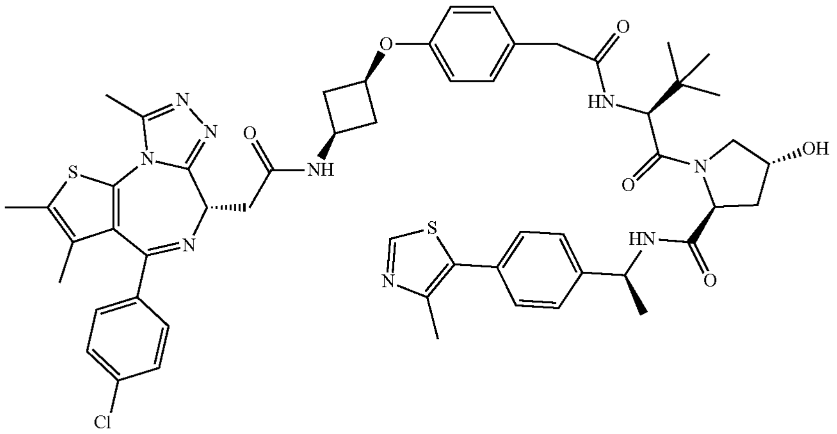 [SMILES: Cc1ncsc1-c1ccc([C@H](C)NC(=O)[C@@H]2C[C@@H](O)CN2C(=O)[C@@H](NC(=O)Cc2ccc(O[C@H]3C[C@@H](NC(=O)C[C@@H]4N=C(c5ccc(Cl)cc5)c5c(sc(C)c5C)-n5c(C)nnc54)C3)cc2)C(C)(C)C)cc1] | 1030.7 | 1030.4 | A | 99.5 |
| 186 | 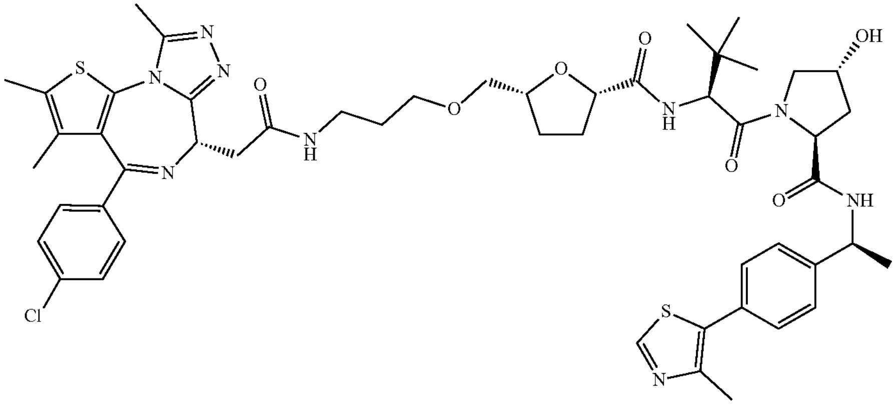 [SMILES: Cc1ncsc1-c1ccc([C@H](C)NC(=O)[C@@H]2C[C@@H](O)CN2C(=O)[C@@H](NC(=O)[C@@H]2CC[C@H](COCCCNC(=O)C[C@@H]3N=C(c4ccc(Cl)cc4)c4c(sc(C)c4C)-n4c(C)nnc43)O2)C(C)(C)C)cc1] | 1012.7 | 1012.4 | B | 94.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 187 | 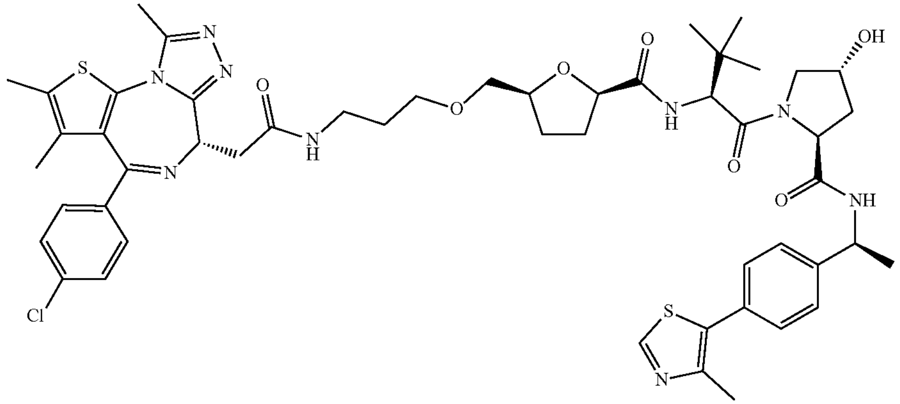 [SMILES: Cc1ncsc1-c1ccc([C@H](C)NC(=O)[C@@H]2C[C@@H](O)CN2C(=O)[C@@H](NC(=O)[C@H]2CC[C@@H](COCCCNC(=O)C[C@@H]3N=C(c4ccc(Cl)cc4)c4c(sc(C)c4C)-n4c(C)nnc43)O2)C(C)(C)C)cc1] | 1012.7 | 1012.5 | B | 98.5 |
| 188 | 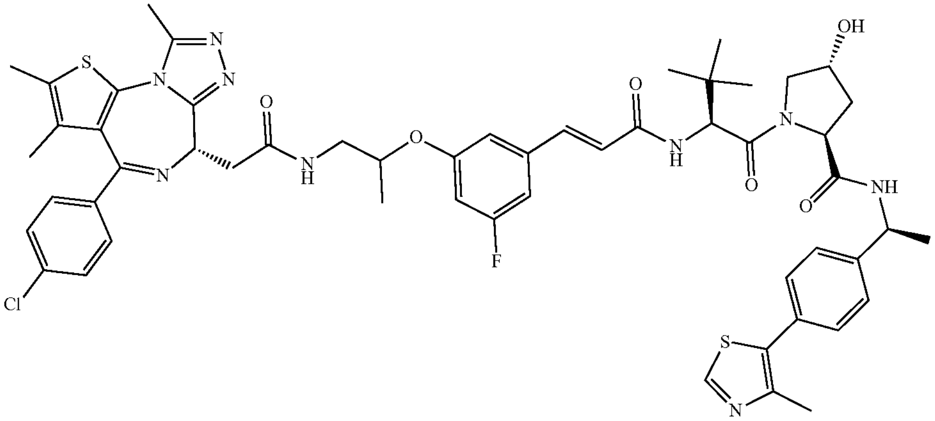 [SMILES: Cc1ncsc1-c1ccc([C@H](C)NC(=O)[C@@H]2C[C@@H](O)CN2C(=O)[C@@H](NC(=O)/C=C/c2cc(F)cc(OC(C)CNC(=O)C[C@@H]3N=C(c4ccc(Cl)cc4)c4c(sc(C)c4C)-n4c(C)nnc43)c2)C(C)(C)C)cc1] | 1048.7 | 1048.4 | A | 95.4 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 189 | 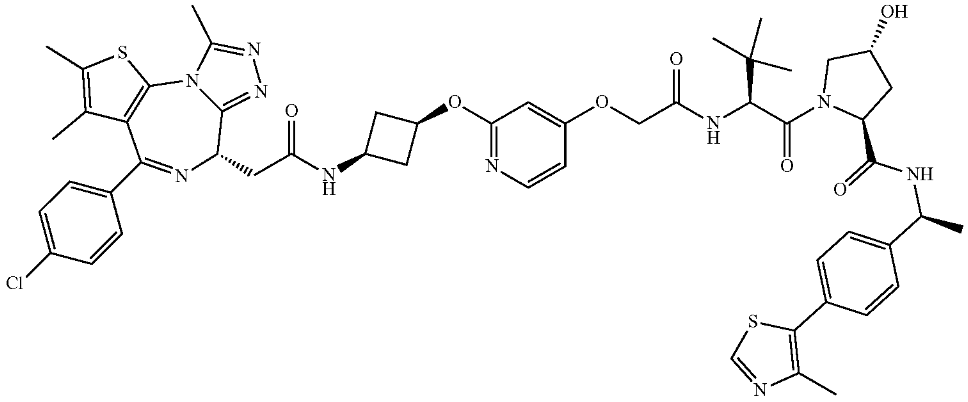 [SMILES: Cc1ncsc1-c1ccc([C@H](C)NC(=O)[C@@H]2C[C@@H](O)CN2C(=O)[C@@H](NC(=O)COc2ccnc(O[C@H]3C[C@@H](NC(=O)C[C@@H]4N=C(c5ccc(Cl)cc5)c5c(sc(C)c5C)-n5c(C)nnc54)C3)c2)C(C)(C)C)cc1] | 1047.7 | 1047.4 | B | 95.9 |
| 190 | 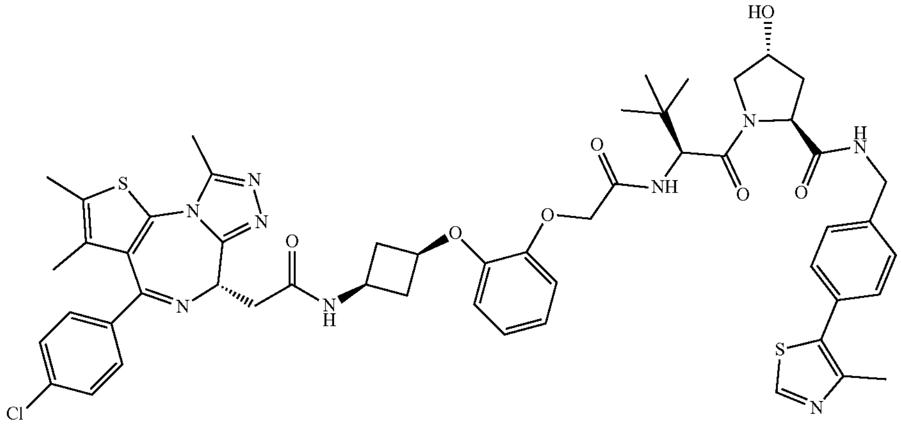 [SMILES: Cc1ncsc1-c1ccc(CNC(=O)[C@@H]2C[C@@H](O)CN2C(=O)[C@@H](NC(=O)COc2ccccc2O[C@H]2C[C@@H](NC(=O)C[C@@H]3N=C(c4ccc(Cl)cc4)c4c(sc(C)c4C)-n4c(C)nnc43)C2)C(C)(C)C)cc1] | 1032.7 | 1032.4 | B | 91.0 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 191 | 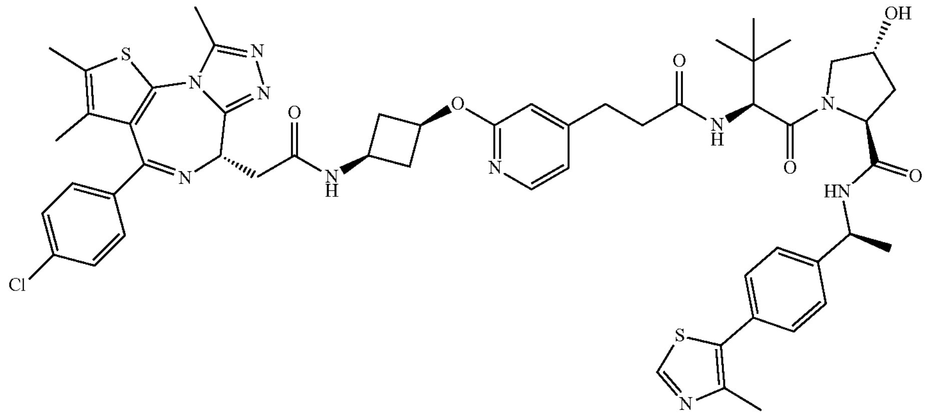 [SMILES: Cc1ncsc1-c1ccc([C@H](C)NC(=O)[C@@H]2C[C@@H](O)CN2C(=O)[C@@H](NC(=O)CCc2ccnc(O[C@H]3C[C@@H](NC(=O)C[C@@H]4N=C(c5ccc(Cl)cc5)c5c(sc(C)c5C)-n5c(C)nnc54)C3)c2)C(C)(C)C)cc1] | 1045.7 | 1045.4 | A | 95.0 |
| 192 | 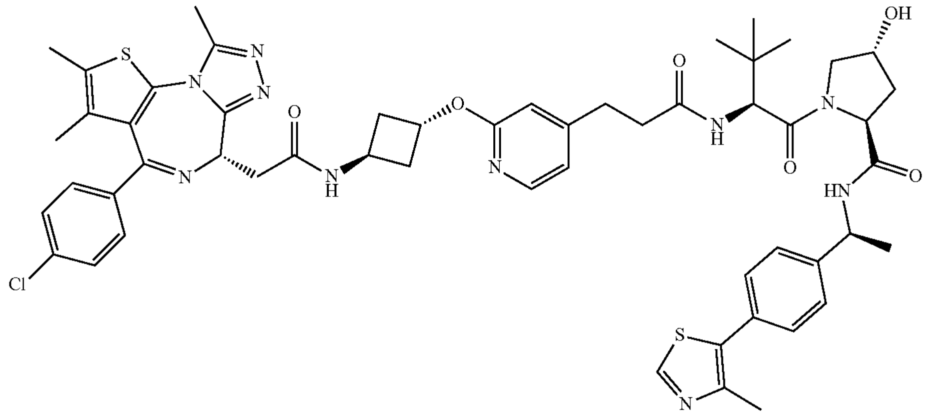 [SMILES: Cc1ncsc1-c1ccc([C@H](C)NC(=O)[C@@H]2C[C@@H](O)CN2C(=O)[C@@H](NC(=O)CCc2ccnc(O[C@H]3C[C@H](NC(=O)C[C@@H]4N=C(c5ccc(Cl)cc5)c5c(sc(C)c5C)-n5c(C)nnc54)C3)c2)C(C)(C)C)cc1] | 1045.7 | 1045.4 | A | 93.0 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 193 | 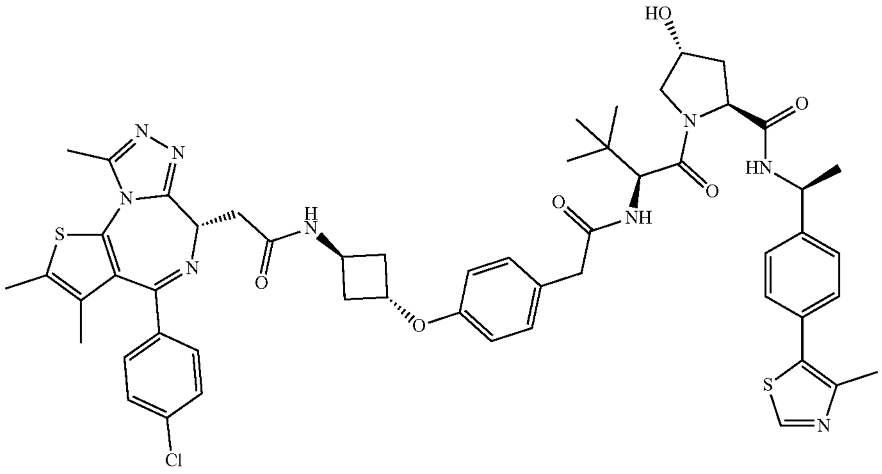 | 1030.7 | 1030.4 | A | 100.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 194 | 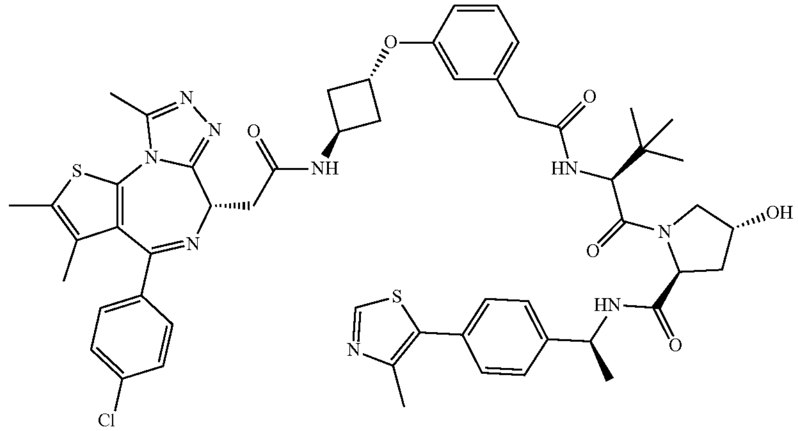 [SMILES: Cc1ncsc1-c1ccc([C@H](C)NC(=O)[C@@H]2C[C@@H](O)CN2C(=O)[C@@H](NC(=O)Cc2cccc(O[C@H]3C[C@H](NC(=O)C[C@@H]4N=C(c5ccc(Cl)cc5)c5c(sc(C)c5C)-n5c(C)nnc54)C3)c2)C(C)(C)C)cc1] | 1030.7 | 1030.4 | A | 92.4 |
| 195 | 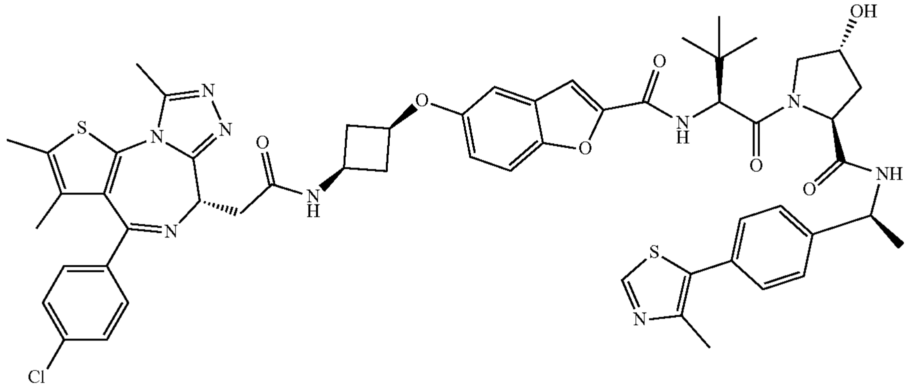 [SMILES: Cc1ncsc1-c1ccc([C@H](C)NC(=O)[C@@H]2C[C@@H](O)CN2C(=O)[C@@H](NC(=O)c2cc3cc(O[C@H]4C[C@@H](NC(=O)C[C@@H]5N=C(c6ccc(Cl)cc6)c6c(sc(C)c6C)-n6c(C)nnc65)C4)ccc3o2)C(C)(C)C)cc1] | 1056.7 | 1056.4 | A | 100.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 196 | 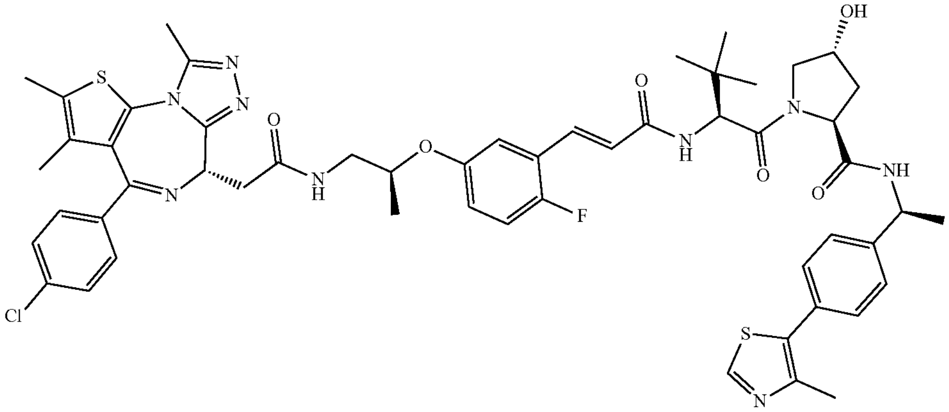 [SMILES: Cc1ncsc1-c1ccc([C@H](C)NC(=O)[C@@H]2C[C@@H](O)CN2C(=O)[C@@H](NC(=O)/C=C/c2cc(O[C@@H](C)CNC(=O)C[C@@H]3N=C(c4ccc(Cl)cc4)c4c(sc(C)c4C)-n4c(C)nnc43)ccc2F)C(C)(C)C)cc1] | 1048.7 | 1048.5 | A | 94.5 |
| 197 | 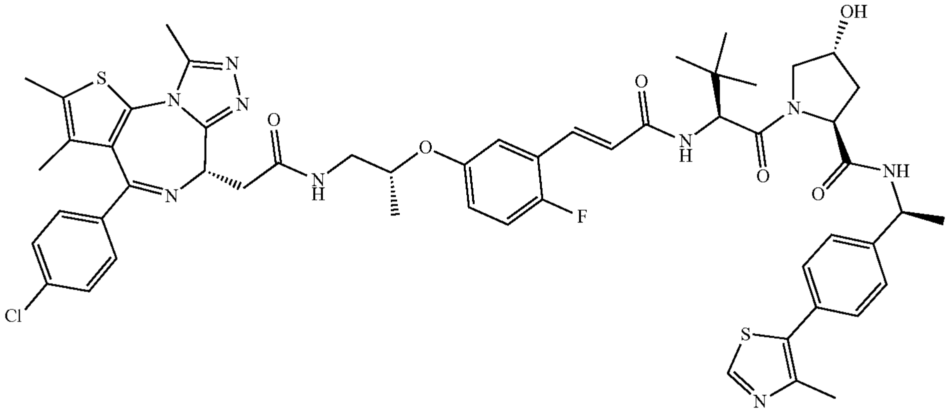 [SMILES: Cc1ncsc1-c1ccc([C@H](C)NC(=O)[C@@H]2C[C@@H](O)CN2C(=O)[C@@H](NC(=O)/C=C/c2cc(O[C@H](C)CNC(=O)C[C@@H]3N=C(c4ccc(Cl)cc4)c4c(sc(C)c4C)-n4c(C)nnc43)ccc2F)C(C)(C)C)cc1] | 1048.7 | 1048.4 | A | 91.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 198 | 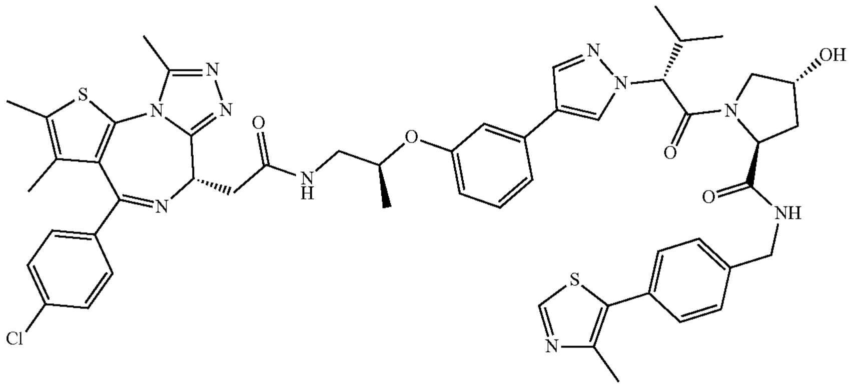 [SMILES: Cc1ncsc1-c1ccc(CNC(=O)[C@@H]2C[C@@H](O)CN2C(=O)[C@@H](C(C)C)n2cc(-c3cccc(O[C@@H](C)CNC(=O)C[C@@H]4N=C(c5ccc(Cl)cc5)c5c(sc(C)c5C)-n5c(C)nnc54)c3)cn2)cc1] | 0999.7 | 0999.4 | D | 16.0 |
| 199 | 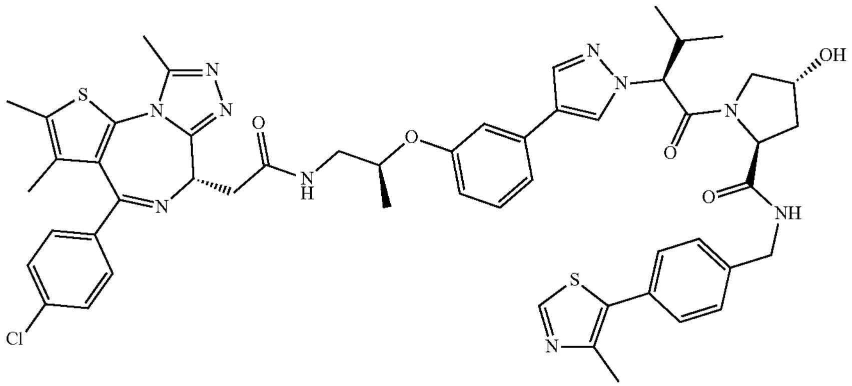 [SMILES: Cc1ncsc1-c1ccc(CNC(=O)[C@@H]2C[C@@H](O)CN2C(=O)[C@H](C(C)C)n2cc(-c3cccc(O[C@@H](C)CNC(=O)C[C@@H]4N=C(c5ccc(Cl)cc5)c5c(sc(C)c5C)-n5c(C)nnc54)c3)cn2)cc1] | 0999.7 | 0999.4 | A | 93.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 200 | 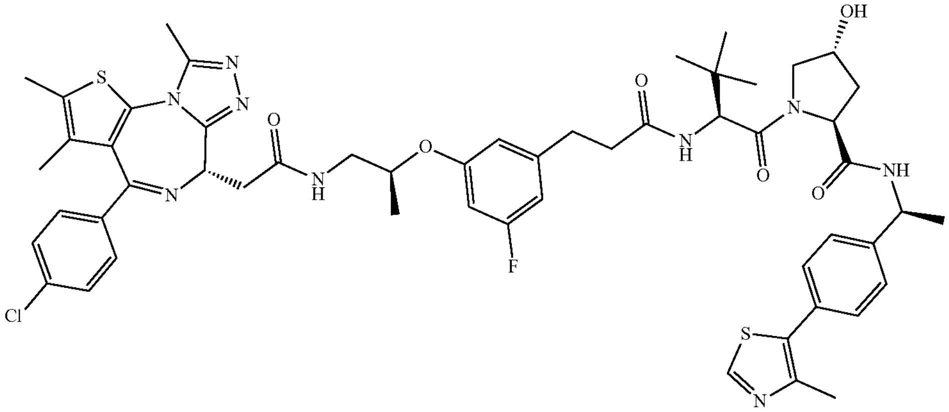 [SMILES: Cc1ncsc1-c1ccc([C@H](C)NC(=O)[C@@H]2C[C@@H](O)CN2C(=O)[C@@H](NC(=O)CCc2cc(F)cc(O[C@@H](C)CNC(=O)C[C@@H]3N=C(c4ccc(Cl)cc4)c4c(sc(C)c4C)-n4c(C)nnc43)c2)C(C)(C)C)cc1] | 1050.7 | 1050.5 | A | 96.5 |
| 201 | 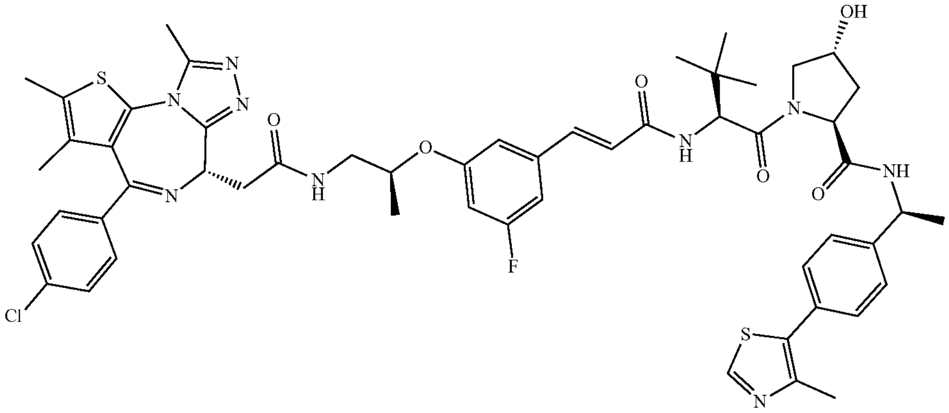 [SMILES: Cc1ncsc1-c1ccc([C@H](C)NC(=O)[C@@H]2C[C@@H](O)CN2C(=O)[C@@H](NC(=O)/C=C/c2cc(F)cc(O[C@@H](C)CNC(=O)C[C@@H]3N=C(c4ccc(Cl)cc4)c4c(sc(C)c4C)-n4c(C)nnc43)c2)C(C)(C)C)cc1] | 1048.7 | 1048.3 | A | 94.1 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 202 | 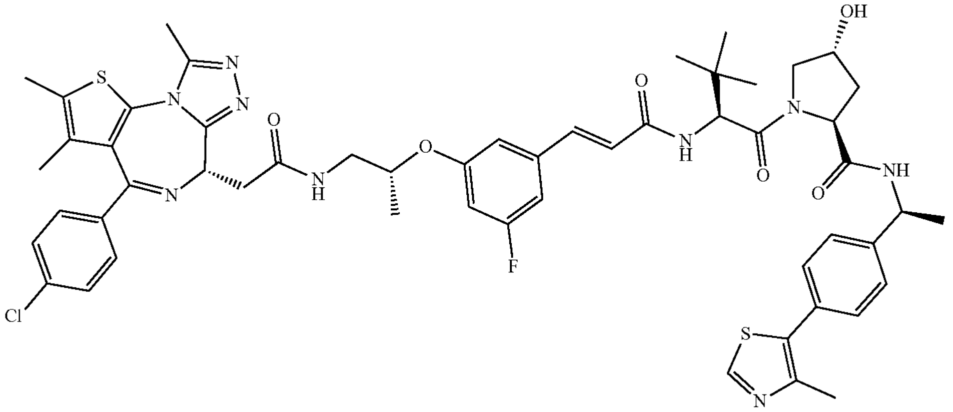 [SMILES: Cc1ncsc1-c1ccc([C@H](C)NC(=O)[C@@H]2C[C@@H](O)CN2C(=O)[C@@H](NC(=O)/C=C/c2cc(F)cc(O[C@H](C)CNC(=O)C[C@@H]3N=C(c4ccc(Cl)cc4)c4c(sc(C)c4C)-n4c(C)nnc43)c2)C(C)(C)C)cc1] | 1048.7 | 1048.3 | A | 94.0 |
| 203 | 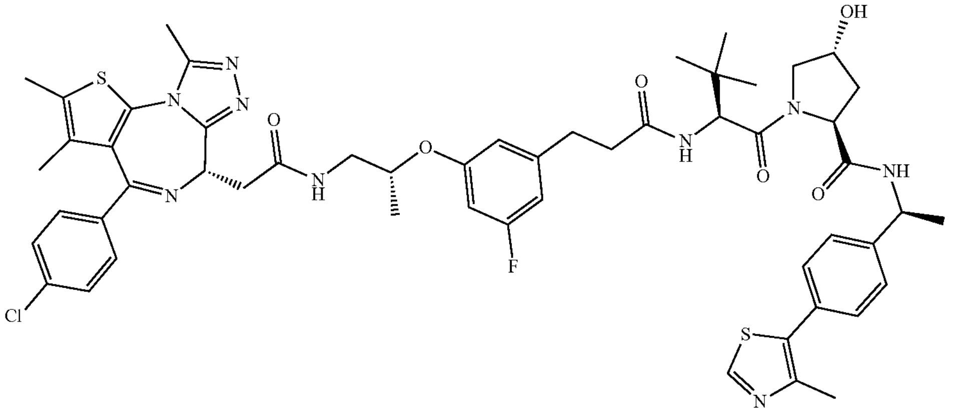 [SMILES: Cc1ncsc1-c1ccc([C@H](C)NC(=O)[C@@H]2C[C@@H](O)CN2C(=O)[C@@H](NC(=O)CCc2cc(F)cc(O[C@H](C)CNC(=O)C[C@@H]3N=C(c4ccc(Cl)cc4)c4c(sc(C)c4C)-n4c(C)nnc43)c2)C(C)(C)C)cc1] | 1050.7 | 1050.1 | A | 92.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 204 | 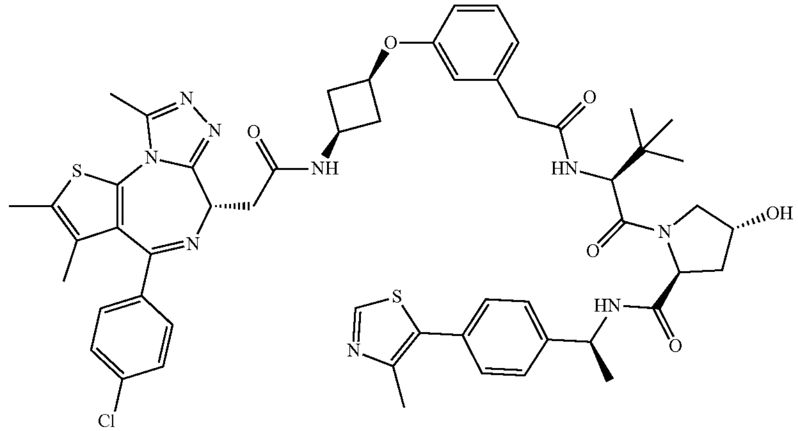 [SMILES: Cc1ncsc1-c1ccc([C@H](C)NC(=O)[C@@H]2C[C@@H](O)CN2C(=O)[C@@H](NC(=O)Cc2cccc(O[C@H]3C[C@@H](NC(=O)C[C@@H]4N=C(c5ccc(Cl)cc5)c5c(sc(C)c5C)-n5c(C)nnc54)C3)c2)C(C)(C)C)cc1] | 1030.7 | 1030.4 | B | 88.0 |
| 205 | 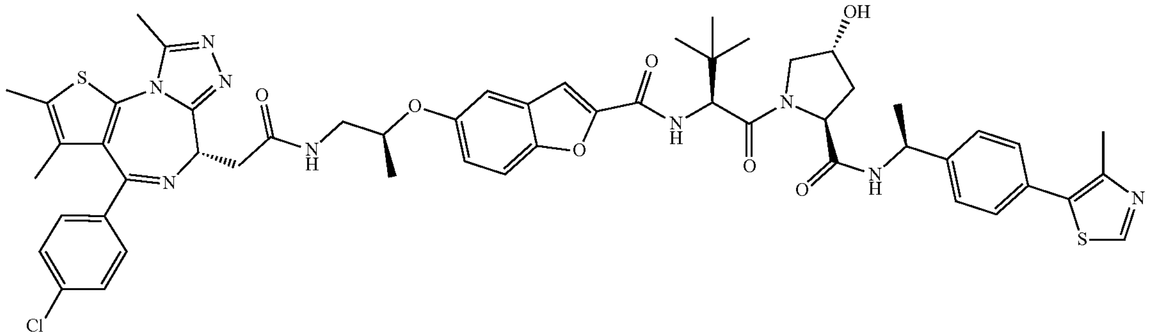 [SMILES: Cc1ncsc1-c1ccc([C@H](C)NC(=O)[C@@H]2C[C@@H](O)CN2C(=O)[C@@H](NC(=O)c2cc3cc(O[C@@H](C)CNC(=O)C[C@@H]4N=C(c5ccc(Cl)cc5)c5c(sc(C)c5C)-n5c(C)nnc54)ccc3o2)C(C)(C)C)cc1] | 1044.7 | 1044.4 | A | 91.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 206 | 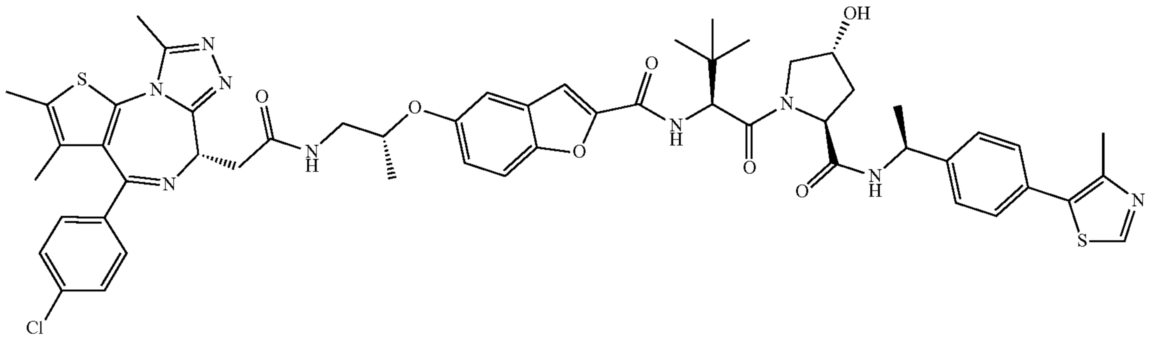 [SMILES: Cc1ncsc1-c1ccc([C@H](C)NC(=O)[C@@H]2C[C@@H](O)CN2C(=O)[C@@H](NC(=O)c2cc3cc(O[C@H](C)CNC(=O)C[C@@H]4N=C(c5ccc(Cl)cc5)c5c(sc(C)c5C)-n5c(C)nnc54)ccc3o2)C(C)(C)C)cc1] | 1044.7 | 1044.4 | A | 90.0 |
| 207 | 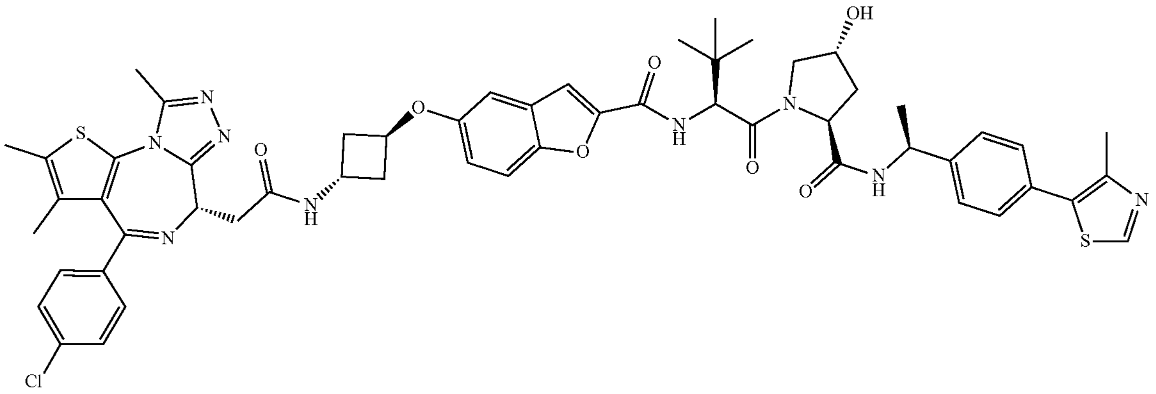 [SMILES: Cc1ncsc1-c1ccc([C@H](C)NC(=O)[C@@H]2C[C@@H](O)CN2C(=O)[C@@H](NC(=O)c2cc3cc(O[C@H]4C[C@H](NC(=O)C[C@@H]5N=C(c6ccc(Cl)cc6)c6c(sc(C)c6C)-n6c(C)nnc65)C4)ccc3o2)C(C)(C)C)cc1] | 1056.7 | 1056.4 | A | 89.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 208 | 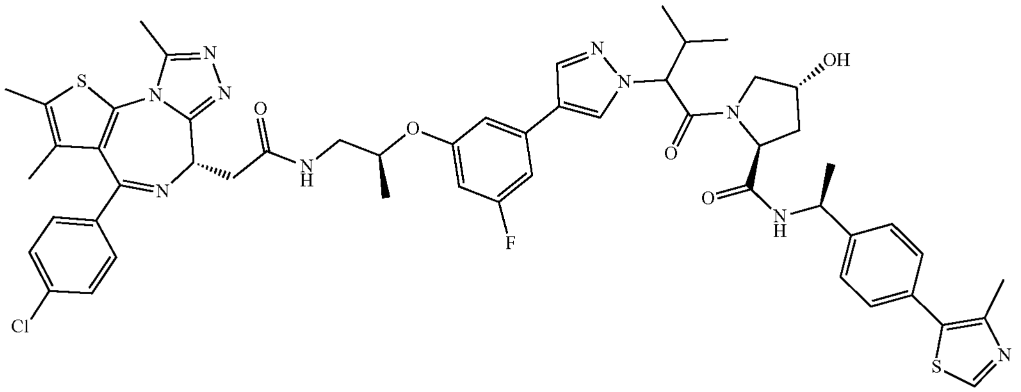 [SMILES: Cc1ncsc1-c1ccc([C@H](C)NC(=O)[C@@H]2C[C@@H](O)CN2C(=O)C(C(C)C)n2cc(-c3cc(F)cc(O[C@@H](C)CNC(=O)C[C@@H]4N=C(c5ccc(Cl)cc5)c5c(sc(C)c5C)-n5c(C)nnc54)c3)cn2)cc1] | 1031.7 | 1031.4 | A | 92.0 |
| 209 | 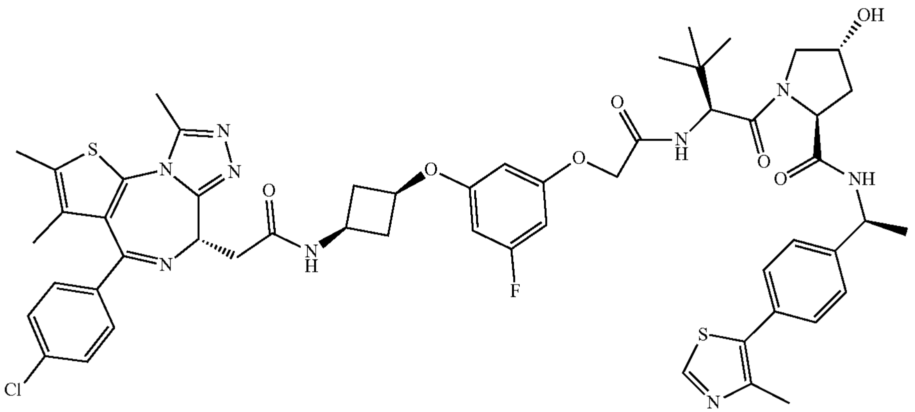 [SMILES: Cc1ncsc1-c1ccc([C@H](C)NC(=O)[C@@H]2C[C@@H](O)CN2C(=O)[C@@H](NC(=O)COc2cc(F)cc(O[C@H]3C[C@@H](NC(=O)C[C@@H]4N=C(c5ccc(Cl)cc5)c5c(sc(C)c5C)-n5c(C)nnc54)C3)c2)C(C)(C)C)cc1] | 1064.7 | 1064.3 | A | 90.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 210 | 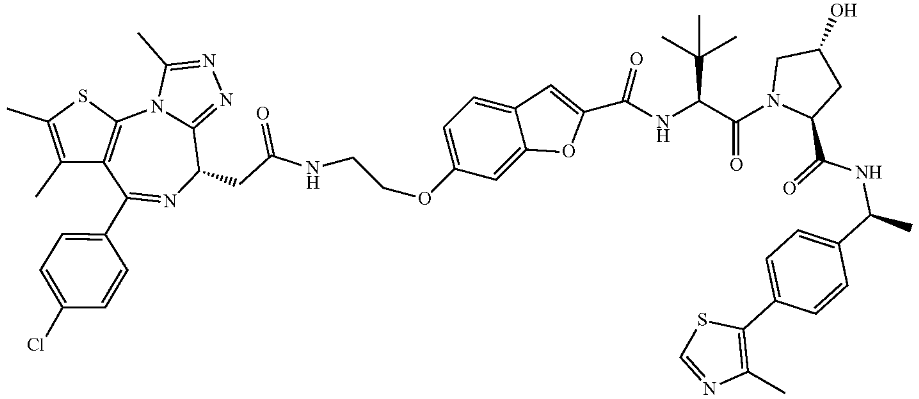 [SMILES: Cc1ncsc1-c1ccc([C@H](C)NC(=O)[C@@H]2C[C@@H](O)CN2C(=O)[C@@H](NC(=O)c2cc3ccc(OCCNC(=O)C[C@@H]4N=C(c5ccc(Cl)cc5)c5c(sc(C)c5C)-n5c(C)nnc54)cc3o2)C(C)(C)C)cc1] | 1030.7 | 1030.3 | A | 100 |
| 211 | 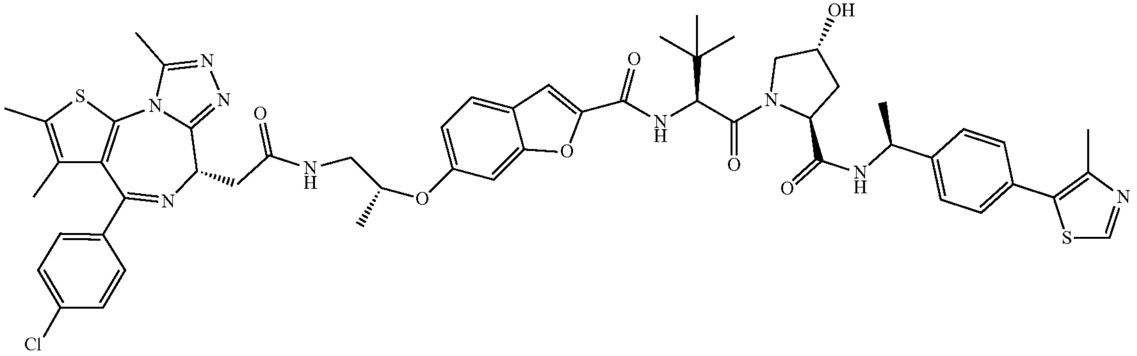 [SMILES: Cc1ncsc1-c1ccc([C@H](C)NC(=O)[C@@H]2C[C@@H](O)CN2C(=O)[C@@H](NC(=O)c2cc3ccc(O[C@H](C)CNC(=O)C[C@@H]4N=C(c5ccc(Cl)cc5)c5c(sc(C)c5C)-n5c(C)nnc54)cc3o2)C(C)(C)C)cc1] | 1044.7 | 1044.1 | A | 99.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 212 | 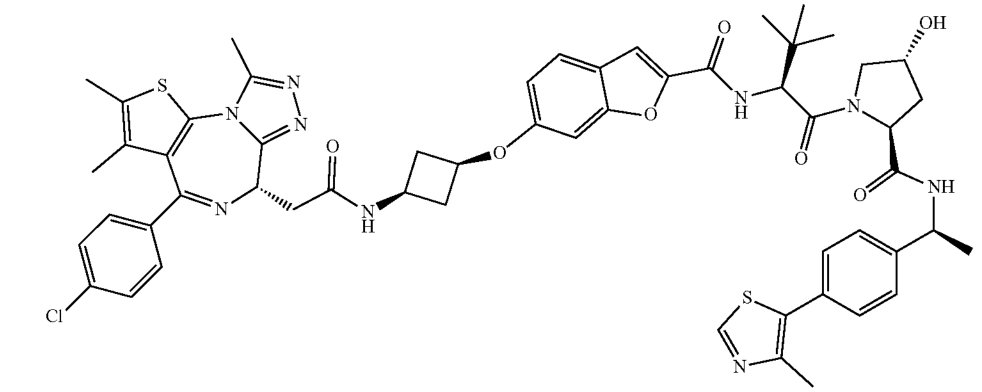 [SMILES: Cc1ncsc1-c1ccc([C@H](C)NC(=O)[C@@H]2C[C@@H](O)CN2C(=O)[C@@H](NC(=O)c2cc3ccc(O[C@H]4C[C@@H](NC(=O)C[C@@H]5N=C(c6ccc(Cl)cc6)c6c(sc(C)c6C)-n6c(C)nnc65)C4)cc3o2)C(C)(C)C)cc1] | 1056.7 | 1056.4 | A | 95.0 |
| 213 | 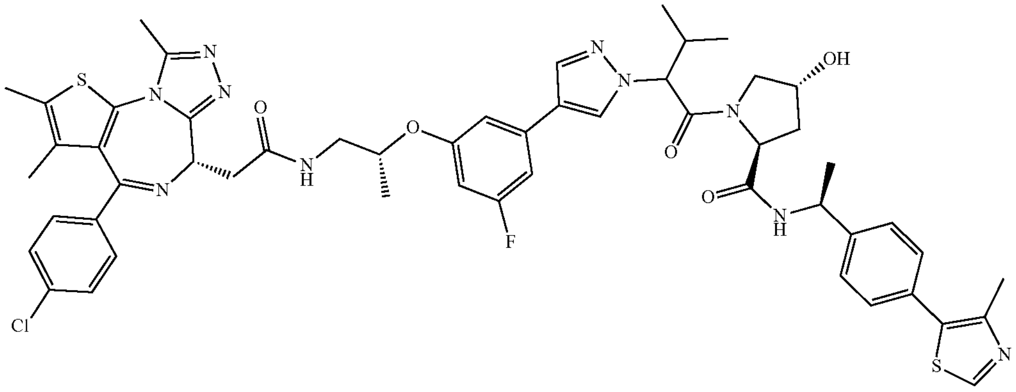 [SMILES: Cc1ncsc1-c1ccc([C@H](C)NC(=O)[C@@H]2C[C@@H](O)CN2C(=O)C(C(C)C)n2cc(-c3cc(F)cc(O[C@H](C)CNC(=O)C[C@@H]4N=C(c5ccc(Cl)cc5)c5c(sc(C)c5C)-n5c(C)nnc54)c3)cn2)cc1] | 1031.7 | 1031.3 | B | 94.3 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 214 | 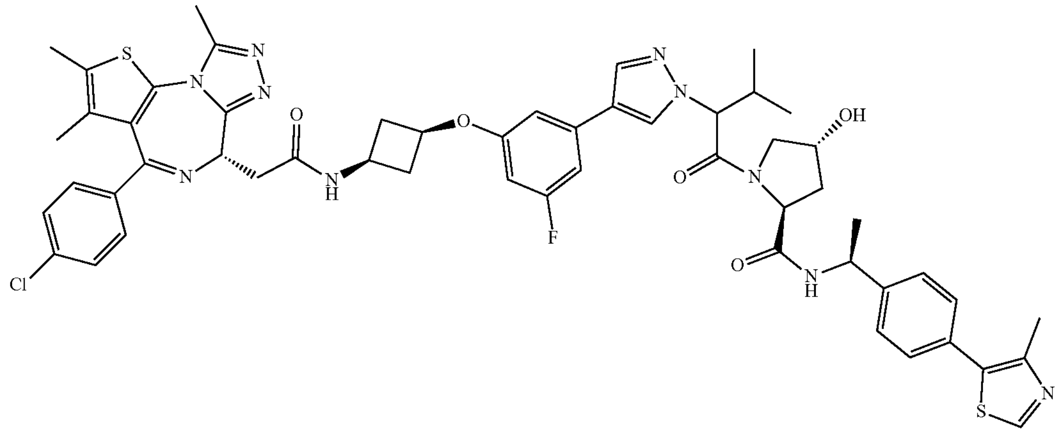 [SMILES: Cc1ncsc1-c1ccc([C@H](C)NC(=O)[C@@H]2C[C@@H](O)CN2C(=O)C(C(C)C)n2cc(-c3cc(F)cc(O[C@H]4C[C@@H](NC(=O)C[C@@H]5N=C(c6ccc(Cl)cc6)c6c(sc(C)c6C)-n6c(C)nnc65)C4)c3)cn2)cc1] | 1043.7 | 1043.3 | B | 97.0 |
| 215 | 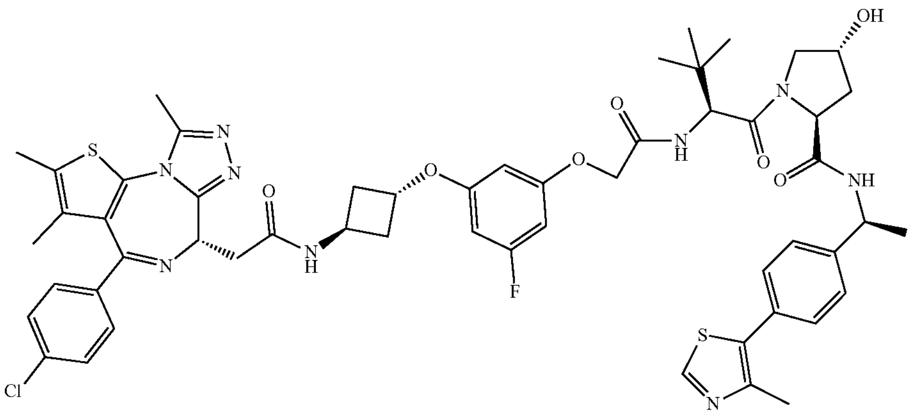 [SMILES: Cc1ncsc1-c1ccc([C@H](C)NC(=O)[C@@H]2C[C@@H](O)CN2C(=O)[C@@H](NC(=O)COc2cc(F)cc(O[C@H]3C[C@H](NC(=O)C[C@@H]4N=C(c5ccc(Cl)cc5)c5c(sc(C)c5C)-n5c(C)nnc54)C3)c2)C(C)(C)C)cc1] | 1064.7 | 1064.3 | A | 98.0 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 216 | 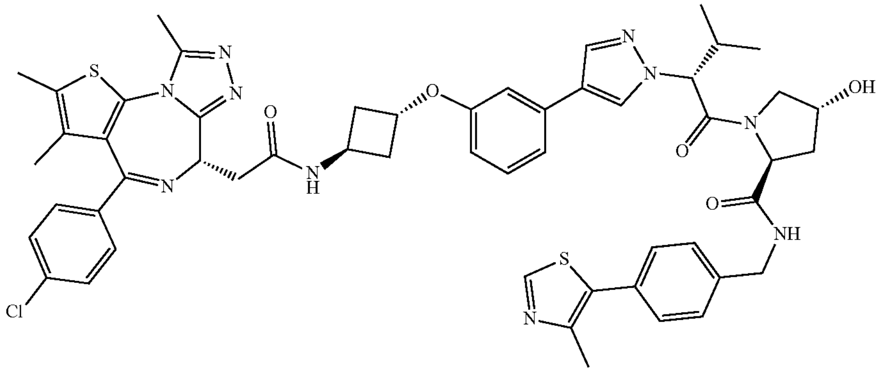 [SMILES: Cc1ncsc1-c1ccc(CNC(=O)[C@@H]2C[C@@H](O)CN2C(=O)[C@@H](C(C)C)n2cc(-c3cccc(O[C@H]4C[C@H](NC(=O)C[C@@H]5N=C(c6ccc(Cl)cc6)c6c(sc(C)c6C)-n6c(C)nnc65)C4)c3)cn2)cc1] | 1011.7 | 1011.5 | D | 14.4 |
| 217 | 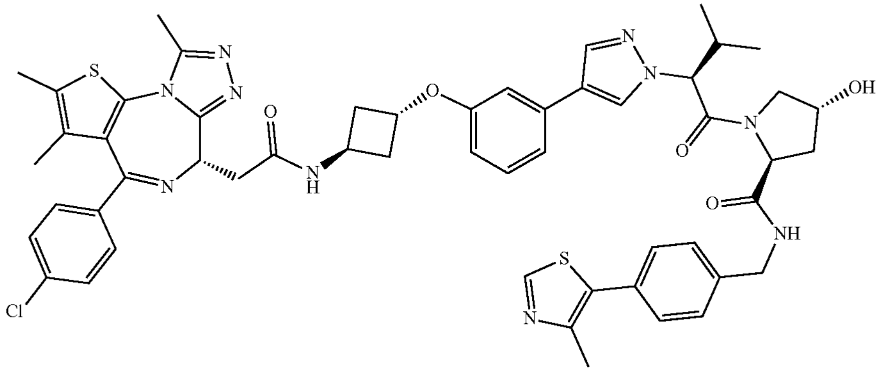 [SMILES: Cc1ncsc1-c1ccc(CNC(=O)[C@@H]2C[C@@H](O)CN2C(=O)[C@H](C(C)C)n2cc(-c3cccc(O[C@H]4C[C@H](NC(=O)C[C@@H]5N=C(c6ccc(Cl)cc6)c6c(sc(C)c6C)-n6c(C)nnc65)C4)c3)cn2)cc1] | 1011.7 | 1011.5 | B | 91.9 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 218 | 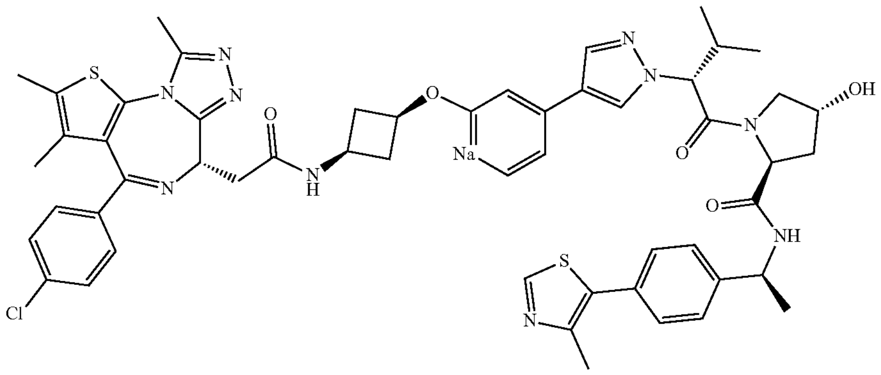 | 1026.7 | 1026.4 | D | 48.0 |
| 219 | 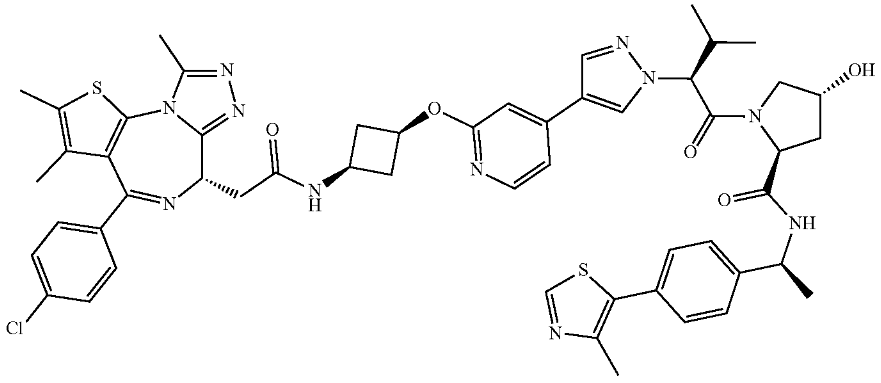 [SMILES: Cc1ncsc1-c1ccc([C@H](C)NC(=O)[C@@H]2C[C@@H](O)CN2C(=O)[C@H](C(C)C)n2cc(-c3ccnc(O[C@H]4C[C@@H](NC(=O)C[C@@H]5N=C(c6ccc(Cl)cc6)c6c(sc(C)c6C)-n6c(C)nnc65)C4)c3)cn2)cc1] | 1026.7 | 1026.5 | A | 95.5 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 220 | 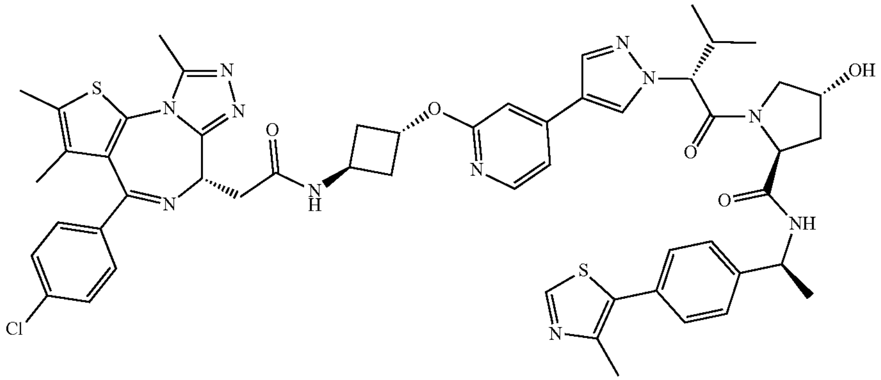 [SMILES: Cc1ncsc1-c1ccc([C@H](C)NC(=O)[C@@H]2C[C@@H](O)CN2C(=O)[C@@H](C(C)C)n2cc(-c3ccnc(O[C@H]4C[C@H](NC(=O)C[C@@H]5N=C(c6ccc(Cl)cc6)c6c(sc(C)c6C)-n6c(C)nnc65)C4)c3)cn2)cc1] | 1026.7 | 1026.5 | C | 66.4 |
| 221 | 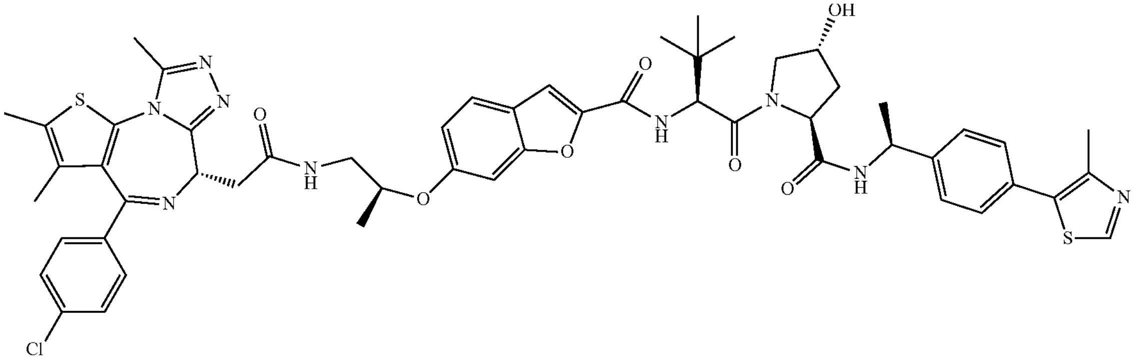 [SMILES: Cc1ncsc1-c1ccc([C@H](C)NC(=O)[C@@H]2C[C@@H](O)CN2C(=O)[C@@H](NC(=O)c2cc3ccc(O[C@@H](C)CNC(=O)C[C@@H]4N=C(c5ccc(Cl)cc5)c5c(sc(C)c5C)-n5c(C)nnc54)cc3o2)C(C)(C)C)cc1] | 1044.7 | 1044.3 | A | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 222 | 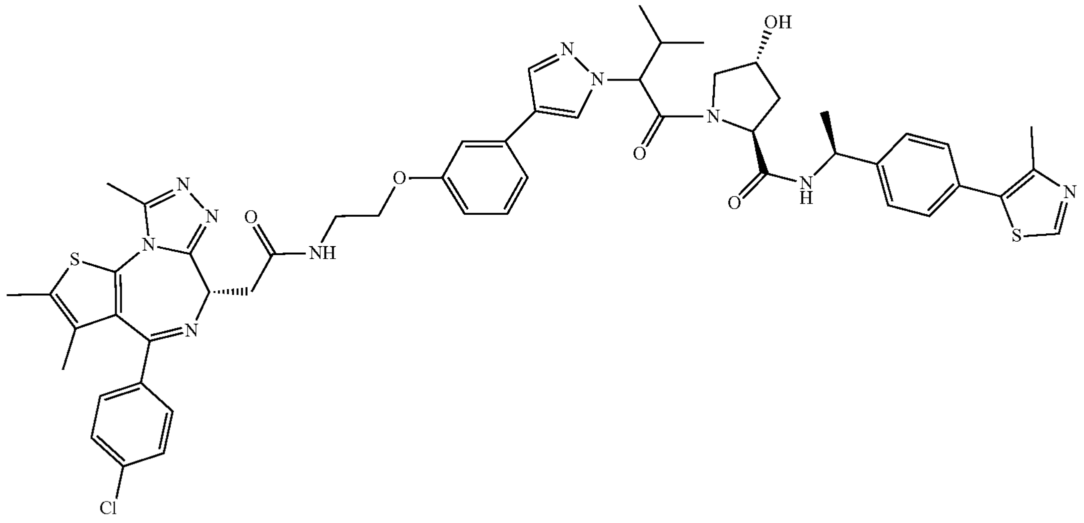 [SMILES: Cc1ncsc1-c1ccc([C@H](C)NC(=O)[C@@H]2C[C@@H](O)CN2C(=O)C(C(C)C)n2cc(-c3cccc(OCCNC(=O)C[C@@H]4N=C(c5ccc(Cl)cc5)c5c(sc(C)c5C)-n5c(C)nnc54)c3)cn2)cc1] | 0999.7 | 0999.4 | A | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 223 | 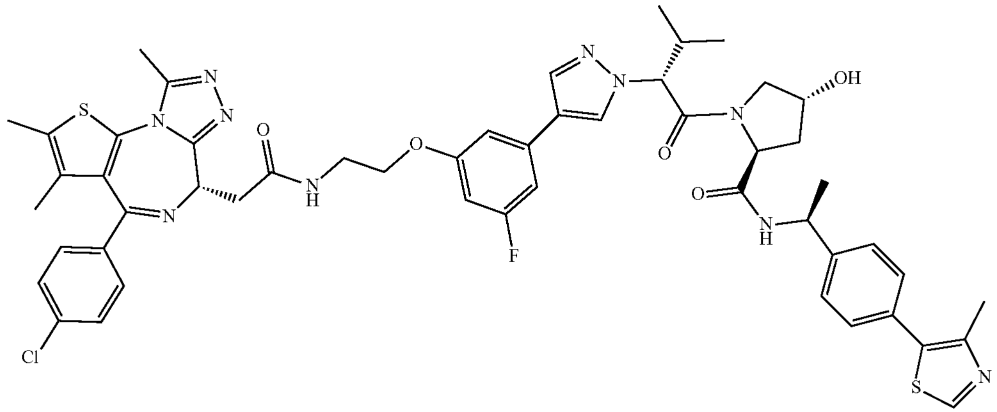 | 1017.6 | 1017.4 | C | 79.0 |
| 224 | 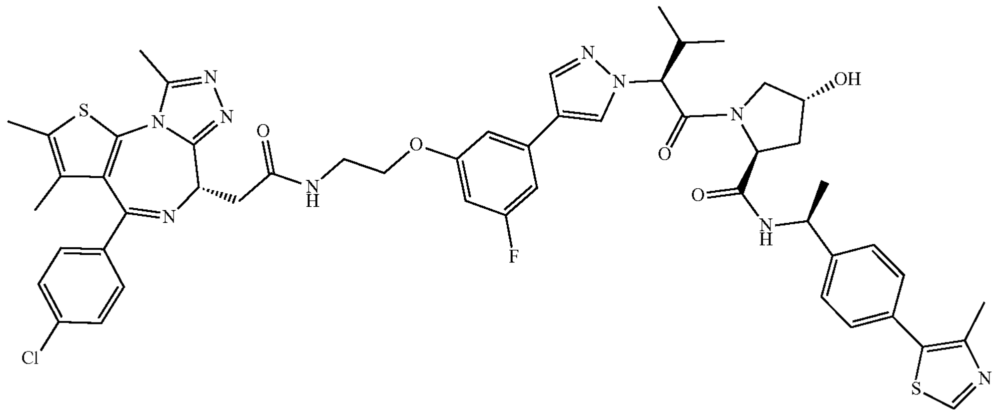 | 1017.6 | 1017.3 | A | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 225 | 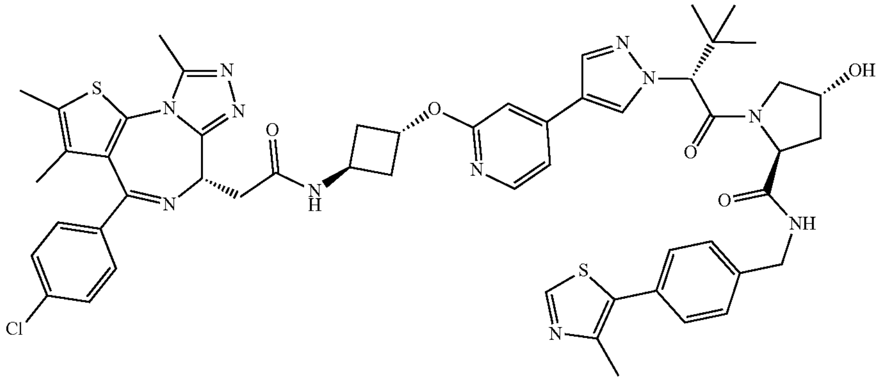 [SMILES: Cc1ncsc1-c1ccc(CNC(=O)[C@@H]2C[C@@H](O)CN2C(=O)[C@H](n2cc(-c3ccnc(O[C@H]4C[C@H](NC(=O)C[C@@H]5N=C(c6ccc(Cl)cc6)c6c(sc(C)c6C)-n6c(C)nnc65)C4)c3)cn2)C(C)(C)C)cc1] | 1012.7 | 1012.4 | D | 50.4 |
| 226 | 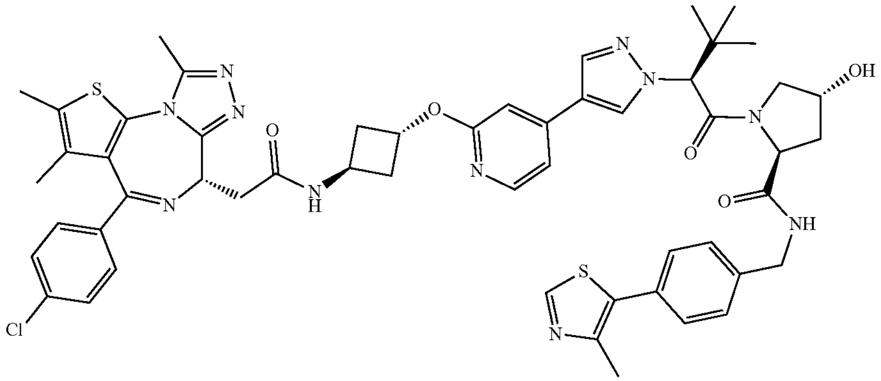 [SMILES: Cc1ncsc1-c1ccc(CNC(=O)[C@@H]2C[C@@H](O)CN2C(=O)[C@@H](n2cc(-c3ccnc(O[C@H]4C[C@H](NC(=O)C[C@@H]5N=C(c6ccc(Cl)cc6)c6c(sc(C)c6C)-n6c(C)nnc65)C4)c3)cn2)C(C)(C)C)cc1] | 1012.7 | 1012.4 | B | 99.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 227 | 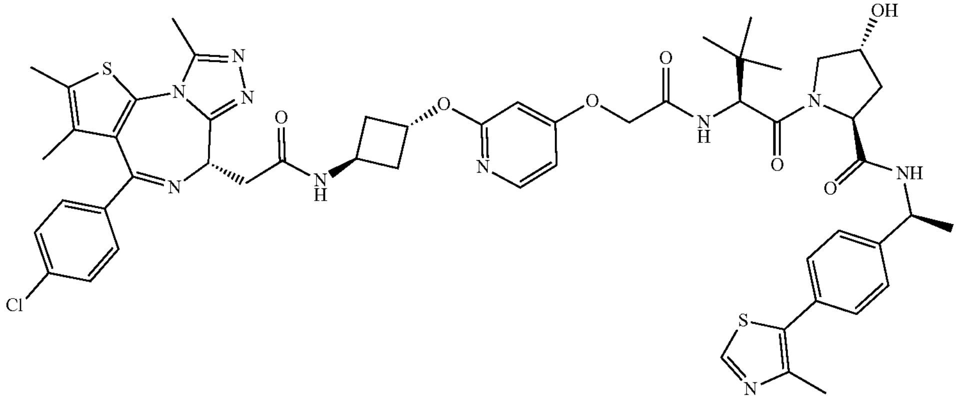 [SMILES: Cc1ncsc1-c1ccc([C@H](C)NC(=O)[C@@H]2C[C@@H](O)CN2C(=O)[C@@H](NC(=O)COc2ccnc(O[C@H]3C[C@H](NC(=O)C[C@@H]4N=C(c5ccc(Cl)cc5)c5c(sc(C)c5C)-n5c(C)nnc54)C3)c2)C(C)(C)C)cc1] | 1047.7 | 1047.6 | A | 100 |
| 228 | 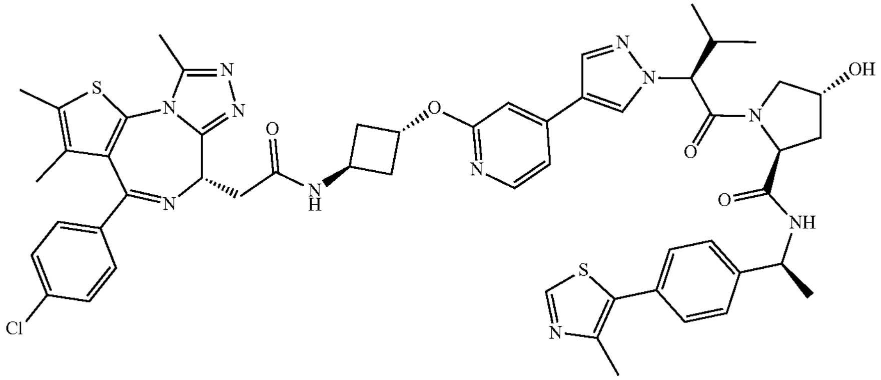 [SMILES: Cc1ncsc1-c1ccc([C@H](C)NC(=O)[C@@H]2C[C@@H](O)CN2C(=O)[C@H](C(C)C)n2cc(-c3ccnc(O[C@H]4C[C@H](NC(=O)C[C@@H]5N=C(c6ccc(Cl)cc6)c6c(sc(C)c6C)-n6c(C)nnc65)C4)c3)cn2)cc1] | 1026.7 | 1026.5 | A | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 229 | 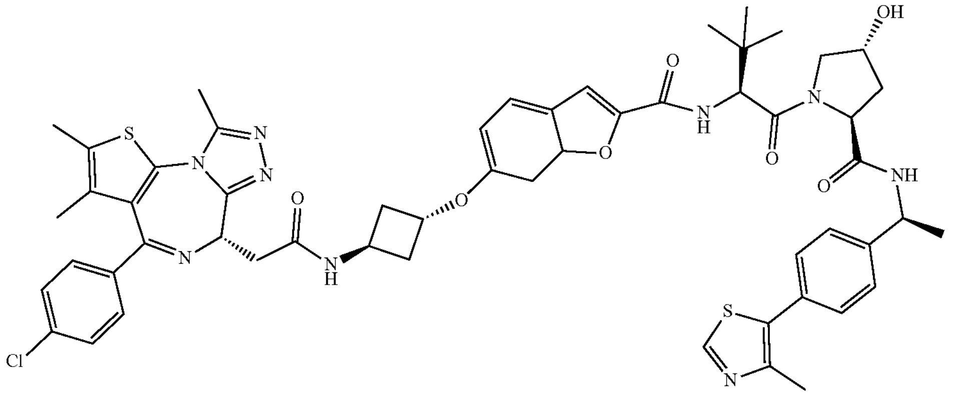 [SMILES: Cc1ncsc1-c1ccc([C@H](C)NC(=O)[C@@H]2C[C@@H](O)CN2C(=O)[C@@H](NC(=O)C2=CC3=CC=C(O[C@H]4C[C@H](NC(=O)C[C@@H]5N=C(c6ccc(Cl)cc6)c6c(sc(C)c6C)-n6c(C)nnc65)C4)CC3O2)C(C)(C)C)cc1] | 1056.7 | 1056.3 | A | 100 |
| 230 | 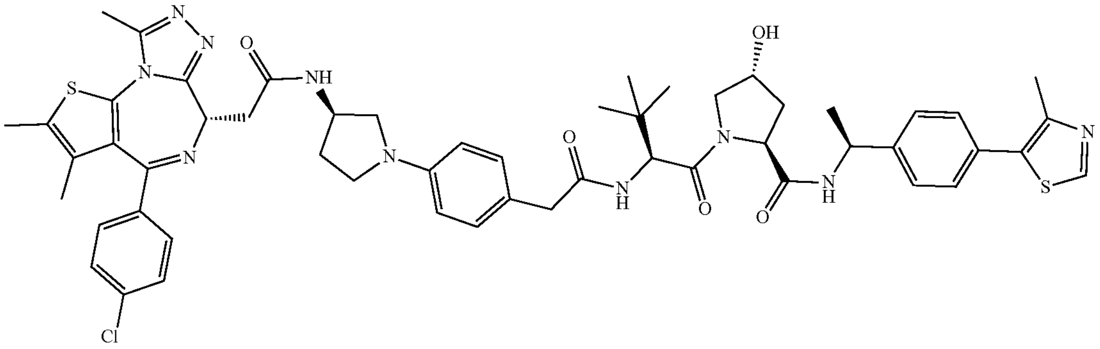 [SMILES: Cc1ncsc1-c1ccc([C@H](C)NC(=O)[C@@H]2C[C@@H](O)CN2C(=O)[C@@H](NC(=O)Cc2ccc(N3CC[C@@H](NC(=O)C[C@@H]4N=C(c5ccc(Cl)cc5)c5c(sc(C)c5C)-n5c(C)nnc54)C3)cc2)C(C)(C)C)cc1] | 1029.7 | 1029.4 | A | 100 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 231 | 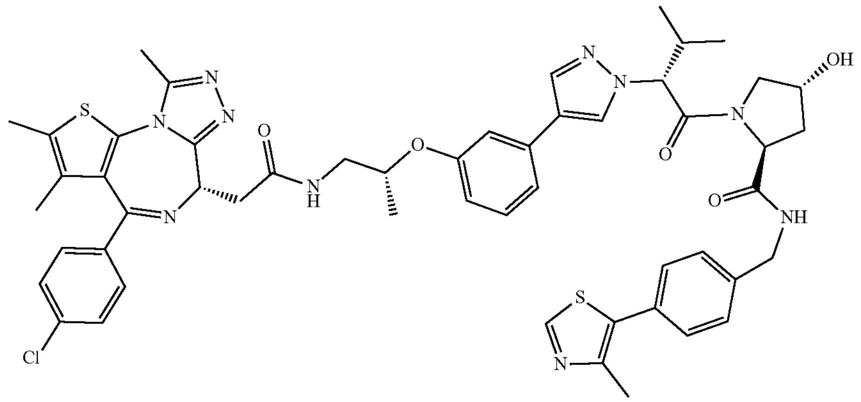 [SMILES: Cc1ncsc1-c1ccc(CNC(=O)[C@@H]2C[C@@H](O)CN2C(=O)[C@@H](C(C)C)n2cc(-c3cccc(O[C@H](C)CNC(=O)C[C@@H]4N=C(c5ccc(Cl)cc5)c5c(sc(C)c5C)-n5c(C)nnc54)c3)cn2)cc1] | 0999.7 | 0999.3 | D | 39.5 |
| 232 | 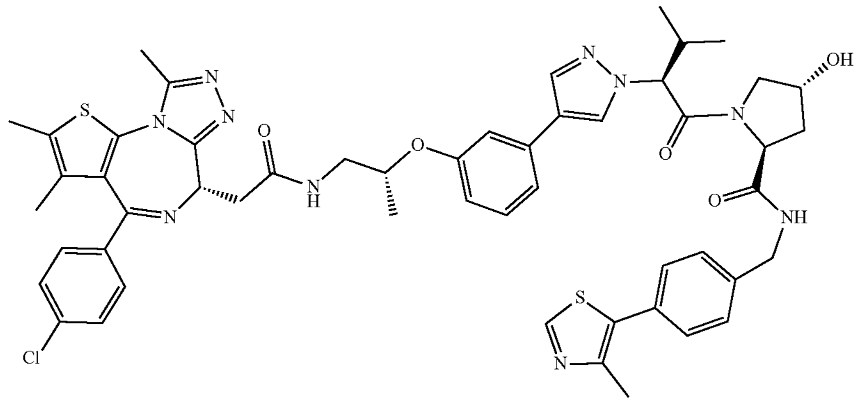 [SMILES: Cc1ncsc1-c1ccc(CNC(=O)[C@@H]2C[C@@H](O)CN2C(=O)[C@H](C(C)C)n2cc(-c3cccc(O[C@H](C)CNC(=O)C[C@@H]4N=C(c5ccc(Cl)cc5)c5c(sc(C)c5C)-n5c(C)nnc54)c3)cn2)cc1] | 0999.7 | 0999.3 | B | 83.0 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 233 | 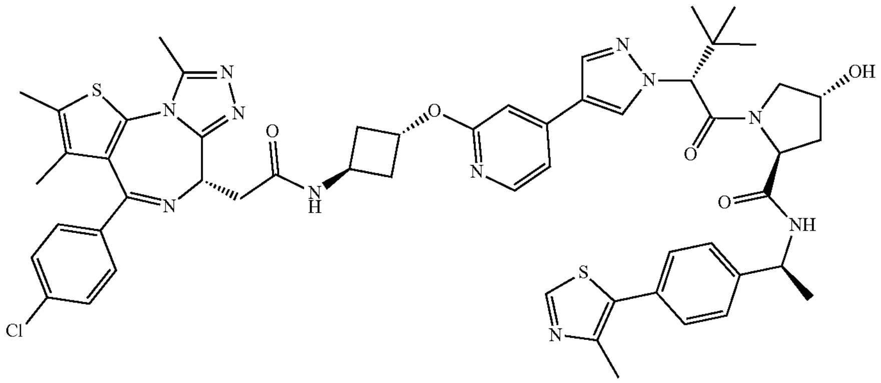 [SMILES: Cc1ncsc1-c1ccc([C@H](C)NC(=O)[C@@H]2C[C@@H](O)CN2C(=O)[C@H](n2cc(-c3ccnc(O[C@H]4C[C@H](NC(=O)C[C@@H]5N=C(c6ccc(Cl)cc6)c6c(sc(C)c6C)-n6c(C)nnc65)C4)c3)cn2)C(C)(C)C)cc1] | 1040.7 | 1040.5 | D | 26.0 |
| 234 | 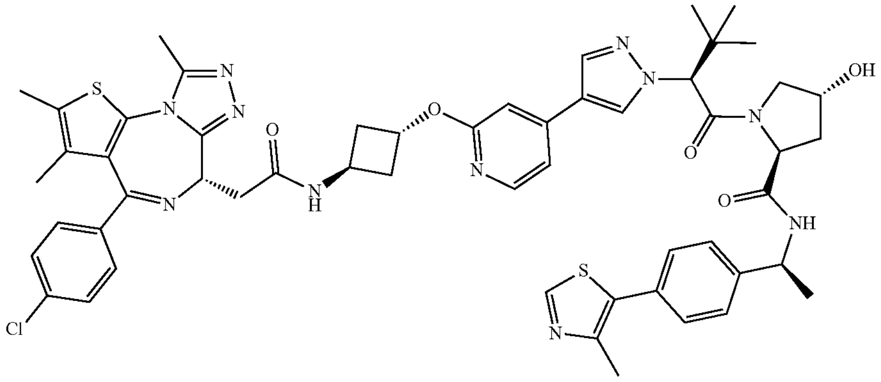 [SMILES: Cc1ncsc1-c1ccc([C@H](C)NC(=O)[C@@H]2C[C@@H](O)CN2C(=O)[C@@H](n2cc(-c3ccnc(O[C@H]4C[C@H](NC(=O)C[C@@H]5N=C(c6ccc(Cl)cc6)c6c(sc(C)c6C)-n6c(C)nnc65)C4)c3)cn2)C(C)(C)C)cc1] | 1040.7 | 1040.5 | B | 80.6 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 235 | 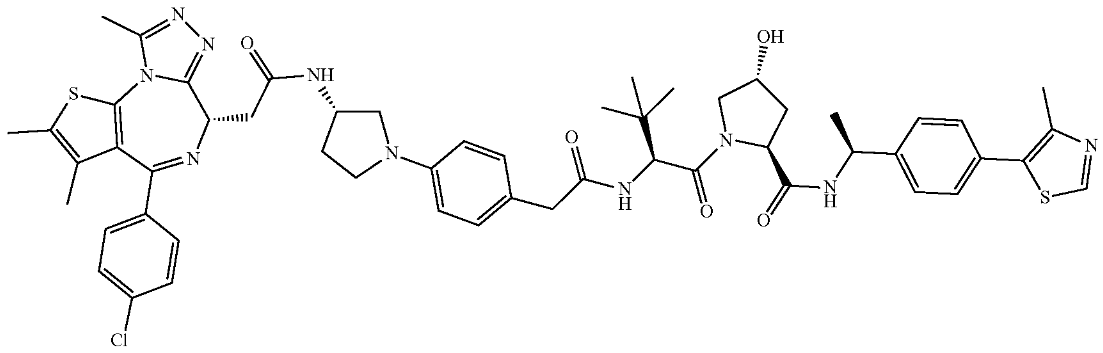 [SMILES: Cc1ncsc1-c1ccc([C@H](C)NC(=O)[C@@H]2C[C@@H](O)CN2C(=O)[C@@H](NC(=O)Cc2ccc(N3CC[C@H](NC(=O)C[C@@H]4N=C(c5ccc(Cl)cc5)c5c(sc(C)c5C)-n5c(C)nnc54)C3)cc2)C(C)(C)C)cc1] | 1029.7 | 1029.4 | A | 97.5 |
| 236 | 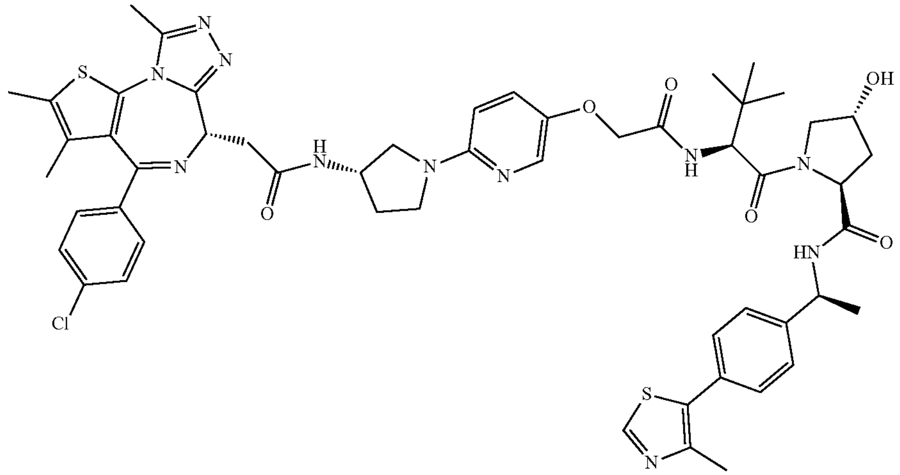 [SMILES: Cc1ncsc1-c1ccc([C@H](C)NC(=O)[C@@H]2C[C@@H](O)CN2C(=O)[C@@H](NC(=O)COc2ccc(N3CC[C@H](NC(=O)C[C@@H]4N=C(c5ccc(Cl)cc5)c5c(sc(C)c5C)-n5c(C)nnc54)C3)nc2)C(C)(C)C)cc1] | 1046.7 | 1046.3 | B | 88.9 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 237 | 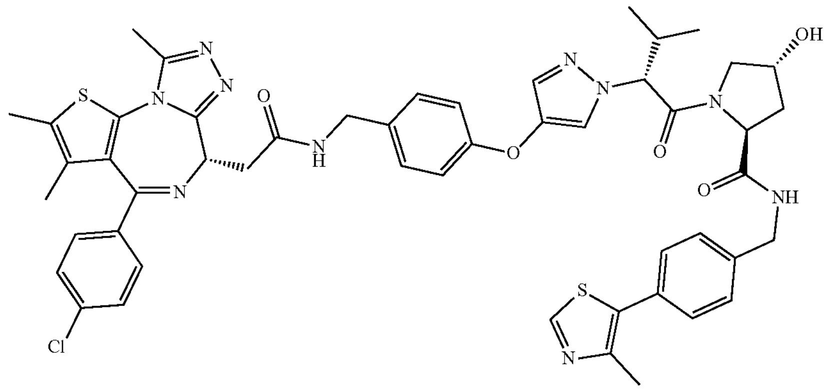 [SMILES: Cc1ncsc1-c1ccc(CNC(=O)[C@@H]2C[C@@H](O)CN2C(=O)[C@@H](C(C)C)n2cc(Oc3ccc(CNC(=O)C[C@@H]4N=C(c5ccc(Cl)cc5)c5c(sc(C)c5C)-n5c(C)nnc54)cc3)cn2)cc1] | 0971.6 | 0971.5 | D | 13.8 |
| 238 | 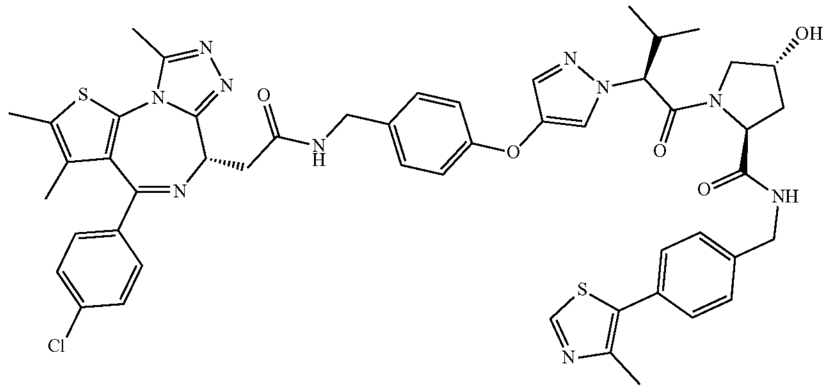 [SMILES: Cc1ncsc1-c1ccc(CNC(=O)[C@@H]2C[C@@H](O)CN2C(=O)[C@H](C(C)C)n2cc(Oc3ccc(CNC(=O)C[C@@H]4N=C(c5ccc(Cl)cc5)c5c(sc(C)c5C)-n5c(C)nnc54)cc3)cn2)cc1] | 0971.6 | 0971.5 | B | 93.3 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 239 | 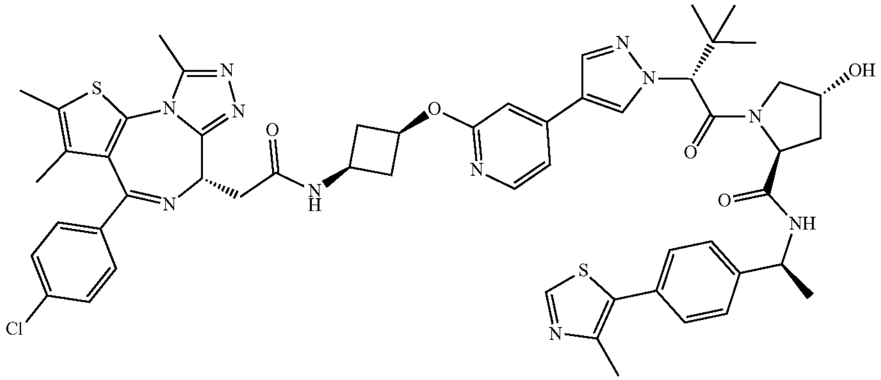 [SMILES: Cc1ncsc1-c1ccc([C@H](C)NC(=O)[C@@H]2C[C@@H](O)CN2C(=O)[C@H](n2cc(-c3ccnc(O[C@H]4C[C@@H](NC(=O)C[C@@H]5N=C(c6ccc(Cl)cc6)c6c(sc(C)c6C)-n6c(C)nnc65)C4)c3)cn2)C(C)(C)C)cc1] | 1040.7 | 1040.0 | D | 39.0 |
| 240 | 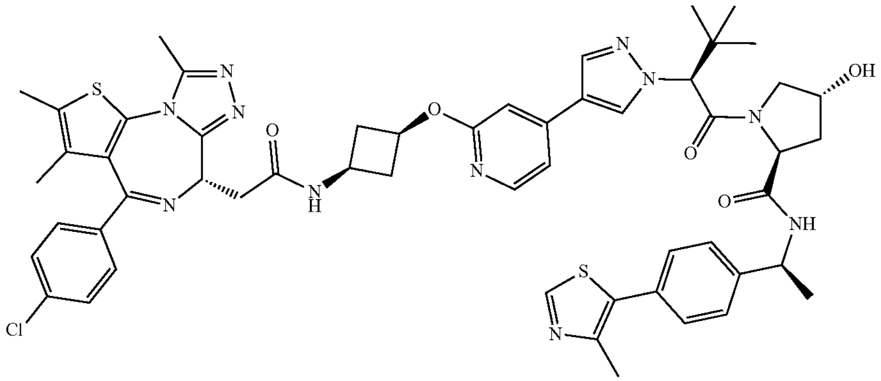 [SMILES: Cc1ncsc1-c1ccc([C@H](C)NC(=O)[C@@H]2C[C@@H](O)CN2C(=O)[C@@H](n2cc(-c3ccnc(O[C@H]4C[C@@H](NC(=O)C[C@@H]5N=C(c6ccc(Cl)cc6)c6c(sc(C)c6C)-n6c(C)nnc65)C4)c3)cn2)C(C)(C)C)cc1] | 1040.7 | 1040.0 | A | 97.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 241 | 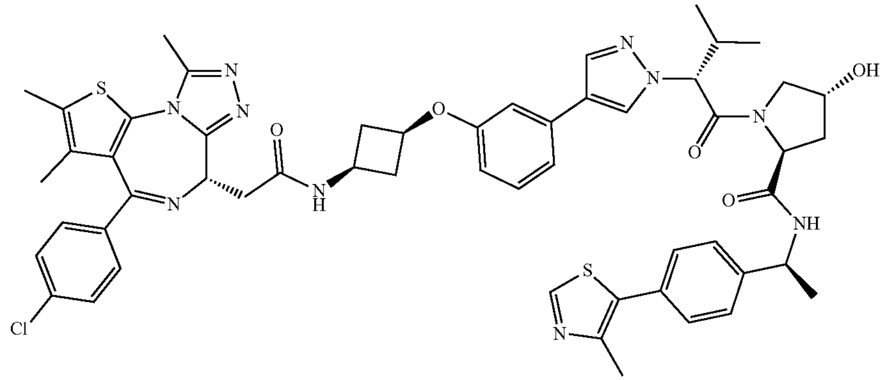 [SMILES: Cc1ncsc1-c1ccc([C@H](C)NC(=O)[C@@H]2C[C@@H](O)CN2C(=O)[C@@H](C(C)C)n2cc(-c3cccc(O[C@H]4C[C@@H](NC(=O)C[C@@H]5N=C(c6ccc(Cl)cc6)c6c(sc(C)c6C)-n6c(C)nnc65)C4)c3)cn2)cc1] | 1025.7 | 1025.4 | D | 49.8 |
| 242 | 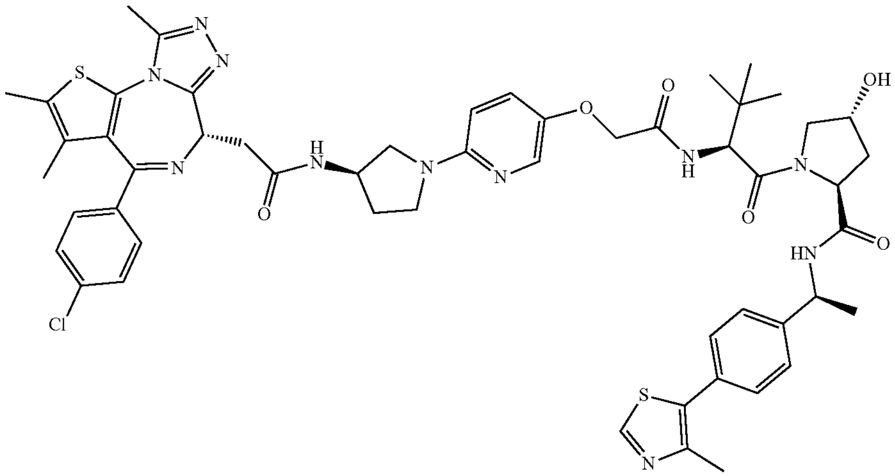 [SMILES: Cc1ncsc1-c1ccc([C@H](C)NC(=O)[C@@H]2C[C@@H](O)CN2C(=O)[C@@H](NC(=O)COc2ccc(N3CC[C@@H](NC(=O)C[C@@H]4N=C(c5ccc(Cl)cc5)c5c(sc(C)c5C)-n5c(C)nnc54)C3)nc2)C(C)(C)C)cc1] | 1046.7 | 1046.5 | A | 98.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 243 | 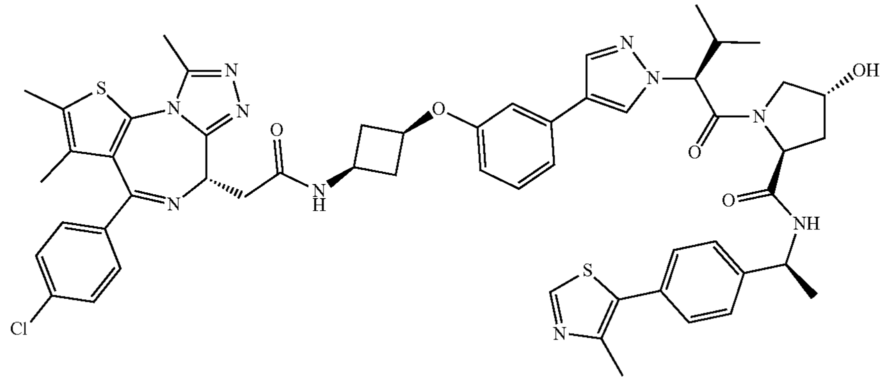 [SMILES: Cc1ncsc1-c1ccc([C@H](C)NC(=O)[C@@H]2C[C@@H](O)CN2C(=O)[C@H](C(C)C)n2cc(-c3cccc(O[C@H]4C[C@@H](NC(=O)C[C@@H]5N=C(c6ccc(Cl)cc6)c6c(sc(C)c6C)-n6c(C)nnc65)C4)c3)cn2)cc1] | 1025.7 | 1025.4 | A | 95.5 |
| 244 | 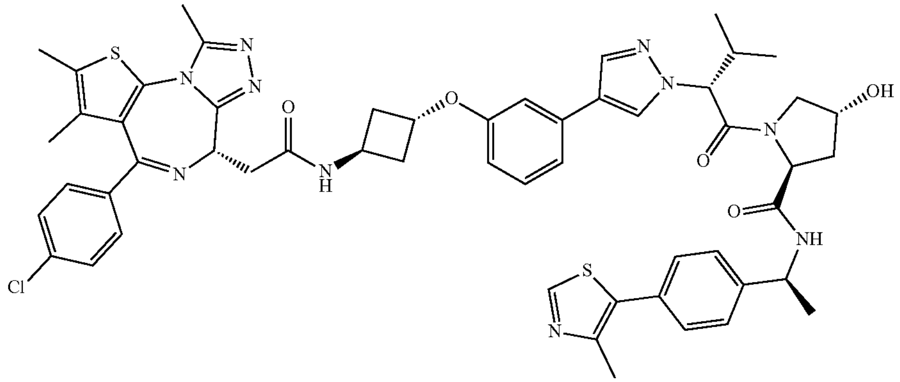 [SMILES: Cc1ncsc1-c1ccc([C@H](C)NC(=O)[C@@H]2C[C@@H](O)CN2C(=O)[C@@H](C(C)C)n2cc(-c3cccc(O[C@H]4C[C@H](NC(=O)C[C@@H]5N=C(c6ccc(Cl)cc6)c6c(sc(C)c6C)-n6c(C)nnc65)C4)c3)cn2)cc1] | 1025.7 | 1025.3 | B | 95.5 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 245 | 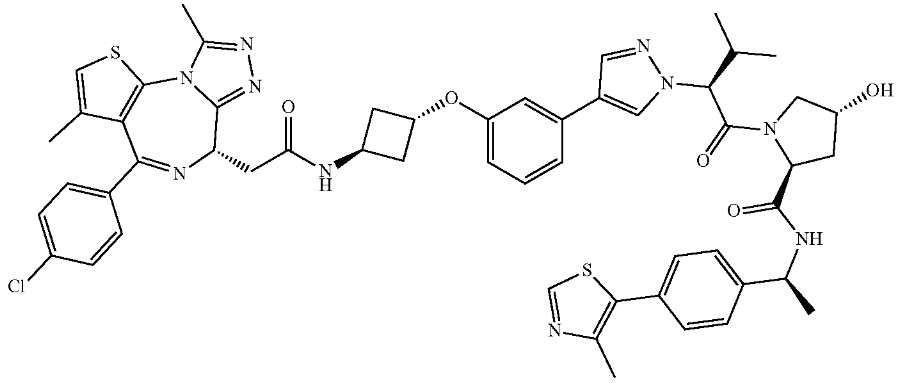 [SMILES: Cc1csc2c1C(c1ccc(Cl)cc1)=N[C@@H](CC(=O)N[C@H]1C[C@H](Oc3cccc(-c4cnn([C@H](C(=O)N5C[C@H](O)C[C@H]5C(=O)N[C@@H](C)c5ccc(-c6scnc6C)cc5)C(C)C)c4)c3)C1)c1nnc(C)n1-2] | 1025.7 | 1025.4 | A | 98.0 |
| 246 | 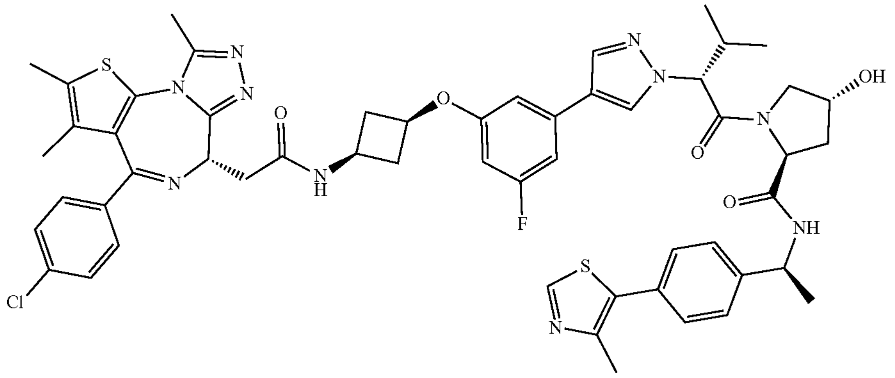 [SMILES: Cc1ncsc1-c1ccc([C@H](C)NC(=O)[C@@H]2C[C@@H](O)CN2C(=O)[C@@H](C(C)C)n2cc(-c3cc(F)cc(O[C@H]4C[C@@H](NC(=O)C[C@@H]5N=C(c6ccc(Cl)cc6)c6c(sc(C)c6C)-n6c(C)nnc65)C4)c3)cn2)cc1] | 1043.7 | 1043.0 | C | 83.0 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 247 | 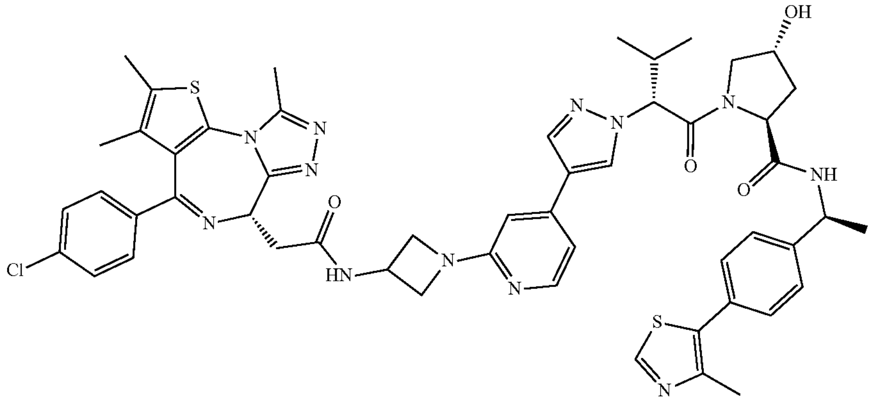 [SMILES: Cc1ncsc1-c1ccc([C@H](C)NC(=O)[C@@H]2C[C@@H](O)CN2C(=O)[C@@H](C(C)C)n2cc(-c3ccnc(N4CC(NC(=O)C[C@@H]5N=C(c6ccc(Cl)cc6)c6c(sc(C)c6C)-n6c(C)nnc65)C4)c3)cn2)cc1] | 1011.7 | 1011.5 | D | 24.1 |
| 248 | 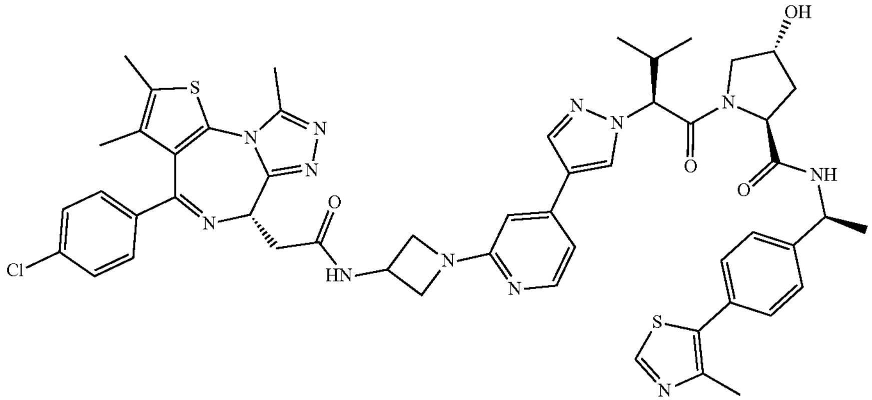 [SMILES: Cc1ncsc1-c1ccc([C@H](C)NC(=O)[C@@H]2C[C@@H](O)CN2C(=O)[C@H](C(C)C)n2cc(-c3ccnc(N4CC(NC(=O)C[C@@H]5N=C(c6ccc(Cl)cc6)c6c(sc(C)c6C)-n6c(C)nnc65)C4)c3)cn2)cc1] | 1011.7 | 1011.5 | B | 95.9 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 249 | 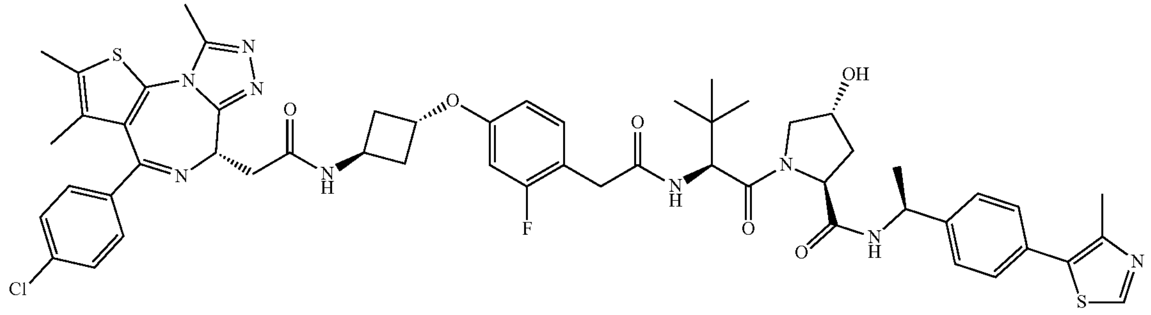 [SMILES: Cc1ncsc1-c1ccc([C@H](C)NC(=O)[C@@H]2C[C@@H](O)CN2C(=O)[C@@H](NC(=O)Cc2ccc(O[C@H]3C[C@H](NC(=O)C[C@@H]4N=C(c5ccc(Cl)cc5)c5c(sc(C)c5C)-n5c(C)nnc54)C3)cc2F)C(C)(C)C)cc1] | 1048.7 | 1048.4 | A | 98.5 |
| 250 | 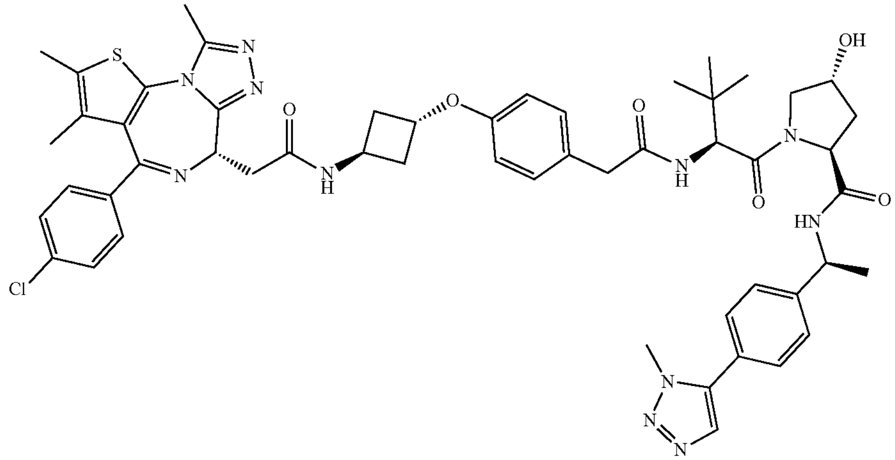 [SMILES: Cc1sc2c(c1C)C(c1ccc(Cl)cc1)=N[C@@H](CC(=O)N[C@H]1C[C@H](Oc3ccc(CC(=O)N[C@H](C(=O)N4C[C@H](O)C[C@H]4C(=O)N[C@@H](C)c4ccc(-c5cnnn5C)cc4)C(C)(C)C)cc3)C1)c1nnc(C)n1-2] | 1014.6 | 1014.5 | D | 16.1 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 251 | 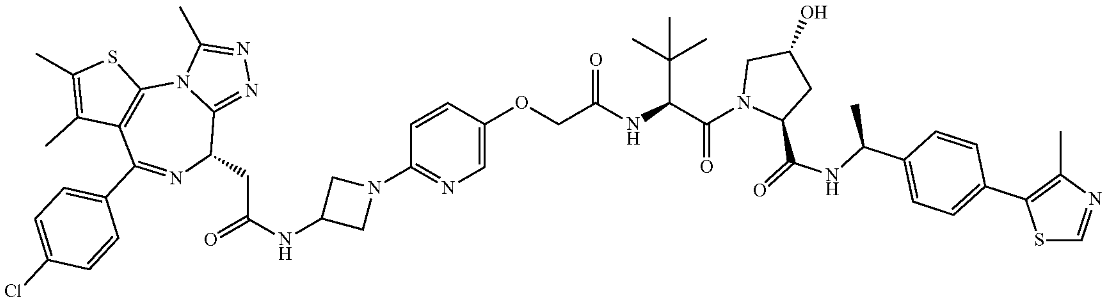 [SMILES: Cc1ncsc1-c1ccc([C@H](C)NC(=O)[C@@H]2C[C@@H](O)CN2C(=O)[C@@H](NC(=O)COc2ccc(N3CC(NC(=O)C[C@@H]4N=C(c5ccc(Cl)cc5)c5c(sc(C)c5C)-n5c(C)nnc54)C3)nc2)C(C)(C)C)cc1] | 1032.7 | 1032.4 | A | 92.3 |
| 252 | 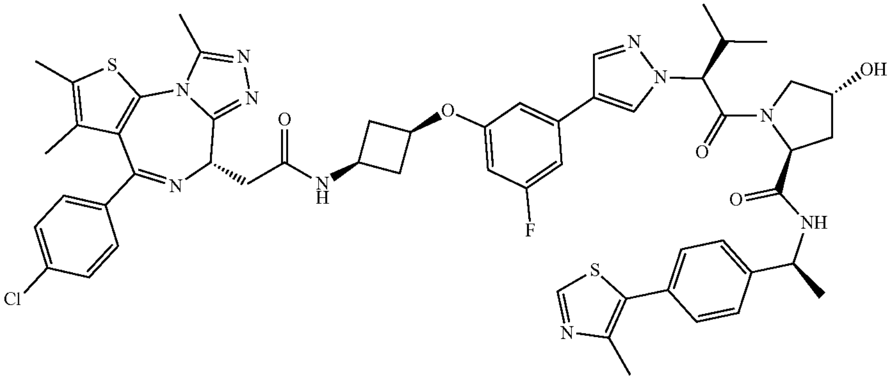 [SMILES: Cc1ncsc1-c1ccc([C@H](C)NC(=O)[C@@H]2C[C@@H](O)CN2C(=O)[C@H](C(C)C)n2cc(-c3cc(F)cc(O[C@H]4C[C@@H](NC(=O)C[C@@H]5N=C(c6ccc(Cl)cc6)c6c(sc(C)c6C)-n6c(C)nnc65)C4)c3)cn2)cc1] | 1043.7 | 1043.0 | A | 97.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 253 | 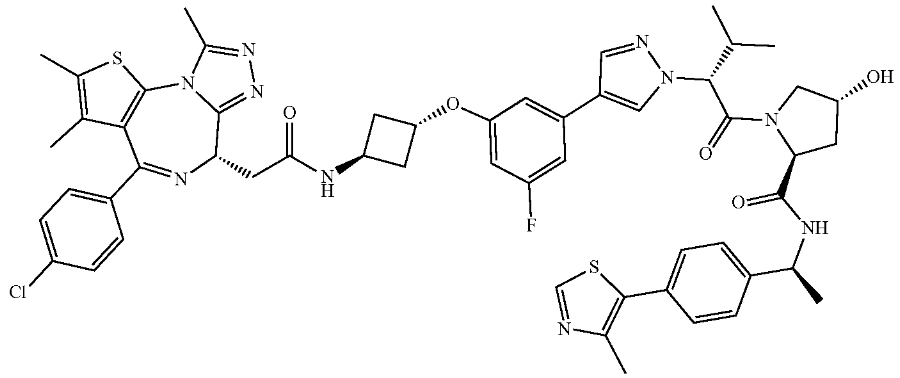 [SMILES: Cc1ncsc1-c1ccc([C@H](C)NC(=O)[C@@H]2C[C@@H](O)CN2C(=O)[C@@H](C(C)C)n2cc(-c3cc(F)cc(O[C@H]4C[C@H](NC(=O)C[C@@H]5N=C(c6ccc(Cl)cc6)c6c(sc(C)c6C)-n6c(C)nnc65)C4)c3)cn2)cc1] | 1043.7 | 1043.1 | D | 33.4 |
| 254 | 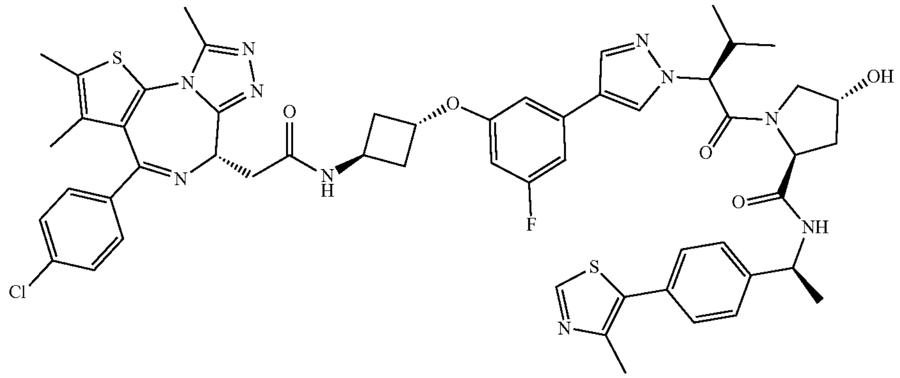 [SMILES: Cc1ncsc1-c1ccc([C@H](C)NC(=O)[C@@H]2C[C@@H](O)CN2C(=O)[C@H](C(C)C)n2cc(-c3cc(F)cc(O[C@H]4C[C@H](NC(=O)C[C@@H]5N=C(c6ccc(Cl)cc6)c6c(sc(C)c6C)-n6c(C)nnc65)C4)c3)cn2)cc1] | 1043.7 | 1043.1 | A | 95.4 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 255 | 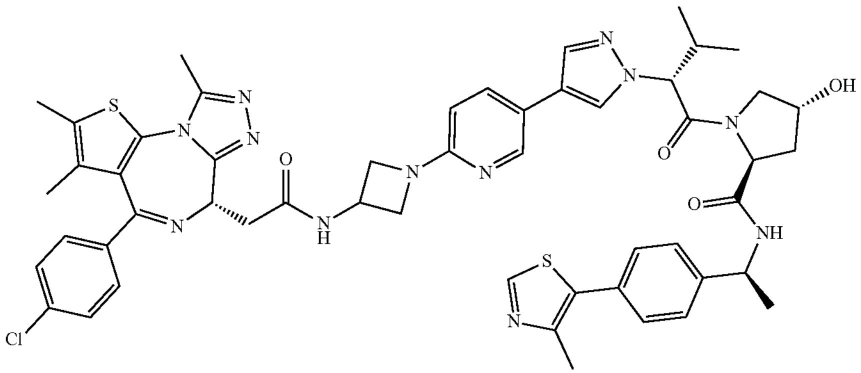 [SMILES: Cc1ncsc1-c1ccc([C@H](C)NC(=O)[C@@H]2C[C@@H](O)CN2C(=O)[C@@H](C(C)C)n2cc(-c3ccc(N4CC(NC(=O)C[C@@H]5N=C(c6ccc(Cl)cc6)c6c(sc(C)c6C)-n6c(C)nnc65)C4)nc3)cn2)cc1] | 1011.7 | 1011.5 | D | 35.5 |
| 256 | 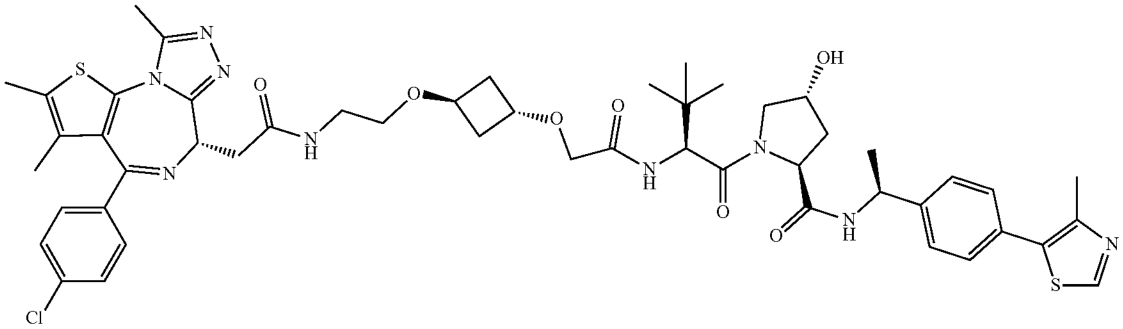 [SMILES: Cc1ncsc1-c1ccc([C@H](C)NC(=O)[C@@H]2C[C@@H](O)CN2C(=O)[C@@H](NC(=O)CO[C@H]2C[C@H](OCCNC(=O)C[C@@H]3N=C(c4ccc(Cl)cc4)c4c(sc(C)c4C)-n4c(C)nnc43)C2)C(C)(C)C)cc1] | 0998.7 | 0998.4 | A | 89.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 257 | 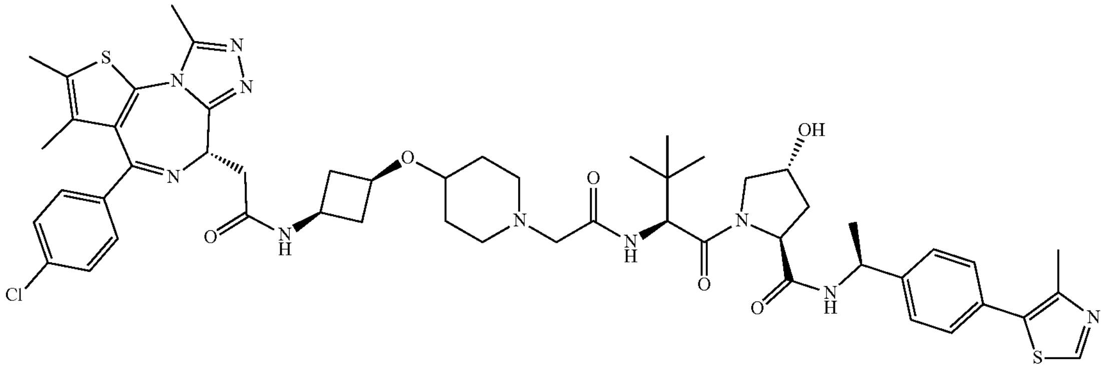 [SMILES: Cc1ncsc1-c1ccc([C@H](C)NC(=O)[C@@H]2C[C@@H](O)CN2C(=O)[C@@H](NC(=O)CN2CCC(O[C@H]3C[C@@H](NC(=O)C[C@@H]4N=C(c5ccc(Cl)cc5)c5c(sc(C)c5C)-n5c(C)nnc54)C3)CC2)C(C)(C)C)cc1] | 1037.7 | 1037.5 | B | 87.0 |
| 258 | 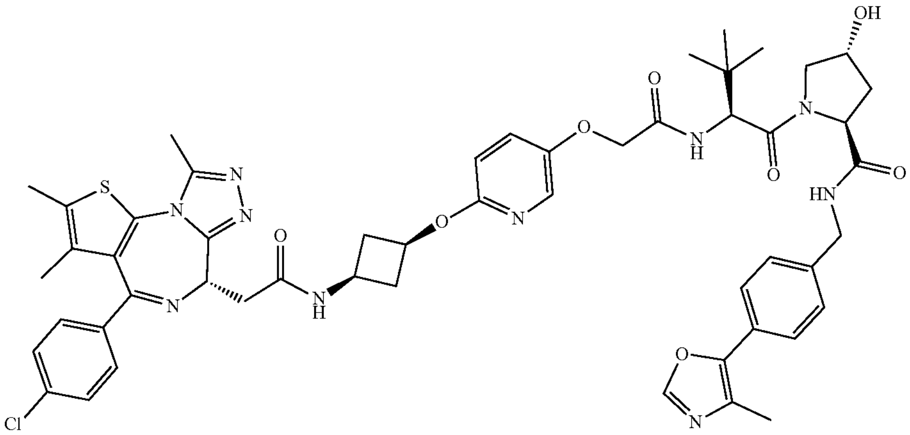 [SMILES: Cc1ncoc1-c1ccc(CNC(=O)[C@@H]2C[C@@H](O)CN2C(=O)[C@@H](NC(=O)COc2ccc(O[C@H]3C[C@@H](NC(=O)C[C@@H]4N=C(c5ccc(Cl)cc5)c5c(sc(C)c5C)-n5c(C)nnc54)C3)nc2)C(C)(C)C)cc1] | 1017.6 | 1017.4 | B | 87.5 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 259 | 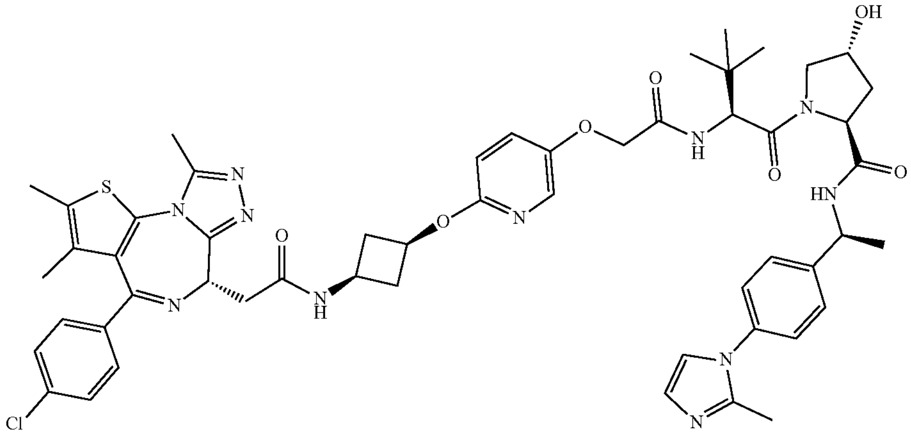 [SMILES: Cc1sc2c(c1C)C(c1ccc(Cl)cc1)=N[C@@H](CC(=O)N[C@H]1C[C@@H](Oc3ccc(OCC(=O)N[C@H](C(=O)N4C[C@H](O)C[C@H]4C(=O)N[C@@H](C)c4ccc(-n5ccnc5C)cc4)C(C)(C)C)cn3)C1)c1nnc(C)n1-2] | 1030.6 | 1030.4 | C | 65.7 |
| 260 | 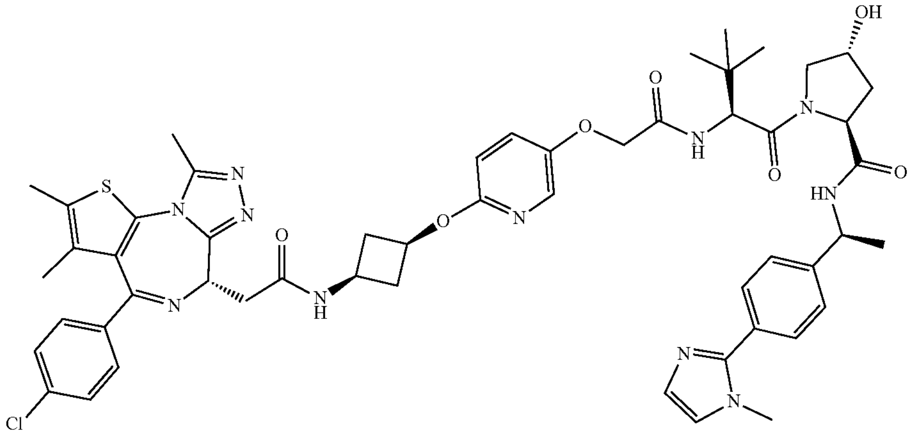 [SMILES: Cc1sc2c(c1C)C(c1ccc(Cl)cc1)=N[C@@H](CC(=O)N[C@H]1C[C@@H](Oc3ccc(OCC(=O)N[C@H](C(=O)N4C[C@H](O)C[C@H]4C(=O)N[C@@H](C)c4ccc(-c5nccn5C)cc4)C(C)(C)C)cn3)C1)c1nnc(C)n1-2] | 1030.6 | 1030.4 | D | 13.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 261 | 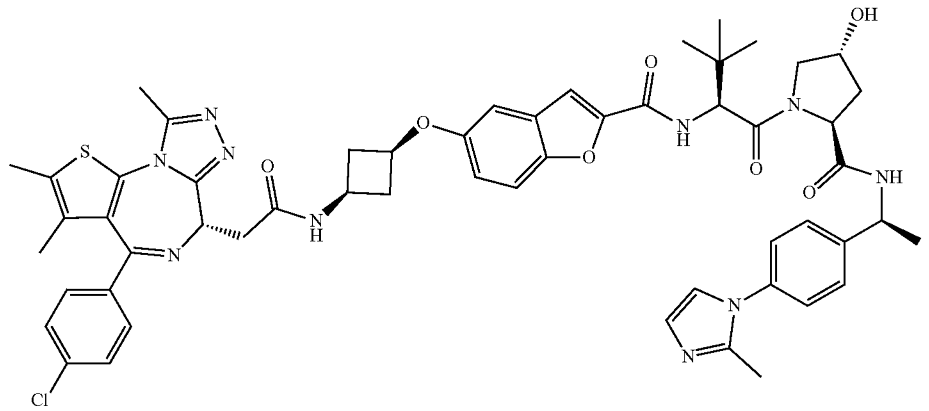 [SMILES: Cc1sc2c(c1C)C(c1ccc(Cl)cc1)=N[C@@H](CC(=O)N[C@H]1C[C@@H](Oc3ccc4oc(C(=O)N[C@H](C(=O)N5C[C@H](O)C[C@H]5C(=O)N[C@@H](C)c5ccc(-n6ccnc6C)cc5)C(C)(C)C)cc4c3)C1)c1nnc(C)n1-2] | 1039.7 | 1039.5 | B | 92.7 |
| 262 | 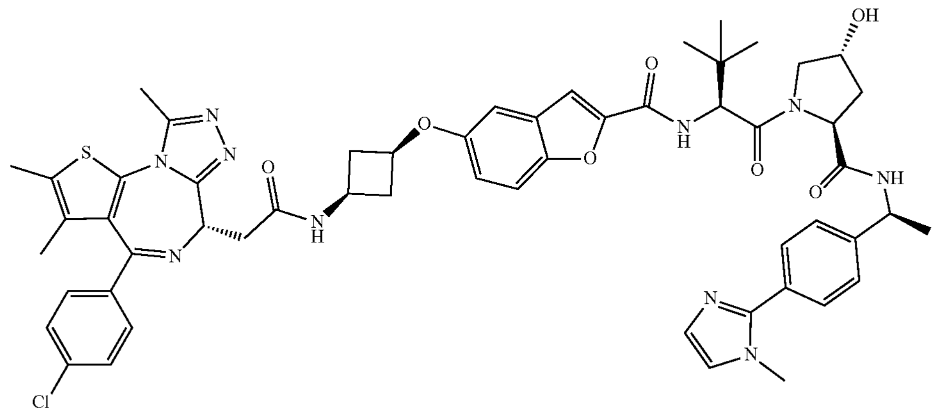 [SMILES: Cc1sc2c(c1C)C(c1ccc(Cl)cc1)=N[C@@H](CC(=O)N[C@H]1C[C@@H](Oc3ccc4oc(C(=O)N[C@H](C(=O)N5C[C@H](O)C[C@H]5C(=O)N[C@@H](C)c5ccc(-c6nccn6C)cc5)C(C)(C)C)cc4c3)C1)c1nnc(C)n1-2] | 1039.7 | 1039.9 | C | 55.5 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 263 | 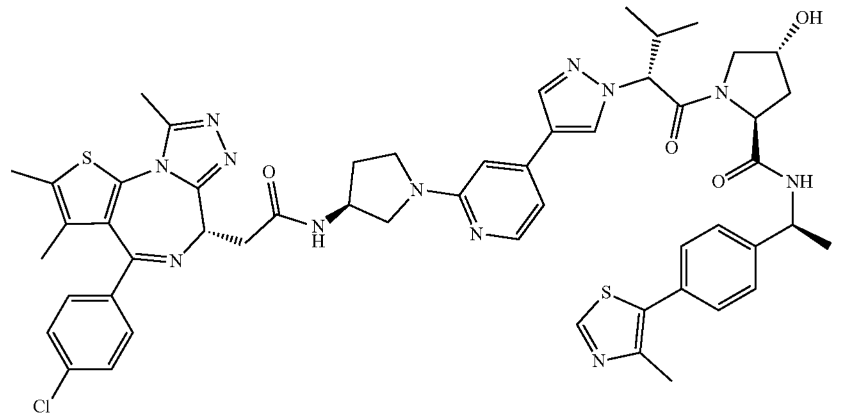 [SMILES: Cc1ncsc1-c1ccc([C@H](C)NC(=O)[C@@H]2C[C@@H](O)CN2C(=O)[C@@H](C(C)C)n2cc(-c3ccnc(N4CC[C@H](NC(=O)C[C@@H]5N=C(c6ccc(Cl)cc6)c6c(sc(C)c6C)-n6c(C)nnc65)C4)c3)cn2)cc1] | 1025.7 | 1025.4 | D | 23.5 |
| 264 | 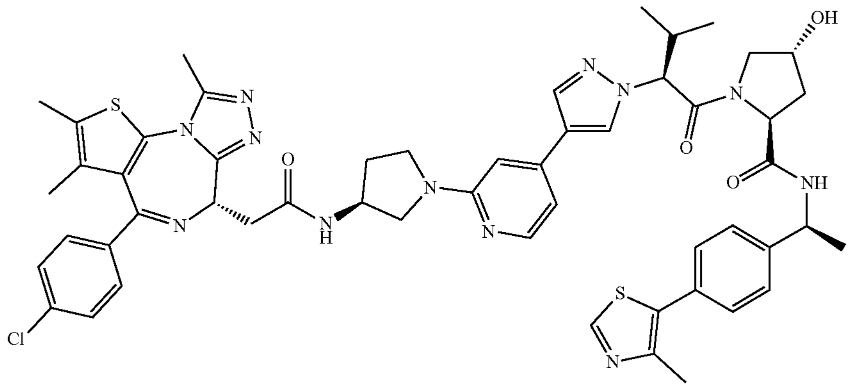 [SMILES: Cc1ncsc1-c1ccc([C@H](C)NC(=O)[C@@H]2C[C@@H](O)CN2C(=O)[C@H](C(C)C)n2cc(-c3ccnc(N4CC[C@H](NC(=O)C[C@@H]5N=C(c6ccc(Cl)cc6)c6c(sc(C)c6C)-n6c(C)nnc65)C4)c3)cn2)cc1] | 1025.7 | 1025.4 | A | 97.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 265 | 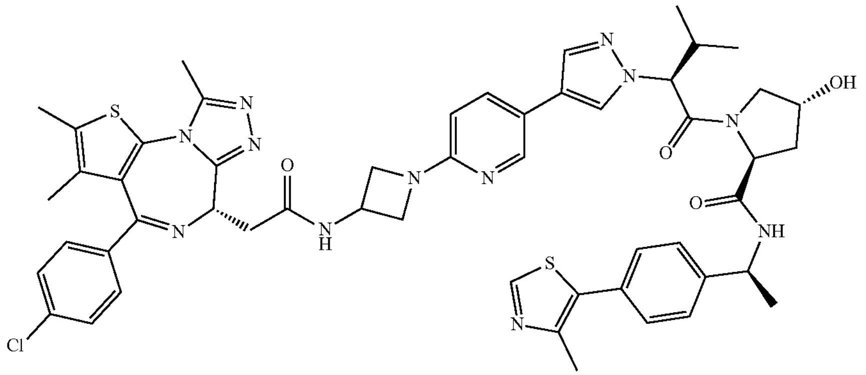 [SMILES: Cc1ncsc1-c1ccc([C@H](C)NC(=O)[C@@H]2C[C@@H](O)CN2C(=O)[C@H](C(C)C)n2cc(-c3ccc(N4CC(NC(=O)C[C@@H]5N=C(c6ccc(Cl)cc6)c6c(sc(C)c6C)-n6c(C)nnc65)C4)nc3)cn2)cc1] | 1011.7 | 1011.5 | B | 95.9 |
| 266 | 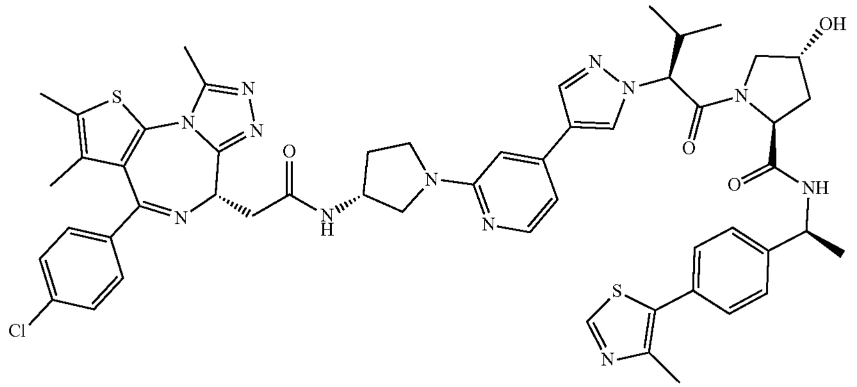 [SMILES: Cc1ncsc1-c1ccc([C@H](C)NC(=O)[C@@H]2C[C@@H](O)CN2C(=O)[C@H](C(C)C)n2cc(-c3ccnc(N4CC[C@@H](NC(=O)C[C@@H]5N=C(c6ccc(Cl)cc6)c6c(sc(C)c6C)-n6c(C)nnc65)C4)c3)cn2)cc1] | 1025.7 | 1025.4 | A | 97.0 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 267 | 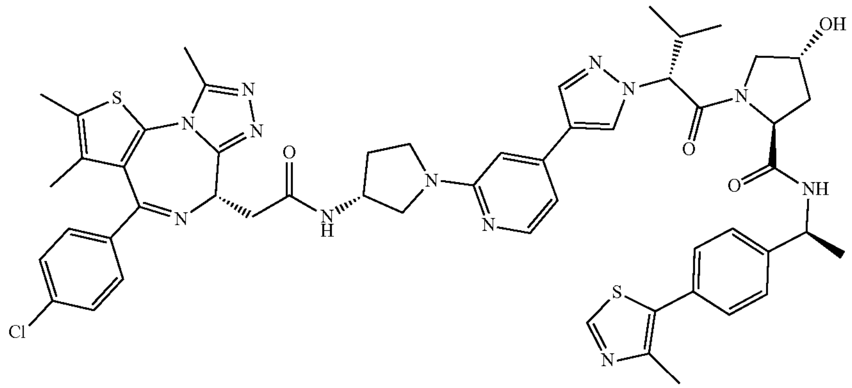 [SMILES: Cc1ncsc1-c1ccc([C@H](C)NC(=O)[C@@H]2C[C@@H](O)CN2C(=O)[C@@H](C(C)C)n2cc(-c3ccnc(N4CC[C@@H](NC(=O)C[C@@H]5N=C(c6ccc(Cl)cc6)c6c(sc(C)c6C)-n6c(C)nnc65)C4)c3)cn2)cc1] | 1025.7 | 1025.4 | D | 51.4 |
| 268 | 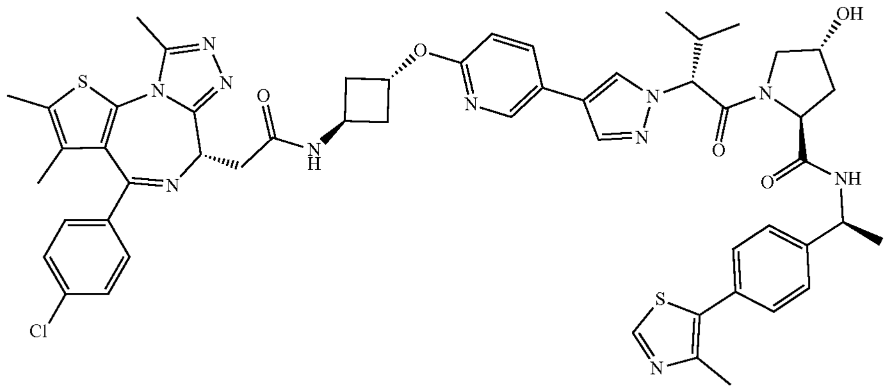 [SMILES: Cc1ncsc1-c1ccc([C@H](C)NC(=O)[C@@H]2C[C@@H](O)CN2C(=O)[C@@H](C(C)C)n2cc(-c3ccc(O[C@H]4C[C@H](NC(=O)C[C@@H]5N=C(c6ccc(Cl)cc6)c6c(sc(C)c6C)-n6c(C)nnc65)C4)nc3)cn2)cc1] | 1026.7 | 1026.4 | B | 98.0 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 269 | 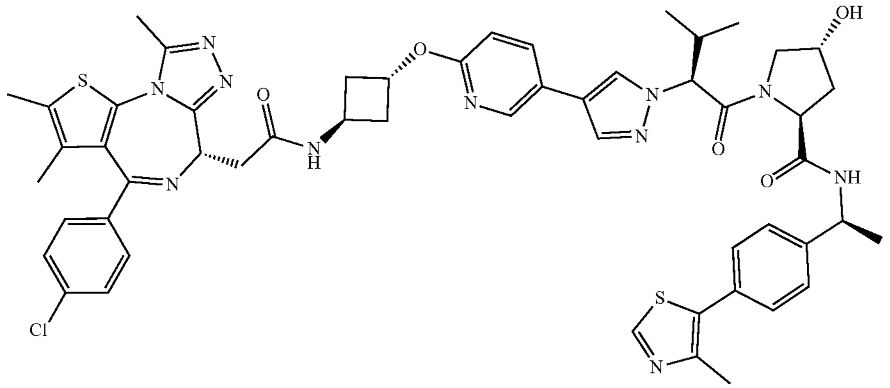 [SMILES: Cc1ncsc1-c1ccc([C@H](C)NC(=O)[C@@H]2C[C@@H](O)CN2C(=O)[C@H](C(C)C)n2cc(-c3ccc(O[C@H]4C[C@H](NC(=O)C[C@@H]5N=C(c6ccc(Cl)cc6)c6c(sc(C)c6C)-n6c(C)nnc65)C4)nc3)cn2)cc1] | 1026.7 | 1026.4 | A | 96.4 |
| 270 | 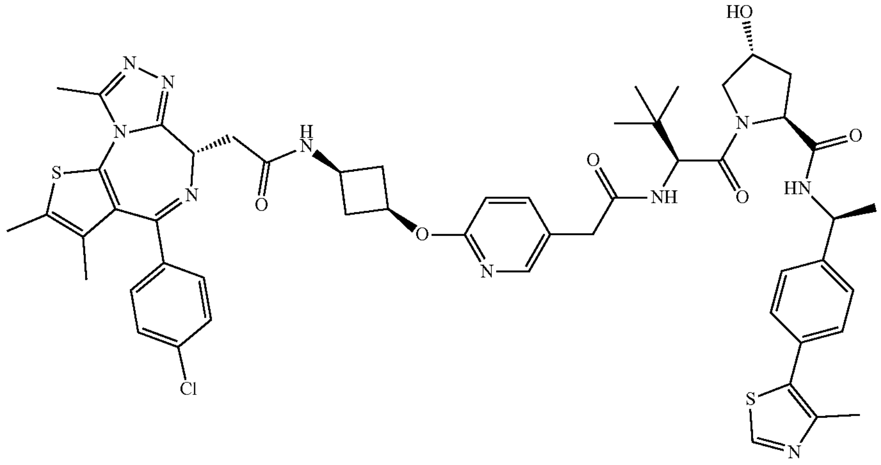 [SMILES: Cc1ncsc1-c1ccc([C@H](C)NC(=O)[C@@H]2C[C@@H](O)CN2C(=O)[C@@H](NC(=O)Cc2ccc(O[C@H]3C[C@@H](NC(=O)C[C@@H]4N=C(c5ccc(Cl)cc5)c5c(sc(C)c5C)-n5c(C)nnc54)C3)nc2)C(C)(C)C)cc1] | 1031.7 | 1031.4 | A | 92.2 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 271 | 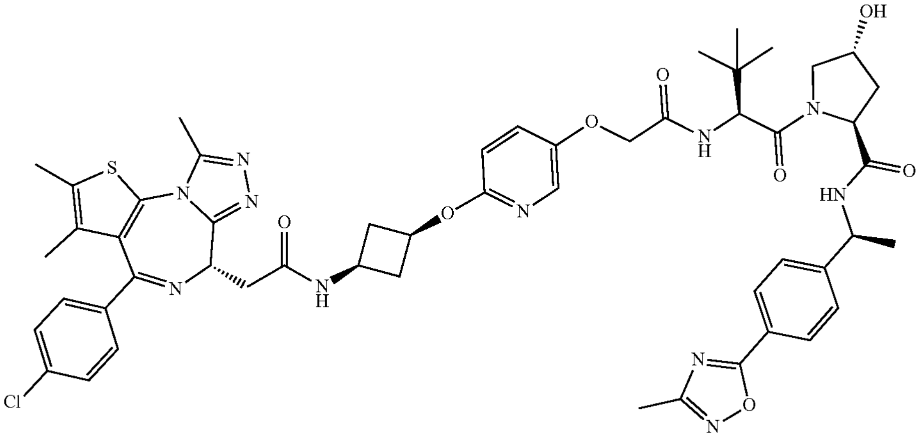 [SMILES: Cc1noc(-c2ccc([C@H](C)NC(=O)[C@@H]3C[C@@H](O)CN3C(=O)[C@@H](NC(=O)COc3ccc(O[C@H]4C[C@@H](NC(=O)C[C@@H]5N=C(c6ccc(Cl)cc6)c6c(sc(C)c6C)-n6c(C)nnc65)C4)nc3)C(C)(C)C)cc2)n1] | 1032.6 | 1032.4 | A | 96.4 |
| 272 | 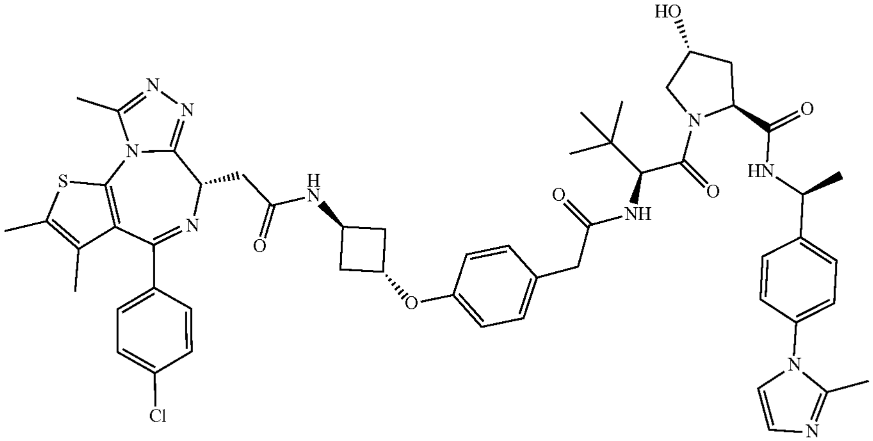 | 1013.7 | 1013.4 | B | 95.9 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 273 | 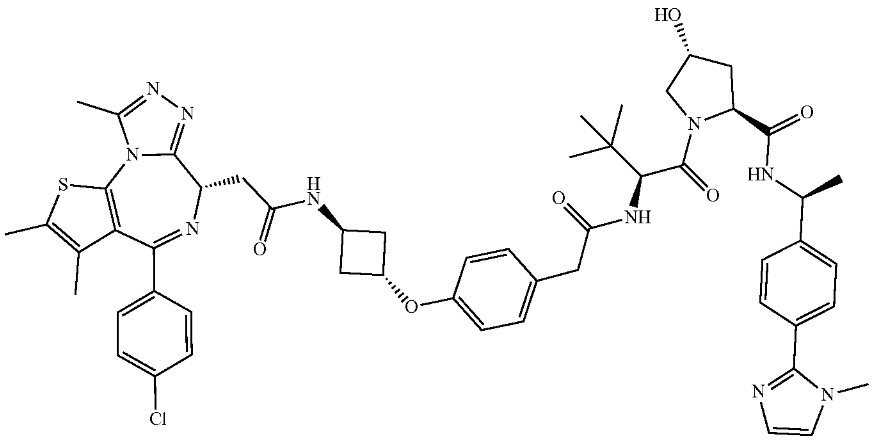 | 1013.7 | 1013.4 | D | <5 |
| 274 | 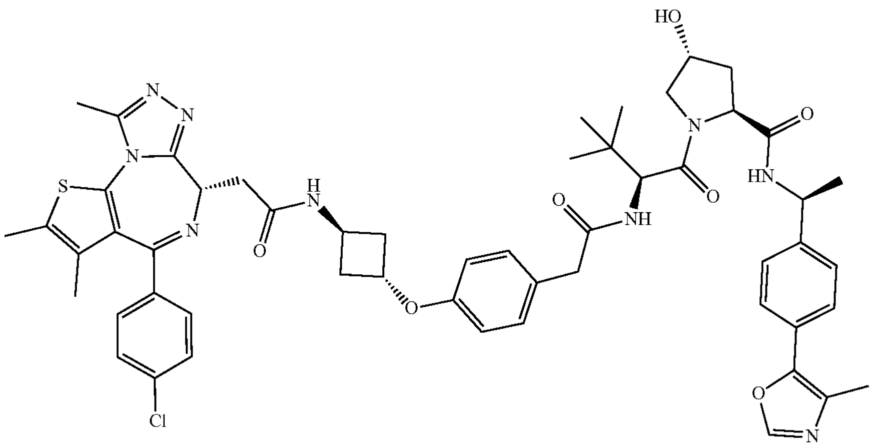 | 1014.6 | 1014.4 | A | 95.4 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 275 | 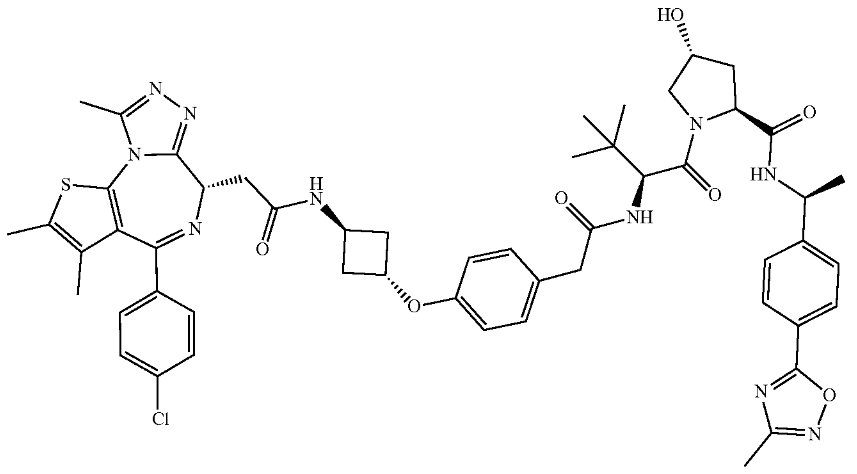 [SMILES: Cc1noc(-c2ccc([C@H](C)NC(=O)[C@@H]3C[C@@H](O)CN3C(=O)[C@@H](NC(=O)Cc3ccc(O[C@H]4C[C@H](NC(=O)C[C@@H]5N=C(c6ccc(Cl)cc6)c6c(sc(C)c6C)-n6c(C)nnc65)C4)cc3)C(C)(C)C)cc2)n1] | 1015.6 | 1015.4 | C | 50.1 |
| 276 | 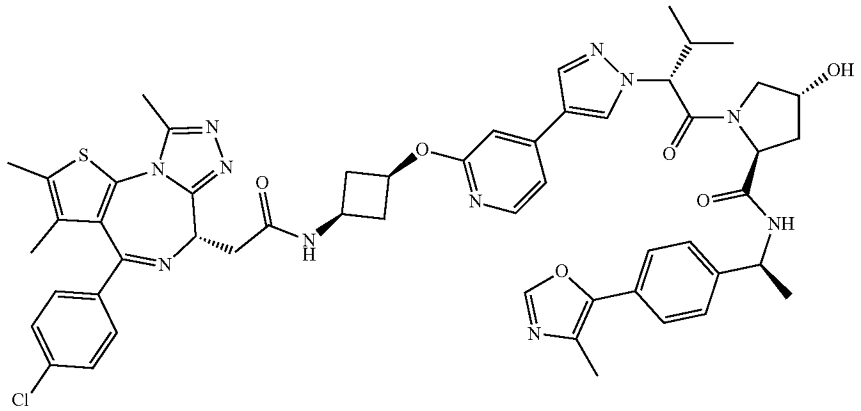 [SMILES: Cc1ncoc1-c1ccc([C@H](C)NC(=O)[C@@H]2C[C@@H](O)CN2C(=O)[C@@H](C(C)C)n2cc(-c3ccnc(O[C@H]4C[C@@H](NC(=O)C[C@@H]5N=C(c6ccc(Cl)cc6)c6c(sc(C)c6C)-n6c(C)nnc65)C4)c3)cn2)cc1] | 1010.6 | 1010.4 | D | 36.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 277 | 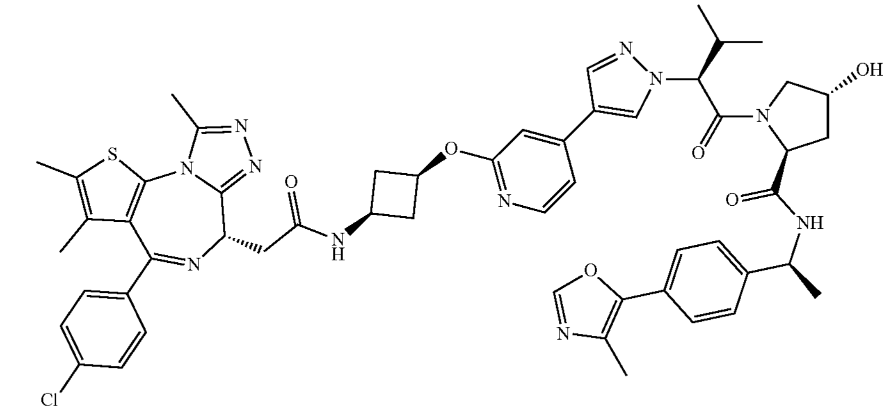 [SMILES: Cc1ncoc1-c1ccc([C@H](C)NC(=O)[C@@H]2C[C@@H](O)CN2C(=O)[C@H](C(C)C)n2cc(-c3ccnc(O[C@H]4C[C@@H](NC(=O)C[C@@H]5N=C(c6ccc(Cl)cc6)c6c(sc(C)c6C)-n6c(C)nnc65)C4)c3)cn2)cc1] | 1010.6 | 1010.4 | B | 94.0 |
| 278 | 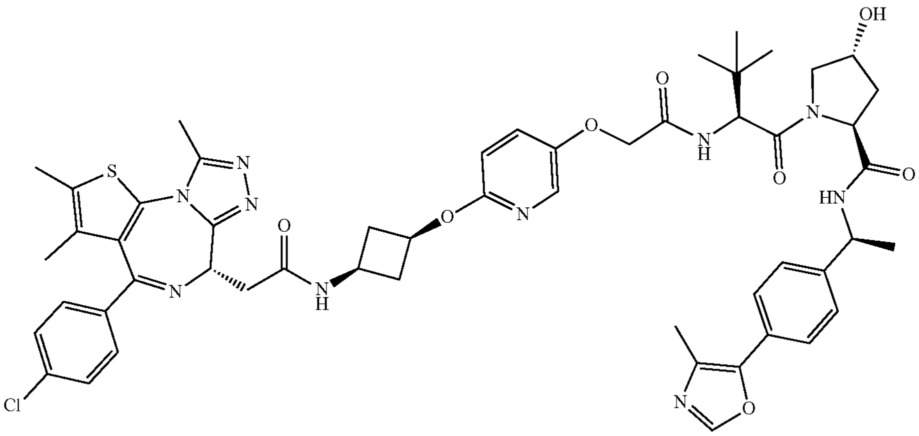 [SMILES: Cc1ncoc1-c1ccc([C@H](C)NC(=O)[C@@H]2C[C@@H](O)CN2C(=O)[C@@H](NC(=O)COc2ccc(O[C@H]3C[C@@H](NC(=O)C[C@@H]4N=C(c5ccc(Cl)cc5)c5c(sc(C)c5C)-n5c(C)nnc54)C3)nc2)C(C)(C)C)cc1] | 1031.6 | 1031.4 | A | 95.4 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 279 | 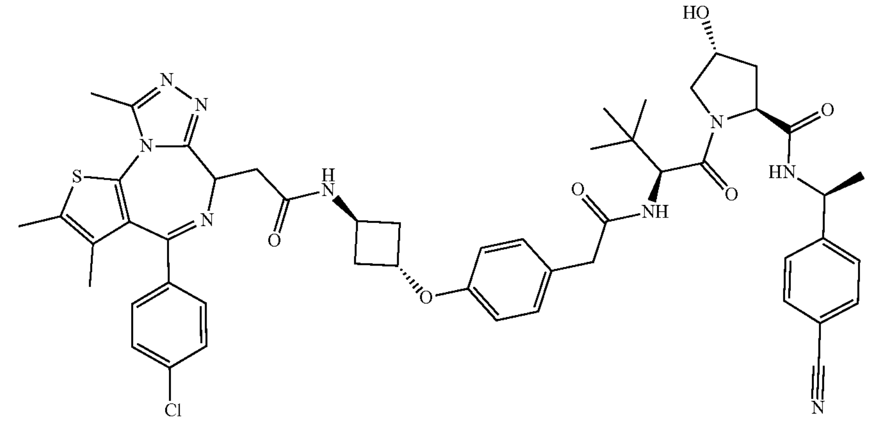 [SMILES: Cc1sc2c(c1C)C(c1ccc(Cl)cc1)=NC(CC(=O)N[C@H]1C[C@H](Oc3ccc(CC(=O)N[C@H](C(=O)N4C[C@H](O)C[C@H]4C(=O)N[C@@H](C)c4ccc(C#N)cc4)C(C)(C)C)cc3)C1)c1nnc(C)n1-2] | 0958.6 | 0958.4 | C | 65.4 |
| 280 | 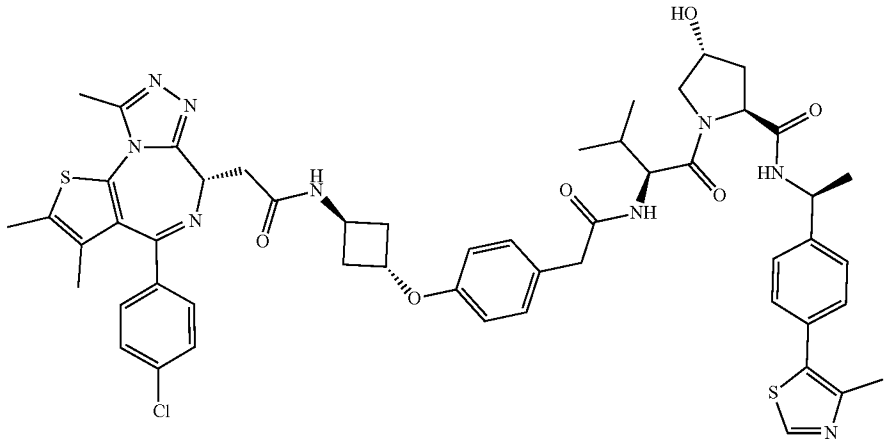 | 1016.7 | 1016.4 | B | 95.4 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 281 | 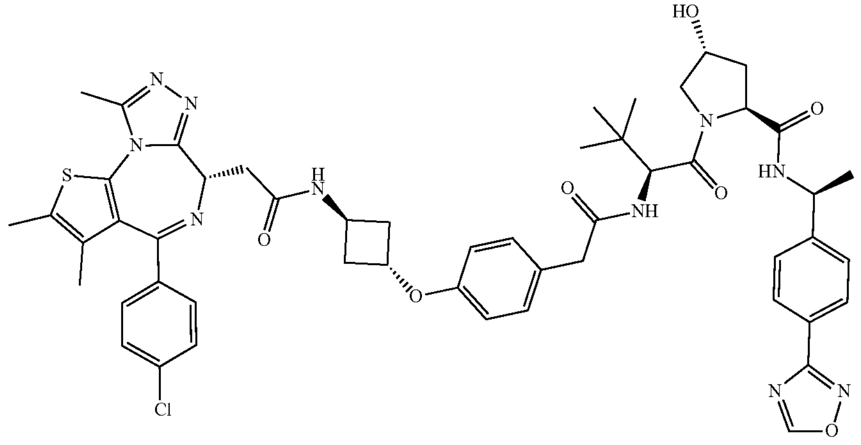 [SMILES: Cc1sc2c(c1C)C(c1ccc(Cl)cc1)=N[C@@H](CC(=O)N[C@H]1C[C@H](Oc3ccc(CC(=O)N[C@H](C(=O)N4C[C@H](O)C[C@H]4C(=O)N[C@@H](C)c4ccc(-c5ncon5)cc4)C(C)(C)C)cc3)C1)c1nnc(C)n1-2] | 1001.6 | 1001.4 | B | 91.4 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 282 | 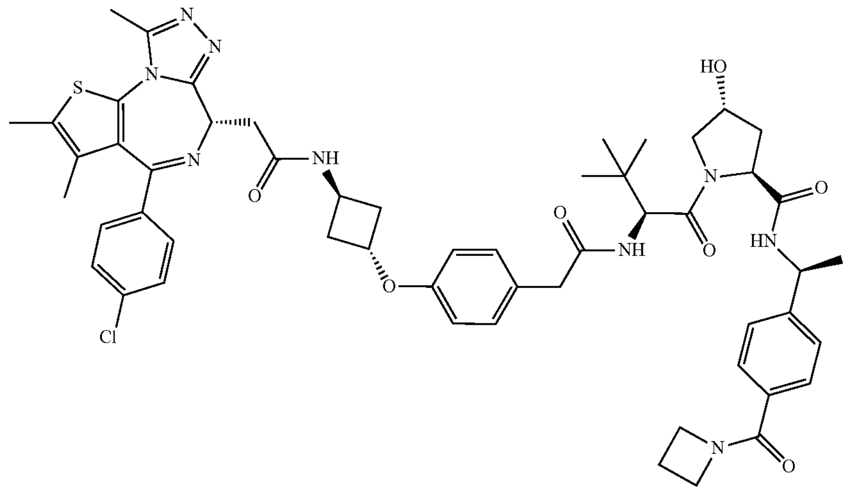 [SMILES: Cc1sc2c(c1C)C(c1ccc(Cl)cc1)=N[C@@H](CC(=O)N[C@H]1C[C@H](Oc3ccc(CC(=O)N[C@H](C(=O)N4C[C@H](O)C[C@H]4C(=O)N[C@@H](C)c4ccc(C(=O)N5CCC5)cc4)C(C)(C)C)cc3)C1)c1nnc(C)n1-2] | 1016.7 | 1016.4 | D | 25.4 |
| 283 | 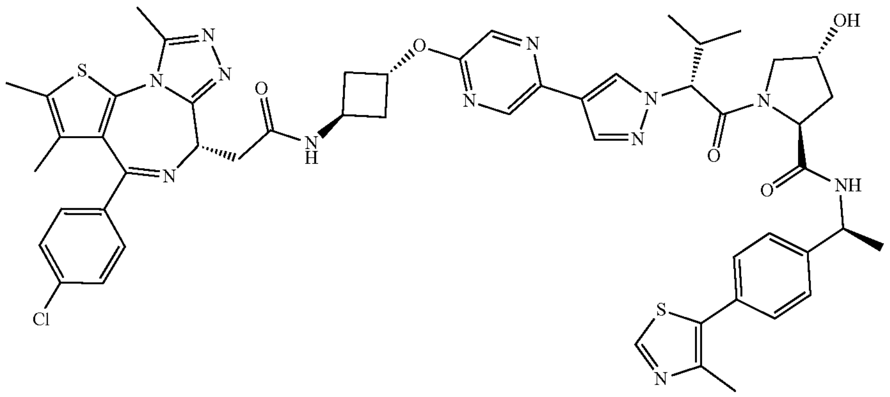 [SMILES: Cc1ncsc1-c1ccc([C@H](C)NC(=O)[C@@H]2C[C@@H](O)CN2C(=O)[C@@H](C(C)C)n2cc(-c3cnc(O[C@H]4C[C@H](NC(=O)C[C@@H]5N=C(c6ccc(Cl)cc6)c6c(sc(C)c6C)-n6c(C)nnc65)C4)cn3)cn2)cc1] | 1027.7 | 1027.5 | B | 89.5 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 284 | 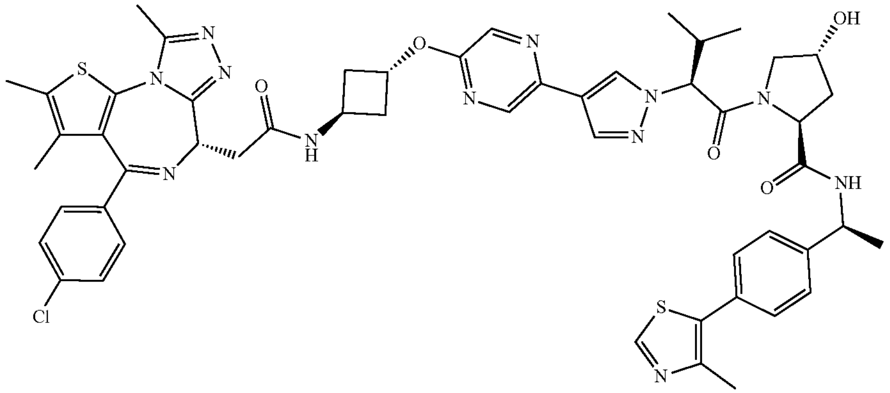 [SMILES: Cc1ncsc1-c1ccc([C@H](C)NC(=O)[C@@H]2C[C@@H](O)CN2C(=O)[C@H](C(C)C)n2cc(-c3cnc(O[C@H]4C[C@H](NC(=O)C[C@@H]5N=C(c6ccc(Cl)cc6)c6c(sc(C)c6C)-n6c(C)nnc65)C4)cn3)cn2)cc1] | 1027.7 | 1027.5 | A | 93.4 |
| 285 | 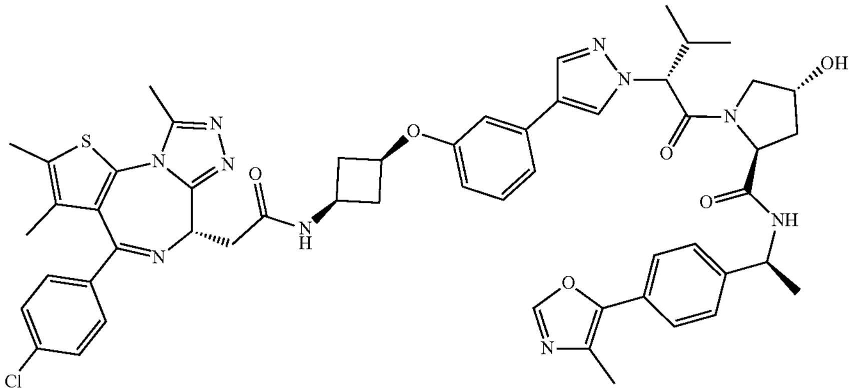 [SMILES: Cc1ncoc1-c1ccc([C@H](C)NC(=O)[C@@H]2C[C@@H](O)CN2C(=O)[C@@H](C(C)C)n2cc(-c3cccc(O[C@H]4C[C@@H](NC(=O)C[C@@H]5N=C(c6ccc(Cl)cc6)c6c(sc(C)c6C)-n6c(C)nnc65)C4)c3)cn2)cc1] | 1009.6 | 1009.6 | D | 44.4 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 286 | 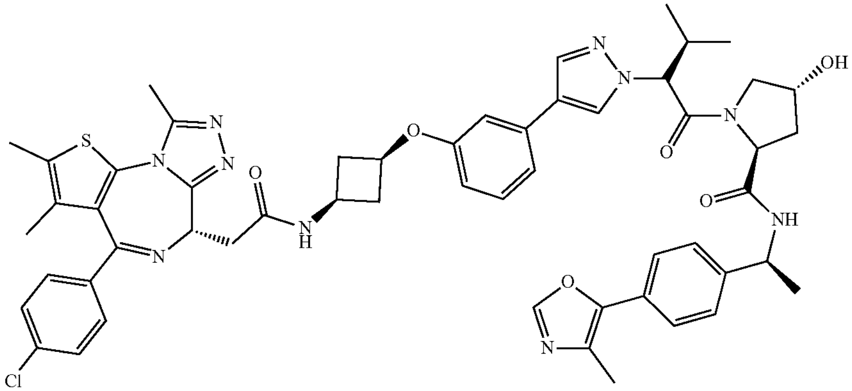 | 1009.6 | 1009.6 | B | 93.0 |
| 287 | 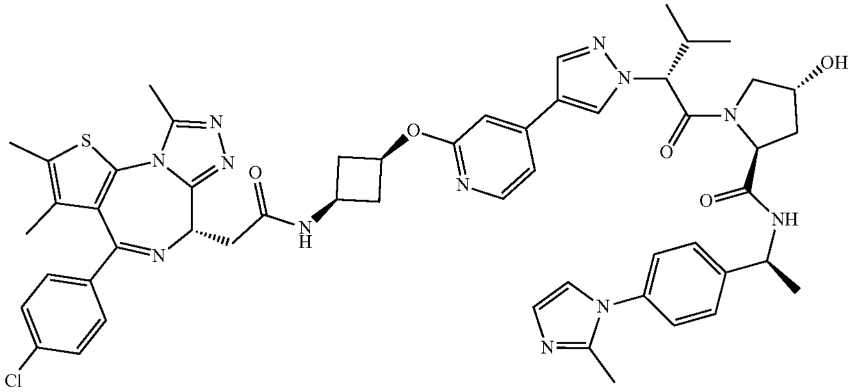 [SMILES: Cc1sc2c(c1C)C(c1ccc(Cl)cc1)=N[C@@H](CC(=O)N[C@H]1C[C@@H](Oc3cc(-c4cnn([C@@H](C(=O)N5C[C@H](O)C[C@H]5C(=O)N[C@@H](C)c5ccc(-n6ccnc6C)cc5)C(C)C)c4)ccn3)C1)c1nnc(C)n1-2] | 1009.6 | 1009.5 | D | 17.3 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 288 | 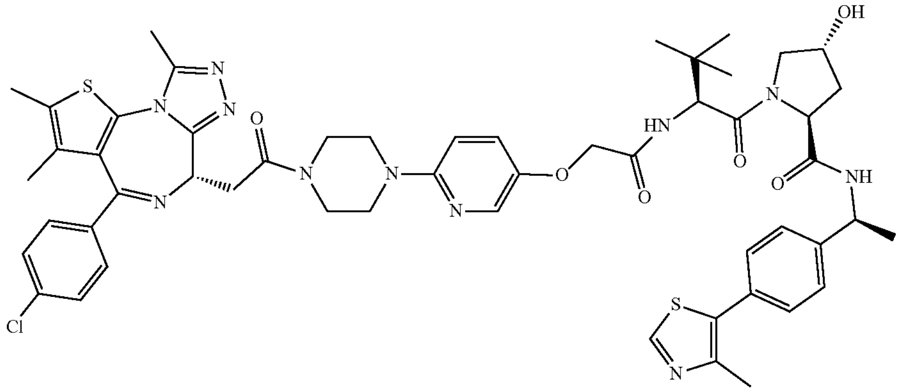 [SMILES: Cc1ncsc1-c1ccc([C@H](C)NC(=O)[C@@H]2C[C@@H](O)CN2C(=O)[C@@H](NC(=O)COc2ccc(N3CCN(C(=O)C[C@@H]4N=C(c5ccc(Cl)cc5)c5c(sc(C)c5C)-n5c(C)nnc54)CC3)nc2)C(C)(C)C)cc1] | 1046.7 | 1046.5 | A | 98.0 |
| 289 | 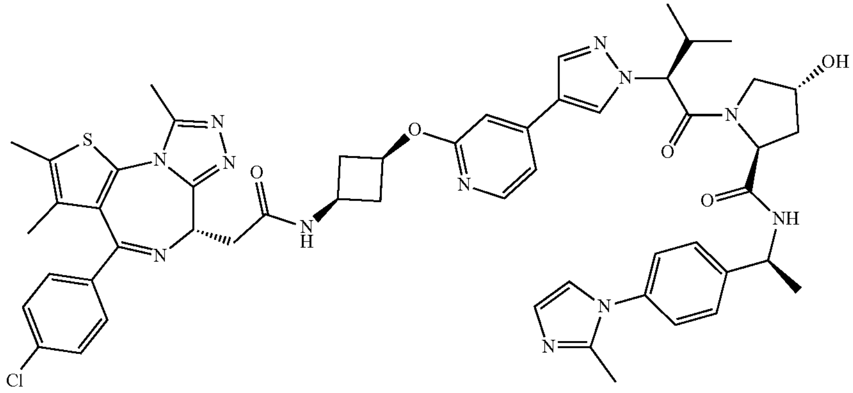 [SMILES: Cc1sc2c(c1C)C(c1ccc(Cl)cc1)=N[C@@H](CC(=O)N[C@H]1C[C@@H](Oc3cc(-c4cnn([C@H](C(=O)N5C[C@H](O)C[C@H]5C(=O)N[C@@H](C)c5ccc(-n6ccnc6C)cc5)C(C)C)c4)ccn3)C1)c1nnc(C)n1-2] | 1009.6 | 1009.6 | C | 93.8 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 290 | 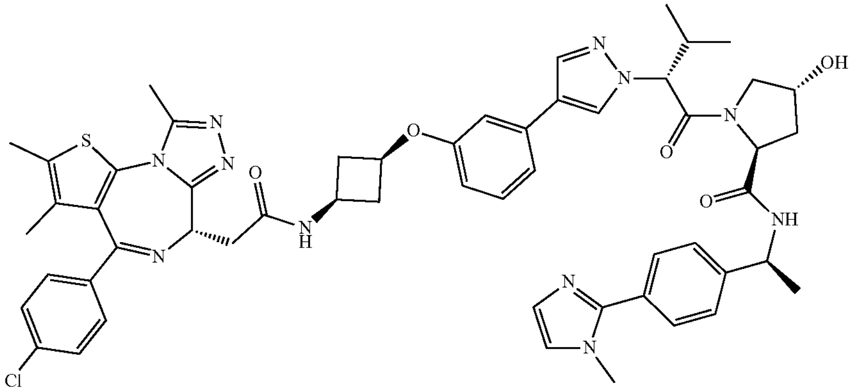 [SMILES: Cc1sc2c(c1C)C(c1ccc(Cl)cc1)=N[C@@H](CC(=O)N[C@H]1C[C@@H](Oc3cccc(-c4cnn([C@@H](C(=O)N5C[C@H](O)C[C@H]5C(=O)N[C@@H](C)c5ccc(-c6nccn6C)cc5)C(C)C)c4)c3)C1)c1nnc(C)n1-2] | 1008.6 | 1008.6 | D | 15.5 |
| 291 | 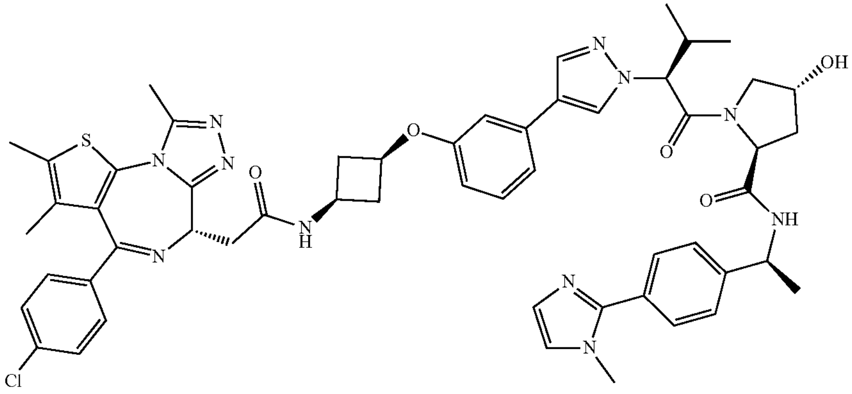 [SMILES: Cc1sc2c(c1C)C(c1ccc(Cl)cc1)=N[C@@H](CC(=O)N[C@H]1C[C@@H](Oc3cccc(-c4cnn([C@H](C(=O)N5C[C@H](O)C[C@H]5C(=O)N[C@@H](C)c5ccc(-c6nccn6C)cc5)C(C)C)c4)c3)C1)c1nnc(C)n1-2] | 1008.6 | 1008.6 | D | 22.2 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 292 | 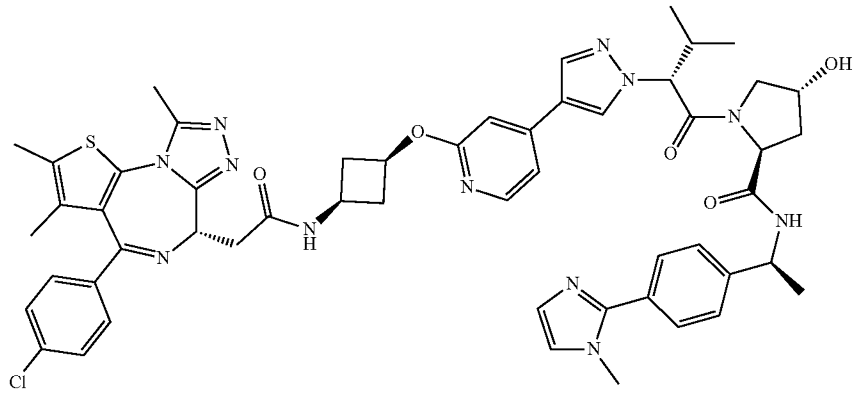 | 1009.6 | 1009.6 | D | 10.0 |
| 293 | 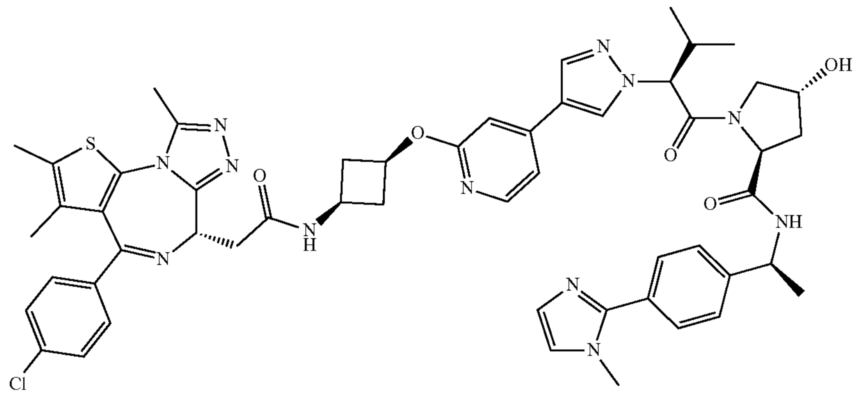 [SMILES: Cc1sc2c(c1C)C(c1ccc(Cl)cc1)=N[C@@H](CC(=O)N[C@H]1C[C@@H](Oc3cc(-c4cnn([C@H](C(=O)N5C[C@H](O)C[C@H]5C(=O)N[C@@H](C)c5ccc(-c6nccn6C)cc5)C(C)C)c4)ccn3)C1)c1nnc(C)n1-2] | 1009.6 | 1009.4 | D | 9.5 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 294 | 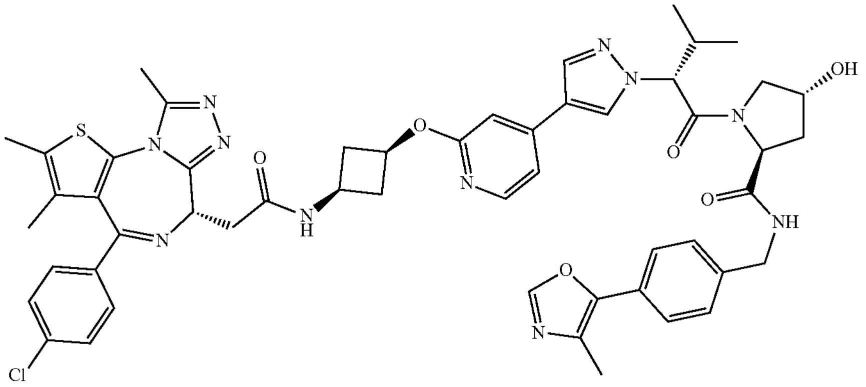 [SMILES: Cc1ncoc1-c1ccc(CNC(=O)[C@@H]2C[C@@H](O)CN2C(=O)[C@@H](C(C)C)n2cc(-c3ccnc(O[C@H]4C[C@@H](NC(=O)C[C@@H]5N=C(c6ccc(Cl)cc6)c6c(sc(C)c6C)-n6c(C)nnc65)C4)c3)cn2)cc1] | 0996.6 | 0996.4 | D | 43.4 |
| 295 | 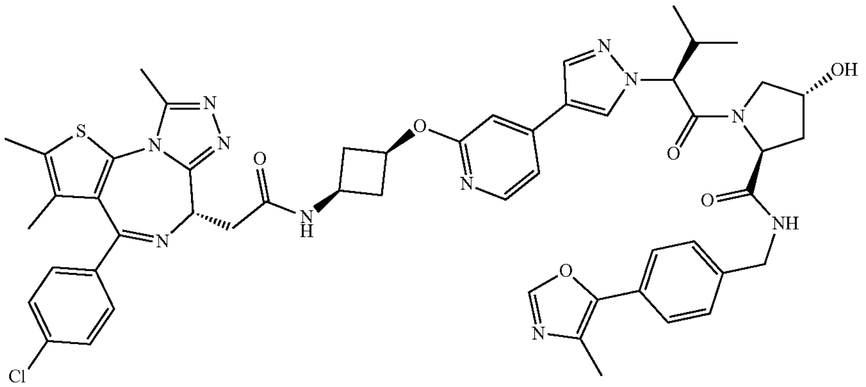 [SMILES: Cc1ncoc1-c1ccc(CNC(=O)[C@@H]2C[C@@H](O)CN2C(=O)[C@H](C(C)C)n2cc(-c3ccnc(O[C@H]4C[C@@H](NC(=O)C[C@@H]5N=C(c6ccc(Cl)cc6)c6c(sc(C)c6C)-n6c(C)nnc65)C4)c3)cn2)cc1] | 0996.6 | 0996.4 | C | 93.8 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 296 | 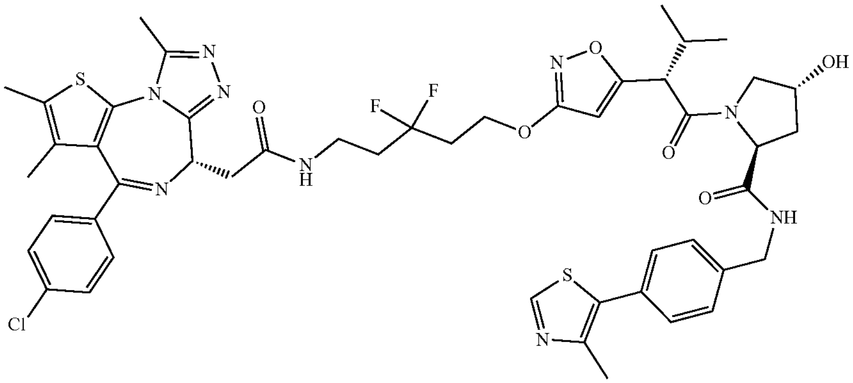 [SMILES: Cc1ncsc1-c1ccc(CNC(=O)[C@@H]2C[C@@H](O)CN2C(=O)[C@H](c2cc(OCCC(F)(F)CCNC(=O)C[C@@H]3N=C(c4ccc(Cl)cc4)c4c(sc(C)c4C)-n4c(C)nnc43)no2)C(C)C)cc1] | 0988.6 | 0988.5 | C | 71.4 |
| 297 | 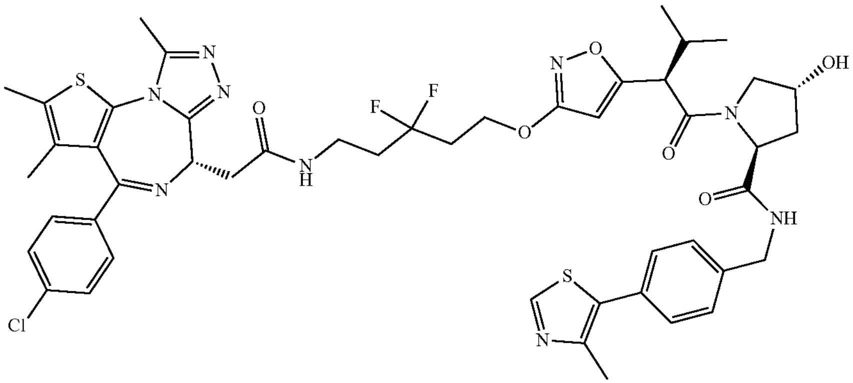 [SMILES: Cc1ncsc1-c1ccc(CNC(=O)[C@@H]2C[C@@H](O)CN2C(=O)[C@@H](c2cc(OCCC(F)(F)CCNC(=O)C[C@@H]3N=C(c4ccc(Cl)cc4)c4c(sc(C)c4C)-n4c(C)nnc43)no2)C(C)C)cc1] | 0988.6 | 0988.5 | A | 97.0 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 298 | 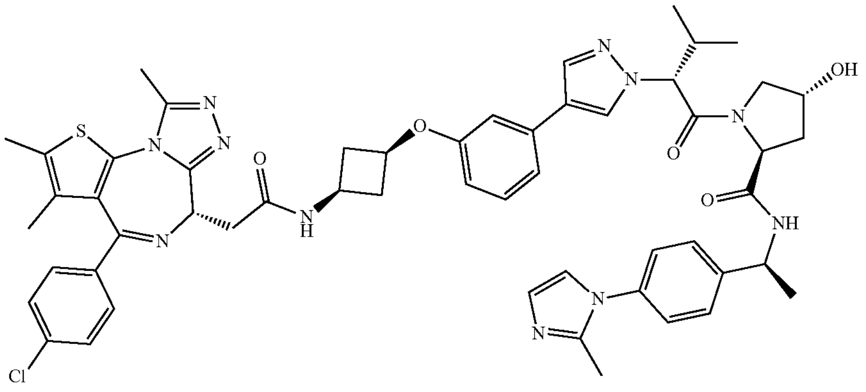 [SMILES: Cc1sc2c(c1C)C(c1ccc(Cl)cc1)=N[C@@H](CC(=O)N[C@H]1C[C@@H](Oc3cccc(-c4cnn([C@@H](C(=O)N5C[C@H](O)C[C@H]5C(=O)N[C@@H](C)c5ccc(-n6ccnc6C)cc5)C(C)C)c4)c3)C1)c1nnc(C)n1-2] | 1008.6 | 1008.6 | D | 25.5 |
| 299 | 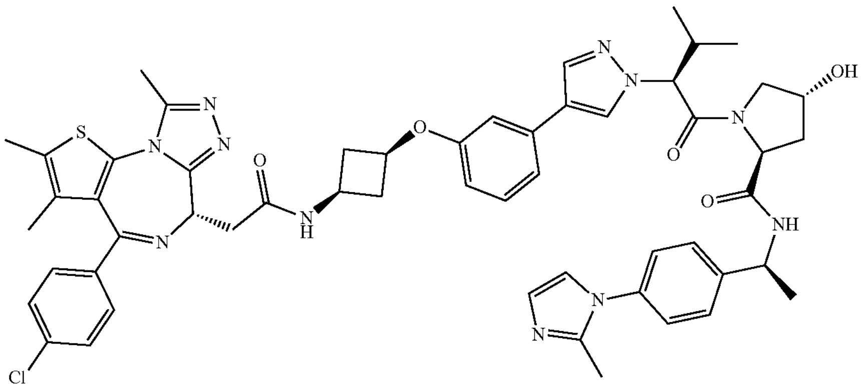 [SMILES: Cc1sc2c(c1C)C(c1ccc(Cl)cc1)=N[C@@H](CC(=O)N[C@H]1C[C@@H](Oc3cccc(-c4cnn([C@H](C(=O)N5C[C@H](O)C[C@H]5C(=O)N[C@@H](C)c5ccc(-n6ccnc6C)cc5)C(C)C)c4)c3)C1)c1nnc(C)n1-2] | 1008.6 | 1008.6 | C | 72.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 300 | 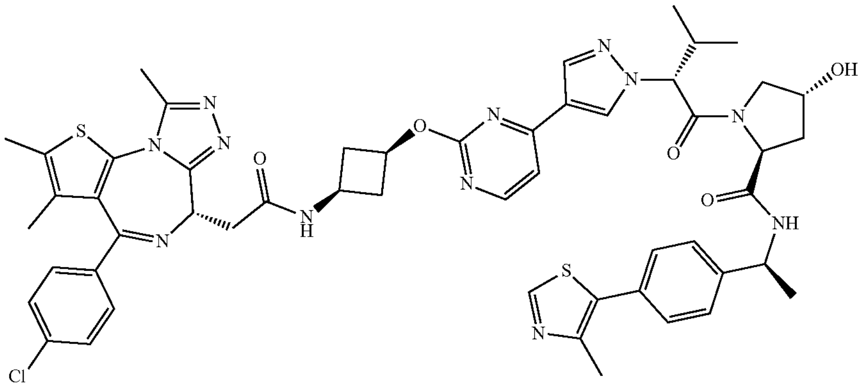 [SMILES: Cc1ncsc1-c1ccc([C@H](C)NC(=O)[C@@H]2C[C@@H](O)CN2C(=O)[C@@H](C(C)C)n2cc(-c3ccnc(O[C@H]4C[C@@H](NC(=O)C[C@@H]5N=C(c6ccc(Cl)cc6)c6c(sc(C)c6C)-n6c(C)nnc65)C4)n3)cn2)cc1] | 1027.7 | 1027.5 | D | 24.0 |
| 301 | 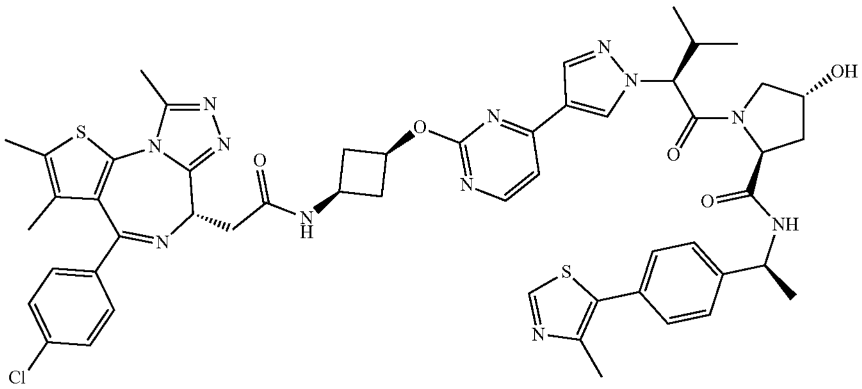 [SMILES: Cc1ncsc1-c1ccc([C@H](C)NC(=O)[C@@H]2C[C@@H](O)CN2C(=O)[C@H](C(C)C)n2cc(-c3ccnc(O[C@H]4C[C@@H](NC(=O)C[C@@H]5N=C(c6ccc(Cl)cc6)c6c(sc(C)c6C)-n6c(C)nnc65)C4)n3)cn2)cc1] | 1027.7 | 1027.5 | B | 95.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 302 | 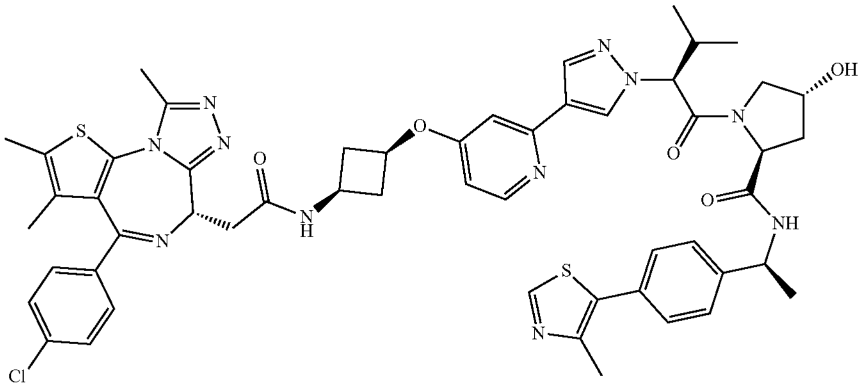 [SMILES: Cc1ncsc1-c1ccc([C@H](C)NC(=O)[C@@H]2C[C@@H](O)CN2C(=O)[C@H](C(C)C)n2cc(-c3cc(O[C@H]4C[C@@H](NC(=O)C[C@@H]5N=C(c6ccc(Cl)cc6)c6c(sc(C)c6C)-n6c(C)nnc65)C4)ccn3)cn2)cc1] | 1026.7 | 1026.5 | B | 92.0 |
| 303 | 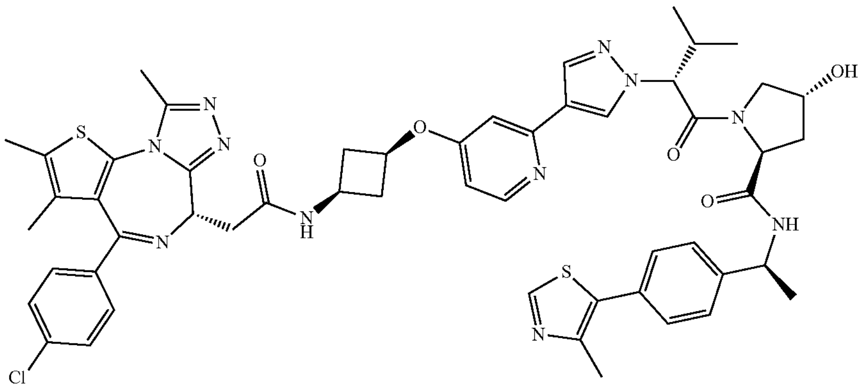 [SMILES: Cc1ncsc1-c1ccc([C@H](C)NC(=O)[C@@H]2C[C@@H](O)CN2C(=O)[C@@H](C(C)C)n2cc(-c3cc(O[C@H]4C[C@@H](NC(=O)C[C@@H]5N=C(c6ccc(Cl)cc6)c6c(sc(C)c6C)-n6c(C)nnc65)C4)ccn3)cn2)cc1] | 1026.7 | 1026.5 | D | 9.8 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 304 | 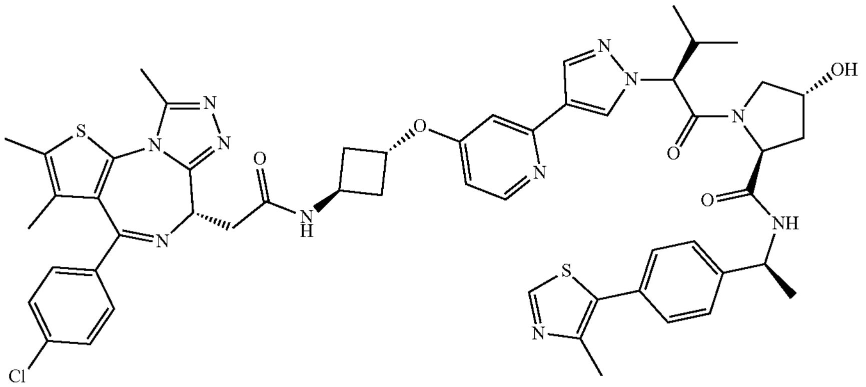 [SMILES: Cc1ncsc1-c1ccc([C@H](C)NC(=O)[C@@H]2C[C@@H](O)CN2C(=O)[C@H](C(C)C)n2cc(-c3cc(O[C@H]4C[C@H](NC(=O)C[C@@H]5N=C(c6ccc(Cl)cc6)c6c(sc(C)c6C)-n6c(C)nnc65)C4)ccn3)cn2)cc1] | 1026.7 | 1026.5 | B | 95.0 |
| 305 | 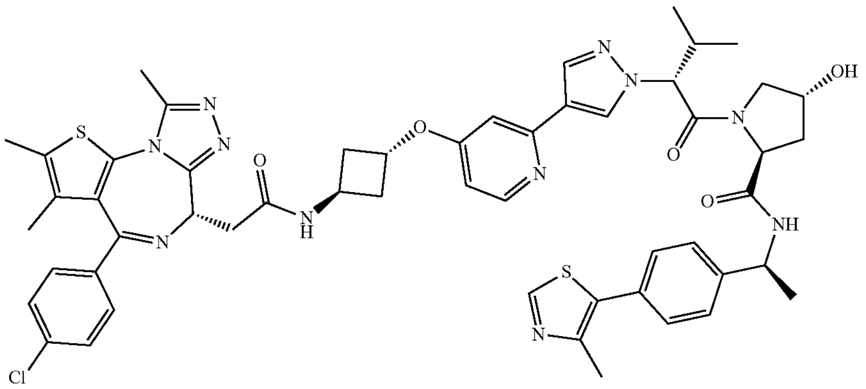 [SMILES: Cc1ncsc1-c1ccc([C@H](C)NC(=O)[C@@H]2C[C@@H](O)CN2C(=O)[C@@H](C(C)C)n2cc(-c3cc(O[C@H]4C[C@H](NC(=O)C[C@@H]5N=C(c6ccc(Cl)cc6)c6c(sc(C)c6C)-n6c(C)nnc65)C4)ccn3)cn2)cc1] | 1026.7 | 1026.4 | D | 6.7 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 306 | 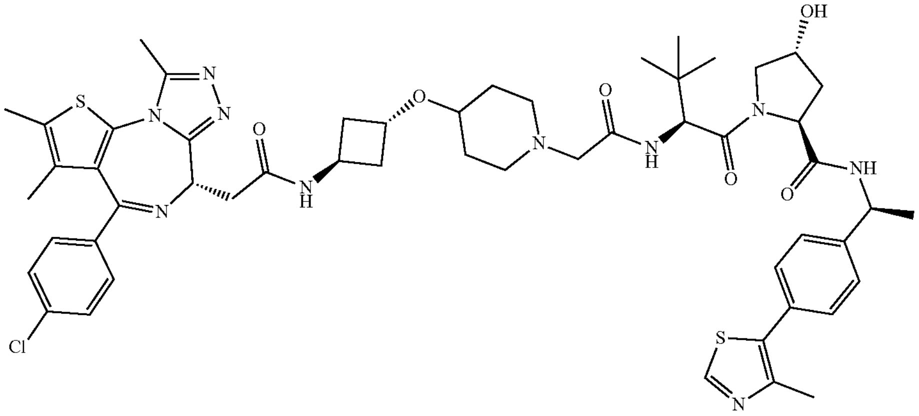 [SMILES: Cc1ncsc1-c1ccc([C@H](C)NC(=O)[C@@H]2C[C@@H](O)CN2C(=O)[C@@H](NC(=O)CN2CCC(O[C@H]3C[C@H](NC(=O)C[C@@H]4N=C(c5ccc(Cl)cc5)c5c(sc(C)c5C)-n5c(C)nnc54)C3)CC2)C(C)(C)C)cc1] | 1037.7 | 1037.4 | A | 100.0 |
| 307 | 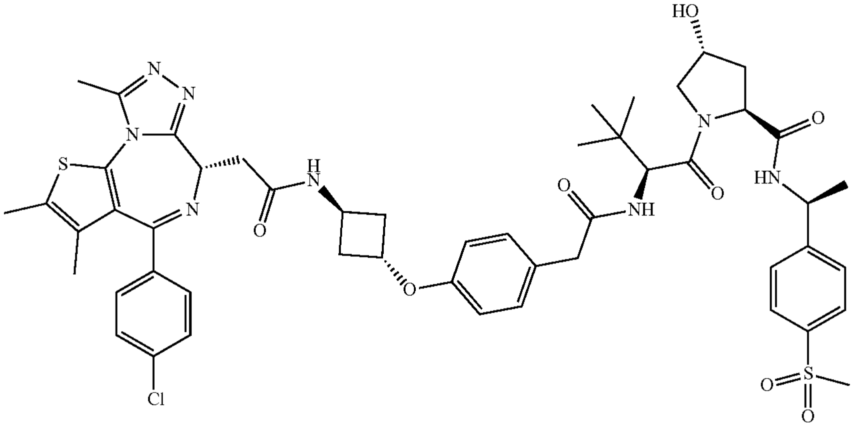 | 1011.7 | 1011.4 | D | 15.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 308 | 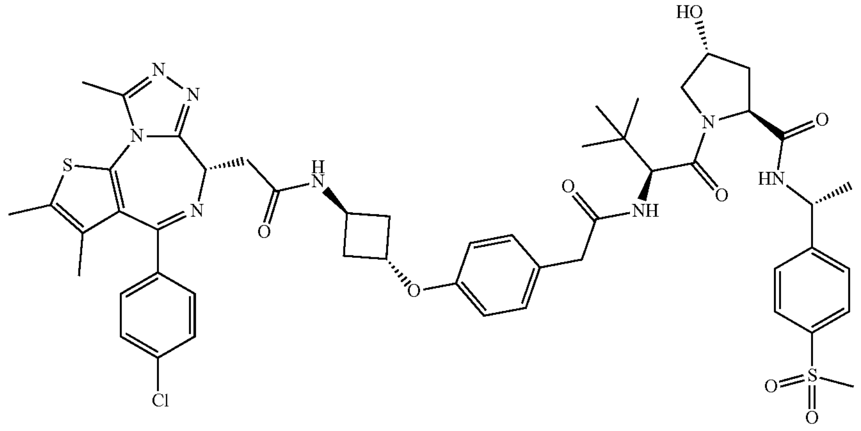 | 1011.7 | 1011.4 | D | 21.0 |
| 309 | 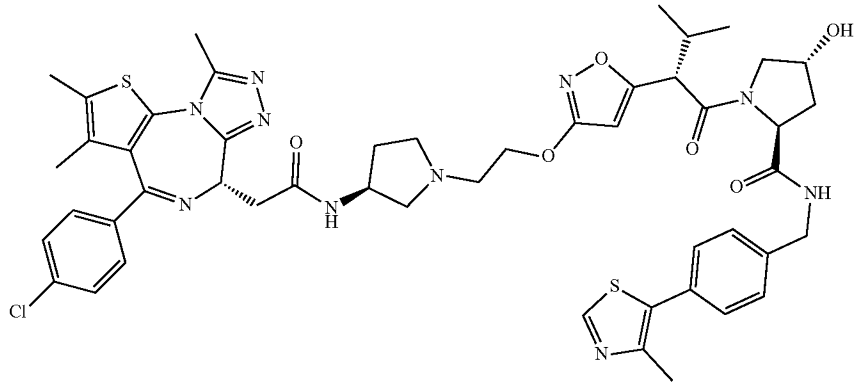 [SMILES: Cc1ncsc1-c1ccc(CNC(=O)[C@@H]2C[C@@H](O)CN2C(=O)[C@H](c2cc(OCCN3CC[C@H](NC(=O)C[C@@H]4N=C(c5ccc(Cl)cc5)c5c(sc(C)c5C)-n5c(C)nnc54)C3)no2)C(C)C)cc1] | 0979.6 | 0979.4 | D | 18.0 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 310 | 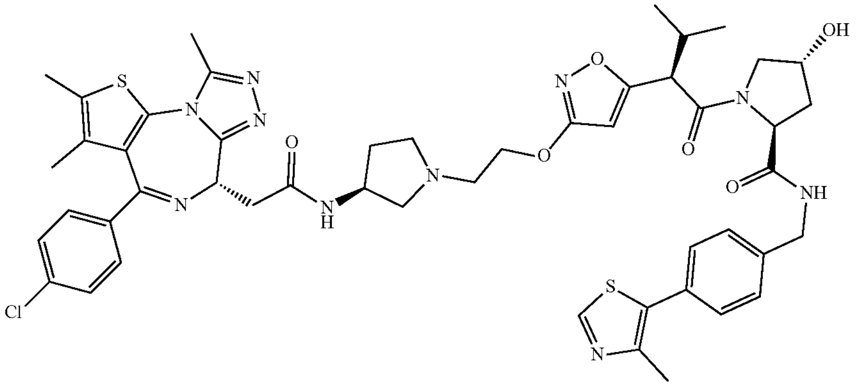 [SMILES: Cc1ncsc1-c1ccc(CNC(=O)[C@@H]2C[C@@H](O)CN2C(=O)[C@@H](c2cc(OCCN3CC[C@H](NC(=O)C[C@@H]4N=C(c5ccc(Cl)cc5)c5c(sc(C)c5C)-n5c(C)nnc54)C3)no2)C(C)C)cc1] | 0979.6 | 0979.4 | A | 94.0 |
| 311 | 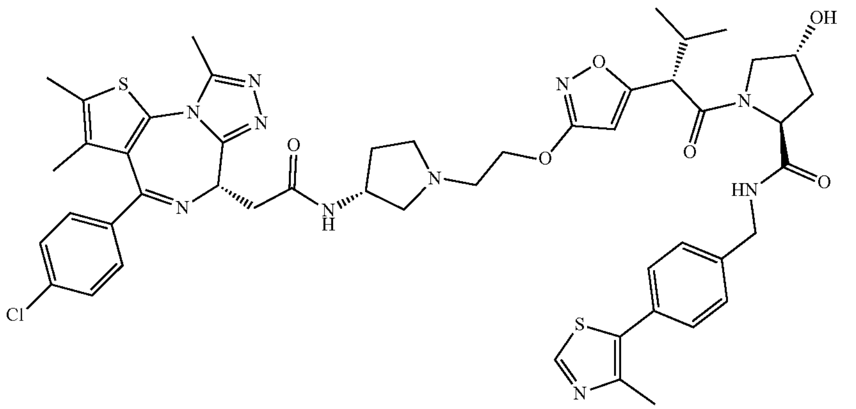 [SMILES: Cc1ncsc1-c1ccc(CNC(=O)[C@@H]2C[C@@H](O)CN2C(=O)[C@H](c2cc(OCCN3CC[C@@H](NC(=O)C[C@@H]4N=C(c5ccc(Cl)cc5)c5c(sc(C)c5C)-n5c(C)nnc54)C3)no2)C(C)C)cc1] | 0979.6 | 0979.4 | D | 43.6 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 312 | 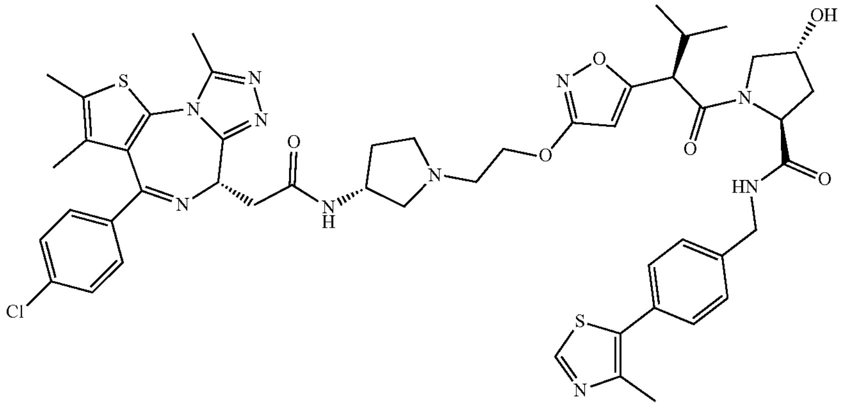 [SMILES: Cc1ncsc1-c1ccc(CNC(=O)[C@@H]2C[C@@H](O)CN2C(=O)[C@@H](c2cc(OCCN3CC[C@@H](NC(=O)C[C@@H]4N=C(c5ccc(Cl)cc5)c5c(sc(C)c5C)-n5c(C)nnc54)C3)no2)C(C)C)cc1] | 0979.6 | 0979.4 | A | 87.5 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 313 | 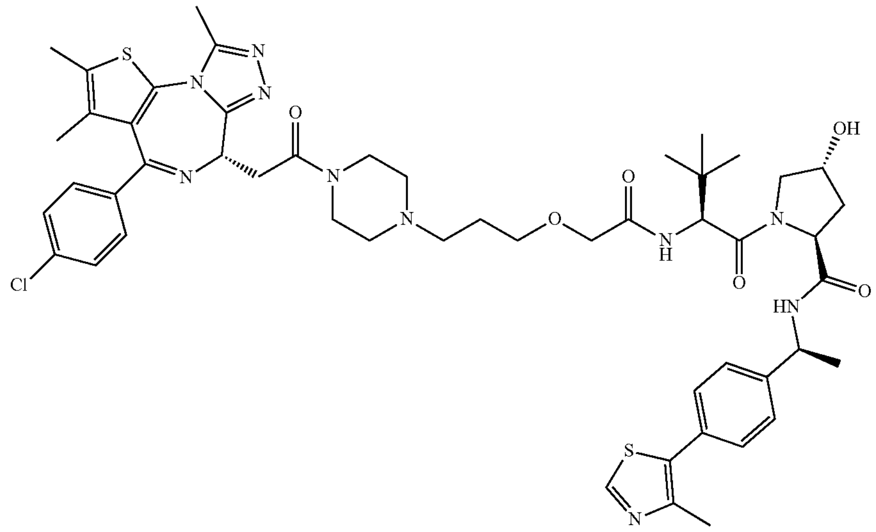 [SMILES: Cc1ncsc1-c1ccc([C@H](C)NC(=O)[C@@H]2C[C@@H](O)CN2C(=O)[C@@H](NC(=O)COCCCN2CCN(C(=O)C[C@@H]3N=C(c4ccc(Cl)cc4)c4c(sc(C)c4C)-n4c(C)nnc43)CC2)C(C)(C)C)cc1] | 1011.7 | 1011.4 | B | 87.5 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 314 | 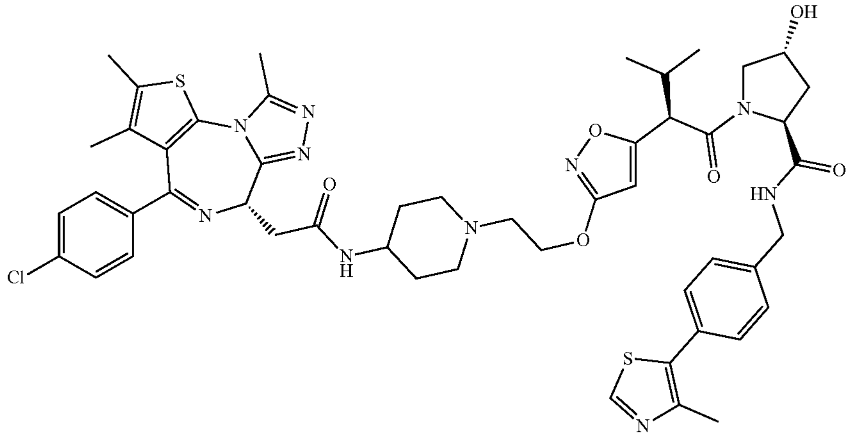 [SMILES: Cc1ncsc1-c1ccc(CNC(=O)[C@@H]2C[C@@H](O)CN2C(=O)[C@@H](c2cc(OCCN3CCC(NC(=O)C[C@@H]4N=C(c5ccc(Cl)cc5)c5c(sc(C)c5C)-n5c(C)nnc54)CC3)no2)C(C)C)cc1] | 0993.6 | 0993.4 | A | 87.0 |
| 315 | 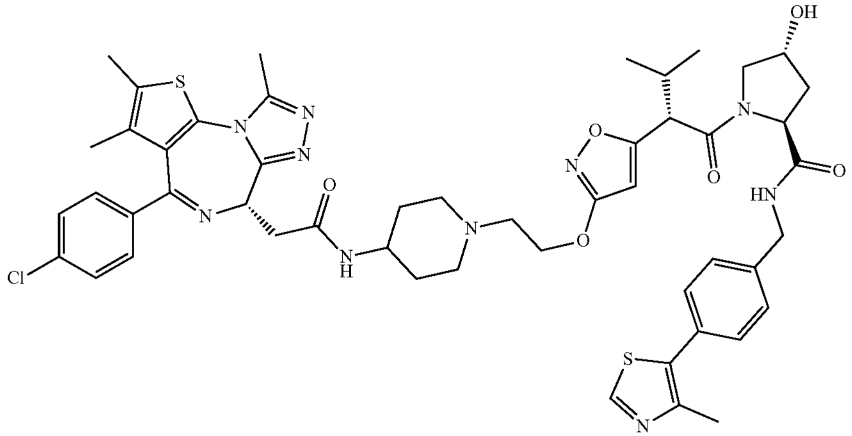 [SMILES: Cc1ncsc1-c1ccc(CNC(=O)[C@@H]2C[C@@H](O)CN2C(=O)[C@H](c2cc(OCCN3CCC(NC(=O)C[C@@H]4N=C(c5ccc(Cl)cc5)c5c(sc(C)c5C)-n5c(C)nnc54)CC3)no2)C(C)C)cc1] | 0993.6 | 0993.4 | D | 11.4 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 316 | 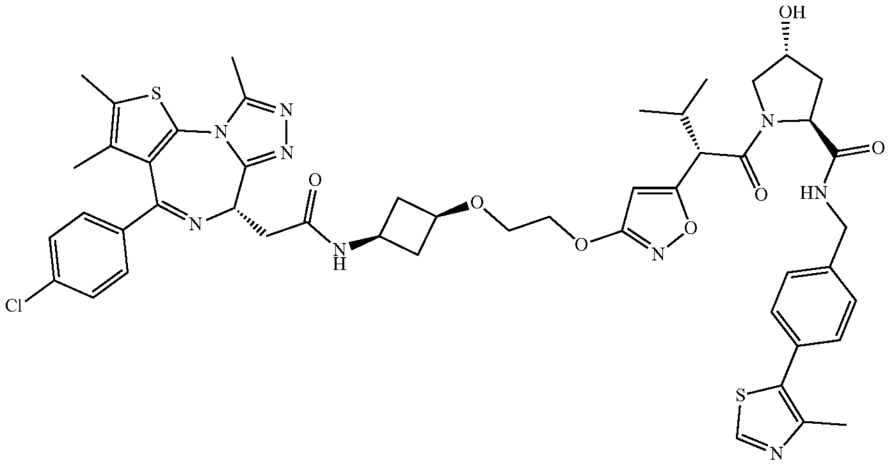 [SMILES: Cc1ncsc1-c1ccc(CNC(=O)[C@@H]2C[C@@H](O)CN2C(=O)[C@H](c2cc(OCCO[C@H]3C[C@@H](NC(=O)C[C@@H]4N=C(c5ccc(Cl)cc5)c5c(sc(C)c5C)-n5c(C)nnc54)C3)no2)C(C)C)cc1] | 0980.6 | 0980.3 | B | 71.4 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 317 | 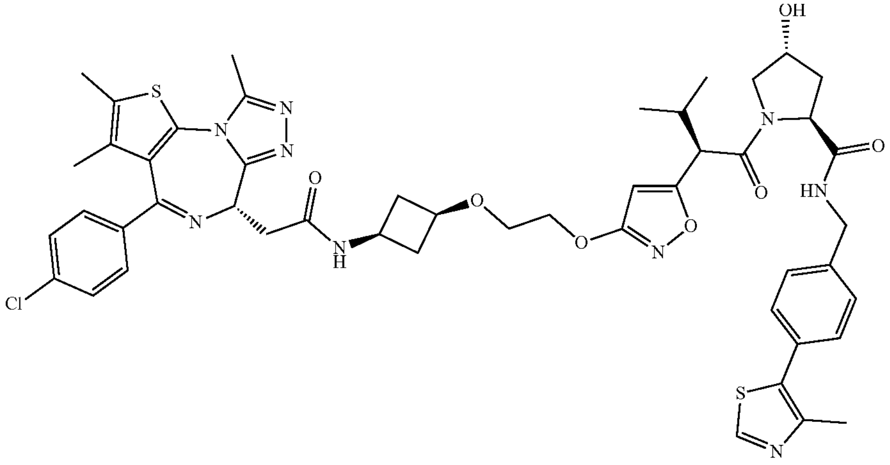 [SMILES: Cc1ncsc1-c1ccc(CNC(=O)[C@@H]2C[C@@H](O)CN2C(=O)[C@@H](c2cc(OCCO[C@H]3C[C@@H](NC(=O)C[C@@H]4N=C(c5ccc(Cl)cc5)c5c(sc(C)c5C)-n5c(C)nnc54)C3)no2)C(C)C)cc1] | 0980.6 | 0980.3 | A | 89.9 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 318 | 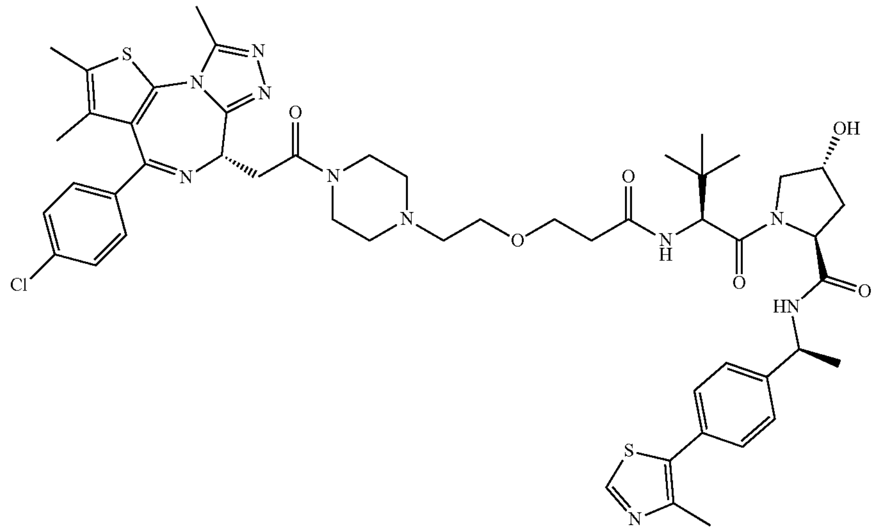 [SMILES: Cc1ncsc1-c1ccc([C@H](C)NC(=O)[C@@H]2C[C@@H](O)CN2C(=O)[C@@H](NC(=O)CCOCCN2CCN(C(=O)C[C@@H]3N=C(c4ccc(Cl)cc4)c4c(sc(C)c4C)-n4c(C)nnc43)CC2)C(C)(C)C)cc1] | 1011.7 | 1011.5 | C | 79.0 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 319 | 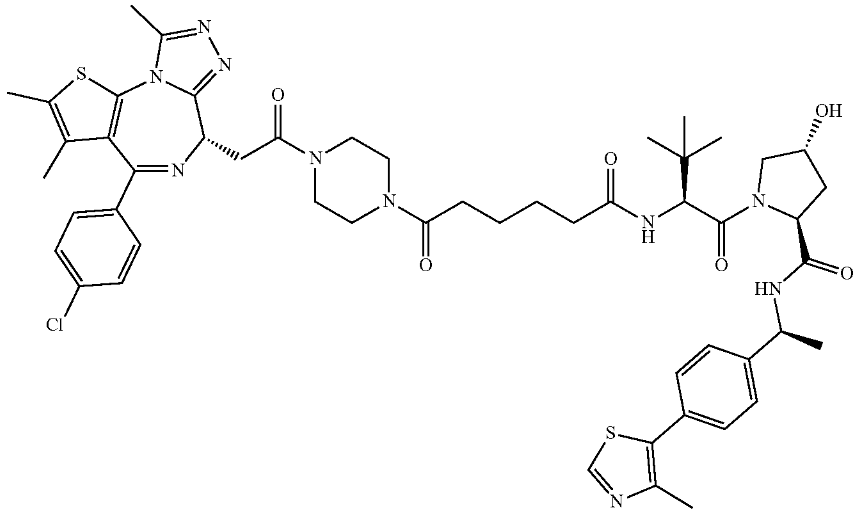 [SMILES: Cc1ncsc1-c1ccc([C@H](C)NC(=O)[C@@H]2C[C@@H](O)CN2C(=O)[C@@H](NC(=O)CCCCC(=O)N2CCN(C(=O)C[C@@H]3N=C(c4ccc(Cl)cc4)c4c(sc(C)c4C)-n4c(C)nnc43)CC2)C(C)(C)C)cc1] | 1023.7 | 1023.4 | C | 78.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 320 | 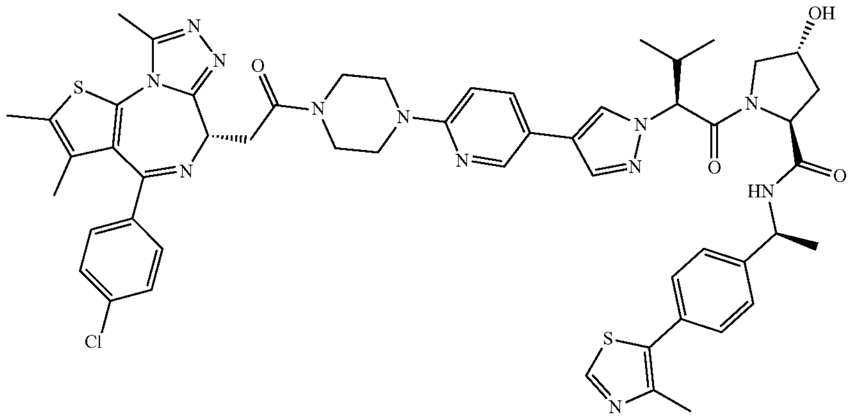 [SMILES: Cc1ncsc1-c1ccc([C@H](C)NC(=O)[C@@H]2C[C@@H](O)CN2C(=O)[C@H](C(C)C)n2cc(-c3ccc(N4CCN(C(=O)C[C@@H]5N=C(c6ccc(Cl)cc6)c6c(sc(C)c6C)-n6c(C)nnc65)CC4)nc3)cn2)cc1] | 1025.7 | 1025.4 | A | 97.8 |
| 321 | 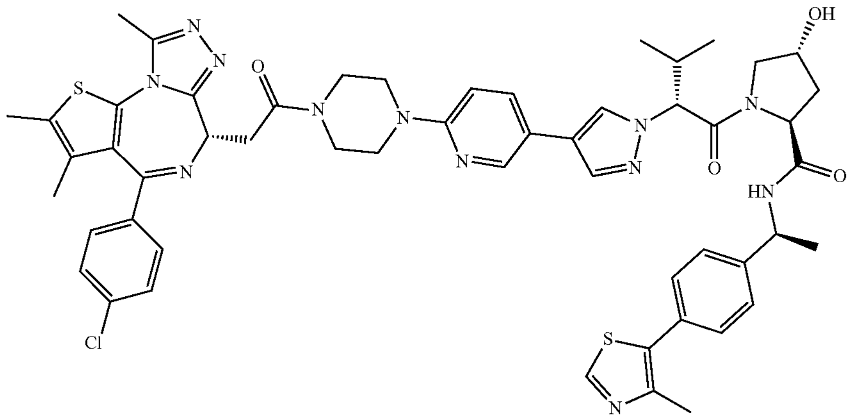 [SMILES: Cc1ncsc1-c1ccc([C@H](C)NC(=O)[C@@H]2C[C@@H](O)CN2C(=O)[C@@H](C(C)C)n2cc(-c3ccc(N4CCN(C(=O)C[C@@H]5N=C(c6ccc(Cl)cc6)c6c(sc(C)c6C)-n6c(C)nnc65)CC4)nc3)cn2)cc1] | 1025.7 | 1025.4 | C | 56.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 322 | 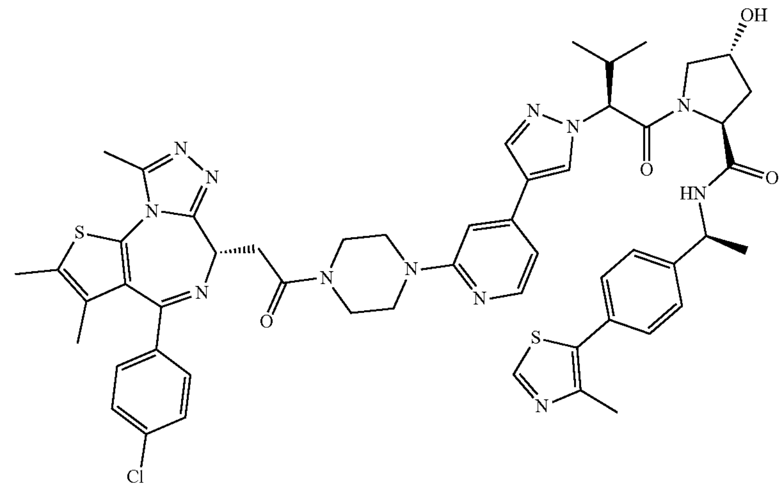 [SMILES: Cc1ncsc1-c1ccc([C@H](C)NC(=O)[C@@H]2C[C@@H](O)CN2C(=O)[C@H](C(C)C)n2cc(-c3ccnc(N4CCN(C(=O)C[C@@H]5N=C(c6ccc(Cl)cc6)c6c(sc(C)c6C)-n6c(C)nnc65)CC4)c3)cn2)cc1] | 1025.7 | 1025.4 | A | 92.6 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 323 | 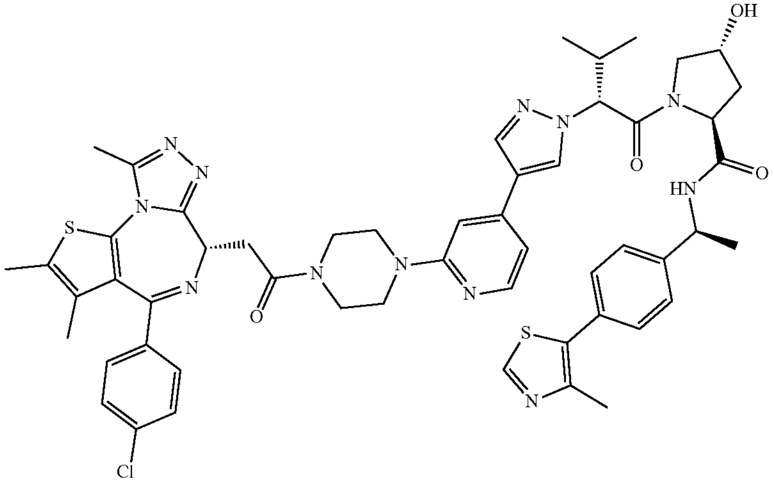 [SMILES: Cc1ncsc1-c1ccc([C@H](C)NC(=O)[C@@H]2C[C@@H](O)CN2C(=O)[C@@H](C(C)C)n2cc(-c3ccnc(N4CCN(C(=O)C[C@@H]5N=C(c6ccc(Cl)cc6)c6c(sc(C)c6C)-n6c(C)nnc65)CC4)c3)cn2)cc1] | 1025.7 | 1025.5 | D | 43.0 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 324 | 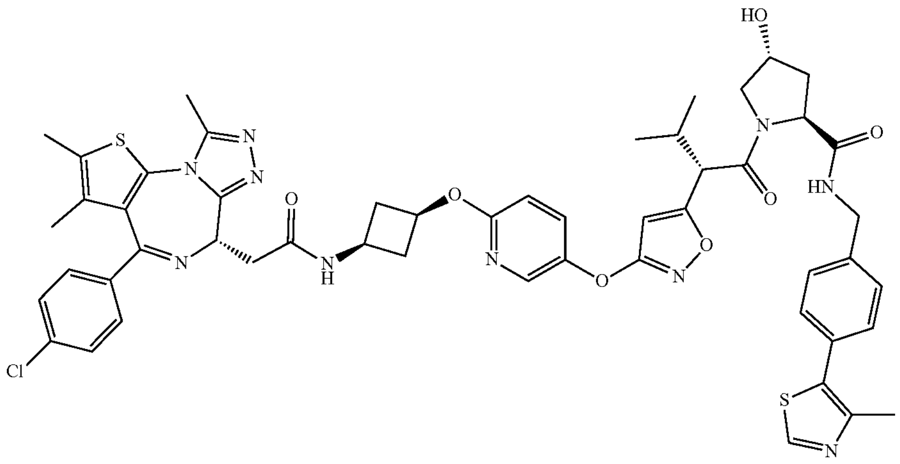 [SMILES: Cc1ncsc1-c1ccc(CNC(=O)[C@@H]2C[C@@H](O)CN2C(=O)[C@H](c2cc(Oc3ccc(O[C@H]4C[C@@H](NC(=O)C[C@@H]5N=C(c6ccc(Cl)cc6)c6c(sc(C)c6C)-n6c(C)nnc65)C4)nc3)no2)C(C)C)cc1] | 1029.6 | 1029.5 | D | 31.6 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 325 | 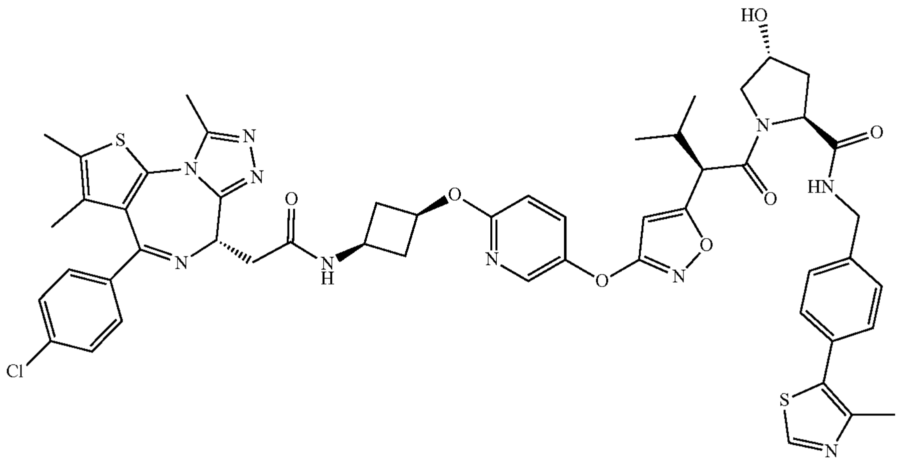 [SMILES: Cc1ncsc1-c1ccc(CNC(=O)[C@@H]2C[C@@H](O)CN2C(=O)[C@@H](c2cc(Oc3ccc(O[C@H]4C[C@@H](NC(=O)C[C@@H]5N=C(c6ccc(Cl)cc6)c6c(sc(C)c6C)-n6c(C)nnc65)C4)nc3)no2)C(C)C)cc1] | 1029.6 | 1029.5 | B | 81.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 326 | 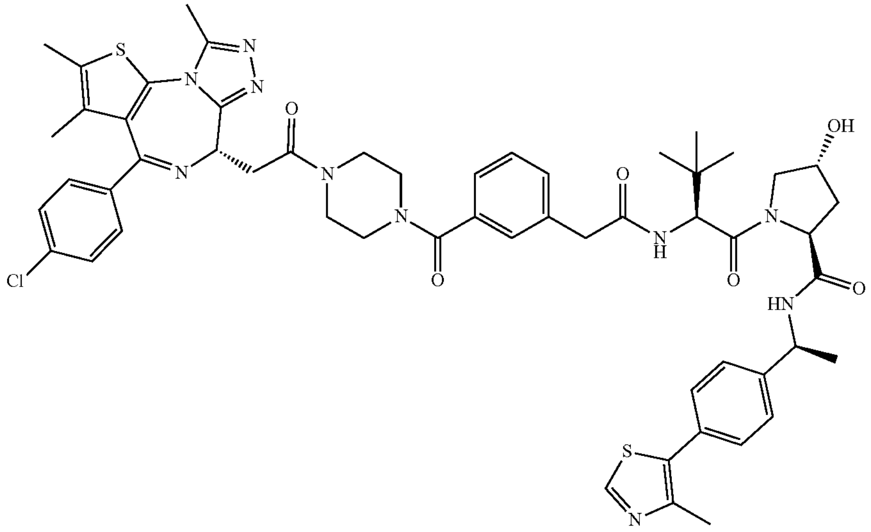 [SMILES: Cc1ncsc1-c1ccc([C@H](C)NC(=O)[C@@H]2C[C@@H](O)CN2C(=O)[C@@H](NC(=O)Cc2cccc(C(=O)N3CCN(C(=O)C[C@@H]4N=C(c5ccc(Cl)cc5)c5c(sc(C)c5C)-n5c(C)nnc54)CC3)c2)C(C)(C)C)cc1] | 1057.7 | 1057.3 | B | 92.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 327 | 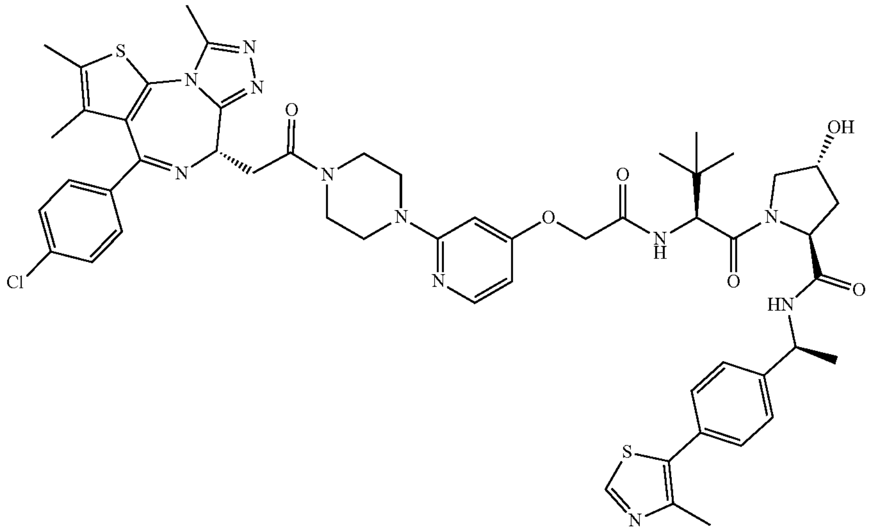 [SMILES: Cc1ncsc1-c1ccc([C@H](C)NC(=O)[C@@H]2C[C@@H](O)CN2C(=O)[C@@H](NC(=O)COc2ccnc(N3CCN(C(=O)C[C@@H]4N=C(c5ccc(Cl)cc5)c5c(sc(C)c5C)-n5c(C)nnc54)CC3)c2)C(C)(C)C)cc1] | 1046.7 | 1046.4 | A | 96.0 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 328 | 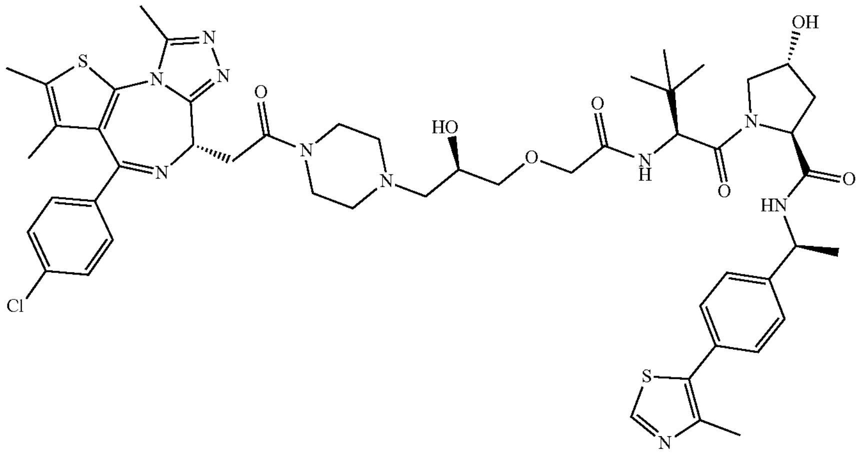 [SMILES: Cc1ncsc1-c1ccc([C@H](C)NC(=O)[C@@H]2C[C@@H](O)CN2C(=O)[C@@H](NC(=O)COC[C@H](O)CN2CCN(C(=O)C[C@@H]3N=C(c4ccc(Cl)cc4)c4c(sc(C)c4C)-n4c(C)nnc43)CC2)C(C)(C)C)cc1] | 1027.7 | 1027.4 | C | 61.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 329 | 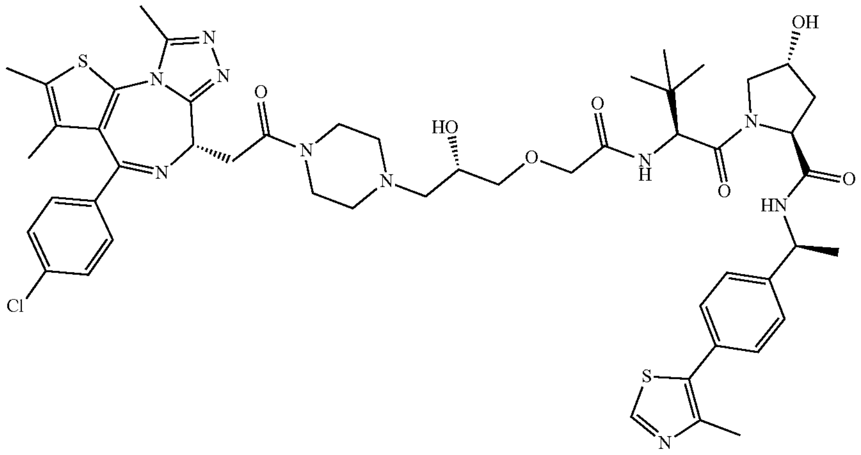 [SMILES: Cc1ncsc1-c1ccc([C@H](C)NC(=O)[C@@H]2C[C@@H](O)CN2C(=O)[C@@H](NC(=O)COC[C@@H](O)CN2CCN(C(=O)C[C@@H]3N=C(c4ccc(Cl)cc4)c4c(sc(C)c4C)-n4c(C)nnc43)CC2)C(C)(C)C)cc1] | 1027.7 | 1027.5 | D | <5 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 330 | 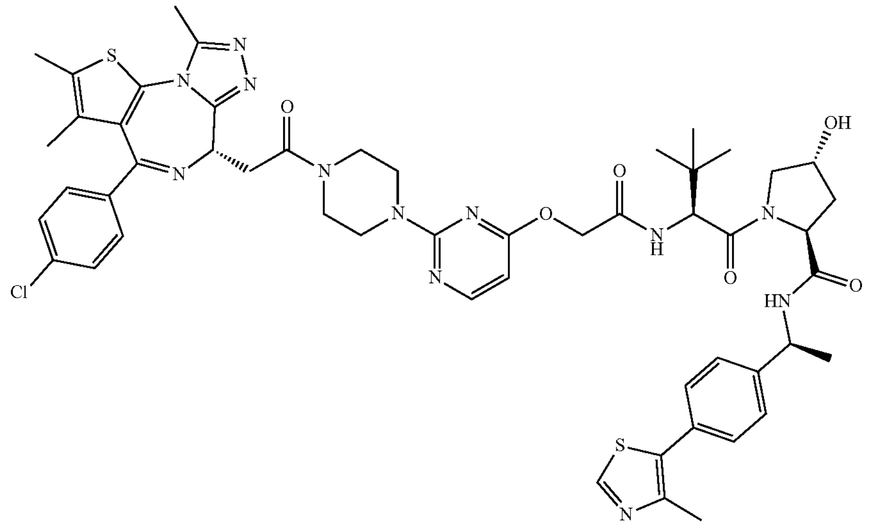 [SMILES: Cc1ncsc1-c1ccc([C@H](C)NC(=O)[C@@H]2C[C@@H](O)CN2C(=O)[C@@H](NC(=O)COc2ccnc(N3CCN(C(=O)C[C@@H]4N=C(c5ccc(Cl)cc5)c5c(sc(C)c5C)-n5c(C)nnc54)CC3)n2)C(C)(C)C)cc1] | 1047.7 | 1047.4 | B | 89.0 |

-continued
| Ex. # | Compound Structure | MW | Obsd $[M+H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 331 | 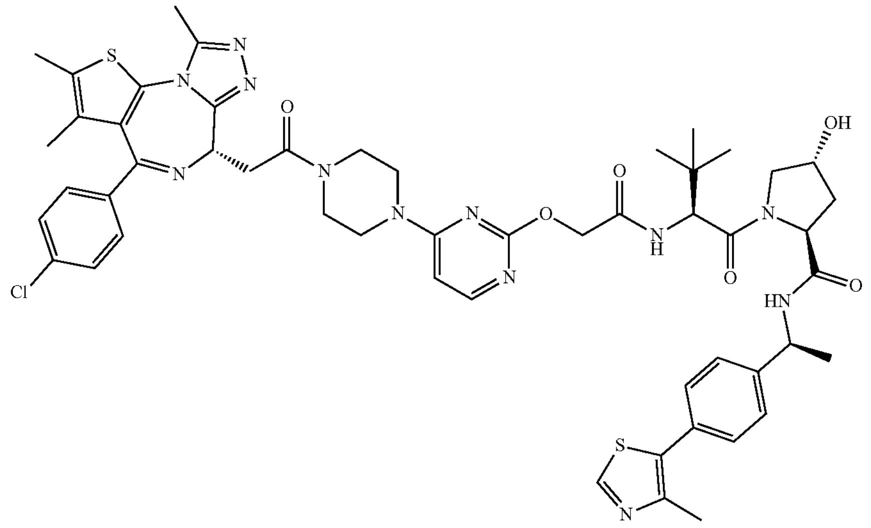 [SMILES: Cc1ncsc1-c1ccc([C@H](C)NC(=O)[C@@H]2C[C@@H](O)CN2C(=O)[C@@H](NC(=O)COc2nccc(N3CCN(C(=O)C[C@@H]4N=C(c5ccc(Cl)cc5)c5c(sc(C)c5C)-n5c(C)nnc54)CC3)n2)C(C)(C)C)cc1] | 1047.7 | 1047.4 | C | 81.5 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 332 | 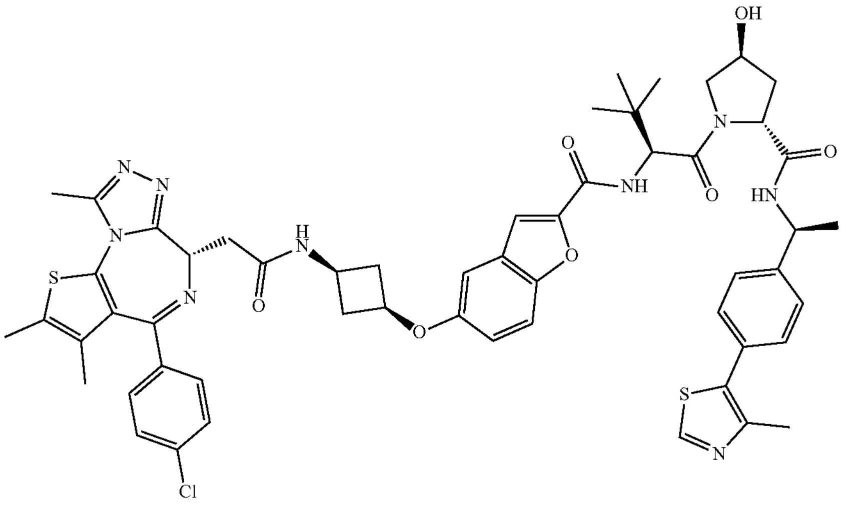 [SMILES: Cc1ncsc1-c1ccc([C@H](C)NC(=O)[C@H]2C[C@H](O)CN2C(=O)[C@@H](NC(=O)c2cc3cc(O[C@H]4C[C@@H](NC(=O)C[C@@H]5N=C(c6ccc(Cl)cc6)c6c(sc(C)c6C)-n6c(C)nnc65)C4)ccc3o2)C(C)(C)C)cc1] | 1056.7 | 1056.3 | C | 61.0 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 333 | 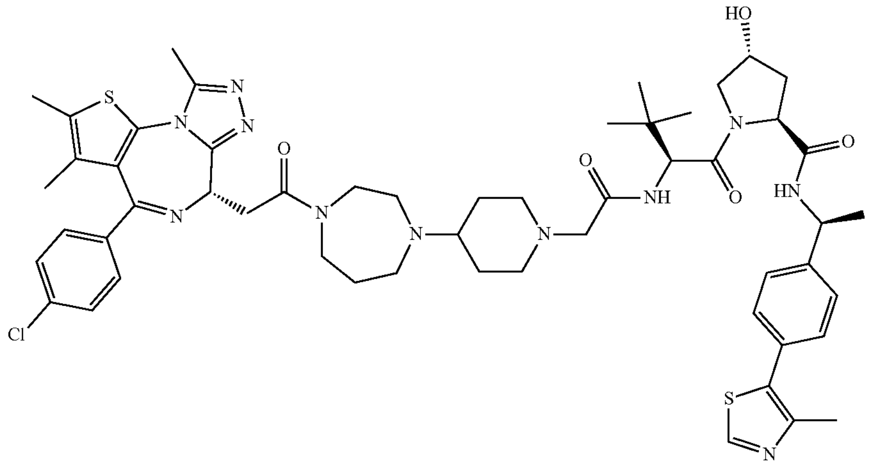 [SMILES: Cc1ncsc1-c1ccc([C@H](C)NC(=O)[C@@H]2C[C@@H](O)CN2C(=O)[C@@H](NC(=O)CN2CCC(N3CCCN(C(=O)C[C@@H]4N=C(c5ccc(Cl)cc5)c5c(sc(C)c5C)-n5c(C)nnc54)CC3)CC2)C(C)(C)C)cc1] | 1050.8 | 1050.5 | B | 88.0 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 334 | 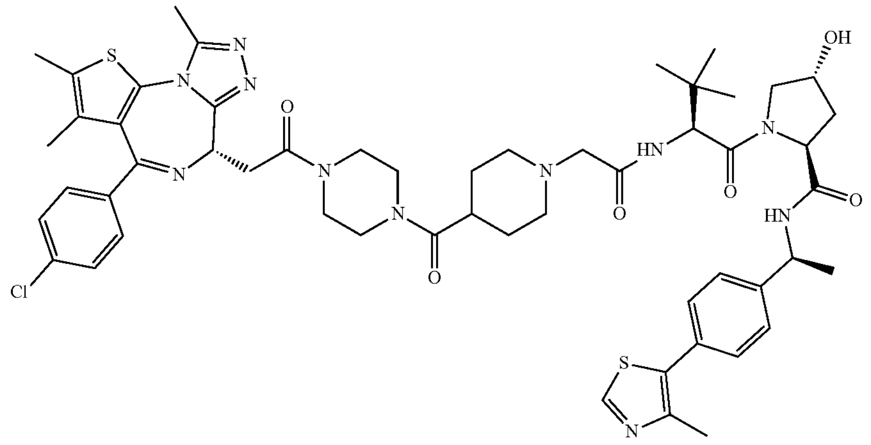 [SMILES: Cc1ncsc1-c1ccc([C@H](C)NC(=O)[C@@H]2C[C@@H](O)CN2C(=O)[C@@H](NC(=O)CN2CCC(C(=O)N3CCN(C(=O)C[C@@H]4N=C(c5ccc(Cl)cc5)c5c(sc(C)c5C)-n5c(C)nnc54)CC3)CC2)C(C)(C)C)cc1] | 1064.8 | 1064.6 | A | 97.0 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 335 | 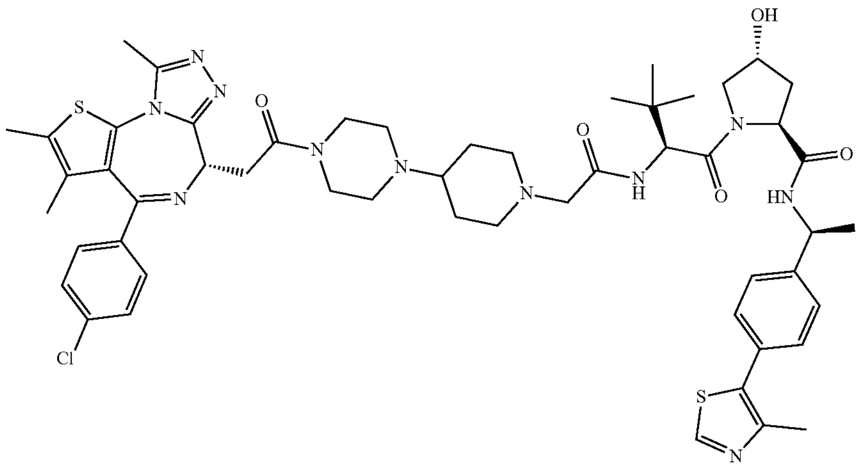 [SMILES: Cc1ncsc1-c1ccc([C@H](C)NC(=O)[C@@H]2C[C@@H](O)CN2C(=O)[C@@H](NC(=O)CN2CCC(N3CCN(C(=O)C[C@@H]4N=C(c5ccc(Cl)cc5)c5c(sc(C)c5C)-n5c(C)nnc54)CC3)CC2)C(C)(C)C)cc1] | 1036.8 | 1036.5 | A | 97.0 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 336 | 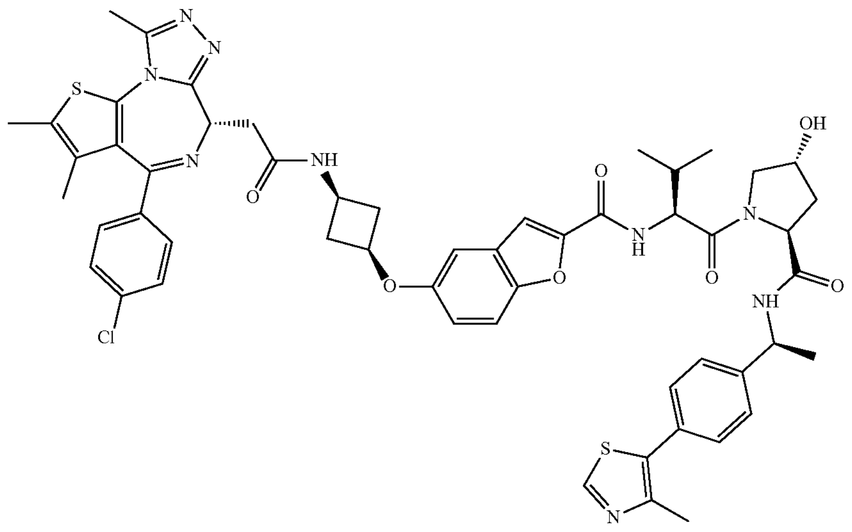 [SMILES: Cc1ncsc1-c1ccc([C@H](C)NC(=O)[C@@H]2C[C@@H](O)CN2C(=O)[C@@H](NC(=O)c2cc3cc(O[C@H]4C[C@@H](NC(=O)C[C@@H]5N=C(c6ccc(Cl)cc6)c6c(sc(C)c6C)-n6c(C)nnc65)C4)ccc3o2)C(C)C)cc1] | 1042.7 | 1042.4 | A | 98.0 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 337 | 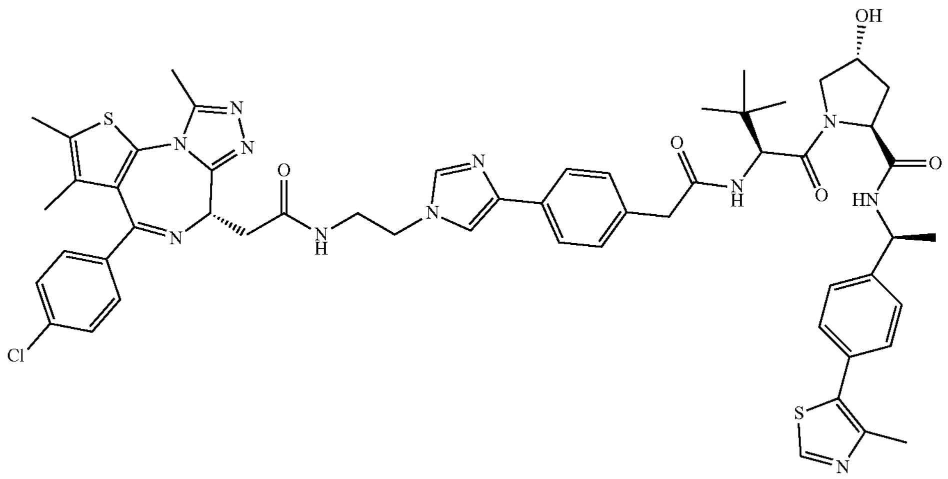 [SMILES: Cc1ncsc1-c1ccc([C@H](C)NC(=O)[C@@H]2C[C@@H](O)CN2C(=O)[C@@H](NC(=O)Cc2ccc(-c3cn(CCNC(=O)C[C@@H]4N=C(c5ccc(Cl)cc5)c5c(sc(C)c5C)-n5c(C)nnc54)cn3)cc2)C(C)(C)C)cc1] | 1054.7 | 1054.3 | A | 96.4 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 338 | 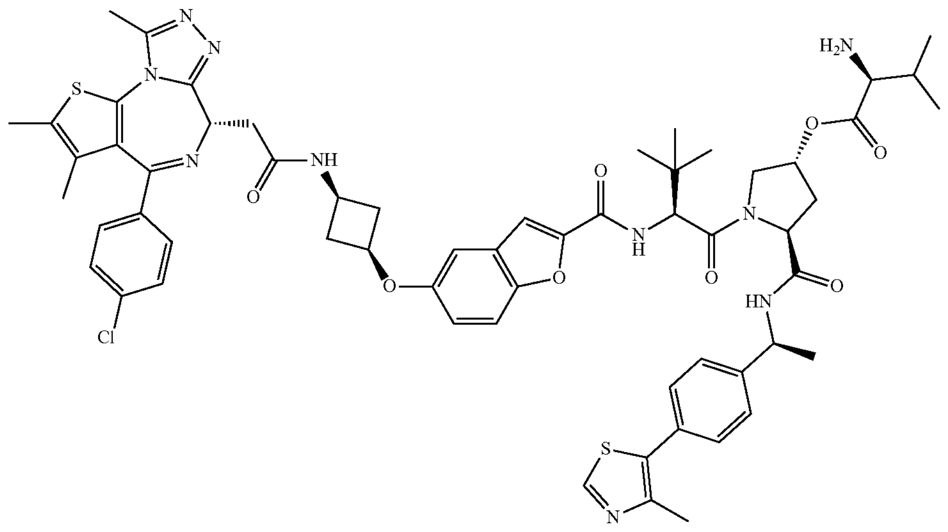 [SMILES: Cc1ncsc1-c1ccc([C@H](C)NC(=O)[C@@H]2C[C@@H](OC(=O)[C@@H](N)C(C)C)CN2C(=O)[C@@H](NC(=O)c2cc3cc(O[C@H]4C[C@@H](NC(=O)C[C@@H]5N=C(c6ccc(Cl)cc6)c6c(sc(C)c6C)-n6c(C)nnc65)C4)ccc3o2)C(C)(C)C)cc1] | 1155.8 | 1155.4 | A | 100 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 339 | 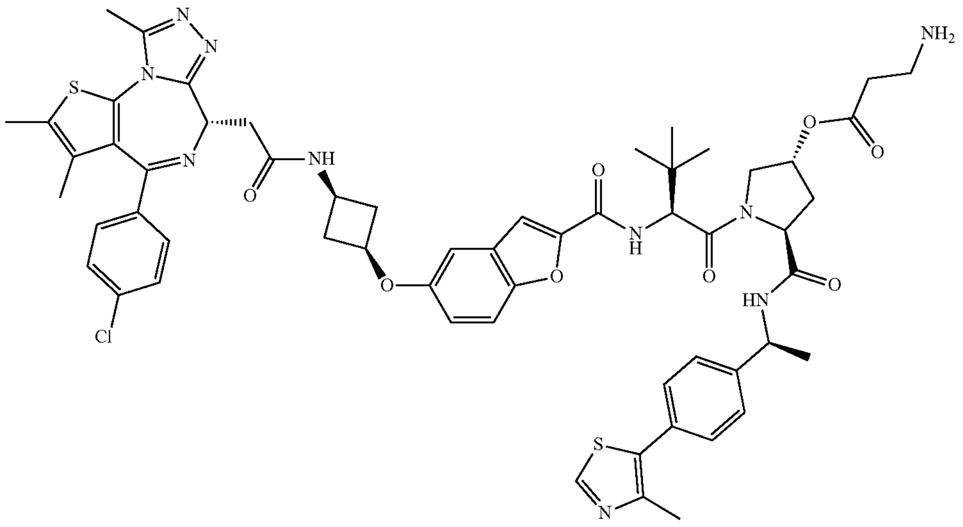 [SMILES: Cc1ncsc1-c1ccc([C@H](C)NC(=O)[C@@H]2C[C@@H](OC(=O)CCN)CN2C(=O)[C@@H](NC(=O)c2cc3cc(O[C@H]4C[C@@H](NC(=O)C[C@@H]5N=C(c6ccc(Cl)cc6)c6c(sc(C)c6C)-n6c(C)nnc65)C4)ccc3o2)C(C)(C)C)cc1] | 1127.8 | 1127.3 | A | 97.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 340 | 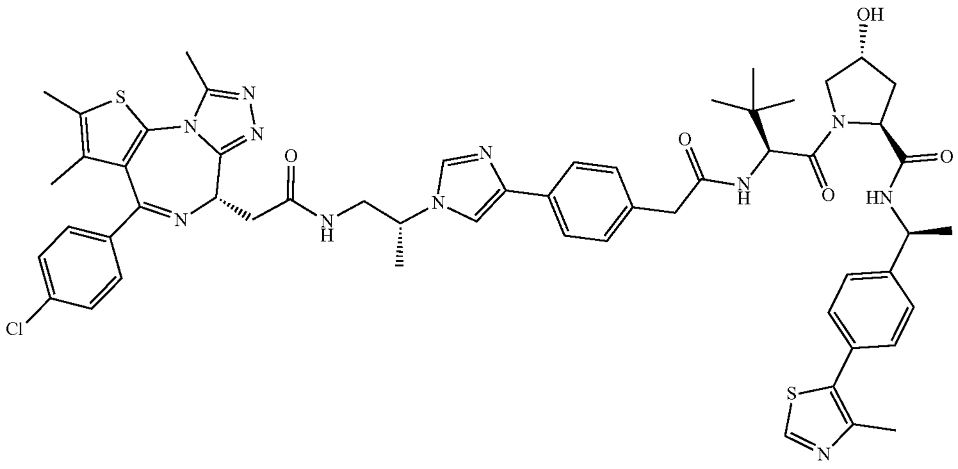 [SMILES: Cc1ncsc1-c1ccc([C@H](C)NC(=O)[C@@H]2C[C@@H](O)CN2C(=O)[C@@H](NC(=O)Cc2ccc(-c3cn([C@H](C)CNC(=O)C[C@@H]4N=C(c5ccc(Cl)cc5)c5c(sc(C)c5C)-n5c(C)nnc54)cn3)cc2)C(C)(C)C)cc1] | 1068.8 | 1068.4 | B | 92.2 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 341 | 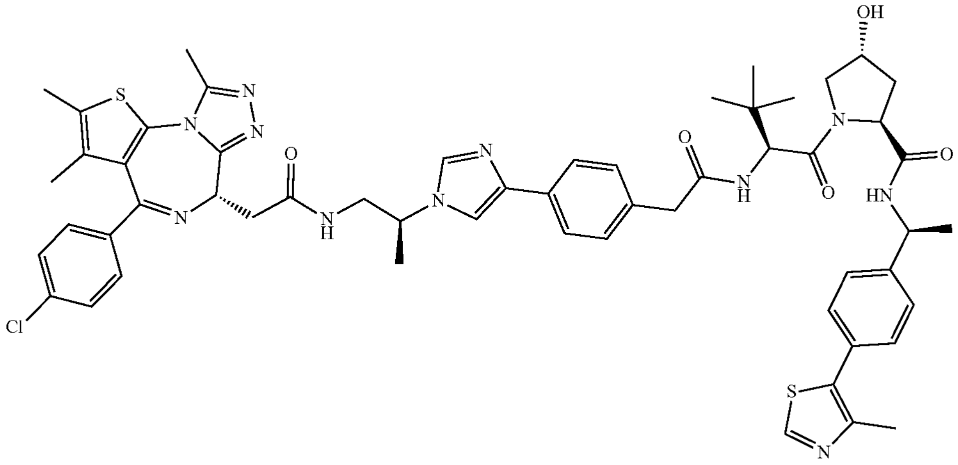 [SMILES: Cc1ncsc1-c1ccc([C@H](C)NC(=O)[C@@H]2C[C@@H](O)CN2C(=O)[C@@H](NC(=O)Cc2ccc(-c3cn([C@@H](C)CNC(=O)C[C@@H]4N=C(c5ccc(Cl)cc5)c5c(sc(C)c5C)-n5c(C)nnc54)cn3)cc2)C(C)(C)C)cc1] | 1068.8 | 1068.4 | A | 98.5 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 342 | 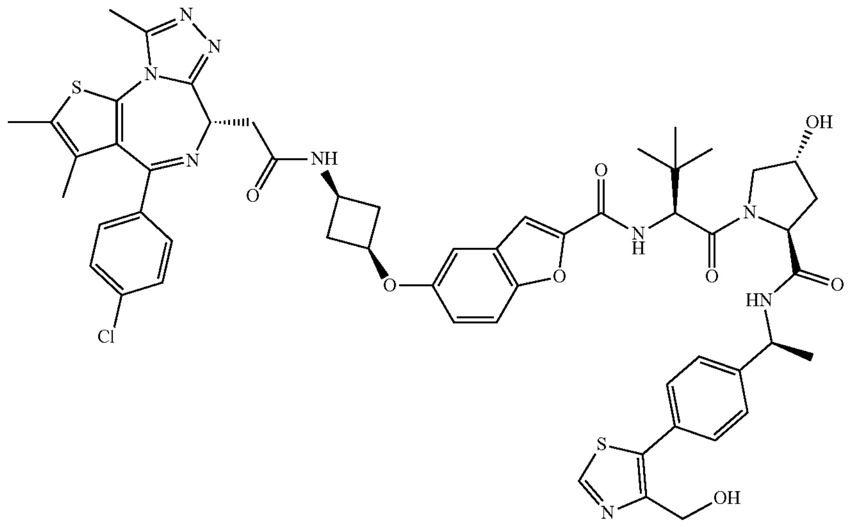 [SMILES: Cc1sc2c(c1C)C(c1ccc(Cl)cc1)=N[C@@H](CC(=O)N[C@H]1C[C@@H](Oc3ccc4oc(C(=O)N[C@H](C(=O)N5C[C@H](O)C[C@H]5C(=O)N[C@@H](C)c5ccc(-c6scnc6CO)cc5)C(C)(C)C)cc4c3)C1)c1nnc(C)n1-2] | 1072.7 | 1072.5 | A | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 343 | 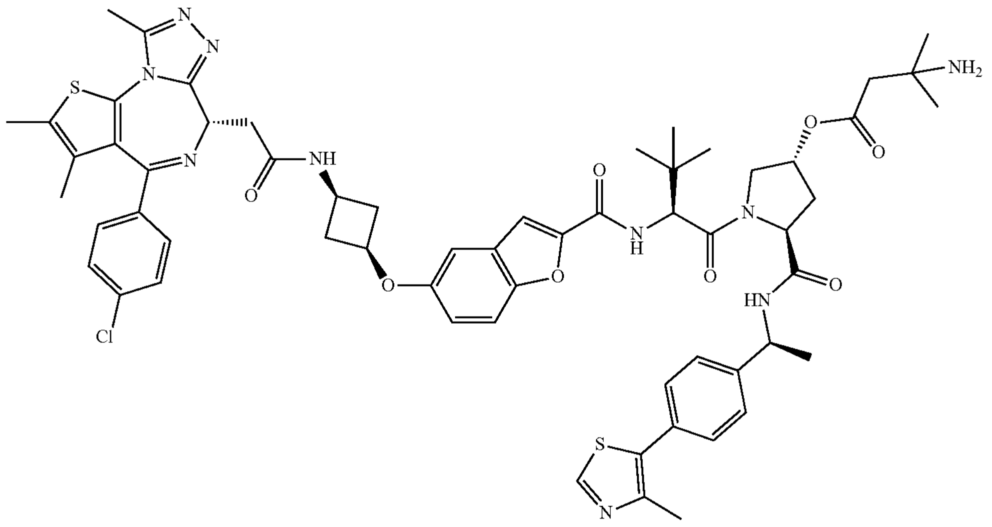 [SMILES: Cc1ncsc1-c1ccc([C@H](C)NC(=O)[C@@H]2C[C@@H](OC(=O)CC(C)(C)N)CN2C(=O)[C@@H](NC(=O)c2cc3cc(O[C@H]4C[C@@H](NC(=O)C[C@@H]5N=C(c6ccc(Cl)cc6)c6c(sc(C)c6C)-n6c(C)nnc65)C4)ccc3o2)C(C)(C)C)cc1] | 1155.8 | 1155.3 | B | 87.0 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 344 | 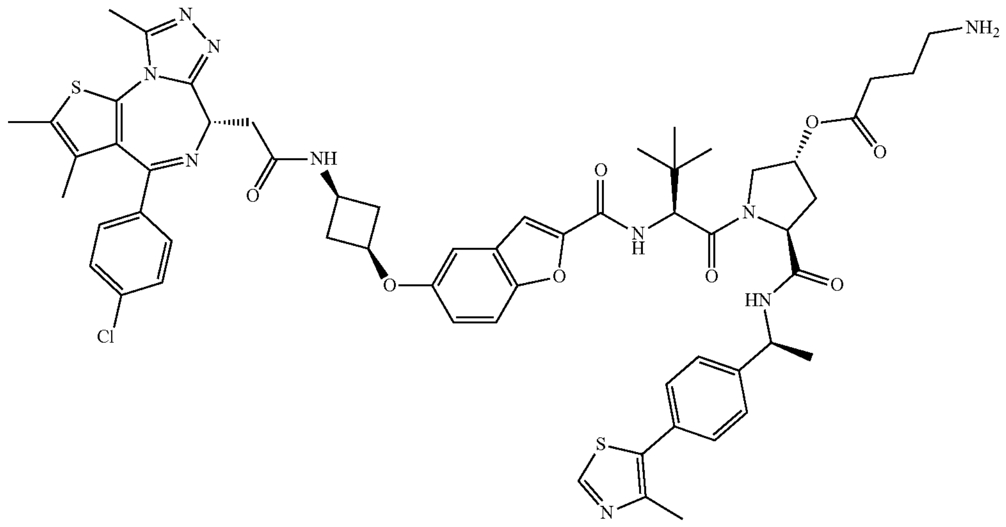 [SMILES: Cc1ncsc1-c1ccc([C@H](C)NC(=O)[C@@H]2C[C@@H](OC(=O)CCCN)CN2C(=O)[C@@H](NC(=O)c2cc3cc(O[C@H]4C[C@@H](NC(=O)C[C@@H]5N=C(c6ccc(Cl)cc6)c6c(sc(C)c6C)-n6c(C)nnc65)C4)ccc3o2)C(C)(C)C)cc1] | 1141.8 | 1141.3 | B | 95.9 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 345 | 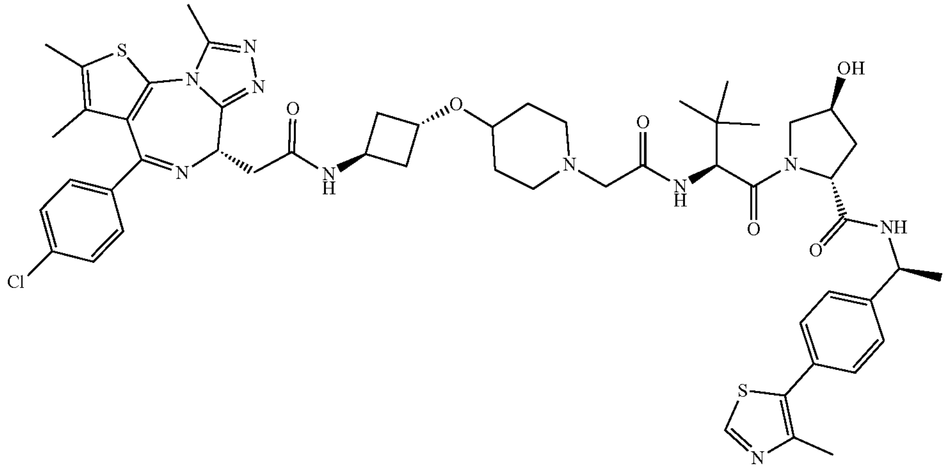 [SMILES: Cc1ncsc1-c1ccc([C@H](C)NC(=O)[C@H]2C[C@H](O)CN2C(=O)[C@@H](NC(=O)CN2CCC(O[C@H]3C[C@H](NC(=O)C[C@@H]4N=C(c5ccc(Cl)cc5)c5c(sc(C)c5C)-n5c(C)nnc54)C3)CC2)C(C)(C)C)cc1] | 1037.7 | 1037.6 | D | <5 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 346 | 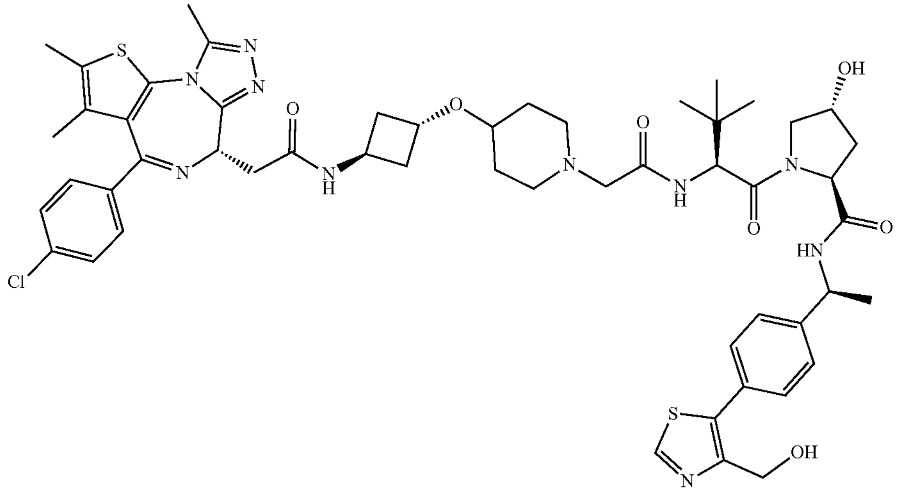 [SMILES: Cc1sc2c(c1C)C(c1ccc(Cl)cc1)=N[C@@H](CC(=O)N[C@H]1C[C@H](OC3CCN(CC(=O)N[C@H](C(=O)N4C[C@H](O)C[C@H]4C(=O)N[C@@H](C)c4ccc(-c5scnc5CO)cc4)C(C)(C)C)CC3)C1)c1nnc(C)n1-2] | 1053.7 | 1053.5 | B | 90 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 347 | 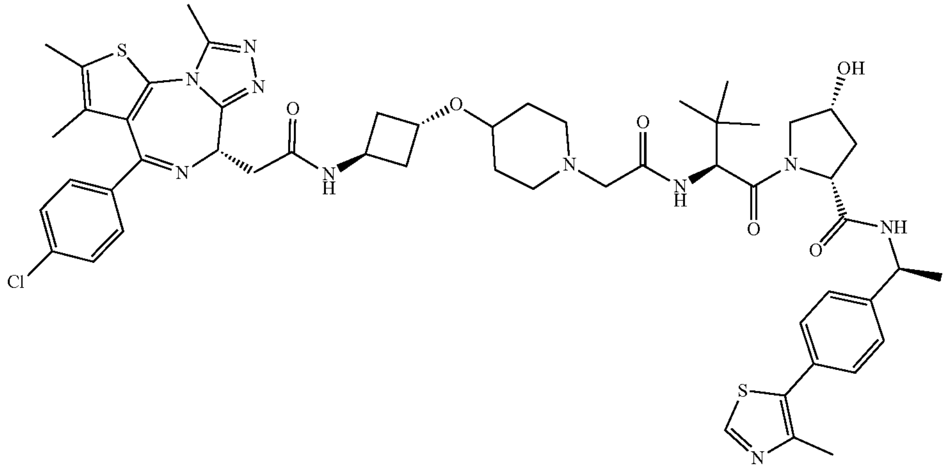 [SMILES: Cc1ncsc1-c1ccc([C@H](C)NC(=O)[C@H]2C[C@@H](O)CN2C(=O)[C@@H](NC(=O)CN2CCC(O[C@H]3C[C@H](NC(=O)C[C@@H]4N=C(c5ccc(Cl)cc5)c5c(sc(C)c5C)-n5c(C)nnc54)C3)CC2)C(C)(C)C)cc1] | 1037.7 | 1037.6 | D | <5 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 348 | 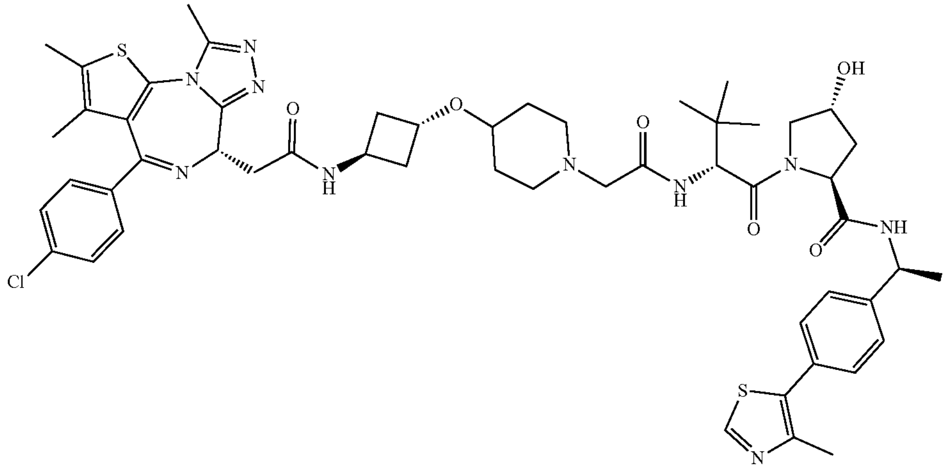 [SMILES: Cc1ncsc1-c1ccc([C@H](C)NC(=O)[C@@H]2C[C@@H](O)CN2C(=O)[C@H](NC(=O)CN2CCC(O[C@H]3C[C@H](NC(=O)C[C@@H]4N=C(c5ccc(Cl)cc5)c5c(sc(C)c5C)-n5c(C)nnc54)C3)CC2)C(C)(C)C)cc1] | 1037.7 | 1037.6 | D | 46 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 349 | 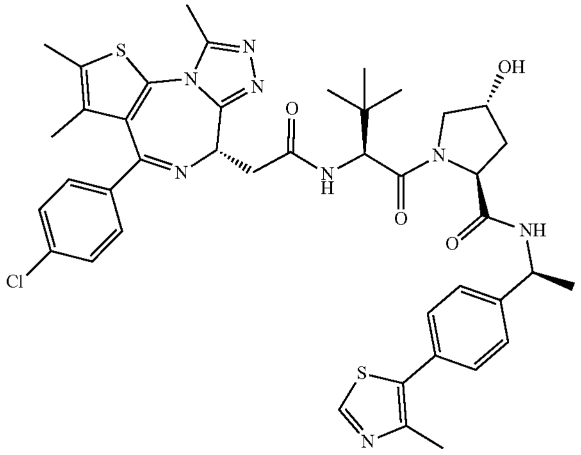 [SMILES: Cc1ncsc1-c1ccc([C@H](C)NC(=O)[C@@H]2C[C@@H](O)CN2C(=O)[C@@H](NC(=O)C[C@@H]2N=C(c3ccc(Cl)cc3)c3c(sc(C)c3C)-n3c(C)nnc32)C(C)(C)C)cc1] | 0827.5 | 0827.4 | D | 22 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 350 | 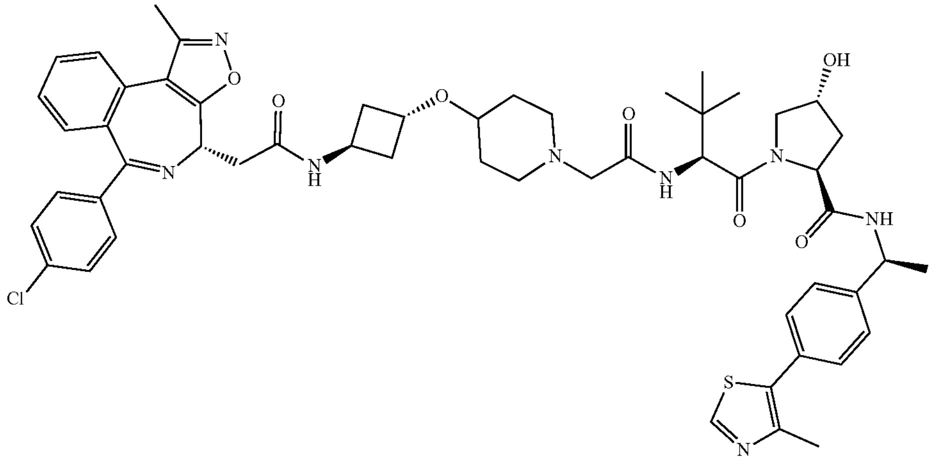 [SMILES: Cc1ncsc1-c1ccc([C@H](C)NC(=O)[C@@H]2C[C@@H](O)CN2C(=O)[C@@H](NC(=O)CN2CCC(O[C@H]3C[C@H](NC(=O)C[C@@H]4N=C(c5ccc(Cl)cc5)c5ccccc5-c5c(C)noc54)C3)CC2)C(C)(C)C)cc1] | 1003.7 | 1003.4 | A | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 351 | 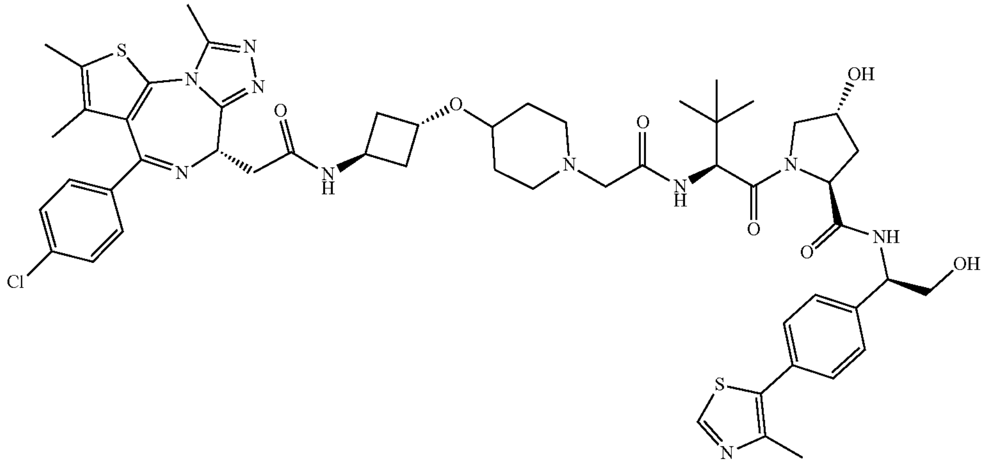 [SMILES: Cc1ncsc1-c1ccc([C@H](CO)NC(=O)[C@@H]2C[C@@H](O)CN2C(=O)[C@@H](NC(=O)CN2CCC(O[C@H]3C[C@H](NC(=O)C[C@@H]4N=C(c5ccc(Cl)cc5)c5c(sc(C)c5C)-n5c(C)nnc54)C3)CC2)C(C)(C)C)cc1] | 1053.7 | 1053.3 | A | 100 |

-continued
| Ex. # | Compound Structure | MW | Obsd [M + H]$^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 352 | 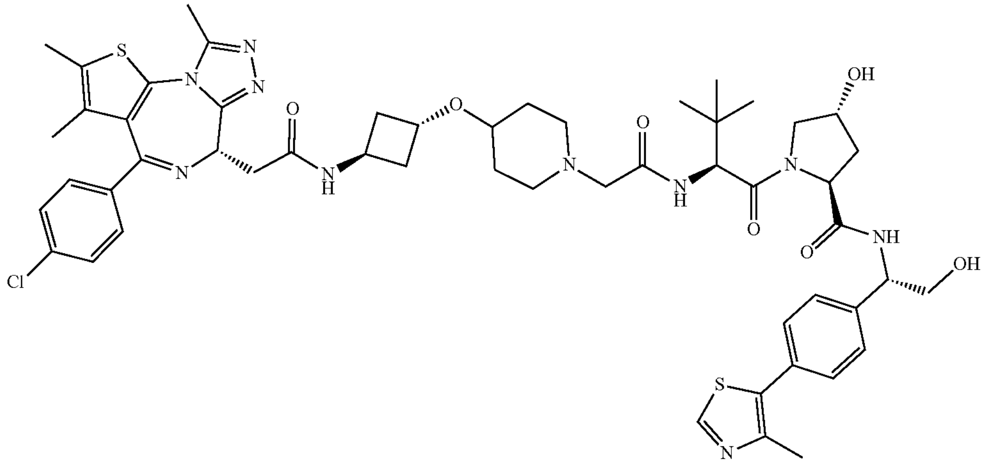 [SMILES: Cc1ncsc1-c1ccc([C@@H](CO)NC(=O)[C@@H]2C[C@@H](O)CN2C(=O)[C@@H](NC(=O)CN2CCC(O[C@H]3C[C@H](NC(=O)C[C@@H]4N=C(c5ccc(Cl)cc5)c5c(sc(C)c5C)-n5c(C)nnc54)C3)CC2)C(C)(C)C)cc1] | 1053.7 | 1053.3 | D | <20 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 353 | 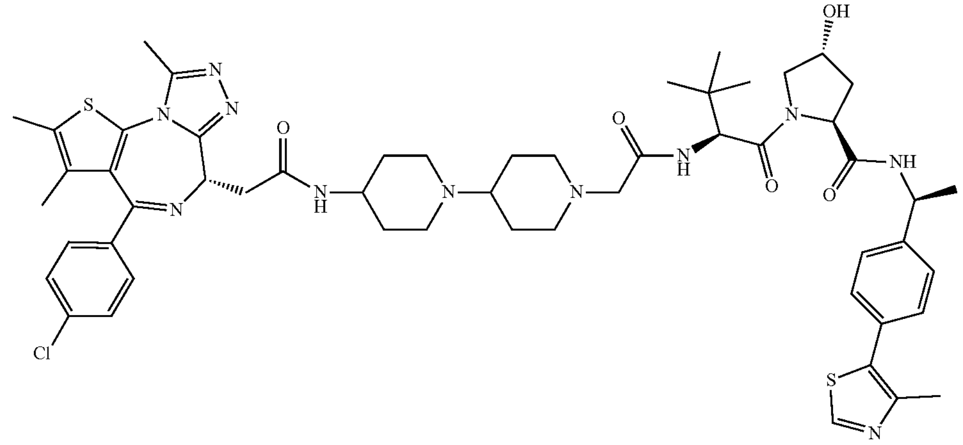 [SMILES: Cc1ncsc1-c1ccc([C@H](C)NC(=O)[C@@H]2C[C@@H](O)CN2C(=O)[C@@H](NC(=O)CN2CCC(N3CCC(NC(=O)C[C@@H]4N=C(c5ccc(Cl)cc5)c5c(sc(C)c5C)-n5c(C)nnc54)CC3)CC2)C(C)(C)C)cc1] | 1050.78 | 525.8* | C | >90 |
| 354 | 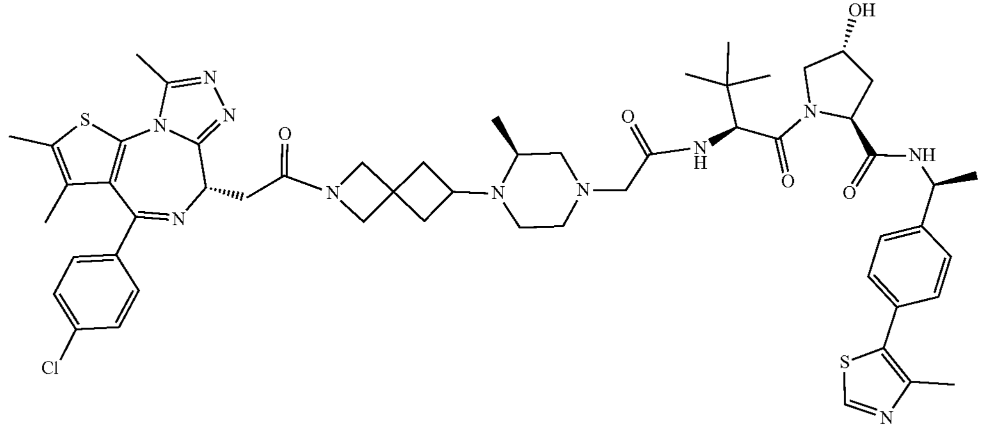 [SMILES: Cc1ncsc1-c1ccc([C@H](C)NC(=O)[C@@H]2C[C@@H](O)CN2C(=O)[C@@H](NC(=O)CN2CCN(C3CC4(C3)CN(C(=O)C[C@@H]3N=C(c5ccc(Cl)cc5)c5c(sc(C)c5C)-n5c(C)nnc53)C4)[C@@H](C)C2)C(C)(C)C)cc1] | 1062.79 | 531.8* | B | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 355 | 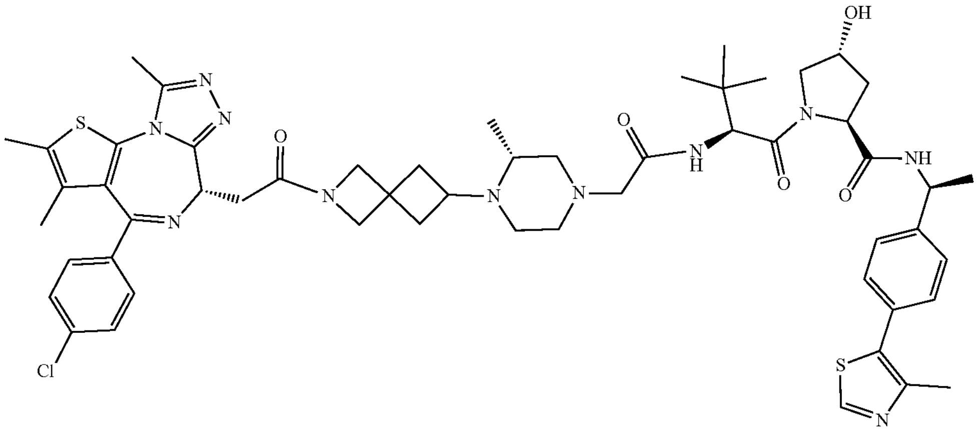 [SMILES: Cc1ncsc1-c1ccc([C@H](C)NC(=O)[C@@H]2C[C@@H](O)CN2C(=O)[C@@H](NC(=O)CN2CCN(C3CC4(C3)CN(C(=O)C[C@@H]3N=C(c5ccc(Cl)cc5)c5c(sc(C)c5C)-n5c(C)nnc53)C4)[C@H](C)C2)C(C)(C)C)cc1] | 1062.79 | 1086.3** | B | 100 |
| 356 | 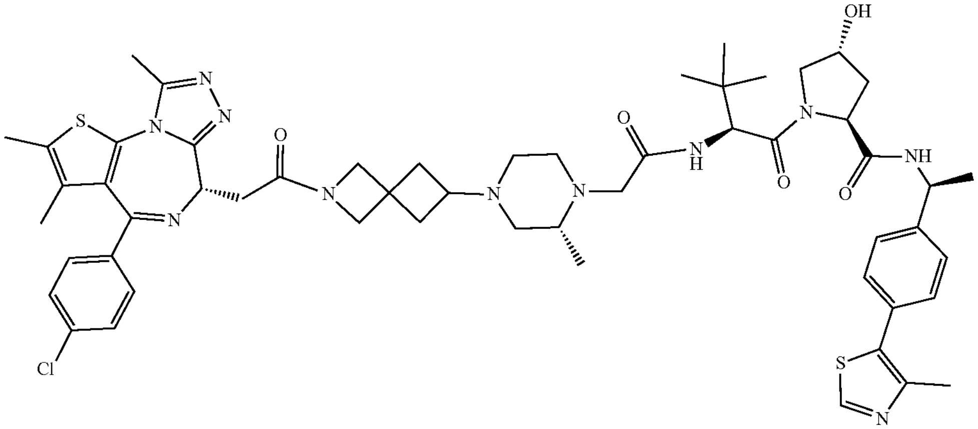 [SMILES: Cc1ncsc1-c1ccc([C@H](C)NC(=O)[C@@H]2C[C@@H](O)CN2C(=O)[C@@H](NC(=O)CN2CCN(C3CC4(C3)CN(C(=O)C[C@@H]3N=C(c5ccc(Cl)cc5)c5c(sc(C)c5C)-n5c(C)nnc53)C4)C[C@H]2C)C(C)(C)C)cc1] | 1062.79 | 532.5* | B | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 357 | 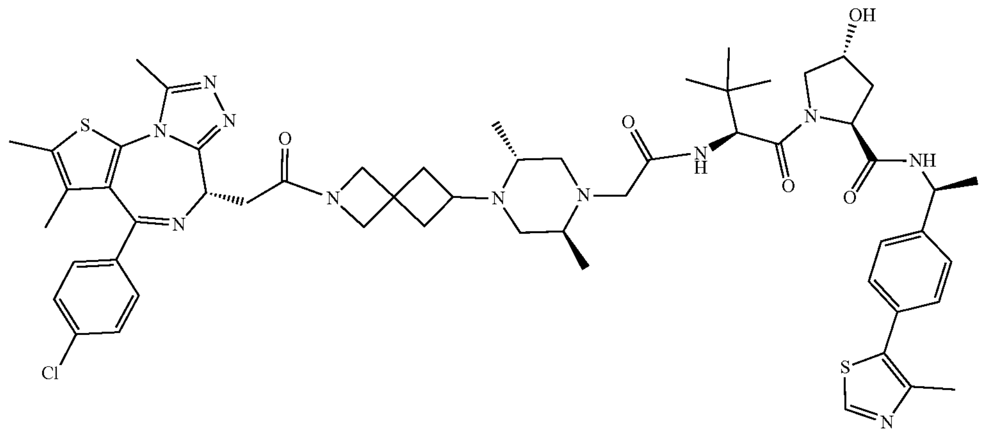 [SMILES: Cc1ncsc1-c1ccc([C@H](C)NC(=O)[C@@H]2C[C@@H](O)CN2C(=O)[C@@H](NC(=O)CN2C[C@@H](C)N(C3CC4(C3)CN(C(=O)C[C@@H]3N=C(c5ccc(Cl)cc5)c5c(sc(C)c5C)-n5c(C)nnc53)C4)C[C@@H]2C)C(C)(C)C)cc1] | 1076.82 | 538.8* | B | 100 |
| 358 | 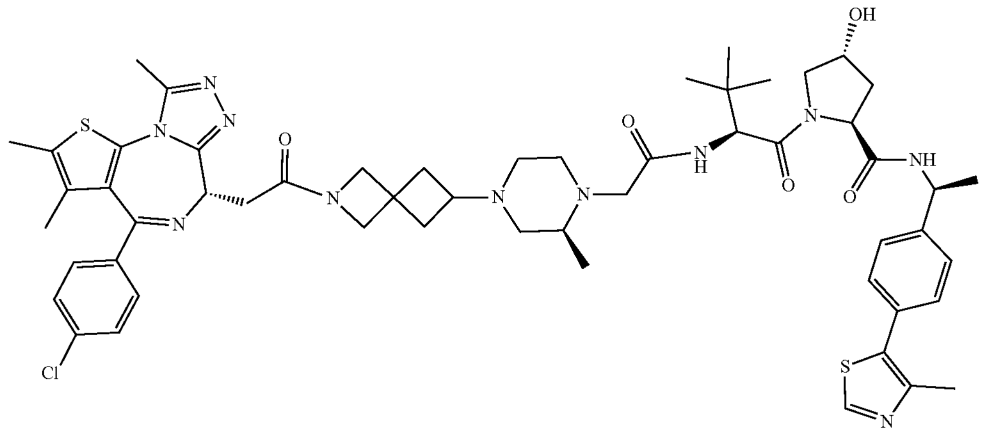 [SMILES: Cc1ncsc1-c1ccc([C@H](C)NC(=O)[C@@H]2C[C@@H](O)CN2C(=O)[C@@H](NC(=O)CN2CCN(C3CC4(C3)CN(C(=O)C[C@@H]3N=C(c5ccc(Cl)cc5)c5c(sc(C)c5C)-n5c(C)nnc53)C4)C[C@@H]2C)C(C)(C)C)cc1] | 1062.79 | 531.8* | B | >90 |

-continued
| Ex. # | Compound Structure | MW | Obsd $[M + H]^+$ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 359 | 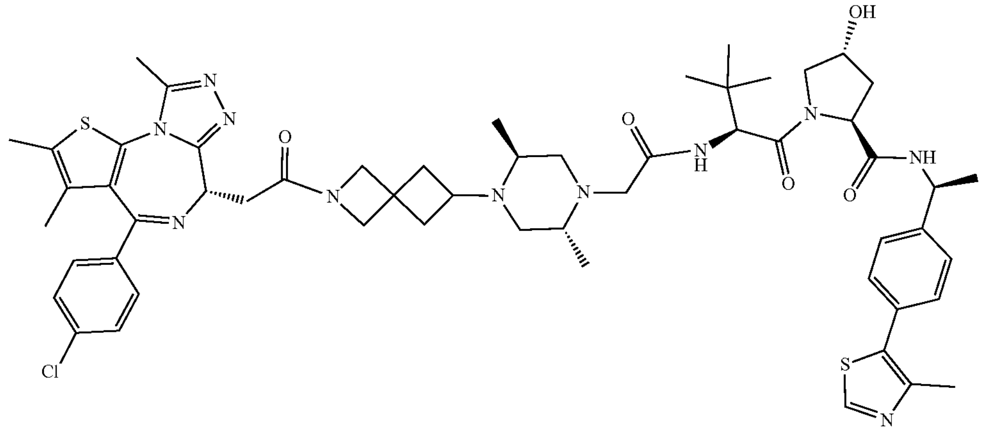 [SMILES: Cc1ncsc1-c1ccc([C@H](C)NC(=O)[C@@H]2C[C@@H](O)CN2C(=O)[C@@H](NC(=O)CN2C[C@H](C)N(C3CC4(C3)CN(C(=O)C[C@@H]3N=C(c5ccc(Cl)cc5)c5c(sc(C)c5C)-n5c(C)nnc53)C4)C[C@H]2C)C(C)(C)C)cc1] | 1076.82 | 538.9* | B | >90 |
| 360 | 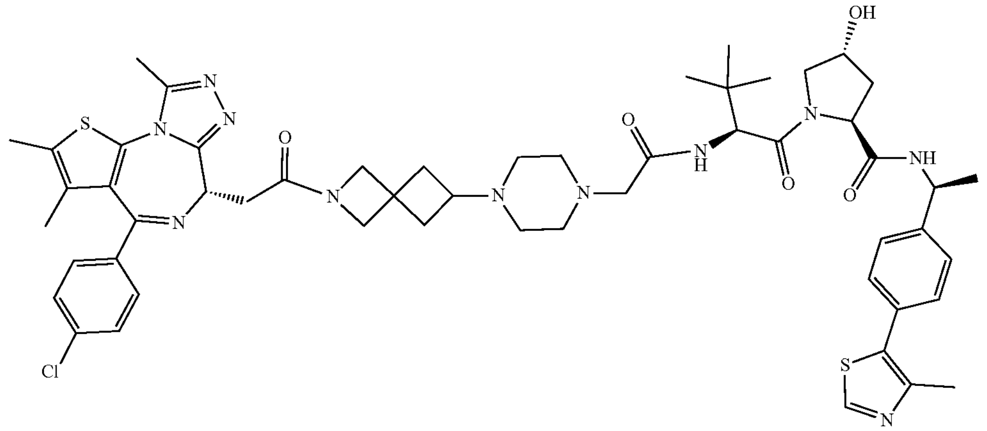 [SMILES: Cc1ncsc1-c1ccc([C@H](C)NC(=O)[C@@H]2C[C@@H](O)CN2C(=O)[C@@H](NC(=O)CN2CCN(C3CC4(C3)CN(C(=O)C[C@@H]3N=C(c5ccc(Cl)cc5)c5c(sc(C)c5C)-n5c(C)nnc53)C4)CC2)C(C)(C)C)cc1] | 1048.76 | 525.3* | C | >90 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
| --- | --- | --- | --- | --- | --- |
| 361 | 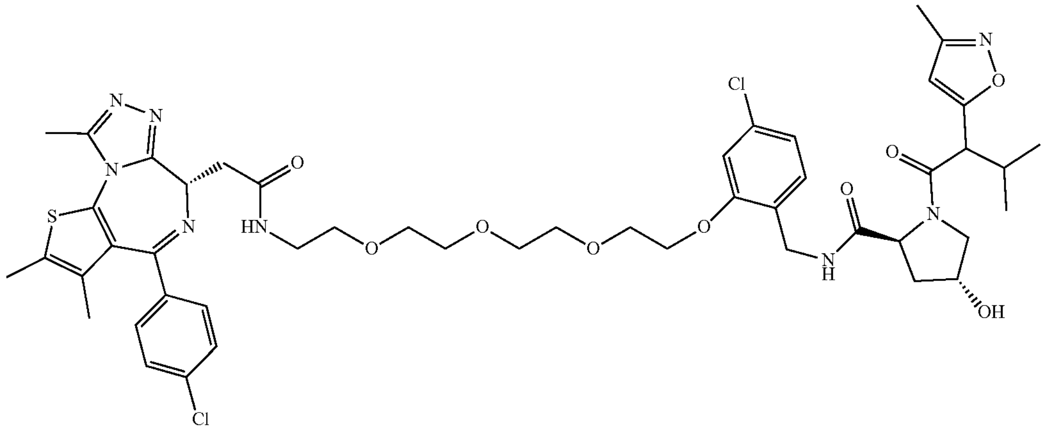 [SMILES: Cc1cc(C(C(=O)N2C[C@H](O)C[C@H]2C(=O)NCc2ccc(Cl)cc2OCCOCCOCCOCCNC(=O)C[C@@H]2N=C(c3ccc(Cl)cc3)c3c(sc(C)c3C)-n3c(C)nnc32)C(C)C)on1] | 994 | 0995.0 | B | 100 |
| 362 | 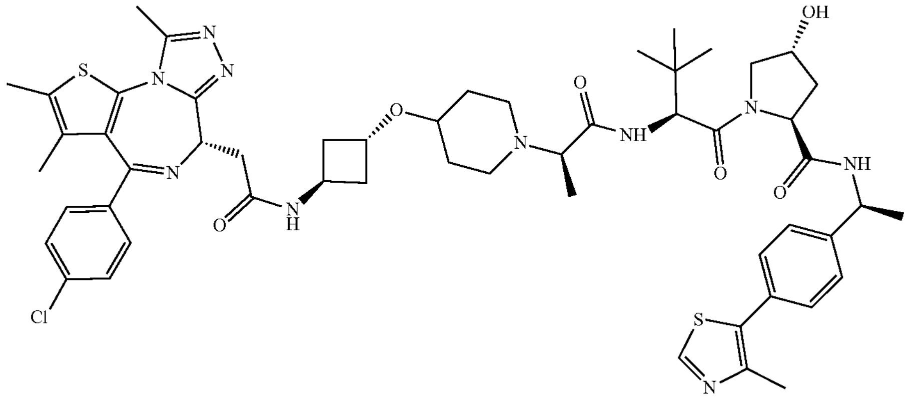 [SMILES: Cc1ncsc1-c1ccc([C@H](C)NC(=O)[C@@H]2C[C@@H](O)CN2C(=O)[C@@H](NC(=O)[C@@H](C)N2CCC(O[C@H]3C[C@H](NC(=O)C[C@@H]4N=C(c5ccc(Cl)cc5)c5c(sc(C)c5C)-n5c(C)nnc54)C3)CC2)C(C)(C)C)cc1] | 1051.76 | 1052.4 | | |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 363 | 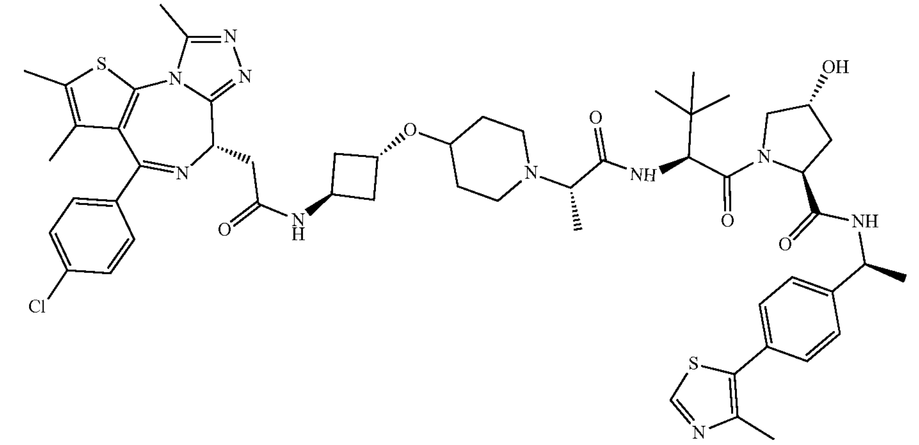 [SMILES: Cc1ncsc1-c1ccc([C@H](C)NC(=O)[C@@H]2C[C@@H](O)CN2C(=O)[C@@H](NC(=O)[C@H](C)N2CCC(O[C@H]3C[C@H](NC(=O)C[C@@H]4N=C(c5ccc(Cl)cc5)c5c(sc(C)c5C)-n5c(C)nnc54)C3)CC2)C(C)(C)C)cc1] | 1051.76 | 1052.4 | | |
| 364 | 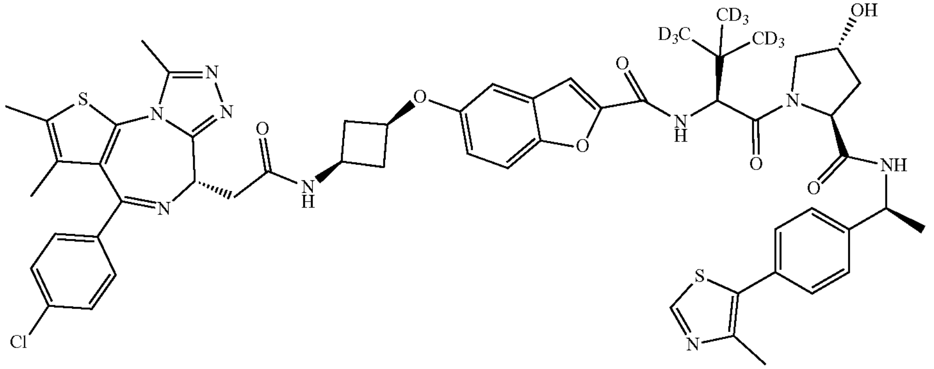 [SMILES: [2H]C([2H])([2H])C([C@H](NC(=O)c1cc2cc(O[C@H]3C[C@@H](NC(=O)C[C@@H]4N=C(c5ccc(Cl)cc5)c5c(sc(C)c5C)-n5c(C)nnc54)C3)ccc2o1)C(=O)N1C[C@H](O)C[C@H]1C(=O)N[C@@H](C)c1ccc(-c2scnc2C)cc1)(C([2H])([2H])[2H])C([2H])([2H])[2H]] | 1065.75 | 1065.4 | A | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 365 | 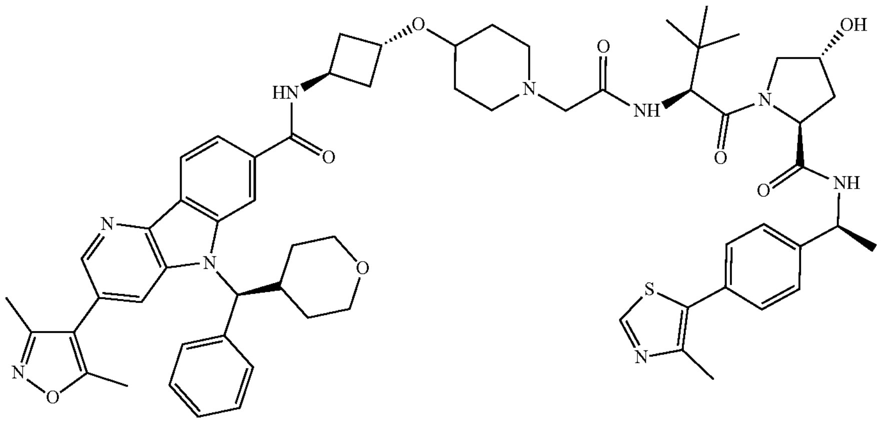 [SMILES: Cc1ncsc1-c1ccc([C@H](C)NC(=O)[C@@H]2C[C@@H](O)CN2C(=O)[C@@H](NC(=O)CN2CCC(O[C@H]3C[C@H](NC(=O)c4ccc5c6ncc(-c7c(C)noc7C)cc6n([C@H](c6ccccc6)C6CCOCC6)c5c4)C3)CC2)C(C)(C)C)cc1] | 1118.4 | 560.1* | A | 100 |
| 366 | 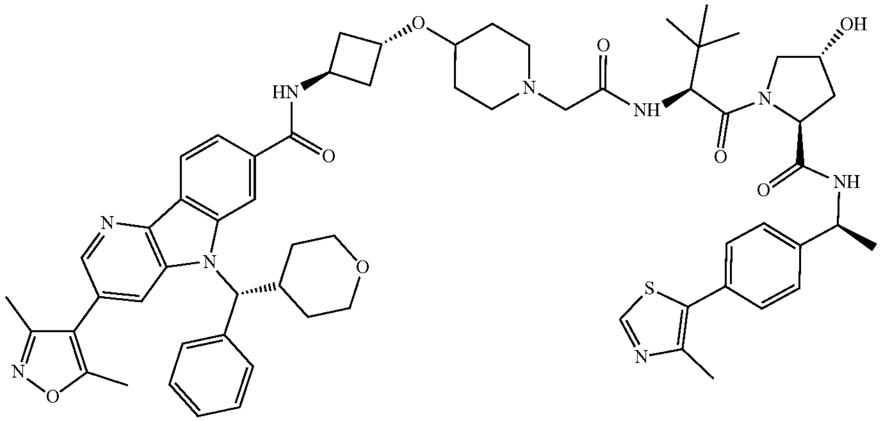 [SMILES: Cc1ncsc1-c1ccc([C@H](C)NC(=O)[C@@H]2C[C@@H](O)CN2C(=O)[C@@H](NC(=O)CN2CCC(O[C@H]3C[C@H](NC(=O)c4ccc5c6ncc(-c7c(C)noc7C)cc6n([C@@H](c6ccccc6)C6CCOCC6)c5c4)C3)CC2)C(C)(C)C)cc1] | 1118.4 | 560.1* | A | 100 |

-continued
| Ex. # | Compound Structure | MW | Obsd [M + H]+ from LC/MS [M/Z] | Degradation of BRD4: DC50 (uM) c-Myc ELISA in 22RV1 cells | Degradation of BRD4: Maximum inhibition (%) c-Myc ELISA in 22RV1 cells |
|---|---|---|---|---|---|
| 367 | 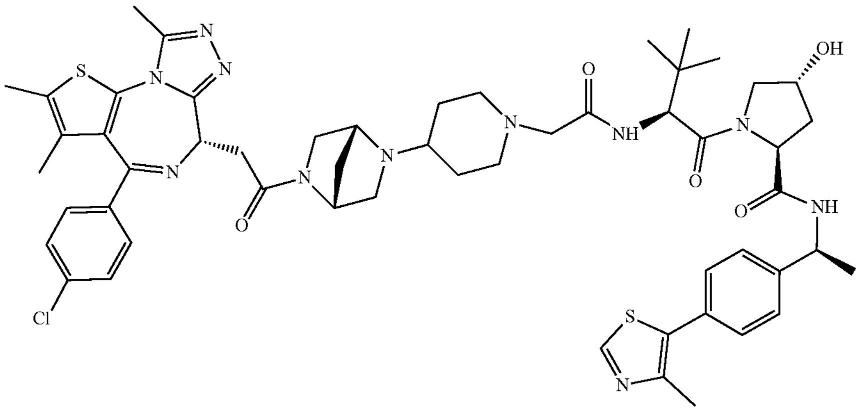 [SMILES: Cc1ncsc1-c1ccc([C@H](C)NC(=O)[C@@H]2C[C@@H](O)CN2C(=O)[C@@H](NC(=O)CN2CCC(N3C[C@H]4C[C@@H]3CN4C(=O)C[C@@H]3N=C(c4ccc(Cl)cc4)c4c(sc(C)c4C)-n4c(C)nnc43)CC2)C(C)(C)C)cc1] | 1048.8 | 1049.4 | | |
| 368 | 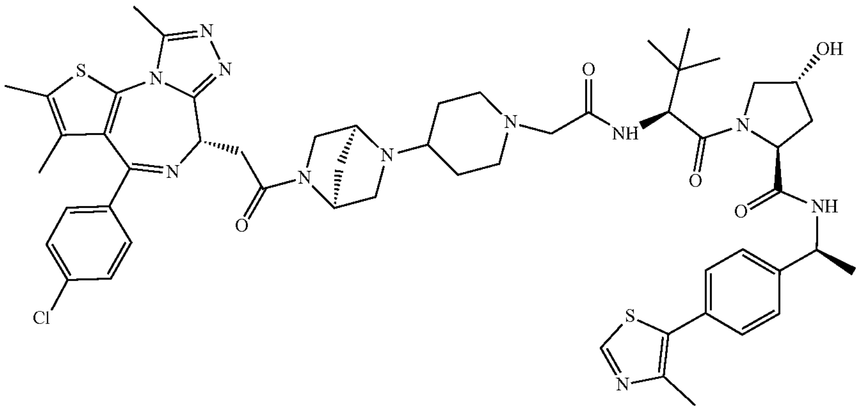 [SMILES: Cc1ncsc1-c1ccc([C@H](C)NC(=O)[C@@H]2C[C@@H](O)CN2C(=O)[C@@H](NC(=O)CN2CCC(N3C[C@@H]4C[C@H]3CN4C(=O)C[C@@H]3N=C(c4ccc(Cl)cc4)c4c(sc(C)c4C)-n4c(C)nnc43)CC2)C(C)(C)C)cc1] | 1048.8 | 1049.4 | B | 100 |
*[M + 2H]/2 as E/Z from LC/MS;
**[M + Na] as E/Z from LC/MS

The invention claimed is:

1. A bifunctional compound according to the structure, PTM-L -UTM, or a pharmaceutically acceptable salt, enantiomer or stereoisomer thereof, wherein:

a) the UTM has a structure according to:

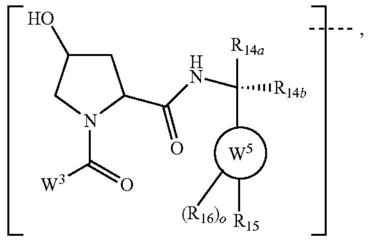

wherein:

$W^3$ is selected from the group of an optionally substituted aryl, optionally substituted heteroaryl, or

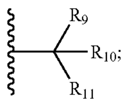

$R_9$ and $R_{10}$ are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ is selected from the group of an optionally substituted heterocyclic, optionally substituted alkoxy, optionally substituted heteroaryl, optionally substituted aryl,

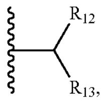

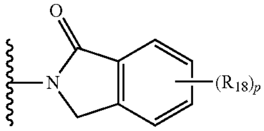

or

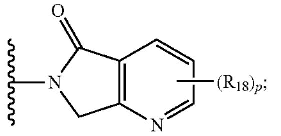

$R_{12}$ is selected from the group of H or optionally substituted alkyl;

$R_{13}$ is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$, are each independently selected from the group of H, haloalkyl, optionally substituted alkyl, methyl, fluoromethyl, hydroxymethyl, ethyl, isopropyl, or cyclopropyl;

$W^5$ is selected from the group of an optionally substituted phenyl or an optionally substituted 5-10 membered heteroaryl, $R_{15}$ is selected from the group of H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; optionally substituted aryl, optionally substituted heteroaryl, optionally substituted cycloalkyl, or optionally substituted heterocycle;

$R_{16}$ is independently selected from the group of halo, optionally substituted alkyl, optionally substituted haloalkyl, hydroxy, or optionally substituted haloalkoxy;

o is 0, 1, 2, 3, or 4;

$R_{18}$ is independently selected from the group of halo, optionally substituted alkoxy, cyano, optionally substituted alkyl, haloalkyl, haloalkoxy or an attachment of L; and p is 0, 1, 2, 3, or 4, b) the PTM has a structure according to:

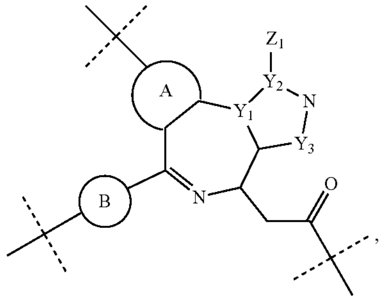

wherein:

$Y_1$ is selected from the group of carbon, or nitrogen;

$Y_2$ and $Y_3$ are independently selected from the group of carbon, nitrogen or oxygen and together with the atoms to form an aromatic fused ring;

A and B are independently selected from the group of a 5-membered aromatic ring, a 6-membered aromatic ring, a heteroaromatic ring, a carbocyclic, each optionally substituted with alkyl, alkoxy, halogen, an aromatic and a heteroaromatic ring; wherein ring A is fused to the central azepine (Y1=C) or diazepine (Y1=N) moiety; and Z1 is selected from the group of methyl or an alkyl group; and wherein the dashed line indicates the site of attachment of a UTM or L coupling the PTM to the UTM;

c) L is a chemical linking moiety connecting UTM and PTM, wherein L has a structure represented by the formula: $-(A^L)_q-$, wherein:

q is an integer greater than or equal to 1, each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}{=}CR^{L2}$, $SiR^{L1}R^{L2}$, $P(O)R^{L1}$, $P(O)OR^{L1}$, $NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 1-6 $R^{L1}$ and/or $R^{L2}$ groups, $C_{3-11}$heterocyclyl optionally substituted with 1-6 $R^{L1}$ and/or $R^{L2}$ groups, aryl optionally substituted with 1-6 $R^{L1}$ and/or $R^{L2}$ groups, heteroaryl optionally substituted with 1-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 1-4 $R^{L5}$ groups;

$R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, $CC—C_{1-8}$alkyl, CCH, $CH{=}CH(C_{1-8}alkyl)$, $C(C_{1-8}alkyl){=}CH(C_{1-8}alkyl)$, $C(C_{1-8}alkyl){=}C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-8}alkyl)_2$, NH $SO_2NH_2$, wherein:

(1) the L includes at least one of S, SO, $SO_2$, $SO_2NR^{L3}$, $SONR^{L3}$, $NR^{L3}CONR^{L4}$, $NR^{L3}SO_2NR^{L4}$, CO, $CR^{L1}{=}CR^{L2}$, C≡C, $SiR^{L1}R^{L2}$, $P(O)R^{L1}$, $P(O)OR^{L1}$, $NR^{L3}C({=}NCN)NR^{L4}$, $NR^{L3}C({=}NCN)$, $NR^{L3}C({=}CNO_2)NR^{L4}$, $C_{3-11}$cycloalkyl optionally substituted with 1-6 $R^{L1}$ and/or $R^{L2}$ groups, $C_{3-11}$heterocyclyl optionally substituted with 1-6 $R^{L1}$ and/or $R^{L2}$ groups, aryl optionally substituted with 1-6 $R^{L1}$ and/or $R^{L2}$ groups, and heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 1-4 $R^{L5}$ groups, or (2) the linker has 6-10 optionally substituted ethylene glycol units wherein each O is optionally replaced with an optionally substituted N, S, P, or Si atom.

2. The compound of claim 1, wherein the UTM has a chemical structure selected from the group of:

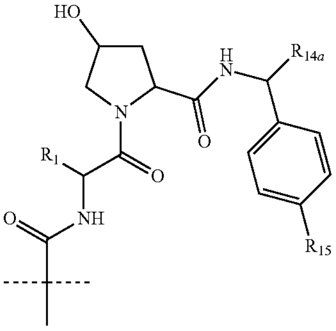

;

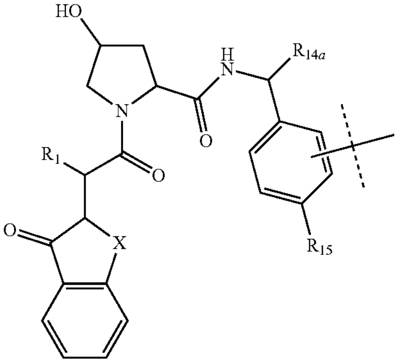

;

-continued

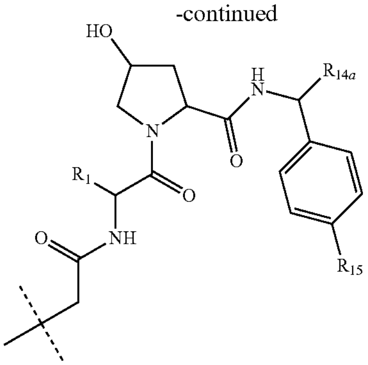

and

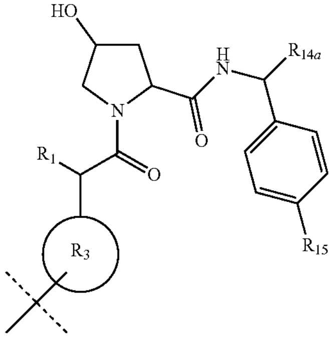

, wherein:

$R_1$ is H, cyclopropyl, cyclobutyl, cyclopentyl, or cyclohexyl; optionally substituted alkyl, optionally substituted hydroxyalkyl, or optionally substituted heteroaryl;

$R_{14a}$ is H, optionally substituted alkyl, or cyclopropyl;

$R_{15}$ is selected from the group consisting of H, halogen, CN, OH, $NO_2$, optionally substituted heteroaryl, optionally substituted aryl; optionally substituted alkyl, optionally substituted haloalkyl, optionally substituted haloalkoxy, cycloalkyl, or cycloheteroalkyl;

X is C or C═O $R_3$ is an optionally substituted 5 or 6 membered heteroaryl;

wherein the dashed line indicates the site of attachment of L coupling the PTM to the UTM.

3. The compound according to claim 2, wherein UTM is a group according to the chemical structure:

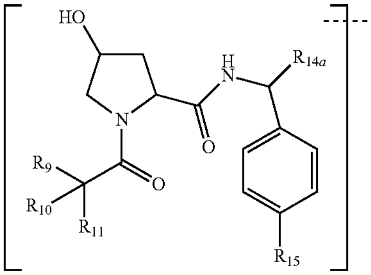

, wherein:

R14a is H, haloalkyl, optionally substituted alkyl, or cyclopropyl;

R9 is H;

R10 is H, ethyl, isopropyl, tert-butyl, sec-butyl, cyclopropyl, cyclobutyl, cyclopentyl, or cyclohexyl;

R11 is

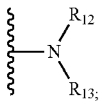

optionally substituted heteroaryl,

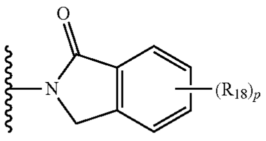 or 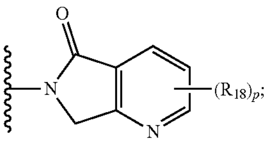

p is 0, 1, 2, 3, or 4; and each $R_{18}$ is independently halo, optionally substituted alkoxy, cyano, optionally substituted alkyl, or a linker;

R12 is H, C═O

R13 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl, $R_{15}$ is selected from the group consisting of H, halogen, Cl, CN, OH, $NO_2$, optionally substituted heteroaryl, optionally substituted aryl;

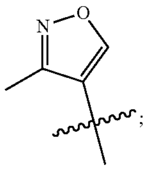; 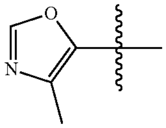; 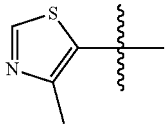;

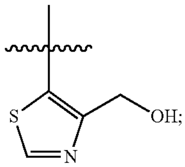 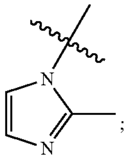;

and wherein the dashed line indicates the site of attachment of at least one PTM, another UTM (UTM') or L coupling at least one PTM or a UTM' or both to UTM-a.

4. The compound according to claim 2, wherein UTM is a group selected from the group consisting of:

UTM-a1

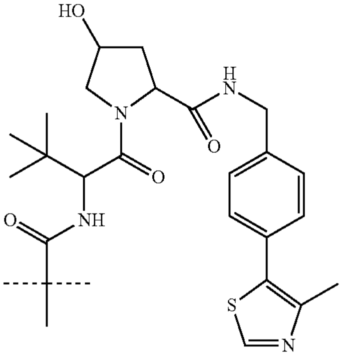

-continued

UTM-a2

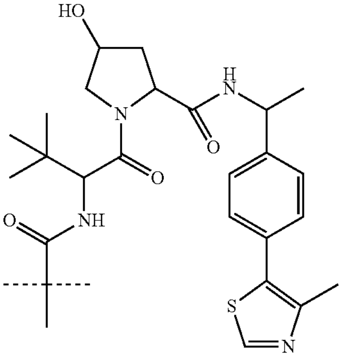

UTM-a3

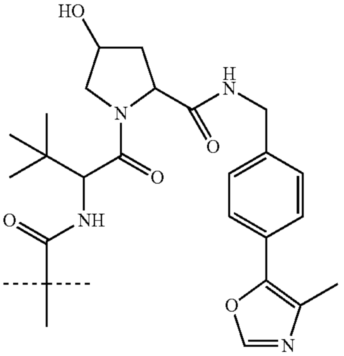

UTM-a4

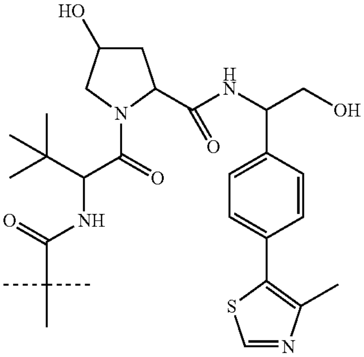

UTM-a5

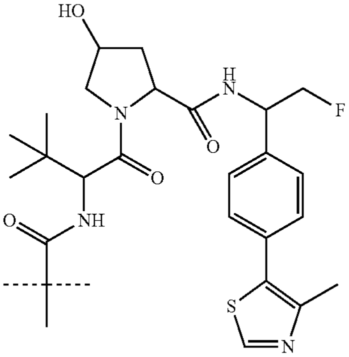

-continued
UTM-a6
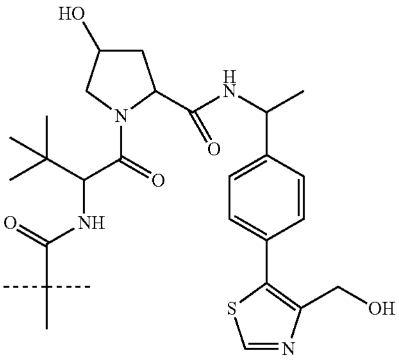
UTM-a7
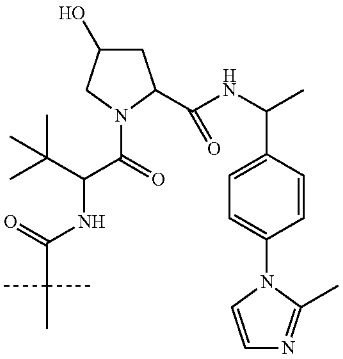
UTM-a8
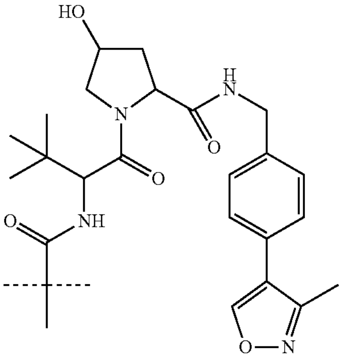
UTM-a9
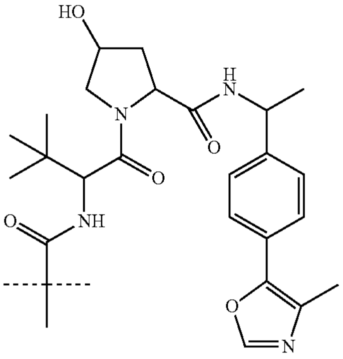
-continued
UTM-a10
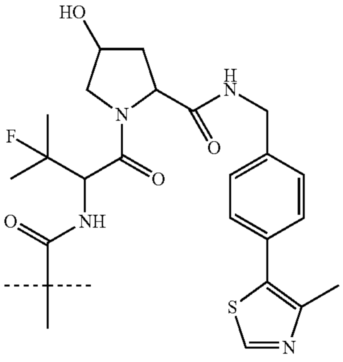
UTM-a11
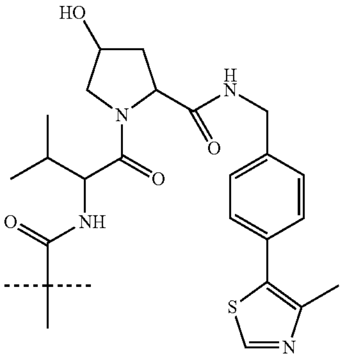
UTM-a12
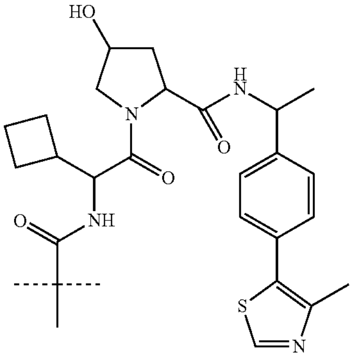
UTM-a13
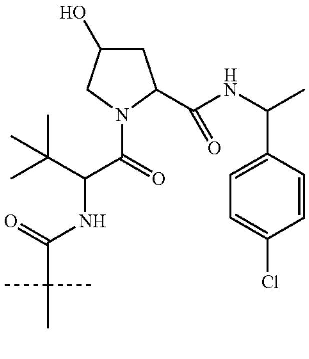

-continued
UTM-a14
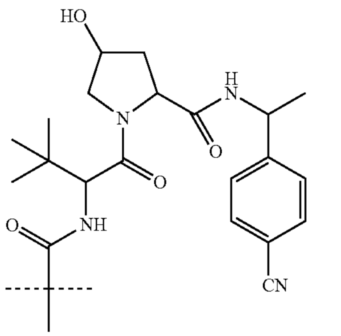
UTM-a15
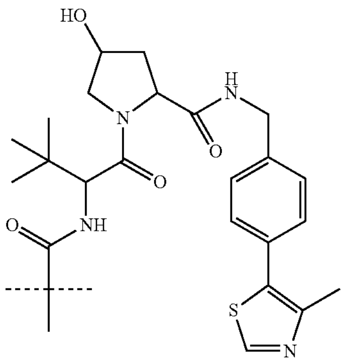
UTM-b1
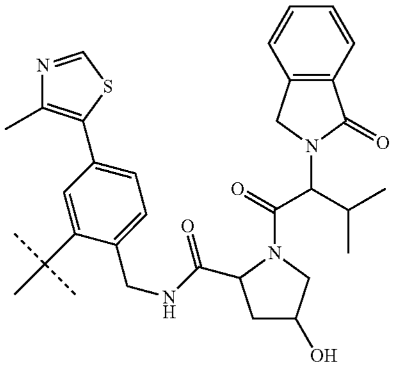
UTM-b2
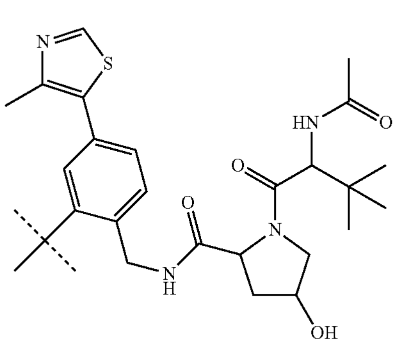
-continued
UTM-b3
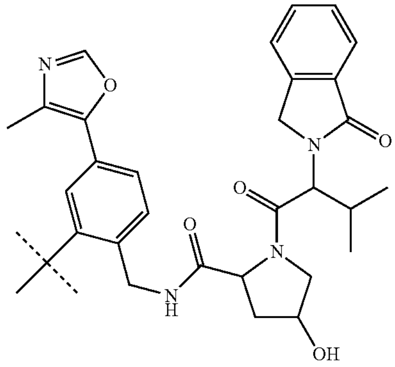
UTM-b4
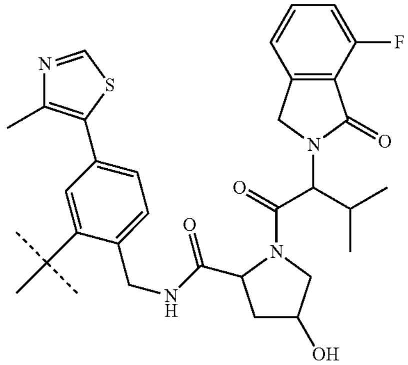
UTM-b5
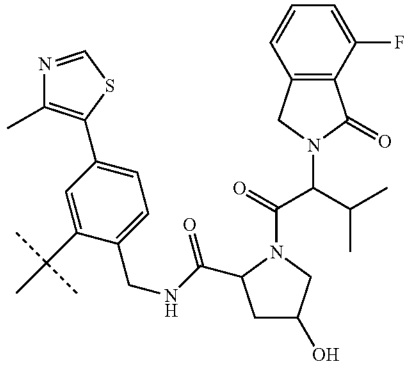
UTM-b6
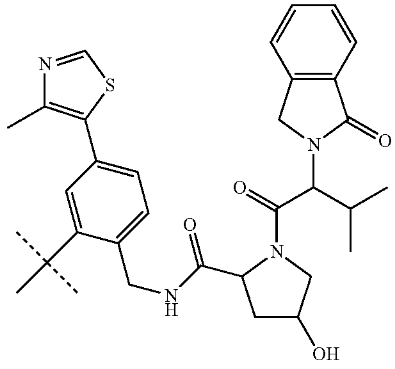

-continued
UTM-b7
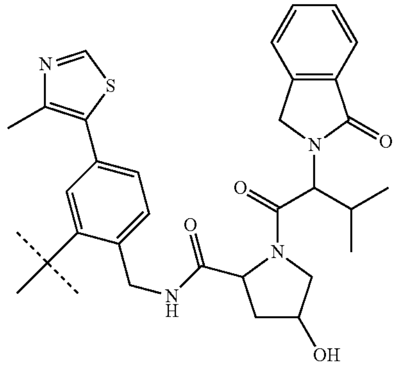
UTM-b8
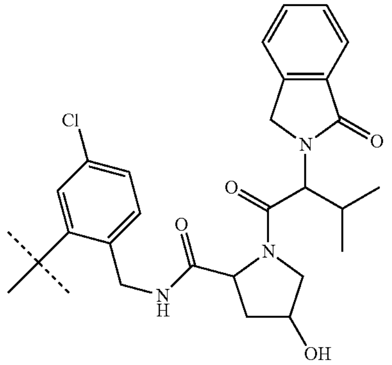
UTM-b9
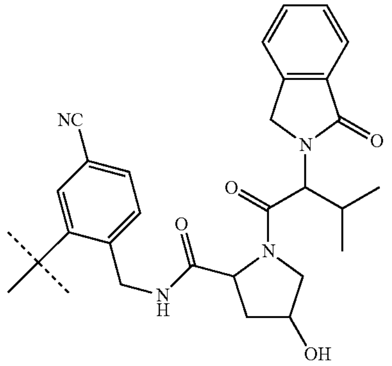
UTM-b10
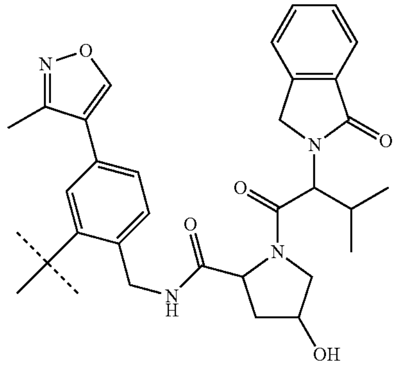
-continued
UTM-b11
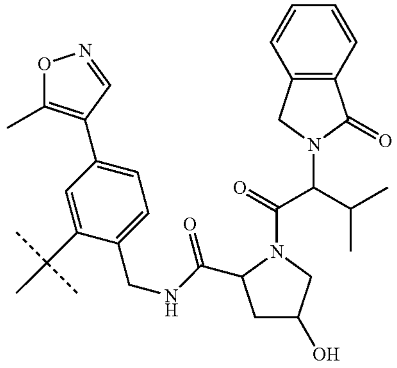
UTM-b12
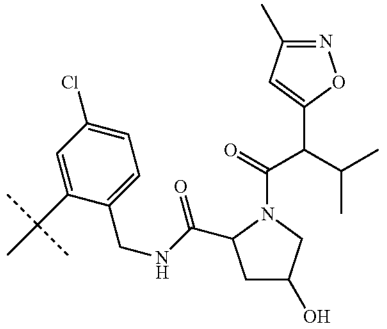
UTM-c1
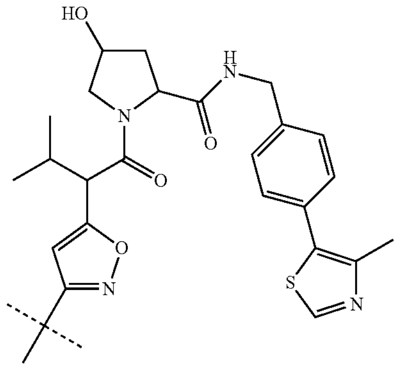
UTM-c2
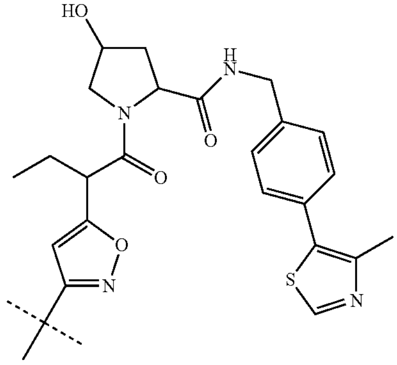

-continued
UTM-c3
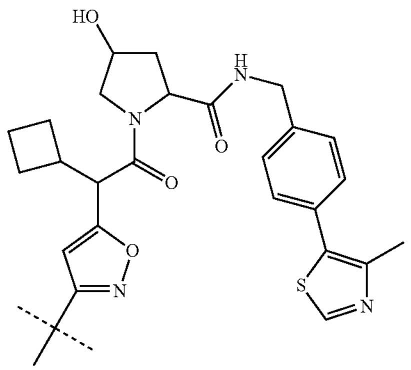
UTM-c4
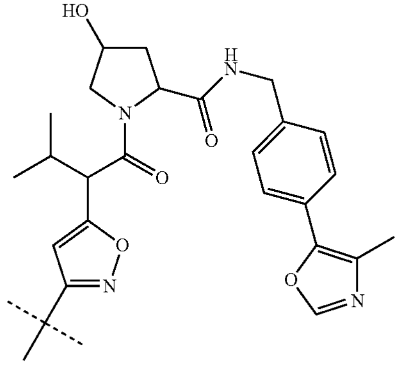
UTM-c5
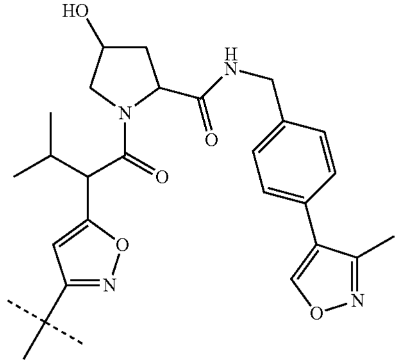
UTM-c6
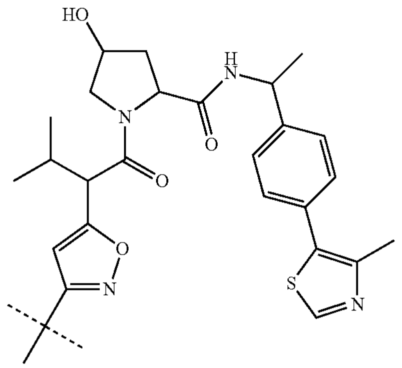
-continued
UTM-c7
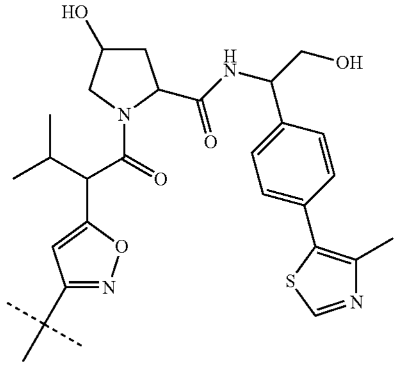
UTM-c8
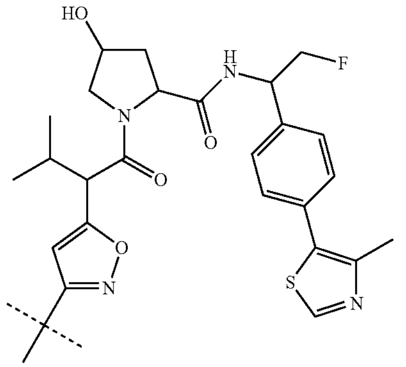
UTM-c9
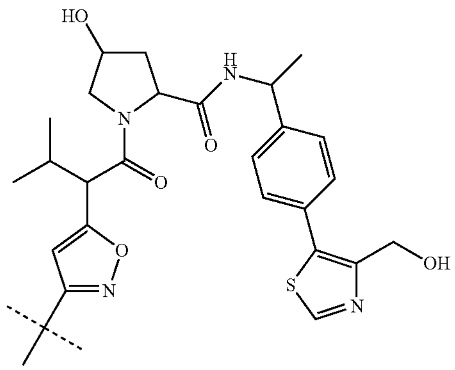
UTM-c10
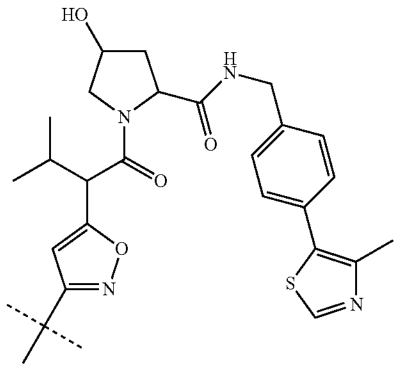

-continued
UTM-c11
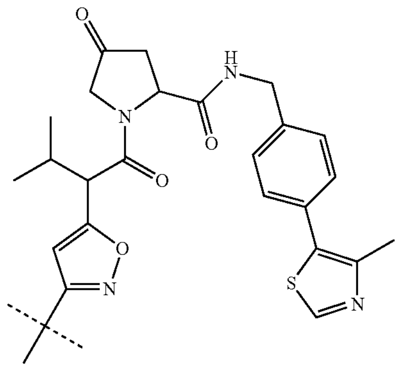
UTM-c12
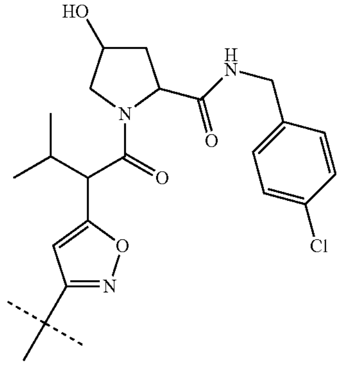
UTM-c13
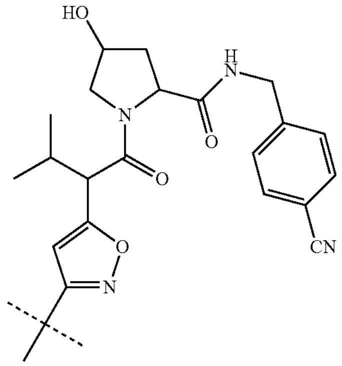
UTM-c14
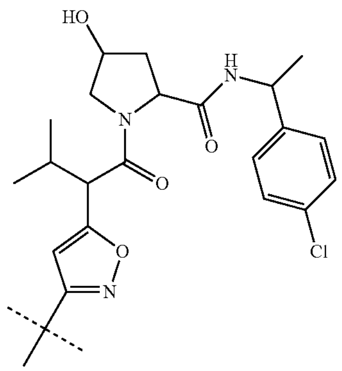
-continued
UTM-c15
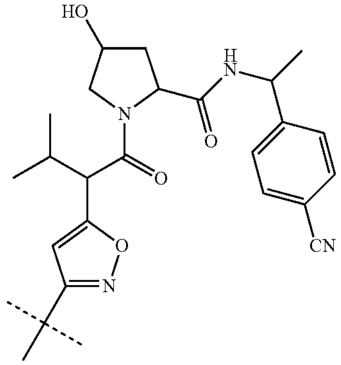
UTM-d1
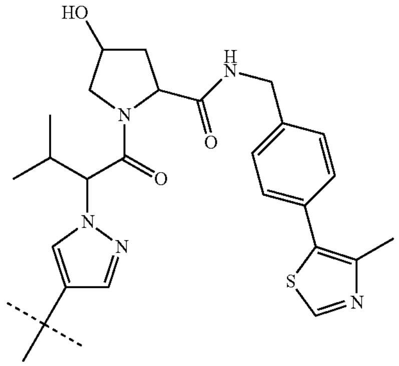
UTM-d2
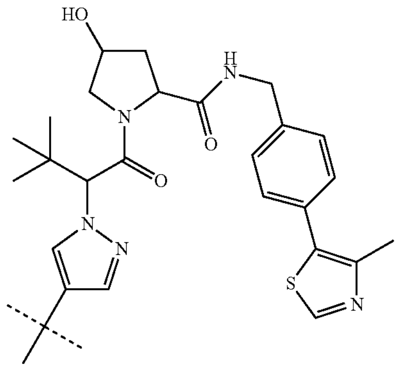
UTM-d3
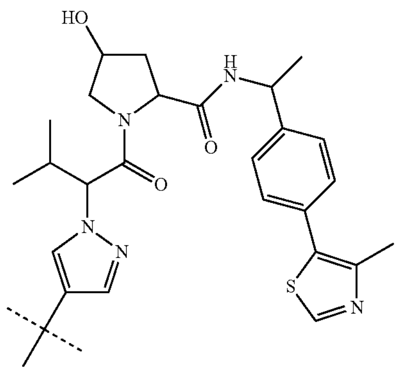

-continued

UTM-d4

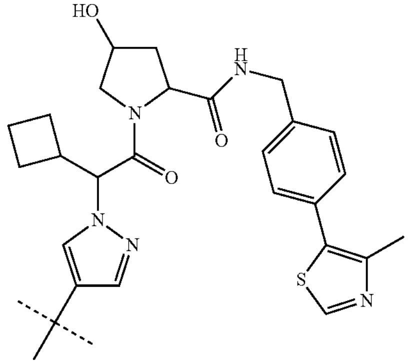

UTM-d5

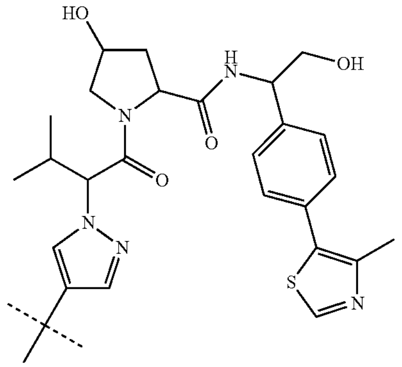

UTM-d6

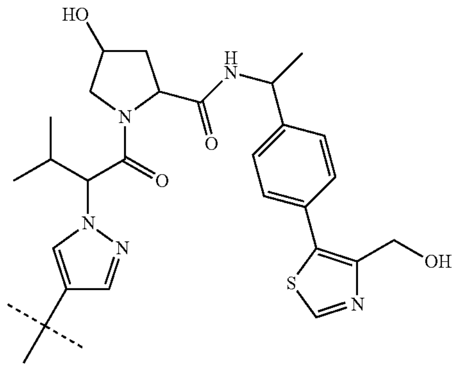

UTM-d7

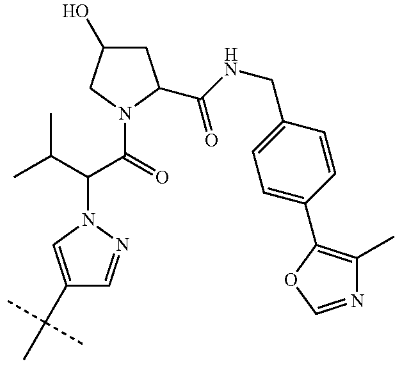

-continued

UTM-d8

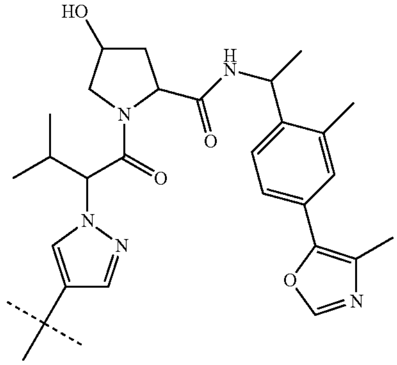

UTM-d9

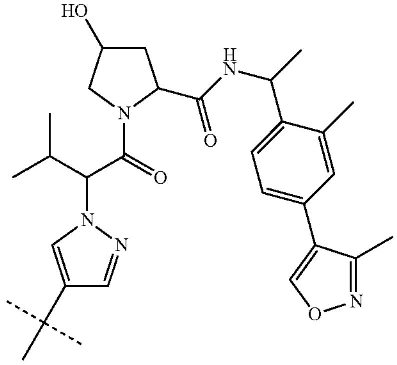

5. The compound according to claim 4, wherein the phenyl ring is substituted with a member selected from fluorine, a lower alkyl, or a lower alkoxy group.

6. The compound according to claim 1, wherein PTM has a chemical structure selected from the group consisting of:

PTM-aa

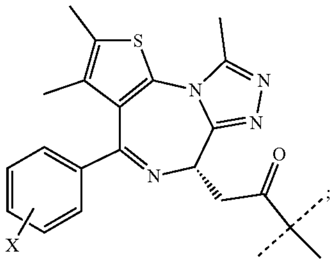

X = Cl, F, Br, H, CN, methyl, ethynyl, methoxy

PTM-ab

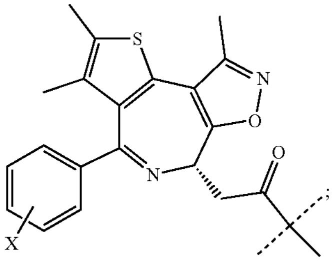

X = Cl, F, Br, H, CN, methyl, ethynyl, methoxy

-continued

PTM-ac

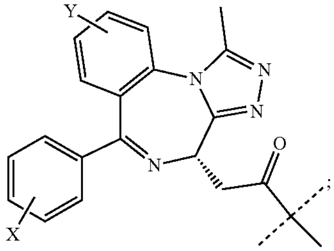

X = Cl, F, Br, H, CN, methyl, methoxy, ethynyl
Y: mono- or di-substitution
Y = Me, OMe, N-methypyrazole/imidazole PTM-ad

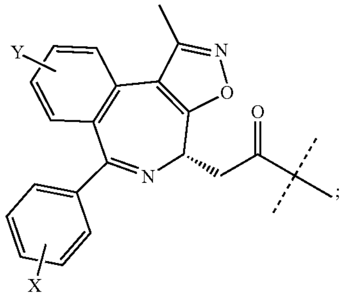

X = Cl, F, Br, H, CN, methyl, methoxy, ethynyl
Y: mono- or di-substitution
Y = Me, OMe, N-methylpyrazole/imidazole PTM-ae

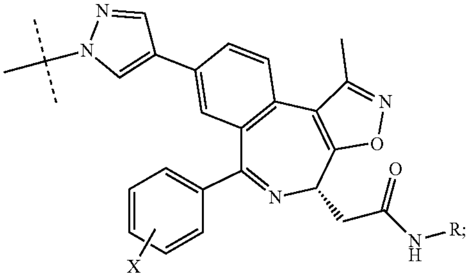

X = Cl, F, Br, H, CN, methyl, ethynyl, methoxy
R = lower alkyl, aryl, substituted aryl PTM-af

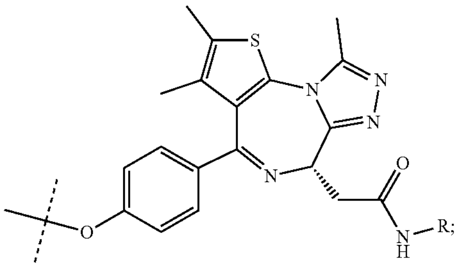

R = lower alkyl, aryl, substituted aryl

-continued

PTM-ag

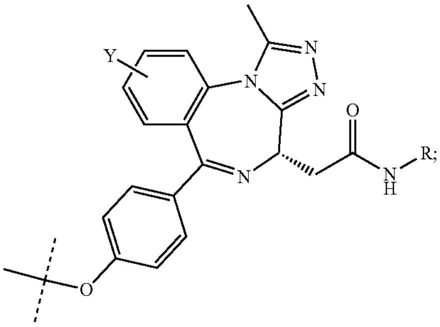

Y: mono- or di-substitution,
Y = Me, OMe, N-methylpyrazole/imidazole
R = lower alkyl, aryl, substituted aryl PTM-ah

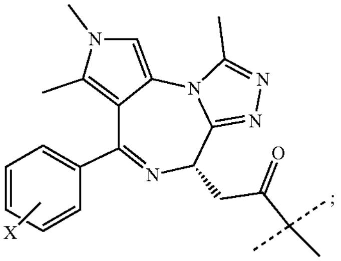

and

X = Cl, F, Br, H, CN, methyl, ethynyl, methoxy

PTM-ai

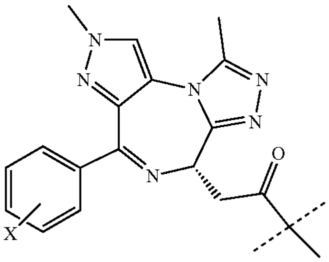

X = Cl, F, Br, H, CN, methyl, ethynyl, methoxy

7. The compound according to any of claim 1 or 6, wherein PTM-a is selected from the group consisting of:

PTM-a1

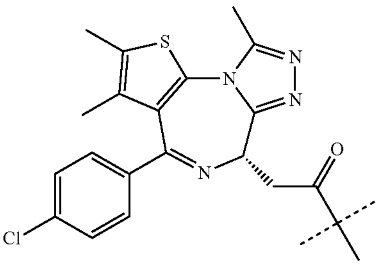

PTM-a2
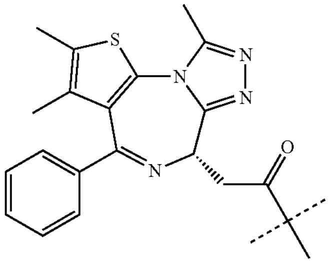
PTM-a3
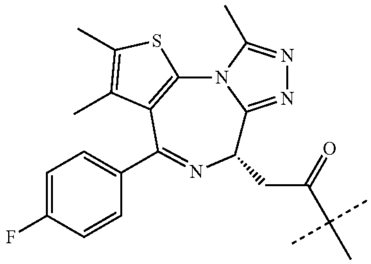
PTM-a4
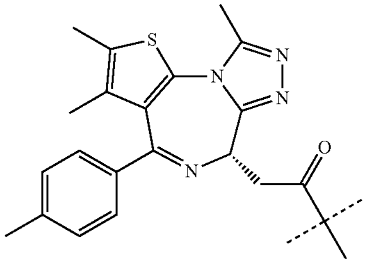
PTM-a5
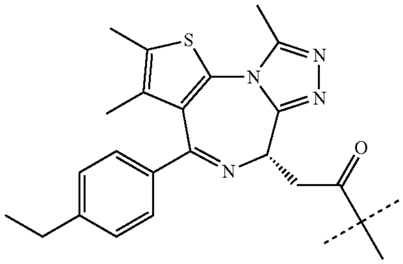
PTM-a6
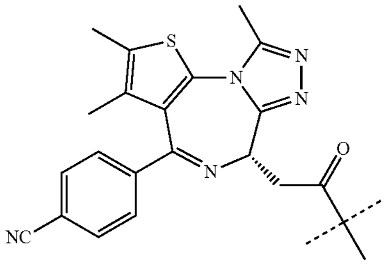
PTM-a7
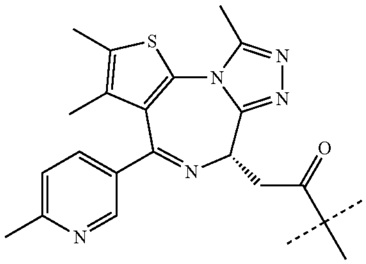
PTM-a8
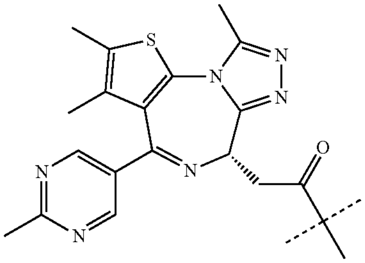
PTM-a9
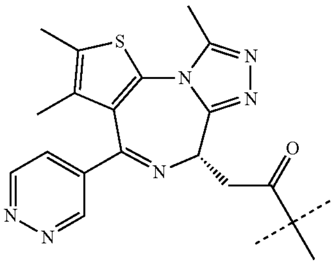
PTM-a10
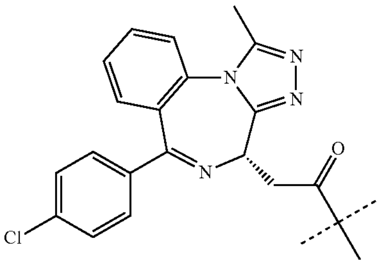
PTM-a11
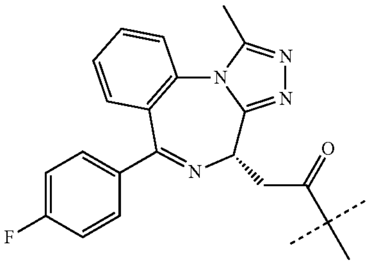
PTM-a12
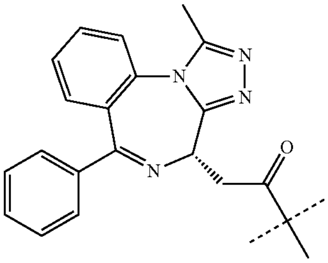
PTM-a13
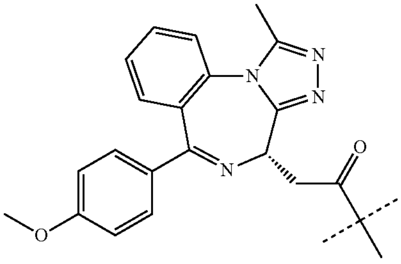

-continued
PTM-a14
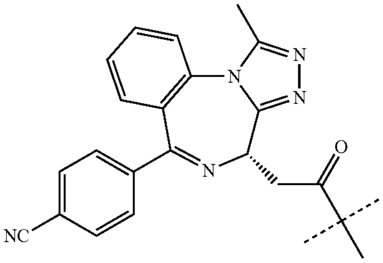
PTM-a15
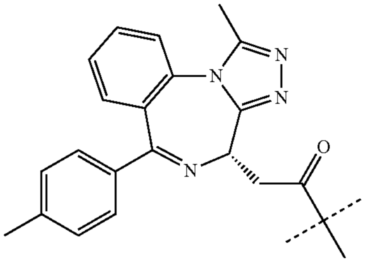
PTM-a16
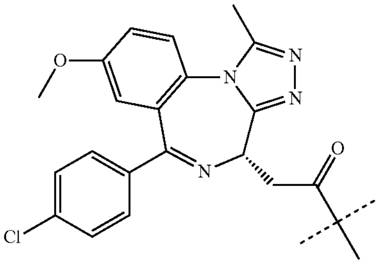
PTM-a17
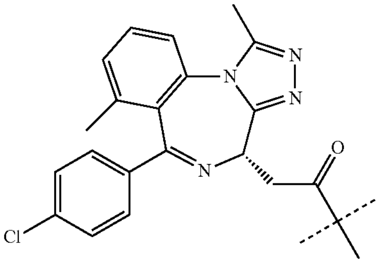
PTM-a18
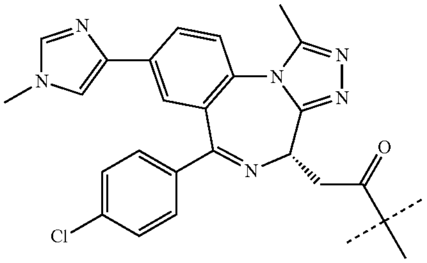
-continued
PTM-a19
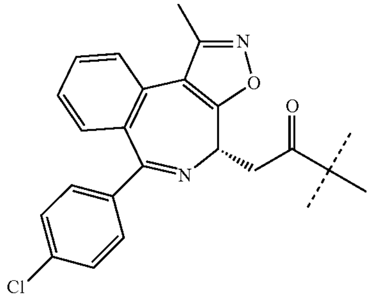
PTM-a20
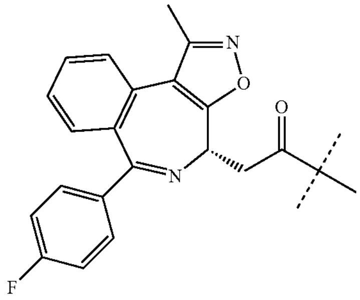
PTM-a21
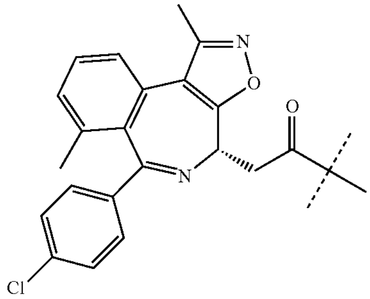
PTM-a22
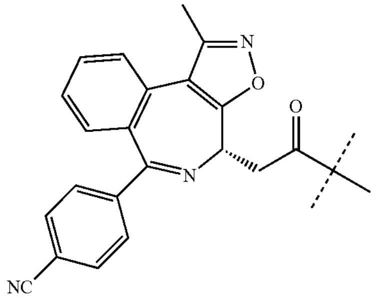
PTM-a23
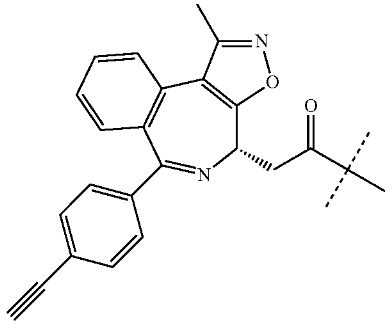

-continued
PTM-a24
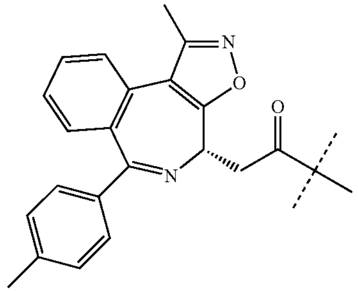
PTM-a25
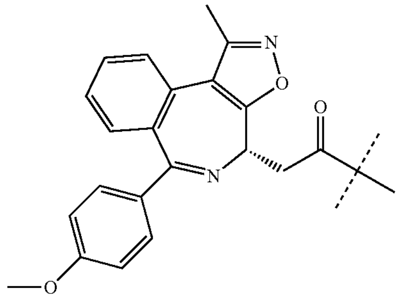
PTM-a26
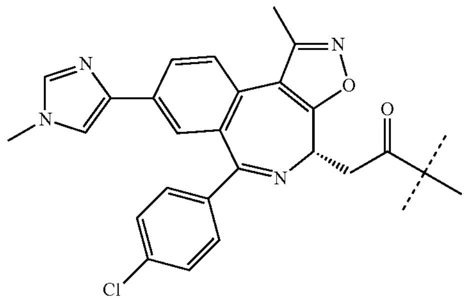
PTM-a27
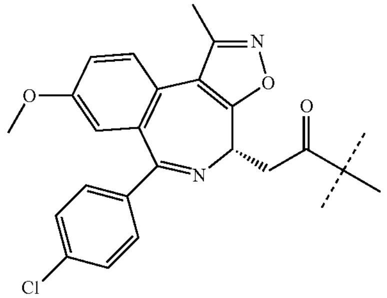
PTM-a28
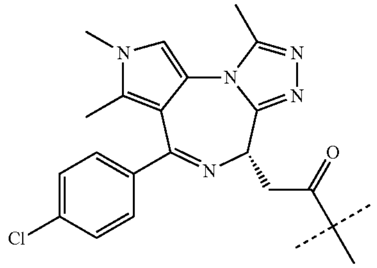
-continued
PTM-a29
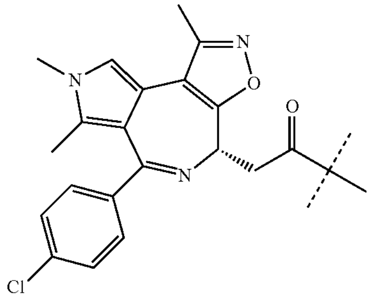
PTM-a30
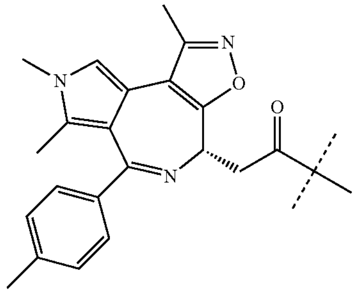
PTM-a31
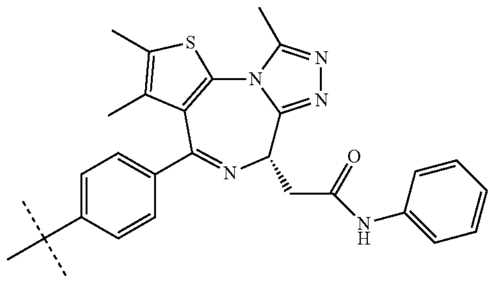
PTM-a32
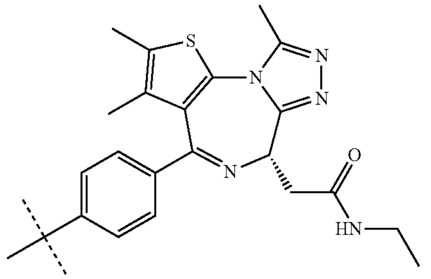
PTM-a33
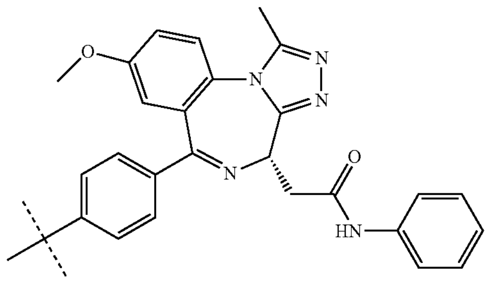

PTM-a34
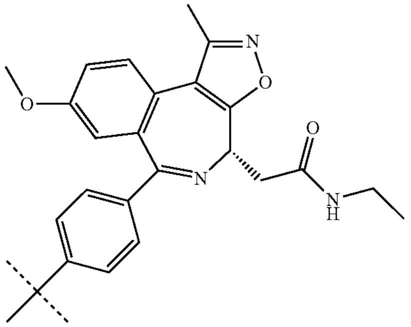
PTM-a35
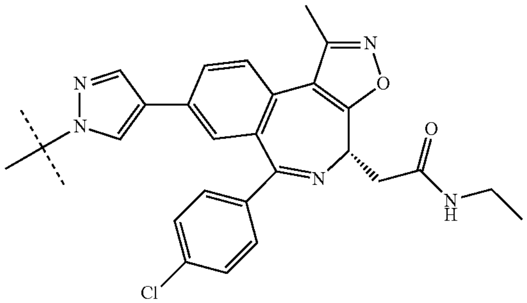
PTM-a36
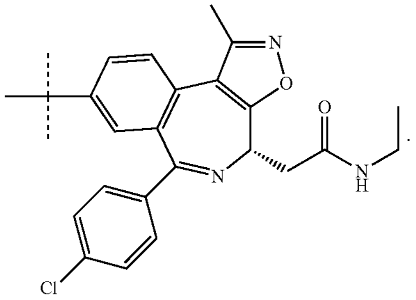
8. The compound according to claim 1, wherein the L is represented by a structure selected from the group consisting of:
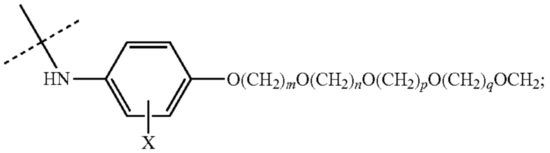
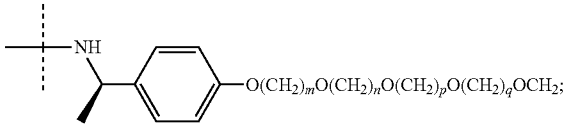
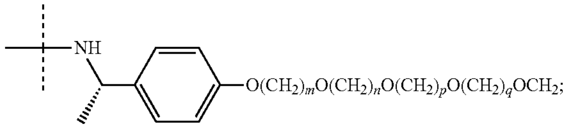
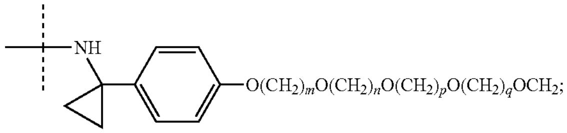
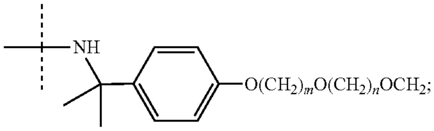
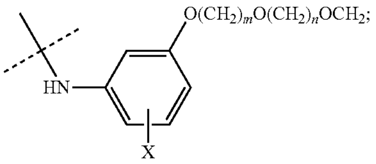
and
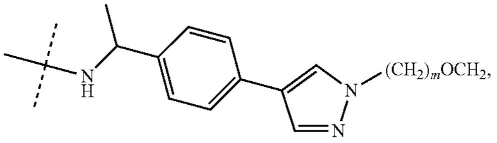
wherein each m, n, o, p, q, and r is independently 0, 1, 2, 3, 4, 5, with the proviso that when the number is zero, there is no N—O or 0-0 bond, R is selected from the group H, methyl and ethyl, and X is selected from the group H and F;
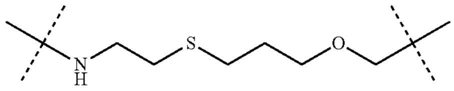
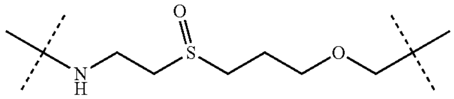
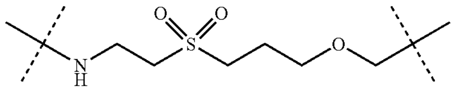
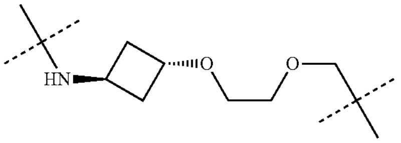
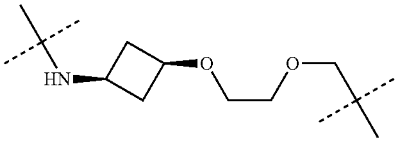
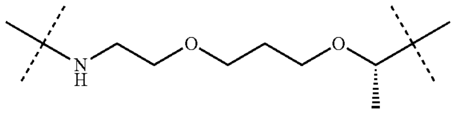
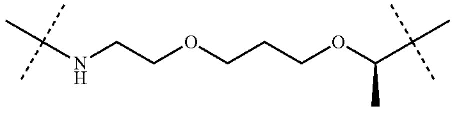
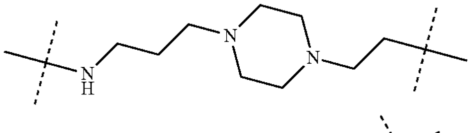
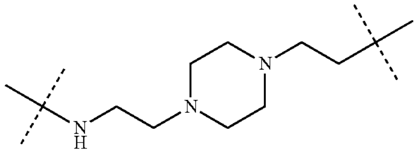

-continued
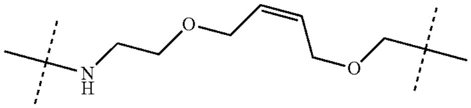
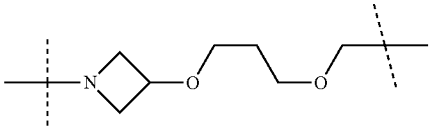
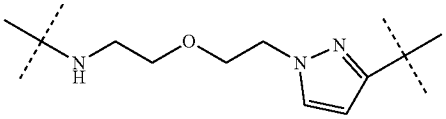
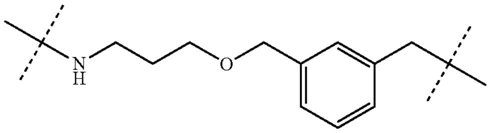
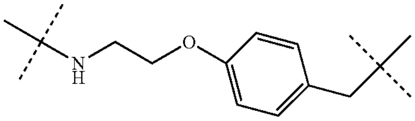
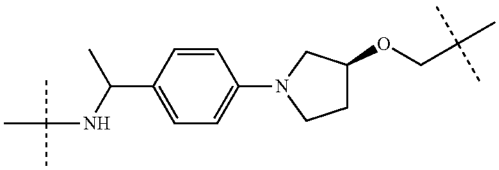
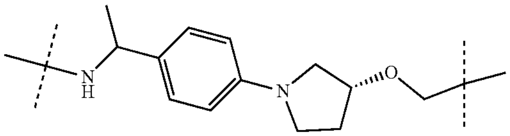
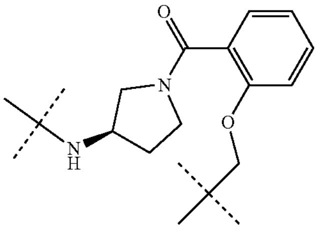
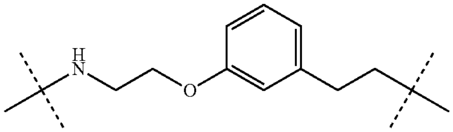
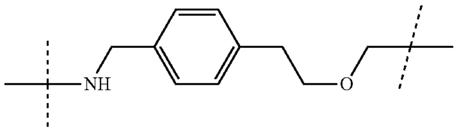
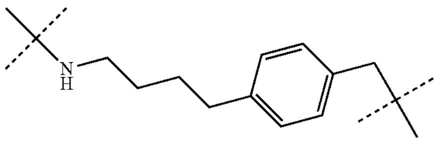
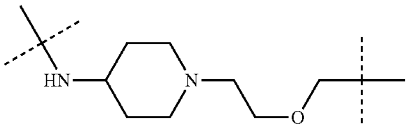
-continued
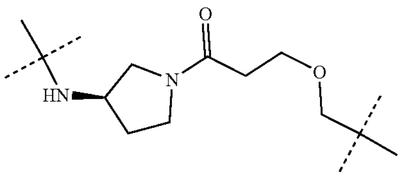
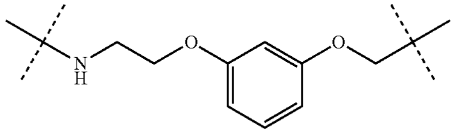
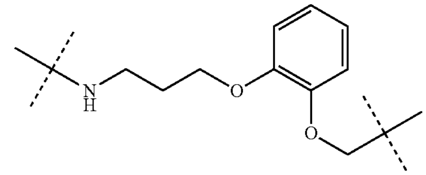
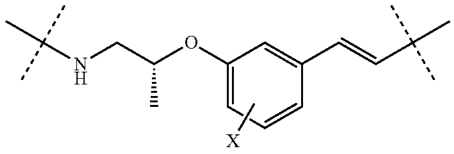
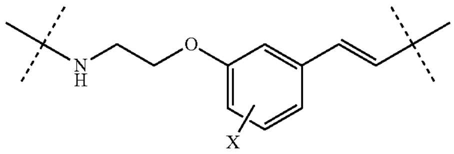
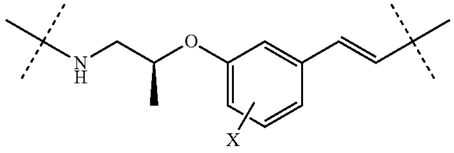
X = H, F
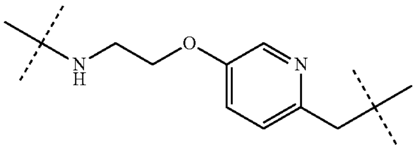
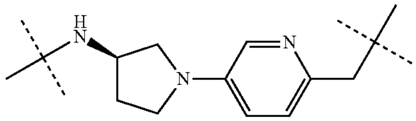
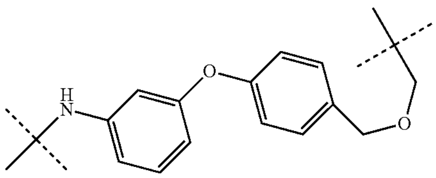
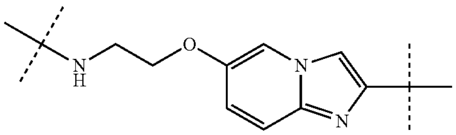
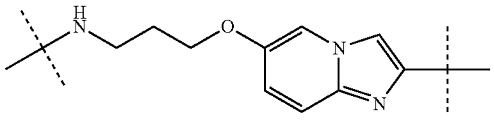

-continued
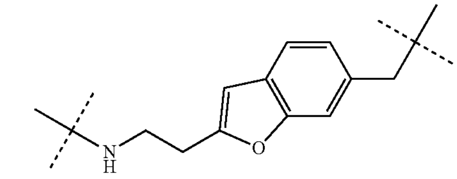
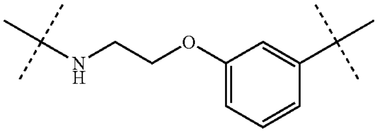
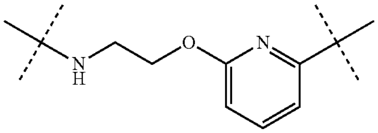
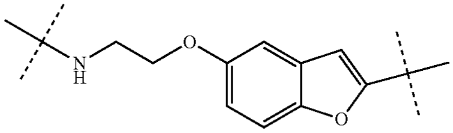
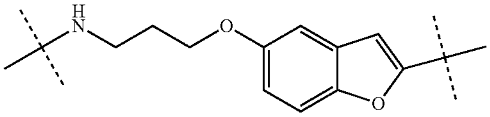
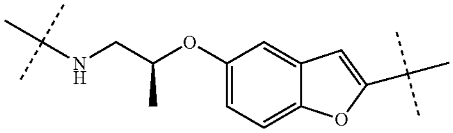
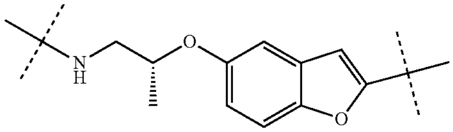
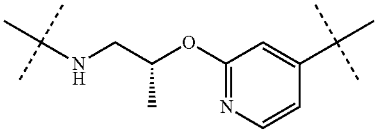
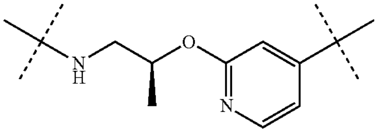
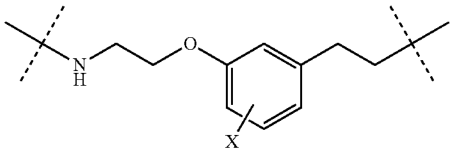
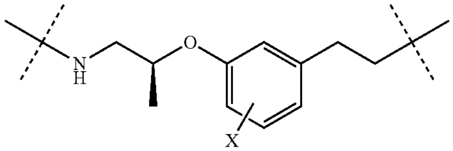
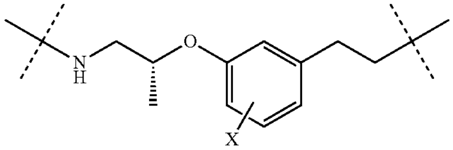
-continued
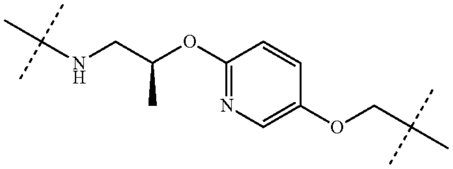
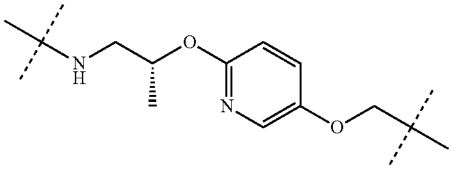
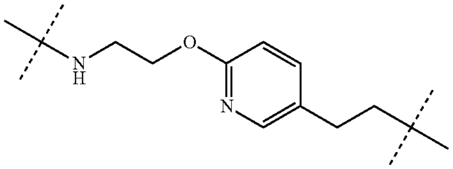
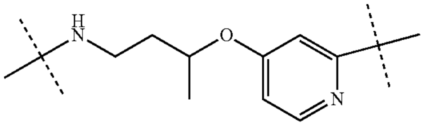
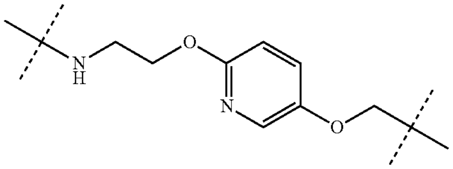
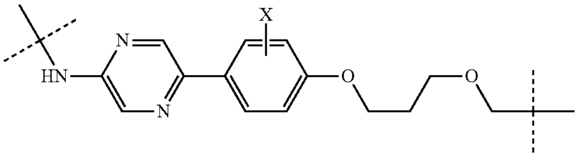
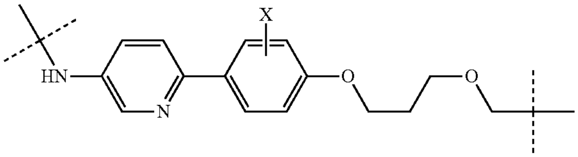
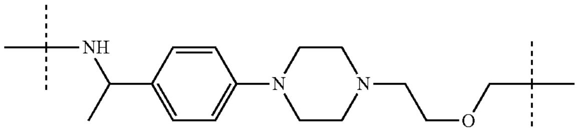
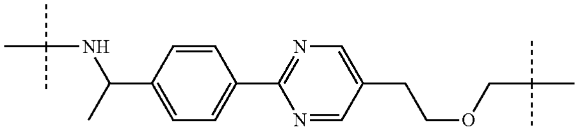
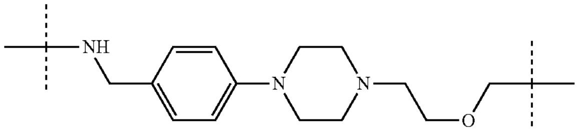
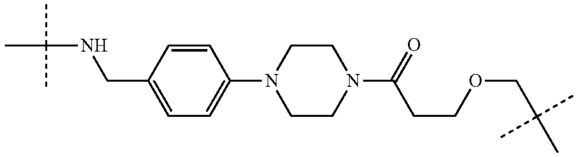

-continued
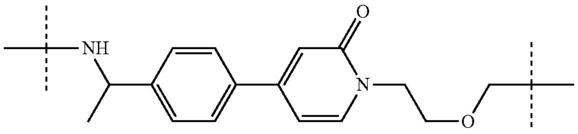
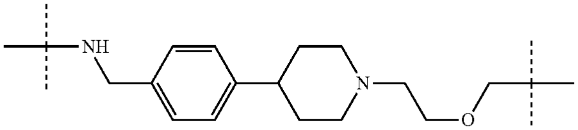
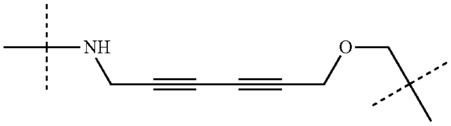
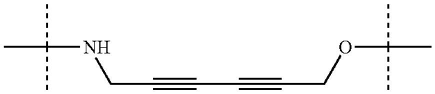
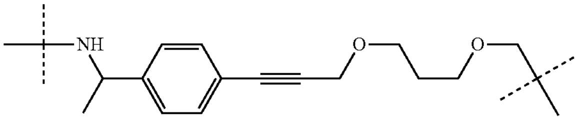
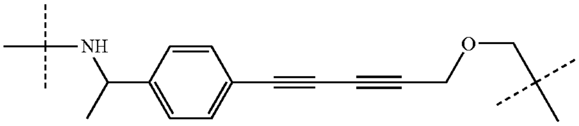
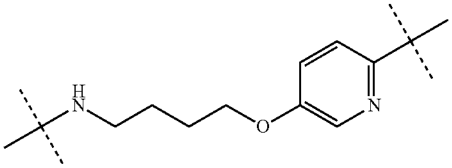
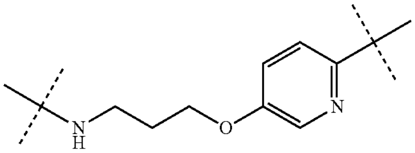
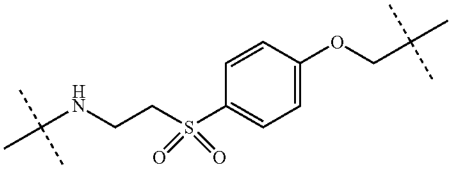
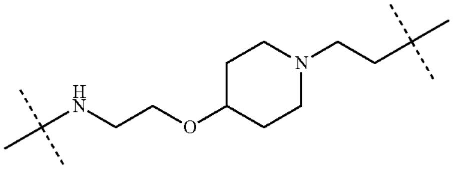
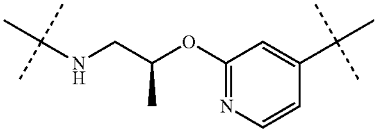
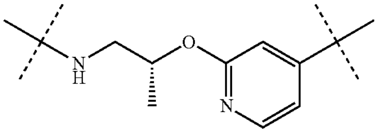
-continued
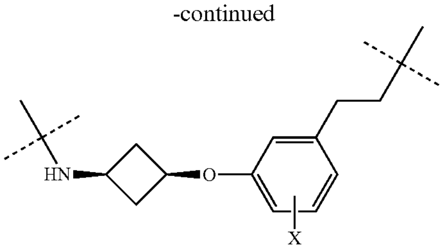
X = H, F
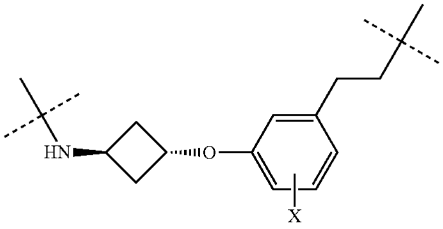
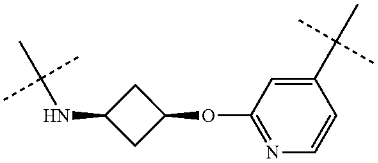
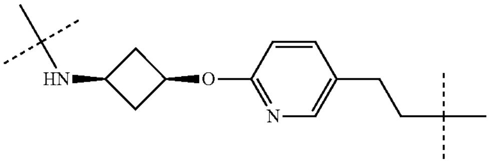
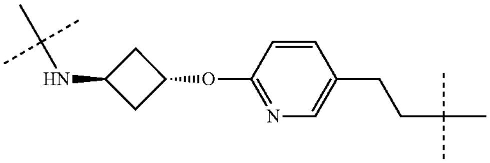
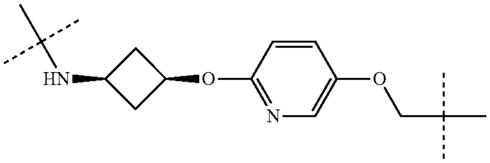
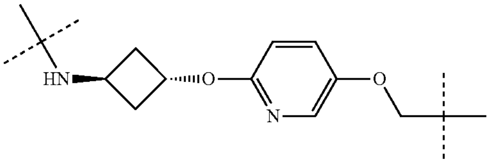
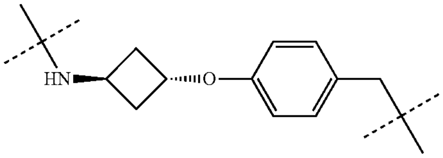
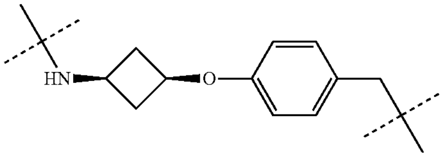
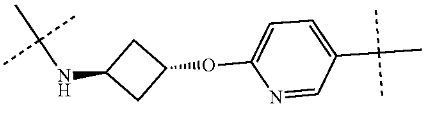

-continued
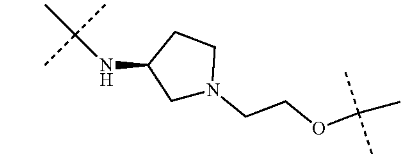
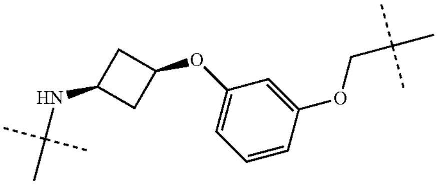
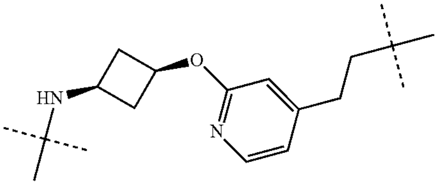
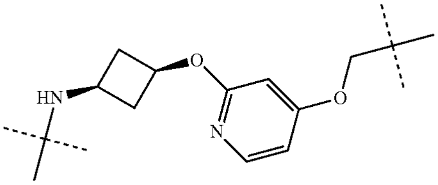
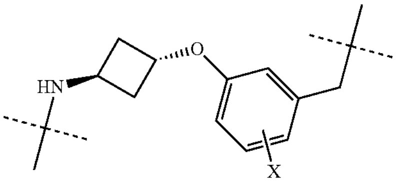
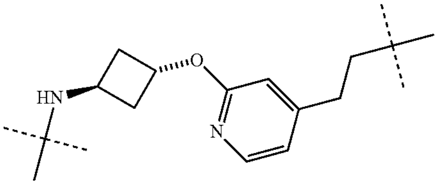
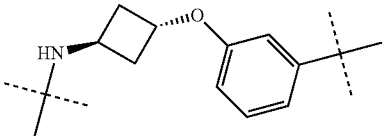
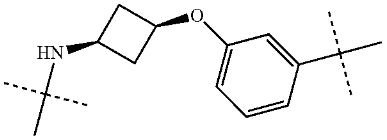
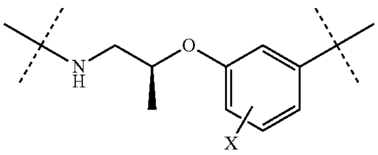
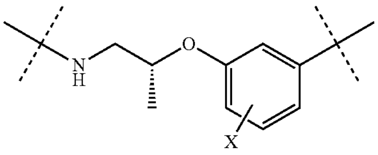
-continued
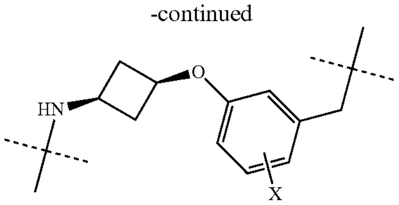
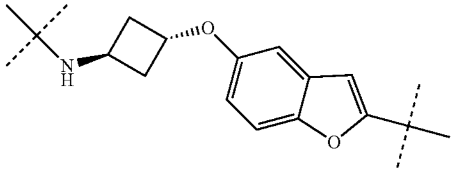
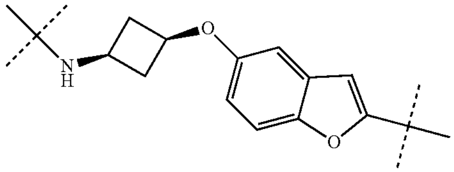
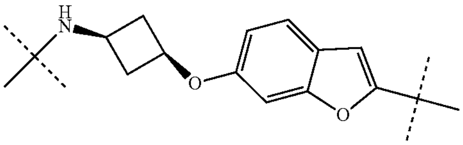
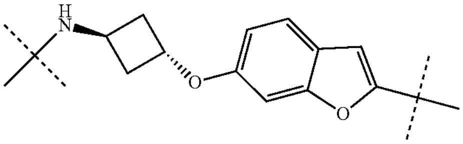
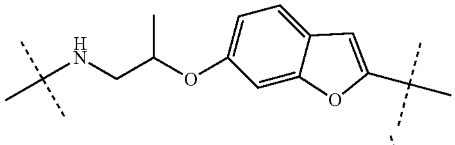
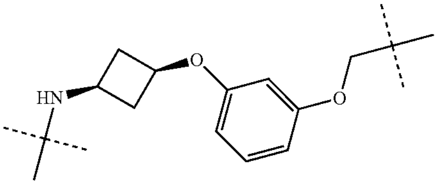
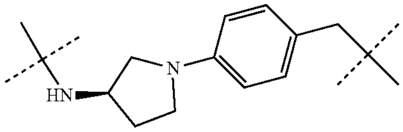
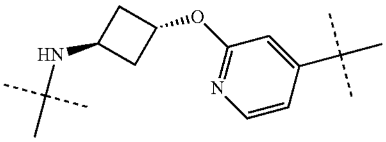
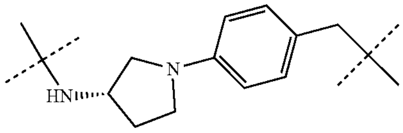
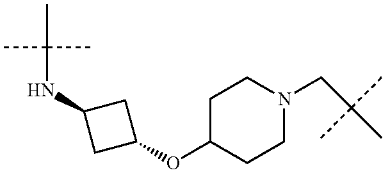

-continued
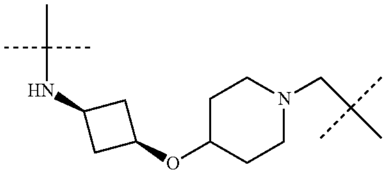
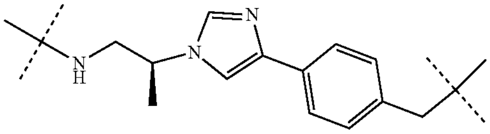
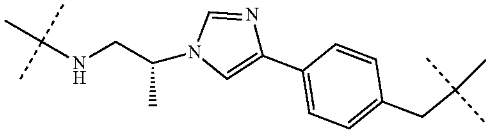
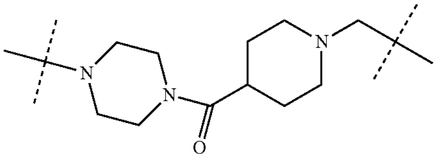
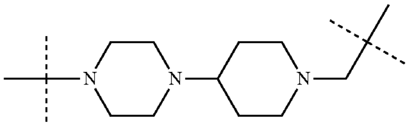
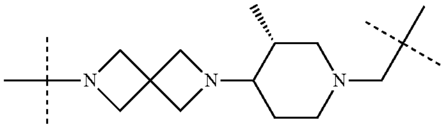
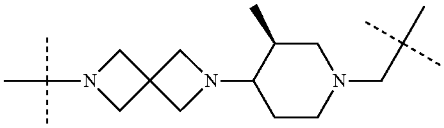
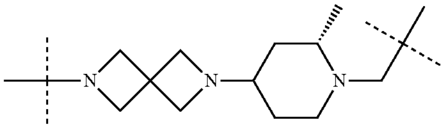
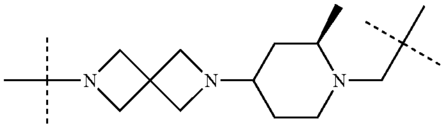
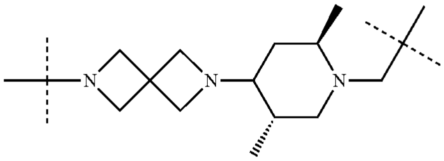
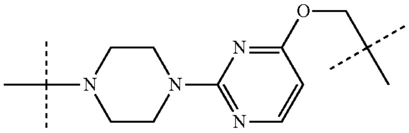
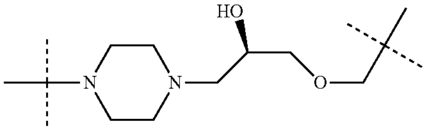
-continued
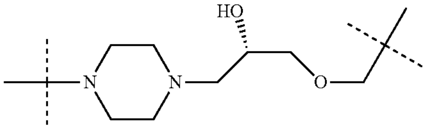
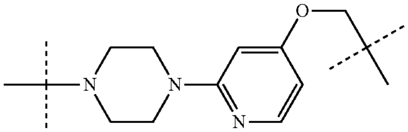
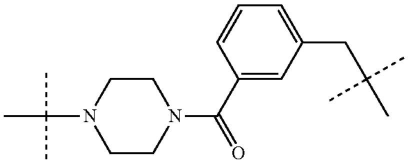
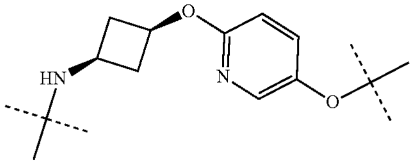
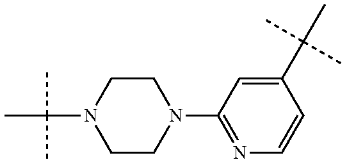
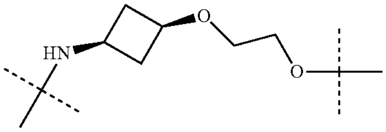
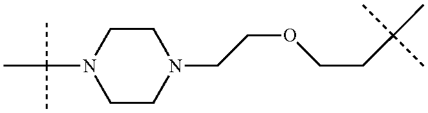
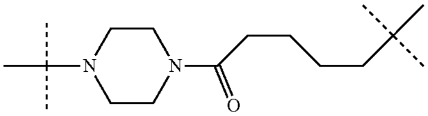
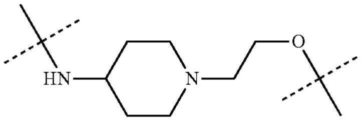
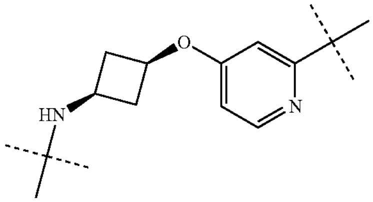
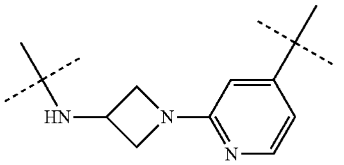
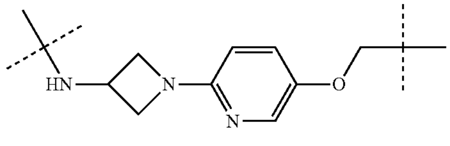

-continued
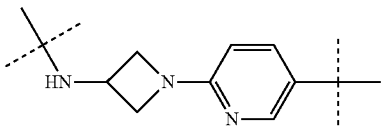
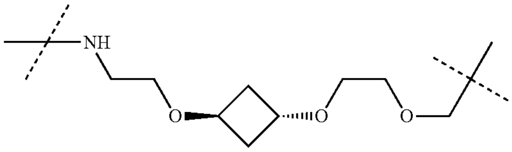
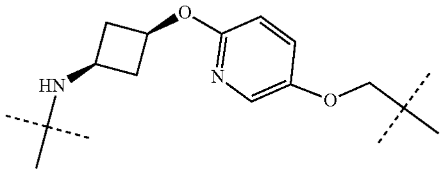
-continued
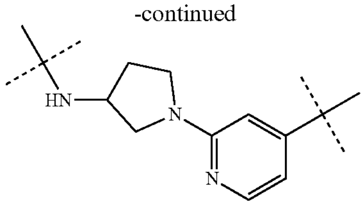
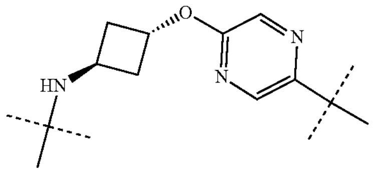
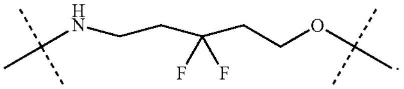
9. The compound according to claim 1, wherein the L is selected from the group consisting of:
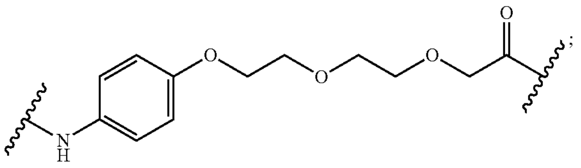
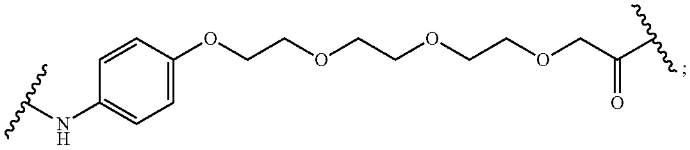
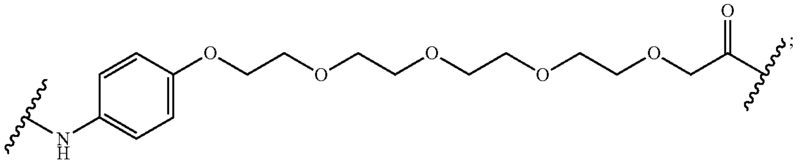
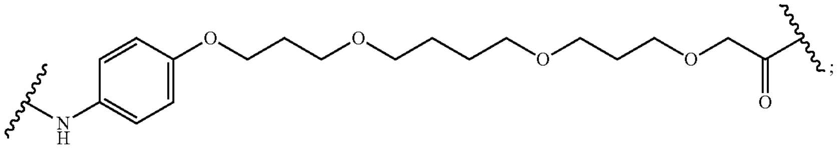
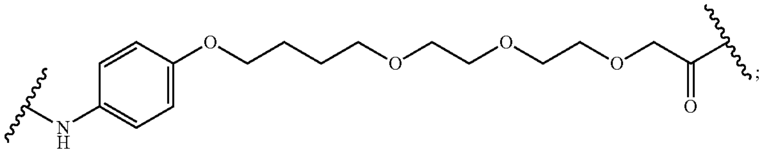
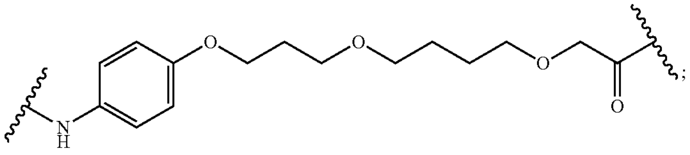
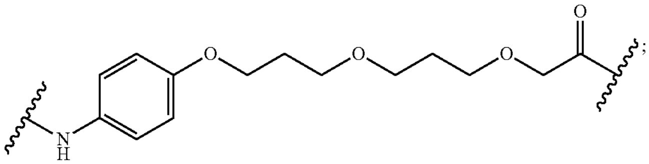

-continued
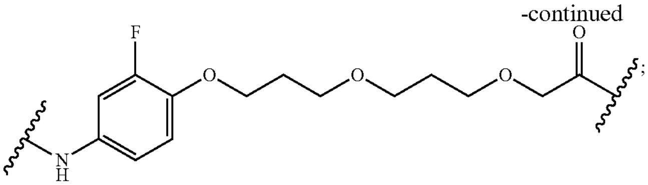
;
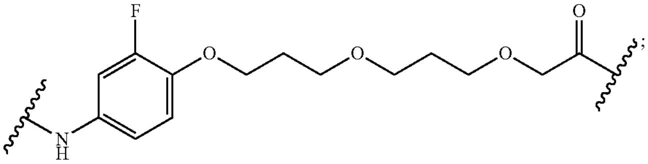
;
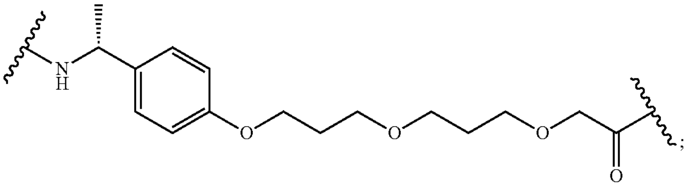
;
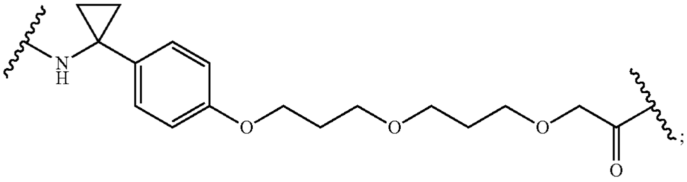
;
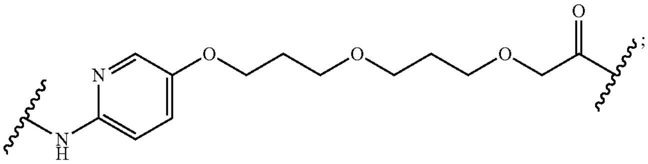
;
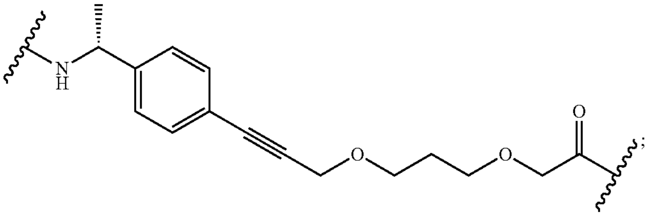
;
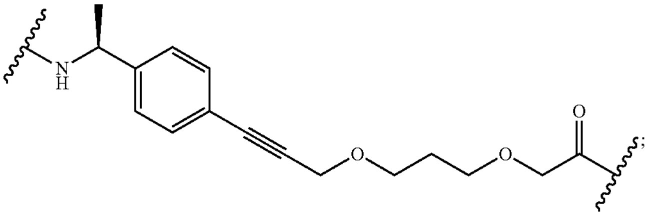
;
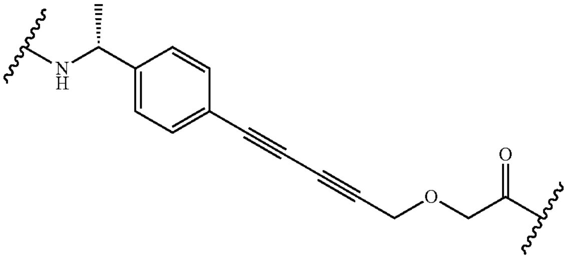
;
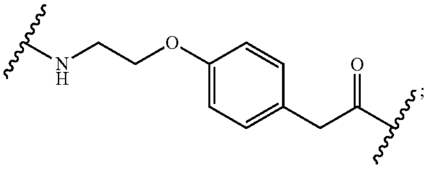
;
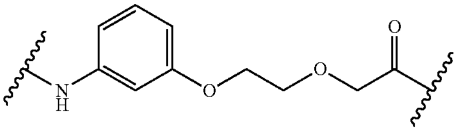
;

-continued
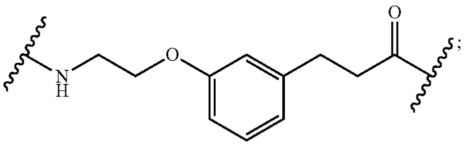;
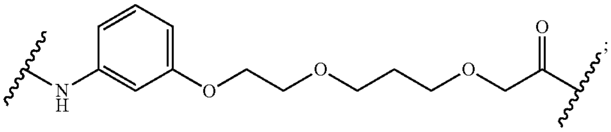;
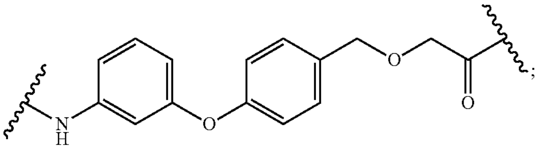;
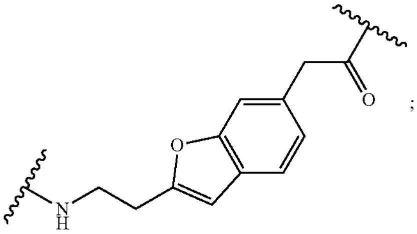;
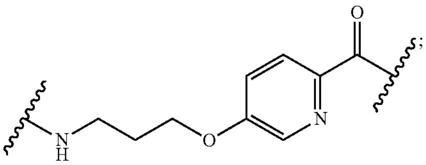;
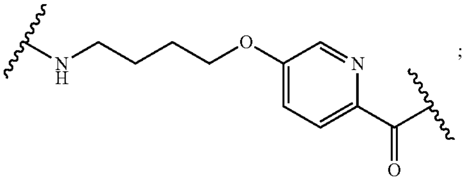;
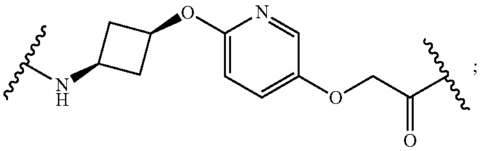;
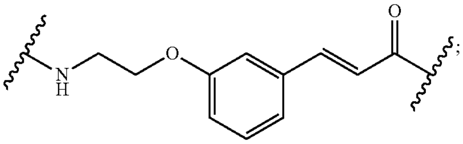;
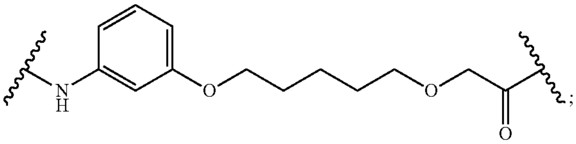;
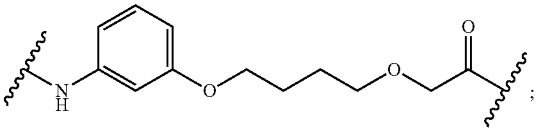;
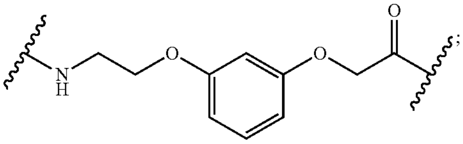;
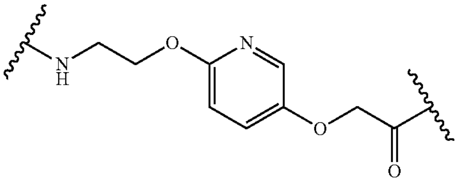;
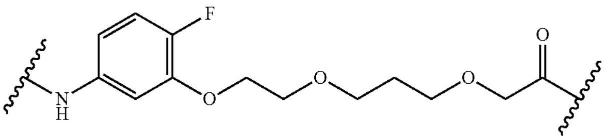;
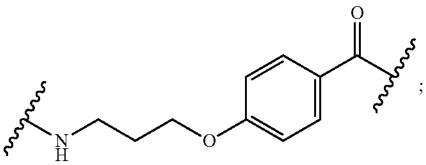;
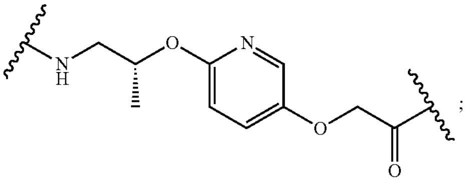;
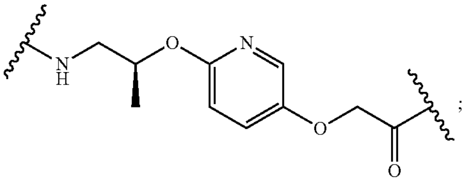;
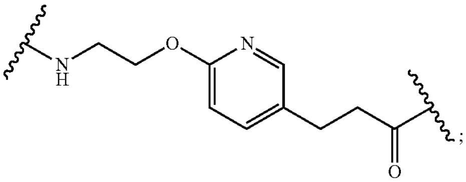;
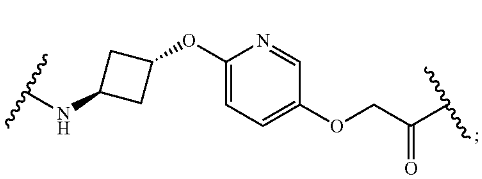;
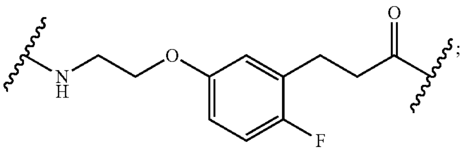;
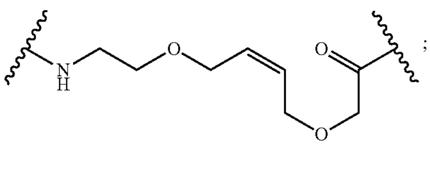;

-continued
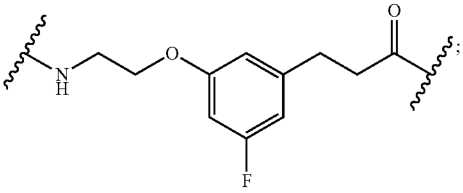
;
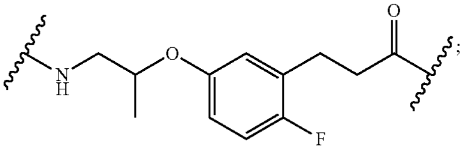
;
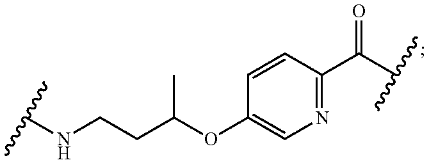
;
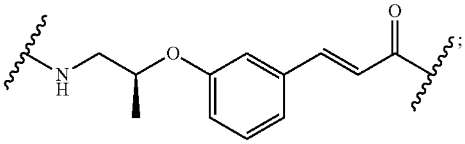
;
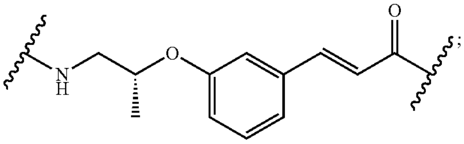
;
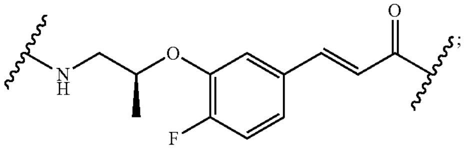
;
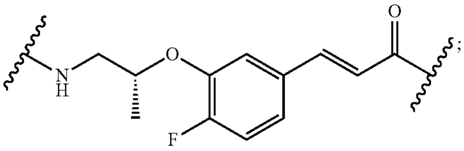
;
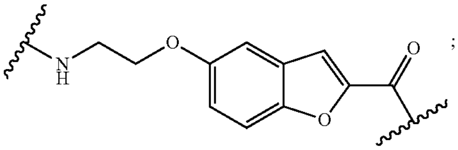
;
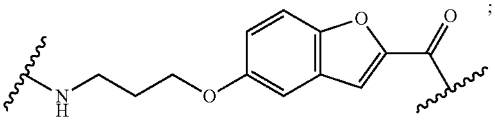
;
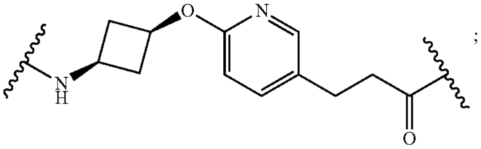
;
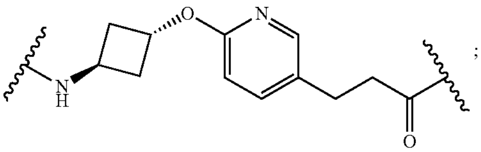
;
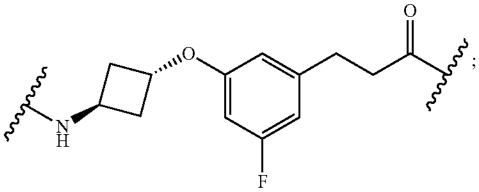
;
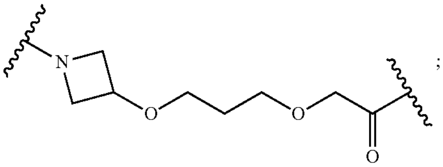
;
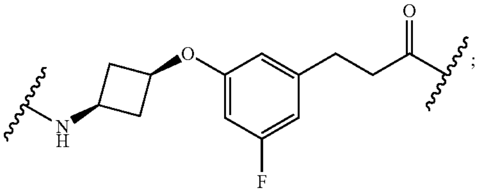
;
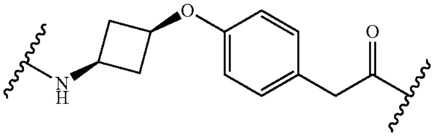
;
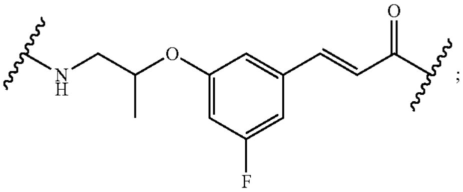
;
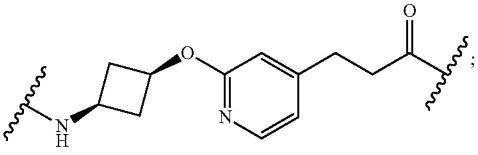
;
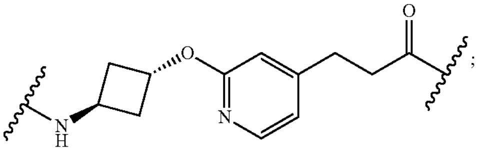
;
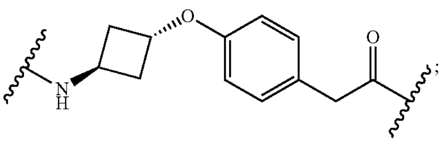
;
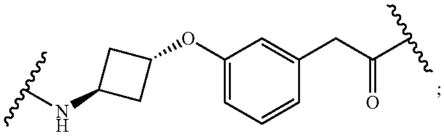
;

-continued
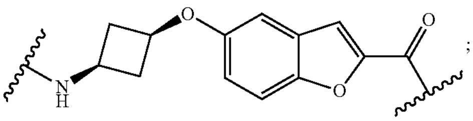;
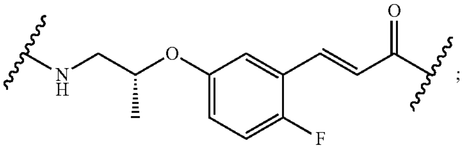;
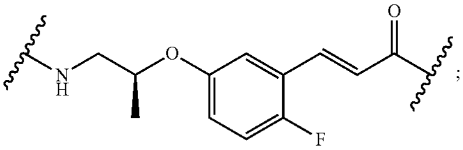;
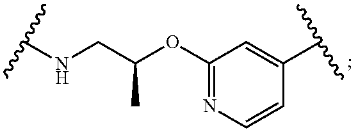;
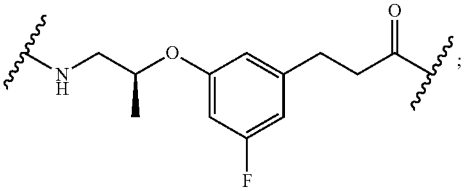;
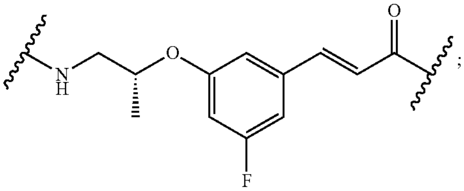;
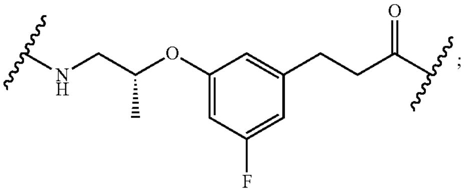;
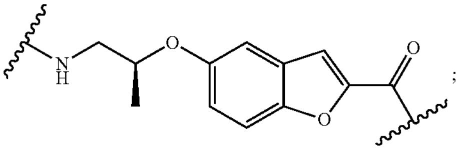;
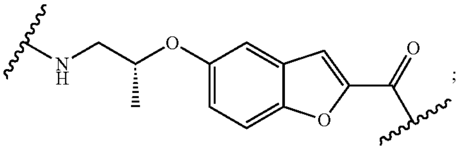;
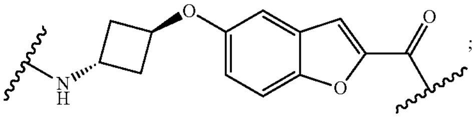;
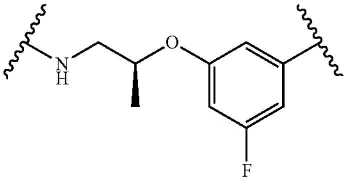;
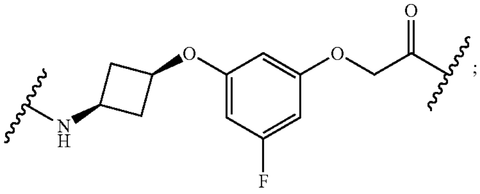;
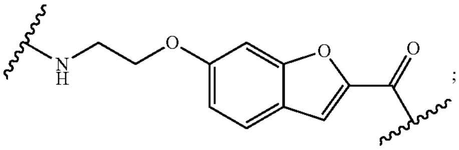;
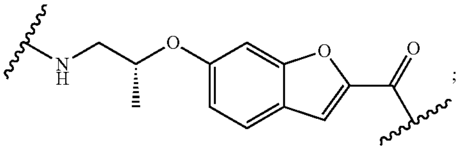;
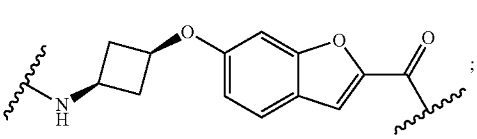;
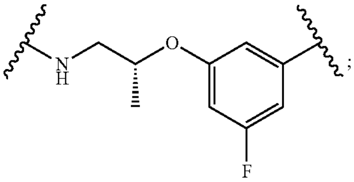;
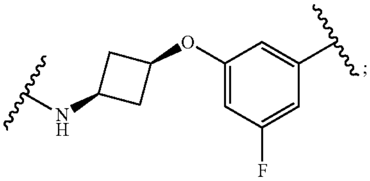;
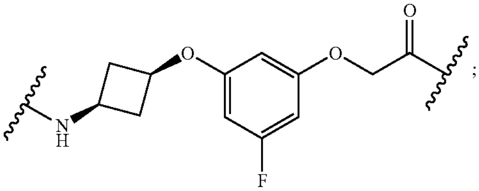;
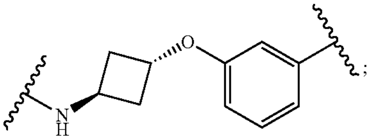;
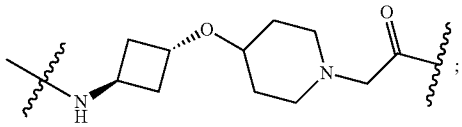;

-continued

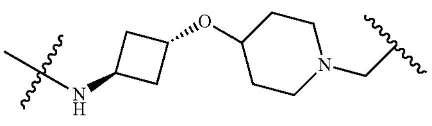

and

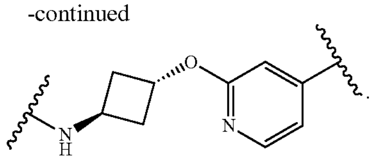

10. The compound according to claim 1, wherein L is a polyethylene group optionally substituted with aryl or phenyl comprising from 5 to 10 ethylene glycol units.

11. A pharmaceutical composition comprising an effective amount of a compound according to claim 1 in combination with a pharmaceutically acceptable carrier, additive or excipient and optionally in further combination with an additional bioactive agent.

12. The pharmaceutical composition according to claim 11, wherein the additional bioactive agent is an anticancer agent.

13. A method of treating cancer in a subject, the method comprising administering to the patient in need thereof an effective amount of a compound according to claim 1, wherein the compound is effective in treating or ameliorating a symptom of the cancer in the subject and the cancer is prostate cancer, ovarian cancer, breast cancer, or B-cell lymphoma.

14. The bifunctional compound according to claim 1, wherein the linker includes S, SO, $SO_2$, $SO_2NR^{L3}$, $SONR^{L3}$, $CONR^{L3}$, $NR^{L3}CONR^{L3}$, $NR^{L3}SO_2NR^{L4}$, CO, $CR^{L1}{=}CR^{L2}$, C≡C, $SiR^{L1}R^{L2}$, $P(O)R^{L1}$, $P(O)OR^{L1}$, $NR^{13}C({=}NCN)NR^{L4}$, $NR^{L3}C({=}NCN)$, $NR^{L3}C({=}CNO_2)NR^{L4}$, $C_{3-11}$cycloalkyl optionally substituted with 1-6 $R^{L1}$ and/or $R^{L2}$ groups, $C_{3-11}$heterocyclyl optionally substituted with 1-6 $R^{L1}$ and/or $R^{L2}$ groups, aryl optionally substituted with 1-6 $R^{L1}$ and/or $R^{L2}$ groups, heteroaryl optionally substituted with 1-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 1-4 $R^{L5}$ groups.

15. The compound according to claim 1, wherein the linker has 6-10 optionally substituted ethylene glycol units wherein each O is optionally replaced with an optionally substituted N atom.

16. The bifunctional compounds according to claim 1, wherein the linker includes 7 optionally substituted ethylene glycol units.

17. The bifunctional compounds according to claim 1, wherein the linker includes 8 optionally substituted ethylene glycol units.

18. The bifunctional compounds according to claim 1, wherein the linker includes 9 optionally substituted ethylene glycol units.

19. The bifunctional compounds according to claim 1, wherein the linker includes 10 optionally substituted ethylene glycol units.

20. The bifunctional compound of claim 1, wherein the bifunctional compound is selected from the group consisting of:

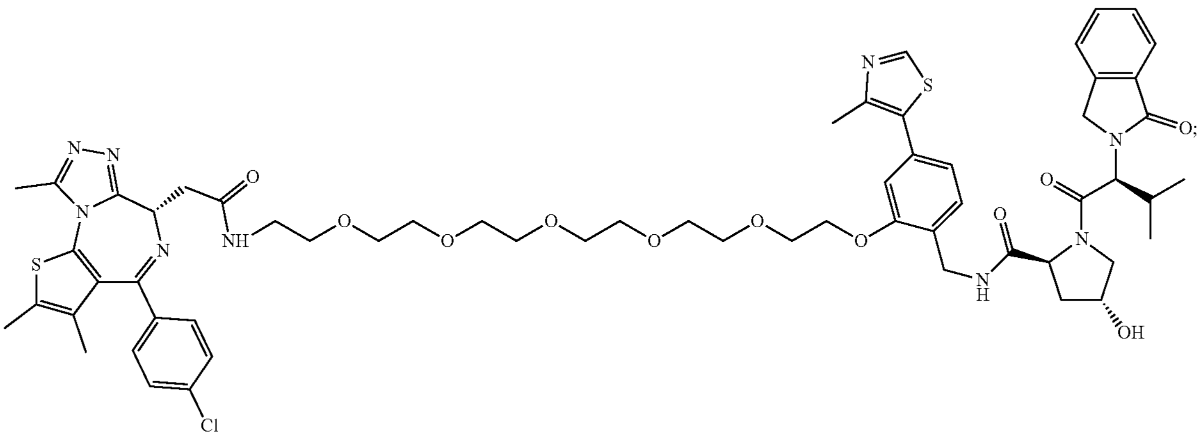

;

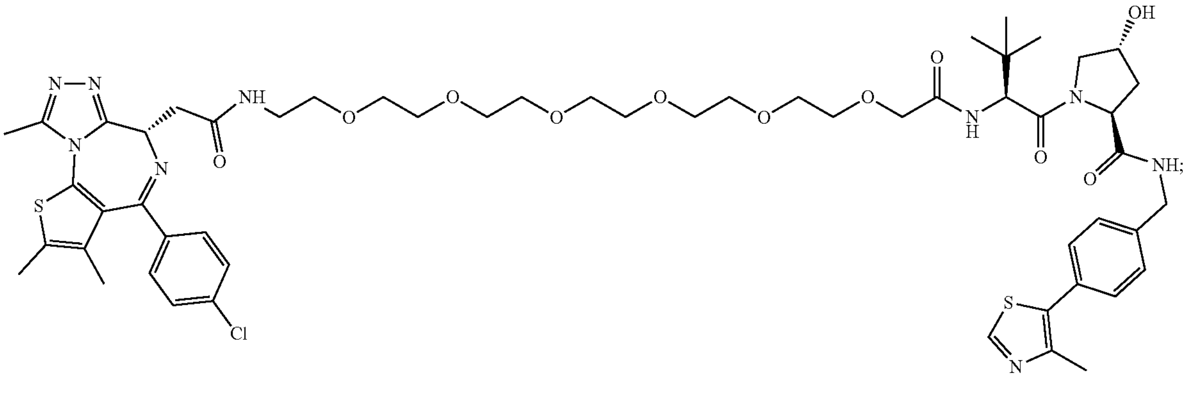

;

-continued
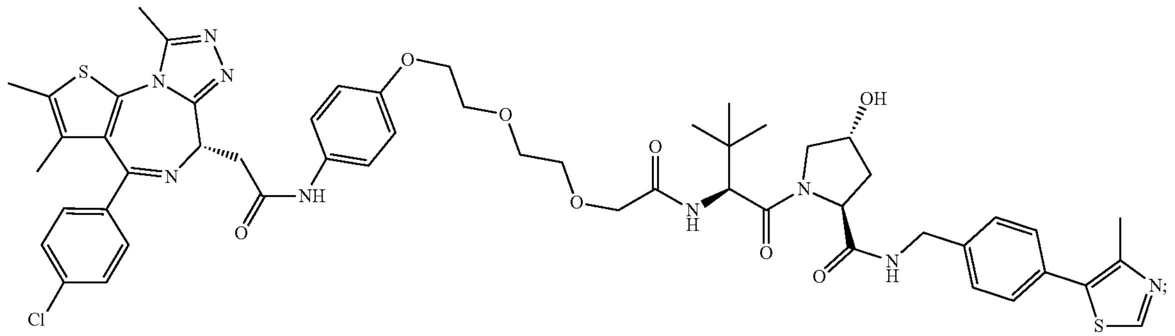
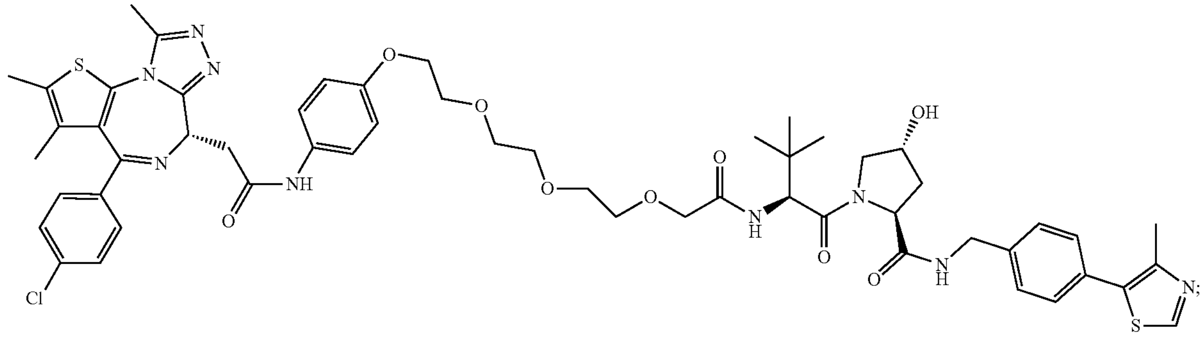
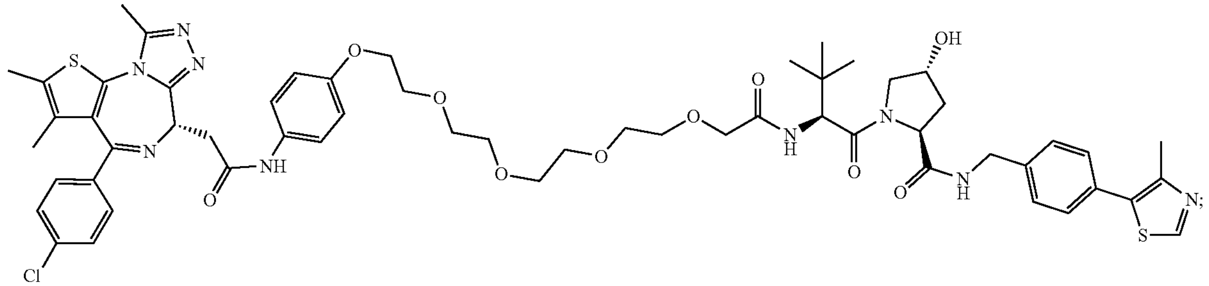
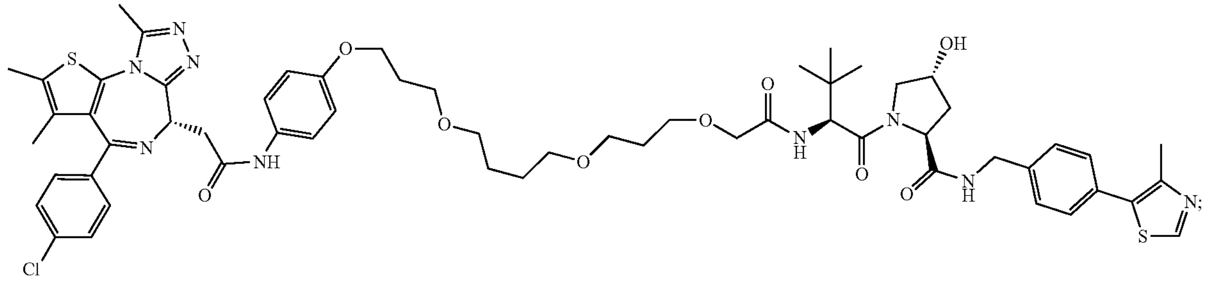
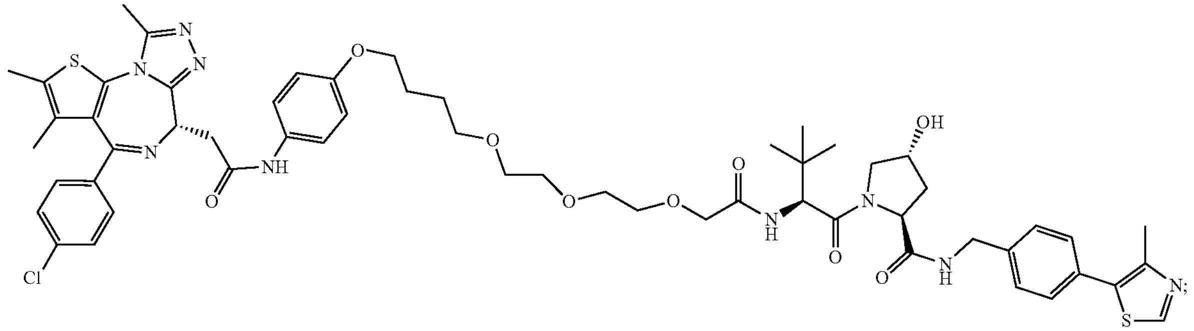

-continued
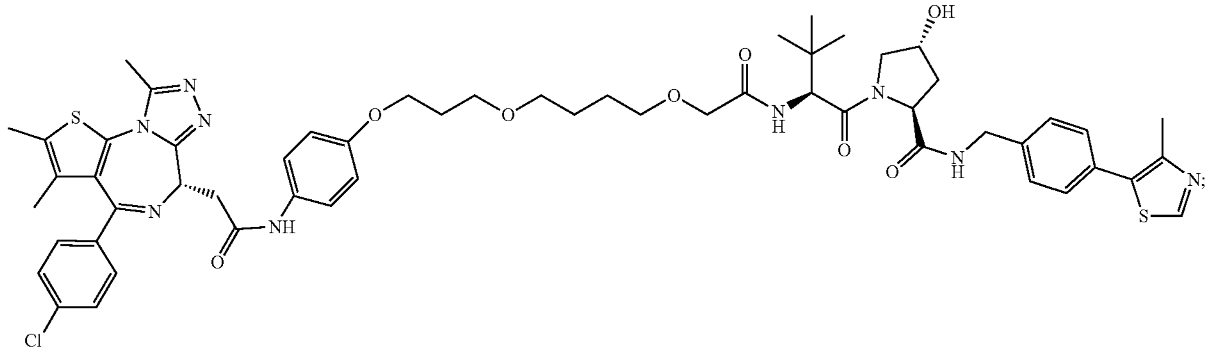
;
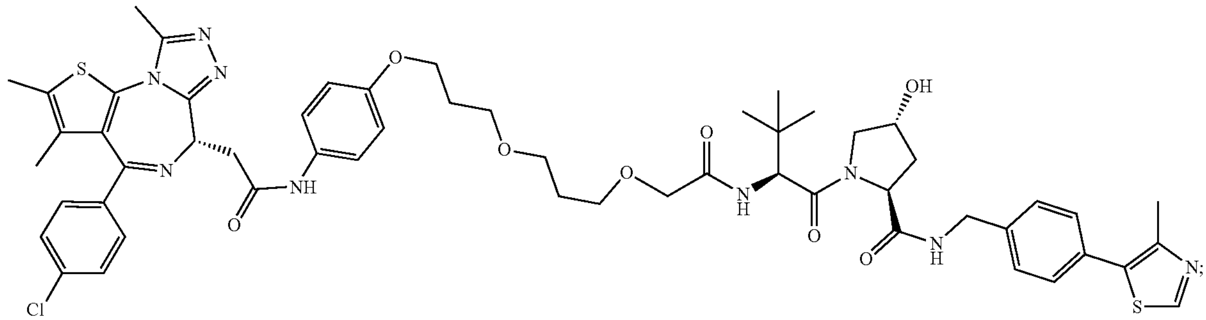
;
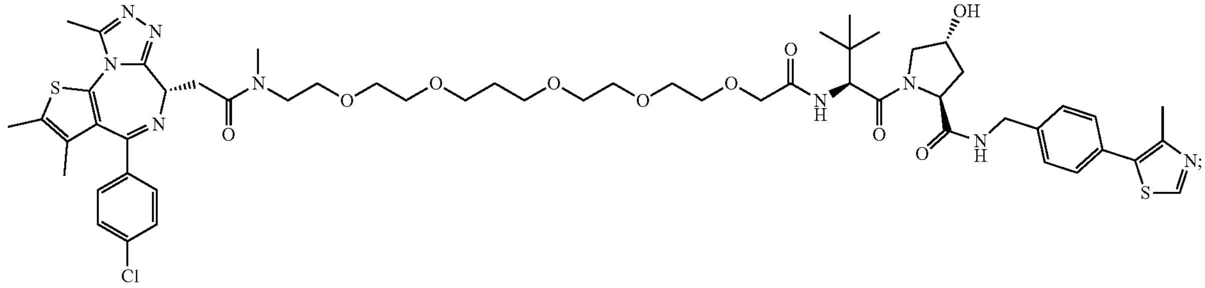
;
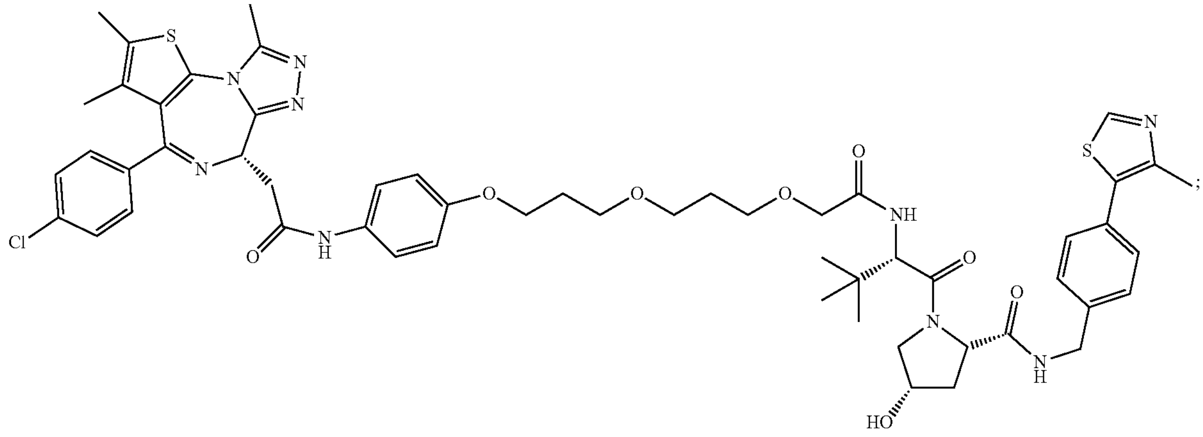
;
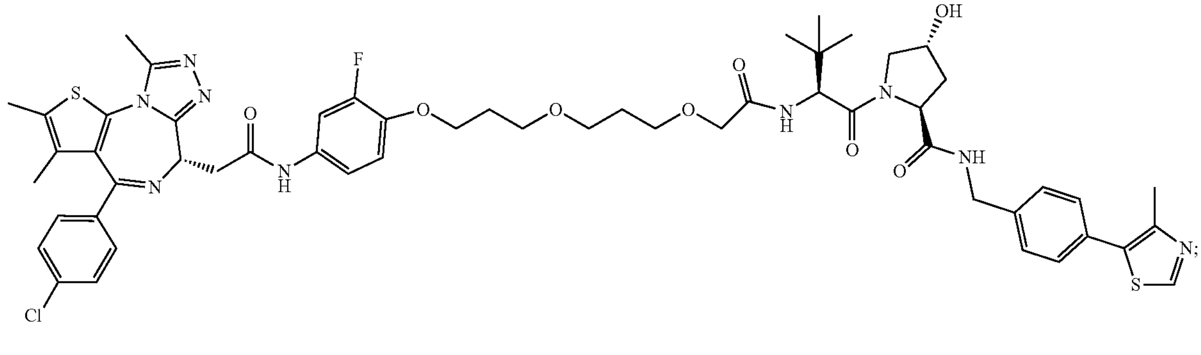
;

-continued
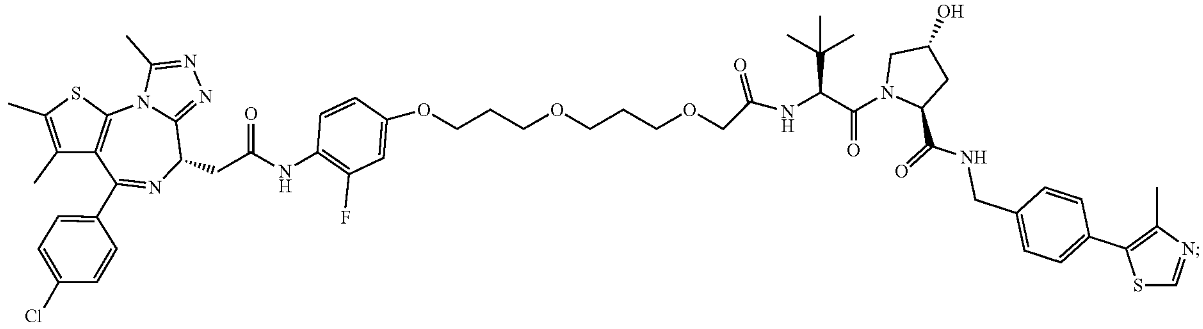
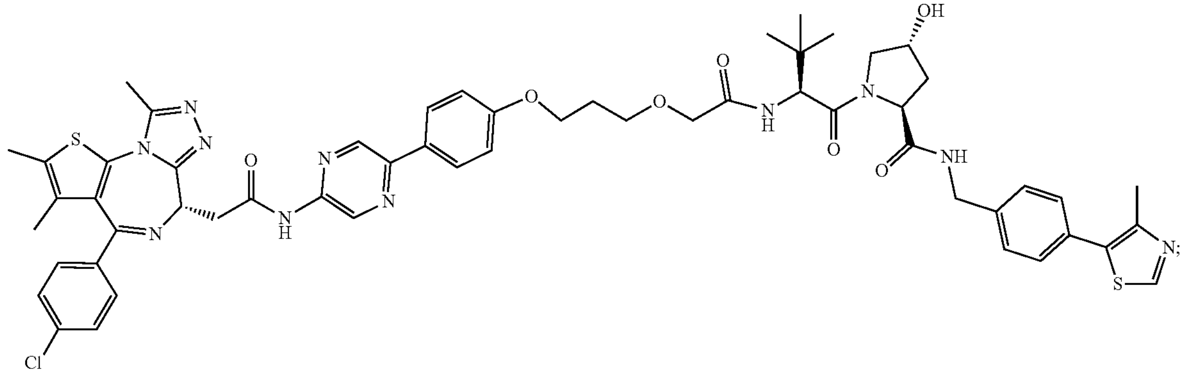
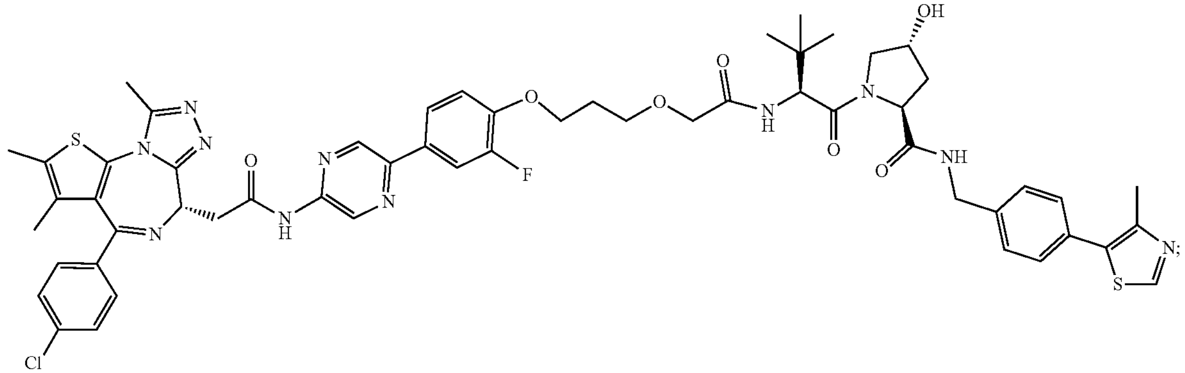
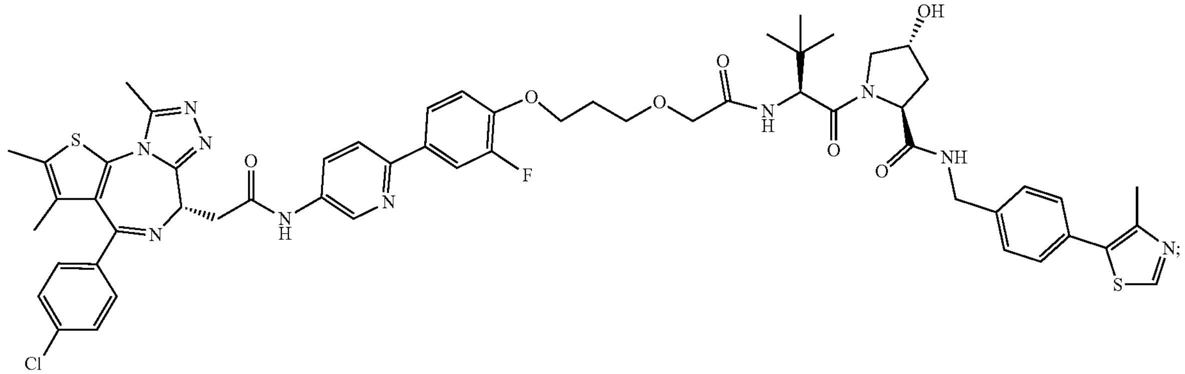

-continued
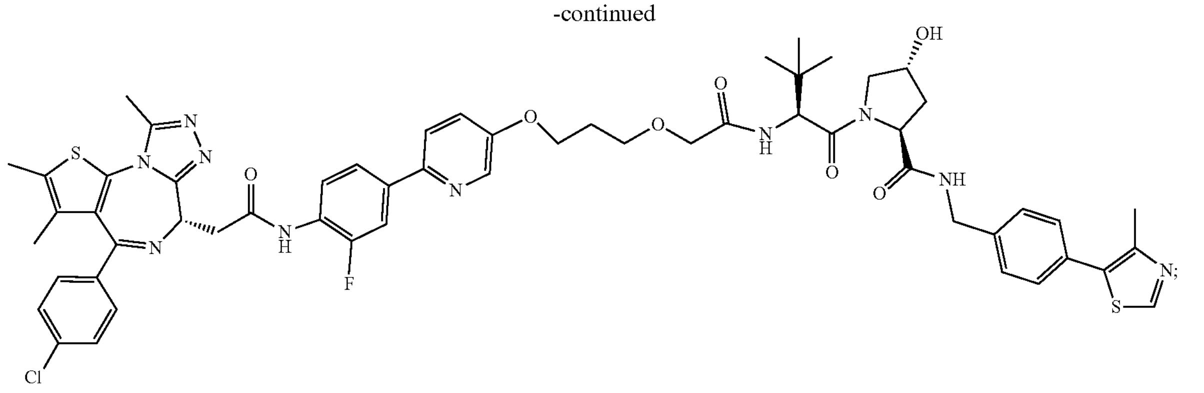
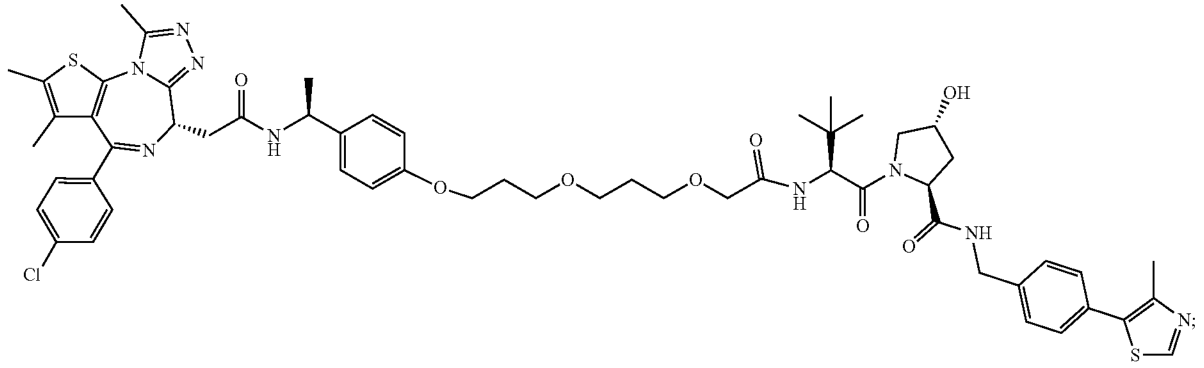
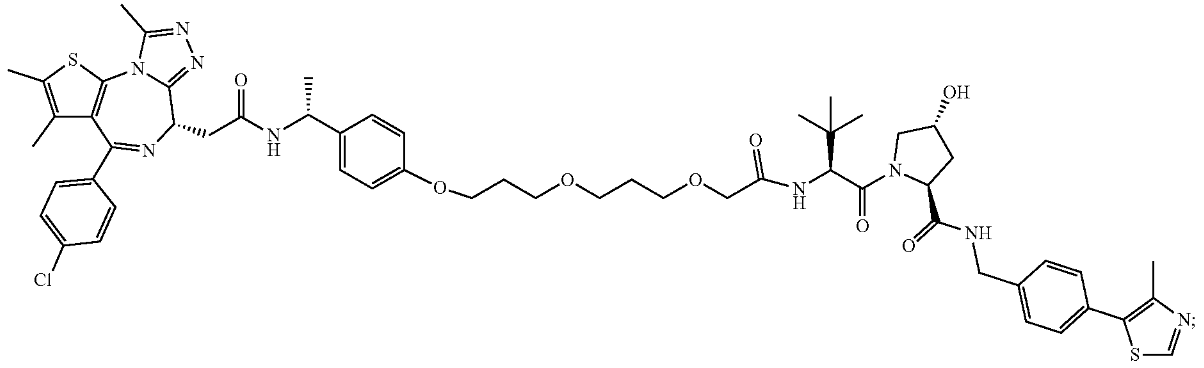
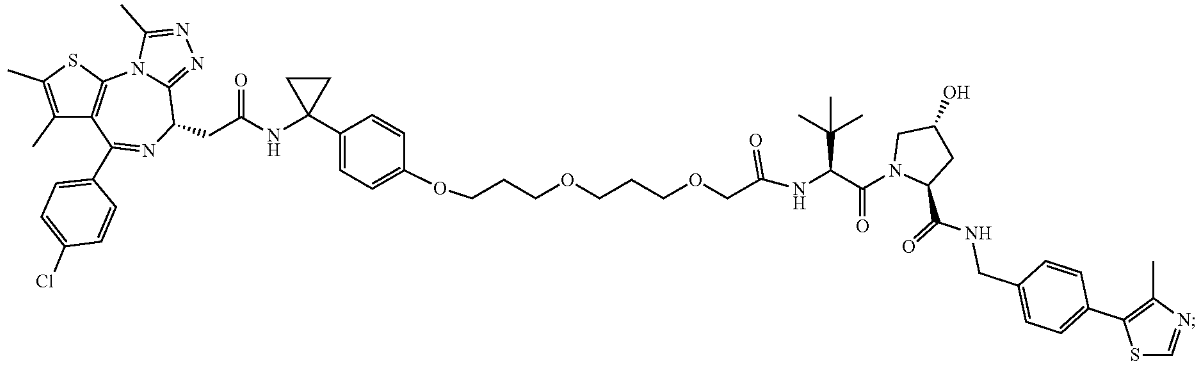

-continued
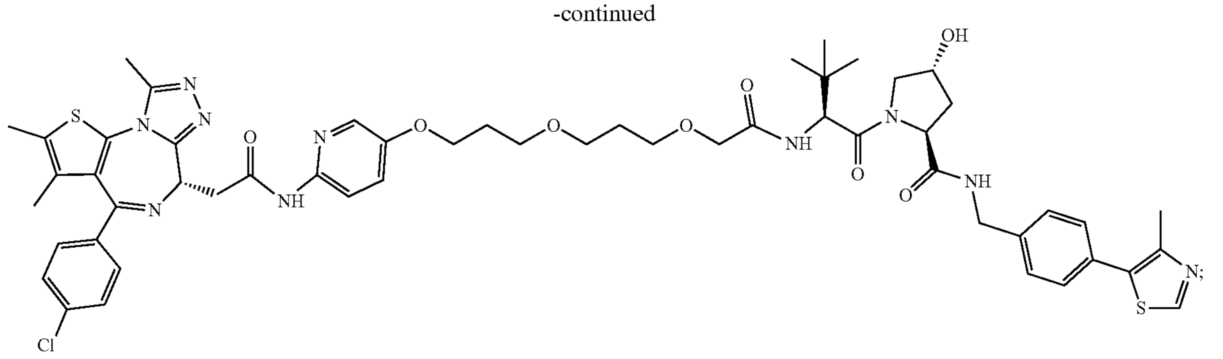
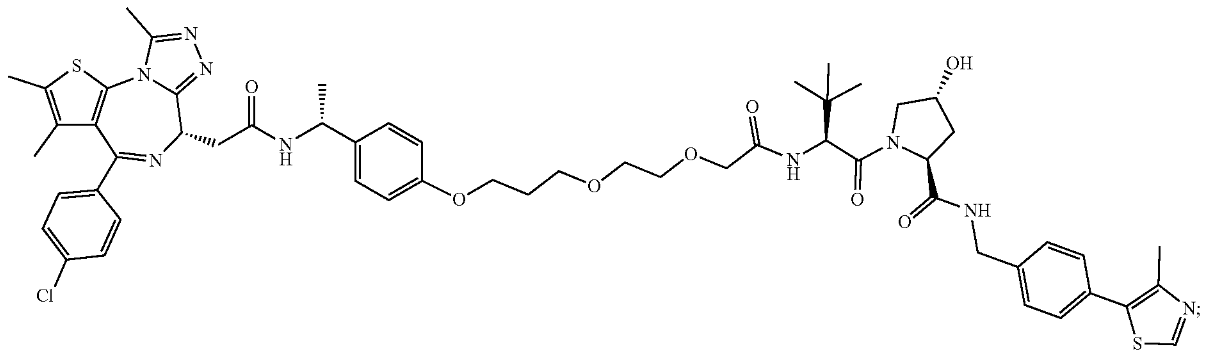
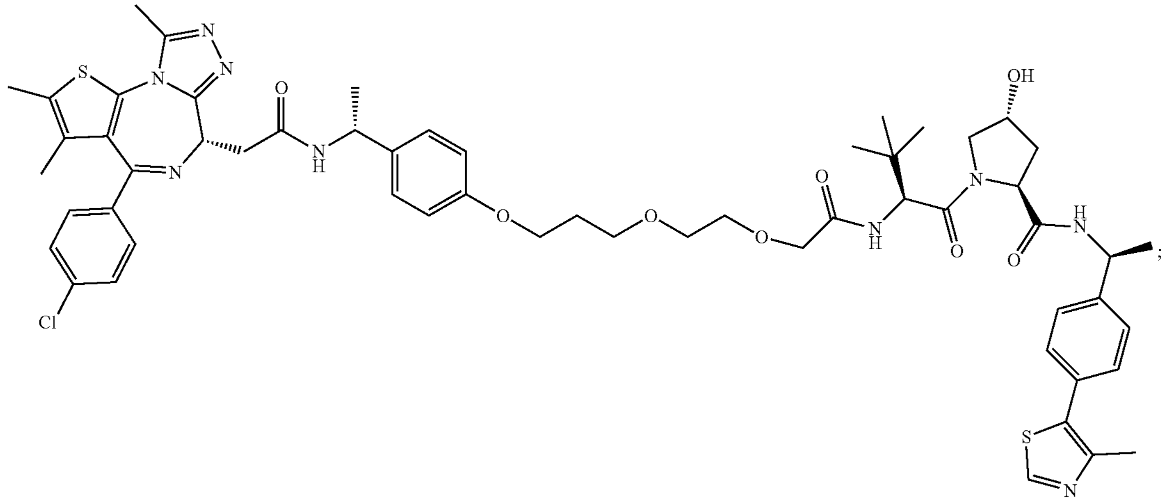
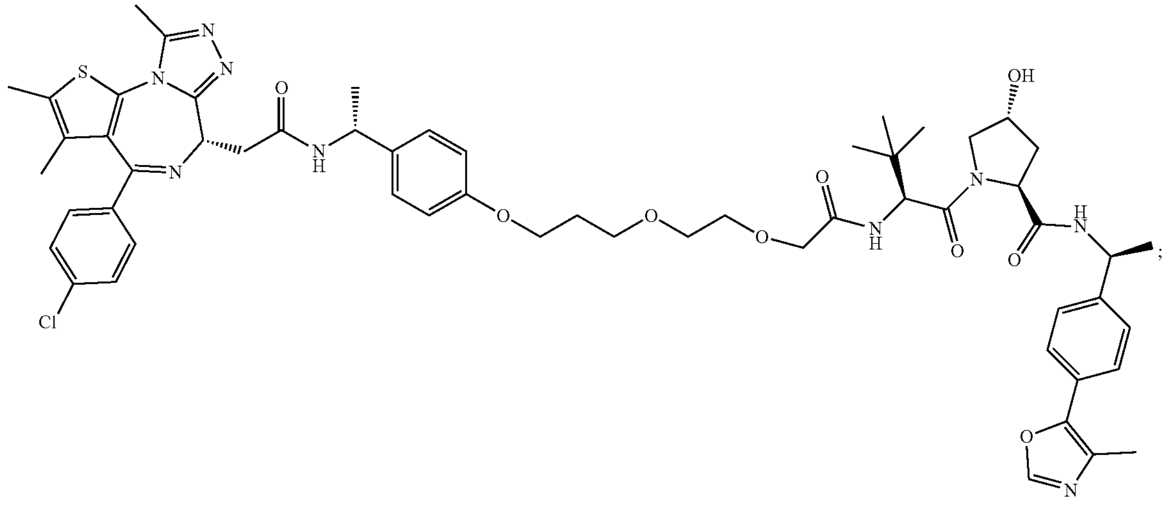

-continued
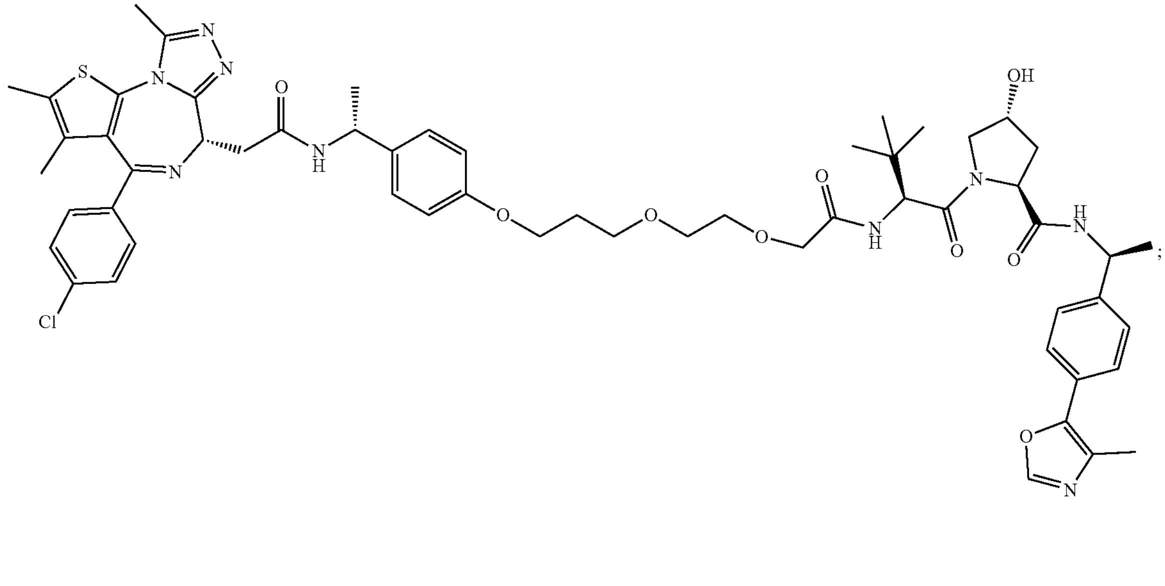
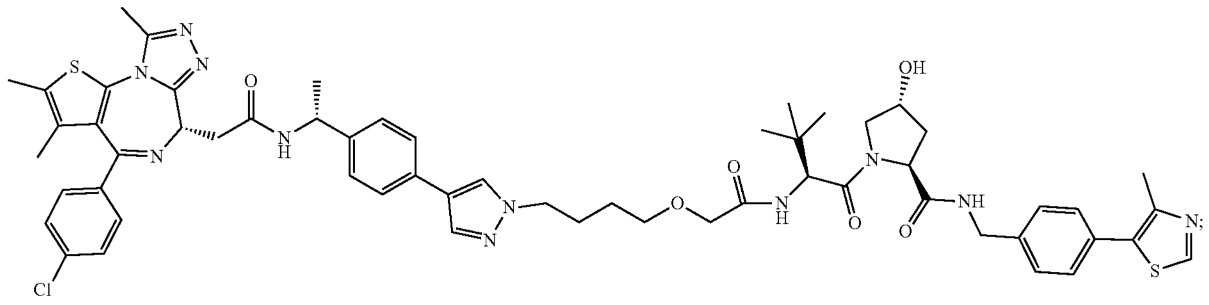
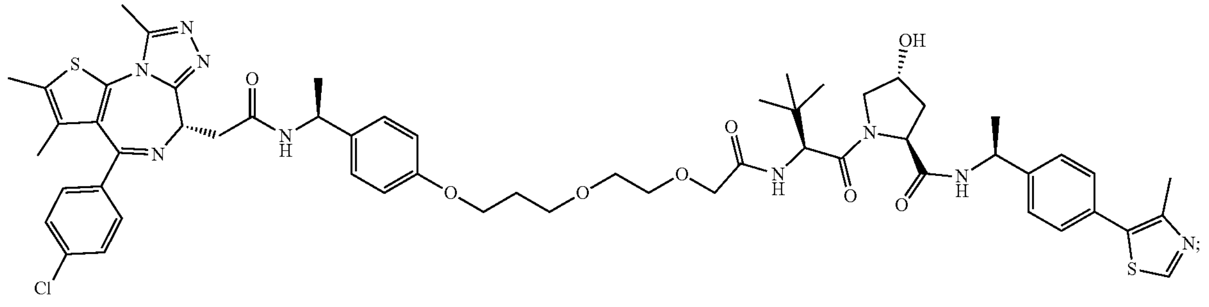
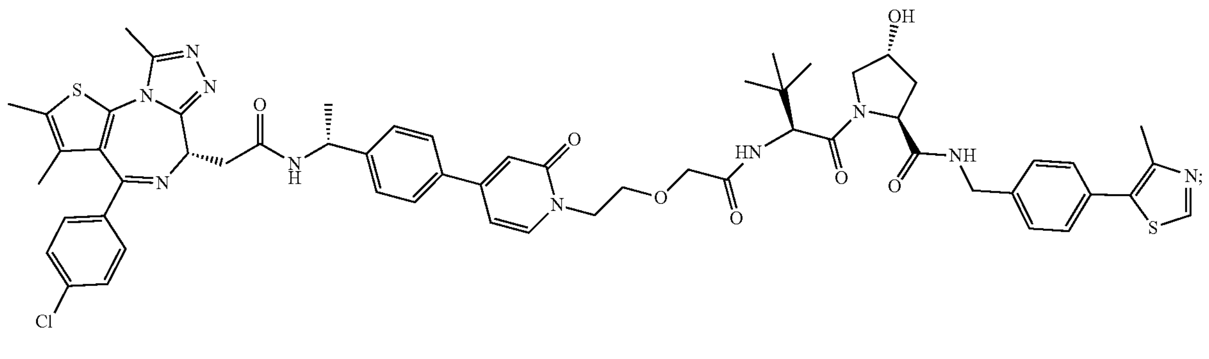

-continued
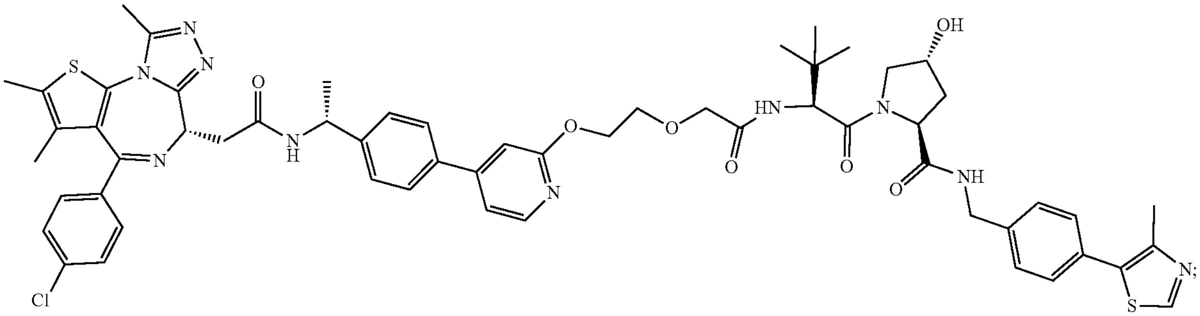
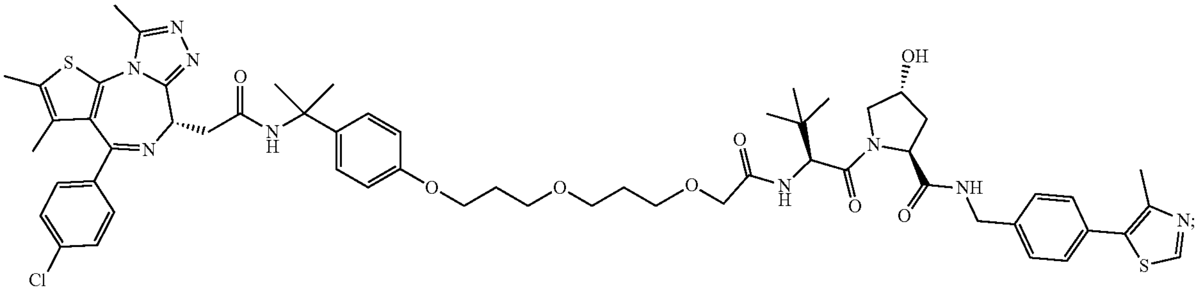
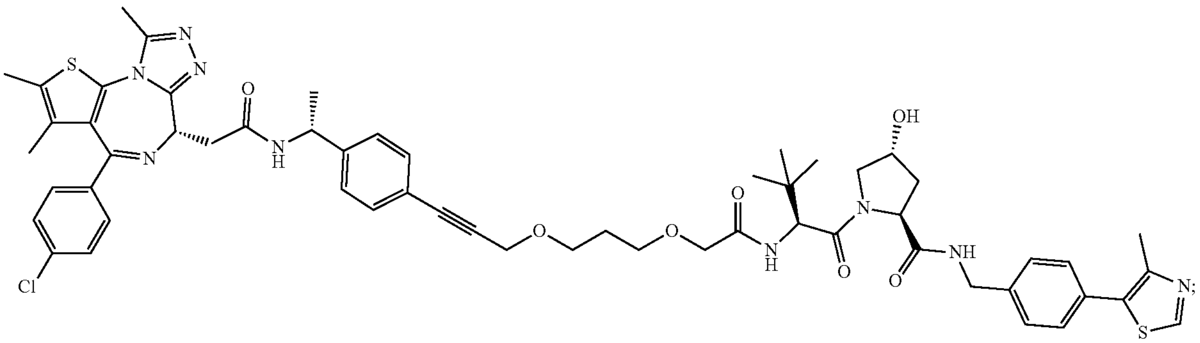
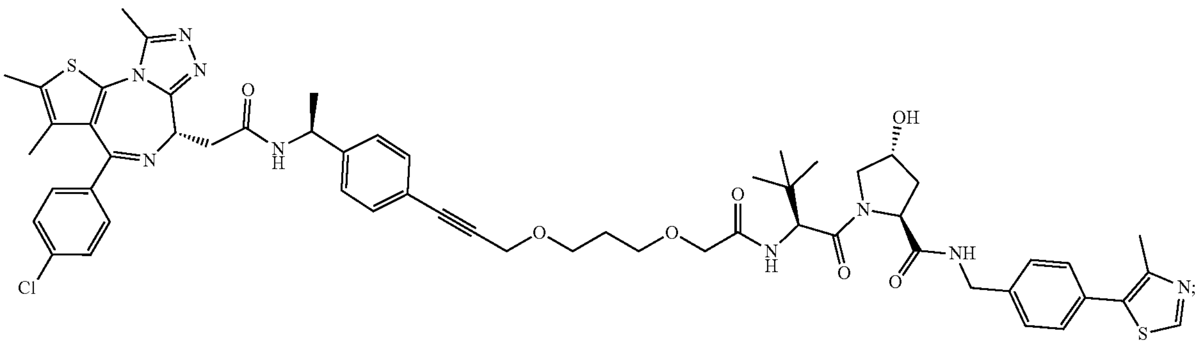
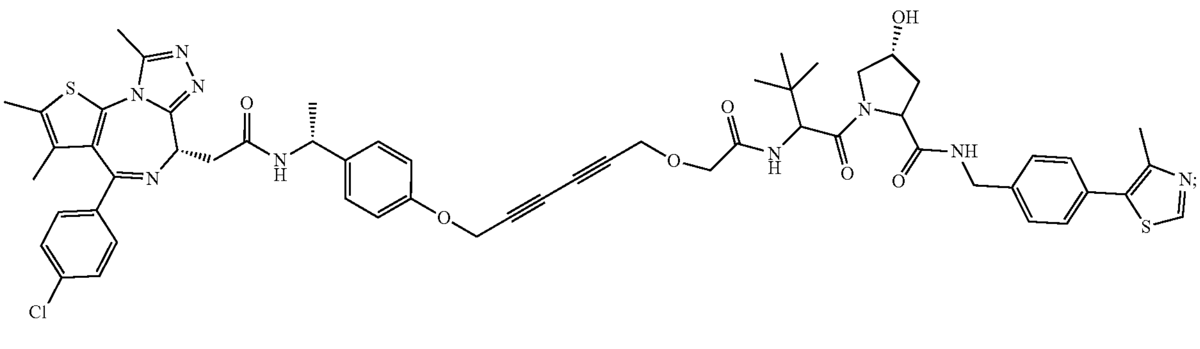

-continued
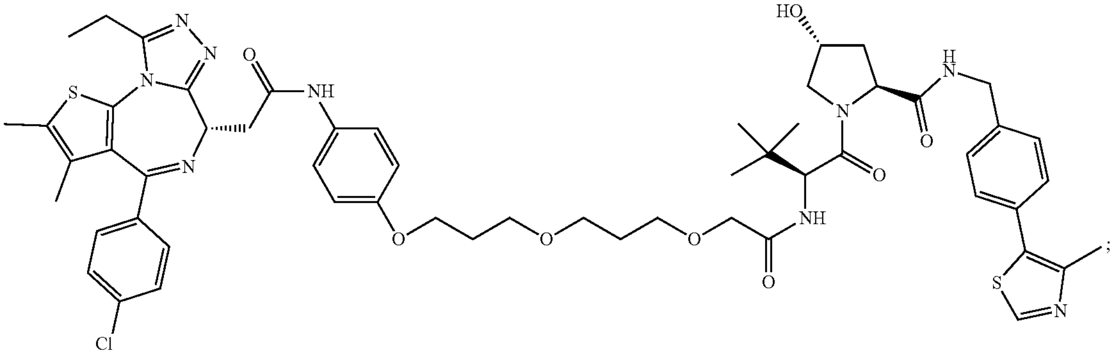
;
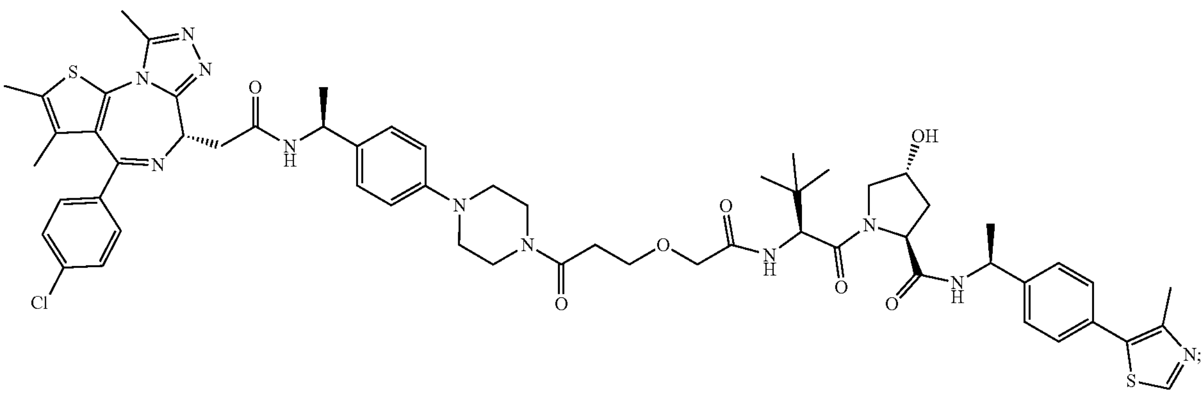
;
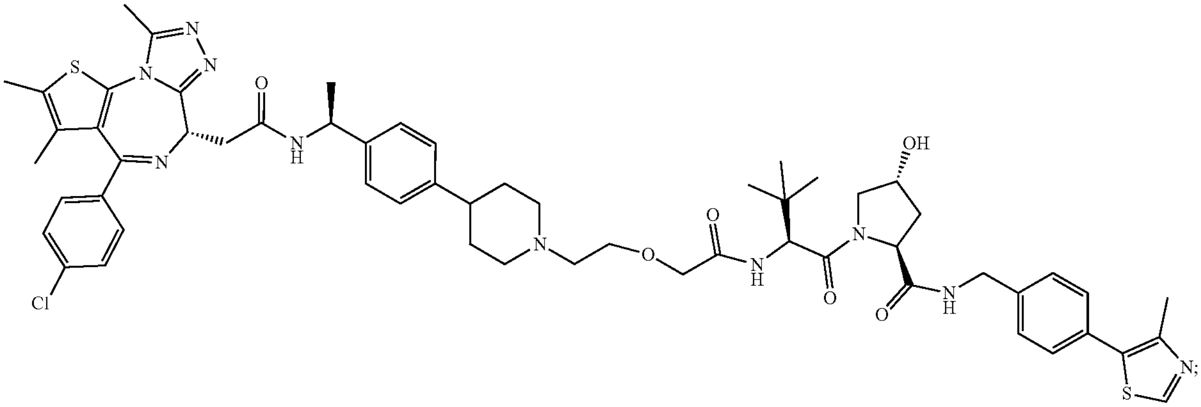
;
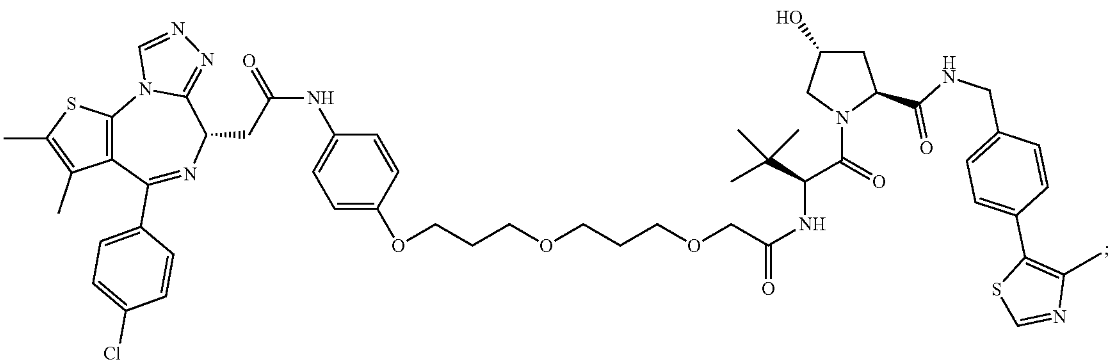
;

-continued
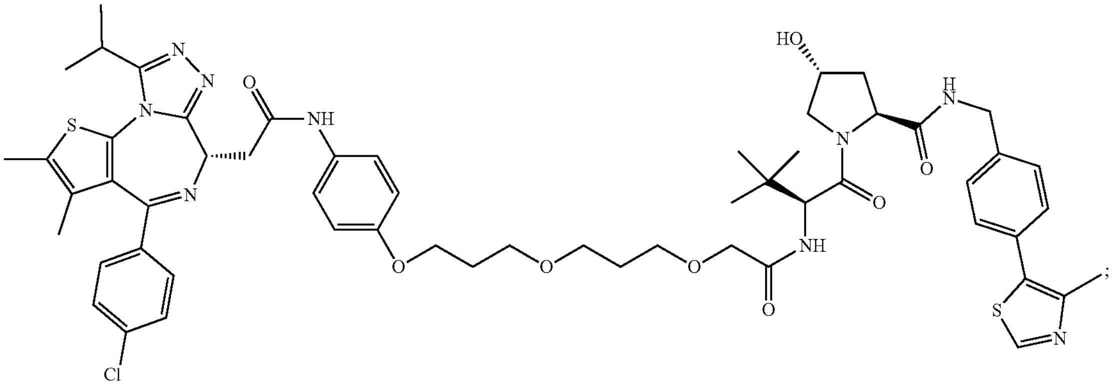
;
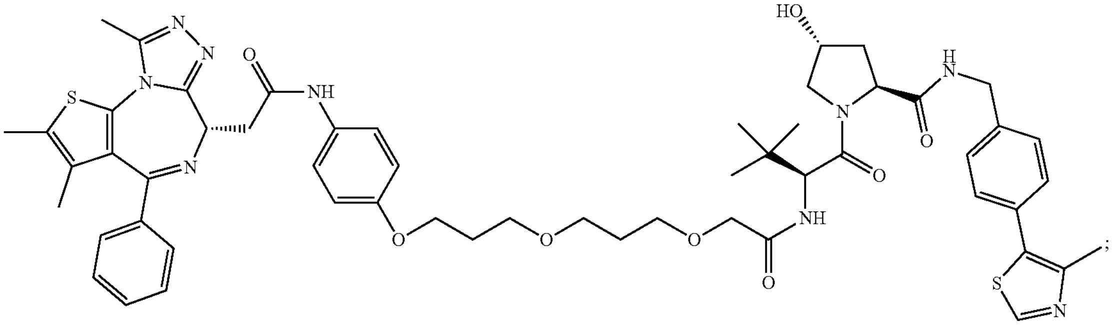
;
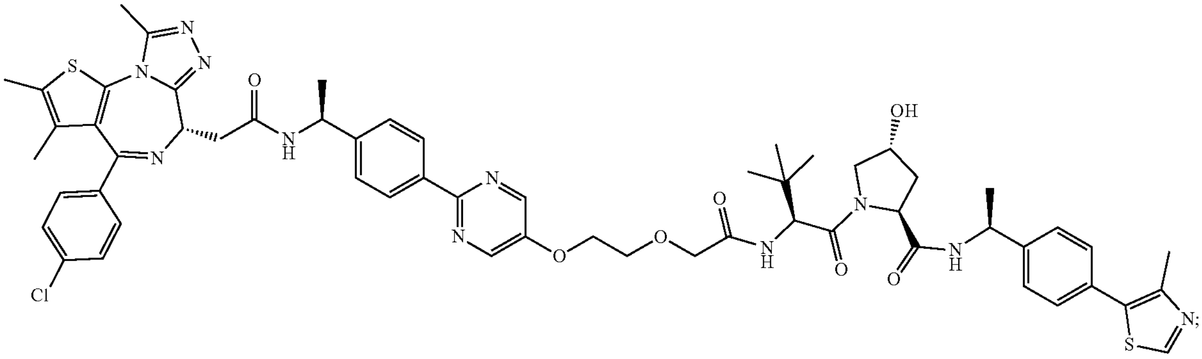
;
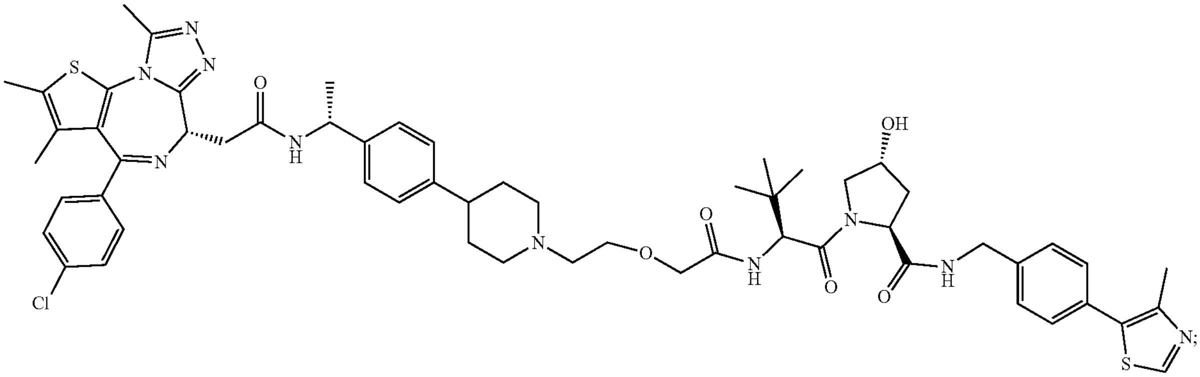
;

-continued
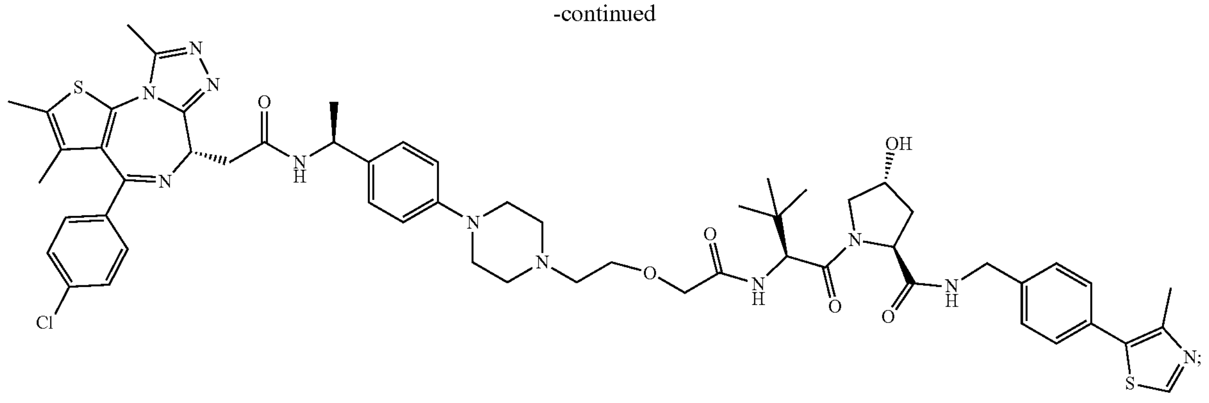
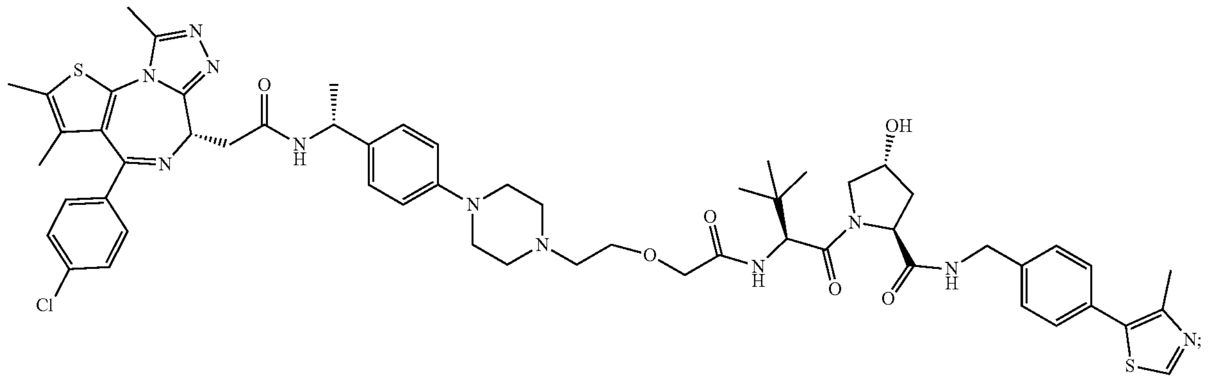
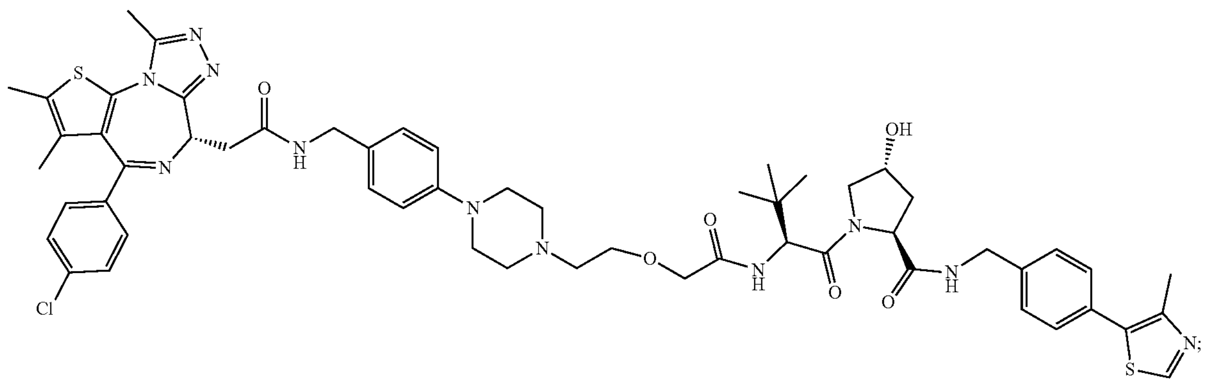
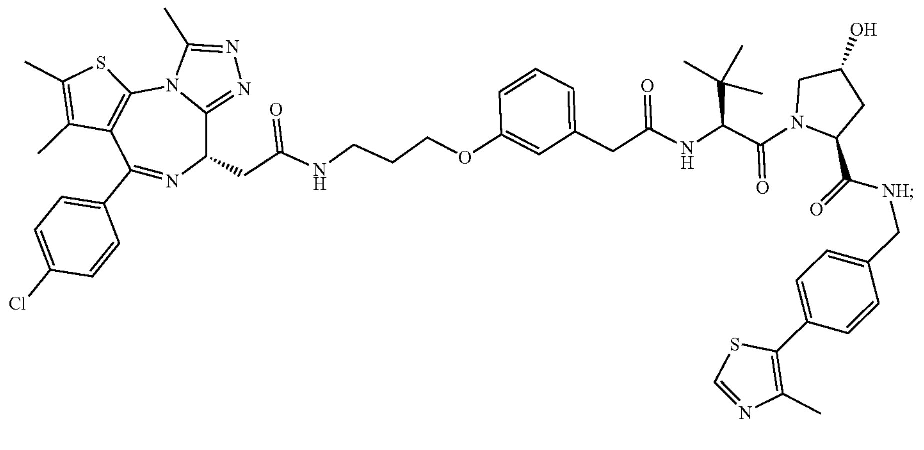

-continued
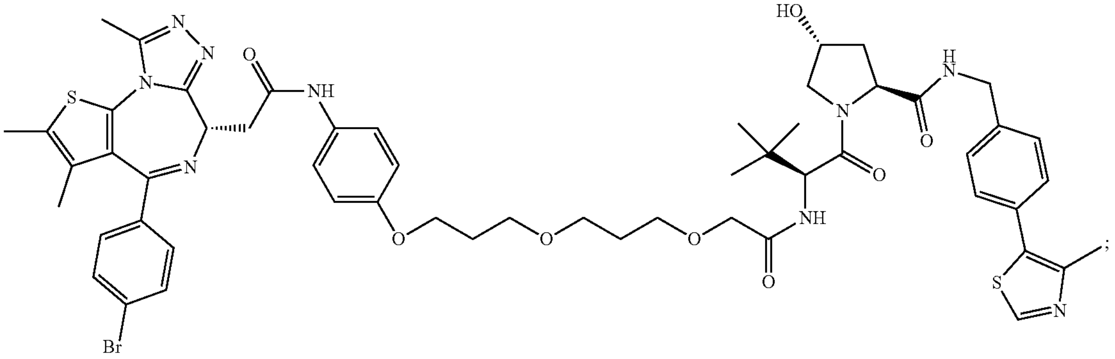
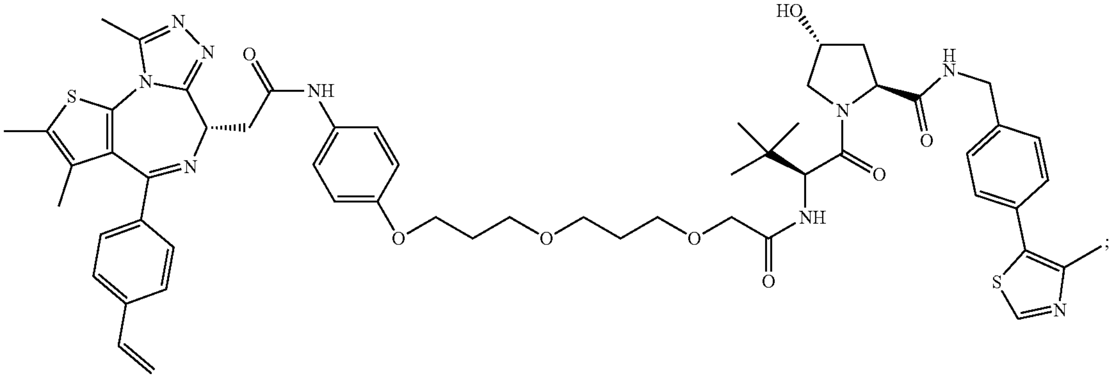
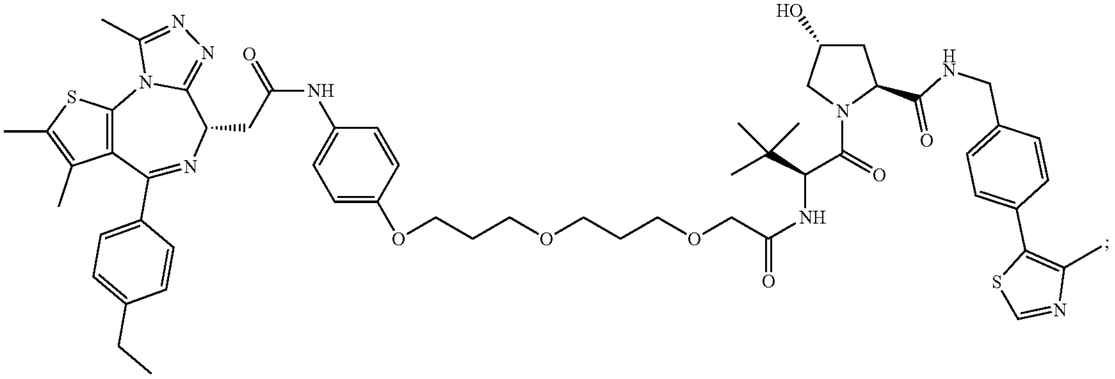
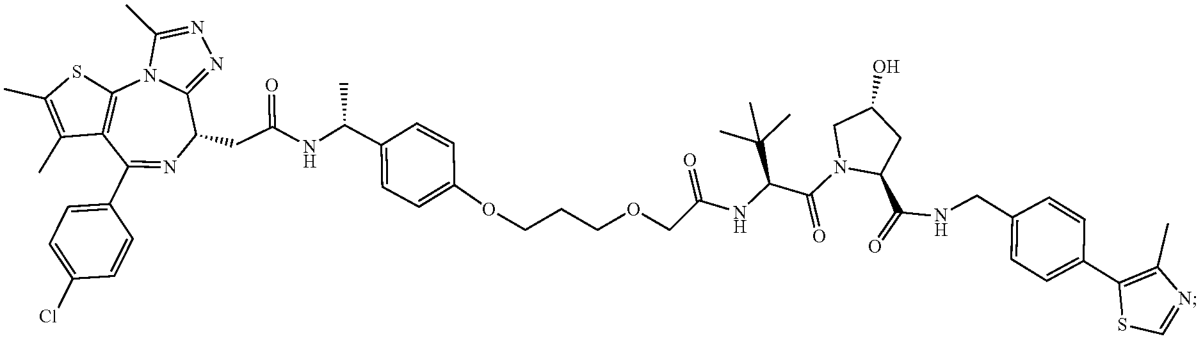

-continued
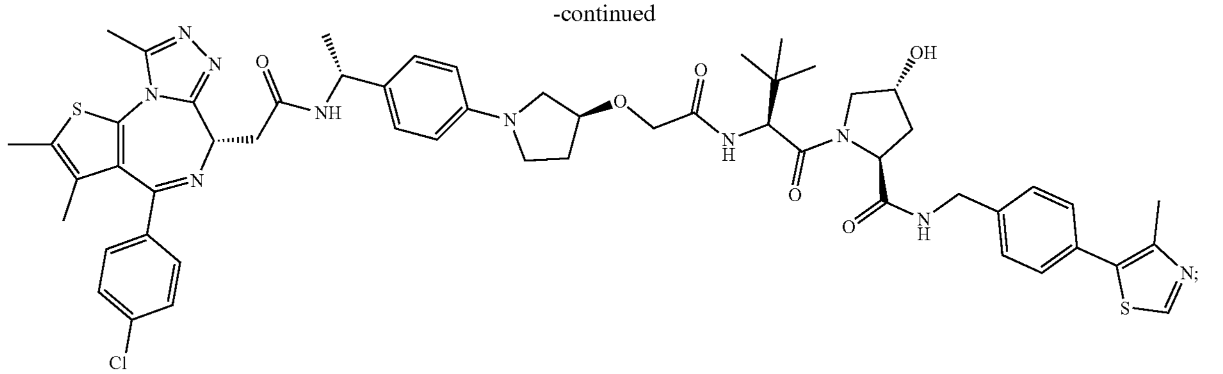
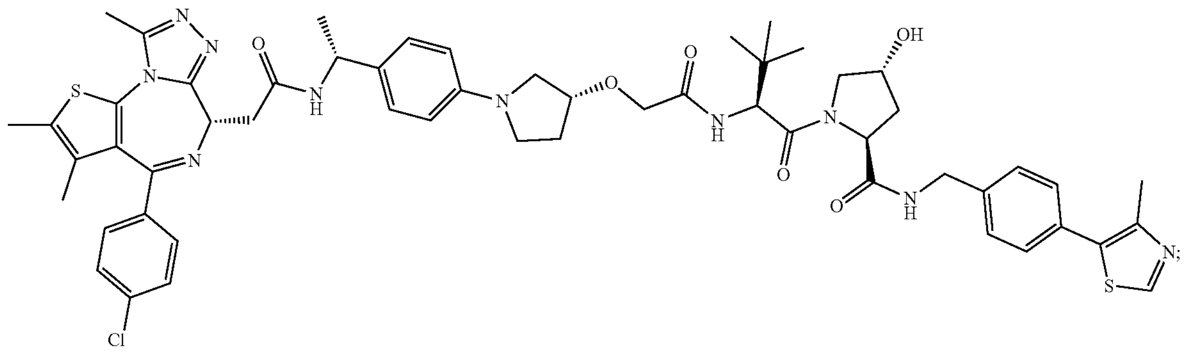
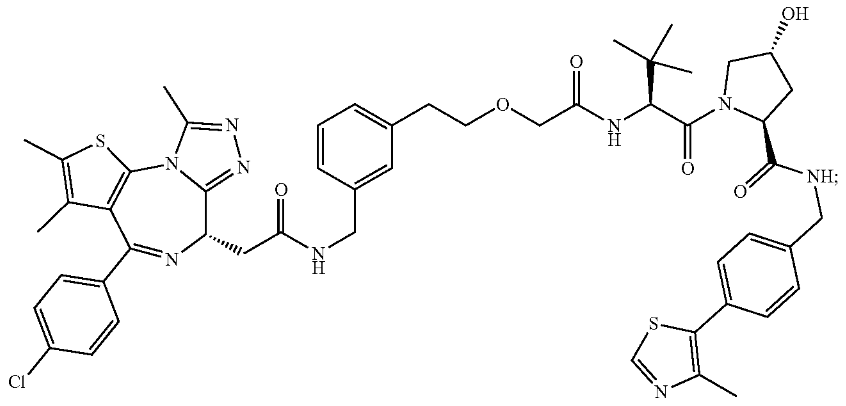
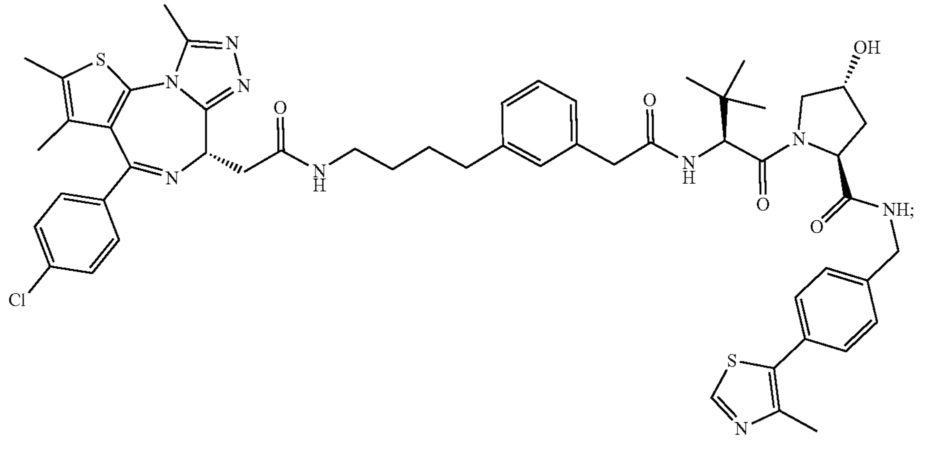

-continued
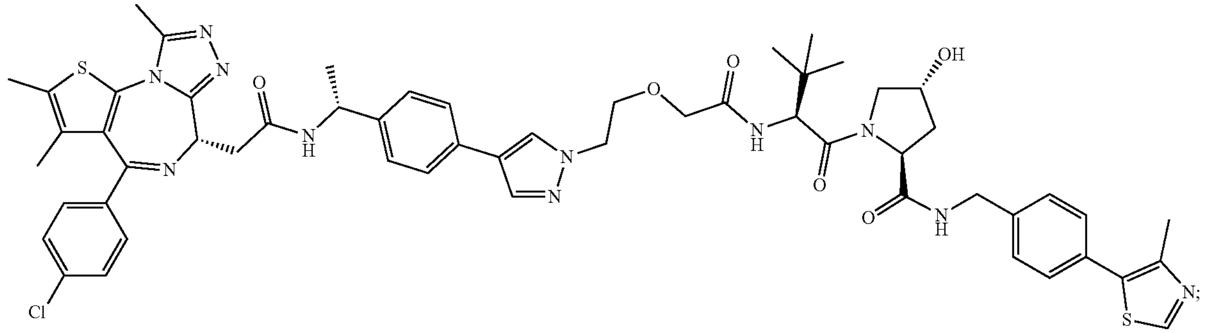
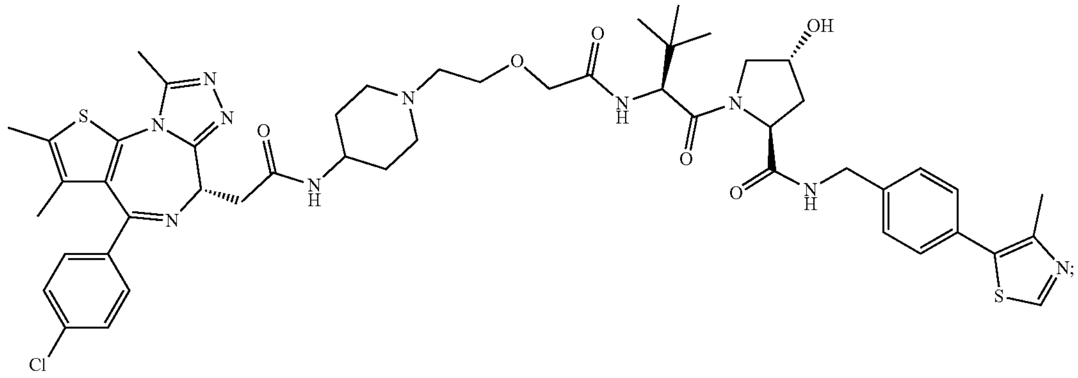
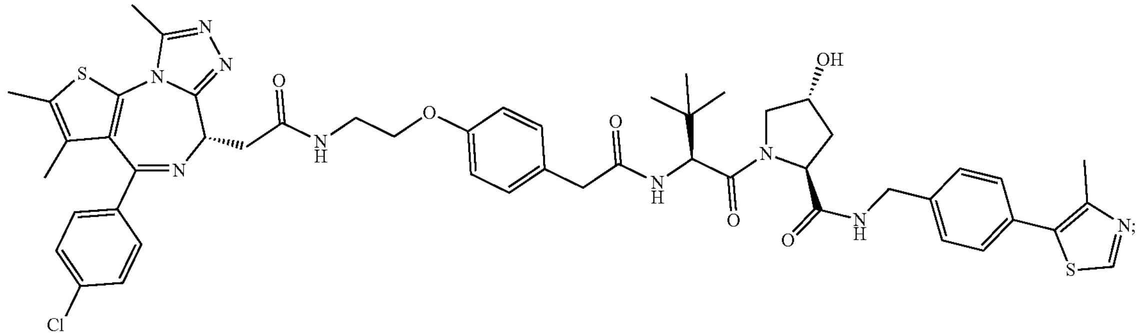
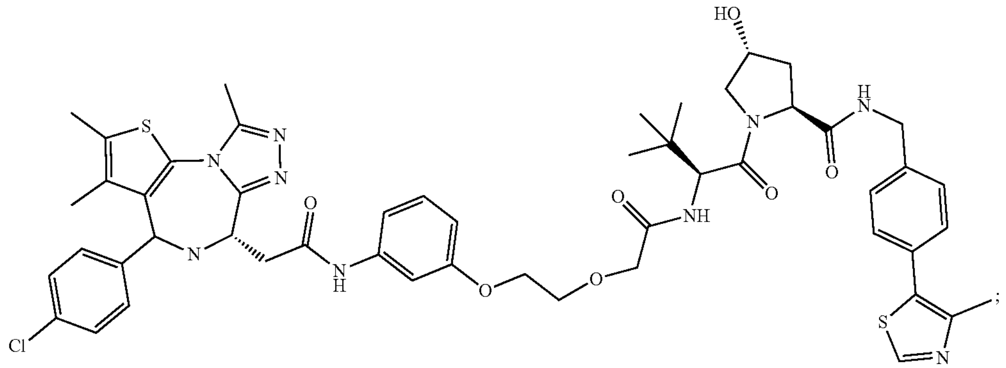
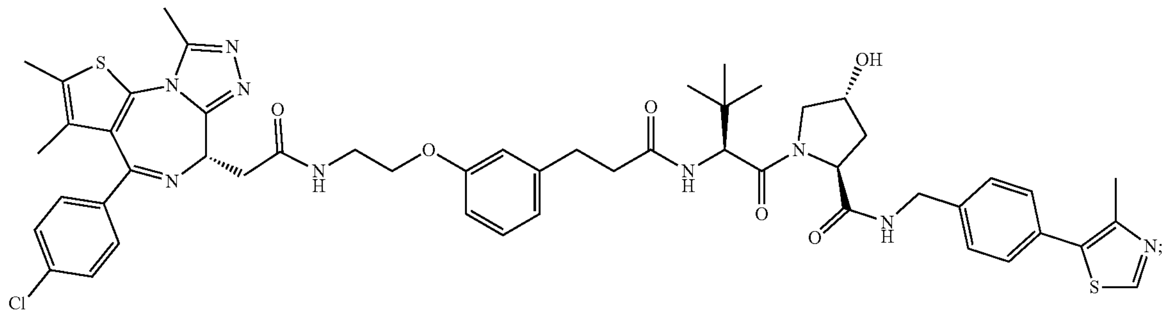

-continued
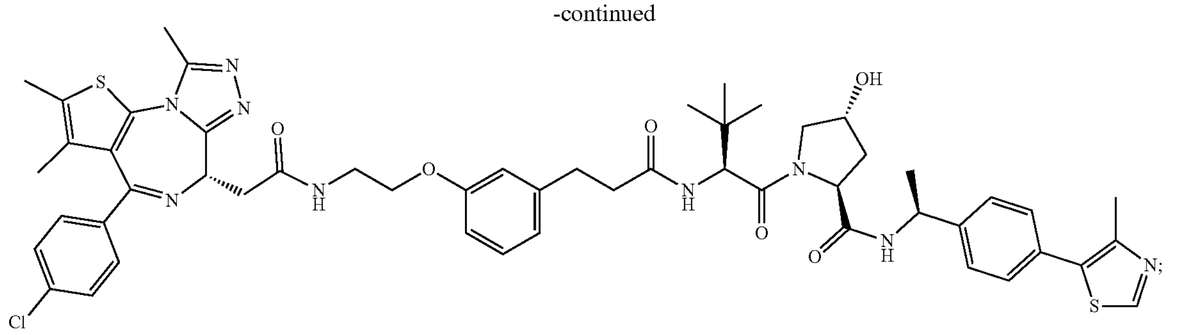
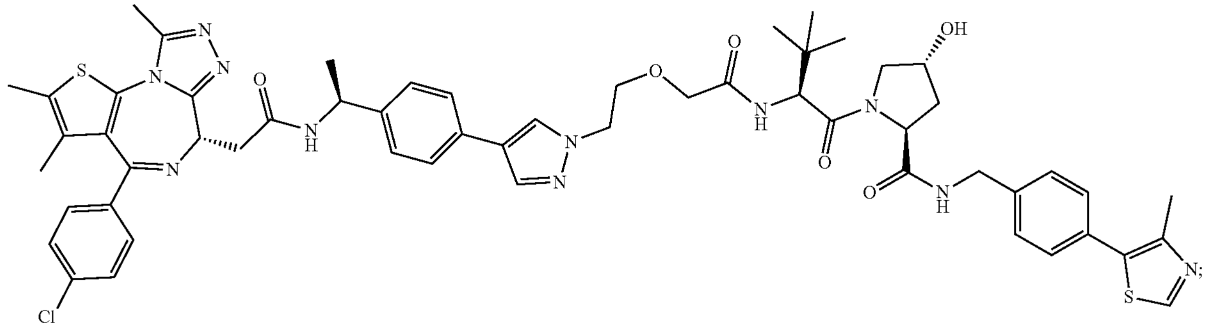
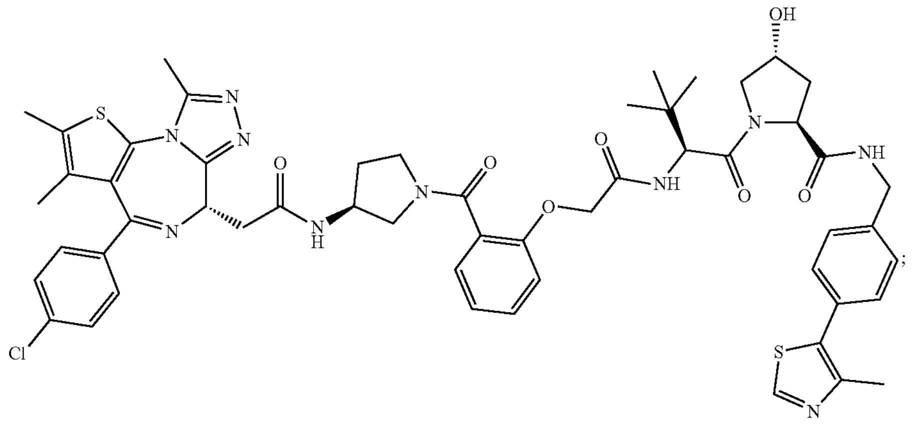
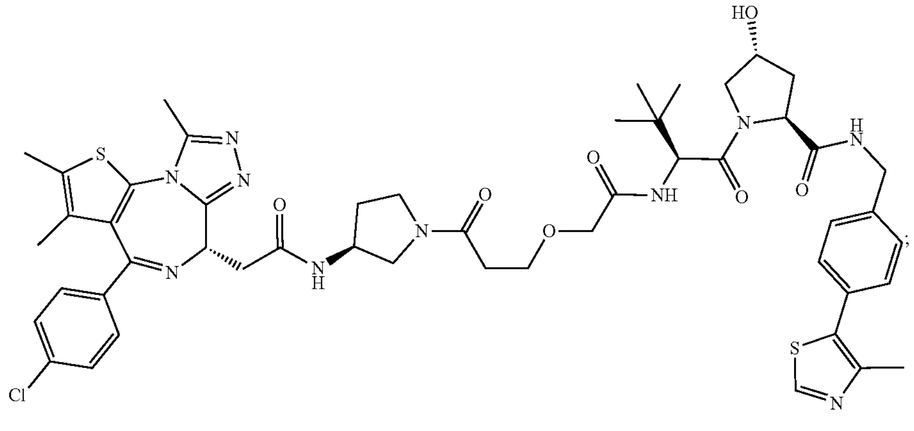

-continued
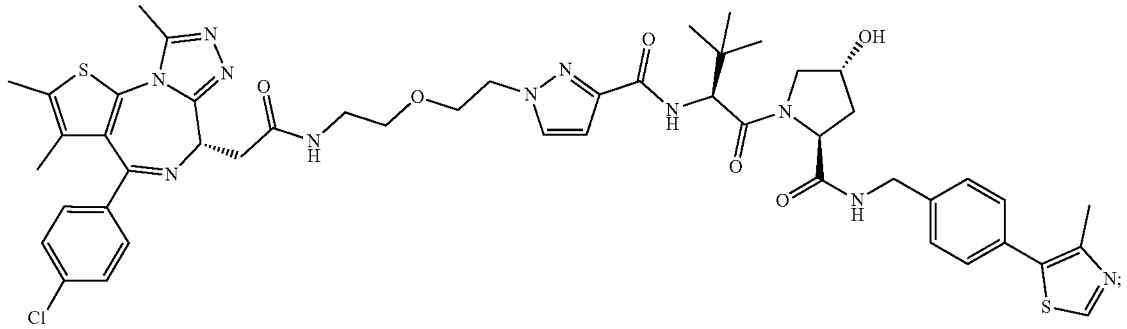
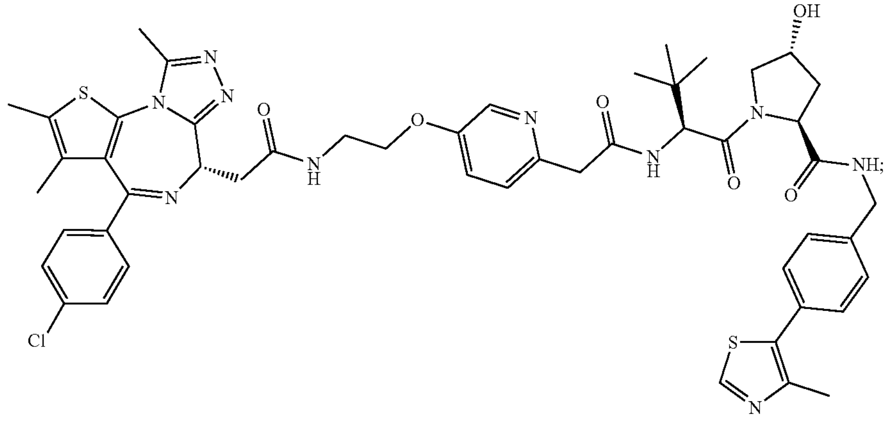
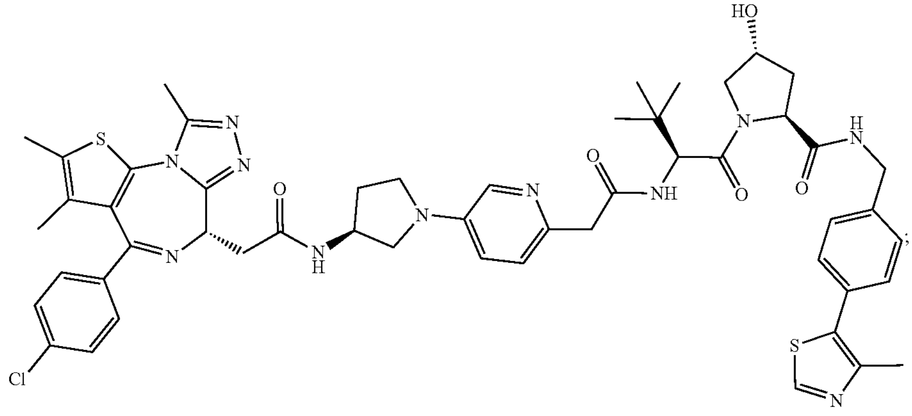
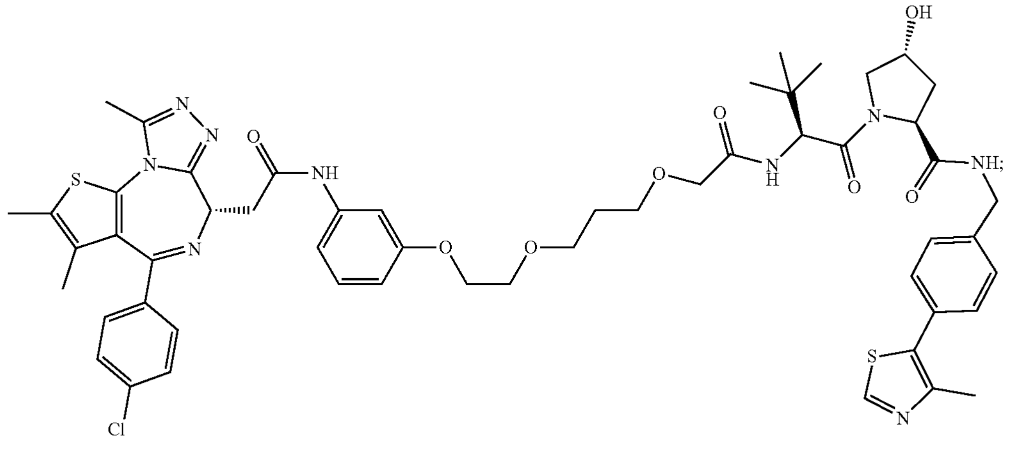

-continued
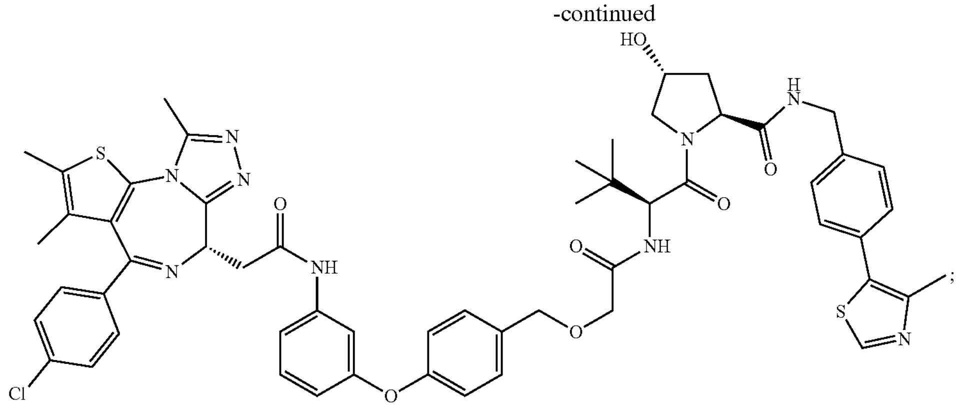
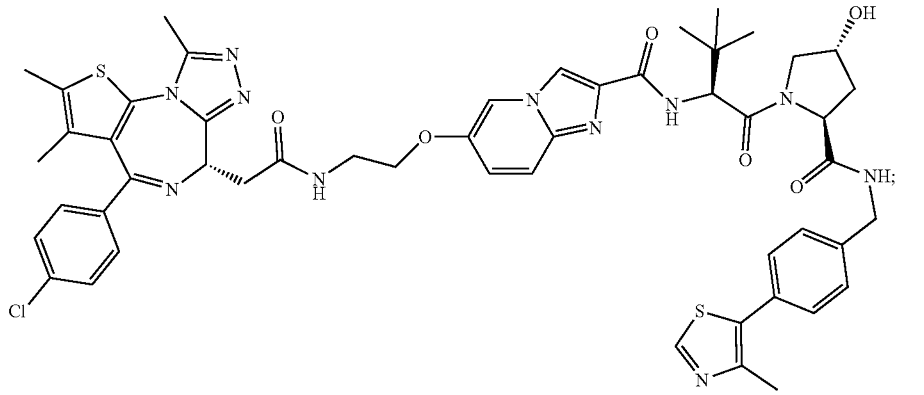
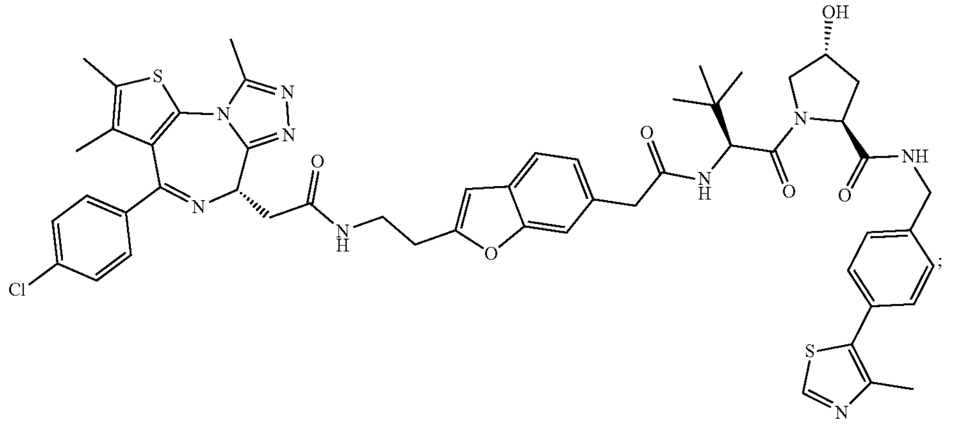
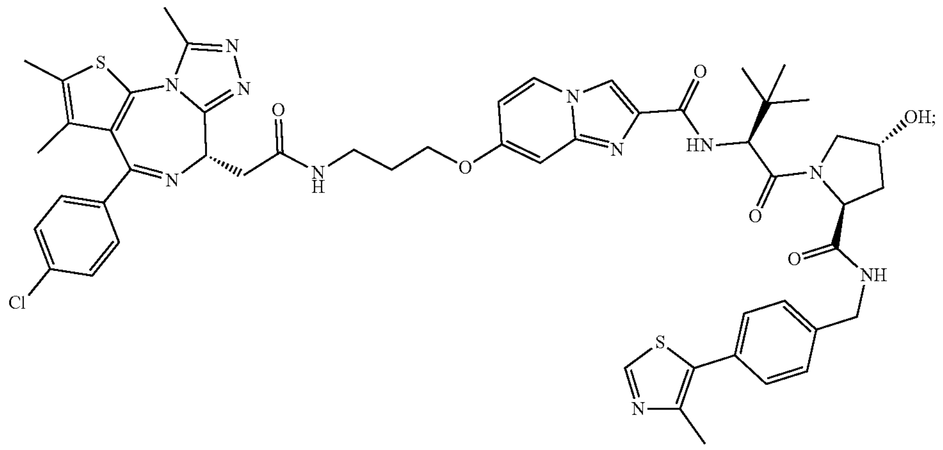

-continued
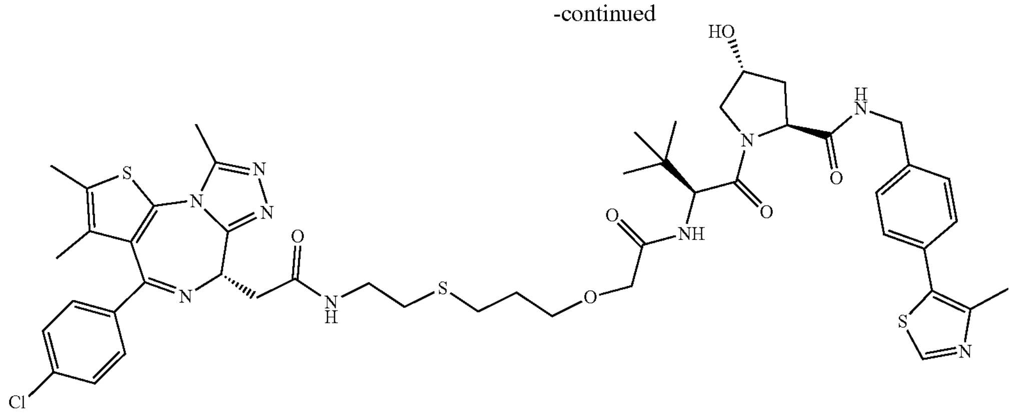
;
or a pharmaceutically acceptable salt, enantiomer, or diastereomers thereof.
21. The bifunctional compound of claim 1, wherein the bifunctional compound is selected from the group consisting of:
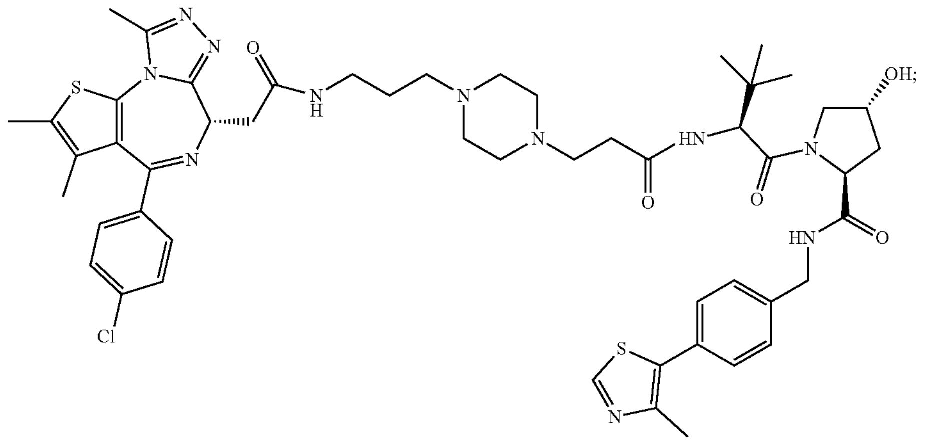
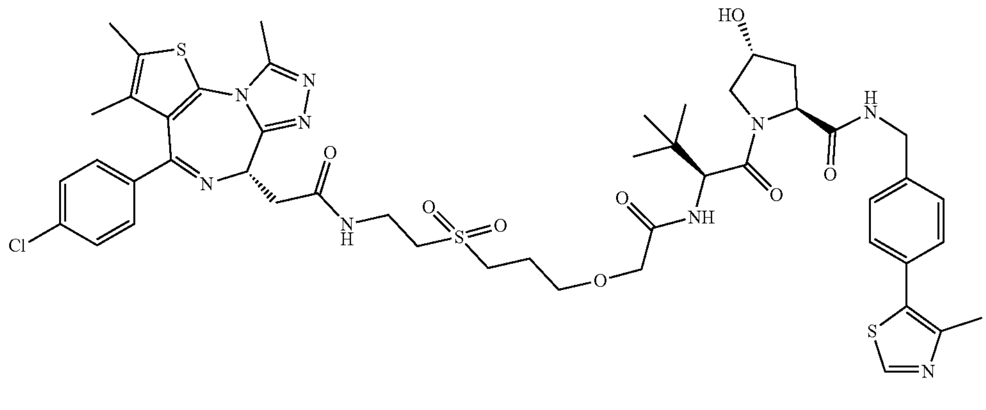
;

-continued
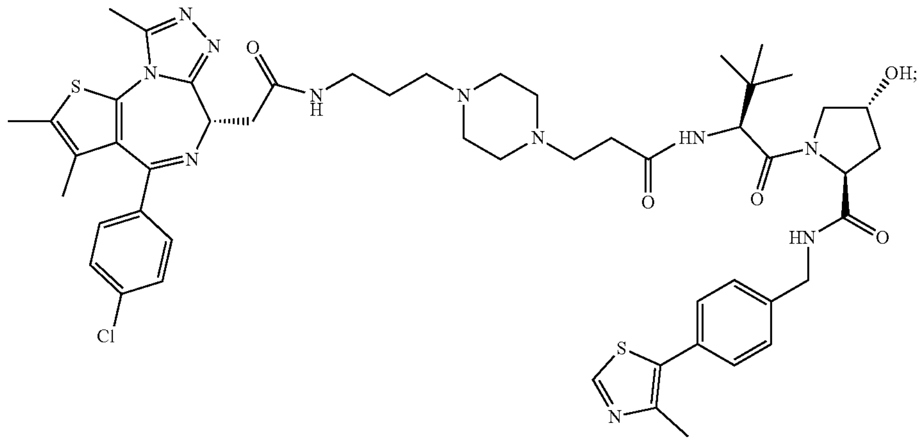
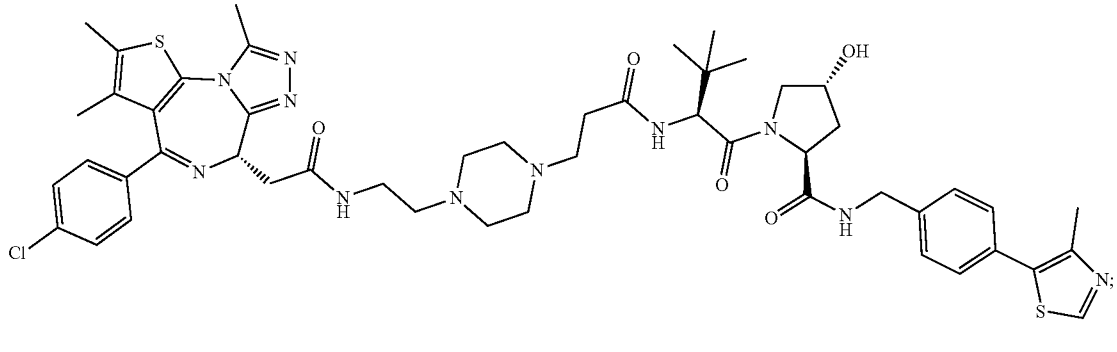
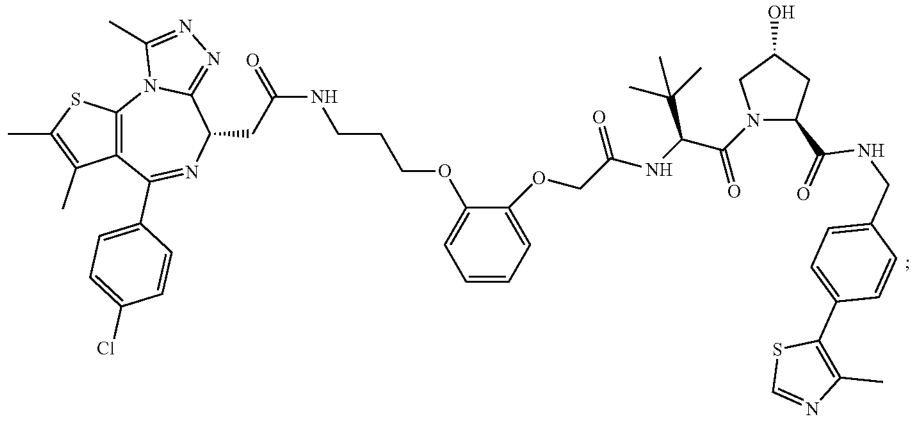
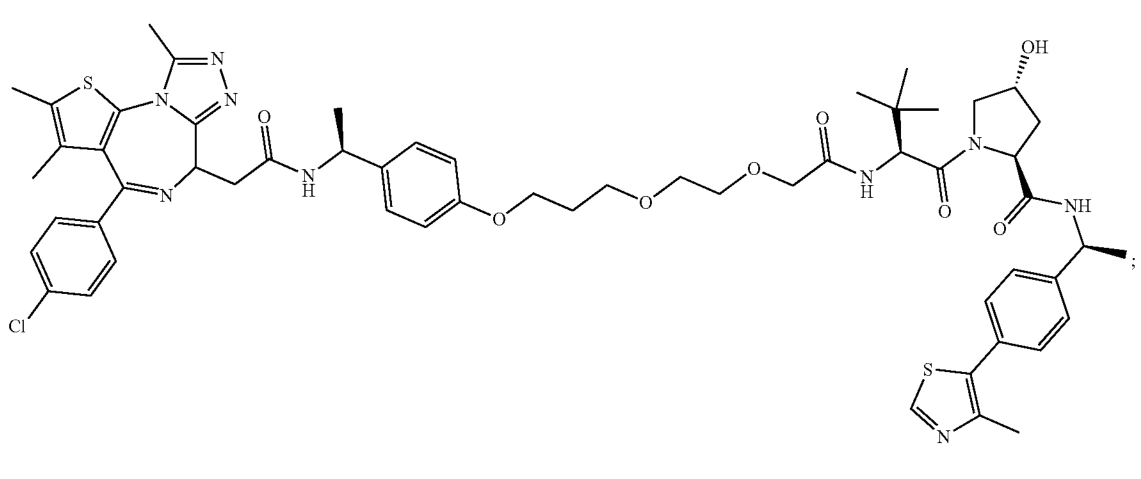

-continued
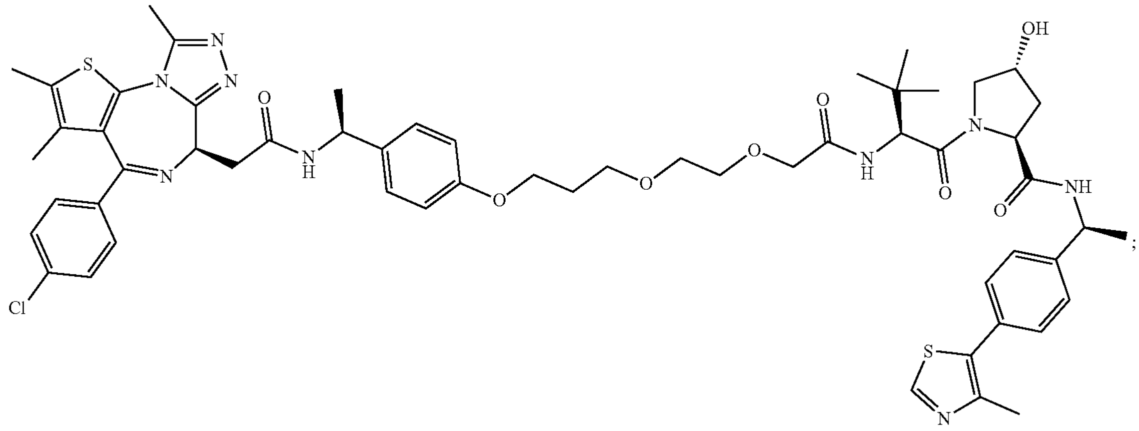
;
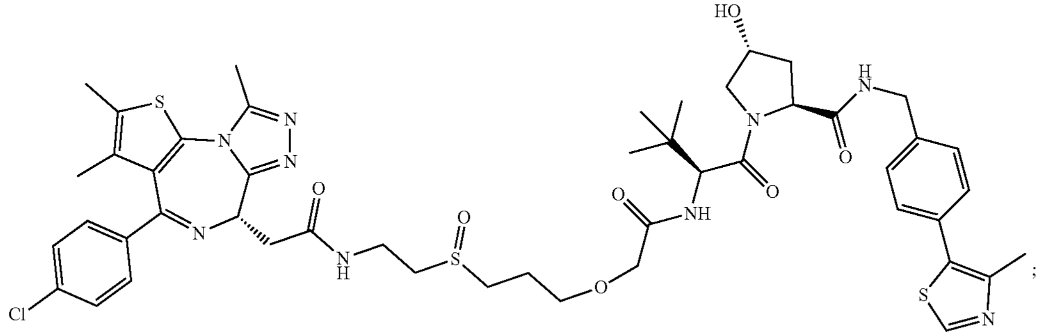
;
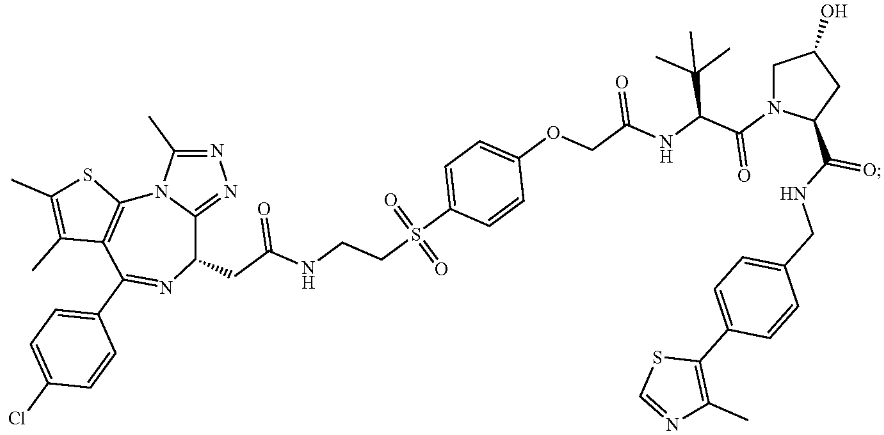
;
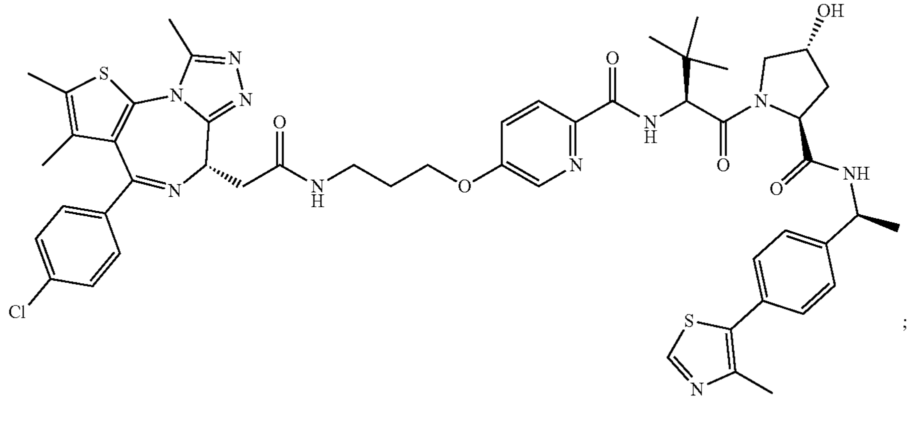
;

-continued
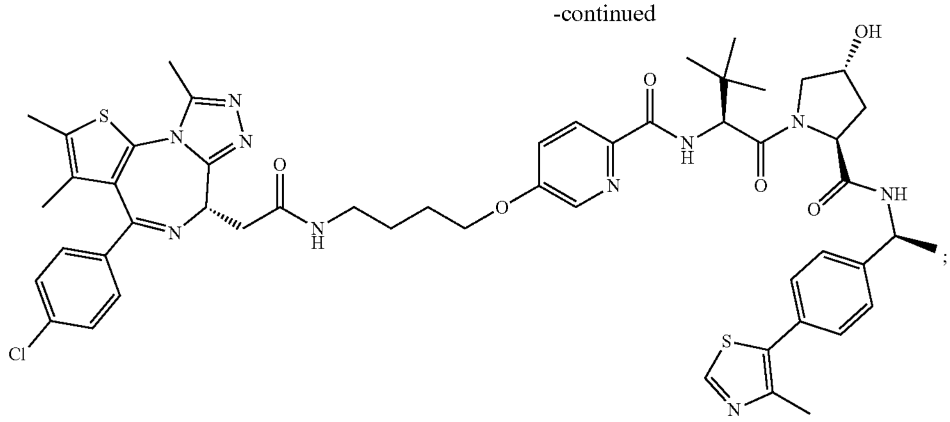
;
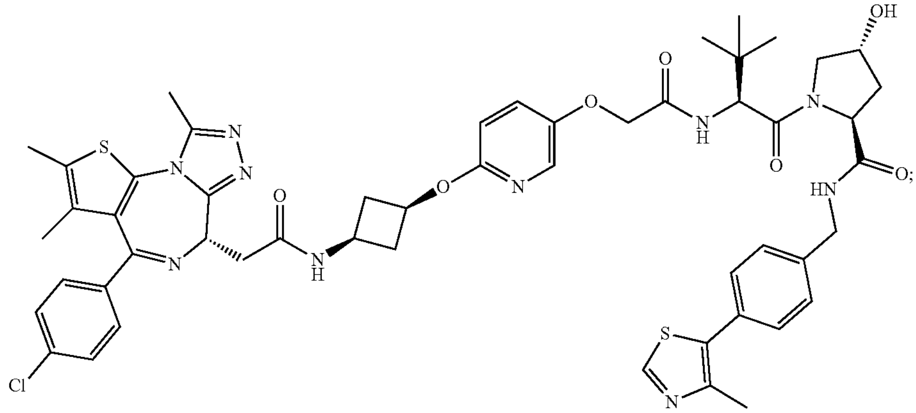
;
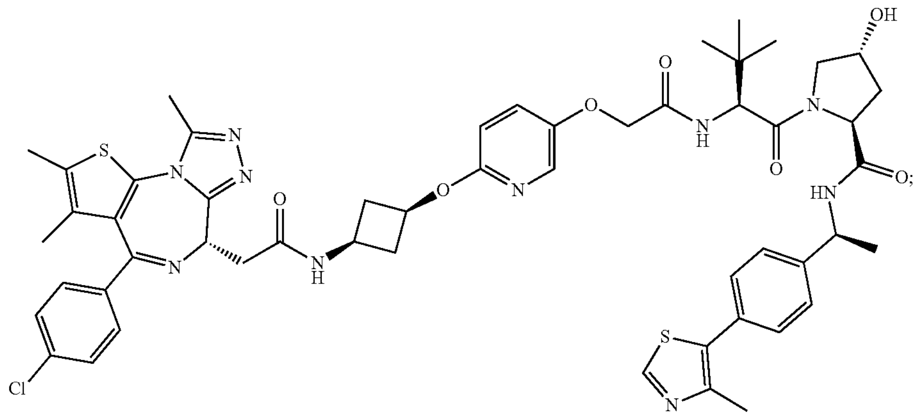
;
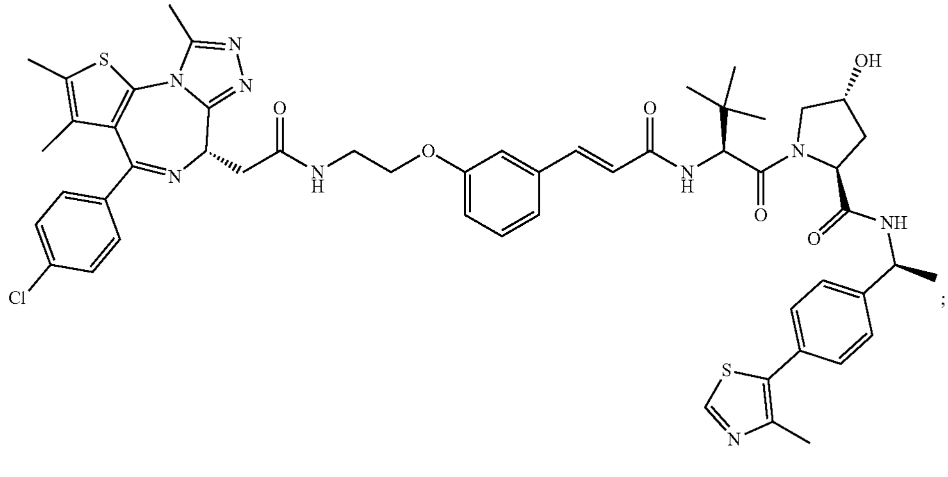
;

-continued
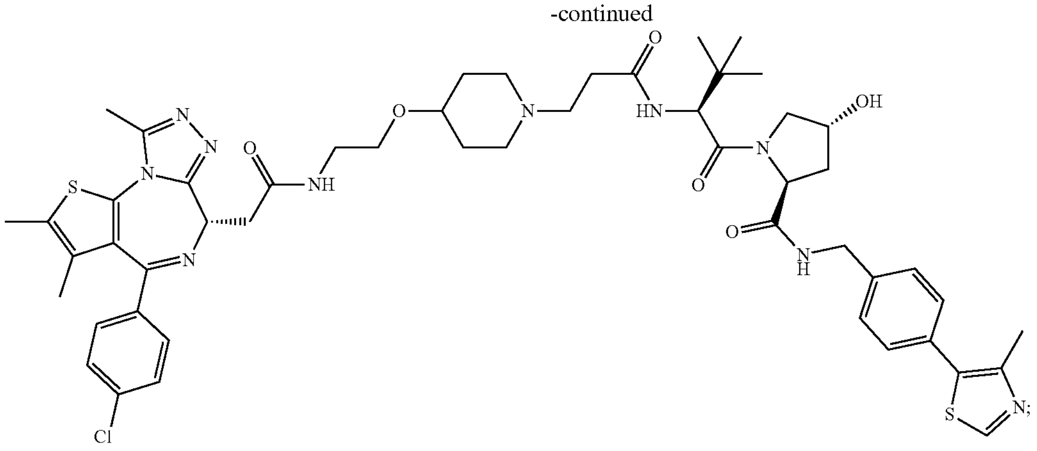
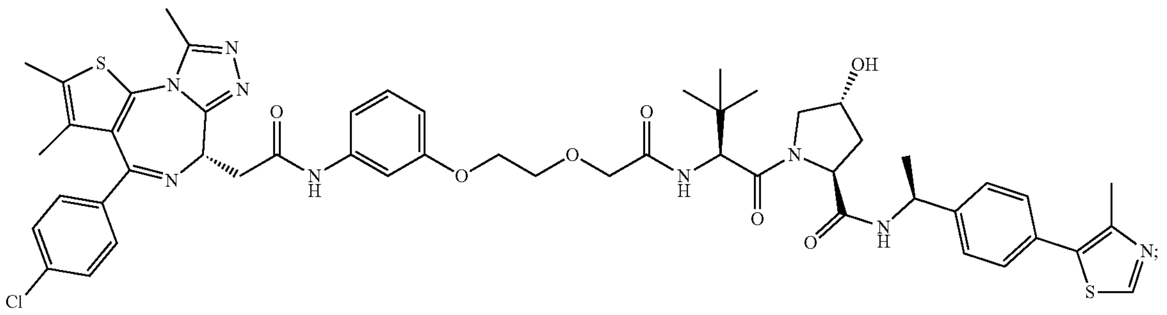
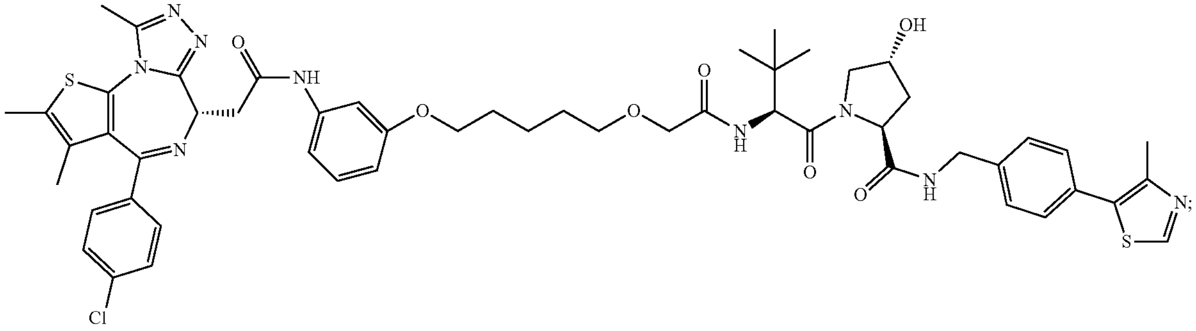
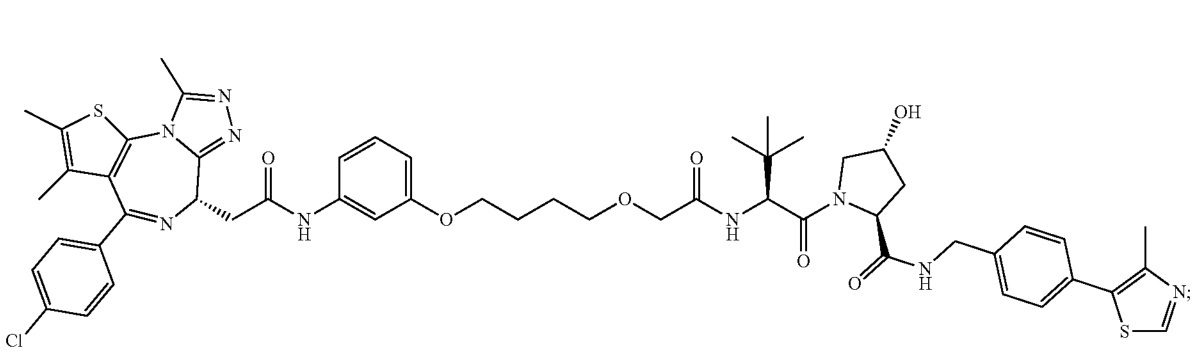

-continued
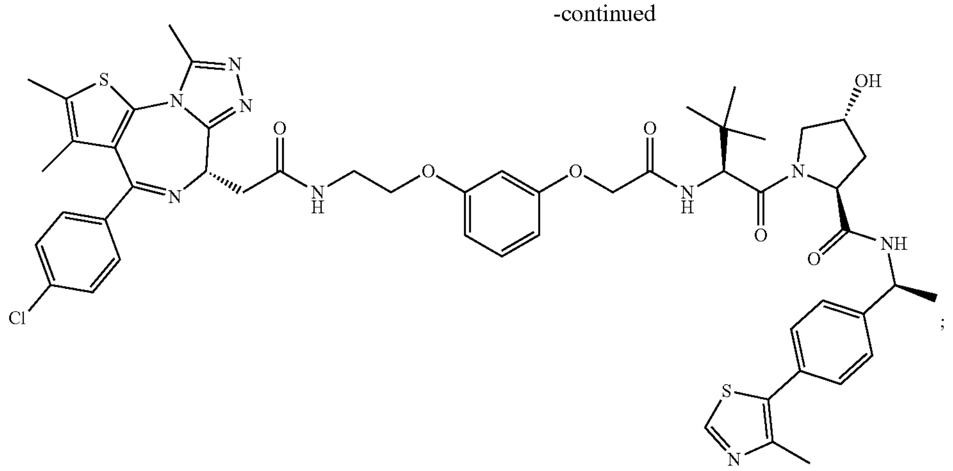
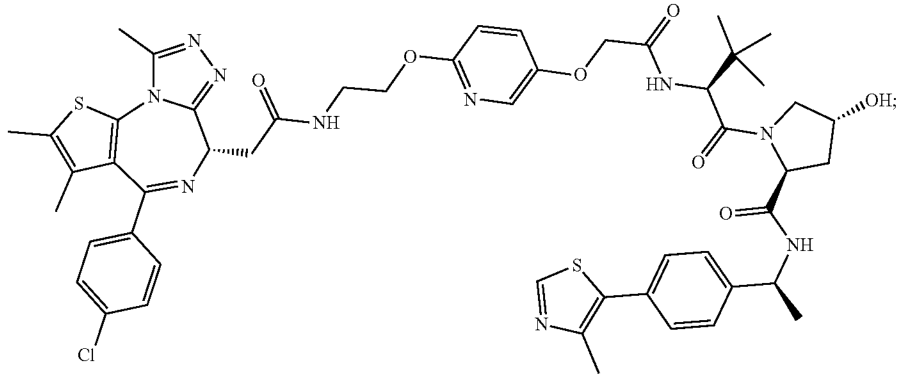
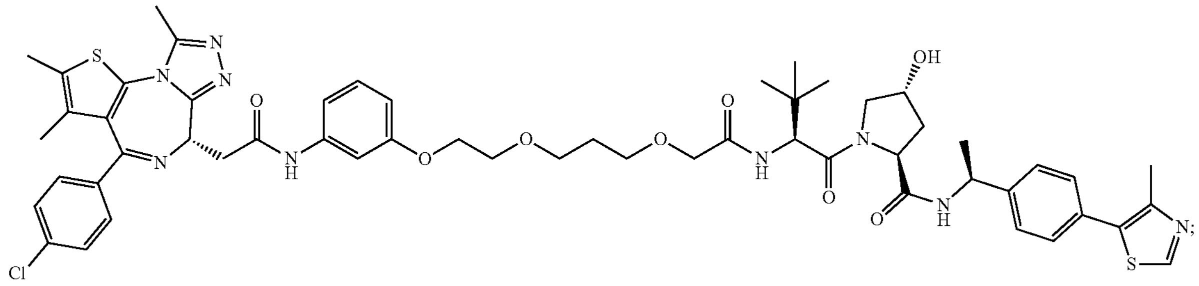
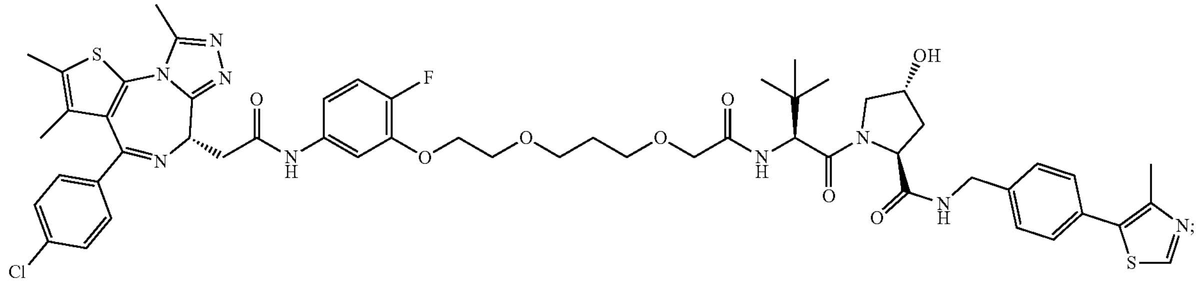
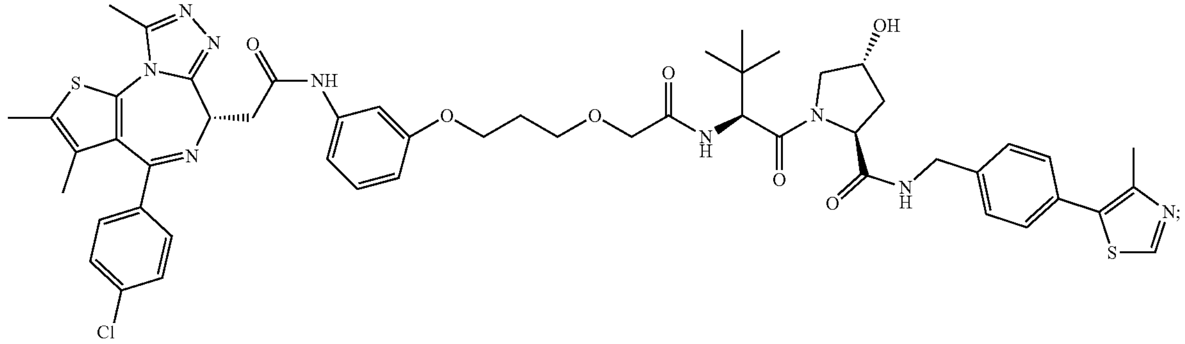

-continued
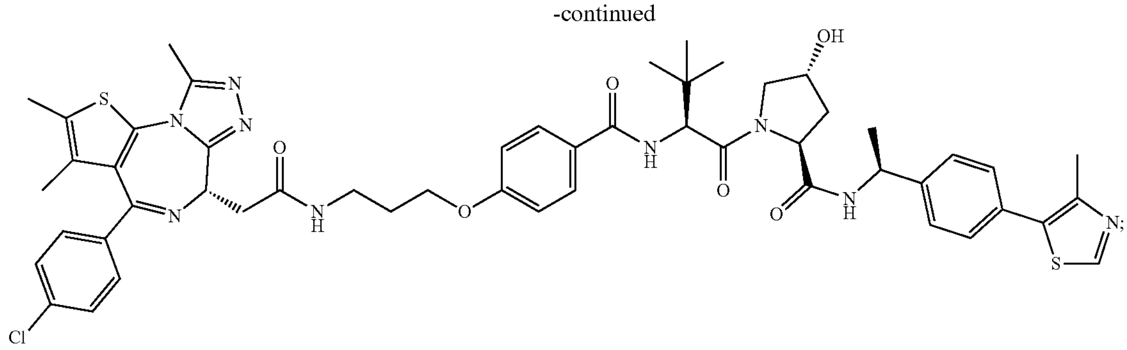
;
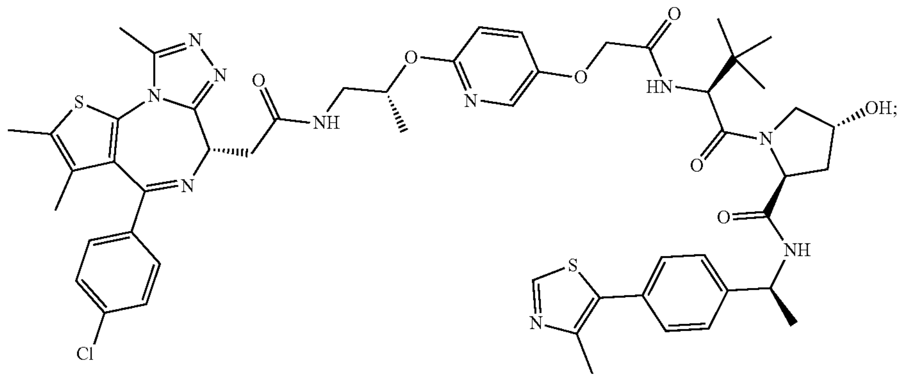
;
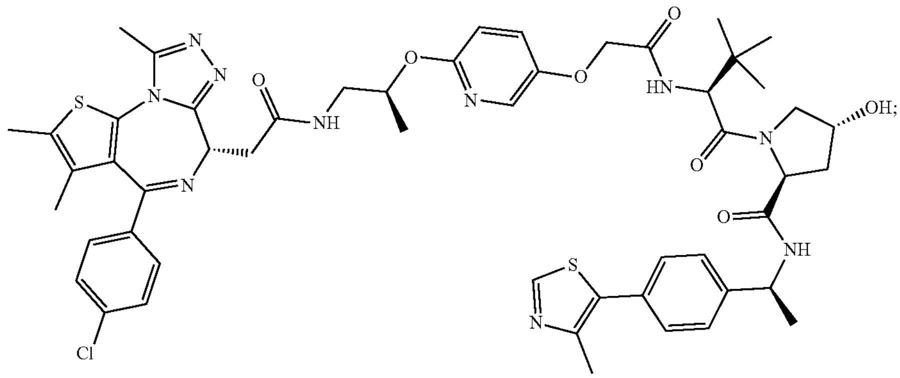
;
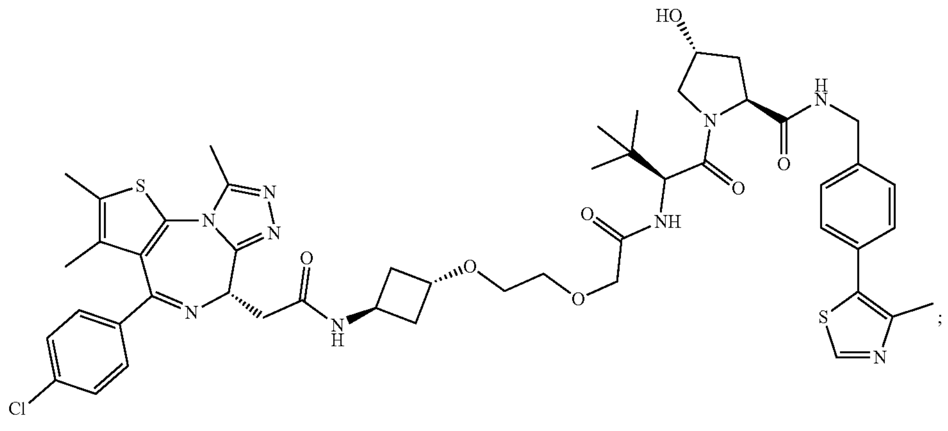
;

-continued
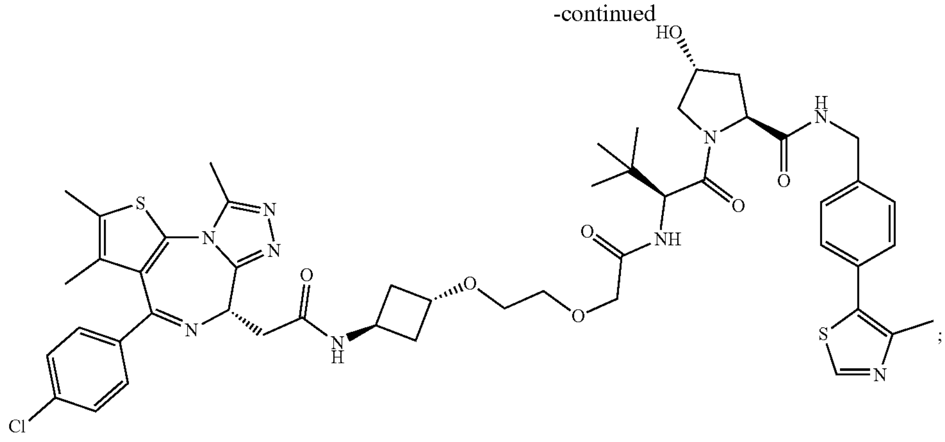
;
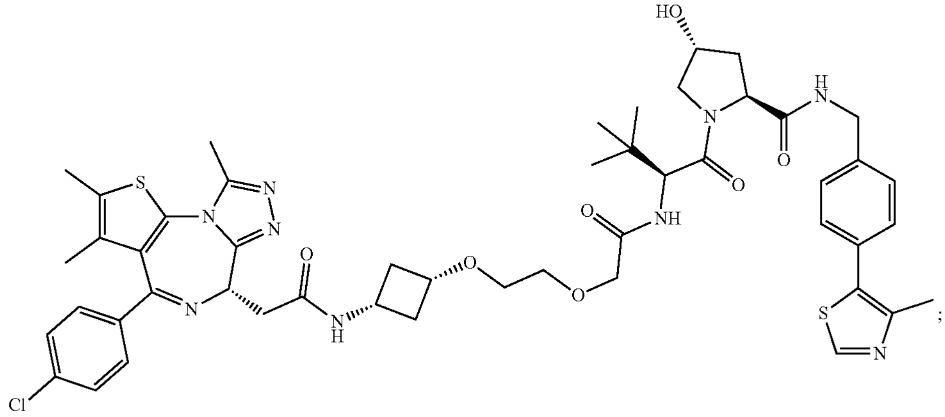
;
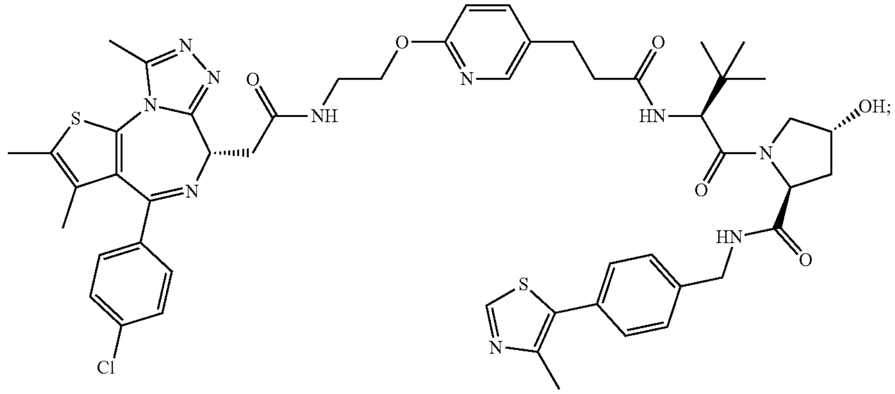
;
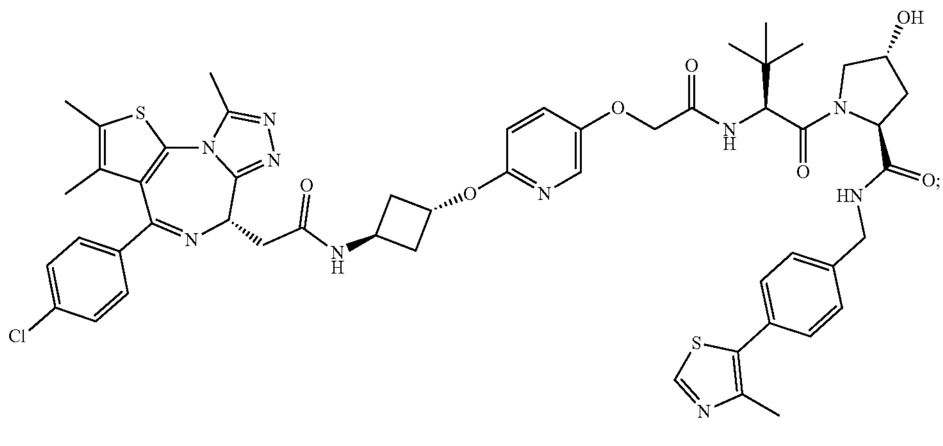
;

-continued
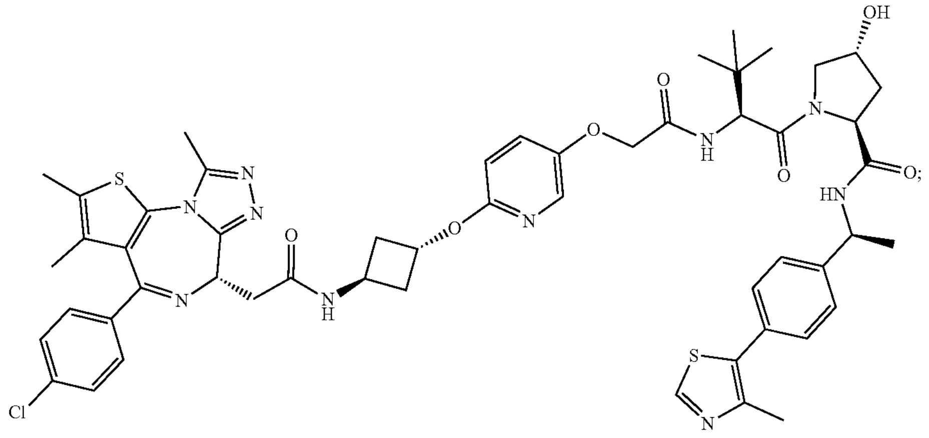
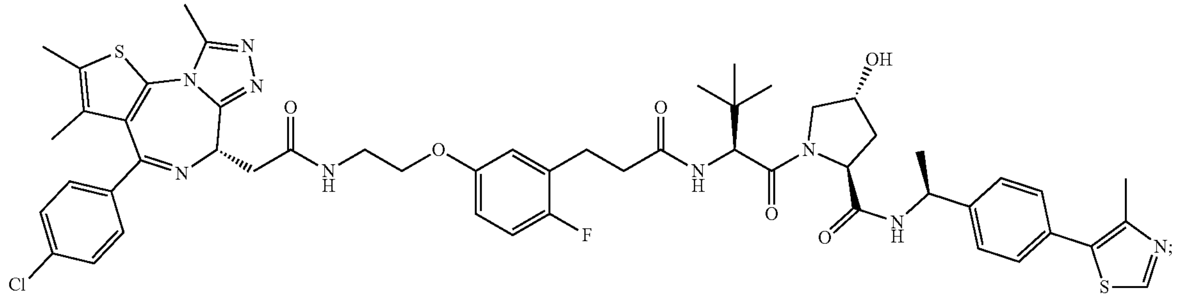
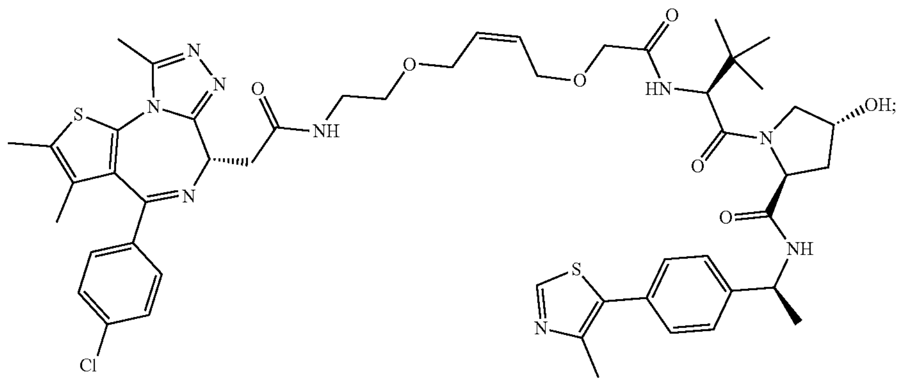
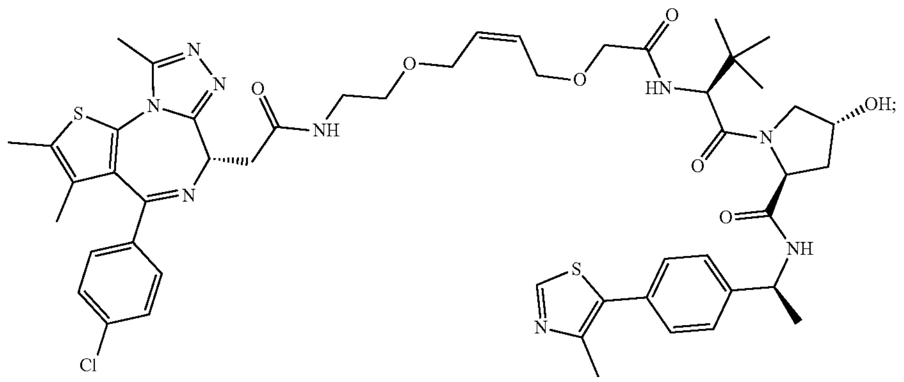

-continued
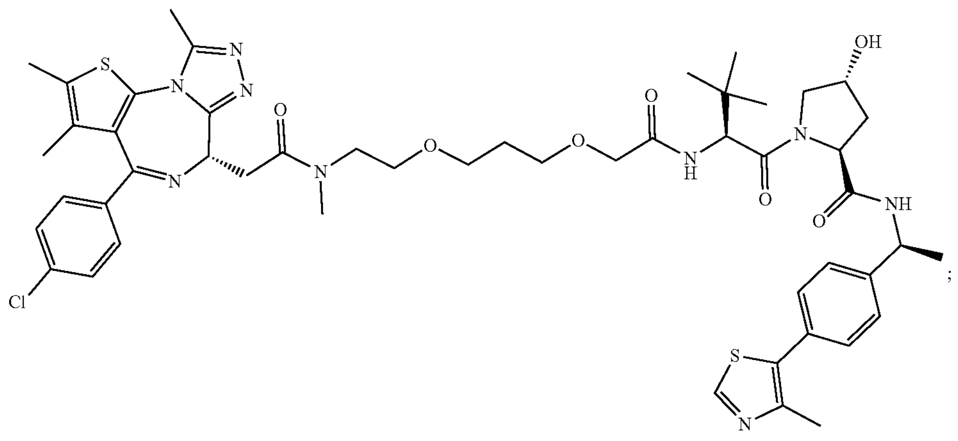
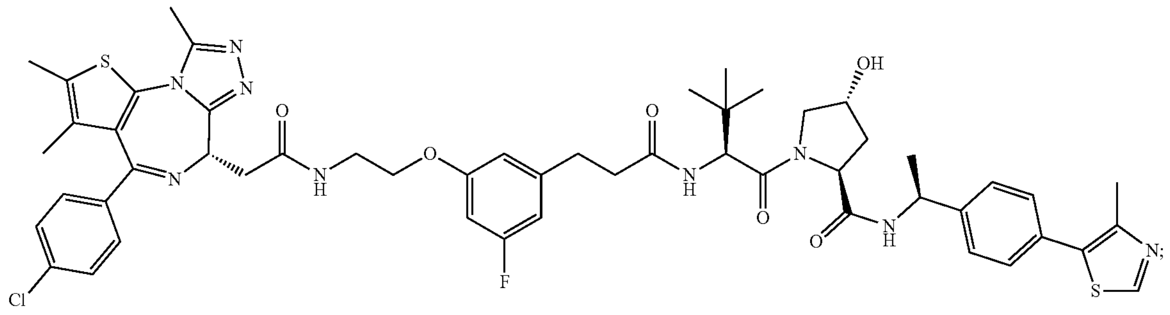
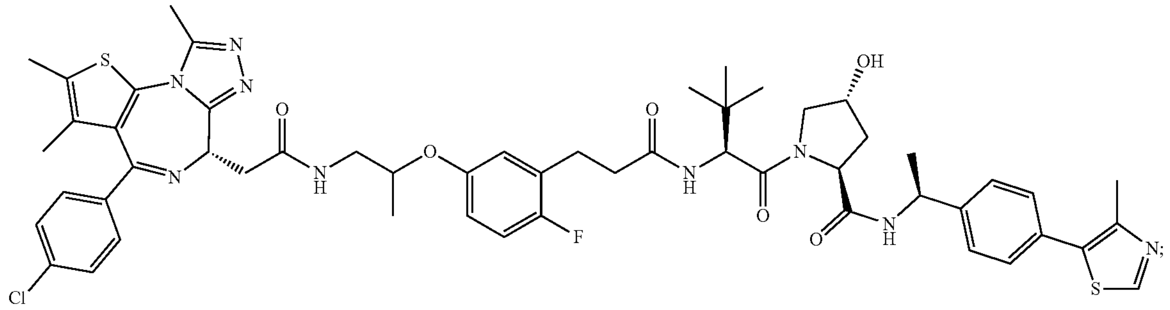
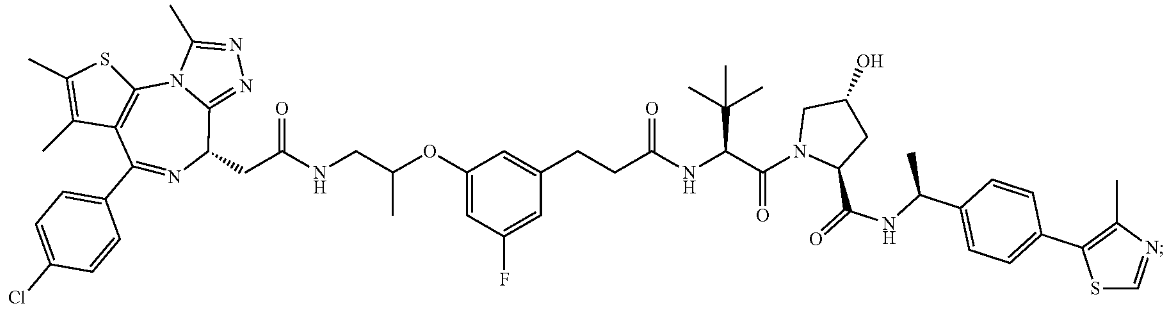
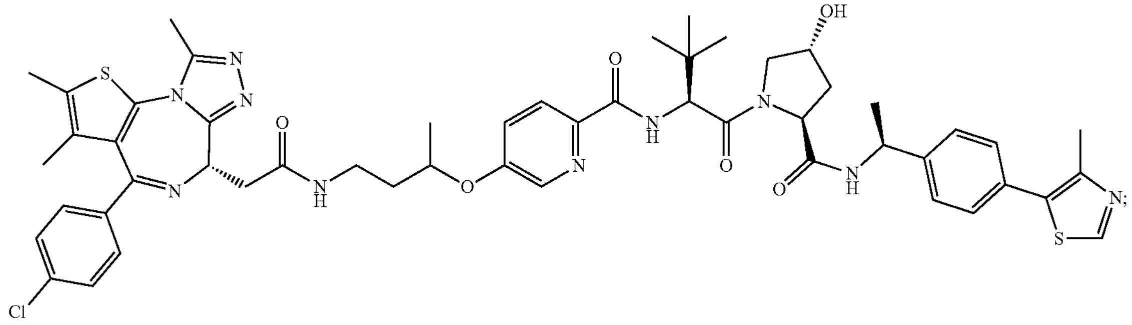

-continued
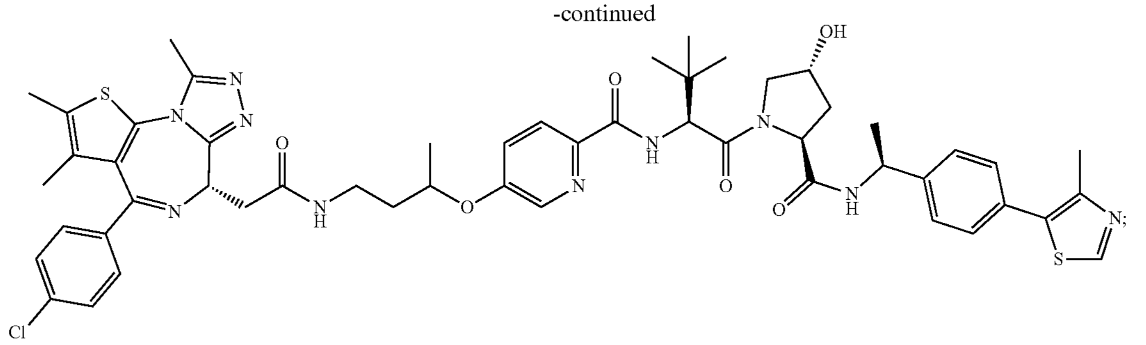
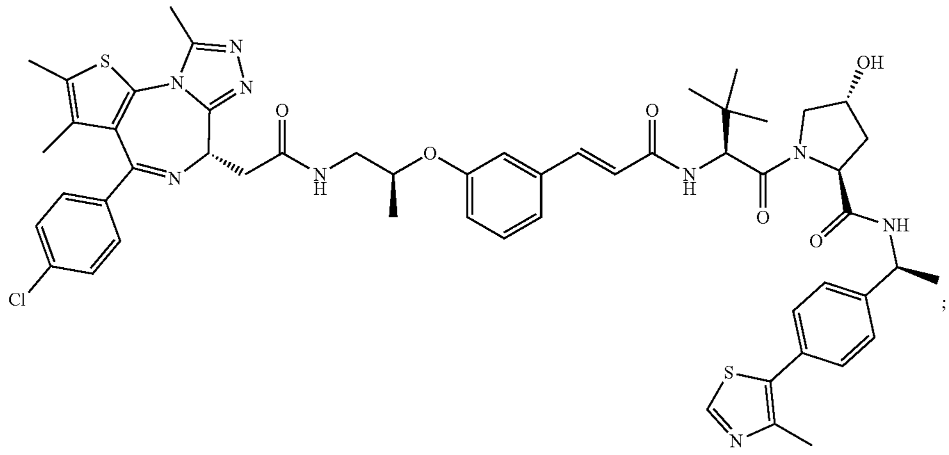
;
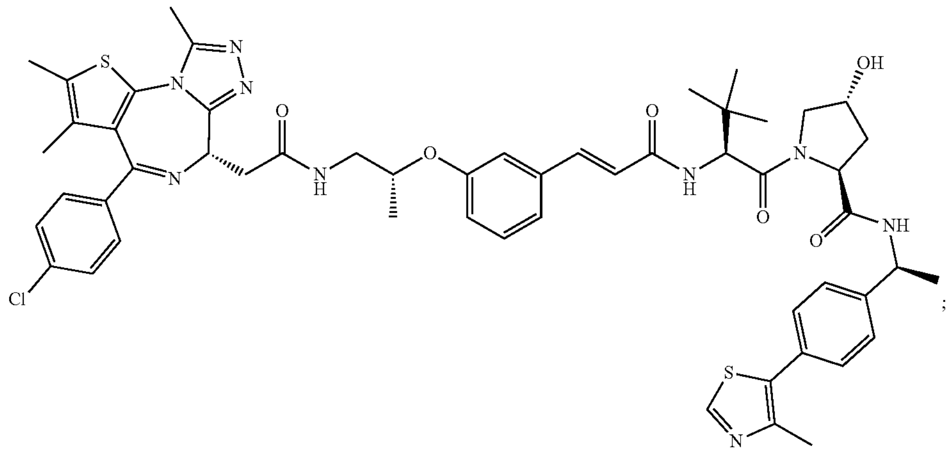
;
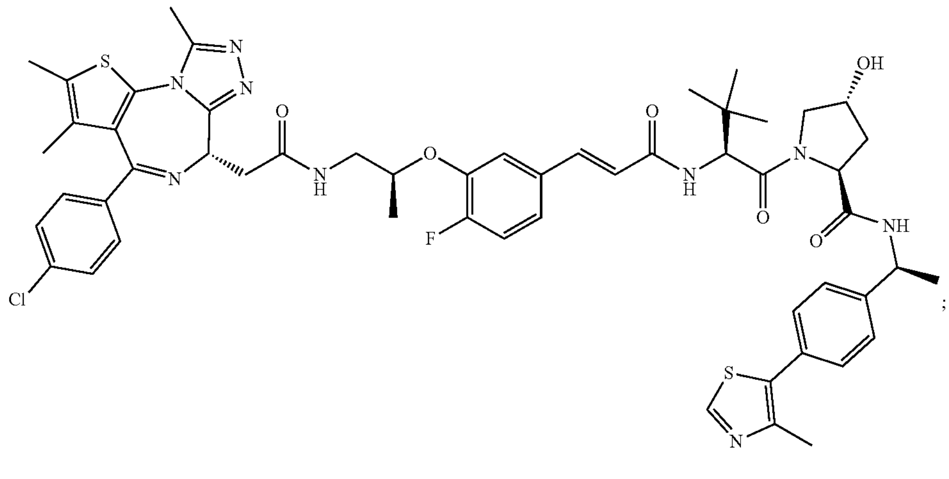
;

-continued
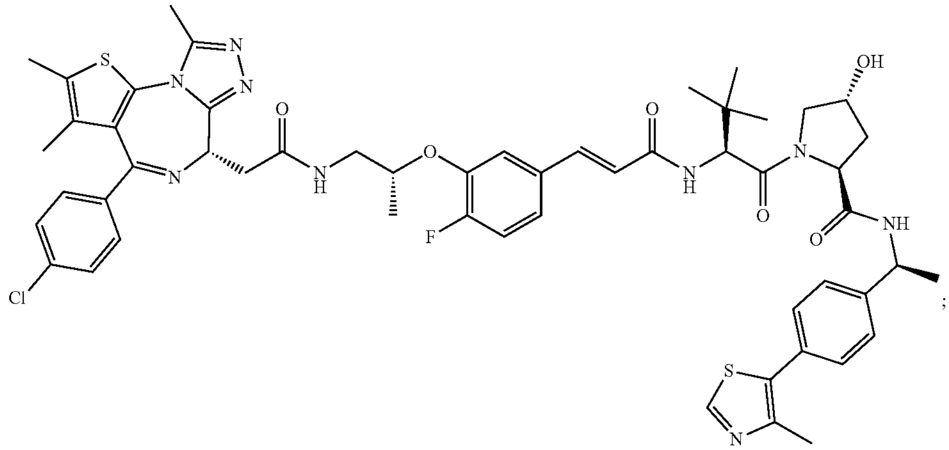
;
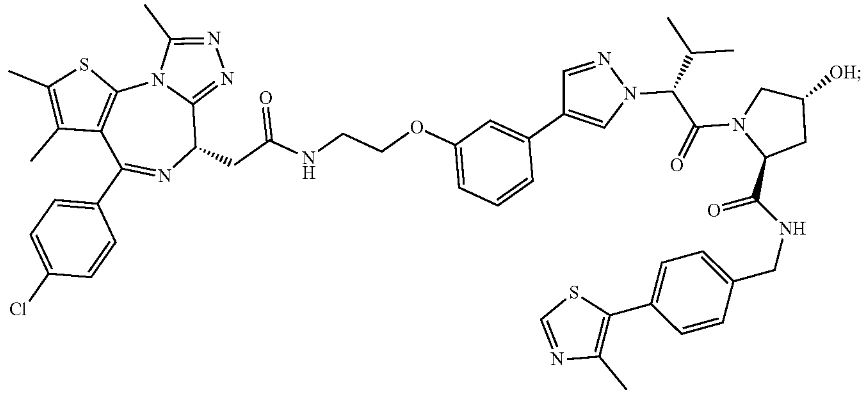
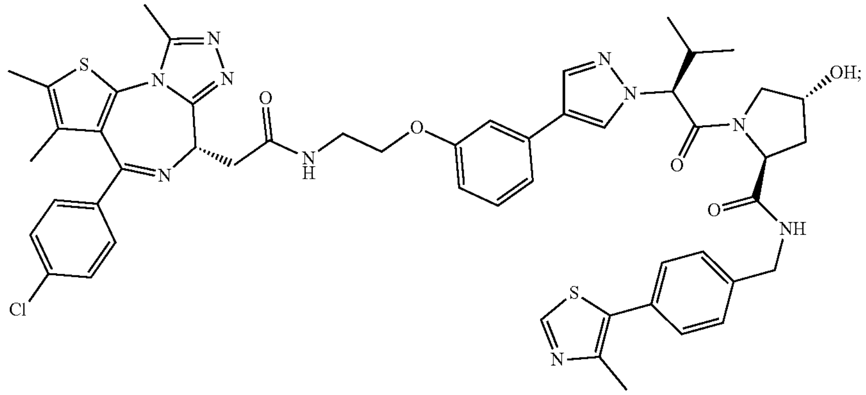
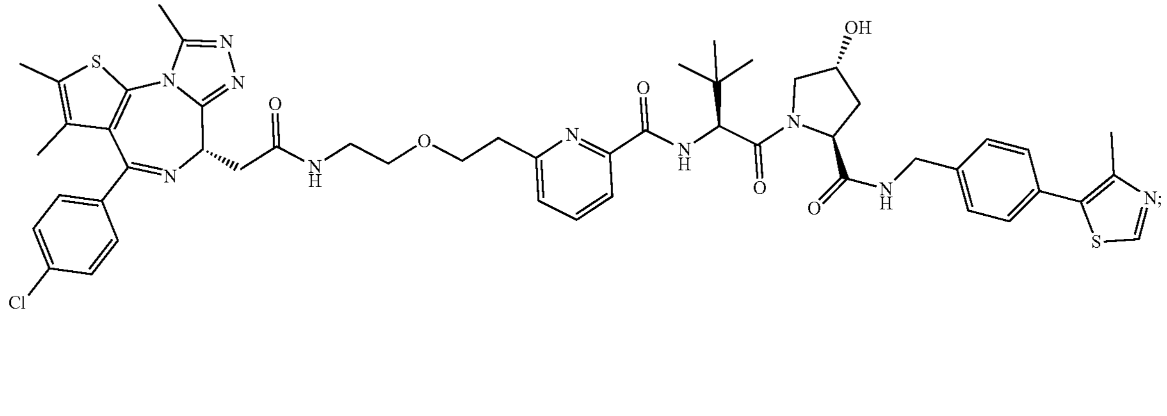

-continued
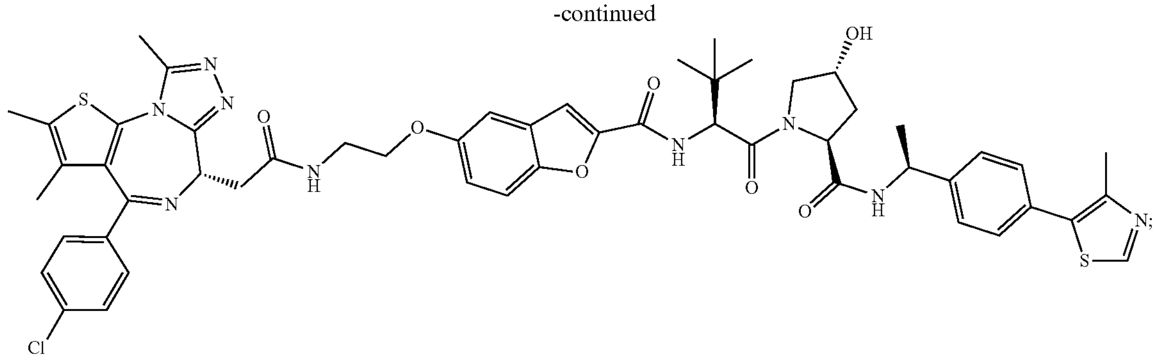
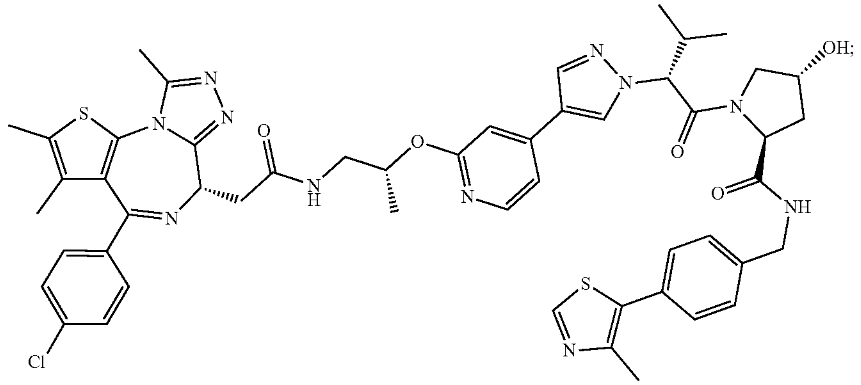
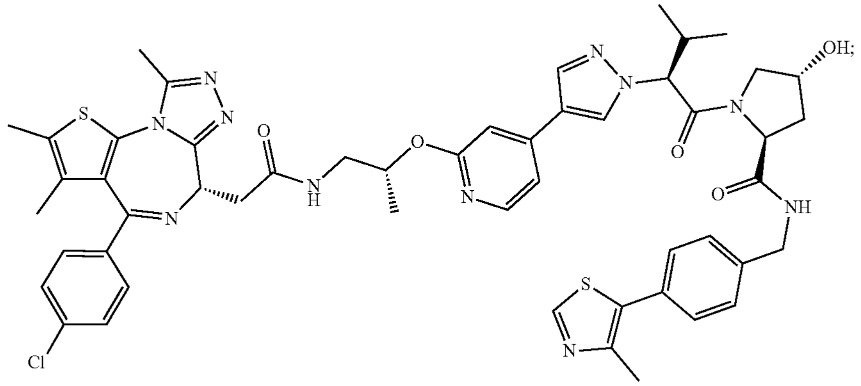
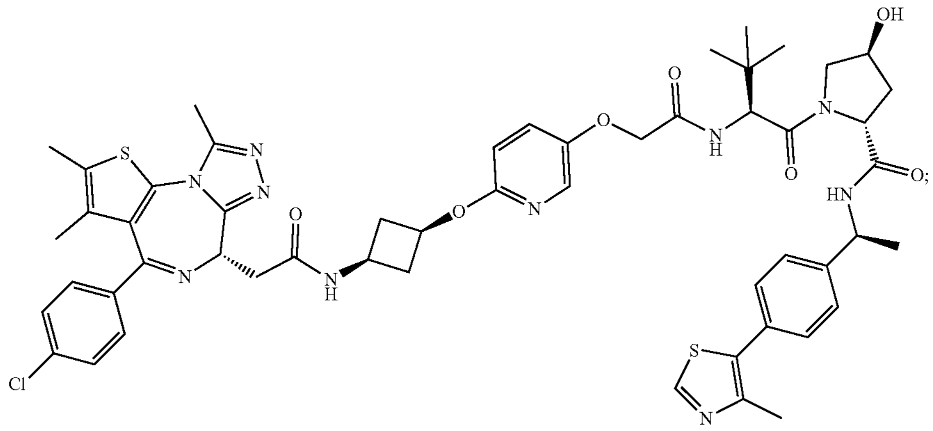

-continued
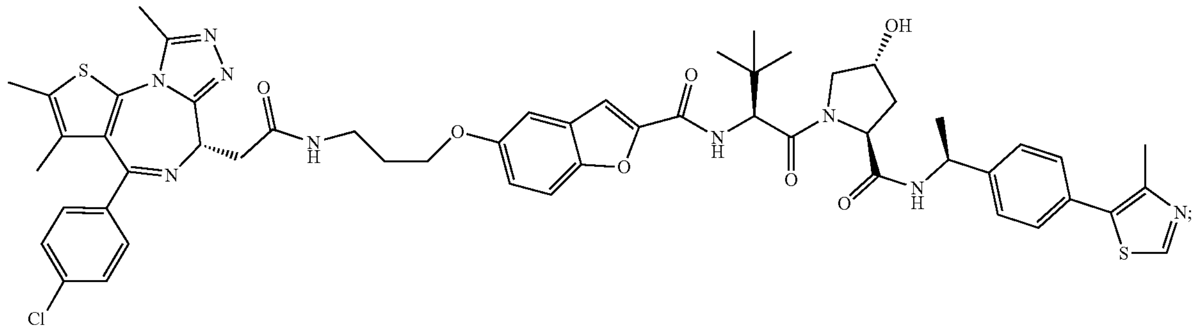
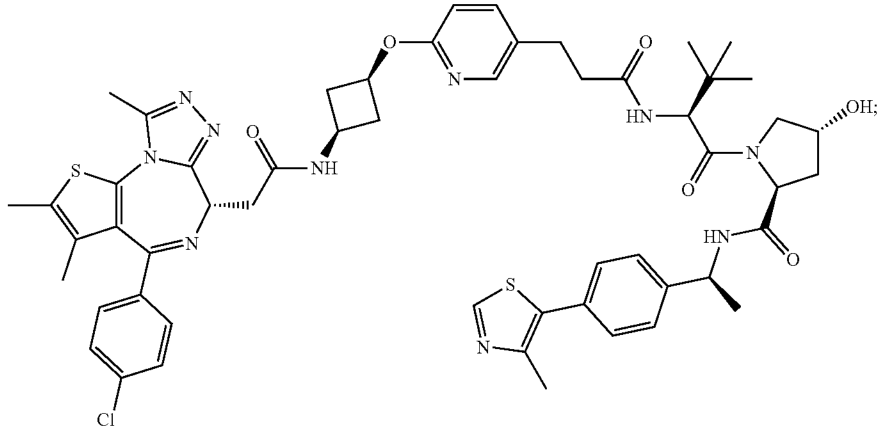
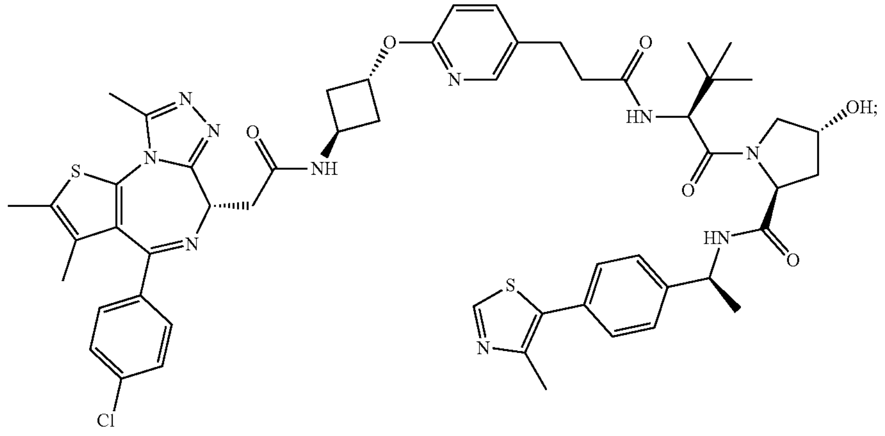
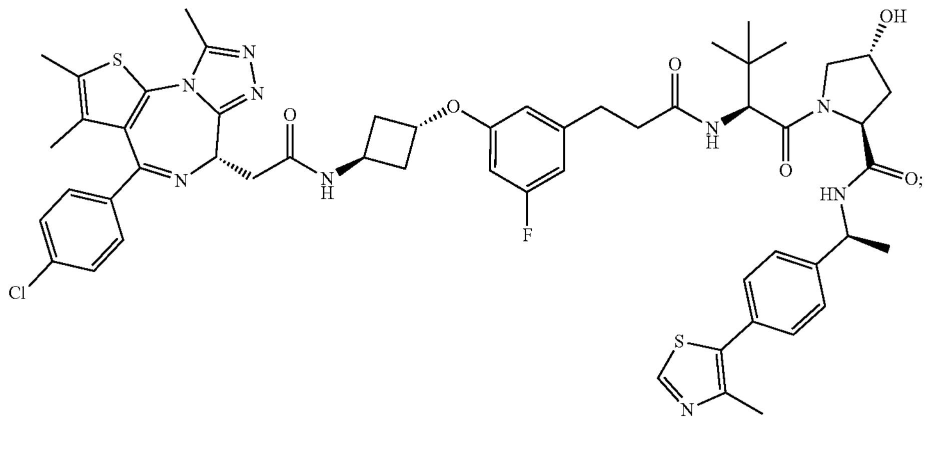

-continued
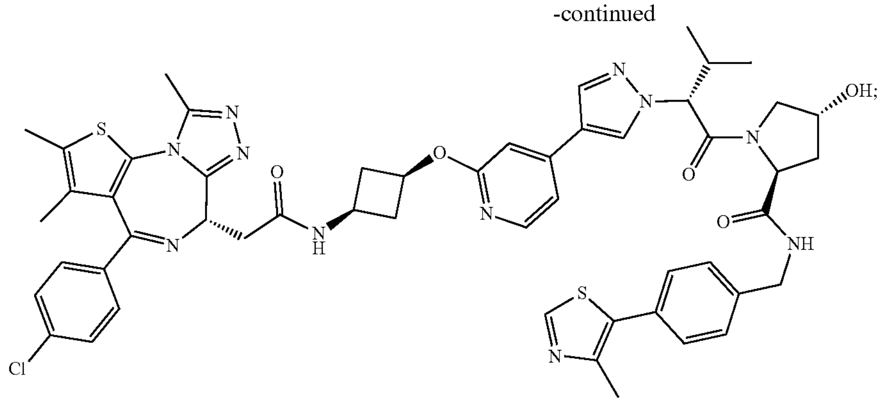
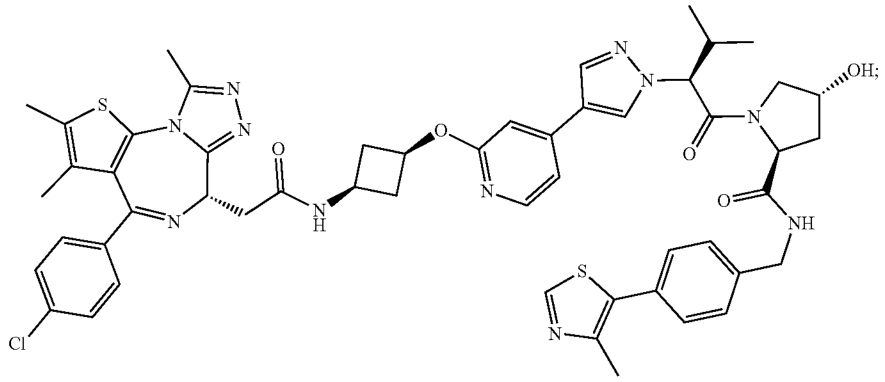
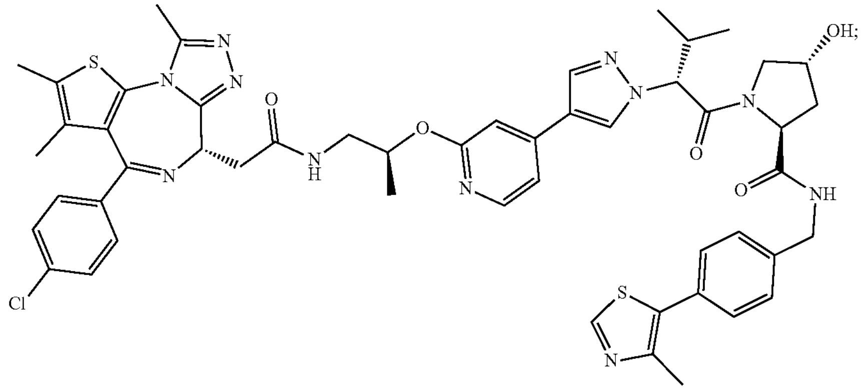
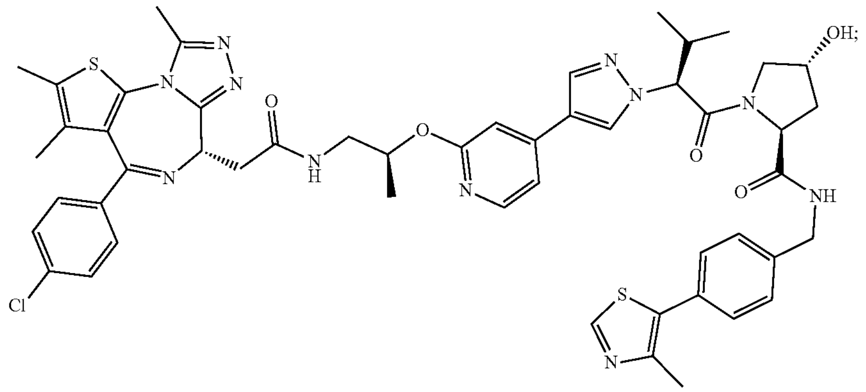

-continued
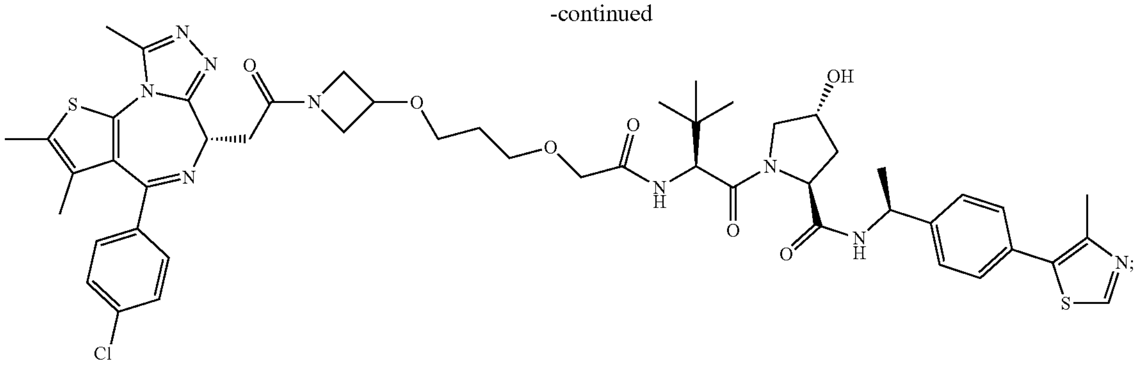
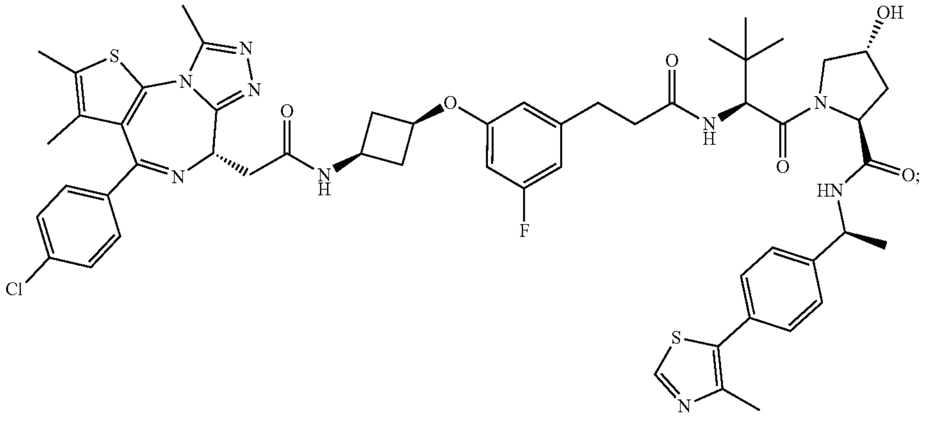
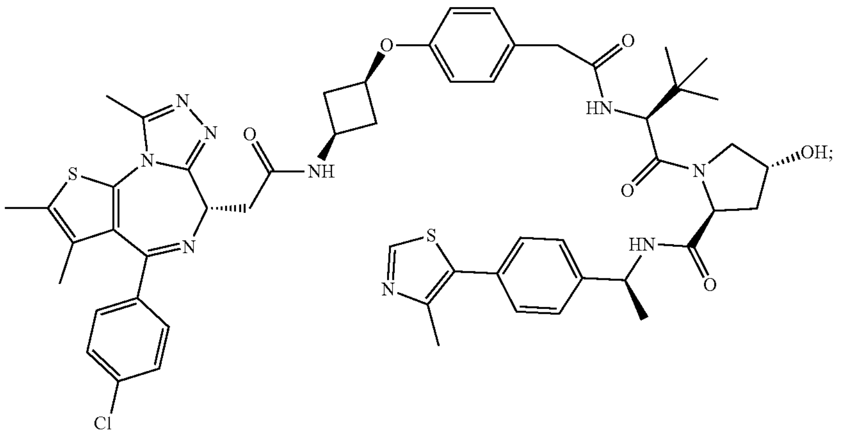
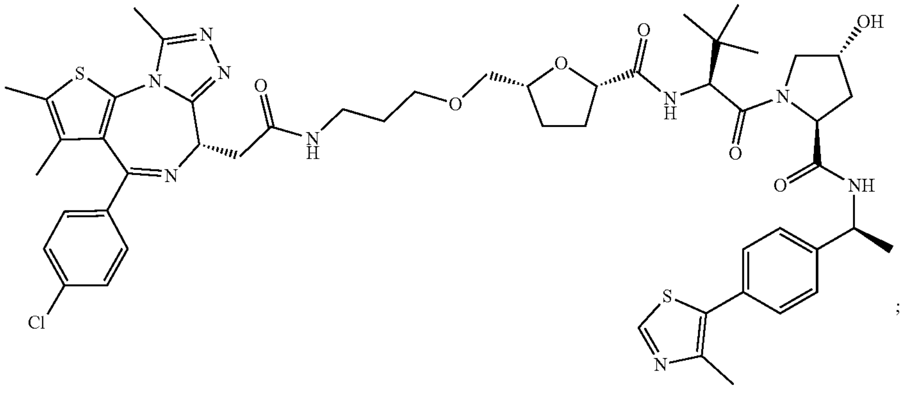
;

-continued
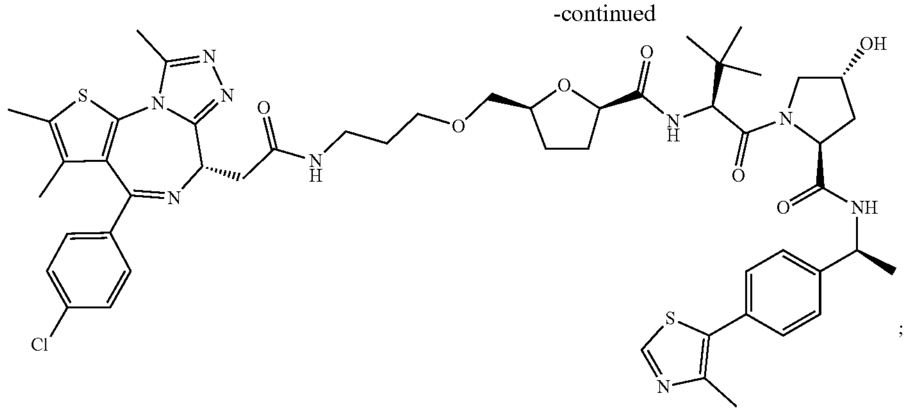
;
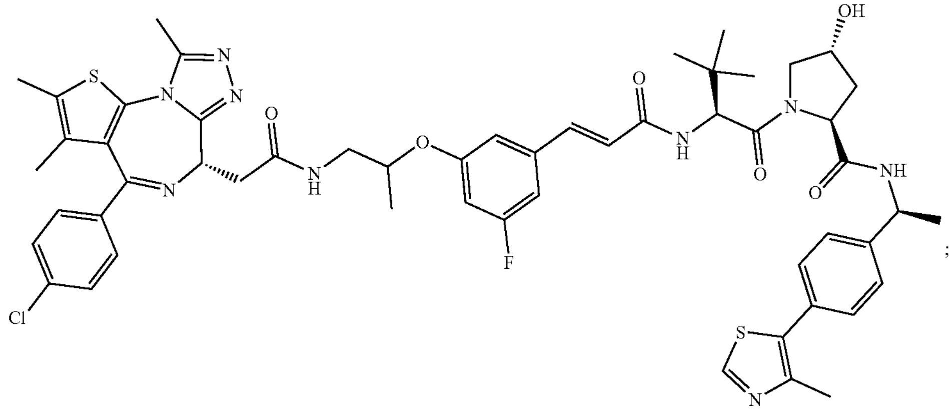
;
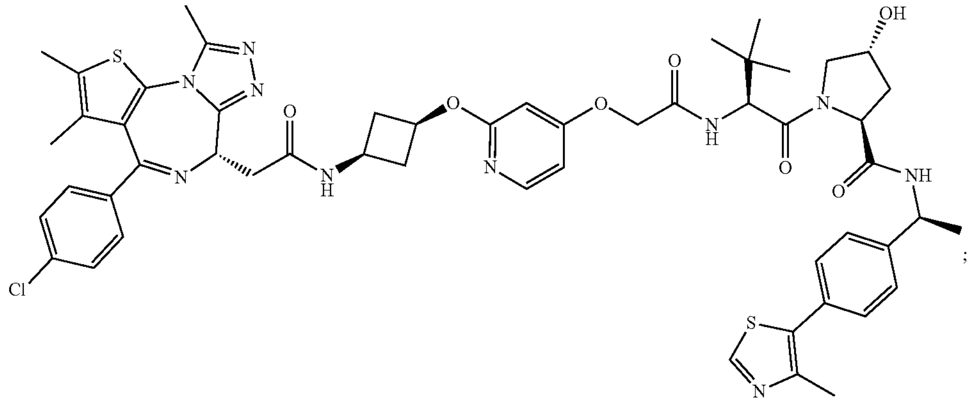
;
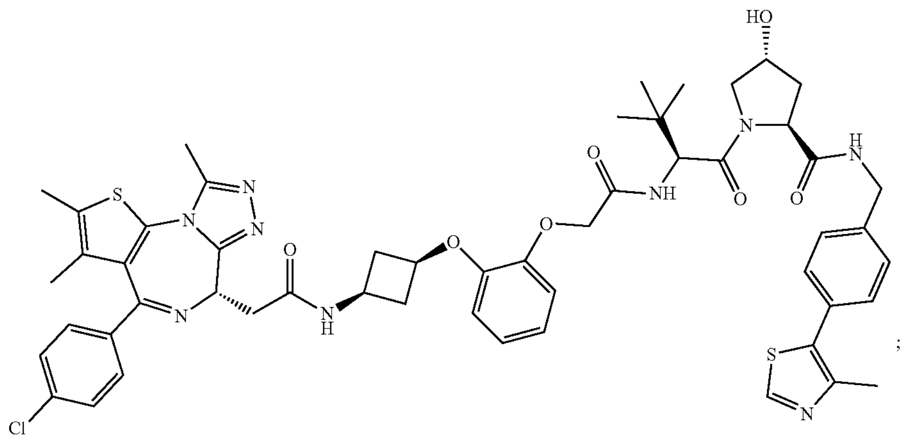
;

-continued
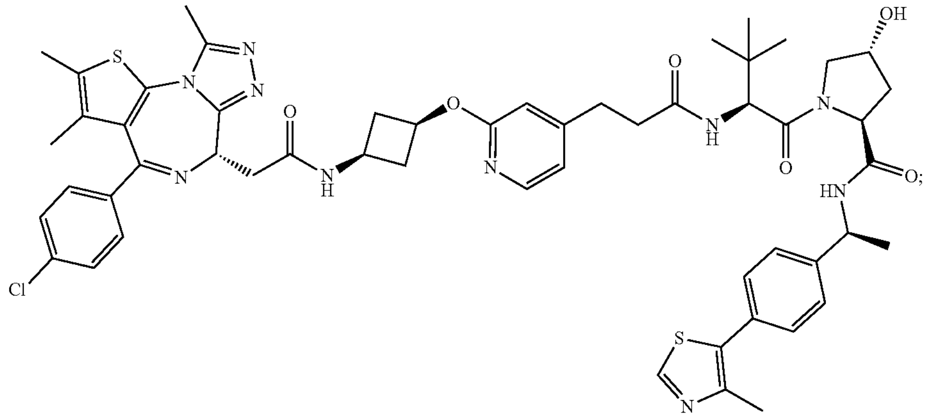
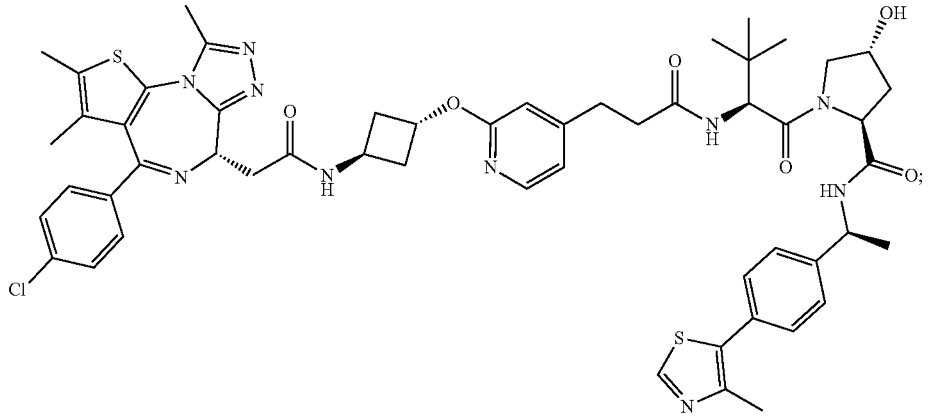
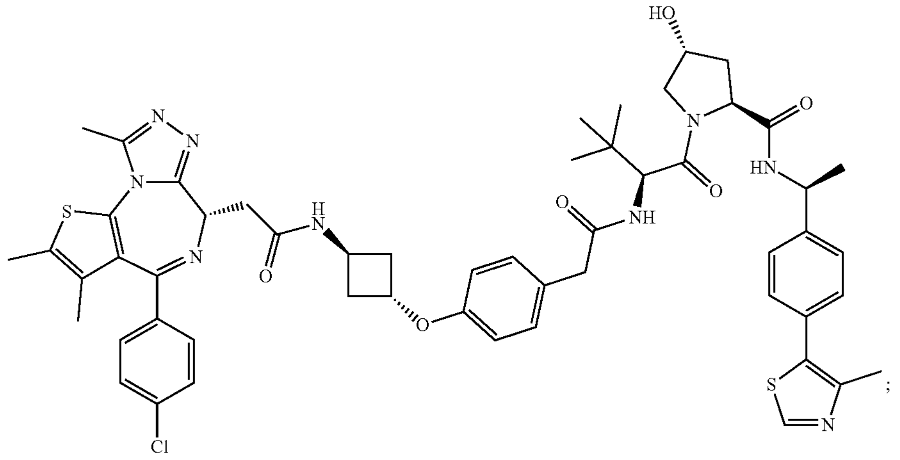
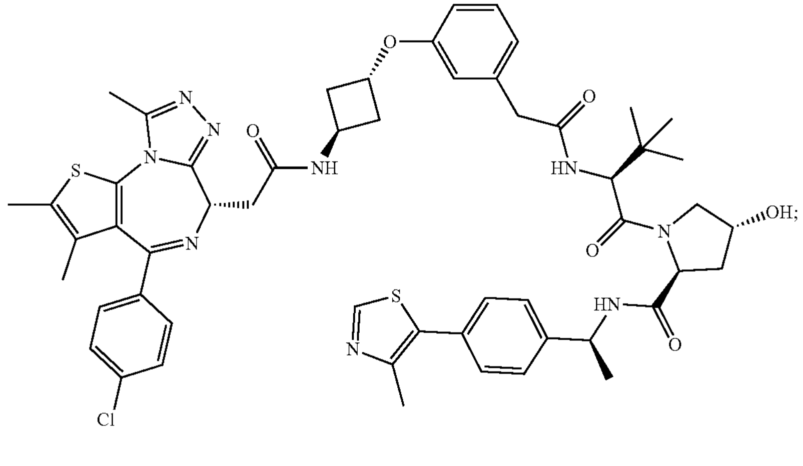

-continued
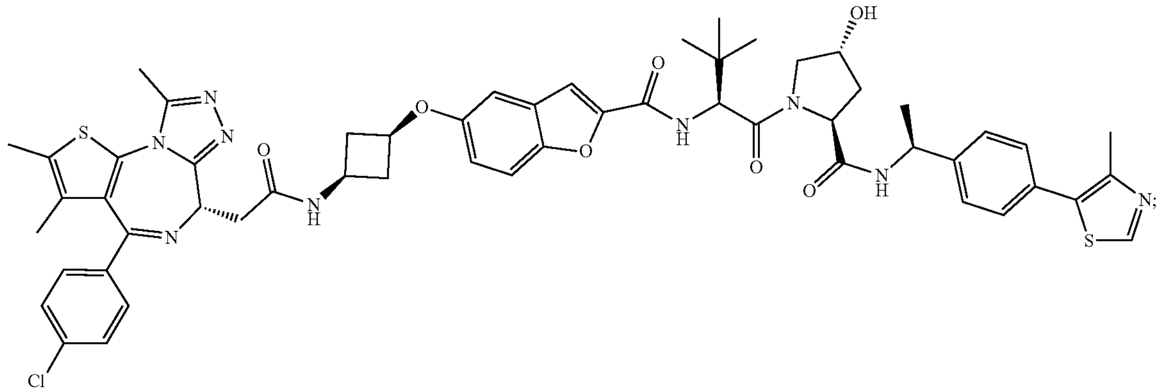
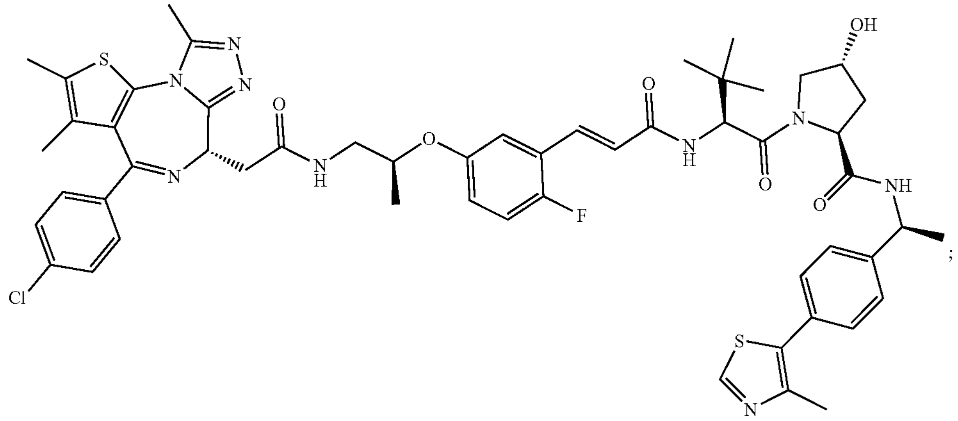
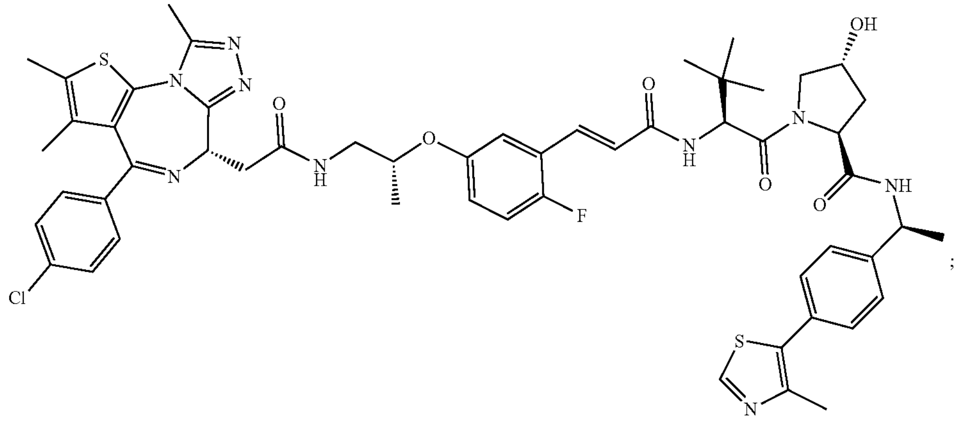
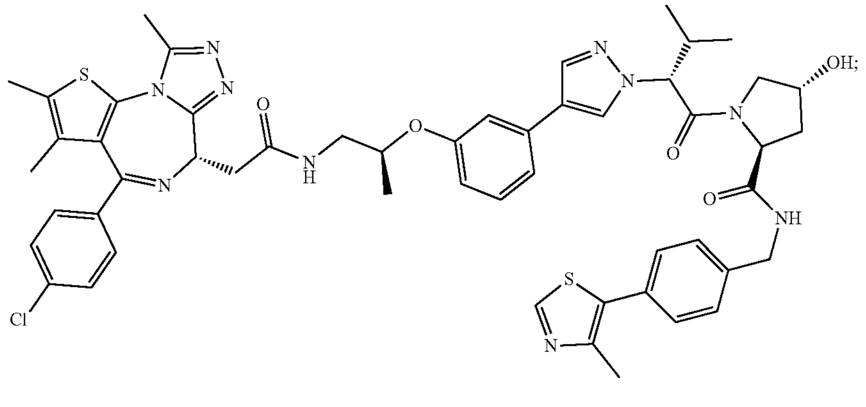

-continued
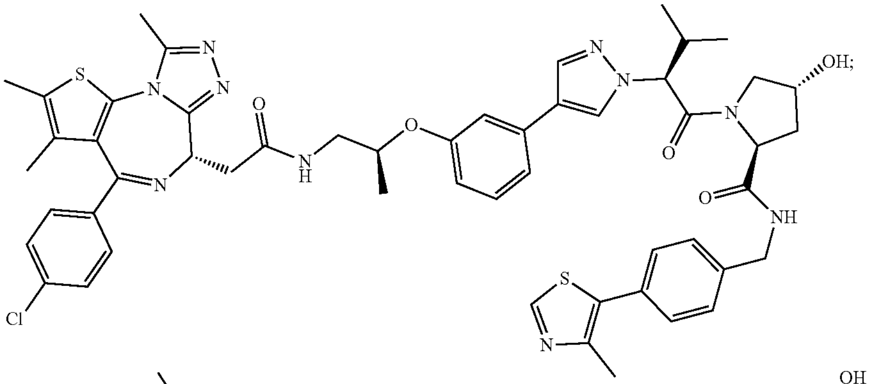
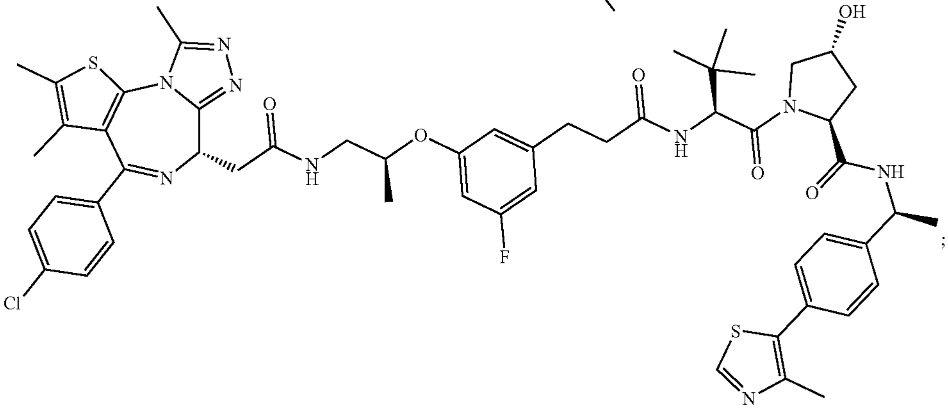
or a pharmaceutically acceptable salt, enantiomer, or diastereomer thereof.
22. The bifunctional compound of claim 1, wherein the bifunctional compound is selected from the group consisting of:
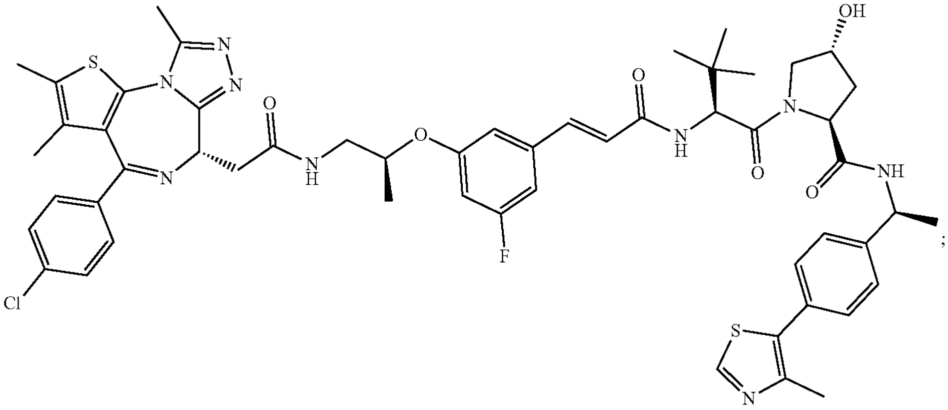
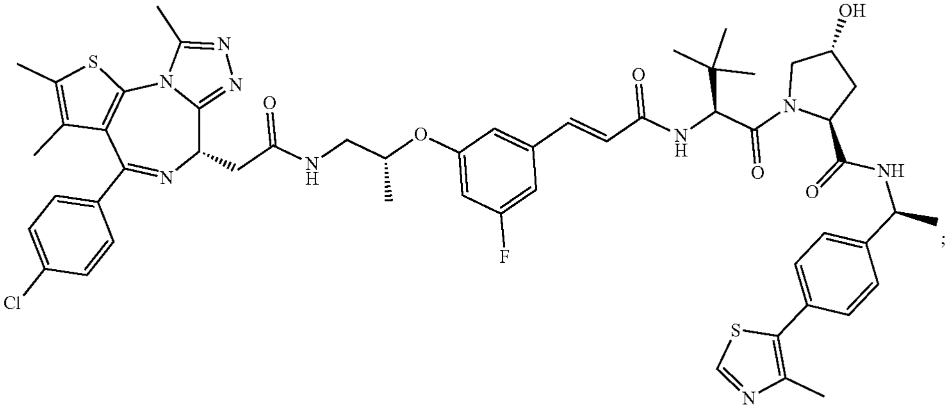

-continued
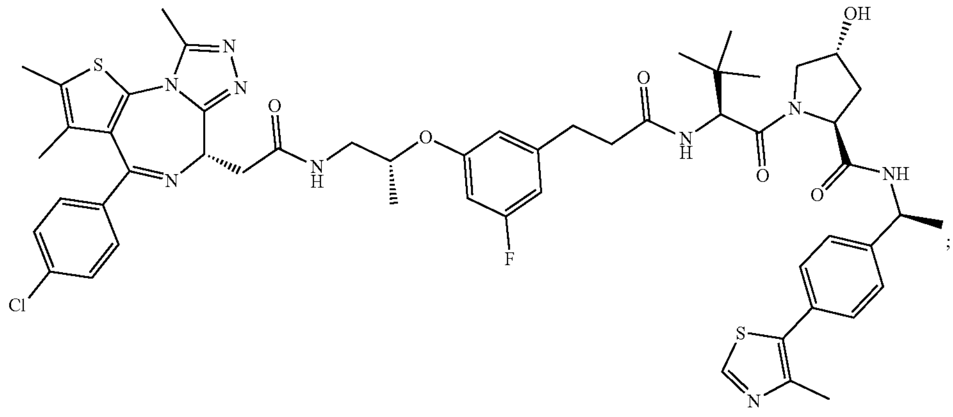
;
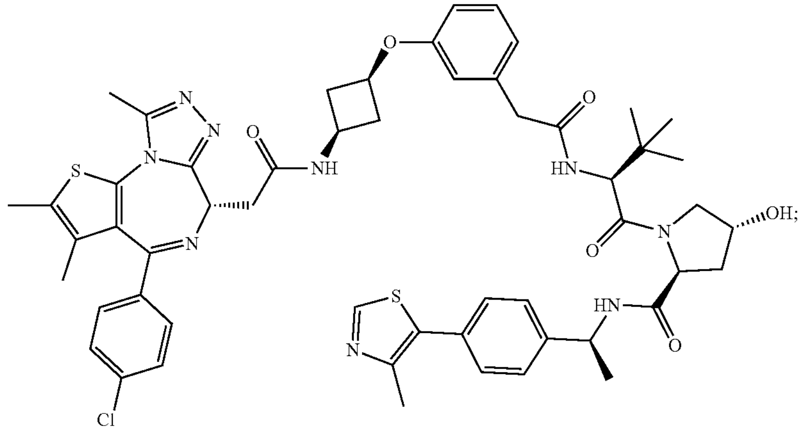
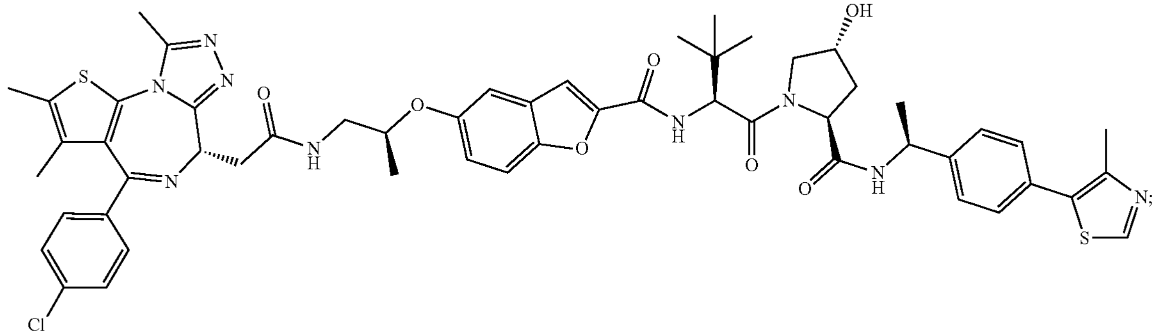
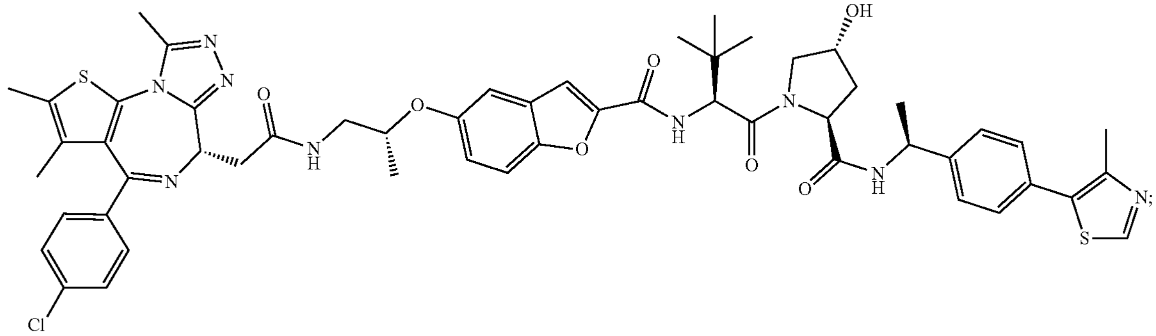

-continued
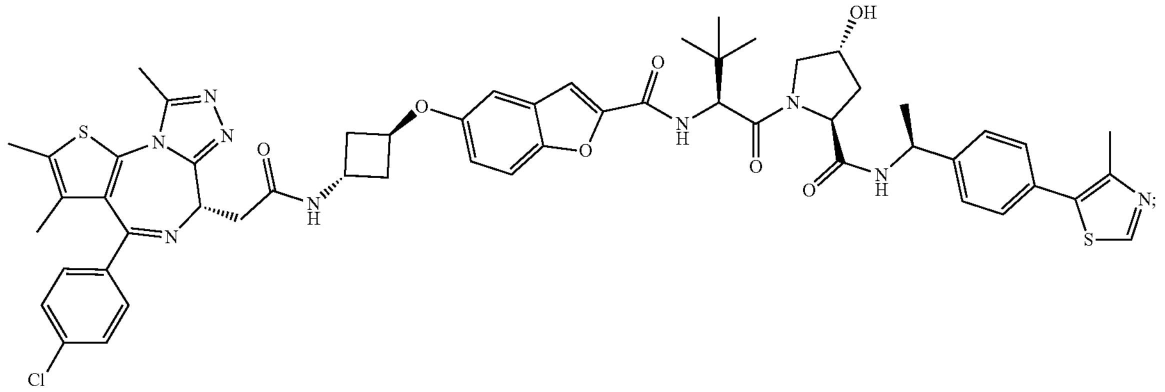
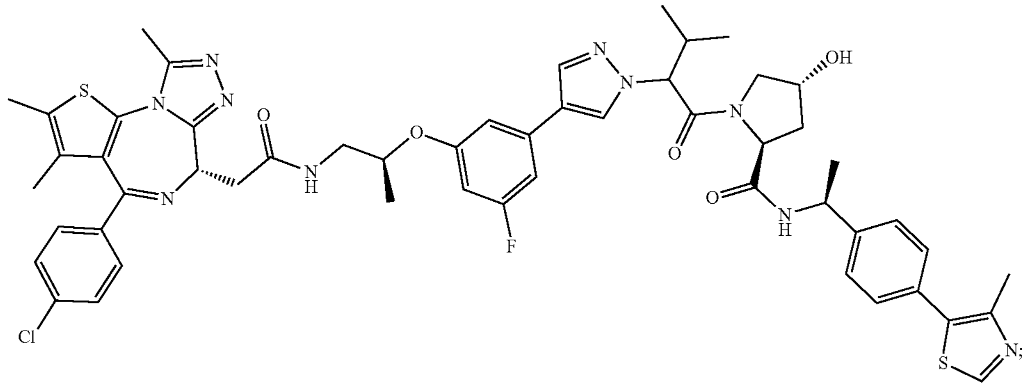
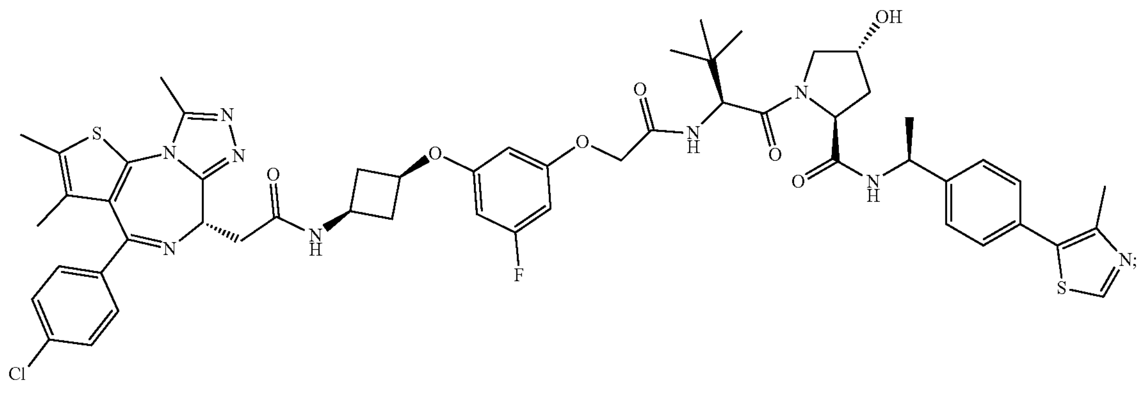
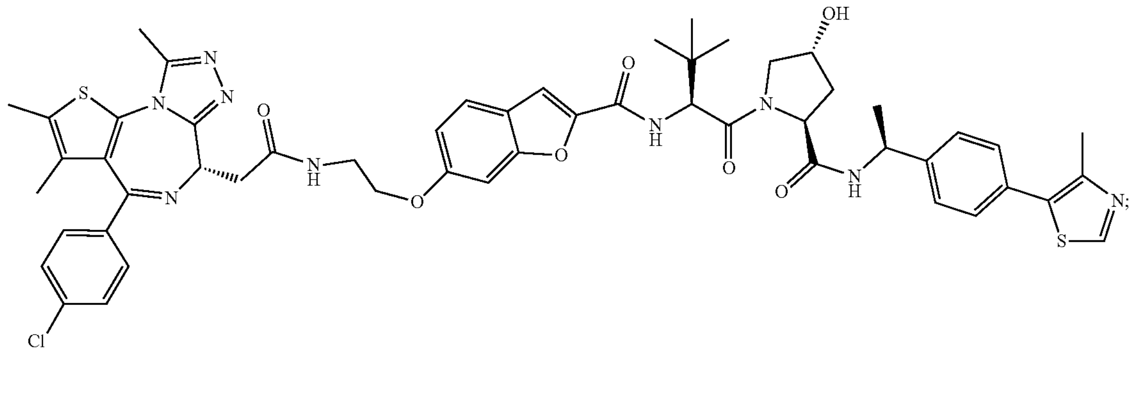

-continued
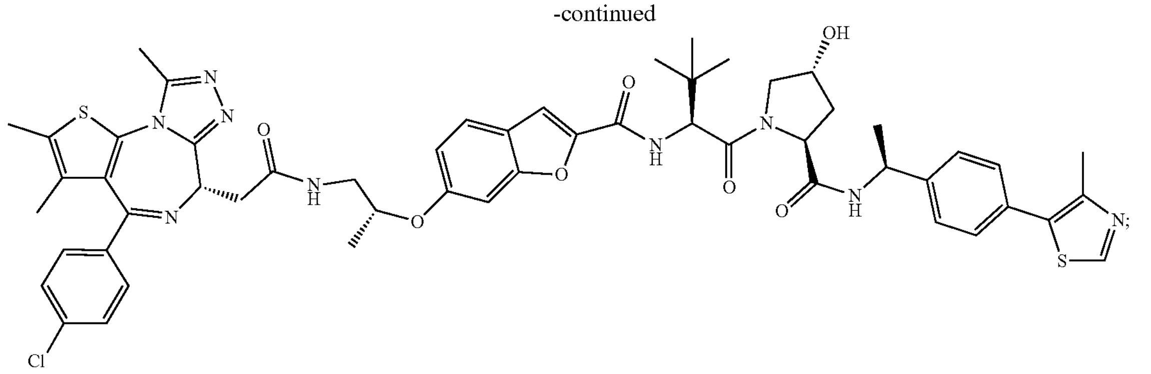
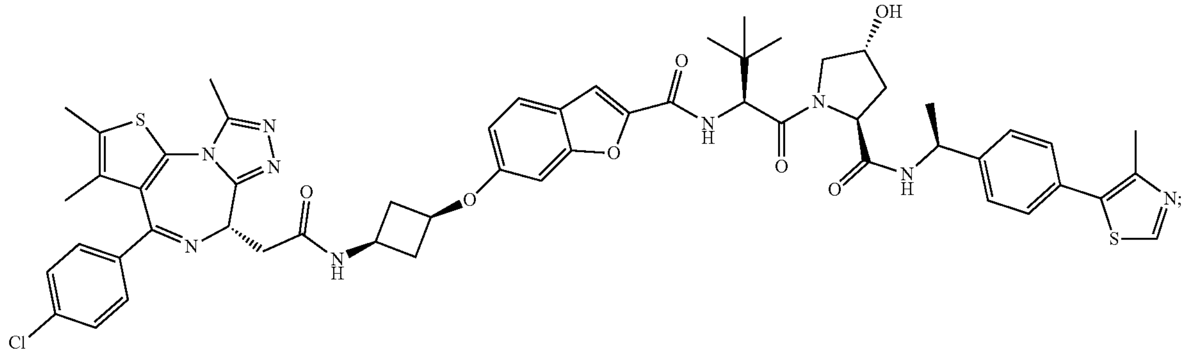
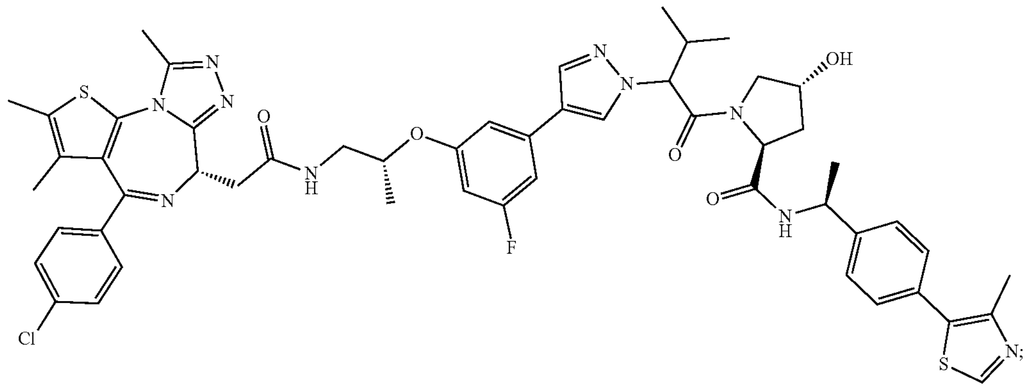
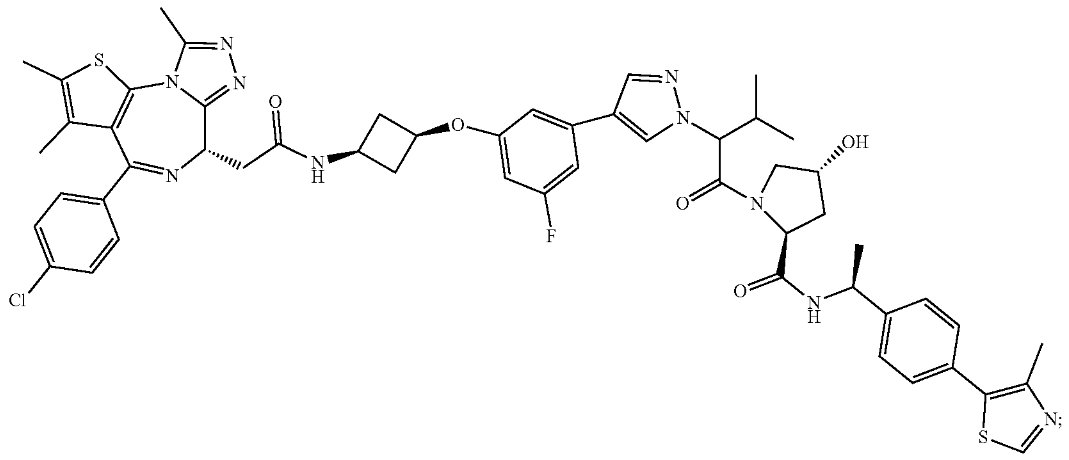

-continued
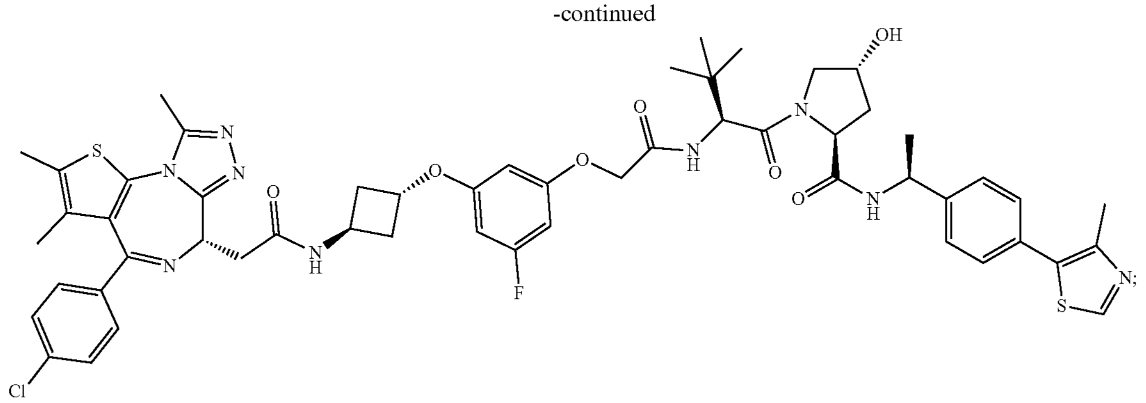
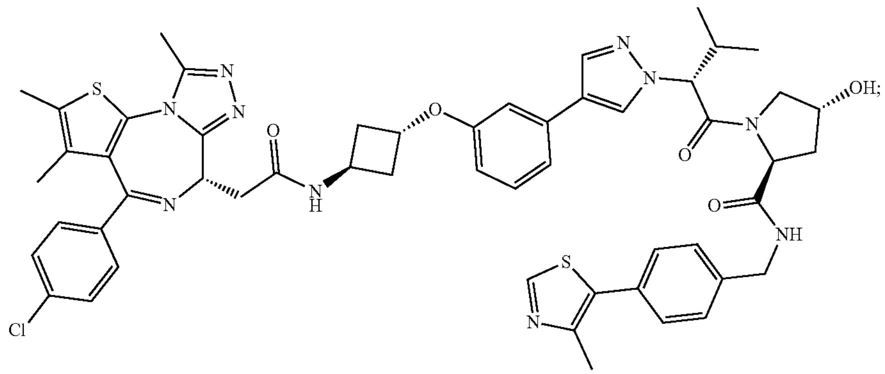
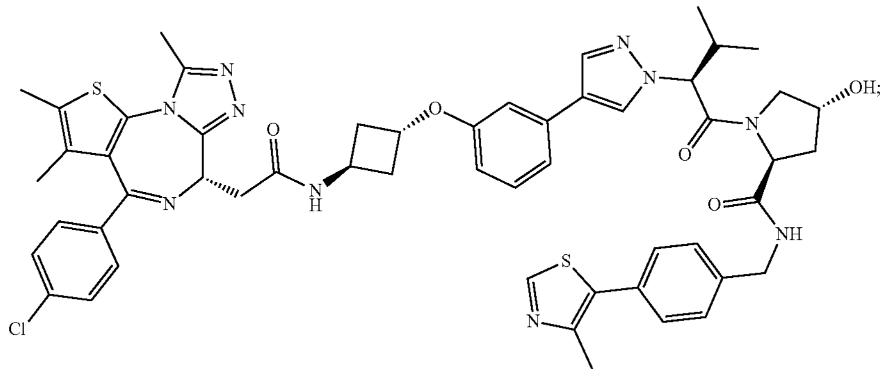
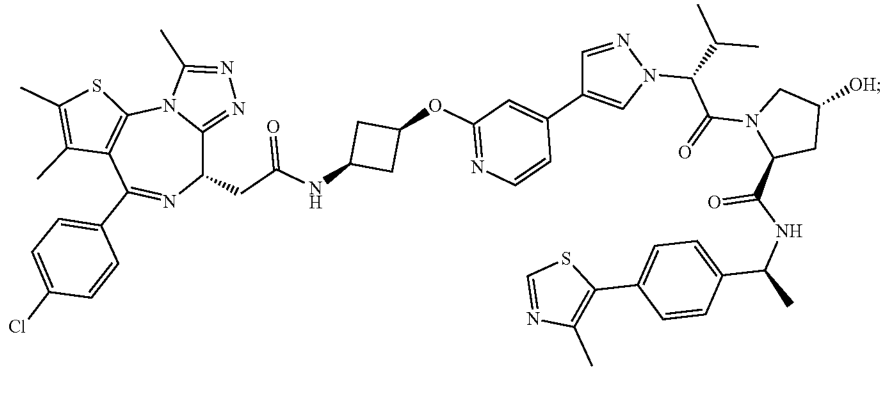

-continued
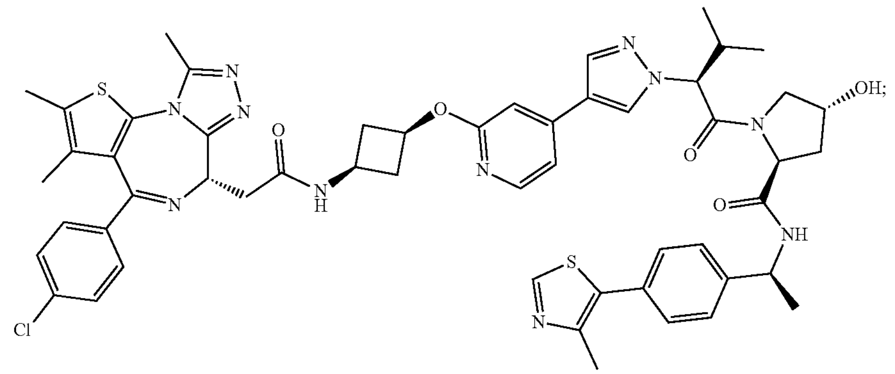
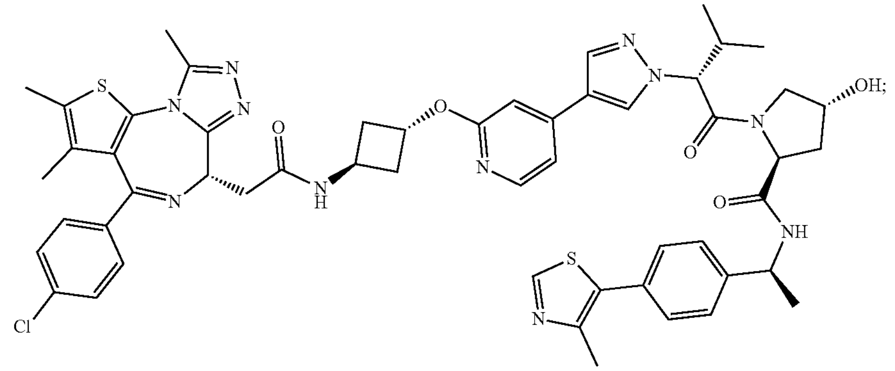
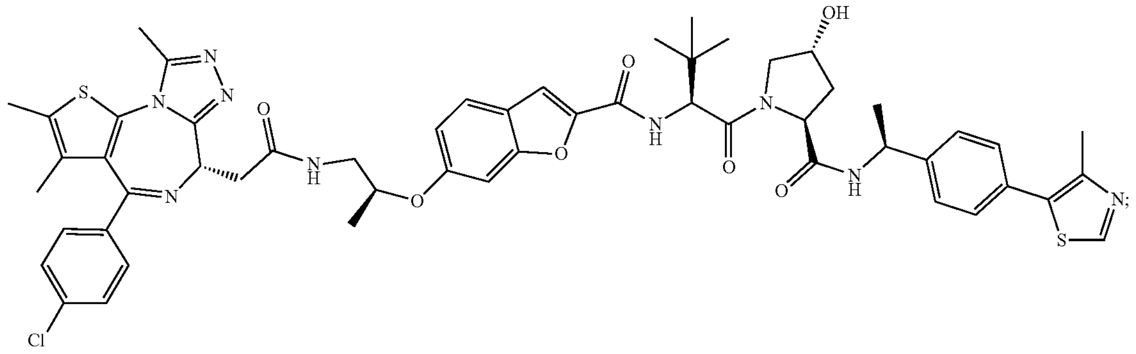
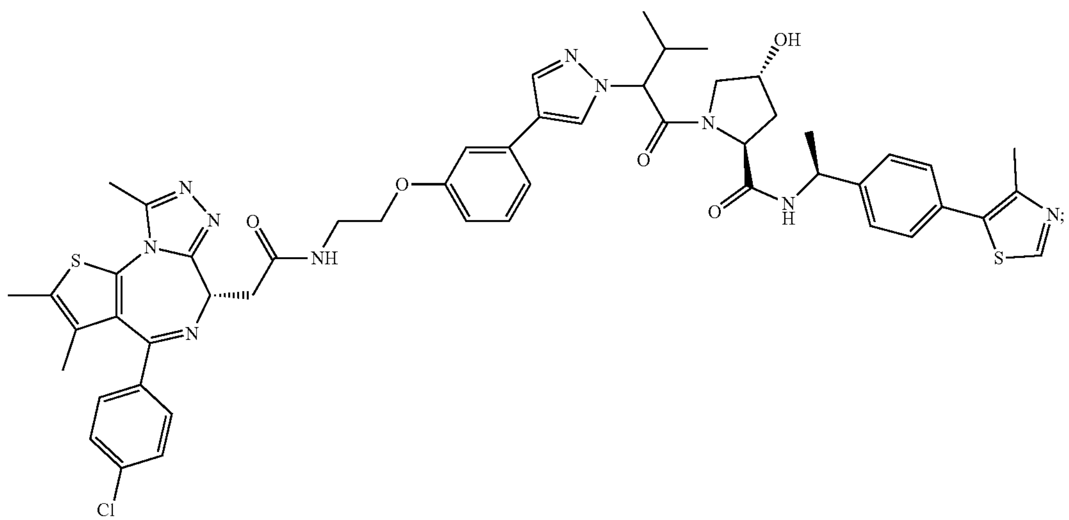

-continued
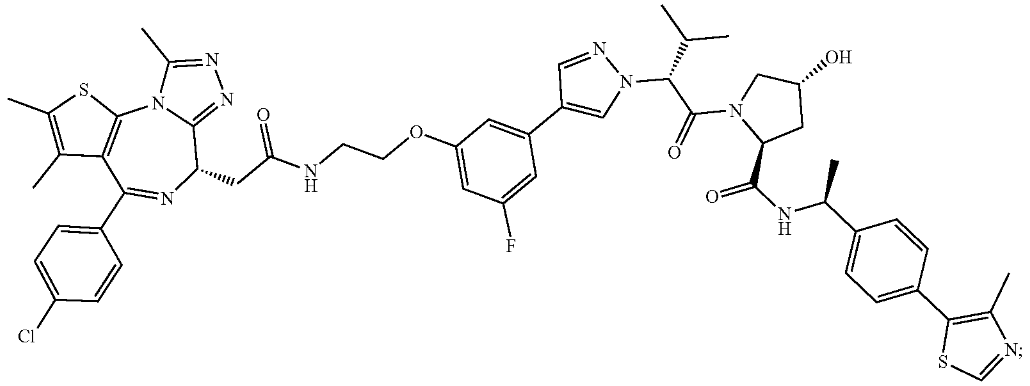
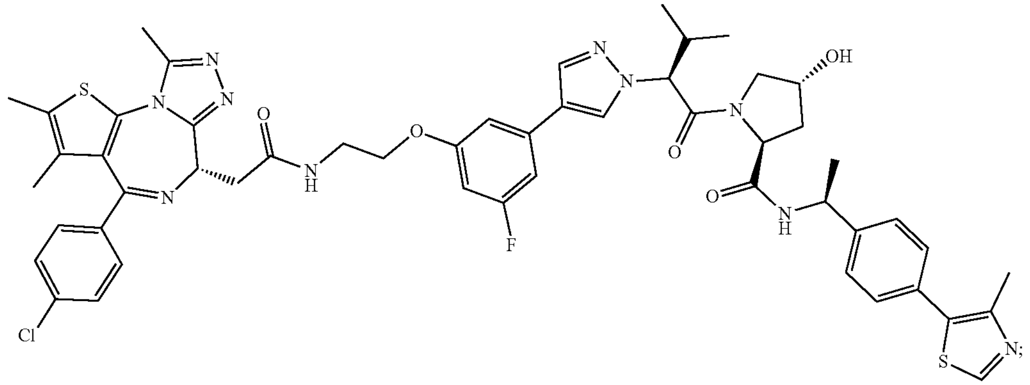
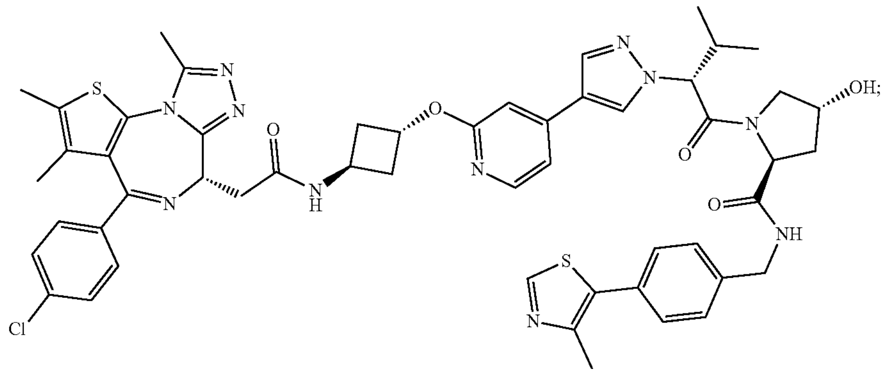
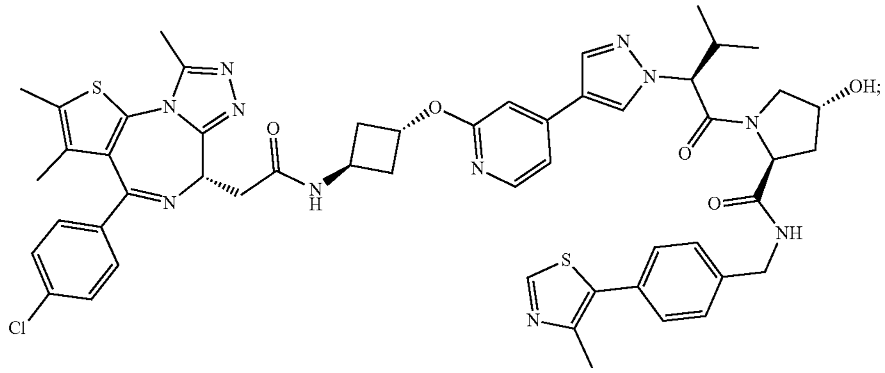

-continued
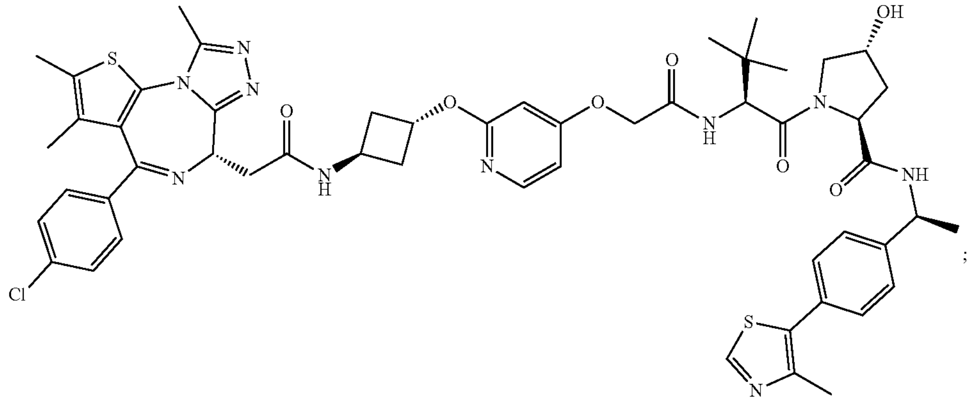
;
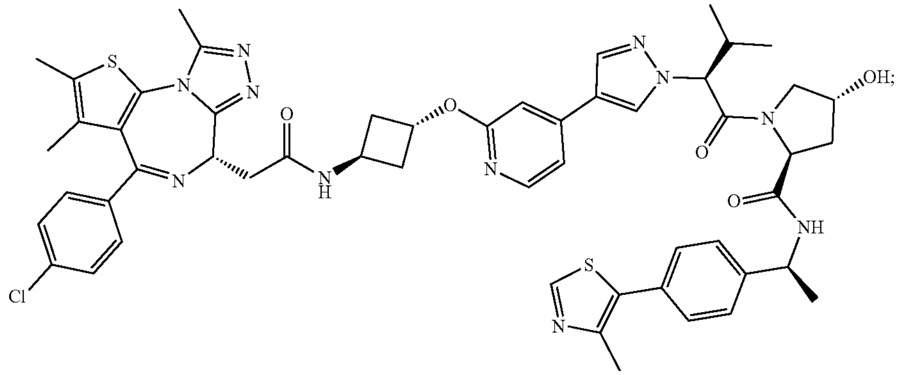
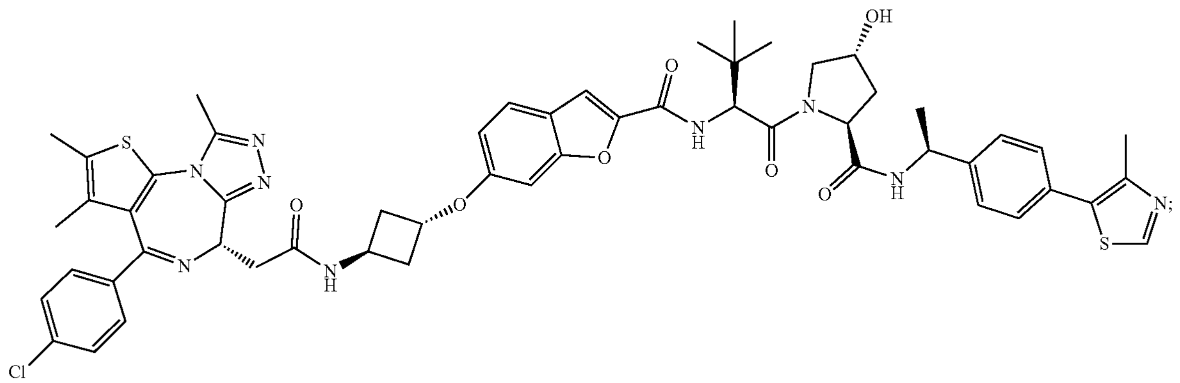
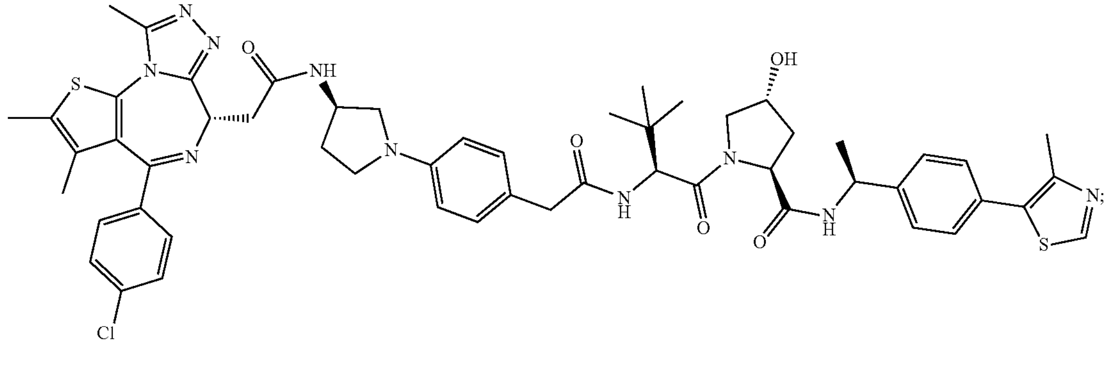

-continued
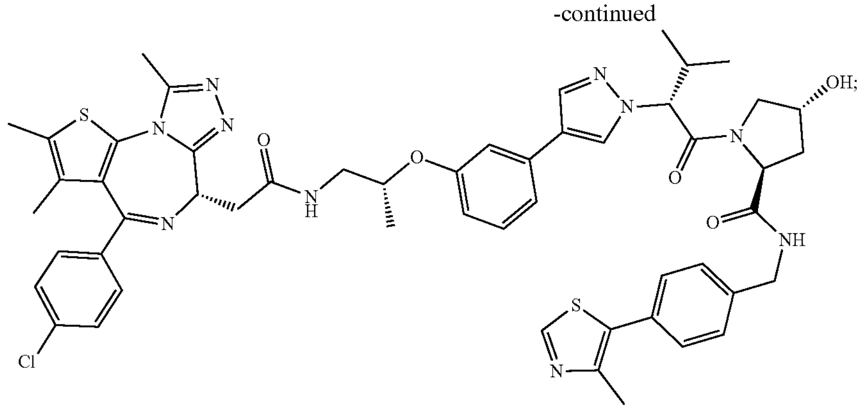
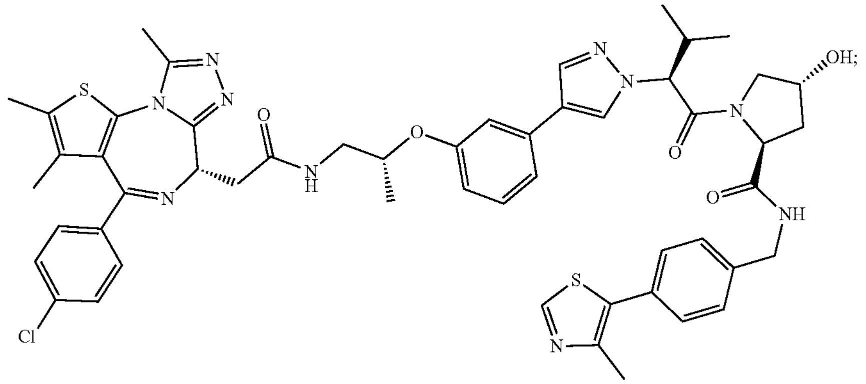
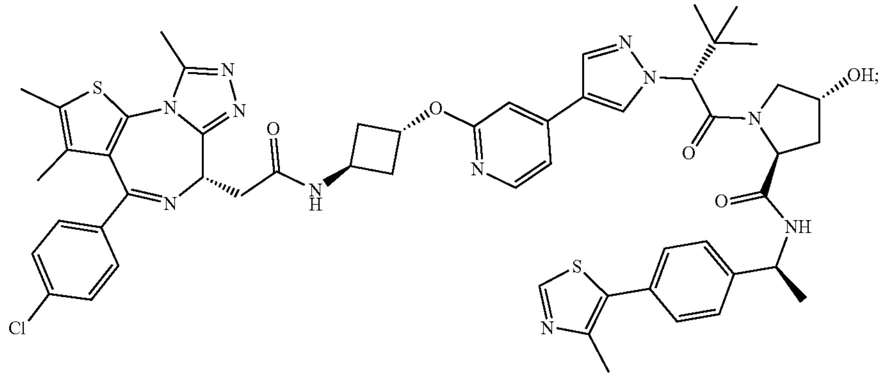
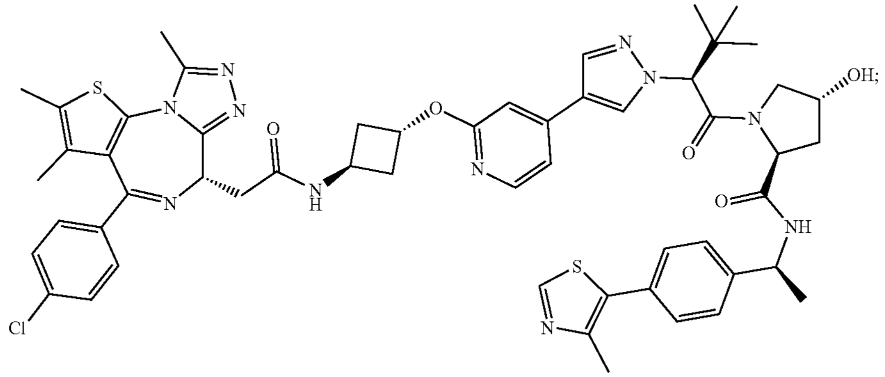

-continued
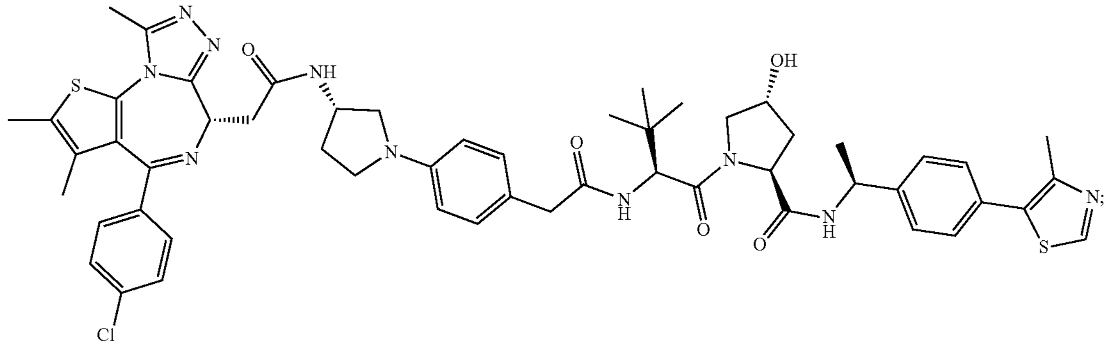
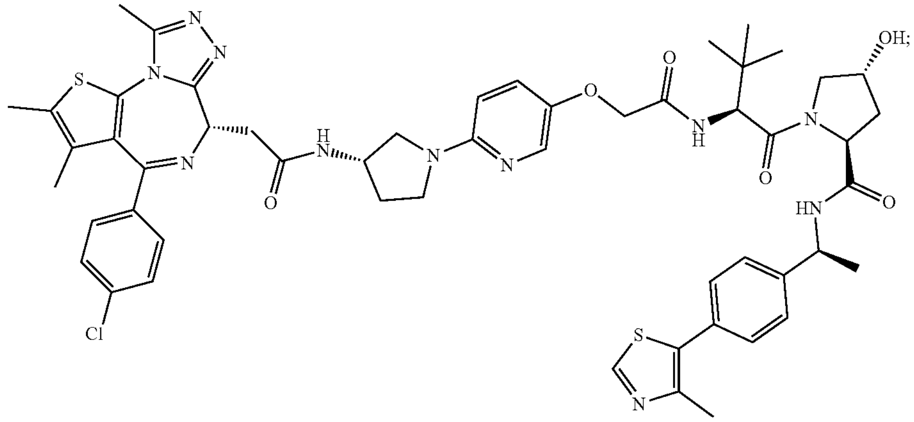
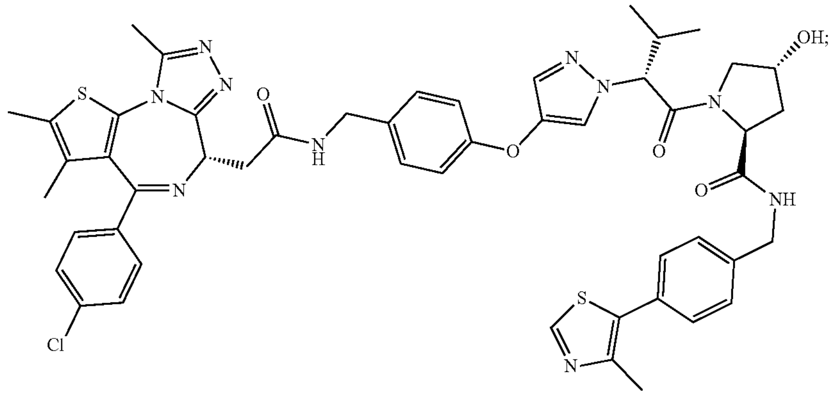
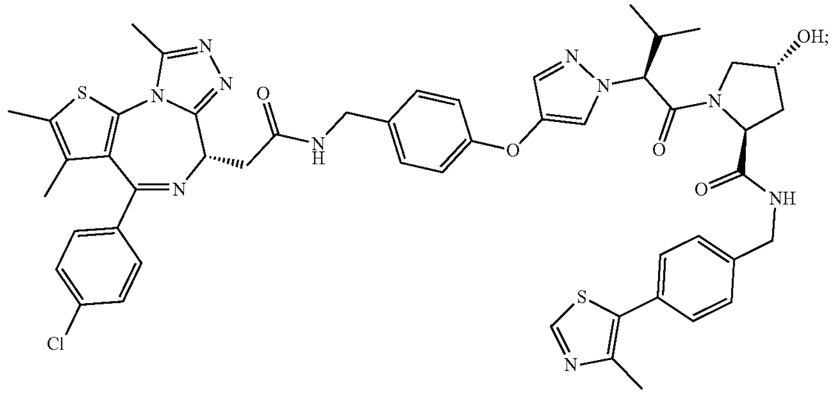

-continued
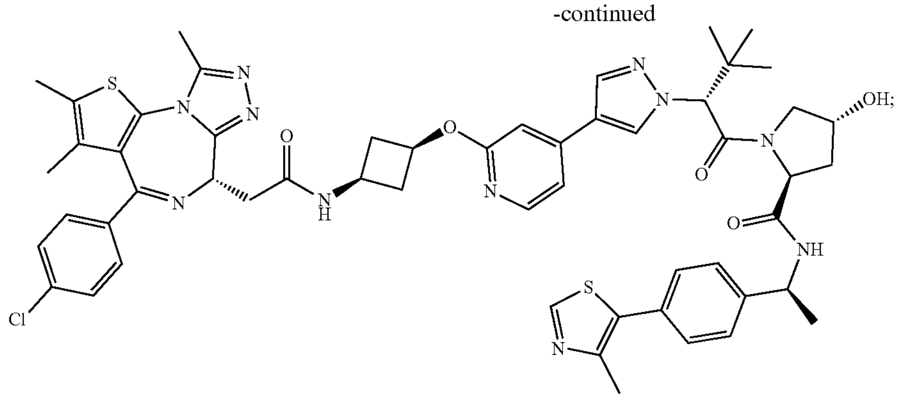
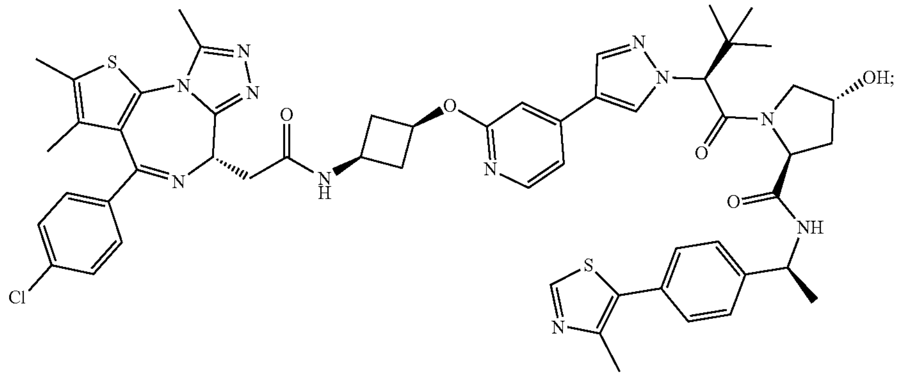
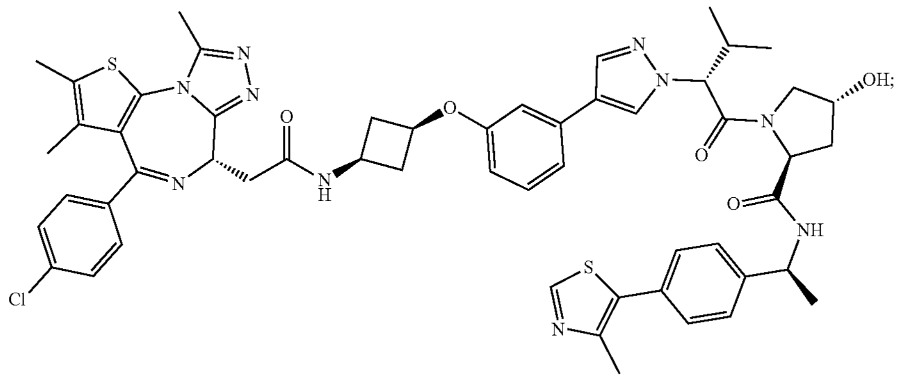
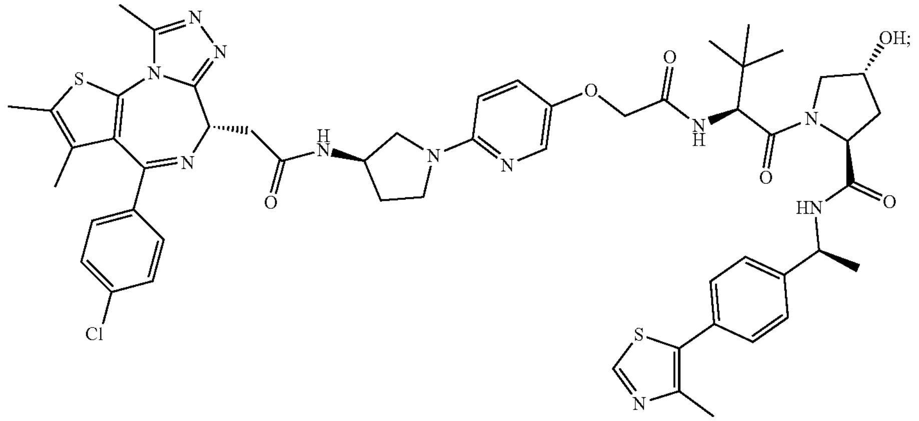

-continued
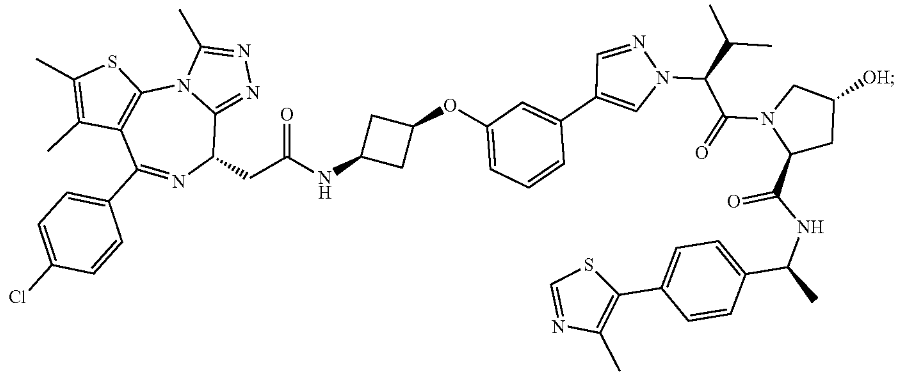
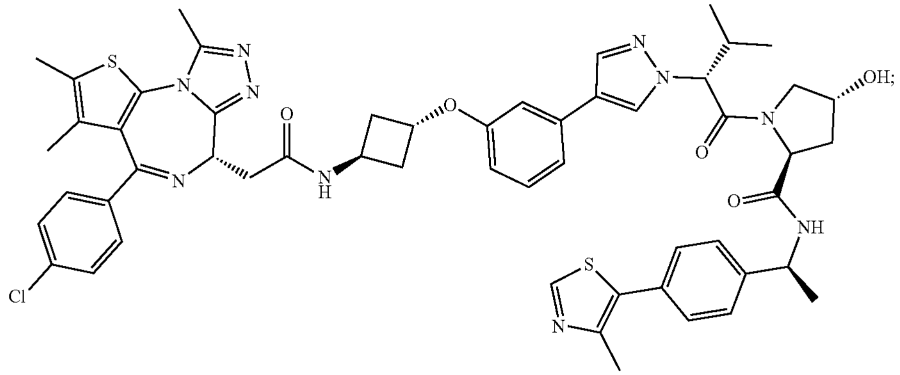
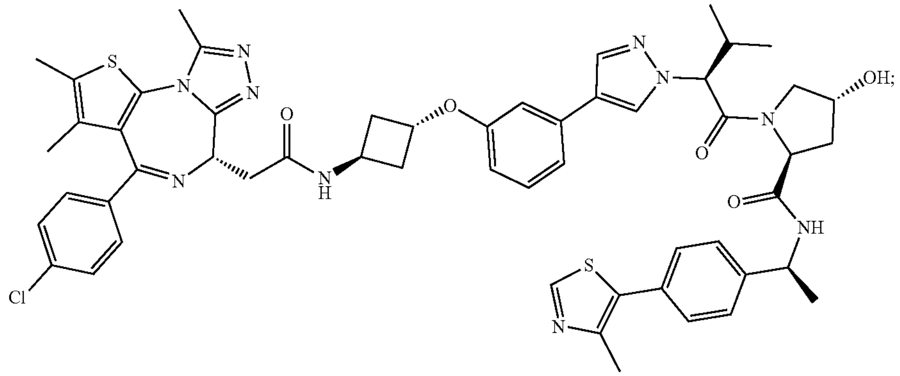
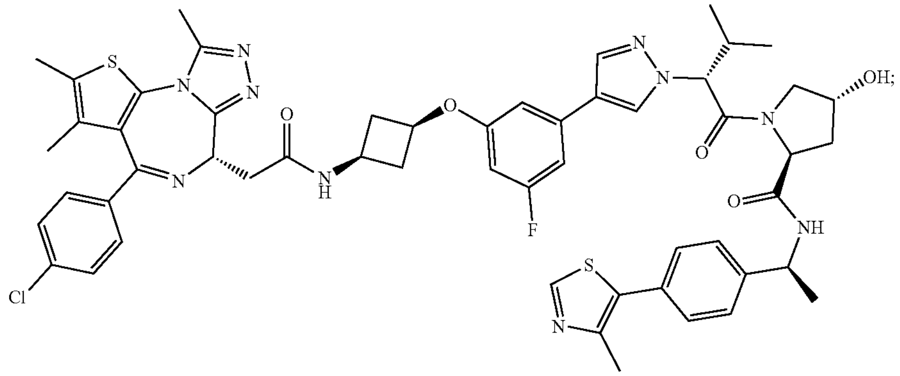

-continued
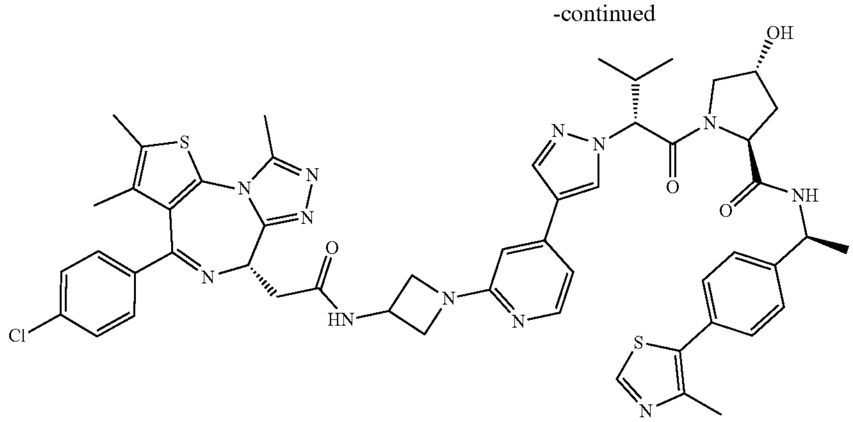
;
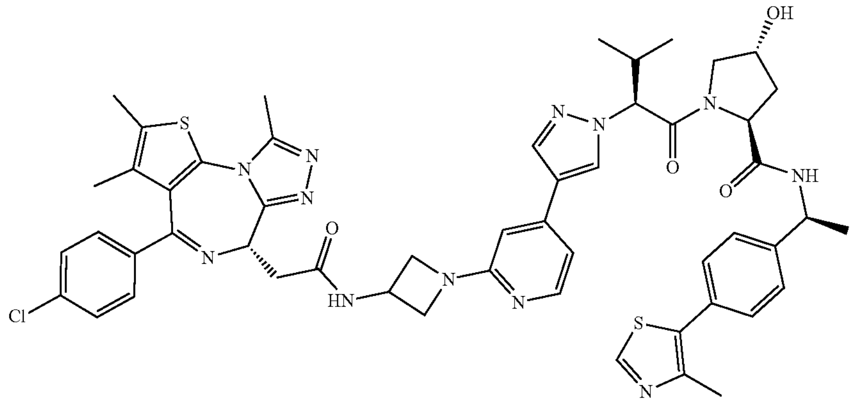
;
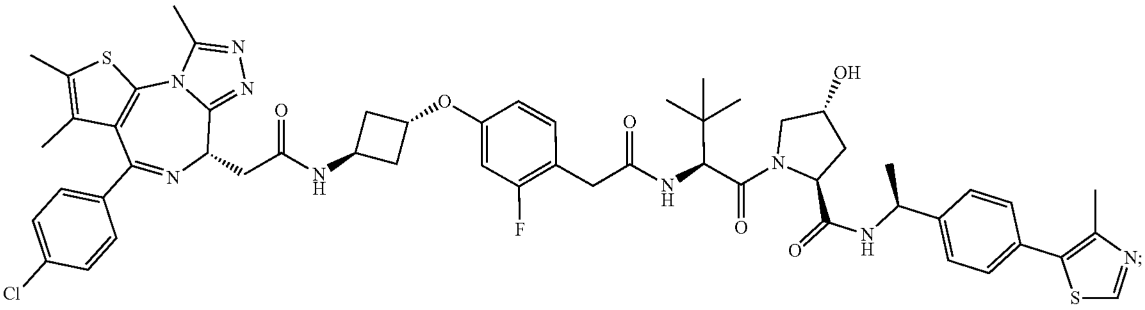
;
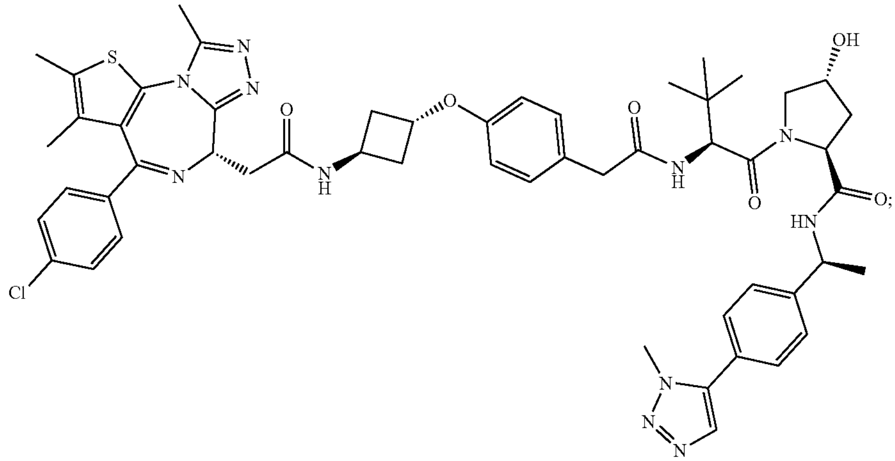
;

-continued
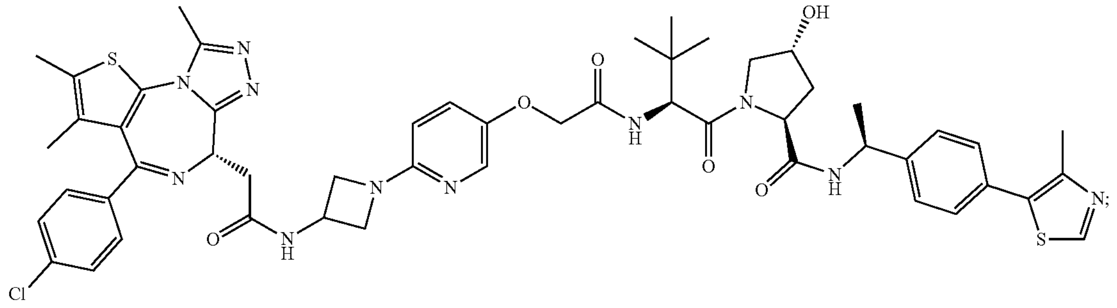
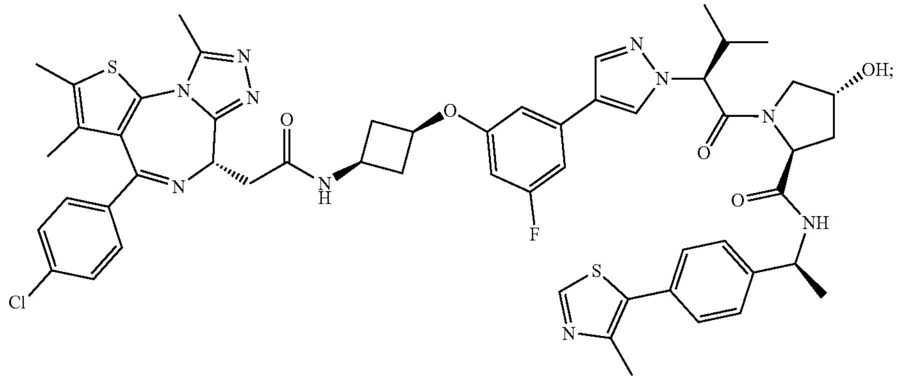
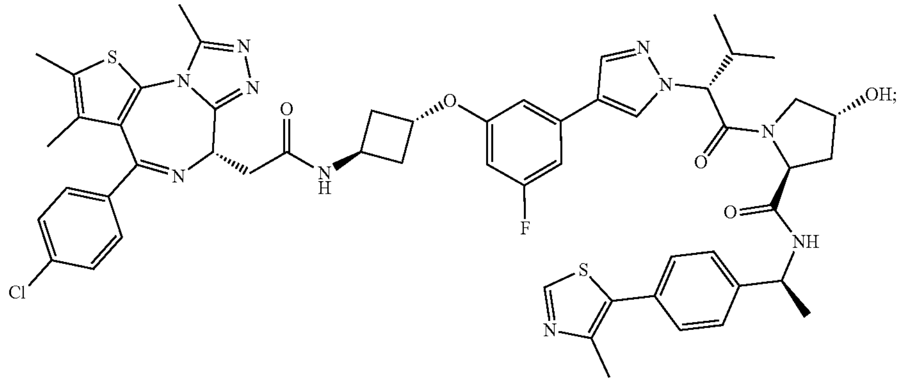
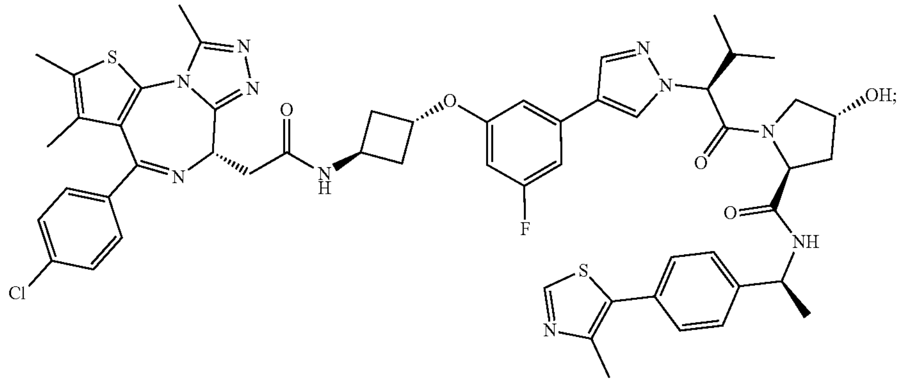

-continued
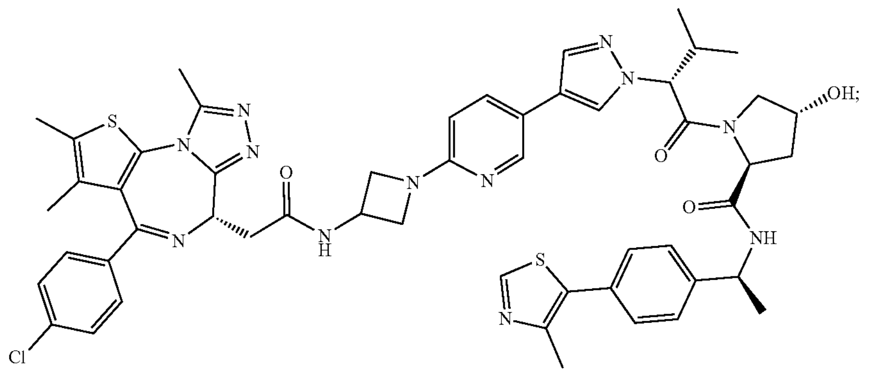
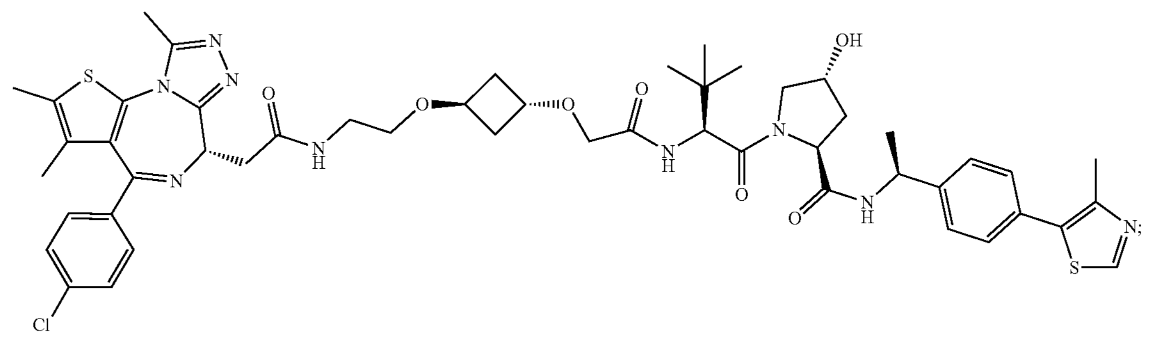
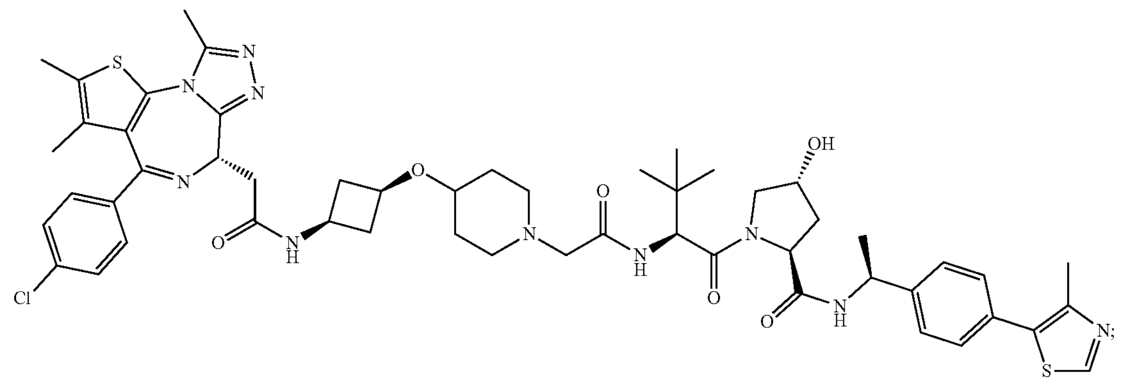
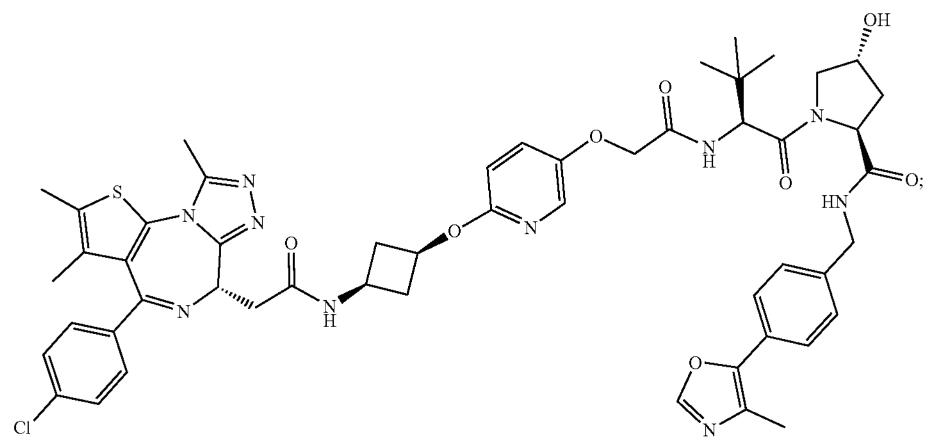

-continued
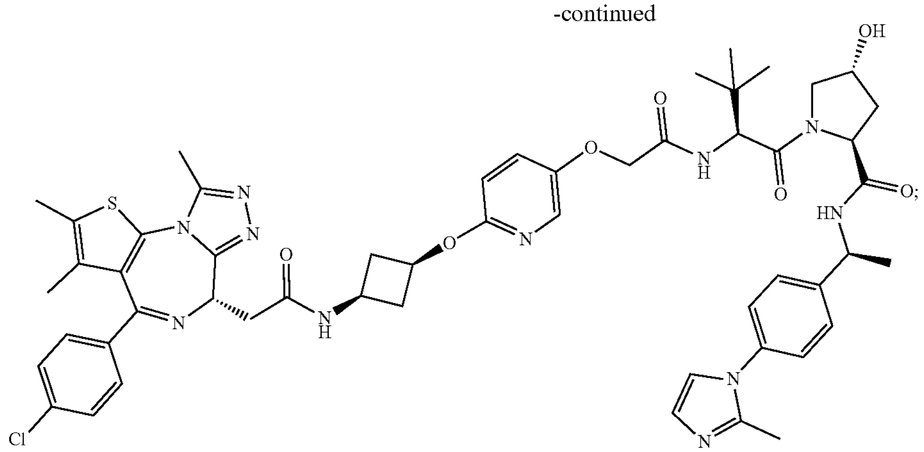
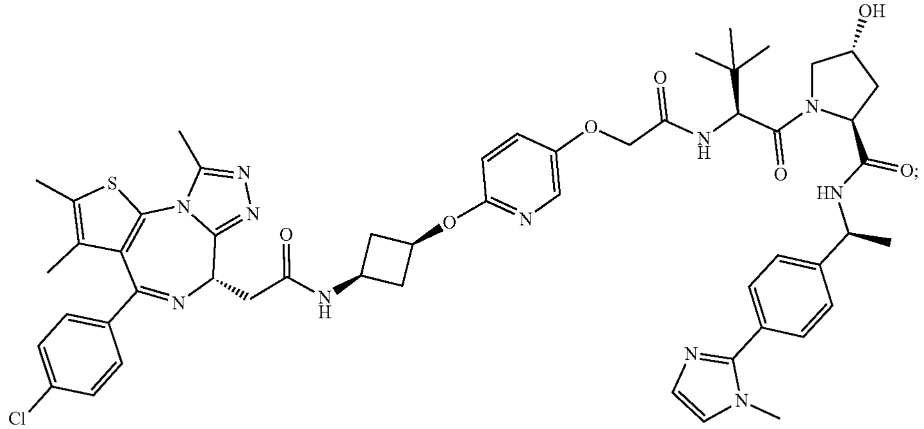
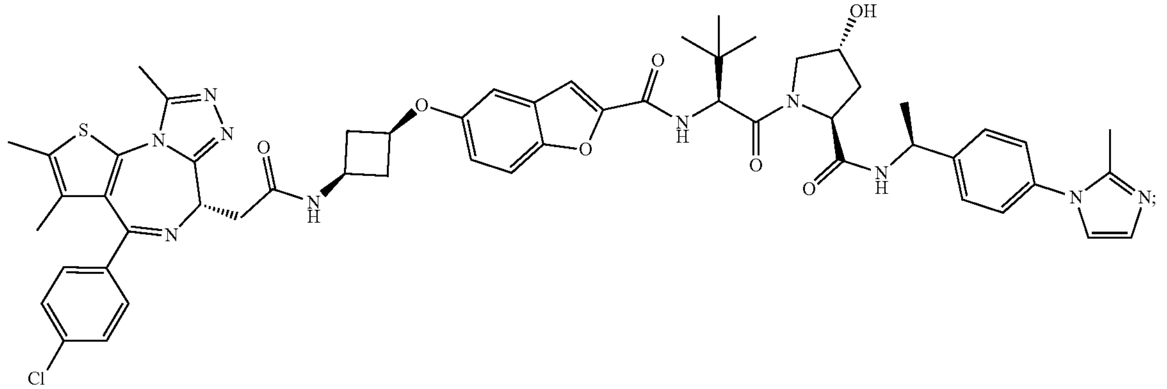
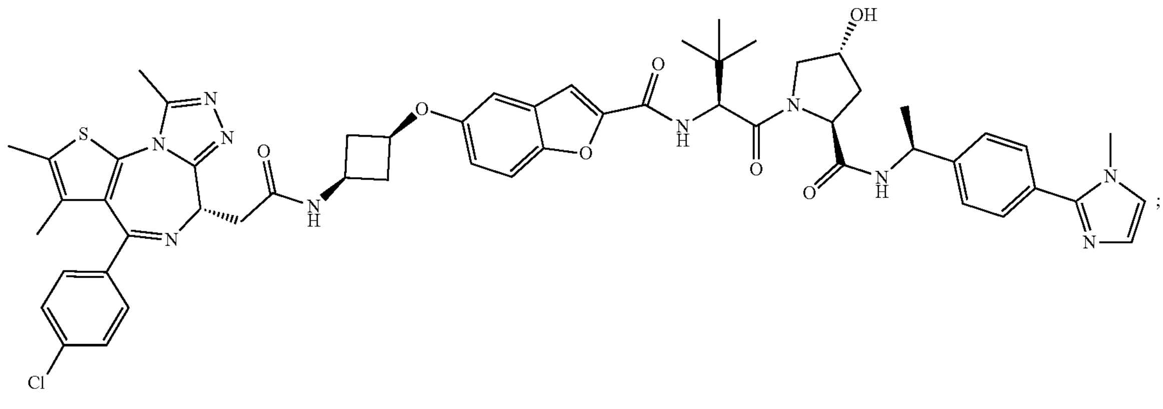
;

-continued
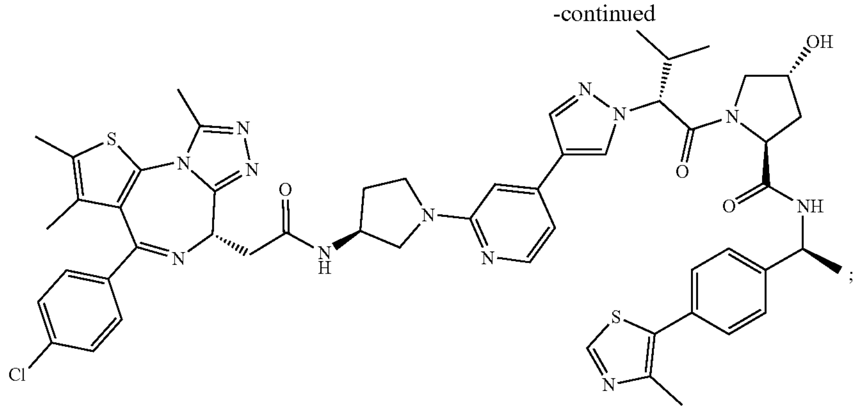
;
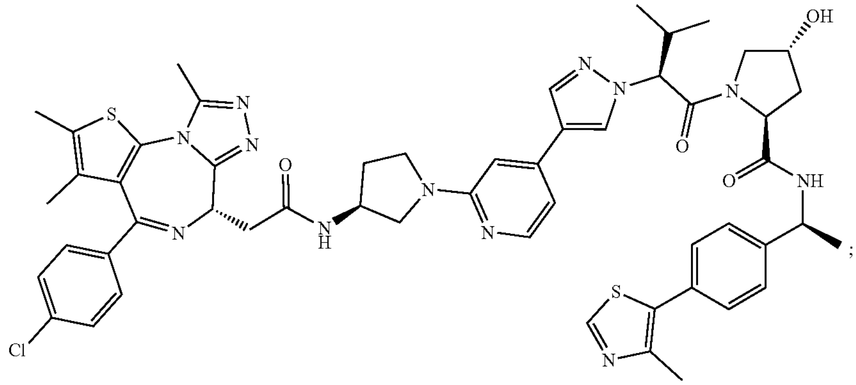
;
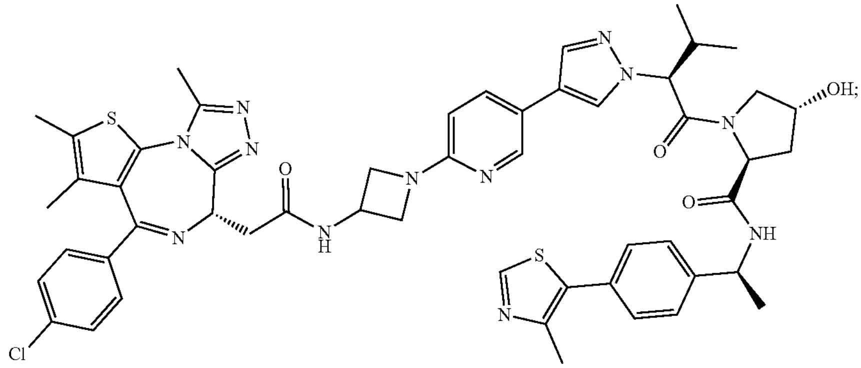
;
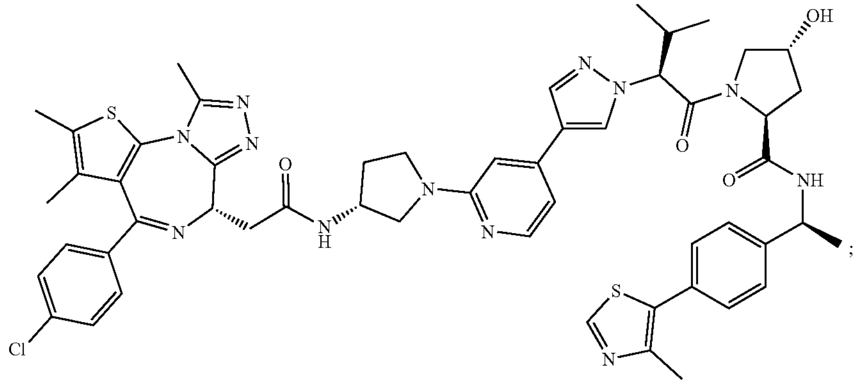
;

-continued
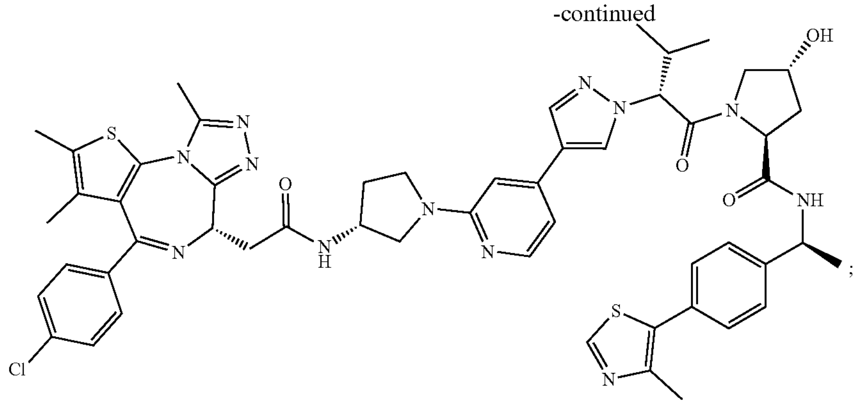
;
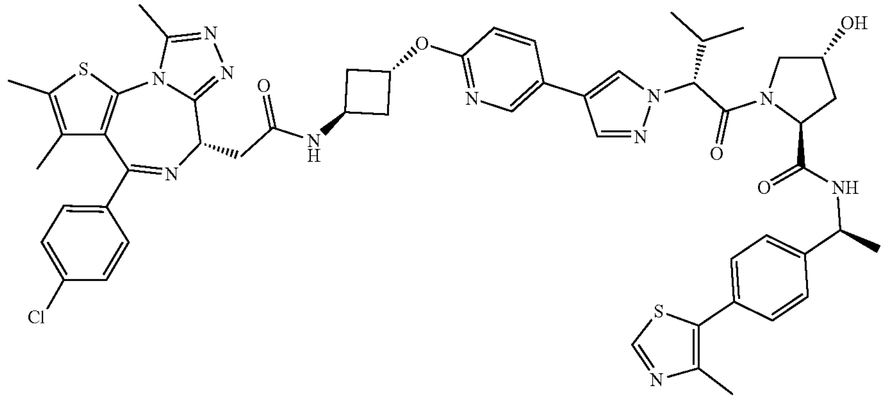
;
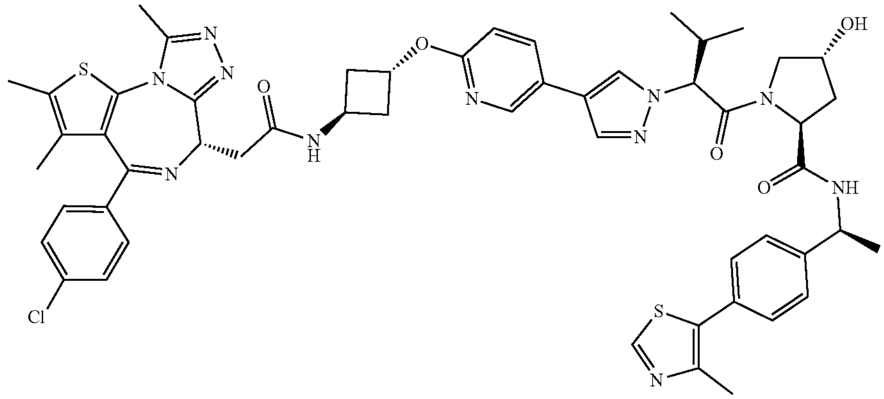
;
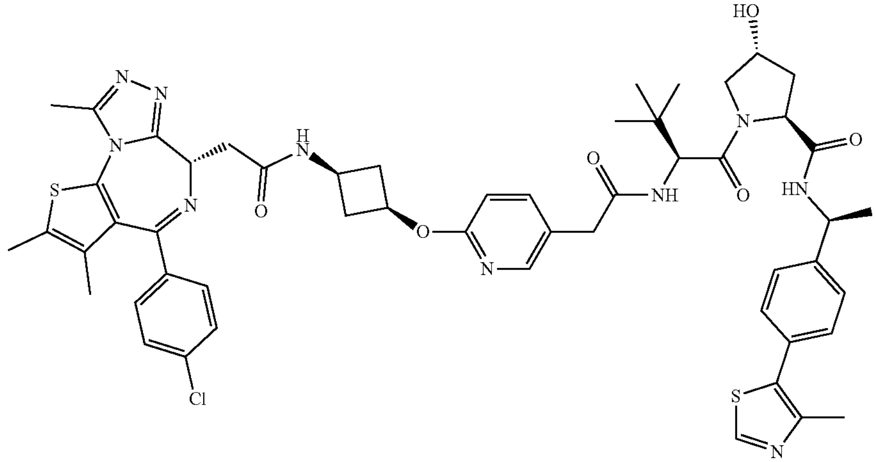
;

-continued
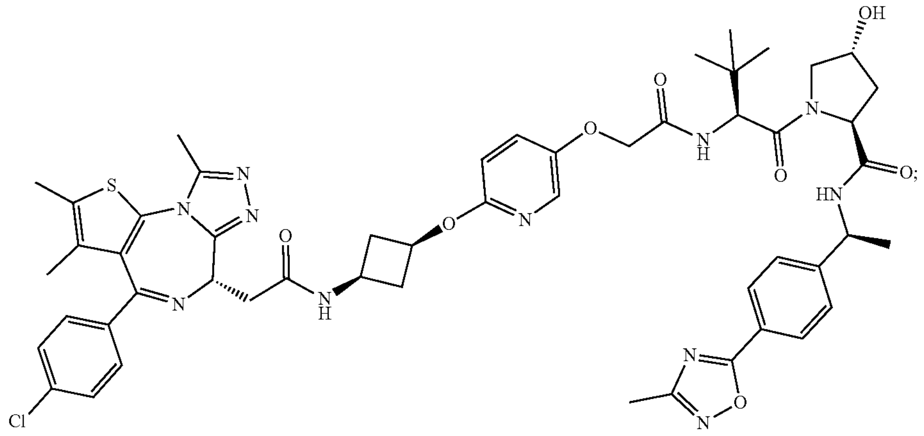
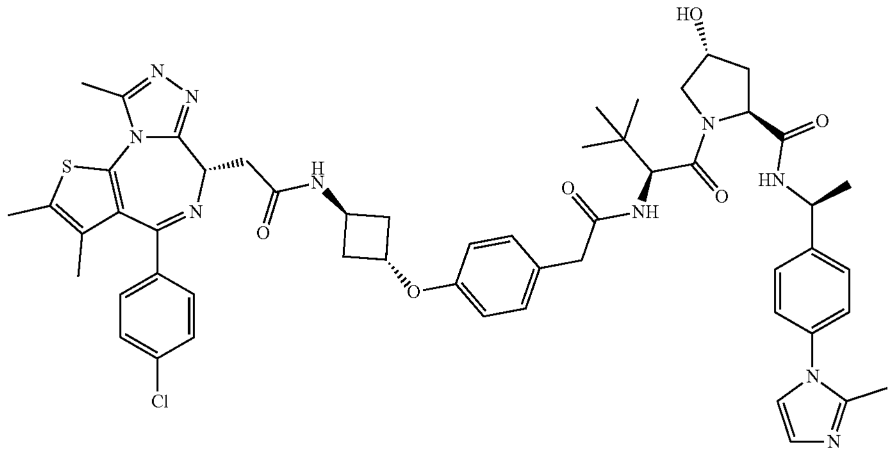
;
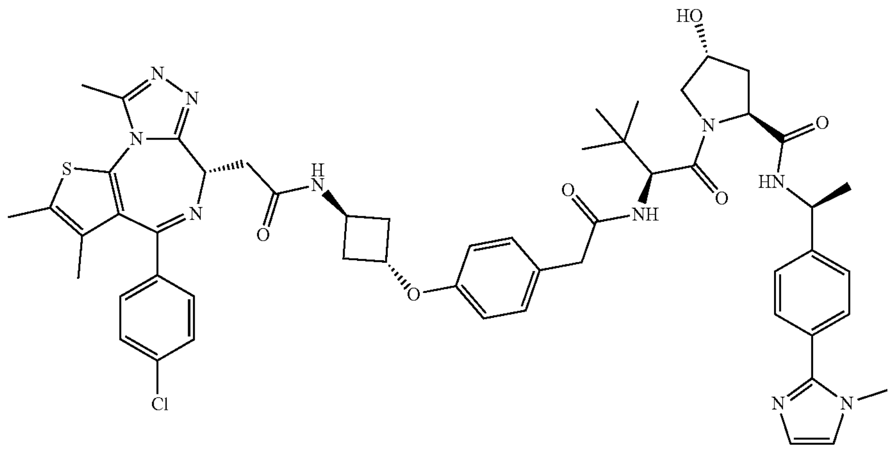
;

-continued
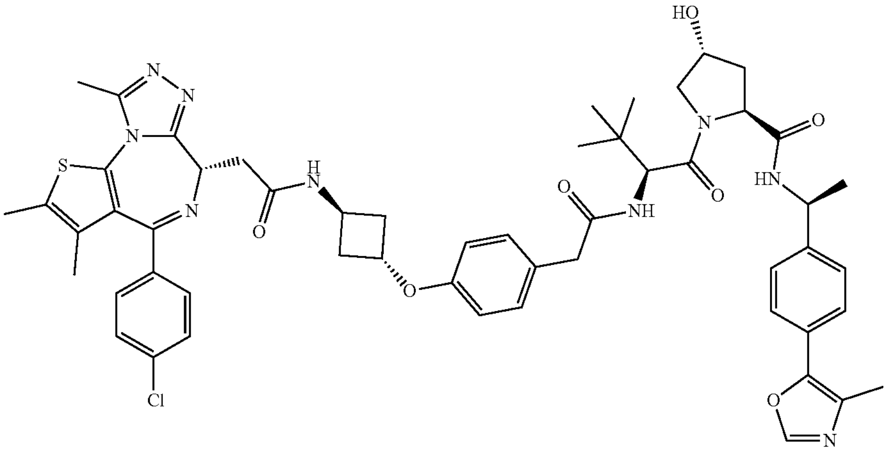
;
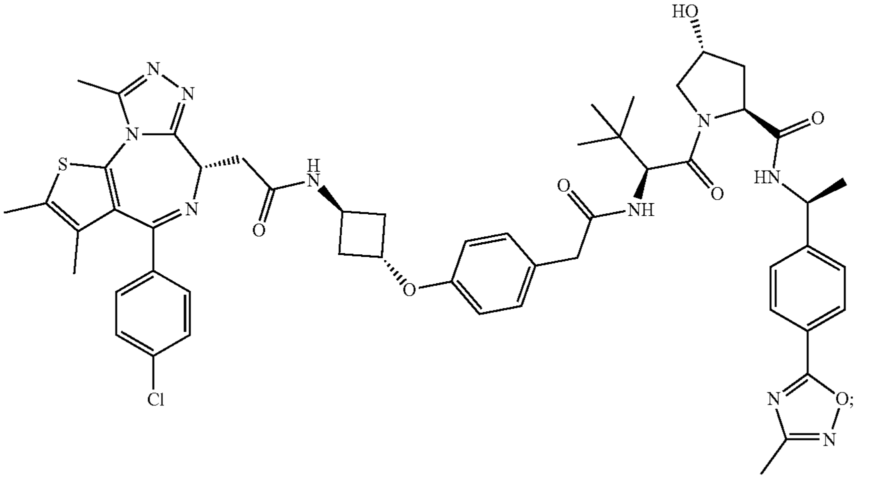
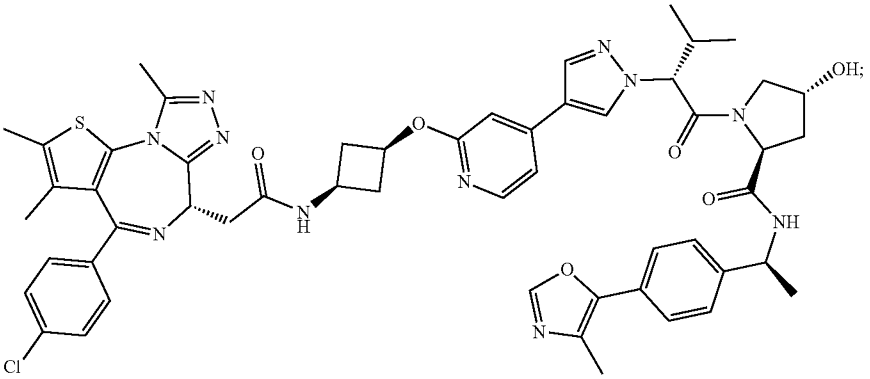
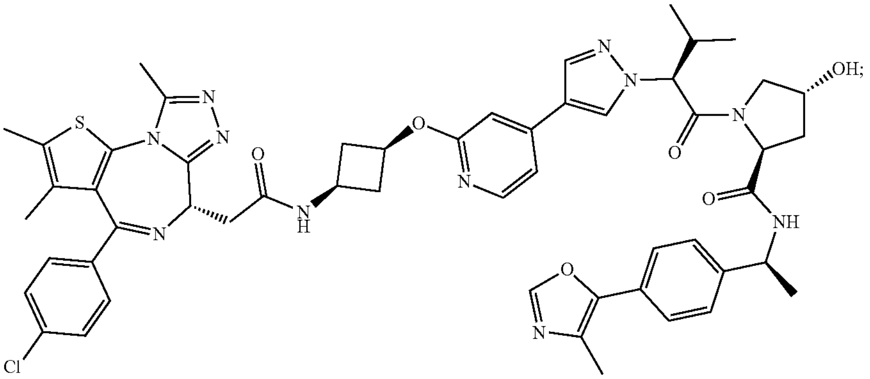

-continued
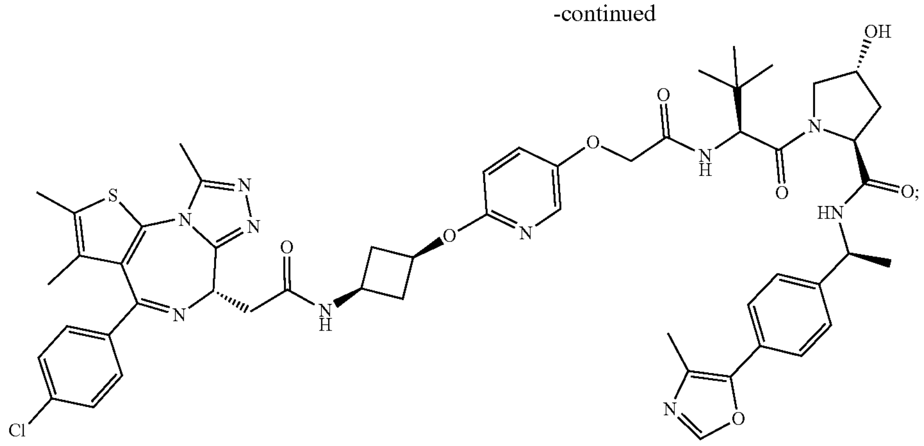
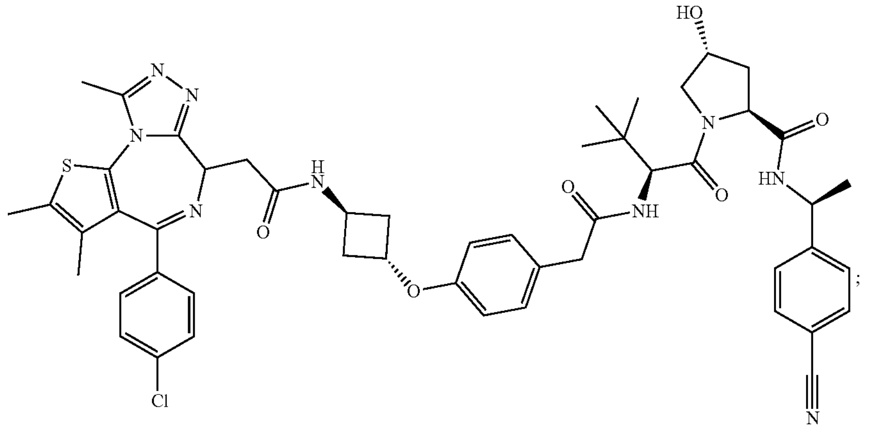
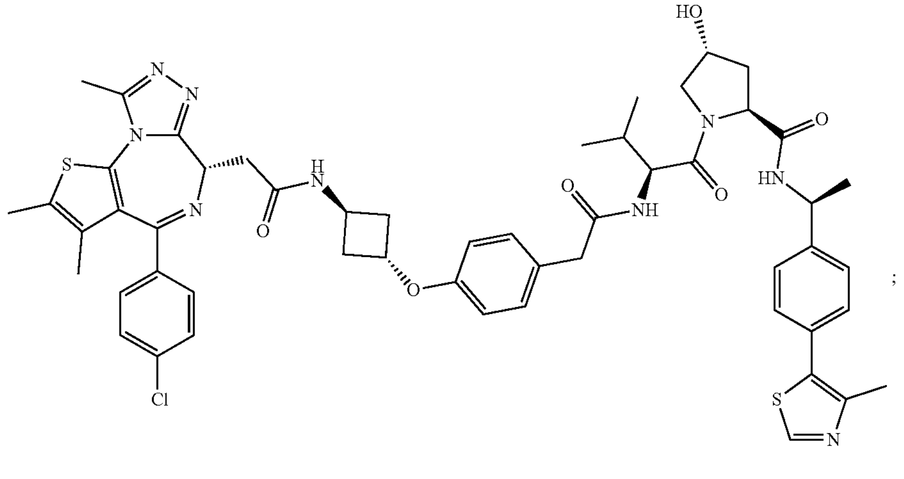

-continued
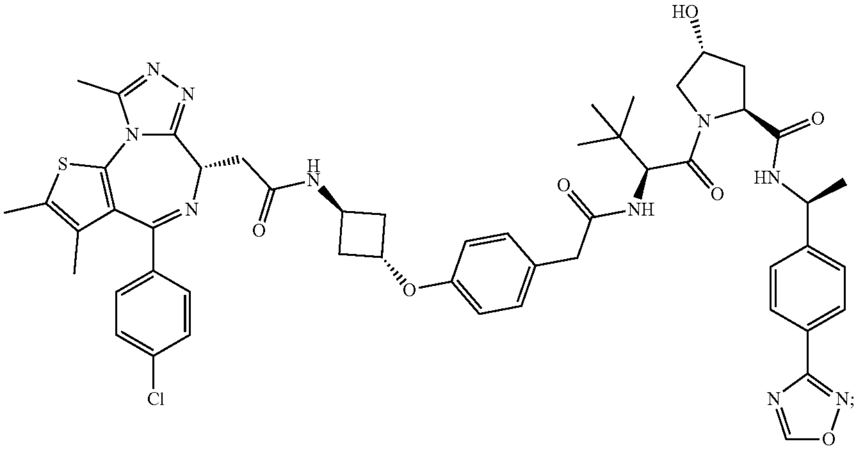
;
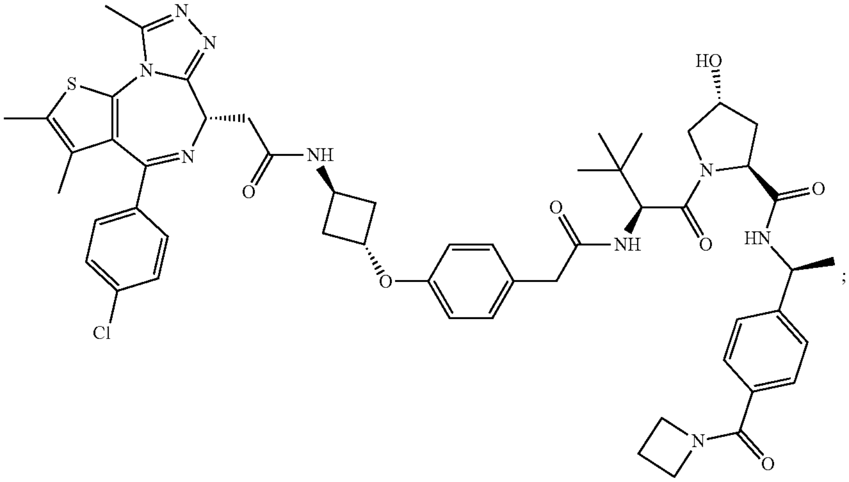
;
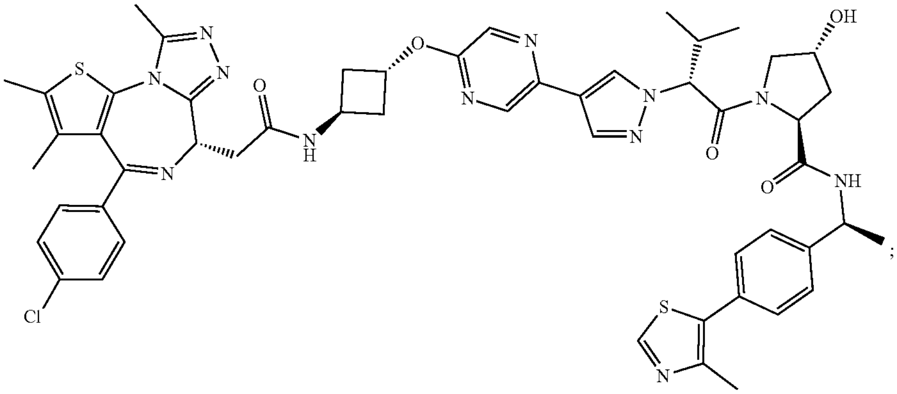
;
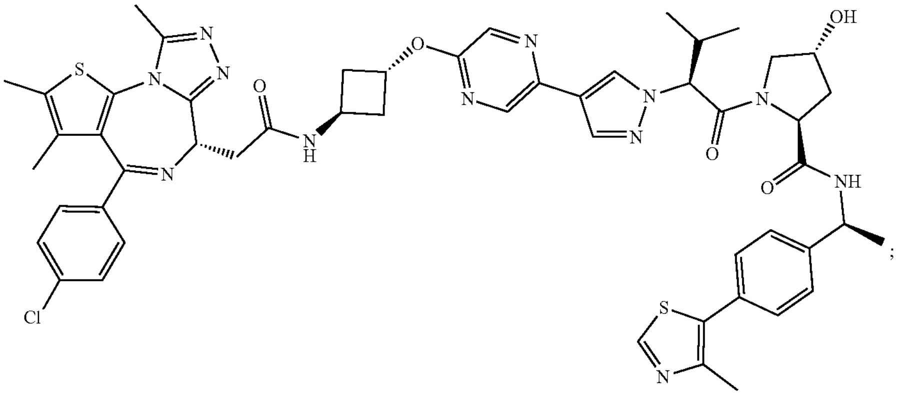
;

-continued
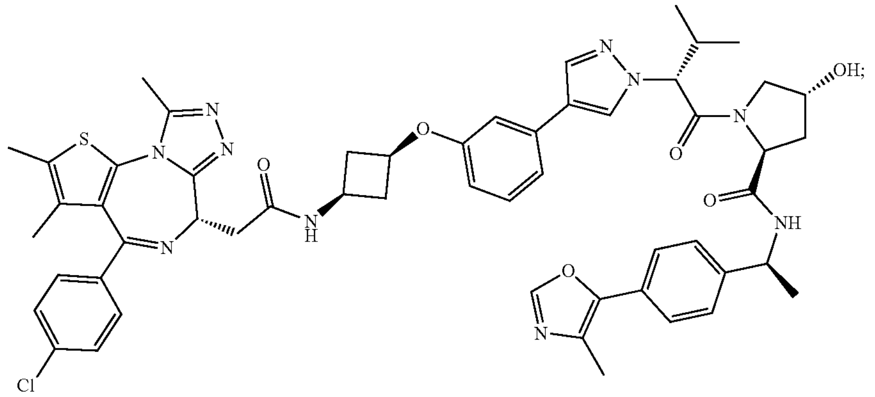
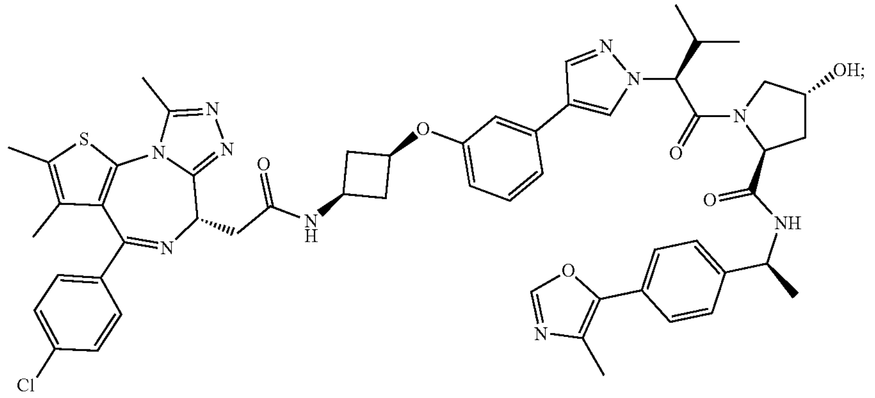
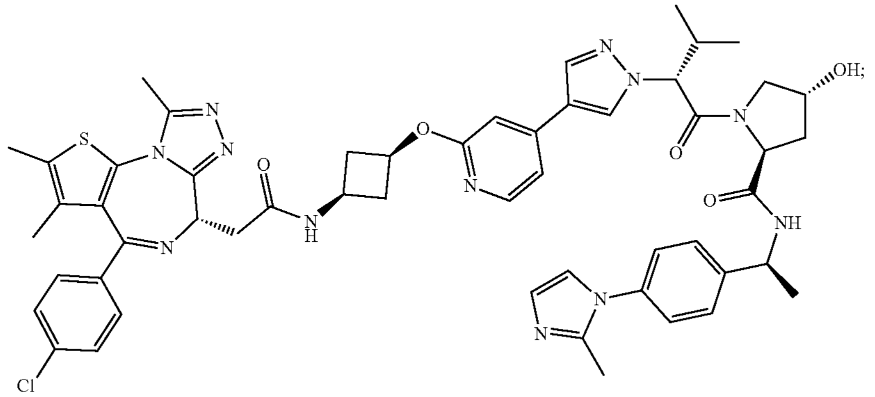
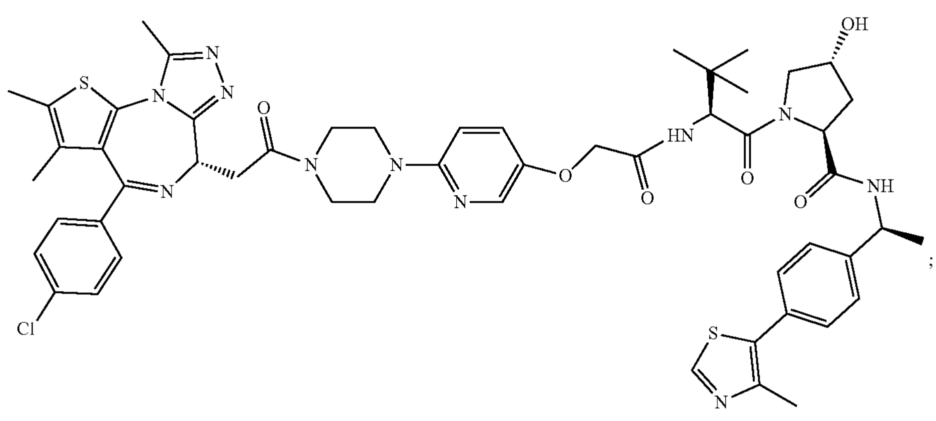
;

-continued
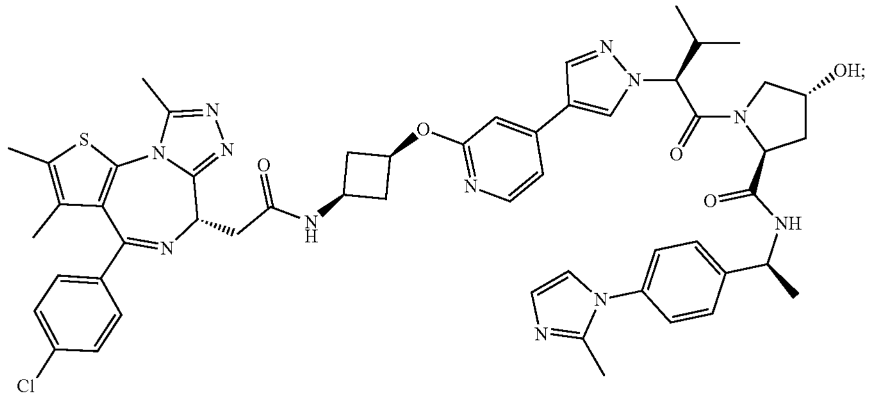
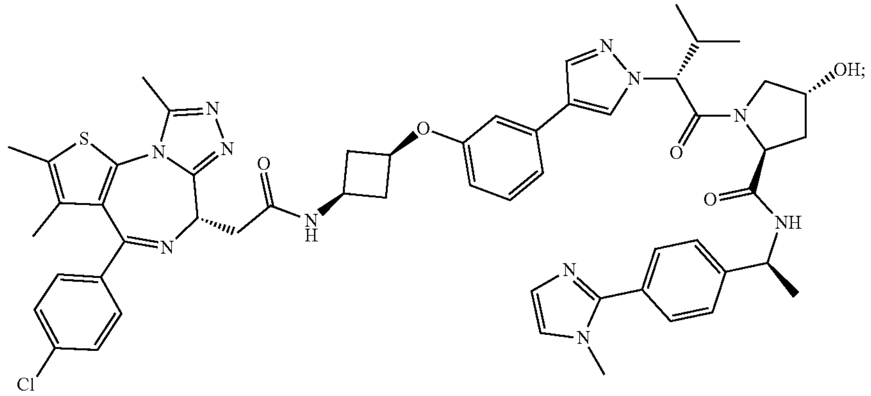
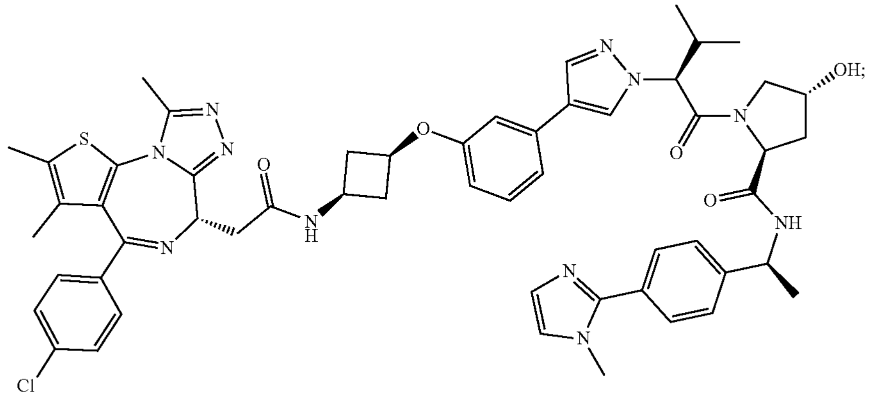
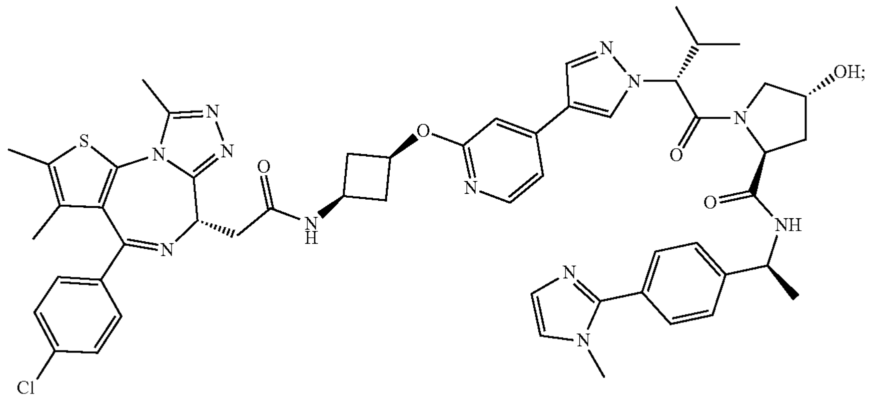

-continued
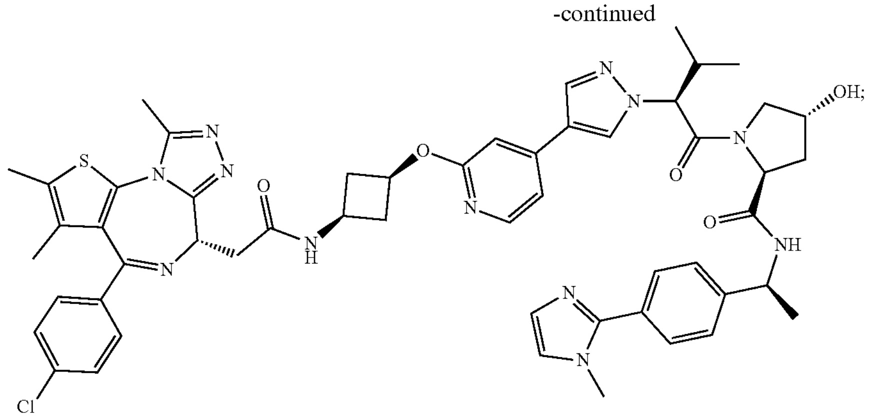
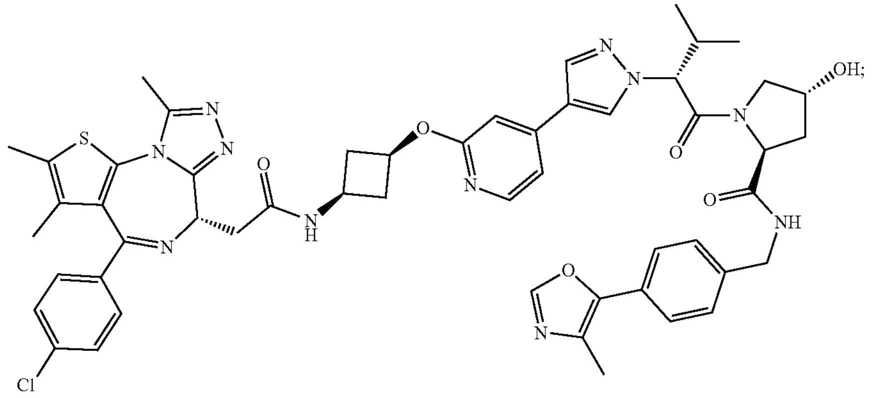
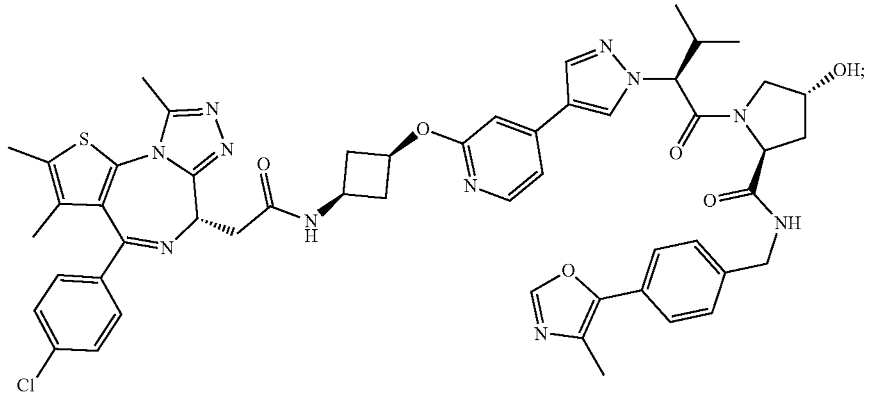
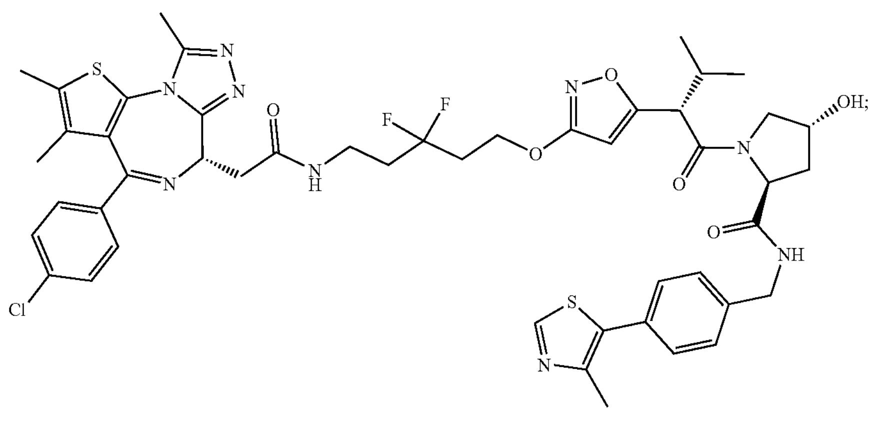

-continued
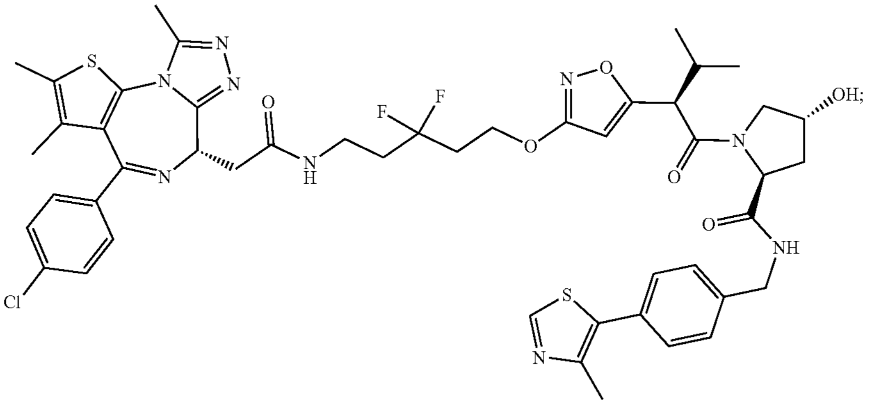
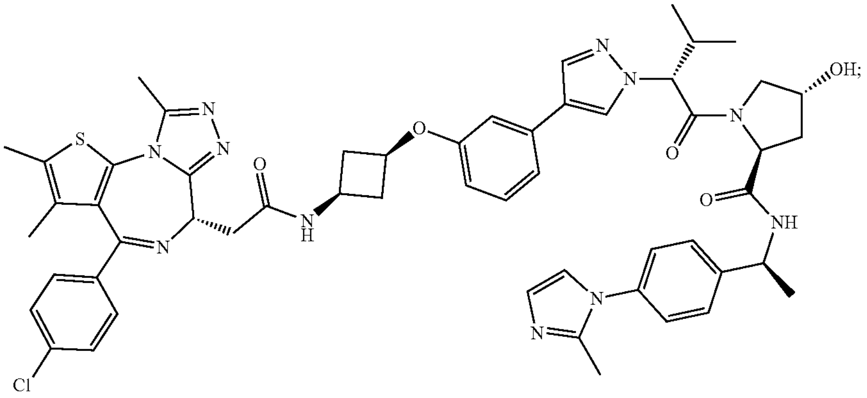
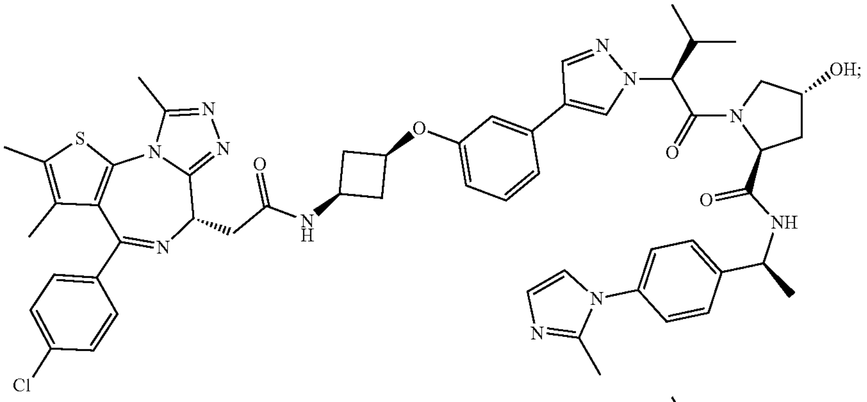
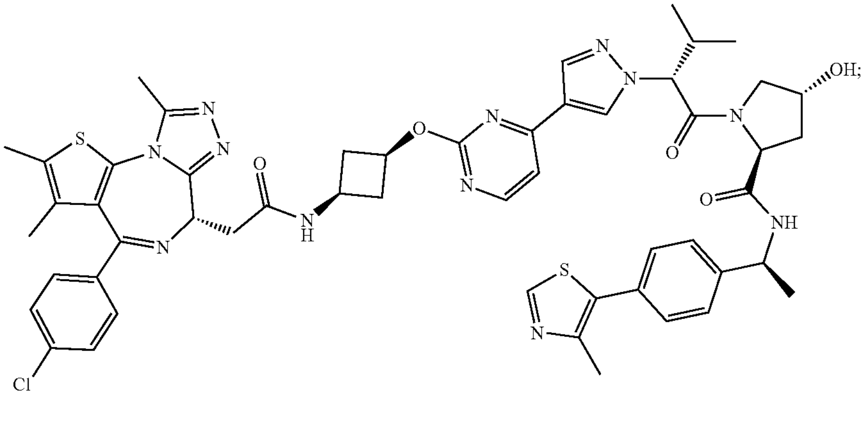
or a pharmaceutically acceptable salt, enantiomer, or diastereomer, thereof.

23. The bifunctional compound according to claim 1, wherein the bifunctional compound is selected from the group consisting of:
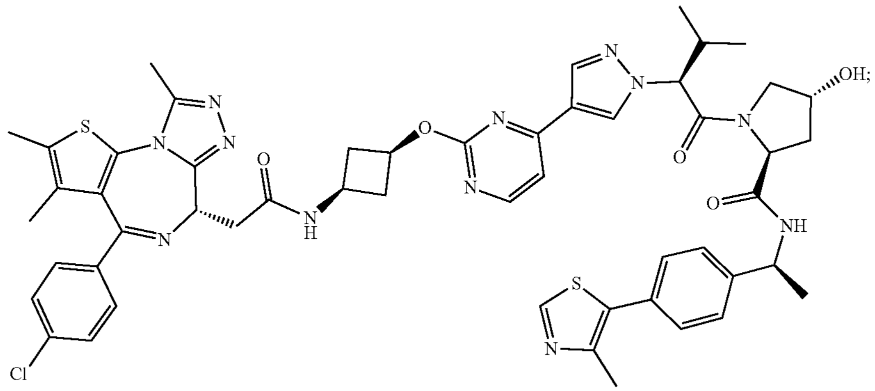
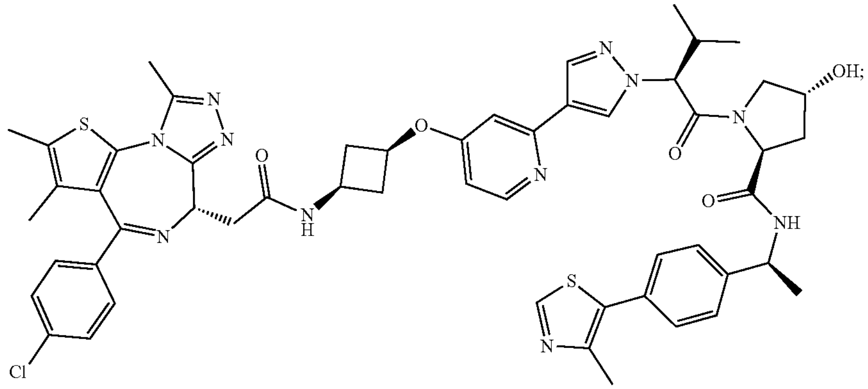
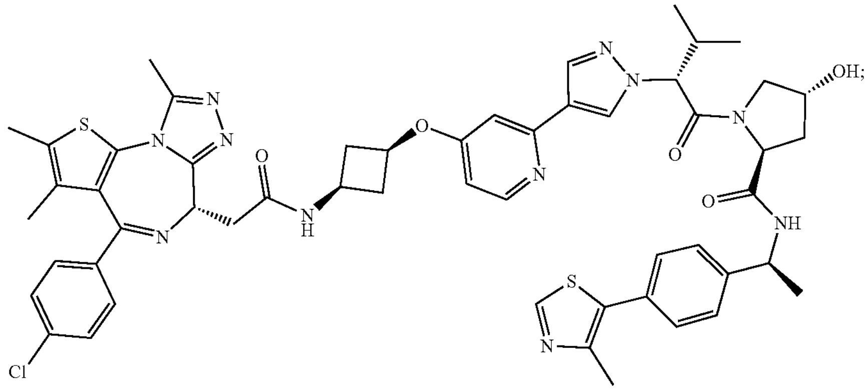
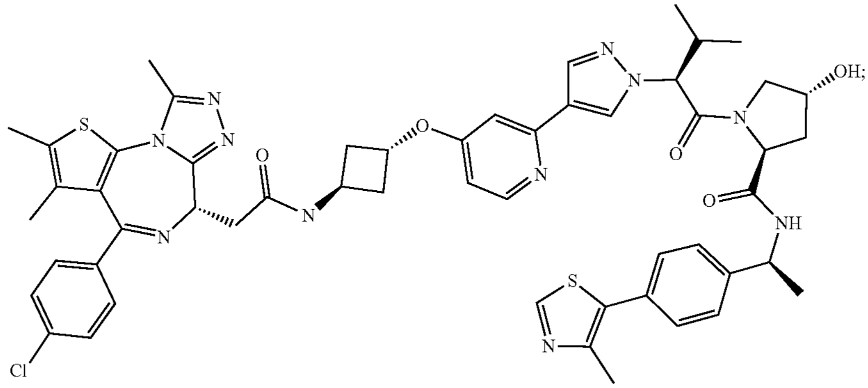

-continued
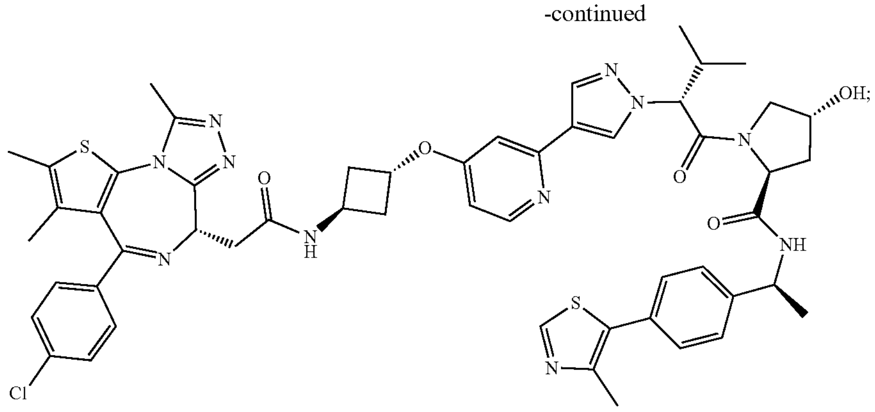
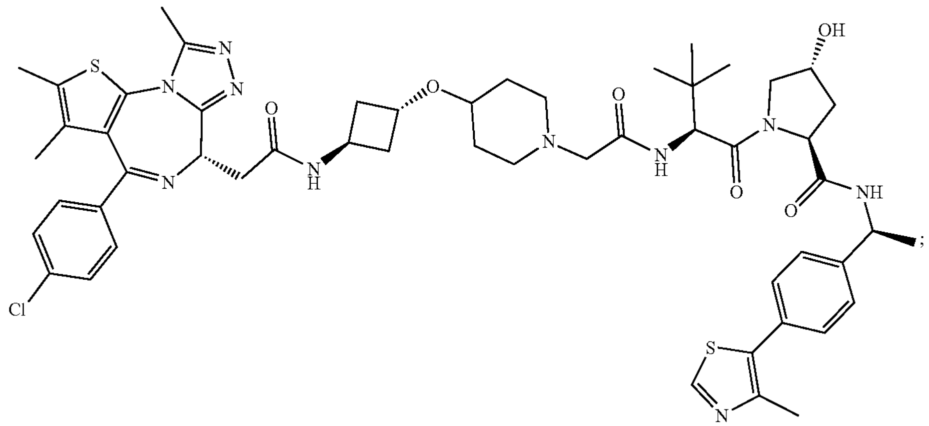
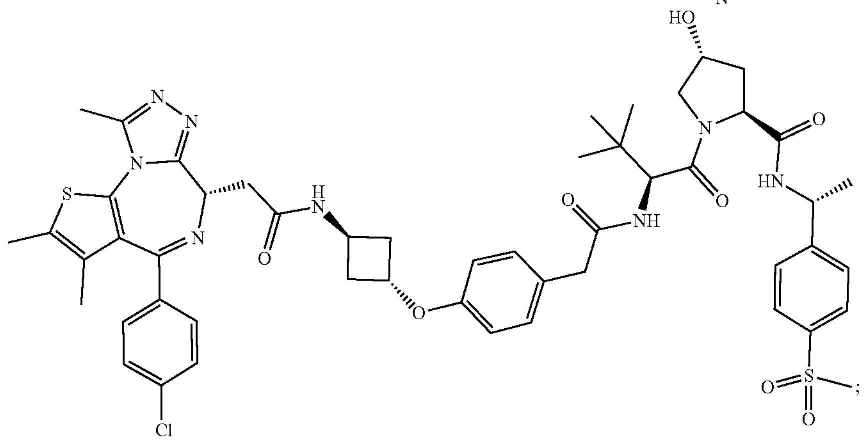
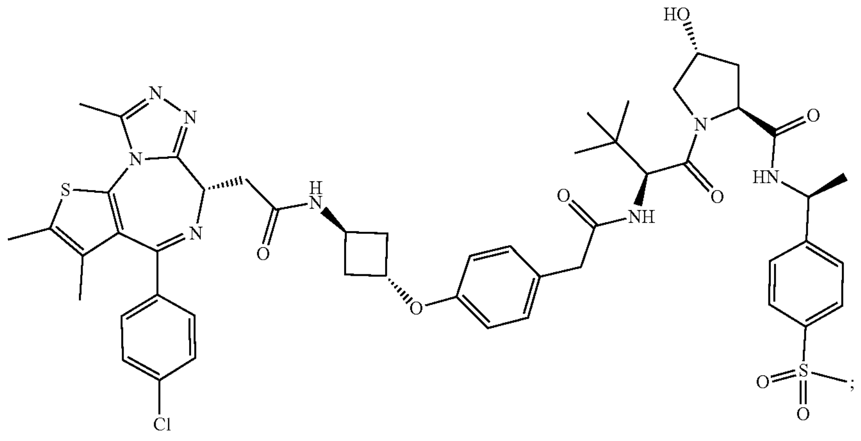

-continued
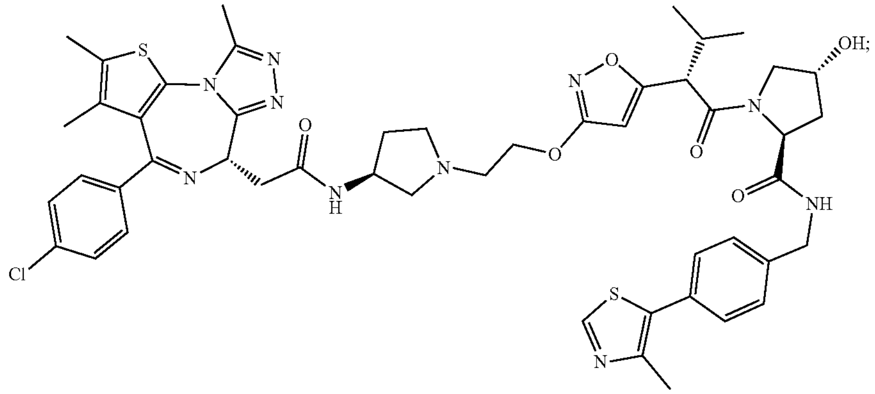
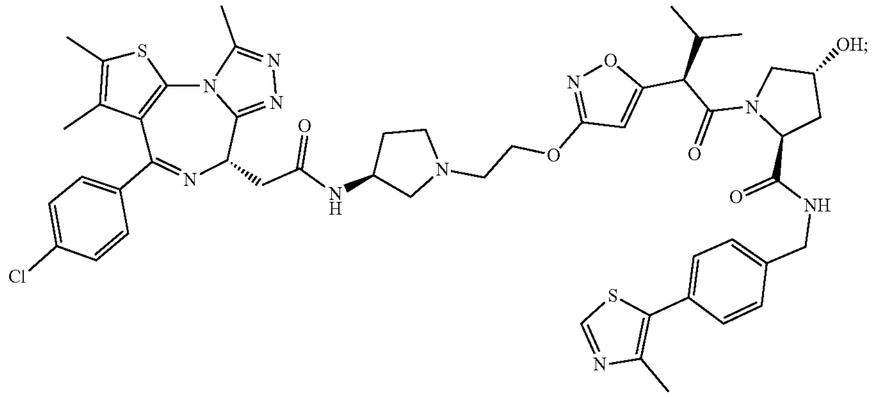
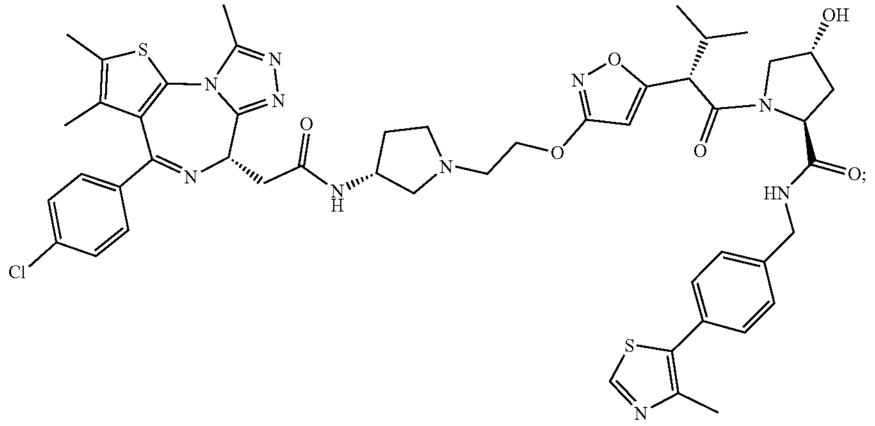
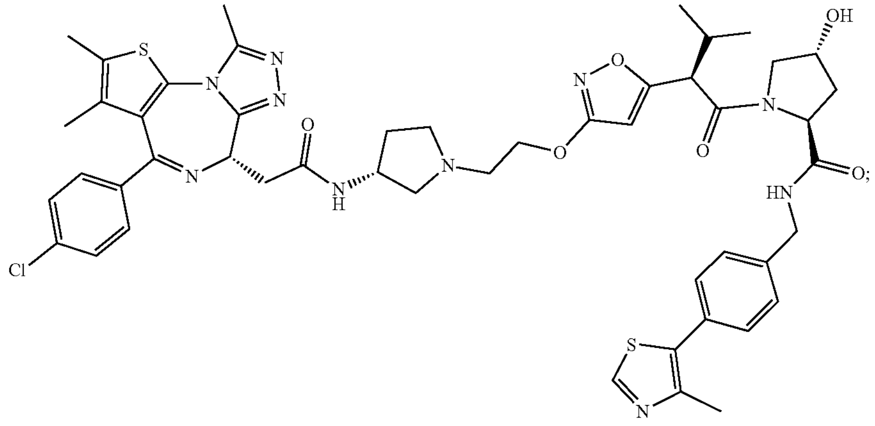

-continued
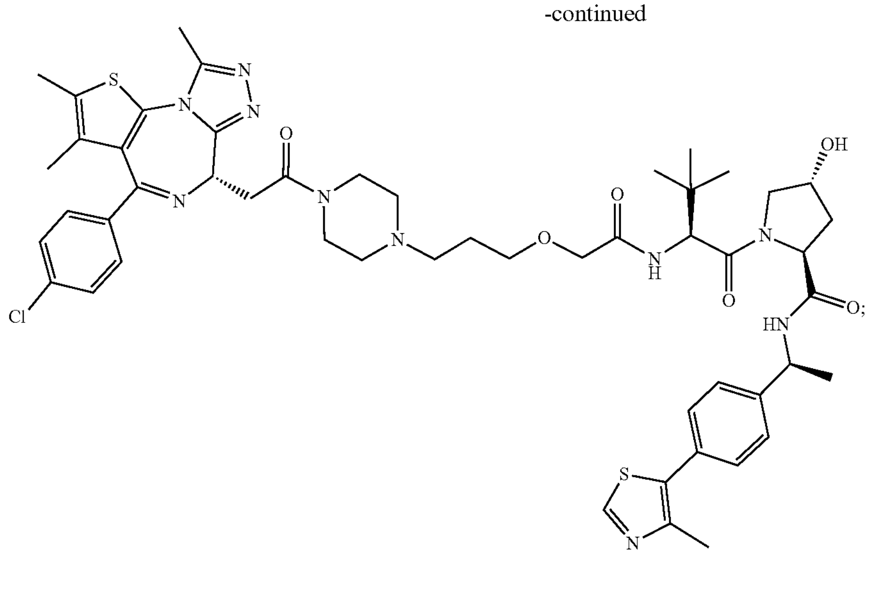
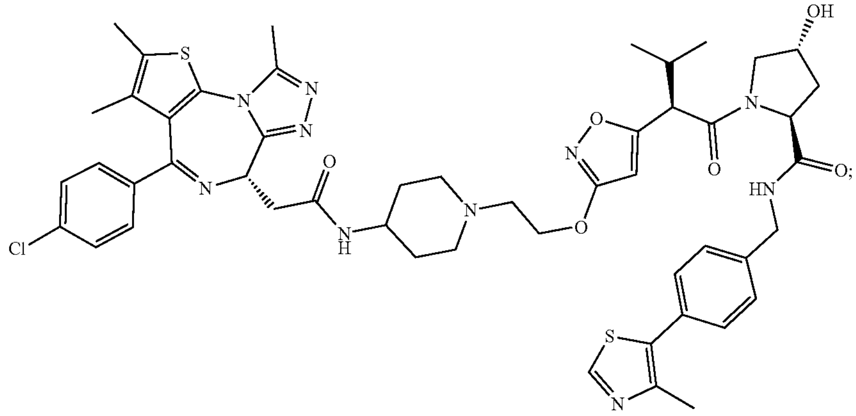
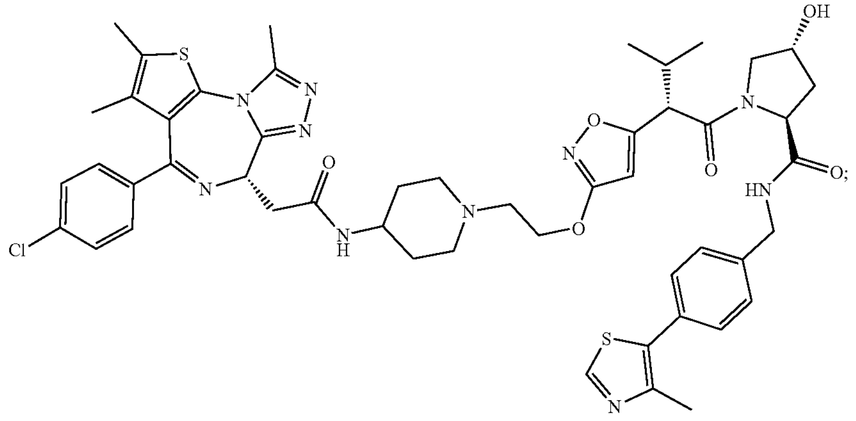

-continued
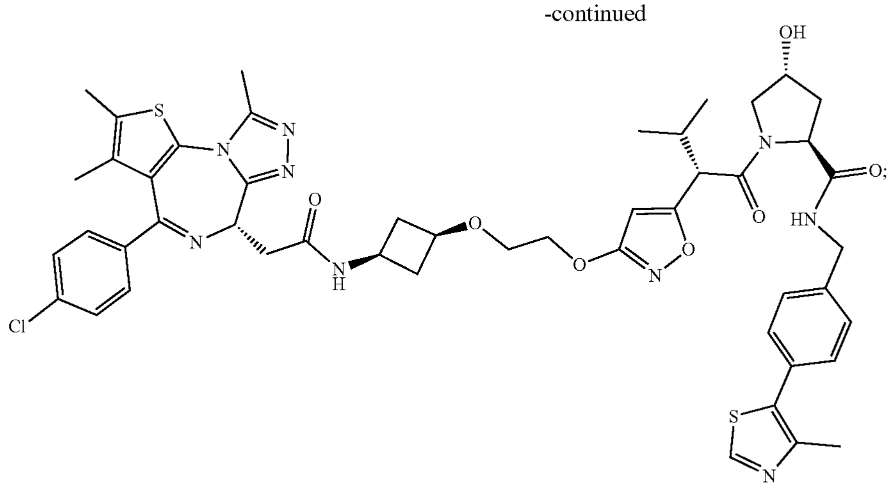
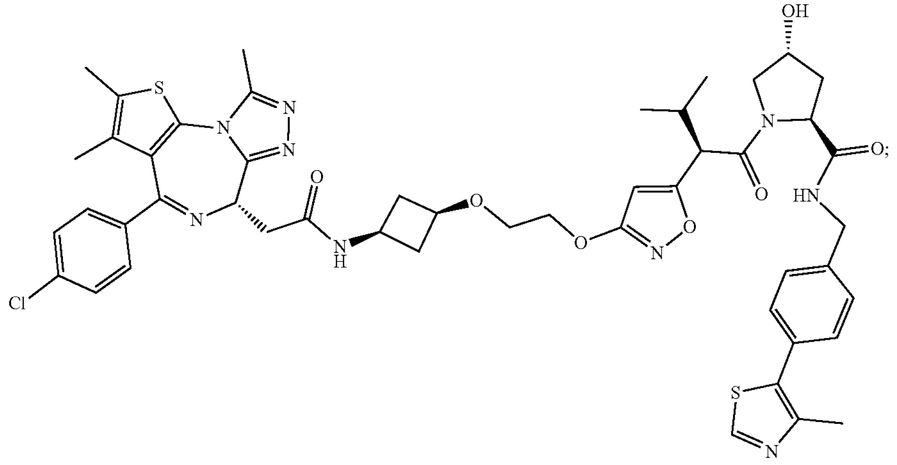
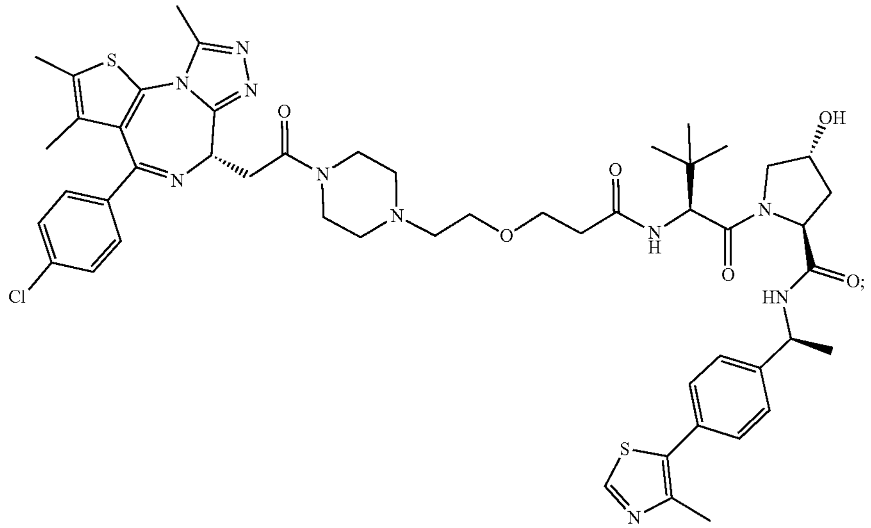

-continued
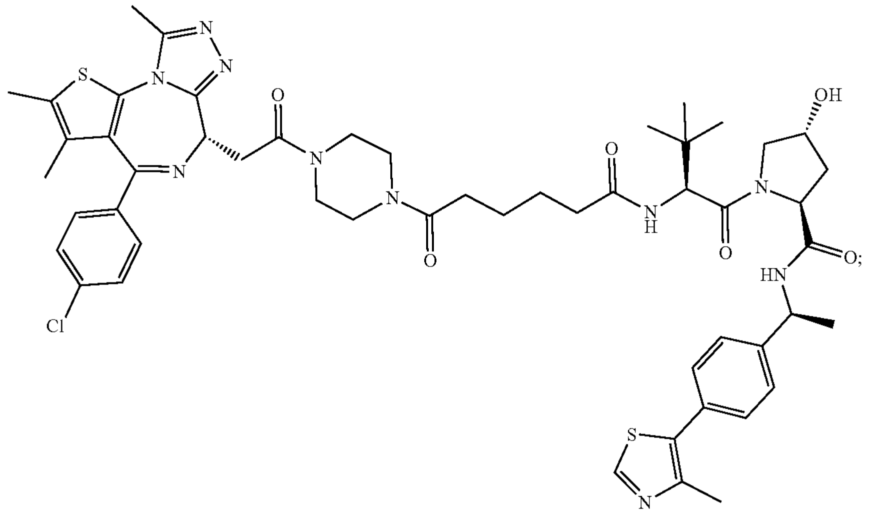
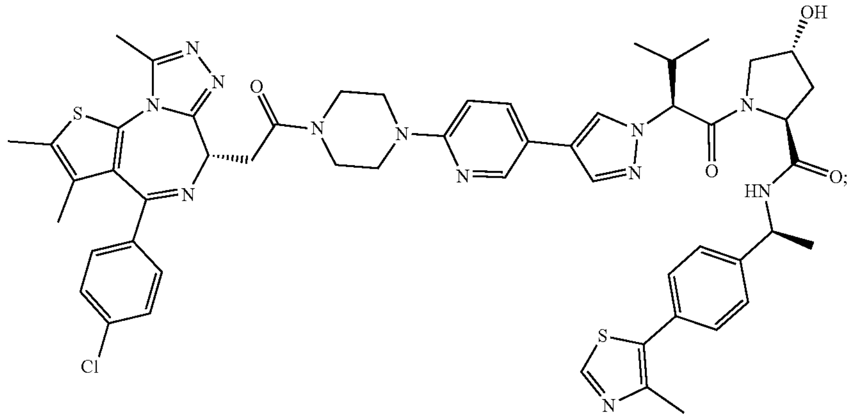
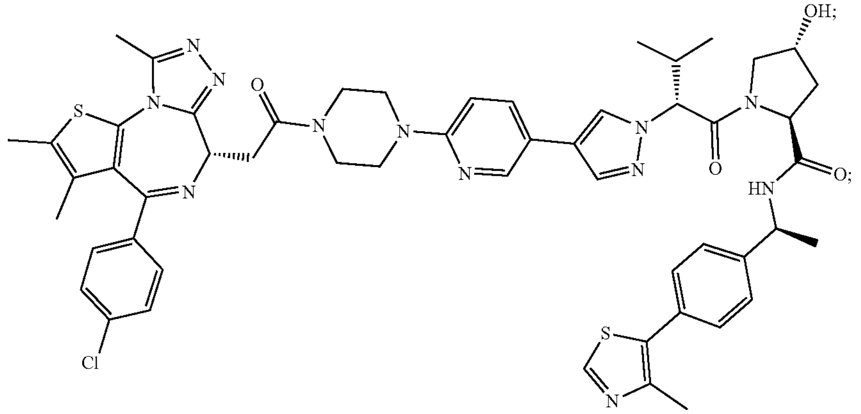

-continued
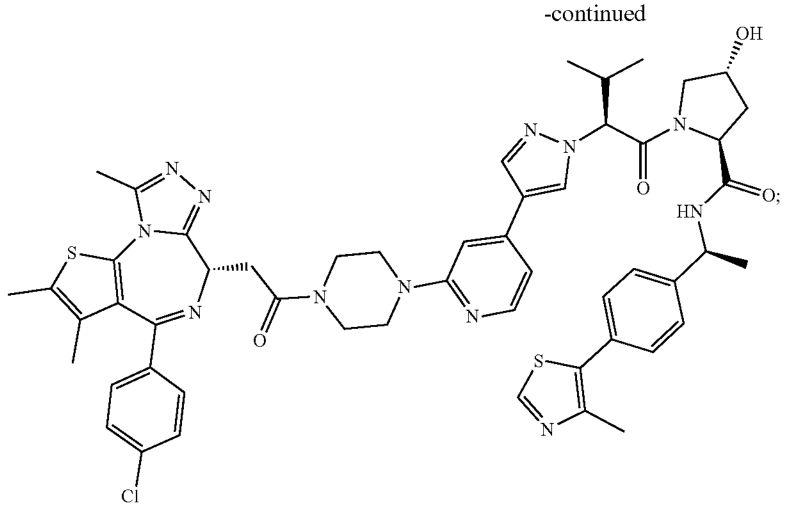
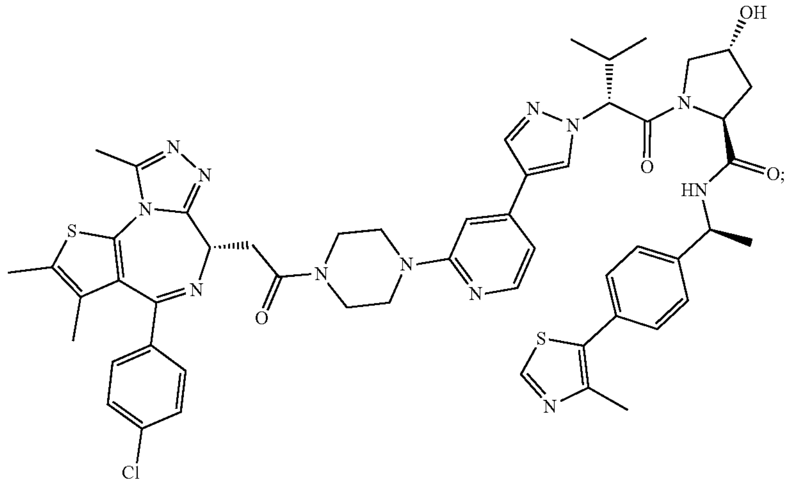
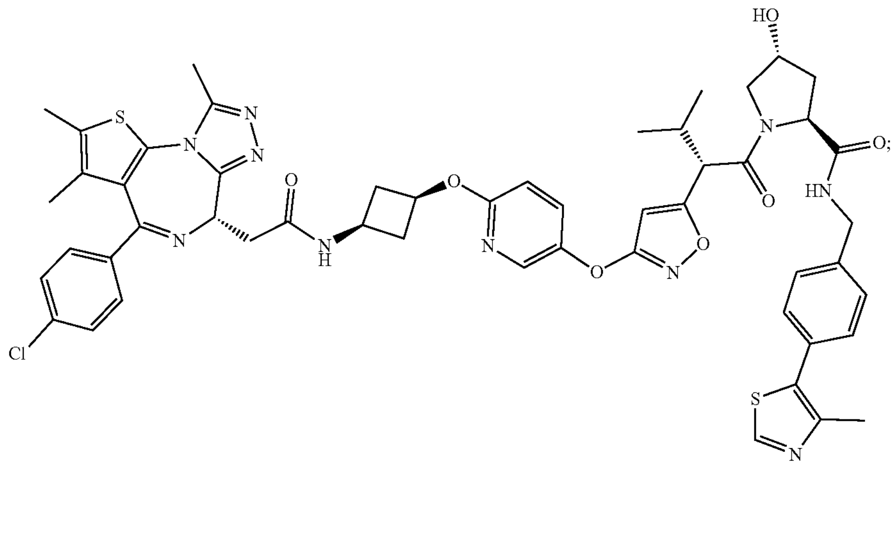

-continued
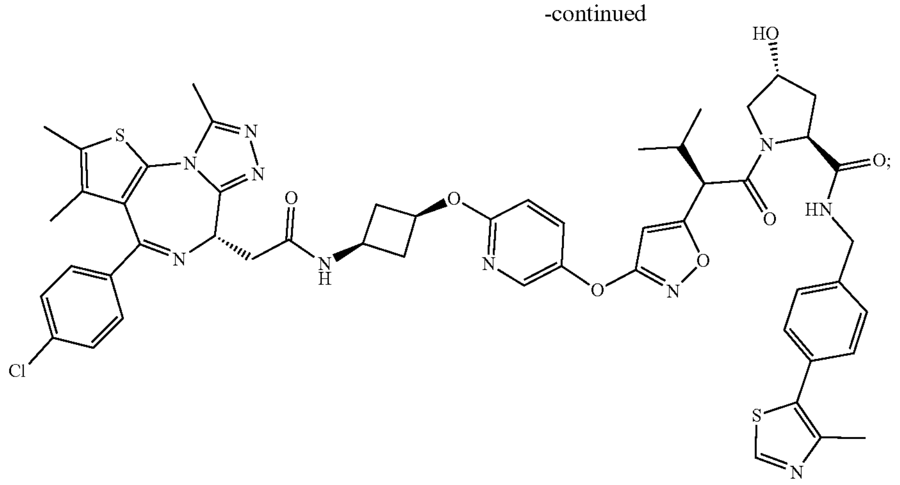
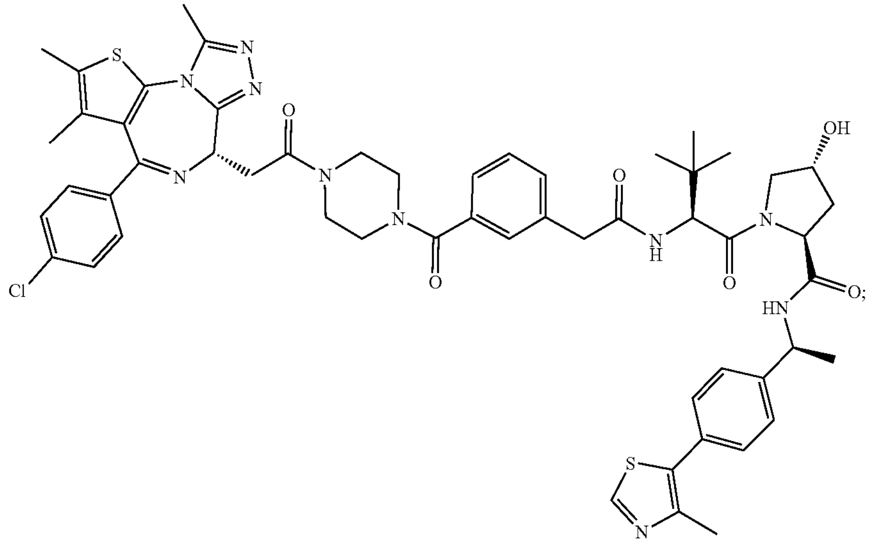
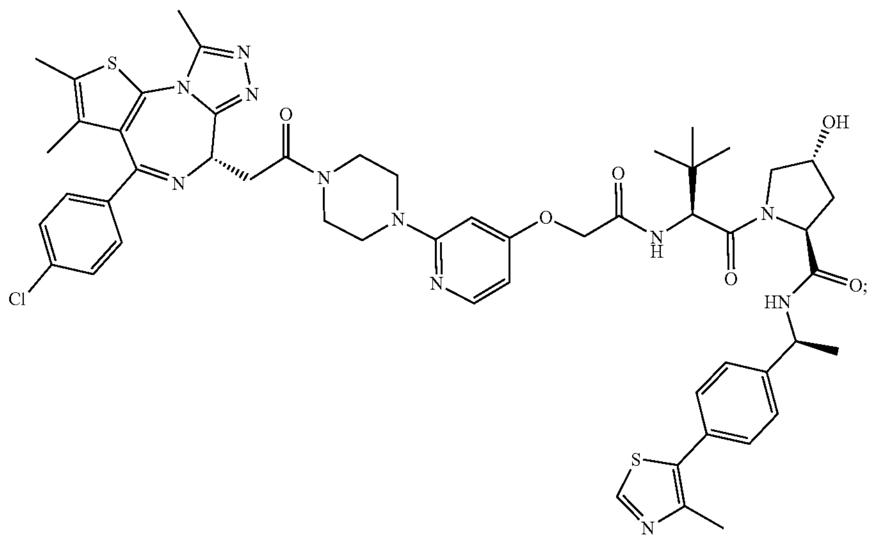

-continued
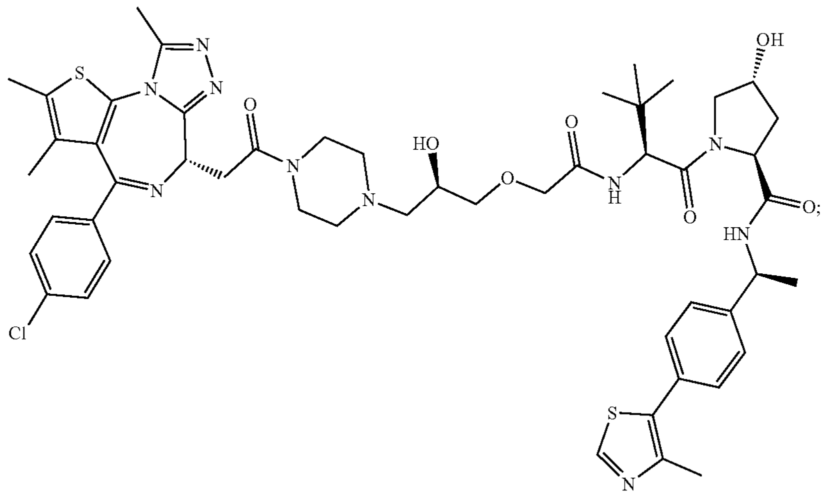
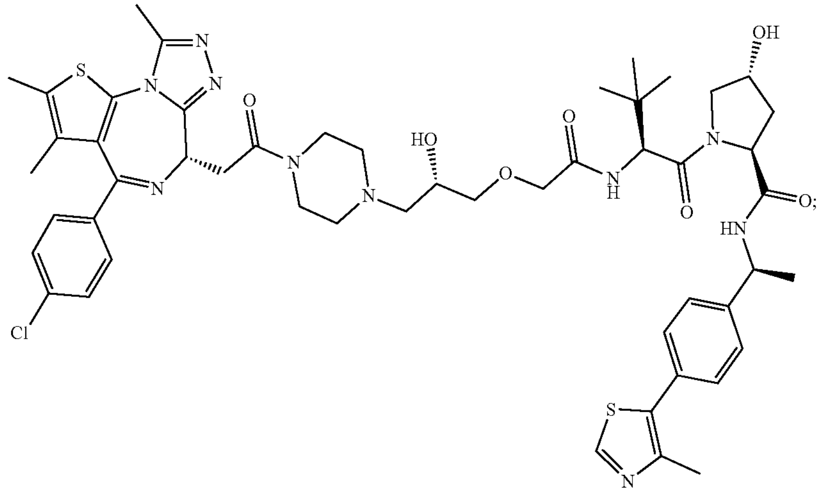
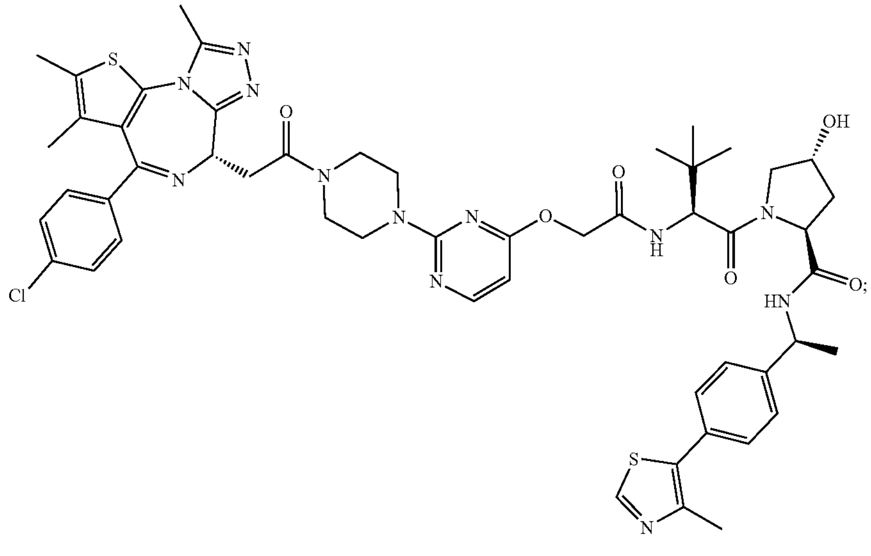

-continued
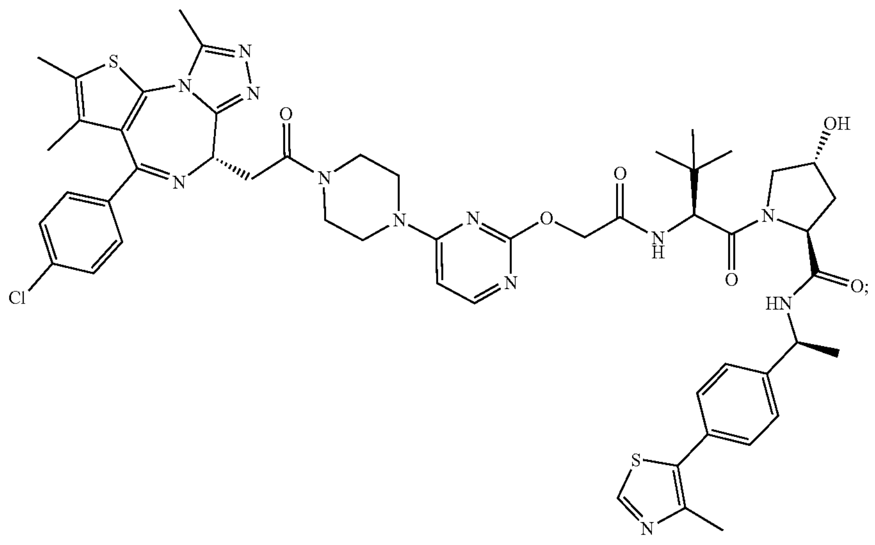
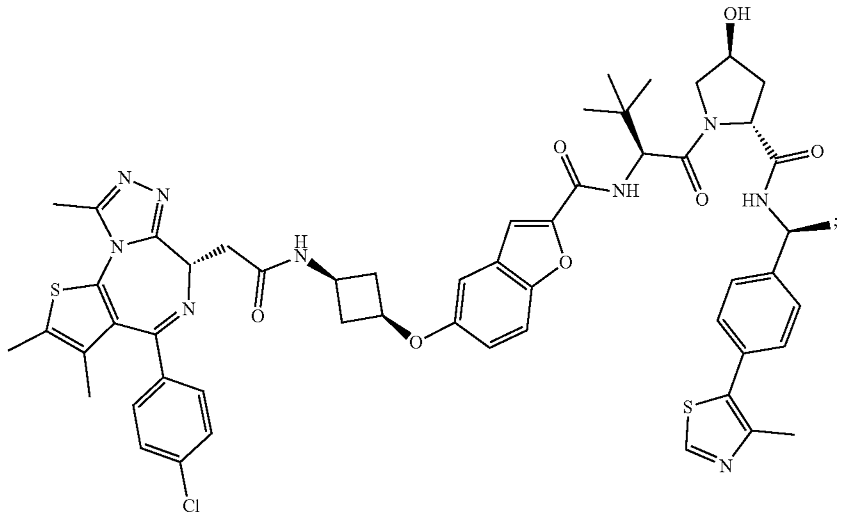
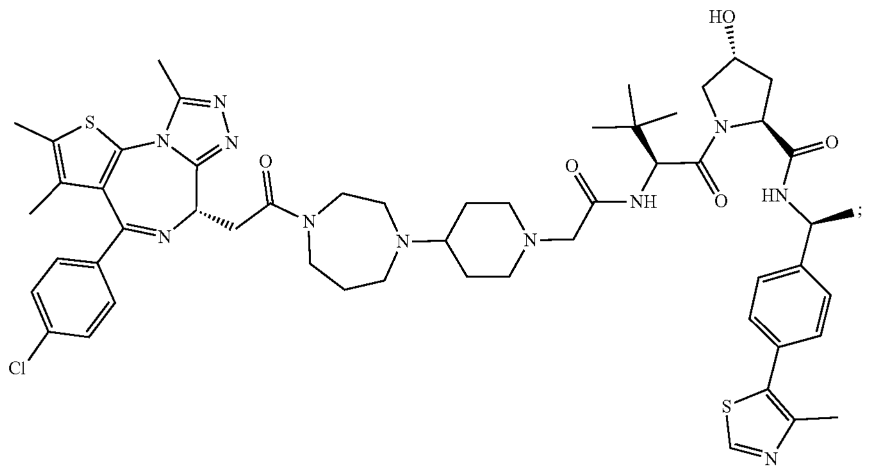

-continued
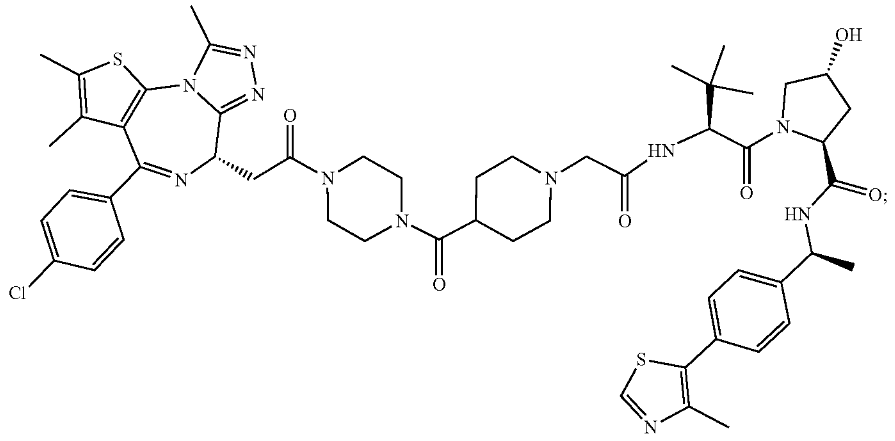
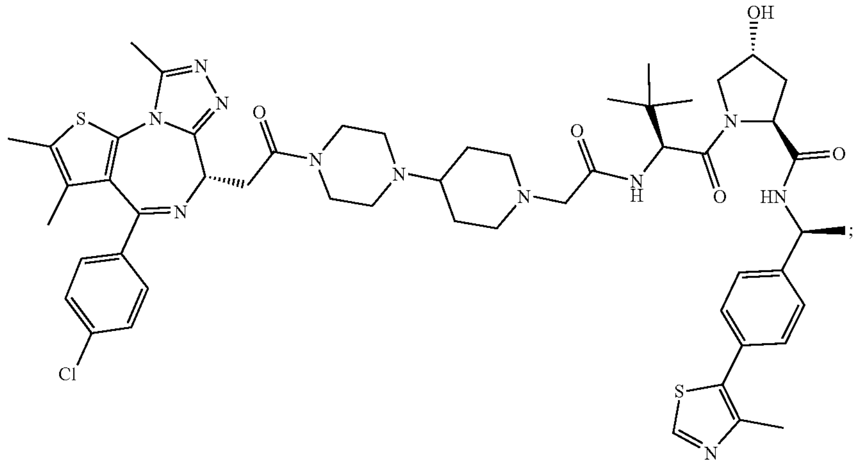
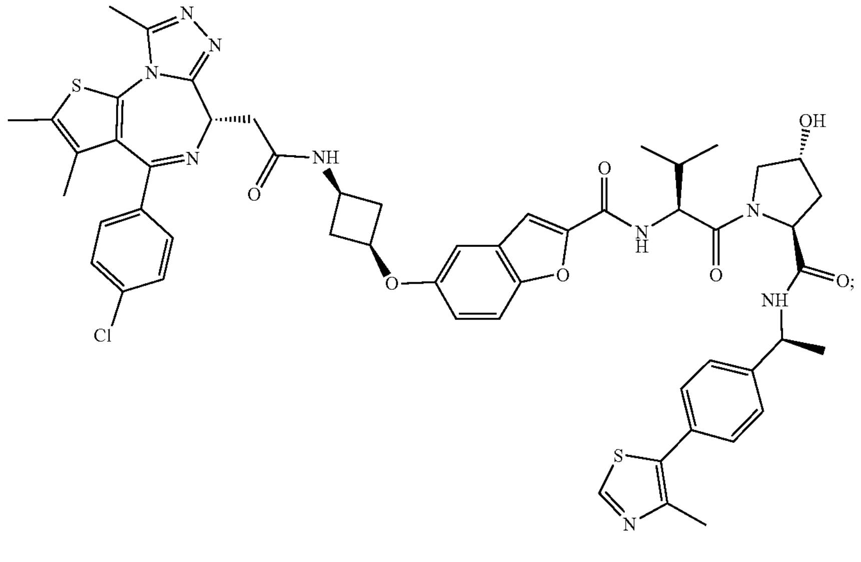

-continued
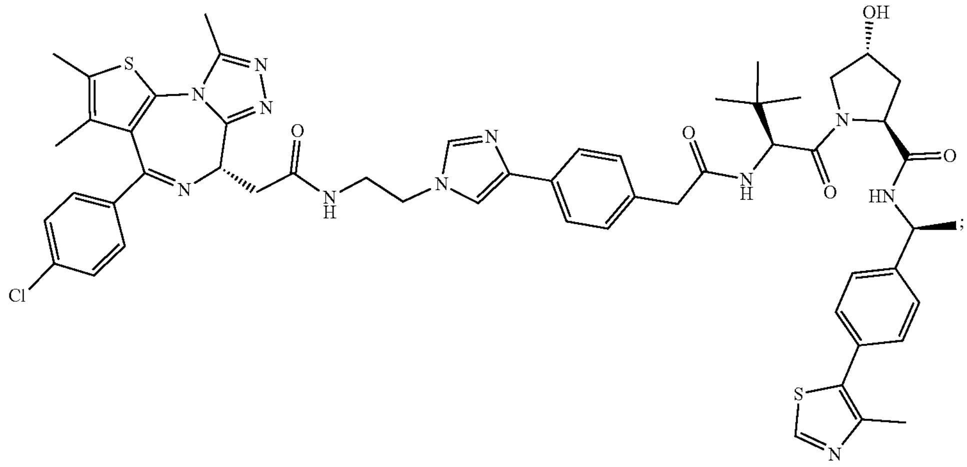
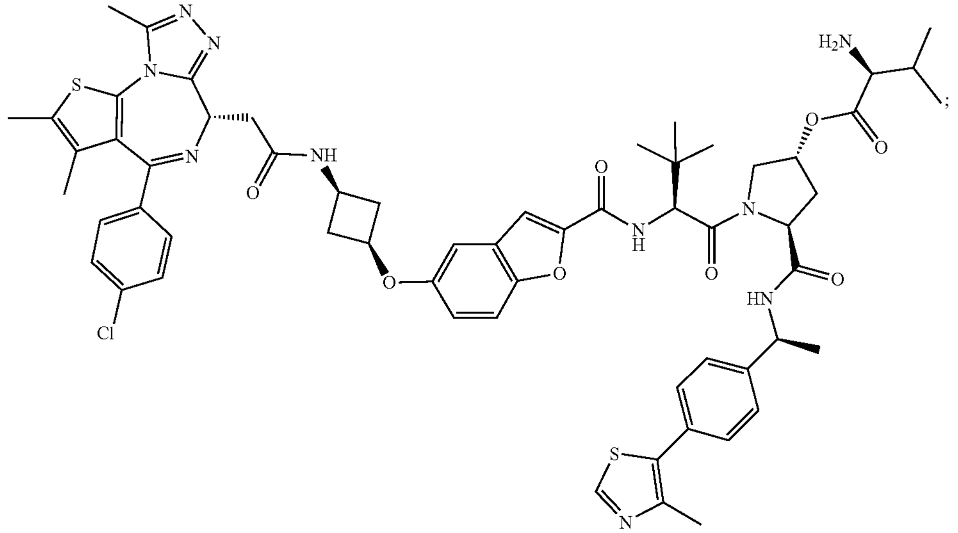
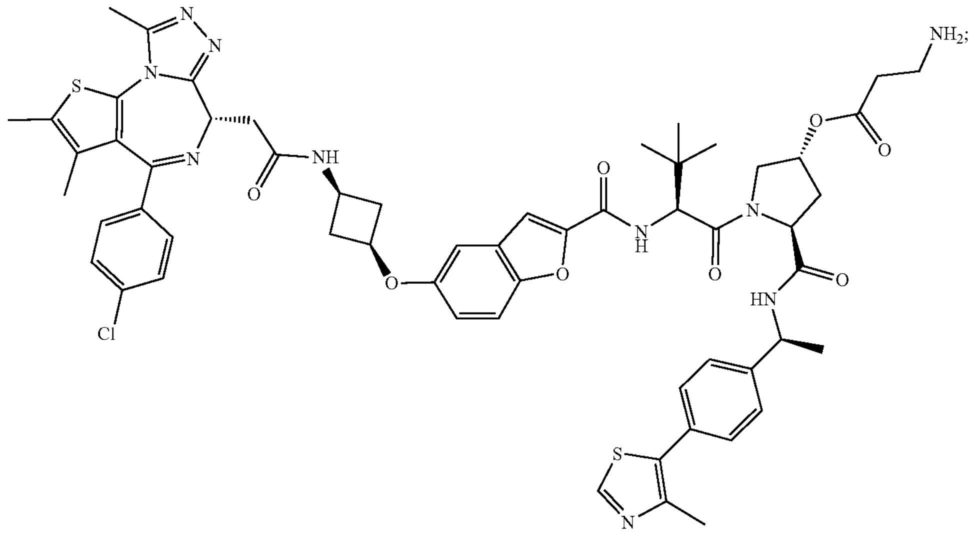

-continued
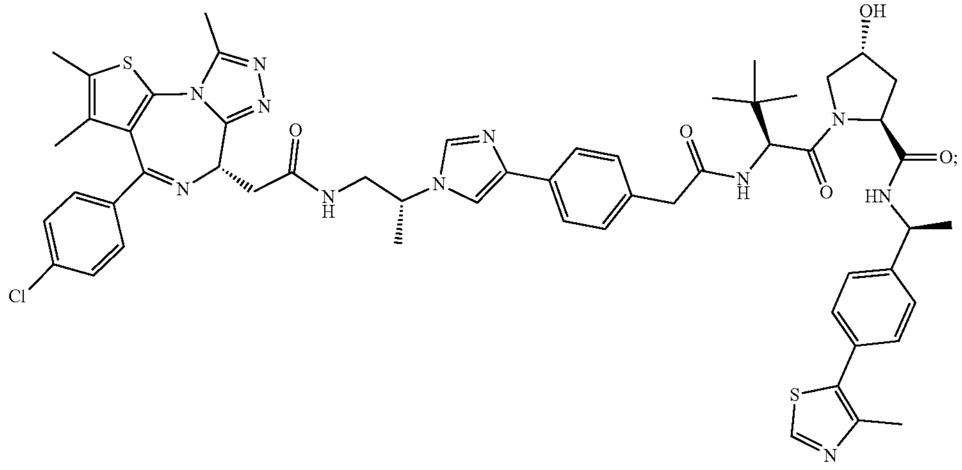
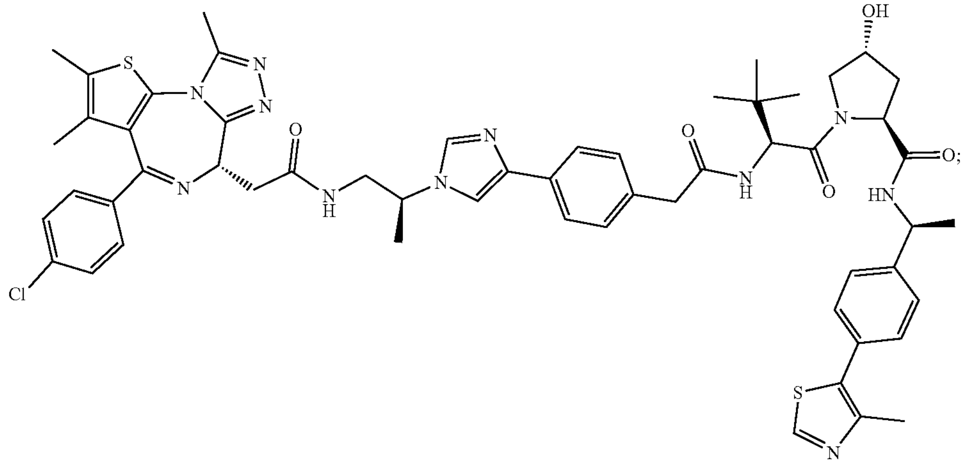
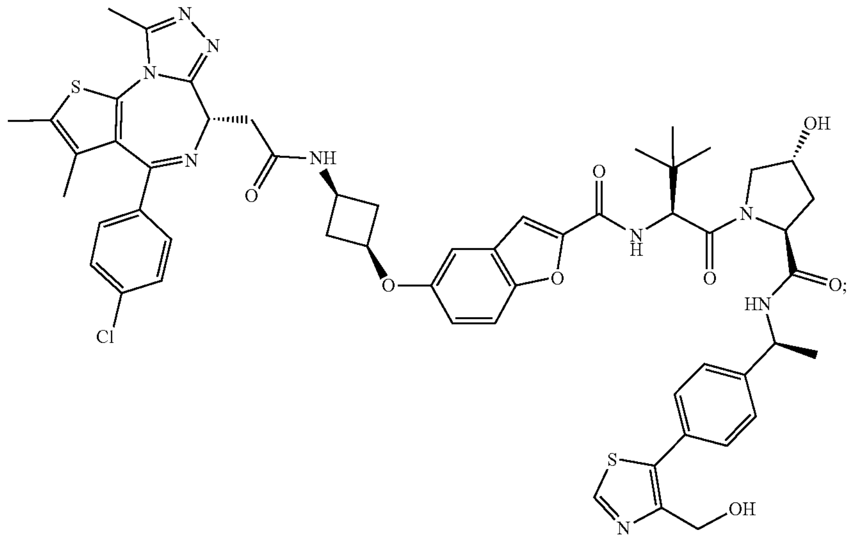

-continued
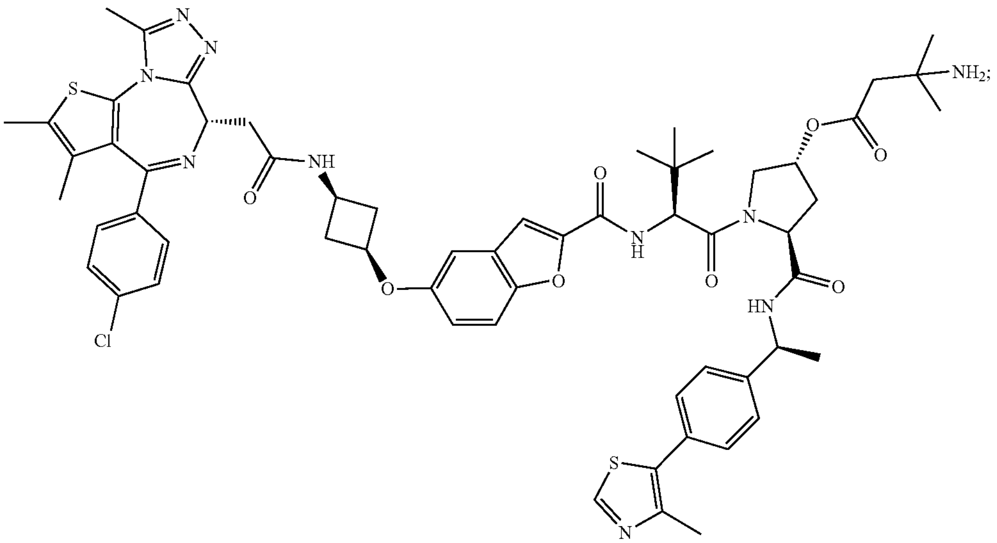
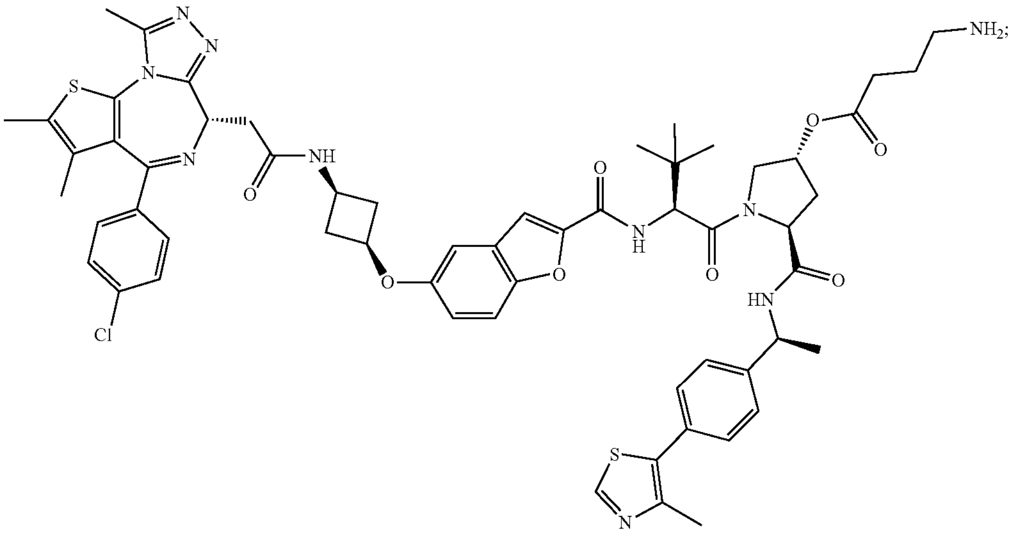
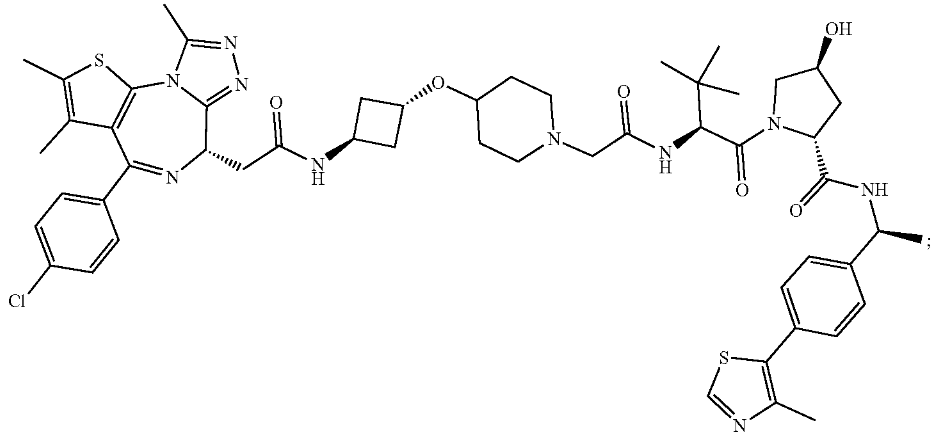

-continued
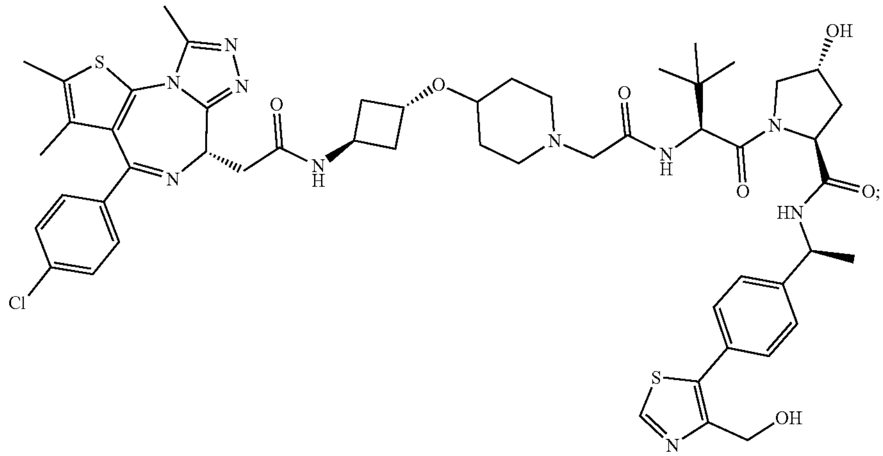
;
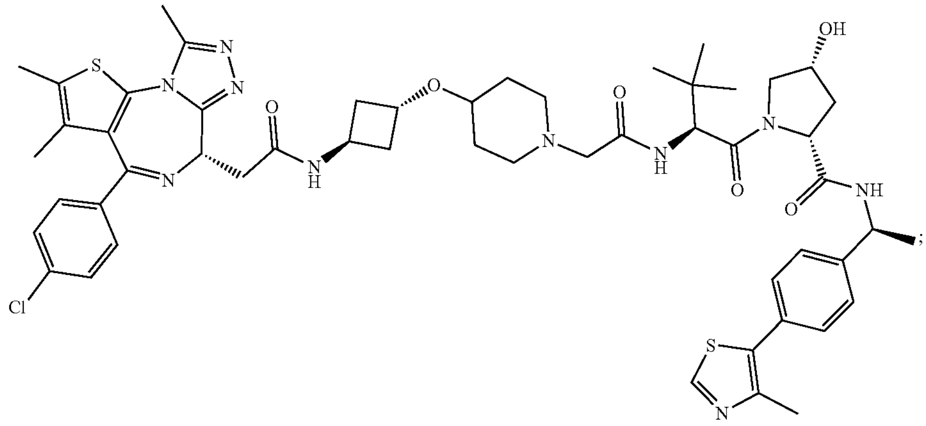
;
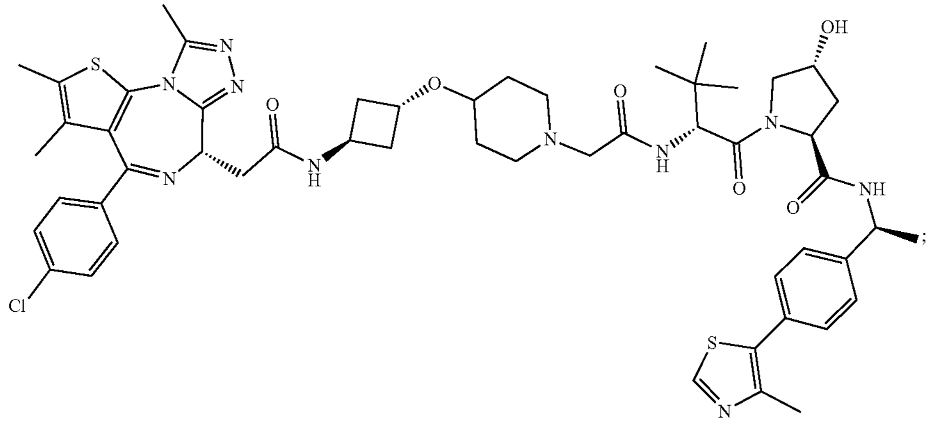
;
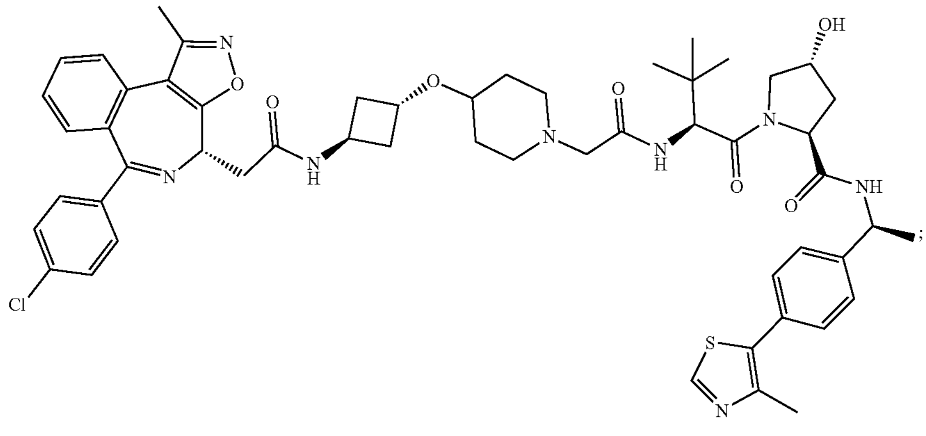
;

-continued
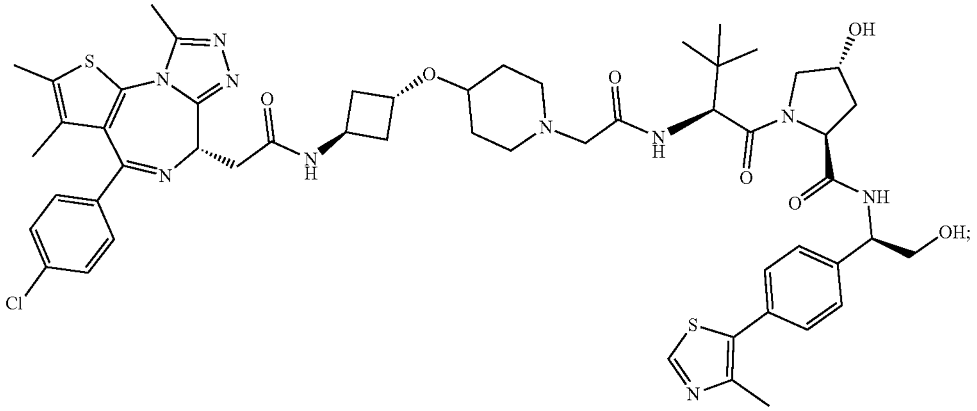
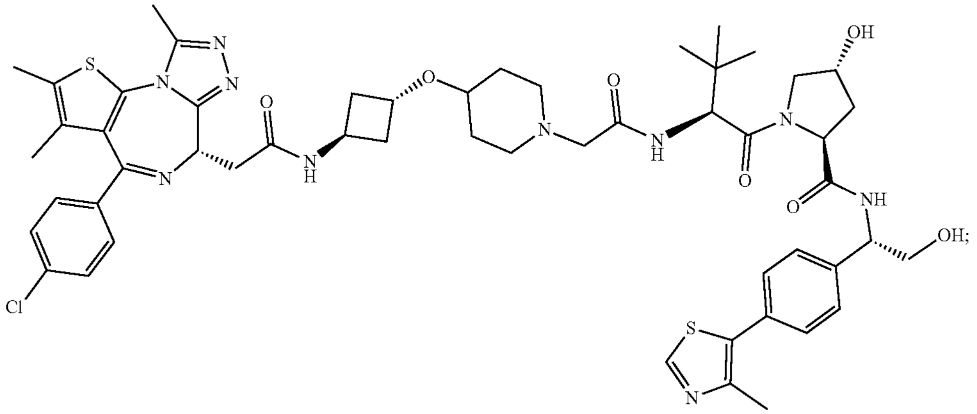
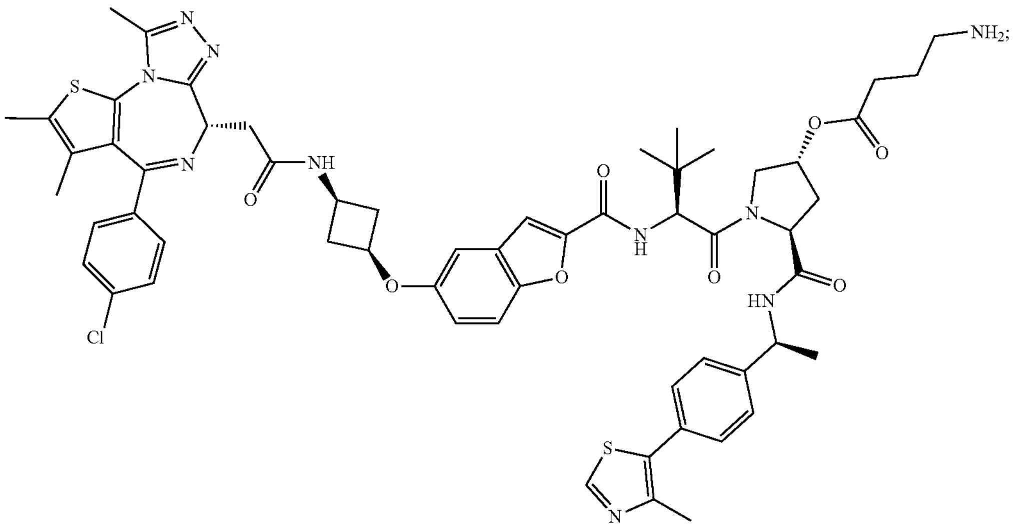

-continued
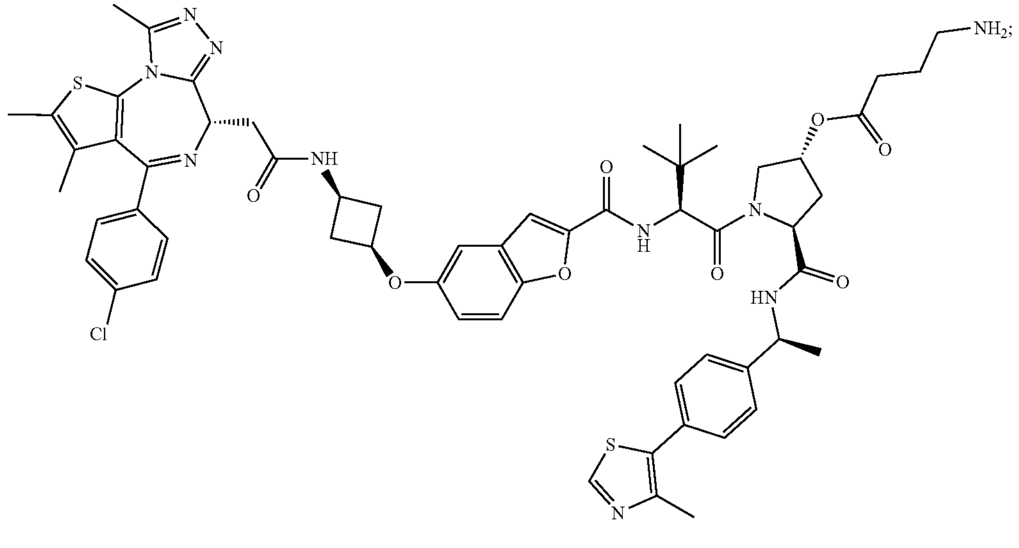
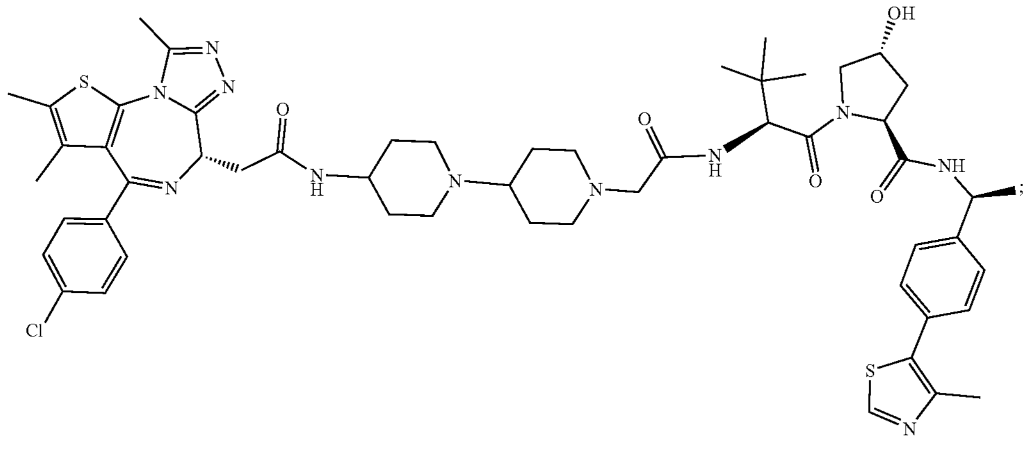
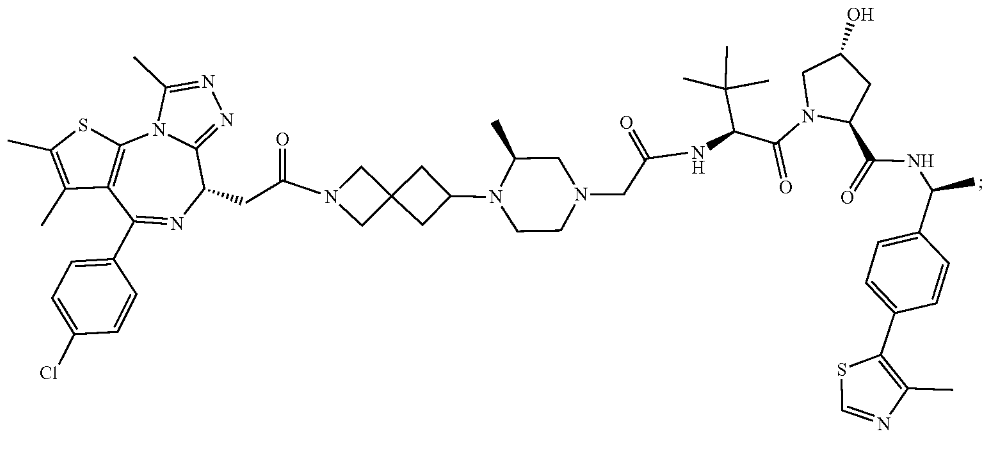

-continued
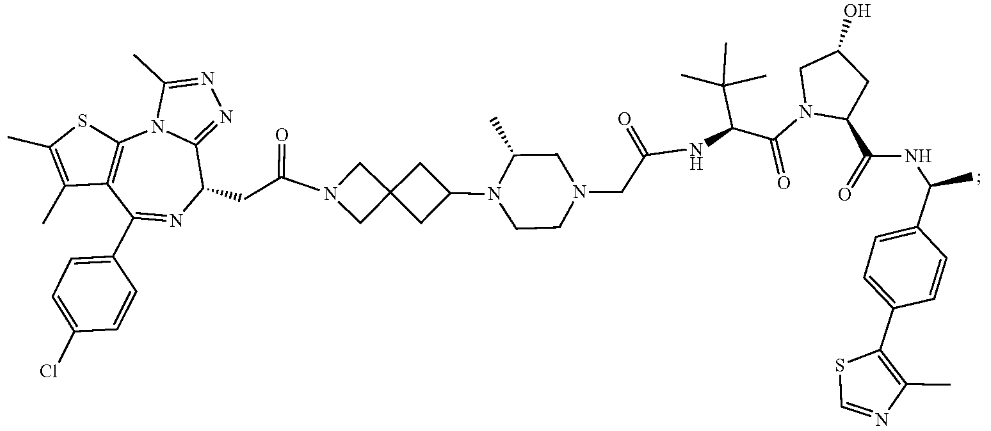
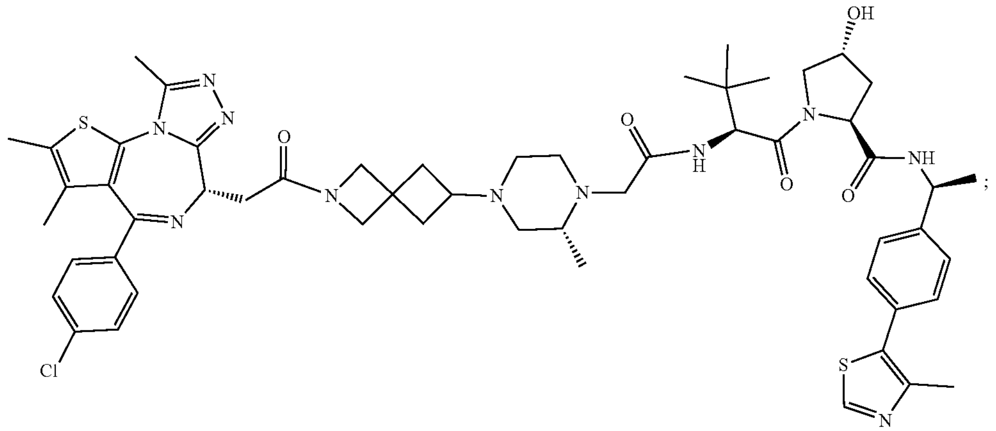
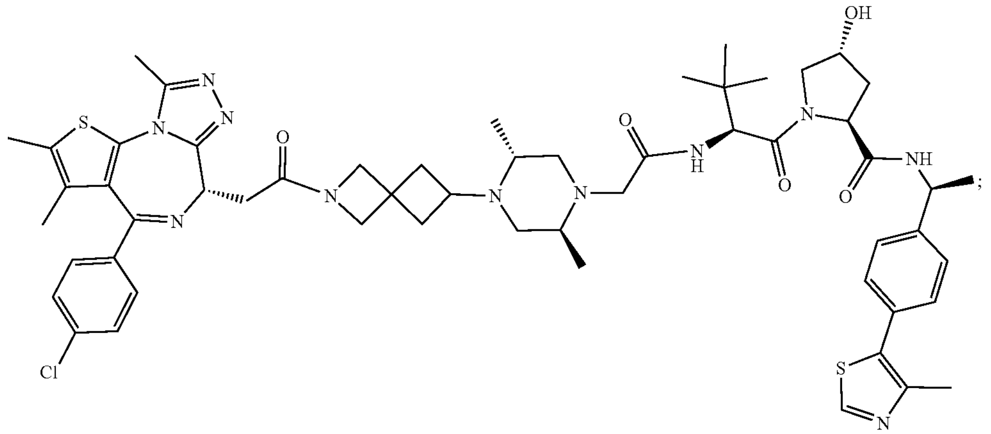
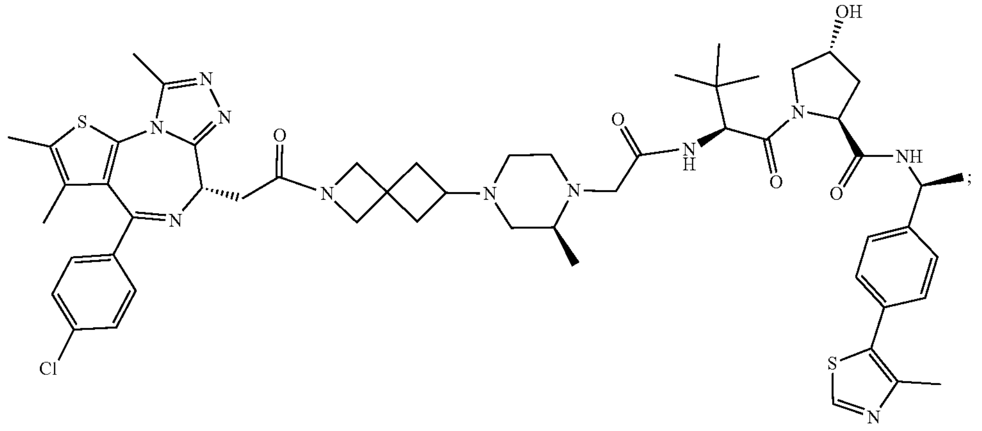

-continued
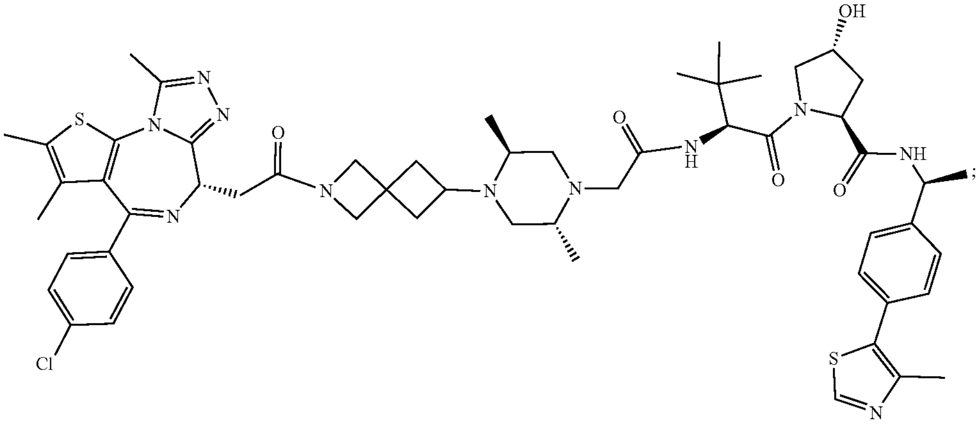
;
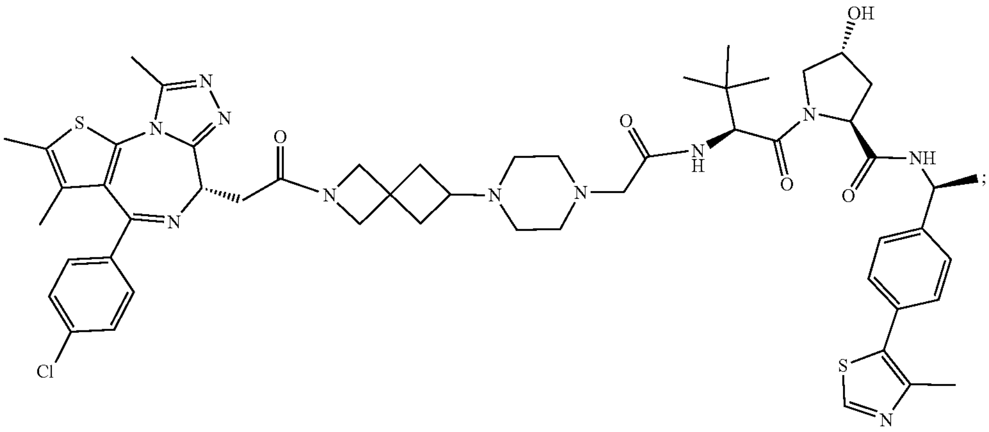
;
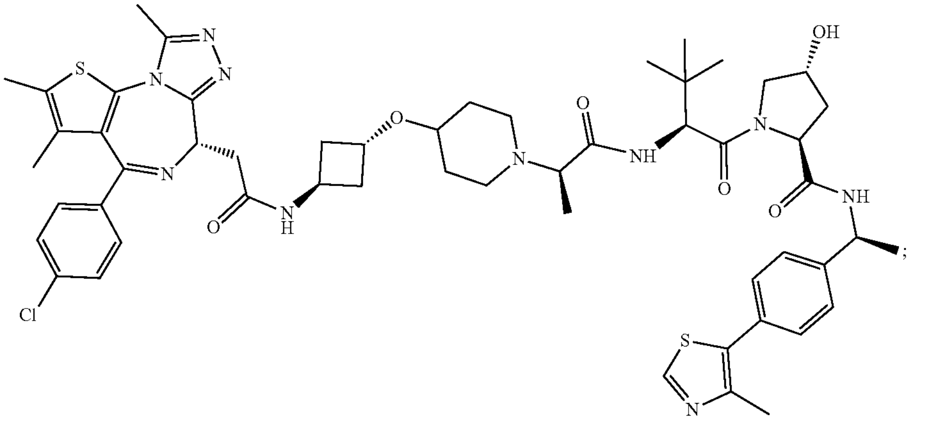
;

-continued
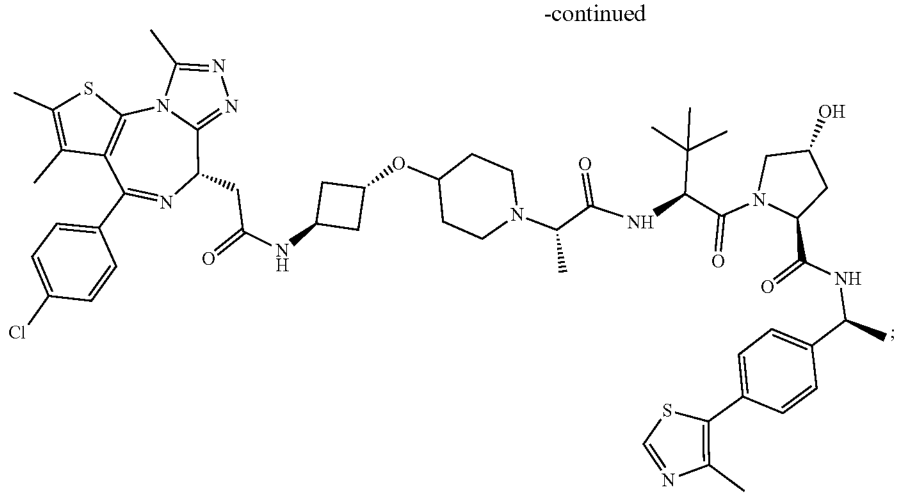
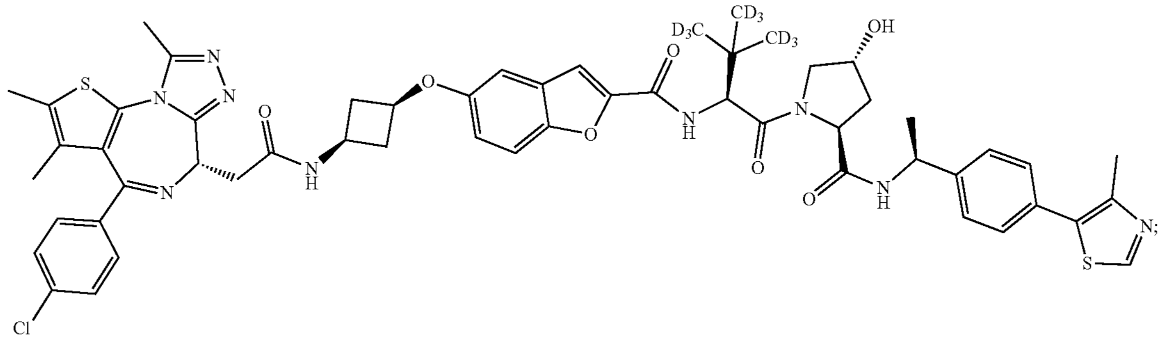
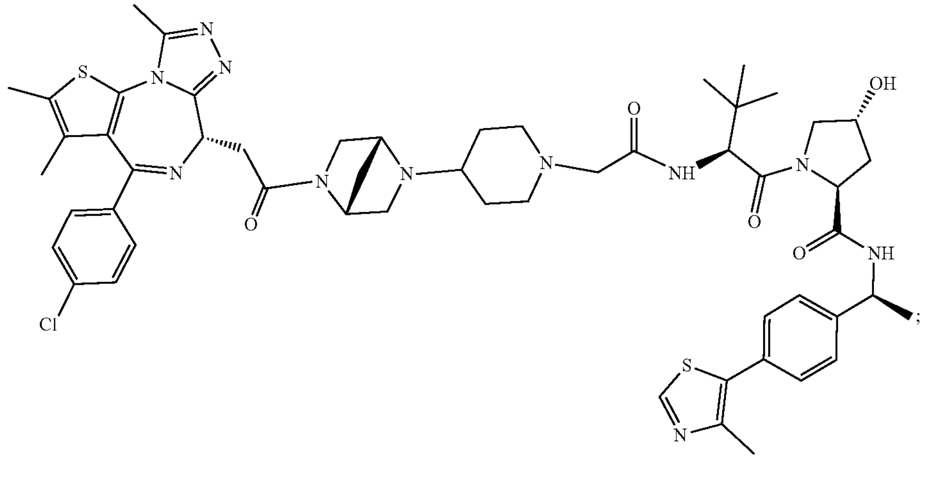

-continued
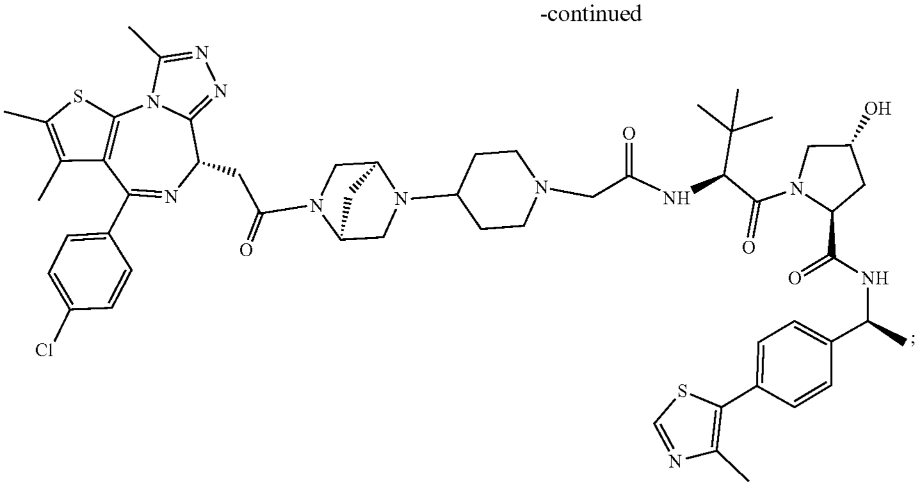
;
or a pharmaceutically acceptable salt, enantiomer, or diastereomer thereof.
* * * * *